US012338256B2

(12) United States Patent
Landry et al.

(10) Patent No.: US 12,338,256 B2
(45) Date of Patent: Jun. 24, 2025

(54) AZA-TETRACYCLIC OXAZEPINE COMPOUNDS AND USES THEREOF

(71) Applicant: Genentech, Inc., South San Francisco, CA (US)

(72) Inventors: Matthew Leo Landry, South San Francisco, CA (US); Christian Nilewski, South San Francisco, CA (US); Michael Siu, South San Francisco, CA (US); Elisia Villemure, South San Francisco, CA (US); BinQing Wei, South San Francisco, CA (US); Steven Do, South San Francisco, CA (US); Lewis John Gazzard, South San Francisco, CA (US); Samantha Alyson Green, South San Francisco, CA (US)

(73) Assignee: GENENTECH, INC., South San Francisco, CA (US)

( * ) Notice: Subject to any disclaimer, the term of this patent is extended or adjusted under 35 U.S.C. 154(b) by 0 days.

(21) Appl. No.: 18/676,200

(22) Filed: May 28, 2024

(65) Prior Publication Data

US 2024/0368186 A1     Nov. 7, 2024

Related U.S. Application Data

(63) Continuation of application No. PCT/US2023/022914, filed on May 19, 2023.

(60) Provisional application No. 63/343,959, filed on May 19, 2022.

(51) Int. Cl.
| | |
|---|---|
| *C07D 519/00* | (2006.01) |
| *A61K 31/553* | (2006.01) |
| *A61K 45/06* | (2006.01) |
| *A61P 35/00* | (2006.01) |
| *C07D 498/22* | (2006.01) |

(52) U.S. Cl.
CPC .......... *C07D 519/00* (2013.01); *A61K 31/553* (2013.01); *A61K 45/06* (2013.01); *A61P 35/00* (2018.01); *C07D 498/22* (2013.01)

(58) Field of Classification Search
CPC .. C07D 519/00; C07D 498/22; A61K 31/553; A61K 45/06; A61P 35/00
See application file for complete search history.

(56) References Cited

U.S. PATENT DOCUMENTS

| | | |
|---|---|---|
| 2022/0281893 A1 | 9/2022 | Gazzard et al. |
| 2023/0100838 A1 | 3/2023 | Pitzen et al. |
| 2023/0174518 A1 | 6/2023 | Kawai |
| 2024/0025919 A1 | 1/2024 | Landry et al. |

FOREIGN PATENT DOCUMENTS

| | | | |
|---|---|---|---|
| CN | 116199703 A | 6/2023 | |
| CN | 116332948 A | 6/2023 | |
| CN | 116514847 A | 8/2023 | |
| CN | 117462688 A | 1/2024 | |
| CN | 117771378 A | 3/2024 | |
| CN | 118221699 A | 6/2024 | |
| EP | 4397664 A1 | 7/2024 | |
| TW | 202416982 A | 5/2024 | |
| WO | 2018/206539 A1 | 11/2018 | |
| WO | 2019/215203 A1 | 11/2019 | |
| WO | 2020/097537 A2 | 5/2020 | |
| WO | 2021/041671 A1 | 3/2021 | |
| WO | 2021/108683 A1 | 6/2021 | |
| WO | 2022/188729 A1 | 9/2022 | |
| WO | 2022/194245 A1 | 9/2022 | |
| WO | WO-2022199587 A1 * | 9/2022 | |
| WO | 2022/206723 A1 | 10/2022 | |
| WO | 2022/268051 A1 | 12/2022 | |
| WO | 2023/001123 A1 | 1/2023 | |
| WO | 2023/001141 A1 | 1/2023 | |
| WO | 2023/274383 A1 | 1/2023 | |
| WO | 2023/018809 A1 | 2/2023 | |
| WO | 2023/018812 A1 | 2/2023 | |
| WO | 2023/030495 A1 | 3/2023 | |
| WO | 2023/046135 A1 | 3/2023 | |
| WO | WO-2023030385 A1 * | 3/2023 | .............. A61P 35/00 |
| WO | 2023/103906 A1 | 6/2023 | |
| WO | 2023/205719 A1 | 10/2023 | |
| WO | 2023/215906 A1 | 11/2023 | |
| WO | 2024/022444 A1 | 2/2024 | |
| WO | 2024/022507 A1 | 2/2024 | |
| WO | 2024/032704 A1 | 2/2024 | |
| WO | 2024/041573 A1 | 2/2024 | |
| WO | 2024/125600 A1 | 6/2024 | |
| WO | 2024/131829 A1 | 6/2024 | |

OTHER PUBLICATIONS

Patani, G. A., "Bioisosterism: a rational approach in drug design." Chemical reviews 96.8 (1996): 3147-3176.*
International Search Report and Written Opinion received for PCT Patent Application No. PCT/US2022/015407, mailed on Apr. 8, 2022, 9 pages.

(Continued)

*Primary Examiner* — John S Kenyon
*Assistant Examiner* — Sara Elizabeth Bell
(74) *Attorney, Agent, or Firm* — HALEY GUILIANO LLP; Karen Mangasarian; Marcus J. Jellen

(57) ABSTRACT

Provided herein are aza-tetracyclic oxazepinyl compounds useful in the treatment of cancers.

28 Claims, 1 Drawing Sheet

(56) References Cited

OTHER PUBLICATIONS

U.S. Appl. No. 17/666,350, filed Feb. 7, 2022 (Not provided; USPTO in possession of specification, claims, and prosecution history).
U.S. Appl. No. 18/199,449, filed May 19, 2023 (Not provided; USPTO in possession of specification, claims, and prosecution history).
U.S. Appl. No. 18/882,588, filed Sep. 11, 2024 (Not provided; USPTO in possession of specification, claims, and prosecution history).

* cited by examiner

| | Compound 6 | Comparator Compound | Compound 7 | Compound 81 | Compound 194 |
|---|---|---|---|---|---|
| G12D GDP HTRF IC50 (nM) (sel. vs. WT) | 0.0736 (7 x) | 0.0700 (7 x) | 0.0588 (5 x) | 0.0849 (5 x) | 0.420 (69 x) |
| HPAC IC50 (nM) (sel. vs. H1975) | 0.25 (2798 x) | 9.0 (33 x) | 1.4 (95 x) | 12 (385 x) | 5.0 (184 x) |
| Mouse | | | | | |
| Blood: CL / Vss / t1/2 (IV, 0.5 mpk) | 13 / 6.7 / 6.7 | 19 / 6.0 / 5.4 | 26 / 4.1 / 3.1 | 32 / 0.61 / 0.66 | 31 / 6.5 / 2.6 |
| B/P@8h | 11 | 5.6 | 7.5 | Not Measurable | 3.4 |
| %F (PO, 5 mpk) | 15% | 0.62% | Not Measureable* | Not Measurable | 19% |
| Rat | | | | | |
| Blood: CL, Vss, t1/2 (IV, 0.5 mpk) | 17 / 18 / 14 | 14 / 6.2 / 28 | 17 / 15 / 15 | - | 20 / 18 / 12 |
| %F (PO, 30 mpk) | 19% | 0.085% | 0.029% | - | 1.4% |
| Plasma: CL, Vss, t1/2 (IV, 0.5 mpk) | 194 / 68 / 16 | 140 / 0.74 / 0.19 | 104 / 9.0 / 3.9 | - | 192 / 88 / 6.7 |
| %F (PO, 30 mpk) | 19% | 0.14% | 0.031% | - | 1.3% |

Not Measurable = Concentration below the lower limit of quantitation (LLOQ: 0.0079 μM for Compound 7; 0.0081 μM for Compound 81). %F could not be determined with insufficient detectable concentrations.

AZA-TETRACYCLIC OXAZEPINE COMPOUNDS AND USES THEREOF

CROSS REFERENCE TO RELATED APPLICATIONS

This application is a continuation of International Patent Application No. PCT/US2023/022914, filed May 19, 2023, which claims priority from and the benefit of U.S. Provisional Application No. 63/343,959, filed May 19, 2022. Each of the foregoing disclosures is hereby incorporated by reference in its entirety.

BACKGROUND

Ras is a small GTP-binding protein that functions as a nucleotide-dependent switch for central growth signaling pathways. In response to extracellular signals, Ras is converted from a GDP-bound ($Ras^{GDP}$) to a GTP-bound ($Ras^{GTP}$) state, as catalyzed by guanine nucleotide exchange factors (GEFs), notably the SOS1 protein. Active $Ras^{GTP}$ mediates its diverse growth-stimulating functions through its direct interactions with effectors including Raf, PI3K, and Ral guanine nucleotide dissociation stimulator. The intrinsic GTPase activity of Ras then hydrolyzes GTP to GDP to terminate Ras signaling. The Ras GTPase activity can be further accelerated by its interactions with GTPase-activating proteins (GAPs), including the neurofibromin 1 tumor suppressor.

Mutant Ras has a reduced GTPase activity, which prolongs its activated state, thereby promoting Ras-dependent signaling and cancer cell survival or growth. Mutation in Ras that affects its ability to interact with GAP or to convert GTP back to GDP will result in a prolonged activation of the protein and consequently a prolonged signal to the cell telling it to continue to grow and divide. Because these signals result in cell growth and division, overactive RAS signaling may ultimately lead to cancer. Mutations in any one of the three main isoforms of RAS (HRas, NRas, or KRas) genes are common events in human tumorigenesis. Among the three Ras isoforms (K, N, and H), KRas is most frequently mutated.

The most common KRas mutations are found at residue G12 and G13 in the P-loop and at residue Q61. G12D is a frequent mutation of KRas gene (glycine-12 to aspartate). Mutations of Ras in cancer are associated with poor prognosis. Inactivation of oncogenic Ras in mice results in tumor shrinkage. Thus, Ras is widely considered an oncology target of exceptional importance.

Accordingly, there is a pressing need for therapies for G12D mutant KRas mediated cancers.

BRIEF SUMMARY

Provided herein are solutions to the problems above and other problems in the art.

In a first aspect provided herein is a compound of formula (I) or a stereoisomer, atropisomer, tautomer, or pharmaceutically acceptable salt thereof as described herein.

In a second aspect provided herein is a compound of formula (IId) or a stereoisomer, atropisomer, tautomer, or pharmaceutically acceptable salt thereof as described herein.

In another aspect provided herein is a compound or pharmaceutically acceptable salt thereof as set forth in Table 1.

In another aspect provided herein is a pharmaceutical composition comprising a compound, stereoisomer, atropisomer, tautomer, or pharmaceutically acceptable salt thereof as described herein.

In another aspect provided herein is a method of treating a cancer comprising a KRas mutation, the method comprising administering to a patient having such cancer, a compound, stereoisomer, atropisomer, tautomer, or pharmaceutically acceptable salt thereof as described herein.

In another aspect provided herein is a method for regulating activity of a KRas mutant protein, the method comprising reacting the mutant protein with a compound, or stereoisomer, atropisomer, tautomer, or pharmaceutically acceptable salt thereof as described herein.

In another aspect provided herein is a method for inhibiting proliferation of a cell population, the method comprising contacting the cell population with a compound, or stereoisomer, atropisomer, tautomer, or pharmaceutically acceptable salt thereof as described herein.

In another aspect provided herein is a method for inhibiting tumor metastasis comprising administering to an individual in need thereof a therapeutically effective amount of the compound or stereoisomer, atropisomer, tautomer, or pharmaceutically acceptable salt thereof as described herein or a pharmaceutical composition as described herein to a subject in need thereof.

In another aspect provided herein is method for preparing a labeled KRas G12D mutant protein, the method comprising reacting a KRas G12D mutant protein with a labeled compound or stereoisomer, atropisomer, tautomer, or pharmaceutically acceptable salt thereof, as described here to result in the labeled KRas G12D mutant protein.

BRIEF DESCRIPTION OF THE DRAWINGS

The Drawing shows the pharmacokinetic profile of compounds 6, 7, 81, and 194, and comparator compound.

DETAILED DESCRIPTION

Definitions

Disclosed herein are 6-aza tetracyclic oxazepine compounds as described herein or a stereoisomer, atropisomer, tautomer, or pharmaceutically acceptable salt thereof and pharmaceutical compositions thereof that, in certain embodiments, are inhibitors or modulators of mutant KRas. In certain instances, such compounds and compositions are inhibitors or modulators of mutant G12D KRas as provided herein. The compounds and compositions described herein are useful in treating diseases and disorders mediated by mutant KRas, including $KRas^{G12D}$ mutations.

While the disclosure herein provides enumerated embodiments, it is understood that they are not intended to limit the compounds and methods described herein to those embodiments. On the contrary, the disclosure is intended to cover all alternatives, modifications, and equivalents that can be included within the scope of the present disclosure as defined by the claims.

Unless otherwise defined, all technical and scientific terms used herein have the same meaning as commonly understood by one of ordinary skill in the art. All publications, patent applications, patents, and other references mentioned herein are incorporated by reference in their entirety. The nomenclature used in this Application is based on IUPAC systematic nomenclature, unless indicated otherwise.

The following definitions are provided to facilitate understanding of certain terms used frequently herein and are not meant to limit the scope of the present disclosure. All references referred to herein are incorporated by reference in their entirety.

The terms "halogen" and "halo" are used interchangeably and refer to F, Cl, Br or I. Additionally, terms such as "haloalkyl," are meant to include monohaloalkyl, polyhaloalkyl, and perhaloalkyl.

The term "alkyl" refers to a saturated linear or branched-chain monovalent hydrocarbon radical. In one example, the alkyl radical is one to eighteen carbon atoms ($C_{1-18}$). In other examples, the alkyl radical is $C_{1-12}$, $C_{1-10}$, $C_{1-8}$, $C_{1-6}$, $C_{1-5}$, $C_{1-4}$, or $C_{1-3}$. Examples of alkyl groups include methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), 1-heptyl and 1-octyl.

The term "oxo" refers to =O.

The term "alkoxy" refers to —O-alkyl.

The terms "cyano" or "nitrile" refers to —C≡N or —CN.

The term "haloalkoxy" refers to —O-haloalkyl.

The terms "hydroxy" and "hydroxyl" refer to —OH.

The term "alkylidene" refers to linear or branched-chain monovalent hydrocarbon radical having formula =CR'R", where R' and R" can be the same or different. In one example, an alkylidene radical is 1 to 6 carbons ($C_{1-6}$). In another example, the alkylidene radical is $C_{1-3}$, $C_{1-2}$, or $C_1$. Exemplary alkylidenes include, but are not limited to, methylidene (=$CH_2$), ethylidene (=$CHCH_3$), and propylidene (=CH—$CH_2$—$CH_3$).

The term "alkenyl" refers to linear or branched-chain monovalent hydrocarbon radical with at least one carbon-carbon double bond and includes radicals having "cis" and "trans" orientations, or alternatively, "E" and "Z" orientations. In one example, the alkenyl radical is two to eighteen carbon atoms ($C_{2-18}$). In other examples, the alkenyl radical is $C_{2-12}$, $C_{2-10}$, $C_{2-8}$, $C_{2-6}$, or $C_{2-3}$. Examples include, but are not limited to, ethenyl or vinyl (—CH=$CH_2$), prop-1-enyl (—CH=$CHCH_3$), prop-2-enyl (—$CH_2$CH=$CH_2$), 2-methylprop-1-enyl, but-1-enyl, but-2-enyl, but-3-enyl, buta-1,3-dienyl, 2-methylbuta-1,3-diene, hex-1-enyl, hex-2-enyl, hex-3-enyl, hex-4-enyl, and hexa-1,3-dienyl.

The term "alkynyl" refers to a linear or branched monovalent hydrocarbon radical with at least one carbon-carbon, triple bond. In one example, the alkynyl radical is two to eighteen carbon atoms ($C_{2-18}$). In other examples, the alkynyl radical is $C_{2-12}$, $C_{2-10}$, $C_{2-8}$, $C_{2-6}$, or $C_{2-3}$. Examples include, but are not limited to, ethynyl (—C≡CH), prop-1-ynyl (—C≡$CCH_3$), prop-2-ynyl (propargyl, —$CH_2$C≡CH), but-1-ynyl, but-2-ynyl, and but-3-ynyl.

The term "alkylene" refers to a saturated, branched, or straight chain hydrocarbon group having two monovalent radical centers derived by the removal of two hydrogen atoms from the same or two different carbon atoms of a parent alkane. In one example, the divalent alkylene group is one to eighteen carbon atoms ($C_{1-18}$). In other examples, the divalent alkylene group is $C_{1-12}$, $C_{1-10}$, $C_{1-8}$, $C_{1-6}$, $C_{1-5}$, $C_{1-4}$, or $C_{1-3}$. Example alkylene groups include methylene (—$CH_2$—), 1,1-ethyl (—$CH(CH_3)$—), (1,2-ethyl —$CH_2CH_2$—), 1,1-propyl (—$CH(CH_2CH_3)$—), 2,2-propyl (—$C(CH_3)_2$—), 1,2-propyl (—$CH(CH_3)CH_2$—), 1,3-propyl (—$CH_2CH_2CH_2$—), 1,1-dimethyleth-1,2-yl (—$C(CH_3)_2CH_2$—), 1,4-butyl (—$CH_2CH_2CH_2CH_2$—), and the like.

The term "cycloalkyl" refers to a saturated hydrocarbon ring group. Cycloalkyl encompasses mono-, bi-, tricyclic, spiro and bridged, saturated ring systems. In one example, the cycloalkyl group is 3 to 12 carbon atoms ($C_{3-12}$). In other examples, cycloalkyl is $C_{3-4}$, $C_{3-5}$, $C_{3-7}$, $C_{3-8}$, $C_{3-10}$, or $C_{5-10}$. In other examples, the cycloalkyl group, as a monocycle, is $C_{3-4}$, $C_{3-8}$, $C_{3-6}$, or $C_{5-6}$. In another example, the cycloalkyl group, as a bicycle, is $C_7$-$C_{12}$. In another example, the cycloalkyl group, as a spiro system, is $C_{5-12}$. Examples of monocyclic cycloalkyl include cyclopropyl, cyclobutyl, cyclopentyl, cyclohexyl, cycloheptyl, cyclooctyl, cyclononyl, cyclodecyl, cycloundecyl and cyclododecyl. Exemplary arrangements of bicyclic cycloalkyls having 7 to 12 ring atoms include, but are not limited to, [4,4], [4,5], [5,5], [5,6] or [6,6] ring systems. Exemplary bridged bicyclic cycloalkyls include, but are not limited to, bicyclo[2.2.1] heptane, bicyclo[2.2.2]octane and bicyclo[3.2.2]nonane. Examples of spirocycloalkyl include, spiro[2.2]pentane, spiro[2.3]hexane, spiro[2.4]heptane, spiro[2.5]octane and spiro[4.5]decane.

The terms "heterocyclic group", "heterocyclic", "heterocycle", "heterocyclyl", or "heterocyclo" are used interchangeably and refer to any mono-, bi-, tricyclic, spiro or bridged, saturated, partially saturated or unsaturated, non-aromatic ring system, having 3 to 20 ring atoms, where the ring atoms are carbon, and at least one atom in the ring or ring system is a heteroatom selected from nitrogen, sulfur or oxygen. If any ring atom of a cyclic system is a heteroatom, that system is a heterocycle, regardless of the point of attachment of the cyclic system to the rest of the molecule. In one example, heterocyclyl includes 3-10 ring atoms ("members") and includes monocycles, bicycles, tricycles, spiro, and bridged ring systems, wherein the ring atoms are carbon, where at least one atom in the ring or ring system is a heteroatom selected from nitrogen, sulfur or oxygen. In other examples, heterocyclyl includes 4-10 or 5-10 ring atoms. In one example, heterocyclyl includes 1 to 4 heteroatoms. In one example, heterocyclyl includes 1 to 3 heteroatoms. In another example, heterocyclyl includes 3- to 7-membered monocycles having 1-2, 1-3 or 1-4 heteroatoms selected from nitrogen, sulfur or oxygen. In another example, heterocyclyl includes 4- to 6-membered monocycles having 1-2, 1-3 or 1-4 heteroatoms selected from nitrogen, sulfur or oxygen. In another example, heterocyclyl includes 3-membered monocycles. In another example, heterocyclyl includes 4-membered monocycles. In another example, heterocyclyl includes 5-6 membered monocycles. In some embodiments, a heterocycloalkyl includes at least one nitrogen. In one example, the heterocyclyl group includes 0 to 3 double bonds. Any nitrogen or sulfur heteroatom may optionally be oxidized (e.g., NO, SO, $SO_2$), and any nitrogen heteroatom may optionally be quaternized (e.g., $[NR_4]^+Cl^-$, $[NR_4]^+OH^-$). Example heterocycles are oxiranyl, aziridinyl, thiiranyl, azetidinyl, oxetanyl, thietanyl, 1,2-dithietanyl, 1,3-dithietanyl, pyrrolidinyl, dihydro-1H-pyrrolyl, dihydrofuranyl, tetrahydrofuranyl, dihydrothienyl, tetrahydrothienyl, imidazolidinyl, piperidinyl, piperazinyl, isoquinolinyl, tetrahydroisoquinolinyl, morpholinyl, thiomorpholinyl, 1,1-dioxo-thiomorpholinyl, dihydropyranyl, tetrahydropyranyl, hexahydrothiopyranyl, hexahydropyrimidinyl, oxazinanyl, thiazinanyl, thioxanyl, homopiperazinyl, homopiperidinyl, azepanyl, oxepanyl, thiepanyl, oxazepinyl, oxazepanyl, diazepanyl, 1,4-diazepanyl, diazepinyl, thiazepinyl, thiazepanyl, tetrahydrothiopyranyl, oxazolidinyl, thiazolidinyl, isothiazolidinyl, 1,1-dioxoisothiazolidinonyl, 1,1-dioxoisothiazolyl, oxazolidinonyl, imidazolidinonyl, 4,5,6,7-tetrahydro[2H]indazolyl, tetrahydrobenzoimidazolyl, 4,5,6,7-tetrahydrobenzo[d]imidazolyl, thiazinyl, oxazinyl, thiadiazinyl, oxadiazinyl, dithiazinyl, dioxazinyl, oxathiazinyl, thiatriazinyl, oxatriazinyl, dithiadiazinyl, imidazolinyl, dihydropyrimidyl, tetrahydropyrimidyl, 1-pyrrolinyl, 2-pyrrolinyl, 3-pyrrolinyl, indolinyl, thiapyranyl, 2H-pyranyl, 4H-pyranyl, dioxanyl, 1,3-dioxolanyl, pyrazolinyl, pyrazolidinyl, dithianyl, dithiolanyl, pyrimidinonyl, pyrimidindionyl, pyrimidin-2,4-dionyl, piperazinonyl, piperazindionyl, pyrazolidinylimidazolinyl, 3-azabicyclo[3.1.0]hexanyl, 3,6-diazabicyclo[3.1.1]heptanyl, 6-azabicyclo[3.1.1]heptanyl, 3-azabicyclo[3.1.1]heptanyl, 3-azabicyclo[4.1.0]heptanyl, azabicyclo[2.2.2]hexanyl, 2-azabicyclo[3.2.1]octanyl, 8-azabicyclo[3.2.1]octanyl, 2-azabicyclo[2.2.2]octanyl, 8-azabicyclo[2.2.2]octanyl, 7-oxabicyclo[2.2.1]heptane, azaspiro[3.5]nonanyl, azaspiro[2.5]octanyl, azaspiro[4.5]decanyl, 1-azaspiro[4.5]decan-2-onyl, azaspiro[5.5]undecanyl, tetrahydroindolyl, octahydroindolyl, tetrahydroisoindolyl, tetrahydroindazolyl, 1,1-dioxohexahydrothiopyranyl.

In particular embodiments, a heterocyclyl group or a heteroaryl group is attached at a carbon atom of the heterocyclyl group or the heteroaryl group. By way of example, carbon bonded heterocyclyl groups include bonding arrangements at position 2, 3, 4, 5, or 6 of a pyridine ring, position 3, 4, 5, or 6 of a pyridazine ring, position 2, 4, 5, or 6 of a pyrimidine ring, position 2, 3, 5, or 6 of a pyrazine ring, position 2, 3, 4, or 5 of a furan, tetrahydrofuran, thiofuran, thiophene, pyrrole or tetrahydropyrrole ring, position 2, 4, or 5 of an oxazole, imidazole or thiazole ring, position 3, 4, or 5 of an isoxazole, pyrazole, or isothiazole ring, position 2 or 3 of an aziridine ring, position 2, 3, or 4 of an azetidine ring, position 2, 3, 4, 5, 6, 7, or 8 of a quinoline ring or position 1, 3, 4, 5, 6, 7, or 8 of an isoquinoline ring.

In certain embodiments, the heterocyclyl group or heteroaryl group is N-attached. By way of example, nitrogen bonded heterocyclyl or heteroaryl groups include bonding arrangements at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline.

"Fused" refers to any ring structure described herein that shares one or more atoms (e.g., carbon or nitrogen atoms) with an existing ring structure in the compounds described herein.

The term "acyl" refers to a carbonyl containing substituent represented by the formula —C(=O)—R in which R is a substituent such as hydrogen, alkyl, cycloalkyl, aryl or heterocyclyl, wherein the alkyl, cycloalkyl, aryl and heterocyclyl are as defined herein. Acyl groups include alkanoyl (e.g., acetyl), aroyl (e.g., benzoyl), and heteroaroyl (e.g., pyridinoyl).

The term "haloalkyl" refers to an alkyl chain in which one or more hydrogen has been replaced by a halogen. Examples of haloalkyls are trifluoromethyl, difluoromethyl, and fluoromethyl. A substituted haloalkyl refers to a haloalkyl having a moiety other than a halogen. An unsubstituted haloalkyl refers to a haloalkyl substituted with no moiety other than hydrogen or halogen as described herein.

As used herein a wavy line "⁓" that intersects a bond in a chemical structure indicate the point of attachment of the atom to which the wavy bond is connected in the chemical structure to the remainder of a molecule, or to the remainder of a fragment of a molecule.

In certain embodiments, divalent groups are described generically without specific bonding configurations. It is understood that the generic description is meant to include both bonding configurations, unless specified otherwise. For example, in the group $R^1$-$R^2$-$R^3$, if the group $R^2$ is described as —$CH_2C(O)$—, then it is understood that this group can be bonded both as $R^1$—$CH_2C(O)$—$R^3$, and as $R^1$—$C(O)CH_2$—$R^3$, unless specified otherwise.

The term "pharmaceutically acceptable" refers to molecular entities and compositions that do not produce an adverse, allergic or other untoward reaction when administered to an animal, such as, for example, a human, as appropriate.

Compounds described herein may be in the form of a salt, such as a pharmaceutically acceptable salt. "Pharmaceutically acceptable salts" include both acid and base addition salts. "Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, carbonic acid, phosphoric acid and the like, and organic acids may be selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, malonic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, benzenesulfonic acid, p-toluenesulfonic acid, salicylic acid and the like.

The term "pharmaceutically acceptable base addition salts" include those derived from inorganic bases such as sodium, potassium, lithium, ammonium, calcium, magnesium, iron, zinc, copper, manganese, aluminum salts and the like. Particular base addition salts are the ammonium, potassium, sodium, calcium and magnesium salts. Salts derived from pharmaceutically acceptable organic nontoxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, tromethamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particular organic non-toxic bases include isopropylamine, diethylamine, ethanolamine, tromethamine, dicyclohexylamine, choline, and caffeine.

In some embodiments, a salt is selected from a hydrochloride, hydrobromide, trifluoroacetate, sulfate, phosphate, acetate, fumarate, maleate, tartrate, lactate, citrate, pyruvate, succinate, oxalate, methanesulfonate, p-toluenesulfonate, bisulfate, benzenesulfonate, ethanesulfonate, malonate, xinafoate, ascorbate, oleate, nicotinate, saccharinate, adipate, formate, glycolate, palmitate, L-lactate, D-lactate, aspartate, malate, L-tartrate, D-tartrate, stearate, furoate (e.g., 2-furoate or 3-furoate), napadisylate (naphthalene-1,5-disulfonate or naphthalene-1-(sulfonic acid)-5-sulfonate), edisylate (ethane-1,2-disulfonate or ethane-1-(sulfonic acid)-2-sulfonate), isothionate (2-hydroxyethylsulfonate), 2-mesitylenesulfonate, 2-naphthalenesulfonate, 2,5-dichlorobenzenesulfonate, D-mandelate, L-mandelate, cinnamate, benzoate, adipate, esylate, malonate, mesitylate (2-mesitylenesulfonate), napsylate (2-naphthalenesulfonate), camsylate (camphor-10-sulfonate, for example (1S)-(+)-10-camphorsulfonic acid salt), glutamate, glutarate, hippurate (2-(benzoylamino)acetate), orotate, xylate (p-xylene-2-sulfonate), and pamoic (2,2'-dihydroxy-1,1'-dinaphthylmethane-3,3'-dicarboxylate).

A "sterile" formulation is aseptic or free from all living microorganisms and their spores.

The term "stereoisomers" refer to compounds that have identical chemical constitution but differ with regard to the arrangement of the atoms or groups in space. Stereoisomers include diastereomers, enantiomers, atropisomers, conformers and the like.

The term "chiral" refers to molecules that have the property of non-superimposability of the mirror image partner, while the term "achiral" refers to molecules which are superimposable on their mirror image partner.

The term "diastereomer" refers to a stereoisomer with two or more centers of chirality and whose molecules are not mirror images of one another. Diastereomers have different physical properties, e.g., melting points, boiling points, spectral properties or biological activities. Mixtures of diastereomers may separate under high resolution analytical procedures such as electrophoresis and chromatography such as HPLC.

The term "enantiomers" refers to two stereoisomers of a compound that are non-superimposable mirror images of one another.

The term "atropisomers" refers to two conformers resulting from hindered rotation about a single bond where the steric strain barrier to rotation can be high enough to allow for the isolation of each conformer.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The term "tautomer" or "tautomeric form" refers to structural isomers of different energies that are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

Certain compounds described herein can exist in unsolvated forms as well as solvated forms, including hydrated forms. A "solvate" refers to an association or complex of one or more solvent molecules and a compound described herein. Examples of solvents that form solvates include water, isopropanol, ethanol, methanol, DMSO, ethyl acetate, acetic acid, and ethanolamine. Certain compounds described herein can exist in multiple crystalline or amorphous forms. In general, all physical forms are contemplated herein. The term "hydrate" refers to the complex where the solvent molecule is water.

The compounds and pharmaceutically acceptable salts thereof described herein also embrace isotopically-labeled compounds that are identical to those recited herein, but for the fact that one or more atoms are replaced by an atom having an atomic mass or mass number different from the atomic mass or mass number usually found in nature. All isotopes of any particular atom or element as specified are contemplated herein, and their uses. Exemplary isotopes that can be incorporated into compounds and pharmaceutically acceptable salts thereof described herein include isotopes of hydrogen, carbon, nitrogen, oxygen, phosphorus, sulfur, fluorine, chlorine and iodine, such as $^2H$, $^3H$, $^{11}C$, $^{13}C$, $^{14}C$, $^{13}N$, $^{15}N$, $^{15}O$, $^{17}O$, $^{18}O$, $^{32}P$, $^{33}P$, $^{35}S$, $^{18}F$, $^{36}Cl$, $^{123}I$, and $^{125}I$. Certain isotopically-labeled compounds or pharmaceutical acceptable salts thereof described herein (e.g., those labeled with $^3H$ and $^{14}C$) are useful in compound and/or substrate tissue distribution assays. Tritiated ($^3H$) and carbon-14 ($^{14}C$) isotopes are useful for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Positron emitting isotopes such as $^{15}O$, $^{13}N$, $^{11}C$ and $^{18}F$ are useful for positron emission tomography (PET) studies to examine substrate receptor occupancy. Isotopically labeled compounds or pharmaceutical acceptable salts thereof described herein can generally be prepared by following procedures analogous to those disclosed in the Examples herein below, by substituting an isotopically labeled reagent for a non-isotopically labeled reagent.

Compounds and pharmaceutically acceptable salts thereof described herein may contain one or more asymmetric carbon atoms. Accordingly, the compounds may exist as diastereomers, enantiomers or mixtures thereof. The syntheses of the compounds may employ racemates, diastereomers or enantiomers as starting materials or as intermediates. Mixtures of particular diastereomeric compounds may be separated, or enriched in one or more particular diastereomers, by chromatographic or crystallization methods. Similarly, enantiomeric mixtures may be separated, or enantiomerically enriched, using the same techniques or others known in the art. Each of the asymmetric carbon or nitrogen atoms may be in the R or S configuration and both of these configurations are contemplated herein.

In the structures shown herein, where the stereochemistry of any particular chiral atom is not specified, then all stereoisomers are contemplated and included. Where stereochemistry is specified by a solid wedge or dashed line representing a particular configuration, then that stereoisomer is so specified and defined. Unless otherwise specified, if solid wedges or dashed lines are used, relative stereochemistry is intended.

A "subject," "individual," or "patient" is a vertebrate and are used interchangeably herein. In certain embodiments, the vertebrate is a mammal. Mammals include, but are not limited to, farm animals (such as cows), sport animals, pets (such as guinea pigs, cats, dogs, rabbits and horses), primates, mice and rats. In certain embodiments, a mammal is a human. In embodiments comprising administration of a compound of to a patient, the patient is typically in need thereof.

The terms "inhibiting" and "reducing," or any variation of these terms, includes any measurable decrease or complete inhibition to achieve a desired result. For example, there may be a decrease of about, at most about, or at least about 5%, 10%, 15%, 20%, 25%, 30%, 35%, 40%, 45%, 50%, 55%, 60%, 65%, 70%, 75%, 80%, 85%, 90%, 95%, 99%, or more, or any range derivable therein, reduction of activity compared to normal.

The term "treatment" refers to clinical intervention designed to alter the natural course of the patient or cell being treated during the course of clinical pathology. Desirable effects of treatment include decreasing the rate of disease progression, ameliorating or palliating the disease state, and remission or improved prognosis. For example, a patient is successfully "treated" if one or more symptoms associated with a cancer described herein are mitigated or eliminated, including, but are not limited to, reducing the proliferation of (or destroying) cancerous cells, decreasing symptoms resulting from the disease, increasing the quality of life of those suffering from the disease, decreasing the dose of other medications required to treat the disease, and/or prolonging survival of patients.

The term "delaying progression" of a disease refers to deferring, hindering, slowing, retarding, stabilizing, and/or postponing development of a cancer described herein. This delay can be of varying lengths of time, depending on the history of the cancer and/or patient being treated. As is evident to one skilled in the art, a sufficient or significant delay can, in effect, encompass prevention, in that the patient does not develop cancer or relapse.

A "mutant KRas mediated disease" and the like refer to a disease described herein (e.g., a cancer described herein) having symptoms or requiring treatment as set forth herein that is/are wholly or partly associated with, a result of, a function of, or otherwise correlated to mutant KRas activity as described herein. In one such embodiment, the mutant KRas is KRas$^{G12D}$.

An "effective amount" or "therapeutically effective amount" is at least the minimum amount required to effect a measurable improvement or prevention of a cancer described herein. An effective amount herein may vary according to factors such as the disease state, age, sex, and weight of the patient, and the ability of the agent to elicit a desired response in the patient. An effective amount is also one in which any toxic or detrimental effects of the treatment are outweighed by the therapeutically beneficial effects. Beneficial or desired results include results such as eliminating or reducing the risk, lessening the severity, delaying the onset of the disease (including biochemical, histological and/or behavioral symptoms of the disease, its complications and intermediate pathological phenotypes presenting during development of the disease), decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. In some embodiments, an effective amount of the drug may have the effect in reducing the number of cancer cells; reducing the tumor size; inhibiting (i.e., slow or stop) cancer cell infiltration into peripheral organs; inhibit (i.e., slow or stop) tumor metastasis; inhibiting (i.e., slow or stop) tumor growth; and/or relieving one or more of the symptoms associated with the disorder. An effective amount can be administered in one or more administrations.

The term "co-administration," "administered in combination with," and their grammatical equivalents, as used herein, encompass administration of two or more agents to an animal, including humans, so that both agents and/or their metabolites are present in the subject at the same time. Co-administration includes simultaneous administration in separate compositions, administration at different times (i.e., sequential administration) in separate compositions, or administration in a composition in which both agents are present.

The term "package insert" is used to refer to instructions customarily included in commercial packages of therapeutic products, that contain information about the indications, usage, dosage, administration, contraindications and/or warnings concerning the use of such therapeutic products.

The terms "antagonist" and "inhibitor" are used interchangeably, and they refer to a compound having the ability to inhibit a biological function of a target protein, whether by inhibiting the activity or expression of the protein, such as a mutant form of KRas. Accordingly, the terms "antagonist" and "inhibitors" are defined in the context of the biological role of the target protein. While preferred antagonists herein specifically interact with (e.g., bind to) the target, compounds that inhibit a biological activity of the target protein by interacting with other members of the signal transduction pathway of which the target protein is a member are also specifically included within this definition. A preferred biological activity inhibited by an antagonist is associated with the development, growth, or spread of a tumor.

The term "agonist" as used herein refers to a compound having the ability to initiate or enhance a biological function of a target protein, whether by inhibiting the activity or expression of the target protein. Accordingly, the term "agonist" is defined in the context of the biological role of the target polypeptide. While preferred agonists herein specifically interact with (e.g., bind to) the target, compounds that initiate or enhance a biological activity of the target polypeptide by interacting with other members of the signal transduction pathway of which the target polypeptide is a member are also specifically included within this definition.

The terms "cancer" and "cancerous", "neoplasm", and "tumor" and related terms are used interchangeably herein and refer to or describe the physiological condition in mammals that is typically characterized by unregulated cell growth. A "tumor" comprises one or more cancerous cells. Examples of cancer include carcinoma, blastoma, sarcoma, seminoma, glioblastoma, melanoma, leukemia, and myeloid or lymphoid malignancies. More particular examples of such cancers include squamous cell cancer (e.g., epithelial squamous cell cancer) and lung cancer including small-cell lung cancer, non-small cell lung cancer ("NSCLC"), adenocarcinoma of the lung and squamous carcinoma of the lung. Other cancers include skin, keratoacanthoma, follicular carcinoma, hairy cell leukemia, buccal cavity, pharynx (oral), lip, tongue, mouth, salivary gland, esophageal, larynx, hepatocellular, gastric, stomach, gastrointestinal, small intestine, large intestine, pancreatic, cervical, ovarian, liver, bladder, hepatoma, breast, colon, rectal, colorectal, genitourinary, biliary passage, thyroid, papillary, hepatic, endometrial, uterine, salivary gland, kidney or renal, prostate, testis, vulval, peritoneum, anal, penile, bone, multiple myeloma, B-cell lymphoma, diffuse large B-Cell lymphoma (DLBCL), central nervous system, brain, head and neck, Hodgkin's, and associated metastases. Other examples of neoplastic disorders include myeloproliferative disorders, such as polycythemia vera, essential thrombocytosis, myelofibrosis, such as primary myelofibrosis, and chronic myelogenous leukemia (CML).

A "chemotherapeutic agent" is an agent useful in the treatment of a given disorder, for example, cancer or inflammatory disorders. Examples of chemotherapeutic agents are well-known in the art. Additionally, chemotherapeutic agents include pharmaceutically acceptable salts, acids or derivatives of any of chemotherapeutic agents, as well as combinations of two or more of them.

Unless otherwise stated, structures depicted herein are also meant to include compounds that differ only in the presence of one or more isotopically enriched atoms. Exemplary isotopes that can be incorporated into compounds and pharmaceutically acceptable salts thereof described herein, include isotopes of hydrogen, carbon, nitrogen, oxygen, phosphorus, sulfur, fluorine, chlorine, and iodine, such as $^2H$, $^3H$, $^{11}C$, $^{13}C$, $^{14}C$, $^{13}N$, $^{15}N$, $^{15}O$, $^{17}O$, $^{18}O$, $^{32}P$, $^{33}P$, $^{35}S$, $^{18}F$, $^{36}Cl$, $^{123}I$, and $^{125}I$, respectively. Isotopically-labeled compounds (e.g., those labeled with $^3H$ and $^{14}C$) can be useful in compound or substrate tissue distribution assays. Tritiated (i.e., $^3H$) and carbon-14 (i.e., $^{14}C$) isotopes can be useful for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements). In some embodiments, in compounds and pharmaceutically acceptable salts thereof described herein, one or more carbon atoms are replaced by $^{13}C$- or $^{14}C$-enriched carbon. Positron emitting isotopes such as $^{15}O$, $^{13}N$, $^{11}C$, and $^{18}F$ are useful for positron emission tomography (PET) studies to examine substrate receptor occupancy. Isotopically labeled compounds can generally be prepared by following procedures analogous to those disclosed in the Schemes or in the Examples herein, by substituting an isotopically labeled reagent for a non-isotopically labeled reagent.

It is specifically contemplated that any limitation discussed with respect to one embodiment provided herein may apply to any other embodiment provided herein. Furthermore, any compound and pharmaceutically acceptable salts thereof described herein or composition described herein may be used in any method provided herein, and any method provided herein may be used to produce or to utilize any compound and pharmaceutically acceptable salts thereof described herein or composition described herein.

Throughout this application, the term "about" is used to indicate that a value includes the standard deviation of error for the device or method being employed to determine the value.

Compounds described herein may have stereochemistry depicted as follows:

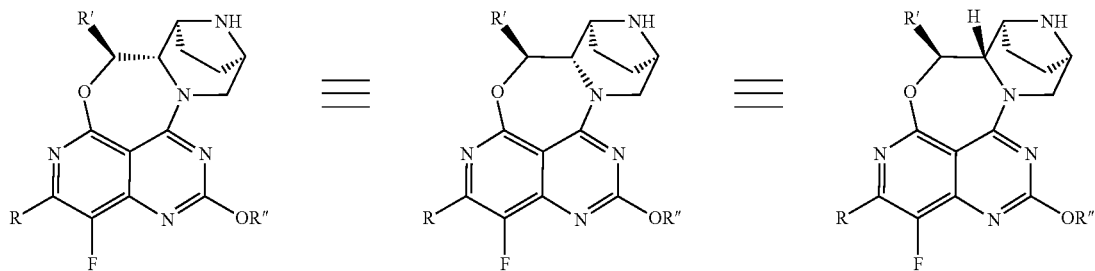

It is understood that all three stereochemical depictions above are equivalent as set forth herein.

Compounds

Provided herein are compounds having the formula: A compound of formula (I):

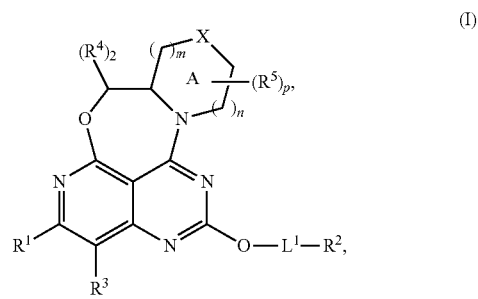

wherein

X is O or $NR^6$ m is 1 or 2;

n is 1 or 2;

wherein n and m together make a 6- or 7-membered ring Ring A;

p is 0, 1, or 2;

$R^1$ is $R^7$-substituted or unsubstituted naphthyl, $R^7$-substituted or unsubstituted isoquinolinyl, $R^7$-substituted or unsubstituted indazolyl, $R^7$-substituted or unsubstituted indanyl, $R^7$-substituted or unsubstituted benzothiazolyl, $R^{7A}$-substituted phenyl, or $R^{7A}$-substituted pyridinyl;

each $R^7$ is independently halogen, OH, $NH_2$, $N(Me)_2$, unsubstituted $C_{1-3}$ alkyl, unsubstituted $C_{1-3}$ alkynyl, unsubstituted $C_{1-3}$ alkoxy, or unsubstituted $C_{1-3}$ haloalkyl each $R^{7A}$ is independently halogen, CN, NH$_2$, N(Me)$_2$, $R^{7B}$ substituted or unsubstituted C$_{1-3}$ alkyl, unsubstituted C$_{1-3}$ haloalkyl, or unsubstituted cyclopropyl $R^{7B}$ is CN, oxo, or C$_{1-3}$ alkyl;

L$^1$ is $R^{L1}$-substituted or unsubstituted C$_{1-4}$ alkylene;

$R^{L1}$ is halogen or unsubstituted C$_{1-3}$ alkyl, or wherein two $R^{L1}$ together form an unsubstituted C$_{3-4}$ cycloalkyl, or;

$R^2$ is $R^9$-substituted or unsubstituted 4-10 membered heterocycle comprising one or more heteroatoms selected from N, S, or O $R^9$ is independently halogen, CN, OH, OCF$_3$, OCHF$_2$, OCH$_2$F, $R^{10}$-substituted or unsubstituted C$_{1-3}$ alkyl, $R^{10}$-substituted or unsubstituted C$_{1-3}$ haloalkyl, unsubstituted C$_{1-3}$ alkoxy, $R^{10}$-substituted or unsubstituted C$_{1-3}$ alkylidene, or $R^{10}$-substituted or unsubstituted C$_{3-4}$ cycloalkyl, or $R^{10}$-substituted or unsubstituted 3 or 4-membered heterocycle; or wherein two $R^9$ together form a $R^{10}$-substituted or unsubstituted C$_{3-5}$ cycloalkyl or a $R^{10}$-substituted or unsubstituted C$_{3-5}$ heterocycle comprising one or more oxygen atoms; or wherein two $R^9$ together form a bridge between two carbon atoms of the cycloalkyl or heterocycle, wherein the bridge comprises 1-3 carbons;

each $R^{10}$ is independently hydrogen, oxo, CN, halogen, or C$_{1-3}$ unsubstituted alkyl;

$R^3$ is hydrogen, —CN, halogen, unsubstituted C$_{1-3}$ alkyl, or unsubstituted cyclopropyl;

each $R^4$ is independently hydrogen, methyl, or C$_{1-3}$ haloalkyl;

$R^5$ is independently halogen, oxo, unsubstituted C$_{1-3}$ alkyl, or unsubstituted C$_{1-3}$ haloalkyl; or wherein two $R^5$ together form a bridge between two carbon atoms of Ring A, wherein the bridge comprises 1-3 carbons and optionally one heteroatom selected from O and N; or two $R^5$ together form a bridge between two carbon atoms of Ring A, wherein the bridge comprises one of O or NR$^{11}$;

$R^{11}$ is hydrogen, C(O)CH$_3$, or unsubstituted C$_{1-3}$ alkyl;

$R^6$ is hydrogen, $R^{6A}$-substituted or unsubstituted C$_{1-6}$ alkyl, $R^{6A}$-substituted or unsubstituted C$_{1-6}$ haloalkyl, $R^{6A}$-substituted or unsubstituted C$_{1-6}$ alkenyl; $R^{6A}$-substituted or unsubstituted C$_{1-6}$ alkynyl, or $R^{6A}$-substituted or unsubstituted 3-4 membered heterocycle $R^{6A}$ is halogen, CN, OR$^{6B}$, SR$^{6C}$, S(O)$_2$R$^{6C}$, C(O)R$^{6B}$, unsubstituted C$_{1-3}$ alkyl, unsubstituted C$_{1-3}$ haloalkyl, or R$^{6B}$ substituted or unsubstituted 3-4 membered heterocycle and R$^{6B}$ and R$^{6C}$ are each independently C$_{1-3}$ alkyl or C$_{1-3}$ haloalkyl.

Still further provided herein, in one embodiment, is a compound of formula (I) or a stereoisomer, atropisomer, tautomer, or pharmaceutically acceptable salt thereof, wherein X is O or NR$^6$;

m is 1 or 2;

n is 1 or 2;

wherein n and m together make a 6- or 7-membered ring Ring A;

p is 0, 1, or 2;

$R^1$ is $R^{7A}$-substituted phenyl or $R^{7A}$-substituted pyridinyl;

each $R^{7A}$ is independently halogen, NH$_2$, unsubstituted C$_{1-3}$ alkyl, or unsubstituted C$_{1-3}$ haloalkyl;

L$^1$ is $R^{L1}$-substituted or unsubstituted C$_{1-4}$ alkylene;

$R^{L1}$ is halogen or unsubstituted C$_{1-3}$ alkyl, or wherein two $R^{L1}$ together form an unsubstituted C$_{3-4}$ cycloalkyl;

$R^2$ is $R^9$-substituted or unsubstituted 4-10 membered heterocycle comprising one or more heteroatoms selected from N, S, or O;

$R^9$ is independently halogen, CN, OH, OCF$_3$, OCHF$_2$, OCH$_2$F, $R^{10}$-substituted or unsubstituted C$_{1-3}$ alkyl, $R^{10}$-substituted or unsubstituted C$_{1-3}$ haloalkyl, unsubstituted C$_{1-3}$ alkoxy, $R^{10}$-substituted or unsubstituted C$_{1-3}$ alkylidene, or $R^{10}$-substituted or unsubstituted C$_{3-4}$ cycloalkyl, or $R^{10}$-substituted or unsubstituted 3 or 4-membered heterocycle; or wherein two $R^9$ together form a $R^{10}$-substituted or unsubstituted C$_{3-5}$ cycloalkyl or a $R^{10}$-substituted or unsubstituted C$_{3-5}$ heterocycle comprising one or more oxygen atoms; or wherein two $R^9$ together form a bridge between two carbon atoms of the cycloalkyl or heterocycle, wherein the bridge comprises 1-3 carbons;

each $R^{10}$ is independently hydrogen, oxo, CN, halogen, or C$_{1-3}$ unsubstituted alkyl;

$R^3$ is hydrogen, —CN, halogen, unsubstituted C$_{1-3}$ alkyl, or unsubstituted cyclopropyl;

each $R^4$ is independently hydrogen, methyl, or C$_{1-3}$ haloalkyl;

$R^5$ is independently halogen, oxo, unsubstituted C$_{1-3}$ alkyl, or unsubstituted C$_{1-3}$ haloalkyl; or wherein two $R^5$ together form a bridge between two carbon atoms of Ring A, wherein the bridge comprises 1-3 carbons and optionally one heteroatom selected from O and N; or two $R^5$ together form a bridge between two carbon atoms of Ring A, wherein the bridge comprises one of O or NR$^{11}$;

$R^{11}$ is hydrogen, C(O)CH$_3$, or unsubstituted C$_{1-3}$ alkyl;

$R^6$ is hydrogen, $R^{6A}$-substituted or unsubstituted C$_{1-6}$ alkyl, $R^{6A}$-substituted or unsubstituted C$_{1-6}$ haloalkyl, $R^{6A}$-substituted or unsubstituted C$_{1-6}$ alkenyl; $R^{6A}$-substituted or unsubstituted C$_{1-6}$ alkynyl, or $R^{6A}$-substituted or unsubstituted 3-4 membered heterocycle;

$R^{6A}$ is halogen, CN, OR$^{6B}$, SR$^{6C}$, S(O)$_2$R$^{6C}$, C(O)R$^{6B}$, unsubstituted C$_{1-3}$ alkyl, unsubstituted C$_{1-3}$ haloalkyl, or R$^{6B}$ substituted or unsubstituted 3-4 membered heterocycle; and $R^{6B}$ and $R^{6C}$ are each independently C$_{1-3}$ alkyl or C$_{1-3}$ haloalkyl.

In another embodiment, is a compound of formula (I-1):

(I-1)

wherein $R^1$, $R^3$, $R^4$, $R^5$, X, m, and n are as described herein.

In one embodiment, each $R^4$ is hydrogen. In another embodiment, one $R^4$ is hydrogen and one $R^4$ is methyl. In another embodiment, one $R^4$ is hydrogen and one $R^4$ is CF$_3$.

In one embodiment, $R^1$ is $R^7$-substituted or unsubstituted naphthyl, $R^7$-substituted or unsubstituted isoquinolinyl, $R^7$-substituted or unsubstituted indazolyl, $R^7$-substituted or unsubstituted indanyl, or R⁷-substituted or unsubstituted benzothiazolyl. In one embodiment, R¹ is R⁷-substituted or unsubstituted naphthyl, R⁷-substituted or unsubstituted isoquinolinyl, or R⁷-substituted or unsubstituted indazolyl. In another embodiment, R¹ is R⁷-substituted or unsubstituted naphthyl. In another embodiment, R¹ is R⁷-substituted or unsubstituted isoquinolinyl. In another embodiment, R¹ is R⁷ᴬ-substituted phenyl or R⁷ᴬ-substituted pyridinyl. In one embodiment, R¹ is R⁷-substituted naphthyl. In one such embodiment, R¹ is R⁷-substituted isoquinolinyl and each R⁴ is hydrogen. In another embodiment, R¹ is R⁷-substituted naphthyl, R⁷-substituted isoquinolinyl, R⁷-substituted indazolyl, R⁷-substituted indanyl, R⁷-substituted benzothiazolyl, or R⁷ᴬ-substituted phenyl. In such embodiments, each R⁴ is hydrogen or one R⁴ is hydrogen and one R⁴ is methyl.

In one embodiment, each R⁷ᴬ is independently halogen, CN, NH₂, N(Me)₂, R⁷ᴮ-substituted or unsubstituted C₁₋₃ alkyl, unsubstituted C₁₋₃ haloalkyl, or unsubstituted cyclopropyl. In another embodiment, each R⁷ᴬ is independently halogen, NH₂, unsubstituted C₁₋₃ alkyl, or unsubstituted C₁₋₃ haloalkyl. In still another embodiment, at least one R⁷ᴬ is NH₂. In one such embodiment, where at least one R⁷ᴬ is NH₂, at least one other R⁷ᴬ is unsubstituted C₁₋₃ alkyl, unsubstituted C₁₋₃ haloalkyl, or halogen.

In one embodiment, each R⁷ is independently halogen, OH, NH₂, N(Me)₂, unsubstituted C₁₋₃ alkyl, unsubstituted C₁₋₃ alkynyl, unsubstituted C₁₋₃ alkoxy, or unsubstituted C₁₋₃ haloalkyl. In one embodiment, each R⁷ is independently halogen, OH, NH₂, unsubstituted C₁₋₃ alkyl, or unsubstituted C₁₋₃ alkynyl. In still another embodiment, at least one R⁷ is NH₂. In another embodiment, at least one R⁷ is OH.

In one embodiment, R¹ is:

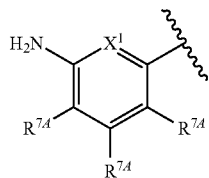

(E)

wherein X¹ is N or CR⁷ᶜ.

In one such embodiment, X¹ is N or CF and each R⁷ᴬ is independently hydrogen, halogen, unsubstituted C₁₋₃ alkyl, or unsubstituted C₁₋₃ haloalkyl. In one such embodiment, each R⁷ᴬ is independently hydrogen, Cl, methyl, ethyl, or CF₃, where no more than one R⁷ᴬ is hydrogen. In one embodiment, at least one R⁷ᴬ is NH₂. In one embodiment, each R⁷ᴬ is independently halogen, NH₂, unsubstituted C₁₋₃ alkyl, or unsubstituted C₁₋₃ haloalkyl. In one embodiment, one R⁷ᴬ is cyclopropyl. In one such embodiment, one R⁷ᴬ is cyclopropyl and is para to the amino group. In another such embodiment, one R⁷ᴬ is cyclopropyl and is meta to the amino group. In one embodiment, X¹ is N. In one embodiment, X¹ is CR⁷ᶜ. In one such embodiment, R⁷ᶜ is hydrogen or halogen.

In another embodiment provided herein is a compound of formula (I) or a stereoisomer, atropisomer, tautomer, or pharmaceutically acceptable salt thereof, wherein
X is O or NR⁶;
m is 1 or 2;
n is 1 or 2;
wherein n and m together make a 6- or 7-membered ring Ring A;
p is 0, 1, or 2;

R¹ is formula

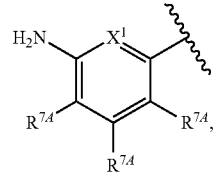

(E)

wherein X¹ is N or CR⁷ᶜ and R⁷ᶜ is hydrogen or halogen;
each R⁷ᴬ is independently halogen, CN, NH₂, N(Me)₂, R⁷ᴮ substituted or unsubstituted C₁₋₃ alkyl, unsubstituted C₁₋₃ haloalkyl, or unsubstituted cyclopropyl;
R⁷ᴮ is CN, oxo, or C₁₋₃ alkyl;
L¹ is R^{L1}-substituted or unsubstituted C₁₋₄ alkylene;
R^{L1} is halogen or unsubstituted C₁₋₃ alkyl, or wherein two R^{L1} together form an unsubstituted C₃₋₄ cycloalkyl;
R² is R⁹-substituted or unsubstituted 4-10 membered heterocycle comprising one or more heteroatoms selected from N, S, or O;
R⁹ is independently halogen, CN, OH, OCF₃, OCHF₂, OCH₂F, R¹⁰-substituted or unsubstituted C₁₋₃ alkyl, R¹⁰-substituted or unsubstituted C₁₋₃ haloalkyl, unsubstituted C₁₋₃ alkoxy, R¹⁰-substituted or unsubstituted C₁₋₃ alkylidene, or R¹⁰-substituted or unsubstituted C₃₋₄ cycloalkyl, or R¹⁰-substituted or unsubstituted 3 or 4-membered heterocycle; or wherein
two R⁹ together form a R¹⁰-substituted or unsubstituted C₃₋₅ cycloalkyl or a R¹⁰-substituted or unsubstituted C₃₋₅ heterocycle comprising one or more oxygen atoms; or wherein
two R⁹ together form a bridge between two carbon atoms of the cycloalkyl or heterocycle, wherein the bridge comprises 1-3 carbons;
each R¹⁰ is independently hydrogen, oxo, CN, halogen, or C₁₋₃ unsubstituted alkyl;
R³ is hydrogen, —CN, halogen, unsubstituted C₁₋₃ alkyl, or unsubstituted cyclopropyl;
each R⁴ is independently hydrogen, methyl, or C₁₋₃ haloalkyl;
R⁵ is independently halogen, oxo, unsubstituted C₁₋₃ alkyl, or unsubstituted C₁₋₃ haloalkyl; or wherein
two R⁵ together form a bridge between two carbon atoms of Ring A, wherein the bridge comprises 1-3 carbons and optionally one heteroatom selected from O and N; or
two R⁵ together form a bridge between two carbon atoms of Ring A, wherein the bridge comprises one of O or NR¹¹;
R¹¹ is hydrogen, C(O)CH₃, or unsubstituted C₁₋₃ alkyl;
R⁶ is hydrogen, R⁶ᴬ-substituted or unsubstituted C₁₋₆ alkyl, R⁶ᴬ-substituted or unsubstituted C₁₋₆ haloalkyl, R⁶ᴬ-substituted or unsubstituted C₁₋₆ alkenyl; R⁶ᴬ-substituted or unsubstituted C₁₋₆ alkynyl, or R⁶ᴬ-substituted or unsubstituted 3-4 membered heterocycle;
R⁶ᴬ is halogen, CN, OR⁶ᴮ, SR⁶ᶜ, S(O)₂R⁶ᶜ, C(O)R⁶ᴮ, unsubstituted C₁₋₃ alkyl, unsubstituted C₁₋₃ haloalkyl, or R⁶ᴮ substituted or unsubstituted 3-4 membered heterocycle; and
R⁶ᴮ and R⁶ᶜ are each independently C₁₋₃ alkyl or C₁₋₃ haloalkyl.

In one such embodiment, X¹ is N and R⁷ᴬ is hydrogen, halogen, unsubstituted C₁₋₃ alkyl, or unsubstituted C₁₋₃ haloalkyl. In another such embodiment, at least one R⁷ᴬ is unsubstituted $C_{1-3}$ haloalkyl (e.g. $CF_3$). Where $X^1$ is N, in some embodiments, $R^1$ comprises the moiety of formula (E1);

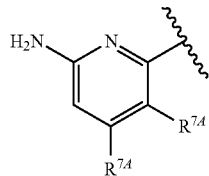
(E1)

In another embodiment is a compound of formula (I) or a stereoisomer, atropisomer, tautomer, or pharmaceutically acceptable salt thereof, wherein
X is O or $NR^6$;
m is 1 or 2;
n is 1 or 2;
wherein n and m together make a 6- or 7-membered ring Ring A;
p is 0, 1, or 2;
$R^1$ is of formula (E1)

each $R^{7A}$ is independently halogen, CN, $NH_2$, $N(Me)_2$, $R^{7B}$ substituted or unsubstituted $C_{1-3}$ alkyl, unsubstituted $C_{1-3}$ haloalkyl, or unsubstituted cyclopropyl;
$R^{7B}$ is CN, oxo, or $C_{1-3}$ alkyl;
$L^1$ is $R^{L1}$-substituted or unsubstituted $C_{1-4}$ alkylene;
$R^{L1}$ is halogen or unsubstituted $C_{1-3}$ alkyl, or wherein two $R^{L1}$ together form an unsubstituted $C_{3-4}$ cycloalkyl;
$R^2$ is $R^9$-substituted or unsubstituted 4-10 membered heterocycle comprising one or more heteroatoms selected from N, S, or O;
$R^9$ is independently halogen, CN, OH, $OCF_3$, $OCHF_2$, $OCH_2F$, $R^{10}$-substituted or unsubstituted $C_{1-3}$ alkyl, $R^{10}$-substituted or unsubstituted $C_{1-3}$ haloalkyl, unsubstituted $C_{1-3}$ alkoxy, $R^{10}$-substituted or unsubstituted $C_{1-3}$ alkylidene, or $R^{10}$-substituted or unsubstituted $C_{3-4}$ cycloalkyl, or $R^{10}$-substituted or unsubstituted 3 or 4-membered heterocycle; or wherein
two $R^9$ together form a $R^{10}$-substituted or unsubstituted $C_{3-5}$ cycloalkyl or a $R^{10}$-substituted or unsubstituted $C_{3-5}$ heterocycle comprising one or more oxygen atoms; or wherein
two $R^9$ together form a bridge between two carbon atoms of the cycloalkyl or heterocycle, wherein the bridge comprises 1-3 carbons;
each $R^{10}$ is independently hydrogen, oxo, CN, halogen, or $C_{1-3}$ unsubstituted alkyl;
$R^3$ is hydrogen, —CN, halogen, unsubstituted $C_{1-3}$ alkyl, or unsubstituted cyclopropyl;
each $R^4$ is independently hydrogen, methyl, or $C_{1-3}$ haloalkyl;
$R^5$ is independently halogen, oxo, unsubstituted $C_{1-3}$ alkyl, or unsubstituted $C_{1-3}$ haloalkyl; wherein two $R^5$ together form a bridge between two carbon atoms of Ring A, wherein the bridge comprises 1-3 carbons and optionally one heteroatom selected from O and N; or
two $R^5$ together form a bridge between two carbon atoms of Ring A, wherein the bridge comprises one of O or $NR^{11}$;
$R^{11}$ is hydrogen, $C(O)CH_3$, or unsubstituted $C_{1-3}$ alkyl;
$R^6$ is hydrogen, $R^{6A}$-substituted or unsubstituted $C_{1-6}$ alkyl, $R^{6A}$-substituted or unsubstituted $C_{1-6}$ haloalkyl, $R^{6A}$-substituted or unsubstituted $C_{1-6}$ alkenyl; $R^{6A}$-substituted or unsubstituted $C_{1-6}$ alkynyl, or $R^{6A}$-substituted or unsubstituted 3-4 membered heterocycle;
$R^{6A}$ is halogen, CN, $OR^{6B}$, $SR^{6C}$, $S(O)_2R^{6C}$, $C(O)R^{6B}$, unsubstituted $C_{1-3}$ alkyl, unsubstituted $C_{1-3}$ haloalkyl, or $R^{6B}$-substituted or unsubstituted 3-4 membered heterocycle; and
$R^{6B}$ and $R^{6C}$ are each independently $C_{1-3}$ alkyl or $C_{1-3}$ haloalkyl.

In one embodiment, where $R^1$ comprises the moiety of formula E1, each $R^7$ is independently hydrogen, Cl, methyl, or $CF_3$. In another such embodiment, each $R^7$ is independently hydrogen, methyl, or $CF_3$.

In one embodiment, where $R^1$ is a moiety of formula (E) and $X^1$ is N, $R^1$ is:

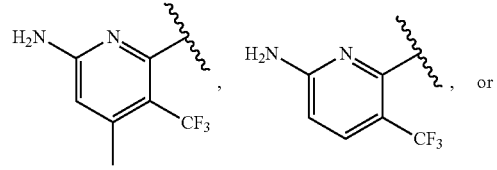

In another embodiment, $R^1$ comprises the moiety of formula (E2);

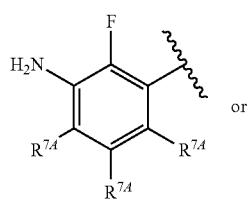
(E2)

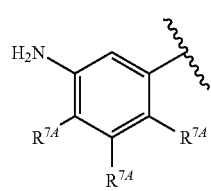
(E3)

wherein each $R^{7A}$ is independently hydrogen, halogen, unsubstituted $C_{1-3}$ alkyl or unsubstituted $C_{1-3}$ haloalkyl. In one such embodiment, no more than one $R^{7A}$ is hydrogen. In another such embodiment, $R^{7A}$ is not hydrogen. In one embodiment of the moieties (E2) and (3), at least one $R^{7A}$ is halogen. In one embodiment of the moieties (E2) and (E3), at least one $R^{7A}$ is unsubstituted $C_{1-3}$ haloalkyl (e.g., $CF_3$, $CHF_2$, $CF_2CF_3$, $CHCF_3$, or $CH_2CF_3$).

In another embodiment is a compound of formula (I) or a stereoisomer, atropisomer, tautomer, or pharmaceutically acceptable salt thereof, wherein X is O or $NR^6$;
m is 1 or 2;
n is 1 or 2;
wherein n and m together make a 6- or 7-membered ring Ring A;
p is 0, 1, or 2;
$R^1$ is (E2) or (E3)

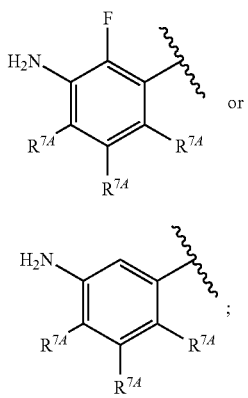

each $R^{7A}$ is independently hydrogen, halogen, unsubstituted $C_{1-3}$ alkyl or unsubstituted $C_{1-3}$ haloalkyl;
$L^1$ is $R^{L1}$-substituted or unsubstituted $C_{1-4}$ alkylene;
$R^{L1}$ is halogen or unsubstituted $C_{1-3}$ alkyl, or wherein two $R^{L1}$ together form an unsubstituted $C_{3-4}$ cycloalkyl;
$R^2$ is $R^9$-substituted or unsubstituted 4-10 membered heterocycle comprising one or more heteroatoms selected from N, S, or O;
$R^9$ is independently halogen, CN, OH, $OCF_3$, $OCHF_2$, $OCH_2F$, $R^{10}$-substituted or unsubstituted $C_{1-3}$ alkyl, $R^{10}$-substituted or unsubstituted $C_{1-3}$ haloalkyl, unsubstituted $C_{1-3}$ alkoxy, $R^{10}$-substituted or unsubstituted $C_{1-3}$ alkylidene, or $R^{10}$-substituted or unsubstituted $C_{3-4}$ cycloalkyl, or $R^{10}$-substituted or unsubstituted 3 or 4-membered heterocycle; or wherein
two $R^9$ together form a $R^{10}$-substituted or unsubstituted $C_{3-5}$ cycloalkyl or a $R^{10}$-substituted or unsubstituted $C_{3-5}$ heterocycle comprising one or more oxygen atoms; or wherein
two $R^9$ together form a bridge between two carbon atoms of the cycloalkyl or heterocycle, wherein the bridge comprises 1-3 carbons;
each $R^{10}$ is independently hydrogen, oxo, CN, halogen, or $C_{1-3}$ unsubstituted alkyl;
$R^3$ is hydrogen, —CN, halogen, unsubstituted $C_{1-3}$ alkyl, or unsubstituted cyclopropyl;
each $R^4$ is independently hydrogen, methyl, or $C_{1-3}$ haloalkyl;
$R^5$ is independently halogen, oxo, unsubstituted $C_{1-3}$ alkyl, or unsubstituted $C_{1-3}$ haloalkyl; or wherein
two $R^5$ together form a bridge between two carbon atoms of Ring A, wherein the bridge comprises 1-3 carbons and optionally one heteroatom selected from O and N; or two $R^5$ together form a bridge between two carbon atoms of Ring A, wherein the bridge comprises one of O or $NR^{11}$;
$R^{11}$ is hydrogen, $C(O)CH_3$, or unsubstituted $C_{1-3}$ alkyl;
$R^6$ is hydrogen, $R^{6A}$-substituted or unsubstituted $C_{1-6}$ alkyl, $R^{6A}$-substituted or unsubstituted $C_{1-6}$ haloalkyl, $R^{6A}$-substituted or unsubstituted $C_{1-6}$ alkenyl; $R^{6A}$-substituted or unsubstituted $C_{1-6}$ alkynyl, or $R^{6A}$-substituted or unsubstituted 3-4 membered heterocycle;
$R^{6A}$ is halogen, CN, $OR^{6B}$, $SR^{6C}$, $S(O)_2R^{6C}$, $C(O)R^{6B}$, unsubstituted $C_{1-3}$ alkyl, unsubstituted $C_{1-3}$ haloalkyl, or $R^{6B}$ substituted or unsubstituted 3-4 membered heterocycle; and
$R^{6B}$ and $R^{6C}$ are each independently $C_{1-3}$ alkyl or $C_{1-3}$ haloalkyl.

In one embodiment, $R^1$ is:

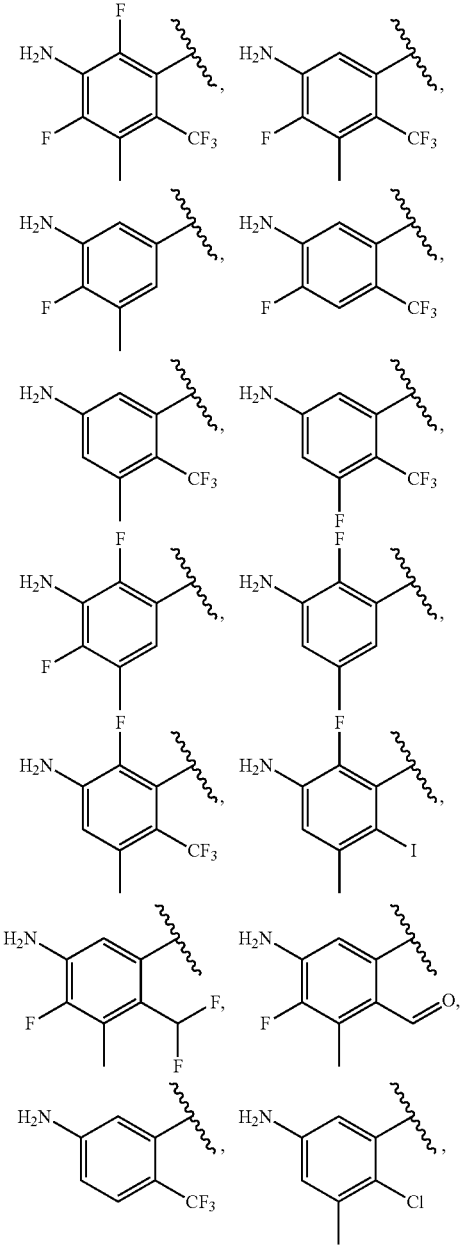

-continued
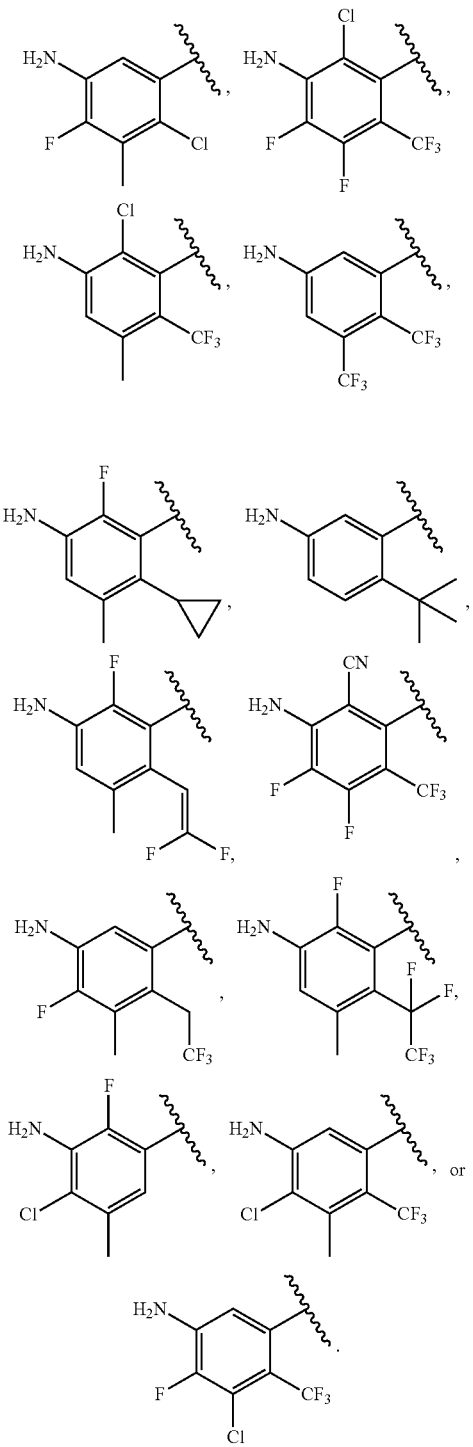
R[1] is
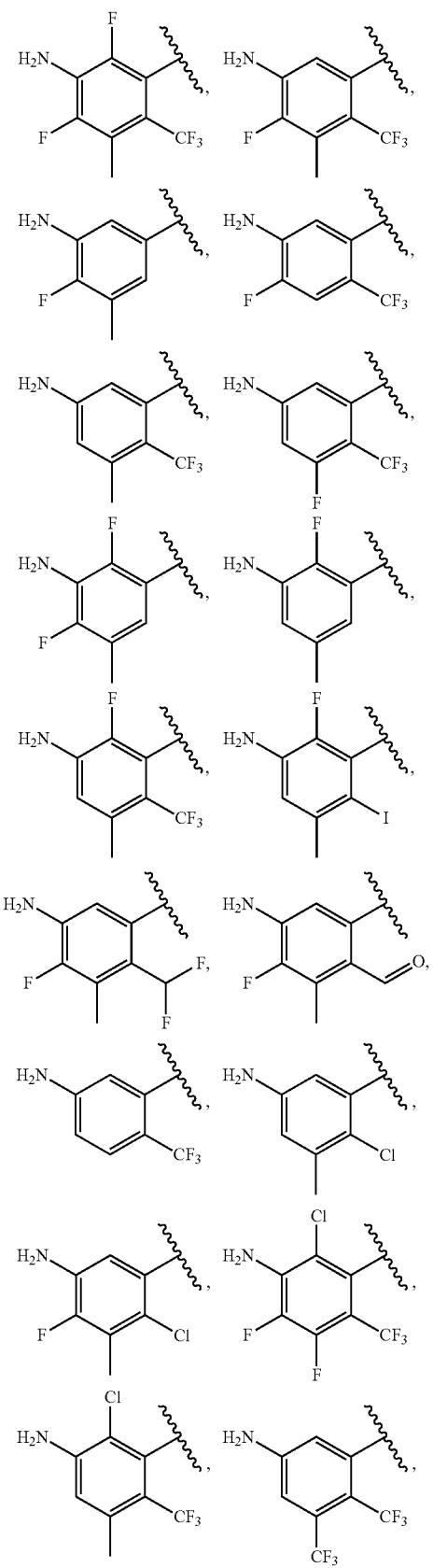
In another embodiment is a compound of formula (I), or a stereoisomer, atropisomer, tautomer, or pharmaceutically acceptable salt thereof, wherein
X is O or NR[6];
m is 1 or 2;
n is 1 or 2;
wherein n and m together make a 6- or 7-membered ring Ring A;

-continued

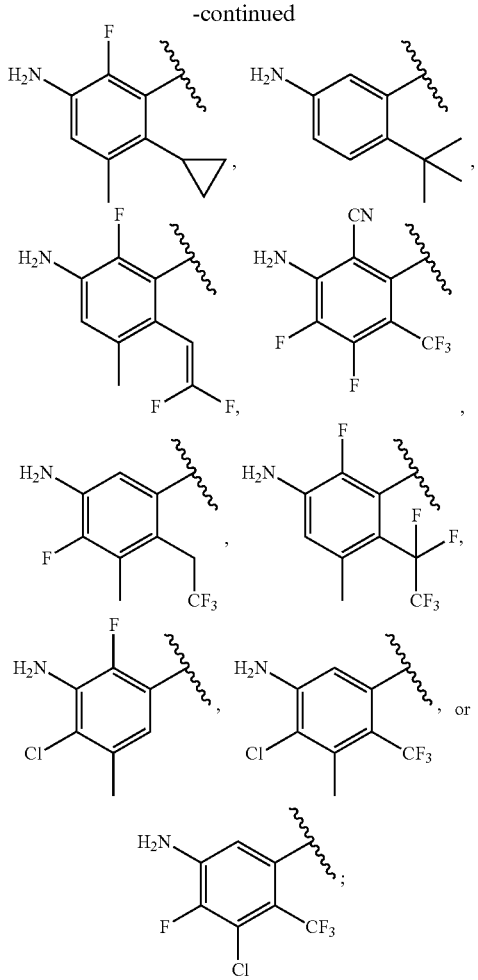

L¹ is $R^{L1}$-substituted or unsubstituted $C_{1-4}$ alkylene;
$R^{L1}$ is halogen or unsubstituted $C_{1-3}$ alkyl, or wherein two $R^{L1}$ together form an unsubstituted $C_{3-4}$ cycloalkyl;
$R^2$ is $R^9$-substituted or unsubstituted 4-10 membered heterocycle comprising one or more heteroatoms selected from N, S, or O;
$R^9$ is independently halogen, CN, OH, $OCF_3$, $OCHF_2$, $OCH_2F$, $R^{10}$-substituted or unsubstituted $C_{1-3}$ alkyl, $R^{10}$-substituted or unsubstituted $C_{1-3}$ haloalkyl, unsubstituted $C_{1-3}$ alkoxy, $R^{10}$-substituted or unsubstituted $C_{1-3}$ alkylidene, or $R^{10}$-substituted or unsubstituted $C_{3-4}$ cycloalkyl, or $R^{10}$-substituted or unsubstituted 3 or 4-membered heterocycle; or wherein
two $R^9$ together form a $R^{10}$-substituted or unsubstituted $C_{3-5}$ cycloalkyl or a $R^{10}$-substituted or unsubstituted $C_{3-5}$ heterocycle comprising one or more oxygen atoms; or wherein
two $R^9$ together form a bridge between two carbon atoms of the cycloalkyl or heterocycle, wherein the bridge comprises 1-3 carbons;
each $R^{10}$ is independently hydrogen, oxo, CN, halogen, or $C_{1-3}$ unsubstituted alkyl;
$R^3$ is hydrogen, —CN, halogen, unsubstituted $C_{1-3}$ alkyl, or unsubstituted cyclopropyl;
each $R^4$ is independently hydrogen, methyl, or $C_{1-3}$ haloalkyl;
$R^5$ is independently halogen, oxo, unsubstituted $C_{1-3}$ alkyl, or unsubstituted $C_{1-3}$ haloalkyl; or wherein two $R^5$ together form a bridge between two carbon atoms of Ring A, wherein the bridge comprises 1-3 carbons and optionally one heteroatom selected from O and N; or
two $R^5$ together form a bridge between two carbon atoms of Ring A, wherein the bridge comprises one of O or $NR^{11}$;
$R^{11}$ is hydrogen, $C(O)CH_3$, or unsubstituted $C_{1-3}$ alkyl;
$R^6$ is hydrogen, $R^{6A}$-substituted or unsubstituted $C_{1-6}$ alkyl, $R^{6A}$-substituted or unsubstituted $C_{1-6}$ haloalkyl, $R^{6A}$-substituted or unsubstituted $C_{1-6}$ alkenyl; $R^{6A}$-substituted or unsubstituted $C_{1-6}$ alkynyl, or $R^{6A}$-substituted or unsubstituted 3-4 membered heterocycle;
$R^{6A}$ is halogen, CN, $OR^{6B}$, $SR^{6C}$, $S(O)_2R^{6C}$, $C(O)R^{6B}$, unsubstituted $C_{1-3}$ alkyl, unsubstituted $C_{1-3}$ haloalkyl, or $R^{6B}$ substituted or unsubstituted 3-4 membered heterocycle; and
$R^{6B}$ and $R^{6C}$ are each independently $C_{1-3}$ alkyl or $C_{1-3}$ haloalkyl.

In one embodiment, $R^1$ is:

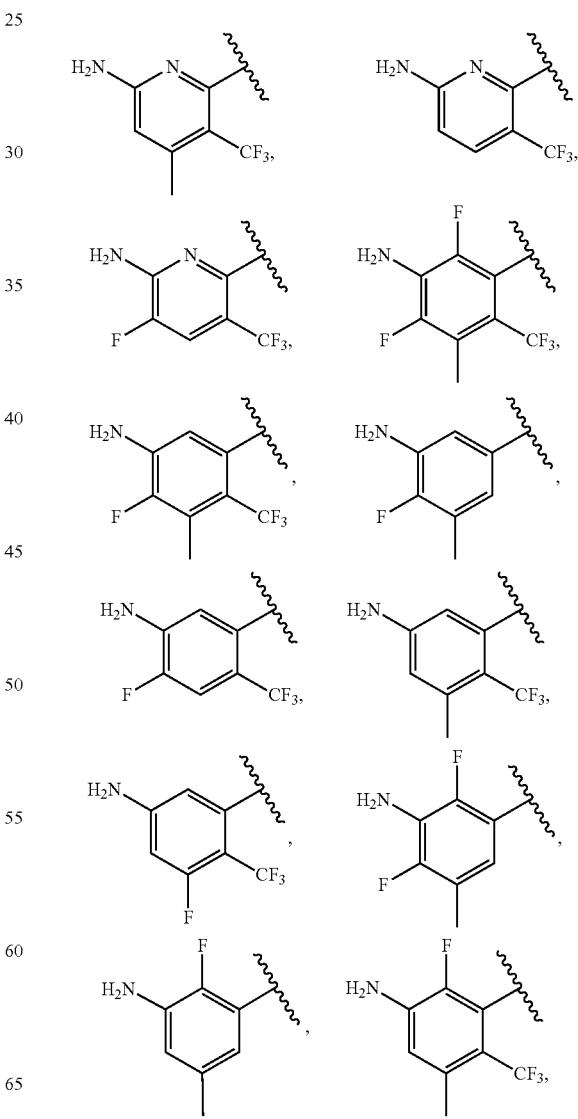

-continued

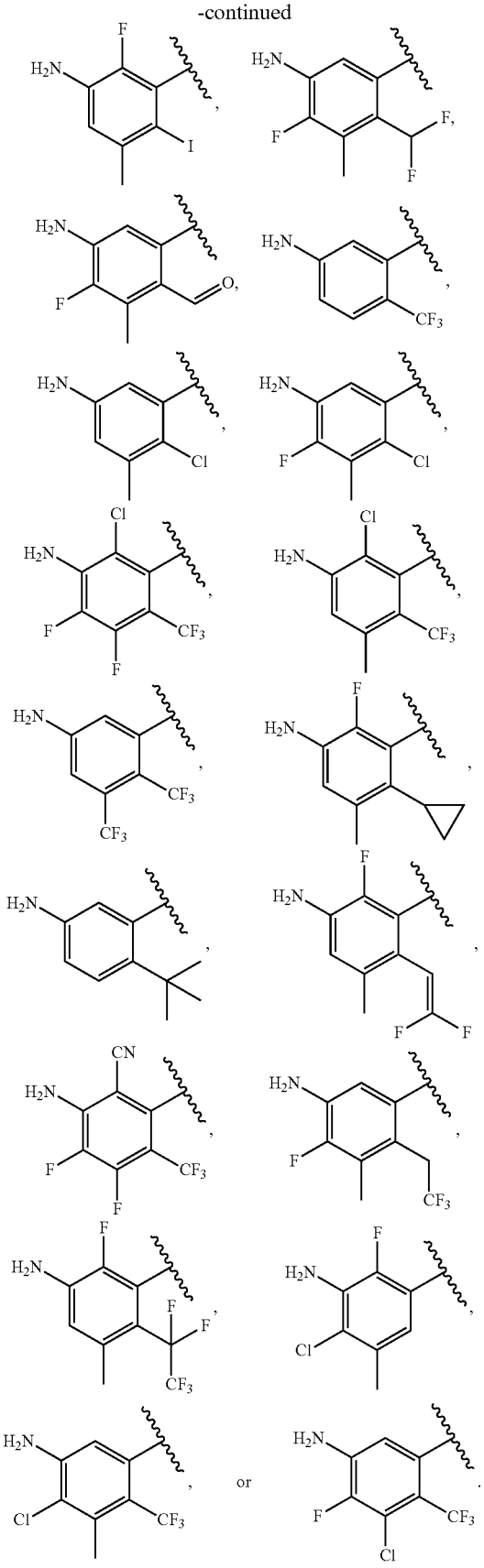

In another embodiment, $R^1$ is:

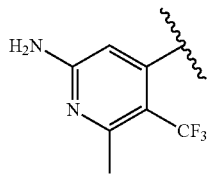

In another embodiment is a compound of formula (I) or a stereoisomer, atropisomer, tautomer, or pharmaceutically acceptable salt thereof, wherein
X is O or $NR^6$;
m is 1 or 2;
n is 1 or 2;
wherein n and m together make a 6- or 7-membered ring Ring A;
p is 0, 1, or 2;
$R^1$ is

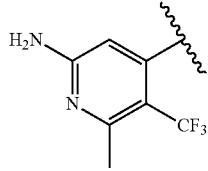

$L^1$ is $R^{L1}$-substituted or unsubstituted $C_{1-4}$ alkylene;
$R^{L1}$ is halogen or unsubstituted $C_{1-3}$ alkyl, or wherein two $R^{L1}$ together form an unsubstituted $C_{3-4}$ cycloalkyl;
$R^2$ is $R^9$-substituted or unsubstituted 4-10 membered heterocycle comprising one or more heteroatoms selected from N, S, or O;
$R^9$ is independently halogen, CN, OH, $OCF_3$, $OCHF_2$, $OCH_2F$, $R^{10}$-substituted or unsubstituted $C_{1-3}$ alkyl, $R^{10}$-substituted or unsubstituted $C_{1-3}$ haloalkyl, unsubstituted $C_{1-3}$ alkoxy, $R^{10}$-substituted or unsubstituted $C_{1-3}$ alkylidene, or $R^{10}$-substituted or unsubstituted $C_{3-4}$ cycloalkyl, or $R^{10}$-substituted or unsubstituted 3 or 4-membered heterocycle; or wherein
two $R^9$ together form a $R^{10}$-substituted or unsubstituted $C_{3-5}$ cycloalkyl or a $R^{10}$-substituted or unsubstituted $C_{3-5}$ heterocycle comprising one or more oxygen atoms; or wherein
two $R^9$ together form a bridge between two carbon atoms of the cycloalkyl or heterocycle, wherein the bridge comprises 1-3 carbons;
each $R^{10}$ is independently hydrogen, oxo, CN, halogen, or $C_{1-3}$ unsubstituted alkyl;
$R^3$ is hydrogen, —CN, halogen, unsubstituted $C_{1-3}$ alkyl, or unsubstituted cyclopropyl;
each $R^4$ is independently hydrogen, methyl, or $C_{1-3}$ haloalkyl;
$R^5$ is independently halogen, oxo, unsubstituted $C_{1-3}$ alkyl, or unsubstituted $C_{1-3}$ haloalkyl; or wherein
two $R^5$ together form a bridge between two carbon atoms of Ring A, wherein the bridge comprises 1-3 carbons and optionally one heteroatom selected from O and N; or
two $R^5$ together form a bridge between two carbon atoms of Ring A, wherein the bridge comprises one of O or $NR^{11}$;
$R^{11}$ is hydrogen, $C(O)CH_3$, or unsubstituted $C_{1-3}$ alkyl;
$R^6$ is hydrogen, $R^{6A}$-substituted or unsubstituted $C_{1-6}$ alkyl, $R^{6A}$-substituted or unsubstituted $C_{1-6}$ haloalkyl, R$^{6A}$-substituted or unsubstituted C$_{1-6}$ alkenyl; R$^{6A}$-substituted or unsubstituted C$_{1-6}$ alkynyl, or R$^{6A}$-substituted or unsubstituted 3-4 membered heterocycle;

R$^{6A}$ is halogen, CN, OR$^{6B}$, SR$^{6C}$, S(O)$_2$R$^{6C}$, C(O)R$^{6B}$, unsubstituted C$_{1-3}$ alkyl, unsubstituted C$_{1-3}$ haloalkyl, or R$^{6B}$ substituted or unsubstituted 3-4 membered heterocycle; and R$^{6B}$ and R$^{6C}$ are each independently C$_{1-3}$ alkyl or C$_{1-3}$ haloalkyl.

In another embodiment, R$^1$ is:

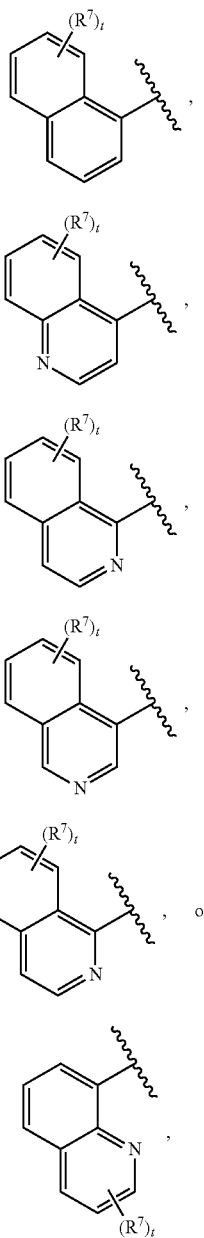

or a stereoisomer thereof, wherein t is 0, 1, 2, or 3. In one embodiment, t is 1 or 2. In another embodiment, t is 3. In one embodiment of the compounds described herein, R$^1$ is not a formula of F, F1, F2, F3, F4, or F5 and is a monocyclic ring.

In another embodiment, R$^1$ is a moiety of formula (F), (F1), (F2), or (F3), wherein t is 0, 1, 2, or 3. In one embodiment, t is 1 or 2. In another embodiment, t is 3.

In one embodiment, R$^1$ is:

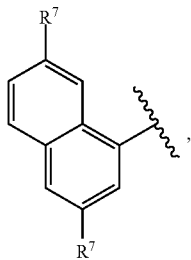

or a stereoisomer thereof, wherein R$^7$ is as described herein.

In another embodiment, R$^1$ is:

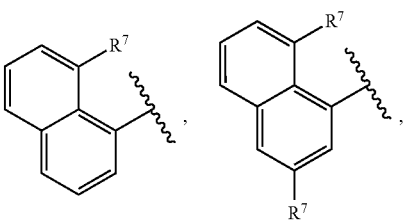

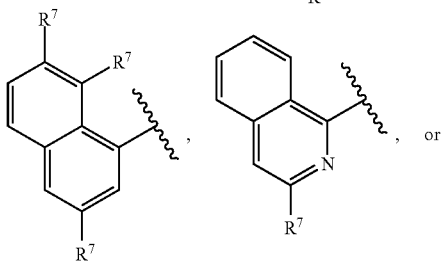

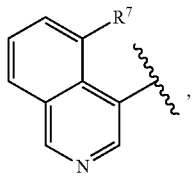

or N or a stereoisomer thereof.

In another embodiment, R$^1$ is:

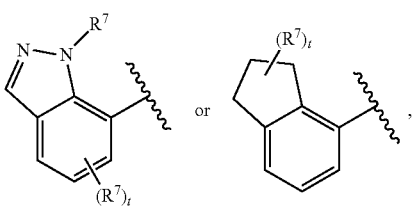

or a stereoisomer thereof, wherein t is 0, 1, 2, or 3. In one embodiment, t is 1 or 2. In one embodiment, R$^7$ is halogen, NH$_2$, OH, C$_{1-3}$alkyl, or C$_{2-3}$alkynyl.

In one embodiment of the compounds or a stereoisomer, atropisomer, tautomer, or pharmaceutically acceptable salt thereof described herein, R$^2$ is R$^9$-substituted or unsubstituted 4-10 membered heterocycle comprising one or more heteroatoms selected from N or O. In another embodiment of the compounds or a stereoisomer, atropisomer, tautomer, or pharmaceutically acceptable salt thereof described herein, $R^2$ is $R^9$-substituted or unsubstituted 4-10 membered heterocycle comprising one or more nitrogen heteroatoms. In another embodiment, $R^2$ is $R^9$-substituted or unsubstituted 5-8 membered heterocycle comprising at least one nitrogen heteroatom.

In one embodiment, each $R^9$ is independently halogen, CN, OH, $OCF_3$, $OCHF_2$, $OCH_2F$, $R^{10}$-substituted or unsubstituted $C_{1-3}$ alkyl, $R^{10}$-substituted or unsubstituted $C_{1-3}$ haloalkyl, unsubstituted $C_{1-3}$ alkoxy, $R^{10}$-substituted or unsubstituted $C_{1-3}$ alkylidene, or $R^{10}$-substituted or unsubstituted $C_{3-4}$ cycloalkyl, or $R^{10}$-substituted or unsubstituted 3 or 4-membered heterocycle. In one embodiment, each $R^9$ is independently halogen, CN, OH, $OCF_3$, $OCHF_2$, or $OCH_2F$. In another such embodiment, each $R^9$ is independently halogen, CN, OH, $OCF_3$, $OCHF_2$, $OCH_2F$, $R^{10}$-substituted or unsubstituted $C_{1-3}$ alkyl, $R^{10}$-substituted or unsubstituted $C_{1-3}$ haloalkyl, unsubstituted $C_{1-3}$ alkoxy, or $R^{10}$-substituted or unsubstituted $C_{1-3}$ alkylidene. In still another embodiment, each $R^9$ is independently $R^{10}$-substituted or unsubstituted $C_{1-3}$ alkyl, $R^{10}$-substituted or unsubstituted $C_{1-3}$ haloalkyl, unsubstituted $C_{1-3}$ alkoxy, or $R^{10}$-substituted or unsubstituted $C_{1-3}$ alkylidene. In another embodiment, each $R^9$ is independently halogen, $R^{10}$-substituted or unsubstituted $C_{3-4}$ cycloalkyl, or $R^{10}$-substituted or unsubstituted 3 or 4-membered heterocycle.

In another embodiment, two $R^9$ together form a $R^{10}$-substituted or unsubstituted $C_{3-5}$ cycloalkyl or a $R^{10}$-substituted or unsubstituted $C_{3-5}$ heterocycle comprising one or more oxygen atoms. In one such embodiment, two $R^9$ together form an unsubstituted cyclopropyl moiety. In another embodiment, two $R^9$ together form an unsubstituted oxetanyl or azetidinyl.

In another embodiment, two $R^9$ together form a bridge between two carbon atoms of the cycloalkyl or heterocycle, wherein the bridge comprises 1-3 carbons. In one such embodiment, the bridge comprises one carbon atom. In another such embodiment, the bridge comprises 2 carbon atoms.

In one embodiment, $R^9$ is halogen or $R^{10}$-substituted or unsubstituted $C_{1-3}$ alkylidene.

In one embodiment, $R^2$ is

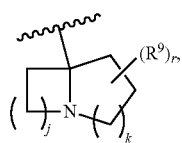

(A)

or a stereoisomer thereof, wherein,
$R^9$ is halogen or $R^{10}$-substituted or unsubstituted $C_{1-3}$ alkylidene
r is an integer of 0-12;
j is 1, 2, or 3; and
k is 1 or 2.

In one embodiment, $R^2$ is a moiety of formula:

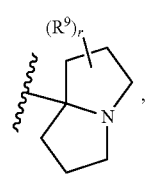

(A-1)

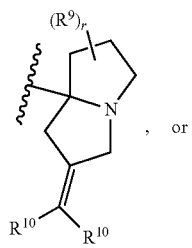

(A-2)

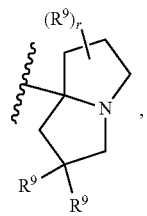

(A-3)

or a stereoisomer thereof, wherein
$R^9$ is independently halogen or $R^{10}$-substituted or unsubstituted $C_{1-3}$ alkylidene;
each $R^{10}$ is independently hydrogen or halogen; and
r is 1 or 2.

In one embodiment, $R^2$ is a moiety of formula:

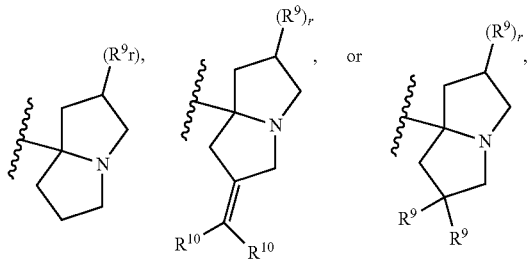

or a stereoisomer thereof.

In one embodiment, $R^2$ is a moiety of formula:

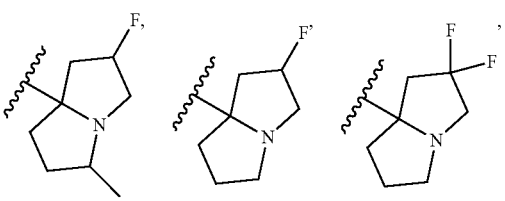

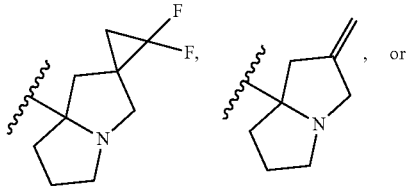

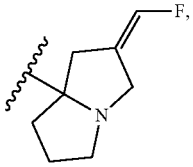

or a stereoisomer thereof.

In one embodiment, $R^2$ is a moiety of formula:

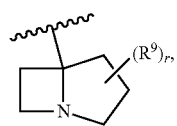
(A-4)

or a stereoisomer thereof, wherein $R^9$ and r are as described herein. In one such embodiment, r is 1 or 2. In one embodiment, each $R^9$ is independently halogen or $R^{10}$-substituted or unsubstituted $C_{1-3}$alkyl.

In one embodiment, $R^2$ is a moiety of formula:

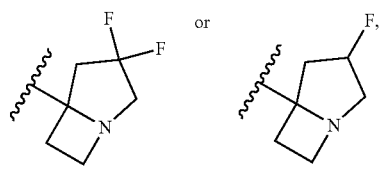 [SMILES: *C12CCN1CC(F)(F)C2 ; *C12CCN1CC(F)C2]

or a stereoisomer thereof.

In another embodiment, $R^2$ is

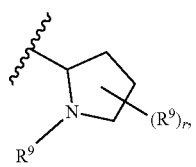
(B)

or a stereoisomer thereof, wherein $R^9$ is independently halogen, oxo, or unsubstituted $C_{1-3}$ alkyl; and r is 1 or 2.

In another embodiment, $R^2$ is

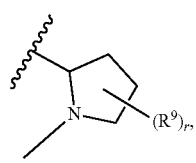

or a stereoisomer thereof.

In another embodiment, $R^2$ is

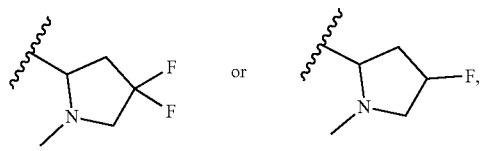

or a stereoisomer thereof.

In still another embodiment, $R^2$ is

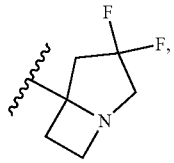 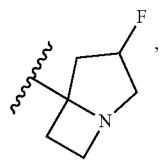

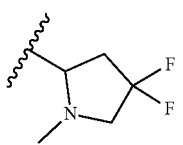 or 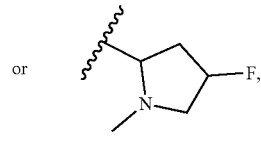

or a stereoisomer thereof.

In another embodiment, $R^2$ is

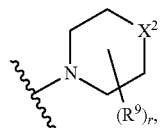
(C)

or a stereoisomer thereof, herein $X^2$ is $CR^9$ or O. In one embodiment, $X^2$ is O. In one such embodiment, $X^2$ is O and r is 0.

In another embodiment, $R^2$ is

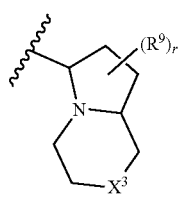
(D)

or

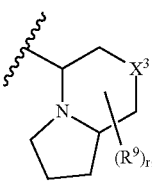
(D1)

or a stereoisomer thereof, wherein $X^3$ is $CR^9$, $NR^9$, or O.

In one embodiment, $R^2$ is a moiety of formula (D), where $X^3$ is $CR^9$, wherein $R^9$ is as described herein. In one such embodiment, $X^3$ is $CH_2$ or $CF_2$. In another such embodiment, $R^2$ is a moiety of formula (D) or (D1) and $X^3$ is O. In one embodiment, $R^2$ is a moiety of formula (D), $X^3$ is O and $R^9$ is unsubstituted $C_{1-3}$alkyl or halogen. In another embodiment, $R^2$ is a moiety of formula (D) $X^3$ is $NR^9$, and $R^9$ is oxo or unsubstituted $C_{1-3}$alkyl.

In one embodiment, $R^2$ is

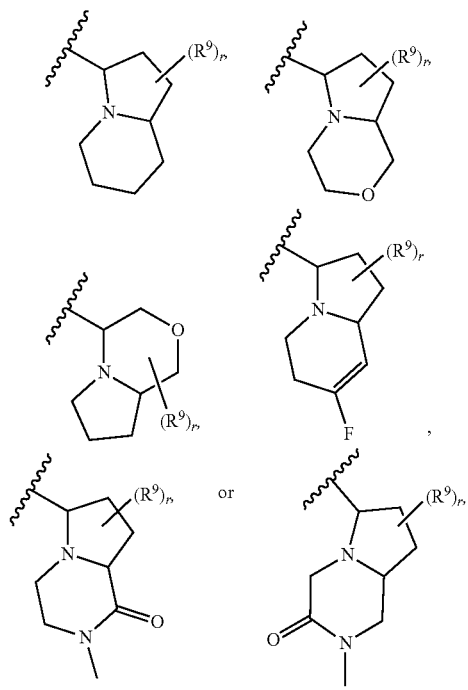

or a stereoisomer thereof. In one embodiment, r is 0 or 1.

In one embodiment, $L^1$ is methylene. In one embodiment, $R^2$ is as described herein and $L^1$ is methylene. In another embodiment, $L^1$ is $R^{L1}$ substituted or unsubstituted $C_{2-3}$ alkylene. In one such embodiment, $L^1$ is unsubstituted $C_{2-3}$ alkylene. In another such embodiment, $L^1$ is $R^{L1}$ substituted $C_{2-3}$ alkylene, where two $R^{L1}$ together form an unsubstituted $C_{3-4}$ cycloalkyl. In one such embodiment, $L^1$ has the formula:

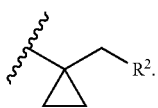

In one embodiment of the compounds or a stereoisomer, atropisomer, tautomer, or pharmaceutically acceptable salt thereof described herein, $R^3$ is halogen. In another embodiment, $R^3$ is —CN.

In one embodiment of the compounds or a stereoisomer, atropisomer, tautomer, or pharmaceutically acceptable salt thereof described herein, each $R^5$ is independently halogen, oxo, unsubstituted $C_{1-3}$ alkyl, or unsubstituted $C_{1-3}$ haloalkyl. In one such embodiment, each $R^5$ is independently unsubstituted $C_{1-3}$ alkyl, or unsubstituted $C_{1-3}$ haloalkyl. In some embodiments, p is 0 or 1.

In another embodiment, two $R^5$ together form a bridge between two carbon atoms of Ring A, wherein the bridge comprises 1-3 carbons and optionally one heteroatom selected from O and N. In one such embodiment, two $R^5$ together form a bridge between two carbon atoms of Ring A, wherein the bridge comprises 1-3 carbons. In one such embodiment, the bridge comprises 1 or 2 carbon atoms. In another such embodiment, the bridge comprises 1 carbon atom. In another such embodiment, the bridge comprises 2 carbon atoms.

In one embodiment, two $R^5$ together form a bridge between two carbon atoms of Ring A, wherein the bridge comprises one of O or $NR^{11}$. In one embodiment, the bridge comprises an O heteroatom. In another embodiment, the bridge comprises $NR^{11}$ where $R^{11}$ is hydrogen or methyl.

In some embodiments, Ring A is a 6 membered ring (i.e., where m and n are both 1). In one embodiment, Ring A is a 7-membered ring where m is 2 and n is 1. In another embodiment, Ring A is a 7-membered ring where m is 1 and n is 2. In one embodiment, X is $NR^6$, where $R^6$ is as described herein.

In one embodiment, $R^6$ is hydrogen or $R^{6A}$-substituted or unsubstituted $C_{1-3}$ alkyl. In one embodiment, $R^6$ is $R^{6A}$-substituted or unsubstituted $C_{1-3}$ alkyl. In one embodiment, $R^6$ is hydrogen. In one embodiment, $R^6$ is methyl.

In some embodiments, $R^6$ is $R^{6A}$-substituted or unsubstituted $C_{1-6}$ alkyl, $R^{6A}$-substituted or unsubstituted $C_{1-6}$ haloalkyl, $R^{6A}$-substituted or unsubstituted $C_{1-6}$ alkenyl; $R^{6A}$-substituted or unsubstituted $C_{1-6}$ alkynyl.

In such embodiments, $R^{6A}$ is halogen, CN, $OR^{6B}$, $SR^{6C}$, $S(O)_2R^{6C}$, $C(O)R^{6B}$, unsubstituted $C_{1-3}$ alkyl, unsubstituted $C_{1-3}$ haloalkyl, or $R^{6B}$ substituted or unsubstituted 3-4 membered heterocycle. In another such embodiment, $R^{6A}$ is halogen, CN, OH, OMe, OEt, $OCF_3$, $SO_2Me$, unsubstituted $C_{1-3}$ alkyl, or 4-membered heterocycle.

In one embodiment, each $R^{6B}$ is independently $C_{1-3}$ alkyl or $C_{1-3}$ haloalkyl. In one such embodiment, $R^{6B}$ is independently $C_{1-3}$ alkyl.

Further provided herein are compounds of formula (I) as described herein having formula:

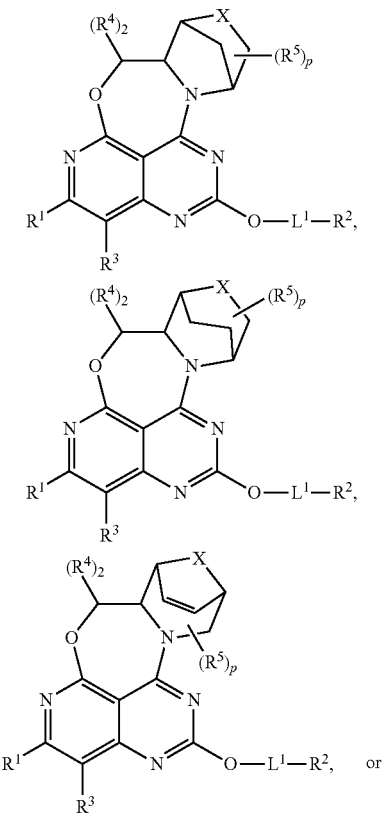

-continued

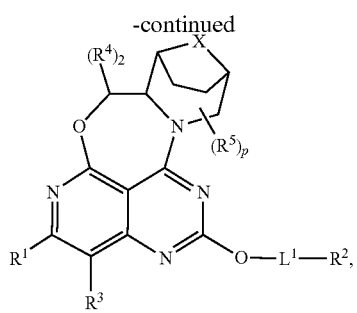

or a stereoisomer, atropisomer, tautomer, or pharmaceutically acceptable salt thereof, wherein $R^1$, $R^2$, $R^3$, $R^4$, $R^5$, X, $L^1$, and p are as described herein.

Further provided herein are compounds of formula (I) as described herein having formula:

(IIa)

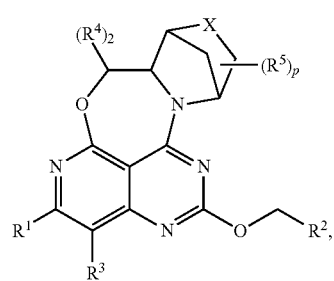

(IIb)

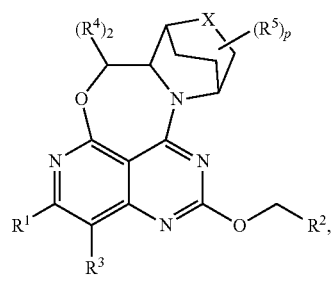

(IIc)

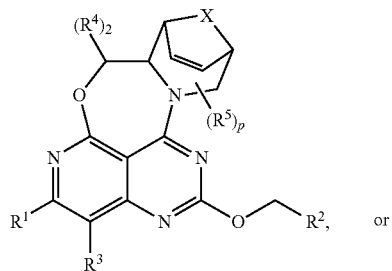

(IId)

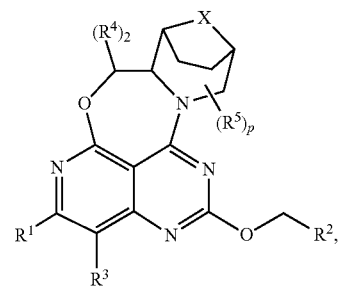

or a stereoisomer, atropisomer, tautomer, or pharmaceutically acceptable salt thereof, wherein $R^1$, $R^2$, $R^3$, $R^4$, $R^5$, X, and p are as described herein.

Further provided herein are compounds of formula (I) as described herein having formula:

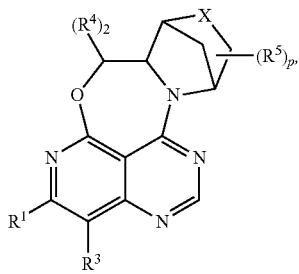

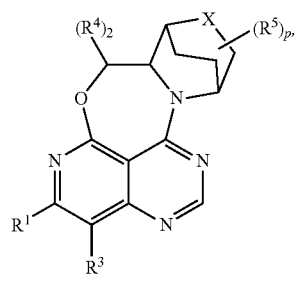

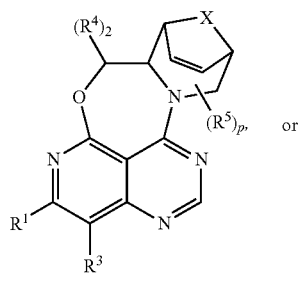

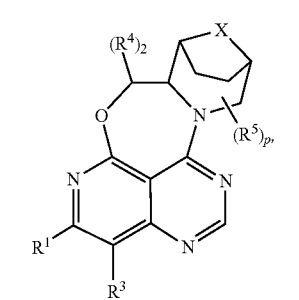

or a stereoisomer, atropisomer, tautomer, or pharmaceutically acceptable salt thereof, wherein $R^1$, $R^3$, $R^4$, $R^5$, X, and p are as described herein.

In one embodiment, the compound of formula (IId) or a stereoisomer, atropisomer, tautomer, or pharmaceutically acceptable salt thereof, comprises formula (IId-1),

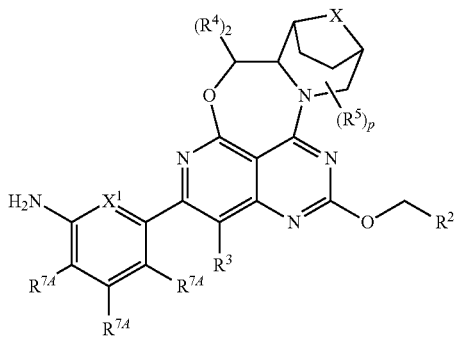

wherein $R^2$, $R^3$, $R^4$, $R^5$, $R^{7A}$, X, $X^1$, and p are as described herein.

In one embodiment, the compound of formula (IId) or a stereoisomer, atropisomer, tautomer, or pharmaceutically acceptable salt thereof, comprises formula (IId-2),

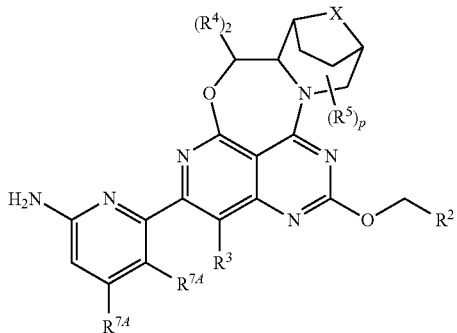

wherein $R^2$, $R^3$, $R^4$, $R^5$, $R^{7A}$, X, and p are as described herein.

In one embodiment, the compound of formula (IId) or a stereoisomer, atropisomer, tautomer, or pharmaceutically acceptable salt thereof, comprises formula (IId-3),

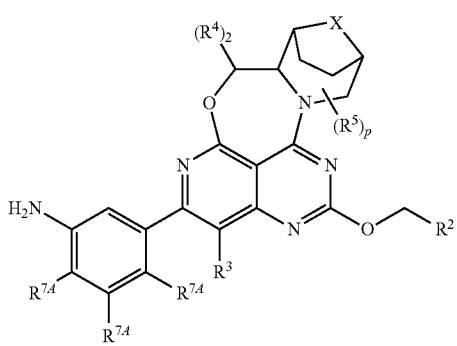

wherein $R^2$, $R^3$, $R^4$, $R^5$, $R^{7A}$, X, and p are as described herein.

In one embodiment, the compound of formula (IId) or a stereoisomer, atropisomer, tautomer, or pharmaceutically acceptable salt thereof, comprises formula (IId-4),

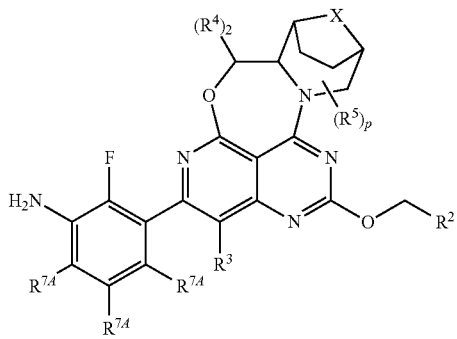

wherein $R^2$, $R^3$, $R^4$, $R^5$, $R^{7A}$, X, and p are as described herein.

In one embodiment, the compound of formula (IId) or a stereoisomer, atropisomer, tautomer, or pharmaceutically acceptable salt thereof, comprises formula (IId-5),

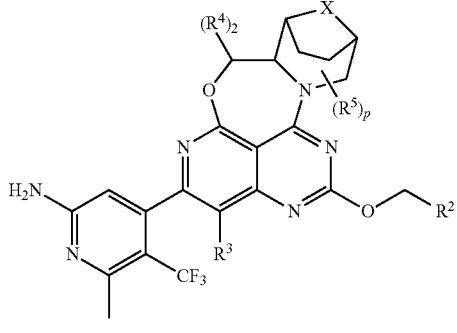

wherein $R^2$, $R^3$, $R^4$, $R^5$, X, and p are as described herein

In one embodiment, X is NH or N(CH$_3$). In one embodiment, $R^1$ is a moiety of formula for (E), (E1), (E2), (E3), (F), (F1), (F2), (F3), (F4), or (F5) as described herein. In one embodiment, $R^2$ is a moiety of formula (A), (A-1), (A-2), (A-3), (A-4), (B), (C), (D), or (D1) as described herein.

In one embodiment of the compounds or a stereoisomer, atropisomer, tautomer, or pharmaceutically acceptable salt thereof described herein of formula (IIa), (IIb), (IIc), or (IId), $R^2$ comprises a moiety of formula:

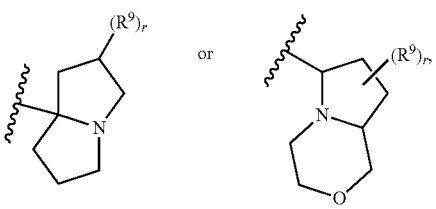

or a stereoisomer thereof. In one such embodiment, the compound, stereoisomer, atropisomer, tautomer, or pharmaceutically acceptable salt thereof described herein comprises formula (IId) as described herein. In another such embodiment, the compound, stereoisomer, atropisomer, tautomer, or pharmaceutically acceptable salt thereof described herein comprises formula (IId-1), (IId-2), (IId-3), (IId-4), or (IId-5), as described herein.

In one such embodiment, the compounds or a stereoisomer, atropisomer, tautomer, or pharmaceutically acceptable salt thereof described herein of formula (IIa), (IIb), (IIc), or (IId), R² comprises a moiety of formula:

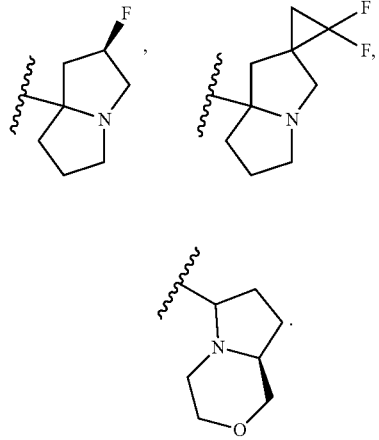

In one such embodiment, the compound, stereoisomer, atropisomer, tautomer, or pharmaceutically acceptable salt thereof described herein comprises formula (IId) as described herein. In another such embodiment, the compound, stereoisomer, atropisomer, tautomer, or pharmaceutically acceptable salt thereof described herein comprises formula (IId-1), (IId-2), (IId-3), (IId-4), or (IId-5), as described herein.

In another embodiment, the compound of formula (I) as described herein has formula:

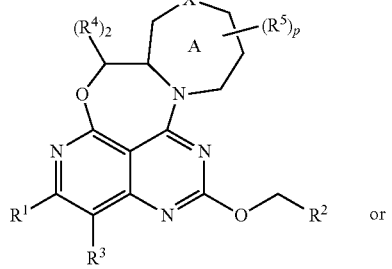

(IIIa)

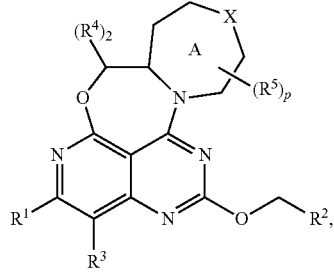

(IIIb)

or a stereoisomer, atropisomer, tautomer, or pharmaceutically acceptable salt thereof, wherein $R^1$, $R^2$, $R^3$, $R^4$, $R^5$, X, and p are as described herein. In one such embodiment, X is $NR^6$, where $R^6$ is hydrogen or $R^{6A}$-substituted or unsubstituted $C_{1-3}$ alkyl.

TABLE 1

| Cmpd. No. | Chemical Structure |
|---|---|
| 1 | 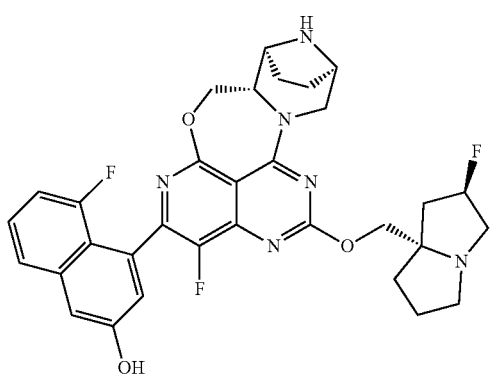 [SMILES: Oc1cc(-c2nc3c4c(nc(OC[C@@]56CCCN5C[C@H](F)C6)nc4c2F)N2C[C@H]4CC[C@H](N4)[C@H]2CO3)c2c(F)cccc2c1]<br>5-fluoro-4-((5aS,6S,9R)-1-fluoro-12-(((2R,7aS)-2-fluorotetrahydro-1H-pyrrolizin-7a(5H)-yl)methoxy)-5a,6,7,8,9,10-hexahydro-5H-4-oxa-3,10a,11,13,14-pentaaza-6,9-methanonaphtho[1,8-ab]heptalen-2-yl)naphthalen-2-ol |

TABLE 1-continued

| Cmpd. No. | Chemical Structure |
|---|---|
| 2 | 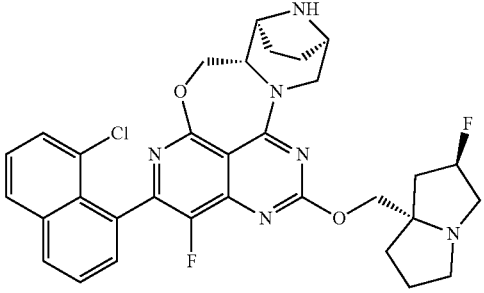 [SMILES: Fc1c(-c2cccc3cccc(Cl)c23)nc2c3c(nc(OC[C@@]45CCCN4C[C@H](F)C5)nc13)N1C[C@H]3CC[C@H](N3)[C@H]1CO2]<br>(5aS,6S,9R)-2-(8-chloronaphthalen-1-yl)-1-fluoro-12-(((2R,7aS)-2-fluorotetrahydro-1H-pyrrolizin-7a(5H)-yl)methoxy)-5a,6,7,9,10-hexahydro-5H-4-oxa-3,10a,11,13,14-pentaaza-6,9-methanonaphtho[1,8-ab]heptalene |
| 3 | 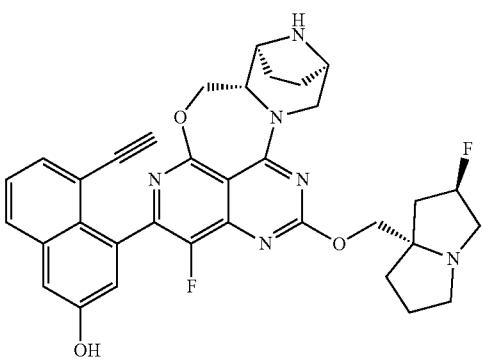 [SMILES: C#Cc1cccc2cc(O)cc(-c3nc4c5c(nc(OC[C@@]67CCCN6C[C@H](F)C7)nc5c3F)N3C[C@H]5CC[C@H](N5)[C@H]3CO4)c12]<br>5-ethynyl-4-((5aS,6S,9R)-1-fluoro-12-(((2R,7aS)-2-fluorotetrahydro-1H-pyrrolizin-7a(5H)-yl)methoxy)-5a,6,7,8,9,10-hexahydro-5H-4-oxa-3,10a,11,13,14-pentaaza-6,9-methanonaphtho[1,8-ab]heptalen-2-yl)naphthalen-2-ol |
| 4 | 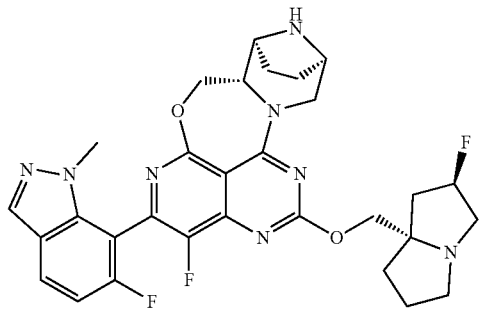 [SMILES: Cn1ncc2ccc(F)c(-c3nc4c5c(nc(OC[C@@]67CCCN6C[C@H](F)C7)nc5c3F)N3C[C@H]5CC[C@H](N5)[C@H]3CO4)c21]<br>(5aS,6S,9R)-1-fluoro-2-(6-fluoro-1-methyl-1H-indazol-7-yl)-12-(((2R,7aS)-2-fluorotetrahydro-1H-pyrrolizin-7a(5H)-yl)methoxy)-5a,6,7,8,9,10-hexahydro-5H-4-oxa-3,10a,11,13,14-pentaaza-6,9-methanonaphtho[1,8-ab]heptalene |
| 5 | 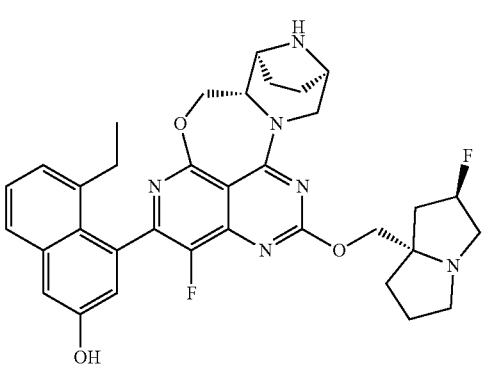 [SMILES: CCc1cccc2cc(O)cc(-c3nc4c5c(nc(OC[C@@]67CCCN6C[C@H](F)C7)nc5c3F)N3C[C@H]5CC[C@H](N5)[C@H]3CO4)c12] |

TABLE 1-continued

| Cmpd. No. | Chemical Structure |
|---|---|
| | 5-ethyl-4-((5aS,6S,9R)-1-fluoro-12-(((2R,7aS)-2-fluorotetrahydro-1H-pyrrolizin-7a(5H)-yl)methoxy)-5a,6,7,8,9,10-hexahydro-5H-4-oxa-3,10a,11,13,14-pentaaza-6,9-methanonaphtho[1,8-ab]heptalen-2-yl)naphthalen-2-ol |
| 6 | 2-Fluoro-5-((5S,5aS,6S,9R)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-3-methyl-4-(trifluoromethyl)aniline |
| 7 | 5-Ethynyl-6-fluoro-4-((5S,5aS,6S,9R)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)naphthalen-2-ol |
| 8 | (5S,5aS,6S,9R)-2-(8-chloronaphthalen-1-yl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene |

TABLE 1-continued

| Cmpd. No. | Chemical Structure |
|---|---|
| 9 | 5-fluoro-4-((5S,5aS,6S,9R)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)naphthalen-2-ol |
| 10 | 5-ethyl-4-((5S,5aS,6S,9R)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)naphthalen-2-ol |
| 11 | 5-ethynyl-4-((5S,5aS,6S,9R)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)naphthalen-2-ol |
| 12 | 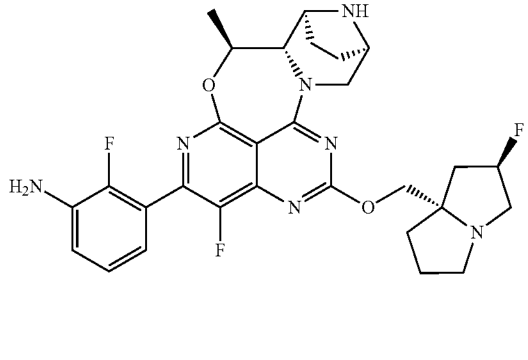 [SMILES: C[C@@H]1Oc2nc(-c3cccc(N)c3F)c(F)c3nc(OC[C@@]45CCCN4C[C@H](F)C5)nc(c23)N2C[C@H]3CC[C@H](N3)[C@@H]12] |

TABLE 1-continued

| Cmpd. No. | Chemical Structure |
|---|---|
| | 2-fluoro-3-((5S,5aS,6S,9R)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)aniline |
| 13 | 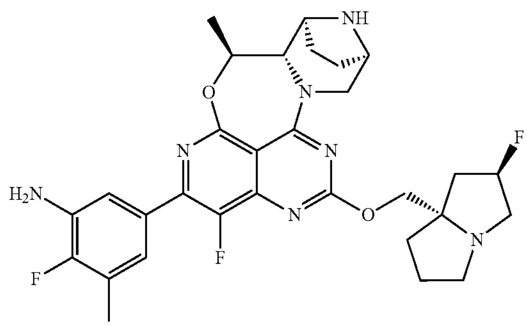 [SMILES: Cc1cc(-c2nc3c4c(nc(OC[C@@]56CCCN5C[C@H](F)C6)nc4c2F)N2C[C@H]4CC[C@H](N4)[C@H]2[C@H](C)O3)cc(N)c1F] |
| | 2-fluoro-5-((5S,5aS,6S,9R)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-3-methylaniline |
| 14 | 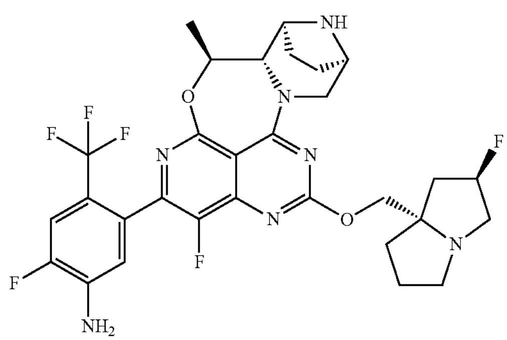 |
| | 2-fluoro-5-((5S,5aS,6S,9R)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-4-(trifluoromethyl)aniline |
| 15 | 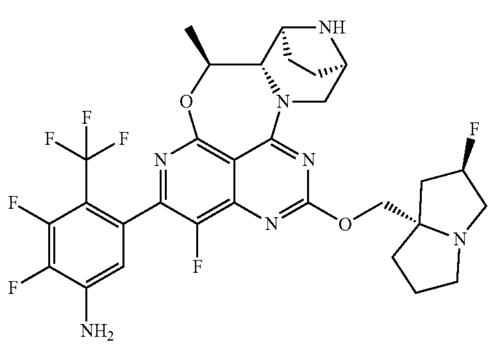 [SMILES: C[C@@H]1Oc2nc(-c3cc(N)c(F)c(F)c3C(F)(F)F)c(F)c3nc(OC[C@@]45CCCN4C[C@H](F)C5)nc(c23)N2C[C@H]3CC[C@H](N3)[C@@H]12] |
| | 2,3-difluoro-5-((5S,5aS,6S,9R)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-4-(trifluoromethyl)aniline |

TABLE 1-continued

| Cmpd. No. | Chemical Structure |
|---|---|
| 16 | 3-((5S,5aS,6S,9R)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-5-methyl-4-(trifluoromethyl)aniline |
| 17 | 3-fluoro-5-((5S,5aS,6S,9R)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-4-(trifluoromethyl)aniline |
| 18 | 2,6-difluoro-3-((5S,5aS,6S,9R)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-5-methylaniline |
| 19 | 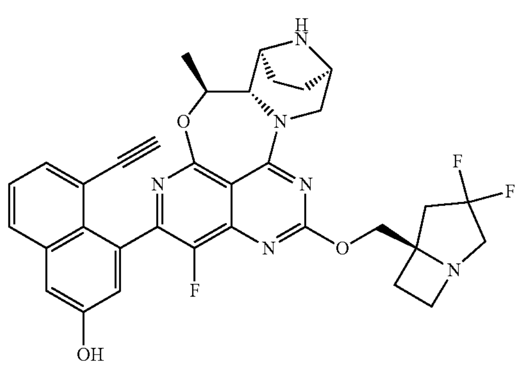 [SMILES: C#Cc1cccc2cc(O)cc(-c3nc4c5c(nc(OC[C@]67CCN6CC(F)(F)C7)nc5c3F)N3C[C@H]5CC[C@H](N5)[C@H]3[C@H](C)O4)c12] |

TABLE 1-continued

| Cmpd. No. | Chemical Structure |
| --- | --- |

4-((5S,5aS,6S,9R)-12-((3,3-Difluoro-1-azabicyclo[3.2.0]heptan-5-yl)methoxy)-1-fluoro-5-methyl-5a,6,7,8,9,10-hexahydro-5H-4-oxa-3,10a,11,13,14-pentaaza-6,9-methanonaphtho[1,8-ab]heptalen-2-yl)-5-ethynylnaphthalen-2-ol

20

4-((5S,5aS,6S,9R)-12-((3,3-Difluoro-1-azabicyclo[3.2.0]heptan-5-yl)methoxy)-1-fluoro-5-methyl-5a,6,7,8,9,10-hexahydro-5H-4-oxa-3,10a,11,13,14-pentaaza-6,9-methanonaphtho[1,8-ab]heptalen-2-yl)-5-ethynylnaphthalen-2-ol

21

(5S,5aS,6S,9R)-2-(8-chloronaphthalen-1-yl)-12-((3,3-difluoro-1-azabicyclo[3.2.0]heptan-5-yl)methoxy)-1-fluoro-5-methyl-5a,6,7,8,9,10-hexahydro-5H-4-oxa-3,10a,11,13,14-pentaaza-6,9-methanonaphtho[1,8-ab]heptalene TABLE 1-continued
| Cmpd. No. | Chemical Structure |
|---|---|
| 22 | 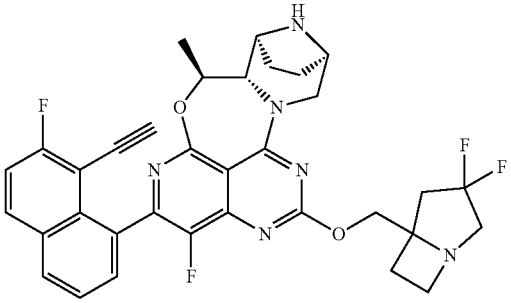 [SMILES: C#Cc1c(F)ccc2cccc(-c3nc4c5c(nc(OCC67CCN6CC(F)(F)C7)nc5c3F)N3C[C@H]5CC[C@H](N5)[C@H]3[C@H](C)O4)c12] |
| | (5S,5aS,6S,9R)-12-((3,3-difluoro-1-azabicyclo[3.2.0]heptan-5-yl)methoxy)-2-(8-ethynyl-7-fluoronaphthalen-1-yl)-1-fluoro-5-methyl-5a,6,7,8,9,10-hexahydro-5H-4-oxa-3,10a,11,13,14-pentaaza-6,9-methanonaphtho[1,8-ab]heptalene |
| 23 | 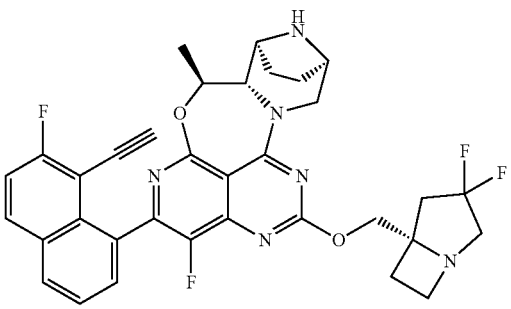 [SMILES: C#Cc1c(F)ccc2cccc(-c3nc4c5c(nc(OC[C@@]67CCN6CC(F)(F)C7)nc5c3F)N3C[C@H]5CC[C@H](N5)[C@H]3[C@H](C)O4)c12] |

TABLE 1-continued

| Cmpd. No. | Chemical Structure |
|---|---|
| | 3-((5S,5aS,6S,9R)-12-((3,3-difluoro-1-azabicyclo[3.2.0]heptan-5-yl)methoxy)-1-fluoro-5-methyl-5a,6,7,8,9,10-hexahydro-5H-4-oxa-3,10a,11,13,14-pentaaza-6,9-methanonaphtho[1,8-ab]heptan-2-yl)-2-fluoro-5-methylaniline |
| 24 | 5-((5S,5aS,6S,9R)-12-(((R)-3,3-difluoro-1-azabicyclo[3.2.0]heptan-5-yl)methoxy)-1-fluoro-5-methyl-5a,6,7,8,9,10-hexahydro-5H-4-oxa-3,10a,11,13,14-pentaaza-6,9-methanonaphtho[1,8-ab]heptalen-2-yl)-2-fluoro-3-methyl-4-(trifluoromethyl)aniline |
| 25 | 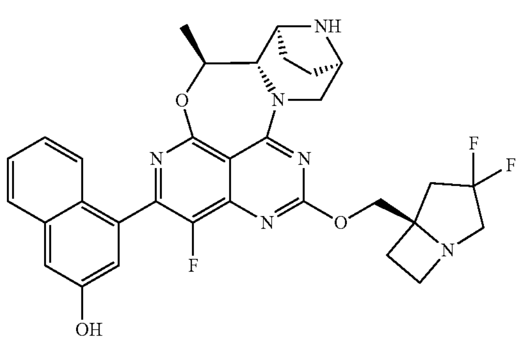 [SMILES: C[C@@H]1Oc2nc(-c3cc(O)cc4ccccc34)c(F)c3nc(OC[C@]45CCN4CC(F)(F)C5)nc(c23)N2C[C@H]3CC[C@H](N3)[C@@H]12] |

| Cmpd. No. | Chemical Structure |
|---|---|
| | 4-((5S,5aS,6S,9R)-12-(((R)-3,3-difluoro-1-azabicyclo[3.2.0]heptan-5-yl)methoxy)-1-fluoro-5-methyl-5a,6,7,8,9,10-hexahydro-5H-4-oxa-3,10a,11,13,14-pentaaza-6,9-methanonaphtho[1,8-ab]heptalen-2-yl)naphthalen-2-ol |
| 26 | 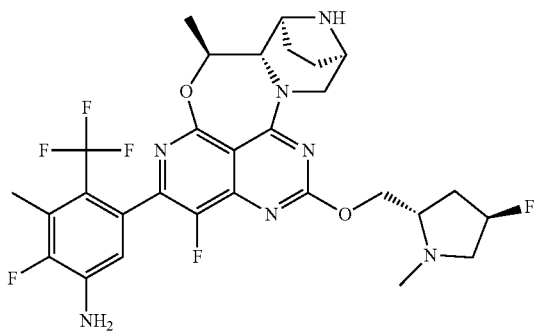 [SMILES: Cc1c(F)c(N)cc(-c2nc3c4c(nc(OC[C@@H]5C[C@@H](F)CN5C)nc4c2F)N2C[C@H]4CC[C@H](N4)[C@H]2[C@H](C)O3)c1C(F)(F)F] |
| | 2-Fluoro-5-((5S,5aS,6S,9R)-1-fluoro-12-(((2S,4R)-4-fluoro-1-methylpyrrolidin-2-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-3-methyl-4-(trifluoromethyl)aniline |
| 27 | 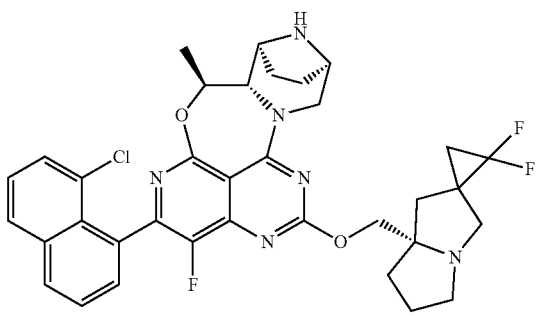 [SMILES: C[C@@H]1Oc2nc(-c3cccc4cccc(Cl)c34)c(F)c3nc(OC[C@@]45CCCN4CC4(CC4(F)F)C5)nc(c23)N2C[C@H]3CC[C@H](N3)[C@@H]12] |
| | (5S,5aS,6S,9R)-2-(8-chloronaphthalen-1-yl)-12-(((7a'S)-2,2-difluorodihydro-1'H,3'H-spiro[cyclopropane-1,2'-pyrrolizin]-7a'(5'H)-yl)methoxy)-1-fluoro-5-methyl-5a,6,7,8,9,10-hexahydro-5H-4-oxa-3,10a,11,13,14-pentaaza-6,9-methanonaphtho[1,8-ab]heptalene |
| 28 | 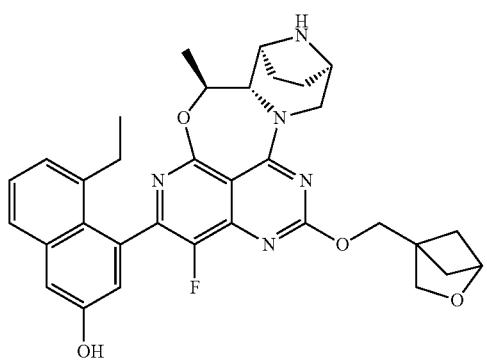 [SMILES: CCc1cccc2cc(O)cc(-c3nc4c5c(nc(OCC67COC(C6)C7)nc5c3F)N3C[C@H]5CC[C@H](N5)[C@H]3[C@H](C)O4)c12] |
| | 4-((5S,5aS,6S,9R)-12-((2-oxabicyclo[2.1.1]hexan-4-yl)methoxy)-1-fluoro-5-methyl-5a,6,7,8,9,10-hexahydro-5H-4-oxa-3,10a,11,13,14-pentaaza-6,9-methanonaphtho[1,8-ab]heptalen-2-yl)-5-ethylnaphthalen-2-ol |

TABLE 1-continued

| Cmpd. No. | Chemical Structure |
|---|---|
| 29 | 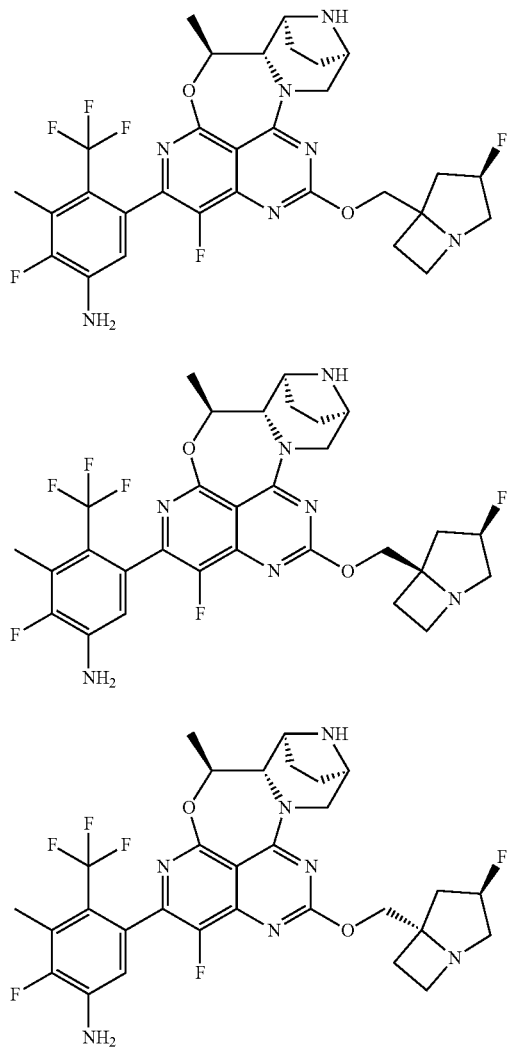 |

2-fluoro-5-((5S,5aS,6S,9R)-1-fluoro-12-(((3R)-3-fluoro-1-azabicyclo[3.2.0]heptan-5-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-3-methyl-4-(trifluoromethyl)aniline

| 30 | 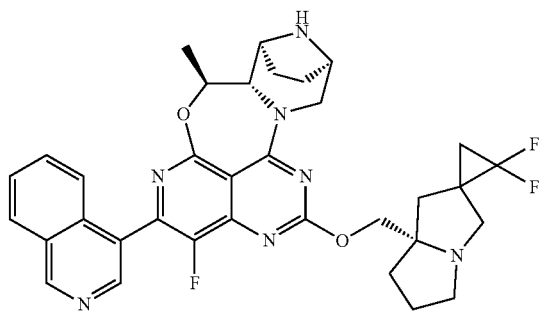 [SMILES: C[C@@H]1Oc2nc(-c3cncc4ccccc34)c(F)c3nc(OC[C@@]45CCCN4CC4(CC4(F)F)C5)nc(c23)N2C[C@H]3CC[C@H](N3)[C@@H]12] |

(5S,5aS,6S,9R)-12-(((7a'S)-2,2-difluorodihydro-1'H,3'H-spiro[cyclopropane-1,2'-pyrrolizin]-7a'(5'H)-yl)methoxy)-1-fluoro-2-(isoquinolin-4-yl)-5-methyl-5a,6,7,8,9,10-hexahydro-5H-4-oxa-3,10a,11,13,14-pentaaza-6,9-methanonaphtho[1,8-ab]heptalene TABLE 1-continued

| Cmpd. No. | Chemical Structure |
|---|---|
| 31 | 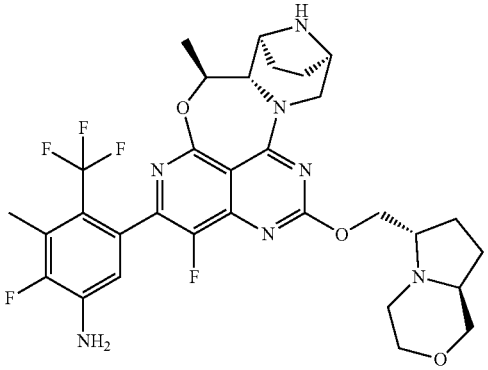 [SMILES: Cc1c(F)c(N)cc(-c2nc3c4c(nc(OC[C@@H]5CC[C@H]6COCCN65)nc4c2F)N2C[C@H]4CC[C@H](N4)[C@H]2[C@H](C)O3)c1C(F)(F)F]<br>2-fluoro-5-(((5S,5aS,6S,9R)-1-fluoro-12-((((6S,8aS)-hexahydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-3-methyl-4-(trifluoromethyl)aniline |
| 32 | 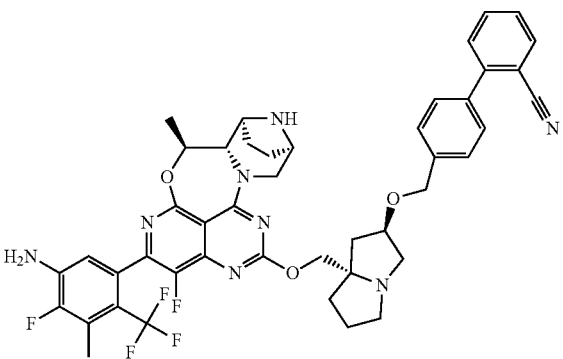 [SMILES: Cc1c(F)c(N)cc(-c2nc3c4c(nc(OC[C@@]56CCCN5C[C@H](OCc5ccc(-c7ccccc7C#N)cc5)C6)nc4c2F)N2C[C@H]4CC[C@H](N4)[C@H]2[C@H](C)O3)c1C(F)(F)F]<br>4'-(((((2R,7aS)-7a-(((((5S,5aS,6S,9R)-2-(5-amino-4-fluoro-3-methyl-2-(trifluoromethyl)phenyl)-1-fluoro-5-methyl-5a,6,7,8,9,10-hexahydro-5H-4-oxa-3,10a,11,13,14-pentaaza-6,9-methanonaphtho[1,8-ab]heptalen-12-yl)oxy)methyl)hexahydro-1H-pyrrolizin-2-yl)oxy)methyl)-[1,1'-biphenyl]-2-carbonitrile |
| 33 | 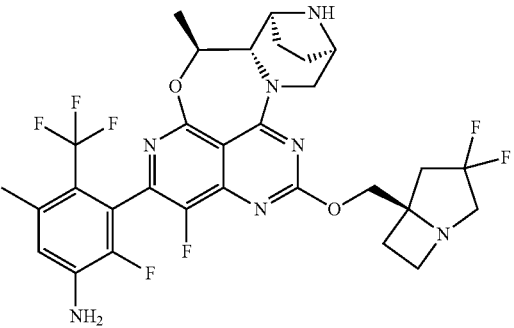 [SMILES: Cc1cc(N)c(F)c(-c2nc3c4c(nc(OC[C@]56CCN5CC(F)(F)C6)nc4c2F)N2C[C@H]4CC[C@H](N4)[C@H]2[C@H](C)O3)c1C(F)(F)F] |

TABLE 1-continued

| Cmpd. No. | Chemical Structure |
|---|---|
| | 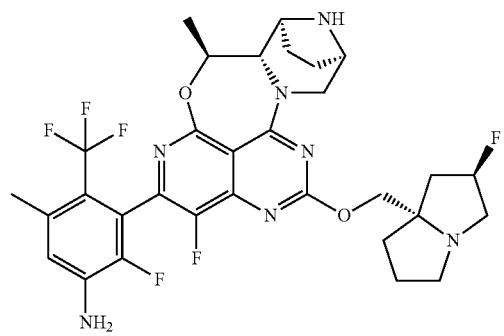 [SMILES: Cc1cc(N)c(F)c(-c2nc3c4c(nc(OC[C@@]56CCCN5C[C@H](F)C6)nc4c2F)N2C[C@H]4CC[C@H](N4)[C@H]2[C@H](C)O3)c1C(F)(F)F]  3-((5S,5aS,6S,9R)-12-((3,3-Difluoro-1-azabicyclo[3.2.0]heptan-5-yl)methoxy)-1-fluoro-5-methyl-5a,6,7,8,9,10-hexahydro-5H-4-oxa-3,10a,11,13,14-pentaaza-6,9-methanonaphtho[1,8-ab]heptalen-2-yl)-2-fluoro-5-methyl-4-(trifluoromethyl)aniline |
| 34 | 2-Fluoro-3-((5S,5aS,6S,9R)-1-fluoro-12-(((2R,7aS)-2-fluorotetrahydro-1H-pyrrolizin-7a(5H)-yl)methoxy)-5-mthyl-5a,6,7,8,9,10-hexahydro-5H-4-oxa-3,10a,11,13,14-pentaaza-6,9-methanonaphtho[1,8-ab]heptalen-2-yl)-5-methyl-4-(trifluoromethyl)aniline |
| 35 | 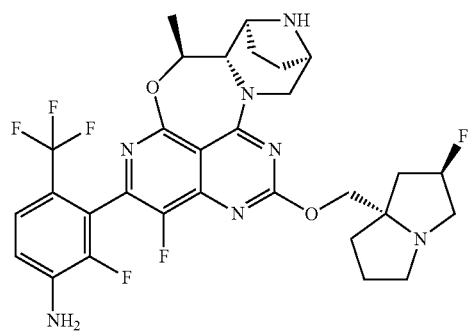 [SMILES: C[C@@H]1Oc2nc(-c3c(C(F)(F)F)ccc(N)c3F)c(F)c3nc(OC[C@@]45CCCN4C[C@H](F)C5)nc(c23)N2C[C@H]3CC[C@H](N3)[C@@H]12]  2-fluoro-3-((5S,5aS,6S,9R)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-4-(trifluoromethyl)aniline |

TABLE 1-continued

| Cmpd. No. | Chemical Structure |
|---|---|
| 36 | 2-fluoro-3-((5aS,6S,9R)-1-fluoro-12-(((2R,7aS)-2-fluorotetrahydro-1H-pyrrolizin-7a(5H)-yl)methoxy)-5a,6,7,8,9,10-hexahydro-5H-4-oxa-3,10a,11,13,14-pentaaza-6,9-methanonaphtho[1,8-ab]heptalen-2-yl)-5-methyl-4-(trifluoromethyl)aniline |
| 38 | (5S,5aS,6S,9R)-2-(5-Chloroisoquinolin-4-yl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene |
| 39 | (5S,5aS,6S,9R)-2-(5-Ethynylisoquinolin-4-yl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene |
| 40 | 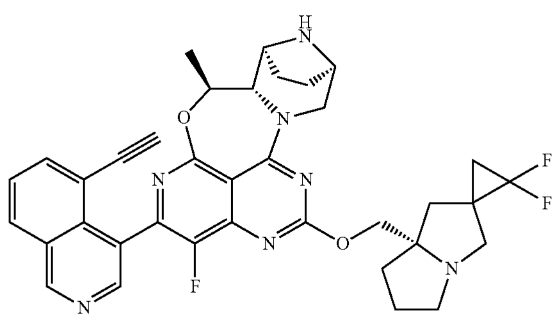 [SMILES: C#Cc1cccc2cncc(-c3nc4c5c(nc(OC[C@@]67CCCN6CC6(CC6(F)F)C7)nc5c3F)N3C[C@H]5CC[C@H](N5)[C@H]3[C@H](C)O4)c12] |

TABLE 1-continued

| Cmpd. No. | Chemical Structure |
|---|---|
| | (5S,5aS,6S,9R)-12-(((7a'S)-2,2-difluorodihydro-1'H,3'H-spiro[cyclopropane-1,2'-pyrrolizin]-7a'(5'H)-yl)methoxy)-2-(5-ethynylisoquinolin-4-yl)-1-fluoro-5-methyl-5a,6,7,8,9,10-hexahydro-5H-4-oxa-3,10a,11,13,14-pentaaza-6,9-methanonaphtho[1,8-ab]heptalene |
| 41 | 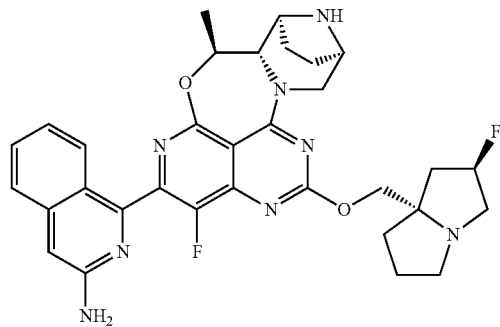 [SMILES: C[C@@H]1Oc2nc(-c3nc(N)cc4ccccc34)c(F)c3nc(OC[C@@]45CCCN4C[C@H](F)C5)nc(c23)N2C[C@H]3CC[C@H](N3)[C@@H]12] |
| | 1-((5S,5aS,6S,9R)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)isoquinolin-3-amine |
| 42 | 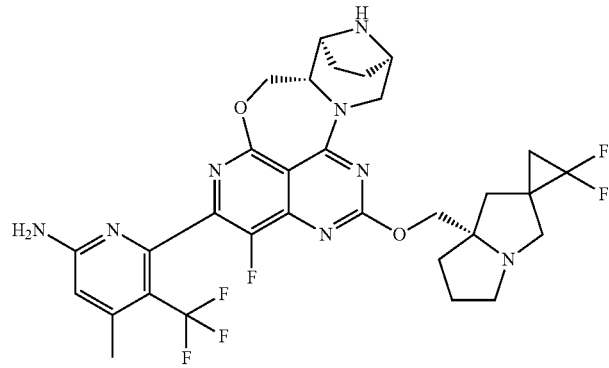 [SMILES: Cc1cc(N)nc(-c2nc3c4c(nc(OC[C@@]56CCCN5CC5(CC5(F)F)C6)nc4c2F)N2C[C@H]4CC[C@H](N4)[C@H]2CO3)c1C(F)(F)F] |
| | 6-((5aS,6S,9R)-12-(((7a'S)-2,2-Difluorodihydro-1'H,3'H-spiro[cyclopropane-1,2'-pyrrolizin]-7a'(5'H)-yl)methoxy)-1-fluoro-5a,6,7,8,9,10-hexahydro-5H-4-oxa-3,10a,11,13,14-pentaaza[6,9]methanonaphtho[1,8-ab]heptalen-2-yl)-4-methyl-5-(trifluoromethyl)pyridin-2-amine |
| 43 | 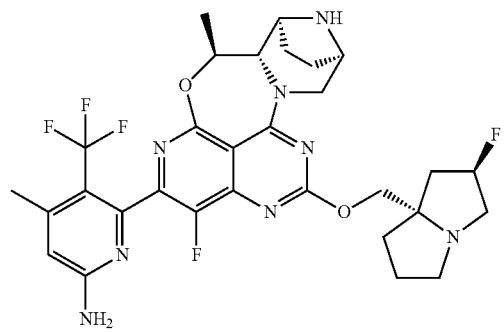 [SMILES: Cc1cc(N)nc(-c2nc3c4c(nc(OC[C@@]56CCCN5C[C@H](F)C6)nc4c2F)N2C[C@H]4CC[C@H](N4)[C@H]2[C@H](C)O3)c1C(F)(F)F] |
| | 6-((5S,5aS,6S,9R)-1-Fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-4-methyl-5-(trifluoromethyl)pyridin-2-amine |

TABLE 1-continued

| Cmpd. No. | Chemical Structure |
|---|---|
| 44 | 6-((5aS,6S,9R)-1-fluoro-12-(((2R,7aS)-2-fluorotetrahydro-1H-pyrrolizin-7a(5H)-yl)methoxy)-5a,6,7,8,9,10-hexahydro-5H-4-oxa-3,10a,11,13,14-pentaaza-6,9-methanonaphtho[1,8-ab]heptalen-2-yl)-4-methyl-5-(trifluoromethyl)pyridin-2-amine |
| 45 | 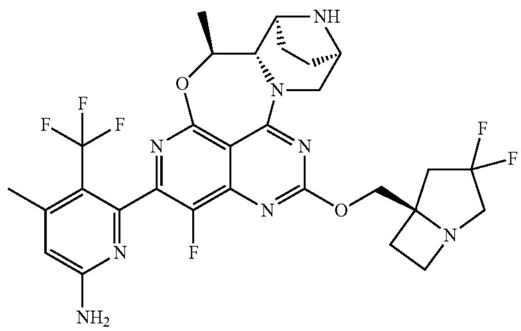 [SMILES: Cc1cc(N)nc(-c2nc3c4c(nc(OC[C@]56CCN5CC(F)(F)C6)nc4c2F)N2C[C@H]4CC[C@H](N4)[C@H]2[C@H](C)O3)c1C(F)(F)F] |
| 46 | 6-((5S,5aS,6S,9R)-12-((3,3-difluoro-1-azabicyclo[3.2.0]heptan-5-yl)methoxy)-1-fluoro-5-methyl-5a,6,7,8,9,10-hexahydro-5H-4-oxa-3,10a,11,13,14-pentaaza-6,9-methanonaphtho[1,8-ab]heptalen-2-yl)-4-methyl-5-(trifluoromethyl)pyridin-2-amine |
| 47 | 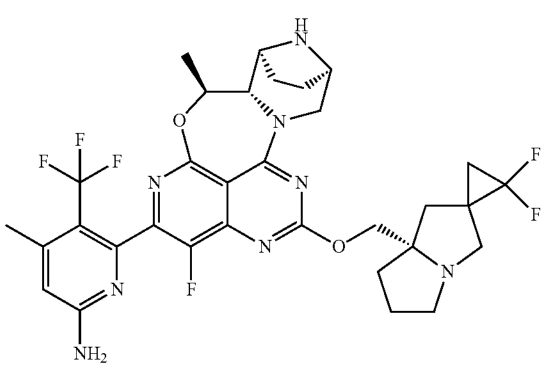 [SMILES: Cc1cc(N)nc(-c2nc3c4c(nc(OC[C@@]56CCCN5CC5(CC5(F)F)C6)nc4c2F)N2C[C@H]4CC[C@H](N4)[C@H]2[C@H](C)O3)c1C(F)(F)F] |

TABLE 1-continued

| Cmpd. No. | Chemical Structure |
|---|---|
| 48 | 6-((5S,5aS,6S,9R)-12-(((7a'S)-2,2-difluorodihydro-1'H,3'H-spiro[cyclopropane-1,2'-pyrrolizin]-7a'(5'H)-yl)methoxy)-1-fluoro-5-methyl-5a,6,7,8,9,10-hexahydro-5H-4-oxa-3,10a,11,13,14-pentaaza[6,9]methanonaphtho[1,8-ab]heptalen-2-yl)-4-methyl-5-(trifluoromethyl)pyridin-2-amine |
| 49 | 6-((5S,5aS,6S,9R)-1-fluoro-5-methyl-12-(((S)-2-methylenetetrahydro-1H-pyrrolizin-7a(5H)-yl)methoxy)-5a,6,7,8,9,10-hexahydro-5H-4-oxa-3,10a,11,13,14-pentaaza-6,9-methanonaphtho[1,8-ab]heptalen-2-yl)-4-methyl-5-(trifluoromethyl)pyridin-2-amine |

TABLE 1-continued

| Cmpd. No. | Chemical Structure |
|---|---|
| | 5-Fluoro-4-(1-fluoro-12-(((2R,7aS)-2-fluorotetrahydro-1H-pyrrolizin-7a(5H)-yl)methoxy)-8-methyl-5a,6,7,8,9,10-hexahydro-5H-4-oxa-3,10a,11,13-pentaazanaphtho[1,8-ab]heptalen-2-yl)naphthalen-2-ol |
| 50 | 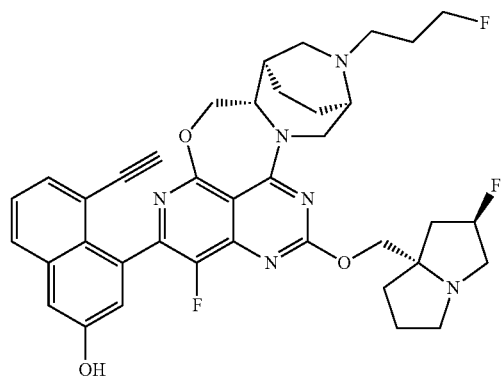 [SMILES: C#Cc1cccc2cc(O)cc(-c3nc4c5c(nc(OC[C@@]67CCCN6C[C@H](F)C7)nc5c3F)N3C[C@H]5CC[C@H](CN5CCCF)[C@H]3CO4)c12]<br>5-Ethynyl-4-((5aS,6R,9R)-1-fluoro-14-(3-fluoropropyl)-12-(((2R,7aS)-2-fluorotetrahydro-1H-pyrrolizin-7a(5H)-yl)methoxy)-5a,6,7,8,9,10-hexahydro-5H-4-oxa-3,10a,11,13,14-pentaaza-6,9-ethanonaphtho[1,8-ab]heptalen-2-yl)naphthalen-2-ol |
| 51 | 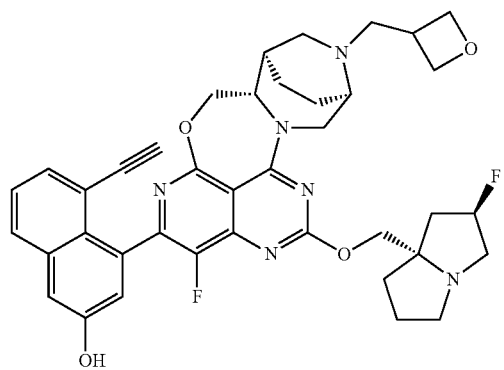 [SMILES: C#Cc1cccc2cc(O)cc(-c3nc4c5c(nc(OC[C@@]67CCCN6C[C@H](F)C7)nc5c3F)N3C[C@H]5CC[C@H](CN5CC5COC5)[C@H]3CO4)c12]<br>5-ethynyl-4-((5aS,6R,9R)-1-fluoro-12-(((2R,7aS)-2-fluorotetrahydro-1H-pyrrolizin-7a(5H)-yl)methoxy)-14-(oxetan-3-ylmethyl)-5a,6,7,8,9,10-hexahydro-5H-4-oxa-3,10a,11,13,14-pentaaza-6,9-ethanonaphtho[1,8-ab]heptalen-2-yl)naphthalen-2-ol |
| 52 | 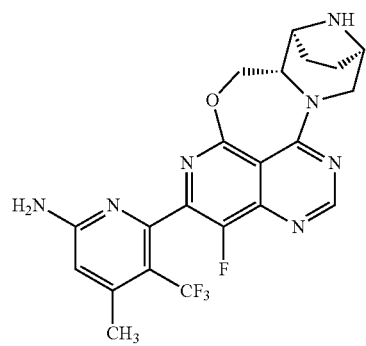 [SMILES: Cc1cc(N)nc(-c2nc3c4c(ncnc4c2F)N2C[C@H]4CC[C@H](N4)[C@H]2CO3)c1C(F)(F)F]<br>6-((5aS,6S,9R)-1-Fluoro-5a,6,7,8,9,10-hexahydro-5H-4-oxa-3,10a,11,13,14-pentaaza-6,9-methanonaphtho[1,8-ab]heptalen-2-yl)-4-methyl-5-(trifluoromethyl)pyridin-2-amine |

TABLE 1-continued

| Cmpd. No. | Chemical Structure |
|---|---|
| 53 | 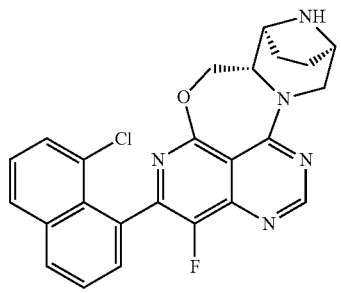 [SMILES: Fc1c(-c2cccc3cccc(Cl)c23)nc2c3c(ncnc13)N1C[C@H]3CC[C@H](N3)[C@H]1CO2]<br>(5aS,6S,9R)-2-(8-Chloronaphthalen-1-yl)-1-fluoro-5a,6,7,8,9,10-hexahydro-5H-4-oxa-3,10a,11,13,14-pentaaza-6,9-methanonaphtho[1,8-ab]heptalene |
| 54 | 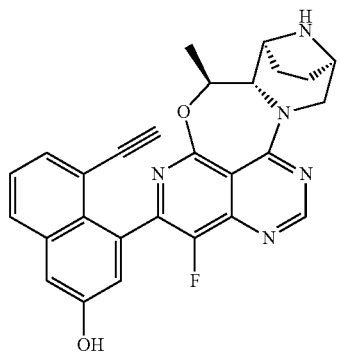 [SMILES: C#Cc1cccc2cc(O)cc(-c3nc4c5c(ncnc5c3F)N3C[C@H]5CC[C@H](N5)[C@H]3[C@H](C)O4)c12]<br>5-Ethynyl-4-((5S,5aS,6S,9R)-1-fluoro-5-methyl-5a,6,7,8,9,10-hexahydro-5H-4-oxa-3,10a,11,13,14-pentaaza-6,9-methanonaphtho[1,8-ab]heptalen-2-yl)naphthalen-2-ol |
| 55 | 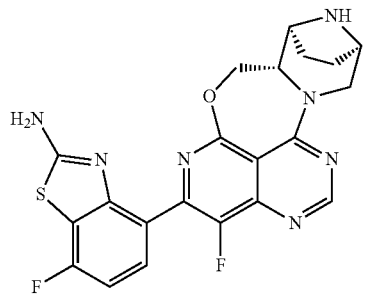 [SMILES: Nc1nc2c(-c3nc4c5c(ncnc5c3F)N3C[C@H]5CC[C@H](N5)[C@H]3CO4)ccc(F)c2s1]<br>7-fluoro-4-((5aS,6S,9R)-1-fluoro-5a,6,7,8,9,10-hexahydro-5H-4-oxa-3,10a,11,13,14-pentaaza-6,9-methanonaphtho[1,8-ab]heptalen-2-yl)benzo[d]thiazol-2-amine |
| 56 | 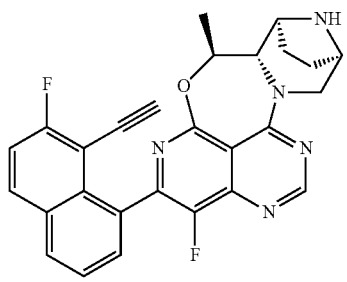 [SMILES: C#Cc1c(F)ccc2cccc(-c3nc4c5c(ncnc5c3F)N3C[C@H]5CC[C@H](N5)[C@H]3[C@H](C)O4)c12]<br>(5S,5aS,6S,9R)-2-(8-ethynyl-7-fluoronaphthalen-1-yl)-1-fluoro-5-methyl-5a,6,7,8,9,10-hexahydro-5H-4-oxa-3,10a,11,13,14-pentaaza-6,9-methanonaphtho[1,8-ab]heptalene |

| Cmpd. No. | Chemical Structure |
|---|---|
| 57 | 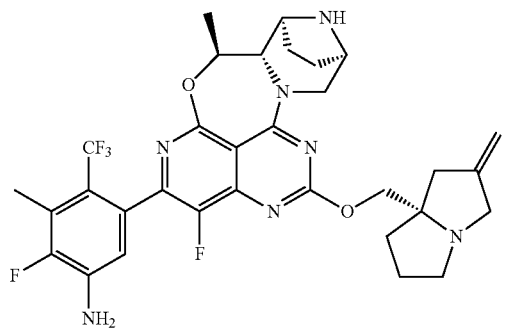 [SMILES: C=C1CN2CCC[C@@]2(COc2nc3c4c(nc(-c5cc(N)c(F)c(C)c5C(F)(F)F)c(F)c4n2)O[C@@H](C)[C@@H]2[C@@H]4CC[C@H](CN32)N4)C1]<br>2-Fluoro-5-(((5S,5aS,6S,9R)-1-fluoro-5-methyl-12-((((S)-2-methylenetetrahydro-1H-pyrrolizin-7a(5H)-yl)methoxy)-5a,6,7,8,9,10-hexahydro-5H-4-oxa-3,10a,11,13,14-pentaaza-6,9-methanonaphtho[1,8-ab]heptalen-2-yl)-3-methyl-4-(trifluoromethyl)aniline |
| 58 | 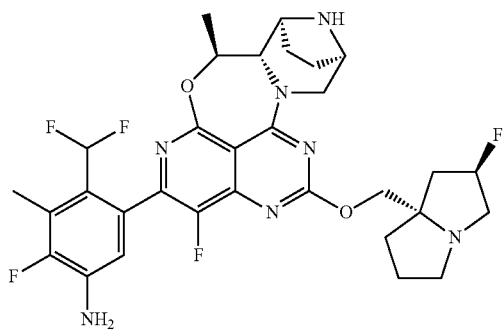 [SMILES: Cc1c(F)c(N)cc(-c2nc3c4c(nc(OC[C@@]56CCCN5C[C@H](F)C6)nc4c2F)N2C[C@H]4CC[C@H](N4)[C@H]2[C@H](C)O3)c1C(F)F]<br>4-(Difluoromethyl)-2-fluoro-5-(((5S,5aS,6S,9R)-1-fluoro-12-((((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-3-methylaniline |
| 59 | 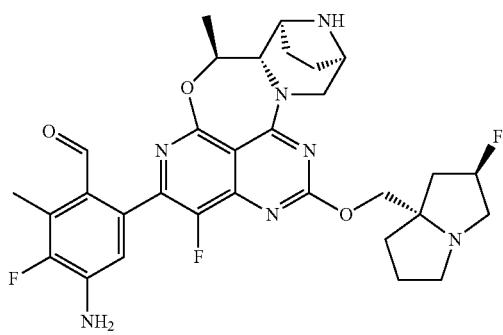 [SMILES: Cc1c(F)c(N)cc(-c2nc3c4c(nc(OC[C@@]56CCCN5C[C@H](F)C6)nc4c2F)N2C[C@H]4CC[C@H](N4)[C@H]2[C@H](C)O3)c1C=O]<br>4-Amino-3-fluoro-6-(((5S,5aS,6S,9R)-1-fluoro-12-((((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-2-methylbenzaldehyde |

TABLE 1-continued

| Cmpd. No. | Chemical Structure |
|---|---|
| 60 | 3-((5S,5aS,6S,9R)-12-(((R)-3,3-Difluoro-1-azabicyclo[3.2.0]heptan-5-yl)methoxy)-1-fluoro-5-methyl-5a,6,7,8,9,10-hexahydro-5H-4-oxa-3,10a,11,13,14-petaaza-6,9-methanonaphtho[1,8-ab]heptalen-2-yl)-5-methyl-4-(trifluoromethyl)aniline |
| 61 | 2-Fluoro-5-((5aS,6S,9R)-1-fluoro-12-(((2R,7aS)-2-fluorotetrahydro-1H-pyrrolizin-7a(5H)-yl)methoxy)-5a,6,7,8,9,10-hexahydro-5H-4-oxa-3,10a,11,13,14-pentaaza-6,9-methanonaphtho[1,8-ab]heptalen-2-yl)-3-methyl-4-(trifluoromethyl)aniline |
| 62 | 5-((5S,5aS,6S,9R)-12-(((7a'S)-2,2-Difluorodihydro-1'H,3'H-spiro[cyclopropane-1,2'-pyrrolizin]-7a'(5'H)-yl)methoxy)-1-fluoro-5-methyl-5a,6,7,8,9,10-hexahydro-5H-4-oxa-3,10a,11,13,14-pentaaza[6,9]methanonaphtho[1,8-ab]heptalen-2-yl)-2-fluoro-3-methyl-4-(trifluoromethyl)aniline |

TABLE 1-continued

| Cmpd. No. | Chemical Structure |
|---|---|
| 64 | 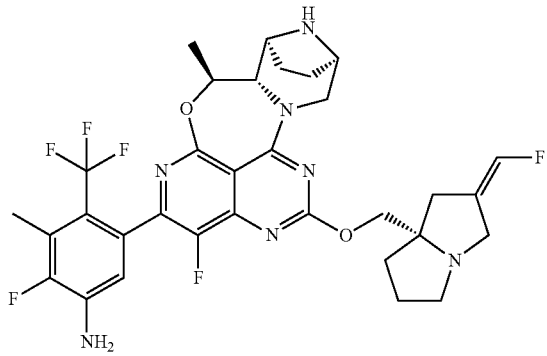 [SMILES: Cc1c(F)c(N)cc(-c2nc3c4c(nc(OC[C@@]56CCCN5C/C(=C\F)C6)nc4c2F)N2C[C@H]4CC[C@H](N4)[C@H]2[C@H](C)O3)c1C(F)(F)F]  2-fluoro-5-(((5S,5aS,6S,9R)-1-fluoro-12-((((S,Z)-2-(fluoromethylene)tetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-3-methyl-4-(trifluoromethyl)aniline |
| 65 | 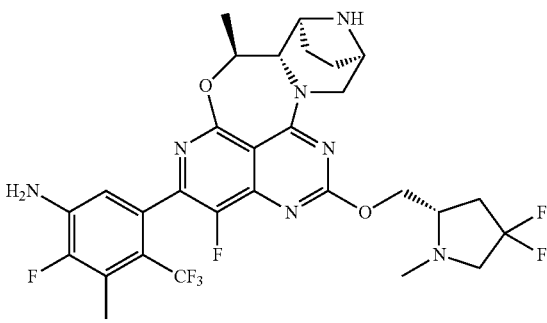 [SMILES: Cc1c(F)c(N)cc(-c2nc3c4c(nc(OC[C@@H]5CC(F)(F)CN5C)nc4c2F)N2C[C@H]4CC[C@H](N4)[C@H]2[C@H](C)O3)c1C(F)(F)F]  5-((5S,5aS,6S,9R)-12-(((S)-4,4-Difluoro-1-methylpyrrolidin-2-yl)methoxy)-1-fluoro-5-methyl-5a,6,7,8,9,10-hexahydro-5H-4-oxa-3,10a,11,13,14-pentaaza-6,9-methanonaphtho[1,8-ab]heptalen-2-yl)-2-fluoro-3-methyl-4-(trifluoromethyl)aniline |
| 66 | 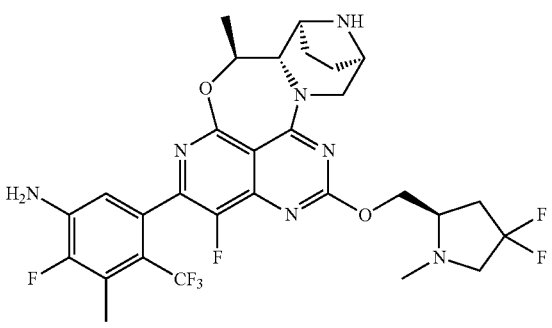 [SMILES: Cc1c(F)c(N)cc(-c2nc3c4c(nc(OC[C@H]5CC(F)(F)CN5C)nc4c2F)N2C[C@H]4CC[C@H](N4)[C@H]2[C@H](C)O3)c1C(F)(F)F]  5-((5S,5aS,6S,9R)-12-(((R)-4,4-difluoro-1-methylpyrrolidin-2-yl)methoxy)-1-fluoro-5-methyl-5a,6,7,8,9,10-hexahydro-5H-4-oxa-3,10a,11,13,14-pentaaza-6,9-methanonaphtho[1,8-ab]heptalen-2-yl)-2-fluoro-3-methyl-4-(trifluoromethyl)aniline |

TABLE 1-continued

| Cmpd. No. | Chemical Structure |
|---|---|
| 67 | 3-((5S,5aS,6S,9R)-1-Fuoro-1-(((6S,8aS)-hexahydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-5-methyl-4-(trifluoromethyl)aniline |
| 68 | 3-((5S,5aS,6S,9R)-12-(((7a'S)-2,2-Difluorodihydro-1'H,3'H-spiro[cyclopropane-1,2'-pyrrolizin]-7a'(5'H)-yl)methoxy)-1-fluoro-5-methyl-5a,6,7,8,9,10-hexahydro-5H-4-oxa-3,10a,11,13,14-pentaaza[6,9]methanonaphtho[1,8-ab]heptalen-2-yl)-5-methyl-4-(trifluoromethyl)aniline |
| 69 | 3-((5S,5aS,6S,9R)-12-(((R)-2,2-Difluorotetrahydro-1H-pyrrolizin-7a(5H)-yl)methoxy)-1-fluoro-5-methyl-5a,6,7,8,9,10-hexahydro-5H-4-oxa-3,10a,11,13,14-pentaaza-6,9-methanonaphtho[1,8-ab]heptalen-2-yl)-5-methyl-4-(trifluoromethyl)aniline |

TABLE 1-continued

| Cmpd. No. | Chemical Structure |
|---|---|
| 70 | 2-Fluoro-5-(((5S,5aS,6S,9R)-1-fluoro-12-((((6S,8aS)-hexahydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-4-(trifluoromethyl)aniline |
| 71 | 5-((5S,5aS,6S,9R)-12-(((R)-3,3-Difluoro-1-azabicyclo[3.2.0]heptan-5-yl)methoxy)-1-fluoro-5-methyl-5a,6,7,8,9,10-hexahydro-5H-4-oxa-3,10a,11,13,14-pentaaza-6,9-methanonaphtho[1,8-ab]heptalen-2-yl)-2-fluoro-4-(trifluoromethyl)aniline |
| 72 | 3-((5S,5aS,6S,9R)-1-Fluoro-12-((((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-4-(trifluoromethyl)aniline |
| 73 | 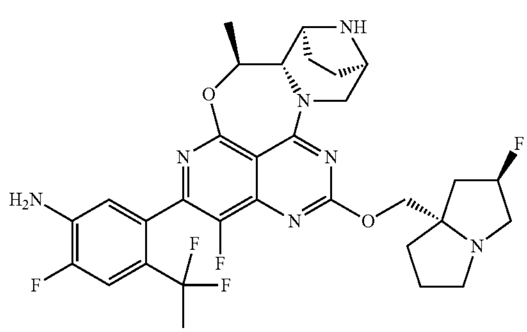 [SMILES: C[C@@H]1Oc2nc(-c3cc(N)c(F)cc3C(C)(F)F)c(F)c3nc(OC[C@@]45CCCN4C[C@H](F)C5)nc(c23)N2C[C@H]3CC[C@H](N3)[C@@H]12] |

TABLE 1-continued

| Cmpd. No. | Chemical Structure |
|---|---|
| | 4-(1,1-difluoroethyl)-2-fluoro-5-((5S,5aS,6S,9R)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)aniline |
| 74 | 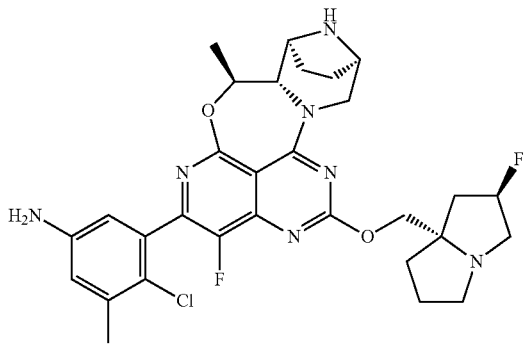 [SMILES: Cc1cc(N)cc(-c2nc3c4c(nc(OC[C@@]56CCCN5C[C@H](F)C6)nc4c2F)N2C[C@H]4CC[C@H](N4)[C@H]2[C@H](C)O3)c1Cl] |
| | 4-Chloro-3-((5S,5aS,6S,9R)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-5-methylaniline |
| 75 | 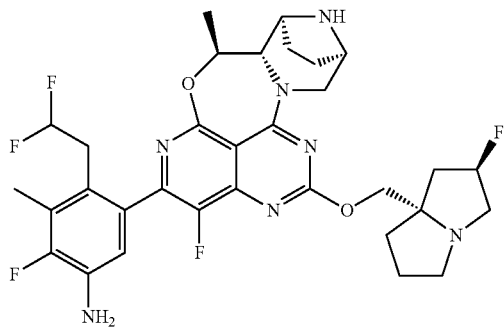 [SMILES: Cc1c(F)c(N)cc(-c2nc3c4c(nc(OC[C@@]56CCCN5C[C@H](F)C6)nc4c2F)N2C[C@H]4CC[C@H](N4)[C@H]2[C@H](C)O3)c1CC(F)F] |
| | 4-(2,2-Difluoroethyl)-2-fluoro-5-((5S,5aS,6S,9R)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-3-methylaniline |
| 76 | 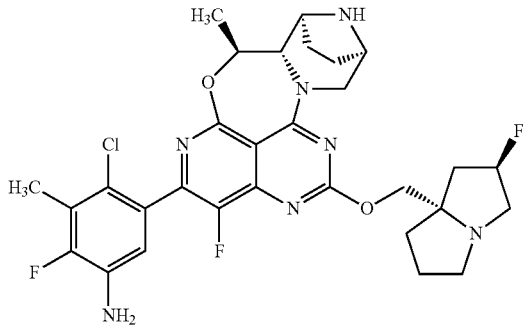 [SMILES: Cc1c(F)c(N)cc(-c2nc3c4c(nc(OC[C@@]56CCCN5C[C@H](F)C6)nc4c2F)N2C[C@H]4CC[C@H](N4)[C@H]2[C@H](C)O3)c1Cl] |
| | 4-Chloro-2-fluoro-5-((5S,5aS,6S,9R)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-3-methylaniline |

TABLE 1-continued

| Cmpd. No. | Chemical Structure |
|---|---|
| 77 | 3-Fluoro-5-((5S,5aS,6S,9R)-1-fluoro-12-((((6S,8aS)-hexahydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-4-(trifluoromethyl)aniline |
| 78 | (5S,5aS,6S,9R)-12-(((R)-3,3-Difluoro-1-azabicyclo[3.2.0]heptan-5-yl)methoxy)-1-fluoro-5-methyl-2-(4-(trifluoromethyl)pyridin-3-yl)-5a,6,7,8,9,10-hexahydro-5H-4-oxa-3,10a,11,13,14-pentaaza-6,9-methanonaphtho[1,8-ab]heptalene |
| 79 | 4-((5S,5aS,6S,9R)-12-(((R)-3,3-Difluoro-1-azabicyclo[3.2.0]heptan-5-yl)methoxy)-1-fluoro-5-methyl-5a,6,7,8,9,10-hexahydro-5H-4-oxa-3,10a,11,13,14-pentaaza-6,9-methanonaphtho[1,8-ab]heptalen-2-yl)quinolin-2-amine |
| 80 | 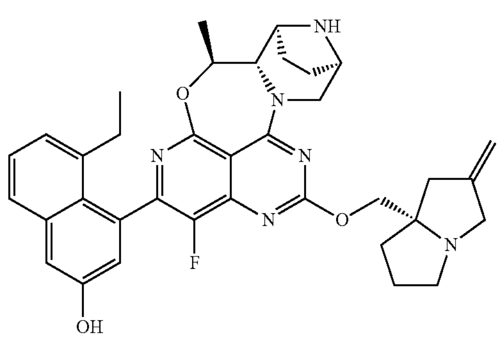 [SMILES: C=C1CN2CCC[C@@]2(COc2nc3c4c(nc(-c5cc(O)cc6cccc(CC)c56)c(F)c4n2)O[C@@H](C)[C@@H]2[C@@H]4CC[C@H](CN32)N4)C1] |

| Cmpd. No. | Chemical Structure |
|---|---|
| | 5-Ethyl-4-((5S,5aS,6S,9R)-1-fluoro-5-methyl-12-(((S)-2-methylenetetrahydro-1H-pyrrolizin-7a(5H)-yl)methoxy)-5a,6,7,8,9,10-hexahydro-5H-4-oxa-3,10a,11,13,14-pentaaza-6,9-methanonaphtho[1,8-ab]heptalen-2-yl)naphthalen-2-ol |
| 81 | 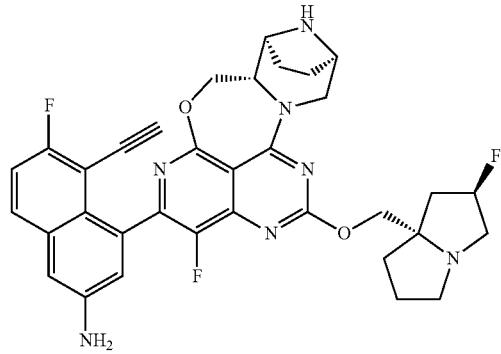 [SMILES: C#Cc1c(F)ccc2cc(N)cc(-c3nc4c5c(nc(OC[C@@]67CCCN6C[C@H](F)C7)nc5c3F)N3C[C@H]5CC[C@H](N5)[C@H]3CO4)c12] |
| | 5-Ethynyl-6-fluoro-4-((5aS,6S,9R)-1-fluoro-12-(((2R,7aS)-2-fluorotetrahydro-1H-pyrrolizin-7a(5H)-yl)methoxy)-5a,6,7,8,9,10-hexahydro-5H-4-oxa-3,10a,11,13,14-pentaaza-6,9-methanonaphtho[1,8-ab]heptalen-2-yl)naphthalen-2-ol |
| 82 | 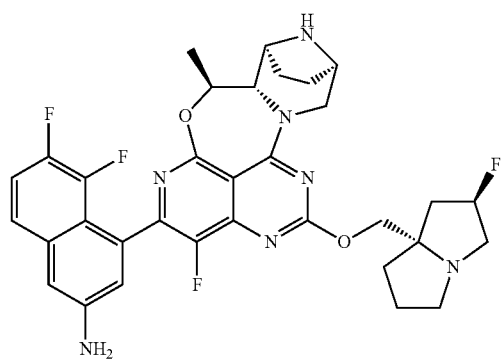 [SMILES: C[C@@H]1Oc2nc(-c3cc(N)cc4ccc(F)c(F)c34)c(F)c3nc(OC[C@@]45CCCN4C[C@H](F)C5)nc(c23)N2C[C@H]3CC[C@H](N3)[C@@H]12] |
| | 5,6-Difluoro-4-((5S,5aS,6S,9R)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)naphthalen-2-ol |
| 83 | 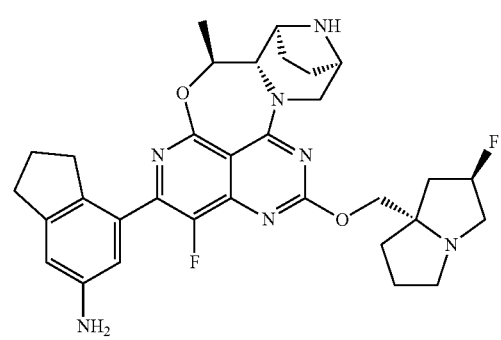 [SMILES: C[C@@H]1Oc2nc(-c3cc(N)cc4c3CCC4)c(F)c3nc(OC[C@@]45CCCN4C[C@H](F)C5)nc(c23)N2C[C@H]3CC[C@H](N3)[C@@H]12] |
| | 7-((5S,5aS,6S,9R)-1-Fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-2,3-dihydro-1H-inden-5-amine |

TABLE 1-continued

| Cmpd. No. | Chemical Structure |
|---|---|
| 84 | 3-Fluoro-6-((5S,5aS,6S,9R)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-5-(trifluoromethyl)pyridin-2-amine |
| 85 | 6-((5S,5aS,6S,9R)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-5-(trifluoromethyl)pyridin-2-amine |
| 86 | 6-((5S,5aS,6S,9R)-12-(((7a'S)-2,2-difluorodihydro-1'H,3'H-spiro[cyclopropane-1,2'-pyrrolizin]-7a'(5'H)-yl)methoxy)-1-fluoro-5-methyl-5a,6,7,8,9,10-hexahydro-5H-4-oxa-3,10a,11,13,14-pentaaza[6,9]methanonaphtho[1,8-ab]heptalen-2-yl)-3-fluoro-5-(trifluoromethyl)pyridin-2-amine |

TABLE 1-continued

| Cmpd. No. | Chemical Structure |
|---|---|
| 87 | 6-((5S,5aS,6S,9R)-12-(((R)-3,3-Difluoro-1-azabicyclo[3.2.0]heptan-5-yl)methoxy)-1-fluoro-5-methyl-5a,6,7,8,9,10-hexahydro-5H-4-oxa-3,10a,11,13,14-pentaaza-6,9-methanonaphtho[1,8-ab]heptalen-2-yl)-3-fluoro-5-(trifluoromethyl)pyridin-2-amine |
| 88 | (5S,5aS,6S,9R)-12-(((R)-3,3-Difluoro-1-azabicyclo[3.2.0]heptan-5-yl)methoxy)-1-fluoro-5-methyl-2-(4-methyl-3-(trifluoromethyl)pyridin-2-yl)-5a,6,7,8,9,10-hexahydro-5H-4-oxa-3,10a,11,13,14-pentaaza-6,9-methanonaphtho[1,8-ab]heptalene |
| 89 | (5S,5aS,6S,9R)-12-(((R)-3,3-Difluoro-1-azabicyclo[3.2.0]heptan-5-yl)methoxy)-1-fluoro-2-(3-methoxyisoquinolin-1-yl)-5-methyl-5a,6,7,8,9,10-hexahydro-5H-4-oxa-3,10a,11,13,14-pentaaza-6,9-methanonaphtho[1,8-ab]heptalene |
| 90 | 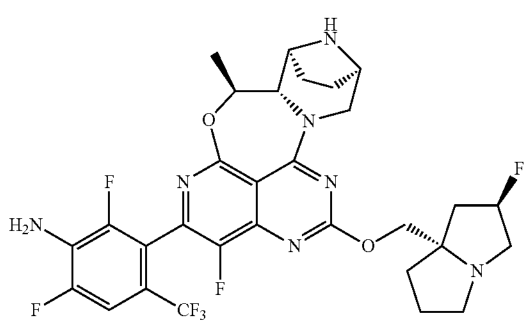 [SMILES: C[C@@H]1Oc2nc(-c3c(C(F)(F)F)cc(F)c(N)c3F)c(F)c3nc(OC[C@@]45CCCN4C[C@H](F)C5)nc(c23)N2C[C@H]3CC[C@H](N3)[C@@H]12] |

TABLE 1-continued

| Cmpd. No. | Chemical Structure |
|---|---|
| 91 | 2,6-Difluoro-3-((5S,5aS,6S,9R)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-4-(trifluoromethyl)aniline |
| 92 | 2,6-Difluoro-3-((5S,5aS,6S,9R)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-5-methyl-4-(trifluoromethyl)aniline |
| 93 | 3-((5S,5aS,6S,9R)-12-(((S)-3,3-Difluoro-1-azabicyclo[3.2.0]heptan-5-yl)methoxy)-1-fluoro-5-methyl-5a,6,7,8,9,10-hexahydro-5H-4-oxa-3,10a,11,13,14-pentaaza-6,9-methanonaphtho[1,8-ab]heptalen-2-yl)-2-fluoro-5-methyl-4-(trifluoromethyl)aniline |

TABLE 1-continued

| Cmpd. No. | Chemical Structure |
|---|---|
| | 3-((5S,5aS,6S,9R)-1-chloro-5-methyl-5a,6,7,8,9,10-hexahydro-5H-4-oxa-3,10a,11,13,14-pentaaza-6,9-methanonaphtho[1,8-ab]heptalen-2-yl)-2-fluoro-5-methyl-4-(trifluoromethyl)aniline (mixture of atropisomers) |
| 94 | 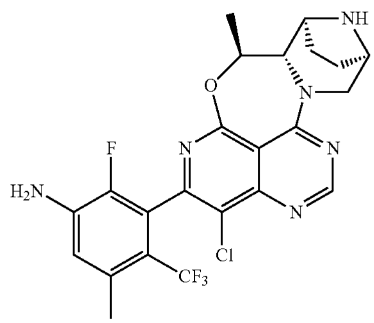 [SMILES: Cc1cc(N)c(F)c(-c2nc3c4c(ncnc4c2Cl)N2C[C@H]4CC[C@H](N4)[C@H]2[C@H](C)O3)c1C(F)(F)F] |
| | 3-((5S,5aS,6S,9R)-1-chloro-5-methyl-5a,6,7,8,9,10-hexahydro-5H-4-oxa-3,10a,11,13,14-pentaaza-6,9-methanonaphtho[1,8-ab]heptalen-2-yl)-2-fluoro-5-methyl-4-(trifluoromethyl)aniline |
| 95 | 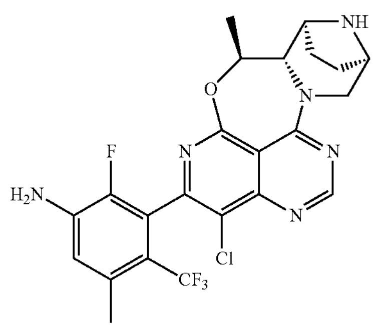 [SMILES: Cc1cc(N)c(F)c(-c2nc3c4c(ncnc4c2Cl)N2C[C@H]4CC[C@H](N4)[C@H]2[C@H](C)O3)c1C(F)(F)F] |
| | 3-((5S,5aS,6S,9R)-1-chloro-5-methyl-5a,6,7,8,9,10-hexahydro-5H-4-oxa-3,10a,11,13,14-pentaaza-6,9-methanonaphtho[1,8-ab]heptalen-2-yl)-2-fluoro-5-methyl-4-(trifluoromethyl)aniline |
| 96 | 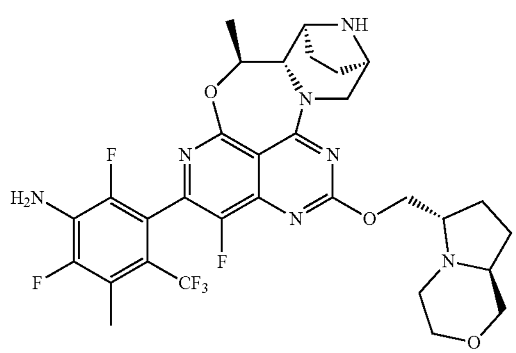 [SMILES: Cc1c(F)c(N)c(F)c(-c2nc3c4c(nc(OC[C@@H]5CC[C@H]6COCCN65)nc4c2F)N2C[C@H]4CC[C@H](N4)[C@H]2[C@H](C)O3)c1C(F)(F)F] |
| | 2,6-difluoro-3-((5S,5aS,6S,9R)-1-fluoro-12-((((6S,8aS)-hexahydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-5-methyl-4-(trifluoromethyl)aniline |

TABLE 1-continued

| Cmpd. No. | Chemical Structure |
|---|---|
| 97 | 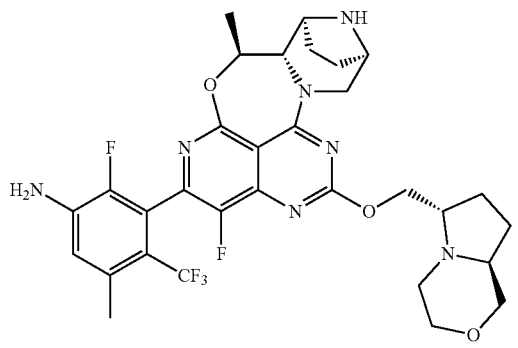 [SMILES: Cc1cc(N)c(F)c(-c2nc3c4c(nc(OC[C@@H]5CC[C@H]6COCCN65)nc4c2F)N2C[C@H]4CC[C@H](N4)[C@H]2[C@H](C)O3)c1C(F)(F)F]<br>2-Fluoro-3-((5S,5aS,6S,9R)-1-fluoro-12-((((6S,8aS)-hexahydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-5-methyl-4-(trifluoromethyl)aniline |
| 98 | 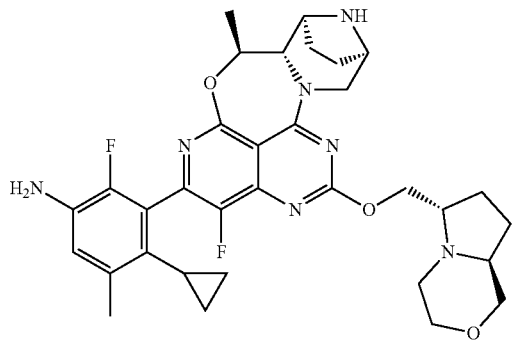 [SMILES: Cc1cc(N)c(F)c(-c2nc3c4c(nc(OC[C@@H]5CC[C@H]6COCCN65)nc4c2F)N2C[C@H]4CC[C@H](N4)[C@H]2[C@H](C)O3)c1C1CC1]<br>4-Cyclopropyl-2-fluoro-3-((5S,5aS,6S,9R)-1-fluoro-12-((((6S,8aS)-hexahydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-5-methylaniline |
| 99 | 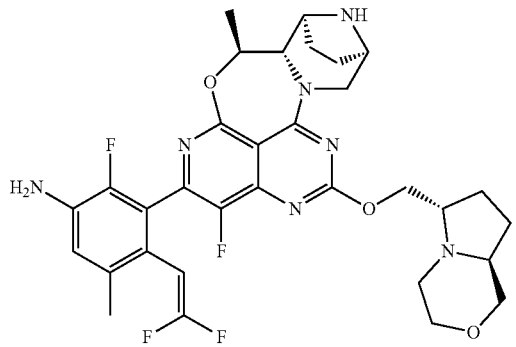 [SMILES: Cc1cc(N)c(F)c(-c2nc3c4c(nc(OC[C@@H]5CC[C@H]6COCCN65)nc4c2F)N2C[C@H]4CC[C@H](N4)[C@H]2[C@H](C)O3)c1C=C(F)F]<br>4-(2,2-Difluorovinyl)-2-fluoro-3-((5S,5aS,6S,9R)-1-fluoro-12-((((6S,8aS)-hexahydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-5-methylaniline |

TABLE 1-continued

| Cmpd. No. | Chemical Structure |
|---|---|
| 100 | 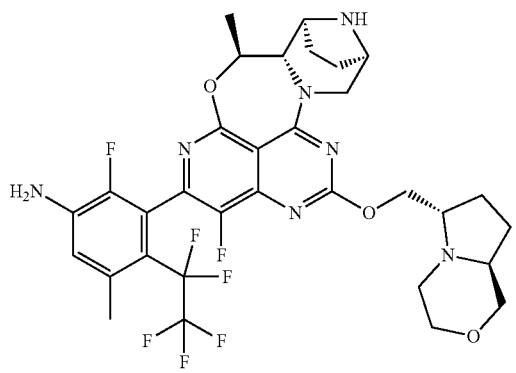 [SMILES: Cc1cc(N)c(F)c(-c2nc3c4c(nc(OC[C@@H]5CC[C@H]6COCCN65)nc4c2F)N2C[C@H]4CC[C@H](N4)[C@H]2[C@H](C)O3)c1C(F)(F)C(F)(F)F]<br>2-Fluoro-3-((5S,5aS,6S,9R)-1-fluoro-12-((((6S,8aS)-hexahydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-5-methyl-4-(perfluoroethyl)aniline |
| 101 | 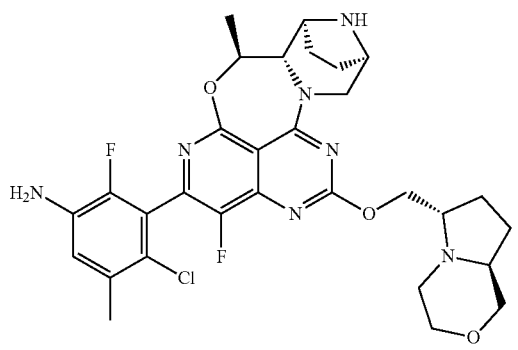 [SMILES: Cc1cc(N)c(F)c(-c2nc3c4c(nc(OC[C@@H]5CC[C@H]6COCCN65)nc4c2F)N2C[C@H]4CC[C@H](N4)[C@H]2[C@H](C)O3)c1Cl]<br>4-Chloro-2-fluoro-3-((5S,5aS,6S,9R)-1-fluoro-12-((((6S,8aS)-hexahydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-5-methylaniline |
| 102 | 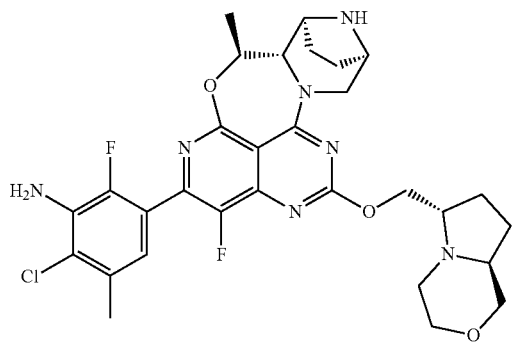 [SMILES: Cc1cc(-c2nc3c4c(nc(OC[C@@H]5CC[C@H]6COCCN65)nc4c2F)N2C[C@H]4CC[C@H](N4)[C@H]2[C@H](C)O3)c(F)c(N)c1Cl]<br>2-Chloro-6-fluoro-5-((5S,5aS,6S,9R)-1-fluoro-12-((((6S,8aS)-hexahydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-3-methylaniline |

TABLE 1-continued

| Cmpd. No. | Chemical Structure |
|---|---|
| 103 | 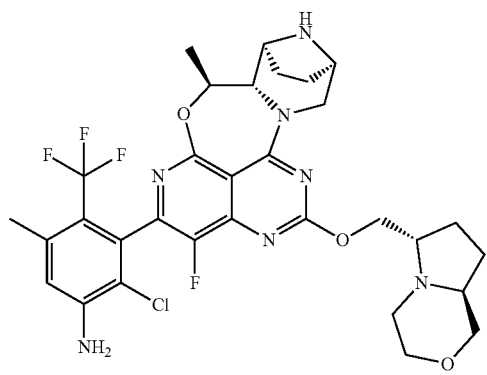 [SMILES: Cc1cc(N)c(Cl)c(-c2nc3c4c(nc(OC[C@@H]5CC[C@H]6COCCN65)nc4c2F)N2C[C@H]4CC[C@H](N4)[C@H]2[C@H](C)O3)c1C(F)(F)F]<br>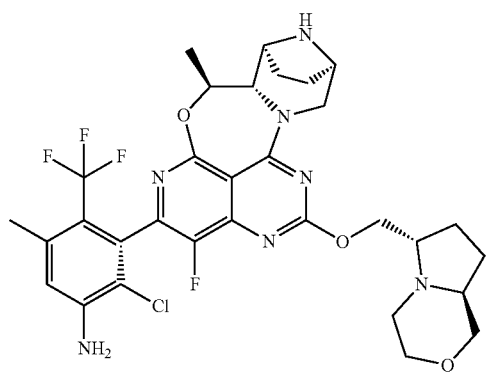<br>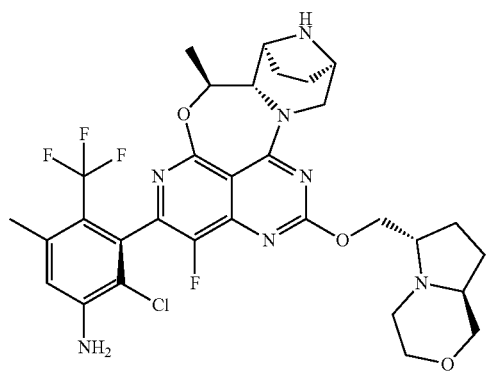<br>2-Chloro-3-((5S,5aS,6S,9R)-1-fluoro-12-(((6S,8aS)-hexahydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-5-methyl-4-(trifluoromethyl)aniline and 2-Chloro-5-((5S,5aS,6S,9R)-1-fluoro-12-(((6S,8aS)-hexahydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-3-methyl-4-(trifluoromethyl)aniline |

TABLE 1-continued

| Cmpd. No. | Chemical Structure |
|---|---|
| 104 | 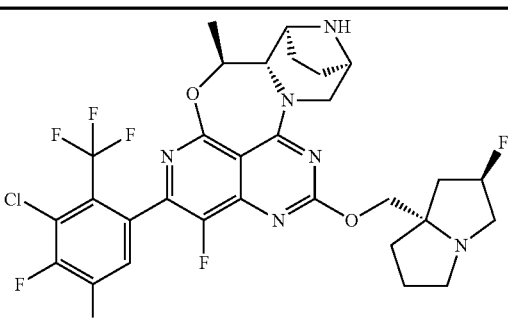<br>3-Chloro-2-fluoro-5-((5S,5aS,6S,9R)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-4-(trifluoromethyl)aniline |
| 105 | 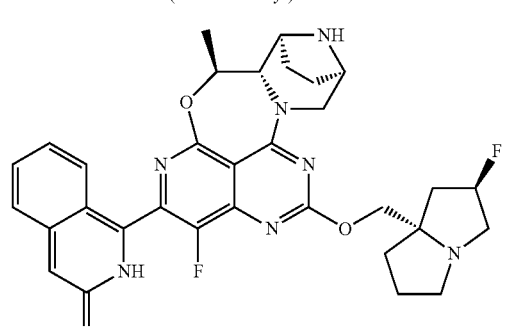<br>1-((5S,5aS,6S,9R)-1-Fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)isoquinolin-3(2H)-one |
| 106 | 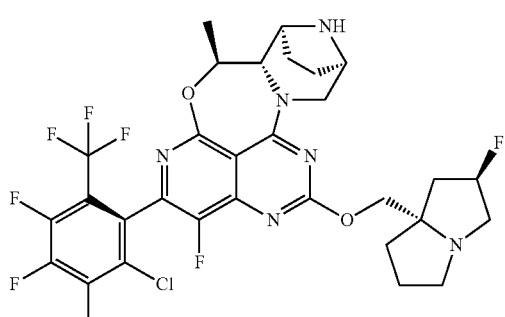<br>2-Chloro-5,6-difluoro-3-((5S,5aS,6S,9R)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa- |

TABLE 1-continued

| Cmpd. No. | Chemical Structure |
|---|---|
| | 3,10a,11,13,14-pentaaza-6,9-methanonaphtho[1,8-ab]heptalen-2-yl)-4-(trifluoromethyl)aniline (two atropisomers) |
| 107 | 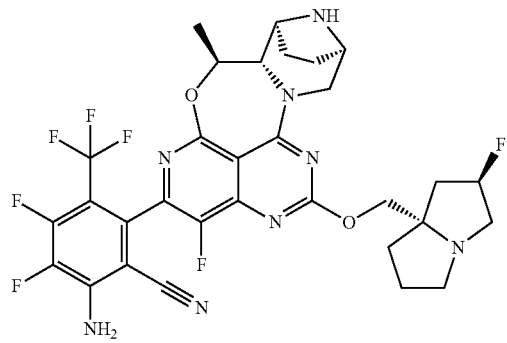 [SMILES: C[C@@H]1Oc2nc(-c3c(C#N)c(N)c(F)c(F)c3C(F)(F)F)c(F)c3nc(OC[C@@]45CCCN4C[C@H](F)C5)nc(c23)N2C[C@H]3CC[C@H](N3)[C@@H]12] |
| | 2-Amino-3,4-difluoro-6-((5S,5aS,6S,9R)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-5-(trifluoromethyl)benzonitrile |
| 108 | 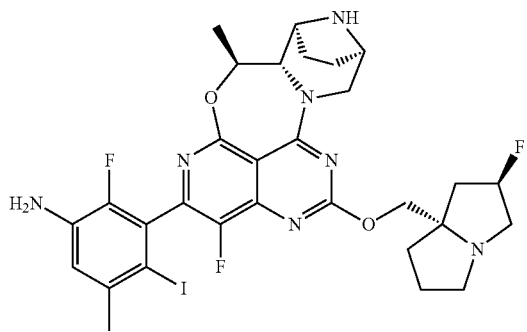 [SMILES: Cc1cc(N)c(F)c(-c2nc3c4c(nc(OC[C@@]56CCCN5C[C@H](F)C6)nc4c2F)N2C[C@H]4CC[C@H](N4)[C@H]2[C@H](C)O3)c1I] |
| | 2-Fluoro-3-((5S,5aS,6S,9R)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-4-iodo-5-methylaniline |
| 110 | 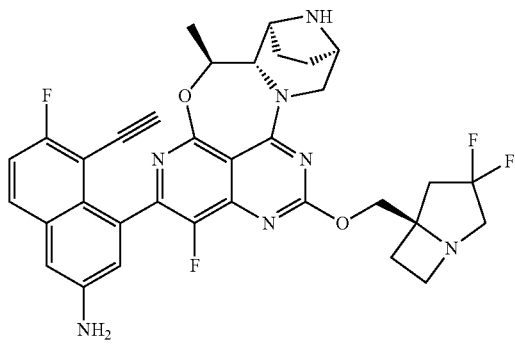 [SMILES: C#Cc1c(F)ccc2cc(N)cc(-c3nc4c5c(nc(OC[C@]67CCN6CC(F)(F)C7)nc5c3F)N3C[C@H]5CC[C@H](N5)[C@H]3[C@H](C)O4)c12] |
| | 4-((5S,5aS,6S,9R)-12-(((R)-3,3-Difluoro-1-azabicyclo[3.2.0]heptan-5-yl)methoxy)-1-fluoro-5-methyl-5a,6,7,8,9,10-hexahydro-5H-4-oxa-3,10a,11,13,14-pentaaza-6,9-methanonaphtho[1,8-ab]heptalen-2-yl)-5-ethynyl-6-fluoronaphthalen-2-amine |

| Cmpd. No. | Chemical Structure |
|---|---|
| 111 | 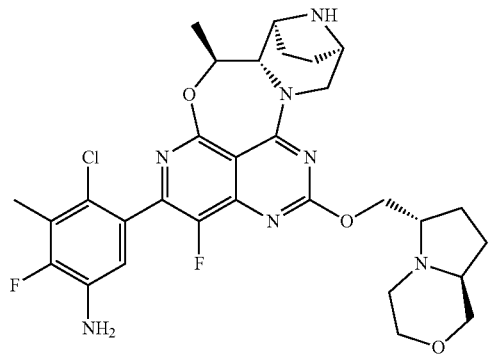 [SMILES: Cc1c(F)c(N)cc(-c2nc3c4c(nc(OC[C@@H]5CC[C@H]6COCCN65)nc4c2F)N2C[C@H]4CC[C@H](N4)[C@H]2[C@H](C)O3)c1Cl]<br>4-Chloro-2-fluoro-5-((5S,5aS,6S,9R)-1-fluoro-12-(((6S,8aS)-hexahydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-3-methylaniline |
| 112 | 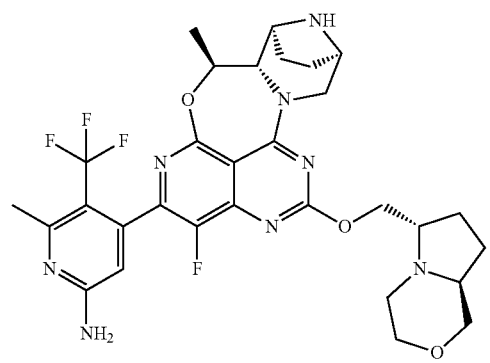 [SMILES: Cc1nc(N)cc(-c2nc3c4c(nc(OC[C@@H]5CC[C@H]6COCCN65)nc4c2F)N2C[C@H]4CC[C@H](N4)[C@H]2[C@H](C)O3)c1C(F)(F)F]<br>4-((5S,5aS,6S,9R)-1-fluoro-12-(((6S,8aS)-hexahydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-6-methyl-5-(trifluoromethyl)pyridin-2-amine |
| 113 | 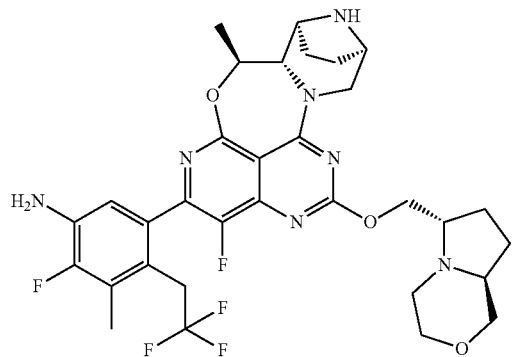 [SMILES: Cc1c(F)c(N)cc(-c2nc3c4c(nc(OC[C@@H]5CC[C@H]6COCCN65)nc4c2F)N2C[C@H]4CC[C@H](N4)[C@H]2[C@H](C)O3)c1CC(F)(F)F]<br>2-fluoro-5-((5S,5aS,6S,9R)-1-fluoro-12-(((6S,8aS)-hexahydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-3-methyl-4-(2,2,2-trifluoroethyl)aniline |

TABLE 1-continued

| Cmpd. No. | Chemical Structure |
| --- | --- |
| 114 | 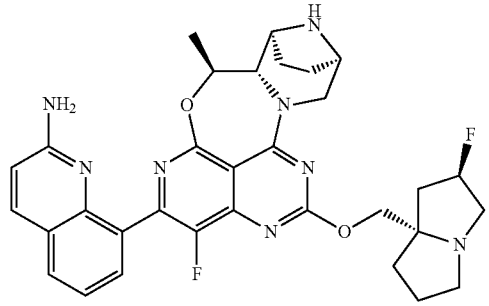 [SMILES: C[C@@H]1Oc2nc(-c3cccc4ccc(N)nc34)c(F)c3nc(OC[C@@]45CCCN4C[C@H](F)C5)nc(c23)N2C[C@H]3CC[C@H](N3)[C@@H]12]
8-((5S,5aS,6S,9R)-1-Fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)quinolin-2-amine |
| 115 | 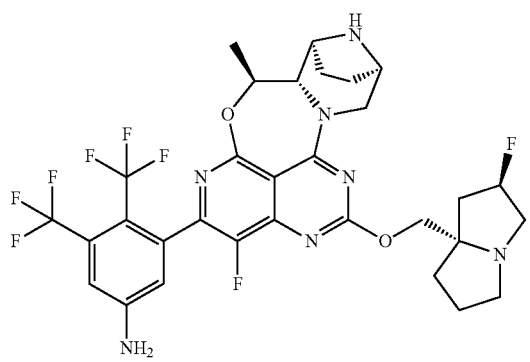 [SMILES: C[C@@H]1Oc2nc(-c3cc(N)cc(C(F)(F)F)c3C(F)(F)F)c(F)c3nc(OC[C@@]45CCCN4C[C@H](F)C5)nc(c23)N2C[C@H]3CC[C@H](N3)[C@@H]12]
3-((5S,5aS,6S,9R)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-4,5-bis(trifluoromethyl)aniline |
| 116 | 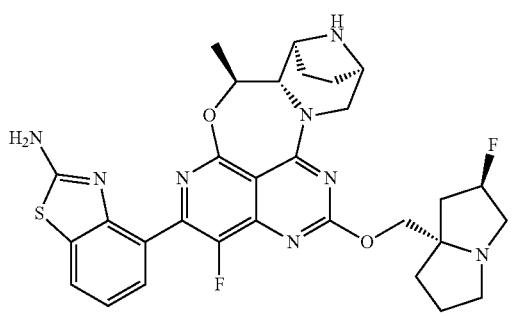 [SMILES: C[C@@H]1Oc2nc(-c3cccc4sc(N)nc34)c(F)c3nc(OC[C@@]45CCCN4C[C@H](F)C5)nc(c23)N2C[C@H]3CC[C@H](N3)[C@@H]12]
4-((5S,5aS,6S,9R)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)benzo[d]thiazol-2-amine |
| 117 | 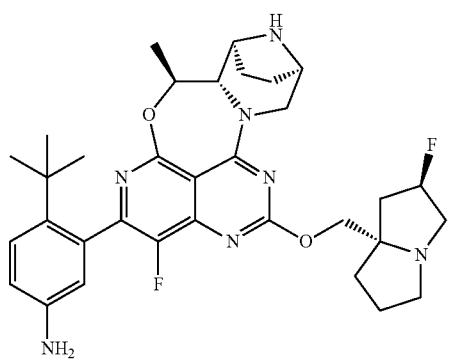 [SMILES: C[C@@H]1Oc2nc(-c3cc(N)ccc3C(C)(C)C)c(F)c3nc(OC[C@@]45CCCN4C[C@H](F)C5)nc(c23)N2C[C@H]3CC[C@H](N3)[C@@H]12] |

TABLE 1-continued

| Cmpd. No. | Chemical Structure |
|---|---|
| | 4-(tert-butyl)-3-((5S,5aS,6S,9R)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)aniline |
| 118 | 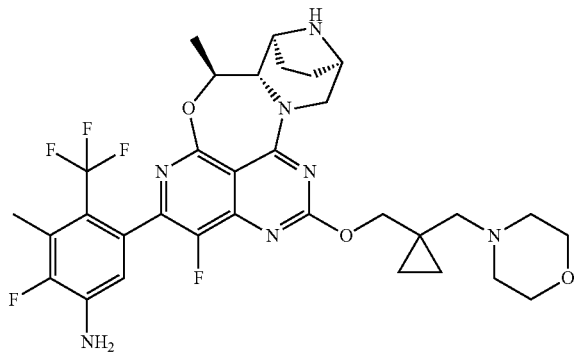 [SMILES: Cc1c(F)c(N)cc(-c2nc3c4c(nc(OCC5(CN6CCOCC6)CC5)nc4c2F)N2C[C@H]4CC[C@H](N4)[C@H]2[C@H](C)O3)c1C(F)(F)F] |
| | 2-Fluoro-5-((5S,5aS,6S,9R)-1-fluoro-5-methyl-12-((1-(morpholinomethyl)cyclopropyl)methoxy)-5a,6,7,8,9,10-hexahydro-5H-4-oxa-3,10a,11,13,14-pentaaza-6,9-methanonaphtho[1,8-ab]heptalen-2-yl)-3-methyl-4-(trifluoromethyl)aniline |
| 119 | 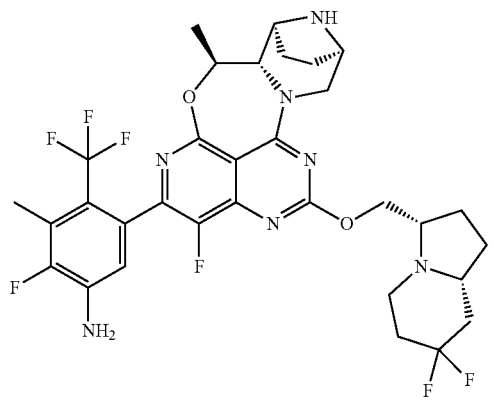 [SMILES: Cc1c(F)c(N)cc(-c2nc3c4c(nc(OC[C@@H]5CC[C@@H]6CC(F)(F)CCN65)nc4c2F)N2C[C@H]4CC[C@H](N4)[C@H]2[C@H](C)O3)c1C(F)(F)F]<br>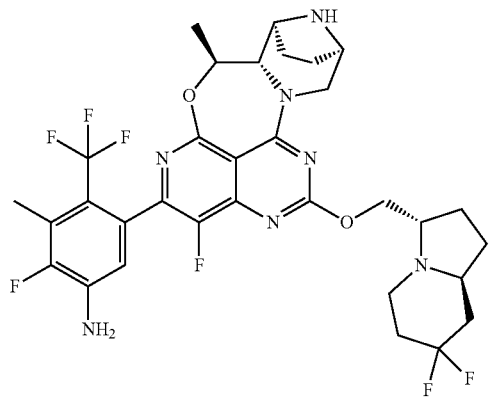 [SMILES: Cc1c(F)c(N)cc(-c2nc3c4c(nc(OC[C@@H]5CC[C@H]6CC(F)(F)CCN56)nc4c2F)N2C[C@H]4CC[C@H](N4)[C@H]2[C@H](C)O3)c1C(F)(F)F] |
| | 5-((5S,5aS,6S,9R)-12-(((3S)-7,7-difluorooctahydroindolizin-3-yl)methoxy)-1-fluoro-5-methyl-5a,6,7,8,9,10-hexahydro-5H-4-oxa-3,10a,11,13,14-pentaaza-6,9-methanonaphtho[1,8-ab]heptalen-2-yl)-2-fluoro-3-methyl-4-(trifluoromethyl)aniline (two isomers) |

TABLE 1-continued

| Cmpd. No. | Chemical Structure |
|---|---|
| 120 | 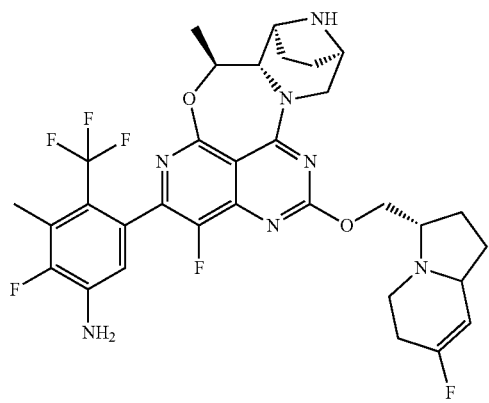 [SMILES: Cc1c(F)c(N)cc(-c2nc3c4c(nc(OC[C@@H]5CCC6C=C(F)CCN65)nc4c2F)N2C[C@H]4CC[C@H](N4)[C@H]2[C@H](C)O3)c1C(F)(F)F]<br>2-fluoro-5-(((5S,5aS,6S,9R)-1-fluoro-12-(((3S)-7-fluoro-1,2,3,5,6,8a-hexahydroindolizin-3-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-3-methyl-4-(trifluoromethyl)aniline |
| 121 | 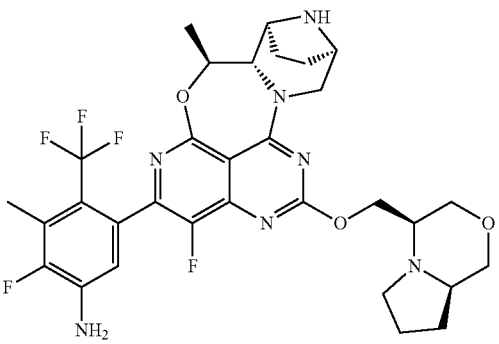 [SMILES: Cc1c(F)c(N)cc(-c2nc3c4c(nc(OC[C@H]5COC[C@H]6CCCN65)nc4c2F)N2C[C@H]4CC[C@H](N4)[C@H]2[C@H](C)O3)c1C(F)(F)F]<br>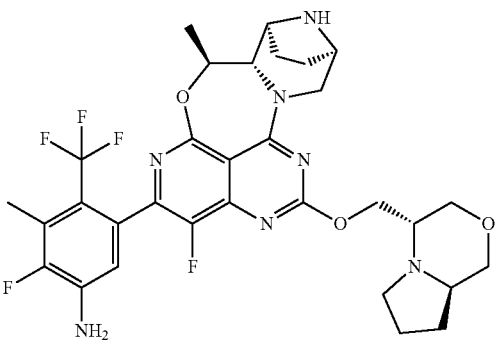 [SMILES: Cc1c(F)c(N)cc(-c2nc3c4c(nc(OC[C@@H]5COC[C@H]6CCCN65)nc4c2F)N2C[C@H]4CC[C@H](N4)[C@H]2[C@H](C)O3)c1C(F)(F)F]<br>2-fluoro-5-(((5S,5aS,6S,9R)-1-fluoro-12-(((8aR)-hexahydro-1H-pyrrolo[2,1-c][1,4]oxazin-4-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-3-methyl-4-(trifluoromethyl)aniline (two isomers) |

TABLE 1-continued

| Cmpd. No. | Chemical Structure |
|---|---|
| 122 | 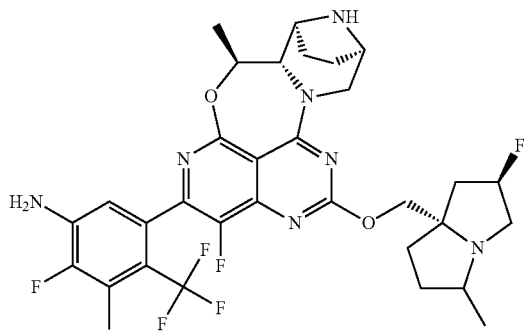 [SMILES: Cc1c(F)c(N)cc(-c2nc3c4c(nc(OC[C@@]56CCC(C)N5C[C@H](F)C6)nc4c2F)N2C[C@H]4CC[C@H](N4)[C@H]2[C@H](C)O3)c1C(F)(F)F]<br>2-fluoro-5-(((5S,5aS,6S,9R)-1-fluoro-12-(((2R,7aS)-2-fluoro-5-methyltetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-3-methyl-4-(trifluoromethyl)aniline |
| 123 | 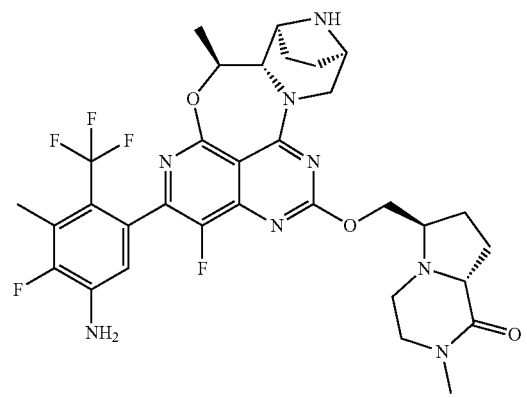 [SMILES: Cc1c(F)c(N)cc(-c2nc3c4c(nc(OC[C@H]5CC[C@@H]6C(=O)N(C)CCN56)nc4c2F)N2C[C@H]4CC[C@H](N4)[C@H]2[C@H](C)O3)c1C(F)(F)F]<br>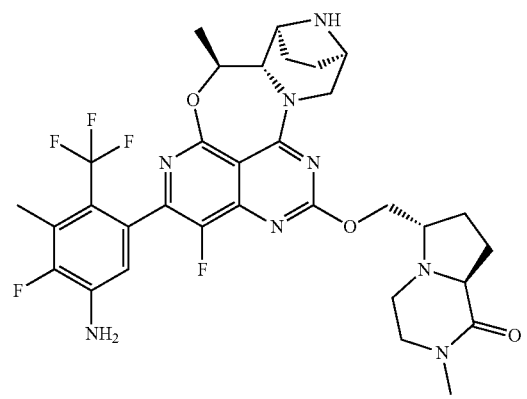 [SMILES: Cc1c(F)c(N)cc(-c2nc3c4c(nc(OC[C@@H]5CC[C@H]6C(=O)N(C)CCN56)nc4c2F)N2C[C@H]4CC[C@H](N4)[C@H]2[C@H](C)O3)c1C(F)(F)F]<br>6-(((((5S,5aS,6S,9R)-2-(5-Amino-4-fluoro-3-methyl-2-(trifluoromethyl)phenyl)-1-fluoro-5-methyl-5a,6,7,8,9,10-hexahydro-5H-4-oxa-3,10a,11,13,14-pentaaza-6,9-methanonaphtho[1,8-ab]heptalen-12-yl)oxy)methyl)-2-methylhexahydropyrrolo[1,2-a]pyrazin-1(2H)-one |

TABLE 1-continued
| Cmpd. No. | Chemical Structure |
|---|---|
| 124 | 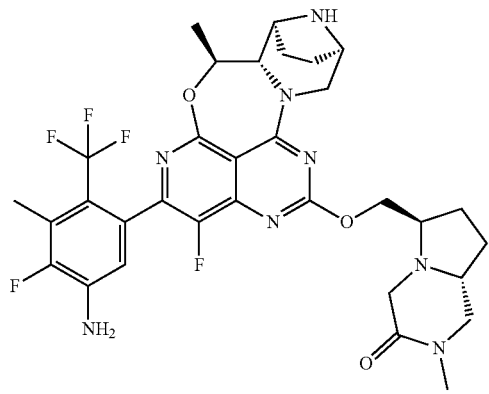 [SMILES: Cc1c(F)c(N)cc(-c2nc3c4c(nc(OC[C@H]5CC[C@@H]6CN(C)C(=O)CN56)nc4c2F)N2C[C@H]4CC[C@H](N4)[C@H]2[C@H](C)O3)c1C(F)(F)F] |
| | 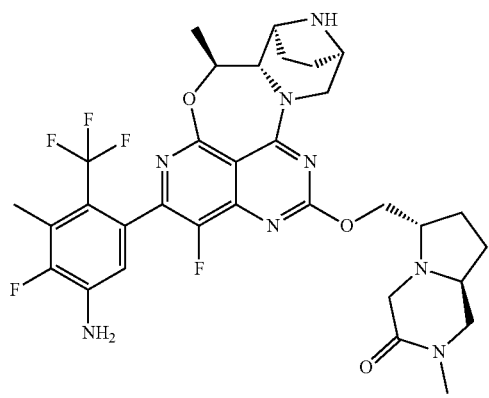 [SMILES: Cc1c(F)c(N)cc(-c2nc3c4c(nc(OC[C@@H]5CC[C@H]6CN(C)C(=O)CN56)nc4c2F)N2C[C@H]4CC[C@H](N4)[C@H]2[C@H](C)O3)c1C(F)(F)F]<br>6-((((5S,5aS,6S,9R)-2-(5-Amino-4-fluoro-3-methyl-2-(trifluoromethyl)phenyl)-1-fluoro-5-methyl-5a,6,7,8,9,10-hexahydro-5H-4-oxa-3,10a,11,13,14-pentaaza-6,9-methanonaphtho[1,8-ab]heptalen-12-yl)oxy)methyl)-2-methylhexahydropyrrolo[1,2-a]pyrazin-3(4H)-one |
| 125 | 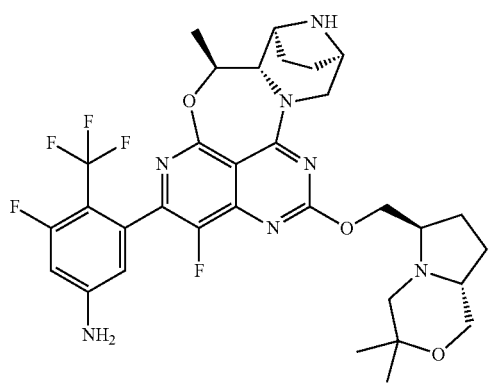 [SMILES: C[C@@H]1Oc2nc(-c3cc(N)cc(F)c3C(F)(F)F)c(F)c3nc(OC[C@H]4CC[C@@H]5COC(C)(C)CN45)nc(c23)N2C[C@H]3CC[C@H](N3)[C@@H]12] |

TABLE 1-continued
| Cmpd. No. | Chemical Structure |
|---|---|
| | 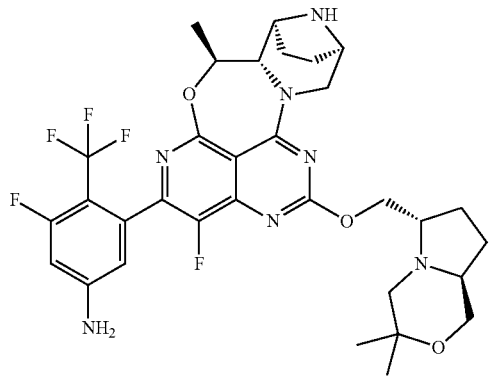 [SMILES: C[C@@H]1Oc2nc(-c3cc(N)cc(F)c3C(F)(F)F)c(F)c3nc(OC[C@@H]4CC[C@H]5COC(C)(C)CN45)nc(c23)N2C[C@H]3CC[C@H](N3)[C@@H]12]<br>3-((5S,5aS,6S,9R)-12-((3,3-dimethylhexahydro-1H-pyrrolo[2,1-c][1,4]oxazin-6-yl)methoxy)-1-fluoro-5-methyl-5a,6,7,8,9,10-hexahydro-5H-4-oxa-3,10a,11,13,14-pentaaza-6,9-methanonaphtho[1,8-ab]heptalen-2-yl)-5-fluoro-4-(trifluoromethyl)aniline |
| 126 | 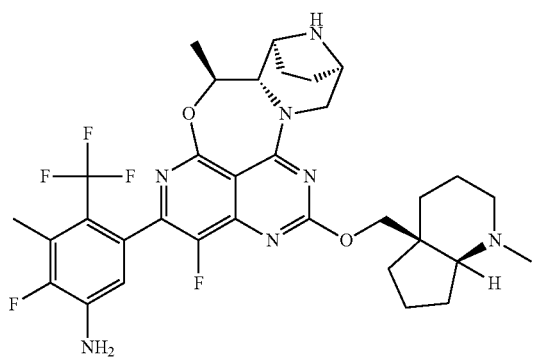 |
| | 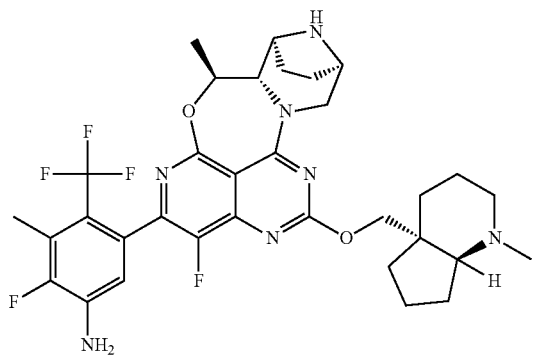 |
| | 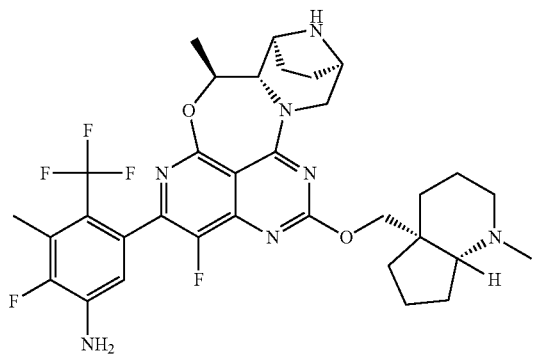 |

TABLE 1-continued

| Cmpd. No. | Chemical Structure |
|---|---|
| | 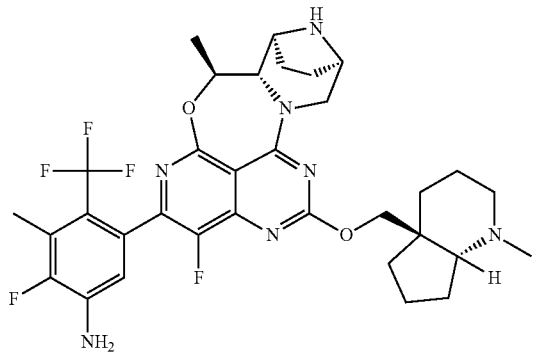
2-Fluoro-5-((5S,5aS,6S,9R)-1-fluoro-5-methyl-12-((1-methyloctahydro-4aH-cyclopenta[b]pyridin-4a-yl)methoxy)-5a,6,7,8,9,10-hexahydro-5H-4-oxa-3,10a,11,13,14-pentaaza-6,9-methanonaphtho[1,8-ab]heptalen-2-yl)-3-methyl-4-(trifluoromethyl)aniline (four isomers) |
| 127 | 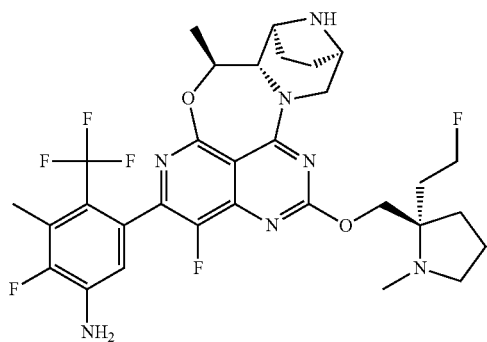 [SMILES: Cc1c(F)c(N)cc(-c2nc3c4c(nc(OC[C@@]5(CCF)CCCN5C)nc4c2F)N2C[C@H]4CC[C@H](N4)[C@H]2[C@H](C)O3)c1C(F)(F)F]

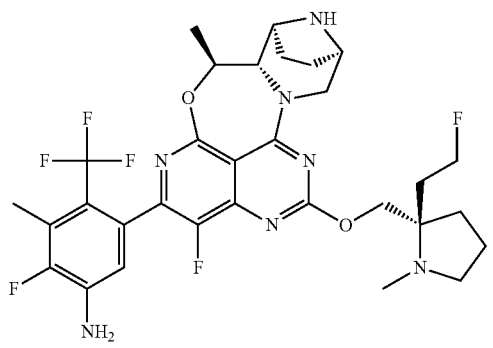 [SMILES: Cc1c(F)c(N)cc(-c2nc3c4c(nc(OC[C@]5(CCF)CCCN5C)nc4c2F)N2C[C@H]4CC[C@H](N4)[C@H]2[C@H](C)O3)c1C(F)(F)F]
2-fluoro-5-((5S,5aS,6S,9R)-1-fluoro-12-((2-(2-fluoroethyl)-1-methylpyrrolidin-2-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-3-methyl-4-(trifluoromethyl)aniline (two isomers) |

TABLE 1-continued

| Cmpd. No. | Chemical Structure |
|---|---|
| 128 | 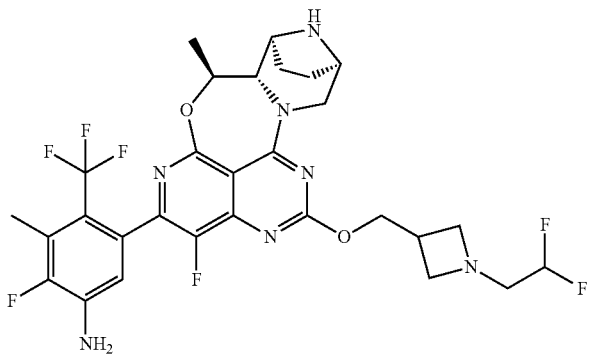 [SMILES: Cc1c(F)c(N)cc(-c2nc3c4c(nc(OCC5CN(CC(F)F)C5)nc4c2F)N2C[C@H]4CC[C@H](N4)[C@H]2[C@H](C)O3)c1C(F)(F)F] 5-((5S,5aS,6S,9R)-12-((1-(2,2-Difluoroethyl)azetidin-3-yl)methoxy)-1-fluoro-5-methyl-5a,6,7,8,9,10-hexahydro-5H-4-oxa-3,10a,11,13,14-pentaaza-6,9-methanonaphtho[1,8-ab]heptalen-2-yl)-2-fluoro-3-methyl-4-(trifluoromethyl)aniline |
| 129 | 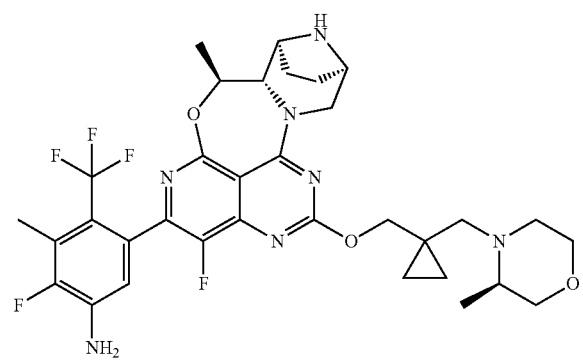 [SMILES: Cc1c(F)c(N)cc(-c2nc3c4c(nc(OCC5(CN6CCOC[C@H]6C)CC5)nc4c2F)N2C[C@H]4CC[C@H](N4)[C@H]2[C@H](C)O3)c1C(F)(F)F] 2-Fluoro-5-((5S,5aS,6S,9R)-1-fluoro-5-methyl-12-((1-(((R)-3-methylmorpholino)methyl)cyclopropyl)methoxy)-5a,6,7,8,9,10-hexahydro-5H-4-oxa-3,10a,11,13,14-pentaaza-6,9-methanonaphtho[1,8-ab]heptalen-2-yl)-3-methyl-4-(trifluoromethyl)aniline |
| 130 | 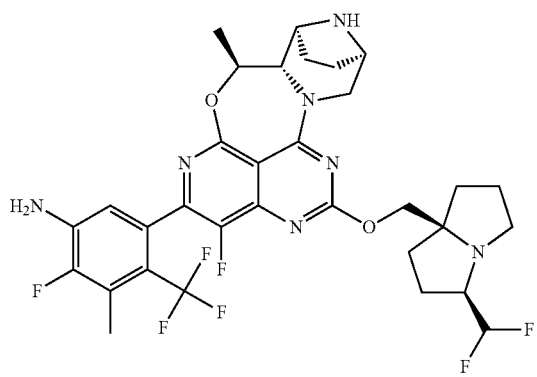 [SMILES: Cc1c(F)c(N)cc(-c2nc3c4c(nc(OC[C@@]56CCCN5[C@@H](C(F)F)CC6)nc4c2F)N2C[C@H]4CC[C@H](N4)[C@H]2[C@H](C)O3)c1C(F)(F)F] |

TABLE 1-continued
| Cmpd. No. | Chemical Structure |
|---|---|
| | 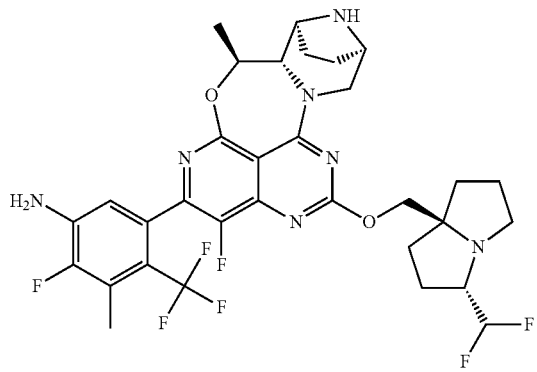 [SMILES: Cc1c(F)c(N)cc(-c2nc3c4c(nc(OC[C@@]56CCCN5[C@H](C(F)F)CC6)nc4c2F)N2C[C@H]4CC[C@H](N4)[C@H]2[C@H](C)O3)c1C(F)(F)F] |
| | 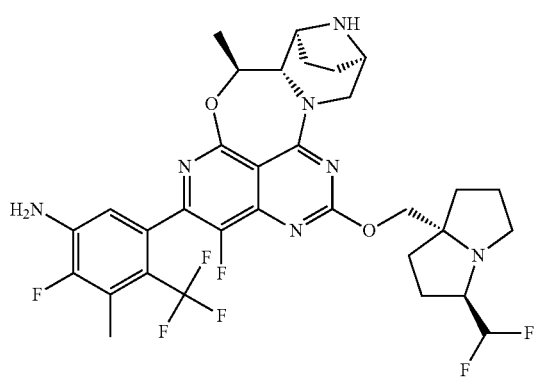 [SMILES: Cc1c(F)c(N)cc(-c2nc3c4c(nc(OC[C@]56CCCN5[C@@H](C(F)F)CC6)nc4c2F)N2C[C@H]4CC[C@H](N4)[C@H]2[C@H](C)O3)c1C(F)(F)F] |
| | 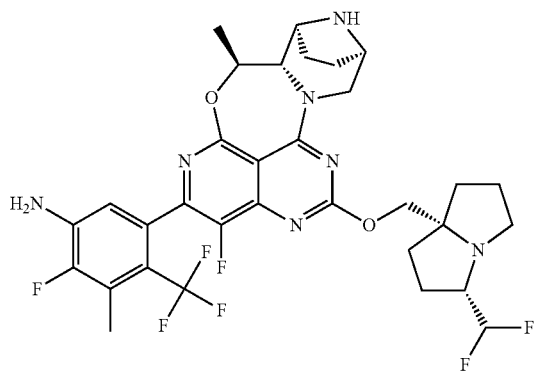 [SMILES: Cc1c(F)c(N)cc(-c2nc3c4c(nc(OC[C@]56CCCN5[C@H](C(F)F)CC6)nc4c2F)N2C[C@H]4CC[C@H](N4)[C@H]2[C@H](C)O3)c1C(F)(F)F]<br>5-((5S,5aS,6S,9R)-12-((3-(Difluoromethyl)tetrahydro-1H-pyrrolizin-7a(5H)-yl)methoxy)-1-fluoro-5-methyl-5a,6,7,8,9,10-hexahydro-5H-4-oxa-3,10a,11,13,14-pentaaza-6,9-methanonaphtho[1,8-ab]heptalen-2-yl)-2-fluoro-3-methyl-4-(trifluoromethyl)aniline (two isomers) |

TABLE 1-continued

| Cmpd. No. | Chemical Structure |
|---|---|
| 131 | 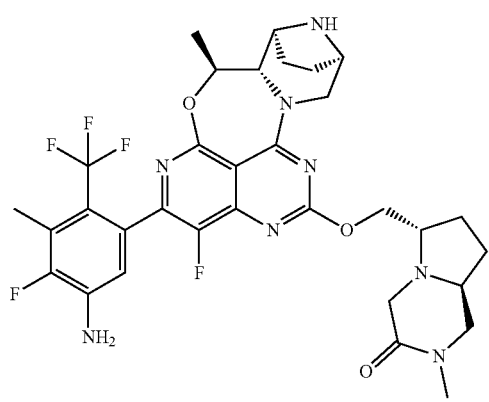 [SMILES: Cc1c(F)c(N)cc(-c2nc3c4c(nc(OC[C@@H]5CC[C@H]6CN(C)C(=O)CN56)nc4c2F)N2C[C@H]4CC[C@H](N4)[C@H]2[C@H](C)O3)c1C(F)(F)F] |
| | 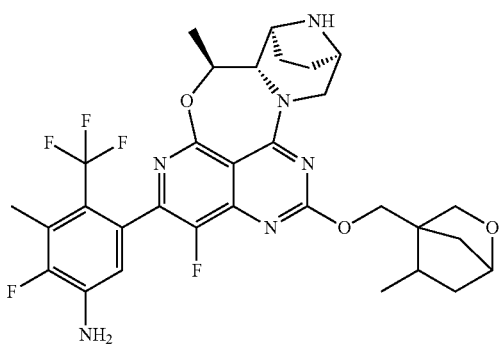 [SMILES: Cc1c(F)c(N)cc(-c2nc3c4c(nc(OCC56COC(CC5C)C6)nc4c2F)N2C[C@H]4CC[C@H](N4)[C@H]2[C@H](C)O3)c1C(F)(F)F] |
| | 6-((((5S,5aS,6S,9R)-2-(5-Amino-4-fluoro-3-methyl-2-(trifluoromethyl)phenyl)-1-fluoro-5-methyl-5a,6,7,8,9,10-hexahydro-5H-4-oxa-3,10a,11,13,14-pentaaza-6,9-methanonaphtho[1,8-ab]heptalen-12-yl)oxy)methyl)-2-methylhexahydropyrrolo[1,2-a]pyrazin-3(4H)-one (four isomers) |
| 132 | 2-Fluoro-5-((5S,5aS,6S,9R)-1-fluoro-5-methyl-12-((5-methyl-2-oxa-5-azabicyclo[2.2.1]heptan-4-yl)methoxy)-5a,6,7,8,9,10-hexahydro-5H-4-oxa-3,10a,11,13,14-pentaaza-6,9-methanonaphtho[1,8-ab]heptalen-2-yl)-3-methyl-4-(trifluoromethyl)aniline (mixture of two isomers) |

TABLE 1-continued
| Cmpd. No. | Chemical Structure |
|---|---|
| 133 | 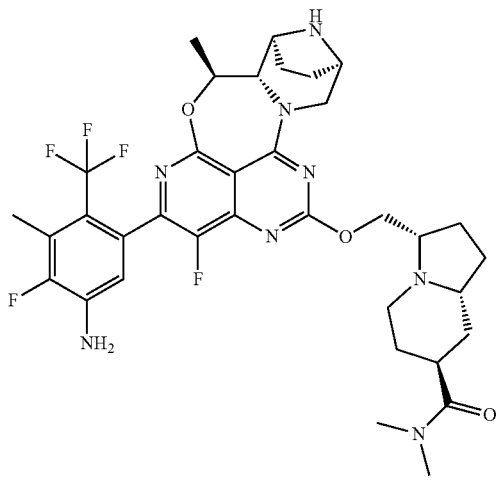 [SMILES: Cc1c(F)c(N)cc(-c2nc3c4c(nc(OC[C@@H]5CC[C@@H]6C[C@@H](C(=O)N(C)C)CCN65)nc4c2F)N2C[C@H]4CC[C@H](N4)[C@H]2[C@H](C)O3)c1C(F)(F)F] |
| | 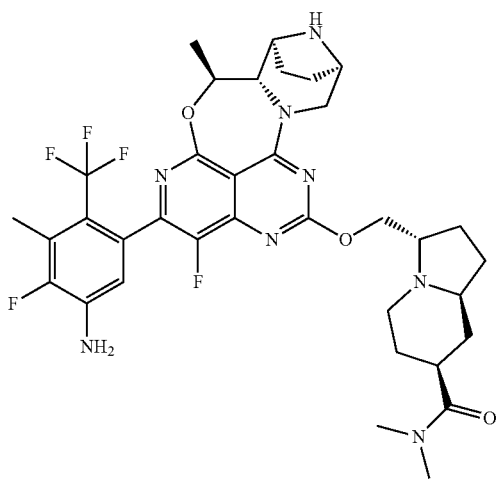 [SMILES: Cc1c(F)c(N)cc(-c2nc3c4c(nc(OC[C@@H]5CC[C@H]6C[C@@H](C(=O)N(C)C)CCN56)nc4c2F)N2C[C@H]4CC[C@H](N4)[C@H]2[C@H](C)O3)c1C(F)(F)F] |
| | 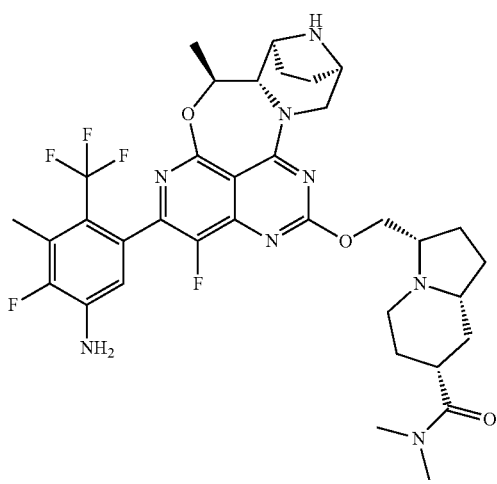 [SMILES: Cc1c(F)c(N)cc(-c2nc3c4c(nc(OC[C@@H]5CC[C@@H]6C[C@H](C(=O)N(C)C)CCN65)nc4c2F)N2C[C@H]4CC[C@H](N4)[C@H]2[C@H](C)O3)c1C(F)(F)F] |

| Cmpd. No. | Chemical Structure |
|---|---|
| | 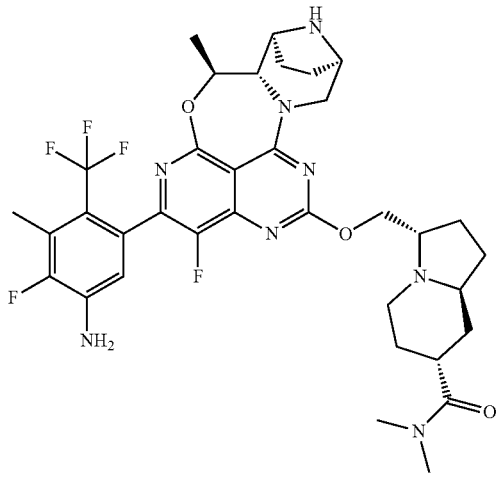 [SMILES: Cc1c(F)c(N)cc(-c2nc3c4c(nc(OC[C@@H]5CC[C@H]6C[C@H](C(=O)N(C)C)CCN56)nc4c2F)N2C[C@H]4CC[C@H](N4)[C@H]2[C@H](C)O3)c1C(F)(F)F]<br>(3S)-3-((((5S,5aS,6S,9R)-2-(5-Amino-4-fluoro-3-methyl-2-(trifluoromethyl)phenyl)-1-fluoro-5-methyl-5a,6,7,8,9,10-hexahydro-5H-4-oxa-3,10a,11,13,14-pentaaza-6,9-methanonaphtho[1,8-ab]heptalen-12-yl)oxy)methyl)-N,N-dimethyloctahydroindolizine-7-carboxamide (four isomers) |
| 134 | 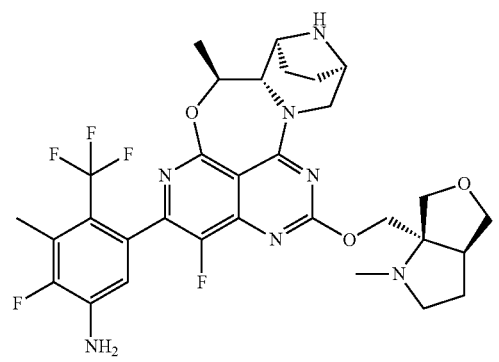 [SMILES: Cc1c(F)c(N)cc(-c2nc3c4c(nc(OC[C@]56COC[C@H]5CCN6C)nc4c2F)N2C[C@H]4CC[C@H](N4)[C@H]2[C@H](C)O3)c1C(F)(F)F]<br>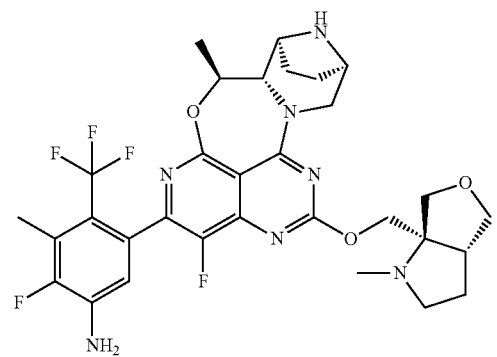 [SMILES: Cc1c(F)c(N)cc(-c2nc3c4c(nc(OC[C@]56COC[C@@H]5CCN6C)nc4c2F)N2C[C@H]4CC[C@H](N4)[C@H]2[C@H](C)O3)c1C(F)(F)F]<br>2-Fluoro-5-((5S,5aS,6S,9R)-1-fluoro-5-methyl-12-((1-methyltetrahydro-1H-furo[3,4-b]pyrrol-6a(6H)-yl)methoxy)-5a,6,7,8,9,10-hexahydro-5H-4-oxa-3,10a,11,13,14-pentaaza-6,9-methanonaphtho[1,8-ab]heptalen-2-yl)-3-methyl-4-(trifluoromethyl)aniline (two isomers) |

TABLE 1-continued

| Cmpd. No. | Chemical Structure |
|---|---|
| 135 | 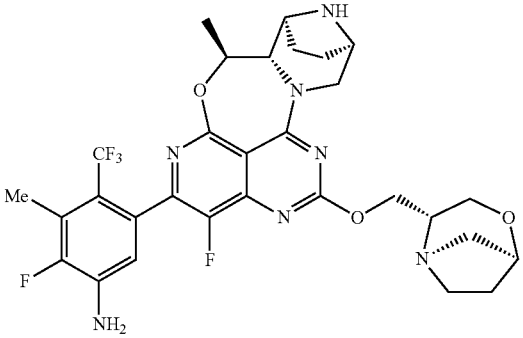 [SMILES: Cc1c(F)c(N)cc(-c2nc3c4c(nc(OC[C@@H]5CO[C@H]6CC[N@]5C6)nc4c2F)N2C[C@H]4CC[C@H](N4)[C@H]2[C@H](C)O3)c1C(F)(F)F]<br>5-((5S,5aS,6S,9R)-12-(((1R,2S,5S)-4-Oxa-1-azabicyclo[3.2.1]octan-2-yl)methoxy)-1-fluoro-5-methyl-5a,6,7,8,9,10-hexahydro-5H-4-oxa-3,10a,11,13,14-pentaaza-6,9-methanonaphtho[1,8-ab]heptalen-2-yl)-2-fluoro-3-methyl-4-(trifluoromethyl)aniline |
| 136 | 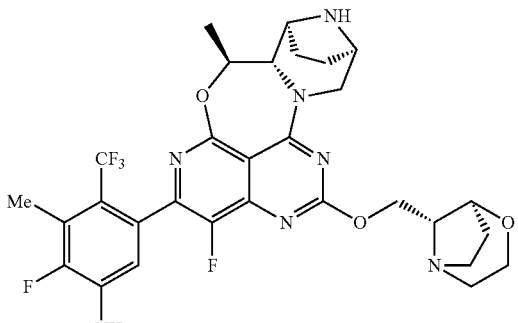<br>5-((5S,5aS,6S,9R)-12-(((5S,8R)-4-Oxa-1-azabicyclo[3.2.1]octan-8-yl)methoxy)-1-fluoro-5-methyl-5a,6,7,8,9,10-hexahydro-5H-4-oxa-3,10a,11,13,14-pentaaza-6,9-methanonaphtho[1,8-ab]heptalen-2-yl)-2-fluoro-3-methyl-4-(trifluoromethyl)aniline |
| 137 | 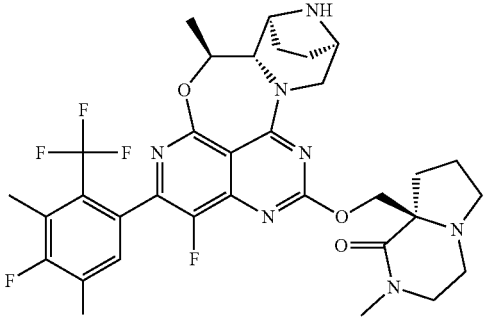<br>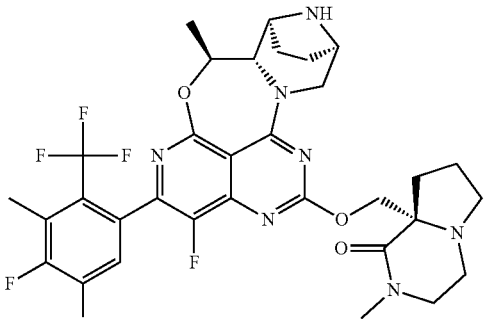 |

TABLE 1-continued

| Cmpd. No. | Chemical Structure |
|---|---|
| | 8a-((((5S,5aS,6S,9R)-2-(5-amino-4-fluoro-3-methyl-2-(trifluoromethyl)phenyl)-1-fluoro-5-methyl-5a,6,7,8,9,10-hexahydro-5H-4-oxa-3,10a,11,13,14-pentaaza-6,9-methanonaphtho[1,8-ab]heptalen-12-yl)oxy)methyl)-2-methylhexahydropyrrolo[1,2-a]pyrazin-1(2H)-one (two isomers) |
| 138 | 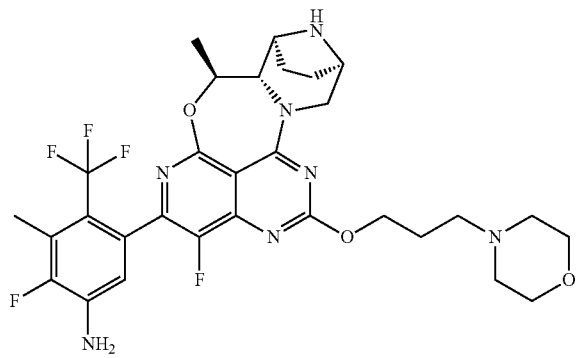 [SMILES: Cc1c(F)c(N)cc(-c2nc3c4c(nc(OCCCN5CCOCC5)nc4c2F)N2C[C@H]4CC[C@H](N4)[C@H]2[C@H](C)O3)c1C(F)(F)F]<br>2-Fluoro-5-((5S,5aS,6S,9R)-1-fluoro-5-methyl-12-(3-morpholinopropoxy)-5a,6,7,8,9,10-hexahydro-5H-4-oxa-3,10a,11,13,14-pentaaza-6,9-methanonaphtho[1,8-ab]heptalen-2-yl)-3-methyl-4-(trifluoromethyl)aniline |
| 139 | 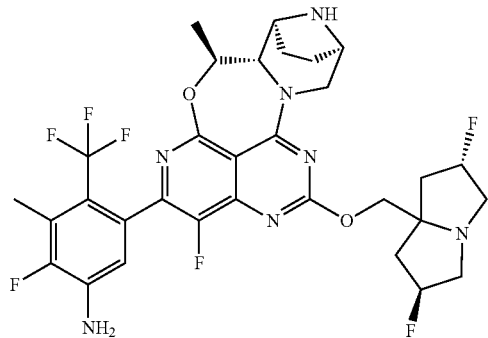 [SMILES: Cc1c(F)c(N)cc(-c2nc3c4c(nc(OCC56C[C@H](F)CN5C[C@@H](F)C6)nc4c2F)N2C[C@H]4CC[C@H](N4)[C@H]2[C@H](C)O3)c1C(F)(F)F]<br>5-((5S,5aS,6S,9R)-12-(((2S,6S)-2,6-Difluorotetrahydro-1H-pyrrolizin-7a(5H)-yl)methoxy)-1-fluoro-5-methyl-5a,6,7,8,9,10-hexahydro-5H-4-oxa-3,10a,11,13,14-pentaaza-6,9-methanonaphtho[1,8-ab]heptalen-2-yl)-2-fluoro-3-methyl-4-(trifluoromethyl)aniline |
| 140 | 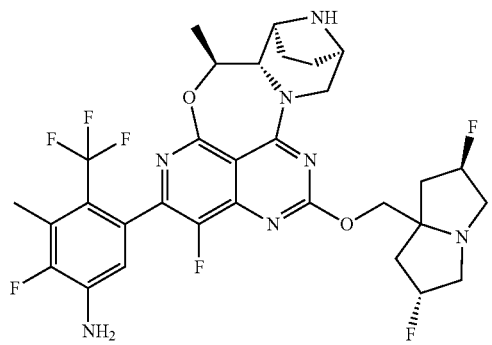 [SMILES: Cc1c(F)c(N)cc(-c2nc3c4c(nc(OCC56C[C@@H](F)CN5C[C@H](F)C6)nc4c2F)N2C[C@H]4CC[C@H](N4)[C@H]2[C@H](C)O3)c1C(F)(F)F]<br>5-((5S,5aS,6S,9R)-12-(((2R,6R)-2,6-Difluorotetrahydro-1H-pyrrolizin-7a(5H)-yl)methoxy)-1-fluoro-5-methyl-5a,6,7,8,9,10-hexahydro-5H-4-oxa-3,10a,11,13,14-pentaaza-6,9-methanonaphtho[1,8-ab]heptalen-2-yl)-2-fluoro-3-methyl-4-(trifluoromethyl)aniline |

TABLE 1-continued

| Cmpd. No. | Chemical Structure |
|---|---|
| 141 | 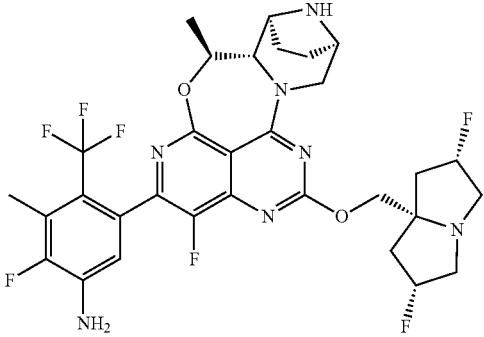 [SMILES: Cc1c(F)c(N)cc(-c2nc3c4c(nc(OC[C@]56C[C@H](F)CN5C[C@H](F)C6)nc4c2F)N2C[C@H]4CC[C@H](N4)[C@H]2[C@H](C)O3)c1C(F)(F)F]<br>5-(((5S,5aS,6S,9R)-12-(((2R,6S,7ar)-2,6-Difluorotetrahydro-1H-pyrrolizin-7a(5H)-yl)methoxy)-1-fluoro-5-methyl-5a,6,7,8,9,10-hexahydro-5H-4-oxa-3,10a,11,13,14-pentaaza-6,9-methanonaphtho[1,8-ab]heptalen-2-yl)-2-fluoro-3-methyl-4-(trifluoromethyl)aniline |
| 142 | 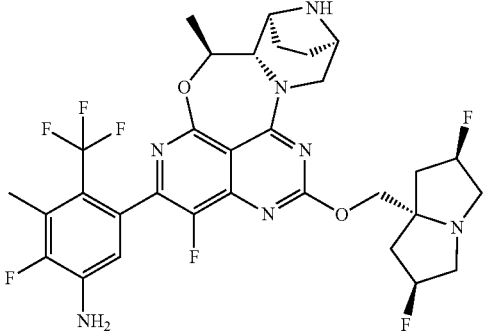 [SMILES: Cc1c(F)c(N)cc(-c2nc3c4c(nc(OC[C@@]56C[C@H](F)CN5C[C@H](F)C6)nc4c2F)N2C[C@H]4CC[C@H](N4)[C@H]2[C@H](C)O3)c1C(F)(F)F]<br>5-(((5S,5aS,6S,9R)-12-(((2R,6S,7as)-2,6-Difluorotetrahydro-1H-pyrrolizin-7a(5H)-yl)methoxy)-1-fluoro-5-methyl-5a,6,7,8,9,10-hexahydro-5H-4-oxa-3,10a,11,13,14-pentaaza-6,9-methanonaphtho[1,8-ab]heptalen-2-yl)-2-fluoro-3-methyl-4-(trifluoromethyl)aniline |
| 143 | 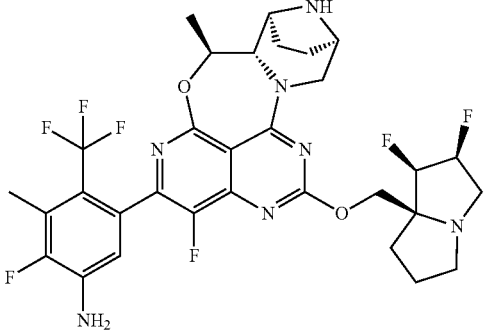 [SMILES: Cc1c(F)c(N)cc(-c2nc3c4c(nc(OC[C@]56CCCN5C[C@H](F)[C@@H]6F)nc4c2F)N2C[C@H]4CC[C@H](N4)[C@H]2[C@H](C)O3)c1C(F)(F)F] |

TABLE 1-continued

| Cmpd. No. | Chemical Structure |
|---|---|
| | 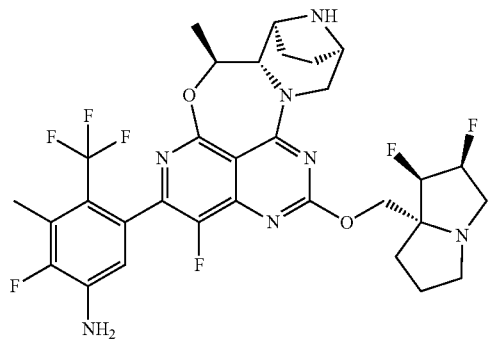 [SMILES: Cc1c(F)c(N)cc(-c2nc3c4c(nc(OC[C@@]56CCCN5C[C@H](F)[C@@H]6F)nc4c2F)N2C[C@H]4CC[C@H](N4)[C@H]2[C@H](C)O3)c1C(F)(F)F]

5-((5S,5aS,6S,9R)-12-((1,2-Difluorotetrahydro-1H-pyrrolizin-7a(5H)-yl)methoxy)-1-fluoro-5-methyl-5a,6,7,8,9,10-hexahydro-5H-4-oxa-3,10a,11,13,14-pentaaza-6,9-methanonaphtho[1,8-ab]heptalen-2-yl)-2-fluoro-3-methyl-4-(trifluoromethyl)aniline
(three isomers) |
| 144 | 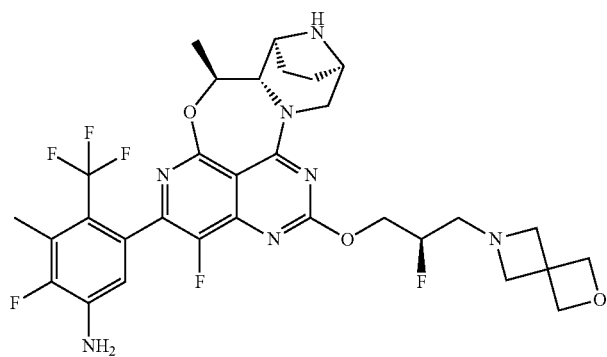 [SMILES: Cc1c(F)c(N)cc(-c2nc3c4c(nc(OC[C@H](F)CN5CC6(COC6)C5)nc4c2F)N2C[C@H]4CC[C@H](N4)[C@H]2[C@H](C)O3)c1C(F)(F)F]

2-Fluoro-5-((5S,5aS,6S,9R)-1-fluoro-12-((1-(((S)-2-(fluoromethyl)morpholino)methyl)cyclopropyl)methoxy)-5-methyl-5a,6,7,8,9,10-hexahydro-5H-4-oxa-3,10a,11,13,14-pentaaza-6,9-methanonaphtho[1,8-ab]heptalen-2-yl)-3-methyl-4-(trifluoromethyl)aniline |
| 145 | 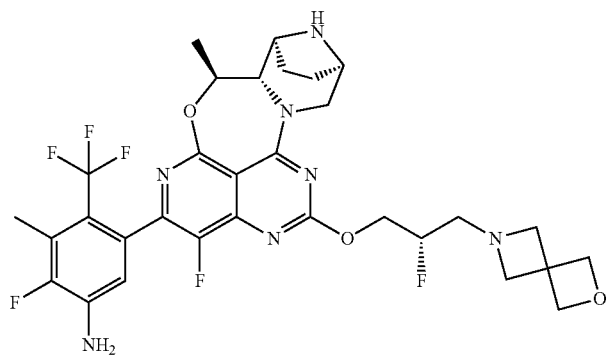 [SMILES: Cc1c(F)c(N)cc(-c2nc3c4c(nc(OC[C@@H](F)CN5CC6(COC6)C5)nc4c2F)N2C[C@H]4CC[C@H](N4)[C@H]2[C@H](C)O3)c1C(F)(F)F]

2-Fluoro-5-((5S,5aS,6S,9R)-1-fluoro-12-((1-(((R)-2-(fluoromethyl)morpholino)methyl)cyclopropyl)methoxy)-5-methyl-5a,6,7,8,9,10-hexahydro-5H-4-oxa-3,10a,11,13,14-pentaaza-6,9-methanonaphtho[1,8-ab]heptalen-2-yl)-3-methyl-4-(trifluoromethyl)aniline |

TABLE 1-continued

| Cmpd. No. | Chemical Structure |
|---|---|
| 146 | 2-Fluoro-5-((5S,5aS,6S,9R)-1-fluoro-12-((1-(((R)-2-(fluoromethyl)morpholino)methyl)cyclopropyl)methoxy)-5-methyl-5a,6,7,8,9,10-hexahydro-5H-4-oxa-3,10a,11,13,14-pentaaza-6,9-methanonaphtho[1,8-ab]heptalen-2-yl)-3-methyl-4-(trifluoromethyl)aniline |
| 149 | 2-Fluoro-5-((5S,5aS,6S,9R)-1-fluoro-5-methyl-12-(2-(3-morpholinooxetan-3-yl)ethoxy)-5a,6,7,8,9,10-hexahydro-5H-4-oxa-3,10a,11,13,14-pentaaza-6,9-methanonaphtho[1,8-ab]heptalen-2-yl)-3-methyl-4-(trifluoromethyl)aniline |
| 150 | |

TABLE 1-continued

| Cmpd. No. | Chemical Structure |
|---|---|
| 151 | 5-((5S,5aS,6S,9R)-12-((2-(2,2-Difluoroethyl)-1-methylpyrrolidin-2-yl)methoxy)-1-fluoro-5-methyl-5a,6,7,8,9,10-hexahydro-5H-4-oxa-3,10a,11,13,14-pentaaza-6,9-methanonaphtho[1,8-ab]heptalen-2-yl)-2-fluoro-3-methyl-4-(trifluoromethyl)aniline (two isomers)<br/>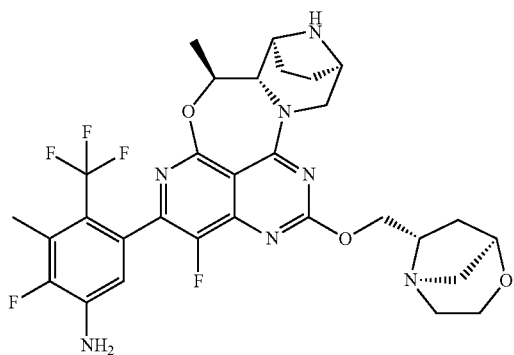 [SMILES: Cc1c(F)c(N)cc(-c2nc3c4c(nc(OC[C@@H]5C[C@@H]6C[N@@]5CCO6)nc4c2F)N2C[C@H]4CC[C@H](N4)[C@H]2[C@H](C)O3)c1C(F)(F)F] |
| | 5-((5S,5aS,6S,9R)-12-(((1R,5R)-4-Oxa-1-azabicyclo[3.2.1]octan-7-yl)methoxy)-1-fluoro-5-methyl-5a,6,7,8,9,10-hexahydro-5H-4-oxa-3,10a,11,13,14-pentaaza-6,9-methanonaphtho[1,8-ab]heptalen-2-yl)-2-fluoro-3-methyl-4-(trifluoromethyl)aniline (two isomers)<br/>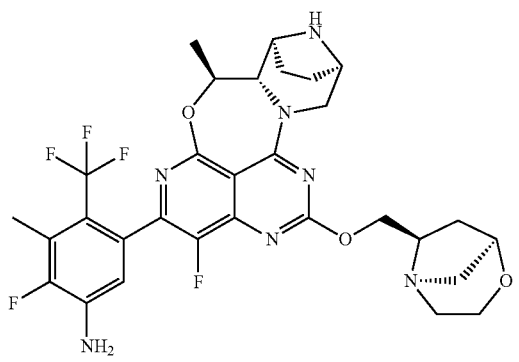 [SMILES: Cc1c(F)c(N)cc(-c2nc3c4c(nc(OC[C@H]5C[C@@H]6C[N@@]5CCO6)nc4c2F)N2C[C@H]4CC[C@H](N4)[C@H]2[C@H](C)O3)c1C(F)(F)F] |
| 152 | 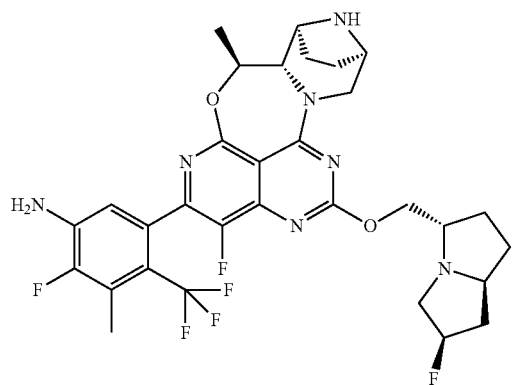 [SMILES: Cc1c(F)c(N)cc(-c2nc3c4c(nc(OC[C@@H]5CC[C@H]6C[C@@H](F)CN56)nc4c2F)N2C[C@H]4CC[C@H](N4)[C@H]2[C@H](C)O3)c1C(F)(F)F] |

TABLE 1-continued

| Cmpd. No. | Chemical Structure |
|---|---|
| | 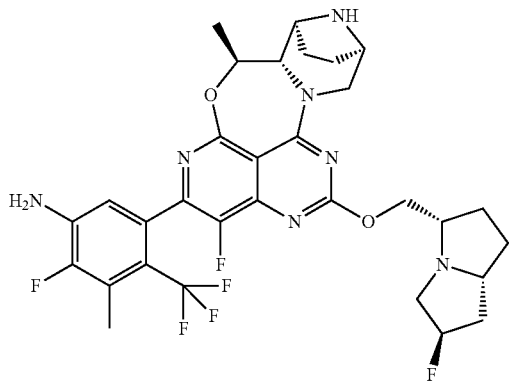 [SMILES: Cc1c(F)c(N)cc(-c2nc3c4c(nc(OC[C@@H]5CC[C@@H]6C[C@@H](F)CN65)nc4c2F)N2C[C@H]4CC[C@H](N4)[C@H]2[C@H](C)O3)c1C(F)(F)F] 2-Fluoro-5-(((5S,5aS,6S,9R)-1-fluoro-12-(((6R)-6-fluorohexahydro-1H-pyrrolizin-3-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-3-methyl-4-(trifluoromethyl)aniline (two isomers) |
| 153 | 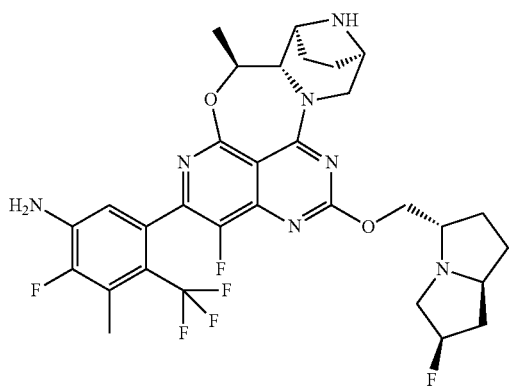 [SMILES: Cc1c(F)c(N)cc(-c2nc3c4c(nc(OC[C@@H]5CC[C@H]6C[C@@H](F)CN56)nc4c2F)N2C[C@H]4CC[C@H](N4)[C@H]2[C@H](C)O3)c1C(F)(F)F]<br>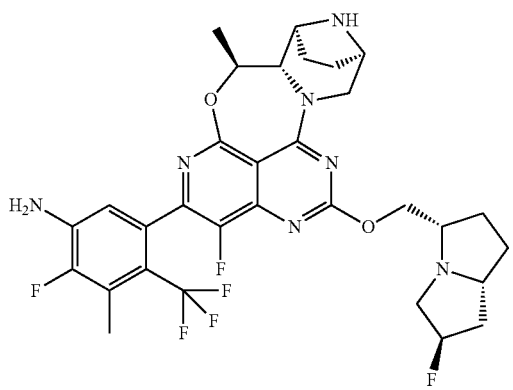 [SMILES: Cc1c(F)c(N)cc(-c2nc3c4c(nc(OC[C@@H]5CC[C@@H]6C[C@@H](F)CN65)nc4c2F)N2C[C@H]4CC[C@H](N4)[C@H]2[C@H](C)O3)c1C(F)(F)F] 5-((5S,5aS,6S,9R)-12-((6,6-Difluorohexahydro-1H-pyrrolizin-3-yl)methoxy)-1-fluoro-5-methyl-5a,6,7,8,9,10-hexahydro-5H-4-oxa-3,10a,11,13,14-pentaaza-6,9-methanonaphtho[1,8-ab]heptalen-2-yl)-2-fluoro-3-methyl-4-(trifluoromethyl)aniline (three isomers) |

TABLE 1-continued

| Cmpd. No. | Chemical Structure |
|---|---|
| 154 | 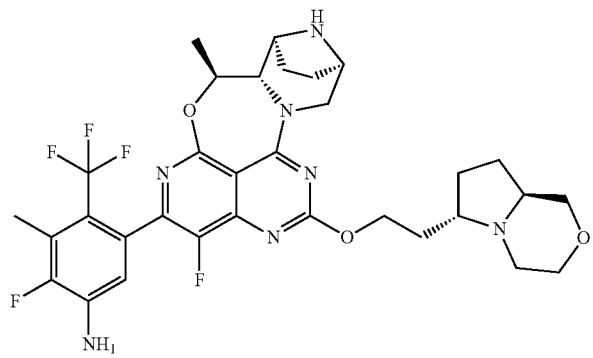 [SMILES: Cc1c(F)c(N)cc(-c2nc3c4c(nc(OCC[C@@H]5CC[C@H]6COCCN56)nc4c2F)N2C[C@H]4CC[C@H](N4)[C@H]2[C@H](C)O3)c1C(F)(F)F]  2-Fluoro-5-((5S,5aS,6S,9R)-1-fluoro-12-(2-((6S,8aS)-hexahydro-1H-pyrrolo[2,1-c][1,4]oxazin-6-yl)ethoxy)-5-methyl-5a,6,7,8,9,10-hexahydro-5H-4-oxa-3,10a,11,13,14-pentaaza-6,9-methanonaphtho[1,8-ab]heptalen-2-yl)-3-methyl-4-(trifluoromethyl)aniline |
| 155 | 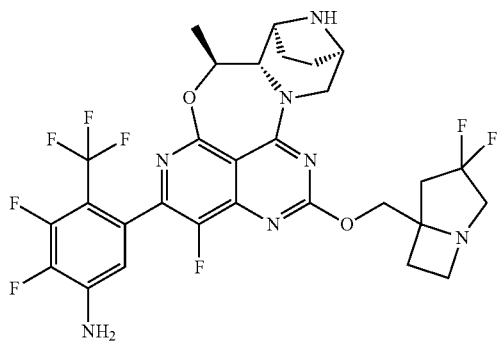 [SMILES: C[C@@H]1Oc2nc(-c3cc(N)c(F)c(F)c3C(F)(F)F)c(F)c3nc(OCC45CCN4CC(F)(F)C5)nc(c23)N2C[C@H]3CC[C@H](N3)[C@@H]12]  5-((5S,5aS,6S,9R)-12-((3,3-difluoro-1-azabicyclo[3.2.0]heptan-5-yl)methoxy)-1-fluoro-5-methyl-5a,6,7,8,9,10-hexahydro-5H-4-oxa-3,10a,11,13,14-pentaaza-6,9-methanonaphtho[1,8-ab]heptalen-2-yl)-2,3-difluoro-4-(trifluoromethyl)aniline |
| 156 | 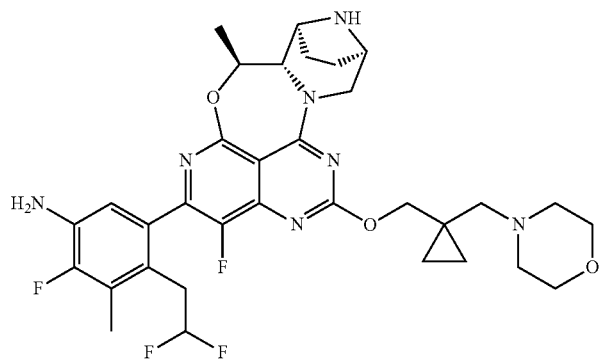 [SMILES: Cc1c(F)c(N)cc(-c2nc3c4c(nc(OCC5(CN6CCOCC6)CC5)nc4c2F)N2C[C@H]4CC[C@H](N4)[C@H]2[C@H](C)O3)c1CC(F)F]  4-(2,2-Difluoroethyl)-2-fluoro-5-((5S,5aS,6S,9R)-1-fluoro-5-methyl-12-((1-(morpholinomethyl)cyclopropyl)methoxy)-5a,6,7,8,9,10-hexahydro-5H-4-oxa-3,10a,11,13,14-pentaaza-6,9-methanonaphtho[1,8-ab]heptalen-2-yl)-3-methylaniline |

TABLE 1-continued

| Cmpd. No. | Chemical Structure |
|---|---|
| 157 | 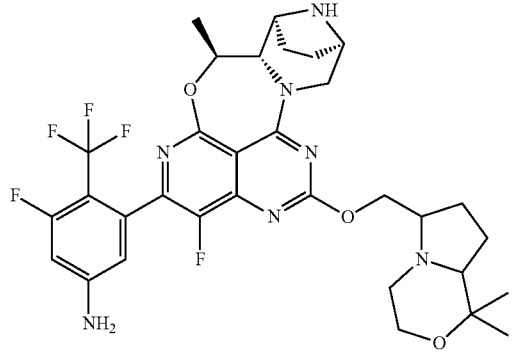 [SMILES: C[C@@H]1Oc2nc(-c3cc(N)cc(F)c3C(F)(F)F)c(F)c3nc(OCC4CCC5N4CCOC5(C)C)nc(c23)N2C[C@H]3CC[C@H](N3)[C@@H]12] 3-((5S,5aS,6S,9R)-12-((1,1-Dimethylhexahydro-1H-pyrrolo[2,1-c][1,4]oxazin-6-yl)methoxy)-1-fluoro-5-methyl-5a,6,7,8,9,10-hexahydro-5H-4-oxa-3,10a,11,13,14-pentaaza-6,9-methanonaphtho[1,8-ab]heptalen-2-yl)-5-fluoro-4-(trifluoromethyl)aniline (mixture of isomers) |
| 158 | 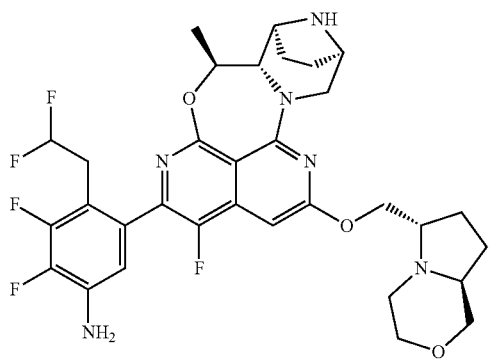 [SMILES: C[C@@H]1Oc2nc(-c3cc(N)c(F)c(F)c3CC(F)F)c(F)c3cc(OC[C@@H]4CC[C@H]5COCCN54)nc(c23)N2C[C@H]3CC[C@H](N3)[C@@H]12] 4-(2,2-Difluoroethyl)-2,3-difluoro-5-((5S,5aS,6S,9R)-1-fluoro-13-(((6S,8aS)-hexahydro-1H-pyrrolo[2,1-c][1,4]oxazin-6-yl)methoxy)-5-methyl-5a,6,7,8,9,10-hexahydro-5H-6,9-epiminoazepino[2',1':3,4][1,4]oxazepino[5,6,7-ij][2,7]naphthyridin-2-yl)aniline |
| 159 | 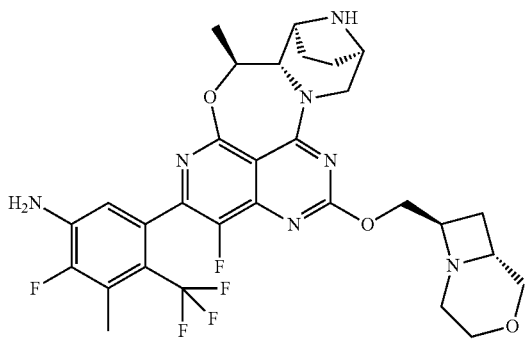 [SMILES: Cc1c(F)c(N)cc(-c2nc3c4c(nc(OC[C@H]5C[C@@H]6COCCN65)nc4c2F)N2C[C@H]4CC[C@H](N4)[C@H]2[C@H](C)O3)c1C(F)(F)F]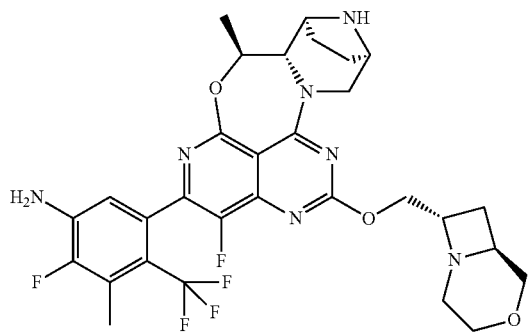 [SMILES: Cc1c(F)c(N)cc(-c2nc3c4c(nc(OC[C@@H]5C[C@H]6COCCN65)nc4c2F)N2C[C@H]4CC[C@H](N4)[C@H]2[C@H](C)O3)c1C(F)(F)F] |

| Cmpd. No. | Chemical Structure |
|---|---|
| | 5-((5S,5aS,6S,9R)-12-((4-Oxa-1-azabicyclo[4.2.0]octan-8-yl)methoxy)-1-fluoro-5-methyl-5a,6,7,8,9,10-hexahydro-5H-4-oxa-3,10a,11,13,14-pentaaza-6,9-methanonaphtho[1,8-ab]heptalen-2-yl)-2-fluoro-3-methyl-4-(trifluoromethyl)aniline (two diastereomers) |
| 160 | 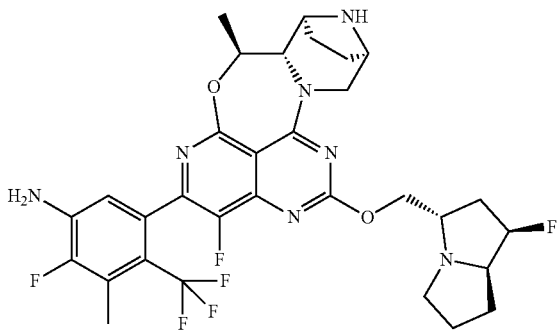 [SMILES: Cc1c(F)c(N)cc(-c2nc3c4c(nc(OC[C@@H]5C[C@@H](F)[C@H]6CCCN56)nc4c2F)N2C[C@H]4CC[C@H](N4)[C@H]2[C@H](C)O3)c1C(F)(F)F]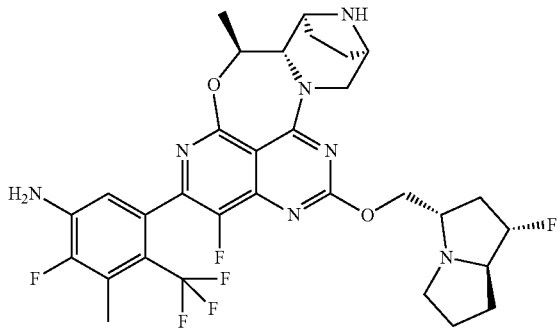 [SMILES: Cc1c(F)c(N)cc(-c2nc3c4c(nc(OC[C@@H]5C[C@H](F)[C@H]6CCCN56)nc4c2F)N2C[C@H]4CC[C@H](N4)[C@H]2[C@H](C)O3)c1C(F)(F)F]2-Fluoro-5-((5S,5aS,6S,9R)-1-fluoro-12-((1-fluorohexahydro-1H-pyrrolizin-3-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-3-methyl-4-(trifluoromethyl)aniline (two diastereomers) |
| 161 | 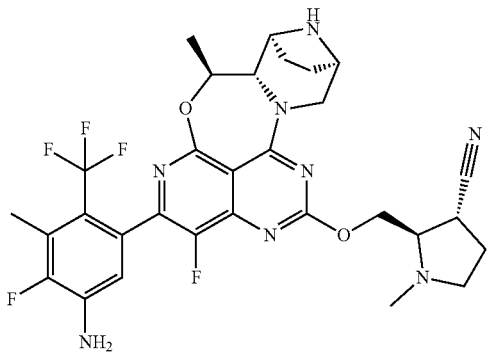 [SMILES: Cc1c(F)c(N)cc(-c2nc3c4c(nc(OC[C@H]5[C@H](C#N)CCN5C)nc4c2F)N2C[C@H]4CC[C@H](N4)[C@H]2[C@H](C)O3)c1C(F)(F)F](2R,3R)-2-((((5S,5aS,6S,9R)-2-(5-Amino-4-fluoro-3-methyl-2-(trifluoromethyl)phenyl)-1-fluoro-5-methyl-5a,6,7,8,9,10-hexahydro-5H-4-oxa-3,10a,11,13,14-pentaaza-6,9-methanonaphtho[1,8-ab]heptalen-12-yl)oxy)methyl)-1-methylpyrrolidine-3-carbonitrile |

TABLE 1-continued

| Cmpd. No. | Chemical Structure |
|---|---|
| 162 | 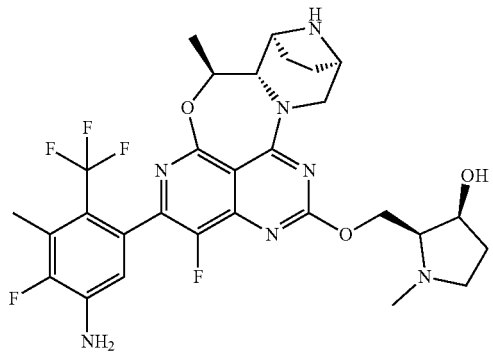 [SMILES: Cc1c(F)c(N)cc(-c2nc3c4c(nc(OC[C@H]5[C@@H](O)CCN5C)nc4c2F)N2C[C@H]4CC[C@H](N4)[C@H]2[C@H](C)O3)c1C(F)(F)F]<br>(2S,3S)-2-(((((5S,5aS,6S,9R)-2-(5-Amino-4-fluoro-3-methyl-2-(trifluoromethyl)phenyl)-1-fluoro-5-methyl-5a,6,7,8,9,10-hexahydro-5H-4-oxa-3,10a,11,13,14-pentaaza-6,9-methanonaphtho[1,8-ab]heptalen-12-yl)oxy)methyl)-1-methylpyrrolidin-3-ol |
| 163 | 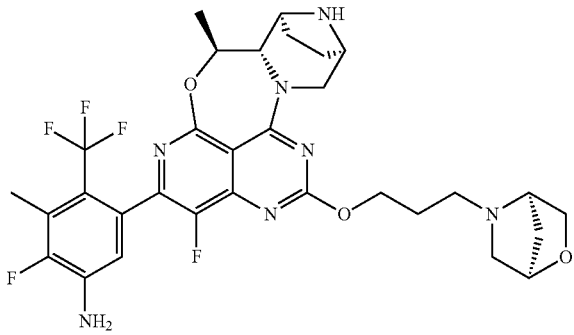 [SMILES: Cc1c(F)c(N)cc(-c2nc3c4c(nc(OCCCN5C[C@H]6C[C@@H]5CO6)nc4c2F)N2C[C@H]4CC[C@H](N4)[C@H]2[C@H](C)O3)c1C(F)(F)F]<br>5-((5S,5aS,6S,9R)-12-(3-((1R,4R)-2-Oxa-5-azabicyclo[2.2.1]heptan-5-yl)propoxy)-1-fluoro-5-methyl-5a,6,7,8,9,10-hexahydro-5H-4-oxa-3,10a,11,13,14-pentaaza-6,9-methanonaphtho[1,8-ab]heptalen-2-yl)-2-fluoro-3-methyl-4-(trifluoromethyl)aniline |
| 164 | 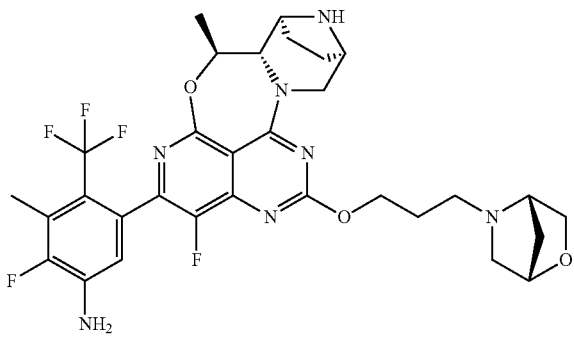 [SMILES: Cc1c(F)c(N)cc(-c2nc3c4c(nc(OCCCN5C[C@@H]6C[C@H]5CO6)nc4c2F)N2C[C@H]4CC[C@H](N4)[C@H]2[C@H](C)O3)c1C(F)(F)F]<br>5-((5S,5aS,6S,9R)-12-(3-((1S,4S)-2-oxa-5-azabicyclo[2.2.1]heptan-5-yl)propoxy)-1-fluoro-5-methyl-5a,6,7,8,9,10-hexahydro-5H-4-oxa-3,10a,11,13,14-pentaaza-6,9-methanonaphtho[1,8-ab]heptalen-2-yl)-2-fluoro-3-methyl-4-(trifluoromethyl)aniline |

| Cmpd. No. | Chemical Structure |
|---|---|
| 165 | 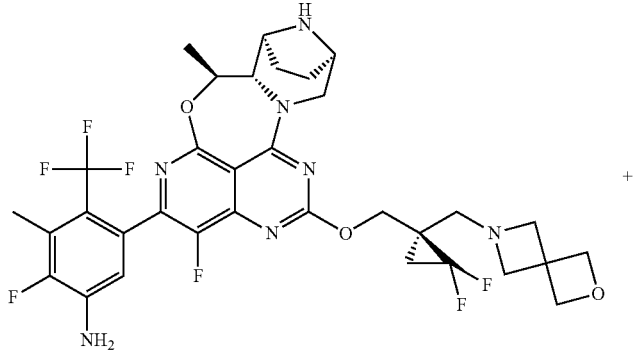 [SMILES: Cc1c(F)c(N)cc(-c2nc3c4c(nc(OC[C@]5(CN6CC7(COC7)C6)CC5(F)F)nc4c2F)N2C[C@H]4CC[C@H](N4)[C@H]2[C@H](C)O3)c1C(F)(F)F] |

5-((5S,5aS,6S,9R)-12-((1-((2-Oxa-6-azaspiro[3,3]heptan-6-yl)methyl)-2,2-difluorocyclopropyl)methoxy)-1-fluoro-5-methyl-5a,6,7,8,9,10-hexahydro-5H-4-oxa-3,10a,11,13,14-pentaaza[6,9]methanonaphtho[1,8-ab]heptalen-2-yl)-2-fluoro-3-methyl-4-(trifluoromethyl)aniline (two diastereomers)

| | |
|---|---|
| 166 | 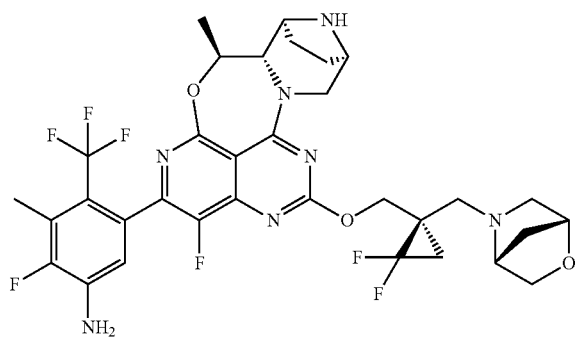 [SMILES: Cc1c(F)c(N)cc(-c2nc3c4c(nc(OC[C@]5(CN6C[C@H]7C[C@@H]6CO7)CC5(F)F)nc4c2F)N2C[C@H]4CC[C@H](N4)[C@H]2[C@H](C)O3)c1C(F)(F)F] |

5-((5S,5aS,6S,9R)-12-((1-(((1R,4R)-2-Oxa-5-azabicyclo[2.2.1]heptan-5-yl)methyl)-2,2-difluorocyclopropyl)methoxy)-1-fluoro-5-methyl-5a,6,7,8,9,10-hexahydro-5H-4-oxa-3,10a,11,13,14-pentaaza-6,9-methanonaphtho[1,8-ab]heptalen-2-yl)-2-fluoro-3-methyl- TABLE 1-continued

| Cmpd. No. | Chemical Structure |
|---|---|

4-(trifluoromethyl)aniline (mixture of two diastereomers)

167

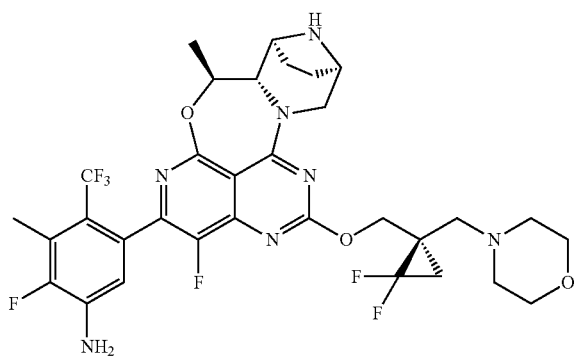 [SMILES: Cc1c(F)c(N)cc(-c2nc3c4c(nc(OC[C@]5(CN6CCOCC6)CC5(F)F)nc4c2F)N2C[C@H]4CC[C@H](N4)[C@H]2[C@H](C)O3)c1C(F)(F)F]

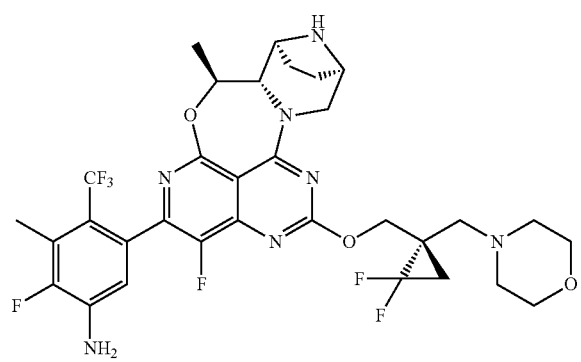 [SMILES: Cc1c(F)c(N)cc(-c2nc3c4c(nc(OC[C@@]5(CN6CCOCC6)CC5(F)F)nc4c2F)N2C[C@H]4CC[C@H](N4)[C@H]2[C@H](C)O3)c1C(F)(F)F]

5-((5S,5aS,6S,9R)-12-((2,2-Difluoro-1-(morpholinomethyl)cyclopropyl)methoxy)-1-fluoro-5-methyl-5a,6,7,8,9,10-hexahydro-5H-4-oxa-3,10a,11,13,14-pentaaza-6,9-methanonaphtho[1,8-ab]heptalen-2-yl)-2-fluoro-3-methyl-4-(trifluoromethyl)aniline (mixture of diastereomers)

168

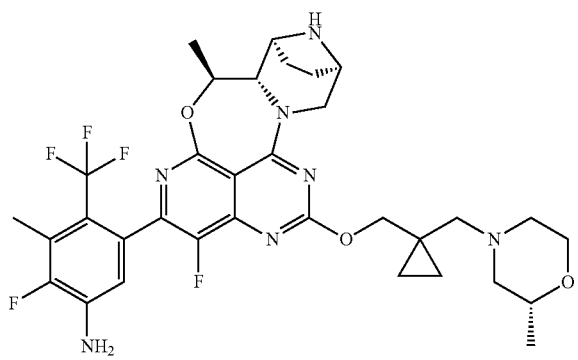 [SMILES: Cc1c(F)c(N)cc(-c2nc3c4c(nc(OCC5(CN6CCO[C@H](C)C6)CC5)nc4c2F)N2C[C@H]4CC[C@H](N4)[C@H]2[C@H](C)O3)c1C(F)(F)F]

2-Fluoro-5-((5S,5aS,6S,9R)-1-fluoro-5-methyl-12-((1-(((R)-2-methylmorpholino)methyl)cyclopropyl)methoxy)-5a,6,7,8,9,10-hexahydro-5H-4-oxa-3,10a,11,13,14-pentaaza-6,9-methanonaphtho[1,8-ab]heptalen-2-yl)-3-methyl-4-(trifluoromethyl)aniline TABLE 1-continued

| Cmpd. No. | Chemical Structure |
|---|---|
| 169 | 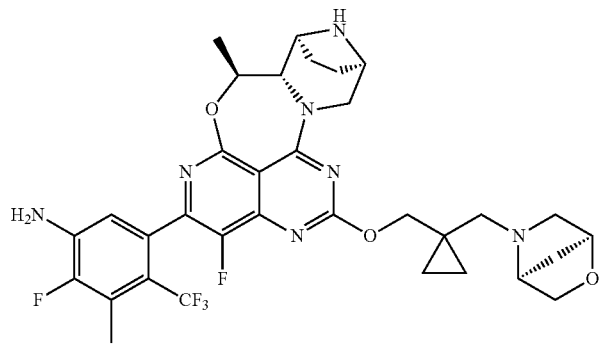 [SMILES: Cc1c(F)c(N)cc(-c2nc3c4c(nc(OCC5(CN6C[C@@H]7C[C@H]6CO7)CC5)nc4c2F)N2C[C@H]4CC[C@H](N4)[C@H]2[C@H](C)O3)c1C(F)(F)F]<br>5-((5S,5aS,6S,9R)-12-((1-((((1S,4S)-2-Oxa-5-azabicyclo[2.2.1]heptan-5-yl)methyl)cyclopropyl)methoxy)-1-fluoro-5-methyl-5a,6,7,8,9,10-hexahydro-5H-4-oxa-3,10a,11,13,14-pentaaza-6,9-methanonaphtho[1,8-ab]heptalene-2-yl)-2-fluoro-3-methyl-4-(trifluoromethyl)aniline |
| 170 | 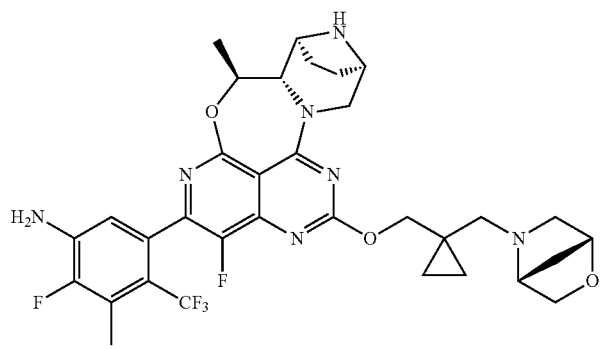 [SMILES: Cc1c(F)c(N)cc(-c2nc3c4c(nc(OCC5(CN6C[C@H]7C[C@@H]6CO7)CC5)nc4c2F)N2C[C@H]4CC[C@H](N4)[C@H]2[C@H](C)O3)c1C(F)(F)F]<br>5-((5S,5aS,6S,9R)-12-((1-((((1R,4R)-2-Oxa-5-azabicyclo[2.2.1]heptan-5-yl)methyl)cyclopropyl)methoxy)-1-fluoro-5-methyl-5a,6,7,8,9,10-hexahydro-5H-4-oxa-3,10a,11,13,14-pentaaza-6,9-methanonaphtho[1,8-ab]heptalene-2-yl)-2-fluoro-3-methyl-4-(trifluoromethyl)aniline |
| 171 | 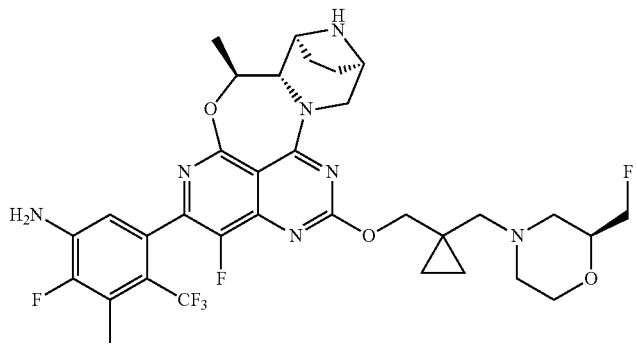 [SMILES: Cc1c(F)c(N)cc(-c2nc3c4c(nc(OCC5(CN6CCO[C@H](CF)C6)CC5)nc4c2F)N2C[C@H]4CC[C@H](N4)[C@H]2[C@H](C)O3)c1C(F)(F)F]<br>2-Fluoro-5-((5S,5aS,6S,9R)-1-fluoro-12-((1-(((S)-2-(fluoromethyl)morpholino)methyl)cyclopropyl)methoxy)-5-methyl-5a,6,7,8,9,10-hexahydro-5H-4-oxa-3,10a,11,13,14-pentaaza-6,9-methanonaphtho[1,8-ab]heptalene-2-yl)-3-methyl-4-(trifluoromethyl)aniline |

TABLE 1-continued

| Cmpd. No. | Chemical Structure |
|---|---|
| 172 | 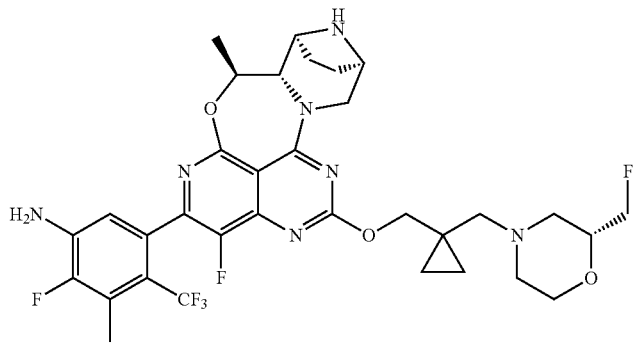 [SMILES: Cc1c(F)c(N)cc(-c2nc3c4c(nc(OCC5(CN6CCO[C@@H](CF)C6)CC5)nc4c2F)N2C[C@H]4CC[C@H](N4)[C@H]2[C@H](C)O3)c1C(F)(F)F]<br>2-Fluoro-5-((5S,5aS,6S,9R)-1-fluoro-12-((1-(((R)-2-(fluoromethyl)morpholino)methyl)cyclopropyl)methoxy)-5-methyl-5a,6,7,8,9,10-hexahydro-5H-4-oxa-3,10a,11,13,14-pentaaza-6,9-methanonaphtho[1,8-ab]heptalen-2-yl)-3-methyl-4-(trifluoromethyl)aniline |
| 173 | 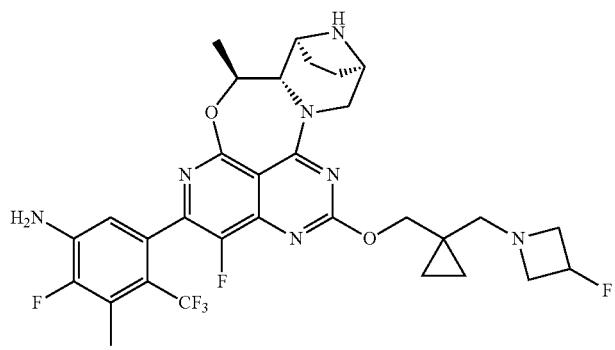 [SMILES: Cc1c(F)c(N)cc(-c2nc3c4c(nc(OCC5(CN6CC(F)C6)CC5)nc4c2F)N2C[C@H]4CC[C@H](N4)[C@H]2[C@H](C)O3)c1C(F)(F)F]<br>2-Fluoro-5-((5S,5aS,6S,9R)-1-fluoro-12-((1-((3-fluoroazetidin-1-yl)methyl)cyclopropyl)methoxy)-5-methyl-5a,6,7,8,9,10-hexahydro-5H-4-oxa-3,10a,11,13,14-pentaaza-6,9-methanonaphtho[1,8-ab]heptalene-2-yl)-3-methyl-4-(trifluoromethyl)aniline |
| 174 | 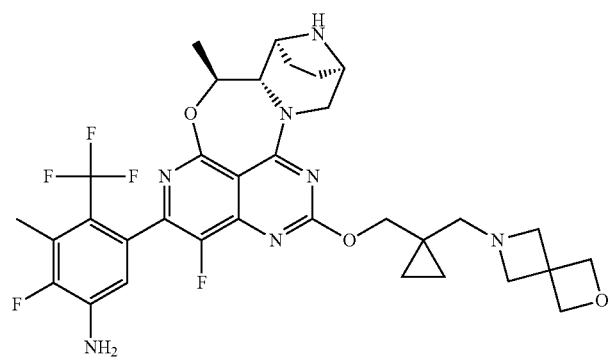 [SMILES: Cc1c(F)c(N)cc(-c2nc3c4c(nc(OCC5(CN6CC7(COC7)C6)CC5)nc4c2F)N2C[C@H]4CC[C@H](N4)[C@H]2[C@H](C)O3)c1C(F)(F)F]<br>5-((5S,5aS,6S,9R)-12-((1-((2-Oxa-6-azaspiro[3.3]heptan-6-yl)methyl)cyclopropyl)methoxy)-1-fluoro-5-methyl-5a,6,7,8,9,10-hexahydro-5H-4-oxa-3,10a,11,13,14-pentaaza[6,9]methanonaphtho[1,8-ab]heptalene-2-yl)-2-fluoro-3-methyl-4-(trifluoromethyl)aniline |

TABLE 1-continued

| Cmpd. No. | Chemical Structure |
|---|---|
| 175 | 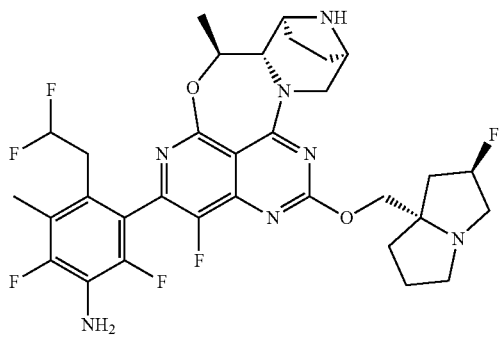 [SMILES: Cc1c(F)c(N)c(F)c(-c2nc3c4c(nc(OC[C@@]56CCCN5C[C@H](F)C6)nc4c2F)N2C[C@H]4CC[C@H](N4)[C@H]2[C@H](C)O3)c1CC(F)F]

4-(2,2-Difluoroethyl)-2,6-difluoro-3-((5S,5aS,6S,9R)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-5-methylaniline |
| 176 | 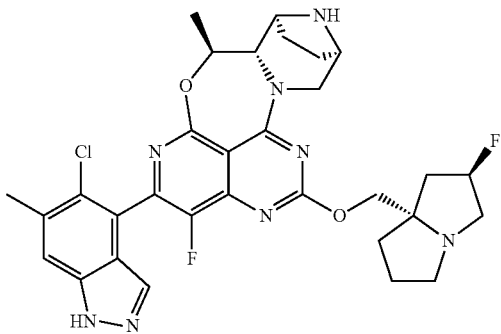 [SMILES: Cc1cc2[nH]ncc2c(-c2nc3c4c(nc(OC[C@@]56CCCN5C[C@H](F)C6)nc4c2F)N2C[C@H]4CC[C@H](N4)[C@H]2[C@H](C)O3)c1Cl]

(5S,5aS,6S,9R)-2-(5-Chloro-6-methyl-1H-indazol-4-yl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene |
| 177 | 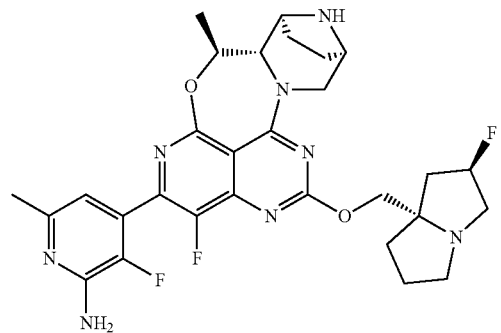 [SMILES: Cc1cc(-c2nc3c4c(nc(OC[C@@]56CCCN5C[C@H](F)C6)nc4c2F)N2C[C@H]4CC[C@H](N4)[C@H]2[C@H](C)O3)c(F)c(N)n1]

3-Fluoro-4-((5S,5aS,6S,9R)-1-fluoro-12-(((2R,7aS)-2-fluorotetrahydro-1H-pyrrolizin-7°(5H)-yl)methoxy)-5-methyl-5°,6,7,8,9,10-hexahydro-5H-4-oxa-3,10°,11,13,14-pentaaza-6,9-methanonaptho[1,8-ab]heptalen-2-yl)-6-methylpyridin-2-amine |

| Cmpd. No. | Chemical Structure |
|---|---|
| 178 | 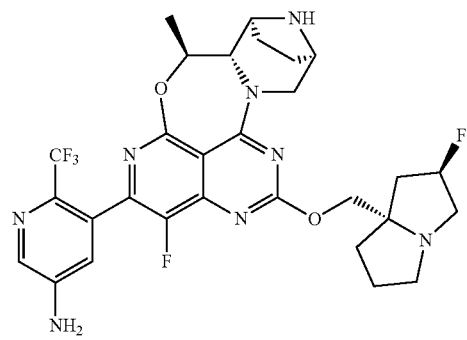 [SMILES: C[C@@H]1Oc2nc(-c3cc(N)cnc3C(F)(F)F)c(F)c3nc(OC[C@@]45CCCN4C[C@H](F)C5)nc(c23)N2C[C@H]3CC[C@H](N3)[C@@H]12]<br>5-((5S,5aS,6S,9R)-1-Fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-2-yl)-6-(trifluoromethyl)pyridin-3-amine |
| 179 | 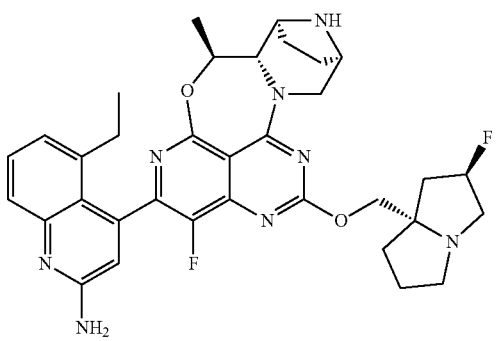 [SMILES: CCc1cccc2nc(N)cc(-c3nc4c5c(nc(OC[C@@]67CCCN6C[C@H](F)C7)nc5c3F)N3C[C@H]5CC[C@H](N5)[C@H]3[C@H](C)O4)c12]<br>5-Ethyl-4-((5S,5aS,6S,9R)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-2-yl)quinolin-2-amine |
| 180 | 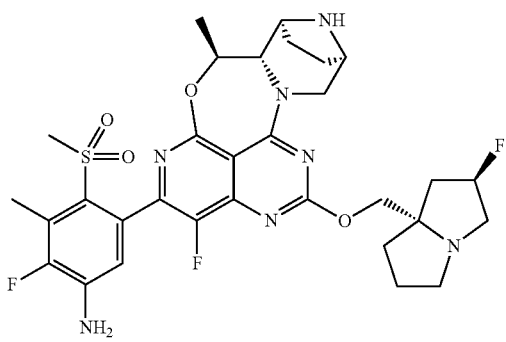 [SMILES: Cc1c(F)c(N)cc(-c2nc3c4c(nc(OC[C@@]56CCCN5C[C@H](F)C6)nc4c2F)N2C[C@H]4CC[C@H](N4)[C@H]2[C@H](C)O3)c1S(C)(=O)=O]<br>2-Fluoro-5-((5S,5aS,6S,9R)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-2-yl)-3-methyl-4-(methylsulfonyl)aniline |

TABLE 1-continued

| Cmpd. No. | Chemical Structure |
|---|---|
| 181 | 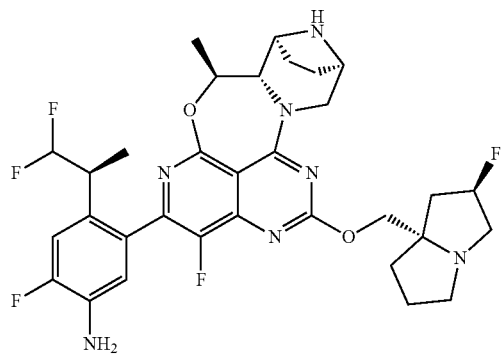 [SMILES: C[C@@H]1Oc2nc(-c3cc(N)c(F)cc3[C@H](C)C(F)F)c(F)c3nc(OC[C@@]45CCCN4C[C@H](F)C5)nc(c23)N2C[C@H]3CC[C@H](N3)[C@@H]12] |
| | 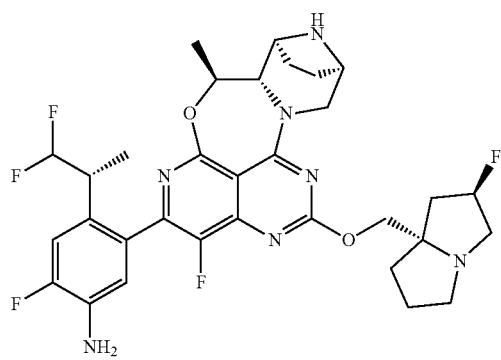 [SMILES: C[C@H](c1cc(F)c(N)cc1-c1nc2c3c(nc(OC[C@@]45CCCN4C[C@H](F)C5)nc3c1F)N1C[C@H]3CC[C@H](N3)[C@H]1[C@H](C)O2)C(F)F] |
| | (1,1-Difluoropropan-2-yl)-2-fluoro-5-((5S,5aS,6S,9R)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-2-yl)aniline (two isomers) |
| 182 | 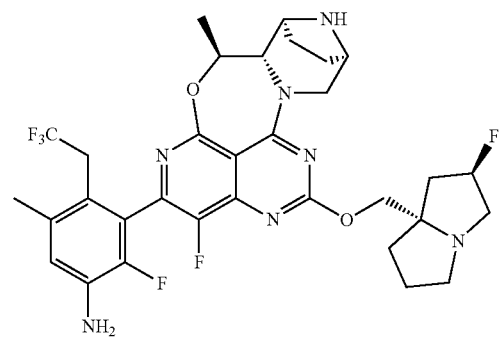 [SMILES: Cc1cc(N)c(F)c(-c2nc3c4c(nc(OC[C@@]56CCCN5C[C@H](F)C6)nc4c2F)N2C[C@H]4CC[C@H](N4)[C@H]2[C@H](C)O3)c1CC(F)(F)F] |
| | 2-Fluoro-3-((5S,5aS,6S,9R)-1-fluoro-12-(((2R,7aS)-2-fluorotetrahydro-1H-pyrrolizin-7°(5H)-yl)methoxy)-5-methyl-5°,6,7,8,9,10-hexahydro-5H-4-oxa-3,10°,11,13,14-pentaaza-6,9-methanonaphtho[1,8-ab]heptalen-2-yl)-5-methyl-4-(2,2,2-trifluoroethyl)aniline |

TABLE 1-continued

| Cmpd. No. | Chemical Structure |
|---|---|
| 183 | 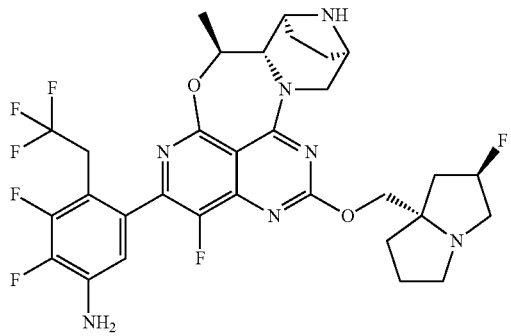 [SMILES: C[C@@H]1Oc2nc(-c3cc(N)c(F)c(F)c3CC(F)(F)F)c(F)c3nc(OC[C@@]45CCCN4C[C@H](F)C5)nc(c23)N2C[C@H]3CC[C@H](N3)[C@@H]12]<br>2,3-Difluoro-5-((5S,5aS,6S,9R)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-2-yl)-4-(2,2,2-trifluoroethyl)aniline |
| 184 | 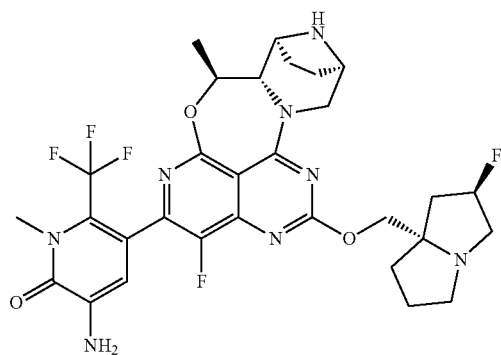 [SMILES: C[C@@H]1Oc2nc(-c3cc(N)c(=O)n(C)c3C(F)(F)F)c(F)c3nc(OC[C@@]45CCCN4C[C@H](F)C5)nc(c23)N2C[C@H]3CC[C@H](N3)[C@@H]12]<br>3-Amino-5-((5S,5aS,6S,9R)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-2-yl)-1-methyl-6-(trifluoromethyl)pyridin-2(1H)-one |
| 185 | 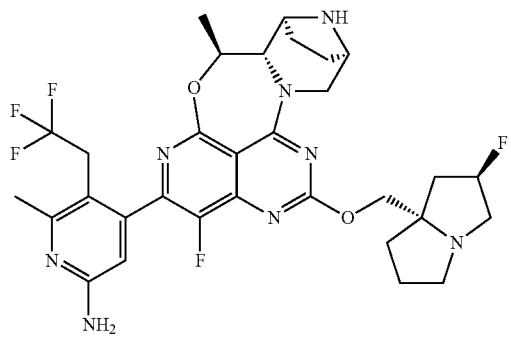 [SMILES: Cc1nc(N)cc(-c2nc3c4c(nc(OC[C@@]56CCCN5C[C@H](F)C6)nc4c2F)N2C[C@H]4CC[C@H](N4)[C@H]2[C@H](C)O3)c1CC(F)(F)F]<br>4-((5S,5aS,6S,9R)-1-Fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-2-yl)-6-methyl-5-(2,2,2-trifluoroethyl)pyridin-2-amine |

| Cmpd. No. | Chemical Structure |
|---|---|
| 186 | 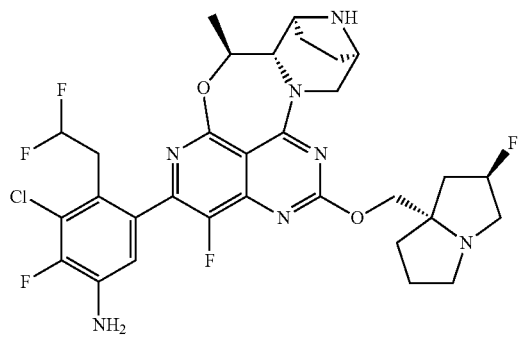 [SMILES: C[C@@H]1Oc2nc(-c3cc(N)c(F)c(Cl)c3CC(F)F)c(F)c3nc(OC[C@@]45CCCN4C[C@H](F)C5)nc(c23)N2C[C@H]3CC[C@H](N3)[C@@H]12] |

3-Chloro-4-(2,2-difluoroethyl)-2-fluoro-5-((5S,5aS,6S,9R)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-2-yl)aniline

| 187 | 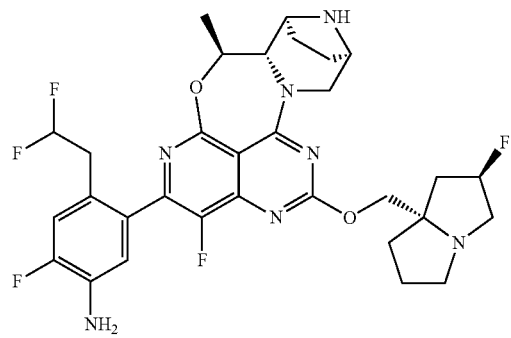 [SMILES: C[C@@H]1Oc2nc(-c3cc(N)c(F)cc3CC(F)F)c(F)c3nc(OC[C@@]45CCCN4C[C@H](F)C5)nc(c23)N2C[C@H]3CC[C@H](N3)[C@@H]12] |

4-(2,2-Difluoroethyl)-2-fluoro-5-((5S,5aS,6S,9R)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-2-yl)aniline
(byproduct of Example 186)

| 188 | 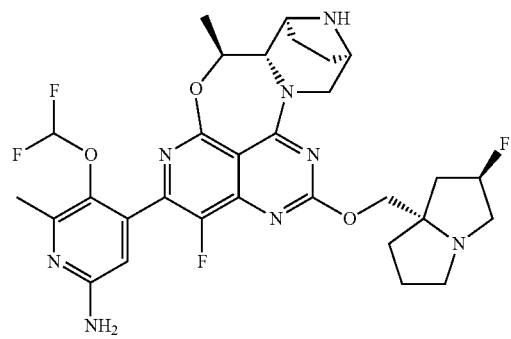 [SMILES: Cc1nc(N)cc(-c2nc3c4c(nc(OC[C@@]56CCCN5C[C@H](F)C6)nc4c2F)N2C[C@H]4CC[C@H](N4)[C@H]2[C@H](C)O3)c1OC(F)F] |

5-(Difluoromethoxy)-4-((5S,5aS,6S,9R)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-2-yl)-6-methylpyridin-2-amine TABLE 1-continued

| Cmpd. No. | Chemical Structure |
|---|---|
| 189 | 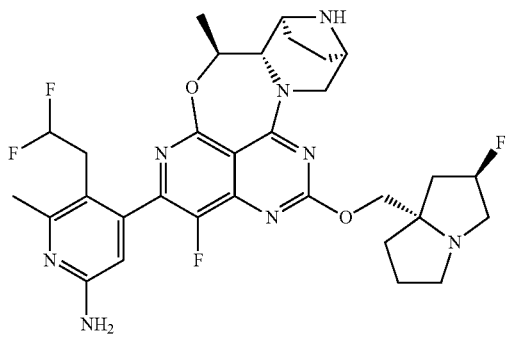 [SMILES: Cc1nc(N)cc(-c2nc3c4c(nc(OC[C@@]56CCCN5C[C@H](F)C6)nc4c2F)N2C[C@H]4CC[C@H](N4)[C@H]2[C@H](C)O3)c1CC(F)F]<br>5-(2,2-Difluoroethyl)-4-((5S,5aS,6S,9R)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-2-yl)-6-methylpyridin-2-amine |
| 190 | 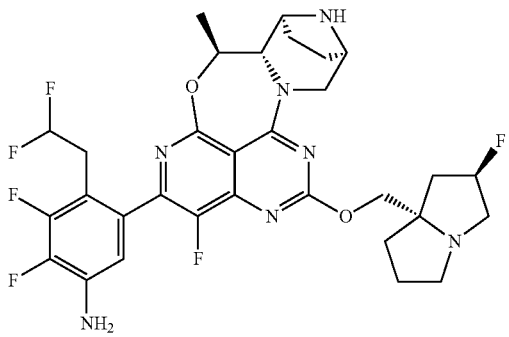 [SMILES: C[C@@H]1Oc2nc(-c3cc(N)c(F)c(F)c3CC(F)F)c(F)c3nc(OC[C@@]45CCCN4C[C@H](F)C5)nc(c23)N2C[C@H]3CC[C@H](N3)[C@@H]12]<br>4-(2,2-Difluoroethyl)-2,3-difluoro-5-((5S,5aS,6S,9R)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-2-yl)aniline |
| 191 | 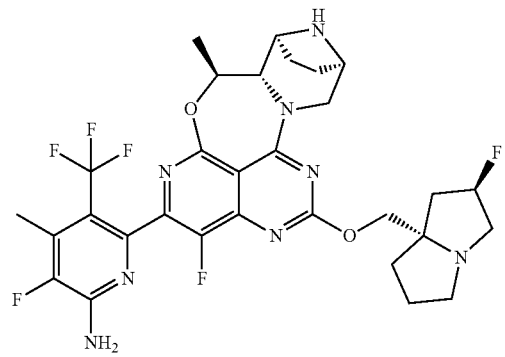 [SMILES: Cc1c(F)c(N)nc(-c2nc3c4c(nc(OC[C@@]56CCCN5C[C@H](F)C6)nc4c2F)N2C[C@H]4CC[C@H](N4)[C@H]2[C@H](C)O3)c1C(F)(F)F]<br>3-Fluoro-6-((5S,5aS,6S,9R)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-2-yl)-4-methyl-5-(trifluoromethyl)pyridin-2-amine |

TABLE 1-continued

| Cmpd. No. | Chemical Structure |
|---|---|
| 192 | 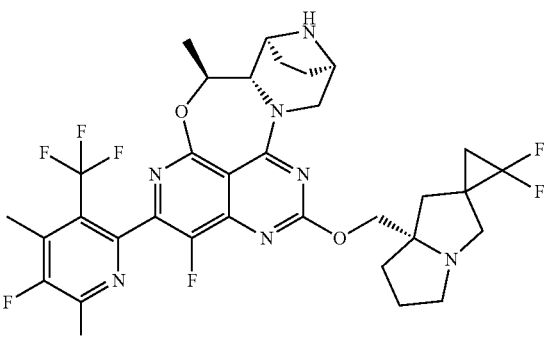 6-((5S,5aS,6S,9R)-12-(((7a'S)-2,2-Difluorodihydro-1'H,3'H-spiro[cyclopropane-1,2'-pyrrolizin]-7a'(5'H)-yl)methoxy)-1-fluoro-5-methyl-5a,6,7,8,9,10-hexahydro-5H-4-oxa-3,10a,11,13,14-pentaaza[6,9]methanonaphtho[1,8-ab]heptalene-2-yl)-3-fluoro-4-methyl-5-(trifluoromethyl)pyridin-2-amine |
| 193 | 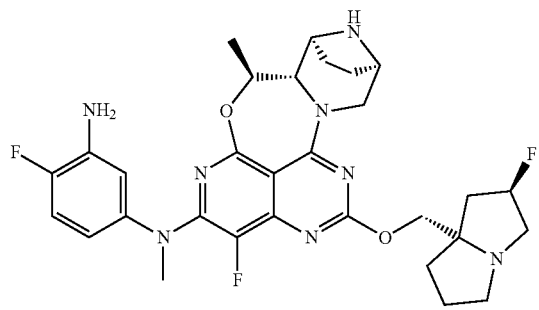 4-Fluoro-N¹-((5S,5aS,6S,9R)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-2-yl)-N¹-methylbenzene-1,3-diamine |
| 194 | 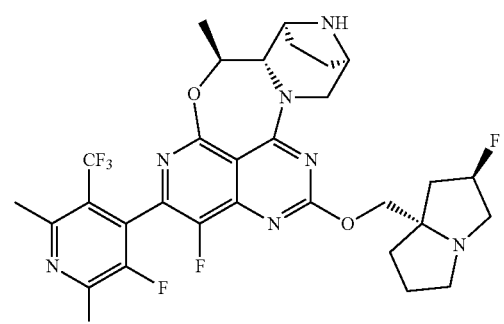 3-Fluoro-4-((5S,5aS,6S,9R)-1-fluoro-12-(((2R,7aS)-2-fluorotetrahydro-1H-pyrrolizin-7°(5H)-yl)methoxy)-5-methyl-5°,6,7,8,9,10-hexahydro-5H-4-oxa-3,10°,11,13,14-pentaaza-6,9-methanonaphtho[1,8-ab]heptalen-2-yl)-6-methyl-5-(trifluoromethyl)pyridin-2-amine |

TABLE 1-continued

| Cmpd. No. | Chemical Structure |
|---|---|
| 195 | 4-chloro-2,6-difluoro-3-((5S,5aS,6S,9R)-1-fluoro-12-(((2R,7aS)-2-fluorotetrahydro-1H-pyrrolizin-7°(5H)-yl)methoxy)-5-methyl-5°,6,7,8,9,10-hexahydro-5H-4-oxa-3,10°,11,13,14-pentaaza-6,9-methanonaphtho[1,8-ab]heptalen-2-yl)-5-methylaniline |
| 196 | 7-Fluoro-8-((5S,5aS,6S,9R)-1-fluoro-12-(((2R,7aS)-2-fluorotetrahydro-1H-pyrrolizin-7°(5H)-yl)methoxy)-5-methyl-5°,6,7,8,9,10-hexahydro-5H-4-oxa-3,10°,11,13,14-pentaaza-6,9-methanonaphtho[1,8-ab]heptalen-2-yl)isoquinolin-1(2H)-one |
| 197 | 3-chloro-4-((5S,5aS,6S,9R)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-6-methyl-5-(trifluoromethyl)pyridin-2-amine |
| 198 | 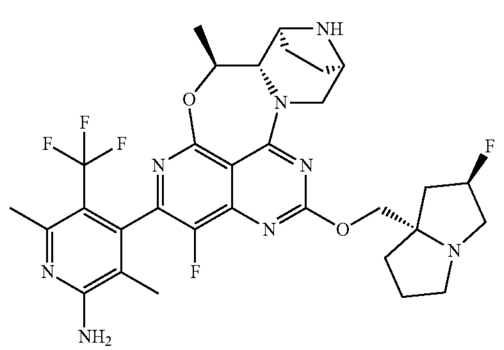 [SMILES: Cc1nc(N)c(C)c(-c2nc3c4c(nc(OC[C@@]56CCCN5C[C@H](F)C6)nc4c2F)N2C[C@H]4CC[C@H](N4)[C@H]2[C@H](C)O3)c1C(F)(F)F] |

TABLE 1-continued

| Cmpd. No. | Chemical Structure |
|---|---|
| | 4-((5S,5aS,6S,9R)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-2-yl)-3,6-dimethyl-5-(trifluoromethyl)pyridin-2-amine |
| 199 | 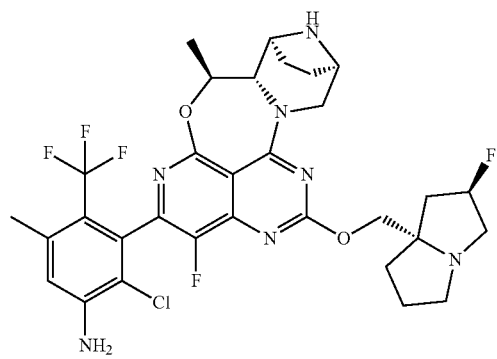 [SMILES: Cc1cc(N)c(Cl)c(-c2nc3c4c(nc(OC[C@@]56CCCN5C[C@H](F)C6)nc4c2F)N2C[C@H]4CC[C@H](N4)[C@H]2[C@H](C)O3)c1C(F)(F)F] |
| | 2-Chloro-3-((5S,5aS,6S,9R)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-2-yl)-5-methyl-4-(trifluoromethyl)aniline |
| 200 | 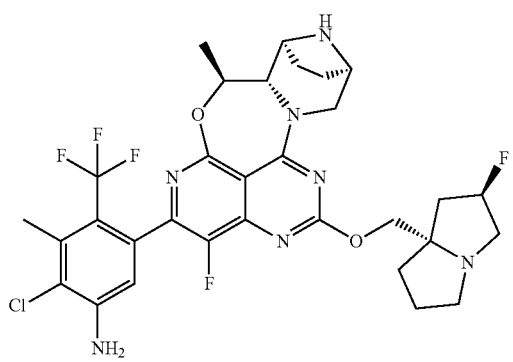 |
| | 2-Chloro-5-((5S,5aS,6S,9R)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-2-yl)-3-methyl-4-(trifluoromethyl)aniline |
| 201 | 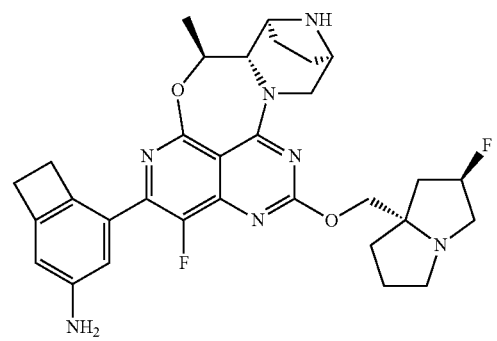 [SMILES: C[C@@H]1Oc2nc(-c3cc(N)cc4c3CC4)c(F)c3nc(OC[C@@]45CCCN4C[C@H](F)C5)nc(c23)N2C[C@H]3CC[C@H](N3)[C@@H]12] |
| | 5-((5S,5aS,6S,9R)-1-Fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-2-yl)bicyclo[4.2.0]octa-1(6),2,4-trien-3-amine |

TABLE 1-continued

| Cmpd. No. | Chemical Structure |
|---|---|
| 202 | 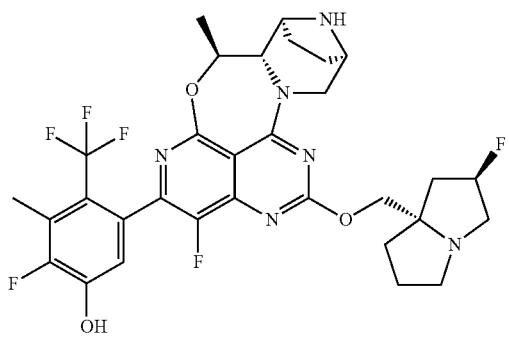 [SMILES: Cc1c(F)c(O)cc(-c2nc3c4c(nc(OC[C@@]56CCCN5C[C@H](F)C6)nc4c2F)N2C[C@H]4CC[C@H](N4)[C@H]2[C@H](C)O3)c1C(F)(F)F]<br>2-Fluoro-5-(((5S,5aS,6S,9R)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-2-yl)-3-methyl-4-(trifluoromethyl)phenol |
| 203 | 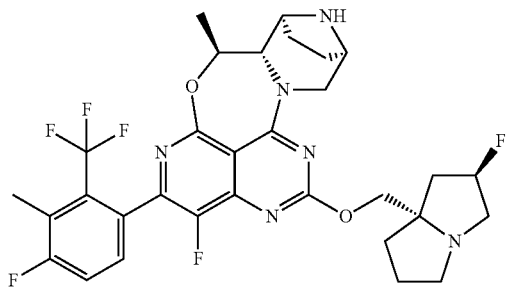 [SMILES: Cc1c(F)ccc(-c2nc3c4c(nc(OC[C@@]56CCCN5C[C@H](F)C6)nc4c2F)N2C[C@H]4CC[C@H](N4)[C@H]2[C@H](C)O3)c1C(F)(F)F]<br>(5S,5aS,6S,9R)-1-fluoro-2-(4-fluoro-3-methyl-2-(trifluoromethyl)phenyl)-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene |
| 204 | 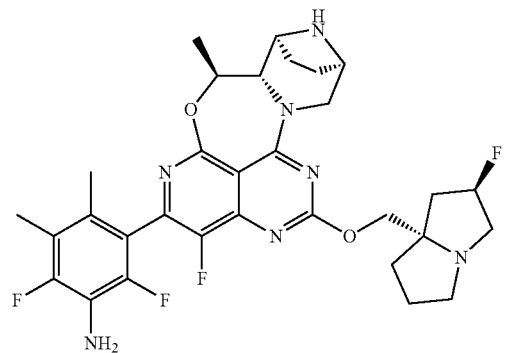 [SMILES: Cc1c(C)c(-c2nc3c4c(nc(OC[C@@]56CCCN5C[C@H](F)C6)nc4c2F)N2C[C@H]4CC[C@H](N4)[C@H]2[C@H](C)O3)c(F)c(N)c1F]<br>2,6-Difluoro-3-((5S,5aS,6S,9R)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-2-yl)-4-iodo-5-methylaniline |

TABLE 1-continued

| Cmpd. No. | Chemical Structure |
|---|---|
| 205 | 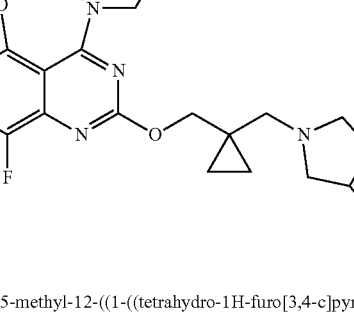<br>4-((5S,5aS,6S,9R)-1-Fluoro-5-methyl-12-((1-(((tetrahydro-1H-furo[3,4-c]pyrrol-5(3H)-yl)methyl)cyclopropyl)methoxy)-5a,6,7,8,9,10-hexahydro-5H-4-oxa-3,10a,11,13,14-pentaaza-6,9-methanonaphtho[1,8-ab]heptalene-2-yl)-6-methyl-5-(trifluoromethyl)pyridin-2-amine |
| 206 | 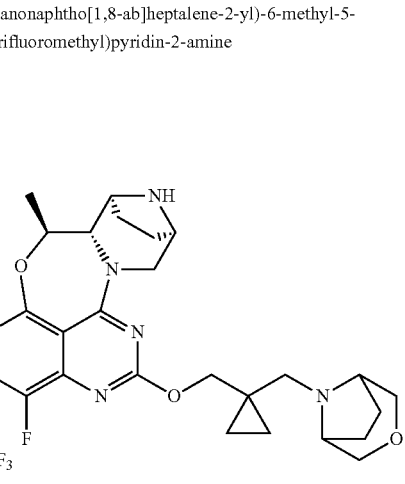<br>4-((5S,5aS,6S,9R)-12-((1-((3-Oxa-8-azabicyclo[3.2.1]octan-8-yl)methyl)cyclopropyl)methoxy)-1-fluoro-5-methyl-5a,6,7,8,9,10-hexahydro-5H-4-oxa-3,10a,11,13,14-pentaaza-6,9-methanonaphtho[1,8-ab]heptalene-2-yl)-6-methyl-5-(trifluoromethyl)pyridin-2-amine |
| 207 | 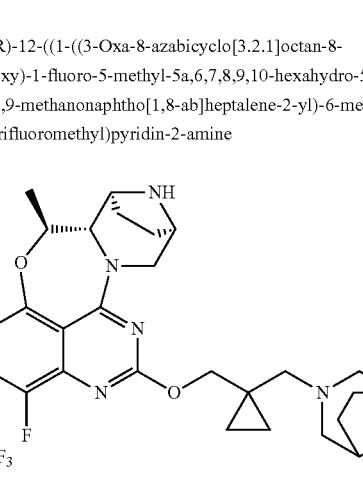<br>4-((5S,5aS,6S,9R)-12-((1-((8-oxa-3-azabicyclo[3.2.1]octan-3-yl)methyl)cyclopropyl)methoxy)-1-fluoro-5-methyl-5a,6,7,8,9,10-hexahydro-5H-4-oxa-3,10a,11,13,14-pentaaza-6,9-methanonaphtho[1,8-ab]heptalene-2-yl)-6-methyl-5-(trifluoromethyl)pyridin-2-amine |

TABLE 1-continued

| Cmpd. No. | Chemical Structure |
|---|---|
| 208 | 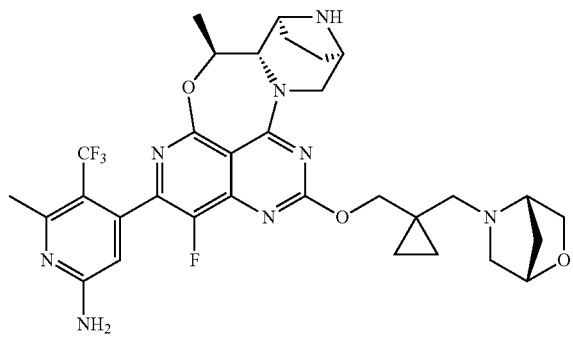 [SMILES: Cc1nc(N)cc(-c2nc3c4c(nc(OCC5(CN6C[C@@H]7C[C@H]6CO7)CC5)nc4c2F)N2C[C@H]4CC[C@H](N4)[C@H]2[C@H](C)O3)c1C(F)(F)F]<br>4-((5S,5aS,6S,9R)-12-((1-(((1S,4S)-2-Oxa-5-azabicyclo[2.2.1]heptan-5-yl)methyl)cyclopropyl)methoxy)-1-fluoro-5-methyl-5a,6,7,8,9,10-hexahydro-5H-4-oxa-3,10a,11,13,14-pentaaza-6,9-methanonaphtho[1,8-ab]heptalene-2-yl)-6-methyl-5-(trifluoromethyl)pyridin-2-amine |
| 209 | 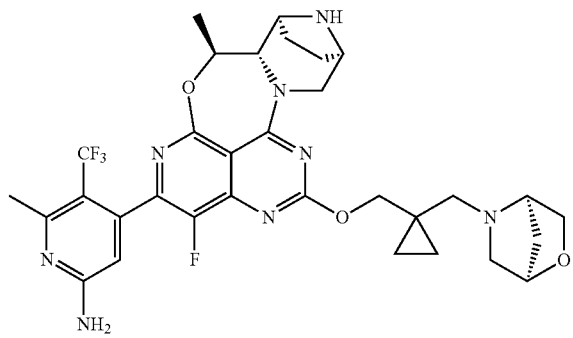 [SMILES: Cc1nc(N)cc(-c2nc3c4c(nc(OCC5(CN6C[C@H]7C[C@@H]6CO7)CC5)nc4c2F)N2C[C@H]4CC[C@H](N4)[C@H]2[C@H](C)O3)c1C(F)(F)F]<br>4-((5S,5aS,6S,9R)-12-((1-(((1R,4R)-2-Oxa-5-azabicyclo[2.2.1]heptan-5-yl)methyl)cyclopropyl)methoxy)-1-fluoro-5-methyl-5a,6,7,8,9,10-hexahydro-5H-4-oxa-3,10a,11,13,14-pentaaza-6,9-methanonaphtho[1,8-ab]heptalene-2-yl)-6-methyl-5-(trifluoromethyl)pyridin-2-amine |
| 210 | 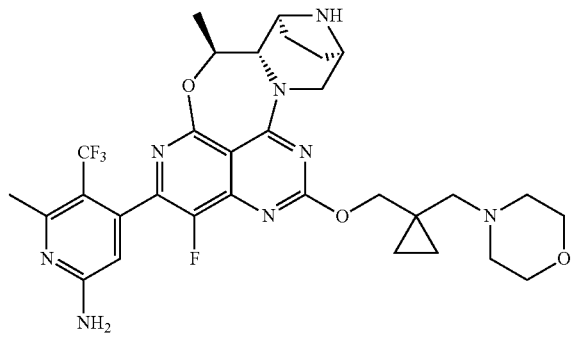 [SMILES: Cc1nc(N)cc(-c2nc3c4c(nc(OCC5(CN6CCOCC6)CC5)nc4c2F)N2C[C@H]4CC[C@H](N4)[C@H]2[C@H](C)O3)c1C(F)(F)F]<br>4-((5S,5aS,6S,9R)-1-Fluoro-5-methyl-12-((1-(morpholinomethyl)cyclopropyl)methoxy)-5a,6,7,8,9,10-hexahydro-5H-4-oxa-3,10a,11,13,14-pentaaza-6,9-methanonaphtho[1,8-ab]heptalene-2-yl)-6-methyl-5-(trifluoromethyl)pyridin-2-amine |

TABLE 1-continued

| Cmpd. No. | Chemical Structure |
|---|---|
| 211 | 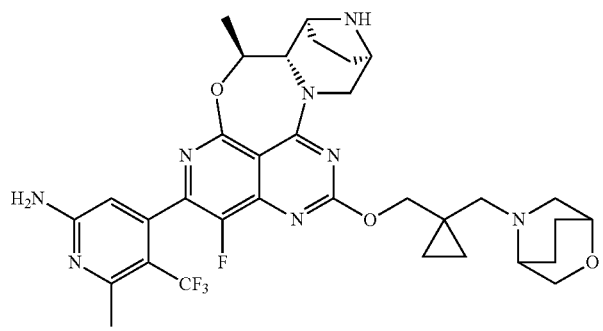 [SMILES: Cc1nc(N)cc(-c2nc3c4c(nc(OCC5(CN6CC7CCC6CO7)CC5)nc4c2F)N2C[C@H]4CC[C@H](N4)[C@H]2[C@H](C)O3)c1C(F)(F)F]<br>4-((5S,5aS,6S,9R)-12-((1-(((2-Oxa-5-azabicyclo[2.2.2]octan-5-yl)methyl)cyclopropyl)methoxy)-1-fluoro-5-methyl-5°,6,7,8,9,10-hexahydro-5H-4-oxa-3,10°,11,13,14-pentaaza-6,9-methanonaphtho[1,8-ab]heptalen-2-yl)-6-methyl-5-(trifluoromethyl)pyridin-2-amine |
| 212 | 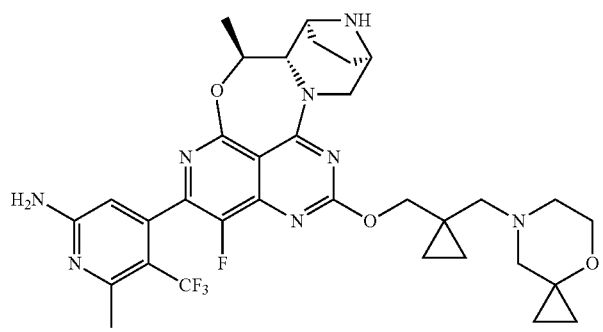 [SMILES: Cc1nc(N)cc(-c2nc3c4c(nc(OCC5(CN6CCOC7(CC7)C6)CC5)nc4c2F)N2C[C@H]4CC[C@H](N4)[C@H]2[C@H](C)O3)c1C(F)(F)F]<br>4-((5S,5aS,6S,9R)-12-((1-(((4-Oxa-7-azaspiro[2.5]octan-7-yl)methyl)cyclopropyl)methoxy)-1-fluoro-5-methyl-5a,6,7,8,9,10-hexahydro-5H-4-oxa-3,10a,11,13,14-pentaaza[6,9]methanonaphtho[1,8-ab]heptalene-2-yl)-6-methyl-5-(trifluoromethyl)pyridin-2-amine |
| 213 | 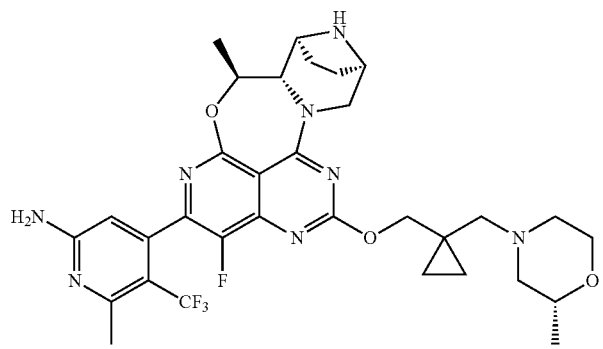 [SMILES: Cc1nc(N)cc(-c2nc3c4c(nc(OCC5(CN6CCO[C@H](C)C6)CC5)nc4c2F)N2C[C@H]4CC[C@H](N4)[C@H]2[C@H](C)O3)c1C(F)(F)F]<br>4-((5S,5aS,6S,9R)-1-Fluoro-5-methyl-12-((1-((((R)-2-methylmorpholino)methyl)cyclopropyl)methoxy)-5a,6,7,8,9,10-hexahydro-5H-4-oxa-3,10a,11,13,14-pentaaza-6,9-methanonaphtho[1,8-ab]heptalen-2-yl)-6-methyl-5-(trifluoromethyl)pyridin-2-amine |

TABLE 1-continued

| Cmpd. No. | Chemical Structure |
|---|---|
| 214 | 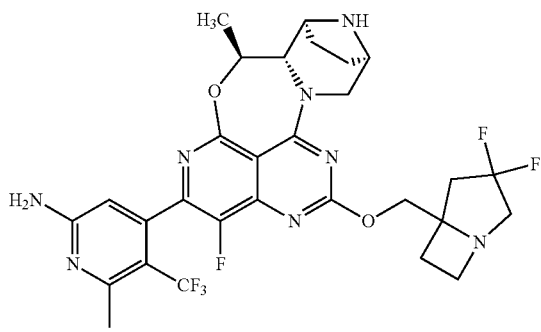 [SMILES: Cc1nc(N)cc(-c2nc3c4c(nc(OCC56CCN5CC(F)(F)C6)nc4c2F)N2C[C@H]4CC[C@H](N4)[C@H]2[C@H](C)O3)c1C(F)(F)F]  4-((5S,5aS,6S,9R)-12-(((3,3-Difluoro-1-azabicyclo[3.2.0]heptan-5-yl)methoxy)-1-fluoro-5-methyl-5°,6,7,8,9,10-hexahydro-5H-4-oxa-3,10°,11,13,14-pentaaza-6,9-methanonaphtho[1,8-ab]heptalen-2-yl)-6-methyl-5-(trifluoromethyl)pyridin-2-amine |
| 215 | 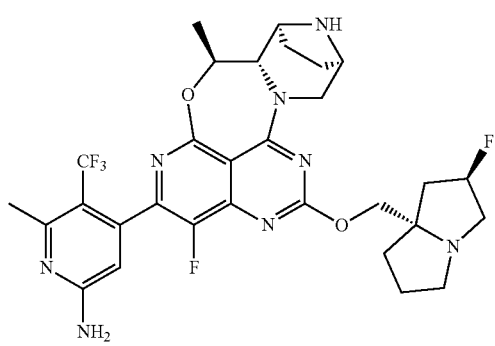 [SMILES: Cc1nc(N)cc(-c2nc3c4c(nc(OC[C@@]56CCCN5C[C@H](F)C6)nc4c2F)N2C[C@H]4CC[C@H](N4)[C@H]2[C@H](C)O3)c1C(F)(F)F]  4-((5S,5aS,6S,9R)-1-Fluoro-12-((((2R,7aS)-2-fluorotetrahydro-1H-pyrrolizin-7°(5H)-yl)methoxy)-5-methyl-5°,6,7,8,9,10-hexahydro-5H-4-oxa-3,10°,11,13,14-pentaaza-6,9-methanonaphtho[1,8-ab]heptalen-2-yl)-6-methyl-5-(trifluoromethyl)pyridin-2-amine |
| 216 | 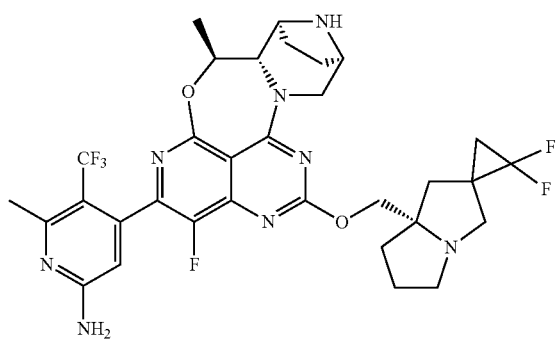 [SMILES: Cc1nc(N)cc(-c2nc3c4c(nc(OC[C@@]56CCCN5CC5(CC5(F)F)C6)nc4c2F)N2C[C@H]4CC[C@H](N4)[C@H]2[C@H](C)O3)c1C(F)(F)F]  4-((5S,5aS,6S,9R)-12-(((7a'S)-2,2-Difluorodihydro-1',3'H-spiro[cyclopropane-1,2'-pyrrolizin]-7a'(5'H)-yl)methoxy)-1-fluoro-5-methyl-5a,6,7,8,9,10-hexahydro-5H-4-oxa-3,10a,11,13,14-pentaaza[6,9]methanonaphtho[1,8-ab]heptalene-2-yl)-6-methyl-5-(trifluoromethyl)pyridin-2-amine |

TABLE 1-continued

| Cmpd. No. | Chemical Structure |
|---|---|
| 217 | 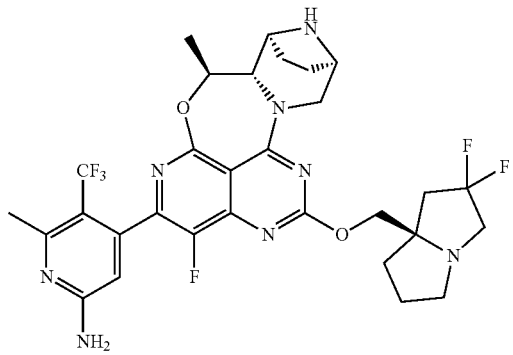 [SMILES: Cc1nc(N)cc(-c2nc3c4c(nc(OC[C@]56CCCN5CC(F)(F)C6)nc4c2F)N2C[C@H]4CC[C@H](N4)[C@H]2[C@H](C)O3)c1C(F)(F)F]<br>4-((5S,5aS,6S,9R)-12-(((R)-2,2-difluorotetrahydro-1H-pyrrolizin-7a(5H)-yl)methoxy)-1-fluoro-5-methyl-5a,6,7,8,9,10-hexahydro-5H-4-oxa-3,10a,11,13,14-pentaaza-6,9-methanonaphtho[1,8-ab]heptalen-2-yl)-6-methyl-5-(trifluoromethyl)pyridin-2-amine |
| 218 | 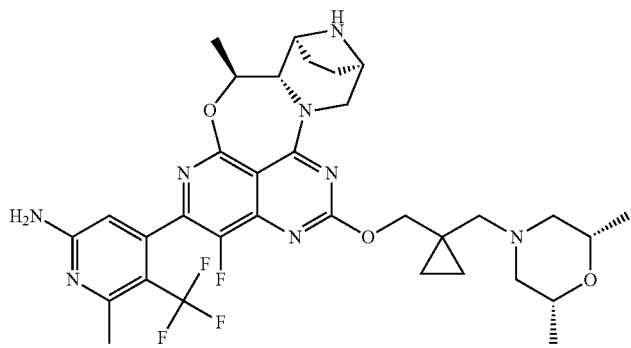 [SMILES: Cc1nc(N)cc(-c2nc3c4c(nc(OCC5(CN6C[C@@H](C)O[C@@H](C)C6)CC5)nc4c2F)N2C[C@H]4CC[C@H](N4)[C@H]2[C@H](C)O3)c1C(F)(F)F]<br>4-((5S,5aS,6S,9R)-12-((1-(((2R,6S)-2,6-Dimethylmorpholino)methyl)cyclopropyl)methoxy)-1-fluoro-5-methyl-5a,6,7,8,9,10-hexahydro-5H-4-oxa-3,10a,11,13,14-pentaaza-6,9-methanonaphtho[1,8-ab]heptalene-2-yl)-6-methyl-5-(trifluoromethyl)pyridin-2-amine |
| 219 | 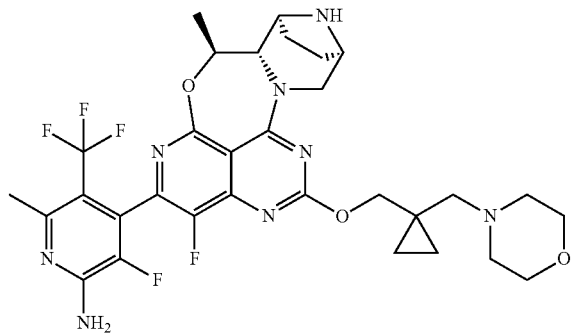 [SMILES: Cc1nc(N)c(F)c(-c2nc3c4c(nc(OCC5(CN6CCOCC6)CC5)nc4c2F)N2C[C@H]4CC[C@H](N4)[C@H]2[C@H](C)O3)c1C(F)(F)F]<br>3-Fluoro-4-((5S,5aS,6S,9R)-1-fluoro-5-methyl-12-((1-(morpholinomethyl)cyclopropyl)methoxy)-5a,6,7,8,9,10-hexahydro-5H-4-oxa-3,10a,11,13,14-pentaaza-6,9-methanonaphtho[1,8-ab]heptalene-2-yl)-6-methyl-5-(trifluoromethyl)pyridin-2-amine |

TABLE 1-continued

| Cmpd. No. | Chemical Structure |
|---|---|
| 220 | 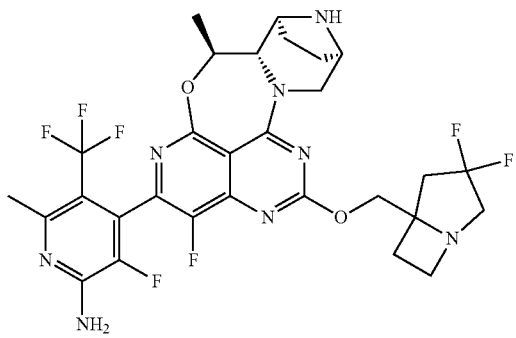 [SMILES: Cc1nc(N)c(F)c(-c2nc3c4c(nc(OCC56CCN5CC(F)(F)C6)nc4c2F)N2C[C@H]4CC[C@H](N4)[C@H]2[C@H](C)O3)c1C(F)(F)F]<br>4-((5S,5aS,6S,9R)-12-((3,3-Difluoro-1-azabicyclo[3.2.0]heptan-5-yl)methoxy)-1-fluoro-5-methyl-5a,6,7,8,9,10-hexahydro-5H-4-oxa-3,10a,11,13,14-pentaaza-6,9-methanonaphtho[1,8-ab]heptalene-2-yl)-3-fluoro-6-methyl-5-(trifluoromethyl)pyridin-2-amine |
| 221 | 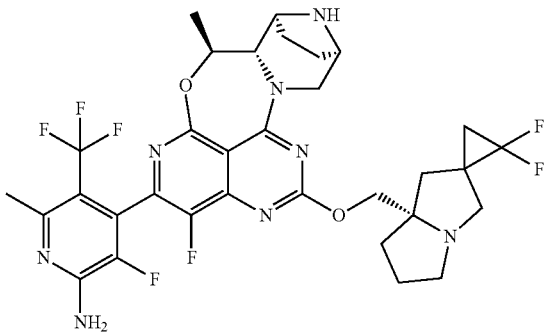 [SMILES: Cc1nc(N)c(F)c(-c2nc3c4c(nc(OC[C@@]56CCCN5CC5(CC5(F)F)C6)nc4c2F)N2C[C@H]4CC[C@H](N4)[C@H]2[C@H](C)O3)c1C(F)(F)F]<br>4-((5S,5aS,6S,9R)-12-(((7a'S)-2,2-Difluorodihydro-1'H,3'H-spiro[cyclopropane-1,2'-pyrrolizin]-7a'(5'H)-yl)methoxy)-1-fluoro-5-methyl-5a,6,7,8,9,10-hexahydro-5H-4-oxa-3,10a,11,13,14-pentaaza[6,9]methanonaphtho[1,8-ab]heptalene-2-yl)-3-fluoro-6-methyl-5-(trifluoromethyl)pyridin-2-amine |
| 222 | 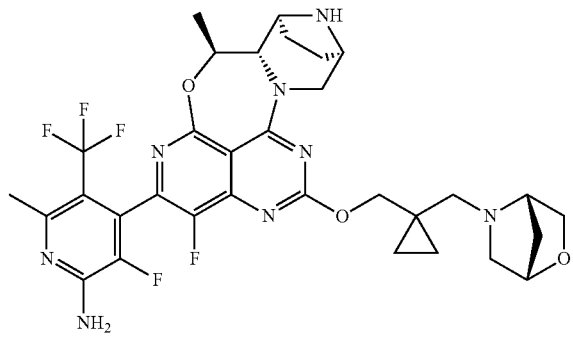 [SMILES: Cc1nc(N)c(F)c(-c2nc3c4c(nc(OCC5(CN6C[C@@H]7C[C@H]6CO7)CC5)nc4c2F)N2C[C@H]4CC[C@H](N4)[C@H]2[C@H](C)O3)c1C(F)(F)F]<br>4-((5S,5aS,6S,9R)-12-((1-((((1S,4S)-2-Oxa-5-azabicyclo[2.2.1]heptan-5-yl)methyl)cyclopropyl)methoxy)-1-fluoro-5-methyl-5a,6,7,8,9,10-hexahydro-5H-4-oxa-3,10a,11,13,14-pentaaza-6,9-methanonaphtho[1,8-ab]heptalene-2-yl)-3-fluoro-6-methyl-5-(trifluoromethyl)pyridin-2-amine |

| Cmpd. No. | Chemical Structure |
|---|---|
| 223 | 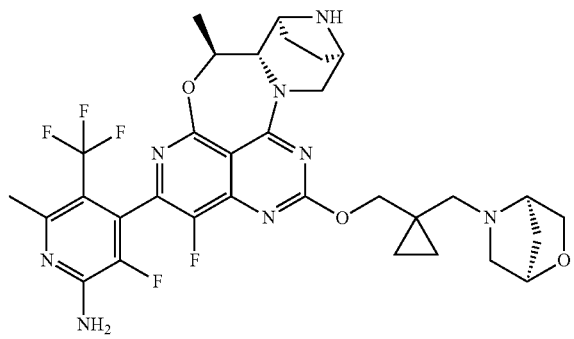 [SMILES: Cc1nc(N)c(F)c(-c2nc3c4c(nc(OCC5(CN6C[C@H]7C[C@@H]6CO7)CC5)nc4c2F)N2C[C@H]4CC[C@H](N4)[C@H]2[C@H](C)O3)c1C(F)(F)F]<br>4-((5S,5aS,6S,9R)-12-((1-((((1R,4R)-2-Oxa-5-azabicyclo[2.2.1]heptan-5-yl)methyl)cyclopropyl)methoxy)-1-fluoro-5-methyl-5a,6,7,8,9,10-hexahydro-5H-4-oxa-3,10a,11,13,14-pentaaza-6,9-methanonaphtho[1,8-ab]heptalene-2-yl)-3-fluoro-6-methyl-5-(trifluoromethyl)pyridin-2-amine |
| 224 | 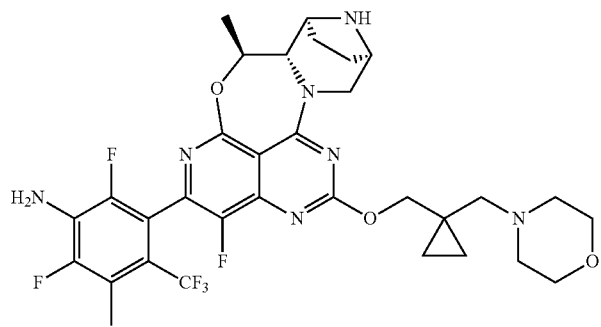 [SMILES: Cc1c(F)c(N)c(F)c(-c2nc3c4c(nc(OCC5(CN6CCOCC6)CC5)nc4c2F)N2C[C@H]4CC[C@H](N4)[C@H]2[C@H](C)O3)c1C(F)(F)F]<br>2,6-Difluoro-3-((5S,5aS,6S,9R)-1-fluoro-5-methyl-12-((1-(morpholinomethyl)cyclopropyl)methoxy)-5a,6,7,8,9,10-hexahydro-5H-4-oxa-3,10a,11,13,14-pentaaza-6,9-methanonaphtho[1,8-ab]heptalene-2-yl)-5-methyl-4-(trifluoromethyl)aniline |
| 225 | 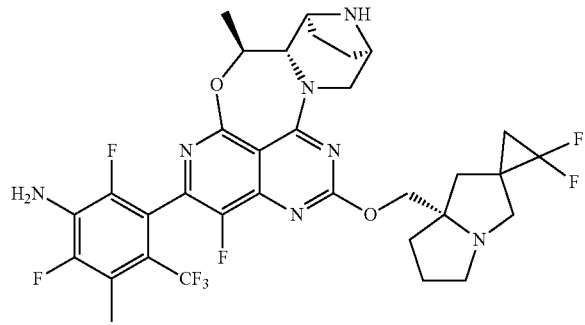 [SMILES: Cc1c(F)c(N)c(F)c(-c2nc3c4c(nc(OC[C@@]56CCCN5CC5(CC5(F)F)C6)nc4c2F)N2C[C@H]4CC[C@H](N4)[C@H]2[C@H](C)O3)c1C(F)(F)F]<br>3-((5S,5aS,6S,9R)-12-(((7'S)-2,2-Difluorodihydro-1'H,3'H-spiro[cyclopropane-1,2'-pyrrolizin]-7a'(5'H)-yl)methoxy)-1-fluoro-5-methyl-5a,6,7,8,9,10-hexahydro-5H-4-oxa-3,10a,11,13,14-pentaaza[6,9]methanonaphtho[1,8-ab]heptalene-2-yl)-2,6-difluoro-5-methyl-4-(trifluoromethyl)aniline |

TABLE 1-continued

| Cmpd. No. | Chemical Structure |
|---|---|
| 226 | 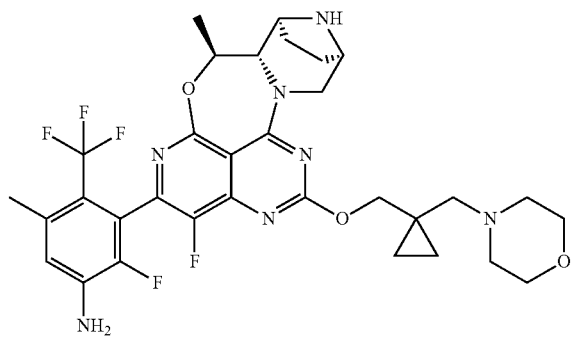 [SMILES: Cc1cc(N)c(F)c(-c2nc3c4c(nc(OCC5(CN6CCOCC6)CC5)nc4c2F)N2C[C@H]4CC[C@H](N4)[C@H]2[C@H](C)O3)c1C(F)(F)F]
2-Fluoro-3-((5S,5aS,6S,9R)-1-fluoro-5-methyl-12-((1-(morpholinomethyl)cyclopropyl)methoxy)-5a,6,7,8,9,10-hexahydro-5H-4-oxa-3,10a,11,13,14-pentaaza-6,9-methanonaphtho[1,8-ab]heptalene-2-yl)-5-methyl-4-(trifluoromethyl)aniline |
| 227 | 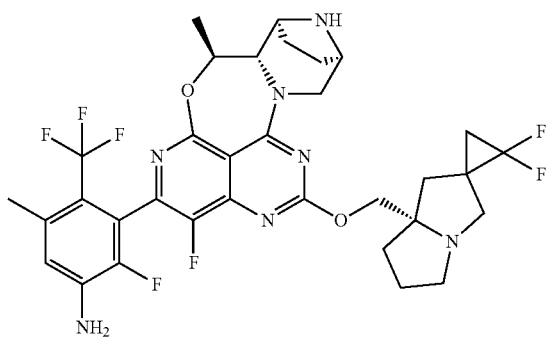 [SMILES: Cc1cc(N)c(F)c(-c2nc3c4c(nc(OC[C@@]56CCCN5CC5(CC5(F)F)C6)nc4c2F)N2C[C@H]4CC[C@H](N4)[C@H]2[C@H](C)O3)c1C(F)(F)F]
3-((5S,5aS,6S,9R)-12-(((7a'S)-2,2-Difluorodihydro-1'H,3'H-spiro[cyclopropane-1,2'-pyrrolizin]-7a'(5'H)-yl)methoxy)-1-fluoro-5-methyl-5a,6,7,8,9,10-hexahydro-5H-4-oxa-3,10a,11,13,14-pentaaza[6,9]methanonaphtho[1,8-ab]heptalene-2-yl)-2-fluoro-5-methyl-4-(trifluoromethyl)aniline |
| 228 | 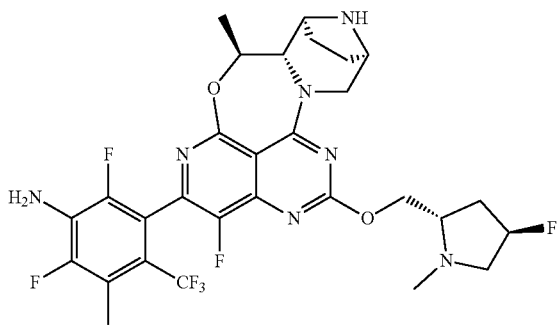 [SMILES: Cc1c(F)c(N)c(F)c(-c2nc3c4c(nc(OC[C@@H]5C[C@@H](F)CN5C)nc4c2F)N2C[C@H]4CC[C@H](N4)[C@H]2[C@H](C)O3)c1C(F)(F)F]
2,6-Difluoro-3-((5S,5aS,6S,9R)-1-fluoro-12-(((2S,4R)-4-fluoro-1-methylpyrrolidin-2-yl)methoxy)-5-methyl-5a,6,7,8,9,10-hexahydro-5H-4-oxa-3,10a,11,13,14-pentaaza-6,9-methanonaphtho[1,8-ab]heptalene-2-yl)-5-methyl-4-(trifluoromethyl)aniline |

TABLE 1-continued

| Cmpd. No. | Chemical Structure |
|---|---|
| 229 | 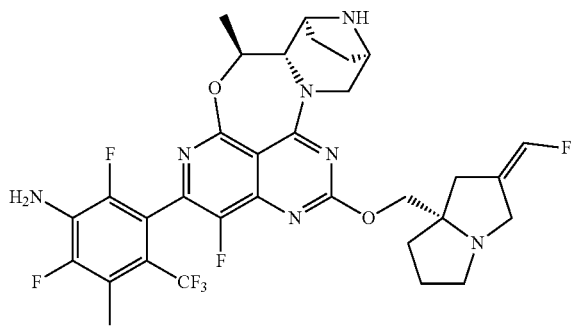 [SMILES: Cc1c(F)c(N)c(F)c(-c2nc3c4c(nc(OC[C@@]56CCCN5C/C(=C\F)C6)nc4c2F)N2C[C@H]4CC[C@H](N4)[C@H]2[C@H](C)O3)c1C(F)(F)F]<br>2,6-Difluoro-3-((5S,5aS,6S,9R)-1-fluoro-12-((((S,Z)-2-(fluoromethylene)tetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-2-yl)-5-methyl-4-(trifluoromethyl)aniline |
| 230 | 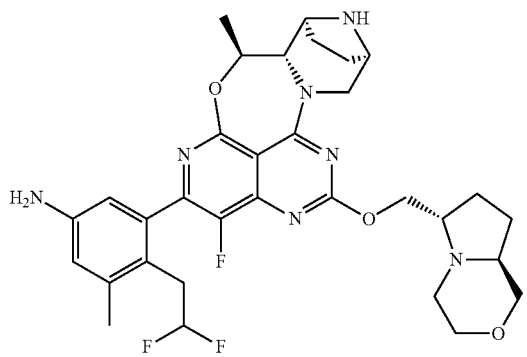 [SMILES: Cc1cc(N)cc(-c2nc3c4c(nc(OC[C@@H]5CC[C@H]6COCCN65)nc4c2F)N2C[C@H]4CC[C@H](N4)[C@H]2[C@H](C)O3)c1CC(F)F]<br>tert-Butyl (5S,5aS,6S,9R)-2-(5-amino-2-(2,2-difluoroethyl)-3-methylphenyl)-1-fluoro-12-(((6S,8aS)-hexahydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate |
| 231 | 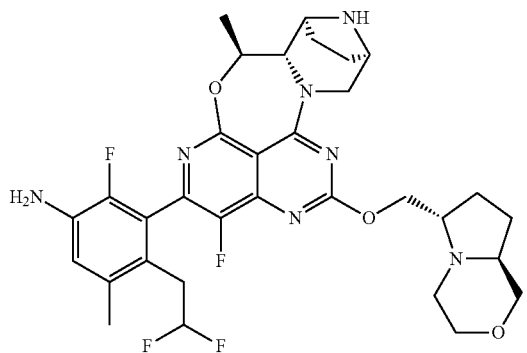 [SMILES: Cc1cc(N)c(F)c(-c2nc3c4c(nc(OC[C@@H]5CC[C@H]6COCCN65)nc4c2F)N2C[C@H]4CC[C@H](N4)[C@H]2[C@H](C)O3)c1CC(F)F]<br>4-(2,2-Difluoroethyl)-2-fluoro-3-((5S,5aS,6S,9R)-1-fluoro-12-(((6S,8aS)-hexahydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalene-2-yl)-5-methylaniline |

TABLE 1-continued

| Cmpd. No. | Chemical Structure |
|---|---|
| 232 | 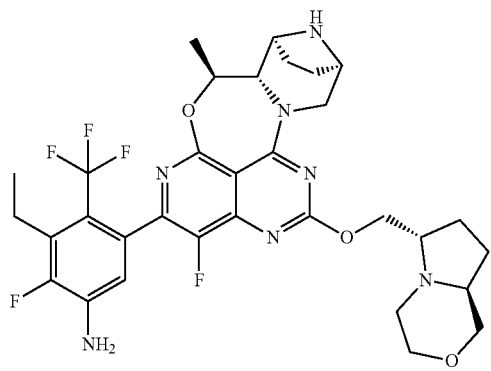 [SMILES: CCc1c(F)c(N)cc(-c2nc3c4c(nc(OC[C@@H]5CC[C@H]6COCCN65)nc4c2F)N2C[C@H]4CC[C@H](N4)[C@H]2[C@H](C)O3)c1C(F)(F)F]<br>3-Ethyl-2-fluoro-5-((5S,5aS,6S,9R)-1-fluoro-12-((((6S,8aS)-hexahydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalene-2-yl)-4-(trifluoromethyl)aniline |
| 233 | 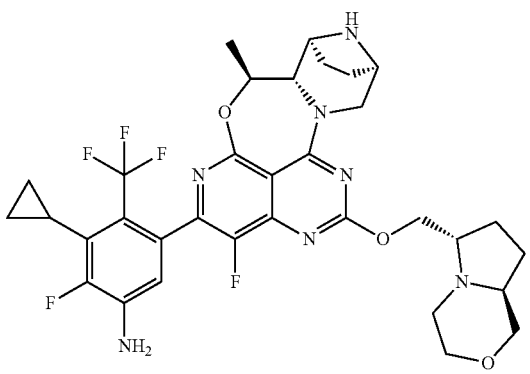 [SMILES: C[C@@H]1Oc2nc(-c3cc(N)c(F)c(C4CC4)c3C(F)(F)F)c(F)c3nc(OC[C@@H]4CC[C@H]5COCCN54)nc(c23)N2C[C@H]3CC[C@H](N3)[C@@H]12]<br>3-Cyclopropyl-2-fluoro-5-((5S,5aS,6S,9R)-1-fluoro-12-(((6S,8aS)-hexahydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalene-2-yl)-4-(trifluoromethyl)aniline |
| 234 | 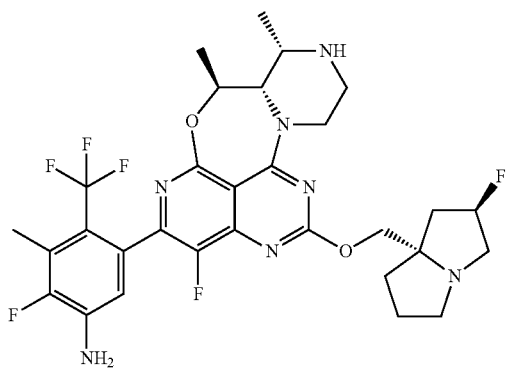 [SMILES: Cc1c(F)c(N)cc(-c2nc3c4c(nc(OC[C@@]56CCCN5C[C@H](F)C6)nc4c2F)N2CCN[C@@H](C)[C@H]2[C@H](C)O3)c1C(F)(F)F] |

TABLE 1-continued
| Cmpd. No. | Chemical Structure |
|---|---|
| | 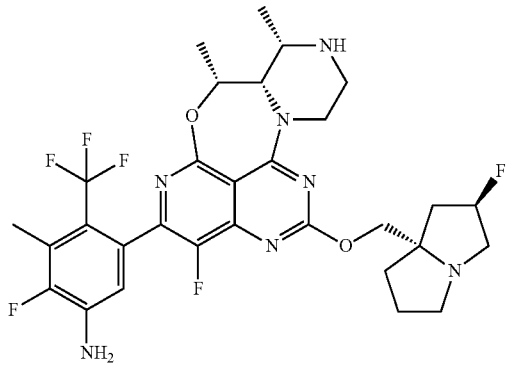 [SMILES: Cc1c(F)c(N)cc(-c2nc3c4c(nc(OC[C@@]56CCCN5C[C@H](F)C6)nc4c2F)N2CCN[C@@H](C)[C@H]2[C@@H](C)O3)c1C(F)(F)F] |
| | 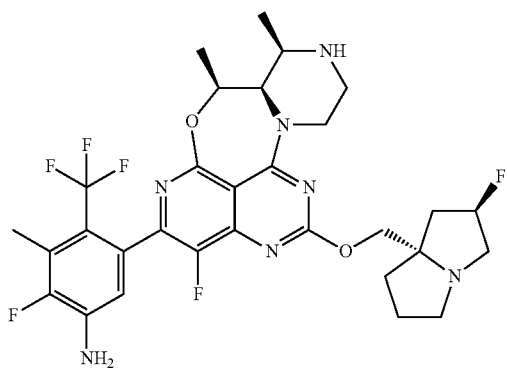 [SMILES: Cc1c(F)c(N)cc(-c2nc3c4c(nc(OC[C@@]56CCCN5C[C@H](F)C6)nc4c2F)N2CCN[C@H](C)[C@@H]2[C@H](C)O3)c1C(F)(F)F] |
| | 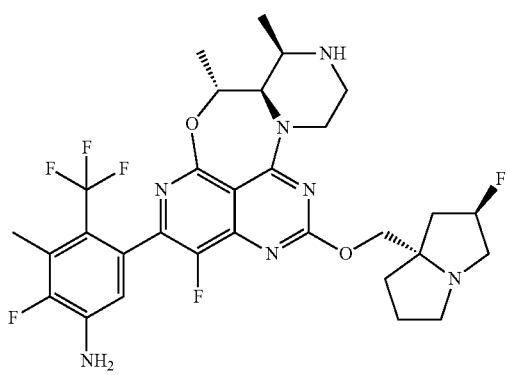 [SMILES: Cc1c(F)c(N)cc(-c2nc3c4c(nc(OC[C@@]56CCCN5C[C@H](F)C6)nc4c2F)N2CCN[C@H](C)[C@@H]2[C@@H](C)O3)c1C(F)(F)F] |
| | 2-Fluoro-5-(1-fluoro-11-(((2R,7aS)-2-fluorotetrahydro-1H-pyrrolizin-7a(5H)-yl)methoxy)-5,6-dimethyl-5,5a,6,7,8,9-hexahydro-4-oxa-3,7,9a,10,12-pentaazabenzo[4,5]cyclohepta[1,2,3-de]naphthalen-2-yl)-3-methyl-4-(trifluoromethyl)aniline (four isomers) |
| 235 | 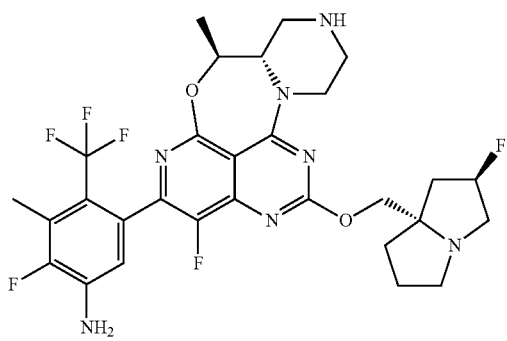 [SMILES: Cc1c(F)c(N)cc(-c2nc3c4c(nc(OC[C@@]56CCCN5C[C@H](F)C6)nc4c2F)N2CCNC[C@H]2[C@H](C)O3)c1C(F)(F)F] |

TABLE 1-continued

| Cmpd. No. | Chemical Structure |
|---|---|

2-Fluoro-5-((5aS)-1-fluoro-11-(((2R,7aS)-2-fluorotetrahydro-1H-pyrrolizin-7a(5H)-yl)methoxy)-5-methyl-5,5a,6,7,8,9-hexahydro-4-oxa-3,7,9a,10,12-pentaazabenzo[4,5]cyclohepta[1,2,3-de]naphthalen-2-yl)-3-methyl-4-(trifluoromethyl)aniline (two isomers)

236

2-Fluoro-5-((5aS,6S,9S)-1-fluoro-12-(((2R,7aS)-2-fluorotetrahydro-1H-pyrrolizin-7a(5H)-yl)methoxy)-5a,6,7,8,9,10-hexahydro-5H-4-oxa-3,10a,11,13,15-pentaaza-6,9-ethanonaphtho[1,8-ab]heptalene-2-yl)-3-methyl-4-(trifluoromethyl)aniline

237

TABLE 1-continued

| Cmpd. No. | Chemical Structure |
|---|---|
| | 2-Fluoro-5-((5aR,6S,9R)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-2-yl)-3-methyl-4-(trifluoromethyl)aniline (two isomers) |
| 238 | 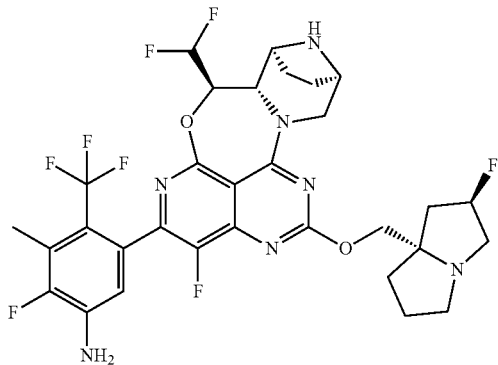 [SMILES: Cc1c(F)c(N)cc(-c2nc3c4c(nc(OC[C@@]56CCCN5C[C@H](F)C6)nc4c2F)N2C[C@H]4CC[C@H](N4)[C@H]2[C@H](C(F)F)O3)c1C(F)(F)F] 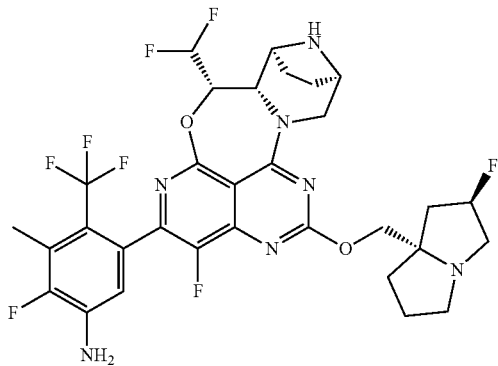 [SMILES: Cc1c(F)c(N)cc(-c2nc3c4c(nc(OC[C@@]56CCCN5C[C@H](F)C6)nc4c2F)N2C[C@H]4CC[C@H](N4)[C@H]2[C@@H](C(F)F)O3)c1C(F)(F)F] |
| | 5-((6S,9R)-5-(Difluoromethyl)-1-fluoro-12-(((2R,7aS)-2-fluorotetrahydro-1H-pyrrolizin-7a(5H)-yl)methoxy)-5a,6,7,8,9,10-hexahydro-5H-4-oxa-3,10a,11,13,14-pentaaza-6,9-methanonaphtho[1,8-ab]heptalene-2-yl)-2-fluoro-3-methyl-4-(trifluoromethyl)aniline (two isomers) |
| 239 | 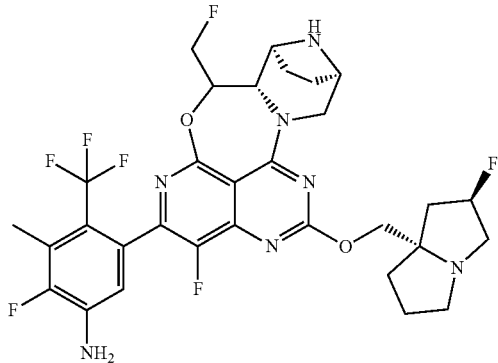 |
| | 2-Fluoro-5-((5aS,6S,9R)-1-fluoro-5-(fluoromethyl)-12-(((2R,7aS)-2-fluorotetrahydro-1H-pyrrolizin-7a(5H)-yl)methoxy)-5a,6,7,8,9,10-hexahydro-5H-4-oxa-3,10a,11,13,14-pentaaza-6,9-methanonaphtho[1,8-ab]heptalene-2-yl)-3-methyl-4-(trifluoromethyl)aniline |

TABLE 1-continued

| Cmpd. No. | Chemical Structure |
|---|---|
| 240 | 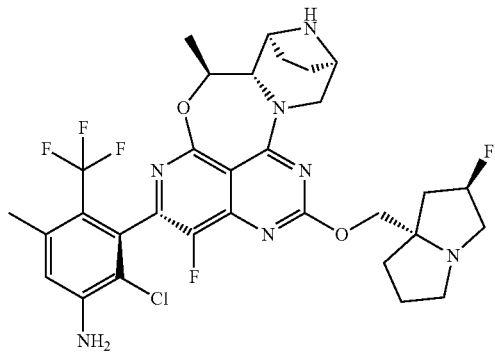 |
| | 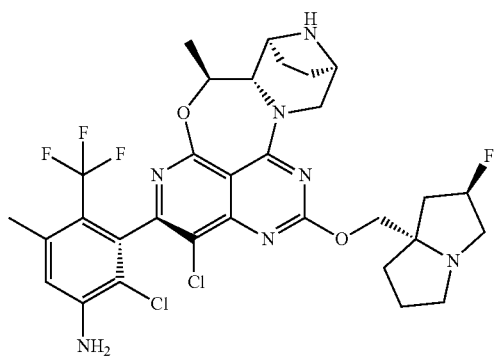 |
| | 2-Chloro-3-((5S,5aS,6S,9R)-1-chloro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-2-yl)-5-methyl-4-(trifluoromethyl)aniline (two atropisomers) |
| 241 | 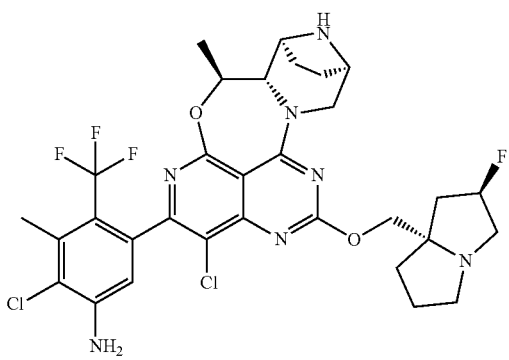 [SMILES: Cc1c(Cl)c(N)cc(-c2nc3c4c(nc(OC[C@@]56CCCN5C[C@H](F)C6)nc4c2Cl)N2C[C@H]4CC[C@H](N4)[C@H]2[C@H](C)O3)c1C(F)(F)F] |
| | 2-Chloro-5-((5S,5aS,6S,9R)-1-chloro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-2-yl)-3-methyl-4-(trifluoromethyl)aniline |

TABLE 1-continued

| Cmpd. No. | Chemical Structure |
|---|---|
| 242 | 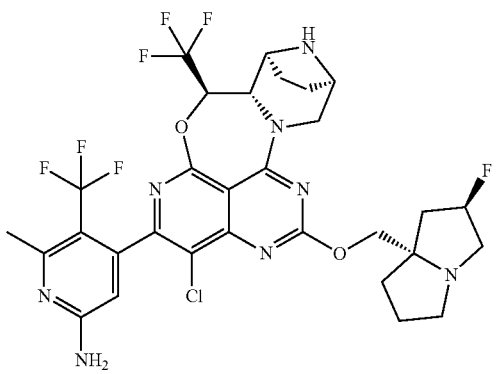 [SMILES: Cc1nc(N)cc(-c2nc3c4c(nc(OC[C@@]56CCCN5C[C@H](F)C6)nc4c2Cl)N2C[C@H]4CC[C@H](N4)[C@H]2[C@H](C(F)(F)F)O3)c1C(F)(F)F]<br>4-((5R,5aS,6S,9R)-1-Fluoro-12-(((2R,7aS)-2-fluorotetrahydro-1H-pyrrolizin-7a(5H)-yl)methoxy)-5-(trifluoromethyl)-5a,6,7,8,9,10-hexahydro-5H-4-oxa-3,10a,11,13,14-pentaaza-6,9-methanonaphtho[1,8-ab]pyridine-2-yl)-6-methyl-5-(trifluoromethyl)pyridine-2-amine |
| 243 | 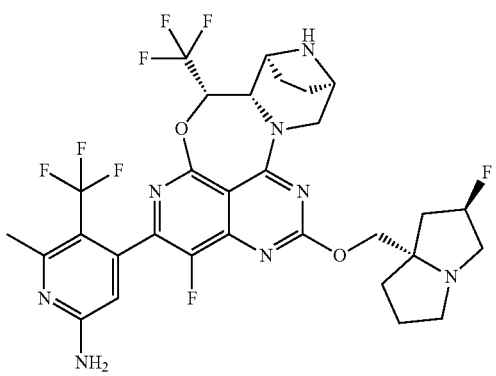 [SMILES: Cc1nc(N)cc(-c2nc3c4c(nc(OC[C@@]56CCCN5C[C@H](F)C6)nc4c2F)N2C[C@H]4CC[C@H](N4)[C@H]2[C@@H](C(F)(F)F)O3)c1C(F)(F)F]<br>4-((6R,9S)-1-fluoro-12-(((2S,7aR)-2-fluorotetrahydro-1H-pyrrolizin-7a(5H)-yl)methoxy)-5-(trifluoromethyl)-5a,6,7,8,9,10-hexahydro-5H-4-oxa-3,10a,11,13,14-pentaaza-6,9-methanonaphtho[1,8-ab]heptalene-2-yl)-6-methyl-5-(trifluoromethyl)pyridin-2-amine |
| 244 | 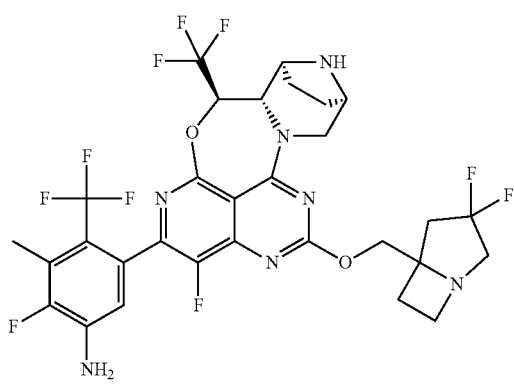 [SMILES: Cc1c(F)c(N)cc(-c2nc3c4c(nc(OCC56CCN5CC(F)(F)C6)nc4c2F)N2C[C@H]4CC[C@H](N4)[C@H]2[C@H](C(F)(F)F)O3)c1C(F)(F)F]<br>5-((5R,5aS,6S,9R)-12-((3,3-Difluoro-1-azabicyclo[3.2.0]heptan-5-yl)methoxy)-1-fluoro-5-(trifluoromethyl)-5a,6,7,8,9,10-hexahydro-5H-4-oxa-3,10a,11,13,14-pentaaza-6,9-methanonaphtho[1,8-ab]heptalene-2-yl)-2-fluoro-3-methyl-4-(trifluoromethyl)aniline (mixture of two diastereomers) |

TABLE 1-continued

| Cmpd. No. | Chemical Structure |
|---|---|
| 245 | 2-Fluoro-5-((5R,5aS,6S,9R)-1-fluoro-12-((((6S,8aS)-hexahydro-1H-pyrrolo[2,1-c][1,4]oxazin-6-yl)methoxy)-5-(trifluoromethyl)-5a,6,7,8,9,10-hexahydro-5H-4-oxa-3,10a,11,13,14-pentaaza-6,9-methanonaphtho[1,8-ab]heptalene-2-yl)-3-methyl-4-(trifluoromethyl)aniline |
| 246 | 2-Fluoro-5-((5S,5aS,6S,9R)-1-fluoro-12-(((2R,7aS)-2-fluorotetrahydro-1H-pyrrolizin-7a(5H)-yl)methoxy)-5-(trifluoromethyl)-5a,6,7,8,9,10-hexahydro-5H-4-oxa-3,10a,11,13,14-pentaaza-6,9-methanonaphtho[1,8-ab]heptalene-2-yl)-3-methyl-4-(trifluoromethyl)aniline |
| 247 | 2-Fluoro-5-((5R,5aS,6S,9R)-1-fluoro-12-(((2R,7aS)-2-fluorotetrahydro-1H-pyrrolizin-7a(5H)-yl)methoxy)-5-(trifluoromethyl)-5a,6,7,8,9,10-hexahydro-5H-4-oxa-3,10a,11,13,14-pentaaza-6,9-methanonaphtho[1,8-ab]heptalene-2-yl)-3-methyl-4-(trifluoromethyl)aniline |

TABLE 1-continued

| Cmpd. No. | Chemical Structure |
|---|---|
| 248 | 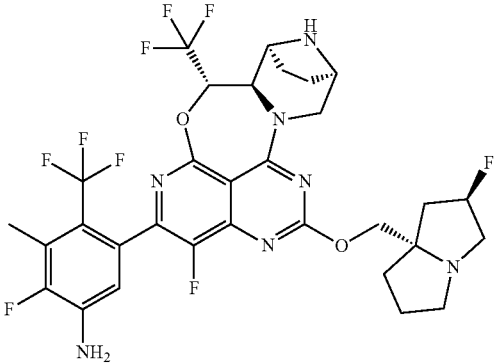 [SMILES: Cc1c(F)c(N)cc(-c2nc3c4c(nc(OC[C@@]56CCCN5C[C@H](F)C6)nc4c2F)N2C[C@H]4CC[C@H](N4)[C@@H]2[C@@H](C(F)(F)F)O3)c1C(F)(F)F] |

2-Fluoro-5-(((5S,5aR,6S,9R)-1-fluoro-12-(((2R,7aS)-2-fluorotetrahydro-1H-pyrrolizin-7a(5H)-yl)methoxy)-5-(trifluoromethyl)-5a,6,7,8,9,10-hexahydro-5H-4-oxa-3,10a,11,13,14-pentaaza-6,9-methanonaphtho[1,8-ab]heptalene-2-yl)-3-methyl-4-(trifluoromethyl)aniline

| 249 | 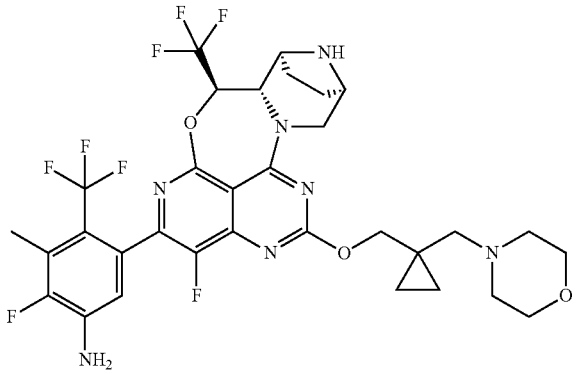 [SMILES: Cc1c(F)c(N)cc(-c2nc3c4c(nc(OCC5(CN6CCOCC6)CC5)nc4c2F)N2C[C@H]4CC[C@H](N4)[C@H]2[C@H](C(F)(F)F)O3)c1C(F)(F)F] |

2-Fluoro-5-(((5R,5aS,6S,9R)-1-fluoro-12-((1-(morpholinomethyl)cyclopropyl)methoxy)-5-(trifluoromethyl)-5a,6,7,8,9,10-hexahydro-5H-4-oxa-3,10a,11,13,14-pentaaza-6,9-methanonaphtho[1,8-ab]heptalene-2-yl)-3-methyl-4-(trifluoromethyl)aniline

| 250 | 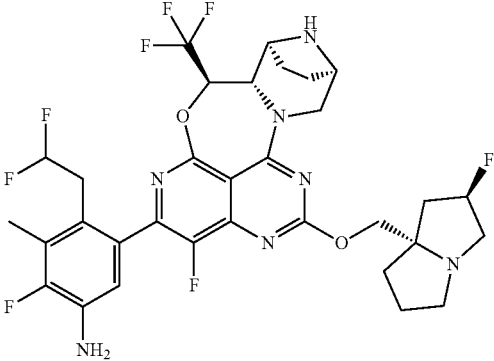 [SMILES: Cc1c(F)c(N)cc(-c2nc3c4c(nc(OC[C@@]56CCCN5C[C@H](F)C6)nc4c2F)N2C[C@H]4CC[C@H](N4)[C@H]2[C@H](C(F)(F)F)O3)c1CC(F)F] |

4-(2,2-Difluoroethyl)-2-fluoro-5-(((5R,5aS,6S,9R)-1-fluoro-12-(((2R,7aS)-2-fluorotetrahydro-1H-pyrrolizin-7a(5H)-yl)methoxy)-5-(trifluoromethyl)-5a,6,7,8,9,10-hexahydro-5H-4-oxa-3,10a,11,13,14-pentaaza-6,9-methanonaphtho[1,8-ab]heptalene-2-yl)-3-methylaniline TABLE 1-continued

| Cmpd. No. | Chemical Structure |
|---|---|
| 251 | 5-Ethynyl-4-((5R,5aS,6S,9R)-1-fluoro-12-(((2R,7aS)-2-fluorotetrahydro-1H-pyrrolizin-7a(5H)-yl)methoxy)-5-(trifluoromethyl)-5a,6,7,8,9,10-hexahydro-5H-4-oxa-3,10a,11,13,14-pentaaza-6,9-methanonaphtho[1,8-ab]heptalene-2-naphthalen-2-ol |
| 252 | 4-((5R,5aS,6S,9R)-12-((3,3-Difluoro-1-azabicyclo[3.2.0]heptan-5-yl)methoxy)-1-fluoro-5-(trifluoromethyl)-5a,6,7,8,9,10-hexahydro-5H-4-oxa-3,10a,11,13,14-pentaaza-6,9-methanonaphtho[1,8-ab]heptalene-2-yl)-6-methyl-5-(trifluoromethyl)pyridin-2-amine (two isomers) |

TABLE 1-continued

| Cmpd. No. | Chemical Structure |
|---|---|
| 253 | 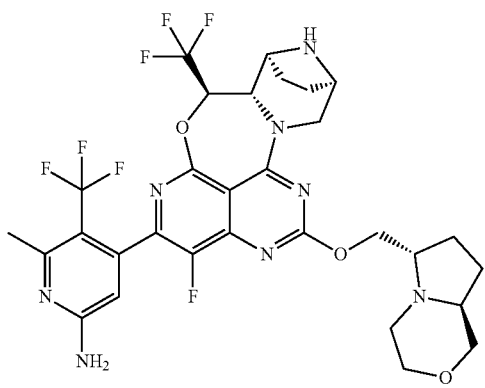 [SMILES: Cc1nc(N)cc(-c2nc3c4c(nc(OC[C@@H]5CC[C@H]6COCCN65)nc4c2F)N2C[C@H]4CC[C@H](N4)[C@H]2[C@H](C(F)(F)F)O3)c1C(F)(F)F]<br>4-((5R,5aS,6S,9R)-1-Fluoro-12-(((6S,8aS)-hexahydro-1H-pyrrolo[2,1-c][1,4]oxazin-6-yl)methoxy)-5-(trifluoromethyl)-5a,6,7,8,9,10-hexahydro-5H-4-oxa-3,10a,11,13,14-pentaaza-6,9-methanonaphtho[1,8-ab]heptalene-2-yl)-6-methyl-5-(trifluoromethyl)pyridin-2-amine |
| 254 | 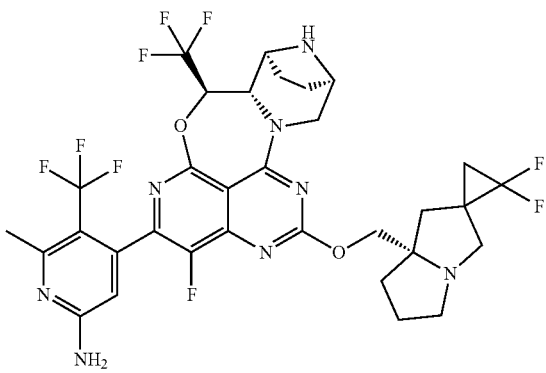 [SMILES: Cc1nc(N)cc(-c2nc3c4c(nc(OC[C@@]56CCCN5CC5(CC5(F)F)C6)nc4c2F)N2C[C@H]4CC[C@H](N4)[C@H]2[C@H](C(F)(F)F)O3)c1C(F)(F)F]<br>4-((5R,5aS,6S,9R)-12-(((7a'S)-2,2-Difluorodihydro-1'H,3'H-spiro[cyclopropane-1,2'-pyrrolizin]-7a'(5'H)-yl)methoxy)-1-fluoro-5-(trifluoromethyl)-5a,6,7,8,9,10-hexahydro-5H-4-oxa-3,10a,11,13,14-pentaaza[6,9]methanonaphtho[1,8-ab]heptalene-2-yl)-6-methyl-5-(trifluoromethyl)pyridin-2-amine |
| 255 | 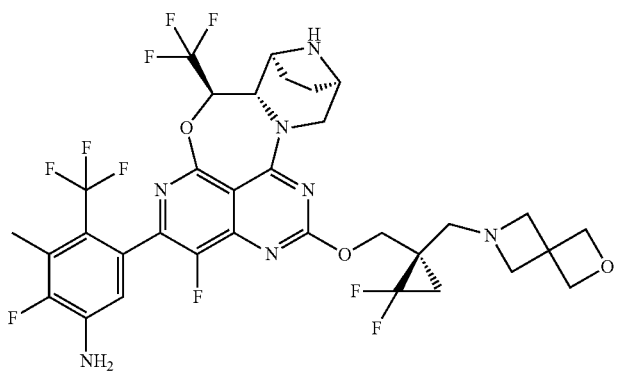 [SMILES: Cc1c(F)c(N)cc(-c2nc3c4c(nc(OC[C@]5(CN6CC7(COC7)C6)CC5(F)F)nc4c2F)N2C[C@H]4CC[C@H](N4)[C@H]2[C@H](C(F)(F)F)O3)c1C(F)(F)F] |

TABLE 1-continued

| Cmpd. No. | Chemical Structure |
|---|---|
| | 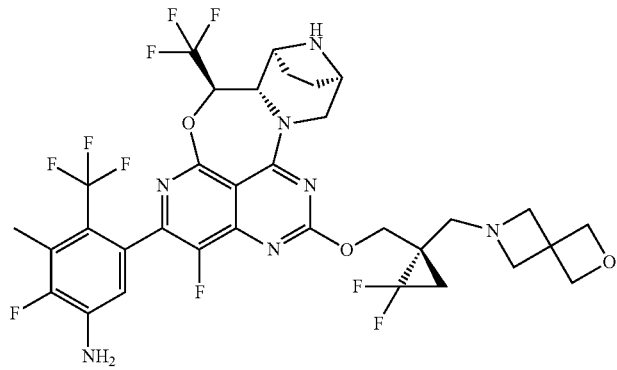 [SMILES: Cc1c(F)c(N)cc(-c2nc3c4c(nc(OC[C@@]5(CN6CC7(COC7)C6)CC5(F)F)nc4c2F)N2C[C@H]4CC[C@H](N4)[C@H]2[C@H](C(F)(F)F)O3)c1C(F)(F)F]
5-((5R,5aS,6S,9R)-12-(((R)-1-((2-oxa-6-azaspiro[3.3]heptan-6-yl)methyl)-2,2-difluorocyclopropyl)methoxy)-1-fluoro-5-(trifluoromethyl)-5a,6,7,8,9,10-hexahydro-5H-4-oxa-3,10a,11,13,14-pentaaza[6,9]methanonaphtho[1,8-ab]heptalen-2-yl)-2-fluoro-3-methyl-4-(trifluoromethyl)aniline (mixture and two separate diastereomers) |
| 256 | 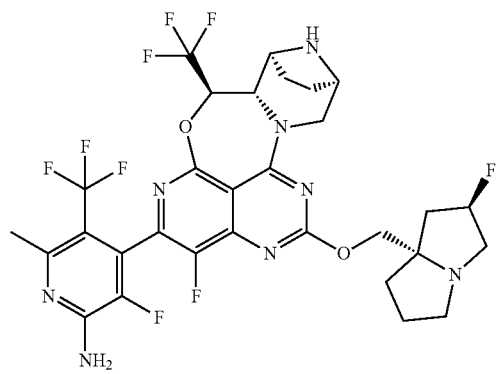 [SMILES: Cc1nc(N)c(F)c(-c2nc3c4c(nc(OC[C@@]56CCCN5C[C@H](F)C6)nc4c2F)N2C[C@H]4CC[C@H](N4)[C@H]2[C@H](C(F)(F)F)O3)c1C(F)(F)F]
3-Fluoro-4-((5R,5aS,6S,9R)-1-fluoro-12-(((2R,7aS)-2-fluorotetrahydro-1H-pyrrolizin-7a(5H)-yl)methoxy)-5-(trifluoromethyl)-5a,6,7,8,9,10-hexahydro-5H-4-oxa-3,10a,11,13,14-pentaaza-6,9-methanonaphtho[1,8-ab]heptalene-2-yl)-6-methyl-5-(trifluoromethyl)pyridin-2-amine |
| 257 | 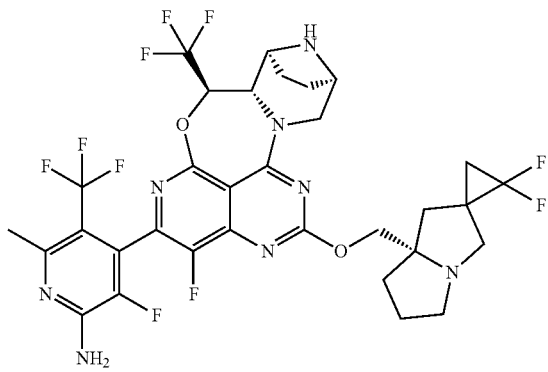 [SMILES: Cc1nc(N)c(F)c(-c2nc3c4c(nc(OC[C@@]56CCCN5CC5(CC5(F)F)C6)nc4c2F)N2C[C@H]4CC[C@H](N4)[C@H]2[C@H](C(F)(F)F)O3)c1C(F)(F)F]
4-((5R,5aS,6S,9R)-12-(((7a'S)-2,2-Difluorodihydro-1'H,3'H-spiro[cyclopropane-1,2'-pyrrolizin]-7a'(5'H)-yl)methoxy)-1-fluoro-5-(trifluoromethyl)-5a,6,7,8,9,10-hexahydro-5H-4-oxa-3,10a,11,13,14-pentaaza[6,9]methanonaphtho[1,8-ab]heptalene-2-yl)-3-fluoro-6-methyl-5-(trifluoromethyl)pyridin-2-amine |

TABLE 1-continued

| Cmpd. No. | Chemical Structure |
|---|---|
| 258 | 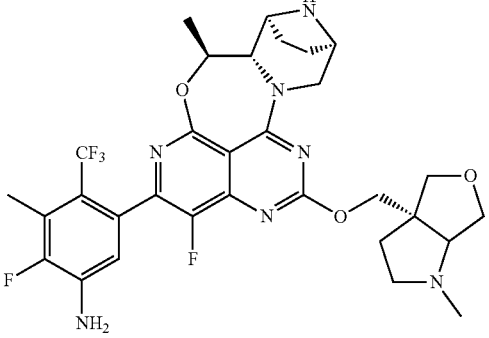 |
| | 2-Fluoro-5-((5S,5aS,6S,9R)-1-fluoro-5-methyl-12-((1-methyltetrahydro-1H-furo[3,4-b]pyrrol-3a(4H)-yl)methoxy)-5a,6,7,8,9,10-hexahydro-5H-4-oxa-3,10a,11,13,14-pentaaza-6,9-methanonaphtho[1,8-ab]heptalene-2-yl)-3-methyl-4-(trifluoromethyl)aniline (two isomers) |
| 259 | 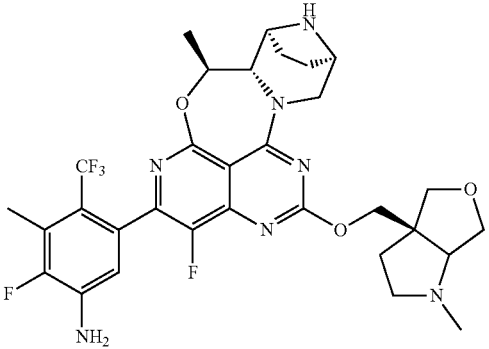 [SMILES: Cc1c(F)c(N)cc(-c2nc3c4c(nc(OC[C@]56CCN(C)C5COC6)nc4c2F)N2C[C@H]4CC[C@H](N4)[C@H]2[C@H](C)O3)c1C(F)(F)F] |
| | 5-((5S,5aS,6S,9R)-12-((1-((2,2-Dimethylaziridin-1-yl)methyl)cyclopropyl)methoxy)-1-fluoro-5-methyl-5a,6,7,8,9,10-hexahydro-5H-4-oxa-3,10a,11,13,14-pentaaza-6,9-methanonaphtho[1,8-ab]heptalene-2-yl)-2-fluoro-3-methyl-4-(trifluoromethyl)aniline |
| 260 | 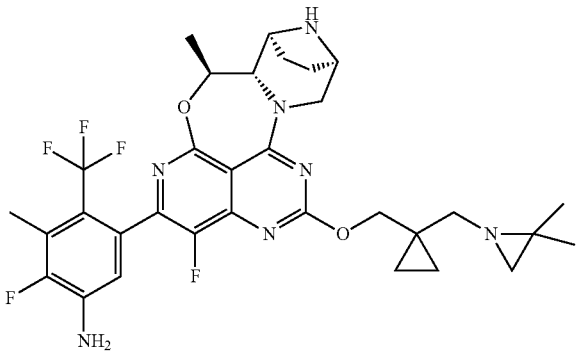 |

TABLE 1-continued

| Cmpd. No. | Chemical Structure |
|---|---|
| 261 | 6-(Difluoromethyl)-4-((5S,5aS,6S,9R)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-2-yl)-5-(trifluoromethyl)pyridin-2-amine 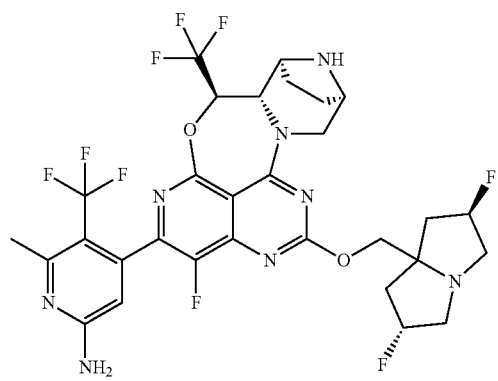 [SMILES: Cc1nc(N)cc(-c2nc3c4c(nc(OCC56C[C@@H](F)CN5C[C@H](F)C6)nc4c2F)N2C[C@H]4CC[C@H](N4)[C@H]2[C@H](C(F)(F)F)O3)c1C(F)(F)F] |
| 262 | 4-((5R,5aS,6S,9R)-12-(((2R,6R)-2,6-Difluorotetrahydro-1H-pyrrolizin-7a(5H)-yl)methoxy)-1-fluoro-5-(trifluoromethyl)-5a,6,7,8,9,10-hexahydro-5H-4-oxa-3,10a,11,13,14-pentaaza-6,9-methanonaphtho[1,8-ab]heptalene-2-yl)-6-methyl-5-(trifluoromethyl)pyridin-2-amine 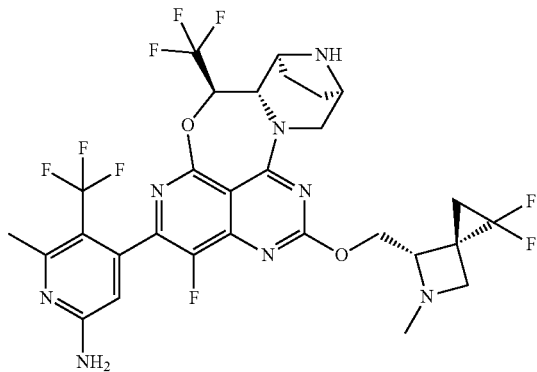 [SMILES: Cc1nc(N)cc(-c2nc3c4c(nc(OC[C@H]5N(C)C[C@]56CC6(F)F)nc4c2F)N2C[C@H]4CC[C@H](N4)[C@H]2[C@H](C(F)(F)F)O3)c1C(F)(F)F] 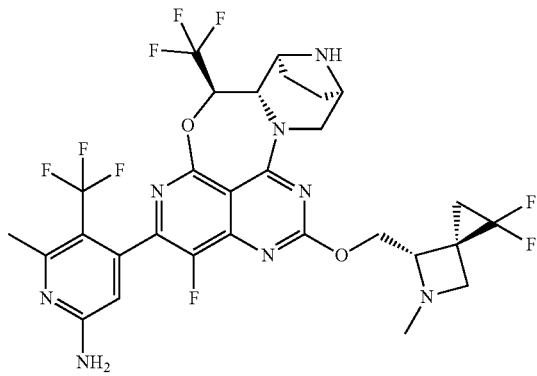 [SMILES: Cc1nc(N)cc(-c2nc3c4c(nc(OC[C@H]5N(C)C[C@@]56CC6(F)F)nc4c2F)N2C[C@H]4CC[C@H](N4)[C@H]2[C@H](C(F)(F)F)O3)c1C(F)(F)F] |

TABLE 1-continued
| Cmpd. No. | Chemical Structure |
|---|---|
| | 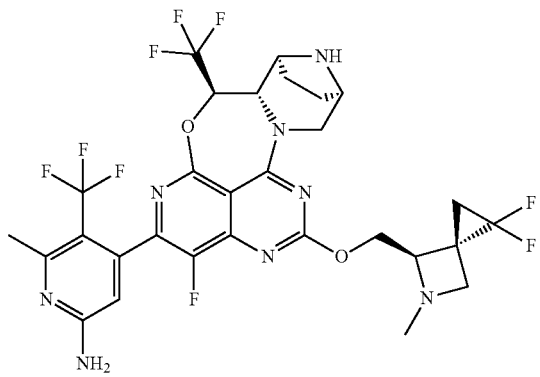 [SMILES: Cc1nc(N)cc(-c2nc3c4c(nc(OC[C@@H]5N(C)C[C@]56CC6(F)F)nc4c2F)N2C[C@H]4CC[C@H](N4)[C@H]2[C@H](C(F)(F)F)O3)c1C(F)(F)F] |
| | 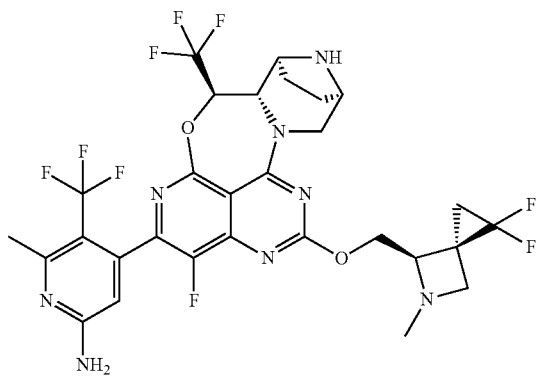 [SMILES: Cc1nc(N)cc(-c2nc3c4c(nc(OC[C@@H]5N(C)C[C@@]56CC6(F)F)nc4c2F)N2C[C@H]4CC[C@H](N4)[C@H]2[C@H](C(F)(F)F)O3)c1C(F)(F)F]
4-((5R,5aS,6S,9R)-12-((1,1-Difluoro-5-methyl-5-azaspiro[2.3]hexan-4-yl)methoxy)-1-fluoro-5-(trifluoromethyl)-5a,6,7,8,9,10-hexahydro-5H-4-oxa-3,10a,11,13,14-pentaaza[6,9]methanonaphtho[1,8-ab]heptalene-2-yl)-6-methyl-5-(trifluoromethyl)pyridin-2-amine (four isomers) |
| 263 | 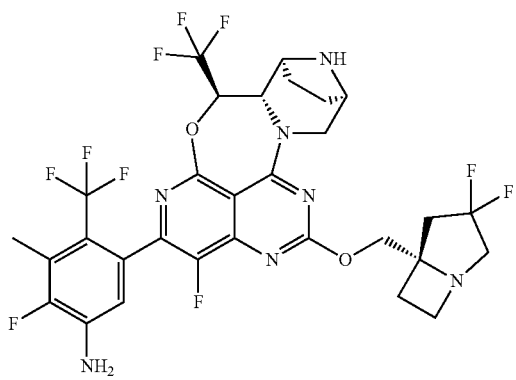 [SMILES: Cc1c(F)c(N)cc(-c2nc3c4c(nc(OC[C@@]56CCN5CC(F)(F)C6)nc4c2F)N2C[C@H]4CC[C@H](N4)[C@H]2[C@H](C(F)(F)F)O3)c1C(F)(F)F] |

| Cmpd. No. | Chemical Structure |
|---|---|
| | 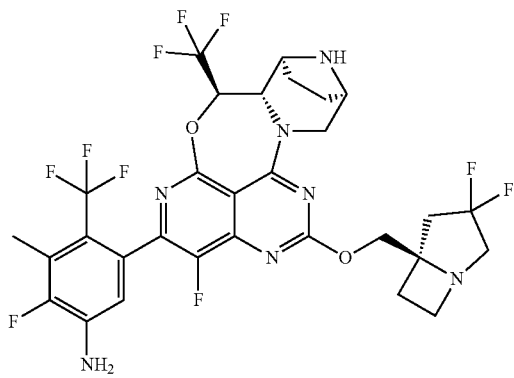 [SMILES: Cc1c(F)c(N)cc(-c2nc3c4c(nc(OC[C@]56CCN5CC(F)(F)C6)nc4c2F)N2C[C@H]4CC[C@H](N4)[C@H]2[C@H](C(F)(F)F)O3)c1C(F)(F)F]<br>5-((5R,5aS,6S,9R)-12-((3,3-Difluoro-1-azabicyclo[3.2.0]heptan-5-yl)methoxy)-1-fluoro-5-(trifluoromethyl)-5a,6,7,8,9,10-hexahydro-5H-4-oxa-3,10a,11,13,14-pentaaza-6,9-methanonaphtho[1,8-ab]heptalene-2-yl)-2-fluoro-3-methyl-4-(trifluoromethyl)aniline (two diastereomers) |
| 264 | 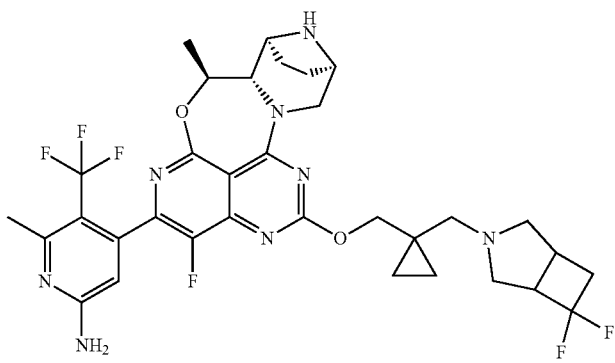 [SMILES: Cc1nc(N)cc(-c2nc3c4c(nc(OCC5(CN6CC7CC(F)(F)C7C6)CC5)nc4c2F)N2C[C@H]4CC[C@H](N4)[C@H]2[C@H](C)O3)c1C(F)(F)F]<br>4-((5S,5aS,6S,9R)-12-((1-((6,6-difluoro-3-azabicyclo[3.2.0]heptan-3-yl)methyl)cyclopropyl)methoxy)-1-fluoro-5-methyl-5a,6,7,8,9,10-hexahydro-5H-4-oxa-3,10a,11,13,14-pentaaza-6,9-methanonaphtho[1,8-ab]heptalene-2-yl)-6-methyl-5-(trifluoromethyl)pyridin-2-amine (mixture of diastereomers) |
| 265 | 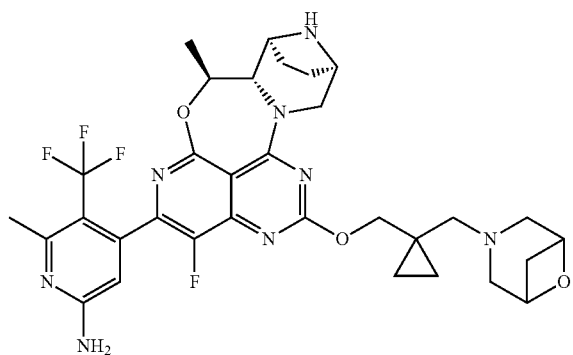 [SMILES: Cc1nc(N)cc(-c2nc3c4c(nc(OCC5(CN6CC7CC(C6)O7)CC5)nc4c2F)N2C[C@H]4CC[C@H](N4)[C@H]2[C@H](C)O3)c1C(F)(F)F]<br>4-((5S,5aS,6S,9R)-12-((1-((6-oxa-3-azabicyclo[3.1.1]heptan-3-yl)methyl)cyclopropyl)methoxy)-1-fluoro-5-methyl-5a,6,7,8,9,10-hexahydro-5H-4-oxa-3,10a,11,13,14-pentaaza-6,9-methanonaphtho[1,8-ab]heptalene-2-yl)-6-methyl-5-(trifluoromethyl)pyridin-2-amine |

TABLE 1-continued

| Cmpd. No. | Chemical Structure |
|---|---|
| 266 | 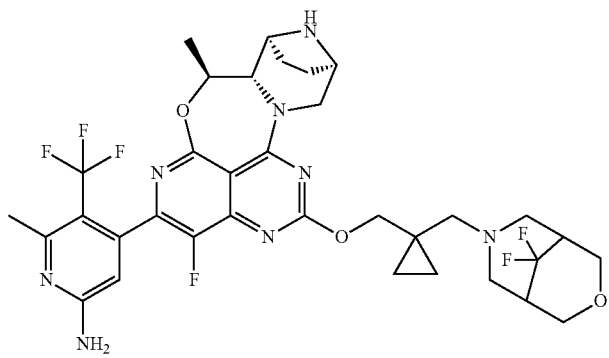 [SMILES: Cc1nc(N)cc(-c2nc3c4c(nc(OCC5(CN6CC7COCC(C6)C7(F)F)CC5)nc4c2F)N2C[C@H]4CC[C@H](N4)[C@H]2[C@H](C)O3)c1C(F)(F)F]<br>4-((5S,5aS,6S,9R)-12-((1-(((9,9-difluoro-3-oxa-7-azabicyclo[3.3.1]nonan-7-yl)methyl)cyclopropyl)methoxy)-1-fluoro-5-methyl-5a,6,7,8,9,10-hexahydro-5H-4-oxa-3,10a,11,13,14-pentaaza-6,9-methanonaphtho[1,8-ab]heptalene-2-yl)-6-methyl-5-(trifluoromethyl)pyridin-2-amine |
| 267 | 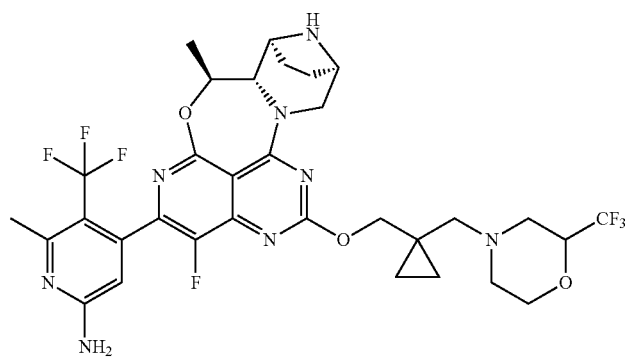 [SMILES: Cc1nc(N)cc(-c2nc3c4c(nc(OCC5(CN6CCOC(C(F)(F)F)C6)CC5)nc4c2F)N2C[C@H]4CC[C@H](N4)[C@H]2[C@H](C)O3)c1C(F)(F)F]<br>4-((5S,5aS,6S,9R)-1-fluoro-5-methyl-12-((1-((2-(trifluoromethyl)morpholino)methyl)cyclopropyl)methoxy)-5a,6,7,8,9,10-hexahydro-5H-4-oxa-3,10a,11,13,14-pentaaza-6,9-methanonaphtho[1,8-ab]heptalene-2-yl)-6-methyl-5-(trifluoromethyl)pyridin-2-amine (mixture of diastereomers) |
| 268 | 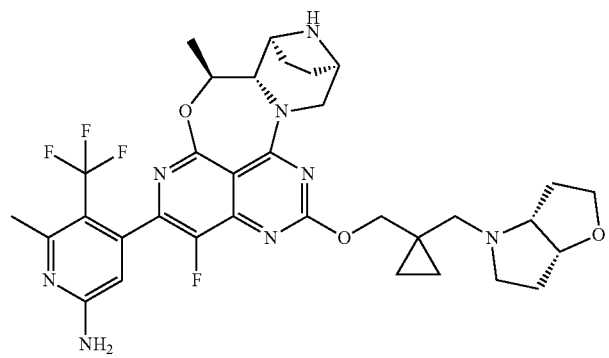 [SMILES: Cc1nc(N)cc(-c2nc3c4c(nc(OCC5(CN6CC[C@H]7OCC[C@H]76)CC5)nc4c2F)N2C[C@H]4CC[C@H](N4)[C@H]2[C@H](C)O3)c1C(F)(F)F]<br>4-((5S,5aS,6S,9R)-1-fluoro-12-((1-(((3aR,6aR)-hexahydro-4H-furo[3,2-b]pyrrol-4-yl)methyl)cyclopropyl)methoxy)-5-methyl-5a,6,7,8,9,10-hexahydro-5H-4-oxa-3,10a,11,13,14-pentaaza-6,9-methanonaphtho[1,8-ab]heptalene-2-yl)-6-methyl-5-(trifluoromethyl)pyridin-2-amine |

TABLE 1-continued

| Cmpd. No. | Chemical Structure |
|---|---|
| 269 | 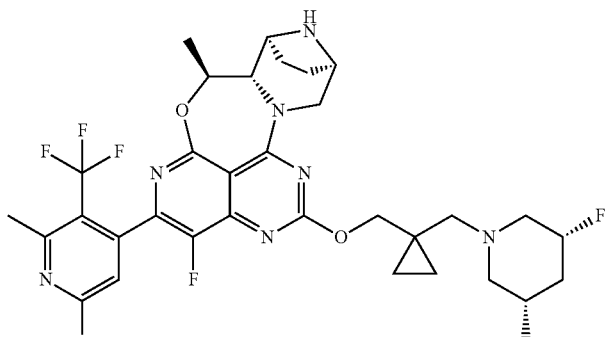<br>4-((5S,5aS,6S,9R)-12-((1-(((3S,5R)-3,5-difluoropiperidin-1-yl)methyl)cyclopropyl)methoxy)-1-fluoro-5-methyl-5a,6,7,8,9,10-hexahydro-5H-4-oxa-3,10a,11,13,14-pentaaza-6,9-methanonaphtho[1,8-ab]heptalene-2-yl)-6-methyl-5-(trifluoromethyl)pyridin-2-amine |
| 270 | 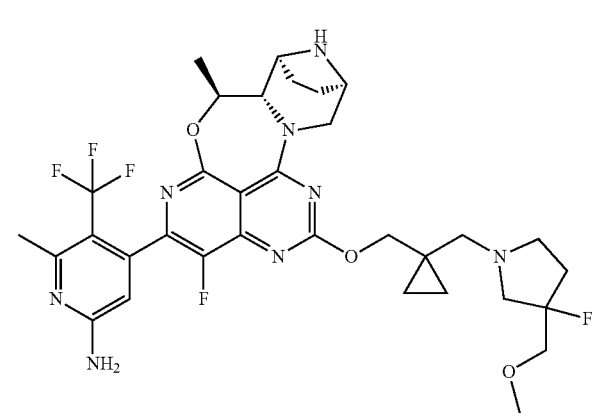 [SMILES: COCC1(F)CCN(CC2(COc3nc4c5c(nc(-c6cc(N)nc(C)c6C(F)(F)F)c(F)c5n3)O[C@@H](C)[C@@H]3[C@@H]5CC[C@H](CN43)N5)CC2)C1]<br>4-((5S,5aS,6S,9R)-1-fluoro-12-((1-((3-fluoro-3-(methoxymethyl)pyrrolidin-1-yl)methyl)cyclopropyl)methoxy)-5-methyl-5a,6,7,8,9,10-hexahydro-5H-4-oxa-3,10a,11,13,14-pentaaza-6,9-methanonaphtho[1,8-ab]heptalen-2-yl)-6-methyl-5-(trifluoromethyl)pyridin-2-amine (mixture of diastereomers) |
| 271 | 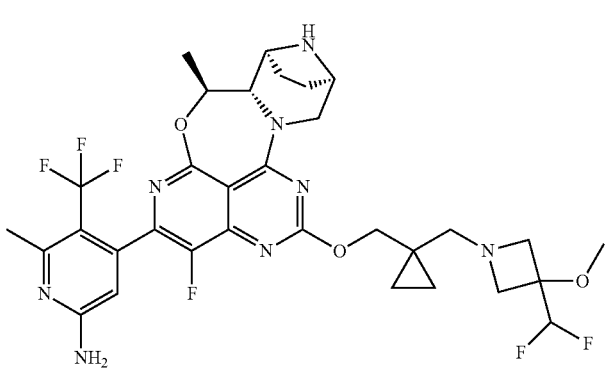<br>4-((5S,5aS,6S,9R)-12-((1-((3-(difluoromethyl)-3-methoxyazetidin-1-yl)methyl)cyclopropyl)methoxy)-1-fluoro-5-methyl-5a,6,7,8,9,10-hexahydro-5H-4-oxa-3,10a,11,13,14-pentaaza-6,9-methanonaphtho[1,8-ab]heptalene-2-yl)-6-methyl-5-(trifluoromethyl)pyridin-2-amine |

| Cmpd. No. | Chemical Structure |
|---|---|
| 272 | 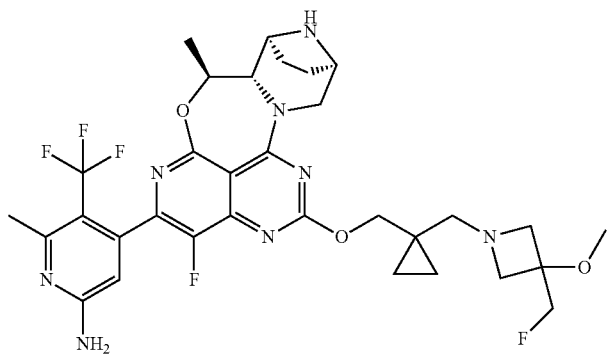<br>4-((5S,5aS,6S,9R)-1-fluoro-12-((1-((3-fluoromethyl)-3-methoxyazetidin-1-yl)methyl)cyclopropyl)methoxy)-5-methyl-5a,6,7,8,9,10-hexahydro-5H-4-oxa-3,10a,11,13,14-pentaaza-6,9-methanonaphtho[1,8-ab]heptalene-2-yl)-6-methyl-5-(trifluoromethyl)pyridin-2-amine |
| 273 | 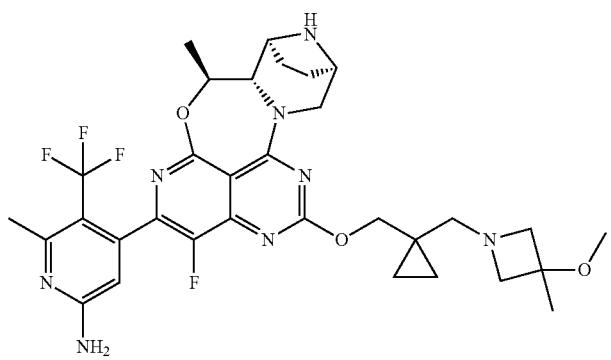<br>4-((5S,5aS,6S,9R)-1-fluoro-12-((1-((3-methoxy-3-methylazetidin-1-yl)methyl)cyclopropyl)methoxy)-5-methyl-5a,6,7,8,9,10-hexahydro-5H-4-oxa-3,10a,11,13,14-pentaaza-6,9-methanonaphtho[1,8-ab]heptalene-2-yl)-6-methyl-5-(trifluoromethyl)pyridin-2-amine |
| 274 | 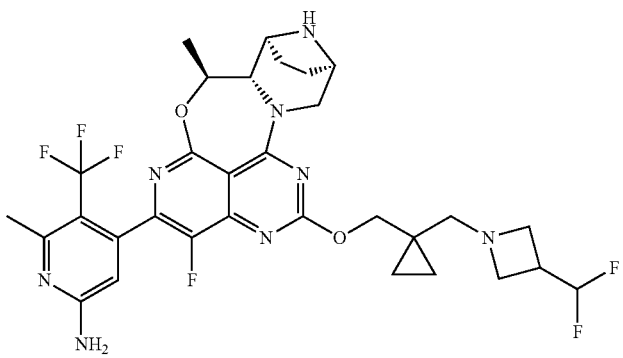 [SMILES: Cc1nc(N)cc(-c2nc3c4c(nc(OCC5(CN6CC(C(F)F)C6)CC5)nc4c2F)N2C[C@H]4CC[C@H](N4)[C@H]2[C@H](C)O3)c1C(F)(F)F]<br>4-((5S,5aS,6S,9R)-12-((1-((3-(difluoromethyl)90eptalene-1-yl)methyl)cyclopropyl)methoxy)-1-fluoro-5-methyl-5a,6,7,8,9,10-hexahydro-5H-4-oxa-3,10a,11,13,14-pentaaza-6,9-methanonaphtho[1,8-ab]heptalene-2-yl)-6-methyl-5-(trifluoromethyl)pyridin-2-amine |

TABLE 1-continued

| Cmpd. No. | Chemical Structure |
|---|---|
| 275 | 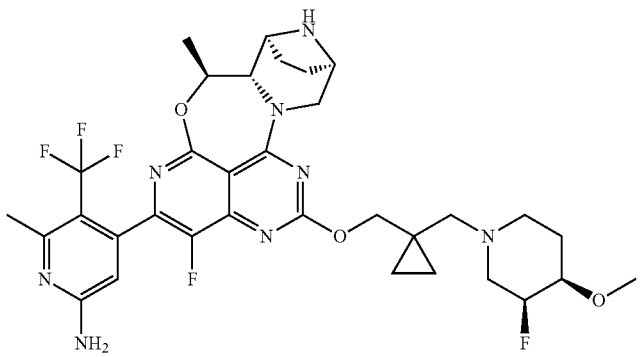
4-((5S,5aS,6S,9R)-1-fluoro-12-((1-(((3S,4R)-3-fluoro-4-methoxypiperidin-1-yl)methyl)cyclopropyl)methoxy)-5-methyl-5a,6,7,8,9,10-hexahydro-5H-4-oxa-3,10a,11,13,14-pentaaza-6,9-methanonaphtho[1,8-ab]heptalene-2-yl)-6-methyl-5-(trifluoromethyl)pyridin-2-amine |
| 276 | 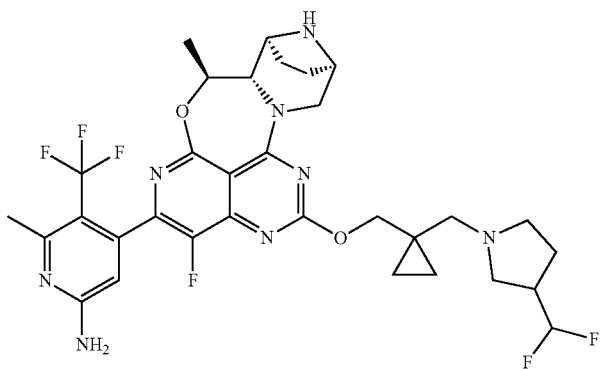 [SMILES: Cc1nc(N)cc(-c2nc3c4c(nc(OCC5(CN6CCC(C(F)F)C6)CC5)nc4c2F)N2C[C@H]4CC[C@H](N4)[C@H]2[C@H](C)O3)c1C(F)(F)F]
4-((5S,5aS,6S,9R)-12-((1-((3-(difluoromethyl)pyrrolidin-1-yl)methyl)cyclopropyl)methoxy)-1-fluoro-5-methyl-5a,6,7,8,9,10-hexahydro-5H-4-oxa-3,10a,11,13,14-pentaaza-6,9-methanonaphtho[1,8-ab]heptalen-2-yl)-6-methyl-5-(trifluoromethyl)pyridin-2-amine (mixture of diastereomers) |
| 277 | 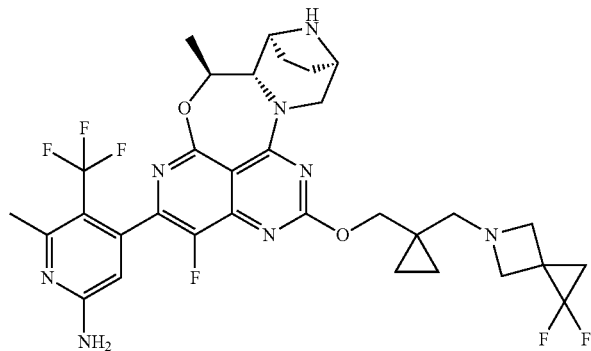 [SMILES: Cc1nc(N)cc(-c2nc3c4c(nc(OCC5(CN6CC7(C6)CC7(F)F)CC5)nc4c2F)N2C[C@H]4CC[C@H](N4)[C@H]2[C@H](C)O3)c1C(F)(F)F]
4-((5S,5aS,6S,9R)-12-((1-((1,1-difluoro-5-azaspiro[2.3]hexan-5-yl)methyl)cyclopropyl)methoxy)-1-fluoro-5-methyl-5a,6,7,8,9,10-hexahydro-5H-4-oxa-3,10a,11,13,14-pentaaza[6,9]methanonaphtho[1,8-ab]heptalene-2-yl)-6-methyl-5-(trifluoromethyl)pyridin-2-amine |

TABLE 1-continued

| Cmpd. No. | Chemical Structure |
|---|---|
| 278 | 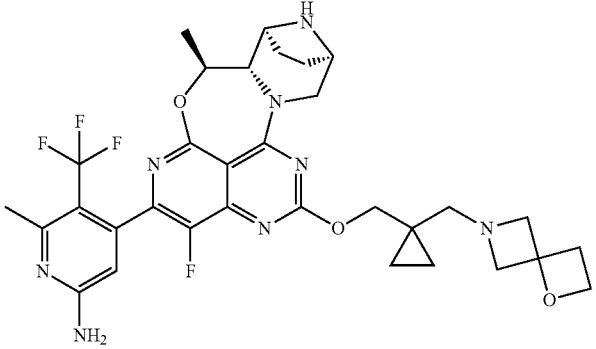 [SMILES: Cc1nc(N)cc(-c2nc3c4c(nc(OCC5(CN6CC7(CCO7)C6)CC5)nc4c2F)N2C[C@H]4CC[C@H](N4)[C@H]2[C@H](C)O3)c1C(F)(F)F] 4-((5S,5aS,6S,9R)-12-((1-((1-oxa-6-azaspiro[3.3]heptan-6-yl)methyl)cyclopropyl)methoxy)-1-fluoro-5-methyl-5a,6,7,8,9,10-hexahydro-5H-4-oxa-3,10a,11,13,14-pentaaza[6,9]methanonaphtho[1,8-ab]heptalene-2-yl)-6-methyl-5-(trifluoromethyl)pyridin-2-amine |
| 279 | 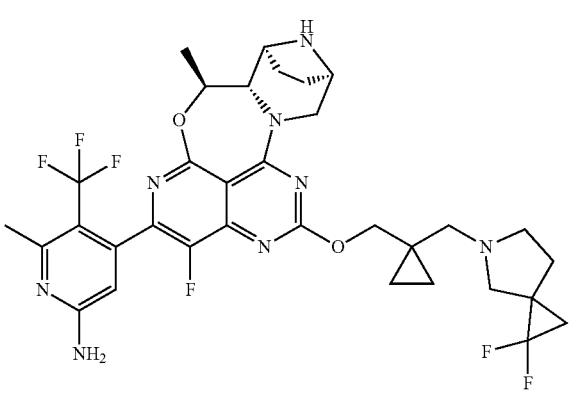 [SMILES: Cc1nc(N)cc(-c2nc3c4c(nc(OCC5(CN6CCC7(C6)CC7(F)F)CC5)nc4c2F)N2C[C@H]4CC[C@H](N4)[C@H]2[C@H](C)O3)c1C(F)(F)F] 4-((5S,5aS,6S,9R)-12-((1-((1,1-difluoro-5-azaspiro[2.4]heptan-5-yl)methyl)cyclopropyl)methoxy)-1-fluoro-5-methyl-5a,6,7,8,9,10-hexahydro-5H-4-oxa-3,10a,11,13,14-pentaaza[6,9]methanonaphtho[1,8-ab]heptalene-2-yl)-6-methyl-5-(trifluoromethyl)pyridin-2-amine (mixture of diastereomers) |
| 280 | 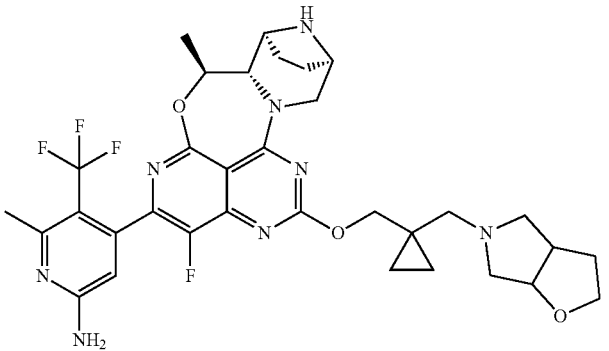 [SMILES: Cc1nc(N)cc(-c2nc3c4c(nc(OCC5(CN6CC7CCOC7C6)CC5)nc4c2F)N2C[C@H]4CC[C@H](N4)[C@H]2[C@H](C)O3)c1C(F)(F)F] 4-((5S,5aS,6S,9R)-1-fluoro-12-((1-((hexahydro-5H-furo[2,3-c]pyrrol-5-yl)methyl)cyclopropyl)methoxy)-5-methyl-5a,6,7,8,9,10-hexahydro-5H-4-oxa-3,10a,11,13,14-pentaaza-6,9-methanonaphtho[1,8-ab]heptalene-2-yl)-6-methyl-5-(trifluoromethyl)pyridin-2-amine (mixture of diastereomers) |

TABLE 1-continued

| Cmpd. No. | Chemical Structure |
|---|---|
| 281 | 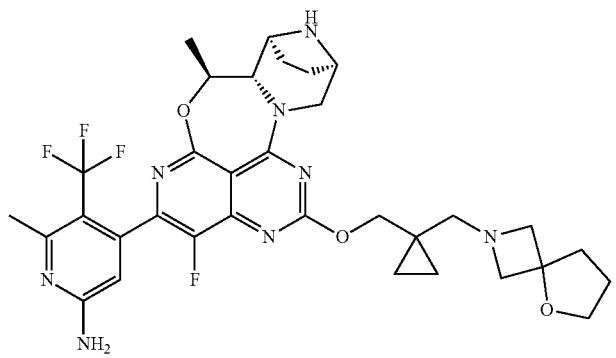 [SMILES: Cc1nc(N)cc(-c2nc3c4c(nc(OCC5(CN6CC7(CCCO7)C6)CC5)nc4c2F)N2C[C@H]4CC[C@H](N4)[C@H]2[C@H](C)O3)c1C(F)(F)F]<br>4-((5S,5aS,6S,9R)-12-((1-(((5-oxa-2-azaspiro[3.4]octan-2-yl)methyl)cyclopropyl)methoxy)-1-fluoro-5-methyl-5a,6,7,8,9,10-hexahydro-5H-4-oxa-3,10a,11,13,14-pentaaza[6,9]methanonaphtho[1,8-ab]heptalene-2-yl)-6-methyl-5-(trifluoromethyl)pyridin-2-amine |
| 282 | 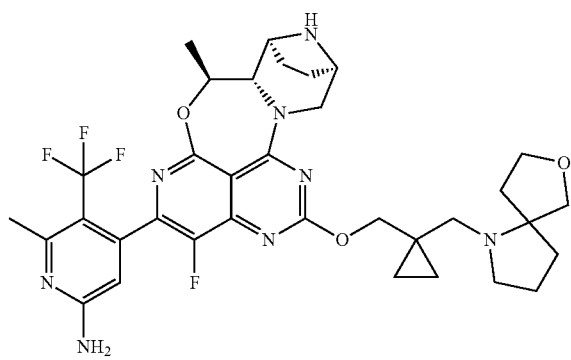 [SMILES: Cc1nc(N)cc(-c2nc3c4c(nc(OCC5(CN6CCCC67CCOC7)CC5)nc4c2F)N2C[C@H]4CC[C@H](N4)[C@H]2[C@H](C)O3)c1C(F)(F)F]<br>4-((5S,5aS,6S,9R)-12-((1-(((7-oxa-1-azaspiro[4.4]nonan-1-yl)methyl)cyclopropyl)methoxy)-1-fluoro-5-methyl-5a,6,7,8,9,10-hexahydro-5H-4-oxa-3,10a,11,13,14-pentaaza[6,9]methanonaphtho[1,8-ab]heptalene-2-yl)-6-methyl-5-(trifluoromethyl)pyridin-2-amine (mixture of diastereomers) |
| 283 | 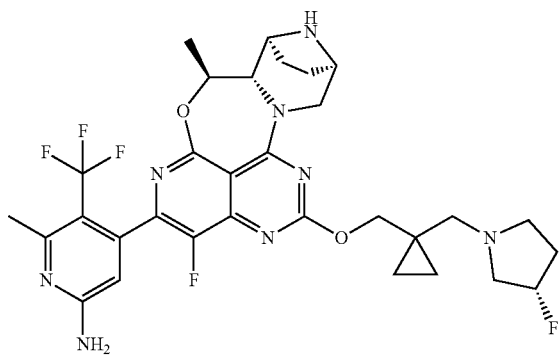 [SMILES: Cc1nc(N)cc(-c2nc3c4c(nc(OCC5(CN6CC[C@H](F)C6)CC5)nc4c2F)N2C[C@H]4CC[C@H](N4)[C@H]2[C@H](C)O3)c1C(F)(F)F]<br>4-((5S,5aS,6S,9R)-1-fluoro-12-((1-(((S)-3-fluoropyrrolidin-1-yl)methyl)cyclopropyl)methoxy)-5-methyl-5a,6,7,8,9,10-hexahydro-5H-4-oxa-3,10a,11,13,14-pentaaza-6,9-methanonaphtho[1,8-ab]heptalene-2-yl)-6-methyl-5-(trifluoromethyl)pyridin-2-amine |

TABLE 1-continued

| Cmpd. No. | Chemical Structure |
|---|---|
| 284 | 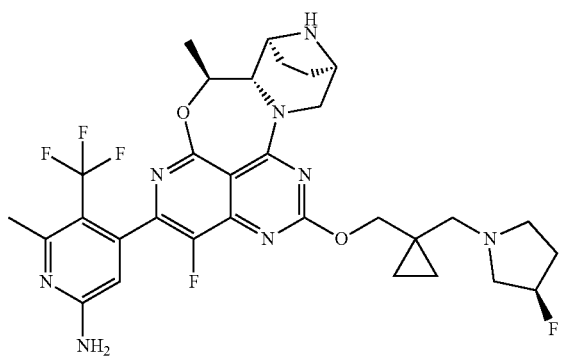 [SMILES: Cc1nc(N)cc(-c2nc3c4c(nc(OCC5(CN6CC[C@@H](F)C6)CC5)nc4c2F)N2C[C@H]4CC[C@H](N4)[C@H]2[C@H](C)O3)c1C(F)(F)F] 4-((5S,5aS,6S,9R)-1-fluoro-12-((1-(((R)-3-fluoropyrrolidin-1-yl)methyl)cyclopropyl)methoxy)-5-methyl-5a,6,7,8,9,10-hexahydro-5H-4-oxa-3,10a,11,13,14-pentaaza-6,9-methanonaphtho[1,8-ab]heptalen-2-yl)-6-methyl-5-(trifluoromethyl)pyridin-2-amine |
| 285 | 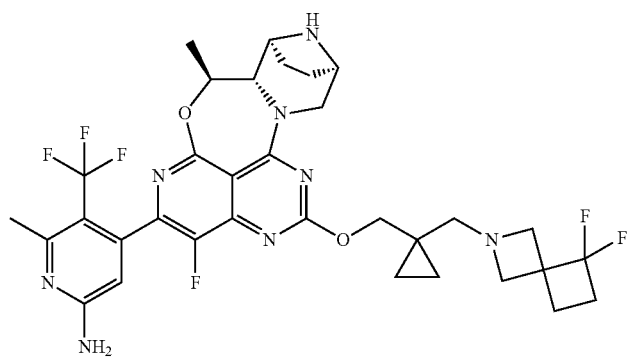 [SMILES: Cc1nc(N)cc(-c2nc3c4c(nc(OCC5(CN6CC7(CCC7(F)F)C6)CC5)nc4c2F)N2C[C@H]4CC[C@H](N4)[C@H]2[C@H](C)O3)c1C(F)(F)F] 4-((5S,5aS,6S,9R)-12-((1-((5,5-difluoro-2-azaspiro[3.3]heptan-2-yl)methyl)cyclopropyl)methoxy)-1-fluoro-5-methyl-5a,6,7,8,9,10-hexahydro-5H-4-oxa-3,10a,11,13,14-pentaaza[6,9]methanonaphtho[1,8-ab]heptalene-2-yl)-6-methyl-5-(trifluoromethyl)pyridin-2-amine |
| 286 | 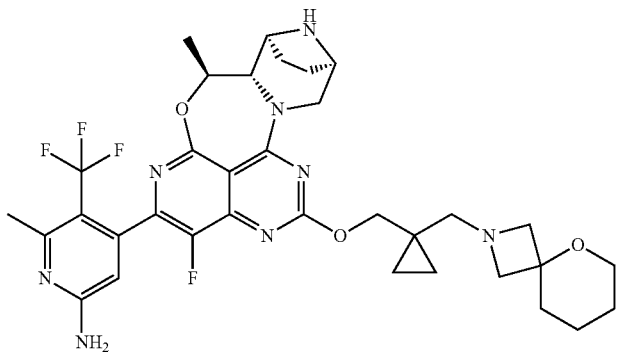 [SMILES: Cc1nc(N)cc(-c2nc3c4c(nc(OCC5(CN6CC7(CCCCO7)C6)CC5)nc4c2F)N2C[C@H]4CC[C@H](N4)[C@H]2[C@H](C)O3)c1C(F)(F)F] 4-((5S,5aS,6S,9R)-12-((1-((5-oxa-2-azaspiro[3.5]nonan-2-yl)methyl)cyclopropyl)methoxy)-1-fluoro-5-methyl-5a,6,7,8,9,10-hexahydro-5H-4-oxa-3,10a,11,13,14-pentaaza[6,9]methanonaphtho[1,8-ab]heptalene-2-yl)-6-methyl-5-(trifluoromethyl)pyridin-2-amine |

TABLE 1-continued

| Cmpd. No. | Chemical Structure |
|---|---|
| 287 | 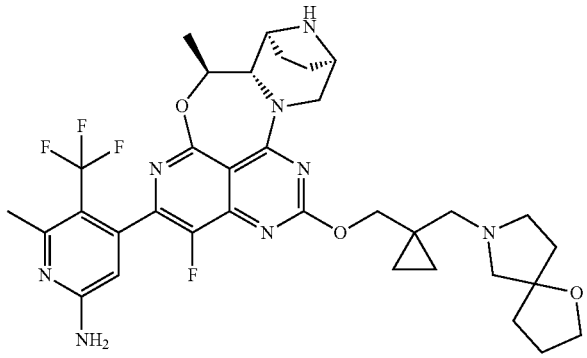 [SMILES: Cc1nc(N)cc(-c2nc3c4c(nc(OCC5(CN6CCC7(CCCO7)C6)CC5)nc4c2F)N2C[C@H]4CC[C@H](N4)[C@H]2[C@H](C)O3)c1C(F)(F)F] 4-((5S,5aS,6S,9R)-12-((1-(((1-oxa-7-azaspiro[4.4]nonan-7-yl)methyl)cyclopropyl)methoxy)-1-fluoro-5-methyl-5a,6,7,8,9,10-hexahydro-5H-4-oxa-3,10a,11,13,14-pentaaza[6,9]methanonaphtho[1,8-ab]heptalene-2-yl)-6-methyl-5-(trifluoromethyl)pyridin-2-amine (mixture of diastereomers) |
| 288 | 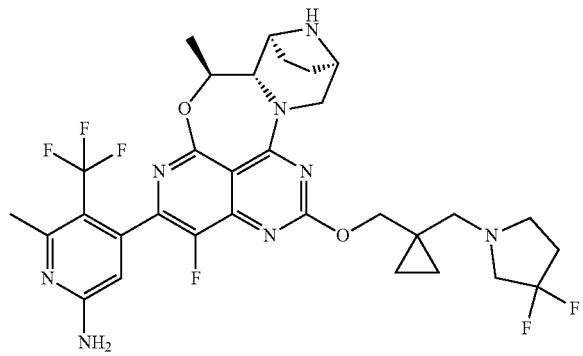 [SMILES: Cc1nc(N)cc(-c2nc3c4c(nc(OCC5(CN6CCC(F)(F)C6)CC5)nc4c2F)N2C[C@H]4CC[C@H](N4)[C@H]2[C@H](C)O3)c1C(F)(F)F] 4-((5S,5aS,6S,9R)-12-((1-((3,3-difluoropyrrolidin-1-yl)methyl)cyclopropyl)methoxy)-1-fluoro-5-methyl-5a,6,7,8,9,10-hexahydro-5H-4-oxa-3,10a,11,13,14-pentaaza-6,9-methanonaphtho[1,8-ab]heptalene-2-yl)-6-methyl-5-(trifluoromethyl)pyridin-2-amine |
| 289 | 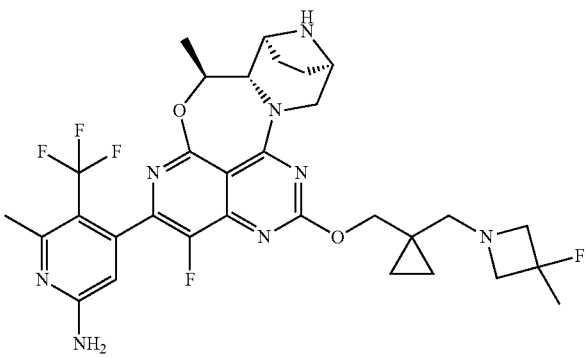 [SMILES: Cc1nc(N)cc(-c2nc3c4c(nc(OCC5(CN6CC(C)(F)C6)CC5)nc4c2F)N2C[C@H]4CC[C@H](N4)[C@H]2[C@H](C)O3)c1C(F)(F)F] 4-((5S,5aS,6S,9R)-1-fluoro-12-((1-((3-fluoro-3-methylazetidin-1-yl)methyl)cyclopropyl)methoxy)-5-methyl-5a,6,7,8,9,10-hexahydro-5H-4-oxa-3,10a,11,13,14-pentaaza-6,9-methanonaphtho[1,8-ab]heptalene-2-yl)-6-methyl-5-(trifluoromethyl)pyridin-2-amine |

TABLE 1-continued

| Cmpd. No. | Chemical Structure |
|---|---|
| 290 | 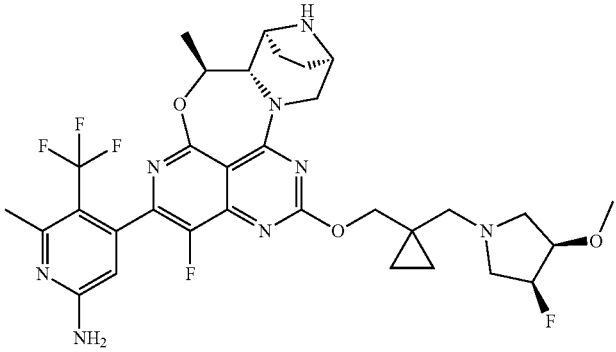  4-((5S,5aS,6S,9R)-1-fluoro-12-((1-(((3S,4R)-3-fluoro-4-methoxypyrrolidin-1-yl)methyl)cyclopropyl)methoxy)-5-methyl-5a,6,7,8,9,10-hexahydro-5H-4-oxa-3,10a,11,13,14-pentaaza-6,9-methanonaphtho[1,8-ab]heptalen-2-yl)-6-methyl-5-(trifluoromethyl)pyridin-2-amine |
| 291 | 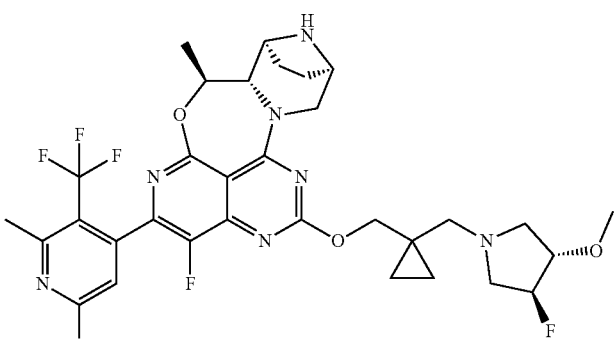  4-((5S,5aS,6S,9R)-1-fluoro-12-((1-(((3S,4S)-3-fluoro-4-methoxypyrrolidin-1-yl)methyl)cyclopropyl)methoxy)-5-methyl-5a,6,7,8,9,10-hexahydro-5H-4-oxa-3,10a,11,13,14-pentaaza-6,9-methanonaphtho[1,8-ab]heptalen-2-yl)-6-methyl-5-(trifluoromethyl)pyridin-2-amine |

In one embodiment is a compound selected from compounds 1-36, 38-45, 47-62, 64-108, 110-146, and 149-291 in Table 1 or a stereoisomer, atropisomer, tautomer, or pharmaceutically acceptable salt thereof.

In one embodiment is a compound selected from compounds 1-36, 38-45, 47-62, 64-108, and 110-125 in Table 1 or a stereoisomer, atropisomer, tautomer, or pharmaceutically acceptable salt thereof.

In one embodiment is a compound selected from compounds 126-146 and 149-291 in Table 1 or a stereoisomer, atropisomer, tautomer, or pharmaceutically acceptable salt thereof.

In one embodiment is a compound selected from compounds 6, 15, 24, 26, 29, 31-32, 57-59, 61-62, 64-66, 75-76, 91, 96, 104, 106, 111, 113, 118-124, 126-146, 149-156, 158-175, 181, 183, 186, 190-192, 195, 200, 204, 224-225, 228-229, 232-239, 241, 244-250, 255, 258-259, and 263 in Table 1 or a stereoisomer, atropisomer, tautomer, or pharmaceutically acceptable salt thereof.

In one embodiment is a compound selected from compounds 6, 12-18, 23-24, 26, 29, 31-36, 57-58, 60-62, 64-77, 90-97, 100-102, 104, 108, 111, 113, 115, 118-146, 149-175, 181-183, 186-187, 190, 195, 200, 204, 224-232, 234-239, 241, 244-250, 255, 258-259, and 263 in Table 1 or a stereoisomer, atropisomer, tautomer, or pharmaceutically acceptable salt thereof.

In one embodiment is a compound selected from compounds 6, 13-14, 16-18, 23-24, 26, 29, 31-34, 36, 57-62, 64-72, 74, 76, 91-104, 106-108, 111, 113, 115, 117-146, 149-154, 157, 159-174, 199, 200, 224-229, 234-241, 244-249, 255, 258-259, and 263 in Table 1 or a stereoisomer, atropisomer, tautomer, or pharmaceutically acceptable salt thereof.

In one embodiment is a compound selected from compounds 6, 12-18, 23-24, 26, 29, 31-36, 42-45, 47-48, 52, 57-58, 60-78, 84-88, 90-97, 100-104, 106, 108, 111-113, 115, 118-146, 149-175, 177-178, 181-183, 185-187, 189-192, 194-195, 197-200, 203-232, 234-250, and 252-291 in Table 1 or a stereoisomer, atropisomer, tautomer, or pharmaceutically acceptable salt thereof.

In one embodiment is a compound selected from compounds 6, 13-14, 16-18, 23-24, 26, 29, 31-34, 36, 42-45, 47-48, 52, 57-62, 64-72, 74, 76, 84-88, 91-104, 106-108, 111, 113, 115, 117-146, 149-154, 157, 159-174, 199, 200, 224-229, 234-241, 244-249, 255, 258-259, and 263 in Table 1 or a stereoisomer, atropisomer, tautomer, or pharmaceutically acceptable salt thereof.

In one embodiment is a compound selected from compounds 42-45, 47-48, and 52 in Table 1 or a stereoisomer, atropisomer, tautomer, or pharmaceutically acceptable salt thereof.

In one embodiment is a compound selected from compounds 112, 205-218, 242-243, 252-254, 261-262, and 264-291 in Table 1 or a stereoisomer, atropisomer, tautomer, or pharmaceutically acceptable salt thereof.

Synthesis of Compounds

Compounds or a stereoisomer, atropisomer, tautomer, or pharmaceutically acceptable salt thereof as described herein of the present disclosure can be made by a variety of methods depicted in the illustrative synthetic reaction schemes shown and described below. The starting materials and reagents used in preparing these compounds generally are either available from commercial suppliers, such as Aldrich Chemical Co., or are prepared by methods known to those skilled in the art following procedures set forth in references such as Fieser and Fieser's *Reagents for Organic Synthesis*; Wiley & Sons: New York, vol. 1-21; R. C. LaRock, *Comprehensive Organic Transformations*, $2^{nd}$ edition Wiley-VCH, New York 1999; *Comprehensive Organic Synthesis*, B. Trost and I. Fleming (Eds.) vol. 1-9 Pergamon, Oxford, 1991; *Comprehensive Heterocyclic Chemistry*, A. R. Katritzky and C. W. Rees (Eds.) Pergamon, Oxford 1984, vol. 1-9; *Comprehensive Heterocyclic Chemistry II*, A. R. Katritzky and C. W. Rees (Eds) Pergamon, Oxford 1996, vol. 1-11; and *Organic Reactions*, Wiley & Sons: New York, 1991, vol. 1-40. The following synthetic reaction schemes are merely illustrative of some methods by which the compounds or pharmaceutical acceptable salts thereof described herein can be synthesized, and various modifications to these synthetic reaction schemes can be made and will be suggested to one skilled in the art having referred to the disclosure contained herein.

Synthetic chemistry transformations and protecting group methodologies (protection and deprotection) useful in synthesizing compounds described herein and necessary reagents and intermediates include, for example, those described in R. Larock, Comprehensive Organic Transformations, VCH Publishers (1989); T. W. Greene and P. G. M. Wuts, Protective Groups in Organic Synthesis, $3^{rd}$ Ed., John Wiley and Sons (1999); and L. Paquette, ed., Encyclopedia of *Reagents for Organic Synthesis*, John Wiley and Sons (1995) and subsequent editions thereof.

Compounds or a stereoisomer, atropisomer, tautomer, or pharmaceutically acceptable salt thereof as described herein described herein can be prepared singly or as compound libraries comprising at least 2, for example 5 to 1,000 compounds, or 10 to 100 compounds. Libraries of compounds or a stereoisomer, atropisomer, tautomer, or pharmaceutically acceptable salt thereof as described herein of the formulae described herein can be prepared by a combinatorial split and mix approach or by multiple parallel syntheses using, for example, either solution phase or solid phase chemistry. Thus, according to a further aspect provided herein is a compound library comprising at least 2 compounds or a stereoisomer, atropisomer, tautomer, or pharmaceutically acceptable salt thereof as described herein.

The Examples provide exemplary methods for preparing compounds or a stereoisomer, atropisomer, tautomer, or pharmaceutically acceptable salt thereof as described herein. Those skilled in the art will appreciate that other synthetic routes can be used to synthesize the compounds or a stereoisomer, atropisomer, tautomer, or pharmaceutically acceptable salt thereof as described herein described herein. Although specific starting materials and reagents are depicted and discussed in the Examples, other starting materials and reagents can be substituted to provide a variety of derivatives and/or reaction conditions. In addition, many of the exemplary compounds prepared by the described methods can be further modified in light of this disclosure using conventional chemistry.

In preparing compounds or a stereoisomer, atropisomer, tautomer, or pharmaceutically acceptable salt thereof as described herein protection of remote functionality (e.g., primary or secondary amine) of intermediates can be necessary. The need for such protection will vary depending on the nature of the remote functionality and the conditions of the preparation methods. Suitable amino-protecting groups include acetyl, trifluoroacetyl, t-butoxycarbonyl (BOC), benzyloxycarbonyl (CBz) and 9-fluorenylmethyleneoxycarbonyl (Fmoc). The need for such protection can be readily determined. For a general description of protecting groups and their use, see T. W. Greene, Protective Groups in Organic Synthesis, John Wiley & Sons, New York, 1991.

In the methods of preparing compounds or a stereoisomer, atropisomer, tautomer, or pharmaceutically acceptable salt thereof as described herein, it can be advantageous to separate reaction products from one another and/or from starting materials. The desired products of each step or series of steps are separated and/or purified to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like. Selection of appropriate methods of separation depends on the nature of the materials involved, such as, boiling point and molecular weight in distillation and sublimation, presence or absence of polar functional groups in chromatography, stability of materials in acidic and basic media in multiphase extraction, and the like.

Diastereomeric mixtures can be separated into their individual diastereomers on the basis of their physical chemical differences by methods such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Also, some of the compounds or a stereoisomer, atropisomer, tautomer, or pharmaceutically acceptable salt thereof as described herein described herein can be atropisomers (e.g., substituted biaryls). Enantiomers can also be separated by use of a chiral HPLC column.

A single stereoisomer, e.g., an enantiomer, substantially free of its stereoisomer can be obtained by resolution of the racemic mixture using a method such as formation of diastereomers using optically active resolving agents (Eliel, E. and Wilen, S. "Stereochemistry of Organic Compounds," John Wiley & Sons, Inc., New York, 1994; Lochmuller, C. H., (1975) J. Chromatogr., 113(3):283-302). Racemic mixtures of chiral compounds or pharmaceutically acceptable salts thereof described herein can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: "Drug Stereochemistry, Analytical Methods and Pharmacology," Irving W. Wainer, Ed., Marcel Dekker, Inc., New York (1993).

Under method (1), diastereomeric salts can be formed by reaction of enantiomerically pure chiral bases such as brucine, quinine, ephedrine, strychnine, a-methyl-b-phenylethylamine (amphetamine), and the like with asymmetric compounds bearing acidic functionality, such as carboxylic acid and sulfonic acid. The diastereomeric salts can be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (E. and Wilen, S. "Stereochemistry of Organic Compounds", John Wiley & Sons, Inc., 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g., (–) menthyl chloroformate in the presence of base, or Mosher ester, a-methoxy-a-(trifluoromethyl)phenyl acetate (Jacob III. J. Org. Chem. (1982) 47:4165), of the racemic mixture, and analyzing the $^1$H NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 96/15111). By method (3), a racemic mixture of two enantiomers can be separated by chromatography using a chiral stationary phase ("Chiral Liquid Chromatography" (1989) W. J. Lough, Ed., Chapman and Hall, New York; Okamoto, J. Chromatogr., (1990) 513:375-378). Enriched or purified enantiomers can be distinguished by methods used to distinguish other chiral molecules with asymmetric carbon atoms, such as optical rotation and circular dichroism.

The chemical reactions described herein may be readily adapted to prepare other compounds and pharmaceutically acceptable salts thereof described herein. For example, the synthesis of non-exemplified compounds and pharmaceutically acceptable salts thereof described herein may be successfully performed by modifications apparent to those skilled in the art, e.g., by appropriately protecting interfering groups, by utilizing other suitable reagents known in the art other than those described, or by making routine modifications of reaction conditions. Alternatively, other reactions disclosed herein or known in the art will be recognized as having applicability for preparing other compounds and pharmaceutically acceptable salts thereof described herein.

Pharmaceutical Formulations

Also provided herein are pharmaceutical compositions comprising compound or a stereoisomer, atropisomer, tautomer, or pharmaceutically acceptable salt thereof as described herein and one or more pharmaceutically acceptable excipients.

Compounds or a stereoisomer, atropisomer, tautomer, or pharmaceutically acceptable salt thereof as described herein as described herein can be formulated in accordance with standard pharmaceutical practice as a pharmaceutical composition. Thus, further provided herein is a pharmaceutical composition comprising a compound or a stereoisomer, atropisomer, tautomer, or pharmaceutically acceptable salt thereof as described herein as described herein and one or more pharmaceutically acceptable excipients.

A typical formulation is prepared by mixing a compound or pharmaceutically acceptable salt thereof as described herein and an excipient. Suitable carriers, diluents and excipients include, but are not limited to, materials such as carbohydrates, waxes, water soluble and/or swellable polymers, hydrophilic or hydrophobic materials, gelatin, oils, solvents, water and the like. The particular excipient used will depend upon the means and purpose for which the compound or pharmaceutically acceptable salt thereof as described herein is being applied. Solvents are generally selected based on solvents recognized as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations can also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound described herein or pharmaceutical composition thereof) or aid in the manufacturing of the pharmaceutical product (i.e., medicament).

The formulations can be prepared using conventional dissolution and mixing procedures. For example, the bulk drug substance (i.e., compound or pharmaceutically acceptable salt thereof as described herein or stabilized form thereof (e.g., complex with a cyclodextrin derivative or other known complexation agent) is dissolved in a suitable solvent in the presence of one or more of the excipients described above. The compound or a stereoisomer, atropisomer, tautomer, or pharmaceutically acceptable salt thereof as described herein as described herein is typically formulated into pharmaceutical dosage forms to provide an easily controllable dosage of the drug and to enable patient compliance with the prescribed regimen.

The pharmaceutical composition (or formulation) for application can be packaged in a variety of ways depending upon the method used for administering the drug. Generally, an article for distribution includes a container having deposited therein the pharmaceutical formulation in an appropriate form. Suitable containers include materials such as bottles (plastic and glass), sachets, ampoules, plastic bags, metal cylinders, and the like. The container can also include a tamper-proof assemblage to prevent indiscreet access to the contents of the package. In addition, the container has deposited thereon a label that describes the contents of the container. The label can also include appropriate warnings.

Pharmaceutical formulations of the compound or a stereoisomer, atropisomer, tautomer, or pharmaceutically acceptable salt thereof as described herein can be prepared for various routes and types of administration. For example, a compound or a stereoisomer, atropisomer, tautomer, or pharmaceutically acceptable salt thereof having the desired degree of purity can optionally be mixed with one or more pharmaceutically acceptable excipients (Remington's Pharmaceutical Sciences (1980) 16$^{th}$ edition, Osol, A. Ed.), in the form of a lyophilized formulation, milled powder, or an aqueous solution. Formulation can be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but can range from about 3 to about 8. For example, formulation in an acetate buffer at pH 5 can be a suitable embodiment.

The pharmaceutical composition ordinarily can be stored as a solid composition, a lyophilized formulation or as an aqueous solution.

The pharmaceutical compositions described herein can be formulated, dosed and administered in a fashion, i.e., amounts, concentrations, schedules, course, vehicles and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The effective amount of the compound or a stereoisomer, atropisomer, tautomer, or pharmaceutically acceptable salt thereof to be administered will be governed by such considerations, and is the minimum amount necessary to ameliorate, or treat the hyperproliferative disorder.

As a general proposition, the initial pharmaceutically effective amount of the compound or a stereoisomer, atropisomer, tautomer, or pharmaceutically acceptable salt thereof administered parenterally per dose will be in the range of about 0.01-100 mg/kg, namely about 0.1 to 20 mg/kg of patient body weight per day, with the typical initial range of compound used being 0.3 to 15 mg/kg/day. In another embodiment, a pharmaceutical composition described herein comprises an effective amount of a compound or a stereoisomer, atropisomer, tautomer, or pharmaceutically acceptable salt thereof described herein in an amount of about: 1 mg-10 mg; 10 mg-25 mg; 20 mg-50 mg; 50 mg-75 mg; 70 mg-100 mg; 100 mg-150 mg; 100 mg-200 mg; 100 mg-500 mg; 200 mg-500 mg; 250 mg-500 mg; 500 mg-1000 mg; or 750 mg-1000 mg.

Acceptable pharmaceutically acceptable excipients are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN®, PLURONICS® or polyethylene glycol (PEG). The active pharmaceutical ingredients can also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nanoparticles and nanocapsules) or in macroemulsions. Such techniques are disclosed in Remington's Pharmaceutical Sciences 16$^{th}$ edition, Osol, A. Ed. (1980).

Sustained-release preparations of compounds or pharmaceutically acceptable salts thereof as described herein may be prepared. Suitable examples of sustained-release preparations include semipermeable matrices of solid hydrophobic polymers containing a compound or pharmaceutically acceptable salt thereof as described herein, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT® (injectable microspheres composed of lactic acid-glycolic acid copolymer and leuprolide acetate) and poly-D-(−)-3-hydroxybutyric acid.

The formulations include those suitable for the administration routes detailed herein. The formulations can conveniently be presented in unit dosage form and can be prepared by any methods. Techniques and formulations generally are found in Remington's Pharmaceutical Sciences (Mack Publishing Co., Easton, PA). Such methods include the step of bringing into association the active ingredient with the carrier which constitutes one or more accessory ingredients. In general, the formulations are prepared by uniformly and intimately bringing into association the active ingredient with liquid carriers or finely divided solid carriers or both, and then, if necessary, shaping the product.

Formulations of a compound or a stereoisomer, atropisomer, tautomer, or pharmaceutically acceptable salt thereof as described herein suitable for oral administration can be prepared as discrete units such as pills, capsules, cachets or tablets each containing a predetermined amount of such compound or a stereoisomer, atropisomer, tautomer, or pharmaceutically acceptable salt thereof. Compressed tablets can be prepared by compressing in a suitable machine the active ingredient in a free-flowing form such as a powder or granules, optionally mixed with a binder, lubricant, inert diluent, preservative, surface active or dispersing agent. Molded tablets can be made by molding in a suitable machine a mixture of the powdered active ingredient moistened with an inert liquid diluent. The tablets can optionally be coated or scored and optionally are formulated so as to provide slow or controlled release of the active ingredient therefrom. Tablets, troches, lozenges, aqueous or oil suspensions, dispersible powders or granules, emulsions, hard or soft capsules, e.g., gelatin capsules, syrups or elixirs can be prepared for oral use. Formulations of compounds or pharmaceutically acceptable salts thereof as described herein intended for oral use can be prepared according to any method for the manufacture of pharmaceutical compositions and such compositions can contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients can be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets can be uncoated or can be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax can be employed.

For treatment of the eye or other external tissues, e.g., mouth and skin, the formulations are preferably applied as a topical ointment or cream containing the active ingredient(s) in an amount of, for example, 0.075 to 20% W/W. When formulated in an ointment, the active ingredients can be employed with either a paraffinic or a water-miscible ointment base. Alternatively, the active ingredients can be formulated in a cream with an oil-in-water cream base. If desired, the aqueous phase of the cream base can include a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations can desirably include a compound which enhances absorption or penetration of the active ingredient through the skin or other affected areas. Examples of such dermal penetration enhancers include dimethyl sulfoxide and related analogs. The oily phase of the emulsions of compositions provided herein can be constituted from known ingredients in a known manner. While the phase can comprise merely an emulsifier, it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations. Emulsifiers and emulsion stabilizers suitable for use in the formulation of described herein include Tween® 60, Span® 80, cetostearyl alcohol, benzyl alcohol, myristyl alcohol, glyceryl mono-stearate and sodium lauryl sulfate.

Aqueous suspensions comprising a compound or a stereoisomer, atropisomer, tautomer, or pharmaceutically acceptable salt thereof as described herein can contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension can also contain one or more preservatives such as ethyl or n-propyl p-hydroxybenzoate, one or more coloring agents, one or more flavoring agents and one or more sweetening agents, such as sucrose or saccharin.

The pharmaceutical compositions of a compound or a stereoisomer, atropisomer, tautomer, or pharmaceutically acceptable salt thereof as described herein can be in the form of a sterile injectable preparation, such as a sterile injectable aqueous or oleaginous suspension. This suspension can be formulated using suitable dispersing or wetting agents and suspending agents which have been mentioned above. The sterile injectable preparation can also be a sterile injectable solution or suspension in a non-toxic parenterally acceptable diluent or solvent, such as a solution in 1,3-butanediol or prepared as a lyophilized powder. Among the acceptable vehicles and solvents that can be employed are water, Ringer's solution and isotonic sodium chloride solution. In addition, sterile fixed oils can conventionally be employed as a solvent or suspending medium. For this purpose, any bland fixed oil can be employed including synthetic mono- or diglycerides. In addition, fatty acids such as oleic acid can likewise be used in the preparation of injectables.

The amount of active ingredient that can be combined with the carrier material to produce a single dosage form will vary depending upon the host treated and the particular mode of administration. For example, a time-release formulation intended for oral administration to humans can contain approximately 1 to 1000 mg of active material compounded with an appropriate and convenient amount of carrier material which can vary from about 5 to about 95% of the total compositions (weight:weight(w/w)). The pharmaceutical composition can be prepared to provide easily measurable amounts for administration. For example, an aqueous solution intended for intravenous infusion can contain from about 3 to 500 µg of the active ingredient per milliliter of solution in order that infusion of a suitable volume at a rate of about 30 mL/hr can occur.

Formulations suitable for parenteral administration include aqueous and non-aqueous sterile injection solutions which can contain anti-oxidants, buffers, bacteriostats and solutes which render the formulation isotonic with the blood of the intended recipient; and aqueous and non-aqueous sterile suspensions which can include suspending agents and thickening agents.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of about 0.5 to 20% w/w, for example about 0.5 to 10% w/w, for example about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration can be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration can be prepared according to conventional methods and can be delivered with other therapeutic agents such as compounds heretofore used in the treatment or prophylaxis disorders as described below.

Formulations suitable for vaginal administration can be presented as pessaries, tampons, creams, gels, pastes, foams or spray formulations containing in addition to the active ingredient such carriers considered to be appropriate.

The formulations can be packaged in unit-dose or multi-dose containers, for example sealed ampoules and vials, and can be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

In one embodiment, the compound or a stereoisomer, atropisomer, tautomer, or pharmaceutically acceptable salt thereof are formulated as a prodrug. The term prodrug as used herein refers to a derivative of a compound that can be hydrolyzed, oxidized, or cleaved under biological conditions to provide the compound or a stereoisomer, atropisomer, tautomer, or pharmaceutically acceptable salt thereof. A prodrug as defined herein includes derivatives comprising one or more moieties that modulate or improve one or more physical, physiological or pharmaceutical property such as, but not limited to, solubility, permeability, uptake, biodistribution, metabolic stability, onset of action or some other druglike property, and is transformed to the bioactive or more biologically active substance as provided herein. In one embodiment, a prodrug herein has no biological activity until release of the compound or pharmaceutically acceptable salt thereof.

Methods of Administration

Compounds or a stereoisomer, atropisomer, tautomer, or pharmaceutically acceptable salt thereof described herein can be administered by any route appropriate to the condition to be treated. Suitable routes include oral, parenteral (including subcutaneous, intramuscular, intravenous (IV), intraarterial, intradermal, intrathecal and epidural), transdermal, rectal, nasal, topical (including buccal and sublingual), vaginal, intraperitoneal, intrapulmonary and intranasal. In one embodiment, a compound or a stereoisomer, atropisomer, tautomer, or pharmaceutically acceptable salt thereof described herein is administered orally or by IV. For local immunosuppressive treatment, the compounds can be administered by intralesional administration, including perfusing or otherwise contacting the graft with the inhibitor before transplantation. It will be appreciated that the preferred route can vary with for example the condition of the recipient. Where the compound or a stereoisomer, atropisomer, tautomer, or pharmaceutically acceptable salt thereof is administered orally, it can be formulated as a pill, capsule, tablet, etc. with a pharmaceutically acceptable carrier or excipient. Where the compound or a stereoisomer, atropisomer, tautomer, or pharmaceutically acceptable salt thereof is administered parenterally, it can be formulated with a pharmaceutically acceptable parenteral vehicle and in a unit dosage injectable form, as detailed below.

Thus, in one aspect provided herein is a pharmaceutical composition comprising a compound or pharmaceutically acceptable salt thereof as described herein and one or more pharmaceutically acceptable excipients. In one embodiment, compounds or a stereoisomer, atropisomer, tautomer, or pharmaceutically acceptable salt thereof described herein are administered as pharmaceutical compositions capable of being administered to a subject orally or parenterally. The compounds or a stereoisomer, atropisomer, tautomer, or pharmaceutically acceptable salt thereof described herein can be formulated for topical or parenteral use where the compound or a stereoisomer, atropisomer, tautomer, or pharmaceutically acceptable salt thereof is dissolved or otherwise suspended in a solution suitable for injections, suspensions, syrups, creams, ointments, gels, sprays, solutions and emulsions.

Oral administration can promote patient compliance in taking the compound (e.g., formulated as a pharmaceutical composition), thereby increasing compliance and efficacy. Oral pharmaceutical compositions comprising a compound described herein include, but are not limited to, tablets (e.g., coated, non-coated and chewable) and capsules (e.g., hard gelatin capsules, soft gelatin capsules, enteric coated capsules, and sustained release capsules). Tablets can be prepared by direct compression, by wet granulation, or by dry granulation. Oral pharmaceutical compositions comprising a compound described herein can be formulated for delayed or prolonged release.

A dose to treat human patients can range from about 10 mg to about 1000 mg of a compound described herein. A typical dose can be about 100 mg to about 300 mg of the compound. A dose can be administered once a day (QID), twice per day (BID), or more frequently, depending on the pharmacokinetic and pharmacodynamic properties, including absorption, distribution, metabolism, and excretion of the particular compound. Administration as used herein refers to the frequency of dosing and not, for example, the number of individual units a patient described herein must take for a dose. Thus, in some embodiments, a patient may take two or more dosage units (e.g., two or more pills/tablets/capsules) QD. In addition, toxicity factors can influence the dosage and administration regimen. When administered orally, the pill, capsule, or tablet can be ingested daily or less frequently for a specified period of time. The regimen can be repeated for a number of cycles of therapy.

Methods of Treating and Uses

The compounds or a stereoisomer, atropisomer, tautomer, or pharmaceutically acceptable salt thereof described herein are useful as Ras inhibitors. In one aspect, the compounds or a stereoisomer, atropisomer, tautomer, or pharmaceutically acceptable salt thereof described herein are useful as KRas inhibitors. In another aspect, the compound or a stereoisomer, atropisomer, tautomer, or pharmaceutically acceptable salt thereof described herein are useful as NRas inhibitors. In another aspect, the compound or a stereoisomer, atropisomer, tautomer, or pharmaceutically acceptable salt thereof described herein are useful as HRas inhibitors. In one embodiment, the compounds or a stereoisomer, atropisomer, tautomer, or pharmaceutically acceptable salt thereof described herein are useful as G12D Ras inhibitors, and as G12D KRas inhibitors.

Provided herein are methods of contacting a cell, such as an ex vivo cell, with a compound or a stereoisomer, atropisomer, tautomer, or pharmaceutically acceptable salt thereof described herein, to inhibit Ras activity (e.g., KRas activity) in the cell. In another embodiment, the activity is mutant G12D KRas activity.

Further provided herein are methods of treating a cancer comprising a KRas mutation, the method comprising administering to a patient having such cancer, an effective amount of a compound or a stereoisomer, atropisomer, tautomer, or pharmaceutically acceptable salt thereof or a pharmaceutical composition as described herein. In one embodiment, the KRas mutation is a KRas$^{G12D}$ mutation.

In one embodiment, the methods further comprise testing a sample (e.g., as set forth herein) from the patient before administration of a compound of pharmaceutically acceptable salt thereof described herein for the absence or presence of a KRas$^{G12D}$ mutation. In one such embodiment, a compound or stereoisomer, atropisomer, tautomer, or pharmaceutically acceptable salt thereof or pharmaceutical composition described herein is administered to the patient after the patient sample is determined to be positive for (e.g., the presence of) a KRas$^{G12D}$ mutation.

The methods of treating a cancer described herein relate to the treatment of cancer such as acute myeloid leukemia, cancer in adolescents, childhood adrenocortical carcinoma, AIDS-related cancers (e.g. lymphoma and Kaposi's sarcoma), anal cancer, appendix cancer, astrocytomas, atypical teratoid rhabdoid tumor, basal cell carcinoma, bile duct cancer, bladder cancer, bone cancer, brain stem glioma, brain tumor, breast cancer, bronchial tumors, Burkitt lymphoma, carcinoid tumor, embryonal tumors, germ cell tumor, primary lymphoma, cervical cancer, childhood cancers, chordoma, cardiac tumors, chronic lymphocytic leukemia (CLL), chronic myelogenous leukemia (CML), chronic myleoproliferative disorders, colon cancer, colorectal cancer, craniopharyngioma, cutaneous T-cell lymphoma, extrahepatic ductal carcinoma in situ (DCIS), embryonal tumors, CNS cancer, endometrial cancer, ependymoma, esophageal cancer, esthesioneuroblastoma, Ewing sarcoma, extracranial germ cell tumor, extragonadal germ cell tumor, eye cancer, fibrous histiocytoma of bone, gall bladder cancer, gastric cancer, gastrointestinal carcinoid tumor, gastrointestinal stromal tumors (GIST), germ cell tumor, gestational trophoblastic tumor, hairy cell leukemia, head and neck cancer, heart cancer, liver cancer, Hodgkin's lymphoma, hypopharyngeal cancer, intraocular melanoma, islet cell tumors, pancreatic neuroendocrine tumors, kidney cancer, laryngeal cancer, lip and oral cavity cancer, lobular carcinoma in situ (LCIS), lung cancer, lymphoma, metastatic squamous neck cancer with occult primary, midline tract carcinoma, mouth cancer, multiple endocrine neoplasia syndromes, multiple myeloma/plasma cell neoplasm, mycosis fungoides, myelodysplastic syndromes, myelodysplastic/myeloproliferative neoplasms, multiple myeloma, Merkel cell carcinoma, malignant mesothelioma, malignant fibrous histiocytoma of bone and osteosarcoma, nasal cavity and paranasal sinus cancer, nasopharyngeal cancer, neuroblastoma, non-Hodgkin's lymphoma, non-small cell lung cancer (NSCLC), oral cancer, oropharyngeal cancer, ovarian cancer, pancreatic cancer, papillomatosis, paraganglioma, parathyroid cancer, penile cancer, pharyngeal cancer, pleuropulmonary blastoma, primary central nervous system (CNS) lymphoma, prostate cancer, rectal cancer, transitional cell cancer, retinoblastoma, rhabdomyosarcoma, salivary gland cancer, skin cancer, small cell lung cancer, small intestine cancer, soft tissue sarcoma, T-Cell lymphoma, testicular cancer, throat cancer, thymoma and thymic carcinoma, thyroid cancer, transitional cell cancer of the renal pelvis and ureter, trophoblastic tumor, unusual cancers of childhood, urethral cancer, uterine sarcoma, vaginal cancer, vulvar cancer, or viral-induced cancer.

In some embodiments, the cancer is a hematological cancer, pancreatic cancer, MYH associated polyposis, colorectal cancer or lung cancer. In one embodiment, the cancer is lung cancer, colorectal cancer, appendiceal cancer, or pancreatic cancer. In one embodiment, the cancer is pancreatic cancer, lung cancer, or colon cancer. The lung cancer can be adenocarcinoma, non-small cell lung cancer (NSCLC), or small cell lung cancer (SCLC). In one embodiment, the cancer is colorectal cancer. In another embodiment, the cancer is pancreatic cancer. In one embodiment, the cancer is lung adenocarcinoma.

The methods provided herein can also comprise testing a sample from the patient before administration of a compound or stereoisomer, atropisomer, tautomer, or pharmaceutically acceptable salt thereof described herein for the absence or presence of a KRas$^{G12D}$ mutation. In one embodiment, a compound, stereoisomer, atropisomer, tautomer, or pharmaceutically acceptable salt thereof or pharmaceutical composition is administered to the patient after the patient sample shows the presence of a KRas$^{G12D}$ mutation. In one embodiment, a compound or stereoisomer, atropisomer, tautomer, or pharmaceutically acceptable salt thereof described herein is not administered unless a patient sample comprises a KRas$^{G12D}$ mutation.

In one embodiment, the cancer is pancreatic cancer, lung cancer, or colorectal cancer. In another embodiment, the cancer is tissue agnostic (comprises a KRas$^{G12D}$ mutation). In one such embodiment, the pancreatic cancer, lung cancer, or colorectal cancer comprises a KRas$^{G12D}$ mutation.

Further provided herein are methods of treating lung cancer comprising a KRas$^{G12D}$ mutation in a patient having such a lung cancer. In one such embodiment, is a method (M1) of treating lung cancer comprising a KRas$^{G12D}$ mutation in a patient having such a lung cancer, the method comprising administering to the patient an effective amount of a compound or a stereoisomer, atropisomer, tautomer, or pharmaceutically acceptable salt thereof (or a pharmaceutical composition comprising the same) described herein. In one embodiment, the lung cancer is non-small cell lung carcinoma (NSCLC). In one embodiment, lung cancer is adenocarcinoma, NSCLC, squamous-cell lung carcinoma (SCLC) or large-cell lung carcinoma. In one embodiment, lung cancer is adenocarcinoma, NSCLC, or SCLC. In another embodiment, the lung cancer is small cell lung carcinoma. In still another embodiment, the lung cancer is glandular tumors, carcinoid tumors or undifferentiated carcinomas. The lung cancer can be stage I or II lung cancer. In one embodiment, the lung cancer is stage III or IV lung cancer. The methods provided herein include administration of the compound as a 1 L therapy.

Still further provided herein are methods of treating pancreatic cancer comprising a KRas$^{G12D}$ mutation in a patient having such pancreatic cancer. In one such embodiment, is a method (M2) of pancreatic lung cancer comprising a KRas$^{G12D}$ mutation in a patient having pancreatic cancer, the method comprising administering to the patient an effective amount of a compound or stereoisomer, atropisomer, tautomer, or pharmaceutically acceptable salt thereof described herein. In one embodiment, the patient has been previously treated with radiation and one or more chemotherapy agents. In one embodiment, the pancreatic cancer is stage 0, I, or II. In another embodiment, the pancreatic cancer is stage III or stage IV.

Still further provided herein are methods of treating colon cancer comprising a KRas$^{G12D}$ mutation in a patient having such colon cancer. In one such embodiment, is a method (M3) of treating colon cancer comprising a KRas$^{G12D}$ mutation in a patient having, the method comprising administering to the patient an effective amount of a compound or stereoisomer, atropisomer, tautomer, or pharmaceutically acceptable salt thereof described herein to the patient. In one embodiment, the colon cancer is stage I or II. In another embodiment, the colon cancer is stage III or stage IV.

In one embodiment of the methods M1, M2, and M3 as described herein, the method further comprises:
(a) determining the absence or presence of a KRas$^{G12D}$ mutation in a sample taken from a patient with a suspected diagnosed cancer; and
(b) administering to the patient an effective amount of a compound or stereoisomer, atropisomer, tautomer, or pharmaceutically acceptable salt thereof described herein.

Further provided herein are methods of treating tissue agnostic cancer comprising a KRas$^{G12D}$ mutation. In one embodiment of such methods, the method comprises:
(a) determining the absence or presence of a KRas$^{G12D}$ mutation in a sample taken from a patient with a suspected diagnosed cancer; and
(b) administering to the patient an effective amount of a compound or stereoisomer, atropisomer, tautomer, or pharmaceutically acceptable salt thereof described herein.

In one embodiment of such methods, the patient is diagnosed with a cancer described herein. In another embodiment of such methods, the sample is a tumor sample taken from the subject. In one such embodiment, the sample is taken before administration of any therapy. In another such embodiment, the sample is taken before administration of a compound or stereoisomer, atropisomer, tautomer, or pharmaceutically acceptable salt thereof described herein and after administration of another chemotherapeutic agent. In another embodiment of such methods, the compound or stereoisomer, atropisomer, tautomer, or pharmaceutically acceptable salt thereof described herein is administered as provided herein (e.g. orally or IV).

Also provided herein is a compound or stereoisomer, atropisomer, tautomer, or pharmaceutically acceptable salt thereof for use as a therapeutically active substance. In one such embodiment, the compound or stereoisomer, atropisomer, tautomer, or pharmaceutically acceptable salt thereof can be for the therapeutic treatment of a cancer comprising a Kras$^{G12D}$ mutation.

Further provided herein is a compound or stereoisomer, atropisomer, tautomer, or pharmaceutically acceptable salt thereof for the therapeutic and/or prophylactic treatment of a cancer comprising a KRas$^{G12D}$ mutation. In one embodiment, the compound or stereoisomer, atropisomer, tautomer, or pharmaceutically acceptable salt thereof is used in the preparation of a medicament for the therapeutic treatment of a cancer comprising a KRas$^{G12D}$ mutation. Still further provided herein are uses of a compound or stereoisomer, atropisomer, tautomer, or pharmaceutically acceptable salt thereof as described herein in the manufacture of a medicament for inhibiting tumor metastasis.

Further provided herein are methods for inhibiting tumor metastasis, the method comprising administering to a patient having a tumor a therapeutically effective amount of a compound or stereoisomer, atropisomer, tautomer, or pharmaceutically acceptable salt thereof described herein. In one embodiment, the inhibition is of a tumor comprising a KRas$^{G12D}$ mutation. In another embodiment, inhibiting tumor metastasis in a patient described herein results in reduction of tumor size. In another embodiment, inhibiting tumor metastasis in a patient described herein results in stabilizing (e.g. no further growth) of tumor size. In another embodiment, inhibiting tumor metastasis in a patient described herein results in remission of the cancer and/or its symptoms.

Further provided herein are methods for inhibiting proliferation of a cell population, the method comprising contacting the cell population with a compound or stereoisomer, atropisomer, tautomer, or pharmaceutically acceptable salt thereof described herein. In one embodiment, the cell population is in a human patient. In another embodiment, the cell population comprises a KRas$^{G12D}$ mutation.

Further provided herein are methods of inhibiting KRas in a patient in need of therapy, comprising administering to the patient a therapeutically effective amount of a compound or stereoisomer, atropisomer, tautomer, or pharmaceutically acceptable salt thereof described herein. In one embodiment, the KRas inhibited is KRas$^{G12D}$. In another embodiment, inhibiting KRas results in decreased tumor size. In another embodiment, inhibiting KRas results in remission of the cancer and/or its symptoms.

Further provided herein are methods for regulating activity of a KRas mutant protein, the method comprising reacting the mutant protein with a compound or stereoisomer, atropisomer, tautomer, or pharmaceutically acceptable salt thereof described herein. In one embodiment, the mutant protein comprises a KRas$^{G12D}$ mutation. In one embodiment, the activity of KRas is decreased after contacting with a compound or stereoisomer, atropisomer, tautomer, or pharmaceutically acceptable salt thereof described herein. In another embodiment, the downregulation of activity of the KRas mutant protein treats a cancer described herein in a patient described herein. In another embodiment, the downregulation of activity of the KRas mutant protein results in decreased tumor size. In another embodiment, the downregulation of activity of the KRas mutant protein results in remission of a cancer described herein and/or its symptoms.

In some embodiments, the methods provided herein comprise inhibiting Kras$^{G12D}$ activity in a cell by contacting said cell with an amount of a compound or stereoisomer, atropisomer, tautomer, or pharmaceutically acceptable salt thereof described herein sufficient to inhibit the activity of KRas$^{G12D}$ in said cell. In some embodiments, the methods provided herein comprise inhibiting KRas$^{G12D}$ activity in a tissue by contacting said tissue with an amount of a compound or stereoisomer, atropisomer, tautomer, or pharmaceutically acceptable salt thereof described herein sufficient to inhibit the activity of KRas$^{G12D}$ in said tissue. In some embodiments, the methods provided herein comprise inhibiting KRas$^{G12D}$ activity in a patient described herein by contacting said patient with an amount of a compound or stereoisomer, atropisomer, tautomer, or pharmaceutically acceptable salt thereof described herein sufficient to inhibit the activity of KRas$^{G12D}$ in said patient.

Further provided herein are methods for preparing a labeled KRas$^{G12D}$ mutant protein, the method comprising reacting a KRas$^{G12D}$ mutant protein with a labeled compound or stereoisomer, atropisomer, tautomer, or pharmaceutically acceptable salt thereof described herein to result in the labeled KRas$^{G12D}$ mutant protein. In one embodiment, the label is an imaging agent. In one embodiment, the labeled KRas$^{G12D}$ can be used to detect the absence or presence of G12D mutant KRas in a patient sample, thereby detecting the presence or absence of a cancer mediated by mutant KRas.

Still further provided herein are methods of inhibiting Ras-mediated cell signaling. In one embodiment, the methods comprise contacting a cell with an effective amount of one or more compounds or a stereoisomer, atropisomer, tautomer, or pharmaceutically acceptable salt thereof disclosed herein thereof. Inhibition of Ras-mediated signal transduction can be assessed and demonstrated by a wide variety of ways known in the art. Non-limiting examples include a showing of (a) a decrease in GTPase activity of Ras; (b) a decrease in GTP binding affinity or an increase in GDP binding affinity; (c) an increase in K off of GTP or a decrease in K off of GDP; (d) a decrease in the levels of signaling transduction molecules downstream in the Ras pathway, such as a decrease in pMEK level; and/or (e) a decrease in binding of Ras complex to downstream signaling molecules including but not limited to Raf. Kits and commercially available assays can be utilized for determining one or more of the above.

KRas mutations, including G12D mutants, have also been identified in hematological malignancies (e.g., cancers that affect blood, bone marrow, and/or lymph nodes). Accordingly, certain embodiments are directed to administration of a disclosed compound or stereoisomer, atropisomer, tautomer, or pharmaceutically acceptable salt thereof (e.g., in the form of a pharmaceutical composition) as described herein to a patient in need of treatment of a hematological malignancy. Such malignancies include but are not limited to leukemias and lymphomas. For example, the presently disclosed compounds can be used for treatment of diseases such as acute lymphoblastic leukemia (ALL), acute myelogenous leukemia (AML), chronic lymphocytic leukemia (CLL), small lymphocytic lymphoma (SLL), chronic myelogenous leukemia (CML), acute monocytic leukemia (AMoL) and/or other leukemias. In other embodiments, the compounds or a pharmaceutically acceptable salt thereof described herein are useful for treatment of lymphomas such as all subtypes of Hodgkin's lymphoma or non-Hodgkin's lymphoma.

Determining whether a tumor or cancer comprises a $KRas^{G12D}$ mutation can be undertaken by assessing the nucleotide sequence encoding the KRas protein, by assessing the amino acid sequence of the KRas protein, or by assessing the characteristics of a putative KRas mutant protein. The sequence of wild-type human KRas (e.g., Accession No. NP203524) is known in the art.

Methods for detecting a mutation in a KRas nucleotide sequence are known by those of skill in the art. These methods include, but are not limited to, polymerase chain reaction-restriction fragment length polymorphism (PCR-RFLP) assays, polymerase chain reaction-single strand conformation polymorphism (PCR-SSCP) assays, real-time PCR assays, PCR sequencing, mutant allele-specific PCR amplification (MASA) assays, direct sequencing, primer extension reactions, electrophoresis, oligonucleotide ligation assays, hybridization assays, TaqMan assays, SNP genotyping assays, high resolution melting assays and microarray analyses. In some embodiments, samples are evaluated for G12d KRas mutations by real-time PCR. In real-time PCR, fluorescent probes specific for the KRas G12D mutation are used. When a mutation is present, the probe binds and fluorescence is detected. In some embodiments, the KRas G12D mutation is identified using a direct sequencing method of specific regions (e.g., exon 2 and/or exon 3) in the KRas gene. This technique will identify all possible mutations in the region sequenced.

Methods for determining whether a tumor or cancer comprises a $KRas^{G12D}$ mutation can use a variety of samples. In some embodiments, the sample is taken from a subject having a tumor or cancer. In some embodiments, the sample is a fresh tumor/cancer sample. In some embodiments, the sample is a frozen tumor/cancer sample. In some embodiments, the sample is a formalin-fixed paraffin-embedded sample. In some embodiments, the sample is processed to a cell lysate. In some embodiments, the sample is processed to DNA or RNA.

Further provided herein are uses of a compound or stereoisomer, atropisomer, tautomer, or pharmaceutically acceptable salt thereof described herein, in the manufacture of a medicament for treating cancer. In some embodiments, the medicament is formulated for oral administration. In some embodiments, the medicament is formulated for injection (e.g. IV administration). In some embodiments, the cancer is comprises a $KRas^{G12D}$ mutation. In some embodiments, the cancer is a hematological cancer, pancreatic cancer, MYH associated polyposis, colorectal cancer or lung cancer. In one embodiment, the cancer is lung cancer, colorectal cancer, or pancreatic cancer. In one embodiment, the cancer is colorectal cancer. In another embodiment, the cancer is pancreatic cancer. In some embodiments, the cancer is lung adenocarcinoma. In some embodiments, are uses of a compound or stereoisomer, atropisomer, tautomer, or pharmaceutically acceptable salt thereof described herein, in the manufacture of a medicament for inhibiting tumor metastasis.

Combination Therapies

The compounds or a stereoisomer, atropisomer, tautomer, or pharmaceutically acceptable salt thereof described herein may be employed alone or in combination with other therapeutic agents for the treatment of a disease or disorder described herein. The second compound of the pharmaceutical combination formulation or dosing regimen preferably has complementary activities to the compound or a pharmaceutically acceptable salt thereof described herein such that they do not adversely affect each other. The combination therapy may provide "synergy" and prove "synergistic", i.e., the effect achieved when the active ingredients used together is greater than the sum of the effects that results from using the compounds separately.

The combination therapy may be administered as a simultaneous or sequential regimen. When administered sequentially, the combination may be administered in two or more administrations. The combined administration includes co-administration, using separate formulations or a single pharmaceutical formulation, and consecutive administration in either order, wherein preferably there is a time period while both (or all) active agents simultaneously exert their biological activities.

Combination therapies herein comprise the administration of a compound or stereoisomer, atropisomer, tautomer, or pharmaceutically acceptable salt thereof described herein, and the use of at least one other treatment method. The amounts of the compound or stereoisomer, atropisomer, tautomer, or pharmaceutically acceptable salt thereof described herein and the other pharmaceutically active agent (s) and the relative timings of administration will be selected in order to achieve the desired combined therapeutic effect.

In various embodiments of the method, the additional therapeutic agent is an epidermal growth factor receptor (EGFR) inhibitor, phosphatidylinositol kinase (PI3K) inhibitor, insulin-like growth factor receptor (IGF1R) inhibitor, a Janus kinase (JAK) inhibitor, a Met kinase inhibitor, a SRC family kinase inhibitor, a mitogen-activated protein kinase (MEK) inhibitor, an extracellular-signal-regulated kinase (ERK) inhibitor, a topoisomerase inhibitor (such as irinotecan, or such as etoposide, or such as doxorubicin), a taxane (such as anti-microtubule agents including paclitaxel and docetaxel), an anti-metabolite agent (such as 5-FU or such as gemcitabine), or an alkylating agent (such as cisplatin or such as cyclophosphamide), or a taxane.

In some embodiments, the additional therapeutic agent is an epidermal growth factor receptor (EGFR) inhibitor, such as Erlotinib or such as Afatinib. In some embodiments the additional therapeutic agent is gefitinib, osimertinib, or dacomitinib. In some embodiments the additional therapeutic agent is a monoclonal antibody such as cetuximab (Erbitux) or panitumumab (Vectibix). In some embodiments the GFR inhibitor is a dual or pan-HER inhibitor. In other embodiments, the additional therapeutic agent is a phosphatidylinositol-3-kinase (PI3K) inhibitor, such as GDC-0077, GDC-0941, MLN1117, BYL719 (Alpelisib) or BKM120 (Buparlisib). GDC-0941 refers to 2-(1H-indazol-4-yl)-6-(4-methanesulfonyl-piperazin-1-ylmethyl)-4-morpholin-4-yl-thieno[3,2-d]pyrimidine or a salt thereof (e.g., bismesylate salt).

In still other embodiments, the additional therapeutic agent is an insulin-like growth factor receptor (IGF1R) inhibitor. For example, in some embodiments the insulin-like growth factor receptor (IGF1R) inhibitor is NVP-AEW541. In other embodiments, the additional therapeutic agent is IGOSI-906 (Linsitinib), BMS-754807, or in other embodiments the additional therapeutic agent is a neutralizing monoclonal antibody specific to IGF1R such as AMG-479 (ganitumab), CP-751,871 (figitumumab), IMC-A12 (cixutumumab), MK-0646 (dalotuzumab), or R-1507 (robatumumab).

In some other embodiments, the additional therapeutic agent is a Janus kinase (JAK) inhibitor. In some embodiments, the additional therapeutic agent is CYT387, GLPG0634, Baricitinib, Lestaurtinib, momelotinib, Pacritinib, Ruxolitinib, or TG101348.

In some other embodiments, the additional therapeutic agent is an anti-glypican 3 antibody. In some embodiments, the anti-glypican 3 antibody is codrituzumab.

In some other embodiments, the additional therapeutic agent is an antibody drug conjugate (ADC). In some embodiments, the ADC is polatuzumab vedotin, RG7986, RG7882, RG6109, or RO7172369.

In some other embodiments, the additional therapeutic agent is an MDM2 antagonist. In some embodiments, the MDM2 antagonist is idasanutlin.

In some other embodiments, the additional therapeutic agent is an agonistic antibody against CD40. In some embodiments, the agonistic antibody against CD40 is selicrelumab (RG7876).

In some other embodiments, the additional therapeutic agent is a bispecific antibody. In some embodiments, the bispecific antibody is RG7828 (BTCT4465A), RG7802, RG7386 (FAP-DR$^5$), RG6160, RG6026, ERY974, or anti-HER2/CD3.

In some other embodiments, the additional therapeutic agent is a targeted immunocytokine. In some embodiments, the targeted immunocytokine is RG7813 or RG7461.

In some other embodiments, the additional therapeutic agent is an antibody targeting colony stimulating factor-1 receptor (CSF-1R). In some embodiments, the CSF-1R antibody is emactuzumab.

In some other embodiments, the additional therapeutic agent is a personalized cancer vaccine. In some embodiments, the personalized cancer vaccine is RG6180.

In some other embodiments, the additional therapeutic agent is an inhibitor of BET (bromodomain and extraterminal family) proteins (BRD2/3/4/T). In some embodiments, the BET inhibitor is RG6146.

In some other embodiments, the additional therapeutic agent is an antibody designed to bind to TIGIT. In some embodiments, the anti-TIGIT antibody is RG6058 (MTIG7192A).

In some other embodiments, the additional therapeutic agent is a selective estrogen receptor degrader (SERD). In some other embodiments, the SERD is RG6047 (GDC-0927) or RG6171 (GDC-9545, giredestrant).

In some other embodiments the additional therapeutic agent is an MET kinase inhibitor, such as Crizotinib, tivantinib, AMG337, cabozantinib, or foretinib. In other embodiments the additional therapeutic agent is a neutralizing monoclonal antibody to MET such as onartuzumab.

In more embodiments, the additional therapeutic agent is a SRC family non-receptor tyrosine kinase inhibitor. For example, in some embodiments the additional therapeutic agent is an inhibitor of the subfamily of SRC family non-receptor tyrosine kinases. Exemplary inhibitors in this respect include Dasatinib. Other examples in this regard include Ponatinib, saracatinib, and bosutinib.

In yet other embodiments, the additional therapeutic agent is a mitogen-activated protein kinase (MEK) inhibitor. In some of these embodiments, the mitogen-activated protein kinase (MEK) inhibitor is trametinib, selumetinib, COTELLIC® (cobimetinib), PD0325901, or RO5126766. In other embodiments the MEK inhibitor is GSK-1120212, also known as trametinib.

In yet other embodiments, the additional therapeutic agent is an extracellular-signal-regulated kinase (ERK) inhibitor. In some of these embodiments, the mitogen-activated protein kinase (MEK) inhibitor is SCH$_{722984}$ or GDC-0994.

In other embodiments the protein kinase inhibitor is taselisib, ipatasertib, GDC-0575, GDC-5573 (HM95573), RG6114 (GDC-0077), CKI27, Afatinib, Axitinib, Atezolizumab, Bevacizumab, Bostutinib, Cetuximab, Crizotinib, Dasatinib, Erlotinib, Fostamatinib, Gefitinib, Imatinib, Lapatinib, Lenvatinib, Ibrutinib, Nilotinib, Panitumumab, Pazopanib, Pegaptanib, Ranibizumab, Ruxolitinib, Sorafenib, Sunitinib, SU6656, Trastuzumab, Tofacitinib, Vandetanib, or Vemurafenib. In still more embodiments, the additional therapeutic agent is a topoisomerase inhibitor. In some of these embodiments, the topoisomerase inhibitor is Irinotecan. In some more embodiments, the additional therapeutic agent is a taxane. Exemplary taxanes include Taxol and Docetaxel.

In addition to the above additional therapeutic agent, other chemotherapeutics are presently known in the art and can be used in combination with the compounds and pharmaceutically acceptable salts thereof described herein. In some embodiments, the chemotherapeutic is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens.

Non-limiting examples are chemotherapeutic agents, cytotoxic agents, and non-peptide small molecules such as Gleevec® (Imatinib Mesylate), Velcade® (bortezomib), Casodex (bicalutamide), Iressa® (gefitinib), and Adriamycin as well as a host of chemotherapeutic agents. Non-limiting examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methyl melamines including altretamine, triethylenemelamine, triethylenephosphoramide, triethylenethiophosphaoramide and trimethylol melamine; nitrogen mustards such as chlorambucil, chlornaphazine, cyclophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, Casodex™, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfornithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; polysaccharide K; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (TAXOL™, Bristol-Myers Squibb Oncology, Princeton, N.J.) and docetaxel (TAXOTERE™, Rhone-Poulenc Rorer, Antony, France); retinoic acid; esperamicins; capecitabine; and pharmaceutically acceptable salts, acids or derivatives of any of the above. Also included as suitable chemotherapeutic cell conditioners are antihormonal agents that act to regulate or inhibit hormone action on tumors such as anti-estrogens including for example tamoxifen, (Nolvadex™), raloxifene, aromatase inhibiting 4(5)-imidazoles, 4-hydroxytamoxifen, trioxifene, keoxifene, LY 117018, onapristone, and toremifene (Fareston); anti-androgens such as flutamide, nilutamide, bicalutamide, leuprolide, and goserelin; chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; Xeloda®; ibandronate; camptothecin-11 (CPT-11); topoisomerase inhibitor RFS 2000; and difluoromethylornithine (DMFO). Where desired, the compounds or pharmaceutical acceptable salts thereof or pharmaceutical composition as described herein can be used in combination with commonly prescribed anti-cancer drugs such as Herceptin®, Avastin®, Gazyva®, Tecentriq®, Alecensa®, Perjeta®, Venclexta™, Erbitux®, Rituxan®, Taxol®, Arimidex®, Taxotere®, ABVD, AVICINE, Abagovomab, Acridine carboxamide, Adecatumumab, 17-N-Allylamino-17-demethoxygeldanamycin, Alpharadin, Alvocidib, 3-Aminopyridine-2-carboxaldehyde thiosemicarbazone, Amonafide, Anthracenedione, Anti-CD22 immunotoxins, Antineoplastic, Antitumorigenic herbs, Apaziquone, Atiprimod, Azathioprine, Belotecan, Bendamustine, BIBW 2992, Biricodar, Brostallicin, Bryostatin, Buthionine sulfoximine, CBV (chemotherapy), Calyculin, cell-cycle nonspecific antineoplastic agents, Dichloroacetic acid, Discodermolide, Elsamitrucin, Enocitabine, Epothilone, Eribulin, Everolimus, Exatecan, Exisulind, Ferruginol, Forodesine, Fosfestrol, ICE chemotherapy regimen, IT-101, Imexon, Imiquimod, Indolocarbazole, Irofulven, Laniquidar, Larotaxel, Lenalidomide, Lucanthone, Lurtotecan, Mafosfamide, Mitozolomide, Nafoxidine, Nedaplatin, Olaparib, Ortataxel, PAC-1, Pawpaw, Pixantrone, Proteasome inhibitor, Rebeccamycin, Resiquimod, Rubitecan, SN-38, Salinosporamide A, Sapacitabine, Stanford V, Swainsonine, Talaporfin, Tariquidar, Tegafur-uracil, Temodar, Tesetaxel, Triplatin tetranitrate, Tris(2-chloroethyl)amine, Troxacitabine, Uramustine, Vadimezan, Vinflunine, ZD6126 or Zosuquidar.

The exact method for administering the compound and the additional therapeutic agent will be apparent to one of ordinary skill in the art. In some exemplary embodiments the compound and the additional therapeutic agent are co-administered. In other embodiments, the compound and the additional therapeutic agent are separately administered.

In some embodiments, the compound and the additional therapeutic agent are administered with the second agent simultaneously or separately. This administration in combination can include simultaneous administration of the two agents in the same dosage form, simultaneous administration in separate dosage forms, and separate administration. That is, the compound and any of the additional therapeutic agents described herein can be formulated together in the same dosage form and administered simultaneously. Alternatively, the compound and any of the additional therapeutic agents described herein can be simultaneously administered, wherein both the agents are present in separate formulations. In another alternative, the compound can be administered just followed by any of the additional therapeutic agents described herein, or vice versa. In some embodiments of the separate administration protocol, the compound and any of the additional therapeutic agents described herein are administered a few minutes apart, or a few hours apart, or a few days apart.

Articles of Manufacture

Also provided herein are articles of manufacture, or "kit", containing materials useful for the treatment of a cancer provided herein. In one embodiment, the kit comprises a container comprising compound or stereoisomer, atropisomer, tautomer, or pharmaceutically acceptable salt thereof described herein. The kit may further comprise a label or package insert on or associated with the container. Suitable containers include, for example, bottles, vials, syringes, blister pack, etc. The container may be formed from a variety of materials such as glass or plastic. The container may hold a compound or a pharmaceutically acceptable salt thereof described herein or a formulation thereof which is effective for treating the condition and may have a sterile access port (for example, the container may be an intravenous solution bag or a vial having a stopper pierceable by a hypodermic injection needle). At least one active agent in the composition is a compound or a pharmaceutically acceptable salt thereof described herein. Alternatively, or additionally, the article of manufacture may further comprise a second container comprising a pharmaceutical diluent, such as bacteriostatic water for injection (BWFI), phosphate-buffered saline, Ringer's solution or dextrose solution. It may further include other materials desirable from a commercial and user standpoint, including other buffers, diluents, filters, needles, and syringes.

In another embodiment, the kits are suitable for the delivery of solid oral forms of a compound or a pharmaceutically acceptable salt thereof described herein, such as tablets or capsules. Such a kit can include a number of unit dosages. An example of such a kit is a "blister pack". Blister packs are well known in the packaging industry and are widely used for packaging pharmaceutical unit dosage forms.

Embodiments

Provided below are exemplary embodiments of the invention.

Embodiment 0. A compound of formula (I) or a stereoisomer, atropisomer, tautomer, or pharmaceutically acceptable salt thereof, wherein X is O or $NR^6$ m is 1 or 2;

n is 1 or 2;

wherein n and m together make a 6- or 7-membered ring Ring A;

p is 0, 1, or 2;

$R^1$ is $R^7$-substituted or unsubstituted naphthyl, $R^7$-substituted or unsubstituted isoquinolinyl, $R^7$-substituted or unsubstituted indazolyl, $R^7$-substituted or unsubstituted indanyl, $R^7$-substituted or unsubstituted benzothiazolyl, $R^{7A}$-substituted phenyl, or $R^{7A}$-substituted pyridinyl;

each $R^7$ is independently halogen, OH, $NH_2$, $N(Me)_2$, unsubstituted $C_{1-3}$ alkyl, unsubstituted $C_{1-3}$ alkynyl, unsubstituted $C_{1-3}$ alkoxy, or unsubstituted $C_{1-3}$ haloalkyl each $R^{7A}$ is independently halogen, CN, $NH_2$, $N(Me)_2$, $R^{7B}$ substituted or unsubstituted $C_{1-3}$ alkyl, unsubstituted $C_{1-3}$ haloalkyl, or unsubstituted cyclopropyl $R^{7B}$ is CN, oxo, or $C_{1-3}$ alkyl;

$L^1$ is $R^{L1}$-substituted or unsubstituted $C_{1-4}$ alkylene;

$R^{L1}$ is halogen or unsubstituted $C_{1-3}$ alkyl, or wherein two $R^{L1}$ together form an unsubstituted $C_{3-4}$ cycloalkyl;

$R^2$ is $R^9$-substituted or unsubstituted 4-10 membered heterocycle comprising one or more heteroatoms selected from N, S, or O;

$R^9$ is independently halogen, CN, OH, $OCF_3$, $OCHF_2$, $OCH_2F$, $R^{10}$-substituted or unsubstituted $C_{1-3}$ alkyl, $R^{10}$-substituted or unsubstituted $C_{1-3}$ haloalkyl, unsubstituted $C_{1-3}$ alkoxy, $R^{10}$-substituted or unsubstituted $C_{1-3}$ alkylidene, or $R^{10}$-substituted or unsubstituted $C_{3-4}$ cycloalkyl, or $R^{10}$-substituted or unsubstituted 3 or 4-membered heterocycle; or wherein two $R^9$ together form a $R^{10}$-substituted or unsubstituted $C_{3-5}$ cycloalkyl or a $R^{10}$-substituted or unsubstituted $C_{3-5}$ heterocycle comprising one or more oxygen atoms; or wherein two $R^9$ together form a bridge between two carbon atoms of the cycloalkyl or heterocycle, wherein the bridge comprises 1-3 carbons;

each $R^{10}$ is independently hydrogen, oxo, CN, halogen, or $C_{1-3}$ unsubstituted alkyl;

$R^3$ is hydrogen, —CN, halogen, unsubstituted $C_{1-3}$ alkyl, or unsubstituted cyclopropyl;

each $R^4$ is independently hydrogen, methyl, or $C_{1-3}$ haloalkyl;

$R^5$ is independently halogen, oxo, unsubstituted $C_{1-3}$ alkyl, or unsubstituted $C_{1-3}$ haloalkyl; or wherein two $R^5$ together form a bridge between two carbon atoms of Ring A, wherein the bridge comprises 1-3 carbons and optionally one heteroatom selected from O and N; or two $R^5$ together form a bridge between two carbon atoms of Ring A, wherein the bridge comprises one of O or $NR^{11}$;

$R^{11}$ is hydrogen, $C(O)CH_3$, or unsubstituted $C_{1-3}$ alkyl;

$R^6$ is hydrogen, $R^{6A}$-substituted or unsubstituted $C_{1-6}$ alkyl, $R^{6A}$-substituted or unsubstituted $C_{1-6}$ haloalkyl, $R^{6A}$-substituted or unsubstituted $C_{1-6}$ alkenyl; $R^{6A}$-substituted or unsubstituted $C_{1-6}$ alkynyl, or $R^{6A}$-substituted or unsubstituted 3-4 membered heterocycle $R^{6A}$ is halogen, CN, $OR^{6B}$, $SR^{6C}$, $S(O)_2R^{6C}$, $C(O)R^{6B}$, unsubstituted $C_{1-3}$ alkyl, unsubstituted $C_{1-3}$ haloalkyl, or $R^{6B}$ substituted or unsubstituted 3-4 membered heterocycle and $R^{6B}$ and $R^{6C}$ are each independently $C_{1-3}$ alkyl or $C_{1-3}$ haloalkyl.

Embodiment 1. A compound of formula (I) or a stereoisomer, atropisomer, tautomer, or pharmaceutically acceptable salt thereof, wherein X is O or $NR^6$;

m is 1 or 2;

n is 1 or 2;

wherein n and m together make a 6- or 7-membered ring Ring A;

p is 0, 1, or 2;

$R^1$ is formula (E), wherein $X^1$ is N or $CR^{7C}$ and $R^{7C}$ is hydrogen or halogen;

each $R^{7A}$ is independently halogen, CN, $NH_2$, $N(Me)_2$, $R^{7B}$-substituted or unsubstituted $C_{1-3}$ alkyl, unsubstituted $C_{1-3}$ haloalkyl, or unsubstituted cyclopropyl;

$R^{7B}$ is CN, oxo, or $C_{1-3}$ alkyl;

$L^1$ is $R^{L1}$-substituted or unsubstituted $C_{1-4}$ alkylene;

$R^{L1}$ is halogen or unsubstituted $C_{1-3}$ alkyl, or wherein two $R^{L1}$ together form an unsubstituted $C_{3-4}$ cycloalkyl;

$R^2$ is $R^9$-substituted or unsubstituted 4-10 membered heterocycle comprising one or more heteroatoms selected from N, S, or O;

$R^9$ is independently halogen, CN, OH, $OCF_3$, $OCHF_2$, $OCH_2F$, $R^{10}$-substituted or unsubstituted $C_{1-3}$ alkyl, $R^{10}$-substituted or unsubstituted $C_{1-3}$ haloalkyl, unsubstituted $C_{1-3}$ alkoxy, $R^{10}$-substituted or unsubstituted $C_{1-3}$ alkylidene, or $R^{10}$-substituted or unsubstituted $C_{3-4}$ cycloalkyl, or $R^{10}$-substituted or unsubstituted 3 or 4-membered heterocycle; or wherein two $R^9$ together form a $R^{10}$-substituted or unsubstituted $C_{3-5}$ cycloalkyl or a $R^{10}$-substituted or unsubstituted $C_{3-5}$ heterocycle comprising one or more oxygen atoms; or wherein two $R^9$ together form a bridge between two carbon atoms of the cycloalkyl or heterocycle, wherein the bridge comprises 1-3 carbons;

each $R^{10}$ is independently hydrogen, oxo, CN, halogen, or $C_{1-3}$ unsubstituted alkyl;

$R^3$ is hydrogen, —CN, halogen, unsubstituted $C_{1-3}$ alkyl, or unsubstituted cyclopropyl;

each $R^4$ is independently hydrogen, methyl, or $C_{1-3}$ haloalkyl;

$R^5$ is independently halogen, oxo, unsubstituted $C_{1-3}$ alkyl, or unsubstituted $C_{1-3}$ haloalkyl; or wherein two $R^5$ together form a bridge between two carbon atoms of Ring A, wherein the bridge comprises 1-3 carbons and optionally one heteroatom selected from O and N; or two $R^5$ together form a bridge between two carbon atoms of Ring A, wherein the bridge comprises one of O or $NR^{11}$;

$R^{11}$ is hydrogen, $C(O)CH_3$, or unsubstituted $C_{1-3}$ alkyl;

$R^6$ is hydrogen, $R^{6A}$-substituted or unsubstituted $C_{1-6}$ alkyl, $R^{6A}$-substituted or unsubstituted $C_{1-6}$ haloalkyl, $R^{6A}$-substituted or unsubstituted $C_{1-6}$ alkenyl; $R^{6A}$-substituted or unsubstituted $C_{1-6}$ alkynyl, or $R^{6A}$-substituted or unsubstituted 3-4 membered heterocycle;

$R^{6A}$ is halogen, CN, $OR^{6B}$, $SR^{6C}$, $S(O)_2R^{6C}$, $C(O)R^{6B}$, unsubstituted $C_{1-3}$ alkyl, unsubstituted $C_{1-13}$ haloalkyl, or $R^{6B}$ substituted or unsubstituted 3-4 membered heterocycle; and $R^{6B}$ and $R^{6C}$ are each independently $C_{1-3}$ alkyl or $C_{1-3}$ haloalkyl.

Embodiment 2. The compound or a stereoisomer, atropisomer, tautomer, or pharmaceutically acceptable salt thereof of embodiment 1, wherein $X^1$ is $CR^{7C}$ and $R^{7C}$ is hydrogen or halogen.

Embodiment 3. The compound or a stereoisomer, atropisomer, tautomer, or pharmaceutically acceptable salt thereof of embodiment 1, wherein $X^1$ is N.

Embodiment 4. A compound of formula (I) or a stereoisomer, atropisomer, tautomer, or pharmaceutically acceptable salt thereof, wherein X is O or $NR^6$;

m is 1 or 2;

n is 1 or 2;

wherein n and m together make a 6- or 7-membered ring Ring A;

p is 0, 1, or 2;

$R^1$ is a moiety of formula (E2) or (E3)

each $R^{7A}$ is independently hydrogen, halogen, unsubstituted $C_{1-3}$ alkyl or unsubstituted $C_{1-3}$ haloalkyl;

$L^1$ is $R^{L1}$-substituted or unsubstituted $C_{1-4}$ alkylene;

$R^{L1}$ is halogen or unsubstituted $C_{1-3}$ alkyl, or wherein two $R^{L1}$ together form an unsubstituted $C_{3-4}$ cycloalkyl;

$R^2$ is $R^9$-substituted or unsubstituted 4-10 membered heterocycle comprising one or more heteroatoms selected from N, S, or O;

$R^9$ is independently halogen, CN, OH, $OCF_3$, $OCHF_2$, $OCH_2F$, $R^{10}$-substituted or unsubstituted $C_{1-3}$ alkyl, $R^{10}$-substituted or unsubstituted $C_{1-3}$ haloalkyl, unsubstituted $C_{1-3}$ alkoxy, $R^{10}$-substituted or unsubstituted $C_{1-3}$ alkylidene, or $R^{10}$-substituted or unsubstituted $C_{3-4}$ cycloalkyl, or $R^{10}$-substituted or unsubstituted 3 or 4-membered heterocycle; or wherein two $R^9$ together form a $R^{10}$-substituted or unsubstituted $C_{3-5}$ cycloalkyl or a $R^{10}$-substituted or unsubstituted $C_{3-5}$ heterocycle comprising one or more oxygen atoms; or wherein two $R^9$ together form a bridge between two carbon atoms of the cycloalkyl or heterocycle, wherein the bridge comprises 1-3 carbons;

each $R^{10}$ is independently hydrogen, oxo, CN, halogen, or $C_{1-3}$ unsubstituted alkyl;

$R^3$ is hydrogen, —CN, halogen, unsubstituted $C_{1-3}$ alkyl, or unsubstituted cyclopropyl;

each $R^4$ is independently hydrogen, methyl, or $C_{1-3}$ haloalkyl;

$R^5$ is independently halogen, oxo, unsubstituted $C_{1-3}$ alkyl, or unsubstituted $C_{1-3}$ haloalkyl; or wherein two $R^5$ together form a bridge between two carbon atoms of Ring A, wherein the bridge comprises 1-3 carbons and optionally one heteroatom selected from O and N; or two $R^5$ together form a bridge between two carbon atoms of Ring A, wherein the bridge comprises one of O or $NR^1$;

$R^{11}$ is hydrogen, $C(O)CH_3$, or unsubstituted $C_{1-3}$ alkyl;

$R^6$ is hydrogen, $R^{6A}$-substituted or unsubstituted $C_{1-6}$ alkyl, $R^{6A}$-substituted or unsubstituted $C_{1-6}$ haloalkyl, $R^{6A}$-substituted or unsubstituted $C_{1-6}$ alkenyl; $R^{6A}$-substituted or unsubstituted $C_{1-6}$ alkynyl, or $R^{6A}$-substituted or unsubstituted 3-4 membered heterocycle;

$R^{6A}$ is halogen, CN, $OR^{6B}$, $SR^{6C}$, $S(O)_2R^{6C}$, $C(O)R^{6B}$, unsubstituted $C_{1-3}$ alkyl, unsubstituted $C_{1-3}$ haloalkyl, or $R^{6B}$ substituted or unsubstituted 3-4 membered heterocycle; and $R^{6B}$ and $R^{6C}$ are each independently $C_{1-3}$ alkyl or $C_{1-3}$ haloalkyl.

Embodiment 5. The compound or a stereoisomer, atropisomer, tautomer, or pharmaceutically acceptable salt thereof of embodiment 4, wherein no more than one $R^{7A}$ is hydrogen.

Embodiment 6. The compound or a stereoisomer, atropisomer, tautomer, or pharmaceutically acceptable salt thereof of embodiment 4, wherein $R^{7A}$ is not hydrogen.

Embodiment 7. The compound or a stereoisomer, atropisomer, tautomer, or pharmaceutically acceptable salt thereof of embodiment 4, wherein at least one $R^{7A}$ is halogen.

Embodiment 8. The compound or a stereoisomer, atropisomer, tautomer, or pharmaceutically acceptable salt thereof of embodiment 4, wherein at least one $R^{7A}$ is unsubstituted $C_{1-3}$ haloalkyl.

Embodiment 9. A compound of formula (I): or a stereoisomer, atropisomer, tautomer, or pharmaceutically acceptable salt thereof, wherein X is O or $NR^6$;

m is 1 or 2;

n is 1 or 2;

wherein n and m together make a 6- or 7-membered ring Ring A;

p is 0, 1, or 2;

$R^1$ is

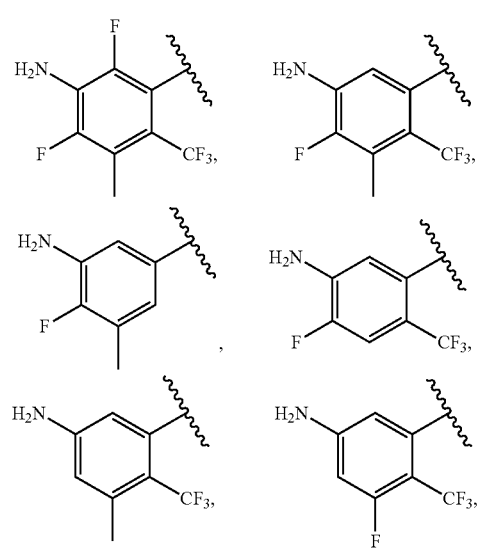

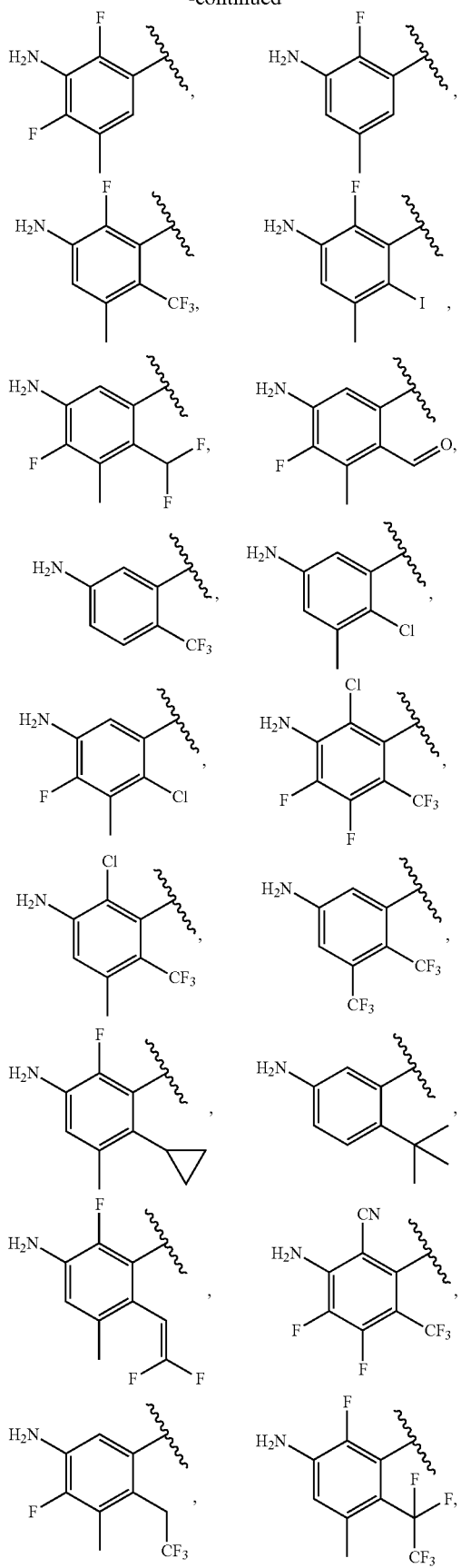

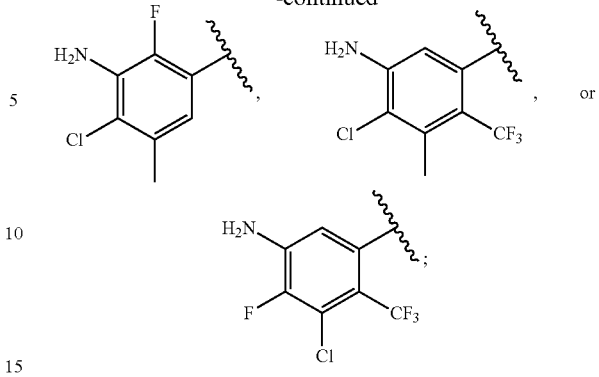

$L^1$ is $R^{L1}$-substituted or unsubstituted $C_{1-4}$ alkylene;

$R^{L1}$ is halogen or unsubstituted $C_{1-3}$ alkyl, or wherein two $R^{L1}$ together form an unsubstituted $C_{3-4}$ cycloalkyl;

$R^2$ is $R^9$-substituted or unsubstituted 4-10 membered heterocycle comprising one or more heteroatoms selected from N, S, or O;

$R^9$ is independently halogen, CN, OH, $OCF_3$, $OCHF_2$, $OCH_2F$, $R^{10}$-substituted or unsubstituted $C_{1-3}$ alkyl, $R^{10}$-substituted or unsubstituted $C_{1-3}$ haloalkyl, unsubstituted $C_{1-3}$ alkoxy, $R^{10}$-substituted or unsubstituted $C_{1-3}$ alkylidene, or $R^{10}$-substituted or unsubstituted $C_{3-4}$ cycloalkyl, or $R^{10}$-substituted or unsubstituted 3 or 4-membered heterocycle; or wherein two $R^9$ together form a $R^{10}$-substituted or unsubstituted $C_{3-5}$ cycloalkyl or a $R^{10}$-substituted or unsubstituted $C_{3-5}$ heterocycle comprising one or more oxygen atoms; or wherein two $R^9$ together form a bridge between two carbon atoms of the cycloalkyl or heterocycle, wherein the bridge comprises 1-3 carbons;

each $R^{10}$ is independently hydrogen, oxo, CN, halogen, or $C_{1-3}$ unsubstituted alkyl;

$R^3$ is hydrogen, —CN, halogen, unsubstituted $C_{1-3}$ alkyl, or unsubstituted cyclopropyl;

each $R^4$ is independently hydrogen, methyl, or $C_{1-3}$ haloalkyl;

$R^5$ is independently halogen, oxo, unsubstituted $C_{1-3}$ alkyl, or unsubstituted $C_{1-3}$ haloalkyl; or wherein two $R^5$ together form a bridge between two carbon atoms of Ring A, wherein the bridge comprises 1-3 carbons and optionally one heteroatom selected from O and N; or two $R^5$ together form a bridge between two carbon atoms of Ring A, wherein the bridge comprises one of O or $NR^{11}$;

$R^{11}$ is hydrogen, $C(O)CH_3$, or unsubstituted $C_{1-3}$ alkyl;

$R^6$ is hydrogen, $R^{6A}$-substituted or unsubstituted $C_{1-6}$ alkyl, $R^{6A}$-substituted or unsubstituted $C_{1-6}$ haloalkyl, $R^{6A}$-substituted or unsubstituted $C_{1-6}$ alkenyl; $R^{6A}$-substituted or unsubstituted $C_{1-6}$ alkynyl, or $R^{6A}$-substituted or unsubstituted 3-4 membered heterocycle;

$R^{6A}$ is halogen, CN, $OR^{6B}$, $SR^{6C}$, $S(O)_2R^{6C}$, $C(O)R^{6B}$, unsubstituted $C_{1-3}$ alkyl, unsubstituted $C_{1-3}$ haloalkyl, or $R^{6B}$ substituted or unsubstituted 3-4 membered heterocycle; and $R^{6B}$ and $R^{6C}$ are each independently $C_{1-3}$ alkyl or $C_{1-3}$ haloalkyl.

Embodiment 10. A compound of formula (I) or a stereoisomer, atropisomer, tautomer, or pharmaceutically acceptable salt thereof, wherein X is O or $NR^6$;

m is 1 or 2;

n is 1 or 2;

wherein n and m together make a 6- or 7-membered ring Ring A;

p is 0, 1, or 2;

$R^1$ is $R^{7A}$-substituted phenyl or $R^{7A}$-substituted pyridinyl;

each $R^{7A}$ is independently halogen, $NH_2$, unsubstituted $C_{1-3}$ alkyl, or unsubstituted $C_{1-3}$ haloalkyl;

$L^1$ is $R^{L1}$-substituted or unsubstituted $C_{1-4}$ alkylene;

$R^{L1}$ is halogen or unsubstituted $C_{1-3}$ alkyl, or wherein two $R^{L1}$ together form an unsubstituted $C_{3-4}$ cycloalkyl;

$R^2$ is $R^9$-substituted or unsubstituted 4-10 membered heterocycle comprising one or more heteroatoms selected from N, S, or O;

$R^9$ is independently halogen, CN, OH, $OCF_3$, $OCHF_2$, $OCH_2F$, $R^{10}$-substituted or unsubstituted $C_{1-3}$ alkyl, $R^{10}$-substituted or unsubstituted $C_{1-3}$ haloalkyl, unsubstituted $C_{1-3}$ alkoxy, $R^{10}$-substituted or unsubstituted $C_{1-3}$ alkylidene, or $R^{10}$-substituted or unsubstituted $C_{3-4}$ cycloalkyl, or $R^{10}$-substituted or unsubstituted 3 or 4-membered heterocycle; or wherein two $R^9$ together form a $R^{10}$-substituted or unsubstituted $C_{3-5}$ cycloalkyl or a $R^{10}$-substituted or unsubstituted $C_{3-5}$ heterocycle comprising one or more oxygen atoms; or wherein two $R^9$ together form a bridge between two carbon atoms of the cycloalkyl or heterocycle, wherein the bridge comprises 1-3 carbons;

each $R^{10}$ is independently hydrogen, oxo, CN, halogen, or $C_{1-3}$ unsubstituted alkyl;

$R^3$ is hydrogen, —CN, halogen, unsubstituted $C_{1-3}$ alkyl, or unsubstituted cyclopropyl;

each $R^4$ is independently hydrogen, methyl, or $C_{1-3}$ haloalkyl;

$R^5$ is independently halogen, oxo, unsubstituted $C_{1-3}$ alkyl, or unsubstituted $C_{1-3}$ haloalkyl; or wherein two $R^5$ together form a bridge between two carbon atoms of Ring A, wherein the bridge comprises 1-3 carbons and optionally one heteroatom selected from O and N; or two $R^5$ together form a bridge between two carbon atoms of Ring A, wherein the bridge comprises one of O or $NR^{11}$;

$R^{11}$ is hydrogen, $C(O)CH_3$, or unsubstituted $C_{1-3}$ alkyl;

$R^6$ is hydrogen, $R^{6A}$-substituted or unsubstituted $C_{1-6}$ alkyl, $R^{6A}$-substituted or unsubstituted $C_{1-6}$ haloalkyl, $R^{6A}$-substituted or unsubstituted $C_{1-6}$ alkenyl; $R^{6A}$-substituted or unsubstituted $C_{1-6}$ alkynyl, or $R^{6A}$-substituted or unsubstituted 3-4 membered heterocycle;

$R^{6A}$ is halogen, CN, $OR^{6B}$, $SR^{6C}$, $S(O)_2R^{6C}$, $C(O)R^{6B}$, unsubstituted $C_{1-3}$ alkyl, unsubstituted $C_{1-3}$ haloalkyl, or $R^{6B}$ substituted or unsubstituted 3-4 membered heterocycle; and $R^{6B}$ and $R^{6C}$ are each independently $C_{1-3}$ alkyl or $C_{1-3}$ haloalkyl.

Embodiment 11. A compound of formula (I) or a stereoisomer, atropisomer, tautomer, or pharmaceutically acceptable salt thereof, wherein X is O or $NR^6$;

m is 1 or 2;

n is 1 or 2;

wherein n and m together make a 6- or 7-membered ring Ring A;

$R^1$ is

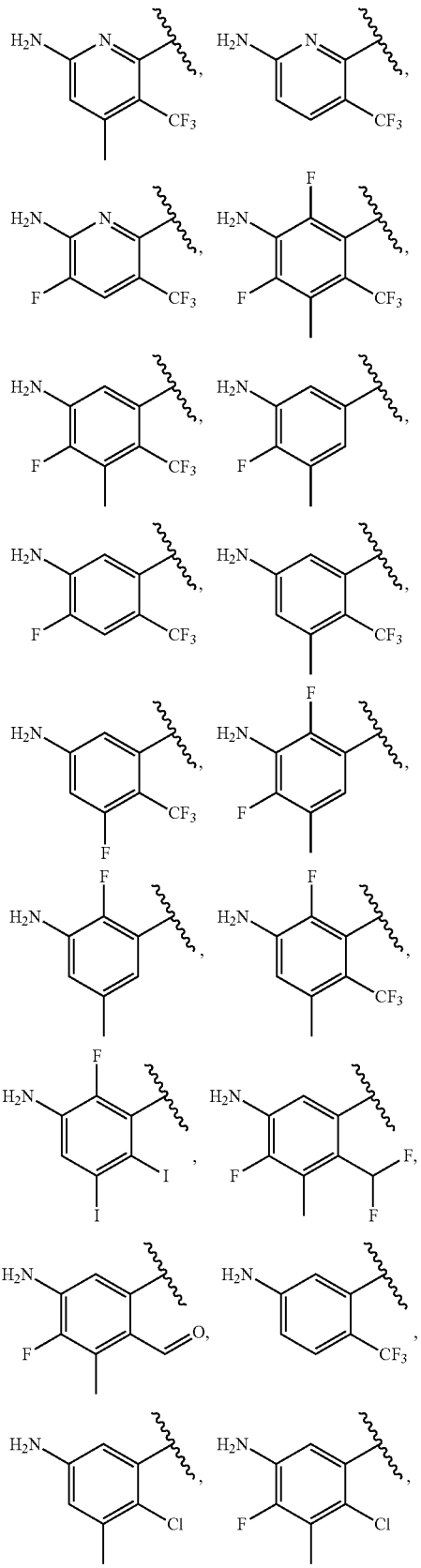

-continued

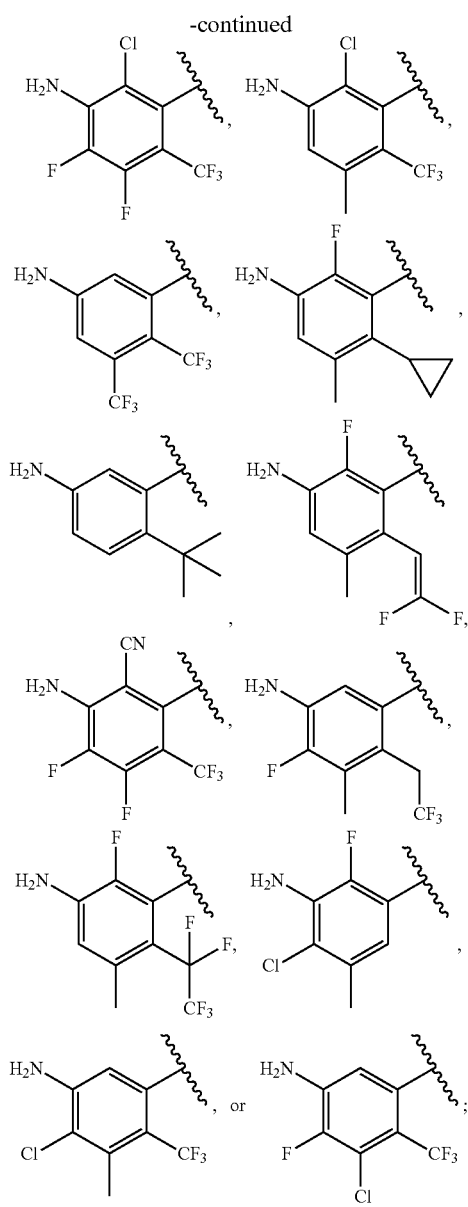

L¹ is $R^{L1}$-substituted or unsubstituted $C_{1-4}$ alkylene;
$R^{L1}$ is halogen or unsubstituted $C_{1-3}$ alkyl, or wherein two $R^{L1}$ together form an unsubstituted $C_{3-4}$ cycloalkyl;
R² is $R^9$-substituted or unsubstituted 4-10 membered heterocycle comprising one or more heteroatoms selected from N, S, or O;
$R^9$ is independently halogen, CN, OH, $OCF_3$, $OCHF_2$, $OCH_2F$, $R^{10}$-substituted or unsubstituted $C_{1-3}$ alkyl, $R^{10}$-substituted or unsubstituted $C_{1-3}$ haloalkyl, unsubstituted $C_{1-3}$ alkoxy, $R^{10}$-substituted or unsubstituted $C_{1-3}$ alkylidene, or $R^{10}$-substituted or unsubstituted $C_{3-4}$ cycloalkyl, or $R^{10}$-substituted or unsubstituted 3 or 4-membered heterocycle; or wherein
two $R^9$ together form a $R^{10}$-substituted or unsubstituted $C_{3-5}$ cycloalkyl or a $R^{10}$-substituted or unsubstituted $C_{3-5}$ heterocycle comprising one or more oxygen atoms; or wherein
two $R^9$ together form a bridge between two carbon atoms of the cycloalkyl or heterocycle, wherein the bridge comprises 1-3 carbons;

each $R^{10}$ is independently hydrogen, oxo, CN, halogen, or $C_{1-3}$ unsubstituted alkyl;
R³ is hydrogen, —CN, halogen, unsubstituted $C_{1-3}$ alkyl, or unsubstituted cyclopropyl;
each R⁴ is independently hydrogen, methyl, or $C_{1-3}$ haloalkyl;
R⁵ is independently halogen, oxo, unsubstituted $C_{1-3}$ alkyl, or unsubstituted $C_{1-3}$ haloalkyl; or wherein
two R⁵ together form a bridge between two carbon atoms of Ring A, wherein the bridge comprises 1-3 carbons and optionally one heteroatom selected from O and N; or
two R⁵ together form a bridge between two carbon atoms of Ring A, wherein the bridge comprises one of O or $NR^{11}$;
$R^{11}$ is hydrogen, $C(O)CH_3$, or unsubstituted $C_{1-3}$ alkyl;
R⁶ is hydrogen, $R^{6A}$-substituted or unsubstituted $C_{1-6}$ alkyl, $R^{6A}$-substituted or unsubstituted $C_{1-6}$ haloalkyl, $R^{6A}$-substituted or unsubstituted $C_{1-6}$ alkenyl; $R^{6A}$-substituted or unsubstituted $C_{1-6}$ alkynyl, or $R^{6A}$-substituted or unsubstituted 3-4 membered heterocycle;
$R^{6A}$ is halogen, CN, $OR^{6B}$, $SR^{6C}$, $S(O)_2R^{6C}$, $C(O)R^{6B}$, unsubstituted $C_{1-3}$ alkyl, unsubstituted $C_{1-3}$ haloalkyl, or $R^{6B}$ substituted or unsubstituted 3-4 membered heterocycle; and
$R^{6B}$ and $R^{6C}$ are each independently $C_{1-3}$ alkyl or $C_{1-3}$ haloalkyl.

Embodiment 12. A compound of formula (I) or a stereoisomer, atropisomer, tautomer, or pharmaceutically acceptable salt thereof, wherein
X is 0 or $NR^6$;
m is 1 or 2;
n is 1 or 2;
wherein n and m together make a 6- or 7-membered ring Ring A;
p is 0, 1, or 2;
R¹ is of formula (E1);
each $R^{7A}$ is independently halogen, CN, $NH_2$, $N(Me)_2$, $R^{7B}$-substituted or unsubstituted $C_{1-3}$ alkyl, unsubstituted $C_{1-3}$ haloalkyl, or unsubstituted cyclopropyl;
$R^{7B}$ is CN, oxo, or $C_{1-3}$ alkyl;
L¹ is $R^{L1}$-substituted or unsubstituted $C_{1-4}$ alkylene;
$R^{L1}$ is halogen or unsubstituted $C_{1-3}$ alkyl, or wherein two $R^{L1}$ together form an unsubstituted $C_{3-4}$ cycloalkyl;
R² is $R^9$-substituted or unsubstituted 4-10 membered heterocycle comprising one or more heteroatoms selected from N, S, or O;
$R^9$ is independently halogen, CN, OH, $OCF_3$, $OCHF_2$, $OCH_2F$, $R^{10}$-substituted or unsubstituted $C_{1-3}$ alkyl, $R^{10}$-substituted or unsubstituted $C_{1-3}$ haloalkyl, unsubstituted $C_{1-3}$ alkoxy, $R^{10}$-substituted or unsubstituted $C_{1-3}$ alkylidene, or $R^{10}$-substituted or unsubstituted $C_{3-4}$ cycloalkyl, or $R^{10}$-substituted or unsubstituted 3 or 4-membered heterocycle; or wherein
two $R^9$ together form a $R^{10}$-substituted or unsubstituted $C_{3-5}$ cycloalkyl or a $R^{10}$-substituted or unsubstituted $C_{3-5}$ heterocycle comprising one or more oxygen atoms; or wherein
two $R^9$ together form a bridge between two carbon atoms of the cycloalkyl or heterocycle, wherein the bridge comprises 1-3 carbons;
each $R^{10}$ is independently hydrogen, oxo, CN, halogen, or $C_{1-3}$ unsubstituted alkyl;
R³ is hydrogen, —CN, halogen, unsubstituted $C_{1-3}$ alkyl, or unsubstituted cyclopropyl;
each R⁴ is independently hydrogen, methyl, or $C_{1-3}$ haloalkyl;

$R^5$ is independently halogen, oxo, unsubstituted $C_{1-3}$ alkyl, or unsubstituted $C_{1-3}$ haloalkyl; or wherein two $R^5$ together form a bridge between two carbon atoms of Ring A, wherein the bridge comprises 1-3 carbons and optionally one heteroatom selected from O and N; or two $R^5$ together form a bridge between two carbon atoms of Ring A, wherein the bridge comprises one of O or $NR^{11}$;

$R^{11}$ is hydrogen, $C(O)CH_3$, or unsubstituted $C_{1-3}$ alkyl;

$R^6$ is hydrogen, $R^{6A}$-substituted or unsubstituted $C_{1-6}$ alkyl, $R^{6A}$-substituted or unsubstituted $C_{1-6}$ haloalkyl, $R^{6A}$-substituted or unsubstituted $C_{1-6}$ alkenyl; $R^{6A}$-substituted or unsubstituted $C_{1-6}$ alkynyl, or $R^{6A}$-substituted or unsubstituted 3-4 membered heterocycle;

$R^{6A}$ is halogen, CN, $OR^{6B}$, $SR^{6C}$, $S(O)_2R^{6C}$, $C(O)R^{6B}$, unsubstituted $C_{1-3}$ alkyl, unsubstituted $C_{1-3}$ haloalkyl, or $R^{6B}$-substituted or unsubstituted 3-4 membered heterocycle; and $R^{6B}$ and $R^{6C}$ are each independently $C_{1-3}$ alkyl or $C_{1-3}$ haloalkyl.

Embodiment 13. A compound of formula (I) or a stereoisomer, atropisomer, tautomer, or pharmaceutically acceptable salt thereof, wherein X is O or $NR^6$;

m is 1 or 2;

n is 1 or 2;

wherein n and m together make a 6- or 7-membered ring Ring A;

p is 0, 1, or 2;

$R^1$ is

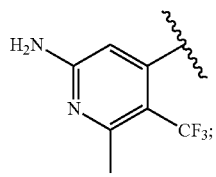 [SMILES: *c1cc(N)nc(C)c1C(F)(F)F]

$L^1$ is $R^{L1}$-substituted or unsubstituted $C_{1-4}$ alkylene;

$R^{L1}$ is halogen or unsubstituted $C_{1-3}$ alkyl, or wherein two $R^{L1}$ together form an unsubstituted $C_{3-4}$ cycloalkyl;

$R^2$ is $R^9$-substituted or unsubstituted 4-10 membered heterocycle comprising one or more heteroatoms selected from N, S, or O;

$R^9$ is independently halogen, CN, OH, $OCF_3$, $OCHF_2$, $OCH_2F$, $R^{10}$-substituted or unsubstituted $C_{1-3}$ alkyl, $R^{10}$-substituted or unsubstituted $C_{1-3}$ haloalkyl, unsubstituted $C_{1-3}$ alkoxy, $R^{10}$-substituted or unsubstituted $C_{1-3}$ alkylidene, or $R^{10}$-substituted or unsubstituted $C_{3-4}$ cycloalkyl, or $R^{10}$-substituted or unsubstituted 3 or 4-membered heterocycle; or wherein two $R^9$ together form a $R^{10}$-substituted or unsubstituted $C_{3-5}$ cycloalkyl or a $R^{10}$-substituted or unsubstituted $C_{3-5}$ heterocycle comprising one or more oxygen atoms; or wherein two $R^9$ together form a bridge between two carbon atoms of the cycloalkyl or heterocycle, wherein the bridge comprises 1-3 carbons;

each $R^{10}$ is independently hydrogen, oxo, CN, halogen, or $C_{1-3}$ unsubstituted alkyl;

$R^3$ is hydrogen, —CN, halogen, unsubstituted $C_{1-3}$ alkyl, or unsubstituted cyclopropyl;

each $R^4$ is independently hydrogen, methyl, or $C_{1-3}$ haloalkyl;

$R^5$ is independently halogen, oxo, unsubstituted $C_{1-3}$ alkyl, or unsubstituted $C_{1-3}$ haloalkyl; or wherein two $R^5$ together form a bridge between two carbon atoms of Ring A, wherein the bridge comprises 1-3 carbons and optionally one heteroatom selected from O and N; or two $R^5$ together form a bridge between two carbon atoms of Ring A, wherein the bridge comprises one of O or $NR^{11}$;

$R^{11}$ is hydrogen, $C(O)CH_3$, or unsubstituted $C_{1-3}$ alkyl;

$R^6$ is hydrogen, $R^{6A}$-substituted or unsubstituted $C_{1-6}$ alkyl, $R^{6A}$-substituted or unsubstituted $C_{1-6}$ haloalkyl, $R^{6A}$-substituted or unsubstituted $C_{1-6}$ alkenyl; $R^{6A}$-substituted or unsubstituted $C_{1-6}$ alkynyl, or $R^{6A}$-substituted or unsubstituted 3-4 membered heterocycle;

$R^{6A}$ is halogen, CN, $OR^{6B}$, $SR^{6C}$, $S(O)_2R^{6C}$, $C(O)R^{6B}$, unsubstituted $C_{1-3}$ alkyl, unsubstituted $C_{1-3}$ haloalkyl, or $R^{6B}$ substituted or unsubstituted 3-4 membered heterocycle; and $R^{6B}$ and $R^{6C}$ are each independently $C_{1-3}$ alkyl or $C_{1-3}$ haloalkyl.

Embodiment 14. The compound or a stereoisomer, atropisomer, tautomer, or pharmaceutically acceptable salt thereof of any one of embodiments 1-13, wherein each $R^4$ is hydrogen.

Embodiment 15. The compound or a stereoisomer, atropisomer, tautomer, or pharmaceutically acceptable salt thereof of any one of embodiments 1-13, wherein one $R^4$ is hydrogen and one $R^4$ is methyl.

Embodiment 16. The compound or a stereoisomer, atropisomer, tautomer, or pharmaceutically acceptable salt thereof of any one of embodiments 1-13, wherein $R^4$ is hydrogen and one $R^4$ is —$CF_3$.

Embodiment 17. The compound or a stereoisomer, atropisomer, tautomer, or pharmaceutically acceptable salt thereof of any one of embodiments 1-3 and 12, wherein each $R^{7A}$ is independently halogen, $NH_2$, unsubstituted $C_{1-3}$ alkyl, or unsubstituted $C_{1-3}$ haloalkyl.

Embodiment 18. The compound or a stereoisomer, atropisomer, tautomer, or pharmaceutically acceptable salt thereof of any one of embodiments 1-3, 10, 12, and 14-17, wherein at least one $R^{7A}$ is $NH_2$ Embodiment 19. The compound or a stereoisomer, atropisomer, tautomer, or pharmaceutically acceptable salt thereof of any one of embodiments 1-18, wherein $L^1$ is methylene.

Embodiment 20. The compound or a stereoisomer, atropisomer, tautomer, or pharmaceutically acceptable salt thereof of any one of embodiments 1-18, wherein $L^1$ is $R^{L1}$-substituted or unsubstituted $C_{2-3}$ alkylene.

Embodiment 21. The compound or a stereoisomer, atropisomer, tautomer, or pharmaceutically acceptable salt thereof of any one of embodiments 1-20, wherein $R^2$ is a moiety of formula (A), or a stereoisomer thereof, wherein, $R^9$ is halogen or $R^{10}$-substituted or unsubstituted $C_{1-3}$ alkylidene r is an integer of 0-12;

j is 1, 2, or 3; and k is 1 or 2.

Embodiment 22. The compound or a stereoisomer, atropisomer, tautomer, or pharmaceutically acceptable salt thereof of any one of embodiments 1-20, wherein $R^2$ is a moiety of formula (B), or a stereoisomer thereof, wherein $R^9$ is independently halogen or unsubstituted $C_{1-3}$ alkyl; and r is 1 or 2.

Embodiment 23. The compound or a stereoisomer, atropisomer, tautomer, or pharmaceutically acceptable salt thereof of any one of embodiments 1-20, wherein R² is:

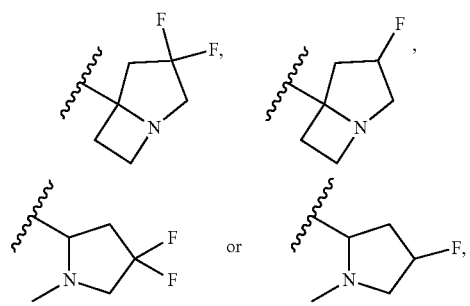

or a stereoisomer thereof.

Embodiment 24. The compound or a stereoisomer, atropisomer, tautomer, or pharmaceutically acceptable salt thereof of any one of embodiments 1-20, wherein R² is:

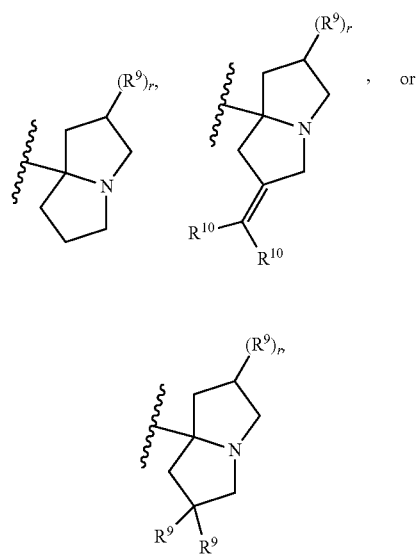

or a stereoisomer thereof, wherein
R⁹ is independently halogen or R¹⁰-substituted or unsubstituted $C_{1-3}$ alkylidene;
each R¹⁰ is independently hydrogen or halogen; and
r is 1 or 2.

Embodiment 25. The compound or a stereoisomer, atropisomer, tautomer, or pharmaceutically acceptable salt thereof of any one of embodiments 1-20, wherein R² is:

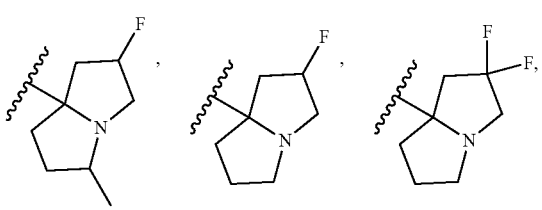

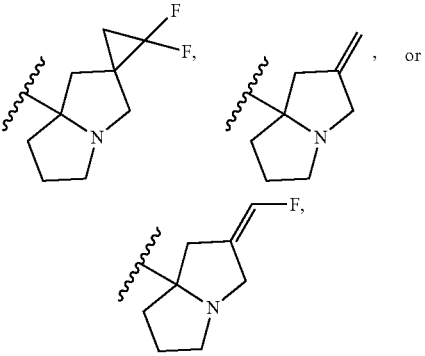

or a stereoisomer thereof.

Embodiment 26. The compound or a stereoisomer, atropisomer, tautomer, or pharmaceutically acceptable salt thereof of any one of embodiments 1-20, wherein R² is a moiety of formula (C) or a stereoisomer thereof, wherein X² is CR⁹ or O.

Embodiment 27. The compound or a stereoisomer, atropisomer, tautomer, or pharmaceutically acceptable salt thereof of any one of embodiments 1-20, wherein R² is a moiety of formula (D) or (D1) or a stereoisomer thereof, wherein X³ is CR⁹, NR⁹, or O.

Embodiment 28. The compound or a stereoisomer, atropisomer, tautomer, or pharmaceutically acceptable salt thereof of any one of embodiments 1-20, wherein R² is:

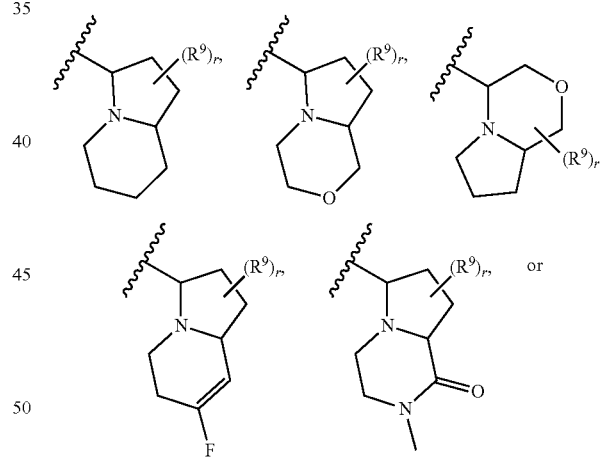

or a stereoisomer thereof.

Embodiment 29. The compound or a stereoisomer, atropisomer, tautomer, or pharmaceutically acceptable salt thereof of any one of embodiments 1-20, wherein R² is:

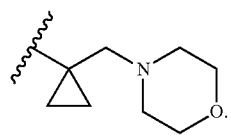 [SMILES: *C1(CN2CCOCC2)CC1]

Embodiment 30. The compound or a stereoisomer, atropisomer, tautomer, or pharmaceutically acceptable salt thereof of any one of embodiments 1-29, wherein $R^3$ is halogen.

Embodiment 31. The compound or a stereoisomer, atropisomer, tautomer, or pharmaceutically acceptable salt thereof of any one of embodiments 1-30, wherein two $R^5$ together form a bridge between two carbon atoms of Ring A, wherein the bridge comprises 1-3 carbons.

Embodiment 32. The compound or a stereoisomer, atropisomer, tautomer, or pharmaceutically acceptable salt thereof of embodiment 31, wherein the bridge comprises 2 carbon atoms.

Embodiment 33. The compound or a stereoisomer, atropisomer, tautomer, or pharmaceutically acceptable salt thereof of embodiment 31, the bridge comprises 1 carbon atom.

Embodiment 34. The compound or a stereoisomer, atropisomer, tautomer, or pharmaceutically acceptable salt thereof of any one of embodiments 1-33, wherein X is $NR^6$.

Embodiment 35. The compound or a stereoisomer, atropisomer, tautomer, or pharmaceutically acceptable salt thereof of embodiment 34, wherein $R^6$ is hydrogen or $R^{6A}$-substituted or unsubstituted $C_{1-3}$ alkyl.

Embodiment 36. The compound or a stereoisomer, atropisomer, tautomer, or pharmaceutically acceptable salt thereof of embodiment 34, wherein $R^6$ is $R^{6A}$-substituted or unsubstituted $C_{1-3}$ alkyl.

Embodiment 37. The compound or a stereoisomer, atropisomer, tautomer, or pharmaceutically acceptable salt thereof of any one of embodiments 34-36, wherein $R^{6A}$ is halogen, CN, OH, OMe, OEt, $OCF_3$, $SO_2Me$, unsubstituted $C_{1-3}$ alkyl, or 4-membered heterocycle.

Embodiment 38. The compound or a stereoisomer, atropisomer, tautomer, or pharmaceutically acceptable salt thereof of embodiment 34, wherein $R^6$ is hydrogen.

Embodiment 39. The compound or a stereoisomer, atropisomer, tautomer, or pharmaceutically acceptable salt thereof of any one of embodiments 1-38, wherein $R^2$ is azetidinyl, oxetanyl, or thietanedioxide.

Embodiment 40. The compound or a stereoisomer, atropisomer, tautomer, or pharmaceutically acceptable salt thereof of any one of embodiments 1-13, wherein the compound of formula (I) comprises formula (IIa), (IIb), (IIc), or (IId), or a stereoisomer, atropisomer, tautomer, or pharmaceutically acceptable salt thereof.

Embodiment 41. The compound or a stereoisomer, atropisomer, tautomer, or pharmaceutically acceptable salt thereof of any one of embodiments 1-13, wherein the compound of formula (I) comprises formula (IIIa) or (IIIb), or a stereoisomer, atropisomer, tautomer, or pharmaceutically acceptable salt thereof.

Embodiment 42. A compound selected from compounds 1-36, 38-45, 47-62, 64-108, 110-146, and 149-291 in Table 1 or a stereoisomer, atropisomer, tautomer, or pharmaceutically acceptable salt thereof.

Embodiment 43. A compound selected from compounds 1-36, 38-45, 47-62, 64-108, and 110-125 in Table 1 or a stereoisomer, atropisomer, tautomer, or pharmaceutically acceptable salt thereof.

Embodiment 44. A compound selected from compounds 126-146 and 149-291 in Table 1 or a stereoisomer, atropisomer, tautomer, or pharmaceutically acceptable salt thereof.

Embodiment 45. A compound selected from compounds 6, 15, 24, 26, 29, 31-32, 57-59, 61-62, 64-66, 75-76, 91, 96, 104, 106, 111, 113, 118-124, 126-146, 149-156, 158-175, 181, 183, 186, 190-192, 195, 200, 204, 224-225, 228-229, 232-239, 241, 244-250, 255, 258-259, and 263 in Table 1 or a stereoisomer, atropisomer, tautomer, or pharmaceutically acceptable salt thereof.

Embodiment 46. A compound selected from compounds 6, 12-18, 23-24, 26, 29, 31-36, 57-58, 60-62, 64-77, 90-97, 100-102, 104, 108, 111, 113, 115, 118-146, 149-175, 181-183, 186-187, 190, 195, 200, 204, 224-232, 234-239, 241, 244-250, 255, 258-259, and 263 in Table 1 or a stereoisomer, atropisomer, tautomer, or pharmaceutically acceptable salt thereof.

Embodiment 47. A compound selected from compounds 6, 13-14, 16-18, 23-24, 26, 29, 31-34, 36, 57-62, 64-72, 74, 76, 91-104, 106-108, 111, 113, 115, 117-146, 149-154, 157, 159-174, 199, 200, 224-229, 234-241, 244-249, 255, 258-259, and 263 in Table 1 or a stereoisomer, atropisomer, tautomer, or pharmaceutically acceptable salt thereof.

Embodiment 48. A compound selected from compounds 6, 12-18, 23-24, 26, 29, 31-36, 42-45, 47-48, 52, 57-58, 60-78, 84-88, 90-97, 100-104, 106, 108, 111-113, 115, 118-146, 149-175, 177-178, 181-183, 185-187, 189-192, 194-195, 197-200, 203-232, 234-250, and 252-291 in Table 1 or a stereoisomer, atropisomer, tautomer, or pharmaceutically acceptable salt thereof.

Embodiment 49. A compound selected from compounds 6, 13-14, 16-18, 23-24, 26, 29, 31-34, 36, 42-45, 47-48, 52, 57-62, 64-72, 74, 76, 84-88, 91-104, 106-108, 111, 113, 115, 117-146, 149-154, 157, 159-174, 199, 200, 224-229, 234-241, 244-249, 255, 258-259, and 263 in Table 1 or a stereoisomer, atropisomer, tautomer, or pharmaceutically acceptable salt thereof.

Embodiment 50. A compound selected from compounds 42-45, 47-48, and 52 in Table 1 or a stereoisomer, atropisomer, tautomer, or pharmaceutically acceptable salt thereof.

Embodiment 51. A compound selected from compounds 112, 205-218, 242-243, 252-254, 261-262, and 264-291 in Table 1 or a stereoisomer, atropisomer, tautomer, or pharmaceutically acceptable salt thereof.

Embodiment 52. A pharmaceutical composition comprising a compound or a stereoisomer, atropisomer, tautomer, or pharmaceutically acceptable salt thereof of any one of embodiments 1-51, and one or more pharmaceutically acceptable excipients.

Embodiment 53. A method of treating cancer, the method comprising administering an effective amount of a compound or a stereoisomer, atropisomer, tautomer, or pharmaceutically acceptable salt thereof of any one of embodiments 1-51, or a pharmaceutical composition of embodiment 52.

Embodiment 54. The method of embodiment 53, wherein the cancer is characterized as comprising a KRas mutation.

Embodiment 55. The method of embodiment 54, wherein the KRas mutation corresponds to a $KRas^{G12D}$ mutation.

Embodiment 56. The method of any one of embodiments 53-55, further comprising testing a sample from the patient before administration for the absence or presence of a $KRas^{G12D}$ mutation.

Embodiment 57. The method of embodiment 56, wherein the compound, stereoisomer, atropisomer, tautomer, or pharmaceutically acceptable salt thereof or pharmaceutical composition is administered to the patient after the patient sample shows the presence of a $KRas^{G12D}$ mutation.

Embodiment 58. The method of any one of embodiments 53-57, wherein the cancer is tissue agnostic.

Embodiment 59. The method of any one of embodiments 53-57, wherein the cancer is pancreatic cancer, lung cancer, or colorectal cancer.

Embodiment 60. The method of embodiment 59, wherein the lung cancer is lung adenocarcinoma, NSCLC, or SCLC.

Embodiment 61. The method of embodiment 59, wherein the cancer is pancreatic cancer.

Embodiment 62. The method of embodiment 59, wherein the cancer is colorectal cancer.

Embodiment 63. The method of any one of embodiments 53-62, further comprising administering at least one additional therapeutic agent.

Embodiment 64. The method of embodiment 63, wherein the additional therapeutic agent comprises an epidermal growth factor receptor (EGFR) inhibitor, phosphatidylinositol kinase (PI3K) inhibitor, insulin-like growth factor receptor (IGF1R) inhibitor, a Janus kinase (JAK) inhibitor, a Met kinase inhibitor, a SRC family kinase inhibitor, a mitogen-activated protein kinase (MEK) inhibitor, an extracellular-signal-regulated kinase (ERK) inhibitor, a topoisomerase inhibitor, a taxane, an anti-metabolite agent, or an alkylating agent.

Embodiment 65. A compound according to any one of embodiments 1-51, or a stereoisomer, atropisomer, tautomer, or pharmaceutically acceptable salt thereof, for use as a therapeutically active substance.

Embodiment 66. Use of a compound of any one of embodiments 1-51, or stereoisomer, atropisomer, tautomer, or pharmaceutically acceptable salt thereof, for the therapeutic treatment of a cancer comprising a $KRas^{G12D}$ mutation.

Embodiment 67. Use of a compound according to any one of embodiments 1-51, or stereoisomer, atropisomer, tautomer, or pharmaceutically salt thereof, in the manufacture of a medicament for inhibiting tumor metastasis.

Embodiment 68. Use of a compound of any one of embodiments 1-51, or stereoisomer, atropisomer, tautomer, or pharmaceutically acceptable salt thereof, for the preparation of a medicament for the therapeutic treatment of a cancer comprising a $KRas^{G12D}$ mutation.

Embodiment 69. A compound according to any one of embodiments 1-51, or stereoisomer, atropisomer, tautomer, or pharmaceutically salt thereof, for the therapeutic and/or prophylactic treatment of a cancer comprising a $KRas^{G12D}$ mutation.

Embodiment 70. A method for regulating activity of a KRas mutant protein, the method comprising reacting the mutant protein with a compound of any one of embodiments 1-51, or stereoisomer, atropisomer, tautomer, or pharmaceutically acceptable salt thereof.

Embodiment 71. A method for inhibiting proliferation of a cell population, the method comprising contacting the cell population with the compound of any one of embodiments 1-51, or stereoisomer, atropisomer, tautomer, or pharmaceutically acceptable salt thereof.

Embodiment 72. A method of embodiment 71, wherein the inhibition of proliferation is measured as a decrease in cell viability of the cell population.

Embodiment 73. A method for inhibiting tumor metastasis comprising administering to an individual in need thereof a therapeutically effective amount of the compound of any one of embodiments 1-51, or stereoisomer, atropisomer, tautomer, or pharmaceutically acceptable salt thereof to a subject in need thereof.

Embodiment 74. A compound of any one of embodiments 1-51, or stereoisomer, atropisomer, tautomer, or pharmaceutically acceptable salt thereof, for use in regulating activity of a KRas mutant protein.

Embodiment 75. A compound of any one of embodiments 1-51, or stereoisomer, atropisomer, tautomer, or pharmaceutically acceptable salt thereof, for use in inhibiting proliferation of a cell population.

Embodiment 76. The compound, stereoisomer, atropisomer, tautomer, or pharmaceutically acceptable salt for use of embodiment 75, wherein the inhibition of proliferation is measured as a decrease in cell viability of the cell population.

Embodiment 77. A compound of any one of embodiments 1-51, or stereoisomer, atropisomer, tautomer, or pharmaceutically acceptable salt thereof, for use in inhibiting tumor metastasis.

Embodiment 78. Use of a compound of any one of embodiments 1-51, or stereoisomer, atropisomer, tautomer, or pharmaceutically acceptable salt thereof, in the manufacture of a medicament for regulating activity of a KRas mutant protein.

Embodiment 79. Use of a compound of any one of embodiments 1-51, or stereoisomer, atropisomer, tautomer, or pharmaceutically acceptable salt thereof, in the manufacture of a medicament for inhibiting proliferation of a cell population.

Embodiment 80. The use of embodiment 79, wherein the inhibition of proliferation is measured as a decrease in cell viability of the cell population.

Embodiment 81. Use of a compound of any one of embodiments 1-51, or stereoisomer, atropisomer, tautomer, or pharmaceutically acceptable salt thereof, in the manufacture of a medicament for inhibiting tumor metastasis.

EXAMPLES

The following Examples are presented by way of illustration, not limitation.

INTERMEDIATES

Intermediate 1:
4-Amino-2,6-dichloro-5-fluoronicotinic acid

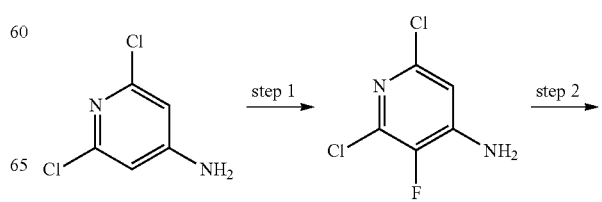

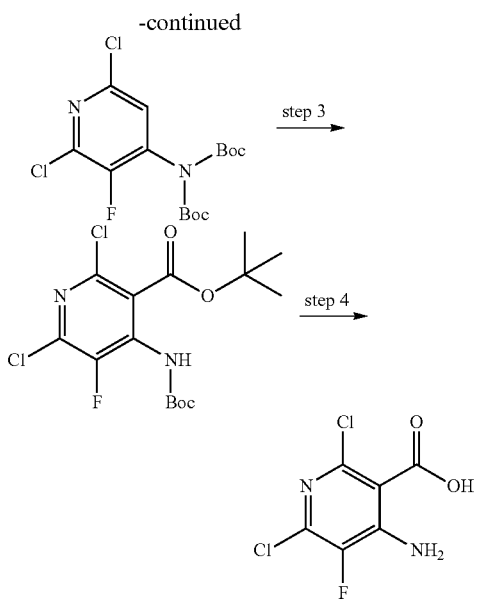

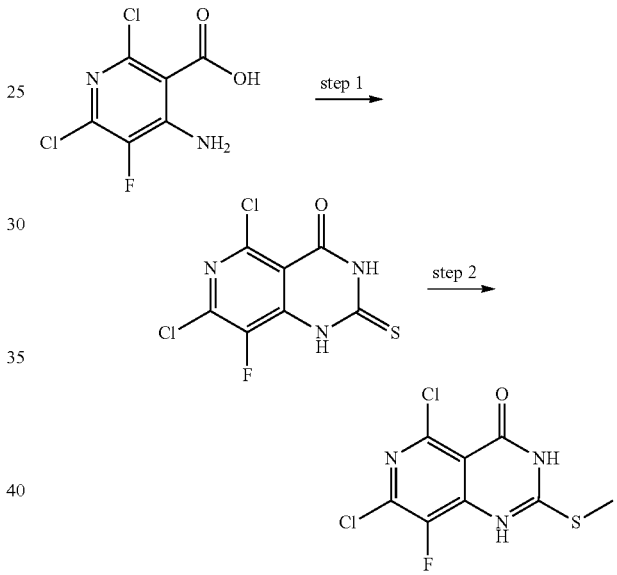

Step 1: 2,6-Dichloro-3-fluoropyridin-4-amine

Under nitrogen, a solution of 2,6-dichloropyridin-4-amine (9.01 g, 55.3 mmol) and SelectFluor (23.6 g, 66.6 mmol) in DMF (90 mL) and acetonitrile (90 mL) was stirred for 30 min at 80° C. The mixture was concentrated under vacuum. The crude product was purified by reverse phase chromatography (gradient: 0-40% acetonitrile in water (0.1% formic acid)) to afford the title compound (4.62 g, 46.2% yield) as a light brown solid. LC-MS: (ESI, m/z): [M+H]$^+$=181. $^1$H NMR (300 MHz, DMSO-d6, ppm) δ 6.99 (s, 2H), 6.70 (d, J=5.4 Hz, 1H).

Step 2: tert-Butyl N-tert-butoxycarbonyl-N-(2,6-dichloro-3-fluoro-4-pyridyl)carbamate Under nitrogen, to a solution of 2,6-dichloro-3-fluoropyridin-4-amine (4.82 g, 26.6 mmol) in THF (100 mL) was added NaHMDS (53.1 mL, 2M in THF) at 0° C. The resulting solution was stirred for 30 min at 0° C. Then Boc$_2$O (29.0 g, 133 mmol) in THF (450 mL) was added at 0° C. and stirred at room temperature overnight. The reaction was quenched with aqueous NH$_4$Cl. A majority of THF was removed under vacuum and the resulting solution was extracted with EtOAc. The combined organic layers were concentrated under vacuum to afford the title compound (9.11 g, crude) as a white solid which was used without further purification. LC-MS: (ESI, m/z): [M+H]$^+$=381. $^1$H NMR (300 MHz, DMSO-d6, ppm) δ 6.13 (s, 1H), 1.42 (s, 9H), 1.38 (d, J=2.4 Hz, 9H).

Step 3: tert-Butyl 4-((tert-butoxycarbonyl)amino)-2,6-dichloro-5-fluoronicotinate Under nitrogen, to a solution of tert-butyl N-tert-butoxycarbonyl-N-(2,6-dichloro-3-fluoro-4-pyridyl)carbamate (9.11 g, 23.9 mmol) in THF (180 mL) was added LDA (41.9 mL, 1M in THF) at −78° C. The resulting solution was stirred for 0.5 h at −78° C. The reaction was quenched with aq. NH$_4$Cl and extracted with EtOAc (300 mL*2). The organic layer was dried over anhydrous sodium sulfate and concentrated under vacuum. The residue was purified by flash chromatography on silica gel eluting with EtOAc/petroleum ether (0-10%) to afford the title compound (4.18 g, 45.9% yield) as a white solid. LC-MS: (ESI, m/z): [M+H]$^+$=381. $^1$H NMR (300 MHz, DMSO-d6, ppm) δ 10.07 (s, 1H), 1.54 (s, 9H), 1.45 (s, 9H).

Step 4: 4-Amino-2,6-dichloro-5-fluoronicotinic acid

A solution of tert-butyl 4-((tert-butoxycarbonyl)amino)-2,6-dichloro-5-fluoronicotinate (4.18 g, 11.0 mmol) in TFA (15 mL) and DCM (15 mL) was stirred at 40° C. for 3 hours. The solvent was concentrated under vacuum to afford the title compound (2.86 g, crude) as a brown solid which was used without further purification. LC-MS: (ESI, m/z): [M+H]$^+$=225.

Intermediate 2: 5,7-Dichloro-8-fluoro-2-(methylthio)pyrido[4,3-d]pyrimidin-4(3H)-one Step 1: 5,7-Dichloro-8-fluoro-2-thioxo-2,3-dihydropyrido[4,3-d]pyrimidin-4(1H)-one To a solution of 4-amino-2,6-dichloro-5-fluoronicotinic acid (2.01 g, 8.92 mmol, intermediate 1) in MeCN (60 mL)/pyridine (20 mL) was added ethoxycarbonyl isothiocyanate (4.20 mL, 35.6 mmol). The resulting solution was stirred at room temperature for 2 hours and concentrated under vacuum. The residue was purified by reverse phase chromatography (gradient: 0-40% acetonitrile in water (0.1% formic acid)) to afford the title compound 1.58 g (46.6% yield) as a yellow solid. LC-MS: (ESI, m/z): [M+H]$^+$=264. $^1$H NMR (400 MHz, DMSO-d6, ppm) δ 13.30 (s, 1H), 12.86 (s, 1H).

Step 2: 5,7-Dichloro-8-fluoro-2-(methylthio)pyrido[4,3-d]pyrimidin-4(3H)-one

Under nitrogen, to a solution of 5,7-dichloro-8-fluoro-2-thioxo-2,3-dihydropyrido[4,3-d]pyrimidin-4(1H)-one (1.58 g, 5.93 mmol) in DMF (20 mL) was added Ch$_3$ONa (320 mg, 5.93 mmol) at 0° C. The resulting solution was stirred for 10 min at room temperature. Then CH$_3$I (842 mg, 5.93 mmol) was added slowly at room temperature. Stirred overnight at room temperature. The reaction solution was added slowly with stirring to cold water. The solid was collected by filtration and dried in an oven to afford the title compound (2.07 g, crude) as a yellow solid which was used for the next step without further purification. LC-MS: (ESI, m/z): [M+H]$^+$=280. $^1$H NMR (300 MHz, DMSO-d6, ppm) δ 13.35 (br, 1H), 2.61 (s, 3H).

Intermediate 3: tert-Butyl (1R,2S,5S)-2-(hydroxymethyl)-3,8-diazabicyclo[3.2.1]octane-8-carboxylate

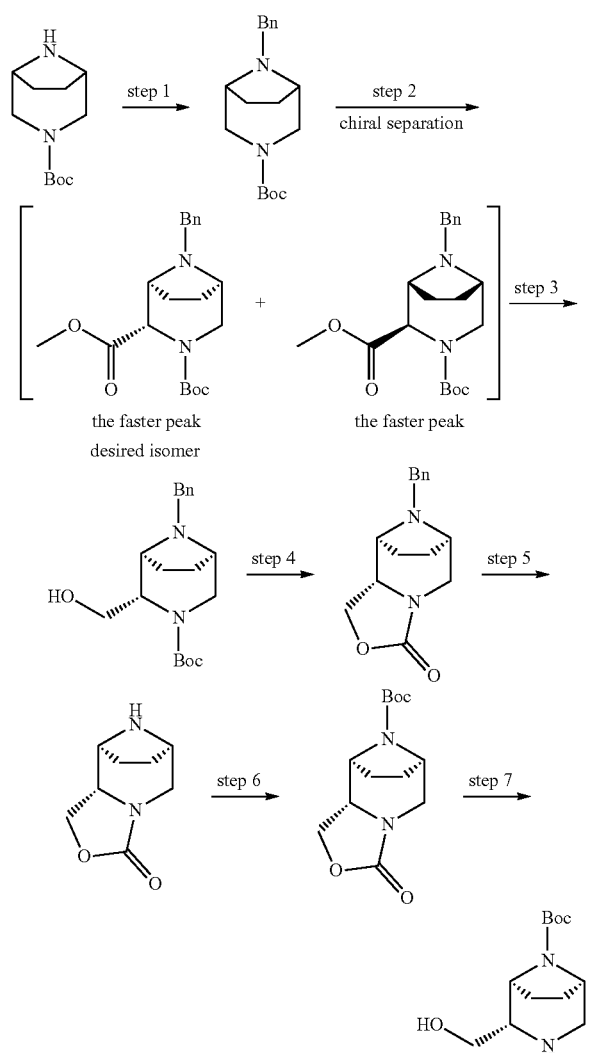

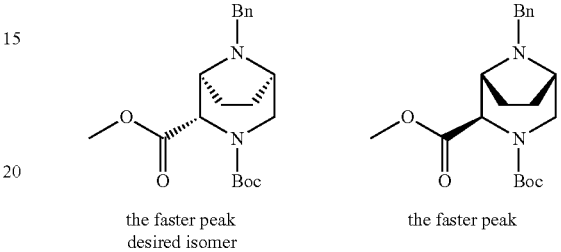

Step 1: tert-Butyl (1R,5S)-8-benzyl-3,8-diazabicyclo[3.2.1]octane-3-carboxylate

To a solution of tert-butyl 3,8-diazabicyclo[3.2.1]octane-3-carboxylate (50.0 g, 236 mmol) in DMF (800 mL) was added K$_2$CO$_3$ (65.1 g, 472 mmol) and BnBr (60.1 g, 353.53 mmol). Stirred at rt for 2 hours. The reaction mixture was diluted with water and extracted with EtOAc. The combined organic phases were washed with water (500 mL×3), dried over Na$_2$SO$_4$ and concentrated under vacuum. The residue was purified by flash chromatography on silica gel eluting with EtOAc/petroleum ether (0~10%) to afford the title compound (69 g, 96.9% yield) as a yellow oil. LC-MS: (ESI, m/z): [M+H]$^+$=303.

Step 2: 3-(tert-Butyl) 2-methyl (1R,2S,5S)-8-benzyl-3,8-diazabicyclo[3.2.1]octane-2,3-dicarboxylate and 3-(tert-Butyl) 2-methyl (1R,2R,5S)-8-benzyl-3,8-diazabicyclo[3.2.1]octane-2,3-dicarboxylate Under N$_2$, to a solution of tert-butyl 8-benzyl-3,8-diazabicyclo[3.2.1]octane-3-carboxylate (23.0 g, 76.06 mmol) and TMEDA (17.7 g, 152.59 mmol) in diethyl ether (500 mL) was added dropwise s-BuLi (117 mL, 1.3 M in hexane) at −78° C., and the mixture was stirred at −78° C. for 1.5 hours. Then methyl carbonochloridate (17.9 g, 189 mmol) in 40 mL Et$_2$O was added dropwise at −78° C. The reaction was warmed to room temperature gradually and stirred an additional 16 hours. The reaction was quenched with saturated NaHCO$_3$ (aq), diluted with water and extracted with EtOAc. The combined organic phases were dried over Na$_2$SO$_4$ and concentrated under vacuum. The crude product was purified by flash chromatography on silica gel eluting with EtOAc/petroleum ether (0~10%) to afford 16 g of racemic mixtures (mixture of cis) as yellow oil. The mixture was separated by chiral-SFC (Column: Lux® 5 μm Cellulose-2, 5×25 cm, 5 um; Mobile Phase A: CO$_2$, Mobile Phase B: MeOH (0.1% 2M NH$_3$—MeOH); Flow rate: 180 mL/min; Gradient: 18% B; 220 nm; RT$_1$:5.07; RT$_2$: 5.57) to afford 5.9 g the faster peak and 5.6 g of the slower peak as yellow oil. LC-MS: (ESI, m/z): [M+H]$^+$=361.

Step 3: tert-Butyl (1R,2S,5S)-8-benzyl-2-(hydroxymethyl)-3,8-diazabicyclo[3.2.1]octane-3-carboxylate Under nitrogen, to a solution of 3-(tert-butyl) 2-methyl (1R,2S,5S)-8-benzyl-3,8-diazabicyclo[3.2.1]octane-2,3-dicarboxylate (20.0 g, 55.5 mmol, faster peak of previous operation) in THF (300 mL) was added LiAlH$_4$ (4.20 g, 111 mmol) at 0° C. The resulting solution was stirred for 30 mins at 0° C. and quenched with Na$_2$SO$_4$·10H$_2$O. The solid was filtered off and the filtrate was concentrated under vacuum. The residue was purified by flash chromatography on silica gel eluting with EtOAc/petroleum ether (0~20%) to afford the title compound (14.3 g, 77.5% yield) as a white solid. LC-MS: (ESI, m/z): [M+H]$^+$=333.

Step 4: (6S,9R,9aS)-10-Benzylhexahydro-1H,3H-6,9-epiminooxazolo[3,4-a]azepin-3-one Under nitrogen, to a solution of tert-butyl 8-benzyl-4-(hydroxymethyl)-3,8-diazabicyclo[3.2.1]octane-3-carboxylate (5.1 g, 15.34 mmol) in THF (100 mL) was added NaH (1.35 g, 33.75 mmol, 60% in mineral oil) at 0° C. The resulting solution was stirred for 3 hours at room temperature, quenched with NH₄Cl (aq) and extracted with EtOAc. The combined organic layers were dried over anhydrous sodium sulfate and concentrated under vacuum. The residue was purified by flash chromatography on silica gel eluting with EtOAc/petroleum ether (0~40%) to afford the title compound (3.5 g, 88.3% yield) as a white solid. LC-MS: (ESI, m/z): [M+H]⁺=259.

Step 5: (6S,9R,9aS)-Hexahydro-1H,3H-6,9-epiminooxazolo[3,4-a]azepin-3-one

A mixture of (6S,9R,9aS)-10-Benzylhexahydro-1H,3H-6,9-epiminooxazolo[3,4-a]azepin-3-one (10.0 g, 38.7 mmol) and Pd/C (3.0 g, 10% dry) in methyl alcohol (200 mL) was stirred under an atmosphere of hydrogen at room temperature for 2 hours at room temperature. The catalyst was filtered off. The filtrate was concentrated under reduced pressure to afford 6 g crude product which was used for next step without further purification. LC-MS: (ESI, m/z): [M+H]⁺=169.

Step 6: tert-Butyl (6S,9R,9aS)-3-oxohexahydro-1H,3H-6,9-epiminooxazolo[3,4-a]azepine-10-carboxylate A solution of (6S,9R,9aS)-Hexahydro-1H,3H-6,9-epiminooxazolo[3,4-a]azepin-3-one (6.00 g, 35.7 mmol), (Boc)₂O (12.6 g, 57.8 mmol) and DIPEA (10.0 g, 77.5 mmol) in dichloromethane (100 mL) was stirred at rt for 2 hours. The reaction mixture was washed with saturated sodium chloride solution. The organic phase was dried over anhydrous Na₂SO₄ and concentrated under vacuum. The residue was purified by flash chromatography on silica gel eluting with EtOAc/petroleum ether (0~40%) to afford the title compound 7.50 g (78.4% yield) as white solid. LC-MS: (ESI, m/z): [M+H]⁺=269.

Step 7: tert-Butyl (1R,2S,5S)-2-(hydroxymethyl)-3,8-diazabicyclo[3.2.1]octane-8-carboxylate A solution of tert-Butyl (6S,9R,9aS)-3-oxohexahydro-1H,3H-6,9-epiminooxazolo[3,4-a]azepine-10-carboxylate (7.50 g, 28.0 mmol) and NaOH (16.8 g, 420 mmol) in ethanol (200 mL) and water (70 mL) was stirred at 80° C. for 16 hours. A majority of EtOH was stripped off under reduced pressure. The residual solution was adjusted to pH=8 with aqueous HCl (1M) and extracted with EtOAc. The combined organic layers were dried over Na₂SO₄ and concentrated under reduced pressure. The residue was purified by flash chromatography on silica gel eluting with DCM/MeOH (5/1) to afford the title compound (5 g, 73.8% yield) as an off white solid. LC-MS: (ESI, m/z): [M+H]⁺=243. ¹H NMR (400 MHz, DMSO-d₆, ppm) δ 4.72-4.57 (m, 1H), 4.02-3.90 (m, 2H), 3.25-3.15 (m, 2H), 2.82-2.68 (m, 2H), 2.64-2.53 (m, 1H), 1.85-1.61 (m, 3H), 1.61-1.47 (m, 1H), 1.41 (s, 9H).

Intermediate 4: tert-Butyl (1R,2S,5S)-2-((S)-1-hydroxyethyl)-3,8-diazabicyclo[3.2.1]octane-8-carboxylate

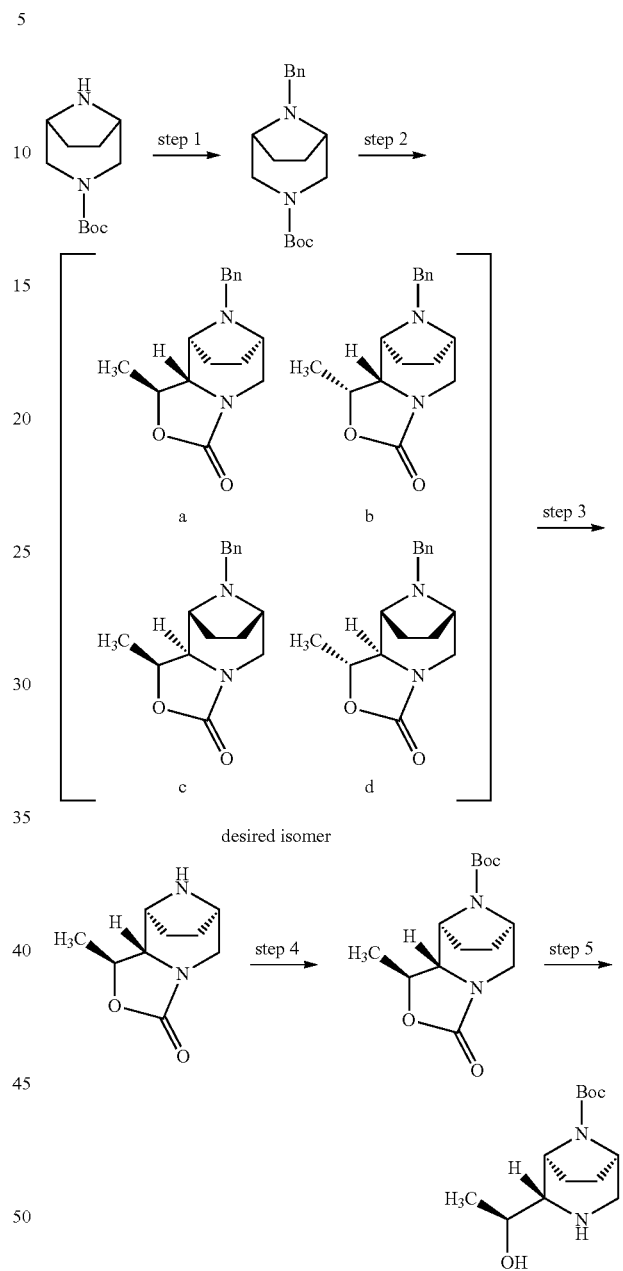

Step 1: tert-Butyl 8-benzyl-3,8-diazabicyclo[3.2.1]octane-3-carboxylate

Under nitrogen, to a solution of tert-butyl 3,8-diazabicyclo[3.2.1]octane-3-carboxylate (5.00 g, 23.5 mmol) in N,N-dimethylformamide (50 mL) was added K₂CO₃ (6.51 g, 47.1 mmol) and (bromomethyl)benzene (6.01 g, 35.1 mmol) at 0° C. Stirred for 1 h at room temperature. The reaction mixture was poured into ice water, extracted with EtOAc. The combined organic layers were dried over anhydrous Na₂SO₄ and concentrated under vacuum. The residue was purified by flash chromatography on silica gel (gradient: 0-30% EtOAc/ petroleum ether) to yield 7 g (98.3% yield) the title compound as a white solid. LC-MS: (ESI, m/z): [M+H]⁺=303.

Step 2: (1S,6S,9R,9aS)-10-Benzyl-1-methylhexahydro-1H,3H-6,9-epiminooxazolo[3,4-a]azepin-3-one

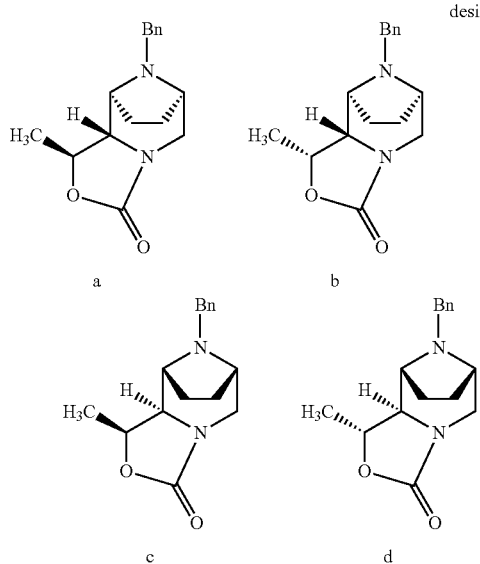

Under nitrogen, to a solution of tert-butyl 8-benzyl-3,8-diazabicyclo[3.2.1]octane-3-carboxylate (7.0 g, 23.1 mmol) and TMEDA (5.38 g, 46.3 mmol) in diethyl ether (70 mL) was added s-BuLi (35.6 mL, 46.3 mmol, 1.3 M in hexane) dropwise at −78° C. The resulting solution was stirred for 1.5 h at −78° C. Then acetaldehyde (2.55 g, 57.8 mmol) was added at −78° C. The reaction was allowed to warm to room temperature gradually and stirred overnight. The mixture was quenched with NH₄Cl (aq.) and extracted with EtOAc. The combined organic layers were dried over anhydrous Na₂SO₄ and concentrated under vacuum. The residue was purified by flash chromatography on silica gel (0-50% EtOAc in petroleum ether) to yield 5.1 g mixture of 4 diastereoisomers. The mixture was separated by Prep-SFC (Column: CHIRALPAK IH, 3*25 cm, 5 μm; Mobile Phase A: CO₂, Mobile Phase B: IPA(0.5% 2M NH₃—MeOH); Flow rate: 70 mL/min; Gradient: isocratic 35% B; Column Temperature(° C.): 35; Back Pressure(bar): 100; Wave Length: 220 n; RT1(min): 6.31; RT2(min): 8.33; Sample Solvent: MeOH—Preparative; Injection Volume: 1.9 mL; Number Of Runs: 50) to yield the compound a (1.39 g, 22% yield) (the first peak) and compound d (1.47 g, 23.3% yield) (the third peak) and mixture of compound b and c (the second peak). The mixture of compound b and c was re-separated by Prep-SFC (Column: CHIRALPAK IH, 5*25 cm, 5 μm; Mobile Phase A: CO₂, Mobile Phase B: IPA(0.5% 2M NH₃—MeOH); Flow rate: 200 mL/min; Gradient: isocratic 50% B; Column Temperature(° C.): 35; Back Pressure (bar): 100; Wave Length: 220 nm; RT1(min): 5.73; RT2 (min): 8.44; Sample Solvent: MeOH—Preparative; Injection Volume: 10 mL; Number Of Runs: 6) to yield compound b (0.500 g, 7.9% yield) (the faster peak) and compound c (0.430 g, 6.8% yield) (the slower peak) as yellow solid. LC-MS: (ESI, m/z): [M+H]⁺=273.

Step 3: (1S,6S,9R,9aS)-1-Methylhexahydro-1H,3H-6,9-epiminooxazolo[3,4-a]azepin-3-one A solution of (1S,6S,9R,9aS)-10-Benzyl-1-methylhexahydro-1H,3H-6,9-epiminooxazolo[3,4-a]azepin-3-one (1.00 g, 3.67 mmol) (the compound a of previous step) and Pd/C (500 mg, 10%) in methyl alcohol (15 mL) was stirred for 1 h at room temperature under an atmosphere of hydrogen gas. The catalyst was filtered off. The filtrate was concentrated under vacuum to yield 658 mg (crude) the title compound as a yellow oil which was used for next step without further purification. LC-MS: (ESI, m/z): [M+H]⁺=183.

Step 4: tert-Butyl (1S,6S,9R,9aS)-1-methyl-3-oxohexahydro-1H,3H-6,9-epiminooxazolo[3,4-a]azepine-10-carboxylate A solution of (1S,6S,9R,9aS)-1-methylhexahydro-1H,3H-6,9-epiminooxazolo[3,4-a]azepin-3-one (658 mg, 3.61 mmol), (Boc)₂O (1.18 g, 5.41 mmol) and DIPEA (1.4 g, 10.8 mmol) in dichloromethane (10 mL) was stirred for 30 min at room temperature. The reaction system was quenched with water, extracted with DCM. The combined organic layers were dried over anhydrous Na₂SO₄ and concentrated under vacuum. The residue was purified by flash chromatography on silica gel (gradient: 0-100% EtOAc/petroleum ether) to yield the title compound (920 mg, 90.2% yield) as a white solid. LC-MS: (ESI, m/z): [M+H]⁺=283.

Step 5: tert-Butyl (1R,2S,5S)-2-((S)-1-hydroxyethyl)-3,8-diazabicyclo[3.2.1]octane-8-carboxylate A solution of tert-butyl (1S,6S,9R,9aS)-1-methyl-3-oxohexahydro-1H,3H-6,9-epiminooxazolo[3,4-a]azepine-10-carboxylate (900 mg, 3.19 mmol) and NaOH (1.28 g, 32.0 mmol) in ethanol (12 mL) and water (4 mL) was stirred for 1 h at 80° C. The reaction solution was cooled to room temperature and diluted with water, extracted with DCM. The combined organic layers were dried over anhydrous Na₂SO₄ and concentrated under vacuum to yield 815 mg (crude) as an oil which was used for next step without further purification. LC-MS: (ESI, m/z): [M+H]⁺=257. ¹H NMR (300 MHz, DMSO-d₆) δ 4.54 (s, 1H), 3.94 (d, J=5.1 Hz, 1H), 3.82 (s, 1H), 2.73 (d, J=11.3 Hz, 1H), 2.60 (d, J=11.5 Hz, 1H), 2.41 (d, J=8.1 Hz, 1H), 2.15 (s, 1H), 179-1.67 (m, 3H), 1.56 (s, 1H), 1.40 (s, 9H), 1.04 (d, J=6.3 Hz, 3H).

Intermediate 5: ((2R,7aS)-2-Fluorotetrahydro-1H-pyrrolizin-7a(5H)-yl)methanol

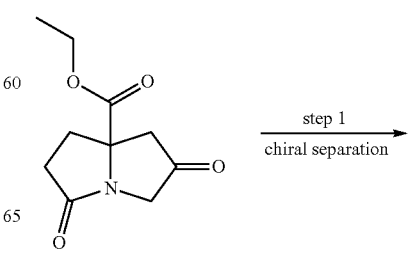

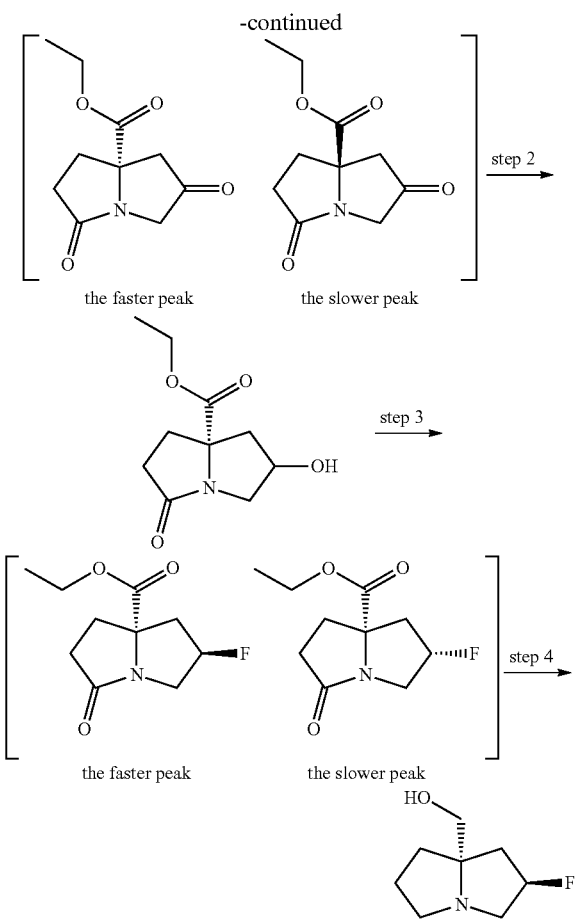

Step 1: Ethyl (S)-2,5-dioxotetrahydro-1H-pyrrolizine-7a(5H)-carboxylate and Ethyl (R)-2,5-dioxotetrahydro-1H-pyrrolizine-7a(5H)-carboxylate 20.0 g ethyl 2,5-dioxotetrahydro-1H-pyrrolizine-7a(5H)-carboxylate (20.0 g, 94.6 mmol) was separated by SFC (Column: AD 2.12*25 cm, 5 um; Mobile Phase A: $CO_2$, Mobile Phase B: EtOH:ACN=1:1; Flow rate: 200 mL/min; Gradient: 50% B; 220 nm; RT1: 2.44; RT2: 3.58; Injection Volume: 10 ml; Number Of Runs: 15) to afford ethyl (S)-2,5-dioxotetrahydro-1H-pyrrolizine-7a(5H)-carboxylate (8.21 g, the faster peak) as a yellow oil and ethyl (R)-2,5-dioxotetrahydro-1H-pyrrolizine-7a(5H)-carboxylate (7.92 g, the slower peak) as a yellow oil. LC-MS: (ESI, m/z): [M+H]$^+$=212. $^1$H NMR (400 MHz, Chloroform-d) δ 4.22 (q, J=7.2 Hz, 2H), 4.14-4.05 (m, 1H), 3.54 (d, J=18.6 Hz, 1H), 3.02-2.91 (m, 2H), 2.87-2.72 (m, 1H), 2.60-2.38 (m, 2H), 2.23-2.11 (m, 1H), 1.28 (t, J=7.1 Hz, 3H).

Step 2: Ethyl (7aS)-2-hydroxy-5-oxotetrahydro-1H-pyrrolizine-7a(5H)-carboxylate

Under nitrogen, to a solution of ethyl (S)-2,5-dioxotetrahydro-1H-pyrrolizine-7a(5H)-carboxylate (1.22 g, 5.68 mmol) in tetrahydrofuran (100 mL) was added $NaBH_4$ (70.3 mg, 1.85 mmol) at 0° C. The mixture was stirred for 30 mins at 0° C. The reaction was quenched with water and concentrated under vacuum. The residue was purified by flash chromatography on silica gel (gradient: 0%-6% MeOH/DCM) to afford the title compound (0.631 g, 62% yield) as a light yellow oil. LC-MS: (ESI, m/z): [M+H]$^+$=214.

Step 3: Ethyl (2R,7aS)-2-fluoro-5-oxotetrahydro-1H-pyrrolizine-7a(5H)-carboxylate and Ethyl (2S,7aS)-2-fluoro-5-oxotetrahydro-1H-pyrrolizine-7a(5H)-carboxylate

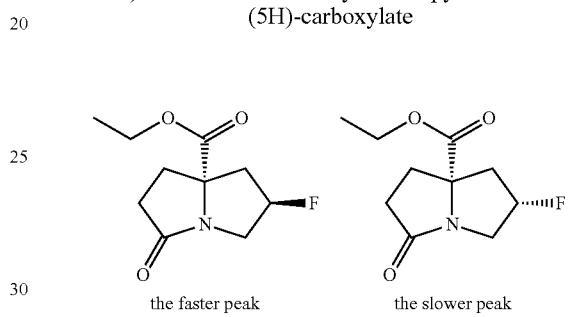

the faster peak         the slower peak

Under nitrogen, to a solution of ethyl (7aS)-2-hydroxy-5-oxotetrahydro-1H-pyrrolizine-7a(5H)-carboxylate (809 mg, 3.80 mmol) was added DAST (923 mg, 5.74 mmol, dissolved in 20 mL DCM) at −15° C. The mixture was stirred for 3 hours at room temperature. The mixture was quenched with EtOH. The solvent was concentrated under reduced pressure. The residue was purified by flash chromatography on silica gel (gradient: 0%-100% EtOAc/petroleum) to afford 425 mg (52% yield) of ethyl (2R,7aS)-2-fluoro-5-oxotetrahydro-1H-pyrrolizine-7a(5H)-carboxylate as a colorless oil and 219 mg (26.9% yield) of ethyl (2S,7aS)-2-fluoro-5-oxotetrahydro-1H-pyrrolizine-7a(5H)-carboxylate as white solid. LC-MS: (ESI, m/z): [M+H]$^+$=216.

Ethyl (2R,7aS)-2-fluoro-5-oxotetrahydro-1H-pyrrolizine-7a(5H)-carboxylate (the faster peak).
$^1$H NMR (400 MHz, Chloroform-d) δ 5.32 (d, J=19.2 Hz, 1H), 4.26-4.11 (m, 3H), 3.25-3.12 (m, 1H), 2.85-2.59 (m, 3H), 2.48-2.39 (m, 1H), 2.37-2.07 (m, 2H), 1.30 (t, J=7.1 Hz, 3H).

Ethyl (2S,7aS)-2-fluoro-5-oxotetrahydro-1H-pyrrolizine-7a(5H)-carboxylate (the slower peak).
$^1$H NMR (400 MHz, Chloroform-d) δ 5.47-5.32 (m, 1H), 4.29-4.24 (m, 2H), 4.08-3.96 (m, 1H), 3.46-3.35 (m, 1H), 2.98-2.78 (m, 2H), 2.53-2.42 (m, 2H), 2.20-2.12 (m, 1H), 1.91-1.76 (m, 1H), 1.31 (t, J=7.1 Hz, 3H).

Step 4: ((2R,7aS)-2-Fluorotetrahydro-1H-pyrrolizin-7a(5H)-yl)methanol

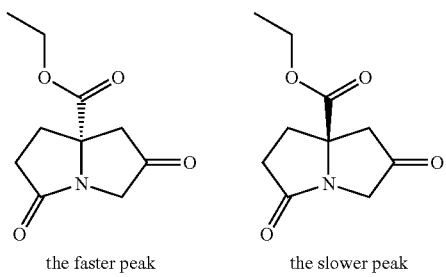

Under nitrogen, to a solution of ethyl (2R,7aS)-2-fluoro-5-oxotetrahydro-1H-pyrrolizine-7a(5H)-carboxylate (310 mg, 1.44 mmol) in tetrahydrofuran (7 mL) was added $LiAlH_4$ (3.1 mL, 1M in THF) at 0° C. The mixture was stirred for 0.5 h at 70° C. The mixture was quenched with Na$_2$SO$_4$·10H$_2$O and filtered. The solvent was removed by blowing N$_2$ and afford the title compound 124 mg (crude) as yellow oil which was used for next step without further purification. LC-MS: (ESI, m/z): [M+H]$^+$=160.

Intermediate 6: (3,3-Difluoro-1-azabicyclo[3.2.0] heptan-5-yl)methanol

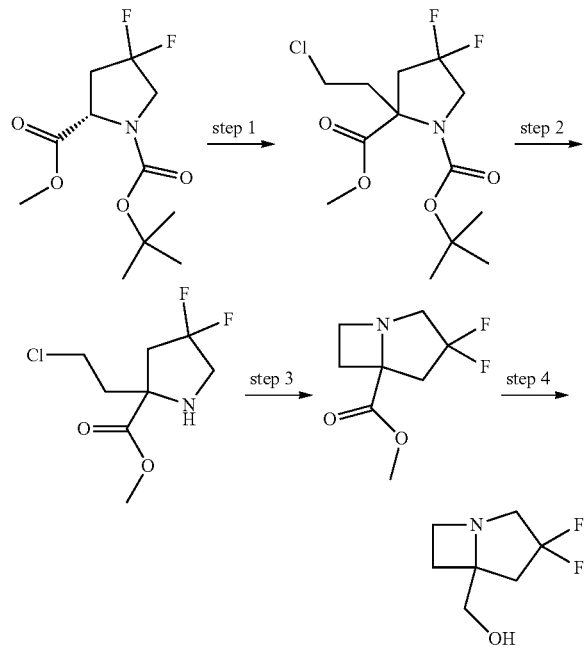

Step 1. 1-(tert-Butyl) 2-methyl 2-(2-chloroethyl)-4,4-difluoropyrrolidine-1,2-dicarboxylate Under nitrogen, to a solution of 1-tert-butyl 2-methyl (2S)-4,4-difluoropyrrolidine-1,2-dicarboxylate (2.0 g, 7.54 mmol) in tetrahydrofuran (30 mL) was added LiHMDS (10 mL, 10 mmol) at −78° C. and stirred at −78° C. for 0.5 hours. Then 1-chloro-2-iodoethane (2.87 g, 15.1 mmol) was added and stirred at room temperature for 1 hour. The reaction was quenched with NH$_4$Cl (aq.), extracted with EtOAc. The combined organic layers were dried over NaSO$_4$ and concentrated under vacuum. The residue was purified by flash chromatography on silica gel eluting with EtOAc/petroleum ether (0~60%) to afford the title compound 900 mg (36.4% yield) as a yellow solid. LC-MS: (ESI, m/z): [M+H]$^+$=328

Step 2. Methyl 2-(2-chloroethyl)-4,4-difluoropyrrolidine-2-carboxylate

Under nitrogen, to a solution of 1-(tert-butyl) 2-methyl 2-(2-chloroethyl)-4,4-difluoropyrrolidine-1,2-dicarboxylate (470 mg, 1.43 mmol) in dichloromethane (5 mL) was added TFA (1 mL) at room temperature. The resulting solution was stirred at room temperature for 1 hour. The solvent was concentrated under vacuum to afford the title compound 300 mg (crude) as a yellow oil which was used for next step without further purification. LC-MS: (ESI, m/z): [M+H]$^+$=228

Step 3. Methyl 3,3-difluoro-1-azabicyclo[3.2.0]heptane-5-carboxylate

Under nitrogen, to a solution of methyl 2-(2-chloroethyl)-4,4-difluoro-pyrrolidine-2-carboxylate (300 mg, 1.32 mmol) in acetonitrile (5 mL) was added Et$_3$N (1 mL) at room temperature and stirred at 85° C. for 12 hours. The solvent was concentrated under vacuum. The residue was purified by flash chromatography on silica gel eluting with DCM/MeOH (0~6%) to afford the title compound 150 mg (59.5% yield) as a yellow solid. LC-MS: (ESI, m/z): [M+H]$^+$=192

Step 4. (3,3-Difluoro-1-azabicyclo[3.2.0]heptan-5-yl)methanol

Under nitrogen, to a solution of methyl 3,3-difluoro-1-azabicyclo[3.2.0]heptane-5-carboxylate (150 mg, 0.780 mmol) in tetrahydrofuran (3 mL) was added LiAlH$_4$ (2.4 mL, 2.4 mmol, 1M in THF) at 0° C. The solution was stirred at 0° C. for 0.5 hours. The solvent was removed by blowing nitrogen to afford 110 mg (crude) the title compound as a yellow oil which was used for next reaction without further purification. LC-MS: (ESI, m/z): [M+H]$^+$=164. purification.

Intermediate 6A: (3,3-Difluoro-1-azabicyclo[3.2.0] heptan-5-yl)methanol

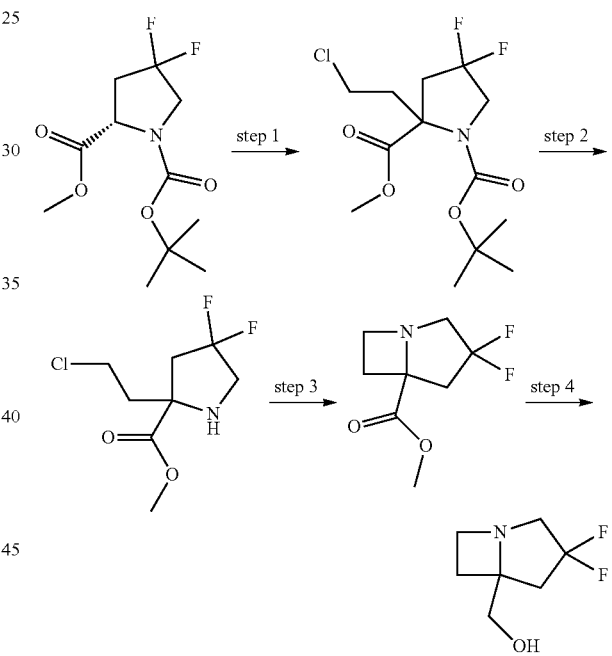

Step 1. 1-(tert-Butyl) 2-methyl 2-(2-chloroethyl)-4,4-difluoropyrrolidine-1,2-dicarboxylate Under nitrogen, to a solution of 1-tert-butyl 2-methyl (2S)-4,4-difluoropyrrolidine-1,2-dicarboxylate (2.0 g, 7.54 mmol) in tetrahydrofuran (30 mL) was added LiHMDS (10 mL, 10 mmol) at −78° C. and the mixture was stirred at −78° C. for 0.5 hours. Then 1-chloro-2-iodoethane (2.87 g, 15.1 mmol) was added and the mixture was stirred at room temperature for 1 hour. The reaction was quenched with NH$_4$Cl (aq.) and then extracted with EtOAc. The combined organic layers were dried over NaSO$_4$ and concentrated under vacuum. The residue was purified by flash chromatography on silica gel eluting with EtOAc/petroleum ether (0~60%) to afford the title compound 900 mg (36.4% yield) as a yellow solid. LC-MS: (ESI, m/z): [M+H]$^+$=328

Step 2. Methyl 2-(2-chloroethyl)-4,4-difluoropyrrolidine-2-carboxylate

Under nitrogen, to a solution of 1-(tert-butyl) 2-methyl 2-(2-chloroethyl)-4,4-difluoropyrrolidine-1,2-dicarboxylate (470 mg, 1.43 mmol) in dichloromethane (5 mL) was added TFA (1 mL) at room temperature. The resulting solution was stirred at room temperature for 1 hour. The solvent was concentrated under vacuum to afford the title compound 300 mg (crude) as a yellow oil which was used for next step without further purification. LC-MS: (ESI, m/z): [M+H]$^+$=228

Step 3. Methyl 3,3-difluoro-1-azabicyclo[3.2.0]heptane-5-carboxylate

Under nitrogen, to a solution of methyl 2-(2-chloroethyl)-4,4-difluoro-pyrrolidine-2-carboxylate (300 mg, 1.32 mmol) in acetonitrile (5 mL) was added Et$_3$N (1 mL) at room temperature and the mixture was stirred at 85° C. for 12 hours. The solvent was concentrated under vacuum. The residue was purified by flash chromatography on silica gel eluting with DCM/MeOH (0~6%) to afford the title compound 150 mg (59.5% yield) as a yellow solid. LC-MS: (ESI, m/z): [M+H]$^+$=192

Step 4. (3,3-Difluoro-1-azabicyclo[3.2.0]heptan-5-yl)methanol

Under nitrogen, to a solution of methyl 3,3-difluoro-1-azabicyclo[3.2.0]heptane-5-carboxylate (150 mg, 0.780 mmol) in tetrahydrofuran (3 mL) was added LiAlH$_4$ (2.4 mL, 2.4 mmol, 1 M in THF) at 0° C. The solution was stirred at 0° C. for 0.5 hours. The solvent was removed by blowing nitrogen through it to afford 110 mg of the crude title compound as a yellow oil which was used for next reaction without further purification. LC-MS: (ESI, m/z): [M+H]$^+$=164. purification.

Intermediate 7: tert-Butyl (5aS,6S,9R)-2-chloro-1-fluoro-12-(methylthio)-5a,6,7,8,9,10-hexahydro-5H-4-oxa-3,10a,11,13,14-pentaaza-6,9-methanonaphtho[1,8-ab]heptalene-14-carboxylate

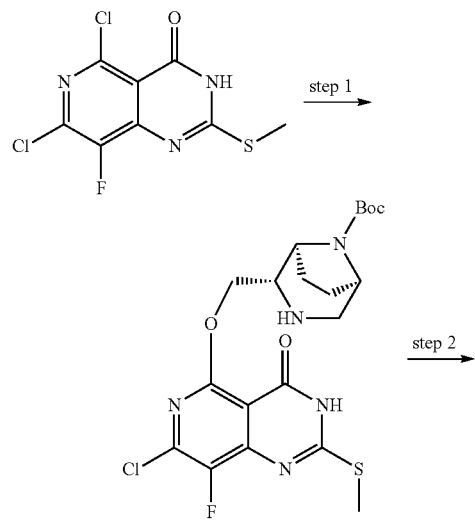

-continued

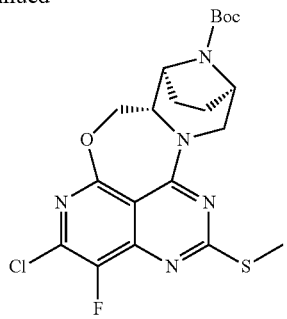

Step 1: tert-Butyl (1S,2S,5R)-2-(((7-chloro-8-fluoro-2-(methylthio)-4-oxo-3,4-dihydropyrido[4,3-d]pyrimidin-5-yl)oxy)methyl)-3,8-diazabicyclo[3.2.1]octane-8-carboxylate Under nitrogen, to a solution of tert-butyl (1S,2S,5R)-2-(hydroxymethyl)-3,8-diazabicyclo[3.2.1]octane-8-carboxylate (289 mg, 1.19 mmol, intermediate 3) in THF (20 mL) was added NaH (191 mg, 4.78 mmol, 60% in mineral oil) at 0° C. The resulting solution was stirred for 0.5 h at room temperature. Then 5,7-dichloro-8-fluoro-2-(methylthio)pyrido[4,3-d]pyrimidin-4(3H)-one (803 mg, 1.43 mmol, intermediate 2) was added at 0° C., and the mixture was stirred for 1 hour at room temperature. The reaction was quenched aqueous NH$_4$Cl, diluted with water and extracted with DCM. The combined organic layers were dried over anhydrous sodium sulfate and concentrated under vacuum to afford the title compound (1.05 g crude) as a white solid which was used for next step without further purification. LC-MS: (ESI, m/z): [M+H]$^+$=486.

Step 2: tert-Butyl (5aS,6S,9R)-2-chloro-1-fluoro-12-(methylthio)-5a,6,7,8,9,10-hexahydro-5H-4-oxa-3,10a,11,13,14-pentaaza-6,9-methanonaphtho[1,8-ab]heptalene-14-carboxylate To a solution of tert-butyl (1S,2S,5R)-2-(((7-chloro-8-fluoro-2-(methylthio)-4-oxo-3,4-dihydropyrido[4,3-d]pyrimidin-5-yl)oxy)methyl)-3,8-diazabicyclo[3.2.1]octane-8-carboxylate (1.05 g, 2.15 mmol) in DCM (10 mL) was added DIPEA (4.16 g, 32.3 mmol) and BOPCl (2.20 g, 8.61 mmol). The resulting solution was stirred at room temperature for 2 hours, diluted with water and extracted with EtOAc. The combined organic layers were dried over anhydrous sodium sulfate and concentrated under vacuum. The residue was purified by flash chromatography on silica gel eluting with EtOAc/petroleum ether (0%-40%) to afford the title compound (381 mg, 37.8% yield) as a light yellow solid. LC-MS: (ESI, m/z): [M+H]$^+$=469

Intermediate 8: tert-Butyl (5aS,6S,9R)-2-chloro-1-fluoro-12-(methylsulfonyl)-5a,6,7,8,9,10-hexahydro-5H-4-oxa-3,10a,11,13,14-pentaaza-6,9-methanonaphtho[1,8-ab]heptalene-14-carboxylate

305

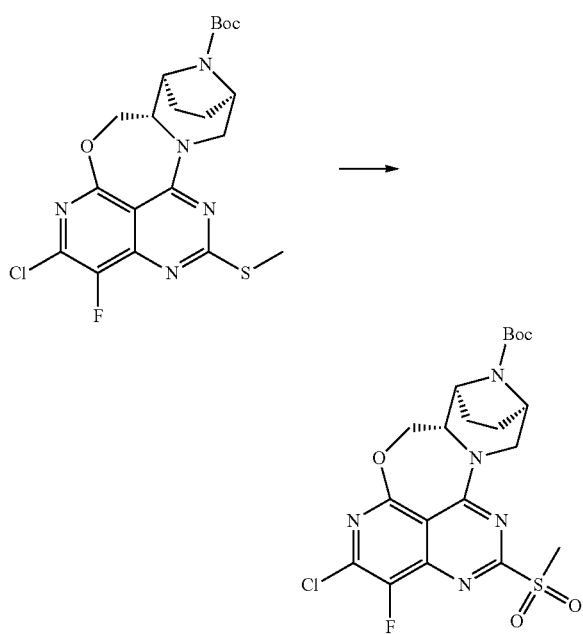

To a solution of tert-butyl (5aS,6S,9R)-2-chloro-1-fluoro-12-(methylthio)-5a,6,7,8,9,10-hexahydro-5H-4-oxa-3,10a,11,13,14-pentaaza-6,9-methanonaphtho[1,8-ab]heptalene-14-carboxylate (381 mg, 0.816 mmol, intermediate 7) in EtOAc (5 mL) was added mCPBA (423 mg, 2.45 mmol) at 0° C. The solution was stirred at room temperature for 1 hour, diluted with saturated NaHCO₃ solution (20 mL) and extracted with EtOAc. The combined organic layers were dried over anhydrous sodium sulfate and concentrated under vacuum. The residue was purified by flash chromatography on silica gel eluting with EtOAc/petroleum ether (0-60%) to afford the title compound 372 mg (91.3% yield) as white solid. LC-MS: (ESI, m/z): [M+H]⁺=500. ¹H NMR (300 MHz, DMSO-d6, ppm) δ 4.99 (d, J=13.5 Hz, 1H), 4.77 (dd, J=13.5, 1.9 Hz, 1H), 4.59 (dd, J=13.5, 7.4 Hz, 1H), 4.38 (d, J=8.3 Hz, 2H), 4.20 (d, J=7.1 Hz, 1H), 3.42 (s, 3H), 3.22 (d, J=13.6 Hz, 1H), 1.93 (d, J=6.7 Hz, 1H), 1.86-1.64 (m, 3H), 1.45 (s, 9H).

Intermediate 9: tert-Butyl (5aS,6S,9R)-2-chloro-1-fluoro-12-(((2R,7aS)-2-fluorotetrahydro-1H-pyrrolizin-7a(5H)-yl)methoxy)-5a,6,7,8,9,10-hexahydro-5H-4-oxa-3,10a,11,13,14-pentaaza-6,9-methanonaphtho[1,8-ab]heptalene-14-carboxylate

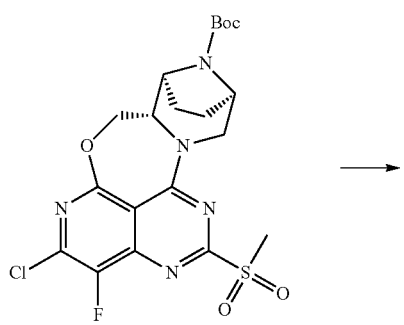

306

-continued

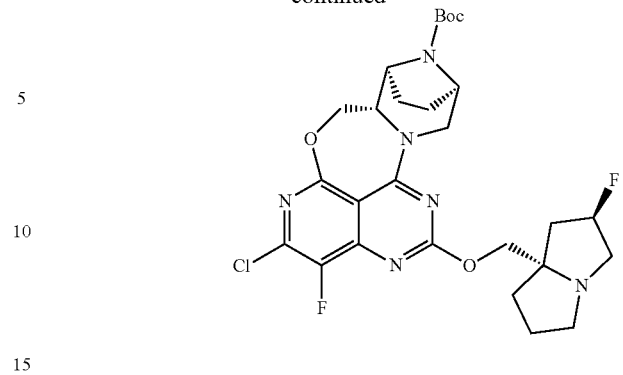

Under nitrogen, to a mixture of tert-butyl (5aS,6S,9R)-2-chloro-1-fluoro-12-(methylsulfonyl)-5a,6,7,8,9,10-hexahydro-5H-4-oxa-3,11a,11,13,14-pentaaza-6,9-methanonaphtho[1,8-ab]heptalene-14-carboxylate (201 mg, 0.401 mmol, intermediate 8) and ((2R,7aS)-2-fluorotetrahydro-1H-pyrrolizin-7a(5H)-yl)methanol (128 mg, 0.802 mmol, intermediate 5) in toluene (2 mL) was added t-BuONa (77.1 mg, 0.802 mmol) at 0° C. The solution was stirred at room temperature for 1 hour, diluted with water (20 mL) and extracted with EtOAc (50 mL*2). The combined organic layers were dried over anhydrous sodium sulfate and concentrated under vacuum. The resulting residue was purified by flash chromatography on silica gel eluting with CH₃OH/DCM (0-10%) to afford the title compound (151 mg, 64.8% yield) as light yellow solid. LC-MS: (ESI, m/z): [M+H]⁺=579. ¹H NMR (300 MHz, DMSO-d6, ppm) δ 5.29 (d, J=54.2 Hz, 1H), 4.89 (d, J=13.4 Hz, 1H), 4.72-4.62 (m, 1H), 4.48 (dd, J=13.3, 7.3 Hz, 1H), 4.40-4.25 (m, 2H), 4.19-3.95 (m, 3H), 3.15-2.97 (m, 4H), 2.89-2.76 (m, 1H), 2.17-2.11 (m, 1H), 2.07-2.02 (m, 1H), 1.94-1.62 (m, 8H), 1.45 (s, 9H).

Intermediate 10: tert-Butyl (5S,5aS,6S,9R)-2-chloro-1-fluoro-5-methyl-12-(methylthio)-5a,6,7,8,9,10-hexahydro-5H-4-oxa-3,10a,11,13,14-pentaaza-6,9-methanonaphtho[1,8-ab]heptalene-14-carboxylate

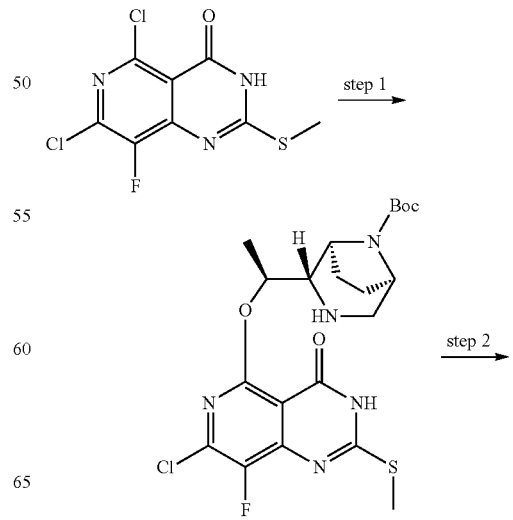

307

Step 1: tert-Butyl (1S,2S,5R)-2-((S)-1-((7-chloro-8-fluoro-2-(methylthio)-4-oxo-3,4-dihydropyrido[4,3-d]pyrimidin-5-yl)oxy)ethyl)-3,8-diazabicyclo[3.2.1]octane-8-carboxylate

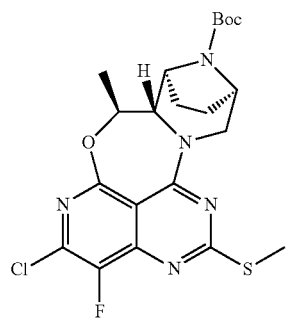

Under nitrogen, to a solution of tert-butyl (1S,2S,5R)-2-((S)-1-hydroxyethyl)-3,8-diazabicyclo[3.2.1]octane-8-carboxylate (769 mg, 3.00 mmol, intermediate 4) in THF (10 mL) was added NaH (480 mg, 12.0 mmol, 60% in mineral oil) at 0° C. The resulting solution was stirred for 0.5 h at room temperature. Then 5,7-dichloro-8-fluoro-2-(methylthio)pyrido[4,3-d]pyrimidin-4(3H)-one (1.01 g, 3.60 mmol, intermediate 2) was added at 0° C., and the mixture was stirred for 2 hours at room temperature. The reaction was quenched with aqueous NH₄Cl, diluted with water and extracted with DCM. The combined organic layers were dried over anhydrous sodium sulfate and concentrated under vacuum to afford the title compound (1.61 g crude) as a white solid, which was used in the next step without further purification. LC-MS: (ESI, m/z): [M+H]⁺=500.

Step 2: tert-Butyl (5S,5aS,6S,9R)-2-chloro-1-fluoro-5-methyl-12-(methylthio)-5a,6,7,8,9,10-hexahydro-5H-4-oxa-3,10a,11,13,14-pentaaza-6,9-methanonaphtho[1,8-ab]heptalene-14-carboxylate To a solution of tert-butyl (1S,2S,5R)-2-((S)-1-((7-chloro-8-fluoro-2-(methylthio)-4-oxo-3,4-dihydropyrido[4,3-d]pyrimidin-5-yl)oxy)ethyl)-3,8-diazabicyclo[3.2.1]octane-8-carboxylate (1.61 g, 3.21 mmol) in DCM (15 mL) was added DIPEA (6.22 g, 48.2 mmol) and BOPCl (3.28 g, 12.9 mmol). The reaction mixture was stirred at room temperature for 2 hours and concentrated under vacuum. The residue was purified by flash chromatography on silica gel eluting with EtOAc/petroleum ether (0%-55%) to afford the title compound (1.21 g, 77.9% yield) as a light yellow solid. LC-MS: (ESI, m/z): [M+H]⁺=482.

308

Intermediate 11: tert-Butyl (5S,5aS,6S,9R)-2-chloro-1-fluoro-5-methyl-12-(methylsulfonyl)-5a,6,7,8,9,10-hexahydro-5H-4-oxa-3,10a,11,13,14-pentaaza-6,9-methanonaphtho[1,8-ab]heptalene-14-carboxylate

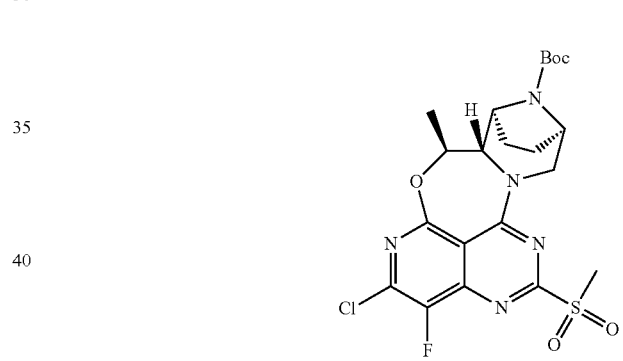

To a solution of tert-butyl (5S,5aS,6S,9R)-2-chloro-1-fluoro-5-methyl-12-(methylthio)-5a,6,7,8,9,10-hexahydro-5H-4-oxa-3,10a,11,13,14-pentaaza-6,9-methanonaphtho[1,8-ab]heptalene-14-carboxylate (1.21 g, 2.5 mmol, intermediate 10) in EtOAc (20 mL) was added mCPBA (1.30 g, 7.52 mmol) at 0° C. The reaction mixture was stirred at room temperature for 1 hour, diluted with NaHCO₃ and extracted with EtOAc. The combined organic layers were dried over anhydrous sodium sulfate and concentrated under vacuum. The residue was purified by flash chromatography on silica gel eluting with EtOAc/petroleum ether (0-60%) to afford the title compound (931 mg, 72.4% yield) as white solid. LC-MS: (ESI, m/z): [M+H]⁺=514. ¹H NMR (300 MHz, DMSO-d6, ppm) δ 5.32-5.16 (m, 1H), 4.74 (t, J=7.7 Hz, 1H), 4.35 (d, J=5.2 Hz, 1H), 4.30-4.10 (m, 2H), 3.42 (s, 3H), 3.20 (d, J=13.4 Hz, 1H), 1.93-1.70 (m, 4H), 1.53 (d, J=6.3 Hz, 3H), 1.47 (s, 9H).

Intermediate 12: tert-Butyl (5S,5aS,6S,9R)-2-chloro-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate

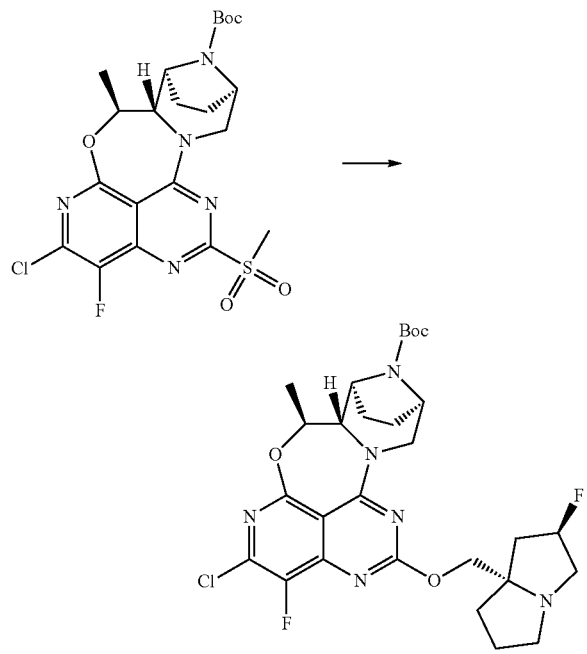

Under nitrogen, to a solution of ((2R,7aS)-2-fluorotetrahydro-1H-pyrrolizin-7a(5H)-yl)methanol (37.5 mg, 0.240 mmol, intermediate 5) and tert-butyl (5S,5aS,6S,9R)-2-chloro-1-fluoro-5-methyl-12-(methylsulfonyl)-5a,6,7,8,9,10-hexahydro-5H-4-oxa-3,10a,11,13,14-pentaaza-6,9-methanonaphtho[1,8-ab]heptalene-14-carboxylate (60.6 mg, 0.120 mmol, intermediate 11) in toluene (1.5 mL) was added t-BuONa (22.6 mg, 0.240 mmol) at 0° C. The reaction mixture was stirred at room temperature for 1 hour, quenched with water, extracted with EtOAc. The combined organic layers were dried over anhydrous sodium sulfate and concentrated under vacuum. The residue was purified by flash chromatography on silica gel eluting with CH$_3$OH/DCM (0-10%) to afford the title compound (40.6 mg, 58.1% yield) as light yellow solid. LC-MS: (ESI, m/z): [M+H]$^+$=593.

Intermediate 13: tert-Butyl (5S,5aS,6S,9R)-2-chloro-12-((3,3-difluoro-1-azabicyclo[3.2.0]heptan-5-yl)methoxy)-1-fluoro-5-methyl-5a,6,7,8,9,10-hexahydro-5H-4-oxa-3,11a,11,13,14-pentaaza-6,9-methanonaphtho[1,8-ab]heptalene-14-carboxylate

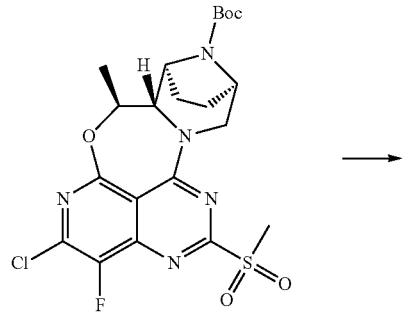

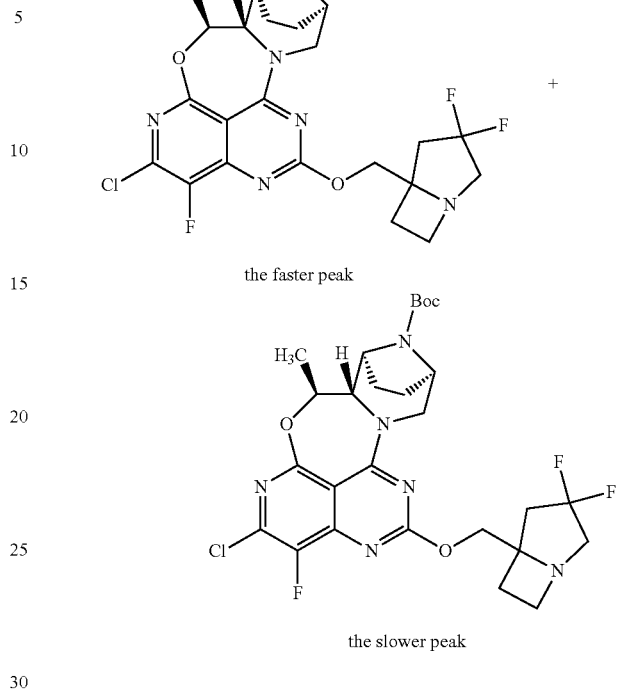

the faster peak the slower peak

Under nitrogen, to a solution of tert-butyl (5S,5aS,6S,9R)-2-chloro-1-fluoro-5-methyl-12-(methylsulfonyl)-5a,6,7,8,9,10-hexahydro-5H-4-oxa-3,10a,11,13,14-pentaaza-6,9-methanonaphtho[1,8-ab]heptalene-14-carboxylate (3.50 g, 6.81 mmol, intermediate 11) and (3,3-difluoro-1-azabicyclo[3.2.0]heptan-5-yl)methanol (1.30 g, 7.97 mmol, intermediate 6) in toluene (35 mL) was added t-BuONa (1.30 g, 13.5 mmol) at 0° C. The resulting solution was stirred at room temperature for 1 h, quenched with water and extracted with EtOAc. The combined organic layers were dried over anhydrous sodium sulfate and concentrated under vacuum. The residue was purified by flash chromatography on silica gel (gradient: 0%-6% MeOH/DCM) to afford 2.06 g (50.7% yield) of a mixture of two diastereoisomers as a white solid. The diastereoisomers were separated by Chiral-Prep-HPLC (Column: CHIRALPAK IE-3, 4.6*50 mm, 3 um; Mobile Phase A: Hex(0.1% DEA): EtOH=50:50; Flow rate: 1 mL/min; Gradient: 0% B to 0% B; Injection Volume: 5 ul mL) to afford yield 643 mg of the faster peak and 676 mg of the slower peak as white solid. LC-MS: (ESI, m/z): [M+H]$^+$=597.

The faster peak (desired isomer): $^1$H NMR (300 MHz, DMSO-d$_6$, ppm): δ 5.18 (d, J=13.2 Hz, 1H), 4.64 (t, J=7.6 Hz, 1H), 4.44-4.29 (m, 3H), 4.16 (s, 1H), 3.99 (d, J=9.0 Hz, 1H), 3.54 (dd, J=9.0, 4.7 Hz, 1H), 3.33-3.15 (m, 1H), 3.15 (d, J=4.4 Hz, 1H), 3.13-2.98 (m, 2H), 2.75-2.52 (m, 1H), 2.50-2.38 (m, 1H), 2.41-2.25 (m, 1H), 1.87 (s, 3H), 1.73 (s, 1H), 1.50 (d, J=6.3 Hz, 3H), 1.47 (s, 9H).

The slower peak: $^1$H NMR (300 MHz, DMSO-d$_6$, ppm): $^1$H NMR (300 MHz, DMSO-d$_6$, ppm): δ 5.18 (d, J=13.2 Hz, 1H), 4.64 (t, J=7.6 Hz, 1H), 4.44-4.29 (m, 3H), 4.16 (s, 1H), 3.99 (d, J=9.0 Hz, 1H), 3.54 (dd, J=9.0, 4.7 Hz, 1H), 3.33-3.15 (m, 1H), 3.15 (d, J=4.4 Hz, 1H), 3.13-2.98 (m, 2H), 2.75-2.52 (m, 1H), 2.50-2.38 (m, 1H), 2.41-2.25 (m, 1H), 1.87 (s, 3H), 1.73 (s, 1H), 1.50 (d, J=6.3 Hz, 3H), 1.47 (s, 9H).

Intermediate 14: tert-Butyl (5aS,6S,9R)-2-chloro-1-fluoro-5a,6,7,8,9,10-hexahydro-5H-4-oxa-3,10a,11,13,14-pentaaza-6,9-methanonaphtho[1,8-ab]heptalene-14-carboxylate

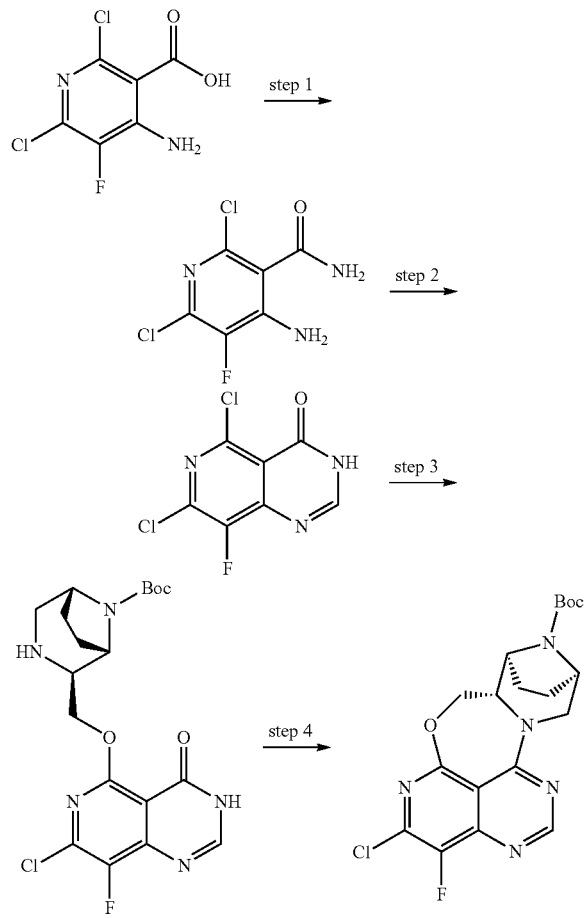

Step 1: 4-Amino-2,6-dichloro-5-fluoronicotinamide

A solution of 4-amino-2,6-dichloro-5-fluoronicotinic acid (2.86 g, 12.7 mmol), NH$_4$Cl (3.38 g, 63.8 mmol), HATU (7.25 g, 19.1 mmol) and DIPEA (16.5 g, 127 mmol) in DMA (28 mL) was stirred at room temperature for 0.5 hour. The resulting solution was diluted with EtOAc (80 mL) and washed with water (60 mL*4). The organic layer was concentrated under vacuum. The residue was purified by flash chromatography on silica gel eluting with CH$_3$OH/DCM (0-5%) to afford the title compound (1.61 g, 56.5% yield) as a white solid. LC-MS: (ESI, m/z): [M+H]$^+$=224. $^1$H NMR (400 MHz, DMSO-d6, ppm) δ 8.06 (s, 1H), 7.81 (s, 1H), 6.87 (s, 2H).

Step 2: 5,7-Dichloro-8-fluoropyrido[4,3-d]pyrimidin-4(3H)-one

A solution of 4-amino-2,6-dichloro-5-fluoronicotinamide (1.51 g, 6.74 mmol) in triethoxymethane (30 mL) was stirred at 150° C. for 3 hours. Then the mixture was concentrated under vacuum. The residue was triturated with EtOAc/petroleum ether (1:1, 10 mL). The solid was collected by filtration to afford the title compound (1.04 g, crude) as a yellow solid which was used for next step without further purification. LC-MS: (ESI, m/z): [M+H]$^+$=234. $^1$H NMR (400 MHz, DMSO-d6, ppm) δ 13.02 (br s, 1H), 8.41 (s, 1H).

Step 3: tert-Butyl (1S,2S,5R)-2-(((7-chloro-8-fluoro-4-oxo-3,4-dihydropyrido[4,3-d]pyrimidin-5-yl)oxy)methyl)-3,8-diazabicyclo[3.2.1]octane-8-carboxylate Under nitrogen, to a solution of tert-butyl (1S,2S,5R)-2-(hydroxymethyl)-3,8-diazabicyclo[3.2.1]octane-8-carboxylate (624 mg, 2.58 mmol, intermediate 3) in DMF (6 mL) was added NaH (134 mg, 3.35 mmol, 60% in mineral oil) at 0° C. The resulting solution was stirred for 30 min at rt. Then 5,7-dichloro-8-fluoropyrido[4,3-d]pyrimidin-4(3H)-one (601 mg, 2.57 mmol) was added and stirred at 80° C. for 1 hour. The reaction mixture was cooled to room temperature and quenched with aq. NH$_4$Cl. The reaction mixture was diluted with EtOAc (50 mL) and washed with brine (50 mL*4). The organic layer was dried over anhydrous sodium sulfate and concentrated under vacuum. The residue was purified by flash chromatography on silica gel eluting with CH$_3$OH/DCM (0-10%) to afford the title compound (452 mg, 40% yield) as a white solid. LC-MS: (ESI, m/z): [M+H]$^+$=440. $^1$H NMR (400 MHz, d6, ppm) δ 8.32 (s, 1H), 4.25-4.05 (m, 3H), 3.98 (d, J=6.4 Hz, 1H), 3.20-3.11 (m, 1H), 2.80 (d, J=11.5 Hz, 1H), 2.60 (s, 1H), 2.03-1.92 (m, 1H), 1.82-1.57 (m, 3H), 1.37 (t, J=9.6 Hz, 9H).

Step 4: tert-Butyl (5aS,6S,9R)-2-chloro-1-fluoro-5a,6,7,8,9,10-hexahydro-5H-4-oxa-3,10a,11,13,14-pentaaza-6,9-methanonaphtho[1,8-ab]heptalene-14-carboxylate Under nitrogen, a solution of tert-butyl (1S,2S,5R)-2-(((7-chloro-8-fluoro-4-oxo-3,4-dihydropyrido[4,3-d]pyrimidin-5-yl)oxy)methyl)-3,8-diazabicyclo[3.2.1]octane-8-carboxylate (452 mg, 1.03 mmol), BOP-Cl (1.05 g, 4.12 mmol) and DIPEA (1.99 g, 15.5 mmol) in DCM (10 mL) was stirred for 2 h at room temperature. Then the mixture was concentrated under vacuum. The residue was purified by flash chromatography on silica gel eluting with EtOAc/petroleum ether (0-40%) to afford the title compound (315 mg, 72.6% yield) as a white solid. LC-MS: (ESI, m/z): [M+H]$^+$=422.

Intermediate 15: tert-Butyl (5S,5aS,6S,9R)-2-chloro-1-fluoro-5-methyl-5a,6,7,8,9,10-hexahydro-5H-4-oxa-3,10a,11,13,14-pentaaza-6,9-methanonaphtho[1,8-ab]heptalene-14-carboxylate

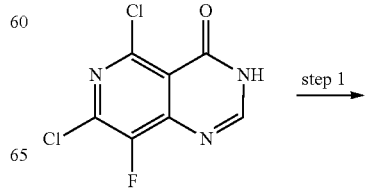

-continued

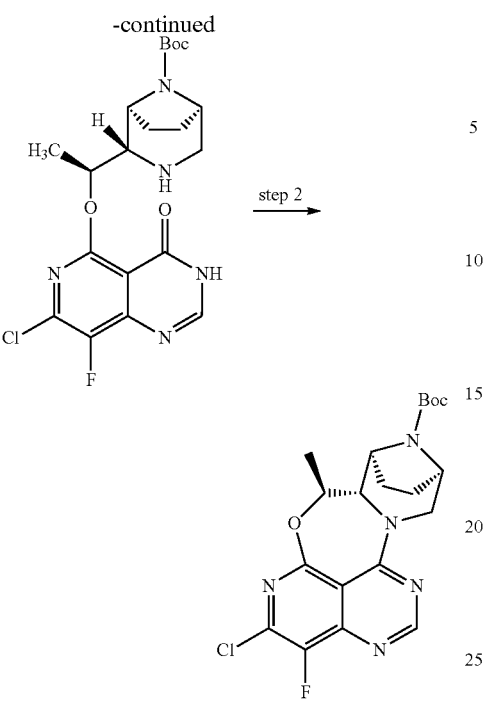

Step 1: tert-Butyl (1R,2S,5S)-2-((S)-1-((7-chloro-8-fluoro-4-oxo-3,4-dihydropyrido[4,3-d]pyrimidin-5-yl)oxy)ethyl)-3,8-diazabicyclo[3.2.1]octane-8-carboxylate Under nitrogen, to a solution of tert-butyl (1R,2S,5S)-2-((S)-1-hydroxyethyl)-3,8-diazabicyclo[3.2.1]octane-8-carboxylate (229 mg, 0.890 mmol, intermediate 4) in DMF (6 mL) was added NaH (71.6 mg, 1.79 mmol, 60% in mineral oil) at 0° C. The resulting solution was stirred for 30 min at rt. Then 5,7-dichloro-8-fluoropyrido[4,3-d]pyrimidin-4(3H)-one (251 mg, 1.07 mmol, intermediate 14, step 2) was added and stirred at 80° C. for 1 hour. The reaction mixture was quenched with aq. NH$_4$Cl, diluted with EtOAc (20 mL) and washed with brine. The organic layer was dried over anhydrous sodium sulfate and concentrated under vacuum to afford the title compound (476 mg, crude) as a white solid which was used for next step without further purification. LC-MS: (ESI, m/z): [M+H]$^+$=454.

Step 2: tert-Butyl (5S,5aS,6S,9R)-2-chloro-1-fluoro-5-methyl-5a,6,7,8,9,10-hexahydro-5H-4-oxa-3,10a,11,13,14-pentaaza-6,9-methanonaphtho[1,8-ab]heptalene-14-carboxylate To a solution of tert-butyl (1R,2R,5S)-2-((S)-1-((7-chloro-8-fluoro-4-oxo-3,4-dihydropyrido[4,3-d]pyrimidin-5-yl)oxy)ethyl)-3,8-diazabicyclo[3.2.1]octane-8-carboxylate (476 mg, 1.05 mmol) in DCM (20 mL) was added DIPEA (2.03 g, 15.71 mmol) and BOPCl (1.07 g, 4.19 mmol). The solution was stirred at rt for 2 hours, then concentrated under vacuum. The residue was purified by flash chromatography on silica gel eluting with EtOAc/petroleum ether (0%-50%) to afford the title compound (221 mg, 48.3% yield) as a white solid. LC-MS: (ESI, m/z): [M+H]$^+$=436.

Intermediate 16: 6-Fluoro-1-methyl-7-(4,4,5,5-tetramethyl-1,3,2-dioxaborolan-2-yl)-1H-indazole

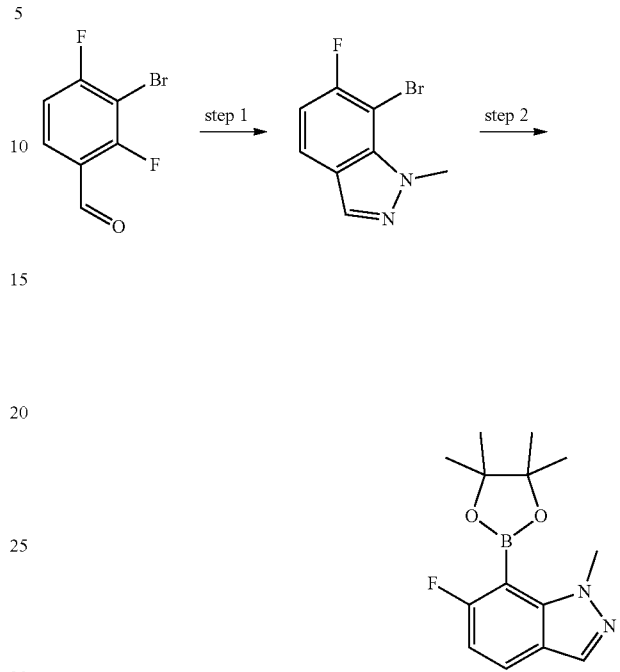

Step 1: 7-Bromo-6-fluoro-1-methyl-1H-indazole

Under nitrogen, a solution of 3-bromo-2,4-difluoro-benzaldehyde (500 mg, 2.26 mmol), 1-methylhydrazine sulfuric acid salt (1.63 g, 11.3 mmol) and K$_2$CO$_3$ (3.12 g, 22.6 mmol) in NMP (15 mL) was stirred at 200° C. for 2 h under microwave irradiation. The reaction system was cooled to room temperature, diluted with water (100 mL) and extracted with EtOAc (100 mL). The organic layer was dried over anhydrous sodium sulfate and concentrated under vacuum. The residue was purified by flash chromatography on silica gel eluting with EtOAc/petroleum ether (0~10%) to afford 7-bromo-6-fluoro-1-methyl-indazole (333.2 mg, 64.3% yield) as a white solid. LC-MS: (ESI, m/z): [M+H]$^+$= 229/231; $^1$H NMR (400 MHz, DMSO-d$_6$) δ 8.13 (s, 1H), 7.80 (dd, J=8.7, 5.0 Hz, 1H), 7.15 (t, J=8.9 Hz, 1H), 4.31 (s, 3H).

Step 2: 6-Fluoro-1-methyl-7-(4,4,5,5-tetramethyl-1,3,2-dioxaborolan-2-yl)-1H-indazole Under nitrogen, a solution of 77-bromo-6-fluoro-1-methyl-1H-indazole (150 mg, 0.660 mmol), Pin$_2$B$_2$ (836 mg, 3.29 mmol), Pd(dppf)Cl (48.2 mg, 0.0700 mmol) and KOAc (258 mg, 2.63 mmol) in DMF (5 mL) was stirred for overnight at 80° C. The resulting solution was purified by reverse phase chromatography (gradient: 0-60% acetonitrile in water (0.05% NH$_4$HCO$_3$)) to afford the title compound (49.9 mg, 27.5% yield) as a white solid. LC-MS: (ESI, m/z): [M+H]$^+$=277. $^1$H-NMR (300 MHz, DMSO-d6, ppm): δ 8.07 (s, 1H), 7.88 (dd, J=8.8, 5.6 Hz, 1H), 6.98 (dd, J=9.5, 8.8 Hz, 1H), 4.05 (s, 3H), 1.38 (s, 12H)

Intermediate 17: 6-(Allylsulfonyl)-N,N-bis(4-methoxybenzyl)-4-methyl-5-(trifluoromethyl)pyridin-2-amine

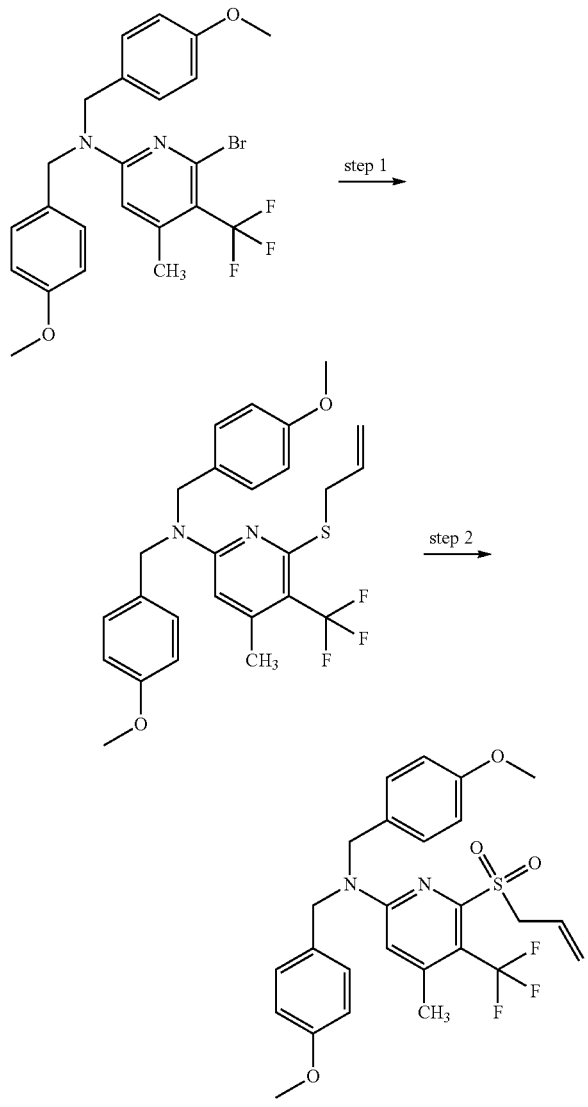

Step 1: 6-(Allylthio)-N,N-bis(4-methoxybenzyl)-4-methyl-5-(trifluoromethyl)pyridin-2-amine Under nitrogen, to a solution of allyl mercaptan (3.74 g, 50.5 mmol) and $K_2CO_3$ (2.79 g, 20.2 mmol) in DMF (20 mL) was added 6-bromo-N,N-bis[(4-methoxyphenyl)methyl]-4-methyl-5-(trifluoromethyl)pyridin-2-amine (5.01 g, 10.1 mmol). The solution was stirred at room temperature overnight and diluted with acetonitrile (20 ml). The solid was filtered off. The filtrate was concentrated under reduced pressure to afford 5.05 g (crude) of the title compound as dark red oil which was used for next step without further purification. LC-MS: (ESI, m/z): [M+H]⁺=489.

Step 2: 6-(Allylsulfonyl)-N, N-bis(4-methoxybenzyl)-4-methyl-5-(trifluoromethyl)pyridin-2 amine To a solution of 6-allylsulfanyl-N,N-bis[(4-methoxyphenyl)methyl]-4-methyl-5-(trifluoromethyl)pyridin-2-amine (5.05 g, 10.3 mmol) in DCM (150 mL) was added mCPBA (14.3 g, 82.7 mmol). The reaction mixture was stirred at room temperature overnight, quenched with saturated $NaHCO_3$ aqueous solution (100 mL) and extracted with DCM. The combined organic layers were dried over anhydrous sodium sulfate and concentrated under vacuum. The residue was purified by silica gel (gradient: 0%-65% ethyl acetate/petroleum ether) to afford 1.70 g (31.6% yield) of the title compound as a white solid. LC-MS: (ESI, m/z): [M+H]⁺=521. ¹H NMR (400 MHz, DMSO-$d_6$, ppm) δ 7.16 (d, J=8.6 Hz, 4H), 7.01 (s, 1H), 6.90 (d, J=8.7 Hz, 4H), 5.61 (ddt, J=18.8, 9.4, 7.1 Hz, 1H), 5.30 (s, 1H), 5.27 (dd, J=6.0, 1.7 Hz, 1H), 4.76 (s, 4H), 4.15 (d, J=7.2 Hz, 2H), 3.72 (s, 6H), 2.38 (s, 3H).

Intermediate 18: ((2-Fluoro-8-(4,4,5,5-tetramethyl-1,3,2-dioxaborolan-2-yl)naphthalen-1-yl)ethynyl)triisopropylsilane

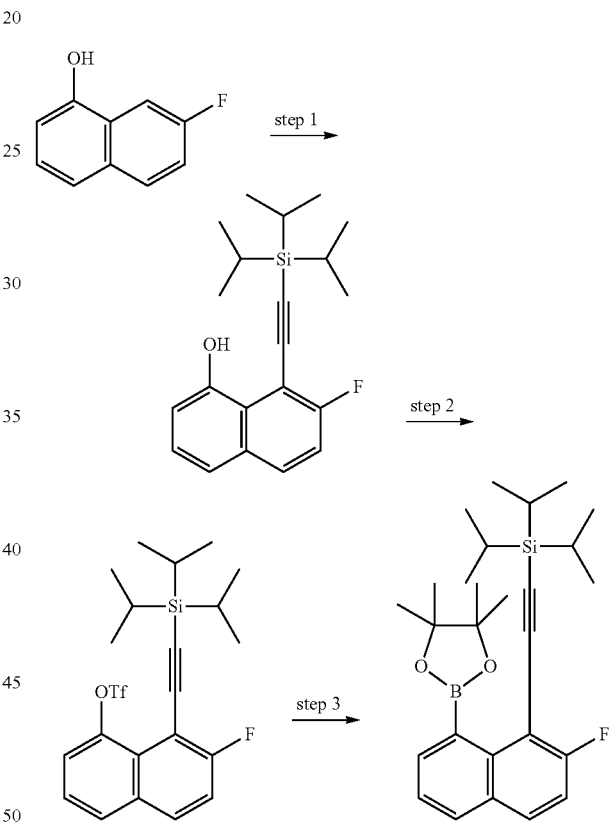

Step 1: 7-Fluoro-8-((triisopropylsilyl)ethynyl)naphthalen-1-ol

Under nitrogen, to a solution of 7-fluoronaphthalen-1-ol (2.50 g, 15.4 mmol) and (bromoethynyl)triisopropylsilane (4.82 g, 18.4 mmol) in DCE (24 mL) were added dichloro(p-cymene)ruthenium(II) dimer (1.42 g, 2.31 mmol), $K_2CO_3$ (2.13 g, 15.4 mmol) and NaOAc (253 mg, 3.09 mmol). The mixture was stirred at 40° C. overnight and concentrated under vacuum. The residue was purified by flash chromatography on silica gel eluting with EtOAc/petroleum ether (0-15%) to afford 5.01 g (94.7% yield) of the title compound as a yellow oil. ¹H-NMR (300 MHz, CDCl₃, ppm) δ 9.00 (s, 1H), 7.68 (dd, J=9.1, 5.8 Hz, 1H), 7.30-7.21 (m, 2H), 7.18-7.06 (m, 1H), 6.96-6.88 (m, 1H), 1.13-1.06 (m, 21H).

Step 2: 7-Fluoro-8-((triisopropylsilyl)ethynyl)naphthalen-1-yl trifluoromethanesulfonate Under nitrogen, to a solution of 7-fluoro-8-((triisopropylsilyl)ethynyl)naphthalen-1-ol (8.95 g, 26.1 mmol) and DIPEA (6.75 g, 52.3 mmol) in DCM (90 mL) was added trifluoromethanesulfonic anhydride (11.1 g, 39.2 mmol) dropwise at −40° C. for 15 min. The solution was stirred at −40° C. for 1 h and concentrated under vacuum. The residue was purified by flash chromatography on silica gel eluting with EtOAc/petroleum ether (0-15%) to afford 10.4 g (83.5% yield) as a yellow oil. $^1$H-NMR (300 MHz, CDCl$_3$, ppm) δ 7.90-7.81 (m, 2H), 7.58 (d, J=7.8 Hz, 1H), 7.48 (t, J=8.0 Hz, 1H), 7.43-7.35 (m, 1H), 1.33-1.15 (m, 21H).

Step 3: ((2-Fluoro-8-(4,4,5,5-tetramethyl-1,3,2-dioxaborolan-2-yl)naphthalen-1-yl)ethynyl)triisopropylsilane Under nitrogen, a solution of 7-fluoro-8-((triisopropylsilyl)ethynyl)naphthalen-1-yl trifluoromethanesulfonate (3.01 g, 6.32 mmol), Pin$_2$B$_2$ (3.22 g, 12.7 mmol), Pd(dppf)Cl$_2$ (486 mg, 0.630 mmol) and KOAc (1.24 g, 12.7 mmol) in 1,4-Dioxane (12 mL) was stirred at 110° C. overnight. The resulting reaction mixture was diluted with EtOAc (100 mL), washed with water (50 mL) and brine (100 mL). The organic layer was dried over anhydrous sodium sulfate and concentrated under vacuum. The residue was purified by flash chromatography on silica gel eluting with EtOAc/petroleum ether (0-13%) to afford 1.61 g (55.9% yield) of the title compound as a yellow solid. $^1$H-NMR (300 MHz, CDCl$_3$, ppm) δ 7.87-7.71 (m, 3H), 7.48-7.37 (m, 1H), 7.32-7.18 (m, 1H), 1.44 (s, 12H), 1.26-1.07 (m, 21H).

Intermediate 19: 2-Fluoro-N,N-bis(4-methoxybenzyl)-5-methyl-3-(4,4,5,5-tetramethyl-1,3,2-dioxaborolan-2-yl)aniline

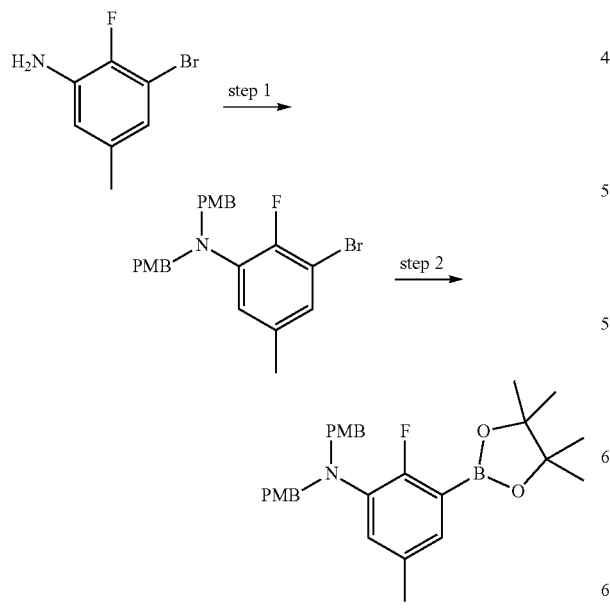

Step 1: 3-Bromo-2-fluoro-N,N-bis(4-methoxybenzyl)-5-methylaniline

Under nitrogen, to a solution of 3-bromo-2-fluoro-5-methylaniline (10.3 g, 50.4 mmol) in THF (90 mL) was added NaH (6.06 g, 151 mmol, 60% in mineral oil) at 0° C. The resulting solution was stirred for 20 min at room temperature. Then PMBCl (19.7 g, 125 mmol) was added at 0° C. and stirred at room temperature for 1.5 hours. The reaction was quenched with aq. NH$_4$Cl and extracted with EtOAc (100 mL). The organic layer was dried over anhydrous sodium sulfate and concentrated under vacuum. The residue was purified by flash chromatography on silica gel (gradient: 0%-9% EtOAc/DCM) to afford 20.4 g (90.9% yield) of the title compound as a yellow solid. LC-MS: (ESI, m/z): [M+H]$^+$=443.

Step 2: 2-Fluoro-N,N-bis(4-methoxybenzyl)-5-methyl-3-(4,4,5,5-tetramethyl-1,3,2-dioxaborolan-2-yl)aniline Under nitrogen, a solution of 3-bromo-2-fluoro-N,N-bis(4-methoxybenzyl)-5-methylaniline (5.01 g, 11.2 mmol), Pin$_2$B$_2$ (5.72 g, 22.5 mmol), Pd(dppf)Cl$_2$ (1.73 g, 2.25 mmol) and KOAc (3.31 g, 33.7 mmol) in 1,4-dioxane (55 mL) was stirred for 5 h at 120° C. The resulting solution was concentrated under vacuum. The residue was purified by flash chromatography on silica gel (gradient: 0%-20% EtOAc/petroleum ether) to afford 4.81 g (79.2% yield) of the title compound as a yellow syrup. LC-MS: (ESI, m/z): [M+H]$^+$=492.

$^1$H NMR (300 MHz, DMSO-d$_6$, ppm): δ 7.28 (s, 6H), 7.24-7.10 (m, 4H), 6.80 (d, J=30.0 Hz, 4H), 3.78 (s, 6H), 2.12 (s, 3H), 1.40 (s, 12H).

Intermediate 20: (5-(Bis(4-methoxybenzyl)amino)-4-fluoro-3-methyl-2-(trifluoromethyl)phenyl)boronic acid

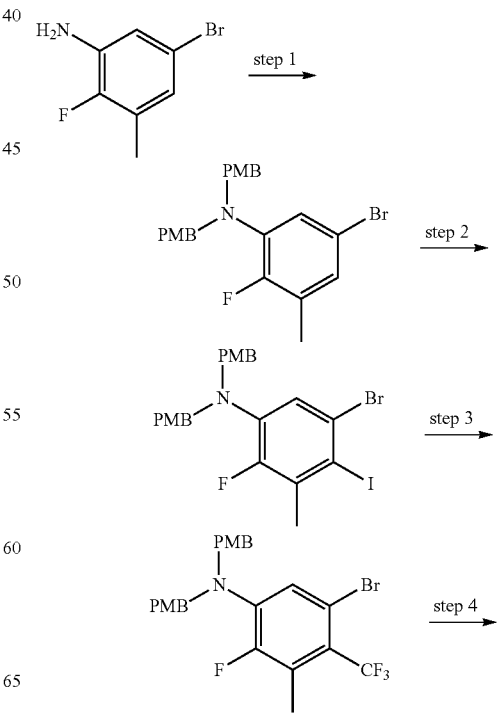

-continued

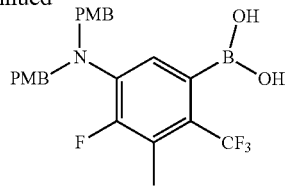

Step 1: 5-Bromo-2-fluoro-N,N-bis(4-methoxybenzyl)-3-methylaniline

Under nitrogen, to a solution of 5-bromo-2-fluoro-3-methylaniline (4.81 g, 23.5 mmol) in DMF (40 mL) was added NaH (2.82 g, 70.5 mmol, 60% in mineral oil) at 0° C. The resulting solution was stirred for 20 min at room temperature. Then PMBCl (7.42 g, 47.3 mmol) was added. Stirred at room temperature for 1 hour and quenched with aq. $NH_4Cl$. The reaction mixture was diluted with $H_2O$ (20 mL) and extracted with EtOAc (2*80 mL). The combined organic layers were dried over anhydrous sodium sulfate and concentrated under vacuum. The residue was slurried with ethanol to yield 6.50 g (crude) of the title compound as an off-white solid which was used for next step without further purification. LC-MS: (ESI, m/z): $[M+H]^+$=444

Step 2: 5-Bromo-2-fluoro-4-iodo-N,N-bis(4-methoxybenzyl)-3-methylaniline

Under nitrogen, to a solution of 5-bromo-2-fluoro-N,N-bis(4-methoxybenzyl)-3-methylaniline (5.70 g, 12.8 mmol) in acetic acid (50 mL) was added NIS (3.20 g, 14.2 mmol) at room temperature. The solution was stirred for 20 min at room temperature. The reaction was quenched with aq. $Na_2S_2O_3$ and diluted with EtOAc (150 mL). Phases were separated. The organic layer was washed with water (4*100 mL), dried over anhydrous sodium sulfate and concentrated under vacuum. The residue was purified by flash chromatography on silica gel eluting with EtOAc/petroleum ether (0-30%) to yield 7.21 g (98.5% yield) of the title compound as a yellow oil. LC-MS: (ESI, m/z): $[M+H]^+$=570.

Step 3: 5-Bromo-2-fluoro-N,N-bis(4-methoxybenzyl)-3-methyl-4-(trifluoromethyl)aniline Under nitrogen, to a solution of 5-bromo-2-fluoro-4-iodo-N,N-bis(4-methoxybenzyl)-3-methylaniline (7.08 g, 12.4 mmol) in DMF (80 mL) was added methyl 2,2-difluoro-2-(fluorosulfonyl)acetate (15.2 mL, 119 mmol) and CuI (23.4 g, 123 mmol) at room temperature. The reaction mixture was stirred for 6 hours at 75° C., diluted with $H_2O$ (40 mL) and extracted with EtOAc (70 mL*2). The combined organic layers were dried over anhydrous sodium sulfate and concentrated under vacuum. The residue was purified by flash chromatography on silica gel eluting with EtOAc/petroleum ether (0-50%) to yield 3.47 g (54.5% yield) of the title compound as a yellow oil. LC-MS: (ESI, m/z): $[M+H]^+$=512.

Step 4: (5-(Bis(4-methoxybenzyl)amino)-4-fluoro-3-methyl-2-(trifluoromethyl)phenyl)boronic acid Under nitrogen, to a solution of 5-bromo-2-fluoro-N,N-bis(4-methoxybenzyl)-3-methyl-4-(trifluoromethyl)aniline (2.40 g, 4.68 mmol) and triisopropyl borate (1.60 mL, 6.91 mmol) in THF (35 mL) was added n-BuLi (2.2 mL, 2.5 M in THF) at −78° C. The resulting solution was stirred for 1 h at −78° C. The reaction was quenched with aq. $NH_4Cl$, diluted with $H_2O$ (20 mL) and extracted with EtOAc (50 mL*2). The combined organic layers were dried over anhydrous sodium sulfate and concentrated under vacuum. The residue was purified by flash chromatography on silica gel eluting with EtOAc(0.1% TEA)/petroleum ether (10% DCM) (0-30%) to yield 1.22 g (54.4% yield) of the title compound as a yellow syrup. LC-MS: (ESI, m/z): $[M+H]^+$=477.

Intermediate 21: 5-Chloro-4-(trimethylstannyl)isoquinoline

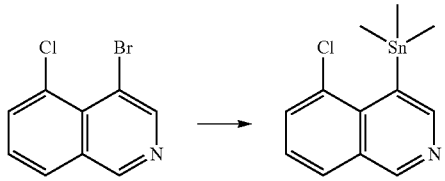

Under nitrogen, a solution of 4-bromo-5-chloroisoquinoline (450 mg, 1.86 mmol), $Sn_2Me_6$ (2.00 g, 6.10 mmol) and $Pd(PPh_3)_4$ (215 mg, 0.190 mmol) in toluene (5 mL) was stirred at 100° C. for 48 h. The reaction system was cooled to room temperature, diluted with water and extracted with EtOAc. The combined organic layers were washed with water, dried over anhydrous sodium sulfate and concentrated under vacuum. The residue was purified by reverse phase chromatography (gradient: 0-78% acetonitrile/water (0.1% FA)) to afford 341 mg (56.3% yield) of the title compound as a yellow oil. LC-MS: (ESI, m/z): $[M+H]^+$=328. $^1$H NMR (400 MHz, Chloroform-d, ppm) δ 9.22 (s, 1H), 8.71 (s, 1H), 7.95-7.88 (m, 1H), 7.85-7.78 (m, 1H), 7.58-7.50 (m, 1H), 0.47 (s, 9H).

Intermediate 22: 2-fluoro-N,N-bis(4-methoxybenzyl)-5-(4,4,5,5-tetramethyl-1,3,2-dioxaborolan-2-yl)-4-(trifluoromethyl)aniline e

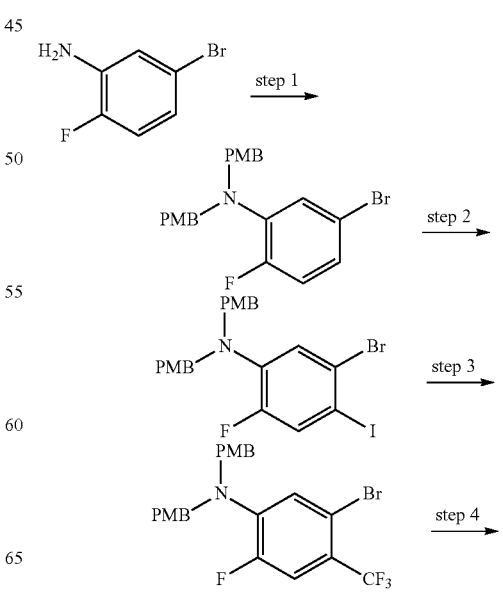

-continued

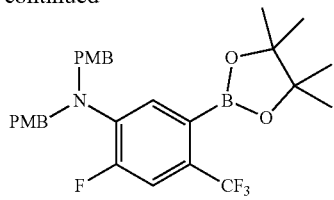

Step 1: 5-Bromo-2-fluoro-N,N-bis(4-methoxybenzyl)aniline

Under nitrogen, to a solution of 5-bromo-2-fluoro-aniline (10.1 g, 53.2 mmol) in DMF (70 mL) was added NaH (6.40 g, 160 mmol, 60% in mineral oil) at 0° C. Stirred for 30 min at room temperature. Then PMBCl (18.2 g, 117 mmol) was added at 0° C., and the mixture was stirred at room temperature for 1 hour. The reaction was quenched with aq. NH$_4$Cl (20 mL), diluted with EtOAc (250 mL) and washed with water (200 mL*4). The organic layer was dried over anhydrous sodium sulfate and concentrated under vacuum. The residue was purified by flash chromatography on silica gel (gradient: 0%-17% EtOAc/petroleum ether) to yield 24.1 g of the title compound as a yellow syrup. LC-MS: (ESI, m/z): [M+H]$^+$=430.

Step 2: 5-Bromo-2-fluoro-4-iodo-N,N-bis(4-methoxybenzyl)aniline

Under nitrogen, a solution of 5-bromo-2-fluoro-N,N-bis(4-methoxybenzyl)aniline (23.9 g, 55.5 mmol) and NIS (14.9 g, 66.5 mmol) in acetic acid (150 mL) was stirred at room temperature for 1.5 hours. The reaction was quenched with aq. Na$_2$S$_2$O$_3$ (15 mL), diluted with EtOAc (300 mL) and washed with water (250 mL). The organic layer was dried over anhydrous sodium sulfate and concentrated under vacuum. The residue was purified by flash chromatography on silica gel (gradient: 0%-22% EtOAc/petroleum ether) to yield 16.7 g (54.0% yield) of the title compound as a white solid. LC-MS: (ESI, m/z): [M+H]$^+$=556.

Step 3: 5-Bromo-2-fluoro-N, N-bis(4-methoxybenzyl)-4-(trifluoromethyl)aniline Under nitrogen, a solution of 5-bromo-2-fluoro-4-iodo-N,N-bis(4-methoxybenzyl)aniline (1.01 g, 1.82 mmol), methyl 2,2-difluoro-2-(fluorosulfonyl)acetate (3.46 g, 18.0 mmol) and CuI (3.42 g, 18.0 mmol) in DMF (10 mL) was stirred at 90° C. for 24 hours. The reaction mixture was diluted with EtOAc (50 mL) and washed with water (35 mL*4). The organic layer was dried over anhydrous sodium sulfate and concentrated under vacuum. The residue was purified by C18 column (solvent gradient: 0-85% ACN in water (0.05% NH$_4$HCO$_3$)) to afford 460 mg (51.3% yield) of the title compound as a yellow oil. LC-MS: (ESI, m/z): [M+H]$^+$=498.

Step 4: 2-fluoro-N,N-bis(4-methoxybenzyl)-5-(4,4,5,5-tetramethyl-1,3,2-dioxaborolan-2-yl)-4-(trifluoromethyl)aniline Under nitrogen, a solution of 5-bromo-2-fluoro-N, N-bis[(4-methoxyphenyl)methyl]-4-(trifluoromethyl)aniline (321 mg, 0.640 mmol), Pin$_2$B$_2$ (327 mg, 1.29 mmol), Pd(dppf)Cl$_2$ (99.1 mg, 0.131 mmol) and KOAc (189 mg, 1.93 mmol) in 1,4-dioxane (2 mL) was stirred for 1 h at 110° C. Then the mixture was concentrated under vacuum. The residue was purified by flash chromatography on silica gel (gradient: 0%-12% EtOAc/petroleum ether) to afford 160 mg (45.5% yield) of the title compound as a yellow oil. LC-MS: (ESI, m/z): [M+H]$^+$=546.

Intermediate 23: 2-Fluoro-3-methyl-5-(4,4,5,5-tetramethyl-1,3,2-dioxaborolan-2-yl)aniline

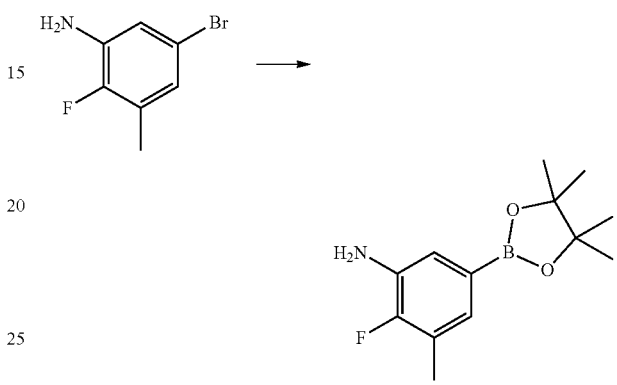

Under nitrogen, a solution of 5-bromo-2-fluoro-3-methylaniline (101 mg, 0.493 mmol), Pin$_2$B$_2$ (253 mg, 0.996 mmol), KOAc (145 mg, 1.48 mmol) and Pd(dppf)Cl$_2$ (38.4 mg, 0.0500 mmol) in 1,4-dioxane (3 mL) was stirred for 3 hours at 110° C. The reaction mixture was diluted with H$_2$O (20 mL), extracted with EtOAc (2*10 mL). The combined organic layers were dried over anhydrous sodium sulfate and concentrated under vacuum. The residue was purified by flash chromatography on silica gel eluting with EtOAc/petroleum ether (0-8%) to yield 184 mg (crude, contain some Pin$_2$B$_2$) of the title compound as a yellow oil which was used for next step without further purification. LC-MS: (ESI, m/z): [M+H]$^+$=251.

Intermediate 24: 4-(4,4,5,5-Tetramethyl-1,3,2-dioxaborolan-2-yl)naphthalen-2-ol

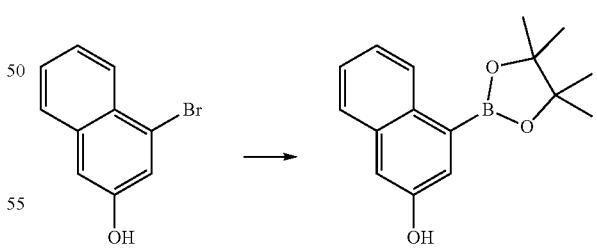

Under nitrogen, a solution of 4-bromonaphthalen-2-ol (400 mg, 1.79 mmol), Pin$_2$B$_2$ (911 mg, 3.59 mmol), Pd(dppf)Cl$_2$ (275 mg, 0.360 mmol) and KOAc (527 mg, 5.38 mmol) in 1,4-dioxane (2 mL) was stirred for 2 h at 110° C. Then the mixture was concentrated under vacuum. The residue was purified by flash chromatography on silica gel (gradient: 0%-15% EtOAc/petroleum ether) to afford 335 mg (92% yield) of the title compound as white solid. LC-MS: (ESI, m/z): [M+H]$^+$=271. $^1$H NMR (300 MHz, DMSO-d$_6$, ppm): δ 9.66 (s, 1H), 8.49 (d, J=8.3 Hz, 1H), 7.70 (d, J=9 Hz, 1H), 7.5 (d, J=3 Hz, 1H), 7.42-7.24 (m, 3H), 1.38 (s, 12H).

Intermediate 25: 2-(8-Fluoro-3-(methoxymethoxy)naphthalen-1-yl)-4,4,5,5-tetramethyl-1,3,2-dioxaborolane

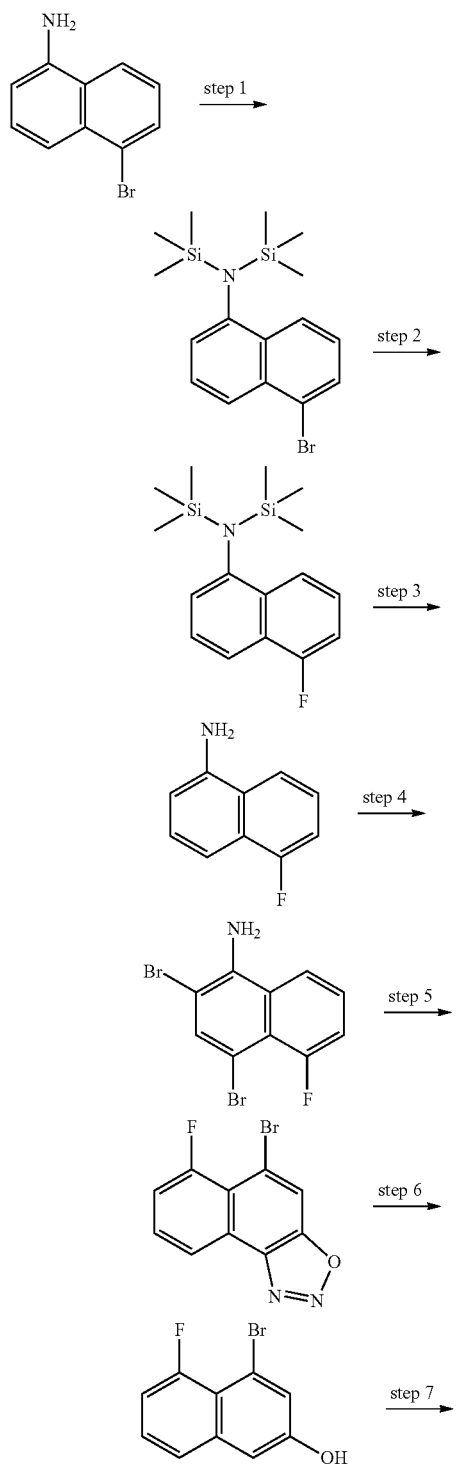

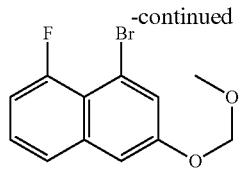

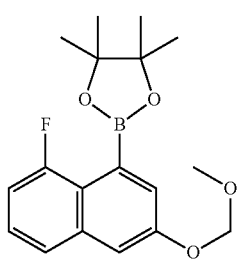 [SMILES: COCOc1cc(B2OC(C)(C)C(C)(C)O2)c2c(F)cccc2c1]

Step 1: N-(5-Bromonaphthalen-1-yl)-1,1,1-trimethyl-N-(trimethylsilyl)silanamine

Under nitrogen, to a solution of 5-bromonaphthalen-1-amine (45.3 g, 204 mmol) in THF (500 mL) was added LiHMDS (451 mL, 1M in THF) at −78° C. and stirred at 20° C. for 3 h. Then the solution cooled back to −78° C. TMSCl (48.7 g, 448 mmol) was added at −78° C. The mixture was warmed naturally to ° C. and stirred at 20° C. for 3 h. Then the mixture was concentrated under vacuum. The residue was treated with hexane. The solid was filtered off. The filtrate was concentrated under vacuum to afford 87.1 g (crude) of the title compound as a red oil which was used for next step without further purification. LC-MS: (ESI, m/z): [M+H]$^+$=443. $^1$H-NMR (300 MHz, CDCl$_3$, ppm) δ 8.21-8.16 (m, 1H), 7.97-7.84 (m, 2H), 7.63-7.55 (m, 1H), 7.49-7.41 (m, 1H), 7.22-7.17 (m, 1H), 0.04 (s, 21H).

Step 2: N-(5-Fluoronaphthalen-1-yl)-1,1,1-trimethyl-N-(trimethylsilyl)silanamine Under nitrogen, to a solution of N-(5-bromonaphthalen-1-yl)-1,1,1-trimethyl-N-(trimethylsilyl)silanamine (87.2 g, 238 mmol) in THF (800 mL) was added n-BuLi (148 mL, 2.5 M in n-hexane) at −78° C. and stirred for 20 min at −78° C. Then N-Fluoro-N-(phenylsulfonyl) benzenesulfonamide (121 g, 382 mmol) was added at this temperature. The reaction mixture was warmed naturally to room temperature and stirred at this temperature for 1 h. The reaction mixture was diluted with water (300 mL) and extracted with EtOAc (500 mL*3). The combined organic layers were dried over anhydrous sodium sulfate and concentrated under vacuum. The residue was purified by flash chromatography on silica gel (gradient: 100% petroleum ether) to afford 45.1 g (62.1%) of the title compound as a light red syrup. LC-MS: (ESI, m/z): [M+H]$^+$=203.

Step 3: 5-Fluoronaphthalen-1-amine

To a solution of N-(5-Fluoronaphthalen-1-yl)-1,1,1-trimethyl-N-(trimethylsilyl)silanamine (45.1 g, 148 mmol) in MeOH (300 mL) was added aqueous HCl (40 mL, 1 M) and stirred at room temperature for 10 min. Then the mixture was concentrated under vacuum. The resulting residue was purified by reverse phase chromatography (gradient: 0-65% acetonitrile in water (0.1% TFA)) to afford 23.4 g (98.4% yield) of the title compound as a brown solid. LC-MS: (ESI, m/z): [M+H]$^+$=162. $^1$H-NMR (300 MHz, CDCl$_3$, ppm) δ

7.69-7.55 (m, 2H), 7.47-7.26 (m, 2H), 7.20-7.11 (m, 1H), 6.88-6.83 (m, 1H), 4.20 (s, 2H).

Step 4: 2,4-Dibromo-5-fluoronaphthalen-1-amine

To a solution of 5-fluoronaphthalen-1-amine (10.0 g, 62.0 mmol) in HOAc (100 mL) was added a solution of bromine (21.4 g, 134 mmol) in HOAc (100 mL) at 0° C. Then the mixture was stirred at 70° C. for 3 h. Cooled to room temperature. The solid was collected by filtration and washed with HOAc (300 mL). Then the solid was suspended in aqueous NaOH (15%, 200 mL) and stirred for 20 min. The solid was collected by filtration and washed with water (200 mL), dried under vacuum to afford 20.1 g (crude) of the title compound as a black solid which was used for next step without further purification. LC-MS: (ESI, m/z): [M+H]$^+$=318. $^1$H-NMR (300 MHz, CDCl$_3$, ppm) δ 7.85 (s, 1H), 7.65-7.59 (m, 1H), 7.51-7.39 (m, 1H), 7.32-7.22 (m, 1H), 4.67 (br s, 2H).

Step 5: 5-Bromo-6-fluoronaphthalen[1,2-d][1,2,3]oxadiazole

To a solution of 2,4-dibromo-5-fluoronaphthalen-1-amine (18.0 g, 56.4 mmol) in propionic acid (45.0 mL, 603 mmol) and HOAc (360 mL) was added NaNO$_2$ (5.84 g, 84.6 mmol) at 0° C. Then the mixture was stirred at 0° C. for 50 min, warmed to 20° C. and stirred for 1.5 h. The solid was collected by filtration, washed with water (200 mL) and dried under vacuum to afford 10.9 g (crude) of the title compound as a brown solid which was used for next step without further purification. LC-MS: (ESI, m/z): [M+H]$^+$=269.

$^1$H-NMR (300 MHz, CDCl$_3$, ppm) δ 7.59-7.50 (m, 1H), 7.20 (s, 1H), 7.14-6.99 (m, 2H).

Step 6: 4-Bromo-5-fluoronaphthalen-2-ol

To a solution of 5-bromo-6-fluoronaphthalen[1,2-d][1,2,3]oxadiazole (10.9 g, 40.8 mmol) in EtOH (150 mL) and THF (75 mL) was added NaBH$_4$ (3.15 g, 82.9 mmol) at 0° C. Then the mixture was stirred at room temperature for 1.5 h and quenched with NaHSO$_4$ (125 mL, 10% in water). A majority of EtOH was stripped off under vacuum. The residual reaction mixture was extracted with EtOAc (3*150 mL). The combined organic phases were washed with water (150 mL), brine (150 mL), dried over anhydrous sodium sulfate and concentrated under vacuum. The residue was purified by flash chromatography on silica gel (gradient: 0-55% EtOAc/petroleum ether) to afford 5.10 g (51.8% yield) of the title compound as a brown solid. LC-MS: (ESI, m/z): [M+H]$^+$=241. $^1$H-NMR (300 MHz, CDCl$_3$, ppm) δ 7.56-7.43 (m, 2H), 7.42-7.33 (m, 1H), 7.22-7.02 (m, 2H).

Step 7: 1-Bromo-8-fluoro-3-(methoxymethoxy)naphthalene

To a solution of 4-bromo-5-fluoronaphthalen-2-ol (4.11 g, 17.0 mmol) in DCM (42.0 mL) was added MOMBr (3.82 g, 30.6 mmol) and DIPEA (5.52 g, 42.7 mmol) at 0° C. Stirred at 0° C. for 0.5 h. The reaction mixture was diluted with water (50 mL) and extracted with DCM (3*50 mL). The combined organic layers were washed with brine (50 mL), dried over anhydrous sodium sulfate and concentrated under vacuum. The residue was purified by flash chromatography on silica gel (gradient: 0-15% EtOAc/petroleum ether) to afford 4.12 g (84.4% yield) of the title compound as a yellow solid. LC-MS: (ESI, m/z): [M+H]$^+$=299. $^1$H-NMR (300 MHz, CDCl$_3$, ppm) δ 7.64-7.50 (m, 2H), 7.45-7.34 (m, 2H), 7.15-7.05 (m, 1H), 5.29 (s, 2H), 3.54 (s, 3H).

Step 8: 2-(8-Fluoro-3-(methoxymethoxy)naphthalen-1-yl)-4,4,5,5-tetramethyl-1,3,2-dioxaborolane Under nitrogen, a solution of 1-bromo-8-fluoro-3-(methoxymethoxy)naphthalene (5.1 g, 17.9 mmol), Pin$_2$B$_2$ (11.4 g, 44.9 mmol), Pd(dppf)Cl$_2$ (1.38 g, 1.80 mmol) and KOAc (5.28 g, 53.8 mmol) in 1,4-dioxane (100 mL) was stirred at 110° C. for 4 h. Cooled to room temperature. The resulting reaction mixture was partitioned between water and EtOAc. The combined organic layers were dried over anhydrous sodium sulfate and concentrated under vacuum. The residue was purified by flash chromatography on silica gel (gradient: 0-25% EtOAc/petroleum ether) to afford 7.60 g (contain 45% Pin$_2$B$_2$) of the title compound as a white solid which was used for next step without further purification. LC-MS: (ESI, m/z): [M+H]$^+$=333.

$^1$H-NMR (300 MHz, CDCl$_3$, ppm) δ 7.54-7.49 (m, 1H), 7.45-7.24 (m, 3H), 7.07-6.99 (m, 1H), 5.31 (s, 2H), 3.52 (s, 3H), 1.46 (s, 12H).

Intermediate 26: Triisopropyl((6-(methoxymethoxy)-8-(4,4,5,5-tetramethyl-1,3,2-dioxaborolan-2-yl)naphthalen-1-yl)ethynyl)silane

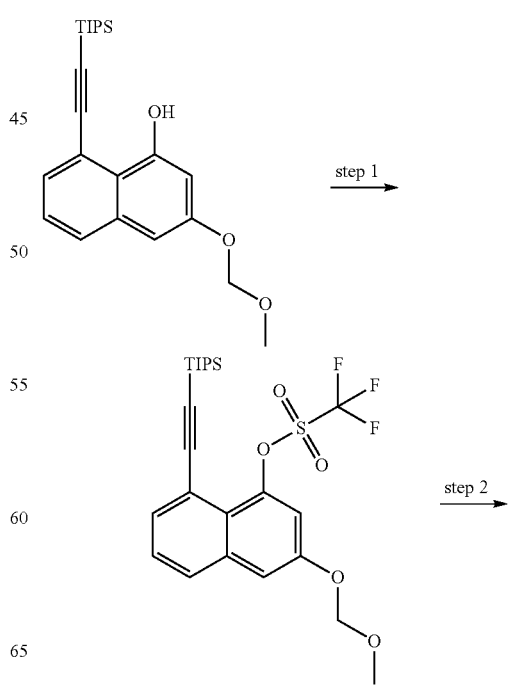

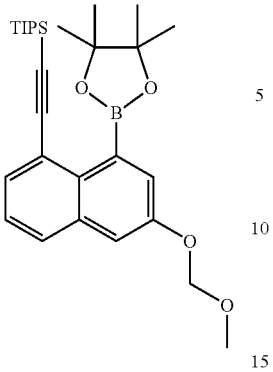

Step 1: 3-(Methoxymethoxy)-8-((triisopropylsilyl)ethynyl)naphthalen-1-yl trifluoromethanesulfonate To a solution of 3-(methoxymethoxy)-8-((triisopropylsilyl)ethynyl)naphthalen-1-ol (1.00 g, 2.60 mmol) and N-(4-chlorophenyl)-1,1,1-trifluoro-N-((trifluoromethyl)sulfonyl)methanesulfonamide (1.23 g, 3.13 mmol) in THF (10 mL) was added NaH (114.6 mg, 2.86 mmol, 60% in oil) at 0° C. The reaction mixture was stirred at room temperature for 1 h. The resulting reaction mixture was diluted with water (30 mL) and extracted with EtOAc (150 mL). The organic layer was washed with brine, dried over anhydrous sodium sulfate and concentrated under vacuum. The residue was purified by flash chromatography on silica gel (gradient: 0%-15% EtOAc/petroleum ether) to afford the title compound (1.41 g, 92.7% yield) as a yellow oil. LC-MS: (ESI, m/z): [M+H]$^+$= 580. $^1$H-NMR (300 MHz, CDCl$_3$, ppm) δ 7.81-7.70 (m, 2H), 7.51-7.39 (m, 2H), 7.35-7.31 (m, 1H), 5.31 (s, 2H), 3.54 (s, 3H), 1.27-1.13 (m, 21H).

Step 2: Triisopropyl((6-(methoxymethoxy)-8-(4,4,5,5-tetramethyl-1,3,2-dioxaborolan-2-yl)naphthalen-1-yl)ethynyl)silane Under nitrogen, a solution of 3-(methoxymethoxy)-8-((triisopropylsilyl)ethynyl)naphthalen-1-yl trifluoromethanesulfonate (1.12 g, 2.17 mmol), Pin$_2$B$_2$ (1.65 g, 6.50 mmol), Pd(dppf)Cl$_2$ (166.7 mg, 0.22 mmol) and KOAc (745 mg, 7.59 mmol) in toluene (11 mL) was stirred at 110° C. overnight. The mixture was partitioned between EtOAc and water. The organic phase was concentrated under vacuum. The residue was purified by flash chromatography on silica gel (gradient: 0%-10% EtOAc/petroleum ether) to afford 833 mg (77.7% yield) of the title compound as a yellow solid. LC-MS: (ESI, m/z): [M+H]$^+$=558. $^1$H-NMR (300 MHz, CDCl$_3$, ppm) δ 7.76-7.66 (m, 2H), 7.49 (d, J=2.6 Hz, 1H), 7.42-7.32 (m, 2H), 5.30 (s, 2H), 3.52 (s, 3H), 1.45 (s, 12H), 1.23-1.15 (m, 21H).

Intermediate 27: 2-(8-Ethyl-3-(methoxymethoxy)naphthalen-1-yl)-4,4,5,5-tetramethyl-1,3,2-dioxaborolane

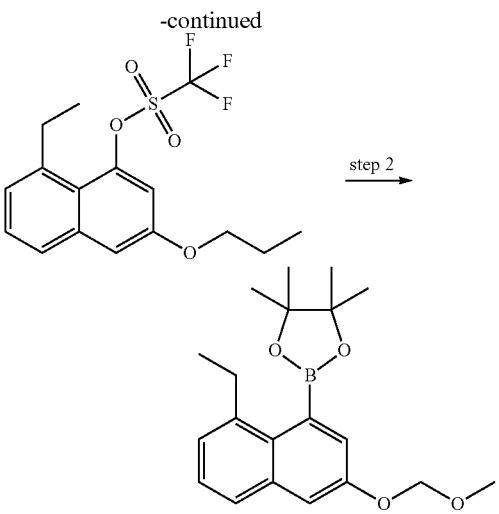

Step 1: 8-Ethyl-3-(methoxymethoxy)naphthalen-1-yl trifluoromethanesulfonate

Under nitrogen, to a solution of 8-ethyl-3-(methoxymethoxy)naphthalen-1-ol (1.00 g, 4.31 mmol) in DCM (15 mL) was added DIPEA (2.22 g, 17.2 mmol) and Tf$_2$O (1.82 g, 6.45 mmol) at −40° C. The resulting solution was stirred at −40° C. for 1 h and concentrated under vacuum. The residue was purified by flash chromatography on silica gel (gradient: 0%-15% EtOAc/petroleum ether) to afford 1.41 g (89.3% yield) of the title compound as a yellow oil. LC-MS: (ESI, m/z): [M+H]$^+$=365. $^1$H-NMR (300 MHz, CDCl$_3$, ppm) δ 7.69-7.63 (m, 1H), 7.50-7.39 (m, 2H), 7.37-7.25 (m, 2H), 5.32 (s, 2H), 3.55 (s, 3H), 3.32-3.22 (m, 2H), 1.35-1.28 (m, 3H).

Step 2: 2-(8-Ethyl-3-(methoxymethoxy)naphthalen-1-yl)-4,4,5,5-tetramethyl-1,3,2-dioxaborolane Under nitrogen, a solution of 8-ethyl-3-(methoxymethoxy)naphthalen-1-yl trifluoromethanesulfonate (1.41 g, 3.87 mmol), Pin$_2$B$_2$ (2.95 g, 11.6 mmol), Pd(dppf)Cl$_2$ (298 mg, 0.390 mmol) and KOAc (949 mg, 9.67 mmol) in 1,4-dioxane (15 mL) was stirred at 110° C. overnight. The mixture was partitioned between EtOAc and water. The organic phase was concentrated under vacuum. The residue was purified by flash chromatography on silica gel (gradient: 0%-15% EtOAc/petroleum ether) to afford 872 mg (65.8% yield) of the title compound as a yellow oil. LC-MS: (ESI, m/z): [M+H]$^+$=343. $^1$H-NMR (300 MHz, CDCl$_3$, ppm) δ 7.65-7.58 (m, 1H), 7.46-7.34 (m, 3H), 7.30-7.25 (m, 1H), 5.31 (s, 2H), 3.53 (s, 3H), 3.26-3.16 (m, 2H), 1.46 (s, 12H), 1.42-1.34 (m, 3H).

Intermediate 28: N,N-bis(4-Methoxybenzyl)-3-methyl-5-(4,4,5,5-tetramethyl-1,3,2-dioxaborolan-2-yl)-4-(trifluoromethyl)aniline

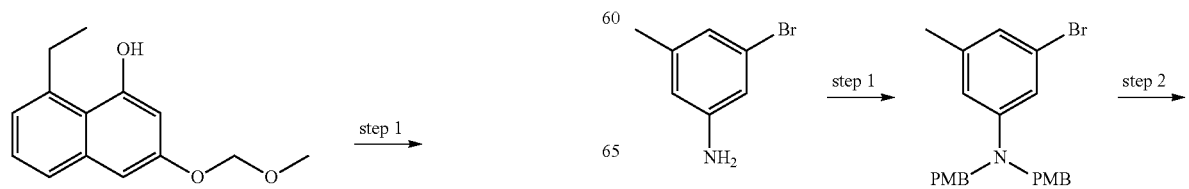

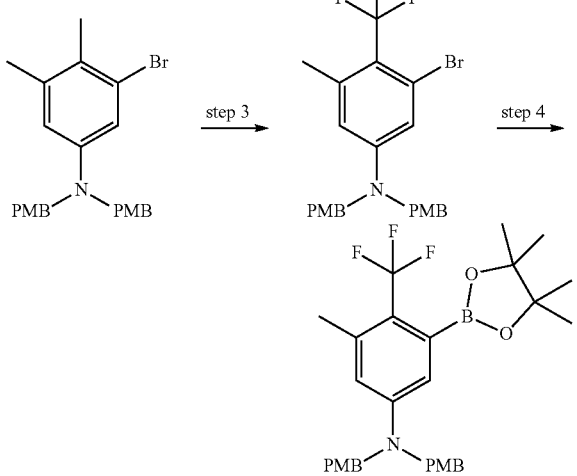

Step 1:
3-Bromo-N,N-bis(4-methoxybenzyl)-5-methylaniline

Under nitrogen, to a solution of 3-bromo-5-methyl-aniline (500 mg, 2.69 mmol) in DMF (5 mL) was added NaH (324 mg, 8.10 mmol, 60% in mineral oil) at 0° C. Stirred for 0.5 hours. Then PMBCl (1.05 g, 6.69 mmol) was added and stirred at room temperature for 12 hours. The reaction was quenched with NH$_4$Cl solution and extracted with EtOAc. The combined organic layers were dried over anhydrous Na$_2$SO$_4$ and concentrated under vacuum. The residue was purified by flash chromatography on silica gel (gradient: 0-10% ethyl acetate/petroleum ether) to afford the title compound (441 mg, 87.8% yield) as a yellow solid. LC-MS: (ESI, m/z): [M+H]$^+$=426/428.

Step 2: 3-Bromo-4-iodo-N,N-bis(4-methoxybenzyl)-5-methylaniline

To a solution of 3-bromo-N,N-bis[(4-methoxyphenyl)methyl]-5-methyl-aniline (2.00 g, 4.69 mmol) in DMF (20 mL) was added NIS (1.58 g, 7.03 mmol) and TsOH (96.0 mg, 0.560 mmol) in portions at room temperature. The resulting solution was stirred at room temperature for 20 min and then quenched with Na$_2$S$_2$O$_3$ aqueous solution. The solution was extracted with EtOAc. The combined organic layers were dried over anhydrous sodium sulfate and concentrated under vacuum. The residue was purified by flash chromatography on silica gel (gradient: 0-18% ethyl acetate/petroleum ether) to afford the title compound (1.58 g, 50.6% yield) as a yellow solid. LC-MS: (ESI, m/z): [M+H]$^+$=552/554.

Step 3: 3-Bromo-N,N-bis(4-methoxybenzyl)-5-methyl-4-(trifluoromethyl)aniline

Under nitrogen, a solution of 3-bromo-4-iodo-N,N-bis[(4-methoxyphenyl)methyl]-5-methyl-aniline (1.58 g, 2.86 mmol), methyl 2,2-difluoro-2-(fluorosulfonyl)acetate (1.82 mL, 14.3 mmol) and CuI (547 mg, 2.86 mmol) in DMF (15 mL) was stirred at 90° C. for 1 hour. The reaction mixture was partitioned between EtOAc and brine. The organic layer was dried over anhydrous sodium sulfate and concentrated under vacuum. The residue was purified by flash chromatography on silica gel (gradient: 0-10% ethyl acetate/petroleum ether) to afford the title compound (695 mg, 43.2% yield) as a yellow solid. LC-MS: (ESI, m/z): [M+H]$^+$=494/496.

Step 4: N,N-Bis(4-methoxybenzyl)-3-methyl-5-(4,4,5,5-tetramethyl-1,3,2-dioxaborolan-2-yl)-4-(trifluoromethyl) aniline Under nitrogen, a solution of 3-bromo-N,N-bis[(4-methoxyphenyl)methyl]-5-methyl-4-(trifluoromethyl)aniline (100 mg, 0.2 mmol), Pin$_2$B$_2$ (153.6 mg, 0.600 mmol), PdCl$_2$(dppf) (15.0 mg, 0.0200 mmol) and KOAc (59.3 mg, 0.610 mmol) in 1,4-dioxane (10 mL) was stirred at 100° C. for 3 hours. Then the mixture was concentrated under vacuum. The residue was purified by flash chromatography on silica gel (gradient: 0-10% ethyl acetate/petroleum ether) to afford the title compound (33.0 mg, 22.7% yield) as a yellow solid. LC-MS: (ESI, m/z): [M+H]$^+$=542.

Intermediate 29: 2,3-Difluoro-N,N-bis(4-methoxybenzyl)-5-(4,4,5,5-tetramethyl-1,3,2-dioxaborolan-2-yl)-4-(trifluoromethyl)aniline

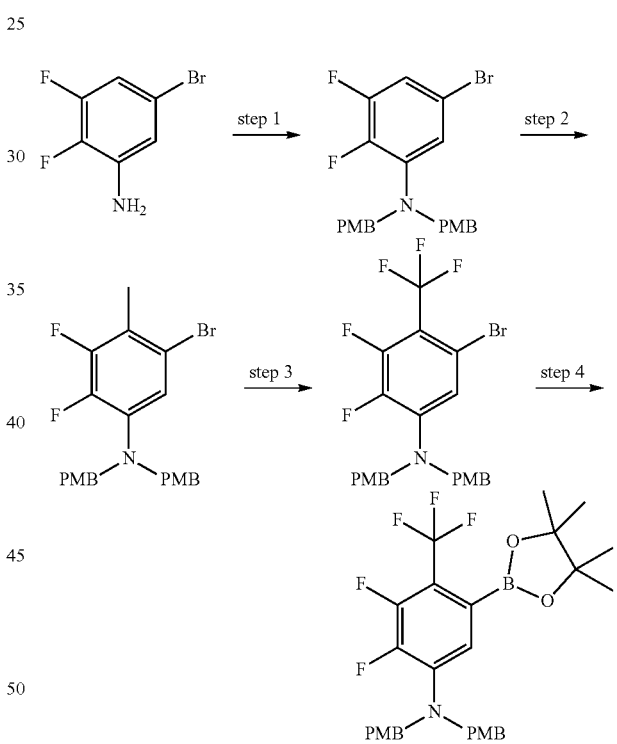

Step 1: 5-Bromo-2,3-difluoro-N,N-bis(4-methoxybenzyl)aniline

Under nitrogen, to a solution of 5-bromo-2,3-difluoro-aniline (500 mg, 2.40 mmol) in DMF (10 mL) was added NaH (384 mg, 9.6 mmol, 60% in mineral oil) at 0° C., and the mixture was stirred at room temperature for 1 hour. Then PMBCl (1.13 g, 7.21 mmol) was added and stirred at room temperature for 4 hours. The reaction was quenched with aqueous NH$_4$Cl solution and extracted with EtOAc. The combined organic layers were dried over anhydrous Na$_2$SO$_4$ and concentrated under vacuum. The residue was purified by flash chromatography on silica gel (gradient: 0-5% ethyl acetate/petroleum ether) to afford the title compound (900 mg, 84.6% yield) as an oil. LC-MS: (ESI, m/z): [M+H]$^+$ =448.

Step 2: 5-Bromo-2,3-difluoro-4-iodo-N,N-bis(4-methoxybenzyl)aniline

A solution of 5-bromo-2,3-difluoro-N,N-bis[(4-methoxyphenyl)methyl]aniline (900 mg, 2.01 mmol) and NIS (676 mg, 3.02 mmol) in acetic acid (10 mL) was stirred at room temperature for 2 hours. Then the mixture was concentrated under vacuum. The residue was purified by flash chromatography on silica gel (gradient: 0-5% ethyl acetate/petroleum ether) to afford the title compound (800 mg, 69.4% yield) as a yellow oil. LC-MS: (ESI, m/z): [M+H]$^+$=574.

Step 3: 5-Bromo-2,3-difluoro-N,N-bis(4-methoxybenzyl)-4-(trifluoromethyl)aniline Under nitrogen, to a solution of 5-bromo-2,3-difluoro-4-iodo-N,N-bis[(4-methoxyphenyl)methyl]aniline (900 mg, 1.57 mmol) and methyl 2,2-difluoro-2-(fluorosulfonyl)acetate (1.50 g, 7.85 mmol) in DMA (9 mL) was added CuI (300 mg, 1.57 mmol) at room temperature. The reaction was stirred at 90° C. for 4 hours. The reaction mixture was partitioned between water and EtOAc. The combined organic layers were dried over anhydrous sodium sulfate and concentrated under vacuum. The residue was purified by flash chromatography on silica gel (gradient: 0-10% ethyl acetate/petroleum ether) to afford the title compound (600 mg, 74.1% yield) as brown oil. LC-MS: (ESI, m/z): [M+H]$^+$= 516.

Step 4: 2,3-Difluoro-N,N-bis(4-methoxybenzyl)-5-(4,4,5,5-tetramethyl-1,3,2-dioxaborolan-2-yl)-4-(trifluoromethyl)aniline Under nitrogen, a solution of 5-bromo-2,3-difluoro-N,N-bis[(4-methoxyphenyl)methyl]-4-(trifluoromethyl)aniline (500 mg, 0.970 mmol), Pin$_2$B$_2$ (739 mg, 2.91 mmol), PdCl$_2$(dppf) (71.0 mg, 0.100 mmol) and KOAc (285 mg, 2.91 mmol) in 1,4-dioxane (5 mL) was stirred at 100° C. for 4 hours. The reaction was cooled to room temperature, diluted with water and extracted with EtOAc. The combined organic layers were dried over anhydrous sodium sulfate and concentrated under vacuum. The residue was purified by flash chromatography on silica gel (gradient: 0-10% ethyl acetate/ petroleum ether) to afford the title compound (260 mg, 47.7% yield) as a white solid. LC-MS: (ESI, m/z): [M+H]$^+$= 564.

Intermediate 30: 3-Fluoro-N,N-bis(4-methoxybenzyl)-5-(4,4,5,5-tetramethyl-1,3,2-dioxaborolan-2-yl)-4-(trifluoromethyl)aniline

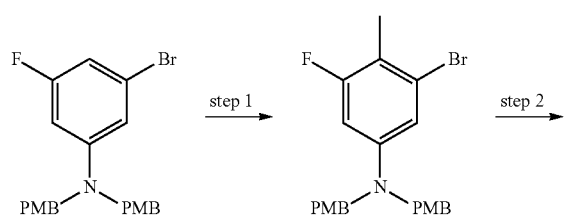

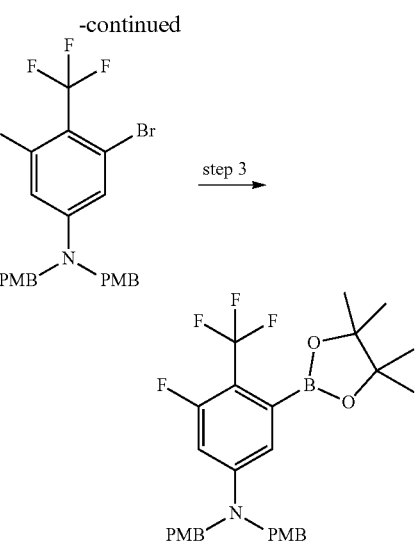

Step 1: 3-Bromo-5-fluoro-4-iodo-N,N-bis(4-methoxybenzyl)aniline

To a solution of 3-bromo-5-fluoro-N,N-bis[(4-methoxyphenyl)methyl]aniline (600 mg, 1.39 mmol) and NIS (484 mg, 2.16 mmol) in DMF (5 mL) was added TsOH (29.0 mg, 0.170 mmol). The resulting mixture was stirred for 1 hour at room temperature. The reaction was quenched with Na$_2$S$_2$O$_3$ aqueous solution and extracted with EtOAc. The combined organic layers were dried over anhydrous sodium sulfate and concentrated under vacuum. The residue was purified by flash chromatography on silica gel (gradient: 0%-25% ethyl acetate/petroleum ether) to yield 200 mg (25.5% yield) of the title compound as a yellow solid. LC-MS: (ESI, m/z): [M+H]$^+$=556.

Step 2: 3-Bromo-5-fluoro-N,N-bis(4-methoxybenzyl)-4-(trifluoromethyl)aniline

Under nitrogen, to a solution of 3-bromo-5-fluoro-4-iodo-N,N-bis[(4-methoxyphenyl)methyl]aniline (100 mg, 0.180 mmol) and CuI (46.0 mg, 0.240 mmol) in DMF (1 mL) was added methyl 2,2-difluoro-2-(fluorosulfonyl)acetate (0.16 mL, 1.19 mmol) at room temperature. The resulting solution was stirred at 90° C. for 2 hours. The reaction mixture was diluted with EtOAc and washed with brine. The organic layer was dried over anhydrous sodium sulfate and concentrated under vacuum. The residue was purified by flash chromatography on silica gel (gradient: 0%-25% ethyl acetate/petroleum ether) to yield 125 mg (crude) of the title compound as a light yellow solid. LC-MS: (ESI, m/z): [M+H]$^+$=498.

Step 3: 3-Fluoro-N,N-bis(4-methoxybenzyl)-5-(4,4,5,5-tetramethyl-1,3,2-dioxaborolan-2-yl)-4-(trifluoromethyl)aniline Under nitrogen, a solution of 3-bromo-5-fluoro-N,N-bis[(4-methoxyphenyl)methyl]-4-(trifluoromethyl)aniline (129 mg, 0.260 mmol), PdCl$_2$(dppf) (19.0 mg, 0.0300 mmol), KOAc (76.0 mg, 0.780 mmol) and Pin$_2$B$_2$ (198 mg, 0.780 mmol) in 1,4-dioxane (2 mL) was stirred at 110° C. overnight. The resulting solution was diluted with EtOAc and washed with brine. The organic layer was dried over anhy-

333 drous sodium sulfate and concentrated under reduced pressure. The residue was purified by reverse phase chromatography (solvent gradient: 0-60% ACN in water (0.05% NH₄HCO₃)) to yield 50 mg (35.4% yield) of the title compound as a colorless oil. LC-MS: (ESI, m/z): [M+H]⁺= 546.

Intermediate 31: 2,6-Difluoro-3-methyl-5-(4,4,5,5-tetramethyl-1,3,2-dioxaborolan-2-yl)aniline

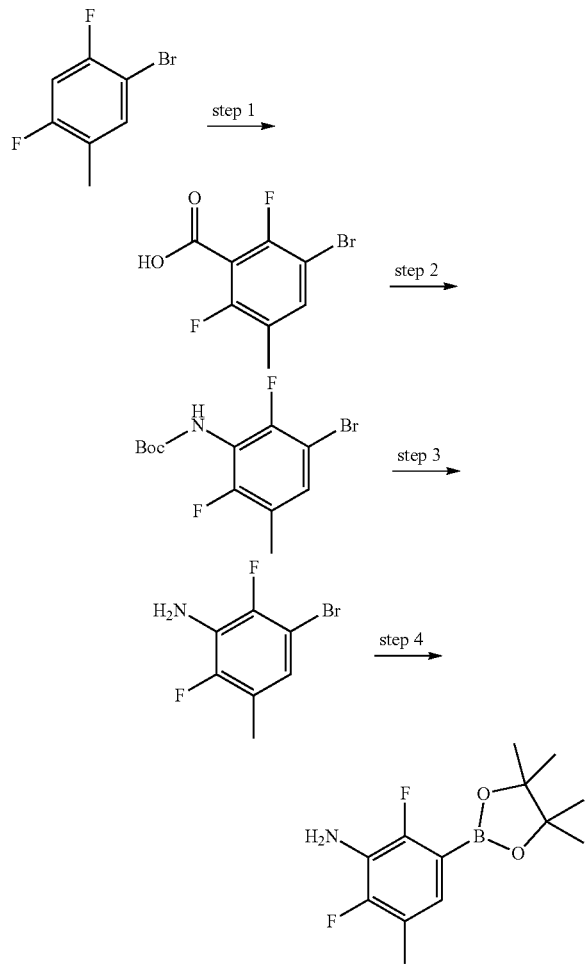

Step 1: 3-Bromo-2,6-difluoro-5-methylbenzoic acid

Under nitrogen, to a stirred solution of 1-bromo-2,4-difluoro-5-methylbenzene (1.00 g, 4.83 mmol) in THF (25 mL) was added LDA (3.14 mL, 6.28 mmol, 2 mol/L in THF) at −85° C. The solution was stirred for 2 h at −85° C. Then the reaction mixture was poured into a solution of dry ice (250 g) in THF (25 mL). The resulting solution was stirred at room temperature for 1 h. The reaction was quenched with NH₄Cl solution (100 mL). THF was stripped off under reduced pressure and the residual solution was acidified to pH=1 with 1 mol/L HCl solution. The solids were collected by filtration and washed with H₂O to afford the titled compound (980 mg, 80.8% yield) as a yellow solid. ¹H NMR (300 MHz, DMSO-d₆) δ 14.14 (s, 1H), 7.90-7.77 (m, 1H), 2.23 (s, 3H).

334

Step 2: tert-Butyl (3-bromo-2,6-difluoro-5-methylphenyl)carbamate

A solution of 3-bromo-2,6-difluoro-5-methyl-benzoic acid (2.00 g, 7.97 mmol), diphenyl azidophosphate (3.28 g, 11.9 mmol) and triethylamine (1.62 g, 16.0 mmol) in 2-methyl-2-propanol (50 mL) was stirred overnight at 90° C., then concentrated under reduced pressure. The residue was purified by flash chromatography on silica gel (gradient: 0-10% EtOAc/petroleum ether) to afford (2.00 g, 77.9% yield) of the title compound as a white solid. LC-MS: (ESI, m/z): [M−H]⁺=320.

Step 3: 3-Bromo-2,6-difluoro-5-methylaniline

A solution of tert-butyl N-(3-bromo-2,6-difluoro-5-methyl-phenyl) carbamate (2.00 g, 6.21 mmol) and HCl (30 mL, 4 mol/L in dioxane) in dichloromethane (30 mL) was stirred for 5 h at room temperature. Then the mixture was concentrated under reduced pressure. The residue was partitioned between saturated NaHCO₃ (aq.) and EtOAc. The combined organic layers were dried over anhydrous Na₂SO₄ and concentrated under vacuum. The residue was purified by flash chromatography on silica gel (gradient: 0-20% EtOAc/petroleum ether) to afford (1 g, 77.9% yield) of the title compound as a white solid. LC-MS: (ESI, m/z): [M+1+MeCN]⁺=263.

Step 4: 2,6-Difluoro-3-methyl-5-(4,4,5,5-tetramethyl-1,3,2-dioxaborolan-2-yl)aniline Under nitrogen, to a stirred solution of 3-bromo-2,6-difluoro-5-methyl-aniline (300 mg, 1.35 mmol) in 1,2-dimethoxyethane (DME) (10 mL) was added Pin₂B₂ (515 mg, 2.03 mmol), Pd(dppf)Cl₂ (98.9 mg, 0.140 mmol) and KOAc (265 mg, 2.70 mmol) at room temperature. The resulting solution was stirred overnight at 90° C. Then the mixture was concentrated under reduced pressure. The residue was purified by flash chromatography on silica gel (gradient: 0-20% EtOAc/petroleum ether) to afford (310 mg, 85.3% yield) of the title compound as a yellow oil. LC-MS: (ESI, m/z): [M+1+MeCN]⁺=311.

Intermediate 32: ((3S)-3-Fluoro-1-azabicyclo[3.2.0]heptan-5-yl)methanol

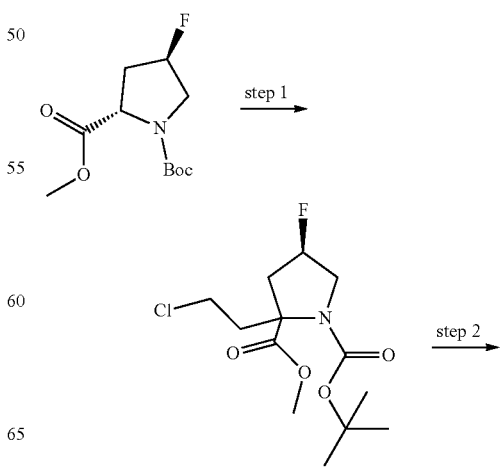

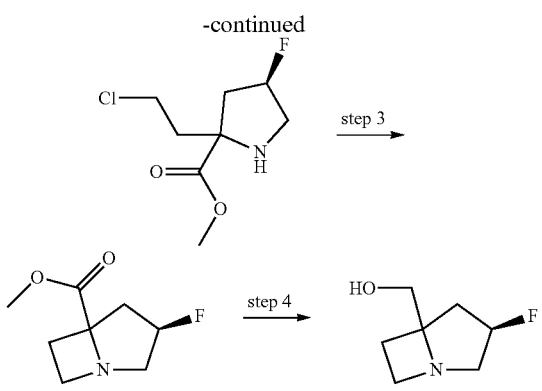

Step 1: 1-(tert-Butyl) 2-methyl (4R)-2-(2-chloro-ethyl)-4-fluoropyrrolidine-1,2-dicarboxylate Under nitrogen, to a solution of 1-(tert-butyl) 2-methyl (2S,4R)-4-fluoropyrrolidine-1,2-dicarboxylate (5.00 g, 20.2 mmol) and HMPA (10.9 g, 60.9 mmol) in tetrahydrofuran (70 mL) was added LiHMDS in THF (60.7 mL, 60.7 mmol, 1 M) at −78° C. The resulting solution was stirred at −78° C. for 1 h. Then 1-bromo-2-chloroethane (8.36 mL, 100 mmol) was added. The resulting solution was stirred at room temperature for 1 h. The mixture was quenched with NH$_4$Cl (aq.), extracted with EtOAc. The combined organic layers were dried over Na$_2$SO$_4$ and concentrated under vacuum. The residual was purified by flash chromatography on silica gel (gradient: 0%-100% EtOAc/petroleum ether) to yield 1.26 g (20.1% yield) of the title compound as a colorless oil. LC-MS: (ESI, m/z): [M+H]$^+$=310.

Step 2: Methyl (4R)-2-(2-chloroethyl)-4-fluoropyrrolidine-2-carboxylate

To a solution of 1-(tert-Butyl) 2-methyl (4R)-2-(2-chloroethyl)-4-fluoropyrrolidine-1,2-dicarboxylate (1.26 g, 3.87 mmol) in dichloromethane (10 mL) was added TFA (5 mL). The resulting solution was stirred at room temperature for 30 min. Solvent was evaporated under vacuum to yield 2 g (crude) of the title compound as a yellow oil which was used for next step without further purification. LC-MS: (ESI, m/z): [M+H]$^+$=210.

Step 3: Methyl (3S)-3-fluoro-1-azabicyclo[3.2.0]heptane-5-carboxylate

A solution of methyl (4R)-2-(2-chloroethyl)-4-fluoropyrrolidine-2-carboxylate (2.00 g, 3.82 mmol) and K$_2$CO$_3$ (1.60 g, 11.6 mmol) in acetonitrile (30 mL) was stirred at 85° C. for 1 h. The solids were filtered off. The filtrate was concentrated under vacuum to yield 2.9 g (crude) of the title compound as a yellow oil which was used for next step without further purification. LC-MS: (ESI, m/z): [M+H]$^+$=174.

Step 4: ((3S)-3-Fluoro-1-azabicyclo[3.2.0]heptan-5-yl)methanol

Under nitrogen, to a solution of methyl (3S)-3-fluoro-1-azabicyclo[3.2.0]heptane-5-carboxylate (2.90 g, 16.7 mmol) in tetrahydrofuran (20 mL) was added LiAlH$_4$ in THF (16.7 mL, 16.7 mmol, 1 M) at 0° C. The resulting solution was stirred at 0° C. for 30 min. The mixture was quenched with Na$_2$SO$_4$·10H$_2$O and filtrated. The solvent was removed by blowing N$_2$ (volatile) to yield 2 g (crude) as a yellow oil which was used for next step without further purification. LC-MS: (ESI, m/z): [M+H]$^+$=146.

Intermediate 33: ((7a'S)-2,2-Difluorodihydro-1'H, 3'H-spiro[cyclopropane-1,2'-pyrrolizin]-7a'(5'H)-yl)methanol

Step 1: Ethyl (R)-2-methylene-5-oxotetrahydro-1H-pyrrolizine-7a(5H)-carboxylate & Ethyl (S)-2-methylene-5-oxotetrahydro-1H-pyrrolizine-7a(5H)-carboxylate

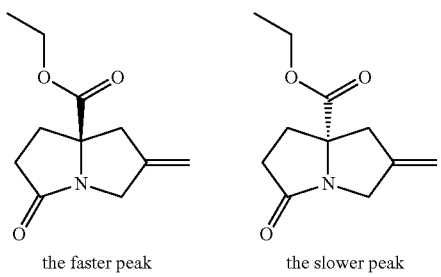

the faster peak     the slower peak

Ethyl 2-methylene-5-oxotetrahydro-1H-pyrrolizine-7a(5H)-carboxylate (19.9 g, was separated by Chiral SFC (Column: CHIRALPAK IH, 50*250 mm; Mobile Phase A: CO2, Mobile Phase B: EtOH; Flow rate: 150 mL/min; Gradient: 26% B; 220 nm; RT1:4.8; RT2:6.43; Injection Volume: 1.8 ml; Number Of Runs: 122) to afford ethyl (R)-2-methylene-5-oxotetrahydro-1H-pyrrolizine-7a(5H)-carboxylate (7.61 g, the faster peak) and ethyl (S)-2-methylene-5-oxotetrahydro-1H-pyrrolizine-7a(5H)-carboxylate (7.29 g, the slower peak). LC-MS: (ESI, m/z): [M+H]$^+$=210. $^1$H NMR (400 MHz, Chloroform-d) 65.12-5.00 (m, 2H), 4.32-4.28 (m, 1H), 4.21 (q, J=7.1 Hz, 2H), 3.73 (d, J=15.7 Hz, 1H), 3.06 (d, J=15.7 Hz, 1H), 2.85-2.72 (m, 1H), 2.66-2.57 (m, 1H), 2.53-2.41 (m, 2H), 2.19-2.08 (m, 1H), 1.28 (t, J=7.1 Hz, 3H). The HNMR of two isomers are the same.

Step 2: Ethyl (7a'S)-2,2-difluoro-5'-oxodihydro-1H, 3H-spiro[cyclopropane-1,2'-pyrrolizine]-7a'(5'H)-carboxylate

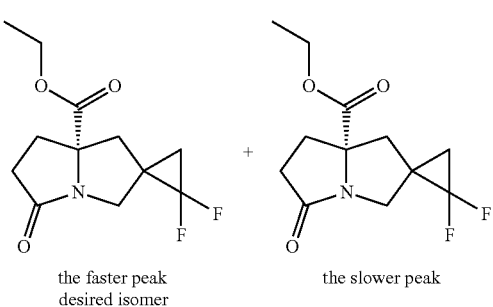 [SMILES: CCOC(=O)[C@@]12CCC(=O)N1CC1(CC1(F)F)C2 ; CCOC(=O)[C@@]12CCC(=O)N1CC1(CC1(F)F)C2]

the faster peak     the slower peak
desired isomer

Under nitrogen, a solution of ethyl (S)-2-methylene-5-oxotetrahydro-1H-pyrrolizine-7a(5H)-carboxylate (200 mg, 0.960 mmol) and NaI (71.7 mg, 0.480 mmol) in THF (5 mL) was added TMSCF$_3$ (476 mg, 3.35 mmol) at room temperature. The resulting solution was stirred for 2.5 h at 65° C. The solution was diluted with DCM, washed with sodium thiosulfate solution and dried over with Na₂SO₄. The organic layer was concentrated under vacuum. The residue was purified by flash chromatography on silica gel (gradient: 0%-35% ethyl acetate/petroleum ether) to afford the faster peak 95.0 mg (38.3% yield) and (gradient: 35%-90% ethyl acetate/petroleum ether) to afford the slower peak 108 mg (43.6% yield) as a yellow solid. LC-MS: (ESI, m/z): [M+H]⁺=260. The faster peak: ¹H NMR (300 MHz, DMSO-d₆, ppm) δ 4.25-4.19 (m, 2H), 3.80-3.70 (m, 1H), 3.04 (d, J=12.1, 3.5 Hz, 1H), 2.62-2.58 (m, 1H), 2.51-2.12 (m, 5H), 1.60 (t, J=9.3 Hz, 2H), 1.24 (t, J=7.1 Hz, 3H). The slower peak: ¹H NMR (300 MHz, DMSO-d₆, ppm) δ 4.24-4.08 (m, 2H), 3.61 (d, J=11.7, 2.7 Hz, 1H), 3.11 (d, J=11.6 Hz, 1H), 2.72-2.54 (m, 1H), 2.44-2.13 (m, 5H), 1.79-1.58 (m, 2H), 1.22 (t, J=7.1 Hz, 3H).

Step 2: ((7a'S)-2,2-difluorodihydro-1'H,3'H-spiro[cyclopropane-1,2'-pyrrolizin]-7a'(5'H)-yl)methanol Under nitrogen, to a solution of ethyl (7a'S)-2,2-difluoro-5'-oxodihydro-1'H,3'H-spiro[cyclopropane-1,2'-pyrrolizine]-7a'(5'H)-carboxylate (95.0 mg, 0.370 mmol, the faster peak of previous step) in THF (2.5 mL) was added LiAlH₄ (1.1 mL, 1 M in THF). The solution was stirred at 65° C. for 1 hour. The reaction was cooled to room temperature and quenched with Na₂SO₄·10H₂O. After filtration, the filtrate was concentrated under reduced pressure to afford 42.0 mg (56.4% yield) of the title compound as a yellow oil. LC-MS: (ESI, m/z): [M+H]⁺=204.

Intermediate 34: (Hexahydro-1H-pyrrolo[2,1-c][1,4]oxazin-6-yl)methanol (mixture of trans

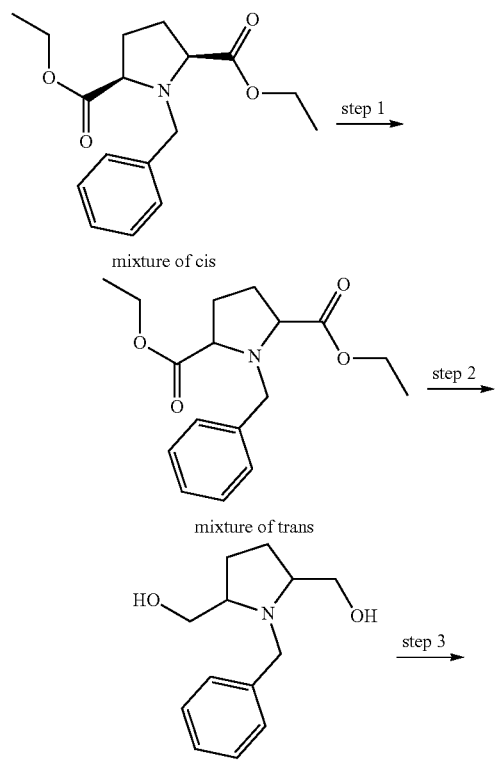

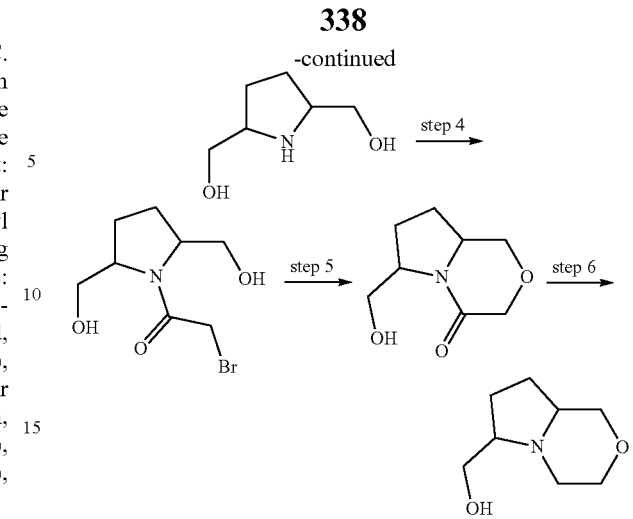

Step 1: Diethyl 1-benzylpyrrolidine-2,5-dicarboxylate (mixture of trans)

To a solution of diethyl cis-1-benzylpyrrolidine-2,5-dicarboxylate (8.60 g, 28.2 mmol) in tetrahydrofuran (120 mL) was added LiHMDS (43.4 mL, 56.4 mmol) at −35° C. After 1 h, the reaction was quenched with saturated aqueous NH₄Cl solution and extracted with EtOAc. The combined organic layers were washed with brine, dried over anhydrous sodium sulfate, and concentrated under vacuum. The residue was purified by flash chromatography on silica gel (gradient: 0-15% ethyl acetate/petroleum ether) to afford 1.27 g (14% yield) of the title compound as a light yellow oil. The cis-isomer was recovered (6.3 g). LC-MS: (ESI, m/z): [M+H]⁺=306.2. ¹H NMR (300 MHz, DMSO-d, ppm) δ 7.32-7.20 (m, 5H), 4.13-3.87 (m, 6H), 3.75-3.60 (m, 3H), 2.25-2.11 (m, 2H), 1.91-1.75 (m, 2H), 1.25-1.06 (m, 3H).

Step 2: (1-Benzylpyrrolidine-2,5-diyl)dimethanol (mixture of trans)

To an ice-cooled solution of diethyl trans-1-benzylpyrrolidine-2,5-dicarboxylate (2.30 g, 7.53 mmol) in tetrahydrofuran (30 mL) under nitrogen was added LiAlH₄ (716 mg, 18.8 mmol) in several portions. The reaction was warmed to room temperature. After 2 h, the mixture was quenched with Na₂SO₄·10H₂O. The solid was filtered, and the filtrate was concentrated under vacuum. The residue was purified by flash chromatography on silica gel (gradient: 0-10% MeOH/DCM) to yield 1.65 g (99% yield) of the title compound as a yellow oil. LC-MS: (ESI, m/z): [M+H]⁺=222.1. ¹H NMR (400 MHz, DMSO-d₆, ppm) δ 7.38-7.15 (m, 5H), 4.34 (s, 2H), 3.95-3.82 (m, 2H), 3.46-3.36 (m, 2H), 3.28-3.20 (m, 2H), 3.01-2.90 (m, 2H), 1.90-1.75 (m, 2H), 1.71-1.58 (m, 2H).

Step 3: Pyrrolidine-2,5-diyldimethanol (mixture of trans)

Under hydrogen (1 atm), a solution of (1-benzylpyrrolidine-2,5-diyl)dimethanol (0.60 g, 2.7 mmol) and Pd/C (180 mg, 10% w/w) in methyl alcohol (10 mL) was stirred at room temperature for 2 h. The catalyst was filtered, and the filtrate was concentrated to afford 405 mg (crude) of the title compound as a light yellow oil. LC-MS: (ESI, m/z): [M+H]= 132.1. The crude product was used without further purification.

Step 4: 1-(2,5-Bis(hydroxymethyl)pyrrolidin-1-yl)-2-bromoethan-1-one (mixture of trans)

To an ice-cooled solution of pyrrolidine-2,5-diyldimethanol (355 mg, 2.71 mmol) and N-methyl morpholine (410 mg, 4.06 mmol) in tetrahydrofuran (10 mL) was added 2-bromoacetyl bromide (539 mg, 2.67 mmol). After 1 h, the reaction was concentrated under vacuum. The residue was purified by flash chromatography on silica gel (gradient: 0-10% MeOH/DCM) to yield 130 mg (19% yield) of the title compound as a yellow oil. LC-MS: (ESI, m/z): [M+H]$^+$= 252.1. $^1$H NMR (400 MHz, DMSO-d$_6$, ppm) δ 5.03 (s, 1H), 4.71 (s, 1H), 4.24 (d, J=11.4 Hz, 1H), 4.09-3.99 (m, 1H), 3.92-3.87 (m, 2H), 3.69 (s, 2H), 3.17 (s, 2H), 2.04-1.72 (m, 4H).

Step 5: 6-(Hydroxymethyl)tetrahydro-1H-pyrrolo[2,1-c][1,4]oxazin-4(3H)-one (mixture of trans)

To an ice-cooled suspension of NaH (65.0 mg, 1.63 mmol, 60% in mineral oil) in tetrahydrofuran (5 mL) was added 1-(2,5-bis(hydroxymethyl)pyrrolidin-1-yl)-2-bromoethan-1-one (130 mg, 0.517 mmol) in 1 mL THF. After 1 h, the resulting solution was warmed to room temperature for 3 h. The reaction was diluted with water and concentrated under vacuum. The residue was purified by flash chromatography on silica gel (gradient: 0-10% MeOH/DCM) to yield the title compound as an oil (37.0 mg, 42% yield). LC-MS: (ESI, m/z): [M+H]$^+$=172.2. $^1$H NMR (400 MHz, DMSO-d, ppm) δ 4.88-4.82 (m, 1H), 4.14-3.97 (m, 3H), 3.84 (d, J=16 Hz, 1H), 3.71-3.61 (m, 1H), 3.59-3.48 (m, 2H), 3.23-3.15 (m, 1H), 2.03-1.87 (m, 2H), 1.82-1.66 (m, 1H), 1.39-1.19 (m, 1H).

Step 6: (Hexahydro-1H-pyrrolo[2,1-c][1,4]oxazin-6-yl)methanol (mixture of trans)

To an ice-cooled suspension of LiAlH$_4$ (27.3 mg, 0.720 mmol) in tetrahydrofuran (5 mL) under nitrogen was added 6-(hydroxymethyl)tetrahydro-1H-pyrrolo[2,1-c][1,4]oxazin-4(3H)-one (60.0 mg, 0.350 mmol) in 0.5 mL THF. The resulting solution warmed to 60° C. for 2 h. The reaction was cooled to room temperature and quenched with Na$_2$SO$_4$·10H$_2$O. The solid was filtered, and the filtrate was concentrated to yield the title compound as a light yellow oil (60 mg, crude). LC-MS: (ESI, m/z): [M+H]$^+$=158.1. The crude product was used for next step without further purification.

Intermediate 34A: ((6S,8aS)-Hexahydro-1H-pyrrolo[2,1-c][1,4]oxazin-6-yl)methanol

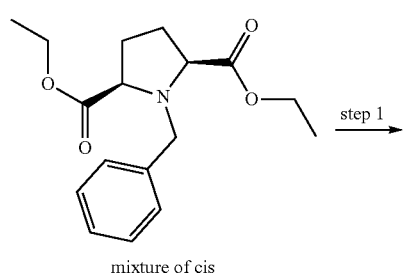

mixture of cis

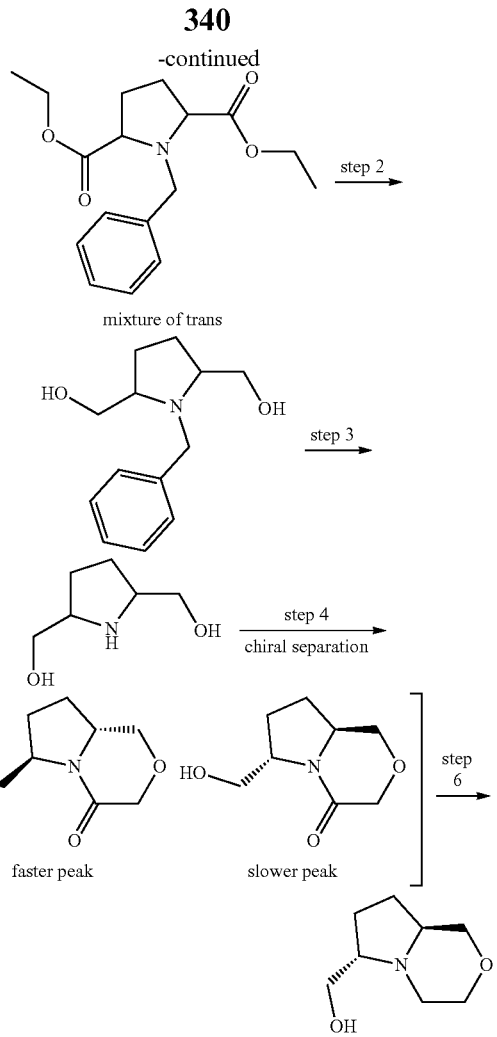

Step 1: Diethyl 1-benzylpyrrolidine-2,5-dicarboxylate (mixture of trans)

To a solution of diethyl cis-1-benzylpyrrolidine-2,5-dicarboxylate (8.60 g, 28.2 mmol) in tetrahydrofuran (120 mL) was added LiHMDS (43.4 mL, 56.4 mmol) at −35° C. After 1 h, the reaction was quenched with saturated aqueous NH$_4$Cl solution and extracted with EtOAc. The combined organic layers were washed with brine, dried over anhydrous sodium sulfate, and concentrated under vacuum. The residue was purified by flash chromatography on silica gel (gradient: 0-15% ethyl acetate/petroleum ether) to afford 1.27 g (14% yield) of the title compound as a light yellow oil. The cis-isomer was recovered (6.3 g). LC-MS: (ESI, m/z): [M+H]$^+$=306.2. $^1$H NMR (300 MHz, DMSO-d, ppm) δ 7.32-7.20 (m, 5H), 4.13-3.87 (m, 6H), 3.75-3.60 (m, 3H), 2.25-2.11 (m, 2H), 1.91-1.75 (m, 2H), 1.25-1.06 (m, 3H).

Step 2: (1-Benzylpyrrolidine-2,5-diyl)dimethanol (mixture of trans)

To an ice-cooled solution of diethyl trans-1-benzylpyrrolidine-2,5-dicarboxylate (2.30 g, 7.53 mmol) in tetrahydrofuran (30 mL) under nitrogen was added LiAlH$_4$ (716 mg, 18.8 mmol) in several portions. The reaction was warmed to room temperature. After 2 h, the mixture was quenched with Na₂SO₄·10H₂O. The solid was filtered, and the filtrate was concentrated under vacuum. The residue was purified by flash chromatography on silica gel (gradient: 0-10% MeOH/DCM) to yield 1.65 g (99% yield) of the title compound as a yellow oil. LC-MS: (ESI, m/z): [M+H]⁺=222.1. ¹H NMR (400 MHz, DMSO-d₆, ppm) δ 7.38-7.15 (m, 5H), 4.34 (s, 2H), 3.95-3.82 (m, 2H), 3.46-3.36 (m, 2H), 3.28-3.20 (m, 2H), 3.01-2.90 (m, 2H), 1.90-1.75 (m, 2H), 1.71-1.58 (m, 2H).

Step 3: Pyrrolidine-2,5-diyldimethanol (mixture of trans)

Under hydrogen (1 atm), a solution of (1-benzylpyrrolidine-2,5-diyl)dimethanol (0.60 g, 2.7 mmol) and Pd/C (180 mg, 10% w/w) in methanol (10 mL) was stirred at room temperature for 2 h. The catalyst was filtered, and the filtrate was concentrated to afford 405 mg (crude) of the title compound as a light yellow oil. LC-MS: (ESI, m/z): [M+H]⁺=132.1. The crude product was used without further purification.

Step 4: (6R,8aR)-6-(Hydroxymethyl)tetrahydro-1H-pyrrolo[2,1-c][1,4]oxazin-4(3H)-one & (6S,8aS)-6-(hydroxymethyl)tetrahydro-1H-pyrrolo[2,1-c][1,4]oxazin-4(3H)-one

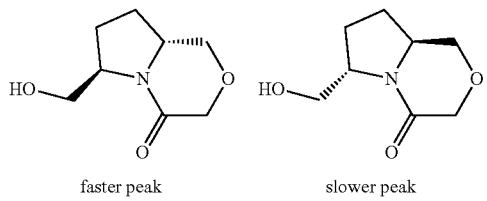

faster peak      slower peak

To a solution of pyrrolidine-2,5-diyldimethanol (7.9 g, 60.305 mmol) in IPA (300.0 mL) was added potassium trimethylsilanolate (16.98 g, 132.671 mmol) at 0° C. Then 2-bromoacetyl bromide (13.27 g, 66.336 mmol) was added. The solution was stirred for 1 min at 0° C. The reaction was quenched with MeOH (20 mL). The solids were filtered out and the filtrate was concentrated under vacuum. The residue was purified by flash chromatography on silica gel (gradient: 0%-10% MeOH/dichloromethane) to yield 3.9 g (mixture of trans) of the title compound as a yellow oil. The enantiomers were separated by chiral SFC with the following conditions (Column, CHIRAL ART Amylose-SA, 3*25 cm, 5 um; mobile phase, CO₂ (70%) and MeOH(0.1% 2 M NH₃—MeOH)(300%)) to afford the faster peak 1.98 g and the slower peak 1.9 g (desired isomer) as a yellow oil. LC-MS: (ESI, m/z): [M+H]⁺=172. H-NMR-PH-GNE-VINT-073-0: ¹H NMR (300 MHz, DMSO-d₆) δ 4.85 (t, J=5.7 Hz, 1H), 4.14-3.99 (m, 3H), 3.84 (d, J=16.5 Hz, 1H), 3.67-3.56 (m, 1H), 3.67-3.51 (m, 2H), 3.23-3.16 (m, 1H), 2.00-1.89 (m, 2H), 1.80-1.69 (m, 1H), 1.34-1.25 (m, 1H).

Step 5: ((6S,8aS)-Hexahydro-1H-pyrrolo[2,1-c][1,4]oxazin-6-yl)methanol

To an ice-cooled suspension of LiAlH₄ (27.3 mg, 0.720 mmol) in tetrahydrofuran (5 mL) under nitrogen was added (6S,8aS)-6-(hydroxymethyl)tetrahydro-1H-pyrrolo[2,1-c][1,4]oxazin-4(3H)-one (60.0 mg, 0.350 mmol) in 0.5 mL THF. The resulting solution warmed to 60° C. for 2 h. The reaction was cooled to room temperature and quenched with Na₂SO₄·10H₂O. The solid was filtered, and the filtrate was concentrated to yield the title compound as a light yellow oil (60 mg, crude). LC-MS: (ESI, m/z): [M+H]⁺=158.1. The crude product was used for next step without further purification.

Intermediate 35: ((2S,4R)-4-Fluoro-1-methylpyrrolidin-2-yl)methanol

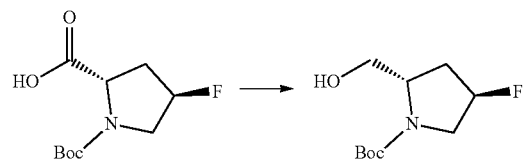 [SMILES: CC(C)(C)OC(=O)N1C[C@H](F)C[C@H]1C(=O)O ; CC(C)(C)OC(=O)N1C[C@H](F)C[C@H]1CO]

Under nitrogen, to a solution (2S,4R)-1-(tert-butoxycarbonyl)-4-fluoropyrrolidine-2-carboxylic acid (60.0 g, 257 mmol) in tetrahydrofuran (1000 mL) was added LiAlH₄ (19.6 g, 515 mmol) at 0° C. The reaction mixture was stirred at room temperature for 1 h, and then stirred at 60° C. for 2 h. The reaction mixture was cooled over ice bath and water (20 mL) was slowly added to quench the reaction, followed 20% aqueous NaOH solution (20 mL) and 20 mL water. The solids were filtered off and filtrate was concentrated under vacuum. The residue was redissolved in DCM, dried over anhydrous Na₂SO₄ and concentrated under vacuum. The residue was purified by flash chromatography on silica gel (gradient: 0%-15% MeOH in DCM (0.1% TEA)) to yield 12.4 g (36% yield) of the title compound as a yellow oil. LC-MS: (ESI, m/z): [M+H]⁺=134. ¹H NMR (300 MHz, DMSO-d4, ppm) δ 5.25-4.97 (m, 1H), 4.44 (dd, J=6.0, 5.0 Hz, 1H), 3.50-3.22 (m, 3H), 2.57-2.50 (m, 1H), 2.46-2.31 (m, 1H), 2.30 (s, 3H), 2.07-1.87 (m, 1H), 1.87-1.60 (m, 1H).

Intermediate 36: (R)-(2-Methylenetetrahydro-1H-pyrrolizin-7a(5H)-yl)methanol and (S)-(2-Methylenetetrahydro-1H-pyrrolizin-7a(5H)-yl)methanol

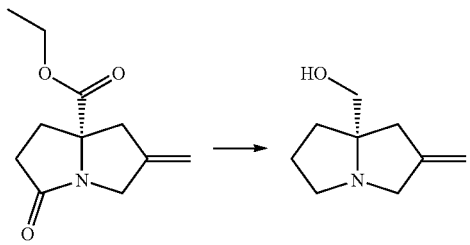

Under nitrogen, to a solution of ethyl (S)-2-methylene-5-oxotetrahydro-1H-pyrrolizine-7a(5H)-carboxylate (110 mg, 0.510 mmol, intermediate 33, step 1) in tetrahydrofuran (5 mL) was added LiAlH₄ (1.1 mL, 1M in THF) at 0° C. The mixture was stirred for 0.5 hours at 70° C. The mixture was quenched with Na₂SO₄·10H₂O and filtered. The solvent was removed by blowing nitrogen (low boiling point for the product) to afford the title compound (62.8 mg, crude) which was used for the next step without further purification. LC-MS: (ESI, m/z): [M+H]⁺=154.

Intermediate 37: 4'-((((2R,7aS)-7a-(Hydroxymethyl)hexahydro-1H-pyrrolizin-2-yl)oxy)methyl)-[1,1'-biphenyl]-2-carbonitrile

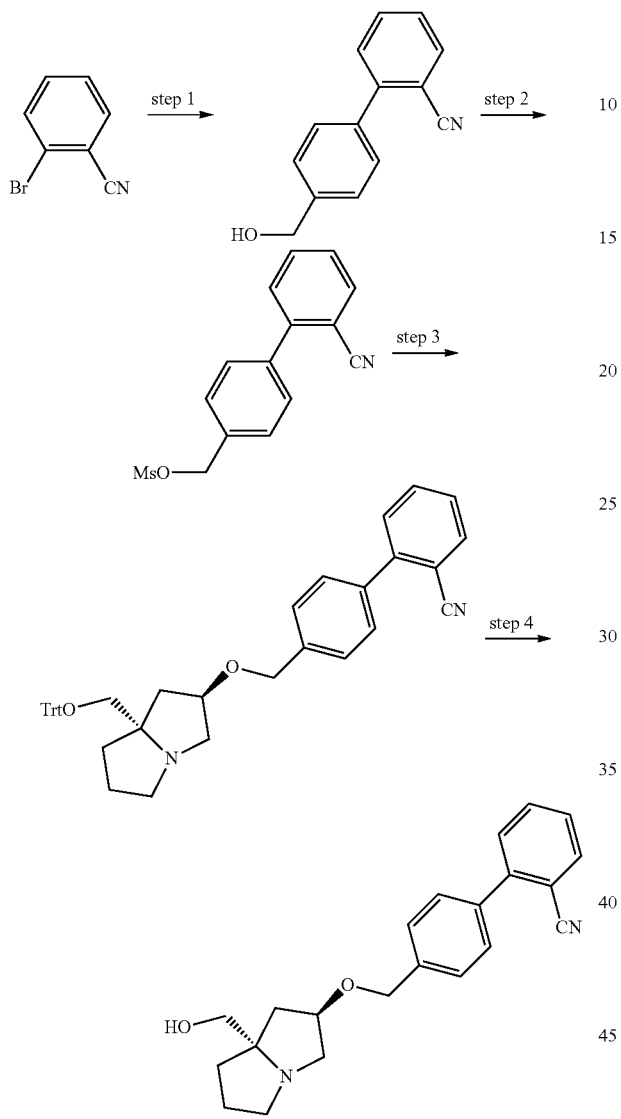

Step 1: 4'-(Hydroxymethyl)-[1,1'-biphenyl]-2-carbonitrile

Under nitrogen, a solution of 2-bromobenzonitrile (1.25 g, 6.87 mmol), Pd(PPh$_3$)$_4$ (793 mg, 0.690 mmol), 4-(hydroxymethyl)phenylboronic acid (1.15 g, 7.55 mmol), K$_2$CO$_3$ (1.90 g, 13.8 mmol) and water (5 mL) in 1,2-dimethoxyethane (50 mL) was stirred for 12 hours at 100° C. The reaction mixture was cooled to room temperature, diluted with water and extracted with EtOAc. The combined organic layers were dried over anhydrous sodium sulfate and concentrated under vacuum. The residue was purified by flash chromatography on silica gel (gradient: 0-30% EtOAc/petroleum ether) to afford the title compound (1.26 g, 87.7% yield) as a yellow solid. $^1$H NMR (300 MHz, DMSO-d$_6$) δ 8.00-7.90 (m, 1H), 7.85-7.75 (m, 1H), 7.69-7.51 (m, 6H), 5.75 (s, 1H), 4.69 (s, 2H).

Step 2: (2'-Cyano-[1,1'-biphenyl]-4-yl)methyl methanesulfonate

To a solution of 2-[4-(hydroxymethyl)phenyl]benzonitrile (235 mg, 1.12 mmol)] and N,N-diisopropylethylamine (0.58 mL, 3.36 mmol) in dichloromethane (10 mL) was added methanesulfonicanhydride (254 mg, 1.46 mmol) at 0° C. under nitrogen. The resulting solution was stirred for 2 h at room temperature, diluted with CH$_2$Cl$_2$ and washed with brine. The organic layer was dried over anhydrous sodium sulfate and concentrated under vacuum to afford the title compound (320 mg, crude) as a yellow oil which was used for next step without further purification. LC-MS: (ESI, m/z): [M+Na]$^+$=310.

Step 3: 4'-((((2R,7aS)-7a-((Trityloxy)methyl)hexahydro-1H-pyrrolizin-2-yl)oxy)methyl)-[1,1'-biphenyl]-2-carbonitrile Under nitrogen, to a solution of (2R,8S)-8-(trityloxymethyl)-1,2,3,5,6,7-hexahydropyrrolizin-2-ol (448 mg, 1.12 mmol) in tetrahydrofuran (4 mL) was added NaH (269 mg, 6.73 mmol, 60% in mineral oil) at 0° C. The resulting solution was stirred for 0.5 h at room temperature. Then [4-(2-cyanophenyl)phenyl]methyl methanesulfonate (322 mg, 1.12 mmol) in tetrahydrofuran (4 mL) was added at room temperature and stirred at 50° C. for 12 hours. The reaction was quenched with saturated NH$_4$Cl solution (20 mL) and extracted with EtOAc (100 mL×3). The combined organic layers were dried over anhydrous sodium sulfate and concentrated under vacuum. The residue was purified by flash chromatography on silica gel (gradient: 0-30% EtOAc/petroleum ether) to afford (440 mg, 66.5% yield) of the title compound as a yellow oil. LC-MS: (ESI, m/z): [M+H]$^+$=591.

Step 4: 4'-((((2R,7aS)-7a-(Hydroxymethyl)hexahydro-1H-pyrrolizin-2-yl)oxy)methyl)-[1,1'-biphenyl]-2-carbonitrile A solution of 4'-((((2R,7aS)-7a-((trityloxy)methyl)hexahydro-1H-pyrrolizin-2-yl)oxy)methyl)-[1,1'-biphenyl]-2-carbonitrile (440 mg, 0.740 mmol) in 2,2,2-trifluoroacetic acid (5 mL) was stirred for 1 h at room temperature, then concentrated under vacuum. The crude product was purified by reverse phase chromatography (gradient: 0-60% acetonitrile in water (0.05% TFA)) to afford the title compound (220 mg, 84.8% yield) as a yellow oil. LC-MS: (ESI, m/z): [M+H]$^+$=349.

Intermediate 38: tert-Butyl 5-(hydroxymethyl)-1,4-diazepane-1-carboxylate

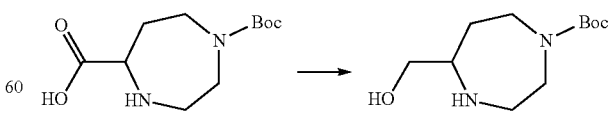

A solution of 1-tert-butoxycarbonyl-1,4-diazepane-5-carboxylic acid (200 mg, 0.820 mmol) and BH$_3$THF (4.91 mL, 4.91 mmol, 1 M in THF) in THF (5 mL) was stirred at 40° C. for 18 hours. The reaction system was quenched with MeOH and concentrated under vacuum to afford the title compound 130 mg (crude) as a yellow oil which was used for next step without further purification. LC-MS: (ESI, m/z): [M+H]$^+$=231.

Intermediate 39: tert-Butyl (1R,2S,5R)-2-(hydroxymethyl)-3,6-diazabicyclo[3.2.2]nonane-6-carboxylate

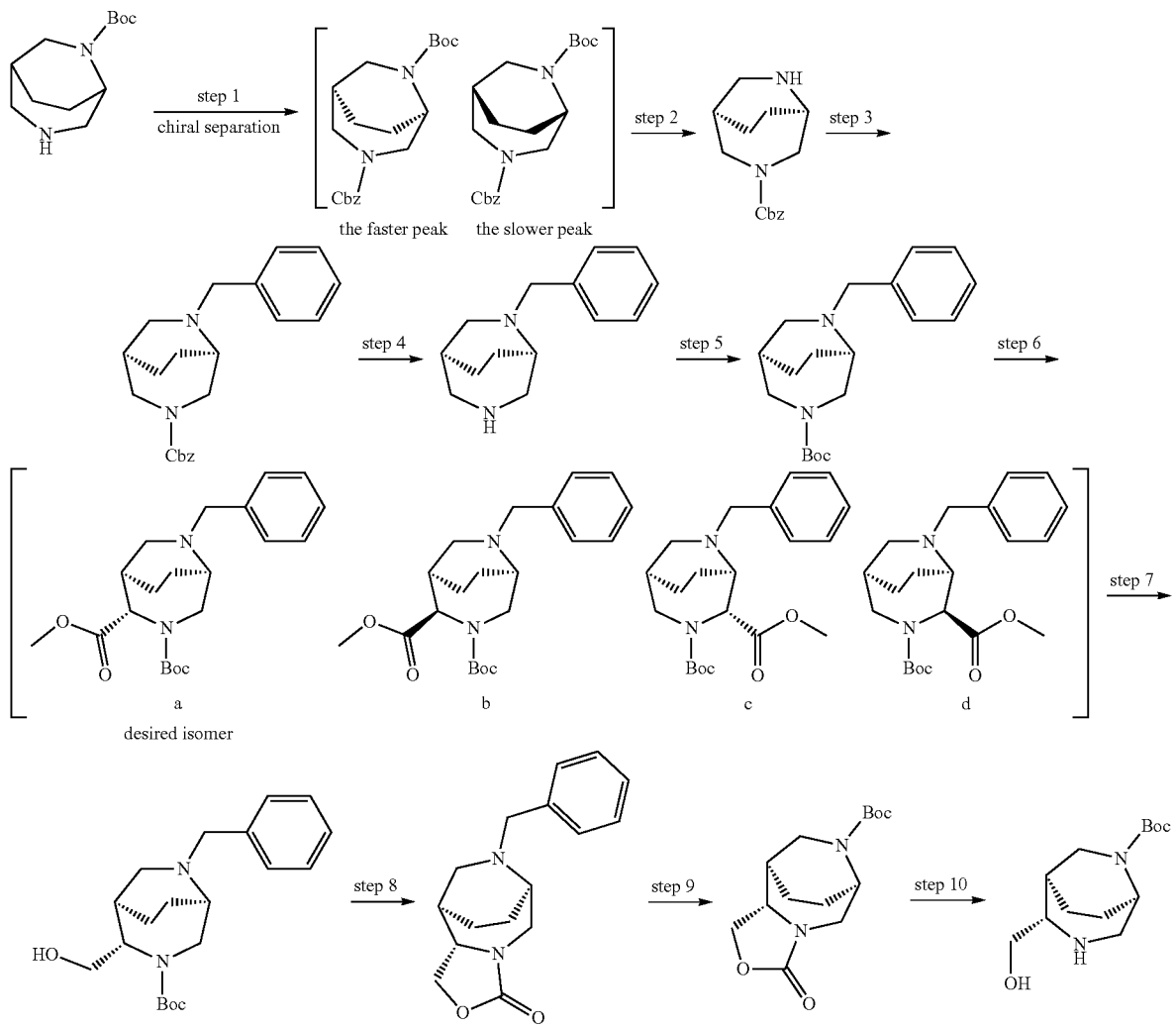

Step 1: 3-Benzyl 6-(tert-butyl) (1S,5R)-3,6-diazabicyclo[3.2.2]nonane-3,6-dicarboxylate Under nitrogen, a solution of tert-butyl 3,6-diazabicyclo[3.2.2]nonane-6-carboxylate (500 mg, 2.21 mmol), CbzCl (492 mg, 2.88 mmol) and DIPEA (1.42 g, 11.1 mmol) in dichloromethane (10 mL) was stirred at room temperature for 1 h. The reaction mixture was diluted with DCM, washed with water. The organic layer was dried over anhydrous sodium sulfate and concentrated under vacuum. The residue was purified by flash chromatography on silica gel (gradient: 0-100% EtOAc/petroleum ether) to afford 800 mg of the title compound as a colorless oil. The two enantiomers were separated by Prep-SFC with the following conditions: (Column: CHIRALPAK IG, 3*25 cm, 5 μm; Mobile Phase A: CO$_2$, Mobile Phase B: IPA(0.5% 2M NH$_3$—MeOH); Flow rate: 70 mL/min; Gradient: 30% B; Column Temperature: 35° C.; Back Pressure: 100 bar; 215 nm; RT1:6.86; RT2: 7.89; Injection Volume: 1.5 ml; Number Of Runs: 20) to yield 330 mg of faster peak and 340 mg slower peak as a white oil. The faster peak is the desired isomer. LC-MS: (ESI, m/z): [M+H]$^+$=361.

Step 2: Benzyl (1R,5R)-3,6-diazabicyclo[3.2.2]nonane-3-carboxylate

A solution of 3-benzyl 6-(tert-butyl) (1S,5R)-3,6-diazabicyclo[3.2.2]nonane-3,6-dicarboxylate (10.0 g, 27.7 mmol) in dichloromethane (60 mL) and 4 M HCl/dioxane (20 mL) was stirred at room temperature for 2 h. Then the mixture was concentrated under vacuum to yield 11.2 g (crude) of the title compound as a yellow solid which was used for next step without further purification. LC-MS: (ESI, m/z): [M+H]⁺=261.

Step 3: Benzyl (1R,5R)-6-benzyl-3,6-diazabicyclo[3.2.2]nonane-3-carboxylate

A solution of benzyl (1R,5R)-3,6-diazabicyclo[3.2.2]nonane-3-carboxylate (11.4 g, 43.7 mmol), benzyl bromide (8.99 g, 52.5 mmol) and DIPEA (11.3 g, 87.5 mmol) in N,N-dimethylformamide (50 mL) was stirred at 80° C. for 3 hours. The reaction mixture was partitioned between EtOAc and water. The organic layers were dried over anhydrous $Na_2SO_4$ and concentrated under vacuum. The residue was purified by flash chromatography on silica gel (gradient: 0-40% EtOAc in petroleum ether) to afford 8.30 g of the title compound as a yellow oil. LC-MS: (ESI, m/z): [M+H]⁺=351

Step 4: (1S,5R)-6-Benzyl-3,6-diazabicyclo[3.2.2]nonane (2,2,2-trifluoroacetic acid salt)

A solution of benzyl (1R,5R)-6-benzyl-3,6-diazabicyclo[3.2.2]nonane-3-carboxylate (8.30 g, 23.6 mmol) in TFA (60 mL) was stirred at 70° C. for 2 hours, then concentrated under vacuum to afford 5.80 g (crude) of the title compound as a yellow oil which was used for the next step without further purification. LC-MS: (ESI, m/z): [M+H]⁺=217.

Step 5: tert-Butyl (1R,5R)-6-benzyl-3,6-diazabicyclo[3.2.2]nonane-3-carboxylate

A solution of (1S,5R)-6-benzyl-3,6-diazabicyclo[3.2.2]nonane (2,2,2-trifluoroacetic acid salt) (5.80 g, crude), $Boc_2O$ (8.60 g, 39.4 mmol) and DIPEA (10.3 g, 79.8 mmol) in dichloromethane (120 mL) was stirred at room temperature for 2 h, then concentrated under vacuum. The residue was purified by reverse phase chromatography (gradient: 0-100% acetonitrile in water (0.05% $NH_4HCO_3$)) to afford 6.30 g of the title compound as a yellow oil. LC-MS: (ESI, m/z): [M+H]⁺=317.

Step 6: 3-(tert-Butyl) 2-methyl (1R,2S,5R)-6-benzyl-3,6-diazabicyclo[3.2.2]nonane-2,3-dicarboxylate Under nitrogen, to a solution of tert-butyl (1R,5R)-6-benzyl-3,6-diazabicyclo[3.2.2]nonane-3-carboxylate (6.09 g, 19.2 mmol) and TMEDA (2.72 g, 23.4 mmol) in diethyl ether (46 mL) was added s-BuLi (18.8 mL, 1.3 M in hexanes) at −78° C. The resulting solution was stirred at −78° C. for 1.5 h. Then methyl chloroformate (1.77 mL, 22.8 mmol) in diethyl ether (4.5 mL) was added and stirred at room temperature for 2 hours. The reaction was quenched with saturated $NaHCO_3$ solution and extracted with EtOAc. The combined organic layers were dried over anhydrous $Na_2SO_4$ and concentrated under vacuum. The residue was purified by flash chromatography on silica gel (gradient: 0-50% EtOAc in petroleum ether) to yield two fractions: faster peak: 2.6 g (undesired regioisomer) and slower peak: 1.50 g (desired isomer, containing trace of endo isomers). LC-MS: (ESI, m/z): [M+H]⁺=375.

Step 7: tert-Butyl (1R,2S,5R)-6-benzyl-2-(hydroxymethyl)-3,6-diazabicyclo[3.2.2]nonane-3-carboxylate Under nitrogen, to a solution of 3-(tert-butyl) 2-methyl (1R,2S,5R)-6-benzyl-3,6-diazabicyclo[3.2.2]nonane-2,3-dicarboxylate (580 mg, 1.54 mmol, slower peak in the previous step) was added $LiAlH_4$ (3.2 mL, 1 M in THF) at 0° C. The resulting solution was stirred at 0° C. for 2 h and quenched with $Na_2SO_4·10H_2O$. The solid was filtered off and the filtrate was concentrated under reduced pressure. The residue was purified by flash chromatography on silica gel (gradient: 0-100% EtOAc in petroleum ether) to yield 520 mg of the title compound as a yellow oil. LC-MS: (ESI, m/z): [M+H]⁺=347. ¹H NMR (400 MHz, DMSO-$d_6$) δ 7.37-7.16 (m, 5H), 4.59 (d, J=42.8 Hz, 1H), 4.39-4.19 (m, 2H), 3.74-3.56 (m, 2H), 3.46 (dt, J=28.9, 10.3 Hz, 2H), 2.84 (s, 1H), 2.78-2.61 (m, 3H), 2.21 (s, 1H), 1.89 (dq, J=29.0, 15.0, 13.0 Hz, 2H), 1.46 (s, 11H).

Step 8: (6R,9R,9aS)-11-Benzylhexahydro-1H,3H-6,9-(epiminomethano)oxazolo[3,4-a]azepin-3-one Under nitrogen, to a solution of tert-butyl (1R,2S,5R)-6-benzyl-2-(hydroxymethyl)-3,6-diazabicyclo[3.2.2]nonane-3-carboxylate (480 mg, 1.39 mmol) in tetrahydrofuran (15 mL) was added NaH (112 mg, 2.82 mmol, 60% in mineral oil) at 0° C. The reaction was stirred at room temperature for 12 h. Aqueous $NH_4Cl$ was added to quench the reaction. Then the mixture was concentrated under vacuum. The residue was purified by flash chromatography on silica gel (gradient: 0-60% EtOAc in petroleum ether) to yield 360 mg of the title compound as a white solid. LC-MS: (ESI, m/z): [M+H]⁺=273.

Step 9: tert-Butyl (6R,9R,9aS)-3-oxohexahydro-1H,3H-6,9-(epiminomethano)oxazolo[3,4-a]azepine-11-carboxylate Under $H_2$ (3 atm), a mixture of (6R,9R,9aS)-11-benzylhexahydro-1H,3H-6,9-(epiminomethano)oxazolo[3,4-a]azepin-3-one (330 mg, 1.20 mmol), 10% Pd/C (99.0 mg, dry) and $Boc_2O$ (530 mg, 2.45 mmol) in methyl alcohol (70 mL) was stirred at room temperature for 1 hour. The catalyst was filtered off and the filtrate was concentrated under reduced pressure. The residue was purified by flash chromatography (gradient: 0-100% EtOAc in petroleum ether) to yield 350 mg of the title compound as a white solid. LC-MS: (ESI, m/z): [M+H]⁺=283.

Step 10: tert-Butyl (1R,2S,5R)-2-(hydroxymethyl)-3,6-diazabicyclo[3.2.2]nonane-6-carboxylate A solution of tert-butyl (6R,9R,9aS)-3-oxohexahydro-1H,3H-6,9-(epiminomethano)oxazolo[3,4-a]azepine-11-carboxylate (275 mg, 0.972 mmol) and NaOH (585 mg, 14.6 mmol) in ethanol (9 mL) and water (3 mL) was stirred at 80° C. for 12 hours. Then the mixture was concentrated under vacuum. The residue was purified by reverse phase flash chromatography on pre-packed C18 column (gradient: 0-100% $CH_3CN$ in water (0.05% $NH_4HCO_3$)) to yield 250 mg of the title compound as a white solid. LC-MS: (ESI, m/z): [M+H]⁺=257. ¹H NMR (300 MHz, DMSO-$d_6$) δ 4.60 (br, 1H), 3.91-4.08 (m, 1H), 3.40-3.01 (m, 4H), 3.00-2.90 (m, 1H), 2.60-2.45 (m, 2H), 2.00 (br, 1H), 1.95-1.85 (m, 1H), 1.80-1.55 (m, 3H), 1.35 (s, 9H), 1.30-1.20 (m, 1H).

Intermediate 40: 1-(Tributylstannyl)isoquinolin-3-amine

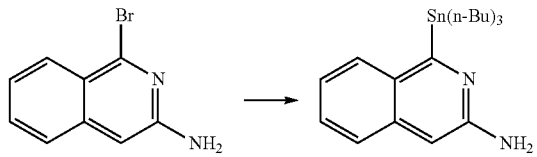

Under nitrogen, a solution of 1-bromoisoquinolin-3-amine (100 mg, 0.450 mmol), Sn$_2$(n-Bu)$_6$ (286 mg, 0.500 mmol), Pd$_2$(dba)$_3$ (41.2 mg, 0.0500 mmol), PCy$_3$ (25.3 mg, 0.0900 mmol) and LiCl (94.6 mg, 2.25 mmol) in 1,4-dioxane (1.5 mL) was stirred at 115° C. for 2 hours. Then the mixture was concentrated under vacuum. The residue was purified by flash chromatography on neutral alumina with EtOAc/petroleum ether (0-15%) to afford the title compound (107 mg, 54.8% yield) as a yellow oil. LC-MS: (ESI, m/z): [M+H]$^+$=435.

Intermediate 41: 2-(8-Chloronaphthalen-1-yl)-4,4,5,5-tetramethyl-1,3,2-dioxaborolane

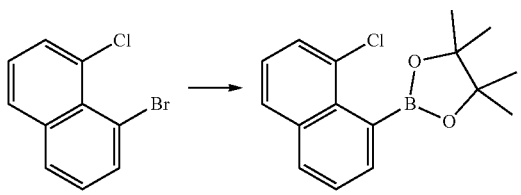 [SMILES: Clc1cccc2cccc(Br)c12 ; CC1(C)OB(c2cccc3cccc(Cl)c23)OC1(C)C]

Under nitrogen, a solution of 1-bromo-8-chloronaphthalene (2.99 g, 12.4 mmol), Pin$_2$B$_2$ (4.71 g, 18.5 mmol), PdCl$_2$(dppf) (908 mg, 1.24 mmol) and KOAc (2.42 g, 24.7 mmol) in DMF (35 mL) was stirred at 80° C. overnight. The reaction mixture was diluted with EtOAc (100 mL), washed with water (100 mL*4). The organic layer was dried over anhydrous sodium sulfate and concentrated under vacuum. The residue was purified by flash chromatography on silica gel eluting with EtOAc/petroleum ether (0-20%) to the title compound (3.01 g, 84.2% yield) as a yellow solid. $^1$H-NMR (300 MHz, DMSO-d$_6$, ppm) δ 8.04 (dd, J=7.5, 2.0 Hz, 1H), 7.96 (dd, J=8.2, 1.3 Hz, 1H), 7.70 (dd, J=7.5, 1.3 Hz, 1H), 7.65-7.58 (m, 2H), 7.58-7.48 (m, 1H), 1.36 (s, 12H)

Intermediate 42: N,N-Bis(4-methoxybenzyl)-4-methyl-6-(tributylstannyl)-5-(trifluoromethyl)pyridin-2-amine

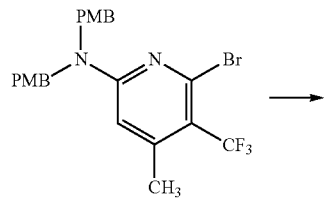

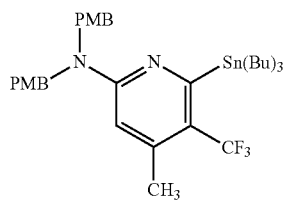

Under nitrogen, a solution of 6-bromo-N,N-bis(4-methoxybenzyl)-4-methyl-5-(trifluoromethyl)pyridin-2-amine (1.51 g, 3.05 mmol), Sn$_2$(n-Bu)$_6$ (2.65 mg, 4.57 mmol), Pd$_2$(dba)$_3$ (279 mg, 0.300 mmol), PCy$_3$ (170 mg, 0.610 mmol) and LiCl (641 mg, 15.3 mmol) in 1,4-dioxane (15 mL) was stirred for 2 h at 110° C. The resulting reaction mixture was cooled to room temperature, diluted with water (35 mL) and extracted with EtOAc. The combined organic layers were dried over anhydrous sodium sulfate and concentrated under vacuum. The residue was purified by flash chromatography on neutral Al$_2$O$_3$ eluting with EtOAc/petroleum ether (0-8%) to afford the title compound (1.01 g, 46.8% yield) as a colorless syrup. The product is not too stable. It is not suitable for long term storage. LC-MS: (ESI, m/z): [M+H]$^+$=707.

Intermediate 43: ((2-Fluoro-6-(methoxymethoxy)-8-(4,4,5,5-tetramethyl-1,3,2-dioxaborolan-2-yl)naphthalen-1-yl)ethynyl)triisopropylsilane

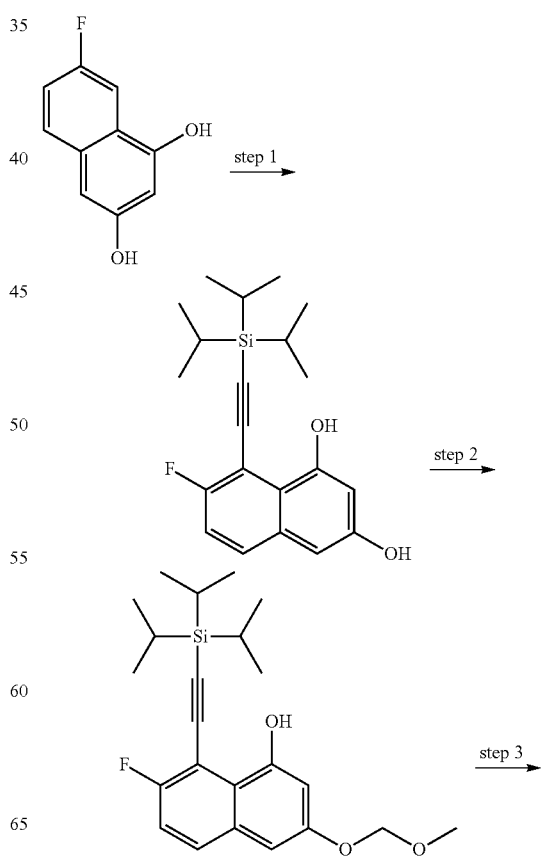

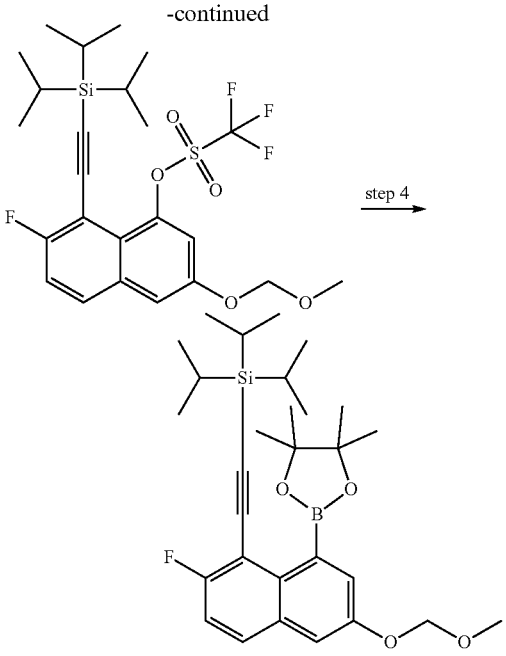

Step 1: 7-Fluoro-8-((triisopropylsilyl)ethynyl)naphthalene-1,3-diol

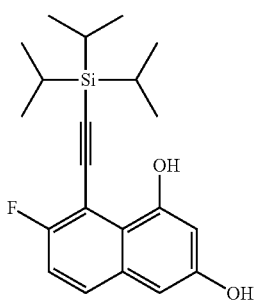 [SMILES: CC(C)[Si](C#Cc1c(F)ccc2cc(O)cc(O)c12)(C(C)C)C(C)C]

Under nitrogen, a solution of 7-fluoronaphthalene-1,3-diol (10.1 g, 56.7 mmol), 2-bromoethynyl(triisopropyl)silane (17.8 g, 68.1 mmol), dichloro(p-cymene)ruthenium (II) dimer (3.50 g, 5.72 mmol) and KOAc (11.2 g, 114 mmol) in 1,4-dioxane (110 mL) was stirred overnight at 110° C., then concentrated under vacuum. The residue was purified by flash chromatography on silica gel eluting with EtOAc/petroleum ether (0-25%) to afford the title compound (16.1 g, 79.2% yield) as a dark brown solid. LC-MS: (ESI, m/z): $[M+H]^+$=359.

Step 2: 7-Fluoro-3-(methoxymethoxy)-8-((triisopropylsilyl)ethynyl)naphthalen-1-ol To a solution of 7-fluoro-8-((triisopropylsilyl)ethynyl)naphthalene-1,3-diol (16.1 g, 44.9 mmol) and DIPEA (17.5 g, 136 mmol) in DCM (160 mL) was added MOMBr (6.70 g, 54.0 mmol) at 0° C. The mixture was stirred at 0° C. for 30 min and concentrated under vacuum. The residue was purified by flash chromatography on silica gel eluting with EtOAc/petroleum ether (0-15%) to afford the title compound (9.90 g, 54.8% yield) as a yellow solid. LC-MS: (ESI, m/z): $[M+H]^+$=403. $^1$H-NMR (300 MHz, CDCl$_3$, ppm) δ 9.01 (s, 1H), 7.55 (dd, J=9.1, 5.7 Hz, 1H), 7.07 (t, J=8.8 Hz, 1H), 6.86 (d, J=2.4 Hz, 1H), 6.70 (dd, J=2.5, 0.9 Hz, 1H), 5.14 (s, 2H), 3.40 (s, 3H), 1.18-0.98 (m, 21H).

Step 3: 7-Fluoro-3-(methoxymethoxy)-8-((triisopropylsilyl)ethynyl)naphthalen-1-yl trifluoromethanesulfonate Under nitrogen, to a solution of 7-fluoro-3-(methoxymethoxy)-8-((triisopropylsilyl)ethynyl)naphthalen-1-ol (5.01 g, 12.4 mmol) and N-(4-chlorophenyl)-1,1,1-trifluoro-N-((trifluoromethyl)sulfonyl)methanesulfonamide (5.85 g, 14.9 mmol) in THF (50 mL) was added NaH (547 mg, 13.7 mmol, 60% in mineral oil) at 0° C. The resulting reaction mixture was stirred at room temperature for 1 h, diluted with water (30 mL) and extracted with EtOAc (150 mL). The combined organic layers were washed with brine, dried over anhydrous sodium sulfate and concentrated under vacuum. The residue was purified by flash chromatography on silica gel (gradient: 0%-8% EtOAc/petroleum ether) to afford 5.11 g (76.8% yield) of the title compound as a yellow oil. $^1$H-NMR (300 MHz, CDCl$_3$, ppm) δ 7.81-7.65 (m, 1H), 7.49-7.30 (m, 3H), 5.30 (s, 2H), 3.54 (s, 3H), 1.35-1.01 (m, 21H).

Step 4: ((2-Fluoro-6-(methoxymethoxy)-8-(4,4,5,5-tetramethyl-1,3,2-dioxaborolan-2-yl)naphthalen-1-yl)ethynyl)triisopropylsilane Under nitrogen, a solution of 7-fluoro-3-(methoxymethoxy)-8-((triisopropylsilyl)ethynyl)naphthalen-1-yl trifluoromethanesulfonate (1.51 g, 2.81 mmol), Pin$_2$B$_2$ (1.43 g, 5.62 mmol), Pd(dppf)Cl$_2$ (216 mg, 0.280 mmol) and KOAc (826 mg, 8.43 mmol) in toluene (12 mL) was stirred overnight at 110° C. The resulting reaction mixture was cooled to room temperature and the solid was filtered off. The filtrate was concentrated under vacuum. The residue was purified by flash chromatography on silica gel (gradient: 0%-10% EtOAc/petroleum ether) to afford 981 mg (68.2% yield) of the title compound as a yellow solid. LC-MS: (ESI, m/z): $[M+H]^+$=513. $^1$H-NMR (300 MHz, CDCl$_3$, ppm) δ 7.66 (dd, J=9.0, 5.6 Hz, 1H), 7.52-7.48 (m, 1H), 7.40-7.35 (m, 1H), 7.22 (t, J=8.8 Hz, 1H), 5.27 (s, 2H), 3.50 (s, 3H), 1.43 (s, 12H), 1.19-1.12 (m, 21H).

Intermediate 44: 2-fluoro-N,N-bis(4-methoxybenzyl)-3-(4,4,5,5-tetramethyl-1,3,2-dioxaborolan-2-yl)aniline

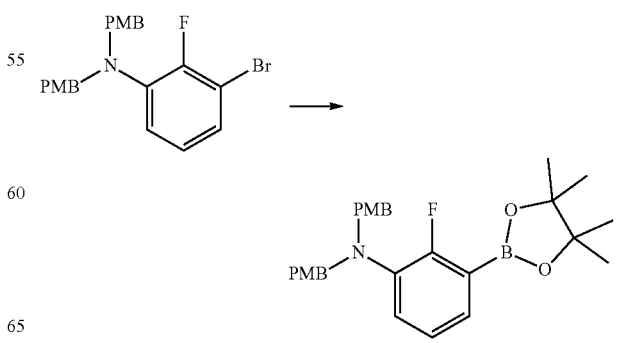

Under nitrogen, a solution of 3-bromo-2-fluoro-N,N-bis[(4-methoxyphenyl)methyl]aniline (12.6 g, 29.3 mmol), Pin$_2$B$_2$ (22.4 g, 88.1 mmol), PdCl$_2$(dppf) (2.15 g, 2.94 mmol) and KOAc (8.64 g, 88.1 mmol) in 1,4-dioxane (20 mL) was stirred at 80° C. for 2 hours. The resulting solution was diluted with water and extracted with petroleum ether. The combined organic layers were dried over anhydrous sodium sulfate and concentrated under vacuum. The residue was purified by flash chromatography on silica gel (gradient: 0%-10% EtOAc/petroleum ether) to afford the title compound (10.4 g, 74.4% yield) as a yellow oil. LC-MS: (ESI, m/z): [M+H]$^+$=478. Z Intermediate 45: 2,4,7-Trichloro-8-fluoropyrido[4,3-d]pyrimidine

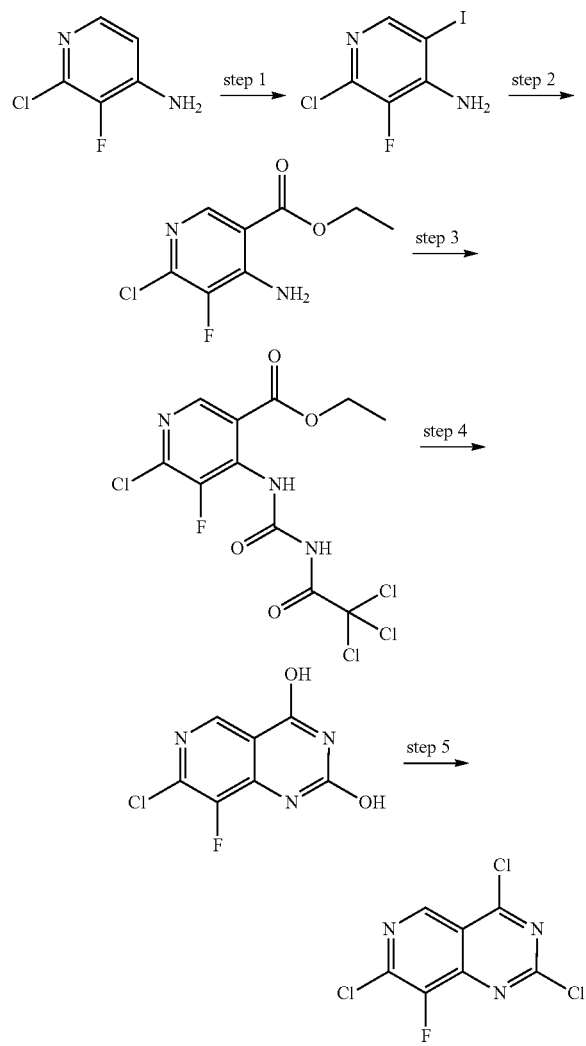

Step 1: 2-Chloro-3-fluoro-5-iodopyridin-4-amine

To a solution of 2-chloro-3-fluoropyridin-4-amine (20.0 g, 136 mmol) and NIS (37.0 g, 164 mmol) in CH$_3$CN (260 mL) was added p-toluene sulfonic acid monohydrate (1.30 g, 6.83 mmol). The solution was stirred at 70° C. for 16 hours. The solvent was evaporated under vacuum. The residue was diluted with EtOAc (600 mL), washed with saturated Na$_2$CO$_3$ solution (2×300 mL), saturated Na$_2$SO$_3$ solution (300 mL) and brine (300 mL). The organic layers were concentrated under vacuum. The residue was purified by flash chromatography on silica gel eluting with EtOAc/petroleum ether (0-35%) to afford 37.0 g (99.5% yield) of the title compound as a white solid. LC-MS: (ESI, m/z): [M+H]$^+$=273. $^1$H-NMR: (400 MHz, methanol-d$_4$, ppm) δ 8.08 (s, 1H).

Step 2: Ethyl 4-amino-6-chloro-5-fluoronicotinate

To a solution of 2-chloro-3-fluoro-5-iodopyridin-4-amine (15.0 g, 55.1 mmol) in EtOH (260 mL) was added Pd(PPh$_3$)$_2$Cl$_2$ (3.87 g, 5.51 mmol) and Et$_3$N (20.1 g, 199 mmol) at room temperature. The mixture was stirred under CO (2 atm) for 15 hours at 80° C., then concentrated under vacuum. The residue was purified by flash chromatography on silica gel eluting with EtOAc/DCM (0-36%) to afford 13.6 g (crude) of the title compound as a yellow solid. LC-MS: (ESI, m/z): [M+H]$^+$=219. $^1$H-NMR: (400 MHz, DMSO-d$_6$, ppm) δ 8.37 (s, 1H), 7.59 (br, 2H), 4.32 (q, J=7.2 Hz, 2H), 1.32 (t, J=7.2 Hz, 3H).

Step 3: Ethyl 6-chloro-5-fluoro-4-(3-(2,2,2-trichloroacetyl)ureido)nicotinate

Under nitrogen, to a solution of ethyl 4-amino-6-chloro-5-fluoronicotinate (12.6 g, 57.5 mmol) in THF (150 mL) was added trichloroacetyl isocyanate (10.3 mL, 86.3 mmol) at 25° C. The resulting solution was stirred for 20 min at 25° C. The mixture was concentrated under vacuum. The residue was washed with MTBE (250 mL). The solid was collected and dried to afford 17.1 g (crude) of the title compound as a pale pink solid. LC-MS: (ESI, m/z): [M+H]$^+$=406.

Step 4: 7-Chloro-8-fluoropyrido[4,3-d]pyrimidine-2,4-diol

To a solution of ethyl 6-chloro-5-fluoro-4-(3-(2,2,2-trichloroacetyl)ureido)nicotinate (16.1 g, 39.6 mmol) in MeOH (160 mL) was added ammonia MeOH solution (29 mL, 7 M). The solution was stirred at 25° C. for 1 hour, then concentrated under vacuum. The residue was washed with MTBE (200 mL) to afford 9.72 g (crude) of the title compound as a white solid. LC-MS: (ESI, m/z): [M+H]$^+$=216. $^1$H-NMR: (400 MHz, DMSO-d$_6$, ppm): δ 8.33 (br, 1H).

Step 5: 2,4,7-Trichloro-8-fluoropyrido[4,3-d]pyrimidine

Under nitrogen, a solution of 7-chloro-8-fluoropyrido[4,3-d]pyrimidine-2,4-diol (7.01 g, 32.5 mmol) and DIPEA (21.0 g, 162.8 mmol) in POCl$_3$ (70 mL) was stirred for 2 h at 100° C. The mixture was added slowly to ice water, maintaining the system at <10° C. The solids were collected by filtration and washed with water (300 mL). The solid was dried under vacuum to afford 6.20 g (crude) of the title compound as a red brown solid. LC-MS: (ESI, m/z): [M+H]$^+$=252. The crude was used for next step without further purification.

Intermediate 46: 5,7,8-Trichloropyrido[4,3-d]pyrimidin-4(3H)-one

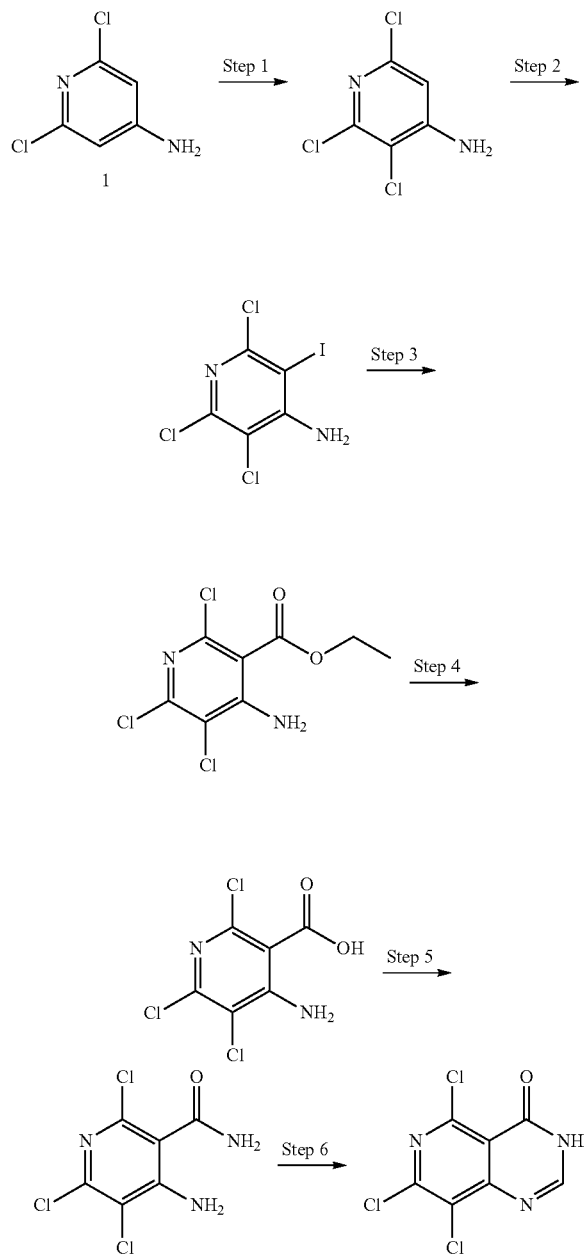

Step 1: 2,3,6-Trichloropyridin-4-amine

A solution of 2,6-dichloropyridin-4-amine (20.0 g, 123 mmol) and NCS (16.4 g, 123 mmol) in tetrahydrofuran (500 mL) was stirred at 50° C. for 24 hours. The reaction system was cooled to room temperature, diluted with water and extracted with EtOAc. The combined organic layers were evaporated under vacuum. The residual was slurried with petroleum ether:EtOAc=10:1 and filtered to afford 21 g of the title compound (crude) as a white solid. LC-MS: (ESI, m/z): $[M+H]^+=197$.

Step 2: 2,3,6-Trichloro-5-iodopyridin-4-amine

To a solution of 2,3,6-trichloropyridin-4-amine (22.0 g, 111 mmol) in ACN (200 mL) was added NIS (30 g, 134 mmol) and TsOH (2.18 g, 11 mmol) at room temperature. The solution was stirred for 2 h at 70° C. The resulting mixture was concentrated under vacuum. The residual was diluted with aqueous $Na_2HSO_3$, extracted with EtOAc. The combined organic layers were washed with aqueous $Na_2CO_3$, dried over anhydrous $Na_2SO_4$ and concentrated under vacuum. The residue was purified by silica gel column chromatography (gradient: 0%-30% EtOAc/petroleum ether) to afford 35 g (97.1% yield) of the title compound as a white solid. LC-MS: (ESI, m/z): $[M+H]^+=323$.

Step 3: Ethyl 4-amino-2,5,6-trichloronicotinate

Under carbon monoxide, a mixture of 2,3,6-trichloro-5-iodo-pyridin-4-amine (8.0 g, 24.7 mmol), $Pd(PPh_3)_2Cl_2$ (1.74 g, 2.47 mmol) and triethylamine (7.51 g, 74.2 mmol) in ethanol (80 mL) was stirred for 48 h at 80° C. The resulting mixture was concentrated under vacuum. The residue was purified by flash chromatography on silica gel (gradient: 0%-20% EtOAc/DCM) to yield 3.7 g (55.5% yield) of the title compound as a white solid. LC-MS: (ESI, m/z): $[M+H]^+=269$.

Step 4: 4-Amino-2,5,6-trichloronicotinic acid

To a solution of ethyl 4-amino-2,5,6-trichloro-pyridine-3-carboxylate (3.0 g, 11.3 mmol) in EtOH (20 mL) was added NaOH (890 mg, 22.3 mmol) and water (60 mL). The resulting mixture was stirred for 2 h at room temperature. The resulting mixture was filtered. The filtrate was acidified to pH 3 with HCl. The precipitated solids were collected by filtration and dried in oven to afford 1.5 g of the title compound (55.8% yield) as a yellow solid. LC-MS: (ESI, m/z): $[M+H]^+=241$.

Step 5: 4-Amino-2,5,6-trichloronicotinamide

A solution of 4-amino-2,5,6-trichloro-pyridine-3-carboxylic acid (300 mg, 1.24 mmol), $NH_4Cl$ (332 mg, 6.21 mmol), HATU (709 mg, 1.86 mmol) and DIPEA (1.6 g, 12.4 mmol) in N,N-dimethylacetamide (5 mL) was stirred at room temperature for 1 hour. The resulting solution was diluted with EtOAc (8 mL), washed with water. The separated organic layer was concentrated under vacuum. The residue was purified by flash chromatography on silica gel (gradient: 0%-5% MeOH/DCM) to yield 200 mg (66.9% yield) of the title compound as a white solid. LC-MS: (ESI, m/z): $[M+H]^+=240$.

Step 6: 5,7,8-Trichloropyrido[4,3-d]pyrimidin-4(3H)-one

A solution of 4-amino-2,5,6-trichloro-pyridine-3-carboxamide (200 mg, 0.83 mmol) in triethoxymethane (3 mL) was stirred at 140° C. for 5 hours. The solvent was removed under vacuum. The residue was diluted with EtOAc/DCM (1/5, 3 mL). After filtration, the solids were collected and dried under vacuum to afford the title compound (120 mg, crude) as a white solid which was used for next reaction without further purification. LC-MS: (ESI, m/z): $[M+H]^+=250$.

Intermediate 47: tert-Butyl (5S,5aS,6S,9R)-1,2-di-
chloro-5-methyl-5a,6,7,8,9,10-hexahydro-5H-4-oxa-
3,10a,11,13,14-pentaaza-6,9-methanonaphtho[1,8-
ab]heptalene-14-carboxylate

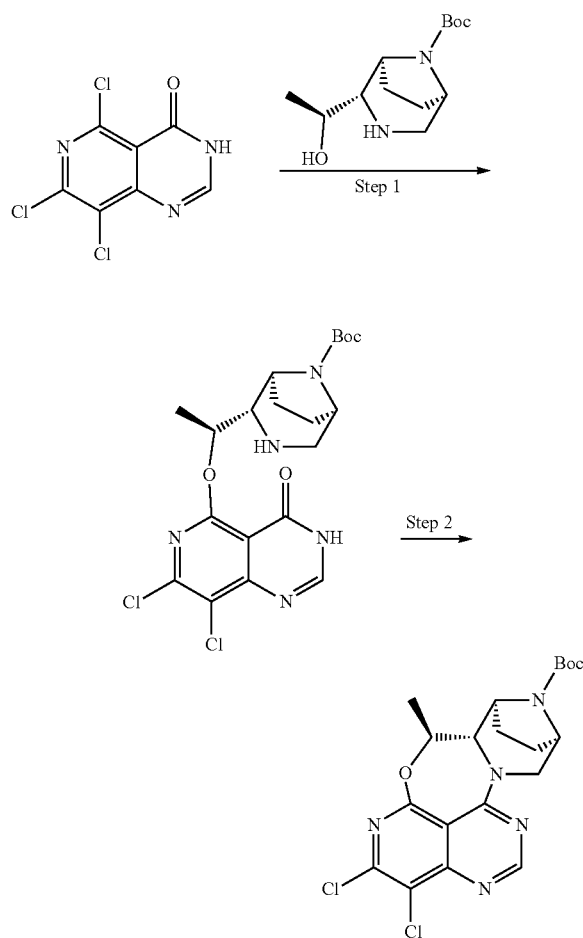

Step 1: tert-Butyl (1S,2S,5R)-2-((S)-1-((7,8-di-
chloro-4-oxo-3,4-dihydropyrido[4,3-d]pyrimidin-5-
yl)oxy)ethyl)-3,8-diazabicyclo[3.2.1]octane-8-car-
boxylate Under nitrogen, to a solution of tert-butyl rac-(1S,2S,5R)-2-[rac-(1S)-1-hydroxyethyl]-3,8-diazabicyclo[3.2.1]octane-8-carboxylate (112 mg, 0.44 mmol, Intermediate 4) in N,N-dimethylformamide (2 mL) was added NaH (69 mg, 1.74 mmol, 60% suspension in oil) at 0° C. The resulting solution was stirred at room temperature for 0.5 h. Then 5,7,8-trichloro-3H-pyrido[4,3-d]pyrimidin-4-one (120 mg, 0.480 mmol, intermediate 46) was added and the mixture was stirred at room temperature for 2 h. The reaction was quenched with water, extracted with EtOAc. The combined organic layers were dried over anhydrous sodium sulfate and concentrated under vacuum. The residue was purified by flash chromatography on silica gel (gradient: 0%-20% MeOH/DCM) to yield 155 mg (68.8% yield) of the title compound as a white solid. LC-MS: (ESI, m/z): [M+H]⁺= 470.

Step 2: tert-Butyl (5S,5aS,6S,9R)-1,2-dichloro-5-
methyl-5a,6,7,8,9,10-hexahydro-5H-4-oxa-3,10a,11,
13,14-pentaaza-6,9-methanonaphtho[1,8-ab]heptal-
ene-14-carboxylate Under nitrogen, a solution of tert-butyl rac-(1S,2S,5R)-2-[rac-(1S)-1-[(7,8-dichloro-4-oxo-3H-pyrido[4,3-d]pyrimidin-5-yl)oxy]ethyl]-3,8-diazabicyclo[3.2.1]octane-8-carboxylate (20.0 mg, 0.04 mmol), BOPCl (32.5 mg, 0.130 mmol) and DIPEA (32.9 mg, 0.260 mmol) in dichloromethane (2 mL) was stirred for 2 h at room temperature. The solvent was concentrated under vacuum. The residue was purified by flash chromatography on silica gel (gradient: 0%-10% MeOH/DCM) to afford 15 mg (78% yield) of the title compound as a white solid. LC-MS: (ESI, m/z): [M+H]⁺=452.

Intermediate 49: tert-Butyl (5aR,6S,9R)-2-chloro-1-
fluoro-4-methyl-12-(methylsulfonyl)-4,5,5a,6,7,8,9,
10-octahydro-3,4,10a,11,13,14-hexaaza-6,9-metha-
nonaphtho[1,8-ab]heptalene-14-carboxylate

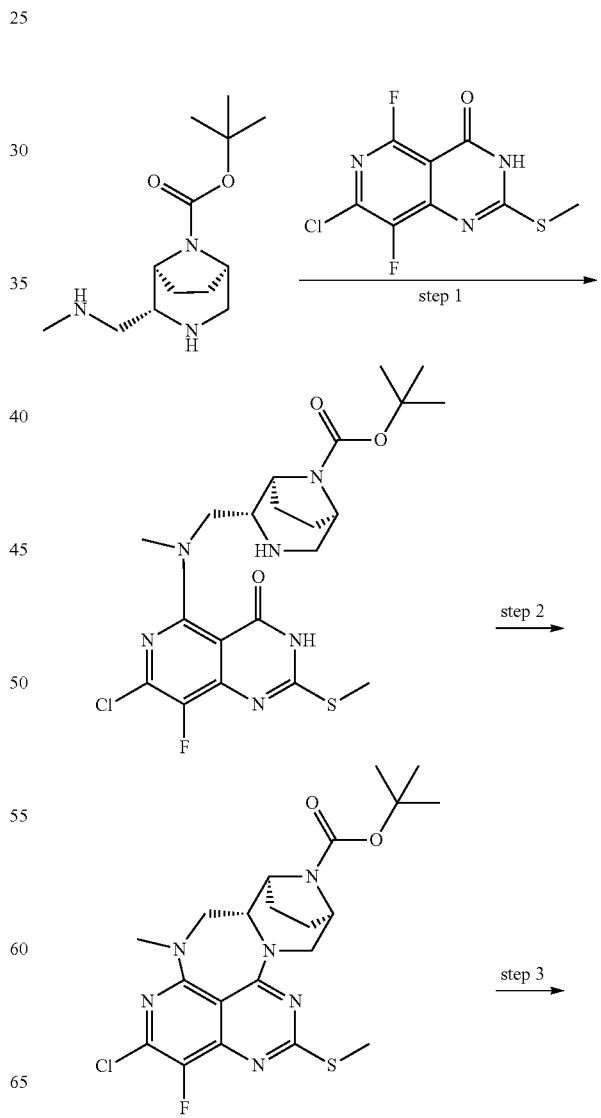

-continued

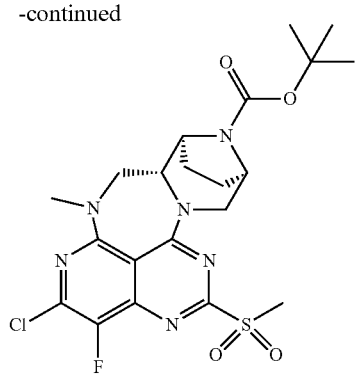

Step 1: tert-Butyl (1S,2R,5R)-2-(((7-chloro-8-fluoro-2-(methylthio)-4-oxo-3,4-dihydropyrido[4,3-d]pyrimidin-5-yl)(methyl)amino)methyl)-3,8-diazabicyclo[3.2.1]octane-8-carboxylate To a solution of tert-butyl (1R,2R,5S)-2-((methylamino)methyl)-3,8-diazabicyclo[3.2.1]octane-8-carboxylate (2.25 g, 8.81 mmol, intermediate 48) and 5,7-dichloro-8-fluoro-2-(methylthio)pyrido[4,3-d]pyrimidin-4(3H)-one (2.78 g, 9.93 mmol, intermediate 2) in N,N-dimethylacetamide (30 mL) was added DIPEA (1.71 g, 13.2 mmol) at room temperature. The solution was stirred for 1 hour at 80° C. The reaction mixture was cooled to room temperature, diluted with EtOAc and washed with water and brine. The separated organic layer was dried over anhydrous sodium sulfate and concentrated under vacuum. The residue was purified by flash chromatography on silica gel (gradient: 0-10% methanol in dichloromethane) to afford the title compound (2.16 g, 49.1% yield) as a white solid. LC-MS: (ESI, m/z): [M+H]$^+$=499. $^1$H NMR (300 MHz, CDCl$_3$, ppm) δ 4.78-4.53 (m, 1H), 4.47-4.29 (m, 1H), 4.08-3.87 (m, 1H), 3.83-3.59 (m, 2H), 3.59-3.35 (m, 2H), 2.82 (s, 3H), 2.67 (s, 3H), 2.27-1.91 (m, 5H), 1.49 (d, J=10.1 Hz, 9H).

Step 2: tert-Butyl (5aR,6S,9R)-2-chloro-1-fluoro-4-methyl-12-(methylthio)-4,5,5a,6,7,8,9,10-octahydro-3,4,10a,11,13,14-hexaaza-6,9-methanonaphtho[1,8-ab]heptalene-14-carboxylate To a solution of tert-butyl (1S,2R,5R)-2-(((7-chloro-8-fluoro-2-(methylthio)-4-oxo-3,4-dihydropyrido[4,3-d]pyrimidin-5-yl)(methyl)amino)methyl)-3,8-diazabicyclo[3.2.1]octane-8-carboxylate (2.16 g, 4.33 mmol) in dichloromethane (20 mL) were added BOPCl (4.41 g, 17.3 mmol) and DIPEA (8.39 g, 64.9 mmol) at room temperature. The solution was stirred for 3 hours at room temperature. The reaction mixture was concentrated under vacuum. The residue was purified by flash chromatography on silica gel (gradient: 0-20% EtOAc in petroleum ether) to afford the title compound (1.70 g, 81.7% yield) as a yellow solid. LC-MS: (ESI, m/z): [M+H]$^+$=481. $^1$H NMR (300 MHz, CDCl$_3$, ppm) δ 5.07-4.93 (m, 1H), 4.82-4.60 (m, 1H), 4.58-4.27 (m, 2H), 3.77-3.62 (m, 1H), 3.49 (d, J=15.4 Hz, 1H), 3.29 (s, 3H), 3.28-3.11 (m, 1H), 2.61 (s, 3H), 2.15-1.93 (m, 2H), 1.78-1.58 (m, 2H), 1.55 (s, 9H).

Step 3: tert-Butyl (5aR,6S,9R)-2-chloro-1-fluoro-4-methyl-12-(methylsulfonyl)-4,5,5a,6,7,8,9,10-octahydro-3,4,10a,11,13,14-hexaaza-6,9-methanonaphtho[1,8-ab]heptalene-14-carboxylate To a solution of tert-butyl (5aR,6S,9R)-2-chloro-1-fluoro-4-methyl-12-(methylthio)-4,5,5a,6,7,8,9,10-octahydro-3,4,10a,11,13,14-hexaaza-6,9-methanonaphtho[1,8-ab]heptalene-14-carboxylate (1.70 g, 3.53 mmol) in EtOAc (20 mL) was added m-CPBA (1.83 g, 10.6 mmol) at 0° C. The resulting solution was stirred for 3 hours at 0° C. The reaction was quenched with aqueous Na$_2$S$_2$O$_3$. The reaction mixture was diluted with water and extracted with EtOAc. The combined organic layers were dried over anhydrous sodium sulfate and concentrated under vacuum. The residue was purified by flash chromatography on silica gel (gradient: 0-60% EtOAc in petroleum ether) to afford the title compound (937 mg, 51.7% yield) as a yellow solid. LC-MS: (ESI, m/z): [M+H]$^+$=513. $^1$H NMR (300 MHz, CDCl$_3$, ppm) δ 5.07-4.93 (m, 1H), 4.82-4.60 (m, 1H), 4.58-4.27 (m, 2H), 3.77-3.62 (m, 1H), 3.49 (d, J=15.4 Hz, 1H), 3.29 (s, 3H), 3.28-3.11 (m, 1H), 2.61 (s, 3H), 2.15-1.93 (m, 2H), 1.78-1.58 (m, 2H), 1.55 (s, 9H).

Intermediate 50: (S,Z/E)-(2-(Fluoromethylene)tetrahydro-1H-pyrrolizin-7a(5H)-yl)methanol (mixture of Z/E

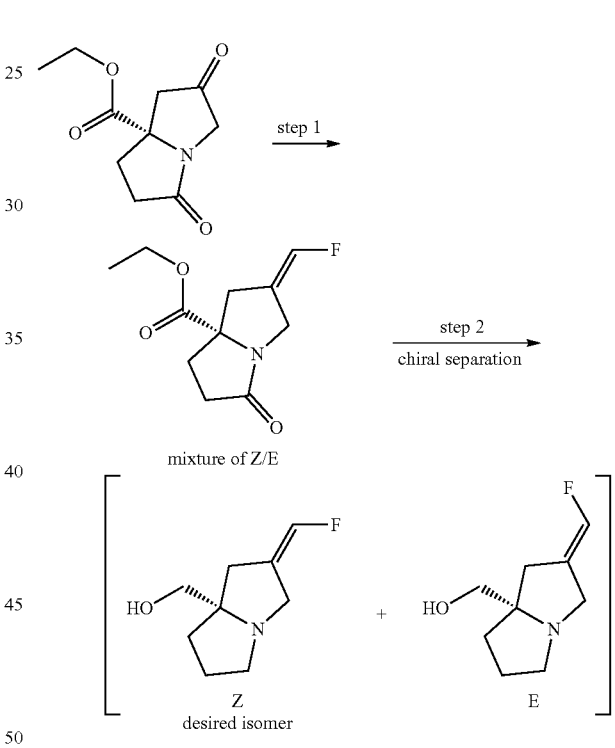

Step 1: Ethyl (S,Z/E)-2-(fluoromethylene)-5-oxotetrahydro-1H-pyrrolizine-7a(5H)-carboxylate Under N$_2$, to a solution of 2-((fluoromethyl)sulfonyl)pyridine (177 mg, 1.01 mmol) in tetrahydrofuran (10 mL) was added KHMDS (1.2 mL, 1.20 mmol) at −78° C. The reaction system was stirred 30 min at −78° C., ethyl (S)-2,5-dioxotetrahydro-1H-pyrrolizine-7a(5H)-carboxylate (200 mg, 0.950 mmol, Intermediate 5, step 1, the faster peak) in THF (5 mL) was added slowly at −78° C. After stirred 3 hours at −78° C., the reaction system was warm to room temperature and stirred another 1 hour at room temperature. The reaction was quenched with aqueous saturated ammonium chloride (1 mL), followed by 3 M HCl (2 mL). The resulting solution was stirred for 1 hour at room temperature.

The solution was diluted with water, extracted with EtOAc. The combined organic layers were dried over anhydrous sodium sulfate and concentrated under vacuum. The residue was purified by flash chromatography on silica gel (gradient: 0%-30% ethyl acetate/petroleum ether) to yield 65.0 mg (30% yield) of the title compound as a yellow oil. LC-MS: (ES, m/z): [M+1]$^+$=228.1. $^1$H NMR (400 MHz, Chloroform-di, ppm) δ 6.75-6.65 (m, 1H), 6.55-6.44 (m, 1H), 4.45-4.32 (m, 2H), 4.27-4.20 (m, 4H), 3.90 (d, J=16 Hz, 1H), 3.73 (d, J=16 Hz, 1H), 3.32 (d, J=16 Hz, 1H), 3.04 (d, J=16 Hz, 1H), 2.89-2.75 (m, 2H), 2.72-2.56 (m, 2H), 2.53-2.35 (m, 4H), 2.25-2.08 (m, 2H), 1.33-1.28 (m, 6H). (diploid H due to it is a mixture of Z/E)

Step 2: (S,Z)-(2-(Fluoromethylene)tetrahydro-1H-pyrrolizin-7a(5H)-yl)methanol and (S,E)-(2-(fluoromethylene)tetrahydro-1H-pyrrolizin-7a(5H)-yl)methanol Under nitrogen, to a solution of ethyl (S,Z/E)-2-(fluoromethylene)-5-oxotetrahydro-1H-pyrrolizine-7a(5H)-carboxylate (60.0 mg, 0.260 mmol) in tetrahydrofuran (5 mL) was added DIBAL-H (2.64 mL, 2.64 mmol) at 0° C. The resulting solution was stirred for 1 hour at room temperature. The reaction was quenched with Na$_2$SO$_4$. 10H$_2$O. After filtration, the filtrate was concentrated under reduced pressure. The residue was purified by flash chromatography on silica gel (gradient: 0%-20% MeOH/DCM(0.1% Et$_3$N)) to yield 26.0 mg (mixture of Z/E, two peaks on normal phase column, but collected together) (57% yield) of the title compound as a yellow oil. LC-MS: (ESI, m/z): [M+H]$^+$=172.1. $^1$H NMR (300 MHz, Chloroform-di, ppm) δ 6.79-6.38 (m, 2H), 3.92-3.70 (m, 2H), 3.61-3.20 (m, 8H), 2.79-2.44 (m, 5H), 2.36-2.26 (m, 1H), 2.14-1.66 (m, 8H). (diploid H due to it is a mixture of Z/E).

The two isomers (Z/E) were separated by normal phase column with the same condition as described above. 2.20 g (Z, the desired isomer) and 2.70 g (E, the undesired isomer) were obtained from 9.7 g ethyl (S,Z/E)-2-(fluoromethylene)-5-oxotetrahydro-1H-pyrrolizine-7a(5H)-carboxylate following the same procedure and purification method described above. Both are yellow oils.

Z isomer: LC-MS: (ESI, m/z): [M+H]$^+$=172. $^1$H NMR (300 MHz, Chloroform-di, ppm) δ 6.64-6.29 (m, 1H), 3.79-3.65 (m, 1H), 3.48-3.37 (m, 1H), 3.35-3.23 (m, 2H), 3.14-3.03 (m, 1H), 2.69-2.58 (m, 1H), 2.46-2.35 (m, 1H), 2.30-2.17 (m, 1H), 2.03-1.59 (m, 4H).

E isomer: LC-MS: (ESI, m/z): [M+H]$^+$=172. $^1$H NMR (300 MHz, Chloroform-di, ppm) δ 6.76-6.42 (m, 1H), 3.75-3.65 (m, 1H), 3.48-3.34 (m, 2H), 3.33-3.18 (m, 2H), 2.73-2.40 (m, 3H), 2.09-1.65 (m, 4H).

Intermediate 51:
(S)-(4,4-Difluoro-1-methylpyrrolidin-2-yl)methanol

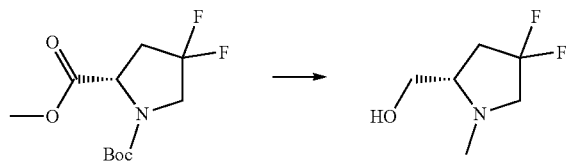

To a solution of 1-(tert-butyl) 2-methyl (S)-4,4-difluoropyrrolidine-1,2-dicarboxylate (300 mg, 1.13 mmol,) in tetrahydrofuran (5 mL) was added LiAlH$_4$ (107 mg, 2.82 mmol) at 0° C. and the mixture was stirred at 60° C. for 1 hour. The reaction was quenched with Na$_2$SO$_4$·10H$_2$O. The reaction mixture was diluted with water and extracted with EtOAc. The combined organic layers were dried over anhydrous sodium sulfate and concentrated under vacuum. The residue was purified by flash chromatography on silica gel (gradient: 0-14% EtOAc in petroleum ether) to afford the title compound (95.0 mg, 55.6% yield, isomer 1) as a white solid. LC-MS: (ESI, m/z): [M+H]$^+$=152.

Analogous to the method described as above, the other enantiomer (R)-(4,4-difluoro-1-methylpyrrolidin-2-yl)methanol (96.6 mg, 56.5% yield) was prepared from 1-(tert-butyl) 2-methyl (R)-4,4-difluoropyrrolidine-1,2-dicarboxylate (300 mg, 1.13 mmol). LC-MS: (ESI, m/z): [M+H]$^+$=152.

Intermediate 52: (5-(Bis(4-methoxybenzyl)amino)-3-methyl-2-(trifluoromethyl)phenyl)boronic acid

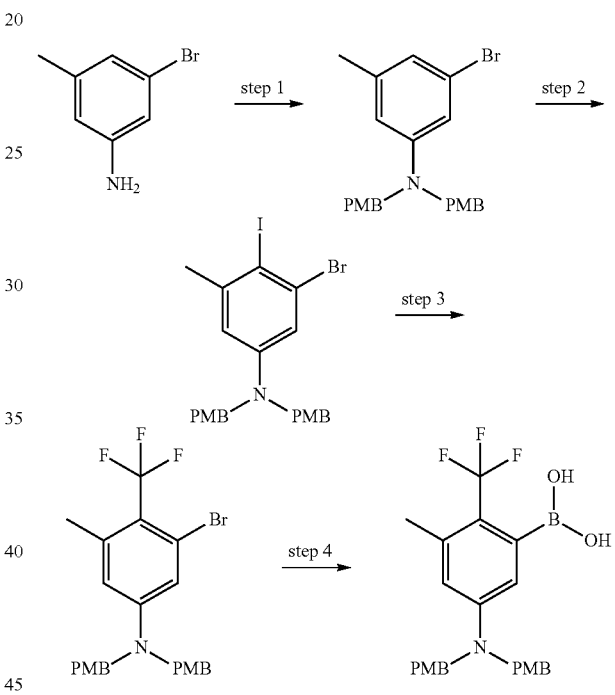

Step 1:
3-Bromo-N,N-bis(4-methoxybenzyl)-5-methylaniline

Under nitrogen, to a solution of 3-bromo-5-methyl-aniline (500 mg, 2.69 mmol) in DMF (5 mL) was added NaH (324 mg, 8.10 mmol, 60% in mineral oil) at 0° C., and the mixture was stirred for 0.5 hours. Then PMBCl (1.05 g, 6.69 mmol) was added and the mixture was stirred at room temperature for 12 hours. The reaction was quenched with NH$_4$Cl solution and extracted with EtOAc. The combined organic layers were dried over anhydrous Na$_2$SO$_4$ and concentrated under vacuum. The residue was purified by flash chromatography on silica gel (gradient: 0-10% ethyl acetate/petroleum ether) to afford the title compound (441 mg, 87.8% yield) as a yellow solid. LC-MS: (ESI, m/z): [M+H]$^+$=426/428.

Step 2: 3-Bromo-4-iodo-N,N-bis(4-methoxybenzyl)-5-methylaniline

To a solution of 3-bromo-N,N-bis[(4-methoxyphenyl)methyl]-5-methyl-aniline (2.00 g, 4.69 mmol) in DMF (20 mL) was added NIS (1.58 g, 7.03 mmol) and TsOH (96.0 mg, 0.560 mmol) in portions at room temperature. The resulting solution was stirred at room temperature for 20 min and then quenched with Na$_2$S$_2$O$_3$ aqueous solution. The solution was extracted with EtOAc. The combined organic layers were dried over anhydrous sodium sulfate and concentrated under vacuum. The residue was purified by flash chromatography on silica gel (gradient: 0-18% ethyl acetate/petroleum ether) to afford the title compound (1.58 g, 50.6% yield) as a yellow solid. LC-MS: (ESI, m/z): [M+H]$^+$=552/554.

Step 3: 3-Bromo-N,N-bis(4-methoxybenzyl)-5-methyl-4-(trifluoromethyl)aniline

Under nitrogen, a solution of 3-bromo-4-iodo-N,N-bis[(4-methoxyphenyl)methyl]-5-methyl-aniline (1.58 g, 2.86 mmol), methyl 2,2-difluoro-2-(fluorosulfonyl)acetate (1.82 mL, 14.3 mmol) and CuI (547 mg, 2.86 mmol) in DMF (15 mL) was stirred at 90° C. for 1 hour. The reaction mixture was partitioned between EtOAc and brine. The organic layer was dried over anhydrous sodium sulfate and concentrated under vacuum. The residue was purified by flash chromatography on silica gel (gradient: 0-10% ethyl acetate/petroleum ether) to afford the title compound (695 mg, 43.2% yield) as a yellow solid. LC-MS: (ESI, m/z): [M+H]$^+$=494/496.

Step 4: (5-(Bis(4-methoxybenzyl)amino)-3-methyl-2-(trifluoromethyl)phenyl)boronic acid Under nitrogen, to a solution of 3-bromo-N,N-bis(4-methoxybenzyl)-5-methyl-4-(trifluoromethyl)aniline (2.43 g, 4.92 mmol) and triisopropyl borate (1.39 g, 7.37 mmol) in tetrahydrofuran (25 mL) was added n-BuLi (3.69 mL, 5.90 mmol, 1.6 M in hexanes) at −65° C. The reaction was stirred at −65° C. for 1 hour. Then the reaction was quenched with water, extracted with EtOAc. The combined organic layers were dried over Na$_2$SO$_4$ and concentrated under vacuum. The residue was purified by reverse phase chromatography (gradient: 0-70% acetonitrile in water (0.5% NH$_4$HCO$_3$)) to afford the title compound (1.16 g, 51.2% yield) as a white solid. LC-MS: (ESI, m/z): [M+H]$^+$=460.

Intermediate 53: N,N-Bis(4-methoxybenzyl)-3-(4,4,5,5-tetramethyl-1,3,2-dioxaborolan-2-yl)-4-(trifluoromethyl)aniline

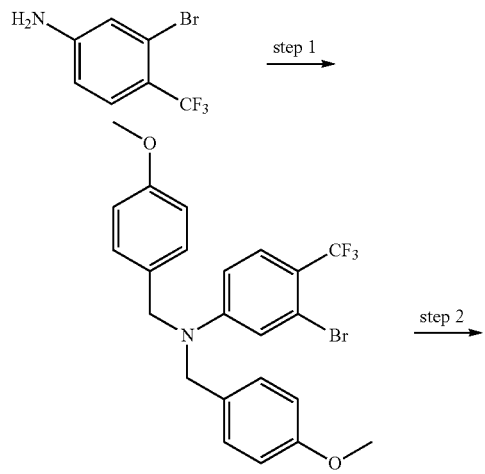

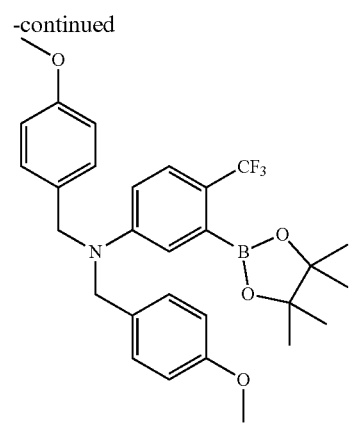

Step 1: 3-Bromo-N,N-bis(4-methoxybenzyl)-4-(trifluoromethyl)aniline

Under nitrogen, to a solution of 3-bromo-4-(trifluoromethyl)aniline (1.00 g, 2.52 mmol) in DMF (14 mL) was added NaH (0.500 g, 12.5 mmol, 60%) at 0° C. The resulting solution was stirred for 0.5 h at room temperature. Then PMB-Cl (1.60 g, 10.2 mmol) was added and the solution was stirred at room temperature overnight. The reaction was quenched with ice water, and the resulting mixture was extracted with EtOAc. The combined organic layers were dried over anhydrous sodium sulfate and concentrated under vacuum. The residue was purified by flash chromatography on silica gel (gradient: 0-5% ethyl acetate in petroleum ether) to afford the title compound 2.20 g (crude) as a yellow solid. LC-MS: (ESI, m/z): [M+H]$^+$=480.

Step 2: N,N-Bis(4-methoxybenzyl)-3-(4,4,5,5-tetramethyl-1,3,2-dioxaborolan-2-yl)-4-(trifluoromethyl)aniline Under nitrogen, to a solution of 3-bromo-N,N-bis(4-methoxybenzyl)-4-(trifluoromethyl)aniline (2.20 g, 4.58 mmol) and Pin$_2$B$_2$ (3.22 g, 12.7 mmol) in 1,4-dioxane (20 mL) was added KOAc (1.24 g, 12.7 mmol) and Pd(dppf)Cl$_2$ (0.620 g, 0.850 mmol) at room temperature. The resulting solution was stirred overnight at 110° C. After cooling to room temperature, the reaction mixture was diluted with water and extracted with EtOAc. The combined organic layers were dried over anhydrous sodium sulfate and concentrated under vacuum. The residue was purified by flash chromatography on silica gel (gradient: 0-10% ethyl acetate in petroleum ether) to afford 900 mg (37.3% yield) of the title compound as a yellow solid. LC-MS: (ESI, m/z): [M+H]$^+$=528.

Intermediate 54: 4-(1,1-Difluoroethyl)-2-fluoro-N,N-bis(4-methoxybenzyl)-5-(4,4,5,5-tetramethyl-1,3,2-dioxaborolan-2-yl)aniline

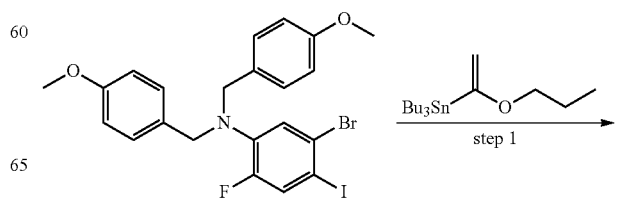

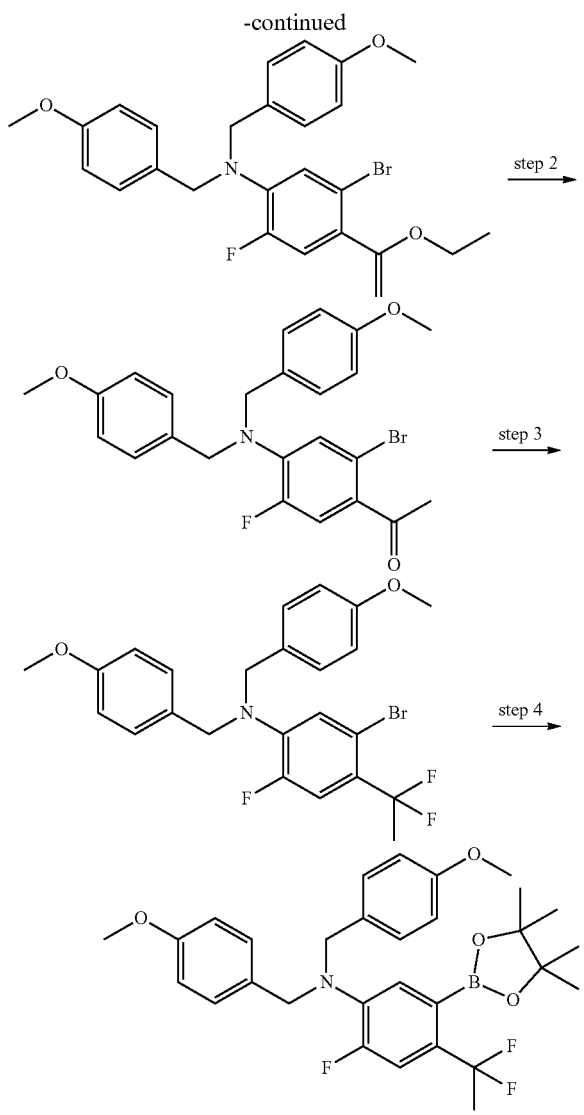

Step 1: 5-Bromo-4-(1-ethoxyvinyl)-2-fluoro-N,N-bis(4-methoxybenzyl)aniline

Under nitrogen, a solution of 5-bromo-2-fluoro-4-iodo-N,N-bis(4-methoxybenzyl)aniline (5.00 g, 8.99 mmol), tributyl(1-ethoxyvinyl)stannane (4.57 mL, 13.5 mmol) and Pd(Ph$_3$)$_2$Cl$_2$ (0.500 g, 0.710 mmol) in N,N-Dimethylformamide (20 mL) was stirred at 80° C. for 16 hours. The reaction was cooled to room temperature, diluted with water and extracted with DCM. The combined organic layers were dried over anhydrous sodium sulfate and concentrated under vacuum to afford 7.0 g crude of the title compound as yellow oil. LC-MS: (ESI, m/z): [M+H]$^+$=500/502. The crude was used for next step without further purification.

Step 2: 1-(4-(Bis(4-methoxybenzyl)amino)-2-bromo-5-fluorophenyl)ethan-1-one

To a solution of 5-bromo-4-(1-ethoxyvinyl)-2-fluoro-N,N-bis(4-methoxybenzyl)aniline (7.0 g, crude) in DMF (10 mL) was added concentrated hydrochloric acid (2.0 mL, 36%) at room temperature. The solution was stirred at room temperature for 1 hour. The solution was concentrated under vacuum. The residue was purified by reverse phase flash chromatography on pre-packed C18 column (gradient: 0-60% CH$_3$CN in water (0.05% NH$_4$HCO$_3$)) to afford 3.0 g (45% yield) of the title compound as a light brown oil. LC-MS: (ESI, m/z): [M+H]$^+$=472, 474.

Step 3: 5-Bromo-4-(1,1-difluoroethyl)-2-fluoro-N,N-bis(4-methoxybenzyl)aniline Under nitrogen, a solution of 1-(4-(bis(4-methoxybenzyl)amino)-2-bromo-5-fluorophenyl)ethan-1-one (970 mg, 2.05 mmol) in BAST (5.0 mL) was stirred at 60° C. for 16 hours. The reaction was cooled to room temperature, quenched with aqueous NaHCO$_3$ solution and extracted with EtOAc. The combined organic layers were dried over anhydrous sodium sulfate and concentrated under vacuum. The residue was purified by flash chromatography on silica gel eluting (gradient: 0-3% EtOAc in petroleum ether) to afford 150 mg (24% yield) of the title compound as brown oil. LC-MS: (ESI, m/z): [M+H]$^+$=494/496.

Step 4: 4-(1,1-Difluoroethyl)-2-fluoro-N,N-bis(4-methoxybenzyl)-5-(4,4,5,5-tetramethyl-1,3,2-dioxaborolan-2-yl)aniline Under nitrogen, a solution of 5-bromo-4-(1,1-difluoroethyl)-2-fluoro-N,N-bis(4-methoxybenzyl)aniline (415 mg, 0.840 mmol), PdCl$_2$(dppf) (122 mg, 0.170 mmol), Pin$_2$B$_2$ (640 mg, 2.52 mmol) and KOAc (247 mg, 2.52 mmol) in 1,4-Dioxane (3 mL) was stirred for 16 hours at 110° C. The reaction was cooled to room temperature, diluted with water and extracted with EtOAc. The combined organic layers were dried over anhydrous sodium sulfate and concentrated under vacuum. The residue was purified by flash chromatography on silica gel eluting (gradient: 0-10% EtOAc in petroleum ether) to afford 120 mg (26% yield) of the title compound as a yellow solid. LC-MS: (ESI, m/z): [M+H]$^+$=542.

Intermediate 55: 4-Chloro-3-methyl-5-(4,4,5,5-tetramethyl-1,3,2-dioxaborolan-2-yl)aniline

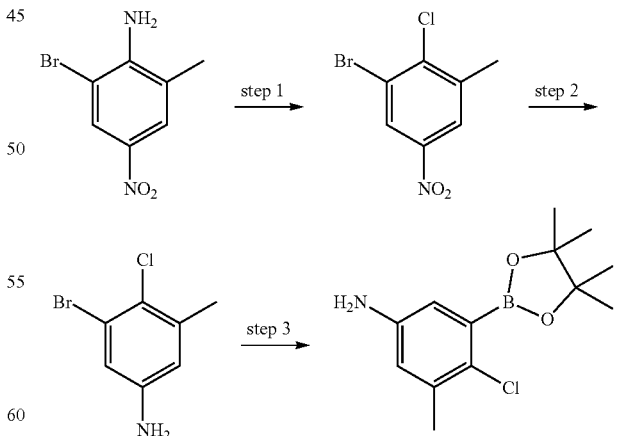

Step 1: 1-Bromo-2-chloro-3-methyl-5-nitrobenzene

To a solution of 2-bromo-6-methyl-4-nitroaniline (500 mg, 2.16 mmol) and CuCl$_2$ (486 mg, 3.61 mmol) in acetonitrile (20 mL) was added tert-butyl nitrite (0.510 mL, 4.33 mmol). The resulting solution was stirred for 12 hours at 50° C. The reaction was quenched with aqueous sodium thiosulfate solution, diluted with water and extracted with ethyl acetate. The combined organic layer was dried over anhydrous sodium sulfate and concentrated under vacuum. The residue was purified by flash chromatography on silica gel (gradient: 0-20% ethyl acetate in petroleum ether) to afford 530 mg (97.8% yield) of the title compound as a white solid. $^1$H NMR (300 MHz, DMSO-d6 ppm) δ 6.82 (d, J=2.4, 0.6 Hz, 1H), 6.68 (dd, J=2.4, 0.8 Hz, 1H), 2.22 (s, 3H).

Step 2: 3-Bromo-4-chloro-5-methylaniline

To a mixture of 1-bromo-2-chloro-3-methyl-5-nitrobenzene (500 mg, 2.00 mmol) and iron powder (559 mg, 9.98 mmol) in ethanol (14 mL) and H$_2$O (6 mL) was added NH$_4$Cl (1.07 g, 20.0 mmol) at room temperature. The resulting solution was stirred for 2 h at 80° C. under nitrogen. The solvent was concentrated under vacuum. The residue was purified by flash chromatography on silica gel (gradient: 0-20% ethyl acetate in petroleum ether) to afford 338 mg (76.8% yield) of the title compound as a yellow solid. LC-MS: (ESI, m/z): [M+H]$^+$=220.

Step 3: 4-Chloro-3-methyl-5-(4,4,5,5-tetramethyl-1,3,2-dioxaborolan-2-yl)aniline Under nitrogen, to a solution of 3-bromo-4-chloro-5-methylaniline (600 mg, 2.72 mmol) and 4,4,4',4',5,5,5',5'-octamethyl-2,2'-bi(1,3,2-dioxaborolane) (2.07 g, 8.16 mmol) in 1,4-dioxane (10 mL) was added Pd(dppf)Cl$_2$ (199 mg, 0.270 mmol) and KOAc (800 mg, 8.16 mmol). The resulting mixture was stirred for 12 h at 100° C. The reaction mixture was diluted with water and extracted with ethyl acetate. The combined organic layers were dried over anhydrous sodium sulfate and concentrated under vacuum. The residue was purified by flash chromatography on silica gel (gradient: 0-100% ethyl acetate in petroleum ether) to afford 556 mg (76.4% yield) of the title compound as a yellow oil. LC-MS: (ESI, m/z): [M+H]$^+$=268.

Intermediate 56: 4-(Difluoromethyl)-2-fluoro-N,N-bis(4-methoxybenzyl)-3-methyl-5-(4,4,5,5-tetramethyl-1,3,2-dioxaborolan-2-yl)aniline

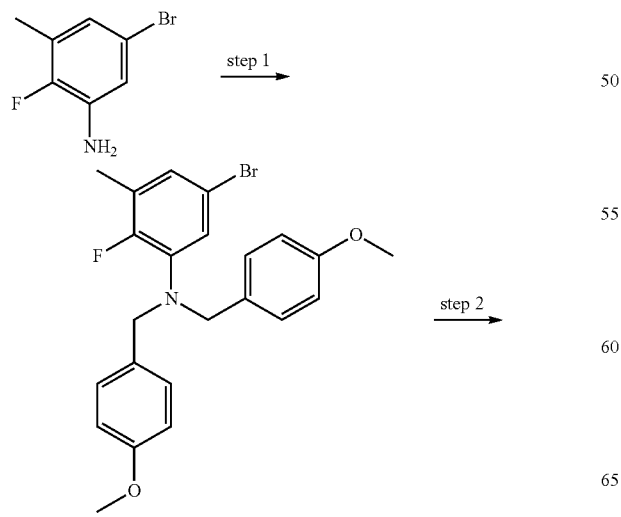

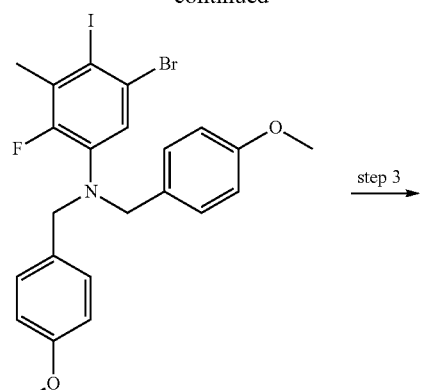

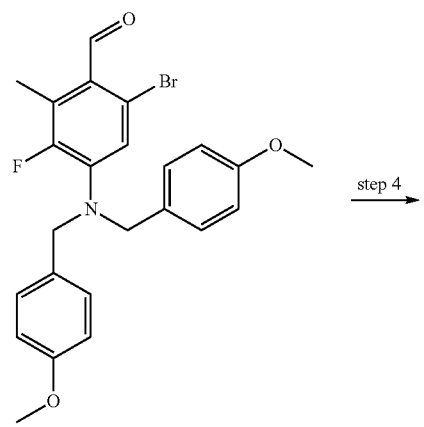

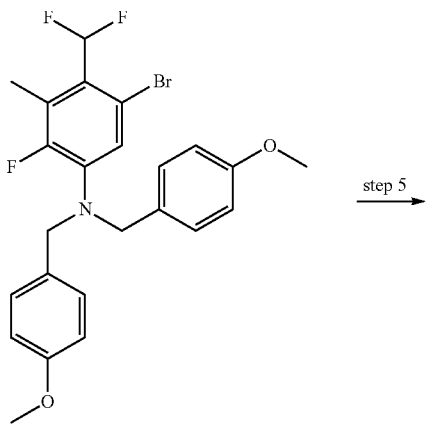

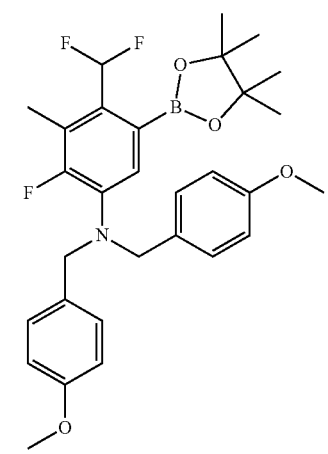

Step 1: 5-Bromo-2-fluoro-N,N-bis(4-methoxyben-zyl)-3-methylaniline

Under nitrogen, to a solution of 5-bromo-2-fluoro-3-methylaniline (5.00 g, 24.5 mmol) in N,N-Dimethylformamide (60 mL) was added NaH (2.94 g, 73.5 mmol, 60% in mineral oil) at 0° C. The resulting solution was stirred at room temperature for 30 min. Then PMB-Cl (8.06 g, 51.5 mmol) was added at 0° C. and the mixture was stirred at room temperature for 2 hours. The reaction was quenched with aqueous NH₄Cl solution and extracted with EtOAc. The combined organic layers were dried over anhydrous sodium sulfate and concentrated under vacuum. The residue was added EtOH (30 mL). The solid was collected by filtration to afford 10.1 g (93% yield) of the title compound as off-white solid. L C-MS: (ESI, m/z): [M+H]⁺ 10=444, 446. ¹H NMR (300 MHz, CDCl₃, ppm) δ 7.21-7.17 (m, 4H), 6.88-6.81 (m, 6H), 4.21 (s, 4H), 3.83 (s, 6H), 2.27 (s, 3H).

Step 2: 5-Bromo-2-fluoro-4-iodo-N,N-bis(4-methoxybenzyl)-3-methylaniline

To a solution of 5-bromo-2-fluoro-N,N-bis(4-methoxybenzyl)-3-methylaniline (7.00 g, 15.7 mmol) in acetic acid (70 mL) was added NIS (4.15 g, 18.4 mmol) at room temperature. The resulting solution was stirred at room temperature for 1 h. The reaction was quenched with aqueous Na₂S₂O₃ solution. The resulting solution was diluted with water and extracted with ethyl acetate. The combined organic layers were washed with brine, dried over anhydrous sodium sulfate and concentrated under vacuum. The residue was purified by flash chromatography on silica gel eluting (gradient: 0-10% EtOAc in petroleum ether) to afford 7.73 g (640 yield) of the title compound as a yellow solid. LC-MS: (ESI, m/z): [M+H]=570, 572.

¹H NMR (300 MHz, CDCl₃, ppm) δ 7.22-7.16 (m, 4H), 7.06 (d, J=8.4 Hz, 1H), 6.88-6.84 (i, 4H), 4.21 (s, 4H), 3.83 (s, 6H), 2.50 (s, 3H).

Step 3: 4-(Bis(4-methoxybenzyl)amino)-6-bromo-3-fluoro-2-methylbenzaldehyde

Under nitrogen, to a solution of 5-bromo-2-fluoro-4-iodo-N,N-bis(4-methoxybenzyl)-3-methylaniline (6.93 g, 12.2 mmol) in tetrahydrofuran (80 mL) was added i-PrMgCl (6.80 mL, 13.6 mmol, 2 M in THF) at −60° C. The solution was stirred at −60° C. for 1 hour. Then DMF (8.89 g, 122 mmol) was added at −60° C. The solution was warmed to room temperature and stirred for 0.5 hour. Then the reaction was quenched with aqueous NH₄Cl solution and extracted with EtOAc. The combined organic layers were dried over anhydrous sodium sulfate and concentrated under vacuum. The residue was purified by flash chromatography on silica gel eluting (gradient: 0-10% EtOAc in petroleum ether) to afford 2.12 g (37% yield) of the title compound as a yellow solid. LC-MS: (ESI, m/z): [M+H]⁺=472, 474. ¹H NMR (300 MHz, CDCl₃, ppm) δ 10.30 (s, 1H), 7.19-7.17 (m, 4H), 6.98 (d, J=7.8 Hz, 1H), 6.91-6.87 (m, 4H), 4.46 (s, 4H), 3.82 (s, 6H), 2.55 (s, 3H).

Step 4: 5-Bromo-4-(difluoromethyl)-2-fluoro-N,N-bis(4-methoxybenzyl)-3-methylaniline Under nitrogen, to a solution of 4-(bis(4-methoxybenzyl)amino)-6-bromo-3-fluoro-2-methylbenzaldehyde (700 mg, 1.48 mmol) in dichloromethane (20 mL) was added DAST (4.80 mL, 39.2 mmol) at −15° C. The solution was stirred at room temperature for 16 hours. The reaction was quenched with aqueous NaHCO₃ solution and extracted with DCM. The combined organic layers were dried over anhydrous sodium sulfate and concentrated under vacuum. The residue was purified by flash chromatography on silica gel eluting (gradient: 0-6% EtOAc in petroleum ether) to afford 647 mg (88% yield) of the title compound as yellow oil. LC-MS: (ESI, m/z): [M+H]⁺=494, 496. ¹H NMR (400 MHz, CDCl₃, ppm) δ 7.22-7.17 (m, 4H), 7.12-6.83 (m, 6H), 4.34 (s, 4H), 3.82 (s, 6H), 2.46 (s, 3H).

Step 5: 4-(Difluoromethyl)-2-fluoro-N,N-bis(4-methoxybenzyl)-3-methyl-5-(4,4,5,5-tetramethyl-1,3,2-dioxaborolan-2-yl)aniline Under nitrogen, a solution of 5-bromo-4-(difluoromethyl)-2-fluoro-N,N-bis(4-methoxybenzyl)-3-methylaniline (647 mg, 1.31 mmol), PdCl₂(dppf) (180 mg, 0.230 mmol), Pin₂B₂ (998 mg, 3.93 mmol) and KOAc (385 mg, 3.92 mmol) in 1,4-dioxane (15 mL) was stirred at 90° C. for 5 hours. The solid was filtered out. The filtrate was washed with brine, dried over anhydrous sodium sulfate and concentrated under vacuum. The residue was purified by flash chromatography on silica gel eluting (gradient: 0-11% EtOAc in petroleum ether) to afford 412 mg (58% yield) of the title compound as a white solid. LC-MS: (ESI, m/z): [M+H]⁺=542. ¹H NMR (400 MHz, CDCl₃, ppm) δ 7.52-7.26 (m, 6H), 6.76 (d, J=8.4 Hz, 4H), 4.59-4.55 (m, 4H), 3.74 (s, 6H), 2.39 (s, 3H), 1.29 (s, 12H).

Intermediate 57: 4-(2,2-Difluoroethyl)-2-fluoro-N,N-bis(4-methoxybenzyl)-3-methyl-5-(4,4,5,5-tetramethyl-1,3,2-dioxaborolan-2-yl)aniline

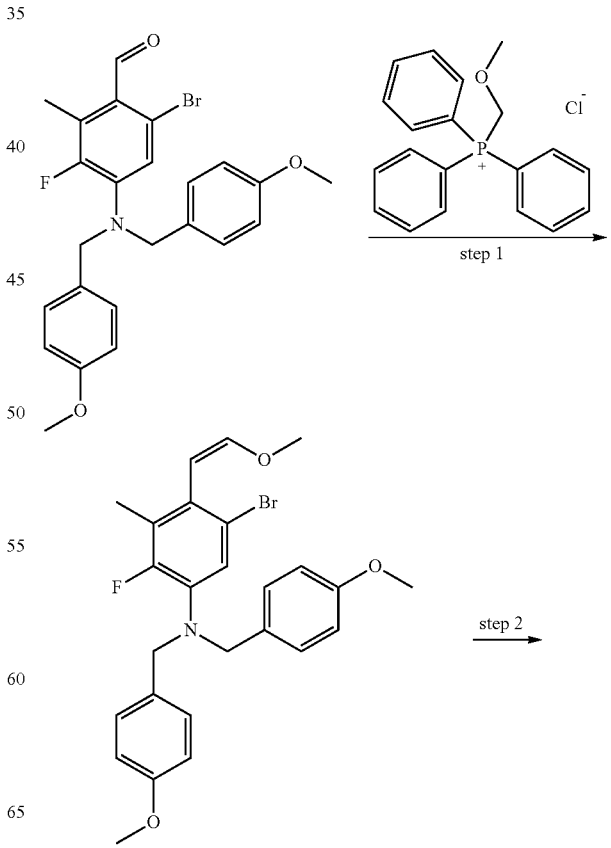

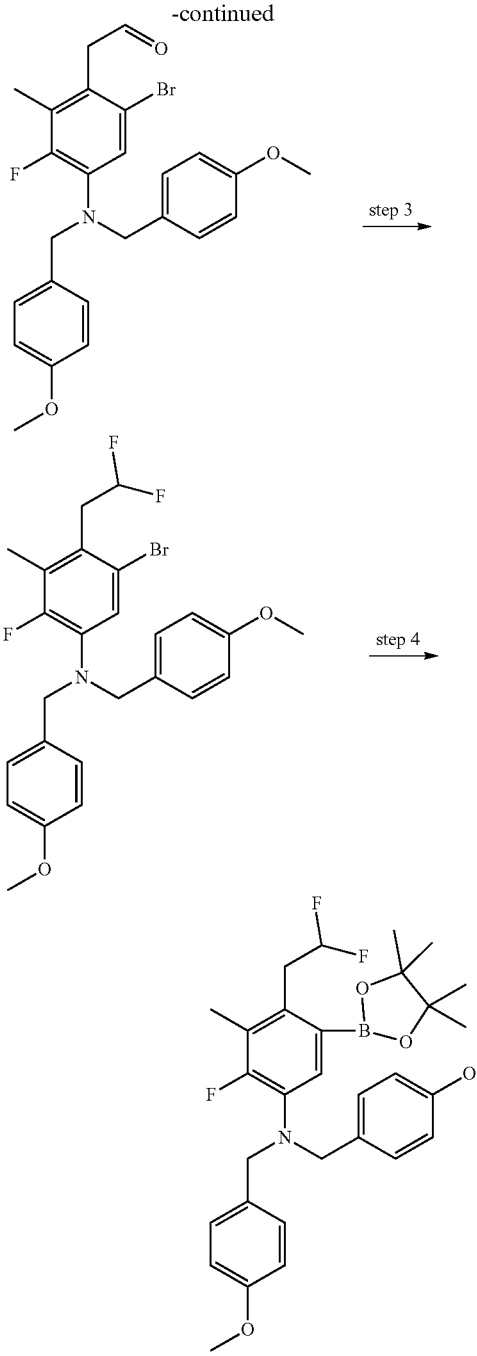

Step 1: 5-Bromo-2-fluoro-N,N-bis(4-methoxybenzyl)-4-(2-methoxyvinyl)-3-methylaniline Under nitrogen, to a solution of (methoxymethyl)triphenylphosphonium chloride (2.04 g, 5.95 mmol) in tetrahydrofuran (30 mL) was added t-BuOK (7.40 mL, 7.40 mmol, 1 M in THF) at 0° C. The solution was stirred at room temperature for 0.5 hour. Then 4-(bis(4-methoxybenzyl)amino)-6-bromo-3-fluoro-2-methylbenzaldehyde (1.41 g, 2.99 mmol, Intermediate 56, step 3) was added at 0° C. The solution was stirred at room temperature for 2 hours. Then the reaction was quenched with aqueous NH$_4$Cl solution and extracted with EtOAc. The combined organic layers were dried over anhydrous sodium sulfate and concentrated under vacuum. The residue was purified by flash chromatography on silica gel eluting (gradient: 0-11% EtOAc in petroleum ether) to afford 1.44 g (96% yield) of the title compound as a yellow oil. LC-MS: (ESI, m/z): [M+H]$^+$=500/502. $^1$H NMR (400 MHz, CDCl$_3$, ppm) δ 7.26-7.22 (m, 4H), 6.82 (d, J=8.8 Hz, 4H), 6.55 (d, J=13.2 Hz, 1H), 6.14 (d, J=6.8 Hz, 0.5H), 5.55 (d, J=13.2 Hz, 1H), 5.18 (d, J=6.8 Hz, 0.5H), 4.27-4.23 (m, 4H), 3.78 (s, 6H), 3.71-3.67 (m, 3H), 2.28-2.21 (m, 3H).

Step 2: 2-(4-(Bis(4-methoxybenzyl)amino)-6-bromo-3-fluoro-2-methylphenyl)acetaldehyde To a solution of 5-bromo-2-fluoro-N,N-bis(4-methoxybenzyl)-4-(2-methoxyvinyl)-3-methylaniline (1.29 g, 2.58 mmol) in tetrahydrofuran (15 mL) was added concentrated hydrochloric acid (1.5 mL, 36%) at −15° C. The solution was stirred at −15° C. for 1 hour. Then the solution was stirred for 5 hours at room temperature. The reaction was quenched with aqueous NaHCO$_3$ solution and extracted with EtOAc. The combined organic layers were dried over anhydrous sodium sulfate and concentrated under vacuum. The residue was purified by flash chromatography on silica gel eluting (gradient: 0-11% EtOAc in petroleum ether) to afford 890 mg (71% yield) of the title compound as an colorless oil. LC-MS: (ESI, m/z): [M+H]$^+$=486/488.

Step 3: 5-Bromo-4-(2,2-difluoroethyl)-2-fluoro-N,N-bis(4-methoxybenzyl)-3-methylaniline Under nitrogen, to a solution of 2-(4-(bis(4-methoxybenzyl)amino)-6-bromo-3-fluoro-2-methylphenyl)acetaldehyde (500 mg, 1.03 mmol) in dichloromethane (15 mL) was added DAST (3.20 mL, 26.2 mmol) at −10° C. The solution was stirred at room temperature for 3 hours. The reaction was quenched with aqueous NaHCO$_3$ solution and extracted with DCM. The combined organic layers were dried over anhydrous sodium sulfate and concentrated under vacuum. The residue was purified by flash chromatography on silica gel eluting (gradient: 0-7% EtOAc in petroleum ether) to afford 518 mg (99% yield) of the title compound as a white solid. LC-MS: (ESI, m/z): [M+H]$^+$=508/510.

Step 4: 4-(2,2-Difluoroethyl)-2-fluoro-N,N-bis(4-methoxybenzyl)-3-methyl-5-(4,4,5,5-tetramethyl-1,3,2-dioxaborolan-2-yl)aniline Under nitrogen, a solution of 5-bromo-4-(2,2-difluoroethyl)-2-fluoro-N,N-bis(4-methoxybenzyl)-3-methylaniline (518 mg, 1.02 mmol), PdCl$_2$(dppf) (140 mg, 0.180 mmol), Pin$_2$B$_2$ (712 mg, 2.80 mmol) and KOAc (300 mg, 3.07 mmol) in 1,4-Dioxane (12 mL) was stirred at 85° C. for 7 hours. The solid was filtered out. The filtrate was washed with brine, dried over anhydrous sodium sulfate and concentrated under vacuum. The residue was purified by flash chromatography on silica gel eluting (gradient: 0-5% EtOAc in petroleum ether) to afford 504 mg (89% yield) of the title compound as an colorless oil. LC-MS: (ESI, m/z): [M+H]$^+$=556. $^1$H NMR (400 MHz, CDCl$_3$, ppm) δ 7.44-7.29 (m, 4H), 6.81-6.76 (m, 4H), 6.01-5.72 (m, 2H), 4.47-4.26 (m, 4H), 3.77 (s, 6H), 3.50-3.43 (m, 2H), 2.25 (s, 3H), 1.27-2.26 (m, 12H).

Intermediate 58: 4-Chloro-2-fluoro-3-methyl-5-(4,4,5,5-tetramethyl-1,3,2-dioxaborolan-2-yl)aniline

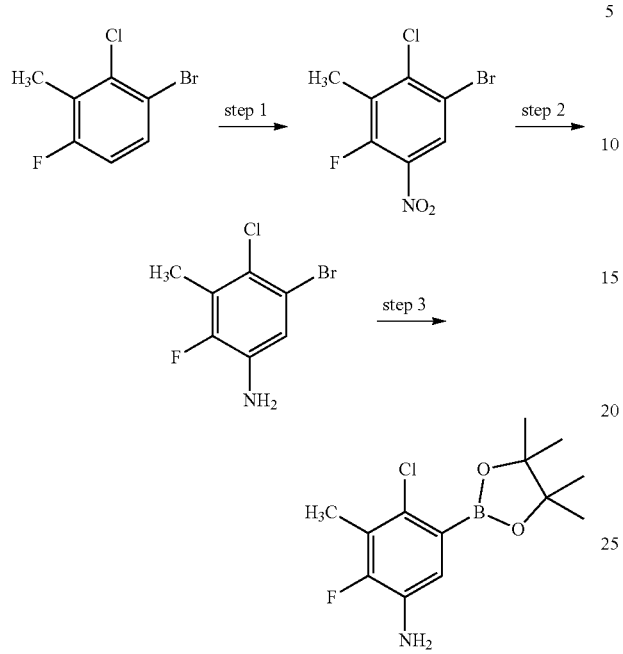

Step 1: 1-Bromo-2-chloro-4-fluoro-3-methyl-5-nitrobenzene

To a solution of 1-bromo-2-chloro-4-fluoro-3-methylbenzene (500 mg, 2.24 mmol) in $H_2SO_4$ (3.8 mL) was added $HNO_3$ (0.200 mL, 2.68 mmol) at 0° C. The solution was stirred at room temperature for 2 h. The reaction was quenched with ice water and extracted with EtOAc. The combined organic layers were dried over anhydrous sodium sulfate and concentrated under vacuum. The residue was purified by TLC (petroleum ether:EtOAc=5:1) to afford 450 mg (74.8% yield) of the title compound as a yellow oil. $^1$H NMR (300 MHz, DMSO-$d_6$, ppm) δ 8.45 (d, J=7.5 Hz, 1H), 2.43 (d, J=2.9 Hz, 3H).

Step 2: 5-Bromo-4-chloro-2-fluoro-3-methylaniline

To a solution of 1-bromo-2-chloro-4-fluoro-3-methyl-5-nitrobenzene (450 mg, 1.68 mmol) and iron powder (472 mg, 8.45 mmol) in ethanol (4.8 mL) and water (0.8 mL) was added $NH_4Cl$ (467 mg, 8.80 mmol) at room temperature. The solution was heated to 80° C. for 2 h. The reaction system was cooled to room temperature. The solid was filtered off. EtOH was evaporated under vacuum. The residual was diluted with water and extracted with EtOAc. The combined organic layers were washed with brine, dried over anhydrous sodium sulfate and concentrated under vacuum. The residue was purified by flash chromatography on silica gel (gradient: 0-50% EtOAc in petroleum ether) to afford 277 mg (69.3% yield) of the title compound as a yellow solid. $^1$H NMR (300 MHz, DMSO-$d_6$, ppm) δ 6.96 (dd, J=13.8, 7.8 Hz, 1H), 5.47 (d, J=30.8 Hz, 2H), 2.24 (t, J=2.8 Hz, 3H).

Step 3: 4-Chloro-2-fluoro-3-methyl-5-(4,4,5,5-tetramethyl-1,3,2-dioxaborolan-2-yl) aniline

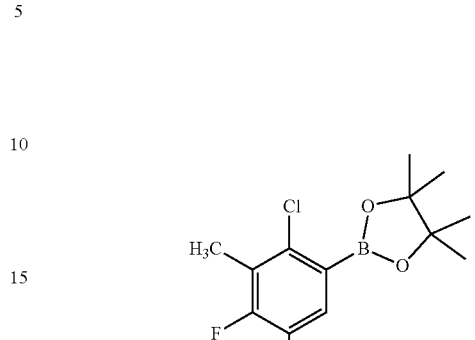

Under nitrogen, a solution of 5-bromo-4-chloro-2-fluoro-3-methylaniline (277 mg, 1.16 mmol), $Pin_2B_2$ (594 mg, 2.34 mmol), KOAc (229 mg, 2.34 mmol) and $PdCl_2(dppf)$ (85.4 mg, 0.120 mmol) in 1,4-dioxane (5 mL) was stirred at 110° C. for 2 h. The reaction system was cooled to room temperature. The solid was filtered off and washed with EtOAc. The combined filtrates were concentrated under reduced pressure The residue was purified by flash chromatography on silica gel (gradient: 0-10% EtOAc in petroleum ether) to yield 120 mg (36.2% yield) of the title compound as a yellow solid. LCMS: (ESI): [M+H]$^+$=286. $^1$H NMR (300 MHz, DMSO-$d_6$, ppm) δ 6.96 (d, J=10.3 Hz, 1H), 5.21 (s, 2H), 2.18 (d, J=2.6 Hz, 3H), 1.29 (s, 12H).

Intermediate 59: (2-Aminoquinolin-4-yl)boronic acid

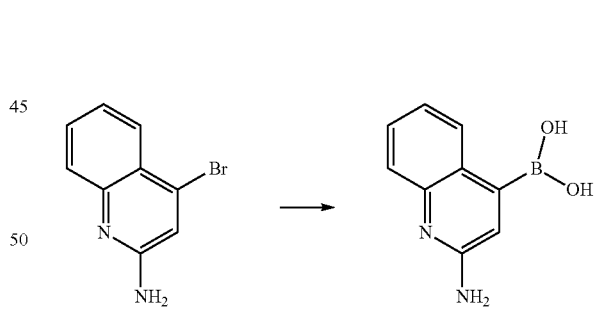

Under nitrogen, a solution of 4-bromoquinolin-2-amine (100 mg, 0.450 mmol), KOAc (132 mg, 1.34 mmol), Pd(dppf)Cl$_2$ (32.7 mg, 0.0400 mmol) and 4,4,4',4',5,5,5',5'-octamethyl-2,2'-bi(1,3,2-dioxaborolane) (342 mg, 1.34 mmol) in 1,4-dioxane (5 mL) was stirred for 2 hours at 100° C. The reaction mixture was diluted with water and extracted with ethyl acetate. The combined organic layers were dried over anhydrous sodium sulfate and concentrated under vacuum. The residue was purified by reverse phase flash chromatography on pre-packed C18 column (gradient: 0-30% CH$_3$CN in water (0.05% TFA) to afford 29.5 mg (24.4% yield) of the title compound as a yellow solid. LC-MS: (ESI, m/z): [M+H]$^+$=189.

Intermediate 60: 2-(7,8-Difluoro-3-(methoxymethoxy)naphthalen-1-yl)-4,4,5,5-tetramethyl-1,3,2-dioxaborolane

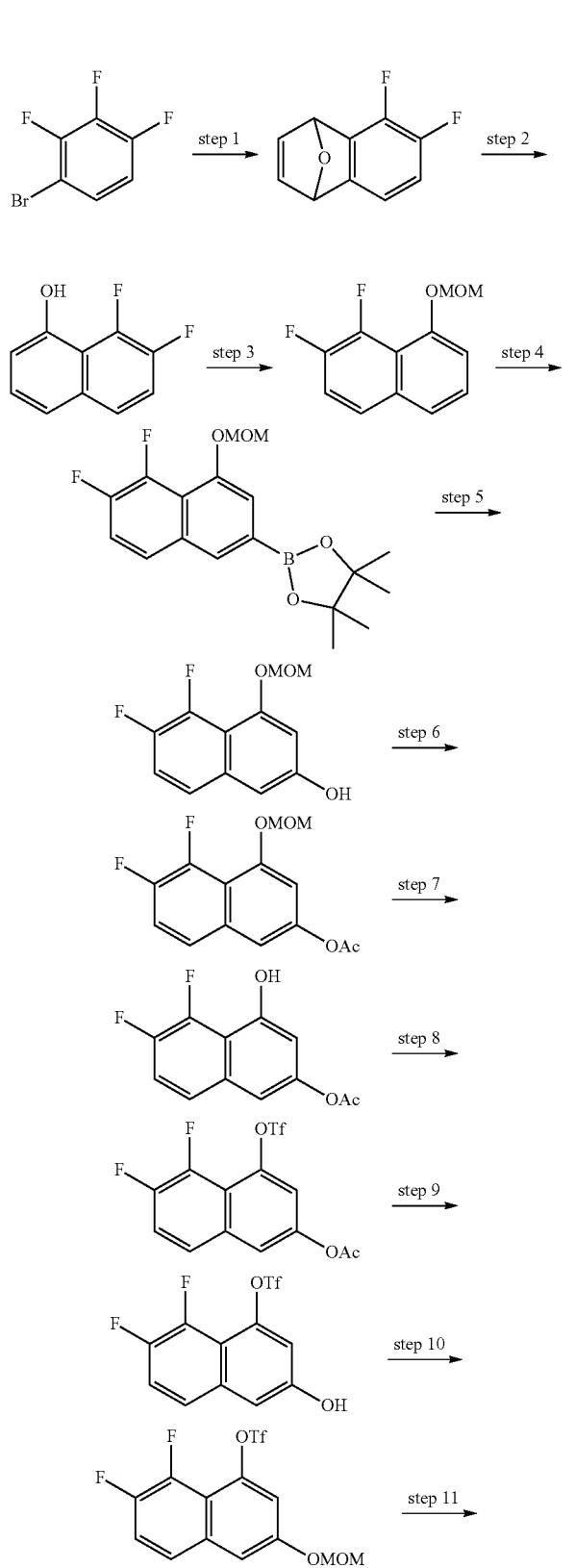

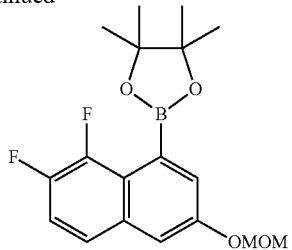

Step 1: 5,6-Difluoro-1,4-dihydro-1,4-epoxynaphthalene

Under nitrogen, to a solution of 1-bromo-2,3,4-trifluorobenzene (24.0 g, 113 mmol) and furan (19.9 g, 293 mmol) in toluene (240 mL) was added n-BuLi (54.8 mL, 2.5 M in hexane) at −15° C. The mixture was stirred at room temperature overnight. The reaction mixture was quenched with water and filtered. The filtrate was extracted with EtOAc. The combined organic layers were dried over $Na_2SO_4$, filtered and concentrated under vacuum. The resulting residue was purified by reverse phase chromatography (gradient: 0-100% ACN in water (0.1% FA)) to yield 6.1 g (29.8% yield) of the title compound as a yellow oil. $^1$H NMR (400 MHz, Chloroform-d) δ 7.16-7.02 (m, 2H), 6.94 (dd, J=7.7, 3.4 Hz, 1H), 6.84-6.64 (m, 1H), 6.00 (s, 1H), 5.74 (s, 1H).

Step 2: 7,8-Difluoronaphthalen-1-ol

A solution of 5,6-difluoro-1,4-dihydro-1,4-epoxynaphthalene (6.01 g, 33.3 mmol) and HCl (38.8 mL, 12 M) in EtOH (60 mL) was stirred at 80° C. for 3 h. The EtOH was concentrated under vacuum. The residue was adjusted pH to 7 with NaOH solid and extracted with EtOAc. The combined organic layers were dried over $Na_2SO_4$, filtered and concentrated under vacuum. The crude product was slurried with petroleum ether at room temperature for 1 h. The solid was collected by filtration to afford 4.50 g (75% yield) of the title compound as a pink solid. $^1$H NMR (400 MHz, Chloroform-d) δ 7.64-7.54 (m, 1H), 7.43-7.36 (m, 2H), 7.33-7.28 (m, 1H), 7.07-6.96 (m, 1H), 6.67 (d, 1H).

Step 3: 1,2-Difluoro-8-(methoxymethoxy)naphthalene

To a solution of 7,8-difluoronaphthalen-1-ol (4.41 g, 24.4 mmol) in DCM (45 mL) was added DIPEA (9.46 g, 73.4 mmol) and MOMBr (6.11 g, 48.9 mmol) at 0° C. The mixture was stirred at room temperature for 2 h. The mixture was diluted with water and extracted with DCM. The combined organic layers were dried over $Na_2SO_4$, filtered and concentrated under vacuum. The residue was purified by flash chromatography on silica gel (gradient: 0%-10% EtOAc/petroleum ether) to yield 4.51 g (82.3% yield) of the title compound as a colorless oil. $^1$H NMR (400 MHz, Chloroform-d) δ 7.59-7.51 (m, 1H), 7.49-7.43 (m, 1H), 7.39-7.30 (m, 2H), 7.20-7.13 (m, 1H), 5.36 (s, 2H), 3.59 (s, 3H).

Step 4: 2-(5,6-Difluoro-4-(methoxymethoxy)naphthalen-2-yl)-4,4,5,5-tetramethyl-1,3,2-dioxaborolane Under nitrogen, to a solution of 1,2-difluoro-8-(methoxymethoxy)naphthalene (1.01 g, 4.46 mmol) and 4,4,5,5-tetramethyl-1,3,2-dioxaborolane (1.43 g, 11.2 mmol) in THF (12 mL) was added (Ir(OMe)(cod))$_2$ (292 mg, 0.450 mmol) and dtbbpy (144 mg, 0.540 mmol). The mixture was stirred at 70° C. for 2 h. The solution was concentrated under vacuum. The residue was purified by flash chromatography on silica gel (gradient: 0%-40% EtOAc/petroleum ether) to yield 1.20 g (crude) of the title compound as a yellow oil.

Step 5:
5,6-Difluoro-4-(methoxymethoxy)naphthalen-2-ol

To a solution of 2-(5,6-difluoro-4-(methoxymethoxy) naphthalen-2-yl)-4,4,5,5-tetramethyl-1,3,2-dioxaborolane (8.41 g, 9.60 mmol) in THF (85 mL) was added HOAc (95 mL) and H$_2$O$_2$ (8.8 mL, 30% in H$_2$O) at 0° C. The mixture was stirred at room temperature for 1 h. The reaction solution was diluted with saturated NaHSO$_3$ aqueous and extracted with EtOAc. The organic layer was dried by anhydrous sodium sulfate and concentrated under vacuum. The residue was purified by flash chromatography on silica gel (gradient: 0%-30% EtOAc/petroleum ether) to yield 493 mg (21.4% yield) of the title compound as a yellow solid. $^1$H NMR (400 MHz, Chloroform-d) δ 7.35-7.30 (m, 2H), 7.16-7.09 (m, 1H), 7.07-6.99 (m, 1H), 5.37 (s, 2H), 3.63 (s, 3H).

Step 6:
5,6-Difluoro-4-(methoxymethoxy)naphthalen-2-yl acetate

To a solution of 5,6-difluoro-4-(methoxymethoxy)naphthalen-2-ol (494 mg, 2.06 mmol), Et$_3$N (415 mg, 4.11 mmol) and DMAP (25.1 mg, 0.210 mmol) in DCM (6.5 mL) was added acetyl chloride (320 mg, 4.08 mmol) at 0° C. The solution was stirred at room temperature for 1 h. The solution was diluted with water and extracted with DCM. The combined organic layers were washed with brine, dried over anhydrous sodium sulfate and concentrated under vacuum. The residue was purified by flash chromatography on silica gel (gradient: 0%-20% EtOAc/petroleum ether) to yield 543 mg (93.6% yield) of the title compound as a colorless oil. $^1$H NMR (400 MHz, Chloroform-d) δ 7.46-7.34 (m, 3H), 7.21-7.11 (m, 1H), 5.38 (s, 2H), 3.59 (s, 3H), 2.42 (s, 3H).

Step 7: 5,6-Difluoro-4-hydroxynaphthalen-2-yl acetate

To a solution of 5,6-difluoro-4-(methoxymethoxy)naphthalen-2-yl acetate (523 mg, 1.85 mmol) in EtOAc (6 mL) was added HCl (2 mL, 4 M in 1,4-dioxane) and the mixture was stirred at −40° C. for 0.5 h. Then the solution was stirred at 0° C. for 0.5 h. The solution diluted with saturated water NaHCO$_3$ and extracted with ethyl acetate. The combined organic layers were washed with brine, dried over anhydrous sodium sulfate and concentrated under vacuum. The residue was purified by flash chromatography on silica gel (gradient: 0%-50% EtOAc/petroleum ether) to yield 302 mg (51.9% yield) of the title compound as a white solid. $^1$H NMR (400 MHz, Chloroform-d) δ 7.47-7.30 (m, 3H), 7.00 (m, 1H), 6.52 (d, J=21.1 Hz, 1H), 2.41 (s, 3H).

Step 8: 5,6-Difluoro-4-(((trifluoromethyl)sulfonyl)oxy)naphthalen-2-yl acetate

To a solution of 5,6-difluoro-4-hydroxynaphthalen-2-yl acetate (250 mg, 1.05 mmol) in DCM (3 mL) was added DIPEA (407 mg, 3.15 mmol) and Tf$_2$O (356 mg, 1.26 mmol) at −78° C. The solution was stirred at −78° C. for 1 h. The solution was warmed to room temperature, diluted with water and extracted with DCM. The combined organic layers were washed with brine, dried over anhydrous sodium sulfate and concentrated under vacuum. The residue was purified by flash chromatography on silica gel eluting (gradient: 0%-25% EtOAc/petroleum ether) to yield 115 mg (29.6% yield) of the title compound as a white solid. $^1$H NMR (400 MHz, Chloroform-d) δ 7.88-7.77 (m, 1H), 7.62-7.47 (m, 3H), 2.44 (s, 3H).

Step 9: 7,8-Difluoro-3-hydroxynaphthalen-1-yl trifluoromethanesulfonate

To a solution of 5,6-difluoro-4-(((trifluoromethyl)sulfonyl)oxy)naphthalen-2-yl acetate (120 mg, 0.320 mmol) in THF (1.5 mL) and H$_2$O (0.5 mL) was added LiOH (9.4 mg, 0.390 mmol) at 0° C. The mixture was stirred at 0° C. for 1 h. The solution was adjusted pH to 6 with AcOH. The solution was diluted with water and extracted with ethyl acetate. The combined organic layers were washed with brine, dried over anhydrous sodium sulfate and concentrated under vacuum to yield 112 mg (crude) of the title compound as a yellow oil. The crude was used for next step without further purification.

Step 10:
7,8-Difluoro-3-(methoxymethoxy)naphthalen-1-yl trifluoromethanesulfonate To a solution of 7,8-difluoro-3-hydroxynaphthalen-1-yl trifluoromethanesulfonate (105 mg, 0.320 mmol) in DCM (1.5 mL) was added DIPEA (124 mg, 0.960 mmol) and MOMBr (80.1 mg, 0.640 mmol) at 0° C. The mixture was stirred at room temperature for 2 h. The solution was diluted with water and extracted with DCM. The combined organic layers were washed with brine, dried over anhydrous sodium sulfate and concentrated under vacuum The residue was purified by flash chromatography on silica gel (gradient: 0%-10% EtOAc/petroleum ether) to yield 96.6 mg (81.0% yield) of the title compound as a yellow solid. $^1$H NMR (400 MHz, Chloroform-d) δ 7.81-7.73 (m, 1H), 7.52-7.34 (m, 3H), 5.40 (s, 2H), 3.59 (s, 3H).

Step 11: 2-(7,8-Difluoro-3-(methoxymethoxy)naphthalen-1-yl)-4,4,5,5-tetramethyl-1,3,2-dioxaborolane Under nitrogen, a solution of 7,8-difluoro-3-(methoxymethoxy)naphthalen-1-yl trifluoromethanesulfonate (90.1 mg, 0.240 mmol), Pin$_2$B$_2$ (122.9 mg, 0.4800 mmol), Pd(dppf)Cl$_2$ (18.6 mg, 0.0200 mmol) and KOAc (119 mg, 1.21 mmol) in DMF (1.5 mL) was stirred at 80° C. overnight. The solution was cooled to room temperature, diluted with water and extracted with ethyl acetate. The combined organic layers were washed with brine, dried over anhydrous sodium sulfate and concentrated under vacuum The residue was purified by flash chromatography on silica gel (gradient: 0%-15% EtOAc/petroleum ether) to yield 59.6 mg (70.3% yield) of the title compound as a white solid. $^1$H NMR (400 MHz, Chloroform-d) δ 7.82-7.71 (m, 1H), 7.65-7.58 (m, 1H), 7.52-7.41 (m, 1H), 7.37-7.31 (m, 1H), 5.37 (s, 2H), 3.58 (s, 3H), 1.46 (s, 12H).

Intermediate 61: 7-(4,4,5,5-Tetramethyl-1,3,2-dioxaborolan-2-yl)-2,3-dihydro-1H-inden-5-amine

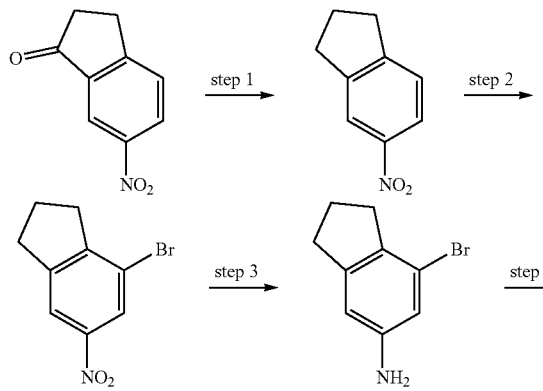

Step 1: 5-Nitro-2,3-dihydro-1H-indene

To a solution of 6-nitro-2,3-dihydro-1H-inden-1-one (3.00 g, 16.9 mmol) in Et$_3$SiH (8 mL) was added TFA (16 mL) at 0° C. The solution was stirred at room temperature for 2 hours. The solvent was concentrated under vacuum. The residue was purified by flash chromatography on silica gel (gradient: 0-7% EtOAc in petroleum ether) to afford the title compound (1.37 g, 49.1% yield) as a white solid. LC-MS: (ESI, m/z): [M+H]$^+$=164.

Step 2: 4-Bromo-6-nitro-2,3-dihydro-1H-indene

To a solution of 5-nitro-2,3-dihydro-1H-indene (300 mg, 1.84 mmol) in sulfuric acid (3 mL) and water (3 mL) was added NBS (327 mg, 1.84 mmol) at room temperature. The solution was stirred at room temperature for 1 hour. The mixture was diluted with water and extracted with ethyl acetate. The combined organic layers were dried over anhydrous sodium sulfate and concentrated under vacuum to afford 350 mg of the title compound (crude) as brown solid. The crude product was used for next step without purification. LC-MS: (ESI, m/z): [M+H]$^+$=243.

Step 3: 7-Bromo-2,3-dihydro-1H-inden-5-amine

A mixture of 4-bromo-6-nitro-2,3-dihydro-1H-indene (350 mg, 1.45 mmol), NH$_4$Cl (781 mg, 14.6 mmol) and iron powder (409 mg, 7.30 mmol) in water (1.5 mL) and EtOAc (3.5 mL) was stirred at 80° C. for 2 hours. The solvent was concentrated under vacuum. The residue was purified by flash chromatography on silica gel (gradient: 0-6% EtOAc in petroleum ether) to afford the title compound (300 mg, 63.6% yield) as a yellow solid. LC-MS: (ESI, m/z): [M+H]$^+$= 222.

Step 4: 7-(4,4,5,5-Tetramethyl-1,3,2-dioxaborolan-2-yl)-2,3-dihydro-1H-inden-5-amine Under nitrogen, a solution of 7-bromo-2,3-dihydro-1H-inden-5-amine (250 mg, 1.18 mmol), Pin$_2$B$_2$ (902 mg, 3.55 mmol), PdCl$_2$(dppf) (86.7 mg, 0.120 mmol) and KOAc (348 mg, 3.55 mmol) in 1,4-dioxane (3 mL) was stirred at 100° C. for 3 hours. The reaction mixture was diluted with water and extracted with EtOAc. The combined organic layers were dried over anhydrous sodium sulfate and concentrated under vacuum. The residue was purified by flash chromatography on silica gel (gradient: 0-94% dichloromethane in petroleum ether) to afford the title compound (150 mg, 43.7% yield) as a yellow solid. LC-MS: (ESI, m/z): [M+H]$^+$= n260.

Intermediate 62: 2,6-Difluoro-3-(4,4,5,5-tetramethyl-1,3,2-dioxaborolan-2-yl)aniline

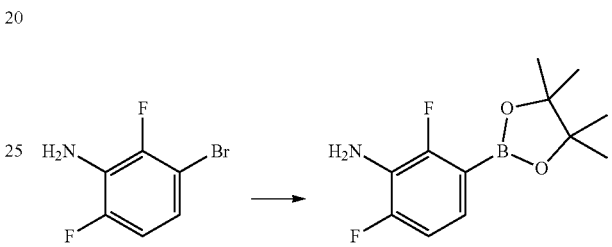

Under nitrogen, a solution of 3-bromo-2,6-difluoroaniline (1.00 g, 4.81 mmol), B$_2$Pin$_2$ (1.83 g, 7.21 mmol), Pd(dppf)Cl$_2$ (703 mg, 0.960 mmol) and KOAc (942 mg, 9.62 mmol) in 1,4-dioxane (15 mL) was stirred at 80° C. overnight. The resulting mixture was filtered. The filtrate was concentrated under reduced pressure. The crude product was diluted with water and extracted with EtOAc. The combined organic layers were washed with brine, dried over anhydrous sodium sulfate. After filtration, the filtrate was concentrated under reduced pressure. The residue was purified by flash chromatography on silica gel (gradient: 0-30% EtOAc in petroleum ether) to afford the title compound (497 mg, 40.5% yield) as a white solid. LC-MS: (ESI, m/z): [M+H]$^+$=256.

Intermediate 63: 6-(Allylsulfonyl)-N,N-bis(4-methoxybenzyl)-5-(trifluoromethyl)pyridin-2-amine

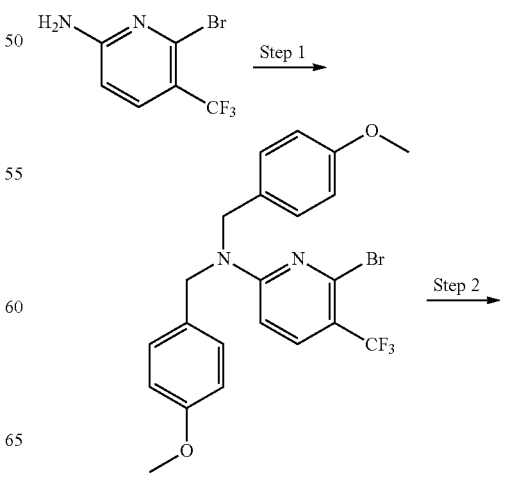

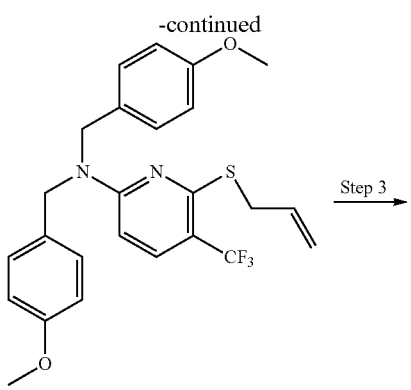

Step 3 →

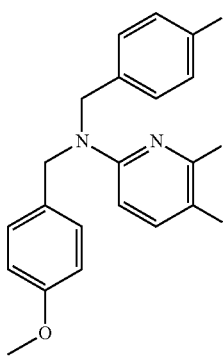

Step 1: 6-Bromo-N,N-bis(4-methoxybenzyl)-5-(trifluoromethyl)pyridin-2-amine

Under nitrogen, to a solution of 6-bromo-5-(trifluoromethyl)pyridin-2-amine (1.81 g, 7.49 mmol) in N,N-dimethylformamide (18 mL) was added NaH (902 mg, 22.6 mmol, 60% suspension in oil) at 0° C. The resulting solution was stirred for 30 min at room temperature. Then PMB-Cl (2932.1 mg, 18.8 mmol) was added at 0° C. and the mixture was stirred at room temperature for 1 hour. The reaction was quenched with aq. NH₄Cl, extracted with EtOAc. The combined organic layers were washed with brine, dried over anhydrous sodium sulfate and concentrated under vacuum. The residue was purified by flash chromatography on silica gel eluting with EtOAc/petroleum ether (0-15%) to afford the title compound (3.56 g, 98.7% yield) as a white solid. LC-MS: (ESI, m/z): [M+H]⁺=481.

Step 2: 6-(Allylthio)-N,N-bis(4-methoxybenzyl)-5-(trifluoromethyl)pyridin-2-amine To a solution of 6-bromo-N,N-bis[(4-methoxyphenyl)methyl]-5-(trifluoromethyl)pyridin-2-amine (500 mg, 1.04 mmol), K₂CO₃ (287 mg, 2.08 mmol) in DMF (10 mL) was added prop-2-ene-1-thiol (0.41 mL, 5.19 mmol). The resulting mixture was stirred for overnight at 50° C. The resulting mixture was diluted with water, extracted with EtOAc. The combined organic layers were dried over anhydrous Na₂SO₄ and concentrated under reduced pressure. The residue was purified by flash chromatography on silica gel (gradient: 0%-20% EtOAc/petroleum ether) to yield 350 mg (70.4% yield) the title compound as a yellow oil. LC-MS: (ESI, m/z): [M+H]⁺=475.

Step 3: 6-(Allylsulfonyl)-N,N-bis(4-methoxybenzyl)-5-(trifluoromethyl)pyridin-2-amine Under nitrogen, to a solution of 6-allylsulfanyl-N,N-bis[(4-methoxyphenyl)methyl]-5-(trifluoromethyl)pyridin-2-amine (165 mg, 0.35 mmol) in dichloromethane (5 mL) was added m-CPBA (240 mg, 1.39 mmol) at 0° C. The solution was stirred at 25° C. for 18 hours. The reaction mixture was partitioned between saturated aqueous NH₄Cl and EtOAc. The organic layer was washed with saturated aqueous NaHCO₃, water and brine, dried over MgSO₄ and concentrated under vacuum. The residue was purified by flash chromatography on silica gel (gradient: 0%-50% EtOAc/petroleum ether) to yield 60 mg (34.1% yield) of the title compound as a yellow oil. LC-MS: (ESI, m/z): [M+H]⁺=507.

Intermediate 64: 6-(Allylsulfonyl)-3-fluoro-N,N-bis(4-methoxybenzyl)-5-(trifluoromethyl)pyridin-2-amine

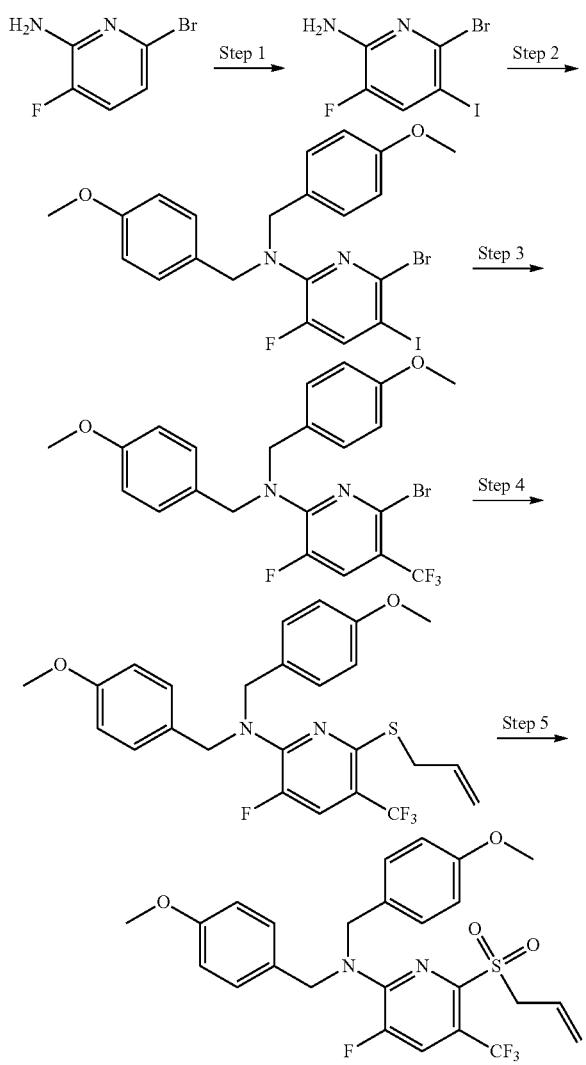

Step 1: 6-Bromo-3-fluoro-5-iodopyridin-2-amine

A solution of 6-bromo-3-fluoro-pyridin-2-amine (200 mg, 1.05 mmol) and NIS (282 mg, 1.26 mmol) in AcOH (10 mL) was stirred at 25° C. for 1 hour. The resulting mixture was diluted with water, extracted with EtOAc. The combined organic layers were dried over anhydrous Na₂SO₄ and concentrated under reduced pressure. The residue was purified by flash chromatography on silica gel (gradient: 0%-20% EtOAc/petroleum ether) to yield the title compound (270 mg, 81.4% yield) as a white solid. LC-MS: (ESI, m/z): [M+H]⁺=317/319.

Step 2: 6-Bromo-3-fluoro-5-iodo-N,N-bis(4-methoxybenzyl)pyridin-2-amine

Under nitrogen, to a solution of 6-bromo-3-fluoro-5-iodo-pyridin-2-amine (100 mg, 0.320 mmol) in N,N-dimethylformamide (2 mL) was added NaH (50.5 mg, 1.26 mmol, 60% suspension in oil) at 0° C. The resulting solution was stirred at room temperature for 30 min. Then PMBCl (98.8 mg, 0.63 mmol) was added. The solution was stirred at 25° C. for 1 hour. The resulting mixture was quenched with NH₄Cl, diluted with water and extracted with EtOAc. The combined organic layers were dried over anhydrous Na₂SO₄. After filtration, the filtrate was concentrated under reduced pressure. The residue was purified by flash chromatography on silica gel (gradient: 0%-20% EtOAc/petroleum ether) to yield the title compound (145 mg, 82.5% yield) as a white solid. LC-MS: (ESI, m/z): [M+H]⁺=557.

Step 3: 6-((2R,5aS,6R,9R)-3-Chloro-1-fluoro-13-(((S,Z)-2-(fluoromethylene)tetrahydro-1H-pyr-rolizin-7a(5H)-yl)methoxy)-15-(3-fluoropropyl)-5a,6,7,8,9,10-hexahydro-5H-9,6-(epiminomethano)azepino[2',1':3,4][1,4]oxazepino[5,6,7-de]quinazolin-2-yl)-4-methyl-5-(trifluoromethyl)pyridin-2-amine Under nitrogen, to a solution of 6-bromo-3-fluoro-5-iodo-N,N-bis[(4-methoxyphenyl)methyl]pyridin-2-amine (2.0 g, 3.59 mmol) in N,N-dimethylformamide (20 mL) was added methyl 2,2-difluoro-2-(fluorosulfonyl)acetate (4.57 mL, 35.9 mmol) and CuI (6.82 g, 35.9 mmol) at 25° C. The resulting solution was stirred at room temperature for 3 h. The resulting mixture was diluted with water, extracted with EtOAc. The combined organic layers were dried over anhydrous Na₂SO₄ and concentrated under reduced pressure. The residue was purified by flash chromatography on silica gel (gradient: 0%-10% EtOAc/petroleum ether) to yield the title compound (1.7 g, 94.9% yield) as a white solid. LC-MS: (ESI, m/z): [M+H]⁺=499.

Step 4: 6-(Allylthio)-3-fluoro-N,N-bis(4-methoxybenzyl)-5-(trifluoromethyl)pyridin-2-amine To a solution of the 6-bromo-3-fluoro-N,N-bis[(4-methoxyphenyl)methyl]-5-(trifluoromethyl)pyridin-2-amine (500 mg, 1.00 mmol) in tetrahydrofuran (5 mL) was added isopropylmagnesium chloride lithium chloride (1 mL, 1.3 mmol) and allyl disulfide (146 mg, 1.00 mmol) at 0° C. The solution was allowed to warm to room temperature and stirred overnight. The reaction was diluted with water, extracted with EtOAc. The combined organic layers were dried over anhydrous Na₂SO₄ and concentrated under reduced pressure. The crude product was purified by reverse phase chromatography (gradient: 0-95% acetonitrile in water (0.10% NH₄HCO₃)) to afford the title compound 350 mg (71% yield) of the title compound as a white solid. LC-MS: (ESI, m/z): [M+H]⁺=493.

Step 5: 6-(Allylsulfonyl)-3-fluoro-N,N-bis(4-methoxybenzyl)-5-(trifluoromethyl)pyridin-2-amine Under nitrogen, to a solution of 6-allylsulfanyl-3-fluoro-N,N-bis[(4-methoxyphenyl)methyl]-5-(trifluoromethyl)pyridin-2-amine (50.0 mg, 0.10 mmol) in dichloromethane (2 mL) was added m-CPBA (52.6 mg, 0.30 mmol) at 0° C. The solution was stirred at 25° C. for 18 hours. The reaction mixture was partitioned between saturated aqueous NH₄Cl and EtOAc. The organic layer was washed with saturated aqueous NaHCO₃, water and brine, dried over MgSO₄ and concentrated under reduced pressure. The residue was purified by flash chromatography on silica gel (gradient: 0%-50% EtOAc/petroleum ether) to yield 20 mg (37.6% yield) of the title compound as a yellow oil. LC-MS: (ESI, miz): [M+H]⁺=525.

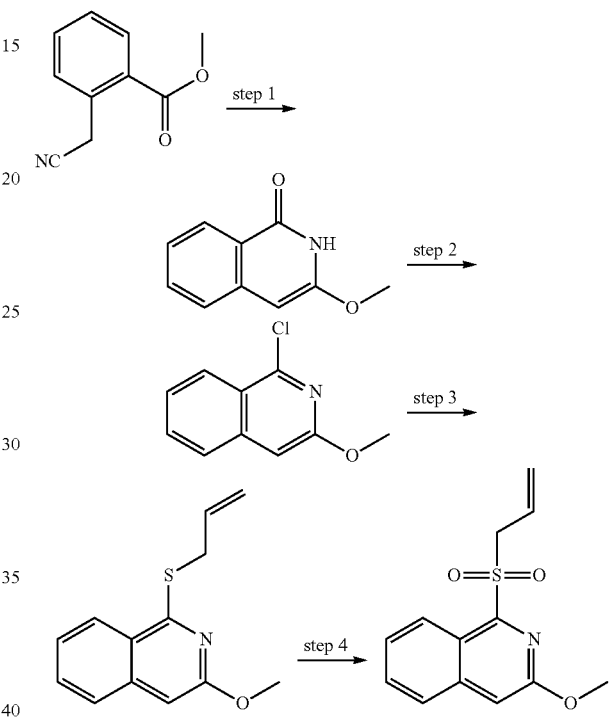

Intermediate 65:
1-(Allylsulfonyl)-3-methoxyisoquinoline

Step 1: 3-Methoxyisoquinolin-1(2H)-one

Under nitrogen, to a stirred solution of methyl 2-(cyanomethyl)benzoate (2.00 g, 11.4 mmol) in methanol (30 mL) was added NaOMe (1.23 g, 22.8 mmol) at 0° C. The resulting solution was stirred at 70° C. for 3 h. After the reaction system was cooled to room temperature, the mixture was acidified with 1 mol/L HCl till the solution turn to yellow from green, then cool to 0° C. till the white solid was precipitated. The solid was collected by filtration, washed with water and dry in oven to afford the title compound 600 mg (30.0% yield) as a white solid. LC-MS: (ESI, m/z): [M+H]⁺=176.

Step 2: 1-Chloro-3-methoxyisoquinoline

Under nitrogen, to a stirred solution of 3-methoxyisoquinolin-1(2H)-one (450 mg, 2.57 mmol) in acetonitrile (20 mL) was added POCl₃ (1.97 mg, 12.8 mmol). The resulting solution was stirred at 80° C. for 3 h. The mixture was concentrated under vacuum. The residue was neutralized by saturated NaHCO₃ solution and extracted with DCM. The combined organic layers were dried over anhydrous sodium sulfate and concentrated under vacuum. The residue was purified by flash chromatography on silica gel (gradient: 0-20% EtOAc in petroleum ether) to afford 240 mg (48.3% yield) of the title compound as a yellow solid. LC-MS: (ESI, m/z): [M+H]$^+$=194.

Step 3: 1-(Allylthio)-3-methoxyisoquinoline

To a stirred solution of 1-chloro-3-methoxy-isoquinoline (200 mg, 1.03 mmol) and K$_2$CO$_3$ (286 mg, 2.07 mmol) in DMF (2.5 mL) was added prop-2-ene-1-thiol (0.39 mL, 4.85 mmol). The resulting solution was stirred at 25° C. overnight. The crude product was purified by reverse phase chromatography (gradient: 0-100% acetonitrile in water (0.05% TFA) to afford 180 mg (75.6% yield) of the title compound as a yellow oil. LC-MS: (ESI, m/z): [M+H]$^+$=232.

Step 4: 1-(Allylsulfonyl)-3-methoxyisoquinoline

To a stirred solution of 1-(allylthio)-3-methoxyisoquinoline (211 mg, 0.912 mmol) in DCM (5 mL) was added m-CPBA (472 mg, 2.74 mmol) at 0° C. The resulting solution was stirred at room temperature for 3 h. The reaction was quenched with aqueous Na$_2$S$_2$O$_3$ solution and extracted with CH$_2$Cl$_2$. The combined organic layer was dried over anhydrous sodium sulfate and concentrated under vacuum. The residue was purified by flash chromatography on silica gel (gradient: 0-50% EtOAc in petroleum ether) to afford 200 mg (83.2% yield) of the title compound as a white solid. LC-MS: (ESI, m/z): [M+H]$^+$=264.

Intermediate 66: 2-(Allylsulfonyl)-4-methyl-3-(trifluoromethyl)pyridine

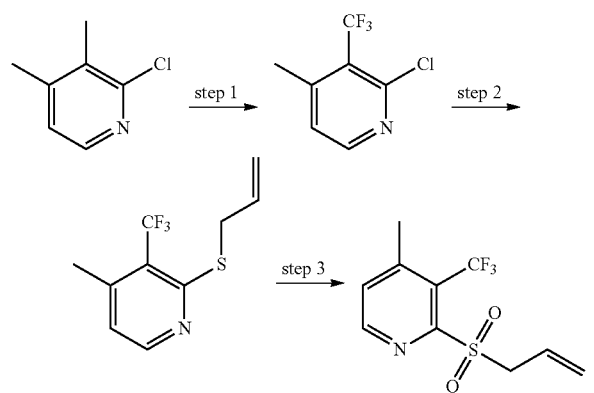

Step 1:
2-Chloro-4-methyl-3-(trifluoromethyl)pyridine

Under nitrogen, to a solution of 2-chloro-3-iodo-4-methylpyridine (1.00 g, 3.95 mmol) and CuI (755 mg, 3.95 mmol) in N, N-dimethylacetamide (10 mL) was added methyl 2,2-difluoro-2-(fluorosulfonyl)acetate (2.51 mL, 19.8 mmol) at 0° C. The mixture was stirred at 90° C. for 1 h. The solution was cooled to room temperature, diluted with water and extracted with EtOAc. The combined organic layers were washed with brine, dried over anhydrous sodium sulfate and concentrated under vacuum. The residue was purified by flash chromatography on silica gel (gradient: 0-10% EtOAc in petroleum ether) to afford 300 mg (38.8% yield) of the title compound as a yellow oil. LC-MS: (ESI, m/z): [M+H]$^+$=196.

Step 2:
2-(Allylthio)-4-methyl-3-(trifluoromethyl)pyridine

A solution of prop-2-ene-1-thiol (1.95 mL, 24.5 mmol), K$_2$CO$_3$ (1.35 g, 9.81 mmol) and 2-chloro-4-methyl-3-(trifluoromethyl)pyridine (956 mg, 4.89 mmol) in N,N-dimethylformamide (10 mL) was stirred at room temperature overnight. The reaction mixture was diluted with water and extracted with EtOAc. The combined organic layers were dried over anhydrous sodium sulfate and concentrated under vacuum. The residue was purified by flash chromatography on silica gel (gradient: 0-5% ethyl acetate in petroleum ether) to afford (1.02 g, 88.5% yield) as a yellow oil. LC-MS: (ESI, m/z): [M+H]$^+$=234.

Step 3: 2-(Allylsulfonyl)-4-methyl-3-(trifluoromethyl)pyridine

To a solution of 2-(allylthio)-4-methyl-3-(trifluoromethyl)pyridine (700 mg, 3.00 mmol) in dichloromethane (10 mL) was added m-CPBA (1.56 g, 9.01 mmol) at 0° C. The resulting solution stirred at room temperature overnight. The reaction was quenched with saturated NaHCO$_3$ solution and extracted with dichloromethane. The combined organic layers were dried over anhydrous sodium sulfate and concentrated under vacuum. The residue was purified by flash chromatography on silica gel (gradient: 0-40% EtOAc in petroleum ether) to afford (370 mg, 43.7% yield) as a yellow oil. LC-MS: (ESI, m/z): [M+H]$^+$=266.

Intermediate 67: 8-Chloro-N,N-bis(4-methoxybenzyl)-1-(trimethylstannyl)isoquinolin-3-amine

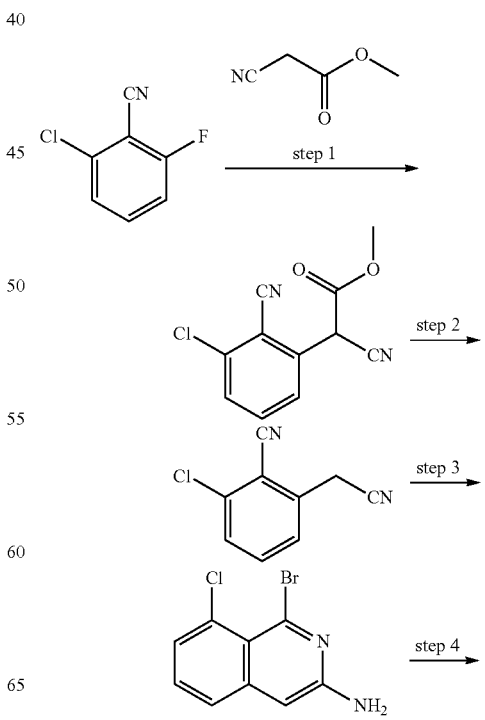

-continued

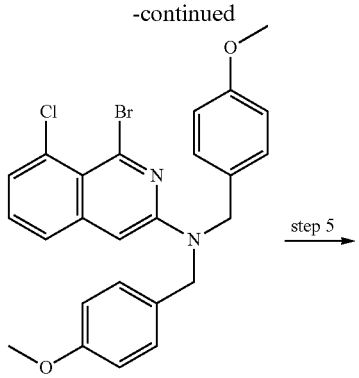

step 5

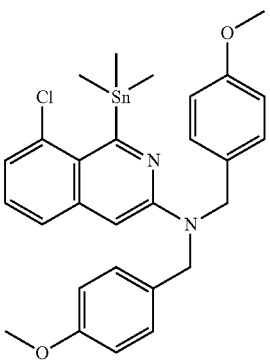

Step 1: Methyl 2-(3-chloro-2-cyanophenyl)-2-cyanoacetate

A solution of 2-chloro-6-fluorobenzonitrile (5.00 g, 32.1 mmol), $K_2CO_3$ (8.87 g, 64.3 mmol) and methyl 2-cyanoacetate (3.69 mL, 41.8 mmol) in dimethyl sulfoxide (50 mL) was stirred at 50° C. for 6 hours. The solution was cooled to room temperature, diluted with EtOAc and washed with water. The organic layer was dried over anhydrous sodium sulfate and concentrated under vacuum. To the crude product was slurried by EtOAc/DCM (1:30) and the solids were collected by filtration to afford the title compound (3.30 g, 43.8% yield) as a yellow solid. $^1$H NMR (300 MHz, DMSO-d6) δ 7.66-7.57 (m, 1H), 7.21 (dd, J=8.4, 7.7 Hz, 1H), 6.88 (dd, J=7.8, 1.0 Hz, 1H), 3.45 (s, 3H).

Step 2: 2-Chloro-6-(cyanomethyl)benzonitrile

To a solution of methyl 2-(3-chloro-2-cyanophenyl)-2-cyanoacetate (3.00 g, 12.8 mmol) in dimethyl sulfoxide (24 mL) was added HCl (6.0 mL, 36.0 mmol, 6 M in water). The reaction system was stirred at 70° C. overnight. The solution was cooled to room temperature, diluted with water and extracted with EtOAc. The combined organic layers were dried over anhydrous sodium sulfate and concentrated under vacuum. The crude product was slurried by DCM/petroleum ether (1:30) to afford the title compound (1.64 g, 50.3% yield) as a green solid. $^1$H NMR (300 MHz, DMSO-d6) δ 7.84-7.70 (m, 2H), 7.70-7.58 (m, 1H), 4.33 (s, 2H).

Step 3: 1-Bromo-8-chloroisoquinolin-3-amine

A solution of 2-chloro-6-(cyanomethyl)benzonitrile (1.54 g, 8.72 mmol) in 40% HBr/HOAc was stirred at 0° C. for 1.5 hours. The reaction mixture was adjusted pH to 8 with saturated $Na_2CO_3$ solution. The reaction mixture was diluted with water and extracted with EtOAc. The combined organic layers were washed with brine, dried over anhydrous sodium sulfate. After filtration, the filtrate was concentrated under reduced pressure. The residue was purified by flash chromatography on silica gel (gradient: 0-80% DCM in petroleum ether) to afford the title compound (714 mg, 31.6% yield) as a yellow solid. LC-MS: (ESI, m/z): $[M+H]^+$=257.

Step 4: 1-Bromo-8-chloro-N,N-bis(4-methoxybenzyl)isoquinolin-3-amine

To a solution of 1-bromo-8-chloroisoquinolin-3-amine (600 mg, 2.33 mmol) in N,N-dimethylacetamide (8 mL) was added NaH (223 mg, 5.83 mmol, 60% suspension in oil) at 0° C. The mixture was stirred for 30 min. PMBCl (804 mg, 5.13 mmol) was added and the mixture was allowed to warm to room temperature and stirred for 1 hour. The reaction mixture was quenched with water. The filtrate was concentrated under reduced pressure. The residual was diluted with water, extracted with EtOAc. The combined organic layers were dried over anhydrous sodium sulfate and concentrated under vacuum. The residue was purified by flash chromatography on silica gel (gradient: 0-20% EtOAc in petroleum ether) to afford the title compound (388 mg, 32.7% yield) as a yellow solid. LC-MS: (ESI, m/z): $[M+H]^+$=497.

Step 5: 8-Chloro-N,N-bis(4-methoxybenzyl)-1-(trimethylstannyl)isoquinolin-3-amine Under nitrogen, a solution of 1-bromo-8-chloro-N,N-bis(4-methoxybenzyl)isoquinolin-3-amine (60.0 mg, 0.120 mmol), $Sn_2Me_6$ (128 mg, 0.390 mmol) and $Pd(PPh_3)_4$ (13.9 mg, 0.0100 mmol) in toluene (1 mL) was stirred at 100° C. overnight. The solution was cooled to room temperature, diluted with water and extracted with DCM. The combined organic layers were dried over anhydrous $Na_2SO_4$ and evaporated to afford 139 mg of the crude product as a green oil which was used for next step without further purification. LC-MS: (ESI, m/z): $[M+H]^+$=583.

Intermediate 68: tert-Butyl (1S,5R)-3,6-diazabicyclo[3.2.2]nonane-6-carboxylate

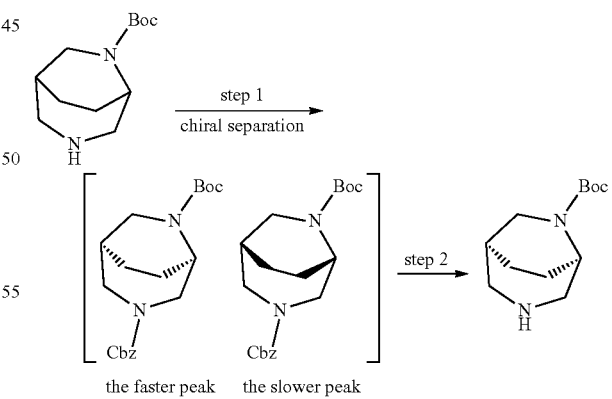

the faster peak    the slower peak

Step 1: 3-Benzyl 6-(tert-butyl) (1S,5R)-3,6-diazabicyclo[3.2.2]nonane-3,6-dicarboxylate Under nitrogen, a solution of tert-butyl 3,6-diazabicyclo[3.2.2]nonane-6-carboxylate (500 mg, 2.21 mmol), CbzCl (492 mg, 2.88 mmol) and DIPEA (1.42 g, 11.1 mmol) in dichloromethane (10 mL) was stirred at room temperature for 1 h. The reaction mixture was diluted with DCM and washed with water. The organic layer was dried over anhydrous sodium sulfate and concentrated under vacuum. The residue was purified by flash chromatography on silica gel (gradient: 0-100% EtOAc/petroleum ether) to afford 800 mg of the title compound as a colorless oil. The two enantiomers were separated by Prep-SFC with the following conditions: (Column: CHIRALPAK IG, 3*25 cm, 5 μm; Mobile Phase A: $CO_2$, Mobile Phase B: IPA(0.5% 2 M $NH_3$—MeOH); Flow rate: 70 mL/min; Gradient: 30% B; Column Temperature: 35° C.; Back Pressure: 100 bar; 215 nm; RT1:6.86; RT2:7.89; Injection Volume: 1.5 ml; Number Of Runs: 20) to yield 330 mg of faster peak and 340 mg slower peak as a white oil. The faster peak is the desired isomer. LC-MS: (ESI, m/z): $[M+H]^+$=361.

Step 2: tert-Butyl (1S,5R)-3,6-diazabicyclo[3.2.2]nonane-6-carboxylate

Under hydrogen, a solution of 3-benzyl 6-(tert-butyl) (1S,5R)-3,6-diazabicyclo[3.2.2]nonane-3,6-dicarboxylate (500 mg, 1.39 mmol) and Pd/C (150.0 mg, 10% wet) in methanol (20 mL) was stirred at 25° C. overnight. After filtration, the filtrate was concentrated under vacuum to yield 300 mg (crude) of the title compound as a colorless oil which was used for next step without further purification. LC-MS: (ESI, m/z): $[M+H]^+$=227.

Intermediate 69: (5-(Bis(4-methoxybenzyl)amino)-2-chloro-4-fluoro-3-methylphenyl)boronic acid

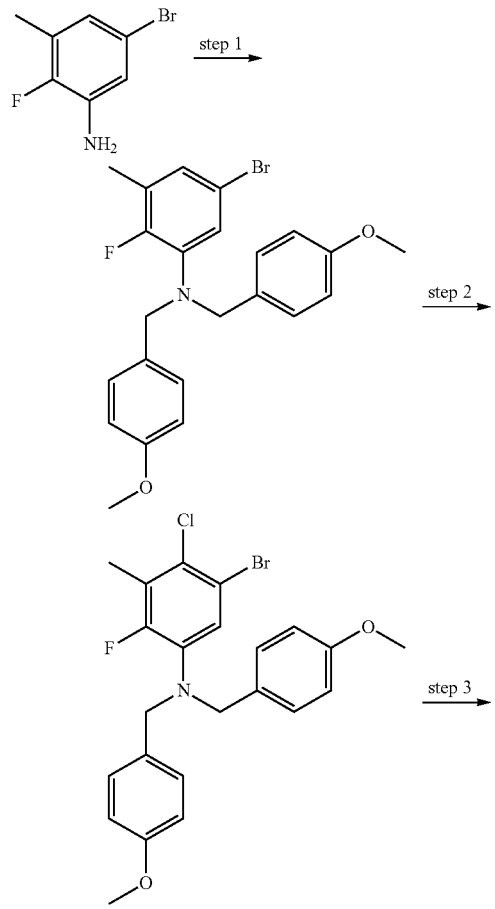

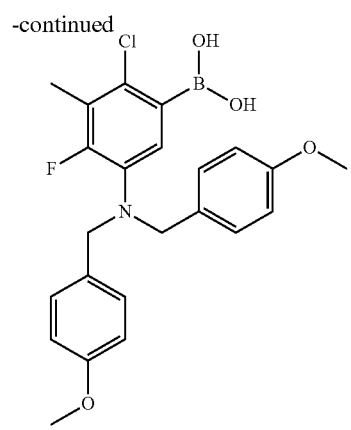

Step 1: 5-Bromo-2-fluoro-N,N-bis(4-methoxybenzyl)-3-methylaniline

Under nitrogen, to a solution of 5-bromo-2-fluoro-3-methyl-aniline (1.00 g, 4.90 mmol) in N,N-dimethylformamide (10 mL) was added NaH (788 mg, 19.7 mmol, 60% oil suspension) at 0° C. The solution was stirred at 0° C. for 30 min. Then PMBCl (1.92 g, 12.3 mmol) was added at 0° C., and the mixture was stirred at room temperature for 1 h. The reaction was quenched with water and extracted with ethyl acetate. The combined organic layers were washed with brine, dried over anhydrous sodium sulfate and concentrated under vacuum. The residue was purified by flash chromatography on silica gel (gradient: 0-20% EtOAc in petroleum ether) to afford the title compound (2.15 g, 98.7% yield) as a yellow solid. LC-MS: (ESI, m/z): $[M+H]^+$=444.

Step 2: 5-Bromo-4-chloro-2-fluoro-N,N-bis(4-methoxybenzyl)-3-methylaniline

A solution of 5-bromo-2-fluoro-N,N-bis[(4-methoxyphenyl)methyl]-3-methyl-aniline (1.00 g, 2.25 mmol) and NCS (300 mg, 2.26 mmol) in 1-methyl-2-pyrrolidinone (10 mL) was stirred at 60° C. for 1 h. EtOAc was added to dilute the reaction mixture, which was then washed with water and brine, dried over anhydrous sodium sulfate and concentrated under vacuum. The residue was purified by flash chromatography on silica gel (gradient: 0-20% EtOAc in petroleum ether) to afford the title compound (1.01 g, 93.7% yield) as a yellow oil. LC-MS: (ESI, m/z): $[M+H]^+$=478.

Step 3: (5-(Bis(4-methoxybenzyl)amino)-2-chloro-4-fluoro-3-methylphenyl)boronic acid Under nitrogen, to a solution of 5-bromo-4-chloro-2-fluoro-N,N-bis[(4-methoxyphenyl)methyl]-3-methyl-aniline (500 mg, 1.04 mmol) and triisopropyl borate (985 mg, 5.24 mmol) in tetrahydrofuran (10 mL) was added n-BuLi (2.5 M in Hex) (0.63 mL, 1.58 mmol) at −78° C. The resulting solution was stirred at −78° C. for 1 h. MeOH was added at −78° C. to quench the reaction. Solvent was evaporated under vacuum. The residue was purified by flash chromatography on silica gel (gradient: 0-300% EtOAC (0.01% $Et_3N$) in petroleum ether (10% DCM)) to afford the title compound (244 mg, 52.7% yield) as a colorless oil. LC-MS: (ESI, m/z): $[M+H]^+$=444.

Intermediate 70: (6-(Bis(4-methoxybenzyl)amino)-2-methyl-3-(trifluoromethyl)pyridin-4-yl)boronic acid

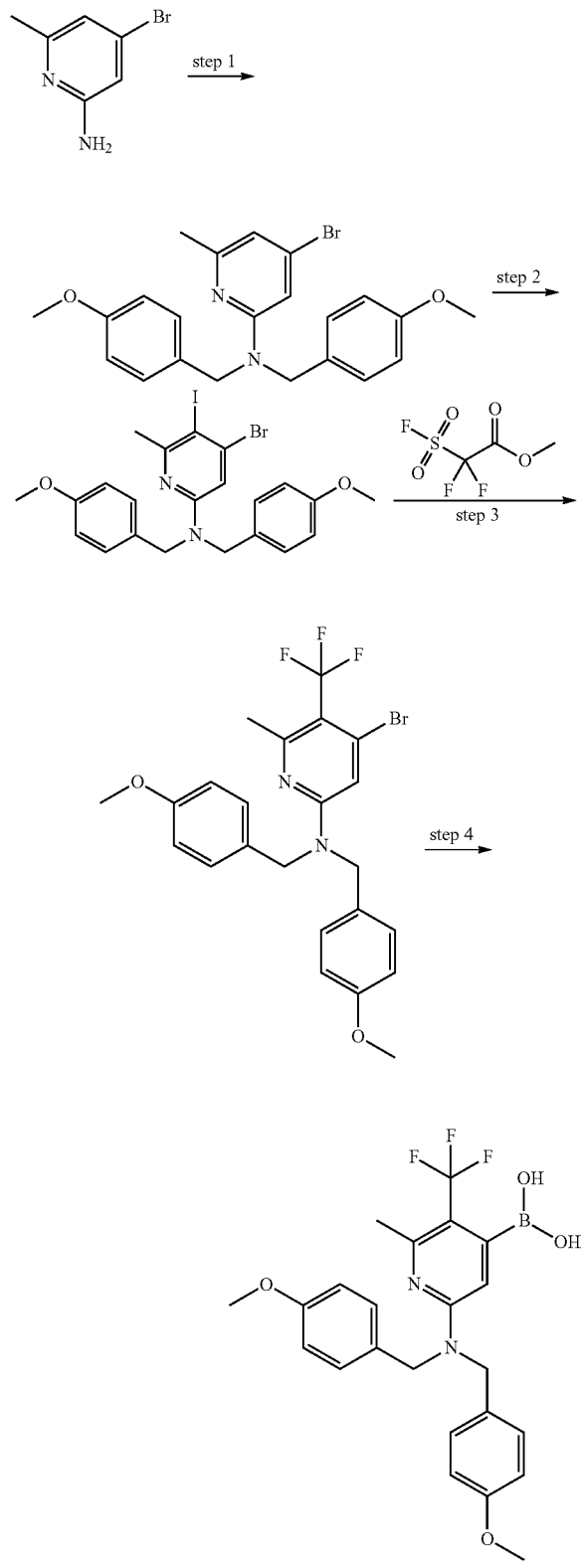

Step 1: 4-Bromo-N,N-bis(4-methoxybenzyl)-6-methylpyridin-2-amine

Under nitrogen, to a solution of 4-bromo-6-methylpyridin-2-amine (1.0 g, 5.35 mmol) was added NaH (535 mg, 13.4 mmol, 60% oil suspension) at 0° C. The mixture was stirred for 20 min. PMBCl (1.85 g, 11.8 mmol) was added, and the mixture was allowed to warm to room temperature and stirred for 1 additional hour. The reaction was quenched with water. The resulting mixture was extracted with EtOAc. The combined organic layers were washed with brine, dried over anhydrous sodium sulfate and concentrated under vacuum. The residue was purified by flash chromatography on silica gel (gradient: 0-20% EtOAc in petroleum ether) to afford the title compound (2.20 g, 94.7% yield) as a white solid. LC-MS: (ESI, m/z): [M+H]$^+$=427.

Step 2: 4-Bromo-5-iodo-N,N-bis(4-methoxybenzyl)-6-methylpyridin-2-amine

A solution of 4-bromo-N,N-bis(4-methoxybenzyl)-6-methylpyridin-2-amine (2.10 g, 4.91 mmol) and NIS (1.11 g, 4.91 mmol) in acetic acid (20 mL) was stirred at room temperature for 30 min. The reaction was quenched with water. The resulting mixture was extracted with EtOAc. The combined organic layers were washed with brine, dried over anhydrous sodium sulfate and concentrated under vacuum. The residue was purified by flash chromatography on silica gel (gradient: 0-20% EtOAc in petroleum ether) to afford the title compound (2.60 g, 88.9% yield) as a white solid. LC-MS: (ESI, m/z): [M+H]$^+$=553.

Step 3: 4-Bromo-N,N-bis(4-methoxybenzyl)-6-methyl-5-(trifluoromethyl)pyridin-2-amine Under nitrogen, a solution of 4-bromo-5-iodo-N,N-bis(4-methoxybenzyl)-6-methylpyridin-2-amine (2.58 g, 4.66 mmol), methyl 2,2-difluoro-2-(fluorosulfonyl)acetate (5.94 mL, 46.6 mmol) and CuI (8.86 g, 46.6 mmol) in N,N-Dimethylacetamide (25 mL) was stirred at 90° C. for 1 hour. The solution was cooled to room temperature. The resulting mixture was filtered. The filtrate was concentrated under reduced pressure. The crude product was diluted with EtOAc, then washed with water. The organic layer was dried over anhydrous Na$_2$SO$_4$ and concentrated under vacuum. The residue was purified by flash chromatography on silica gel (gradient: 0-20% EtOAc in petroleum ether) to afford the title compound (1.92 g, 70.5% yield) as a white solid. LC-MS: (ESI, m/z): [M+H]$^+$=495.

Step 4: (6-(Bis(4-methoxybenzyl)amino)-2-methyl-3-(trifluoromethyl)pyridin-4-yl)boronic acid Under nitrogen, to a solution of 4-bromo-N,N-bis(4-methoxybenzyl)-6-methyl-5-(trifluoromethyl)pyridin-2-amine (1.83 g, 3.69 mmol) and triisopropyl borate (1.28 mL, 5.54 mmol) in tetrahydrofuran (20 mL) was added a solution of n-BuLi (2.77 mL, 1.6 M in hexane) at −78° C., and the mixture was stirred at −78° C. for 1 hour. The reaction was quenched with water. The resulting mixture was extracted with EtOAc. The combined organic layers were washed with brine, dried over anhydrous sodium sulfate and concentrated under vacuum. The residue was purified by flash chromatography on silica gel (gradient: 0-40% EtOAc in petroleum ether) to afford the title compound (562 mg, 31.3% yield) as a white oil. LC-MS: (ESI, m/z): [M+H]$^+$=461.

393

Intermediate 71: 2-Fluoro-N,N-bis(4-methoxybenzyl)-3-methyl-5-(4,4,5,5-tetramethyl-1,3,2-dioxaborolan-2-yl)-4-(2,2,2-trifluoroethyl)aniline

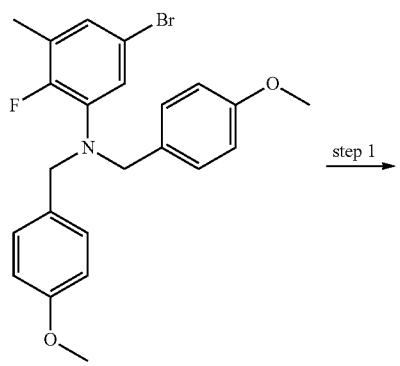

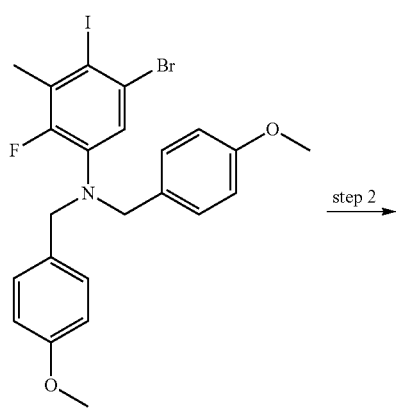

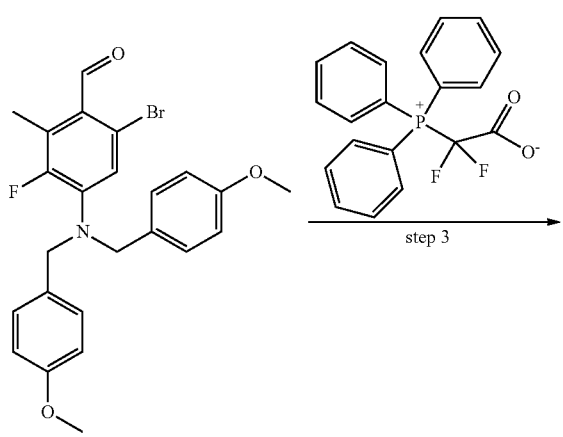

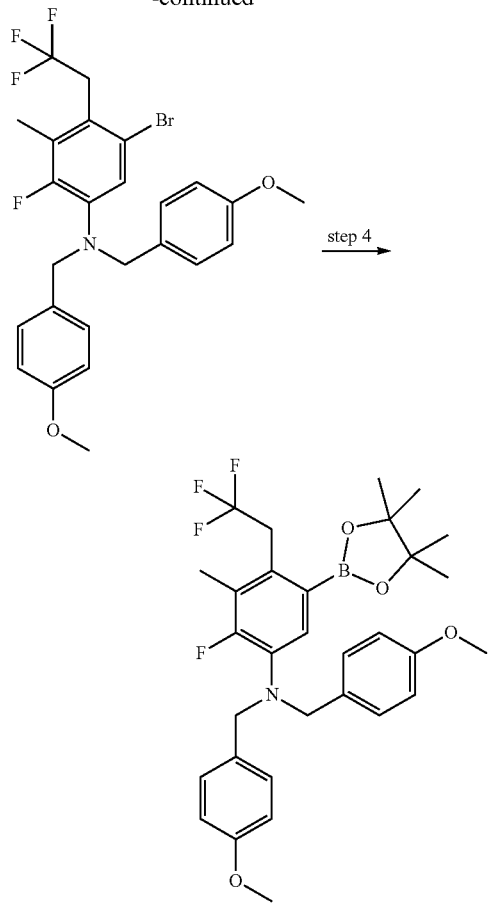

Step 1: 5-Bromo-2-fluoro-4-iodo-N,N-bis(4-methoxybenzyl)-3-methylaniline

A solution of 5-bromo-2-fluoro-N,N-bis(4-methoxybenzyl)-3-methylaniline (4.11 g, 9.25 mmol, intermediate 69, step 1) and NIS (2.71 g, 12.0 mmol) in acetic acid (40 mL) was stirred at room temperature for 1 hour. Then the reaction was quenched with aqueous $Na_2S_2O_3$ solution and extracted with EtOAc. The combined organic layers were dried over anhydrous sodium sulfate and concentrated under vacuum. The residue was purified by flash chromatography on silica gel (gradient: 0-8% EtOAc in petroleum ether) to afford 4.22 g (80% yield) of the title compound as a yellow solid. LC-MS: (ESI, m/z): $[M+H]^+$=570, 572.

Step 2: 4-(Bis(4-methoxybenzyl)amino)-6-bromo-3-fluoro-2-methylbenzaldehyde

Under nitrogen, to a solution of 5-bromo-2-fluoro-4-iodo-N,N-bis(4-methoxybenzyl)-3-methylaniline (4.17 g, 7.31 mmol) in tetrahydrofuran (45 mL) was added i-PrMgCl (4.10 mL, 2M in THF) at −60° C. The solution was stirred at −60° C. for 1 hour. Then DMF (5.34 g, 73.2 mmol) was added at −60° C. The solution was warmed to room temperature and stirred for 0.5 hour. Then the reaction was quenched with aqueous $NH_4Cl$ solution and extracted with EtOAc. The combined organic layers were dried over anhydrous sodium sulfate and concentrated under vacuum. The residue was purified by flash chromatography on silica gel (gradient: 0-10% EtOAc in petroleum ether) to afford 1.72 g (50% yield) of the title compound as yellow solid. LC-MS: (ESI, m/z): [M+H]⁺=472, 474.

Step 3: 5-Bromo-2-fluoro-N,N-bis(4-methoxybenzyl)-3-methyl-4-(2,2,2-trifluoroethyl)aniline A solution of 4-(bis(4-methoxybenzyl)amino)-6-bromo-3-fluoro-2-methylbenzaldehyde (660 mg, 1.40 mmol) and 2,2-difluoro-2-(triphenylphosphonio)acetate (998 mg, 2.80 mmol) in N,N-Dimethylformamide (16 mL) was stirred at 60° C. for 2.5 hours. To the reaction solution was added TBAF (12.0 mL, 1M in THF), and the mixture was stirred at 60° C. for 3 hours. The reaction was cooled to room temperature, quenched with brine and extracted with EtOAc. The combined organic layers were dried over anhydrous sodium sulfate and concentrated under vacuum. The residue was purified by flash chromatography on silica gel (gradient: 0-5% EtOAc in petroleum ether) to afford 424 mg (58% yield) of the title compound as colorless oil. LC-MS: (ESI, m/z): [M+H]⁺=526/528. ¹H NMR (300 MHz, DMSO-d6, ppm) δ 7.21 (d, J=8.7 Hz, 4H), 7.04 (d, J=8.4 Hz, 1H), 6.88 (d, J=8.7 Hz, 4H), 4.25 (s, 4H), 3.81-3.75 (m, 2H), 3.72 (s, 6H), 2.27 (s, 3H).

Step 4: 2-Fluoro-N,N-bis(4-methoxybenzyl)-3-methyl-5-(4,4,5,5-tetramethyl-1,3,2-dioxaborolan-2-yl)-4-(2,2,2-trifluoroethyl)aniline Under nitrogen, a solution of 5-bromo-2-fluoro-N,N-bis(4-methoxybenzyl)-3-methyl-4-(2,2,2-trifluoroethyl)aniline (510 mg, 0.970 mmol), PdCl₂(dppf) (149 mg, 0.190 mmol), Pin₂B₂ (738 mg, 2.91 mmol) and KOAc (286 mg, 2.91 mmol) in 1,4-dioxane (15 mL) was stirred at 110° C. for 4 hours. The reaction system was cooled to room temperature, diluted with brine and extracted with EtOAc. The combined organic layers were dried over anhydrous sodium sulfate and concentrated under vacuum. The residue was purified by flash chromatography on silica gel (gradient: 0-7% EtOAc in petroleum ether) to afford 330 mg (59% yield) of the title compound as a white solid. LC-MS: (ESI, m/z): [M+H]⁺=574. ¹H NMR (300 MHz, CDCl₃, ppm) δ 7.33-7.23 (m, 5H), 6.84-6.81 (m, 4H), 4.24 (s, 4H), 3.93-3.86 (m, 2H), 3.80 (s, 6H), 2.27 (s, 3H), 1.30 (s, 12H).

Intermediate 72: (2-Aminoquinolin-8-yl)boronic acid

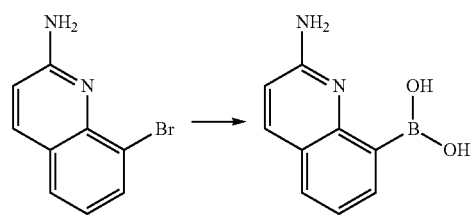 [SMILES: Nc1ccc2cccc(Br)c2n1 ; Nc1ccc2cccc(B(O)O)c2n1]

Under nitrogen, a mixture of 8-bromoquinolin-2-amine (100 mg, 0.450 mmol), Pin₂B₂ (342 mg, 1.34 mmol), Pd(dppf)Cl₂ (32.7 mg, 0.0400 mmol) and KOAc (132 mg, 1.34 mmol) in 1,4-dioxane (5 mL) was stirred at 100° C. for 3 hours. The reaction mixture was diluted with water and extracted with ethyl acetate. The combined organic layers were dried over anhydrous sodium sulfate and concentrated under vacuum. The residue was purified by reverse phase flash chromatography on a pre-packed C18 column (gradient: 0-30% CH₃CN in water (0.05% TFA) to afford 55.0 mg (45.4% yield) of the title compound as a yellow solid. LC-MS: (ESI, m/z): [M+H]⁺=189.

Intermediate 73: (5-(Bis(4-methoxybenzyl)amino)-2,3-bis(trifluoromethyl)phenyl)boronic acid

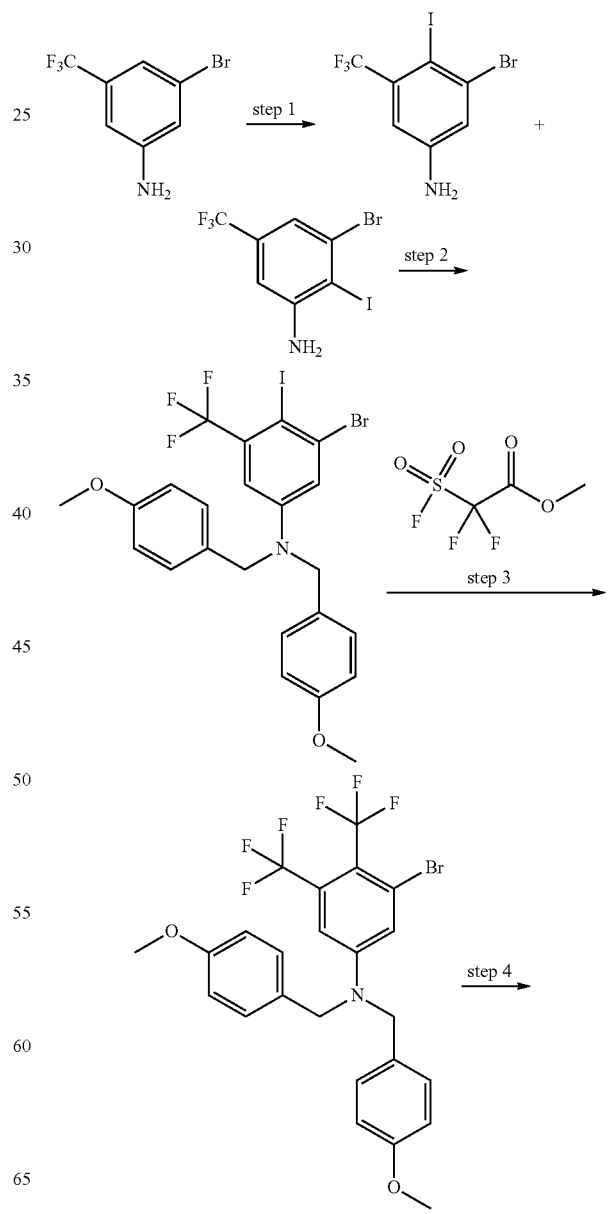

-continued

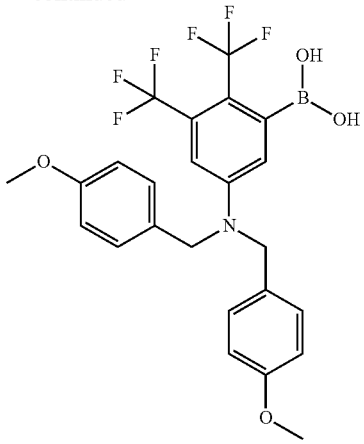 [SMILES: COc1ccc(CN(Cc2ccc(OC)cc2)c2cc(B(O)O)c(C(F)(F)F)c(C(F)(F)F)c2)cc1]

Step 1: 3-Bromo-4-iodo-5-(trifluoromethyl)aniline and 3-bromo-2-iodo-5-(trifluoromethyl)aniline A solution of 3-bromo-5-(trifluoromethyl)aniline (1.00 g, 4.17 mmol) and NIS (937 mg, 4.17 mmol) in acetic acid (10 mL) was stirred at room temperature for 1 hour. The reaction was quenched with water, and the mixture was extracted with EtOAc. The combined organic layers were washed with brine, dried over anhydrous sodium sulfate and concentrated under vacuum. The residue was purified by flash chromatography on silica gel (gradient: 0-20% EtOAc in petroleum ether) to afford the title compound 1 (185 mg, 12.0% yield) as a yellow solid, together with by-product 2 (980 mg, 63.1% yield) as a yellow oil. LC-MS: (ESI, m/z): [M+H]$^+$=366.

Step 2: 3-Bromo-4-iodo-N,N-bis(4-methoxybenzyl)-5-(trifluoromethyl)aniline

To a solution of 3-bromo-4-iodo-5-(trifluoromethyl)aniline (165 mg, 0.450 mmol) was added NaH (45.1 mg, 1.13 mmol) at 0° C. The mixture was stirred for 20 min. PMBCl (156 mg, 0.990 mmol) was added, and the mixture was allowed to warm to room temperature and stirred for 1 additional hour. The reaction was quenched with water, and the mixture was extracted with EtOAc. The combined organic layers were washed with brine, dried over anhydrous sodium sulfate and concentrated under vacuum. The residue was purified by flash chromatography on silica gel (gradient: 0-30% EtOAc in petroleum ether) to afford the title compound (238 mg, 81.0% yield) as a light yellow solid. LC-MS: (ESI, m/z): [M+H]$^+$=606.

Step 3: 3-Bromo-N,N-bis(4-methoxybenzyl)-4,5-bis(trifluoromethyl)aniline

Under nitrogen, a solution of 3-bromo-4-iodo-N,N-bis(4-methoxybenzyl)-5-(trifluoromethyl)aniline (200 mg, 0.330 mmol), methyl 2,2-difluoro-2-(fluorosulfonyl)acetate (0.42 mL, 3.30 mmol) and CuI (627 mg, 3.30 mmol) in N,N-dimethylacetamide (3 mL) was stirred at 80° C. for 1 hour. The solution was cooled to room temperature. The resulting mixture was diluted with EtOAc and washed with water. The separated organic layer was concentrated under reduce pressure. The residual was purified by flash chromatography on silica gel (gradient: 0-20% EtOAc in petroleum ether) to afford the title compound (108 mg, 57.9% yield) as a white solid. LC-MS: (ESI, m/z): [M+H]$^+$=548.

Step 4: (5-(Bis(4-methoxybenzyl)amino)-2,3-bis(trifluoromethyl)phenyl)boronic acid Under nitrogen, to a solution of 3-bromo-N,N-bis(4-methoxybenzyl)-4,5-bis(trifluoromethyl)aniline (95.0 mg, 0.170 mmol) and triisopropyl borate (0.06 mL, 0.260 mmol) in tetrahydrofuran (2 mL) was added a solution of n-BuLi (0.13 mL, 1.6 M in hexane) at −78° C. The reaction was stirred at −78° C. for 1 hour. The reaction was quenched with water, and the mixture was extracted with EtOAc. The combined organic layers were washed with brine, dried over anhydrous sodium sulfate and concentrated under vacuum. The residue was purified by flash chromatography on silica gel (gradient: 0-20% EtOAc in petroleum ether) to afford the title compound (25.0 mg, 28.1% yield) as a white solid. LC-MS: (ESI, m/z): [M+H]$^+$=514.

Intermediate 74: (2-Aminobenzo[d]thiazol-4-yl)boronic acid

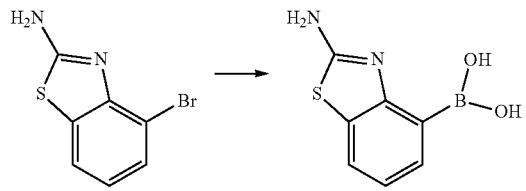 [SMILES: Nc1nc2c(Br)cccc2s1 ; Nc1nc2c(B(O)O)cccc2s1]

Under nitrogen, a mixture of 4-bromobenzo[d]thiazol-2-amine (200 mg, 0.873 mmol), Pin$_2$B$_2$ (665 mg, 2.62 mmol), Pd(dppf)Cl$_2$ (63.8 mg, 0.0873 mmol) and KOAc (257 mg, 2.62 mmol) in 1,4-dioxane (6 mL) was stirred at 100° C. for 2 hours. The reaction mixture was diluted with water and extracted with ethyl acetate. The combined organic layers were dried over anhydrous sodium sulfate and concentrated under vacuum. The residue was purified by reverse phase flash chromatography on a pre-packed C18 column (gradient: 0-30% CH$_3$CN in water (0.05% NH$_4$HCO$_3$) to afford 90.0 mg (53.1% yield) of the title compound as a white solid. LC-MS: (ESI, m/z): [M+H]$^+$=195.

Intermediate 75: 4-(tert-Butyl)-N,N-bis(4-methoxybenzyl)-3-(4,4,5,5-tetramethyl-1,3,2-dioxaborolan-2-yl)aniline

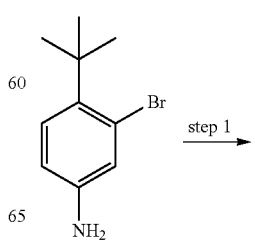

-continued

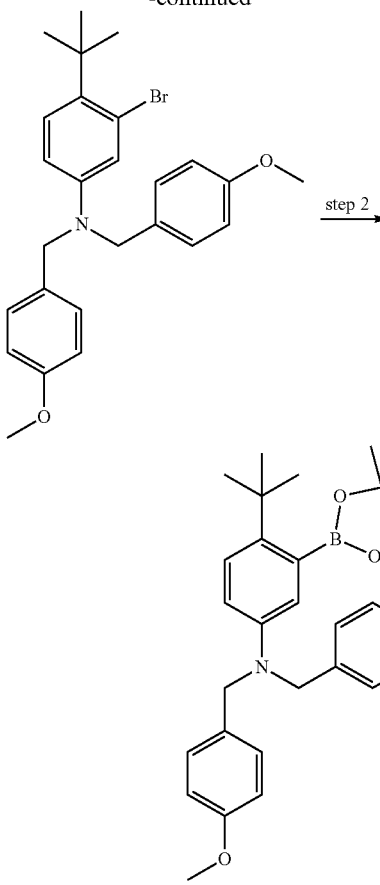

Step 1: 3-Bromo-4-(tert-butyl)-N,N-bis(4-methoxybenzyl)aniline

Under nitrogen, to a solution of 3-bromo-4-(tert-butyl) aniline (190 mg, 0.833 mmol) in N,N-dimethylformamide (3 mL) was added NaH (200 mg, 8.33 mmol) at 0° C., and the mixture was stirred at room temperature for 30 minutes. Then PMBCl (325 mg, 2.08 mmol) was added, and the mixture stirred at room temperature for 12 hours. The reaction was quenched with saturated $NH_4Cl$ aqueous solution, diluted with water and extracted with ethyl acetate. The combined organic layers were washed with brine, dried over anhydrous sodium sulfate and concentrated under vacuum. The residue was purified by flash chromatography on silica gel (gradient: 0-12% ethyl acetate/petroleum ether) to afford the title compound (290 mg, 74.4% yield) as a yellow solid. LC-MS: (ESI, m/z): $[M+H]^+=470$.

Step 2: 4-(tert-Butyl)-N,N-bis(4-methoxybenzyl)-3-(4,4,5,5-tetramethyl-1,3,2-dioxaborolan-2-yl)aniline Under nitrogen, a mixture of 3-bromo-4-(tert-butyl)-N,N-bis(4-methoxybenzyl)aniline (280 mg, 0.598 mmol), $Pin_2B_2$ (228 mg, 0.898 mmol), $Pd(dppf)Cl_2$ (44.0 mg, 0.0600 mmol) and KOAc (117 mg, 1.19 mmol) in 1,4-dioxane (5 mL) was stirred at 90° C. overnight. The reaction mixture was diluted with water and extracted with ethyl acetate. The combined organic layers were dried over anhydrous sodium sulfate and concentrated under vacuum. The residue was purified by flash chromatography on silica gel (gradient: 0-20% ethyl acetate in petroleum ether) to afford the title compound (300 mg, 97% yield) as a yellow oil. LC-MS: (ESI, m/z): $[M+H]^+=516$.

Intermediate 76: 3-Chloro-2-fluoro-5-(4,4,5,5-tetramethyl-1,3,2-dioxaborolan-2-yl)aniline

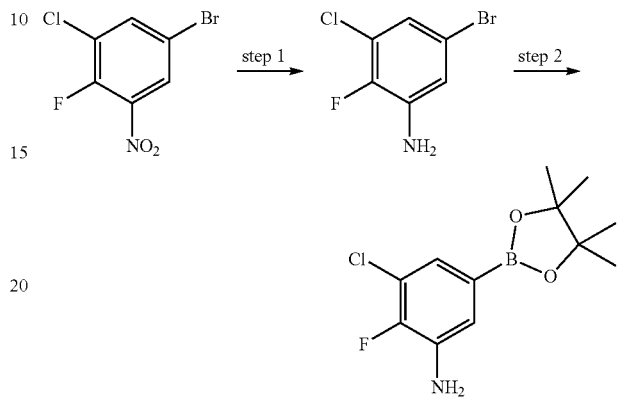

Step 1: 5-Bromo-3-chloro-2-fluoroaniline

To a stirred solution of 5-bromo-1-chloro-2-fluoro-3-nitrobenzene (2.00 g, 7.86 mmol) in ethanol (70 mL) was added $NH_4Cl$ (4.20 g, 78.6 mmol), Fe (2.19 g, 39.3 mmol) and $H_2O$ (30 mL). The resulting solution was stirred at 80° C. overnight. The reaction system was cooled to room temperature and extracted with EtOAc. The combined organic layers were washed with saturated NaCl solution, dried over anhydrous sodium sulfate and concentrated under vacuum. The residue was purified by flash chromatography on silica gel (gradient: 0-20% EtOAc in petroleum ether) to afford 1.5 g (85% yield) of the title compound as a yellow solid. LC-MS: (ESI, m/z): $[M+MeCN]^+=265$.

Step 2: 3-Chloro-2-fluoro-5-(4,4,5,5-tetramethyl-1,3,2-dioxaborolan-2-yl)aniline Under nitrogen, a solution of 5-bromo-3-chloro-2-fluoroaniline (200 mg, 0.890 mmol), $Pin_2B_2$ (339 mg, 1.34 mmol), $Pd(dppf)Cl_2$ (65.2 mg, 0.0900 mmol) and KOAc (175 mg, 1.78 mmol) in 1,2-dimethoxyethane (8 mL) was stirred at 100° C. overnight. The mixture was concentrated under vacuum. The residue was purified by flash chromatography on silica gel (gradient: 0-20% EtOAc in petroleum ether) to afford 230 mg (95.1% yield) of the title compound as a yellow oil. LC-MS: (ESI, m/z): $[M+H]^+=272$.

Intermediate 77: 1-(Allylsulfonyl)-3-methoxyisoquinoline

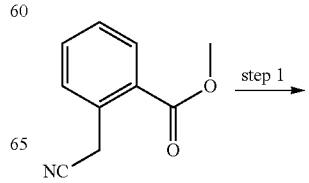

Step 4: 1-(Allylsulfonyl)-3-methoxyisoquinoline

To a stirred solution of 1-(allylthio)-3-methoxyisoquinoline (211 mg, 0.910 mmol) in dichloromethane (5 mL) was added m-CPBA (472 mg, 2.74 mmol) in batches during 1 h at 0° C. The resulting solution was stirred at 25° C. for 3 h. The reaction mixture was quenched with aqueous Na₂S₂O₃ solution and extracted with EtOAc. The combined organic layers were washed with brine and dried over anhydrous sodium sulfate. The solvent was concentrated under vacuum. The residue was purified by flash chromatography on silica gel (gradient: 0-60% EtOAc in petroleum ether) to afford 200 mg (83.3% yield) of the title compound as a yellow solid. LC-MS: (ESI, m/z): [M+H]⁺=264.

Intermediate 78: ((8aR)-Hexahydro-1H-pyrrolo[2,1-c][1,4]oxazin-4-yl)methanol

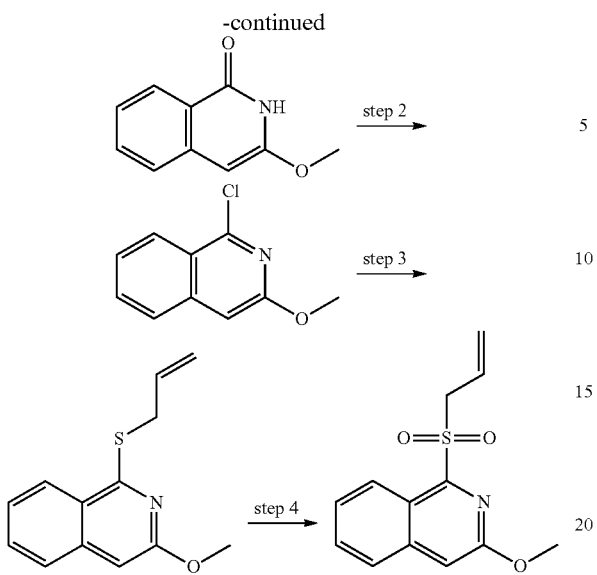

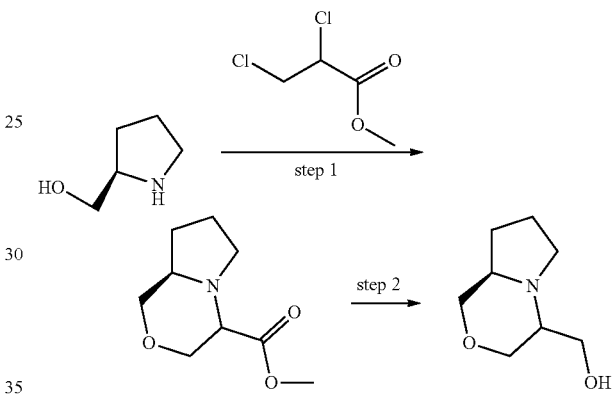

Step 1: 3-Methoxyisoquinolin-1(2H)-one

Under nitrogen, to a stirred solution of methyl 2-(cyanomethyl)benzoate (2.00 g, 11.4 mmol) in methanol (30 mL) was added NaOMe (1.23 g, 22.8 mmol) at 0° C. The result solution was stirred for 3 h at 70° C. The mixture was cooled to room temperature and acidified with 1 mol/L HCl until the solution turned from green to yellow. Then the solution was cooled to 0° C., and the white solid was precipitated. The solid was collected by filtration and dry under vacuum to afford the title compound 600 mg (30.0% yield) as a white solid. LC-MS: (ESI, m/z): [M+H]⁺=176.

Step 2: 1-Chloro-3-methoxyisoquinoline

Under nitrogen, to a stirred solution of 3-methoxyisoquinolin-1(2H)-one (500 mg, 2.85 mmol) in acetonitrile (50 mL) was added POCl₃ (1.31 g, 8.56 mmol). The resulting solution was stirred at 80° C. for 3 h. The mixture was concentrated under vacuum. The residue was dissolved by CH₂Cl₂ (50 mL), the pH was adjusted to pH=7 with saturated NaHCO₃ solution, and the mixture was extracted with CH₂Cl₂. The combined organic layers were washed with brine and dried over anhydrous sodium sulfate. The solvent was concentrated under vacuum. The residue was purified by flash chromatography on silica gel (gradient: 0-40% EtOAc in petroleum ether) to afford 240 mg (43.4% yield) of the title compound as a yellow solid. LC-MS: (ESI, m/z): [M+H]⁺=194.

Step 3: 1-(Allylthio)-3-methoxyisoquinoline

Under nitrogen, to a stirred solution of 1-chloro-3-methoxyisoquinoline (200 mg, 1.03 mmol) in N,N-dimethylformamide (3 mL) were added K₂CO₃ (285 mg, 2.07 mmol) and allyl mercaptan (0.39 mL, 4.85 mmol). The resulting solution was stirred at 25° C. overnight. The residue was purified by reverse phase flash chromatography on a pre-packed C18 column (gradient: 0-100% CH₃CN in water (0.05% TFA)) to yield 200 mg (83.7% yield) the title compound as a yellow solid. LC-MS: (ESI, m/z): [M+H]⁺=232.

Step 1: Methyl (8aR)-hexahydro-1H-pyrrolo[2,1-c][1,4]oxazine-4-carboxylate

Under nitrogen, to a solution of (R)-pyrrolidin-2-ylmethanol (1.01 g, 9.99 mmol) in N,N-dimethylformamide (20 mL) was added methyl 2,3-dichloropropanoate (1.56 g, 9.94 mmol) at 0° C. The resulting solution was stirred at 0° C. for 2 hours and at room temperature for 1 hour. The solution was cooled to 0° C. and NaH (1.04 g, 26.0 mmol, 60% in mineral oil) was added. The solution was stirred at 40° C. for 5 hours. Then the reaction was quenched with aqueous NH₄Cl solution, and the mixture was extracted with EtOAc. The combined organic layers were dried over anhydrous sodium sulfate and concentrated under vacuum. The residue was purified by flash chromatography on silica gel (gradient: 0-70% EtOAc in petroleum ether) to afford 871 mg (47% yield) of the title compound as a yellow oil. LC-MS: (ESI, m/z): [M+H]⁺=186.

Step 2: ((8aR)-Hexahydro-1H-pyrrolo[2,1-c][1,4]oxazin-4-yl)methanol

Under nitrogen, to a solution of methyl (8aR)-hexahydro-1H-pyrrolo[2,1-c][1,4]oxazine-4-carboxylate (125 mg, 0.680 mmol) in tetrahydrofuran (8 mL) was added LiAlH₄ (1.30 mL, 1.30 mmol, 1 M in THF) at 0° C. The solution was stirred at room temperature for 2 hours. The reaction was quenched with Na₂SO₄·10H₂O. The solid was filtered out. The solvent of filtrate was removed by nitrogen blowing to afford 90 mg (crude) of the title compound as colorless oil.

The crude product was used for next step without further purification. LC-MS: (ESI, m/z): [M+H]⁺=158.

Intermediate 79: ((3S)-7,7-Difluorooctahydroindolizin-3-yl)methanol and ((3S)-7-Fluoro-1,2,3,5,6,8a-hexahydroindolizin-3-yl)methanol and ((3S)-7-fluoro-1,2,3,5,6,8a-hexahydroindolizin-3-yl)methanol

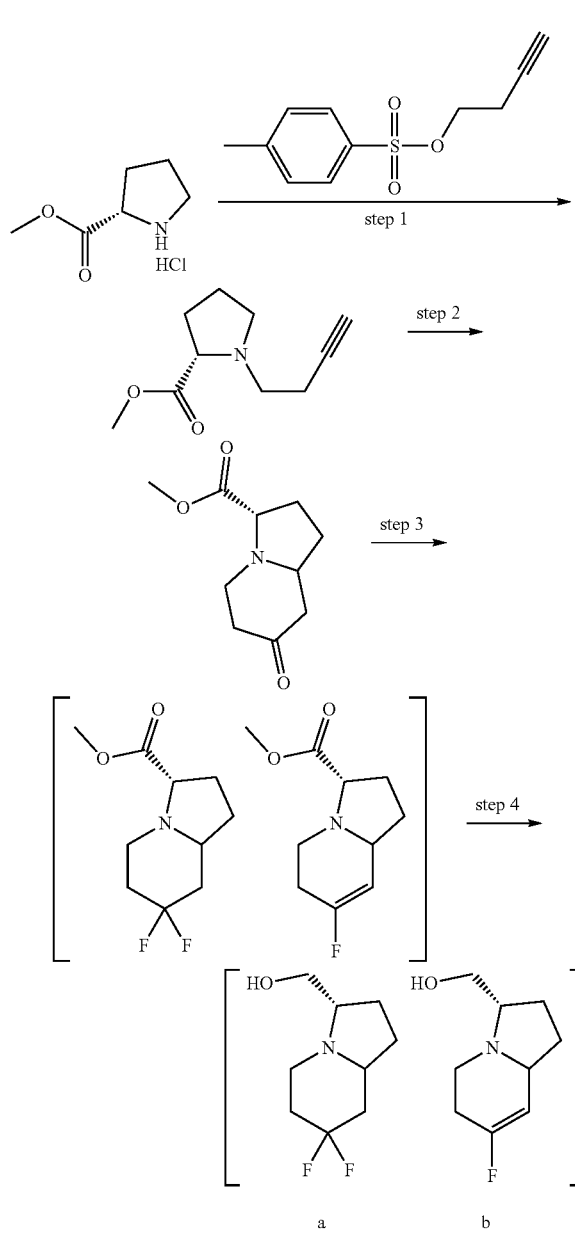

Step 1: Methyl but-3-yn-1-yl-L-prolinate

To a solution of methyl L-prolinate hydrochloride (3.99 g, 24.1 mmol) in acetonitrile (500 mL) were added but-3-yn-1-yl 4-methylbenzenesulfonate (13.6 g, 60.7 mmol), NaI (1.80 g, 12.0 mmol) and Cs₂CO₃ (54.9 g, 168 mmol). The solution was stirred at 80° C. for 6 hours. The system was cooled to room temperature and the solid was filtered out. The filtrate was concentrated under vacuum. The residue was purified by flash chromatography on silica gel (gradient: 0-20% EtOAc in petroleum ether) to afford 3.41 g (78% yield) of the title compound as a brown oil. LC-MS: (ESI, m/z): [M+H]⁺=182.

Step 2: Methyl (3S)-7-oxooctahydroindolizine-3-carboxylate

Under nitrogen, to a solution of methyl but-3-yn-1-yl-L-prolinate (3.41 g, 18.8 mmol) and 4 Å MS (10 g) in dichloromethane (100 mL) was added m-CPBA (4.35 g, 21.4 mmol) at 0° C. The solution was stirred at 0° C. for 2 hours. Then the resulting solution was cooled to −78° C. and added triphenylphosphine gold(I) bis(trifluoromethanesulfonyl)imidate (616 mg, 0.830 mmol). The solution was stirred at −78° C. for 5 hours. The solution was diluted with DCM, washed with aqueous Na₂CO₃ solution and brine. The organic layer was dried over anhydrous sodium sulfate and concentrated under vacuum. The residue was purified by flash chromatography on silica gel eluting (gradient: 0-60% EtOAc in petroleum ether) to afford 1.73 g (47% yield) of the title compound as a brown oil. LC-MS: (ESI, m/z): [M+H]⁺=198. ¹H NMR (300 MHz, CDCl₃, ppm) δ 3.93-3.88 (m, 1H), 3.72 (s, 3H), 3.39-3.23 (m, 2H), 2.99-2.88 (m, 1H), 2.62-2.44 (m, 2H), 2.40-2.148 (m, 4H), 2.09-1.97 (m, 1H), 1.65-1.52 (m, 1H).

Step 3: ((3S)-7,7-Difluorooctahydroindolizin-3-yl)methanol and ((3S)-7-Fluoro-1,2,3,5,6,8a-hexahydroindolizin-3-yl)methanol & ((3S)-7-fluoro-1,2,3,5,6,8a-hexahydroindolizin-3-yl)methanol Under nitrogen, to a solution of methyl (3S)-7-oxooctahydroindolizine-3-carboxylate (1.73 g, 8.77 mmol) in dichloromethane (30 mL) was added DAST (3.0 mL, 24.4 mmol) at −5° C. The solution was stirred at room temperature for 2 hours. The reaction was quenched with aqueous NaHCO₃ solution and extracted with DCM. The combined organic layers were dried over anhydrous sodium sulfate and concentrated under vacuum. The residue was purified by flash chromatography on silica gel (gradient: 0-26% EtOAc in petroleum ether) to afford 90 mg (5% yield) of the mixture of two title compounds as a brown oil. LC-MS: (ESI, m/z): [M+H]⁺=220 and 200.

Step 4: ((3S)-7,7-Difluorooctahydroindolizin-3-yl)methanol and ((3S)-7-Fluoro-1,2,3,5,6,8a-hexahydroindolizin-3-yl)methanol Under nitrogen, to a solution of the mixture of methyl (3S)-7,7-difluorooctahydroindolizine-3-carboxylate and methyl (3S)-7-fluoro-1,2,3,5,6,8a-hexahydroindolizine-3-carboxylate (90.2 mg, 0.410 mmol) in tetrahydrofuran (5 mL) was added LiAlH₄ (0.84 mL, 0.84 mmol, 1 M in THF) at 0° C. The solution was stirred at room temperature for 2 hours. Then the reaction was quenched with Na₂SO₄·10H₂O. The solid was filtered out. The filtrate was concentrated by nitrogen blowing to afford 80 mg mixture of the title compounds as a crude brown oil. The crude mixture was used for next step without further purification. LC-MS: (ESI, m/z): [M+H]⁺=192 and 172.

Intermediate 80: ((2R,7aS)-2-Fluoro-5-methyltetra-hydro-1H-pyrrolizin-7a(5H)-yl)methanol (single unknown stereoisomer

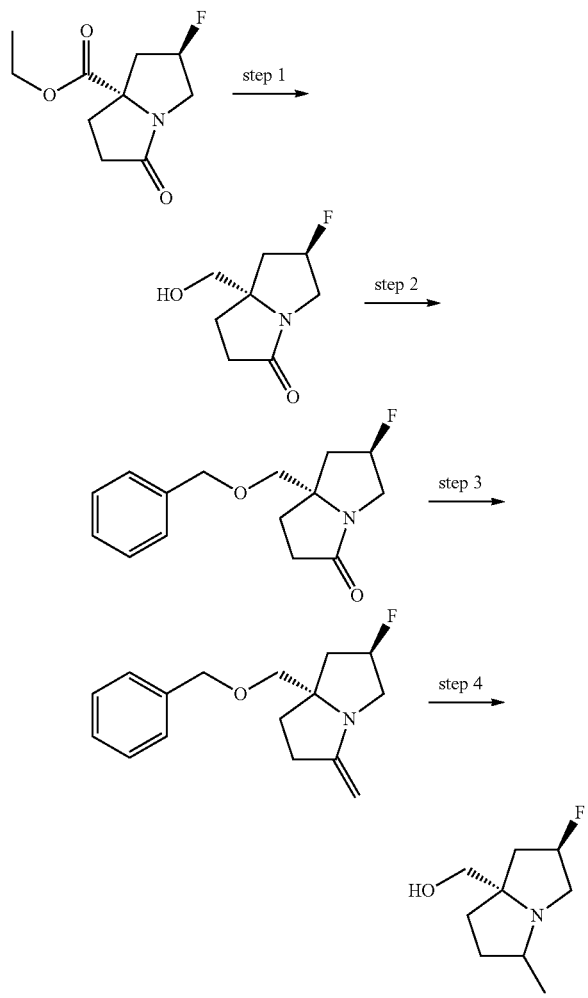

Step 1: (6R,7aS)-6-Fluoro-7a-(hydroxymethyl)hexa-hydro-3H-pyrrolizin-3-one

To a solution of ethyl (2R,7aS)-2-fluoro-5-oxotetrahydro-1H-pyrrolizine-7a(5H)-carboxylate (1.08 g, 5.02 mmol) in methanol (10 mL) was added NaBH$_4$ (284 mg, 7.50 mmol) at 0° C. The solution was stirred at room temperature for 1 hour. The reaction was quenched with saturated NH$_4$Cl aqueous solution. The solvent was concentrated under vacuum. The residue was re-dissolved in dichloromethane, dried over anhydrous sodium sulfate and concentrated under vacuum to afford the title compound (636 mg, 73.2% yield) as a yellow oil. LC-MS: (ESI, m/z): [M+H]$^+$=174.

Step 2: (6R,7aS)-7a-((Benzyloxy)methyl)-6-fluoro-hexahydro-3H-pyrrolizin-3-one To a solution of (6R,7aS)-6-fluoro-7a-(hydroxymethyl)hexahydro-3H-pyrrolizin-3-one in tetrahydrofuran (10 mL) was added NaH (60% dispersion in mineral oil, 340 mg, 8.50 mmol) at 0° C. Then a solution of benzyl bromide (1.16 g, 6.80 mmol) in tetrahydrofuran (10 mL) was added at 0° C., and the mixture was stirred at room temperature for 6 hours. The reaction was quenched with saturated NH$_4$Cl aqueous solution. The reaction mixture was diluted with water and extracted with ethyl acetate. The combined organic layers were washed with brine, dried over anhydrous sodium sulfate and concentrated under vacuum. The residue was purified by flash chromatography on silica gel (gradient: 0-60% ethyl acetate in petroleum ether) to afford the title compound (696 mg, 77.3% yield) as a yellow oil. LC-MS: (ESI, m/z): [M+H]$^+$=264. $^1$H NMR (300 MHz, CDCl$_3$, ppm) δ 7.43-7.29 (m, 5H), 5.44-5.16 (m, 1H), 4.63-4.48 (m, 2H), 4.23-4.02 (m, 1H), 3.41 (d, J=614.8 Hz, 2H), 3.28-3.06 (m, 1H), 2.88-2.70 (m, 1H), 2.49-2.34 (m, 1H), 2.33-2.14 (m, 1H), 2.12-1.94 (m, 2H), 1.60 (s, 1H).

Step 3: (2R,7aS)-7a-((Benzyloxy)methyl)-2-fluoro-5-methylenehexahydro-1H-pyrrolizine Under nitrogen, to a solution of (6R,7aS)-7a-((benzyloxy)methyl)-6-fluorohexahydro-3H-pyrrolizin-3-one (298 mg, 1.13 mmol) in tetrahydrofuran (10 mL) was added Tebbe reagent (0.5M solution in toluene, 6.60 mL, 3.30 mmol) dropwise over a period of 30 minutes at −40° C. The temperature was warmed to room temperature, and the mixture was stirred for 2 hours. The reaction was quenched with saturated NaHCO$_3$ aqueous at 0° C. until effervescence ceased. The reaction mixture was diluted with water and extracted with ethyl acetate. The combined organic layers were washed with brine, dried over anhydrous sodium sulfate and concentrated under vacuum to afford the title compound (1.06 g, crude) as a yellow oil. The crude product was used for next step without further purification. LC-MS: (ESI, m/z): [M+H]$^+$=262.

Step 4: ((2R,7aS)-2-Fluoro-5-methyltetrahydro-1H-pyrrolizin-7a(5H)-yl)methanol (single unknown stereoisomer)

Under hydrogen, to a solution of (2R,7aS)-7a-((benzyloxy)methyl)-2-fluoro-5-methylenehexahydro-1H-pyrrolizine (261 mg, 1.00 mmol) in methanol (10 mL) were added 10% Pd/C (106 mg, wet) and 20% Pd(OH)$_2$/C (140 mg) at room temperature. The solution was stirred at 50° C. for 2 hours. The resulting mixture was filtered. the filter cake was washed with methanol. The combined filtrate was concentrated under vacuum to afford the title compound (single unknown stereoisomer, 140 mg, crude) as an orange oil. The crude product was used for the next step without further purification. LC-MS: (ESI, m/z): [M+H]$^+$=174.

Intermediate 81: 6-(Hydroxymethyl)-2-methylhexa-hydropyrrolo[1,2-a]pyrazin-1(2H)-one (mixture of trans isomers

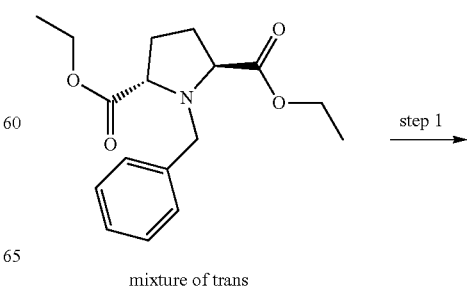

mixture of trans

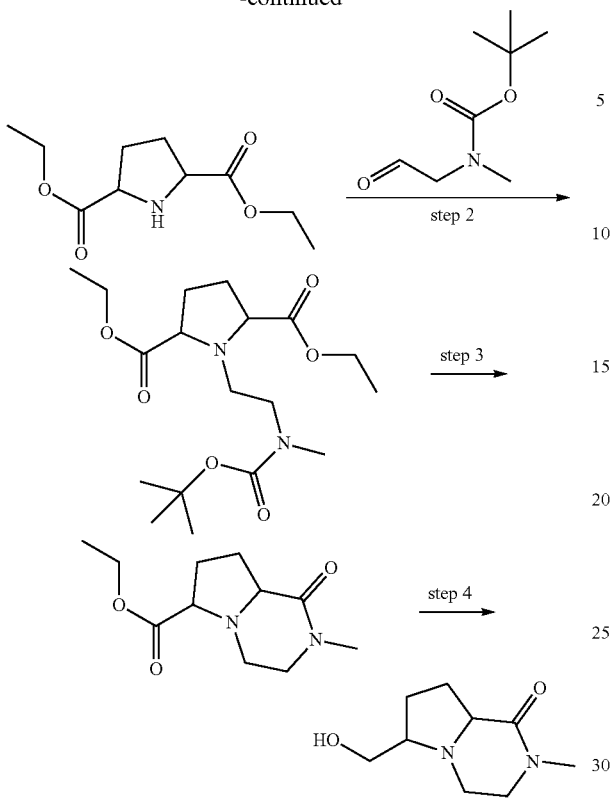

Step 1: Diethyl pyrrolidine-2,5-dicarboxylate (mixture of trans isomers)

Under hydrogen, to a solution of diethyl 1-benzylpyrrolidine-2,5-dicarboxylate (mixture of trans isomers, 730 mg, 2.39 mmol) in methanol (10 mL) were added 10% Pd/C (255 mg) and 20% Pd(OH)$_2$/C (440 mg) at room temperature. The resulting mixture was stirred at room temperature for 2 hours. The resulting mixture was filtered. The filter cake was washed with methanol. The combined filtrate was concentrated under vacuum to afford the title compound (mixture of trans isomers, 507 mg, 98.4% yield) as a light yellow oil. LC-MS: (ESI, m/z): [M+H]$^+$=216. $^1$H NMR (300 MHz, CDCl$_3$, ppm) δ 4.21 (q, J=7.1 Hz, 4H), 4.06-3.93 (m, 2H), 2.31-2.10 (m, 2H), 2.04-1.88 (m, 2H), 1.30 (t, J=7.1 Hz, 6H).

Step 2: Diethyl 1-(2-((tert-butoxycarbonyl)(methyl)amino)ethyl)pyrrolidine-2,5-dicarboxylate (mixture of trans isomers)

To a solution of diethyl pyrrolidine-2,5-dicarboxylate (mixture of trans isomers, 300 mg, 1.39 mmol) in dichloromethane (10 mL) was added a solution of tert-butyl methyl(2-oxoethyl)carbamate (1.21 g, 6.99 mmol) in dichloromethane (2 mL) at 0° C., and the mixture was stirred for 30 minutes. Then NaBH(OAc)$_3$ (1.48 g, 6.98 mmol) was added at 0° C., and the mixture was stirred at room temperature for 3 hours. The reaction was quenched with water and extracted with dichloromethane. The combined organic layers were washed with brine, dried over anhydrous sodium sulfate and concentrated under vacuum. The residue was purified by flash chromatography on silica gel (gradient: 0-30% ethyl acetate in petroleum ether) to afford the title compound (mixture of trans isomers, 488 mg, 94.0% yield) as a light yellow oil. LC-MS: (ESI, m/z): [M+H]$^+$=373. $^1$H NMR (300 MHz, CDCl$_3$, ppm) δ 4.19 (q, J=7.1 Hz, 4H), 3.97-3.89 (m, 2H), 3.48-3.20 (m, 2H), 3.04-2.93 (m, 2H), 2.87 (s, 3H), 2.43-2.21 (m, 2H), 2.03-1.86 (m, 2H), 1.47 (s, 9H), 1.30 (t, J=7.1 Hz, 6H).

Step 3: Ethyl 2-methyl-1-oxooctahydropyrrolo[1,2-a]pyrazine-6-carboxylate (mixture of trans isomers)

To a solution of diethyl 1-(2-((tert-butoxycarbonyl)(methyl)amino)ethyl)pyrrolidine-2,5-dicarboxylate (mixture of trans isomers, 438 mg, 1.18 mmol) in ethyl acetate (5 mL) was added hydrogen chloride (4M solution in ethyl acetate, 6 mL) at 0° C., and the mixture was stirred at room temperature for 2 hours. The solvent was concentrated under vacuum. The residue was dissolved in methanol, and DIPEA (2 mL) was added. The resulting mixture was stirred at room temperature overnight. The solvent was concentrated under vacuum and the residue was purified by flash chromatography on silica gel (gradient: 0-10% methanol in dichloromethane) to afford the title compound (mixture of trans isomers, 157 mg, 58.8% yield) as a yellow oil. LC-MS: (ESI, m/z): [M+H]$^+$=227.

Step 4: 6-(Hydroxymethyl)-2-methylhexahydropyrrolo[1,2-a]pyrazin-1(2H)-one (mixture of trans isomers)

Under nitrogen, to a mixture of ethyl 2-methyl-1-oxooctahydropyrrolo[1,2-a]pyrazine-6-carboxylate (mixture of trans isomers, 134 mg, 0.592 mmol) in tetrahydrofuran (10 mL) was added LiBH$_4$ (64.5 mg, 2.96 mmol) at room temperature. The solution was stirred at 60° C. for 6 hours. After filtration, the filtrate was concentrated under reduced pressure to afford the title compound (mixture of trans isomers, 84.9 mg, crude) as a colorless solid. The crude product was used for next step without further purification. LC-MS: (ESI, m/z): [M+H]$^+$=185.

Intermediate 82: 6-(hydroxymethyl)-2-methylhexahydropyrrolo[1,2-a]pyrazin-3(4H)-one (mixture of trans isomers

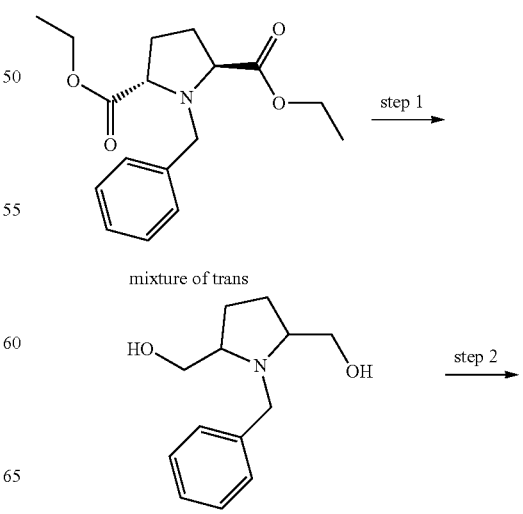

mixture of trans

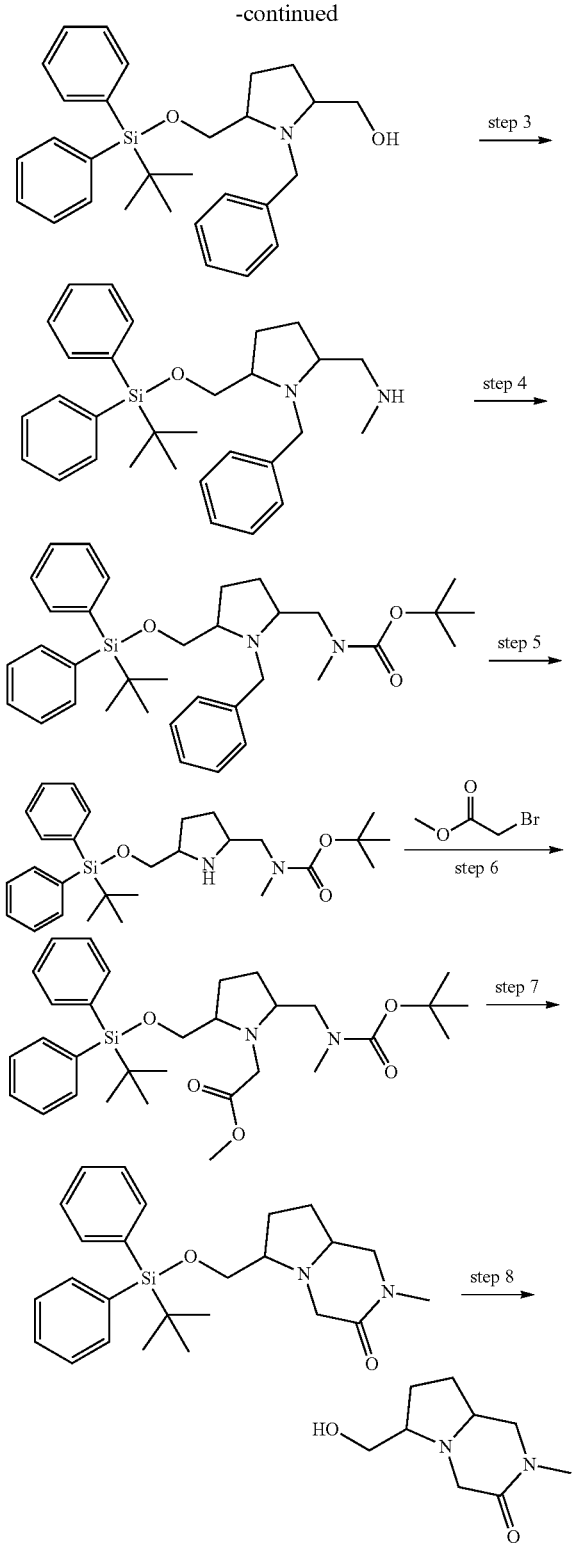

Step 1: (1-Benzylpyrrolidine-2,5-diyl)dimethanol (mixture of trans isomers)

Under nitrogen, to a solution of diethyl 1-benzylpyrrolidine-2,5-dicarboxylate (mixture of trans isomers, 1.00 g, 3.28 mmol) in tetrahydrofuran (8 mL) was added LiAlH$_4$ (311 mg, 8.2 mmol) at 0° C. The solution was stirred at room temperature for 2 hours. The reaction was quenched with Na$_2$SO$_4$·10H$_2$O. After filtration, the filtrate was collected and concentrated under vacuum. The residue was purified by flash chromatography on silica gel (gradient: 0-7% ethyl acetate in petroleum ether) to afford the title compound (mixture of trans isomers, 700 mg, 96.6% yield) as a white solid. LC-MS: (ESI, m/z): [M+H]$^+$=222.

Step 2: (1-Benzyl-5-(((tert-butyldiphenylsilyl)oxy)methyl)pyrrolidin-2-yl)methanol (mixture of trans isomers)

To a solution of (1-benzylpyrrolidine-2,5-diyl)dimethanol (mixture of trans isomers, 720 mg, 2.36 mmol) and DMAP (40.0 mg, 0.330 mmol) in N,N-dimethylformamide (8 mL) were added TBDMSCl (896 mg, 3.26 mmol) and DIPEA (841 mg, 6.52 mmol). The solution was stirred at room temperature for 5 hours. The solvent was concentrated under vacuum. The residue was purified by flash chromatography on silica gel (gradient: 0-13% EtOAc in petroleum ether) to afford the title compound (mixture of trans isomers, 370 mg, 56.7% yield) as a yellow oil. LC-MS: (ESI, m/z): [M+H]$^+$=460.

Step 3: 1-(1-Benzyl-5-(((tert-butyldiphenylsilyl)oxy)methyl)pyrrolidin-2-yl)-N-methylmethanamine (mixture of trans isomers)

Under nitrogen, to a solution of (1-benzyl-5-(((tert-butyldiphenylsilyl)oxy)methyl)pyrrolidin-2-yl)methanol (mixture of trans isomers, 370 mg, 0.806 mmol) and DIPEA (208 mg, 1.61 mmol) in dichloromethane (3 mL) was added trifluoromethanesulfonic anhydride (364 mg, 1.29 mmol) at −78° C. The resulting solution was stirred for 15 minutes at −78° C. Then CH$_3$NH$_2$ (1 mL, 2 M solution in THF) was added at −78° C. The solution was stirred at room temperature for 1 hour. The reaction mixture concentrated under vacuum. The residue was purified by flash chromatography on silica gel (gradient: 0-30% ethyl acetate in petroleum ether) to afford the title compound (mixture of trans isomers, 300 mg, 78.9% yield) as a light yellow oil. LC-MS: (ESI, m/z): [M+H]$^+$=473.

Step 4: tert-Butyl ((1-benzyl-5-(((tert-butyldiphenylsilyl)oxy)methyl)pyrrolidin-2-yl)methyl)(methyl)carbamate (mixture of trans isomers)

To a solution of 1-(1-benzyl-5-(((tert-butyldiphenylsilyl)oxy)methyl)pyrrolidin-2-yl)-N-methylmethanamine (mixture of trans isomers, 612 mg, 1.30 mmol) and DIPEA (201 mg, 1.56 mmol) in dichloromethane (5 mL) was added Boc$_2$O (311 mg, 1.43 mmol) at 0° C. The solution was stirred at room temperature for 2 hours. The solvent was concentrated under vacuum and the residue was purified by flash chromatography on silica gel (gradient: 0-10% methanol in dichloromethane) to afford the title compound (mixture of trans isomers, 270 mg, 36.5% yield) as a light yellow oil. LC-MS: (ESI, m/z): [M+H]$^+$=573.

Step 5: tert-Butyl ((5-(((tert-butyldiphenylsilyl)oxy)methyl)pyrrolidin-2-yl)methyl)(methyl)carbamate (mixture of trans isomers)

Under hydrogen, to a solution of tert-butyl ((1-benzyl-5-(((tert-butyldiphenylsilyl)oxy)methyl)pyrrolidin-2-yl)methyl)(methyl)carbamate(mixture of trans isomers, 290 mg, 0.507 mmol) in methanol (10 mL) were added 10% Pd/C (54.0 mg) and 20% Pd(OH)$_2$/C (71.0 mg) at room temperature. The resulting mixture was stirred at room temperature for 2 hours and then filtered. The filter cake was washed with methanol. The combined filtrate was concentrated under vacuum to afford the title compound (mixture of trans isomers, 210 mg, crude) as a light yellow oil. The crude product was used for next step without further purification. LC-MS: (ESI, m/z): [M+H]$^+$=483.

Step 6: Methyl 2-(2-(((tert-butoxycarbonyl)(methyl) amino)methyl)-5-(((tert-butyldiphenylsilyl)oxy) methyl)pyrrolidin-1-yl)acetate (mixture of trans isomers)

To a mixture of tert-butyl ((5-(((tert-butyldiphenylsilyl) oxy)methyl)pyrrolidin-2-yl)methyl)(methyl)carbamate (mixture of trans isomers, 200 mg, 0.415 mmol) and K$_2$CO$_3$ (170 mg, 1.23 mmol) in acetonitrile (10 mL) was added methyl 2-bromoacetate (100 mg, 0.654 mmol) at room temperature. The solution was stirred at 50° C. for 5 hours. The reaction mixture was diluted with water and extracted with ethyl acetate. The combined organic layers were dried over anhydrous sodium sulfate and concentrated under vacuum. The residue was purified by flash chromatography on silica gel (gradient: 0-18% ethyl acetate in petroleum ether) to afford the title compound (mixture of trans isomers, 215 mg, 93.5% yield) as a light yellow oil. LC-MS: (ESI, m/z): [M+H]$^+$=555.

Step 7: 6-(((tert-butyldiphenylsilyl)oxy)methyl)-2-methylhexahydropyrrolo[1,2-a]pyrazin-3(4H)-one (mixture of trans isomers)

To a solution of methyl 2-(2-(((tert-butoxycarbonyl) (methyl)amino)methyl)-5-(((tert-butyldiphenylsilyl)oxy) methyl)pyrrolidin-1-yl)acetate (mixture of trans isomers, 185 mg, 0.334 mmol) in ethyl acetate (5 mL) was added hydrogen chloride (6 mL, 4 M solution in ethyl acetate) at 0° C. The solution was stirred at room temperature for 2 hours. The solvent was concentrated under vacuum. The residue was dissolved in methanol and added DIPEA (1 mL, 6.00 mmol). The resulting mixture was stirred at room temperature overnight. The solvent was concentrated under vacuum. The residue was purified by flash chromatography on silica gel (gradient: 0-10% methanol in dichloromethane) to afford the title compound (mixture of trans isomers, 130 mg, 92.2% yield) as a yellow oil. LC-MS: (ESI, m/z): [M+H]$^+$=423.

Step 8: 6-(hydroxymethyl)-2-methylhexahydropyrrolo[1,2-a]pyrazin-3(4H)-one (mixture of trans isomers)

A solution of 6-(((tert-butyldiphenylsilyl)oxy)methyl)-2-methylhexahydropyrrolo[1,2-a]pyrazin-3(4H)-one (mixture of trans isomers, 100 mg, 0.237 mmol) and hydrogen chloride (1 mL, 4 M solution in methanol) in methanol (10 mL) was stirred at 60° C. for 2 hours. The solvent was concentrated under vacuum to afford the title compound (mixture of trans isomers, 35.0 mg, crude) as a colorless solid. The crude product was used for next step without further purification. LC-MS: (ESI, m/z): [M+H]$^+$=185.

Intermediate 83: ((6S,8aS)-3,3-Dimethylhexahydro-1H-pyrrolo[2,1-c][1,4]oxazin-6-yl)methanol

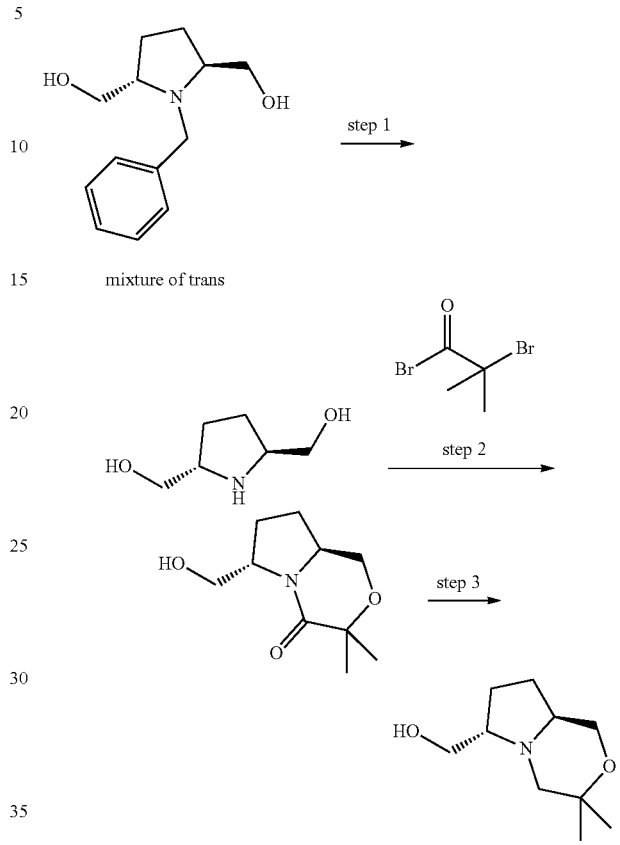

Step 1: ((2S,5S)-Pyrrolidine-2,5-diyl)dimethanol

Under hydrogen, to a solution of ((2S,5S)-1-benzylpyrrolidine-2,5-diyl)dimethanol (305 mg, 1.38 mmol) in methanol (5 mL) was added 10% Pd/C (200 mg) at room temperature. The resulting solution was stirred at room temperature for 3 hours. The resulting mixture was filtered. The filtrate was concentrated under reduced pressure to afford 194 mg (crude) as a yellow oil. LC-MS: (ESI, m/z): [M+H]$^+$=132.

Step 2: (6S,8aS)-6-(Hydroxymethyl)-3,3-dimethyltetrahydro-1H-pyrrolo[2,1-c][1,4]oxazin-4(3H)-one Under nitrogen, to a solution of ((2S,5S)-pyrrolidine-2,5-diyl)dimethanol (180 mg, 1.37 mmol) and TMSOK (351 mg, 2.74 mmol) in IPA (5 mL) was added 2-bromo-2-methylpropanoyl bromide (0.2 mL, 1.65 mmol) at 0° C. The resulting solution was stirred at 0° C. for 0.5 hour. The residue was purified by flash chromatography on silica gel (gradient: 0-10% MeOH in DCM) to afford the title compound (67 mg, 24.5% yield) as a yellow oil. LC-MS: (ESI, m/z): [M+H]$^+$=200.

Step 3: ((6S,8aS)-3,3-Dimethylhexahydro-1H-pyrrolo[2,1-c][1,4]oxazin-6-yl)methanol Under nitrogen, to a solution of (6S,8aS)-6-(hydroxymethyl)-3,3-dimethyltetrahydro-1H-pyrrolo[2,1-c][1,4]

oxazin-4(3H)-one (57.0 mg, 0.290 mmol) in tetrahydrofuran (1 mL) was added a solution of LiAlH₄ in THF (0.29 mL, 2.5 M in THF) at 0° C. The resulting solution was stirred at 70° C. for 0.5 hour. Then Na₂SO₄·10H₂O was added at 0° C. The solids were filtered and washed with tetrahydrofuran. The filtrate was concentrated under reduced pressure to afford 65 mg (crude) of the title compound as a white oil. The crude product was used for next step without further purification LC-MS: (ESI, m/z): [M+H]⁺=186.

Intermediate 84: (2-(2-Fluoroethyl)-1-methylpyrrolidin-2-yl)methanol

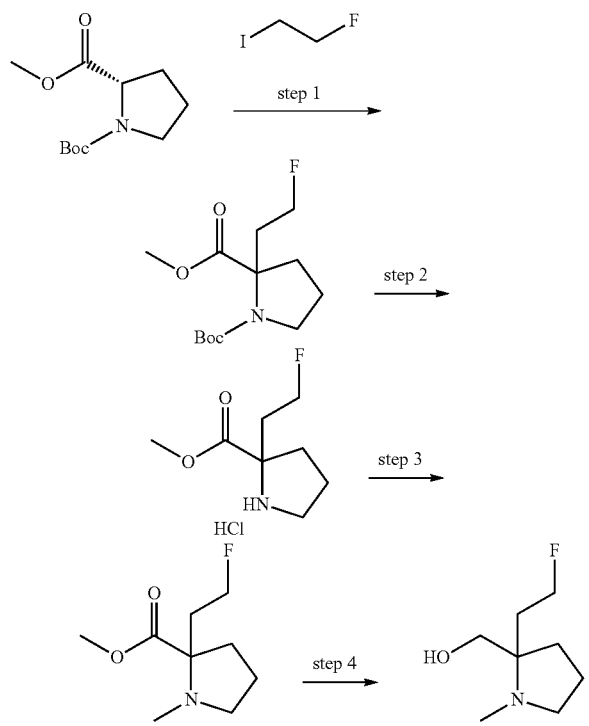

Step 1: 1-(tert-Butyl) 2-methyl 2-(2-fluoroethyl) pyrrolidine-1,2-dicarboxylate

Under nitrogen, to a solution of 1-(tert-butyl) 2-methyl (S)-pyrrolidine-1,2-dicarboxylate (1.0 g, 4.36 mmol) in tetrahydrofuran (40 mL) was added LiHMDS (1 M in THF, 9 mL) at −15° C. The solution was stirred at −15° C. for 1 hour. Then 1-fluoro-2-iodoethane (1.89 g, 10.9 mmol) was added and the solution was stirred additional 0.5 hour at −15° C. Then the mixture was warmed to room temperature and stirred for 2 hours. The reaction was quenched with aqueous NH₄Cl solution and extracted with EtOAc. The combined organic layers were dried over anhydrous sodium sulfate and concentrated under vacuum. The residue was purified by flash chromatography on silica gel (gradient: 0-10% EtOAc/petroleum ether) to afford 1.01 g of the title compound as a colorless oil. LC-MS: (ESI, m/z): [M+H]⁺=276.

Step 2: Methyl 2-(2-fluoroethyl) pyrrolidine-2-carboxylate HCl salt

To a solution of 1-(tert-butyl) 2-methyl 2-(2-fluoroethyl) pyrrolidine-1,2-dicarboxylate (750 mg, 2.72 mmol) in dichloromethane (4 mL) was added HCl (4 M in 1,4-dioxane, 6 mL). The solution and was stirred at room temperature for 1 hour. Then the solution was concentrated under vacuum to afford 561 mg (crude) of the title compound as white solid. LC-MS: (ESI, m/z): [M+H]⁺=176.

Step 3: Methyl 2-(2-fluoroethyl)-1-methylpyrrolidine-2-carboxylate

A solution of methyl 2-(2-fluoroethyl) pyrrolidine-2-carboxylate HCl salt (560 mg, 2.65 mmol), (HCHO)n (676 mg, 22.5 mmol) and NaOAc (440 mg, 5.37 mmol) in dichloromethane (10 mL) and methanol (5 mL) was stirred at room temperature for 2 hours. Then NaBH(OAc)₃ (1.13 g, 5.33 mmol) was added. The solution was stirred at room temperature for 16 hours. The solution was concentrated under vacuum. The residue was diluted with brine and extracted with EtOAc. The combined organic layers were dried over anhydrous sodium sulfate and concentrated under vacuum. The residue was purified by flash chromatography on silica gel (gradient: 0-35% EtOAc/petroleum ether) to afford 421 mg of the title compound as a yellow oil. LC-MS: (ESI, m/z): [M+H]⁺=190.

Step 4: (2-(2-Fluoroethyl)-1-methylpyrrolidin-2-yl)methanol

Under nitrogen, to a solution of methyl 2-(2-fluoroethyl)-1-methylpyrrolidine-2-carboxylate (470 mg, 2.48 mmol) in tetrahydrofuran (15 mL) was added LiAlH₄ (1 M in THF, 5 mL) at 0° C. The solution was stirred at room temperature for 1 hour. The reaction was quenched by Na₂SO₄·10H₂O. The solid was filtered out. The filtrate was concentrated under vacuum to afford 390 mg (crude) of the title compound as colorless oil. LC-MS: (ESI, m/z): [M+H]⁺=162. The crude was used for next step without further purification.

Intermediate 85: (1-(2,2-Difluoroethyl) azetidin-3-yl)methanol

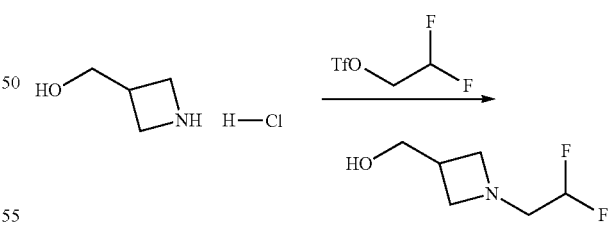

To a solution of azetidin-3-ylmethanol hydrochloride (500 mg, 4.05 mmol) in dichloromethane (5 mL) was added DIPEA (1.57 g, 12.2 mmol) at room temperature, and the mixture was stirred for 30 minutes. Then 2,2-difluoroethyl trifluoromethanesulfonate (870 mg, 4.06 mmol) was added, and the mixture was stirred for 2 hours at room temperature. The solvent was concentrated under vacuum to afford the title compound (2.00 g, crude) as a yellow solid. LC-MS: (ESI, m/z): [M+H]⁺=152. The crude was used for next step without further purification.

Intermediate 86: (R)-(1-((3-Methylmorpholino)methyl)cyclopropyl) methanol

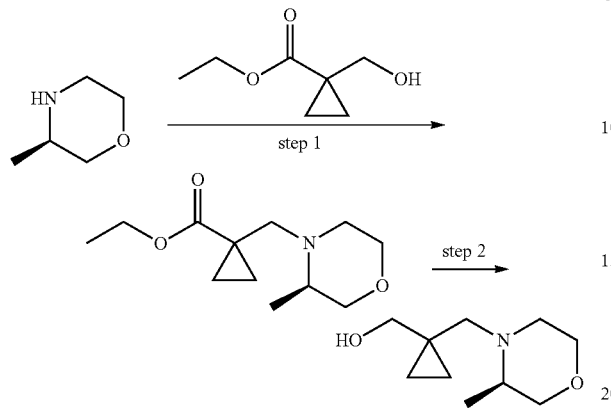

Step 1: Ethyl (R)-1-((3-methylmorpholino)methyl)cyclopropane-1-carboxylate

Under nitrogen, to a solution of ethyl 1-(hydroxymethyl)cyclopropane-1-carboxylate (500 mg, 3.47 mmol) and DIPEA (1.84 mL, 10.4 mmol) in dichloromethane (5 mL) was added Tf$_2$O (1.2 mL, 7.1 mmol) dropwise at −10° C. and the solution was stirred for 5 minutes. Then a solution of (R)-3-methylmorpholine (351 mg, 3.47 mmol) in dichloromethane (1 mL) was added at −10° C., and the mixture was stirred for 1 hour at room temperature. The solvent was concentrated under vacuum to afford the title compound (1.80 g, crude) as a yellow solid. LC-MS: (ESI, m/z): [M+H]$^+$=228.

Step 2: (R)-(1-((3-Methylmorpholino)methyl)cyclopropyl) methanol

Under nitrogen, to a solution of ethyl (R)-1-((3-methylmorpholino)methyl) cyclopropane-1-carboxylate (1.80 g, crude) in THF (20 mL) was added LiAlH$_4$ (600 mg, 15.8 mmol) in portions at 0° C., and the mixture was stirred for 1 hour at room temperature. The reaction was quenched with Na$_2$SO$_4$·10H$_2$O and filtrated. The filtrate was concentrated under reduced pressure to afford the title compound (714 mg, crude) as a yellow oil. LC-MS: (ESI, m/z): [M+H]$^+$= 186. The crude was used for next step without further purification.

Intermediate 87: (3-(Difluoromethyl)tetrahydro-1H-pyrrolizin-7a(5H)-yl) methanol

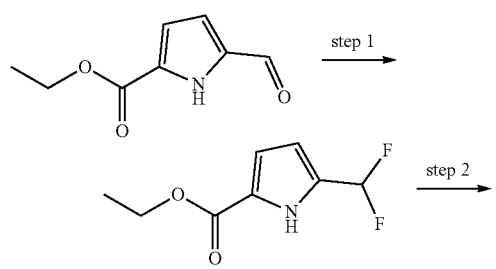

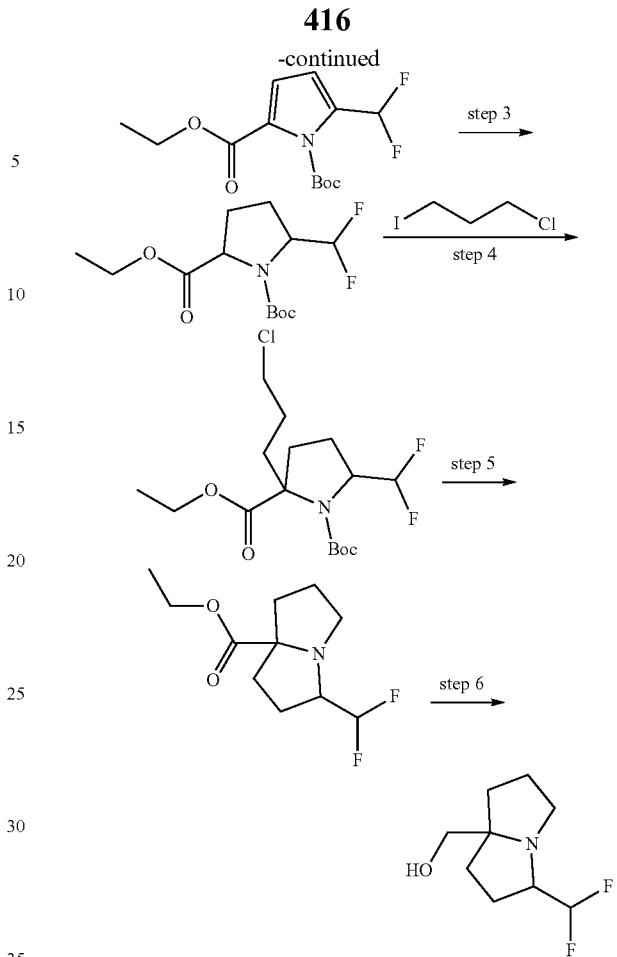

Step 1: Ethyl 5-(difluoromethyl)-1H-pyrrole-2-carboxylate

Under nitrogen, a solution of ethyl 5-formyl-1H-pyrrole-2-carboxylate (5.00 g, 29.9 mmol) and BAST (19.9 g, 89.7 mmol) in 1,2-dichlorobenzene (300 mL) was stirred for 2 hours at 80° C. The reaction was quenched with saturated NaHCO$_3$ aqueous solution. The reaction mixture was diluted with water and extracted with ethyl acetate. The combined organic layers were washed with brine, dried over anhydrous sodium sulfate and concentrated under vacuum. The residue was purified by flash chromatography on silica gel (gradient: 0-10% ethyl acetate in petroleum ether) to afford the title compound (5.00 g) as a white solid. LC-MS: (ESI, m/z): [M+H]$^+$=190.

Step 2: 1-(tert-Butyl) 2-ethyl 5-(difluoromethyl)-1H-pyrrole-1,2-dicarboxylate To a solution of ethyl 5-(difluoromethyl)-1H-pyrrole-2-carboxylate (5.00 g, 26.3 mmol), DMAP (650 mg, 5.30 mmol) and DIPEA (10.2 g, 79.0 mmol) in dichloromethane (300 mL) was added a solution of (Boc)$_2$O (46.2 g, 212 mmol) in dichloromethane (200 mL) dropwise at 0° C., and the mixture was stirred at room temperature for 1 hour. The reaction mixture was diluted with water and extracted with ethyl acetate. The combined organic layers were washed with brine, dried over anhydrous sodium sulfate and concentrated under vacuum. The residue was purified by flash chromatography on silica gel (gradient: 0-10% ethyl acetate in petroleum ether) to afford the title compound (5.40 g) as a yellow solid. LC-MS: (ESI, m/z): [M−56+H]$^+$=234.

Step 3: 1-(tert-Butyl) 2-ethyl 5-(difluoromethyl) pyrrolidine-1,2-dicarboxylate

Under hydrogen (1 atm), a solution of 1-(tert-butyl) 2-ethyl 5-(difluoromethyl)-1H-pyrrole-1,2-dicarboxylate (5.40 g, 18.7 mmol) and 10% Pd/C (2.45 g) in ethanol (100 mL) was stirred for 1 hour at room temperature. The resulting mixture was filtered. The filter cake was washed with ethanol. The combined filtrate was concentrated under vacuum to afford the title compound (4.6 g, crude) as a yellow solid. LC-MS: (ESI, m/z): [M−100+H]$^+$=194.

Step 4: 1-(tert-Butyl) 2-ethyl 2-(3-chloropropyl)-5-(difluoromethyl) pyrrolidine-1,2-dicarboxylate Under nitrogen, to a solution of 1-(tert-butyl) 2-ethyl 5-(difluoromethyl) pyrrolidine-1,2-dicarboxylate (3.80 g, 13.0 mmol) in tetrahydrofuran (100 mL) was added LDA (2M solution in tetrahydrofuran, 32.5 mL) dropwise at −78° C., and the mixture was stirred for 1 h at −78° C. Then a solution of 1-chloro-3-iodopropane (18.6 g, 91.0 mmol) in tetrahydrofuran (100 mL) was added dropwise at −78° C. and the solution was warmed to room temperature and stirred an additional 1 hour. The reaction was quenched with saturated NH$_4$Cl aqueous solution. The reaction mixture was diluted with water and extracted with ethyl acetate. The combined organic layers were washed with brine, dried over anhydrous sodium sulfate and concentrated under vacuum. The residue was purified by flash chromatography on silica gel (gradient: 0-30% ethyl acetate in petroleum ether) to afford the title compound (2.54 g) as a yellow oil. LC-MS: (ESI, m/z): [M−100+H]$^+$=270.

Step 5: Ethyl 3-(difluoromethyl)tetrahydro-1H-pyrrolizine-7a(5H)-carboxylate

To a solution of 1-(tert-butyl) 2-ethyl 2-(3-chloropropyl)-5-(difluoromethyl) pyrrolidine-1,2-dicarboxylate (2.54 g, 6.88 mmol) in HFIP (100 mL) was added 2,2,2-trifluoroacetic acid (5 mL) at room temperature, and the mixture was stirred for 3 hours. The solvent was concentrated under vacuum. The residue was re-dissolved in ethanol (100 mL) and treated with K$_2$CO$_3$ (2.85 g, 20.6 mmol) and KI (114 mg, 0.688 mmol). The resulting mixture was stirred for 1 hour at 40° C. After filtration, the filtrate was collected and concentrated under vacuum to afford the title compound (3.20 g, crude) as a yellow oil. LC-MS: (ESI, m/z): [M+H]$^+$= 234.

Step 6: (3-(Difluoromethyl)tetrahydro-1H-pyrrolizin-7a(5H)-yl) methanol

Under nitrogen, to a solution of ethyl 3-(difluoromethyl) tetrahydro-1H-pyrrolizine-7a(5H)-carboxylate (3.20 g, crude) in tetrahydrofuran (40 mL) was added LiAlH$_4$ (779 mg, 20.5 mmol) in portions at 0° C., and the mixture was stirred for 1 hour at room temperature. The reaction was quenched with Na$_2$SO$_4$·10H$_2$O. After filtration, the filtrate was collected and concentrated under vacuum to afford the title compound (600 mg, crude) as a yellow oil. LC-MS: (ESI, m/z): [M+H]$^+$=192. The crude was used for next step without further purification.

Intermediate 88: 6-(Hydroxymethyl)-2-methylhexahydropyrrolo[1,2-a] pyrazin-3(4H)-one (mixture of trans isomers

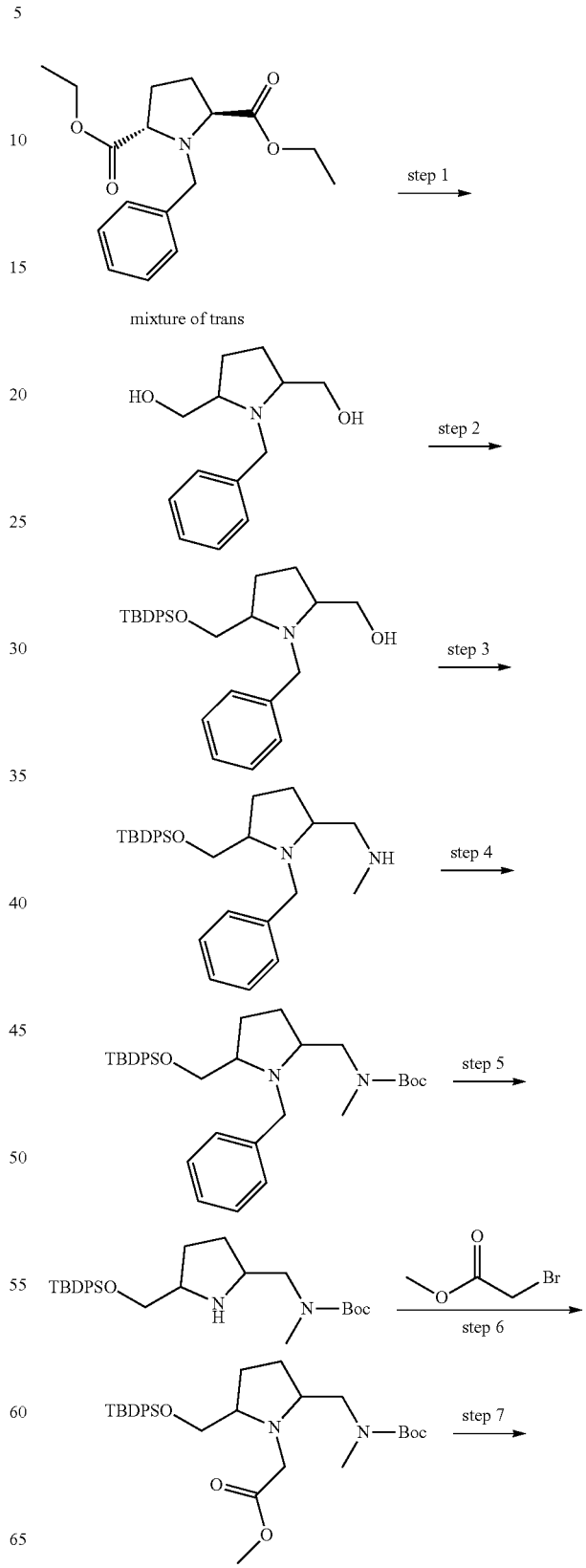

-continued

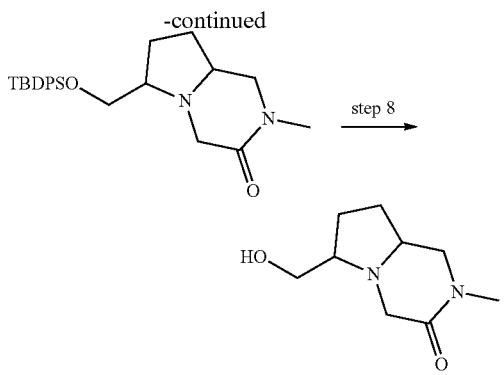

Step 1: (1-Benzylpyrrolidine-2,5-diyl)dimethanol (mixture of trans isomers)

Under nitrogen, to a solution of diethyl 1-benzylpyrrolidine-2,5-dicarboxylate (mixture of trans isomers, 1.00 g, 3.28 mmol) in tetrahydrofuran (10 mL) was added LiAlH$_4$ (311 mg, 8.18 mmol) slowly at 0° C. and stirred for 2 hours at room temperature. The reaction was quenched with Na$_2$SO$_4$·10H$_2$O. After filtration, the filtrate was collected and concentrated under vacuum. The residue was purified by flash chromatography on silica gel (gradient: 0-10% ethyl acetate in petroleum ether) to afford the title compound (700 mg, mixture of trans isomers) as a white solid. LC-MS: (ESI, m/z): [M+H]$^+$=222.

Step 2: (1-Benzyl-5-(((tert-butyldiphenylsilyl)oxy) methyl) pyrrolidin-2-yl) methanol (mixture of trans isomers)

To a solution of (1-benzylpyrrolidine-2,5-diyl)dimethanol (700 mg, 3.17 mmol), DIPEA (818 mg, 6.34 mmol) and DMAP (38.7 mg, 0.317 mmol) in N, N-dimethylformamide (10 mL) was added TBDPSCl (959 mg, 3.49 mmol) at room temperature. The solution was stirred for 5 hours at room temperature. The reaction mixture was diluted with water and extracted with ethyl acetate. The combined organic layers were washed with brine, dried over anhydrous sodium sulfate and concentrated under vacuum. The residue was purified by flash chromatography on silica gel (gradient: 0-20% EtOAc in petroleum ether) to afford the title compound (370 mg) as a yellow oil. LC-MS: (ESI, m/z): [M+H]$^+$=460.

Step 3: 1-(1-Benzyl-5-(((tert-butyldiphenylsilyl)oxy) methyl) pyrrolidin-2-yl)-N-methylmethanamine (mixture of trans isomers)

Under nitrogen, to a solution of (1-benzyl-5-(((tert-butyldiphenylsilyl)oxy) methyl) pyrrolidin-2-yl) methanol (370 mg, 0.806 mmol) and DIPEA (208 mg, 1.61 mmol) in dichloromethane (3 mL) was added trifluoromethanesulfonic anhydride (364 mg, 1.29 mmol) at -78° C., and the mixture was stirred for 15 minutes. Then CH$_3$NH$_2$ (2M solution in THF, 1 mL) was added at -78° C., and the mixture was stirred for 1 hour at room temperature. The reaction mixture concentrated under vacuum. The residue was purified by flash chromatography on silica gel (gradient: 0-30% ethyl acetate in petroleum ether) to afford the title compound (300 mg) as a light yellow oil. LC-MS: (ESI, m/z): [M+H]$^+$=473.

Step 4: tert-Butyl ((1-benzyl-5-(((tert-butyldiphenylsilyl)oxy) methyl) pyrrolidin-2-yl)methyl) (methyl) carbamate (mixture of trans isomers)

To a solution of 1-(1-benzyl-5-(((tert-butyldiphenylsilyl)oxy) methyl) pyrrolidin-2-yl)-N-methylmethanamine (300 mg, 0.634 mmol) and DIPEA (98.2 mg, 0.761 mmol) in dichloromethane (5 mL) was added (Boc)$_2$O (152 mg, 0.697 mmol) at 0° C., and the mixture was stirred at room temperature for 2 hours. The reaction mixture was diluted with water and extracted with ethyl acetate. The combined organic layers were washed with brine, dried over anhydrous sodium sulfate and concentrated under vacuum. The residue was purified by flash chromatography on silica gel (gradient: 0-10% methanol in dichloromethane) to afford the title compound (270 mg) as a light yellow oil. LC-MS: (ESI, m/z): [M+H]$^+$=573.

Step 5: tert-Butyl ((5-(((tert-butyldiphenylsilyl)oxy) methyl) pyrrolidin-2-yl)methyl)(methyl) carbamate (mixture of trans isomers)

Under hydrogen (1 atm), to a solution of tert-butyl ((1-benzyl-5-(((tert-butyldiphenylsilyl)oxy) methyl) pyrrolidin-2-yl)methyl)(methyl) carbamate (270 mg, 0.471 mmol) in methanol (10 mL) was added 10% Pd/C (49.9 mg) and 20% Pd(OH)$_2$/C (contain 61.7% water, 87.9 mg) at room temperature. The resulting mixture was stirred for 2 hours at room temperature. The resulting mixture was filtered. The filter cake was washed with methanol. The combined filtrate was concentrated under vacuum to afford the title compound (210 mg, crude) as a light yellow oil. LC-MS: (ESI, m/z): [M+H]$^+$=483.

Step 6: Methyl 2-(2-(((tert-butoxycarbonyl)(methyl) amino) methyl)-5-(((tert-butyldiphenylsilyl)oxy) methyl) pyrrolidin-1-yl)acetate (mixture of trans isomers)

A mixture of tert-butyl ((5-(((tert-butyldiphenylsilyl)oxy) methyl) pyrrolidin-2-yl)-methyl)(methyl)carbamate (200 mg, 0.414 mmol), methyl 2-bromoacetate (95.2 mg, 0.623 mmol) and K$_2$CO$_3$ (172 mg, 1.23 mmol) in acetonitrile (10 mL) was stirred for 5 hours at 50° C. The reaction mixture was diluted with water and extracted with ethyl acetate. The combined organic layer was dried over anhydrous sodium sulfate and concentrated under vacuum. The residue was purified by flash chromatography on silica gel (gradient: 0-20% ethyl acetate in petroleum ether) to afford the title compound (215 mg) as a light yellow oil. LC-MS: (ESI, m/z): [M+H]$^+$=555.

Step 7: 6-(((tert-Butyldiphenylsilyl)oxy)methyl)-2-methylhexahydropyrrolo[1,2-a] pyrazin-3(4H)-one (mixture of trans isomers)

To a solution of methyl 2-(2-(((tert-butoxycarbonyl) (methyl)amino) methyl)-5-(((tert-butyldiphenylsilyl)oxy) methyl) pyrrolidin-1-yl)acetate (185 mg, 0.334 mmol) in dioxane (5 mL) was added hydrogen chloride (4M solution in ethyl acetate, 6 mL) at 0° C., and the mixture was stirred for 2 hours at room temperature. The solvent was concentrated under vacuum. The residue was re-dissolved in methanol and treated with DIPEA (1 mL). The resulting mixture was stirred at room temperature overnight. The solvent was concentrated under vacuum and the residue was purified by flash chromatography on silica gel (gradient: 0-10% methanol in dichloromethane) to afford the title compound (130 mg) as a yellow oil. LC-MS: (ESI, m/z): [M+H]$^+$=423.

Step 8: 6-(Hydroxymethyl)-2-methylhexahydropyr-rolo[1,2-a] pyrazin-3(4H)-one (mixture of trans isomers)

Under nitrogen, to a solution of 6-(((tert-butyldiphenyl-silyl)oxy) methyl)-2-methylhexahydropyrrolo[1,2-a] pyrazin-3(4H)-one (100 mg, 0.237 mmol) in methanol (10 mL) was added hydrogen chloride (4M solution in methanol, 1 mL, 4.00 mmol) at room temperature, and the mixture was stirred for 2 hours at 60° C. The solvent was concentrated under vacuum to afford the title compound (65.0 mg, crude) as a white solid. LC-MS: (ESI, m/z): [M+H]$^+$=185. The crude was used for next step without further purification.

Intermediate 89: (5-Methyl-2-oxa-5-azabicyclo [2.2.1] heptan-4-yl)methanol

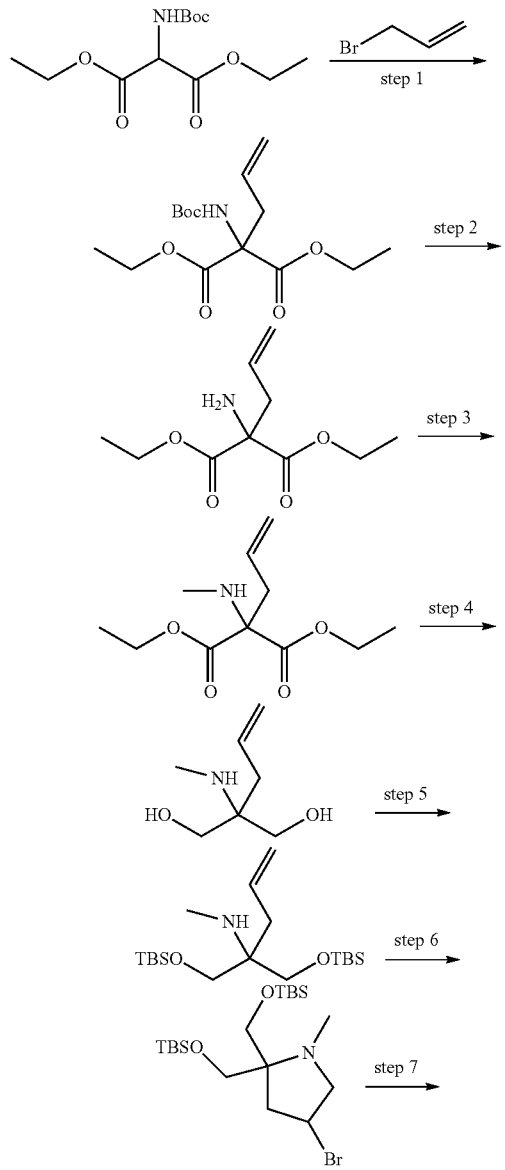

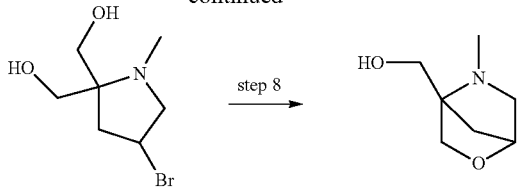

Step 1: Diethyl 2-allyl-2-((tert-butoxycarbonyl)amino) malonate

Under nitrogen, to a solution of diethyl 2-((tert-butoxycarbonyl)amino) malonate (10.0 g, 36.3 mmol) in tetrahydrofuran (100 mL) was added NaH (2.90 g, 72.5 mmol, 60% in mineral oil) and 3-bromoprop-1-ene (5.18 g, 43.2 mmol) at 0° C. The resulting solution was stirred for 2 h at 80° C. Then cooled to room temperature, quenched with NH$_4$Cl aqueous and extracted with EtOAc. The organic layers were dried over anhydrous sodium sulfate and concentrated under vacuum. The residue was purified by flash chromatography on silica gel (gradient: 0-20% EtOAc/petroleum ether) to afford 5.18 g of the title compound as a yellow oil. LC-MS: (ESI, m/z): [M+H]$^+$=316.

Step 2: Diethyl 2-allyl-2-aminomalonate

To a solution of diethyl 2-allyl-2-((tert-butoxycarbonyl) amino) malonate (4.68 g, 14.8 mmol) in dichloromethane (27.9 mL) was added TFA (9.30 mL). The resulting solution was stirred for 1 h at room temperature. Solvent was evaporated under vacuum to afford 6.5 g (crude) of the title compound (TFA salt) as yellow solid. LC-MS: (ESI, m/z): [M+H]$^+$=216.

Step 3: Diethyl 2-allyl-2-(methylamino)malonate

A solution of crude diethyl 2-allyl-2-aminomalonate (6.5 g) from step 2, formaldehyde (1.11 g, 14.8 mmol, 40% in water) and NaOAc (2.44 g, 29.8 mmol) in dichloromethane (50 mL) was stirred for 2 h at room temperature. Then NaBH(OAc)$_3$ (6.30 g, 29.7 mmol) was added at room temperature, and the mixture was stirred for 1 h. Water was added to quench the reaction, extracted with DCM The combined organic layers were dried over anhydrous sodium sulfate and concentrated under vacuum. The residue was purified by flash chromatography on silica gel (gradient: 0-30% EtOAc/petroleum ether) to afford 1.09 g of the title compound as a yellow oil. LC-MS: (ESI, m/z): [M+H]$^+$=230.

Step 4: 2-Allyl-2-(methylamino) propane-1,3-diol

Under nitrogen, to a solution of diethyl 2-allyl-2-(methylamino) propanedioate (990 mg, 4.32 mmol) in tetrahydrofuran (10 mL) was added LiAlH$_4$ (3.46 mL, 2.5 M in THF) at 0° C. The resulting solution was stirred for 30 min at room temperature The reaction was quenched by Na$_2$SO$_4$·10H$_2$O and filtrated. The solvent was evaporated under vacuum to afford 491 mg (crude) as a yellow oil. LC-MS: (ESI, m/z): [M+H]$^+$=146.

Step 5: 6-Allyl-N,2,2,3,3,9,9,10,10-nonamethyl-4,8-dioxa-3,9-disilaundecan-6-amine To a solution of 2-allyl-2-(methylamino) propane-1,3-diol (491 mg, 3.38 mmol) and triethylamine (1.71 g, 16.9 mmol)

in dichloromethane (10 mL) was added tert-butylchlorodimethylsilane (1.52 g, 10.1 mmol) at 0° C. The resulting solution was stirred for 2 h at room temperature. The reaction was quenched with NH₄Cl aqueous and extracted with EtOAc. The combined organic layers were dried over anhydrous sodium sulfate and concentrated under vacuum. The residue was purified by flash chromatography on silica gel (gradient: 0-50% EtOAc/petroleum ether) to afford 960 mg of the title compound as a yellow oil. LC-MS: (ESI, m/z): [M+H]⁺=374.

Step 6: 4-Bromo-2,2-bis(((tert-butyldimethylsilyl)oxy)methyl)-1-methylpyrrolidine To a solution of 6-allyl-N,2,2,3,3,9,9,10,10-nonamethyl-4,8-dioxa-3,9-disilaundecan-6-amine (760 mg, 2.03 mmol) in acetonitrile (10.0 mL) was added 1-bromopyrrolidine-2,5-dione (361 mg, 2.04 mmol) at room temperature. The resulting solution was stirred for 15 min at room temperature. Solvent was evaporated under vacuum to afford 240 mg (crude) as a yellow oil. LC-MS: (ESI, m/z): [M+H]⁺=452.

Step 7: (4-Bromo-1-methylpyrrolidine-2,2-diyl)dimethanol

To a mixture of 4-bromo-2,2-bis(((tert-butyldimethylsilyl)oxy)methyl)-1-methylpyrrolidine (240 mg, 0.530 mmol) in methanol methyl alcohol (2.00 mL) and tetrahydrofuran (2.00 mL) was added HCl (6.00 mL, 4 M in water). The resulting solution was stirred for overnight at room temperature. Solvent was evaporated under vacuum to afford 200 mg (crude) of the title compound as a yellow oil. LC-MS: (ESI, m/z): [M+H]⁺=224.

Step 8: (5-Methyl-2-oxa-5-azabicyclo [2.2.1] heptan-4-yl) methanol

Under nitrogen, to a solution of (4-bromo-1-methylpyrrolidine-2,2-diyl)dimethanol (200 mg, 0.890 mmol) in N,N-dimethylformamide (5 mL) was added NaH (71.4 mg, 1.79 mmol, 60% in mineral oil) at 0° C. The resulting solution was stirred at room temperature for 2 h. The reaction was quenched with sat. NH₄Cl aqueous. Solvent was evaporated under vacuum. The residue was washed by DCM and filtrated. The solvent was evaporated under vacuum to afford 90 mg as a yellow oil. LC-MS: (ESI, m/z): [M+H]⁺=144.

Intermediate 90: 6-(Hydroxymethyl)-2-methylhexahydropyrrolo[1,2-a] pyrazin-1(2H)-one (mixture of trans isomers

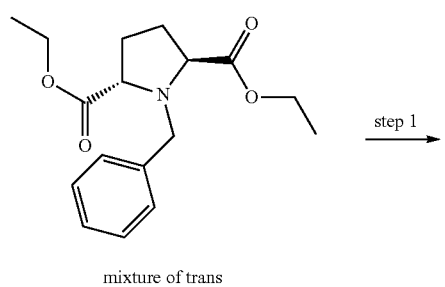

mixture of trans

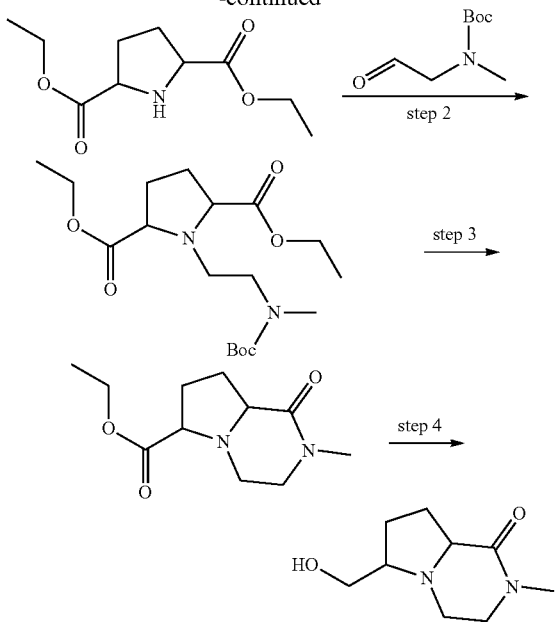

Step 1: Diethyl pyrrolidine-2,5-dicarboxylate (mixture of trans isomers)

Under nitrogen, to a solution of diethyl 1-benzylpyrrolidine-2,5-dicarboxylate (mixture of trans isomers, 730 mg, 2.39 mmol) in ethanol (10 mL) was added 10% Pd/C (255 mg) and 20% Pd(OH)₂/C (contained 61.7% water, 440 mg) at room temperature. The flask was evacuated and back fed with hydrogen three times. The resulting mixture was stirred under hydrogen (1 atm) for 2 hours at room temperature. The resulting mixture was filtered over celite and the filter cake was washed with ethanol. The combined filtrate was concentrated under vacuum to afford the title compound (507 mg, crude) as a light yellow oil. LC-MS: (ESI, m/z): [M+H]⁺=216. ¹H NMR (300 MHz, CDCl₃, ppm) δ 4.21 (q, J=7.1 Hz, 4H), 4.06-3.93 (m, 2H), 2.31-2.10 (m, 2H), 2.04-1.88 (m, 2H), 1.30 (t, J=7.1 Hz, 6H).

Step 2: Diethyl 1-(2-((tert-butoxycarbonyl)(methyl)amino)ethyl) pyrrolidine-2,5-dicarboxylate (mixture of trans isomers)

To a solution of diethyl pyrrolidine-2,5-dicarboxylate (300 mg, 1.39 mmol) in dichloromethane (10 mL) was added a solution of tert-butyl methyl(2-oxoethyl)carbamate (1.21 g, 6.99 mmol) in dichloromethane (2 mL) at 0° C., and the mixture was stirred for 30 minutes. Then NaBH(OAc)₃ (1.48 g, 6.98 mmol) was added at 0° C., and the mixture was stirred for 3 hours at room temperature. The reaction was quenched with water and extracted with dichloromethane. The combined organic layers were washed with brine, dried over anhydrous sodium sulfate and concentrated under vacuum. The residue was purified by flash chromatography on silica gel (gradient: 0-30% ethyl acetate in petroleum ether) to afford the title compound (488 mg) as a light yellow oil. LC-MS: (ESI, m/z): [M+H]⁺=373. ¹H NMR (300 MHz, CDCl₃, ppm) δ 4.19 (q, J=7.1 Hz, 4H), 3.97-3.89 (m, 2H), 3.48-3.20 (m, 2H), 3.04-2.93 (m, 2H), 2.87 (s, 3H), 2.43-2.21 (m, 2H), 2.03-1.86 (m, 2H), 1.47 (s, 9H), 1.30 (t, J=7.1 Hz, 6H).

Step 3: Ethyl 2-methyl-1-oxooctahydropyrrolo[1,2-a]pyrazine-6-carboxylate (mixture of trans isomers)

To a solution of diethyl 1-(2-((tert-butoxycarbonyl)(methyl)amino) ethyl) pyrrolidine-2,5-dicarboxylate (438 mg, 1.18 mmol) in ethyl acetate (5 mL) was added hydrogen chloride (4M solution in ethyl acetate, 6 mL) at 0° C., and the mixture was stirred for 2 hours at room temperature. The solvent was concentrated under vacuum. The residue was re-dissolved in ethanol (20 mL) and treated with DIPEA (2 mL, 12.0 mmol). The resulting mixture was stirred at room temperature overnight. The solvent was concentrated under vacuum and the residue was purified by flash chromatography on silica gel (gradient: 0-10% methanol in dichloromethane) to afford the title compound (157 mg) as a yellow oil. LC-MS: (ESI, m/z): [M+H]$^+$=227.

Step 4: 6-(Hydroxymethyl)-2-methylhexahydropyrrolo[1,2-a] pyrazin-1(2H)-one (mixture of trans isomers)

To a mixture of ethyl 2-methyl-1-oxooctahydropyrrolo[1,2-a] pyrazine-6-carboxylate (134 mg, 0.592 mmol) in tetrahydrofuran (10 mL) was added LiBH$_4$ (64.5 mg, 2.96 mmol) at room temperature, and the mixture was stirred for 6 hours at 60° C. The reaction was quenched with Na$_2$SO$_4$·10H$_2$O. After filtration, the filtrate was concentrated under reduced pressure to afford the title compound (84.9 mg, crude) as a colorless solid. LC-MS: (ESI, m/z): [M+H]$^+$=185. The crude was used for next step without further purification.

Intermediate 91: (3S)-3-(Hydroxymethyl)-N N-dimethyloctahydroindolizine-7-carboxamide (four isomers

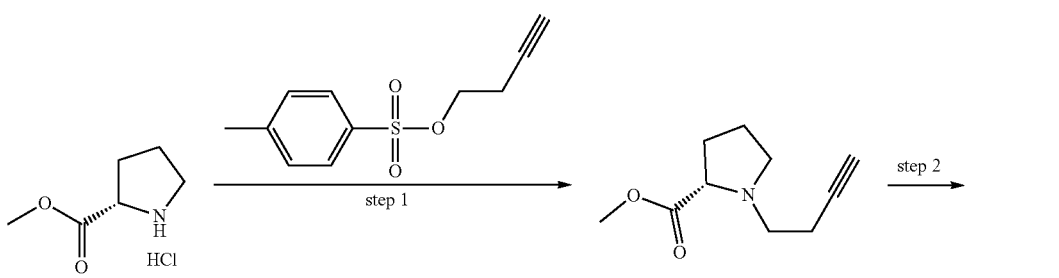

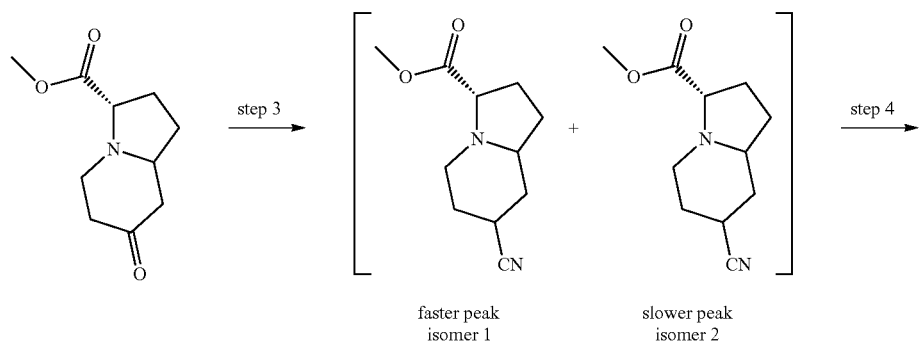

faster peak isomer 1     slower peak isomer 2

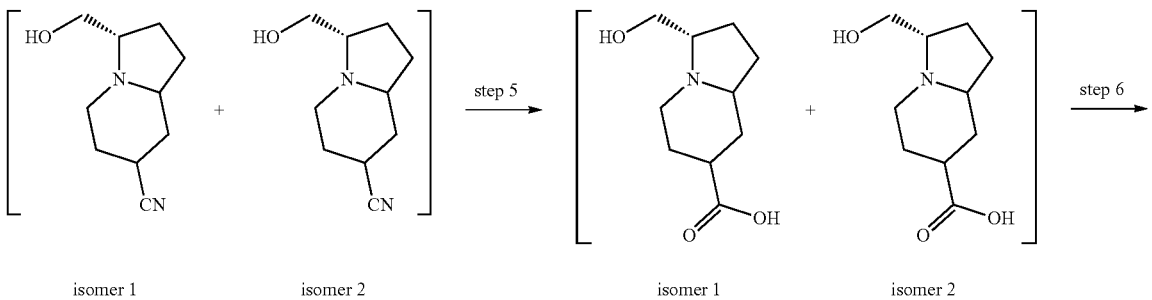

isomer 1     isomer 2        isomer 1     isomer 2

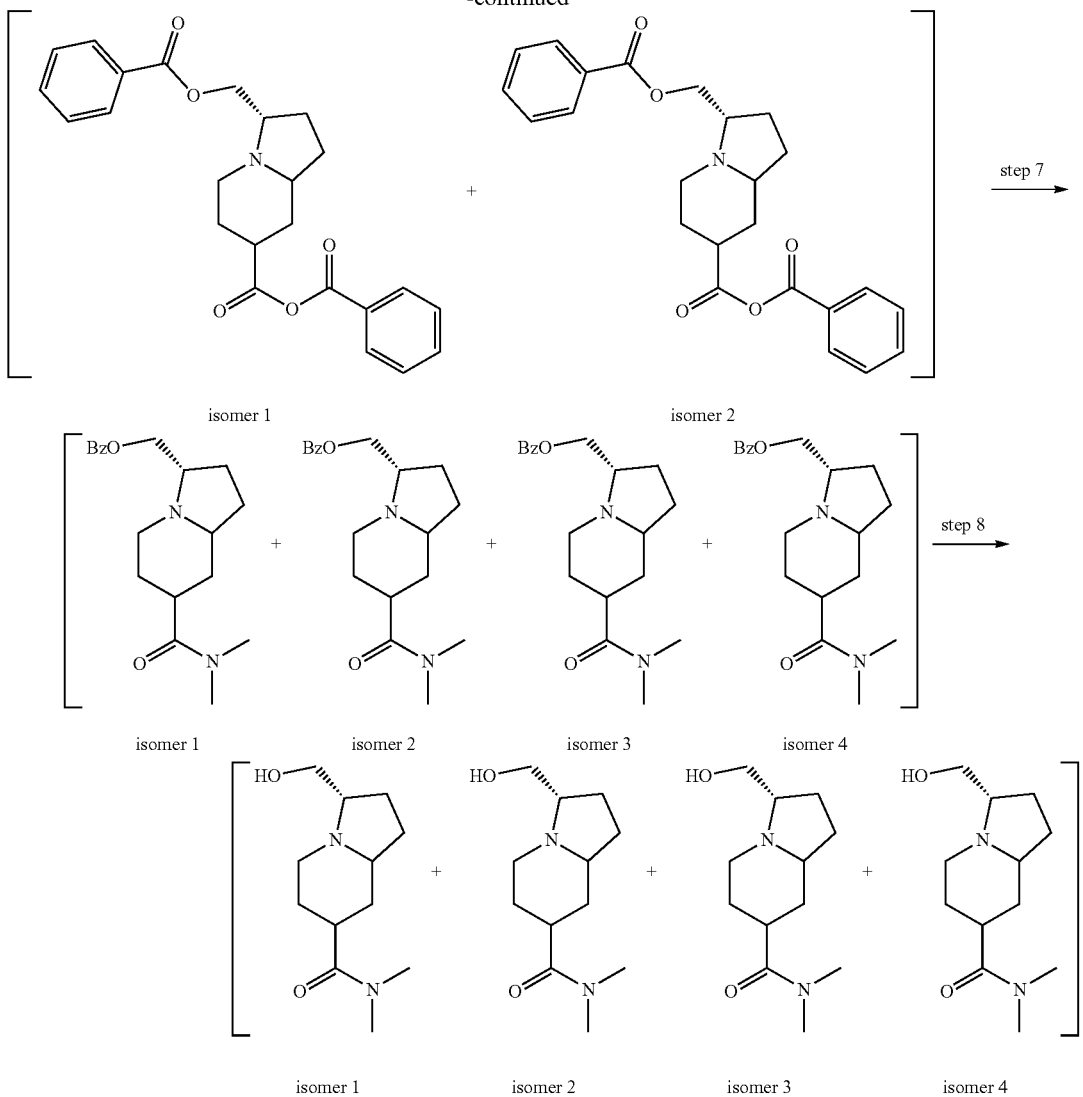

Step 1: Methyl but-3-yn-1-yl-L-prolinate

A solution of methyl L-prolinate hydrochloride salt (10.1 g, 60.7 mmol), but-3-yn-1-yl 4-methylbenzenesulfonate (32.4 g, 145 mmol), NaI (4.58 g, 30.5 mmol) and NaHCO$_3$ (20.5 g, 243 mmol) in acetonitrile (500 mL) was stirred at 80° C. for 16 hours. The solid was filtered out. The filtrate was concentrated under vacuum. The residue was diluted with DCM, washed with aqueous NaOH solution (5%), water and brine. The organic phase was concentrated under vacuum. The residue was purified by flash chromatography on silica gel eluting (gradient: 0-20% EtOAc/petroleum ether) to afford 11.1 g (crude) of the title compound as a yellow oil. LC-MS: (ESI, m/z): [M+H]$^+$=182.

Step 2: Methyl (3S)-7-oxooctahydroindolizine-3-carboxylate

Under nitrogen, to a solution of methyl but-3-yn-1-yl-L-prolinate (9.48 g, 52.3 mmol) and 4 Å MS (10 g) in dichloromethane (300 mL) was added m-CPBA (12.9 g, 63.3 mmol) at 0° C. The solution was stirred at 0° C. for 2 hours. Then the solution was cooled to −78° C., a solution of PPh$_3$AuNTf$_2$ (1.95 g, 2.64 mmol) in DCM was added at −78° C. The solution was stirred at −78° C. for 5 hours. The solution was diluted with DCM and the molecular sieves were filtered out. The filtrate was washed with aqueous NaHCO$_3$ solution and brine, dried over with anhydrous sodium sulfate and concentrated under vacuum. The residue was purified by flash chromatography on silica gel eluting (gradient: 0-60% EtOAc/petroleum ether) to afford 5.58 g of the title compound as a brown oil. LC-MS: (ESI, m/z): [M+H]$^+$=198.

Step 3: Methyl (3S)-7-cyanooctahydroindolizine-3-carboxylate (two isomers)

Under nitrogen, to a solution of methyl (3S)-7-oxooctahydroindolizine-3-carboxylate (2.01 g, 10.2 mmol) and 1-((isocyanomethyl)sulfonyl)-4-methylbenzene (3.3 g, 16.9 mmol) in 1,2-dimethoxyethane (100 mL) and methanol (0.4 mL) was added t-BuOK (1 M in THF, 25 mL) at 0° C. The solution was stirred at room temperature for 3 hours. The solid was filtered out. The filtrate was concentrated under vacuum. The residue was purified by flash chromatography on silica gel (gradient: 0-60% EtOAc/petroleum ether) to afford 361 mg of the faster peak (isomer 1) and 362 mg of the slower peak (isomer 2) as brown oils. LC-MS: (ESI, m/z): [M+H]$^+$=209.

Step 4: (3S)-3-(Hydroxymethyl) octahydroindolizine-7-carbonitrile (two isomers)

Under nitrogen, to a solution of methyl (3S)-7-cyanooctahydroindolizine-3-carboxylate (500 mg, 2.4 mmol) (isomer 1 of last step) in tetrahydrofuran (14 mL) was added LiBH$_4$ (2 M in THF, 2.5 mL) at 0° C. The solution was stirred at room temperature for 16 hours. The reaction was quenched by EtOAc. The solution was purified by ion exchange resin (Si-Propysulfonic acid) and concentrated under vacuum to afford 433 mg (crude) of the title compound (isomer 1) as a brown oil. LC-MS: (ESI, m/z): [M+H]$^+$=181.

Analogous to method described as above, the other isomer (isomer 2) 441 mg (crude) was prepared from methyl (3S)-7-cyanooctahydroindolizine-3-carboxylate (800 mg, 3.84 mmol) (isomer 2 of last step) as a crude brown oil. LC-MS: (ESI, m/z): [M+H]$^+$=181.

Step 5: (3S)-3-(Hydroxymethyl) octahydroindolizine-7-carboxylic acid (two isomers)

A solution of (3S)-3-(hydroxymethyl) octahydroindolizine-7-carbonitrile (181 mg, 1 mmol) (isomer 1 of last step) in hydrochloric acid (6 mL, 12M) was stirred at 80° C. for 2 hours. The solution was concentrated under vacuum to afford 270 mg (crude) of the title compound (isomer 1) as a brown oil. LC-MS: (ESI, m/z): [M+H]$^+$=200.

Analogous to method described as above, the other isomer (isomer 2) 1.03 g (crude) was prepared from (3S)-3-(hydroxymethyl) octahydroindolizine-7-carbonitrile (440 mg, 2.44 mmol) (isomer 2 of last step) as a brown oil. LC-MS: (ESI, m/z): [M+H]$^+$=200.

Step 6: Benzoic (3S)-3-((benzoyloxy)methyl) octahydroindolizine-7-carboxylic anhydride (two isomers)

To a solution of (3S)-3-(hydroxymethyl) octahydroindolizine-7-carboxylic acid (271 mg, crude) (isomer 1 of last step) in dichloromethane (8 mL) were added DIPEA (1.19 g, 9.22 mmol) and benzoyl chloride (585 mg, 4.16 mmol) at 0° C. The solution was stirred at room temperature for 16 hours. The solution was quenched by water, extracted with DCM. The combined organic layers were dried over anhydrous sodium sulfate and concentrated under vacuum to afford 810 mg (crude) of the title compound (isomer 1) as a brown oil. LC-MS: (ESI, m/z): [M+H]$^+$=408.

Analogous to method described as above, the other isomer (isomer 2) 4.31 g (crude) was prepared from (3S)-3-(hydroxymethyl) octahydroindolizine-7-carboxylic acid (1.03 g, crude) (isomer 2 of last step) as a crude brown oil. LC-MS: (ESI, m/z): [M+H]$^+$=408.

Step 7: ((3S)-7-(Dimethylcarbamoyl) octahydroindolizin-3-yl)methyl benzoate (four isomers)

A mixture of benzoic (3S)-3-((benzoyloxy)methyl) octahydroindolizine-7-carboxylic anhydride (810 mg, crude) (isomer 1 of last step) and dimethylamine (2 M in THF, 12 mL) was stirred at room temperature for 4 hours. The solution was concentrated under vacuum. The residue was purified by C18 column (solvent gradient: 0-40% ACN in water (0.05% NH$_4$HCO$_3$)) to afford 95 mg of the faster peak (isomer 1) and 67 mg of the slower peak (isomer 2) as brown oils. LC-MS: (ESI, m/z): [M+H]$^+$=331.

Analogous to method described as above, the other isomers (the mixture of isomer 3 and isomer 4) 277 mg was prepared from (3S)-3-((benzoyloxy)methyl) octahydroindolizine-7-carboxylic anhydride (4.31 g, crude, 2.44 mmol) (isomer 2 of last step) as a brown oil. LC-MS: (ESI, m/z): [M+H]$^+$=331.

Step 8: (3S)-3-(Hydroxymethyl)-N,N-dimethyloctahydroindolizine-7-carboxamide (four isomers)

To a solution of ((3S)-7-(dimethylcarbamoyl) octahydroindolizin-3-yl)methyl benzoate (65.1 mg, 0.200 mmol) (isomer 1 of last step) in ethanol (1.5 mL) was added a solution of NaOH (24.8 mg, 0.620 mmol) in water (0.5 mL). The solution was stirred at room temperature for 2 hours. The reaction solution was adjusted to pH=7 with 2N HCl aqueous. Then the solution was purified by ion exchange resin (Si-Propysulfonic acid) and concentrated under vacuum to afford 43 mg (crude) of the title compound (isomer 1) as a brown oil. LC-MS: (ESI, m/z): [M+H]$^+$=227. The crude was used for next step without further purification.

Analogous to method described as above, the other isomer (isomer 2) 46 mg (crude) was prepared from ((3S)-7-(dimethylcarbamoyl) octahydroindolizin-3-yl)methyl benzoate (66.5 mg, 0.200 mmol) (isomer 2 of last step) as a brown oil. LC-MS: (ESI, m/z): [M+H]$^+$=227.

Analogous to method described as above, the other isomers (the mixture of isomer 3 and isomer 4) 145 mg (crude) was prepared from ((3S)-7-(dimethylcarbamoyl) octahydroindolizin-3-yl)methyl benzoate (277 mg, 0.840 mmol) (the mixture of isomer 3 and isomer 4) as a brown oil. LC-MS: (ESI, m/z): [M+H]$^+$=227. These two isomers were separated at the target compound.

Intermediate 92: (1-Methyltetrahydro-1H-furo[3,4-b] pyrrol-6a(6H)-yl) methanol

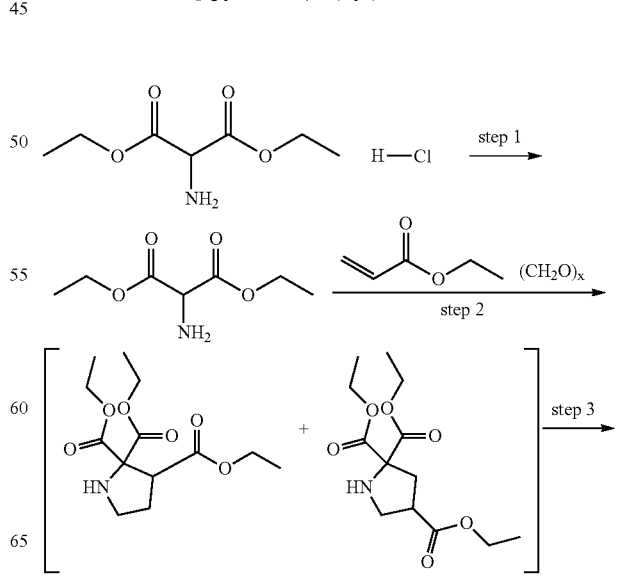

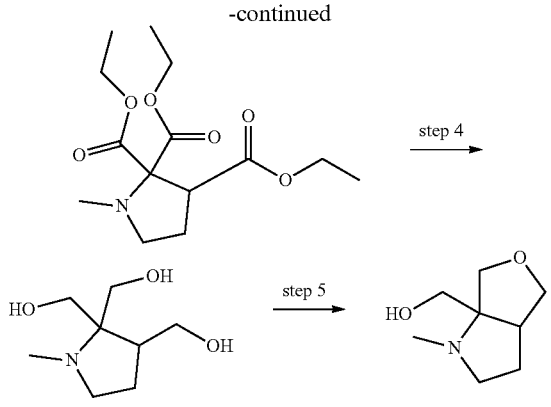

Step 1: Diethyl 2-aminomalonate

To a solution of diethyl 2-aminomalonate hydrochloride (25.0 g, 118 mmol) in ethanol (10 mL) was added NaHCO$_3$ (19.8 g, 236 mmol) at room temperature in portions, and the mixture was stirred for 1 hour. The resulting mixture was filtered and the filtrate was concentrated under vacuum to afford the title compound (20.0 g, crude) as a light yellow oil. LC-MS: (ESI, m/z): [M+H]$^+$=176.

Step 2: Triethyl pyrrolidine-2,2,3-tricarboxylate & Triethyl pyrrolidine-2,2,4-tricarboxylate (~3:1 mixture)

A solution of diethyl 2-aminomalonate (20.0 g, 114 mmol), ethyl acrylate (11.4 g, 114 mmol) and polyformaldehyde (3.42 g, 38.0 mmol) in toluene (500 mL) was stirred overnight at 110° C. The solvent was concentrated under vacuum. The residue was purified by flash chromatography on silica gel (gradient: 0-50% ethyl acetate in petroleum ether) to afford the title compounds (25.0 g) as a yellow oil. LC-MS: (ESI, m/z): [M+H]$^+$=288.

Step 3: Triethyl 1-methylpyrrolidine-2,2,3-tricarboxylate

To a solution of triethyl pyrrolidine-2,2,3-tricarboxylate and triethyl pyrrolidine-2,2,4-tricarboxylate (~3:1 mixture, 25.0 g, 87.1 mmol) and polyformaldehyde (13.1 g, 145 mmol) in dichloromethane (500 mL) was added NaBH(OAc)$_3$ (92.3 g, 436 mmol) at room temperature in portions, and the mixture was stirred overnight. The reaction was quenched with water at 0° C. and extracted with dichloromethane. The combined organic layers were washed with brine, dried over anhydrous sodium sulfate and concentrated under vacuum. The residue was purified by flash chromatography on silica gel (gradient: 0-30% EtOAc in petroleum ether) to afford the title compound (15.7 g) as a light yellow oil. LC-MS: (ESI, m/z): [M+H]$^+$=302. $^1$H NMR (300 MHz, CDCl$_3$, ppm) δ 4.33-4.07 (m, 6H), 3.72-3.61 (m, 1H), 3.16-3.05 (m, 1H), 2.95-2.82 (m, 1H), 2.54 (s, 3H), 2.36-2.11 (m, 2H), 1.36-1.20 (m, 9H).

Step 4: (1-Methylpyrrolidine-2,2,3-triyl)trimethanol

Under nitrogen, to a solution of triethyl 1-methylpyrrolidine-2,2,3-tricarboxylate (9.00 g, 30.0 mmol) in tetrahydrofuran (200 mL) was added LiAlH$_4$ (2M solution in tetrahydrofuran, 30 mL) dropwise at 0° C., and the mixture was stirred for 2 hours at room temperature. The reaction was quenched with Na$_2$SO$_4$·10H$_2$O. After filtration, the filtrate was collected and concentrated under vacuum to afford the title compound (5.10 g, crude) as a yellow oil. LC-MS: (ESI, m/z): [M+H]$^+$=176.

Step 5: (1-Methyltetrahydro-1H-furo[3,4-b] pyrrol-6a(6H)-yl)methanol

Under nitrogen, to a solution of (1-methylpyrrolidine-2,2,3-triyl)trimethanol (175 mg, 1.00 mmol) and TEA (0.4 mL) in dichloromethane (4 mL) was added Tf$_2$O (0.3 mL, 1.78 mmol) dropwise at –10° C., and the mixture was stirred for 30 minutes at room temperature. The solvent was concentrated under vacuum to afford the title compound (300 mg, crude) as a brown oil. LC-MS: (ESI, m/z): [M+H]$^+$=158. The crude was used for next step without further purification.

Intermediate 93: ((2R,5S)-4-Oxa-1-azabicyclo [3.2.1] octan-2-yl) methanol

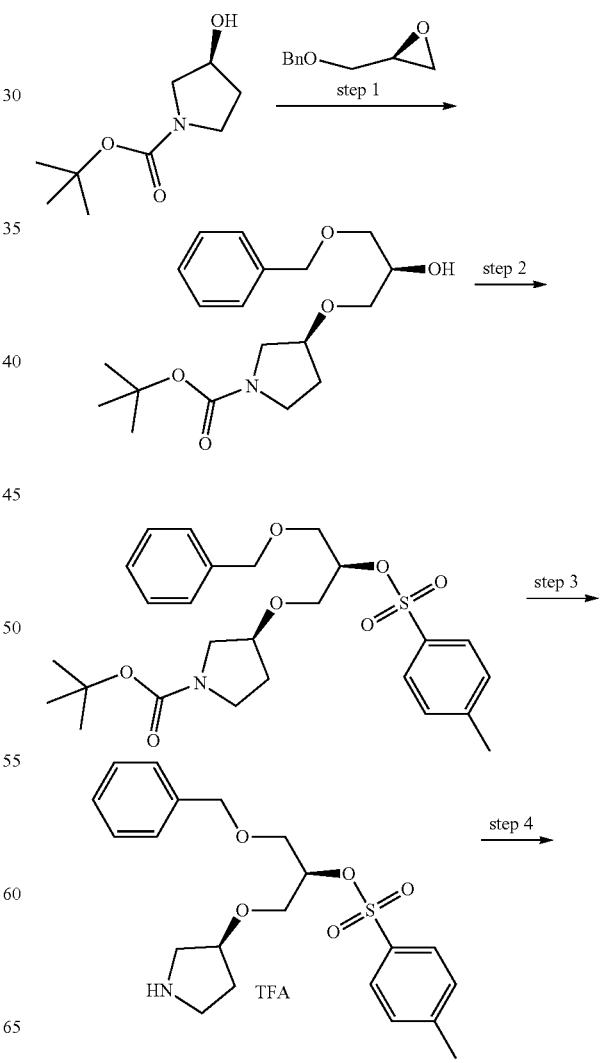

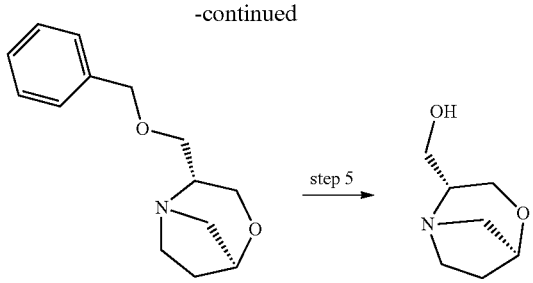

Step 1: tert-Butyl (S)-3-((R)-3-(benzyloxy)-2-hydroxypropoxy) pyrrolidine-1-carboxylate Under nitrogen, to a solution of tert-butyl (S)-3-hydroxypyrrolidine-1-carboxylate (5.00 g, 26.7 mmol) in THF (80 mL) was added NaH (2.67 g, 66.7 mmol) at 0° C. The resulting solution was stirred at 0° C. for 20 min. Then (S)-2-((benzyloxy)methyl) oxirane (4.38 g, 26.7 mmol) was added. The solution was stirred at 50° C. overnight. The reaction was quenched with water, extracted with EtOAc. The combined organic layers were dried over anhydrous sodium sulfate and concentrated under vacuum. The residue was purified by C18 column (solvent gradient: 0-60% ACN in water (0.05% NH$_4$HCO$_3$)) to afford the title compound (2.55 g) as a yellow oil. LC-MS: (ESI, m/z): [M+H]$^+$=352.

Step 2: tert-Butyl (S)-3-((R)-3-(benzyloxy)-2-(tosyloxy) propoxy) pyrrolidine-1-carboxylate To a solution of tert-butyl (S)-3-((R)-3-(benzyloxy)-2-hydroxypropoxy) pyrrolidine-1-carboxylate (2.65 g, 7.54 mmol) in dichloromethane (20 mL) was added Et$_3$N (2.84 g, 28.0 mmol), TsCl (1.75 g, 9.18 mmol) and 4-DMAP (46.0 mg, 0.38 mmol) at 0° C. The resulting solution was stirred at room temperature overnight. The reaction was quenched with water, washed with 0.1 M HCl and brine. The organic layer was dried over anhydrous Na$_2$SO$_4$ and concentrated under vacuum. The residue was purified by flash chromatography on silica gel (gradient: 0%-40% EtOAc/petroleum ether) to afford the title compound (2.57 g) as a yellow oil. LC-MS: (ESI, m/z): [M+H]$^+$=506.

Step 3: (R)-1-(Benzyloxy)-3-(((S)-pyrrolidin-3-yl)oxy)propan-2-yl 4-methylbenzenesulfonate (TFA salt)

A solution of tert-butyl (S)-3-((R)-3-(benzyloxy)-2-(tosyloxy) propoxy) pyrrolidine-1-carboxylate (2.57 g, 5.08 mmol) in 2,2,2-trifluoroacetic acid (3 mL) and dichloromethane (9 mL) was stirred at room temperature for 1 hour. The mixture was concentrated under vacuum to afford crude product (3.30 g) as a yellow oil. LC-MS: (ESI, m/z): [M+H]$^+$=406.

Step 4: (2R,5S)-2-((Benzyloxy)methyl)-4-oxa-1-azabicyclo [3.2.1] octane

A solution of (R)-1-(benzyloxy)-3-(((S)-pyrrolidin-3-yl)oxy) propan-2-yl 4-methylbenzenesulfonate (TFA salt) (3.30 g, 6.35 mmol) and K$_2$CO$_3$ (3.37 g, 24.4 mmol) in acetonitrile (30 mL) was stirred at 70° C. overnight. The resulting mixture was concentrated under reduced pressure. The residue was purified by C18 column (solvent gradient: 0-100% ACN in water (0.05% NH$_4$HCO$_3$)) to afford the title compound (890 mg) as a yellow solid. LC-MS: (ESI, m/z): [M+H]$^+$=234.

Step 5: ((2R,5S)-4-Oxa-1-azabicyclo [3.2.1] octan-2-yl) methanol

Under hydrogen (1 atm), a solution of ((2R,5S)-2-((benzyloxy)methyl)-4-oxa-1-azabicyclo [3.2.1]octane (139 mg, 0.600 mmol) and 10% Pd/C (180 mg) in methyl alcohol (4 mL) was stirred at room temperature overnight. The resulting mixture was filtered. The filtrate was concentrated under reduced pressure to afford the title compound (51 mg crude) as a white oil. LC-MS: (ESI, m/z): [M+H]$^+$=144. The crude was used for next step without further purification.

Intermediate 94: ((5S,8R)-4-Oxa-1-azabicyclo [3.2.1] octan-8-yl) methanol

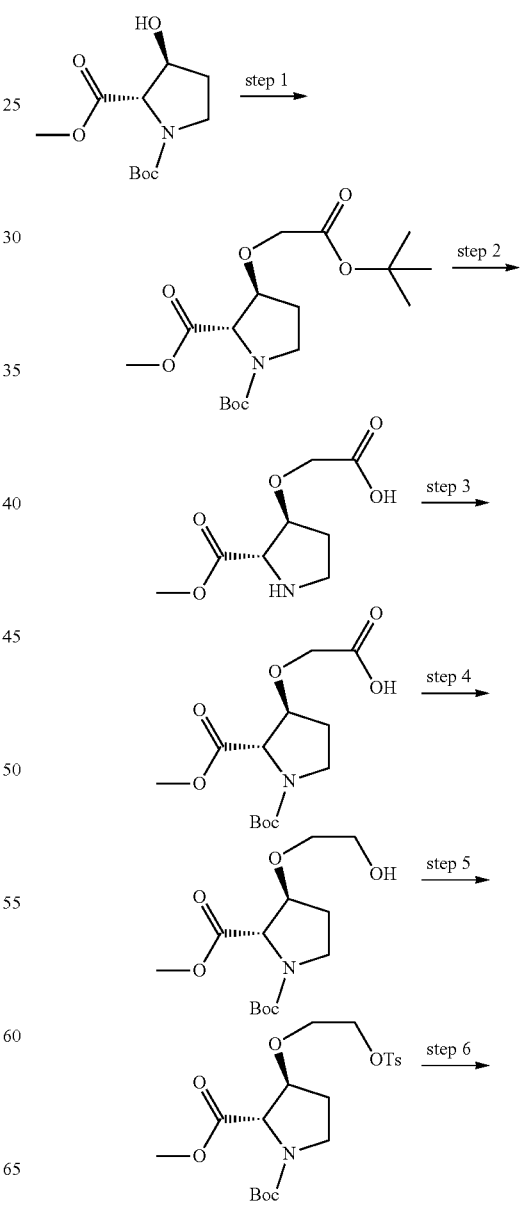

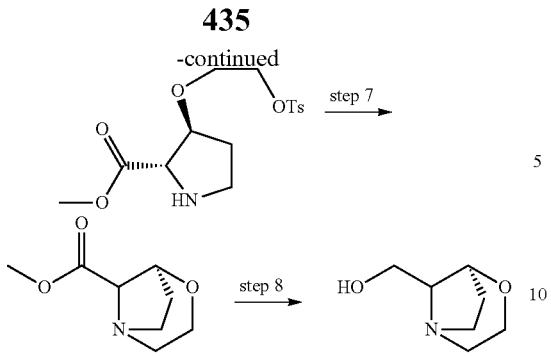

Step 1: 1-(tert-Butyl) 2-methyl (2S,3S)-3-(2-(tert-butoxy)-2-oxoethoxy) pyrrolidine-1,2-dicarboxylate Under nitrogen, to a solution of 1-(tert-butyl) 2-methyl (2S,3S)-3-hydroxypyrrolidine-1,2-dicarboxylate (1.01 g, 4.12 mmol) in THF (8 mL) was added NaH (247 mg, 6.18 mmol, 60% in mineral oil) at 0° C. The resulting solution was stirred for 0.5 hours at 0° C. Then tert-butyl 2-chloroacetate (1.22 mL, 8.25 mmol) was added, and the mixture was stirred at 0° C. for 1 hour. The reaction was quenched with NH₄Cl aqueous and extracted with EtOAc. The combined organic layers were dried over anhydrous sodium sulfate and concentrated under vacuum. The residue was purified by flash chromatography on silica gel (gradient: 0-20% EtOAc in petroleum ether) to afford 351 mg of the title compound as a yellow oil. LC-MS: (ESI, m/z): [M+H]⁺= 360.

Step 2: 2-(((2S,3S)-2-(Methoxycarbonyl) pyrrolidin-3-yl)oxy) acetic acid

To a solution of 1-(tert-butyl) 2-methyl (2S,3S)-3-(2-(tert-butoxy)-2-oxoethoxy) pyrrolidine-1,2-dicarboxylate (351 mg, 0.970 mmol) in acetonitrile (3 mL) was added HCl/1,4-dioxane (1 mL, 4 mol/L), and the mixture was stirred at room temperature for 3 hours. The solvent was concentrated under vacuum to afford 298 mg (crude) of the title compound as a yellow oil. LC-MS: (ESI, m/z): [M+H]⁺=204.

Step 3: 2-(((2S,3S)-1-(tert-Butoxycarbonyl)-2-(methoxycarbonyl)pyrrolidin-3-yl)oxy)acetic acid To a solution of 2-(((2S,3S)-2-(methoxycarbonyl) pyrrolidin-3-yl)oxy)acetic acid (261 mg, 1.28 mmol) in DCM (2 mL) was added DIPEA (1.30 g, 10.1 mmol) and (Boc)₂O (837 mg, 3.84 mmol). The solution was stirred at room temperature for 1 hour. The resulting mixture was diluted with DCM and washed with water and brine. The organic layer was concentrated under vacuum to afford 319 mg (crude) of the title compound as a yellow oil. LC-MS: (ESI, m/z): [M+H]⁺=304.

Step 4: 1-(tert-Butyl) 2-methyl (2S,3S)-3-(2-hydroxyethoxy) pyrrolidine-1,2-dicarboxylate Under nitrogen, to a solution of 2-(((2S,3S)-1-(tert-butoxycarbonyl)-2-(methoxycarbonyl) pyrrolidin-3-yl)oxy) acetic acid (262 mg, 0.860 mmol) in THF (3 mL) was added BH₃ (1.6 mL, 1M in THF) at 0° C. The resulting solution was stirred for 3 hours at 0° C. The reaction was quenched with MeOH. The reaction mixture concentrated under vacuum to afford 349 mg (crude) of the title compound as a colorless oil. LC-MS: (ESI, m/z): [M+H]⁺=290.

Step 5: 1-(tert-Butyl) 2-methyl (2S,3S)-3-(2-(tosyloxy) ethoxy) pyrrolidine-1,2-dicarboxylate Under nitrogen, to a solution of 1-(tert-butyl) 2-methyl (2S,3S)-3-(2-hydroxyethoxy) pyrrolidine-1,2-dicarboxylate (301 mg, 1.04 mmol), Et₃N (207 mg, 2.05 mmol) and 4-DMAP (12.7 mg, 0.100 mmol) in DCM (10 mL) was added TsCl (217 mg, 1.14 mmol) at room temperature. The solution was stirred for 8 hours at room temperature. The resulting mixture was diluted with EtOAc and washed with water and brine. The organic layer was concentrated under vacuum. The residue was purified by flash chromatography on silica gel (gradient: 0-10% MeOH/DCM) to afford 128 mg of the title compound as a yellow oil. LC-MS: (ESI, m/z): [M+H]⁺=444.

Step 6: Methyl (2S,3S)-3-(2-(tosyloxy) ethoxy) pyrrolidine-2-carboxylate

To a solution of 1-(tert-butyl) 2-methyl (2S,3S)-3-(2-(tosyloxy) ethoxy) pyrrolidine-1,2-dicarboxylate (111 mg, 0.250 mmol) in acetonitrile (4.5 mL) was added HCl/1,4-dioxane (1.5 mL, 4 mol/L), and the mixture was stirred at room temperature for 1 hour. The solvent was concentrated under vacuum to afford 103 mg (crude) of the title compound as a yellow oil. LC-MS: (ESI, m/z): [M+H]⁺=344.

Step 7: Methyl (5S,8S)-4-oxa-1-azabicyclo [3.2.1] octane-8-carboxylate

To a solution of methyl (2S,3S)-3-(2-(tosyloxy) ethoxy) pyrrolidine-2-carboxylate (103 mg, 0.300 mmol) in acetonitrile (5 mL) was added K₂CO₃ (227 mg, 1.64 mmol), and the mixture was stirred at 70° C. for 3 hours. After filtration, the filtrate was concentrated under reduced pressure to afford 110 mg (crude) of the title compound as a colorless oil. LC-MS: (ESI, m/z): [M+H]⁺=172.

Step 8: ((5S,8R)-4-Oxa-1-azabicyclo [3.2.1] octan-8-yl)methanol

Under nitrogen, to a solution of methyl (5S,8S)-4-oxa-1-azabicyclo [3.2.1] octane-8-carboxylate (110 mg, crude) in THF (3 mL) was added LiAlH₄ (1.3 mL, 1M in THF) at 0° C. The resulting solution was stirred for 1 hour at room temperature. The reaction was quenched by Na₂SO₄·10H₂O. After filtration, the filtrate was concentrated under reduced pressure to afford 63.1 mg (crude) of the title compound as a colorless oil. LC-MS: (ESI, m/z): [M+H]⁺=144. The crude was used for next step without further purification.

Intermediate 95: (1-Methyloctahydro-4aH-cyclopenta[b]pyridin-4a-yl)methanol

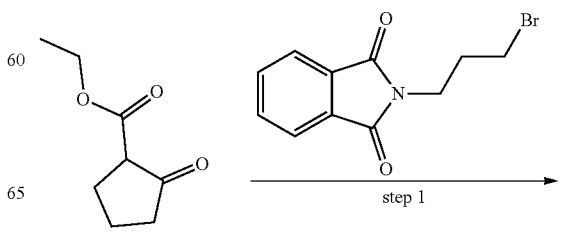

Step 3: Ethyl 1-methyloctahydro-4aH-cyclopenta[b]pyridine-4a-carboxylate

To a solution of ethyl 2,3,4,5,6,7-hexahydro-4aH-cyclopenta[b]pyridine-4a-carboxylate (4.40 g, 22.4 mmol) and polyformaldehyde (3.36 g, 37.3 mmol) in dichloromethane (300 mL) was added NaBH(OAc)$_3$ (23.7 g, 112 mmol) at room temperature in portions, and the mixture was stirred overnight. The reaction was quenched with water at 0° C. and extracted with dichloromethane. The combined organic layers were washed with brine, dried over anhydrous sodium sulfate and concentrated under vacuum. The residue was purified by flash chromatography on silica gel (gradient: 0-40% EtOAc in petroleum ether) to afford the title compound (1.50 g) as a light colorless oil. LC-MS: (ESI, m/z): [M+H]$^+$=212.

Step 4: (1-Methyloctahydro-4aH-cyclopenta[b]pyridin-4a-yl) methanol

To a solution of ethyl 1-methyloctahydro-4aH-cyclopenta[b]pyridine-4a-carboxylate (1.50 g, 7.08 mmol) in tetrahydrofuran (20 mL) was added LiAlH$_4$ (2M solution in tetrahydrofuran, 7.1 mL) dropwise at 0° C., and the mixture was stirred for 1 hour at room temperature. The reaction was quenched with Na$_2$SO$_4$·10H$_2$O. After filtration, the filtrate was collected and concentrated under vacuum to afford the title compound (600 mg crude) as a yellow oil. LC-MS: (ESI, m/z): [M+H]$^+$=170. The crude was used for next step without further purification.

Intermediate 96: 8a-(Hydroxymethyl)-2-methylhexahydropyrrolo[1,2-a]pyrazin-1(2H)-one

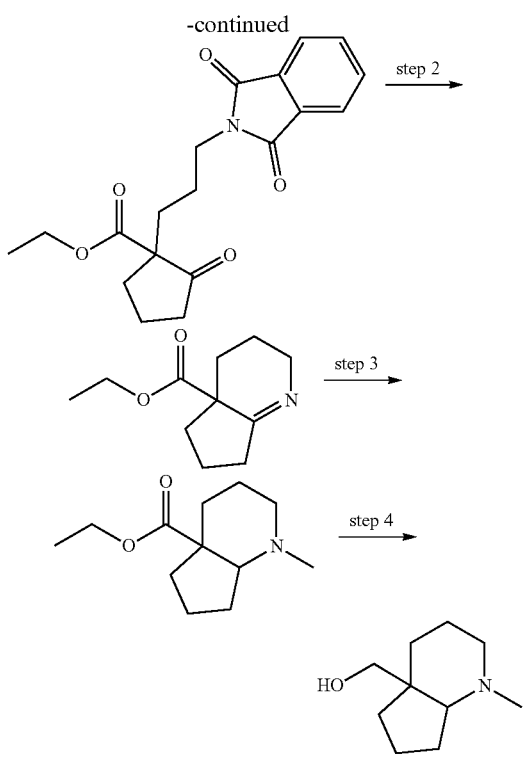

Step 1: Ethyl 1-(3-(1,3-dioxoisoindolin-2-yl) propyl)-2-oxocyclopentane-1-carboxylate To a solution of ethyl 2-oxocyclopentane-1-carboxylate (10.0 g, 64.1 mmol) in tetrahydrofuran (50 mL) and DMF (50 mL) was added NaH (60% dispersion in mineral oil, 3.08 g, 76.9 mmol) in 3 portions at 0° C., and the mixture was stirred for 30 minutes. Then 2-(3-bromopropyl) isoindoline-1,3-dione (18.9 g, 70.5 mmol) in tetrahydrofuran (50 mL) was added at 0° C., and the mixture was stirred overnight at 65° C. The reaction was quenched with/saturated NH$_4$Cl aqueous solution. The reaction mixture was diluted with water and extracted with ethyl acetate. The combined organic layers were washed with brine, dried over anhydrous sodium sulfate and concentrated under vacuum. The residue was purified by flash chromatography on silica gel (gradient: 0-20% EtOAc in petroleum ether) to afford the title compound (13.5 g) as a white solid. LC-MS: (ESI, m/z): [M+H]$^+$=344. $^1$H NMR (300 MHz, CDCl$_3$, ppm) δ 7.88-7.77 (m, 2H), 7.76-7.65 (m, 2H), 4.23-4.04 (m, 2H), 3.88-3.56 (m, 2H), 2.60-2.13 (m, 4H), 2.06-1.70 (m, 4H), 1.70-1.50 (m, 2H), 1.32-1.15 (m, 3H).

Step 2: Ethyl 2,3,4,5,6,7-hexahydro-4aH-cyclopenta[b]pyridine-4a-carboxylate

To a solution of ethyl 1-(3-(1,3-dioxoisoindolin-2-yl) propyl)-2-oxocyclopentane-1-carboxylate (13.5 g, 39.2 mmol) in ethanol (200 mL) was added hydrazine hydrate (80%, 7.2 mL) at room temperature, and the mixture was stirred for 1 hour at 80° C. The mixture was cooled to room temperature and the solid was filtered. The filtrate was concentrated under reduced pressure to afford the title compound (4.40 g, crude) as an off white solid. LC-MS: (ESI, m/z): [M+H]$^+$=196.

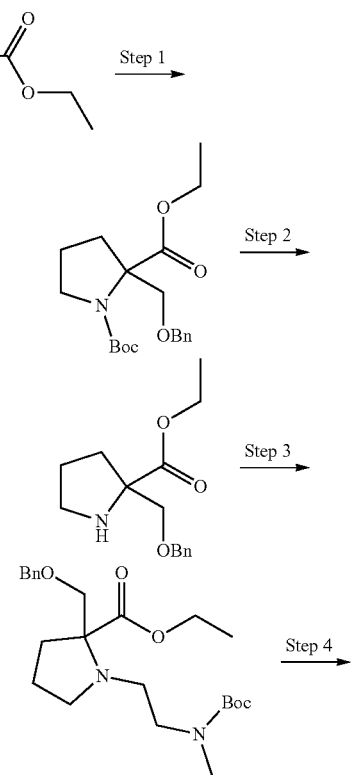

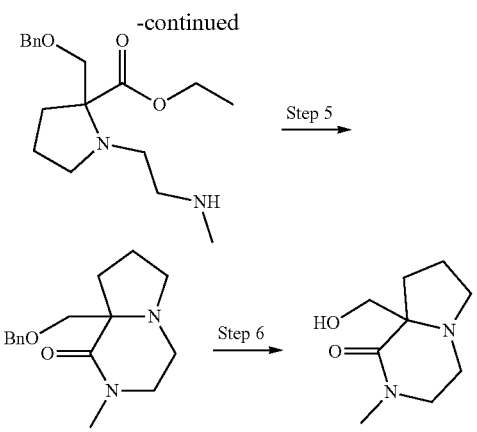

Step 1: 1-(tert-Butyl) 2-ethyl 2-((benzyloxy)methyl) pyrrolidine-1,2-dicarboxylate Under nitrogen, to a solution of 1-(tert-butyl) 2-ethyl pyrrolidine-1,2-dicarboxylate (10.0 g, 41.1 mmol) in tetrahydrofuran (100 mL) was added LiHMDS (1M in THF, 100 mL, 100 mmol) at −40° C. The resulting solution was stirred at −40° C. for 30 min. Then BOMCl (9.62 g, 61.7 mmol) was added at −40° C. The solution was stirred at 25° C. for 1 hour. The reaction mixture was partitioned between saturated aqueous NH₄Cl and EtOAc. The organic layer was washed with saturated aqueous NaHCO₃, water and brine, dried over MgSO₄ and concentrated. The residue was purified by flash chromatography on silica gel (gradient: 0%-20% EtOAc/petroleum ether) to afford 12 g of the title compound as a yellow oil. LC-MS: (ESI, m/z): [M+H]⁺=364.

Step 2: Ethyl 2-((benzyloxy)methyl) pyrrolidine-2-carboxylate

A solution of 1-(tert-butyl) 2-ethyl 2-(benzyloxymethyl) pyrrolidine-1,2-dicarboxylate (5.0 g, 13.8 mmol) in dichloromethane (50 mL) and TFA (20 mL) was stirred at room temperature for 2 hours. The resulting mixture was concentrated under reduced pressure. The residue was purified by C18 column (solvent gradient: 0-80% ACN in water (0.05% NH₄HCO₃)) to afford 3.4 g of the title compound as a yellow oil. LC-MS: (ESI, m/z): [M+H]⁺=264.

Step 3: Ethyl 2-((benzyloxy)methyl)-1-(2-((tert-butoxycarbonyl)(methyl)amino)ethyl) pyrrolidine-2-carboxylate To a solution of ethyl 2-(benzyloxymethyl) pyrrolidine-2-carboxylate (2.5 g, 9.49 mmol) in dichloromethane (50 mL) was added a solution of tert-butyl N-methyl-N-(2-oxoethyl)carbamate (8.2 g, 47.5 mmol) in dichloromethane (10 mL) at 0° C., and the mixture was stirred for 30 minutes. Then NaBH(OAc)₃ (10 g, 48 mmol) was added at 0° C., and the mixture was stirred at room temperature for 3 hours. The reaction was quenched with water and extracted with dichloromethane. The combined organic layers were washed with brine, dried over anhydrous sodium sulfate and concentrated under vacuum. The residue was purified by flash chromatography on silica gel (gradient: 0-30% EtOAc/petroleum ether) to afford 3.9 g as a light yellow oil. LC-MS: (ESI, m/z): [M+H]⁺=421.

Step 4: Ethyl 2-((benzyloxy)methyl)-1-(2-(methylamino)ethyl) pyrrolidine-2-carboxylate A solution of ethyl 2-(benzyloxymethyl)-1-[2-[tert-butoxycarbonyl(methyl)amino]ethyl]pyrrolidine-2-carboxylate (100 mg, 0.24 mmol) in aqueous HCl (1M) in EtOAc solution (1.5 mL) and dichloromethane (3 mL) was stirred at 25° C. for 4 hours. The resulting mixture was concentrated under reduced pressure to afford 50 mg (crude) of the title compound as a yellow solid. LC-MS: (ESI, m/z): [M+H]⁺=321. The crude was used for next step without further purification.

Step 5: 8a-((Benzyloxy)methyl)-2-methylhexahydropyrrolo[1,2-a] pyrazin-1(2H)-one A solution of ethyl 2-(benzyloxymethyl)-1-[2-(methylamino)ethyl] pyrrolidine-2-carboxylate (1.0 g, 3.12 mmol) and DIPEA (4.02 g, 31.2 mmol) in MeOH was stirred at 25° C. for 72 hours. The resulting mixture was extracted with DCM. The combined organic layers were dried over anhydrous Na₂SO₄. After filtration, the filtrate was concentrated under reduced pressure. The residue was purified by flash chromatography on silica gel (gradient: 0%-10% MeOH/DCM) to afford 200 mg of the title compound as a yellow oil. LC-MS: (ESI, m/z): [M+H]⁺=275.

Step 6: 8a-(Hydroxymethyl)-2-methylhexahydropyrrolo[1,2-a] pyrazin-1(2H)-one Under nitrogen, to a solution of 8a-(benzyloxymethyl)-2-methyl-4,6,7,8-tetrahydro-3H-pyrrolo[1,2-a] pyrazin-1-one (300 mg, 1.09 mmol) in methyl alcohol (5 mL) was added Pd/C (10%, 20.0 mg) at 25° C. The resulting solution was stirred at room temperature for 18 h. After filtration, the filtrate was concentrated under reduced pressure to afford the title compound 250 mg crude. LC-MS: (ESI, m/z): [M+H]⁺=185. The crude product was used for next step without further purification.

Intermediate 97: (1,2-Difluorotetrahydro-1H-pyrrolizin-7a(5H)-yl) methanol

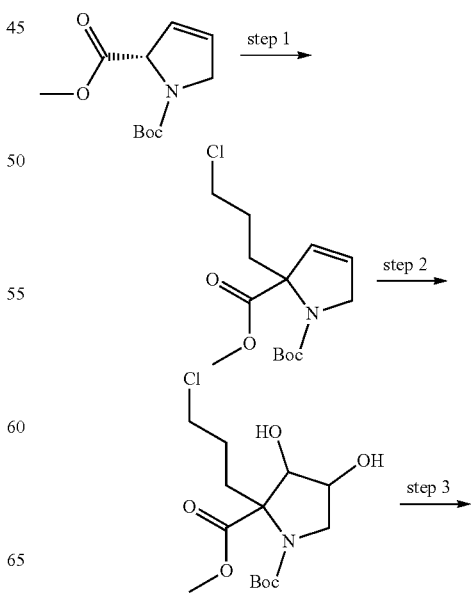

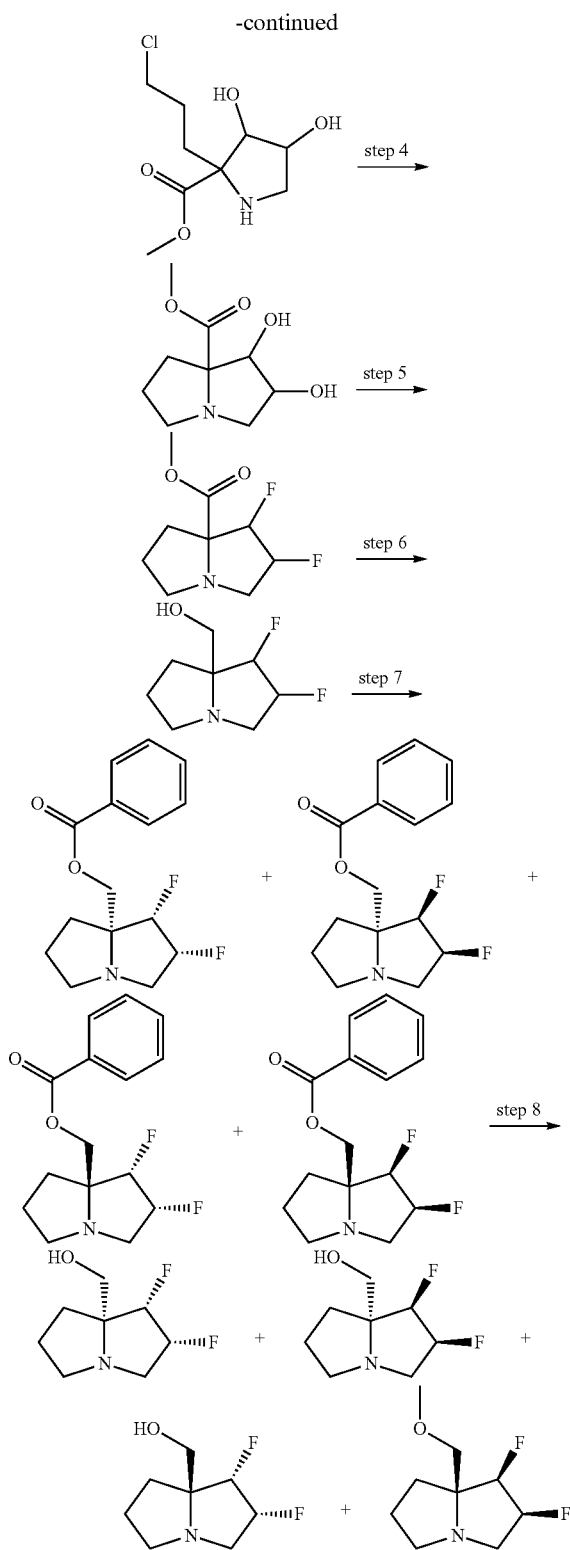

Step 1: 1-(tert-Butyl) 2-methyl 2-(3-chloropropyl)-2,5-dihydro-1H-pyrrole-1,2-dicarboxylate Under nitrogen, to a solution of 1-(tert-butyl) 2-methyl (S)-2,5-dihydro-1H-pyrrole-1,2-dicarboxylate (10.8 g, 47.5 mmol) in THF (50 mL) was added LiHMDS (95.3 mL, 1 M in THF) dropwise at −30° C., and the mixture was stirred for 1 hour at −30° C. Then 1-bromo-3-chloropropane (22.4 g, 142 mmol) was added dropwise at −30° C., and the mixture was stirred for 30 min. The mixture was warmed to room temperature and stirred for 1.5 h. The reaction was quenched with NH$_4$Cl aqueous and extracted with EtOAc. The combined organic layers were dried over anhydrous sodium sulfate and concentrated under vacuum. The residue was purified by flash chromatography on silica gel (gradient: 0%-40% EtOAc/petroleum ether) to afford 10.7 g of the title compound as a light yellow syrup. LC-MS: (ESI, m/z): [M+H]$^+$=304.

Step 2: 1-(tert-Butyl) 2-methyl 2-(3-chloropropyl)-3,4-dihydroxypyrrolidine-1,2-dicarboxylate A solution of 1-(tert-butyl) 2-methyl 2-(3-chloropropyl)-2,5-dihydro-1H-pyrrole-1,2-dicarboxylate (10.7 g, 35.2 mmol), NMMO (10.2 g, 88.3 mmol) and K$_2$OSO$_2$(OH)$_4$ (1.62 g, 4.40 mmol) in acetone (60 mL) and water (40 mL) was stirred at room temperature for 2 hours. The solvent was concentrated under vacuum. The residue was purified by flash chromatography on silica gel (gradient: 0%-4% MeOH/DCM) to afford 10.4 g of the title compound as a brown syrup. LC-MS: (ESI, m/z): [M+H]$^+$=338.

Step 3: Methyl 2-(3-chloropropyl)-3,4-dihydroxy-pyrrolidine-2-carboxylate

A solution of 1-(tert-butyl) 2-methyl 2-(3-chloropropyl)-3,4-dihydroxypyrrolidine-1,2-dicarboxylate (10.4 g, 30.7 mmol) and TFA (25 mL) in DCM (75 mL) was stirred at room temperature for 2 hours. The solvent was concentrated under vacuum to afford 8.26 g crude of the title compound as a brown syrup. LC-MS: (ESI, m/z): [M+H]$^+$=238.

Step 4: Methyl 1,2-dihydroxytetrahydro-1H-pyrrolizine-7a(5H)-carboxylate

A solution of methyl 2-(3-chloropropyl)-3,4-dihydroxy-pyrrolidine-2-carboxylate (8.26 g, 34.8 mmol) and K$_2$CO$_3$ (14.2 g, 103 mmol) in acetonitrile (60 mL) was stirred at room temperature for 1.5 hours. The solvent was concentrated under vacuum. The residue was purified by C18 column (solvent gradient: 0-70% ACN in water (0.05% NH$_4$HCO$_3$)) to yield 13.0 g (crude) as a yellow solid. LC-MS: (ESI, m/z): [M+H]$^+$=202.

Step 5: Methyl 1,2-difluorotetrahydro-1H-pyrrolizine-7a(5H)-carboxylate

Under nitrogen, a solution of methyl 1,2-dihydroxytetrahydro-1H-pyrrolizine-7a(5H)-carboxylate (13.0 g, 64.7 mmol) (crude) in DAST (65 mL) was stirred for 2 days at 40° C., quenched by NaHCO$_3$ aqueous and extracted with DCM. The combined organic layers were dried over anhydrous sodium sulfate and concentrated under vacuum. The residue was dissolved with CH$_3$OH (30 mL). After filtration, the filtrate was concentrated under reduced pressure to afford 3.91 g crude of the title compound as a brown syrup. LC-MS: (ESI, m/z): [M+H]$^+$=206.

Step 6: (1,2-Difluorotetrahydro-1H-pyrrolizin-7a(5H)-yl)methanol

Under nitrogen, a solution of methyl 1,2-difluorotetrahydro-1H-pyrrolizine-7a(5H)-carboxylate (2.65 g, crude) in THF (20 mL) was added LiAlH₄ (8.1 mL, 2.4 M in THF) at 0° C. The resulting solution was stirred for 1 h at room temperature. The reaction was quenched with Na₂SO₄·10H₂O. After filtration, the filtrate was concentrated under reduced pressure to afford 1.19 g crude of the title compound as a brown syrup. LC-MS: (ESI, m/z): [M+H]⁺=178.

Step 7: (1,2-Difluorotetrahydro-1H-pyrrolizin-7a (5H)-yl)methyl benzoate

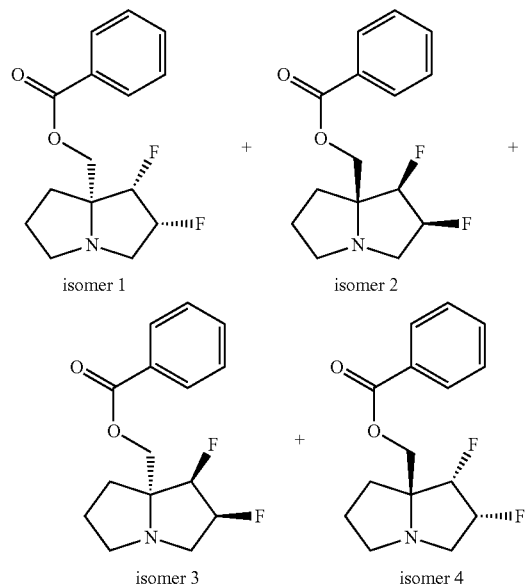

isomer 1    isomer 2 isomer 3    isomer 4

To a solution of (1,2-difluorotetrahydro-1H-pyrrolizin-7a (5H)-yl) methanol (1.19 g, 6.72 mmol) and Et₃N (1.36 g, 13.5 mmol) in DCM (12 mL) was added benzoyl chloride (1.42 g, 10.1 mmol) at 0° C., and the mixture was stirred at room temperature for 2 hours. The solvent was concentrated under vacuum. The residue was purified by flash chromatography on silica gel (gradient: 0%-4% MeOH/DCM) to afford mixture product. The mixture was purified by C18 column (solvent gradient: 0-60% ACN in water (0.05% NH₄HCO₃)) to yield 633.3 mg of the mixture of isomer 1 and isomer 2 (faster peak) as a yellow syrup and 295.1 mg of the isomer 3 and isomer 4 (slower peak) as a yellow syrup. The isomer 1 and isomer 2 were separated by Chiral-Prep-HPLC (conditions: Column: CHIRAL ART Cellulose-SC, 2*25 cm, 5 um; Mobile Phase A: — (0.5% 2 M NH₃—MeOH)—C, Mobile Phase B: IPA-HPLC; Flow rate: 20 mL/min; Gradient: 30 B to 30 B in 15 min; 220/254 nm; $R_{T1}$:8.505; $R_{T2}$:10.259) to afford 229 mg of isomer 1 as a colorless syrup (single cis isomer, complete configuration not determined) and 223 mg of isomer 2 as a colorless syrup (single cis isomer, complete configuration not determined). The isomer 3 and isomer 4 were separated by Chiral-Prep-HPLC (conditions: Column: LUX 5 um Cellulose-2, 2.12*25 cm; Mobile Phase A: -x (0.5% 2 M NH₃—MeOH)—H—, Mobile Phase B: EtOH—HPLC; Flow rate: 20 mL/min; Gradient: 5 B to 5 B in 15 min; 220/254 n; $R_T$1:9.533; $R_{T2}$:13.438) to afford 117 mg of isomer 3 as a colorless syrup (single trans isomer, the exact structure is not sure) and 108 mg of isomer 4 as a colorless syrup (single trans isomer, the exact structure is not sure). LC-MS: (ESI, m/z): [M+H]⁺=282.

Step 8: (1,2-Difluorotetrahydro-1H-pyrrolizin-7a(5H)-yl) methanol

A solution of (1,2-difluorotetrahydro-1H-pyrrolizin-7a (5H)-yl)methyl benzoate (50.3 mg, 0.180 mmol) (isomer 1 from last step) and LiOH·H₂O (45.3 mg, 1.08 mmol) in THF (1 mL) and water (0.25 mL) was stirred at room temperature overnight. The solution was diluted with water and extracted with DCM. The combined organic layers were washed with brine, dried over anhydrous sodium sulfate and concentrated under vacuum to afford 30.6 mg (crude) as a yellow oil. LC-MS: (ESI, m/z): [M+H]⁺=178.

Analogous to method described as above, another 3 isomers were prepared.

Intermediate 100:
2-(3-Morpholinooxetan-3-yl)ethan-1-ol

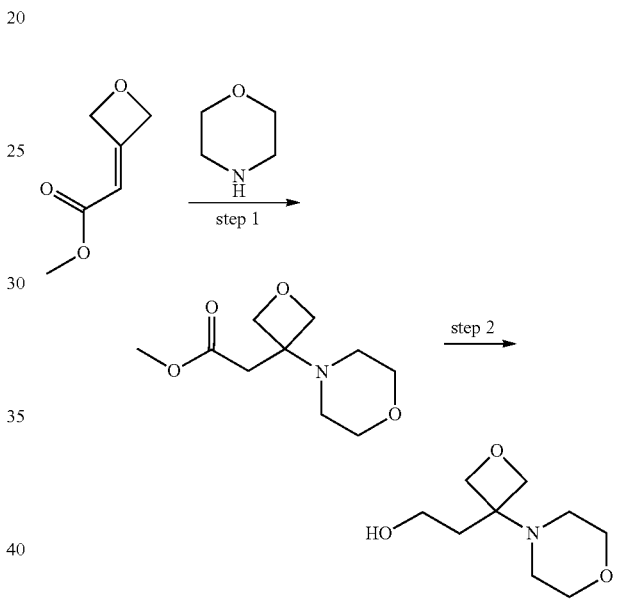

Step 1: Methyl 2-(3-morpholinooxetan-3-yl)acetate

A mixture of methyl 2-(oxetan-3-ylidene)acetate (1.01 g, 7.11 mmol) and morpholine (2.25 g, 25.8 mmol) was stirred at room temperature for 3 hours. The solution was diluted with EtOAc, washed with water and brine. The organic layer was dried over anhydrous sodium sulfate and concentrated under vacuum. The residue was purified by flash chromatography on silica gel eluting (gradient: 0-40% EtOAc/ petroleum ether) to afford 1.01 g of the title compound as a light brown oil. LC-MS: (ESI, m/z): [M+H]⁺=216.

Step 2: 2-(3-Morpholinooxetan-3-yl)ethan-1-ol

Under nitrogen, to a solution of methyl 2-(3-morpholinooxetan-3-yl)acetate (600 mg, 2.79 mmol) in tetrahydrofuran (15 mL) was added LiAlH₄ (2 mL, 2.5 M in THF) at 0° C. The solution was stirred at room temperature for 2 hours. The reaction was quenched by Na₂SO₄·10H₂O, and the solid was filtered out. The filtrate was concentrated under vacuum to afford 487 mg (crude) of the title compound as an colorless oil. LC-MS: (ESI, m/z): [M+H]⁺=188. The crude was used for next step without further purification.

Intermediate 103: (2-(2,2-Difluoroethyl)-1-methylpyrrolidin-2-yl)methanol

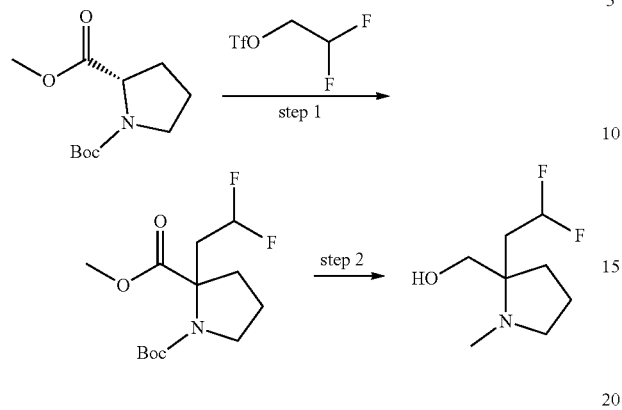

Step 1: 1-(tert-Butyl) 2-methyl 2-(2,2-difluoroethyl) pyrrolidine-1,2-dicarboxylate To a solution of 1-(tert-butyl) 2-methyl (S)-pyrrolidine-1,2-dicarboxylate (2.50 g, 10.9 mmol) in tetrahydrofuran (50 mL) was added LiHMDS (1M in THF, 22 mL) dropwise at −40° C., and the mixture was stirred for 1 hour. Then a solution of 2,2-difluoroethyl trifluoromethanesulfonate (3.50 g, 16.4 mmol) in tetrahydrofuran (50 mL) was added dropwise at −40° C., and the mixture was stirred for additional 1 hour at room temperature. The reaction was quenched with saturated NH$_4$Cl. The reaction mixture was diluted with water and extracted with ethyl acetate. The combined organic layers were washed with brine, dried over anhydrous sodium sulfate and concentrated under vacuum. The residue was purified by flash chromatography on silica gel (gradient: 0-20% ethyl acetate in petroleum ether) to afford the title compound (1.50 g) as a light yellow oil. LC-MS: (ESI, m/z): [M+H]$^+$=294.

Step 2: (2-(2,2-Difluoroethyl)-1-methylpyrrolidin-2-yl)methanol

To a solution of 1-(tert-butyl) 2-methyl 2-(2,2-difluoroethyl)pyrrolidine-1,2-dicarboxylate (1.50 g, 5.11 mmol) in tetrahydrofuran (15 mL) was added LiAlH$_4$ (389 mg, 10.3 mmol) in portions at 0° C., and the mixture was stirred for 2 hours at 60° C. The reaction was quenched with Na$_2$SO$_4$·10H$_2$O. The reaction mixture was diluted with water and extracted with ethyl acetate. The combined organic layers were dried over anhydrous sodium sulfate and concentrated under vacuum. The residue was purified by flash chromatography on silica gel (gradient: 0-15% ethyl acetate in petroleum ether) to afford the title compound (700 mg) as a white solid. LC-MS: (ESI, m/z): [M+H]$^+$=180.

Intermediate 104: ((1R,5R)-4-Oxa-1-azabicyclo[3.2.1]octan-7-yl)methanol

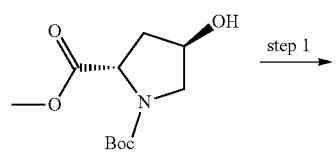

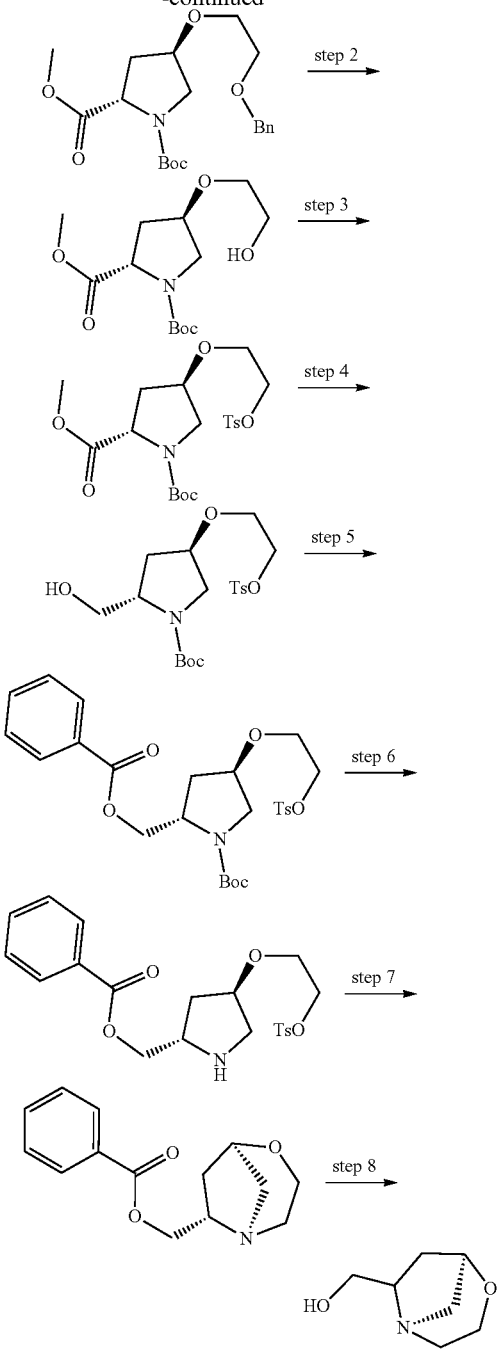

Step 1: 1-(tert-Butyl) 2-methyl (2S,4R)-4-(2-(benzyloxy)ethoxy)pyrrolidine-1,2-dicarboxylate Under nitrogen, to a solution of 1-(tert-butyl) 2-methyl (2S,4R)-4-hydroxypyrrolidine-1,2-dicarboxylate (20.0 g, 81.6 mmol) in DMF (200 mL) was added NaI (1.22 g, 8.16 mmol) and NaH (3.92 g, 98.0 mmol, 60% dispersion in mineral oil) at 0° C. The resulting solution was stirred at 0° C. for 20 min. Then ((2-bromoethoxy)methyl)benzene (19.2 g, 89.4 mmol) was added, and the mixture was stirred at room temperature for 1 h. The reaction was quenched by NH$_4$Cl aqueous and extracted with EtOAc. The combined organic layers were dried over anhydrous sodium sulfate and concentrated under vacuum. The residue was purified by flash chromatography on silica gel (gradient: 0%-50% EtOAc/petroleum ether) to afford 12.8 g of the title compound as a colorless oil. LC-MS: (ESI, m/z): [M+H]⁺=280.

Step 2: 1-(tert-Butyl) 2-methyl (2S,4R)-4-(2-hydroxyethoxy)pyrrolidine-1,2-dicarboxylate Under hydrogen (1 atm), a suspension of Pd/C (1.68 g, 10%) and 1-(tert-butyl) 2-methyl (2S,4R)-4-(2-(benzyloxy)ethoxy)pyrrolidine-1,2-dicarboxylate (6.70 g, 17.7 mmol) in MeOH (700 mL) was stirred at room temperature for 2 days. The solution was filtered and the filtrate was concentrated under vacuum to afford 4.89 g (crude) of the title compound as a yellow oil. LC-MS: (ESI, m/z): [M-100+H]⁺=190.

Step 3: 1-(tert-Butyl) 2-methyl (2S,4R)-4-(2-(tosyloxy)ethoxy)pyrrolidine-1,2-dicarboxylate To a solution of 1-(tert-butyl) 2-methyl (2S,4R)-4-(2-hydroxyethoxy)pyrrolidine-1,2-dicarboxylate (5.01 g, 17.3 mmol), DIPEA (2.46 g, 19.0 mmol) and 4-DMAP (211 mg, 1.73 mmol) in DCM (55 mL) was added TsCl (3.64 g, 19.0 mmol) at 0° C. The solution was stirred at room temperature overnight. The resulting solution was partitioned between water and DCM. The organic layer was dried over anhydrous sodium sulfate and concentrated under vacuum. The residue was purified by flash chromatography on silica gel (gradient: 0%-50% EtOAc/petroleum ether) to afford 4.76 g of the title compound as a yellow oil. LC-MS: (ESI, m/z): [M-100+H]⁺=344.

Step 4: tert-Butyl (2S,4R)-2-(hydroxymethyl)-4-(2-(tosyloxy)ethoxy)pyrrolidine-1-carboxylate Under nitrogen, a solution of 1-(tert-butyl) 2-methyl (2S,4R)-4-(2-(tosyloxy)ethoxy)pyrrolidine-1,2-dicarboxylate (9.46 g, 21.3 mmol) in THF (100 mL) was added LiAlH₄ (8.54 mL, 2.5 M in THF) at 0° C. The result solution was stirred at 0° C. for 30 min. The solution was quenched with Na₂SO₄·10H₂O at 0° C. and filtrated. The solvent was concentrated under vacuum to afford 7.50 g (crude) of the title compound as a yellow crude oil. LC-MS: (ESI, m/z): [M-100+H]⁺=316.

Step 5: tert-Butyl (2S,4R)-2-((benzoyloxy)methyl)-4-(2-(tosyloxy)ethoxy)pyrrolidine-1-carboxylate To a solution of tert-butyl (2S,4R)-2-(hydroxymethyl)-4-(2-(tosyloxy)ethoxy)pyrrolidine-1-carboxylate (7.50 g, 18.1 mmol) and Et₃N (48 g, 54.2 mmol) in DCM (80 mL) was added benzoyl chloride (3.82 g, 27.2 mmol) at 0° C. The result solution was stirred at room temperature for 3 h. The resulting solution was partitioned between water and EtOAc. The organic layer was dried over anhydrous sodium sulfate and concentrated under vacuum. The residue was purified by flash chromatography on silica gel (gradient: 0%-60% EtOAc/petroleum ether) to afford 5.84 g of the title compound as a yellow oil. LC-MS: (ESI, m/z): [M-100+H]⁺=420.

Step 6: ((2S,4R)-4-(2-(Tosyloxy)ethoxy)pyrrolidin-2-yl)methyl benzoate

A solution of tert-butyl (2S,4R)-2-((benzoyloxy)methyl)-4-(2-(tosyloxy)ethoxy)pyrrolidine-1-carboxylate (6.70 g, 12.9 mmol) in DCM (80 mL) and TFA (40 mL) was stirred at room temperature for 0.5 h. The solution was concentrated under vacuum to afford 9.40 g (crude) of the title compound as a yellow oil. LC-MS: (ESI, m/z): [M+H]⁺=420.

Step 7: ((1R,5R,7S)-4-Oxa-1-azabicyclo[3.2.1]octan-7-yl)methyl benzoate

To a solution of ((2S,4R)-4-(2-(tosyloxy)ethoxy)pyrrolidin-2-yl)methyl benzoate (9.40 g, 22.4 mmol) in DMA (285 mL) was added K₂CO₃ (21.7 g, 157 mmol). The solution was stirred at 40° C. for overnight. After filtrated, the solution was concentrated under vacuum. The residue was purified by C18 column (solvent gradient: 0-50% ACN in water (0.05% NH₄HCO₃)) to afford 1.80 g of the title compound as a yellow oil. LC-MS: (ESI, m/z): [M+H]⁺=248.

Step 8: ((1R,5R)-4-Oxa-1-azabicyclo[3.2.1]octan-7-yl)methanol

Under nitrogen, to a solution of ((1R,5R,7S)-4-Oxa-1-azabicyclo[3.2.1]octan-7-yl)methyl benzoate (500 mg, 2.02 mmol) in THF (5.5 mL) was added LiAlH₄ (3.04 mL, 1 M in THF) at 0° C. The result solution was stirred at room temperature for 1 h. The solution was quenched with Na₂SO₄·10H₂O at 0° C. and filtrated. The filtrate was concentrated under vacuum to afford 188 mg (crude) of the title compound as a yellow oil. LC-MS: (ESI, m/z): [M+H]⁺= 144. The crude was used for next step without further purification.

Intermediate 105:
((6R)-6-Fluorohexahydro-1H-pyrrolizin-3-yl)methanol

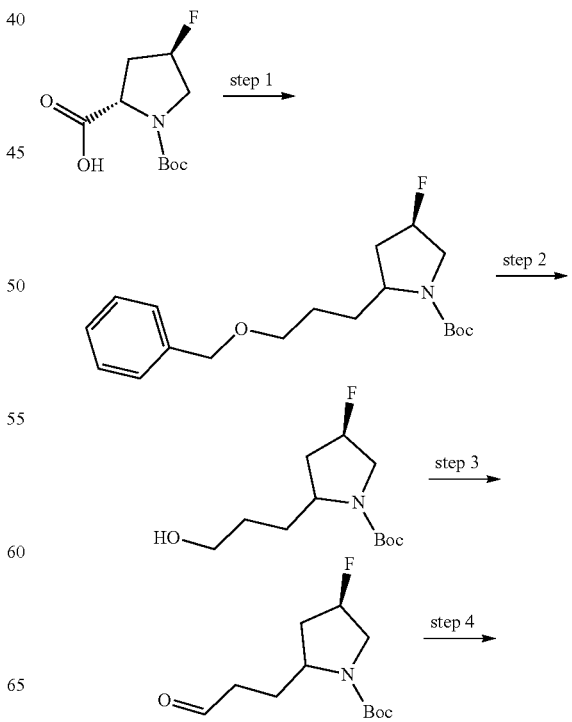

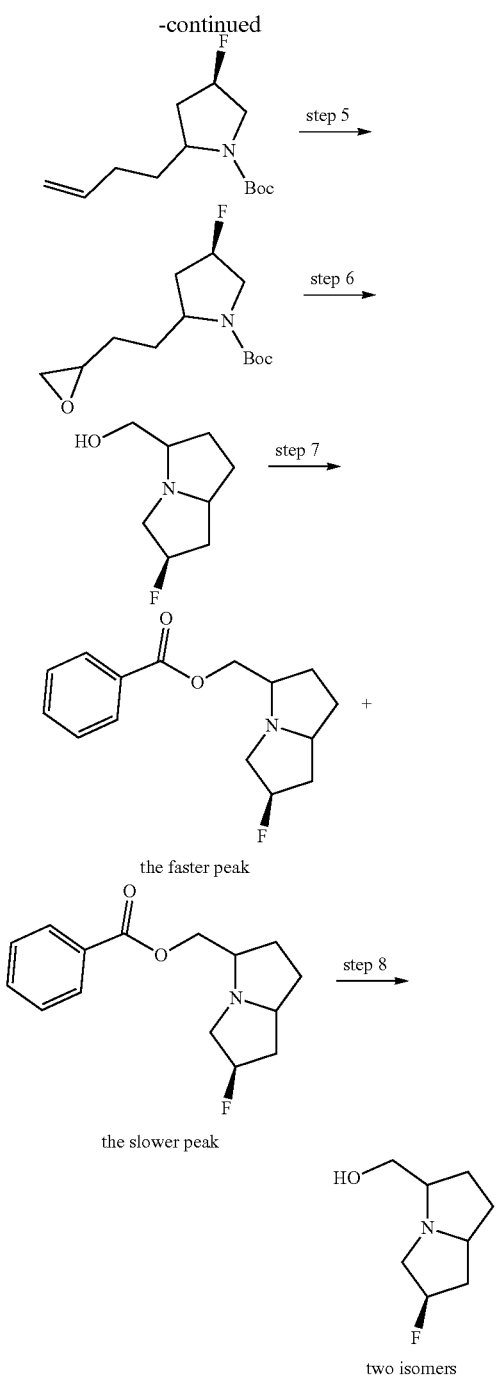

the faster peak the slower peak two isomers

Step 1: tert-Butyl (4R)-2-(3-(benzyloxy) propyl)-4-fluoropyrrolidine-1-carboxylate Under nitrogen, to a solution of (2S,4R)-1-(tert-butoxycarbonyl)-4-fluoropyrrolidine-2-carboxylic acid (1.53 g, 6.56 mmol), (Ir[dF(CF$_3$) ppy]2 (dtbpy)) PF6 (89.0 mg, 0.0900 mmol), 4,4-dOMe-bpy (94.0 mg, 0.430 mmol), NiCl$_2$-glyme (96.1 mg, 0.431 mmol) and K$_2$CO$_3$ (1.19 g, 8.70 mmol) in ACN (2.5 mL) was added ((3-bromopropoxy) methyl) benzene (1.00 g, 4.36 mmol) and H$_2$O (1.58 mL) at 0° C. The resulting solution was stirred overnight at room temperature irradiation under blue LED light. After filtration, the filtrate was diluted with water, extracted with EtOAc. The combined organic layers were concentrated under vacuum. The residue was purified by flash chromatography on silica gel (gradient: 0%-50% EtOAc/petroleum ether) to afford 525 mg of the title compound as a yellow oil. LC-MS: (ESI, m/z): [M-100+H]$^+$=238.

Step 2: tert-Butyl (4R)-4-fluoro-2-(3-hydroxypropyl) pyrrolidine-1-carboxylate Under nitrogen (1 atm), to a solution of tert-butyl (4R)-2-(3-(benzyloxy) propyl)-4-fluoropyrrolidine-1-carboxylate (2.60 g, 7.71 mmol) in MeOH (25 mL) was added Pd/C (801 mg, 10%) at room temperature. The resulting solution was stirred overnight at room temperature. After filtration, the filtrate was concentrated under vacuum to afford 2.01 g (crude) of the title compound as a yellow oil. LC-MS: (ESI, m/z): [M+H]$^+$=248.

Step 3: tert-Butyl (4R)-4-fluoro-2-(3-oxopropyl) pyrrolidine-1-carboxylate

To a solution of tert-butyl (4R)-4-fluoro-2-(3-hydroxypropyl) pyrrolidine-1-carboxylate (400 mg, 1.62 mmol) in DCM (10 mL) was added Dess-Martin (1.03 g, 2.43 mmol) at 0° C., and the mixture was stirred at room temperature for 3 h. After filtration, the filtrate was partitioned between water and EtOAc. The organic layer was dried over anhydrous sodium sulfate and concentrated under vacuum. The residue was purified by flash chromatography on silica gel (gradient: 0%-30% EtOAc/petroleum ether) to afford 132 mg of the title compound as a yellow oil. LC-MS: (ESI, m/z): [M+H]$^+$=246.

Step 4: tert-Butyl (4R)-2-(but-3-en-1-yl)-4-fluoropyrrolidine-1-carboxylate

Under nitrogen, to a solution of methyltriphenylphosphonium bromide (2.71 g, 7.60 mmol) in THF (15 mL) was added t-BuOK (9.53 mL, 1 M in THF) at 0° C., and the mixture was stirred at room temperature for 30 min, then tert-butyl (4R)-4-fluoro-2-(3-oxopropyl) pyrrolidine-1-carboxylate (934 mg, 3.81 mmol) in THF (8 mL) was added at 0° C. The mixture solution was stirred at room temperature for 2 h. The reaction was quenched with aqueous NH$_4$Cl and extracted with EtOAc. The combined organic layers were dried over anhydrous sodium sulfate and concentrated under vacuum. The residue was purified by flash chromatography on silica gel (gradient: 0%-10% EtOAc/petroleum ether) to afford 792 mg of the title compound as a yellow oil. LC-MS: (ESI, m/z): [M+H]$^+$=244.

Step 5: tert-Butyl (4R)-4-fluoro-2-(2-(oxiran-2-yl) ethyl)pyrrolidine-1-carboxylate To a solution of tert-butyl (4R)-2-(but-3-en-1-yl)-4-fluoropyrrolidine-1-carboxylate (792 mg, 3.26 mmol) in DCM (9 mL) was added m-CPBA (959 mg, 5.54 mmol) at 0° C. The mixture was stirred at room temperature overnight. The reaction was quenched with aqueous Na$_2$S$_2$O$_3$ and extracted with EtOAc. The combined organic layers were dried over anhydrous sodium sulfate and concentrated under vacuum. The residue was purified by flash chromatography on silica gel (gradient: 0%-50% EtOAc/petroleum ether) to afford 781 mg of the title compound as a yellow oil. LC-MS: (ESI, m/z): [M-56+H]$^+$=204.

Step 6: ((6R)-6-Fluorohexahydro-1H-pyrrolizin-3-yl) methanol

A solution of tert-butyl (4R)-4-fluoro-2-(2-(oxiran-2-yl)ethyl)pyrrolidine-1-carboxylate (500 mg, 1.93 mmol) in TFA (1.5 mL) and DCM (6 mL) was stirred at room temperature overnight. The solvent was concentrated under vacuum to afford 568 mg (crude) of the title compound as a brown oil. LC-MS: (ESI, m/z): $[M+H]^+=160$.

Step 7: ((6R)-6-Fluorohexahydro-1H-pyrrolizin-3-yl)methyl benzoate

To a solution of ((6R)-6-fluorohexahydro-1H-pyrrolizin-3-yl)methanol (200 mg, 1.26 mmol) and Et$_3$N (381 mg, 3.77 mmol) in DCM (3 mL) was added BzCl (213 mg, 1.51 mmol) at 0° C. The solution was stirred at room temperature for 1.5 h. The solution was concentrated under vacuum. The residue was purified by C18 column (solvent gradient: 0-50% ACN in water (0.05% NH$_4$HCO$_3$)) to afford 35.2 mg of the faster peak and 49.3 mg of the slower peak as a yellow oil. LC-MS: (ESI, m/z): $[M+H]^+=264$.

Step 8: ((6R)-6-Fluorohexahydro-1H-pyrrolizin-3-yl)methanol

Under nitrogen, to a solution of ((6R)-6-fluorohexahydro-1H-pyrrolizin-3-yl)methyl benzoate (35.1 mg, 0.130 mmol) (the faster peak from last step) in THF (1.5 mL) was added LiAlH$_4$ (0.2 mL, 1 M in THF) at 0° C. The solution was stirred at room temperature for 1 h. The mixture was quenched by Na$_2$SO$_4$·10H$_2$O and filtrated. The solvent was removed by nitrogen blowing to afford 27.1 mg (crude) of the title compound as a yellow crude oil. LC-MS: (ESI, m/z): $[M+H]^+=160$. The crude was used for next step without further purification.

Intermediate 106: (6,6-Difluorohexahydro-1H-pyrrolizin-3-yl) methanol

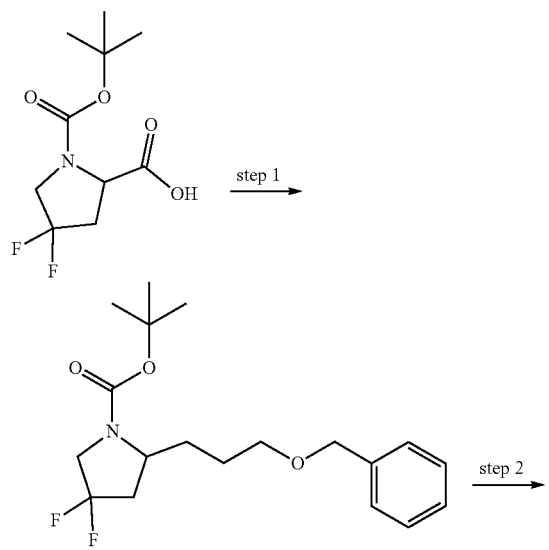

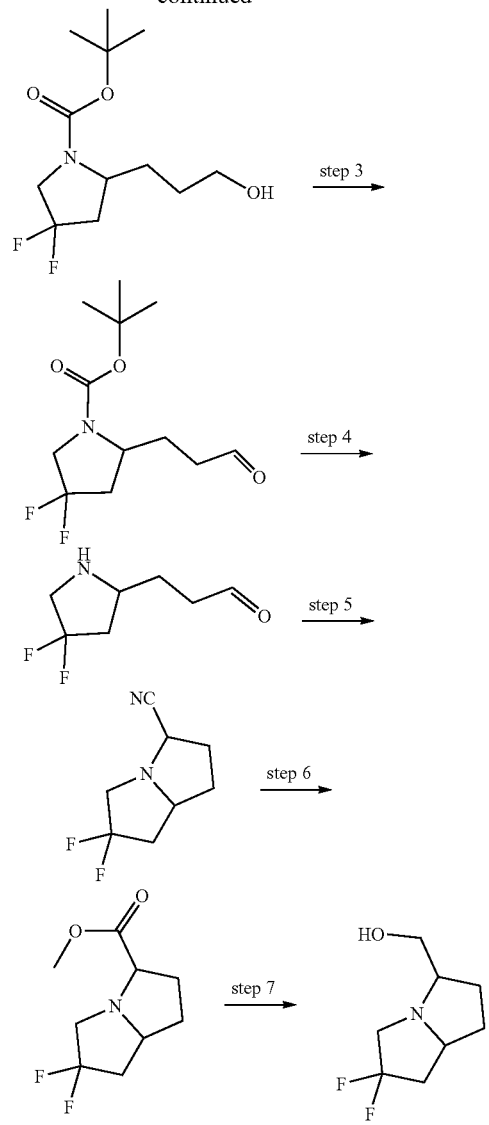

Step 1: tert-Butyl 2-(3-(benzyloxy)propyl)-4,4-difluoropyrrolidine-1-carboxylate Under nitrogen, a solution of (2S)-1-(tert-butoxycarbonyl)-4,4-difluoro-2-pyrrolidinecarboxylic acid (164 mg, 0.65 mmol), NiCl$_2$-glyme (9.59 mg, 0.04 mmol), 4,4-dOMe-bpy (9.44 mg, 0.04 mmol), ((3-bromopropoxy)methyl) benzene (0.08 mL, 0.44 mmol), (Ir[dF(CF$_3$)ppy]2(dtbpy))PF6 (8.83 mg, 0.01 mmol), K$_2$CO$_3$ (120 mg, 0.87 mmol), water (0.16 mL, 8.73 mmol) and acetonitrile (5 mL) was stirred for 48 h under irradiated with 34 W blue LEDs. The resulting mixture was extracted with EtOAc. The combined organic layers were dried over anhydrous Na$_2$SO$_4$. The residue was purified by flash chromatography on silica gel (gradient: 0%-20% EtOAc/petroleum ether) to yield 23 mg of the title compound as a yellow oil. LC-MS: (ESI, m/z): $[M+H]^+=356$.

Step 2: tert-Butyl 4,4-difluoro-2-(3-hydroxypropyl) pyrrolidine-1-carboxylate

Under hydrogen (1 atm), to a solution of tert-butyl 2-(3-benzyloxypropyl)-4,4-difluoro-pyrrolidine-1-carboxylate (1.9 g, 5.35 mmol) in methanol (10 mL) was added 10% Pd/C (200 mg) at 25° C. The resulting solution was stirred at room temperature for 24 hours. After filtration, the filtrate was concentrated under reduced pressure to afford the crude product 1.09 g. LC-MS: (ESI, m/z): [M+H]+=266.

Step 3: tert-Butyl 4,4-difluoro-2-(3-oxopropyl) pyrrolidine-1-carboxylate

To a solution of DMSO (2.12 g, 27.2 mmol) in dichloromethane (5 mL) was added oxalyl chloride (2M in DCM, 11.3 mL, 22.6 mmol) at −78° C. After stirring for 10 min, the tert-butyl 4,4-difluoro-2-(3-hydroxypropyl) pyrrolidine-1-carboxylate (1.2 g, 4.52 mmol) dissolved in CH$_2$Cl$_2$ (5 mL) was added, and the mixture was stirred at −78° C. for 45 min. Then Et$_3$N (4.58 g, 45.2 mmol) was added dropwise. The solution was stirred at −78° C. for 15 min and then allowed to warm up to room temperature over 30 min. The resulting mixture was diluted with water, extracted with EtOAc. The combined organic layers were dried over anhydrous Na$_2$SO$_4$. After filtration, the filtrate was concentrated under reduced pressure to afford the crude product 0.83 g as yellow oil. LC-MS: (ESI, m/z): [M+H]+=264.

Step 4: 3-(4,4-Difluoropyrrolidin-2-yl)propanal

Under nitrogen, to a solution of tert-butyl 4,4-difluoro-2-(3-oxopropyl) pyrrolidine-1-carboxylate (100 mg, 0.38 mmol) in acetonitrile (2 mL) was added TMSI (380 mg, 1.9 mmol) at 0° C. The resulting solution was stirred at room temperature for 2 hours. The resulting mixture was concentrated under reduced pressure. The crude product 53 mg was used for the next step without further purification. LC-MS: (ESI, m/z): [M+H]+=164.

Step 5: 6,6-Difluorohexahydro-1H-pyrrolizine-3-carbonitrile

To a solution of 3-(4,4-difluoropyrrolidin-2-yl)propanal (100 mg, 0.61 mmol) in acetonitrile (2 mL) was added TMSCN (303 mg, 3.06 mmol) at 0° C. The resulting mixture was stirred for overnight at room temperature. The reaction was diluted with water, extracted with EtOAc. The combined organic layers were dried over anhydrous Na$_2$SO$_4$ and concentrated under vacuum to afford the title compound 91 mg (crude). LC-MS: (ESI, m/z): [M+H]+=173. The crude was used for next step without further purification.

Step 6: Methyl 6,6-difluorohexahydro-1H-pyrrolizine-3-carboxylate

A solution of 6,6-difluorohexahydro-1H-pyrrolizine-3-carbonitrile (150 mg, 0.87 mmol) in hydrochloric acid solution (2 mL) and methanol (2 mL) was stirred at 40° C. for 18 hours. The resulting mixture was concentrated under reduced pressure to afford the crude product 129 mg. LC-MS: (ESI, m/z): [M+H]+=206.

Step 7: (6,6-Difluorohexahydro-1H-pyrrolizin-3-yl) methanol

Under nitrogen, to a solution of methyl 6,6-difluorohexahydro-1H-pyrrolizine-3-carboxylate (50.0 mg, 0.24 mmol) in tetrahydrofuran (2 mL) was added LiAlH$_4$ (0.32 mL, 1.5 M in THF) at 0° C. The resulting solution was stirred at room temperature for 2 hours. The resulting mixture was quenched with Na$_2$SO$_4$·10H$_2$O. After filtration, the filtrate was concentrated under reduced pressure to afford the crude product 30 mg as yellow oil. LC-MS: (ESI, m/z): [M+H]+=178. The crude was used for next step without further purification.

Intermediate 107: 2-((6S,8aS)-Hexahydro-1H-pyrrolo[2,1-c][1,4]oxazin-6-yl)ethan-1-ol

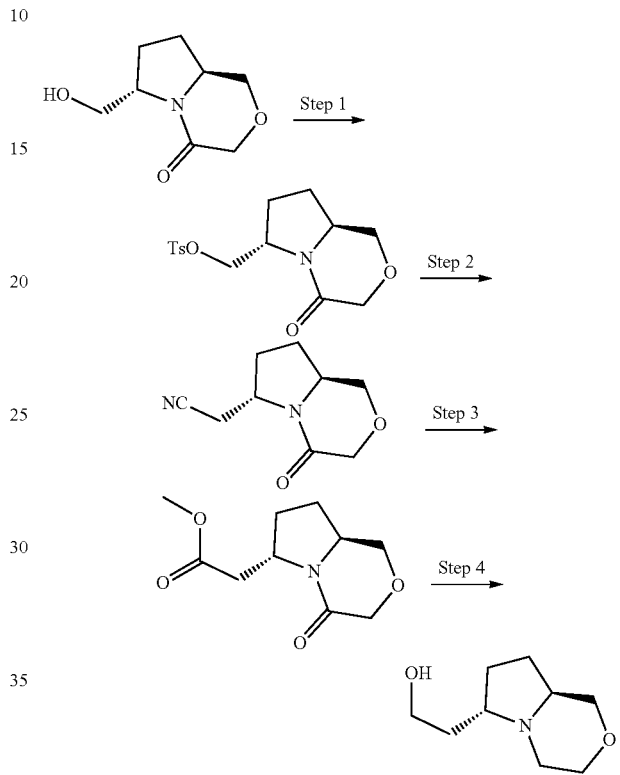

Step 1: ((6S,8aS)-4-Oxohexahydro-1H-pyrrolo[2,1-c][1,4]oxazin-6-yl)methyl 4-methylbenzenesulfonate To a solution of rac-(6S,8aS)-6-(hydroxymethyl)-6,7,8,8a-tetrahydro-1H-pyrrolo[2,1-c][1,4]oxazin-4-one (500 mg, 2.92 mmol), Et$_3$N (886 mg, 8.76 mmol) in dichloromethane (10 mL) was added TsCl (835 mg, 4.38 mmol) and DMAP (17.8 mg, 0.15 mmol) at 0° C. The resulting mixture was stirred overnight at room temperature. The resulting mixture was diluted with water, extracted with DCM. The combined organic layers were dried over anhydrous Na$_2$SO$_4$ and concentrated under vacuum. The residue was purified by flash chromatography on silica gel (gradient: 0%-20% MeOH/DCM) to yield 650 mg of the title compound as a white solid. LC-MS: (ESI, m/z): [M+H]+=326.

Step 2: 2-((6S,8aS)-4-Oxohexahydro-1H-pyrrolo[2,1-c][1,4]oxazin-6-yl)acetonitrile To a solution of [rac-(6S,8aS)-4-oxo-6,7,8,8a-tetrahydro-1H-pyrrolo[2,1-c][1,4]oxazin-6-yl]methyl 4-methylbenzenesulfonate (50.0 mg, 0.15 mmol), TBAF (161 mg, 0.61 mmol) in acetonitrile (3 mL) was added TMSCN (91 mg, 0.92 mmol) at 0° C. The resulting solution was stirred at 80° C. for 6 h. The resulting mixture was extracted with EtOAc. The combined organic layers were dried over anhydrous $Na_2SO_4$. After filtration, the filtrate was concentrated under reduced pressure. The residue was purified by flash chromatography on silica gel (gradient: 0%-20% MeOH/DCM) to yield 20 mg of the title compound as a white solid. LC-MS: (ESI, m/z): $[M+H]^+=181$.

Step 3: Methyl 2-((6S,8aS)-4-oxohexahydro-1H-pyrrolo[2,1-c][1,4]oxazin-6-yl)acetate A solution of 2-[rac-(6S,8aS)-4-Oxohexahydro-1H-pyrrolo[2,1-c][1,4]oxazin-6-yl]acetonitrile (50 mg, 0.3 mmol) in methanol (1 mL) and hydrochloric acid solution (1 ml) was stirred at 40 degrees C. for 72 hours. The resulting mixture was concentrated under reduced pressure to afford 40 mg of the title compound as a yellow solid which was used without further purification. LC-MS: (ESI, m/z): $[M+H]^+=214$.

Step 4: 2-((6S,8aS)-Hexahydro-1H-pyrrolo[2,1-c][1,4]oxazin-6-yl)ethan-1-ol

Under nitrogen, to a solution of Methyl 2-[rac(6S,8aS)-4-oxohexahydro-1H-pyrrolo[2,1-c][1,4]oxazin-6-yl]acetate (100 mg, 0.47 mmol) in tetrahydrofuran (2 mL) was added $LiAlH_4$ (1.5M in THF, 0.46 mL) at 0° C. The resulting solution was stirred at 60° C. for 1 h. The reaction was quenched with $Na_2SO_4 \cdot 10H_2O$ and filtration. The filtrate was concentrated under reduced pressure to afford 60 mg (crude) of the title compound as a yellow solid. LC-MS: (ESI, m/z): $[M+H]^+=172$. The crude was used for next step without further purification.

Intermediate 108: ((2S)-2,6-Difluorotetrahydro-1H-pyrrolizin-7a(51)-yl) methanol

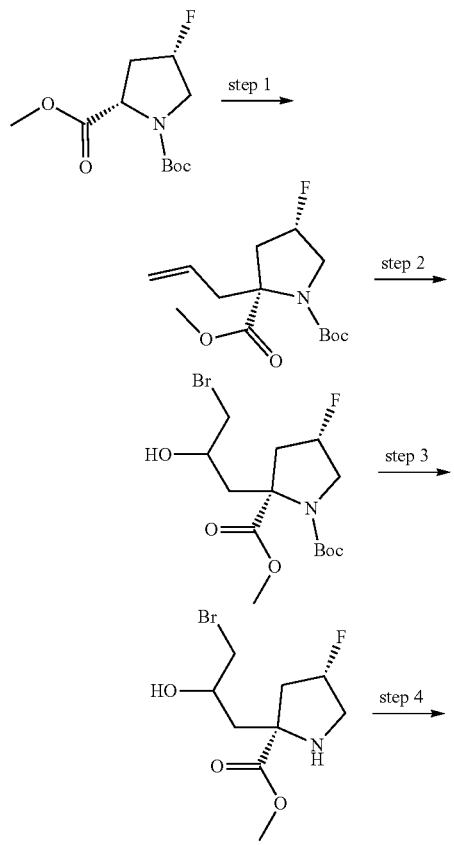

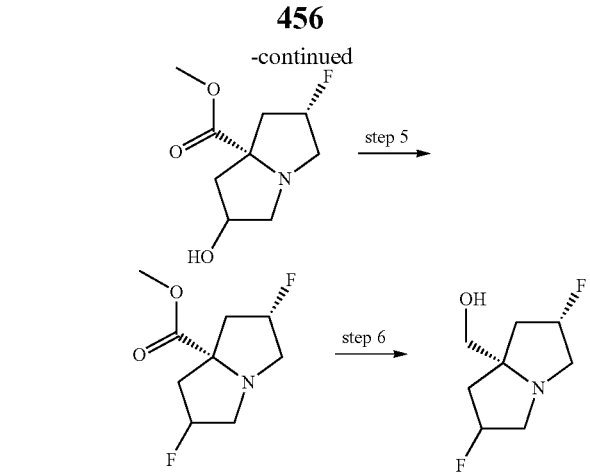

Step 1: 1-(tert-Butyl) 2-methyl (2S,4S)-2-allyl-4-fluoropyrrolidine-1,2-dicarboxylate Under nitrogen, to a solution of 1-(tert-butyl) 2-methyl (2S,4S)-4-fluoropyrrolidine-1,2-dicarboxylate (5.00 g, 20.2 mmol) in tetrahydrofuran (45.0 mL) was added LHMDS (40.5 mL, 1 M in THF) at −78° C., and the mixture was stirred for 1 hour at −50° C. Then allyl bromide (4.90 g, 40.5 mmol) was added, and the mixture was stirred at −50° C. The mixture was wormed to 25° C. and stirred for 1 hour. The reaction was quenched by $Na_2S_2O_3$ aqueous and extracted with EtOAc. The combined organic layers were dried over anhydrous sodium sulfate and concentrated under vacuum. The residue was purified by flash chromatography on silica gel (gradient: 0%-25% EtOAc/petroleum ether) to afford 5.30 g of the title compound as a yellow oil. LC-MS: (ESI, m/z): $[M+H]^+=288$.

Step 2: 1-(tert-Butyl) 2-methyl (2S,4S)-2-(3-bromo-2-hydroxypropyl)-4-fluoropyrrolidine-1,2-dicarboxylate To a solution of 1-(tert-butyl) 2-methyl (2S,4S)-2-allyl-4-fluoropyrrolidine-1,2-dicarboxylate (4.07 g, 14.2 mmol) in DMSO (30 mL) and water (10 mL) was added NBS (5.83 g, 32.9 mmol), and the mixture was stirred at room temperature for 1 hour. The solvent was concentrated under vacuum. The residue was purified by C18 column (solvent gradient: 0-75% ACN in water (0.1% TFA)) to afford 1.29 g of the title compound as a yellow oil. LC-MS: (ESI, m/z): $[M+H]^+=384$.

Step 3: Methyl (2S,4S)-2-(3-bromo-2-hydroxypropyl)-4-fluoropyrrolidine-2-carboxylate A solution of 1-(tert-butyl) 2-methyl (2S,4S)-2-(3-bromo-2-hydroxypropyl)-4-fluoropyrrolidine-1,2-dicarboxylate (730 mg, 1.90 mmol) in DCM (10 mL) and TFA (1 mL) was stirred at room temperature for 1 h. The solvent was concentrated under vacuum to afford 1.11 g (crude) of the title compound as a red oil. LC-MS: (ESI, m/z): $[M+H]^+=284$.

Step 4: Methyl (2S,7aS)-2-fluoro-6-hydroxytetrahydro-1H-pyrrolizine-7a(5H)-carboxylate To a solution of methyl (2S,4S)-2-(3-bromo-2-hydroxypropyl)-4-fluoropyrrolidine-2-carboxylate (1.11 g, 3.89 mmol)] in ACN (5 mL) was added $K_2CO_3$ (2.69 g, 19.5 mmol), and the mixture was stirred at room temperature for 1 h. The solvent was concentrated under vacuum. The residue was purified by flash chromatography on silica gel (gradient: 0%-8% MeOH/DCM) to afford 307 mg of the title compound as a yellow oil. LC-MS: (ESI, m/z): [M+H]+= 204.

Step 5: Methyl (2S)-2,6-difluorotetrahydro-1H-pyrrolizine-7a(5H)-carboxylate

Under nitrogen, to a solution of methyl (2S,7aS)-2-fluoro-6-hydroxytetrahydro-1H-pyrrolizine-7a(5H)-carboxylate (307 mg, 1.51 mmol)] in DCM (6 mL) was added DAST (365 mg, 2.27 mmol) at −20° C. The solution was stirred at −20° C. for 1 h. The reaction was quenched with NaHCO3 aqueous, extracted with EtOAc. The combined organic layers were dried over anhydrous sodium sulfate and concentrated under vacuum. The residue was purified by flash chromatography on silica gel (gradient: 0%-10% MeOH/DCM) to afford 165 mg of the title compound as a yellow oil. LC-MS: (ESI, m/z): [M+H]+=206.

Step 6: ((2S)-2,6-Difluorotetrahydro-1H-pyrrolizin-7a(5H)-yl)methanol

Under nitrogen, to a solution of methyl (2S)-2,6-difluorotetrahydro-1H-pyrrolizine-7a(5H)-carboxylate (165 mg, 0.800 mmol) in THF (5 mL) was added LiAlH4 (0.32 mL, 2.5M in THF) 0° C., and the mixture was stirred at room temperature for 0.5 h. The reaction was quenched with Na2SO4·10H2O. After filtration, the filtrate was concentrated under reduced pressure to afford 70.1 mg (crude) of the title compound as a yellow oil. LC-MS: (ESI, m/z): [M+H]+= 178. The crude was used for next step without further purification.

Intermediate 109: ((2R,7aR)-2,6-Difluorotetrahydro-1H-pyrrolizin-7a(5H)-yl) methanol

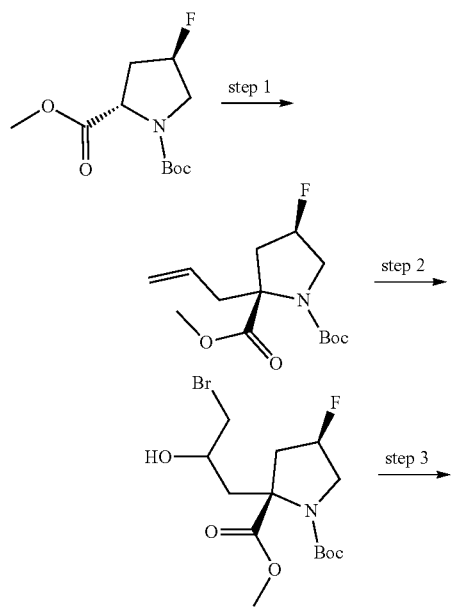

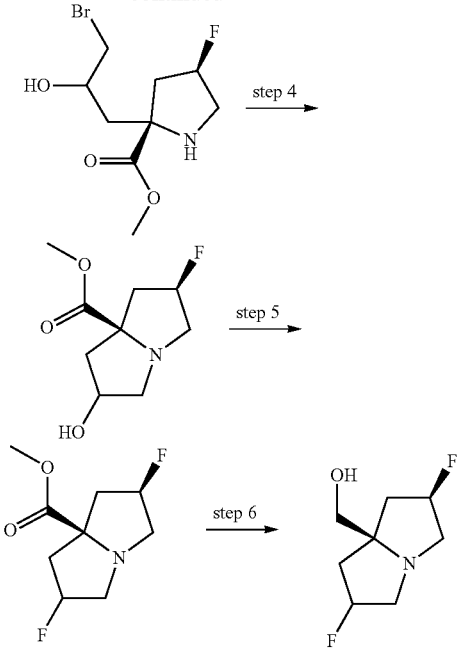

Step 1: 1-(tert-Butyl) 2-methyl (2R,4R)-2-allyl-4-fluoropyrrolidine-1,2-dicarboxylate Under nitrogen, to a solution of 1-(tert-butyl) 2-methyl (2S,4R)-4-fluoropyrrolidine-1,2-dicarboxylate (10.0 g, 40.4 mmol) in tetrahydrofuran (20 mL) was added LHMDS (80.8 mL, 1 M in THF) at −30° C. The resulting solution was stirred for 1 hour at −30° C. Then 3-bromoprop-1-ene (7.0 mL, 80.8 mmol) was added, and the mixture was stirred at room temperature overnight. The reaction was quenched with saturated NH4Cl solution and extracted with EtOAc. The combined organic layers were dried over anhydrous sodium sulfate and concentrated under vacuum. The residue was purified by C18 column (solvent gradient: 0-60% ACN in water (0.05% NH4HCO3)) to afford the title compound (5.27 g) as a yellow oil. LC-MS: (ESI, m/z): [M+H]+=288.

Step 2: 1-(tert-Butyl) 2-methyl (2R,4R)-2-(3-bromo-2-hydroxypropyl)-4-fluoropyrrolidine-1,2-dicarboxylate To a solution of 1-(tert-butyl) 2-methyl (2R,4R)-2-allyl-4-fluoropyrrolidine-1,2-dicarboxylate (5.27 g, 18.3 mmol) in dimethyl sulfoxide (21 mL) and water (6 mL) was added NBS (6.53 g, 36.7 mmol) at room temperature. The reaction was stirred at room temperature for 2 hours. The crude was purified by C18 column (solvent gradient: 0-50% ACN in water (0.05% NH4HCO3)) to afford the title compound (1.46 g) as a yellow oil. LC-MS: (ESI, m/z): [M+H]+=384.

Step 3: Methyl (2R,4R)-2-(3-bromo-2-hydroxypropyl)-4-fluoropyrrolidine-2-carboxylate A solution of 1-(tert-butyl) 2-methyl (2R,4R)-2-(3-bromo-2-hydroxypropyl)-4-fluoropyrrolidine-1,2-dicarboxylate (1.46 g, 3.8 mmol) in 2,2,2-trifluoroacetic acid (7.5 mL) and dichloromethane (7.5 mL) was stirred at room temperature for 0.5 hour. The solution was concentrated under vacuum to afford the title compound (1.88 g, crude) as a yellow oil. LC-MS: (ESI, m/z): [M+H]+=284.

Step 4: Methyl (2R,7aR)-2-fluoro-6-hydroxytetrahydro-1H-pyrrolizine-7a(5H)-carboxylate A solution of methyl (2R,4R)-2-(3-bromo-2-hydroxypropyl)-4-fluoropyrrolidine-2-carboxylate (1.88 g, 6.62 mmol) and K$_2$CO$_3$ (4.56 g, 33.1 mmol) in acetonitrile (15 mL) was stirred at room temperature overnight. The resulting mixture was filtered. The filtrate was concentrated under reduced pressure. The residue was purified by C18 column (solvent gradient: 0-10% ACN in water (0.05% NH$_4$HCO$_3$)) to afford the title compound (673 mg) as a yellow oil. LC-MS: (ESI, m/z): [M+H]+=204.

Step 5: Methyl (2R,7aR)-2,6-difluorotetrahydro-1H-pyrrolizine-7a(5H)-carboxylate To a solution of methyl (2R,7aR)-2-fluoro-6-hydroxytetrahydro-1H-pyrrolizine-7a(5H)-carboxylate (600 mg, 2.95 mmol) in dichloromethane (6 mL) was added DAST (950 mg, 5.91 mmol) at −20° C. and was stirred at room temperature overnight. The reaction was quenched by MeOH. The solution was concentrated under vacuum. The residue was purified by flash chromatography on silica gel (gradient: 0-2% MeOH in DCM (0.1% 7M NH$_3$/MeOH)) to afford the title compound (120 mg) as a brown oil. LC-MS: (ESI, m/z): [M+H]+=206.

Step 6: ((2R,7aR)-2,6-Difluorotetrahydro-1H-pyrrolizin-7a(5H)-yl)methanol

Under nitrogen, to a solution of methyl (2R,7aR)-2,6-difluorotetrahydro-1H-pyrrolizine-7a(5H)-carboxylate (90.0 mg, 0.440 mmol) in tetrahydrofuran (2 mL) was added LiAlH$_4$ (0.18 mL, 2.5 M in THF) at 0° C. The resulting solution was stirred at room temperature for 1 hour. Then 200 mg Na$_2$SO$_4$·10H$_2$O was added, and the mixture was stirred at room temperature for 10 min. After filtration, the filtrate was concentrated under reduced pressure to afford the title compound (80 mg, crude) as a brown oil. LC-MS: (ESI, m/z): [M+H]+=178. The crude was used for next step without further purification.

Intermediate 110: ((2R,6S,7aS)-2,6-Difluorotetrahydro-1H-pyrrolizin-7a(5H)-yl) methanol

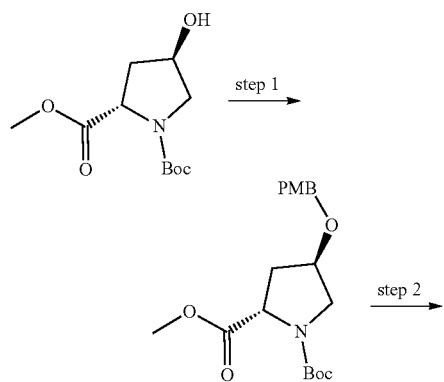

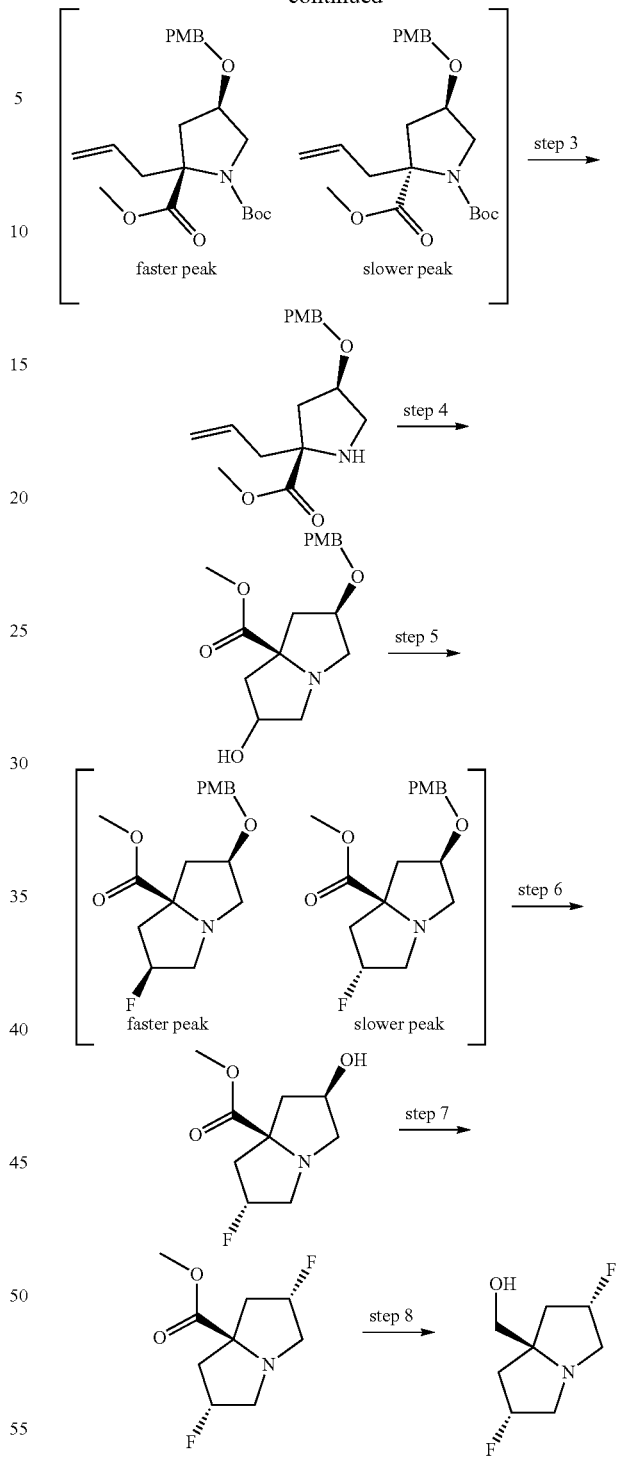

Step 1: 1-(tert-Butyl) 2-methyl (2S,4R)-4-((4-methoxybenzyl)oxy)pyrrolidine-1,2-dicarboxylate To a solution of 1-(tert-butyl) 2-methyl (2S,4R)-4-hydroxypyrrolidine-1,2-dicarboxylate (20 g, 81.6 mmol) was added NaH (3.92 g, 98.0 mmol, 60% dispersion in mineral oil) at 0° C. The mixture was stirred for 30 min at 0° C. PMBCl (14.1 g, 89.8 mmol) was added and the mixture was allowed to warm to room temperature and stirred for 2 hours. The reaction was quenched with aqueous NH₄Cl solution. The resulting solution was extracted with EtOAc. The combined organic layers were dried over anhydrous sodium sulfate and concentrated under vacuum. The residue was purified by C18 column (solvent gradient: 0-50% ACN in water (0.05% NH₄HCO₃)) to afford the title compound (11.0 g) as a yellow oil. LC-MS: (ESI, m/z): [M+H]⁺=366.

Step 2: 1-(tert-Butyl) 2-methyl (2S,4R)-2-allyl-4-((4-methoxybenzyl)oxy)pyrrolidine-1,2-dicarboxylate

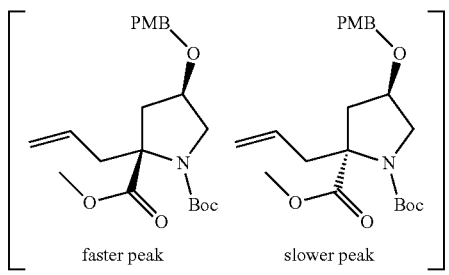

faster peak    slower peak

Under nitrogen, to a solution of 1-(tert-butyl) 2-methyl (2S,4R)-4-((4-methoxybenzyl)oxy) pyrrolidine-1,2-dicarboxylate (18 g, 49.3 mmol) in tetrahydrofuran (150 mL) was added LHMDS (98.6 mL, 1M in THF) at −78° C. The resulting solution was stirred for 1 hour at −78° C. Then 3-bromoprop-1-ene (11.8 g, 98.6 mmol) was added, and the mixture was stirred at −78° C. for 2 hours. The reaction was quenched with aqueous NH₄Cl solution. The organic solvent was removed under vacuum. The residual was diluted with water, extracted with EtOAc. The combined organic layers were dried over anhydrous sodium sulfate and concentrated under vacuum. The residue was purified by flash chromatography on silica gel (gradient: 0%-15% EtOAc/petroleum ether) to afford 18.4 g mixture of two isomers as a yellow oil. The isomers were separated by Prep Chiral-SFC with the following conditions: (Column: Mobile Phase A: CO₂, Mobile Phase B: IPA; Flow rate: 100 mL/min; Gradient: isocratic 10% B; Column Temperature(° C.): 35; Back Pressure(bar): 100; Wave Length: 220 nm; R_T1(min): 4.37; R_T2(min): 5.73) to afford faster peak (12.6 g) and slower peak (6.06 g) as a yellow oil (LC-MS: (ESI, m/z): [M+H]⁺=406).

Step 3: Methyl (2R,4R)-2-allyl-4-((4-methoxybenzyl)oxy)pyrrolidine-2-carboxylate Under nitrogen, to a solution of 1-(tert-butyl) 2-methyl (2S,4R)-2-allyl-4-((4-methoxybenzyl)oxy) pyrrolidine-1,2-dicarboxylate (12.0 g, 29.6 mmol, the faster peak of last step) and 2,6-di-tert-butylpyridine (13.3 mL, 59.3 mmol) in dichloromethane (120 mL) was added TMSOTf (13.2 g, 59.3 mmol) at room temperature. The resulting solution was stirred at room temperature overnight. The solvent was concentrated under vacuum. The residue was purified by C18 column (solvent gradient: 0-60% ACN in water (0.05% NH₄HCO₃)) to afford the title compound (5.1 g) as a yellow oil. LC-MS: (ESI, m/z): [M+H]⁺=306.

Step 4: Methyl (6R,7aR)-2-hydroxy-6-((4-methoxybenzyl)oxy) tetrahydro-1H-pyrrolizine-7a(5H)-carboxylate A solution of methyl (2R,4R)-2-allyl-4-((4-methoxybenzyl)oxy)pyrrolidine-2-carboxylate (3.5 g, 11.5 mmol), TFA (1.44 g, 12.6 mmol) and NBS (2.45 mg, 13.7 mmol) in acetone (28 mL) and water (7 mL) was stirred at room temperature for 2 hours. Then K₂CO₃ (1.58 mg, 11.4 mmol) was added, and the mixture was stirred at room temperature overnight. The solution was concentrated under vacuum. The residue was purified by C18 column (solvent gradient: 0-25% ACN in water (0.05% NH₄HCO₃)) to afford the title compound (1.99 g) as a yellow oil. LC-MS: (ESI, m/z): [M+H]⁺=322.

Step 5: Methyl (2R,6R,7aS)-2-fluoro-6-((4-methoxybenzyl)oxy) tetrahydro-1H-pyrrolizine-7a(5H)-carboxylate

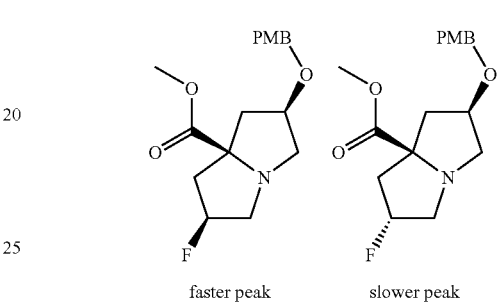

faster peak    slower peak

Under nitrogen, to a solution of methyl (6R,7aR)-2-hydroxy-6-((4-methoxybenzyl)oxy) tetrahydro-1H-pyrrolizine-7a(5H)-carboxylate (1.99 g, 6.19 mmol) in dichloromethane (20 mL) was added DAST (1.50 g, 9.29 mmol) at −40° C. The resulting solution was stirred for 1 hour at room temperature. The reaction was quenched with MeOH. The solution was concentrated under vacuum. The residue was purified by C18 column (solvent gradient: 0-25% ACN in water (0.05% NH₄HCO₃)) to afford faster peak (253 mg) and slower peak (425 mg) as a yellow oil (LC-MS: (ESI, m/z): [M+H]⁺=324.

Step 6: Methyl (2R,6R,7aS)-2-fluoro-6-hydroxytetrahydro-1H-pyrrolizine-7a(5H)-carboxylate A solution of methyl (2R,6R,7aS)-2-fluoro-6-((4-methoxybenzyl)oxy) tetrahydro-1H-pyrrolizine-7a(5H)-carboxylate (420 mg, 1.30 mmol, the slower peak of last step) in dichloromethane (1 mL) and 2,2,2-trifluoroacetic acid (1 mL) was stirred at room temperature for 1 hour. The solution was concentrated under vacuum. The residue was purified by flash chromatography on silica gel (gradient: 0-4% MeOH in DCM(0.1% 7M NH₃/MeOH)) to afford the title compound (182 mg) as a yellow solid. LC-MS: (ESI, m/z): [M+H]⁺=204.

Step 7: Methyl (2R,6S,7as)-2,6-difluorotetrahydro-1H-pyrrolizine-7a(5H)-carboxylate Under nitrogen, to a solution of methyl (2R,6R,7aS)-2-fluoro-6-hydroxytetrahydro-1H-pyrrolizine-7a(5H)-carboxylate (182 mg, 0.900 mmol) in dichloromethane (2 mL) was added DAST (288 mg, 1.79 mmol) at −30° C. The resulting solution was stirred for 3 hours at room temperature. The reaction was quenched with MeOH. The solution was concentrated under vacuum. The residue was purified by flash chromatography on silica gel (gradient: 0-2%

MeOH in DCM(0.1% NH₃—MeOH)) to afford the title compound (61 mg) as a brown oil. LC-MS: (ESI, m/z): [M+H]⁺=206.

Step 8:((2R,6S,7aS)-2,6-Difluorotetrahydro-1H-pyrrolizin-7a(5H)-yl)methanol

Under nitrogen, to a solution of methyl (2R,6S,7as)-2,6-difluorotetrahydro-1H-pyrrolizine-7a(5H)-carboxylate (60 mg, 0.292 mmol) in tetrahydrofuran (2 mL) was added LiAlH₄ (0.12 mL, 2.4 M in THF) at 0° C. The resulting solution was stirred at room temperature for 1 hour. Then Na₂SO₄·10H₂O was added, and the mixture was stirred at room temperature for 5 min. After filtration, the filtrate was concentrated under vacuum to afford the title compound (65 mg, crude) as a brown oil. LC-MS: (ESI, m/z): [M+H]⁺= 178. The crude was used for next step without further purification.

Intermediate 111: 8-(Hydroxymethyl)-4-oxa-1-azabicyclo [4.2.0] octan-2-one (mixture trans

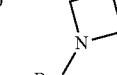

Step 1: ((2S,4S)-Azetidine-2,4-diyl)dimethanol

Under nitrogen, a solution of tert-butyl rac-(2S,4S)-2,4-bis(hydroxymethyl)azetidine-1-carboxylate (700 mg, 3.22 mmol) in DCM (3.2 mL) was added TFA (0.8 mL) at room temperature, and the mixture was stirred for 1 h. The resulting solution was concentrated under vacuum to afford 1.20 g (crude) of the title compound as a yellow oil. LC-MS: (ESI, m/z): [M+H]⁺=118.

Step 2: 8-(Hydroxymethyl)-4-oxa-1-azabicyclo [4.2.0]octan-2-one

To a solution of ((2S,4S)-azetidine-2,4-diyl)dimethanol (1.20 g, 10.2 mmol) in i-PrOH (60 mL) was added TMSOK (9.81 g, 76.4 mmol) and chloroacetyl chloride (3.17 mL, 39.84 mmol) at 0° C., and the mixture was stirred at room temperature for overnight. The solvent was concentrated under vacuum. The residue was purified by flash chromatography on silica gel (gradient: 0%-10% MeOH/DCM) to afford 210 mg of the title compound as a yellow oil. LC-MS: (ESI, m/z): [M+H]⁺=158.

Intermediate 112: 3-(Hydroxymethyl) hexahydro-1H-pyrrolizin-1-ol

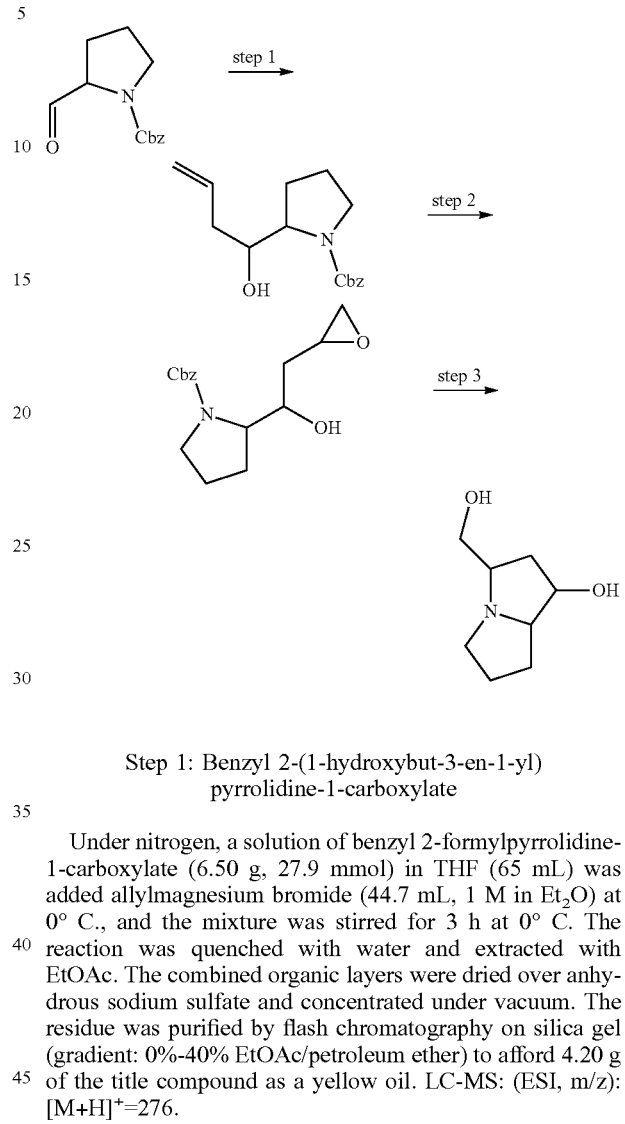

Step 1: Benzyl 2-(1-hydroxybut-3-en-1-yl) pyrrolidine-1-carboxylate

Under nitrogen, a solution of benzyl 2-formylpyrrolidine-1-carboxylate (6.50 g, 27.9 mmol) in THF (65 mL) was added allylmagnesium bromide (44.7 mL, 1 M in Et₂O) at 0° C., and the mixture was stirred for 3 h at 0° C. The reaction was quenched with water and extracted with EtOAc. The combined organic layers were dried over anhydrous sodium sulfate and concentrated under vacuum. The residue was purified by flash chromatography on silica gel (gradient: 0%-40% EtOAc/petroleum ether) to afford 4.20 g of the title compound as a yellow oil. LC-MS: (ESI, m/z): [M+H]⁺=276.

Step 2: Benzyl 2-(1-hydroxy-2-(oxiran-2-yl)ethyl) pyrrolidine-1-carboxylate

To a solution of benzyl 2-(1-hydroxybut-3-en-1-yl) pyrrolidine-1-carboxylate (4.11 g, 14.9 mmol) in DCM (50 mL) was added m-CPBA (4.4 g, 25.43 mmol) at 0° C., and the mixture was stirred at room temperature for 3 h. The reaction was quenched with saturated NaHCO₃ aqueous, extracted with EtOAc. The combined organic layers were dried over anhydrous sodium sulfate and concentrated under vacuum. The residue was purified by flash chromatography on silica gel (gradient: 0%-35% EtOAc/petroleum ether) to afford 2.60 g of the title compound as a yellow oil. LC-MS: (ESI, m/z): [M+H]⁺=292.

Step 3: 3-(Hydroxymethyl) hexahydro-1H-pyrrolizin-1-ol

Under hydrogen (1 atm), to a solution of benzyl 2-(1-hydroxy-2-(oxiran-2-yl)ethyl)pyrrolidine-1-carboxylate (2.60 g, 8.92 mmol) in MeOH (25 mL) was added Pd/C (780 mg, 10%), and the mixture was stirred for 3 h at room temperature. After filtration, the filtrate was concentrated under vacuum to afford 1.41 g (crude) of the title compound as a yellow oil. LC-MS: (ESI, m/z): [M+H]+=158. The crude was used for next step without further purification.

Intermediate 113: ((2S,3S)-3-((tert-Butyldiphenylsilyl)oxy)-1-methylpyrrolidin-2-yl) methanol

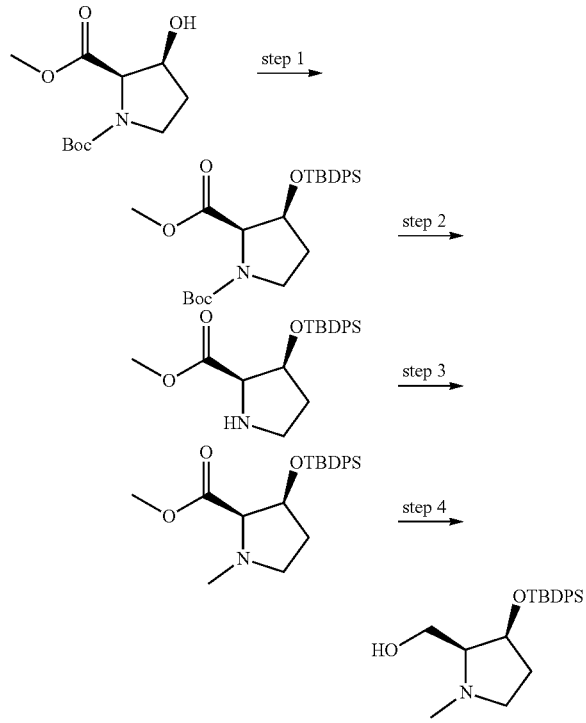

Step 1: 1-(tert-Butyl) 2-methyl (2R,3S)-3-((tert-butyldiphenylsilyl)oxy)pyrrolidine-1,2-dicarboxylate To a solution of 1-(tert-butyl) 2-methyl (2R,3S)-3-hydroxypyrrolidine-1,2-dicarboxylate (2.10 g, 8.56 mmol) and imidazole (1.75 g, 25.7 mmol) in N, N-dimethylacetamide (20 mL) was added TBDPSCl (4.71 g, 17.1 mmol) at room temperature. The resulting solution was stirred at room temperature overnight. Some starting material remained. Then additional imidazole (1.75 g, 25.7 mmol) and TBDPSCl (4.71 g, 17.1 mmol) was added, and the mixture was stirred at room temperature overnight. The resulting mixture was diluted with EtOAc, washed with brine and dried over anhydrous sodium sulfate. The solvent was concentrated under vacuum and the residue was purified by flash chromatography on silica gel (gradient: 0-50% DCM/petroleum ether) to afford the title compound (2.74 g) as a pink oil. LC-MS: (ESI, m/z): [M+H]+=484.

Step 2: Methyl (2R,3S)-3-((tert-butyldiphenylsilyl)oxy) pyrrolidine-2-carboxylate A solution of 1-(tert-butyl) 2-methyl (2R,3S)-3-((tert-butyldiphenylsilyl)oxy) pyrrolidine-1,2-dicarboxylate (2.74 g, 5.67 mmol) in dichloromethane (15 mL) and 2,2,2-trifluoroacetic acid (5 mL) was stirred at room temperature for 1 hour. The reaction mixture was adjusted pH to 8 with aqueous NaHCO3 solution. The resulting solution was extracted with DCM. The combined organic layers were dried over anhydrous Na2SO4 and concentrated under vacuum to afford the title compound (2.39 g, crude) as a yellow oil. LC-MS: (ESI, m/z): [M+H]+=384.

Step 3: Methyl (2R,3S)-3-((tert-butyldiphenylsilyl)oxy)-1-methylpyrrolidine-2-carboxylate A solution of methyl (2R,3S)-3-((tert-butyldiphenylsilyl)oxy)pyrrolidine-2-carboxylate (2.39 g, 6.23 mmol), paraformaldehyde (935 mg, 31.2 mmol) and AcOH (374 mg, 6.23 mmol) in methanol (21 mL) was stirred at room temperature for 1 hour. Then NaBH3CN (1.57 g, 24.9 mmol) was added, and the mixture was stirred at room temperature overnight. The reaction was quenched with water, extracted with EtOAc. The combined organic layers were washed with brine, dried over anhydrous sodium sulfate and concentrated under vacuum to afford the title compound (2.71 g, crude) as a white oil. LC-MS: (ESI, m/z): [M+H]+=398.

Step 4: ((2S,3S)-3-((tert-Butyldiphenylsilyl)oxy)-1-methylpyrrolidin-2-yl)methanol A solution of methyl (2R,3S)-3-((tert-butyldiphenylsilyl)oxy)-1-methylpyrrolidine-2-carboxylate (900 mg, 2.26 mmol), KBH4 (733 mg, 13.5 mmol) and ZnCl2 (924 mg, 6.79 mmol) in 1,4-dioxane (10 mL) was stirred at 100° C. for 2 hours. The resulting mixture was filtered. The filtrate was concentrated under reduced pressure. The crude product was diluted with EtOAc and was washed with water. The organic layer was dried over anhydrous Na2SO4 and concentrated under reduced pressure. The residue was purified by C18 column (solvent gradient: 0-50% ACN in water (0.05% TFA)) to afford the title compound (515 mg) as a colorless oil. LC-MS: (ESI, m/z): [M+H]+=370.

Intermediate 114: tert-Butyl (5S,5aS,6S,9R)-2-(5-(bis(4-methoxybenzyl)amino)-4-fluoro-3-methyl-2-(trifluoromethyl)phenyl)-1-fluoro-5-methyl-12-(methylsulfonyl)-5a,6,7,8,9,10-hexahydro-5H-4-oxa-3,10a,11,13,14-pentaaza-6,9-methanonaphtho[1,8-ab]heptalene-14-carboxylate

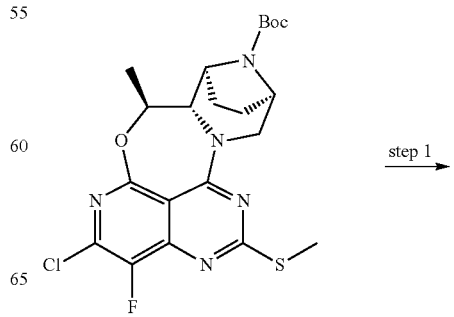

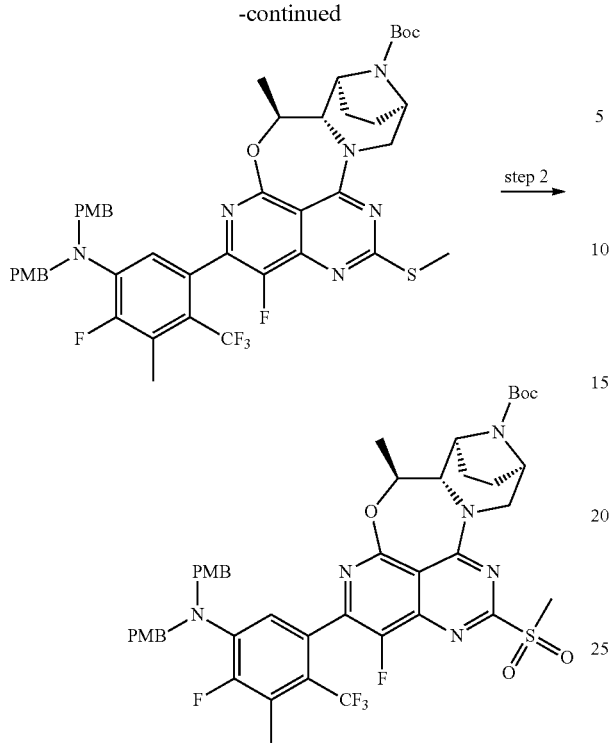

Step 1: tert-Butyl (5S,5aS,6S,9R)-2-(5-(bis(4-methoxybenzyl)amino)-4-fluoro-3-methyl-2-(trifluoromethyl)phenyl)-1-fluoro-5-methyl-12-(methylthio)-5a,6,7,8,9,10-hexahydro-5H-4-oxa-3,10a,11,13,14-pentaaza-6,9-methanonaphtho[1,8-ab]heptalene-14-carboxylate Under nitrogen, to a solution of tert-butyl (5S,5aS,6S,9R)-2-chloro-1-fluoro-5-methyl-12-(methylthio)-5a,6,7,8,9,10-hexahydro-5H-4-oxa-3,10a,11,13,14-pentaaza-6,9-methanonaphtho[1,8-ab]heptalene-14-carboxylate (701 mg, 1.45 mmol) and (5-(bis(4-methoxybenzyl)amino)-4-fluoro-3-methyl-2-(trifluoromethyl)phenyl)boronic acid (1.73 g, 3.63 mmol) in THF (9 mL) was added cataCXium A Pd G$_3$ (317 mg, 0.440 mmol) and K$_3$PO$_4$ (1.8 mL, 1.5 M in H$_2$O) at room temperature. The resulting solution was stirred for 3 h at 60° C. The reaction mixture was cooled to room temperature and concentrated under vacuum. The residue was purified by reverse phase flash chromatography on pre-packed C18 column (gradient: 0-100% CH$_3$CN in water (0.05% NH$_4$HCO$_3$)) to yield 941 mg of the title compound as a yellow solid. LC-MS: (ESI, m/z): [M+H]$^+$=879.

Step 2: tert-Butyl (5S,5aS,6S,9R)-2-(5-(bis(4-methoxybenzyl)amino)-4-fluoro-3-methyl-2-(trifluoromethyl)phenyl)-1-fluoro-5-methyl-12-(methylsulfonyl)-5a,6,7,8,9,10-hexahydro-5H-4-oxa-3,10a,11,13,14-pentaaza-6,9-methanonaphtho[1,8-ab]heptalene-14-carboxylate Under nitrogen, to a solution of tert-butyl (5S,5aS,6S,9R)-2-(5-(bis(4-methoxybenzyl)amino)-4-fluoro-3-methyl-2-(trifluoromethyl)phenyl)-1-fluoro-5-methyl-12-(methylthio)-5a,6,7,8,9,10-hexahydro-5H-4-oxa-3,10a,11,13,14-pentaaza-6,9-methanonaphtho[1,8-ab]heptalene-14-carboxylate (910 mg, 1.04 mmol) in DCM (10 mL) was added m-CPBA (537 mg, 3.11 mmol) at 0° C. The resulting solution was stirred for 2 h at room temperature. The solution was diluted with NaHCO$_3$ solution and extracted with DCM. The combined organic layers were washed with brine, dried over anhydrous sodium sulfate and concentrated under vacuum. The residue was purified by flash chromatography on silica gel (gradient: 0-51% EtOAc in petroleum ether) to afford 378 mg of the title compound as a yellow solid. LC-MS: (ESI, m/z): [M+H]$^+$=911.

Intermediates 115 and 116: 3-((1R,4R)-2-Oxa-5-azabicyclo[2.2.1]heptan-5-yl)propan-1-ol and (3-((1S,4S)-2-oxa-5-azabicyclo[2.2.1]heptan-5-yl)propan-1-ol

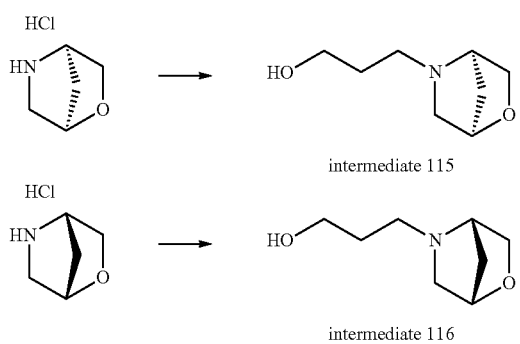

intermediate 115 intermediate 116

Under nitrogen, a solution of (1R,4R)-2-oxa-5-azabicyclo[2.2.1]heptane hydrochloride (100 mg, 0.740 mmol), 3-iodopropan-1-ol (276 mg, 1.48 mmol) and K$_2$CO$_3$ (287 mg, 2.08 mmol) in ACN (1.5 mL) was stirred at 80° C. for 2 h. The solution was cooled to room temperature, filtrated and concentrated under vacuum. The residue was purified by SCX-2 column (ion exchange resin) to afford 15 mg (crude) of the title compound as a yellow oil. LC-MS: (ESI, m/z): [M+H]$^+$=158.

Analogous to method described as above, (3-((1S,4S)-2-oxa-5-azabicyclo [2.2.1] heptan-5-yl) propan-1-ol) was prepared.

Intermediate 117_(1-(((tert-Butyldiphenylsilyl)oxy)methyl)-2,2-difluorocyclopropyl)methanol

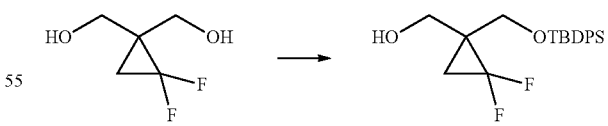

To a solution of (2,2-difluorocyclopropane-1,1-diyl)dimethanol (200 mg, 1.45 mmol) and imidazole (197 mg, 2.90 mmol) in dichloromethane (10 mL) was added TBDPSCl (398 mg, 1.45 mmol) at 0° C., and the mixture was stirred for 1 hour at room temperature. The solvent was concentrated under vacuum. The residue was purified by flash chromatography on silica gel eluting (gradient: 0-10% EtOAc in petroleum ether) to afford the title compound (320 mg) as a colorless oil. LC-MS: (ESI, m/z): [M+H]$^+$=377.

Intermediate 118: tert-Butyl (5S,5aS,6S,9R)-2-(5-(bis(4-methoxybenzyl)amino)-4-fluoro-3-methyl-2-(trifluoromethyl)phenyl)-12-((2,2-difluoro-1-(hydroxymethyl)cyclopropyl)methoxy)-1-fluoro-5-methyl-5a,6,7,8,9,10-hexahydro-5H-4-oxa-3,10a,11,13,14-pentaaza-6,9-methanonaphtho[1,8-ab]heptalene-14-carboxylate (two isomers

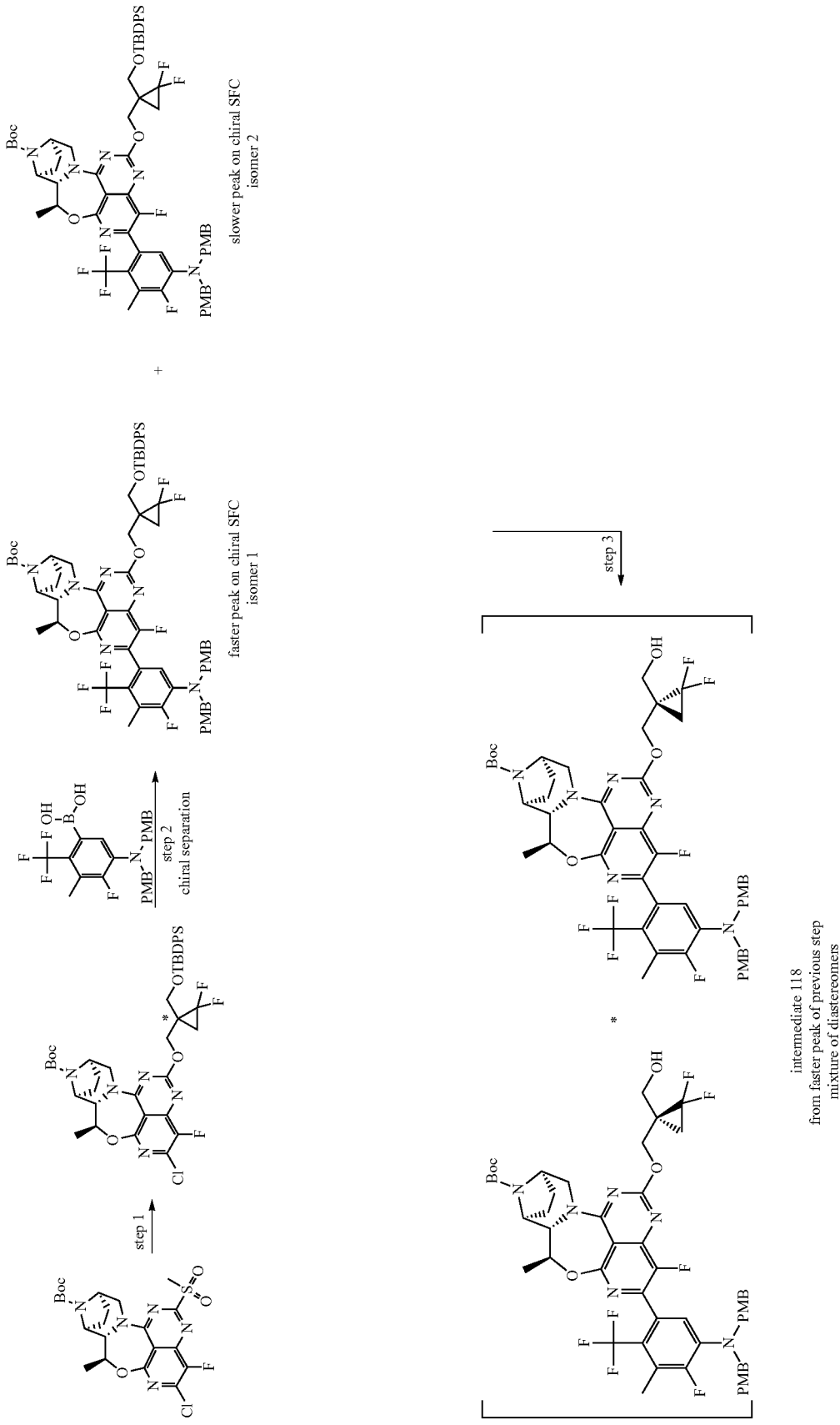

Step 1: tert-Butyl (5S,5aS,6S,9R)-12-((1-(((tert-butyldiphenylsilyl)oxy)methyl)-2,2-difluorocyclopropyl)methoxy)-2-chloro-1-fluoro-5-methyl-5a,6,7,8,9,10-hexahydro-5H-4-oxa-3,10a,11,13,14-pentaaza-6,9-methanonaphtho[1,8-ab]heptalene-14-carboxylate To a solution of (1-(((tert-Butyldiphenylsilyl)oxy)methyl)-2,2-difluorocyclopropyl)methanol (800 mg, 2.12 mmol, intermediate 117) in tetrahydrofuran (40 mL) was added NaH (60% dispersion in mineral oil, 424 mg, 10.6 mmol) at 0° C., and the mixture was stirred for 30 minutes at room temperature. Then tert-butyl (5S,5aS,6S,9R)-2-chloro-1-fluoro-5-methyl-12-(methylsulfonyl)-5a,6,7,8,9,10-hexahydro-5H-4-oxa-3,10a,11,13,14-pentaaza-6,9-methanonaphtho[1,8-ab]heptalene-14-carboxylate (546 mg, 1.06 mmol) was added, and the mixture was stirred for 1 hour at room temperature. The reaction was quenched with saturated NH₄Cl aqueous solution. The reaction mixture was diluted with water and extracted with ethyl acetate. The combined organic layers were washed with brine, dried over anhydrous sodium sulfate and concentrated under vacuum. The residue was purified by flash chromatography on silica gel eluting (gradient: 0-20% EtOAc in petroleum ether) to afford the title compound (566 mg) as a yellow solid. LC-MS: (ESI, m/z): [M+H]⁺=811.

Step 2: tert-Butyl (5S,5aS,6S,9R)-2-(5-(bis(4-methoxybenzyl)amino)-4-fluoro-3-methyl-2-(trifluoromethyl)phenyl)-12-((1-(((tert-butyldiphenylsilyl)oxy)methyl)-2,2-difluorocyclopropyl)methoxy)-1-fluoro-5-methyl-5a,6,7,8,9,10-hexahydro-5H-4-oxa-3,10a,11,13,14-pentaaza-6,9-methanonaphtho[1,8-ab]heptalene-14-carboxylate (two isomers)

Under nitrogen, a solution of tert-butyl (5S,5aS,6S,9R)-12-((1-(((tert-butyldiphenylsilyl)oxy)methyl)-2,2-difluorocyclopropyl)methoxy)-2-chloro-1-fluoro-5-methyl-5a,6,7,8,9,10-hexahydro-5H-4-oxa-3,10a,11,13,14-pentaaza-6,9-methanonaphtho[1,8-ab]heptalene-14-carboxylate (1.70 g, 2.10 mmol), (5-(bis(4-methoxybenzyl)amino)-4-fluoro-3-methyl-2-(trifluoromethyl)phenyl)boronic acid (3.01 g, 6.30 mmol), K₃PO₄ (1.5M aqueous solution, 7 mL, 10.5 mmol) and cataCXium A Pd G3 (320 mg, 0.440 mmol) in tetrahydrofuran (35 mL) stirred for 3 hours at 60° C. The reaction mixture was diluted with water and extracted with ethyl acetate. The combined organic layer was dried over anhydrous sodium sulfate and concentrated under vacuum. The residue was purified by flash chromatography on silica gel (gradient: 0-30% EtOAc in petroleum ether) to afford a mixture of isomers (2.40 g) as a yellow solid. The two diastereomers were separated by Chiral-Prep-SFC with the following conditions: (Column: (S, S)-Whelk-O 1 5 μm Kromasil 3*25 cm, 5 μm; Mobile Phase A: CO₂, Mobile Phase B: IPA(0.1% 2M NH₃-MEOH); Flow rate: 100 mL/min; Gradient: isocratic 50% B; Column Temperature(° C.): 35; Back Pressure(bar): 100; Wave Length: 220 nm; RT1(min): 5.53; RT2(min): 6.6; Sample Solvent: ACN; Injection Volume: 1.9 mL; Number Of Runs: 7) to afford isomer 1 (1.10 g, the faster peak) and isomer 2 (1.04 g, the slower peak) as white solids. LC-MS: (ESI, m/z): [M+H]⁺= 1208.

Step 3: tert-Butyl (5S,5aS,6S,9R)-2-(5-(bis(4-methoxybenzyl)amino)-4-fluoro-3-methyl-2-(trifluoromethyl)phenyl)-12-((2,2-difluoro-1-(hydroxymethyl)cyclopropyl)methoxy)-1-fluoro-5-methyl-5a,6,7,8,9,10-hexahydro-5H-4-oxa-3,10a,11,13,14-pentaaza-6,9-methanonaphtho[1,8-ab]heptalene-14-carboxylate (two isomers)

To a solution of tert-butyl (5S,5aS,6S,9R)-2-(5-(bis(4-methoxybenzyl)amino)-4-fluoro-3-methyl-2-(trifluoromethyl)phenyl)-12-((1-(((tert-butyldiphenylsilyl)oxy)methyl)-2,2-difluorocyclopropyl)methoxy)-1-fluoro-5-methyl-5a,6,7,8,9,10-hexahydro-5H-4-oxa-3,10a,11,13,14-pentaaza-6,9-methanonaphtho[1,8-ab]heptalene-14-carboxylate (1.10 g, 0.911 mmol, isomer 1 of last step) in tetrahydrofuran (30 mL) was added TBAF (1M solution in tetrahydrofuran, 3 mL, 3.00 mmol), and the mixture was stirred for 2 hours at room temperature. The reaction mixture was diluted with water and extracted with ethyl acetate. The combined organic layer was dried over anhydrous sodium sulfate and concentrated under vacuum. The residue was purified by flash chromatography on silica gel (gradient: 0-50% EtOAc in petroleum ether) to afford the title compound (810 mg, intermediate 118) as a yellow solid. LC-MS: (ESI, m/z): [M+H]⁺=969. It appears that isomerization took place in the TBDPS deprotection step to give a mixture of diastereomers of the title compound with respect to the stereogenic center of the difluorocyclopropyl moiety. This mixture was used as such in the following steps.

Intermediate 119: (R)-(1-((2-methylmorpholino)methyl)cyclopropyl)methanol

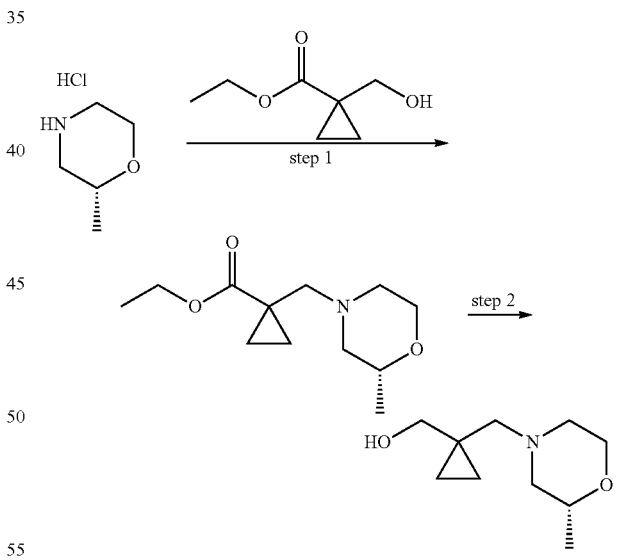

Step 1: Ethyl (R)-1-((2-methylmorpholino)methyl)cyclopropane-1-carboxylate

Under nitrogen, to a solution of ethyl 1-(hydroxymethyl)cyclopropane-1-carboxylate (500 mg, 3.47 mmol) and DIPEA (1.84 mL, 10.4 mmol) in dichloromethane (5 mL) was added Tf₂O (1.2 mL, 6.94 mmol) dropwise at −10° C., and the mixture was stirred for 5 minutes. Then a solution of (R)-2-methylmorpholine in dichloromethane (5 mL) (pre-treated (R)-2-methylmorpholine hydrochloride (477 mg, 3.47 mmol) with DIPEA (1.23 mL, 6.94 mmol)) was added at −10° C., and the mixture was stirred for 1 hour at room temperature. The solvent was concentrated under vacuum to afford the title compound (1.90 g, crude) as a yellow solid. LC-MS: (ESI, m/z): [M+H]$^+$=228.

Step 2: (R)-(1-((2-methylmorpholino)methyl)cyclopropyl)methanol

To a solution of ethyl (R)-1-((2-methylmorpholino)methyl)cyclopropane-1-carboxylate (1.90 g, crude) in THF (20 mL) was added LiAlH$_4$ (600 mg, 15.8 mmol) in portions at 0° C., and the mixture was stirred for 1 hour at room temperature. The reaction was quenched with Na$_2$SO$_4$·10H$_2$O and filtrated. The filtrate was concentrated under reduced pressure to afford the title compound (1.00 g, crude) as a yellow oil. LC-MS: (ESI, m/z): [M+H]$^+$=186. The crude was used for next step without further purification.

Intermediates 120 and 121: (1-(((1S,4S)-2-Oxa-5-azabicyclo[2.2.1]heptan-5-yl)methyl)cyclopropyl)methanol and (1-(((1R,4R)-2-oxa-5-azabicyclo[2.2.1]heptan-5-yl)methyl)cyclopropyl)methanol

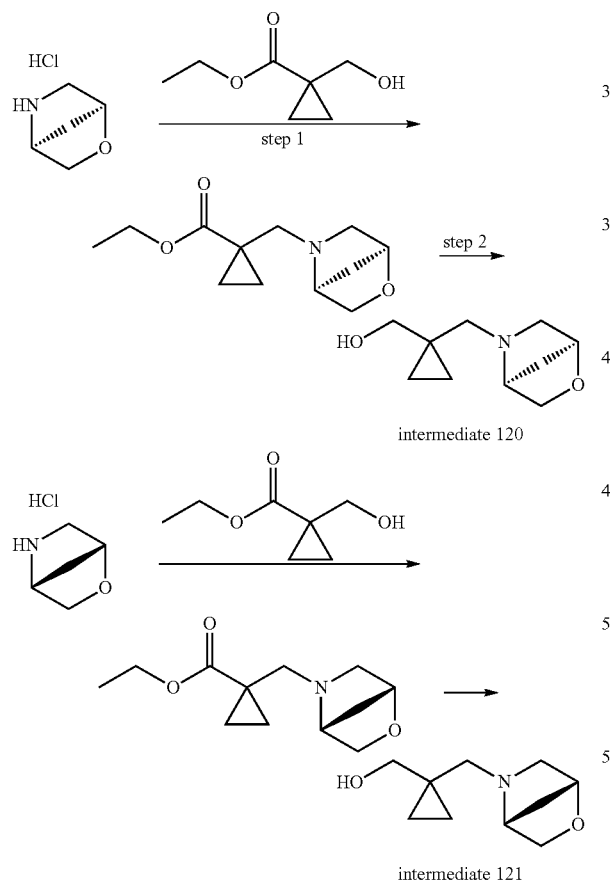

intermediate 120 intermediate 121

Step 1: Ethyl 1-(((1S,4S)-2-oxa-5-azabicyclo[2.2.1]heptan-5-yl)methyl)cyclopropane-1-carboxylate Under nitrogen, to a solution of ethyl 1-(hydroxymethyl)cyclopropane-1-carboxylate (500 mg, 3.47 mmol) and DIPEA (1.84 mL, 10.4 mmol) in dichloromethane (10 mL) was added Tf$_2$O (1.2 mL, 6.94 mmol) dropwise at −10° C., and the mixture was stirred for 5 minutes. Then a solution of (1S,4S)-2-oxa-5-azabicyclo[2.2.1]heptane in dichloromethane (5 mL) (pretreated (1S,4S)-2-oxa-5-azabicyclo[2.2.1]heptane hydrochloride (490 mg, 3.47 mmol) with DIPEA (1.23 mL, 6.94 mmol)) was added at −10° C., and the mixture was stirred for 1 hour at room temperature. The solvent was concentrated under vacuum to afford the title compound (1.50 g, crude) as a brown solid. LC-MS: (ESI, m/z): [M+H]$^+$=226.

Analogous to method described as above, the enantiomer (1.30 g, crude) was prepared from (1R,4R)-2-oxa-5-azabicyclo[2.2.1]heptane hydrochloride (490 mg, 3.47 mmol) as a brown solid. LC-MS: (ESI, m/z): [M+H]$^+$=226.

Step 2: (1-(((1S,4S)-2-Oxa-5-azabicyclo[2.2.1]heptan-5-yl)methyl)cyclopropyl)methanol To a solution of ethyl 1-(((1S,4S)-2-oxa-5-azabicyclo[2.2.1]heptan-5-yl)methyl)cyclopropane-1-carboxylate (1.50 g, crude) in THF (20 mL) was added LiAlH$_4$ (505 mg, 13.3 mmol) in portions at 0° C., and the mixture was stirred for 1 hour at room temperature. The reaction was quenched with Na$_2$SO$_4$·10H$_2$O and filtrated. The filtrate was concentrated under reduced pressure to afford the title compound (2.50 g, crude, intermediate 120) as a brown solid. LC-MS: (ESI, m/z): [M+H]$^+$=184.

Analogous to method described as above, the other isomer intermediate 121 (2.40 g, crude) was prepared from ethyl 1-(((1R,4R)-2-oxa-5-azabicyclo[2.2.1]heptan-5-yl)methyl)cyclopropane-1-carboxylate (1.30 g, crude) as a brown solid. LC-MS: (ESI, m/z): [M+H]$^+$=184.

Intermediate 122: tert-Butyl (5S,5aS,6S,9R)-2-(5-(bis(4-methoxybenzyl)amino)-4-fluoro-3-methyl-2-(trifluoromethyl)phenyl)-1-fluoro-12-((1-(hydroxymethyl)cyclopropyl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate

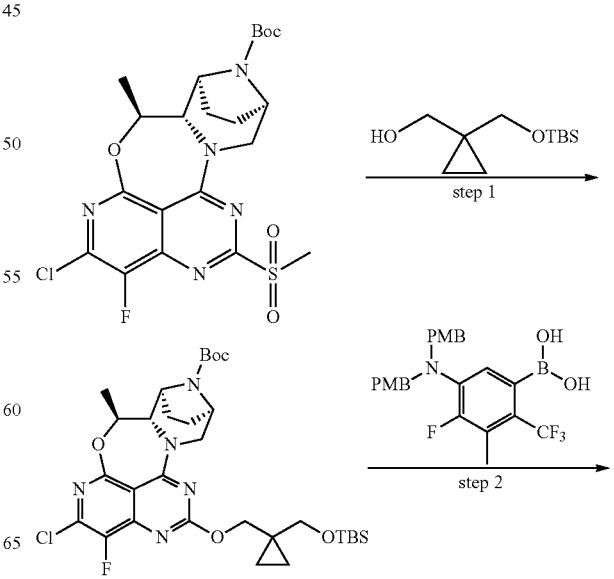

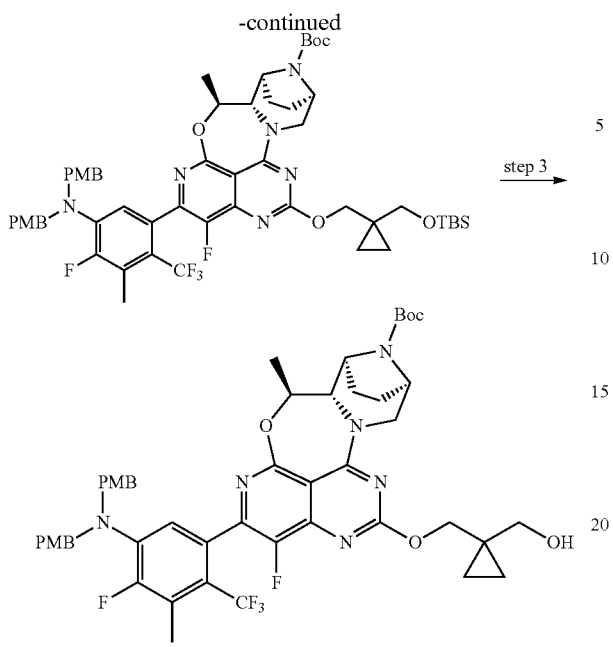

Step 1: tert-Butyl (5S,5aS,6S,9R)-12-((1-(((tert-butyldimethylsilyl)oxy)methyl)cyclopropyl)methoxy)-2-chloro-1-fluoro-5-methyl-5a,6,7,8,9,10-hexahydro-5H-4-oxa-3,10a,11,13,14-pentaaza-6,9-methanonaphtho[1,8-ab]heptalene-14-carboxylate To a solution of (1-(((tert-butyldimethylsilyl)oxy)methyl)cyclopropyl)methanol (842 mg, 3.89 mmol) in tetrahydrofuran (10 mL) was added NaH (60% dispersion in mineral oil, 390 mg, 9.75 mmol) at 0° C. in 3 portions, and the mixture was stirred for 30 minutes at room temperature. Then tert-butyl (5S,5aS,6S,9R)-2-chloro-1-fluoro-5-methyl-12-(methylsulfonyl)-5a,6,7,8,9,10-hexahydro-5H-4-oxa-3,10a,11,13,14-pentaaza-6,9-methanonaphtho[1,8-ab]heptalene-14-carboxylate (1.00 g, 1.95 mmol) was added, and the mixture was stirred for 2 hours at room temperature. The reaction was quenched with saturated NH$_4$Cl aqueous solution. The reaction mixture was diluted with water and extracted with ethyl acetate. The combined organic layers were washed with brine, dried over anhydrous sodium sulfate and concentrated under vacuum. The residue was purified by flash chromatography on silica gel (gradient: 0-20% EtOAc in petroleum ether) to afford the title compound (800 mg) as a white solid. LC-MS: (ESI, m/z): [M+H]$^+$=650.

Step 2: tert-Butyl (5S,5aS,6S,9R)-2-(5-(bis(4-methoxybenzyl)amino)-4-fluoro-3-methyl-2-(trifluoromethyl)phenyl)-12-((1-(((tert-butyldimethylsilyl)oxy)methyl)cyclopropyl)methoxy)-1-fluoro-5-methyl-5a,6,7,8,9,10-hexahydro-5H-4-oxa-3,10a,11,13,14-pentaaza-6,9-methanonaphtho[1,8-ab]heptalene-14-carboxylate Under nitrogen, a solution of tert-butyl (5S,5aS,6S,9R)-12-((1-(((tert-butyldimethylsilyl)oxy)methyl)cyclopropyl)methoxy)-2-chloro-1-fluoro-5-methyl-5a,6,7,8,9,10-hexahydro-5H-4-oxa-3,10a,11,13,14-pentaaza-6,9-methanonaphtho[1,8-ab]heptalene-14-carboxylate (800 mg, 1.23 mmol), (5-(bis(4-methoxybenzyl)amino)-4-fluoro-3-methyl-2-(trifluoromethyl)phenyl)boronic acid (1.17 g, 2.45 mmol), K$_3$PO$_4$ (1.5M in H$_2$O, 4 mL, 6.00 mmol) and cataCXium A Pd G3 (179 mg, 0.246 mmol) in tetrahydrofuran (20 mL) was stirred for 3 hours at 60° C. The reaction mixture was diluted with water and extracted with EtOAc. The combined organic layer was dried over anhydrous sodium sulfate and concentrated under vacuum. The residue was purified by flash chromatography on silica gel (gradient: 0-10% methanol in dichloromethane) to afford the title compound (1.20 g) as a brown solid. LC-MS: (ESI, m/z): [M+H]$^+$=1047.

Step 3: tert-Butyl (5S,5aS,6S,9R)-2-(5-(bis(4-methoxybenzyl)amino)-4-fluoro-3-methyl-2-(trifluoromethyl)phenyl)-1-fluoro-12-((1-(hydroxymethyl)cyclopropyl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate To a solution of tert-butyl (5S,5aS,6S,9R)-2-(5-(bis(4-methoxybenzyl)amino)-4-fluoro-3-methyl-2-(trifluoromethyl)phenyl)-12-((1-(((tert-butyldimethylsilyl)oxy)methyl)cyclopropyl)methoxy)-1-fluoro-5-methyl-5a,6,7,8,9,10-hexahydro-5H-4-oxa-3,10a,11,13,14-pentaaza-6,9-methanonaphtho[1,8-ab]heptalene-14-carboxylate (1.20 g, 1.15 mmol) in tetrahydrofuran (10 mL) was added TBAF (1M solution in tetrahydrofuran, 2.3 mL) at room temperature, and the mixture was stirred for 1 hour. The solvent was concentrated under vacuum. The residue was purified by flash chromatography on silica gel (gradient: 0-10% methanol in dichloromethane) to afford the title compound (1.00 g) as a white solid. LC-MS: (ESI, m/z): [M+H]$^+$=933. $^1$H NMR (300 MHz, DMSO-d6, ppm) δ 7.16 (d, J=8.0 Hz, 4H), 6.86 (d, J=8.1 Hz, 4H), 6.78-6.46 (m, 1H), 5.15 (d, J=13.1 Hz, 1H), 4.71-4.48 (m, 2H), 4.48-4.20 (m, 5H), 4.19-3.85 (m, 3H), 3.71 (s, 6H), 3.49-3.34 (m, 2H), 3.05 (d, J=13.3 Hz, 1H), 2.35 (s, 3H), 1.96-1.61 (m, 4H), 1.54-1.39 (m, 12H), 0.62-0.40 (m, 4H).

Intermediate 123: 5-Chloro-6-methyl-4-(4,4,5,5-tetramethyl-1,3,2-dioxaborolan-2-yl)-1-((2-(trimethylsilyl)ethoxy)methyl)-1H-indazole

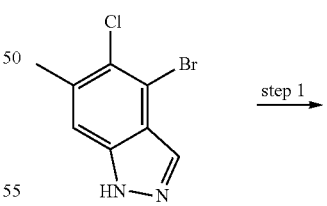

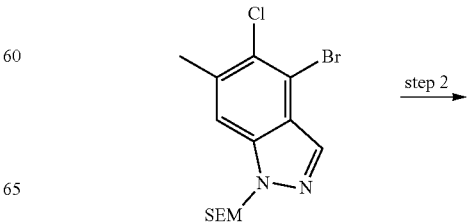

-continued

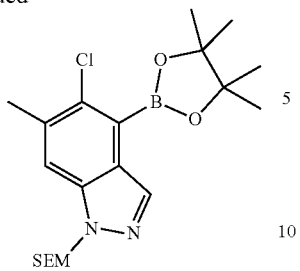

Step 1: 4-Bromo-5-chloro-6-methyl-1-((2-(trimethylsilyl)ethoxy)methyl)-1H-indazole Under nitrogen, to a solution of 4-bromo-5-chloro-6-methyl-1H-indazole (300 mg, 1.22 mmol) in DMF (3.00 mL) was added NaH (59.0 mg, 1.48 mmol, 60% in mineral oil) at 0° C. The resulting solution was stirred for 30 min at 0° C. Then SEMCl (266 mg, 1.60 mmol) was added at 0° C., and the mixture was stirred for 1 h at room temperature. The mixture was cooled to 0° C., quenched with water and extracted with EtOAc. The organic layers were dried over anhydrous sodium sulfate and concentrated under vacuum. The residue was purified by flash chromatography on silica gel (gradient: 0%-20% EtOAc/petroleum ether) to afford 317 mg of the title compound as a white solid. LCMS: (ESI, m/z): [M+H]$^+$=375.

Step 2: 5-Chloro-6-methyl-4-(4,4,5,5-tetramethyl-1,3,2-dioxaborolan-2-yl)-1-((2-(trimethylsilyl)ethoxy)methyl)-1H-indazole Under nitrogen, a solution of 4-bromo-5-chloro-6-methyl-1-((2-(trimethylsilyl)ethoxy)methyl)-1H-indazole (267 mg, 0.714 mmol), Pd(dppf)Cl$_2$·DCM (58.3 mg, 0.0710 mmol), Pin$_2$B$_2$ (274 mg, 1.08 mmol) and KOAc (212 mg, 2.16 mmol) in 1,4-dioxane (3.00 mL) was stirred for 16 h at 100° C. The reaction mixture was cooled to room temperature, filtered through a celite pad and washed with EtOAc. The filtrate was concentrated in vacuo. The residue was purified by flash chromatography on silica gel (gradient: 0%-20% EtOAc/petroleum ether) to afford 166 mg of the title compound as a white solid. LCMS: (ESI, m/z): [M+H]$^+$= 423.

Intermediate 124: (3-(bis(4-Methoxybenzyl)amino)-6-(2,2-difluoroethyl)-2,4-difluoro-5-methylphenyl)boronic acid

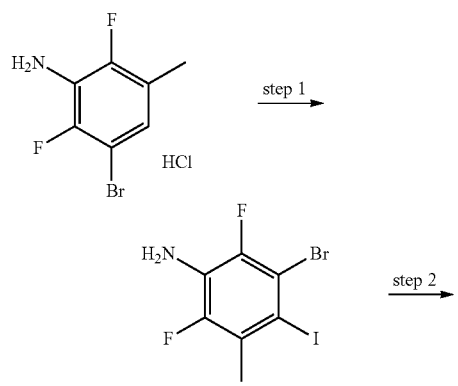

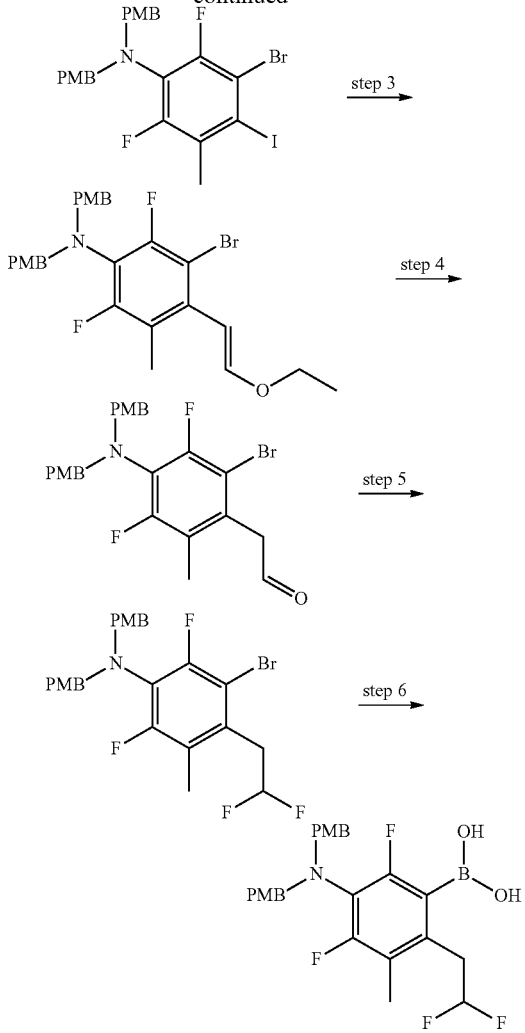

Step 1:
3-Bromo-2,6-difluoro-4-iodo-5-methylaniline

A solution of 3-bromo-2,6-difluoro-5-methyl-aniline (2.01 g, 9.02 mmol) and NIS (2.42 g, 10.8 mmol) in AcOH (10 mL) was stirred for 30 min at room temperature. The solution was quenched by Na$_2$S$_2$O$_3$ aqueous and extracted with EtOAc. The combined organic layers were dried over anhydrous sodium sulfate and concentrated under vacuum. The residue was purified by flash chromatography on silica gel (gradient: 0%-6% EtOAc/petroleum ether) to afford 2.15 g of the title compound as a yellow solid. LC-MS: (ESI, m/z): [M+H]$^+$=348.

Step 2: 3-Bromo-2,6-difluoro-4-iodo-N,N-bis(4-methoxybenzyl)-5-methylaniline

Under nitrogen, to a solution of 3-bromo-2,6-difluoro-4-iodo-5-methylaniline (2.13 g, 6.13 mmol) in DMF (20 mL) was added NaH (0.980 g, 24.5 mmol) at 0° C. The resulting solution was stirred for 30 min at 0° C. Then PMB-Cl (2.39 g, 15.3 mmol) was added, and the mixture was stirred at room temperature for 2 h. The solution was quenched with NH$_4$Cl aqueous and extracted with EtOAc. The combined organic layers were dried over anhydrous sodium sulfate and concentrated under vacuum. The residue was purified by flash chromatography on silica gel (gradient: 0%-8% EtOAc/petroleum ether) to afford 3.73 g of the title compound as a yellow solid. LC-MS: (ESI, m/z): [M+H]⁺=588.

Step 3: (E)-3-Bromo-4-(2-ethoxyvinyl)-2,6-difluoro-N,N-bis(4-methoxybenzyl)-5-methylaniline Under nitrogen, a solution of 3-bromo-2,6-difluoro-4-iodo-N,N-bis(4-methoxybenzyl)-5-methylaniline (3.77 g, 6.41 mmol), (E)-2-(2-ethoxyvinyl)-4,4,5,5-tetramethyl-1,3,2-dioxaborolane (1.40 g, 7.05 mmol), Pd(dppf)Cl₂ (0.980 g, 1.28 mmol) and K₂CO₃ (1.77 g, 12.8 mmol) in 1,4-dioxane (38 mL) and water (7.6 mL) was stirred for 5 h at 90° C. The resulting reaction was cooled to room temperature and concentrated under vacuum. The residue was purified by flash chromatography on silica gel (gradient: 0%-10% EtOAc/petroleum ether) to afford 1.62 g of the title compound as a yellow oil. LC-MS: (ESI, m/z): [M+H]⁺=532.

Step 4: 2-(4-(bis(4-Methoxybenzyl)amino)-2-bromo-3,5-difluoro-6-methylphenyl)acetaldehyde Under nitrogen, to a solution of (E)-3-bromo-4-(2-ethoxyvinyl)-2,6-difluoro-N,N-bis(4-methoxybenzyl)-5-methylaniline (1.61 g, 3.01 mmol) in THF (16 mL) was added HCl (3.2 mL, 36%) and stirred for 2 h at room temperature. The solution was quenched by NaHCO₃ aqueous and extracted with EtOAc. The combined organic layers were dried over anhydrous sodium sulfate and concentrated under vacuum to afford 1.51 g (crude) of the title compound as a yellow oil. LC-MS: (ESI, m/z): [M+H]⁺=504.

Step 5: 3-Bromo-4-(2,2-difluoroethyl)-2,6-difluoro-N,N-bis(4-methoxybenzyl)-5-methylaniline Under nitrogen, to a solution of 2-(4-(bis(4-methoxybenzyl)amino)-2-bromo-3,5-difluoro-6-methylphenyl)acetaldehyde (1.51 g, 2.99 mmol) in DCM (16 mL) was added DAST (4.83 g, 29.9 mmol) at −10° C., and the mixture was stirred for 2 h at room temperature. The solution was quenched with NaHCO₃ aqueous and extracted with DCM. The combined organic layers were dried over anhydrous sodium sulfate and concentrated under vacuum. The residue was purified by flash chromatography on silica gel (gradient: 0%-9% EtOAc/petroleum ether) to afford 1.01 g of the title compound as a yellow oil. LC-MS: (ESI, m/z): [M+H]⁺=526.

Step 6: (3-(bis(4-Methoxybenzyl)amino)-6-(2,2-difluoroethyl)-2,4-difluoro-5-methylphenyl) boronic acid Under nitrogen, a solution of 3-bromo-4-(2,2-difluoroethyl)-2,6-difluoro-N,N-bis(4-methoxybenzyl)-5-methylaniline (500 mg, 0.950 mmol) and triisopropyl borate (893 mg, 4.75 mmol) in THF (5 mL) was added n-BuLi (1.9 mL, 2.5 M in THF) at −60° C., and the mixture was stirred for 2 h at −60° C. The solution was quenched by MeOH and the solution was concentrated under vacuum. The residue was purified by flash chromatography on silica gel (gradient: 0%-29% EtOAc (0.1% TEA)/petroleum ether (10% DCM)) to afford 201 mg of the title compound as a yellow oil. LC-MS: (ESI, m/z): [M+H]⁺=492.

Intermediate 125: 3-Fluoro-N,N-bis(4-methoxybenzyl)-6-methyl-4-(4,4,5,5-tetramethyl-1,3,2-dioxaborolan-2-yl)pyridin-2-amine

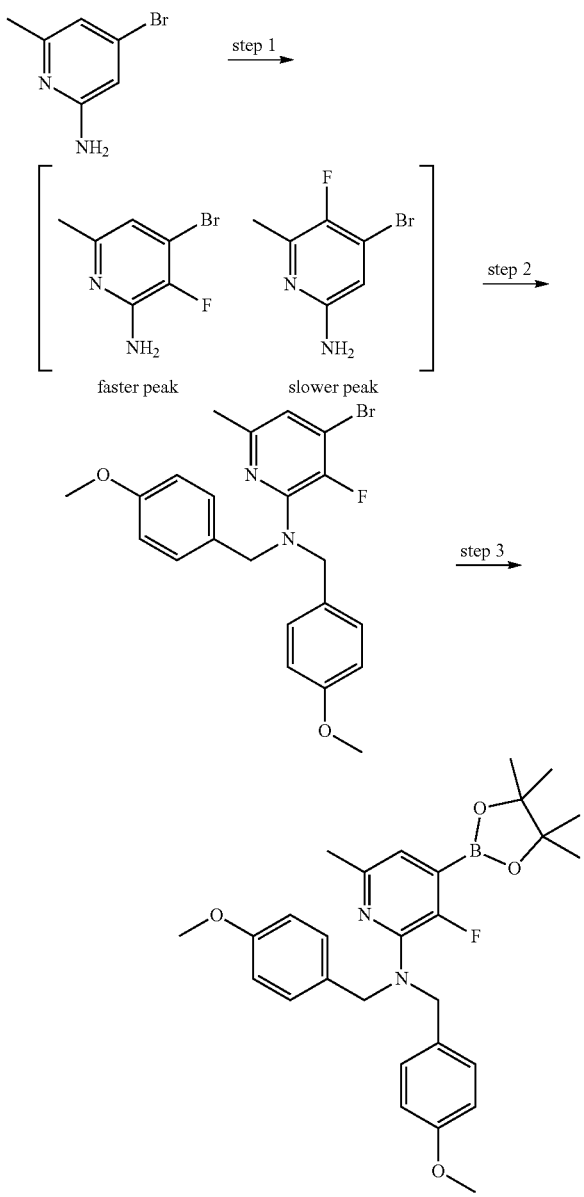

Step 1: 4-Bromo-3-fluoro-6-methylpyridin-2-amine

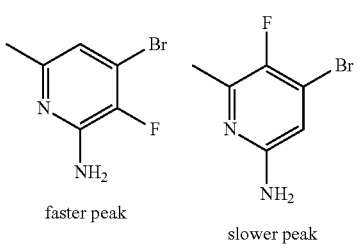

To a solution of 4-bromo-6-methylpyridin-2-amine (1.00 g, 5.35 mmol) in CHCl$_3$ (6 mL) and water (6 mL) was added SelectFluor (946 mg, 2.67 mmol) at room temperature. The reaction was stirred at room temperature overnight. The reaction mixture was concentrated under vacuum. EtOAc was added and washed with water. The organic layer was dried over anhydrous sodium sulfate and concentrated under vacuum. The residue was purified by flash chromatography on silica gel (gradient: 0-100% EtOAc in petroleum ether) to afford faster peak (112 mg) and slower peak (215 mg) as yellow solids.

Faster peak: LC-MS: (ESI, m/z): [M+H]$^+$=205. $^1$H NMR (300 MHz, DMSO-d$_6$) δ 6.64 (d, J=3.7 Hz, 1H), 6.40 (s, 2H), 2.21 (d, J=1.2 Hz, 3H).

Slower peak: LC-MS: (ESI, m/z): [M+H]$^+$=205. $^1$H NMR (300 MHz, DMSO-d$_6$) δ 6.54 (d, J=3.8 Hz, 1H), 5.99 (s, 2H), 2.25 (d, J=3.2 Hz, 3H).

Step 2: 4-Bromo-3-fluoro-N,N-bis(4-methoxybenzyl)-6-methylpyridin-2-amine

To a solution of 4-bromo-3-fluoro-6-methylpyridin-2-amine (110 mg, 0.540 mmol, the faster peak of last step) in DMF (1 mL) was added NaH (53.6 mg, 1.34 mmol, 60% dispersion in mineral oil) at 0° C. The mixture was stirred for 20 min at 0° C. PMBCl (185 mg, 1.18 mmol) was added and the mixture was allowed to warm to room temperature and stirred for 1 hour. The reaction was quenched by water. The resulting mixture was extracted with EtOAc. The combined organic layers were washed with brine, dried over anhydrous sodium sulfate and concentrated under vacuum. The residue was purified by flash chromatography on silica gel (gradient: 0-40% EtOAc in petroleum ether) to afford the title compound (175 mg) as a white solid. LC-MS: (ESI, m/z): [M+H]$^+$=445.

Step 3: 3-Fluoro-N,N-bis(4-methoxybenzyl)-6-methyl-4-(4,4,5,5-tetramethyl-1,3,2-dioxaborolan-2-yl)pyridin-2-amine Under nitrogen, a solution of 4-bromo-3-fluoro-N,N-bis(4-methoxybenzyl)-6-methylpyridin-2-amine (150 mg, 0.340 mmol), B$_2$Pin$_2$ (128 mg, 0.510 mmol), Pd(dppf)Cl$_2$ (49.3 mg, 0.0700 mmol) and KOAc (66.0 mg, 0.670 mmol) in 1,4-dioxane (3 mL) was stirred at 80° C. for 4 hours. The solution was cooled to room temperature. The resulting mixture was filtered. The filtrate was concentrated under reduced pressure. The crude product was diluted with water and extracted with EtOAc. The combined organic layers were washed with brine, dried over anhydrous sodium sulfate. The solvent was concentrated under reduced pressure. The residue was purified by flash chromatography on silica gel (gradient: 0-5% MeOH in DCM) to afford the title compound (150 mg) as a yellow oil. LC-MS: (ESI, m/z): [M+H]$^+$=411 (Mass of the boronic acid). $^1$H NMR (300 MHz, DMSO-d$_6$) δ 7.20-7.11 (m, 4H), 6.91-6.80 (m, 4H), 6.68 (d, J=2.4 Hz, 1H), 4.50 (s, 4H), 3.70 (s, 6H), 2.27 (s, 3H), 1.26 (s, 12H).

Intermediate 126: N,N-Bis(4-methoxybenzyl)-5-(4,4,5,5-tetramethyl-1,3,2-dioxaborolan-2-(trifluoromethyl)pyridin-3-amine

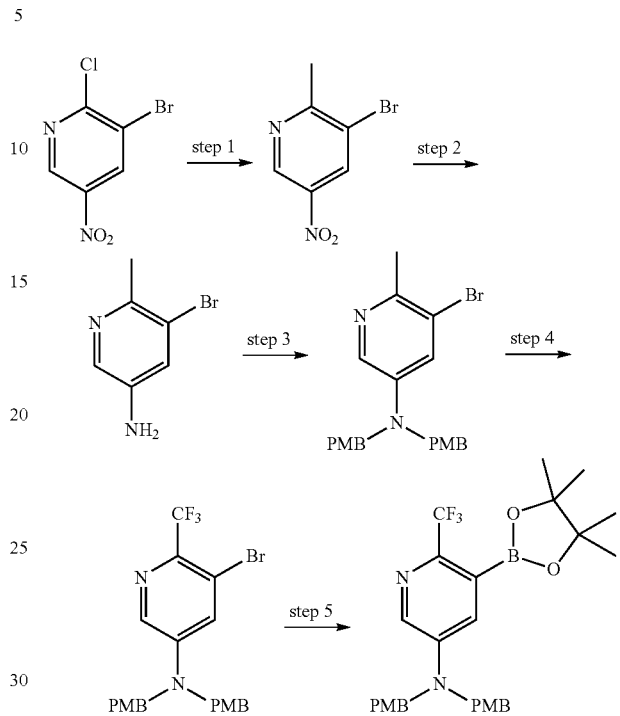

Step 1: 3-Bromo-2-iodo-5-nitropyridine

A solution of 3-bromo-2-chloro-5-nitropyridine (2.0 g, 8.42 mmol) and NaI (12.9 g, 86 mmol) in 2,2,2-trifluoroacetic acid (20 mL) was stirred at room temperature for 24 hours. The reaction was quenched by aqueous NaHCO$_3$ solution and extracted with EtOAc. The combined organic layers were dried over anhydrous sodium sulfate and concentrated under vacuum. The residue was purified by flash chromatography on silica gel (gradient: 0-10% EtOAc/petroleum ether) to afford 990 mg of the title compound as a brown solid. LC-MS: (ESI, m/z): [M+H]$^+$=329; 331.

Step 2: 5-Bromo-6-iodopyridin-3-amine

A solution of 3-bromo-2-iodo-5-nitropyridine (700 mg, 2.13 mmol), NH$_4$Cl (577 mg, 10.9 mmol) and ferrous powder (605 mg, 10.8 mmol) in ethanol (30 mL) and water (10 mL) was stirred at 80° C. for 2.5 hours. The solution was concentrated under vacuum. The residue was diluted with brine, extracted with EtOAc. The combined organic layers were dried over anhydrous sodium sulfate and concentrated under vacuum. The residue was purified by flash chromatography on silica gel (gradient: 0-40% EtOAc/petroleum ether) to afford 570 mg of the title compound as a yellow solid. LC-MS: (ESI, m/z): [M+H]$^+$=299; 301.

Step 3: 5-Bromo-6-iodo-N,N-bis(4-methoxybenzyl) pyridin-3-amine

Under nitrogen, to a solution of 5-bromo-6-iodopyridin-3-amine (570 mg, 1.91 mmol) in N,N-dimethylformamide (18 mL) was added NaH (392 mg, 9.81 mmol, 60% dispersion in mineral oil) at 0° C. The solution was stirred at room temperature for 0.5 hour. Then PMB-Cl (906 mg, 5.78 mmol) was added. The solution was stirred at room temperature for 2 hours. The reaction was quenched with aqueous NH$_4$Cl solution and extracted with EtOAc. The combined organic layers were dried over anhydrous sodium sulfate and concentrated under vacuum. The residue was purified by flash chromatography on silica gel (gradient: 0-20% EtOAc/petroleum ether) to afford 925 mg of the title compound as a yellow solid. LC-MS: (ESI, m/z): [M+H]$^+$=539; 541.

Step 4: 5-Bromo-N,N-bis(4-methoxybenzyl)-6-(trifluoromethyl)pyridin-3-amine

A solution of 5-bromo-6-iodo-N,N-bis(4-methoxybenzyl)pyridin-3-amine (1.05 g, 1.95 mmol), methyl 2,2-difluoro-2-(fluorosulfonyl)acetate (1.89 g, 9.84 mmol) and CuI (1.97 g, 10.4 mmol) in N,N-dimethylacetamide (14 mL) was stirred at 70° C. for 7 hours. The solution diluted with brine, extracted with EtOAc. The combined organic layers were dried over anhydrous sodium sulfate and concentrated under vacuum. The residue was purified by flash chromatography on silica gel eluting (gradient: 0-20% EtOAc/petroleum ether) to afford 802 mg of the title compound as a yellow solid. LC-MS: (ESI, m/z): [M+H]$^+$=481; 483.

Step 5: N,N-Bis(4-methoxybenzyl)-5-(4,4,5,5-tetramethyl-1,3,2-dioxaborolan-2-yl)-6-(trifluoromethyl)pyridin-3-amine Under nitrogen, a solution of 5-bromo-N,N-bis(4-methoxybenzyl)-6-(trifluoromethyl)pyridin-3-amine (800 mg, 1.66 mmol), Pin$_2$B$_2$ (1.28 g, 5.04 mmol), PdCl$_2$(dppf) (263 mg, 0.359 mmol) and KOAc (498 mg, 5.08 mmol) in 1,4-Dioxane (25 mL) was stirred at 110° C. for 6 hours. The solution was added brine and extracted with EtOAc. The combined organic layers were dried over anhydrous sodium sulfate and concentrated under vacuum. The residue was purified by flash chromatography on silica gel (gradient: 0-20% EtOAc/petroleum ether) to afford 392 mg of the title compound as a yellow oil. LC-MS: (ESI, m/z): [M+H]$^+$=529.

Intermediate 127: 5-Ethyl-N,N-bis(4-methoxybenzyl)-4-(4,4,5,5-tetramethyl-1,3,2-dioxaborolan-2-yl)quinolin-2-amine

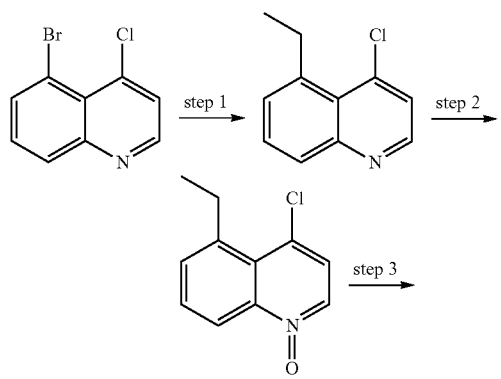

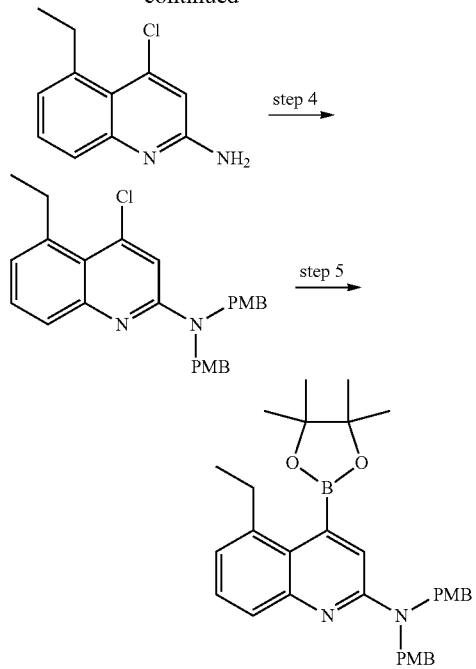

Step 1: 4-Chloro-5-ethylquinoline

Under nitrogen, a solution of 5-bromo-4-chloro-quinoline (2.01 g, 8.29 mmol), ethylboronic acid (798 mg, 10.8 mmol), dichloro[9,9-dimethyl-4,5-bis(diphenylphosphino)xanthene]palladium(II) (603 mg, 0.800 mmol) and Cs$_2$CO$_3$ (5.69 g, 17.5 mmol) in toluene (64 mL) and water (8 mL) was stirred at 100° C. for 16 hours. The solution was diluted with water, extracted with EtOAc. The combined organic layers were dried over anhydrous sodium sulfate and concentrated under vacuum. The residue was purified by flash chromatography on silica gel (gradient: 0-20% EtOAc/petroleum ether) to afford 1.12 g of the title compound as a colorless oil. LC-MS: (ESI, m/z): [M+H]$^+$=192.

Step 2: 4-Chloro-5-ethylquinoline 1-oxide

Under nitrogen, to a solution of 4-chloro-5-ethylquinoline (1.11 g, 5.79 mmol) in dichloromethane (35 mL) was added m-CPBA (2.12 g, 12.3 mmol) at 0° C. The solution was stirred at room temperature for 5 hours. The reaction was quenched with saturated NaS$_2$O$_3$ aqueous and extracted with DCM. The combined organic layers were dried over anhydrous sodium sulfate and concentrated under vacuum to afford 1.21 g (crude) of the title compound as a crude brown oil. LC-MS: (ESI, m/z): [M+H]$^+$=208.

Step 3: 4-Chloro-5-ethylquinolin-2-amine

A solution of 4-chloro-5-ethylquinoline 1-oxide (1.21 g, 5.83 mmol) and TsCl (1.86 g, 9.76 mmol) in dichloromethane (60 mL) was stirred at room temperature for 1 hour. Then the above solution was added to a solution of Et$_3$N (9.89 g, 97.9 mmol) and NH$_4$Cl (5.27 g, 98.5 mmol) in dichloromethane (60 mL). The solution was stirred at room temperature for 16 hours. The solid was filtered out and the filtrate was concentrated under vacuum. The residue was purified by C18 column (solvent gradient: 0-45% ACN in

Step 4: 4-Chloro-5-ethyl-N,N-bis(4-methoxybenzyl) quinolin-2-amine

Under nitrogen, to a solution of 4-chloro-5-ethylquinolin-2-amine (520 mg, 2.52 mmol) in N,N-dimethylformamide (12 mL) was added NaH (401 mg, 10.0 mmol, 60% dispersion in mineral oil) at 0° C. The solution was stirred at room temperature for 0.5 hour. Then PMB-Cl (1.17 g, 7.45 mmol) was added and the solution was stirred at room temperature for 3 hours. The reaction was quenched with aqueous $NH_4Cl$ solution and extracted with EtOAc. The combined organic layers were dried over anhydrous sodium sulfate and concentrated under vacuum. The residue was purified by flash chromatography on silica gel (gradient: 0-5% EtOAc/petroleum ether) to afford 993 mg of the title compound as a colorless oil. LC-MS: (ESI, m/z): [M+H]$^+$=447.

Step 5: 5-Ethyl-N,N-bis(4-methoxybenzyl)-4-(4,4,5,5-tetramethyl-1,3,2-dioxaborolan-2-yl)quinolin-2-amine Under nitrogen, a solution of 4-chloro-5-ethyl-N,N-bis(4-methoxybenzyl)quinolin-2-amine (990 mg, 2.22 mmol), $Pin_2B_2$ (1.72 g, 6.77 mmol), $PdCl_2(dppf)$ (345 mg, 0.472 mmol) and KOAc (659 mg, 6.72 mmol) in 1,4-Dioxane (25 mL) was stirred at 110° C. for 3 hours. The solution was concentrated under vacuum. The residue was purified by flash chromatography on silica gel (gradient: 0-10% EtOAc/petroleum ether) to afford 651 mg of the title compound as a yellow oil. LC-MS: (ESI, m/z): [M+H]$^+$=539.

Intermediate 128: 2-Fluoro-3-methyl-4-(methylsulfonyl)-5-(4,4,5,5-tetramethyl-1,3,2-dioxaborolan-2-yl)aniline

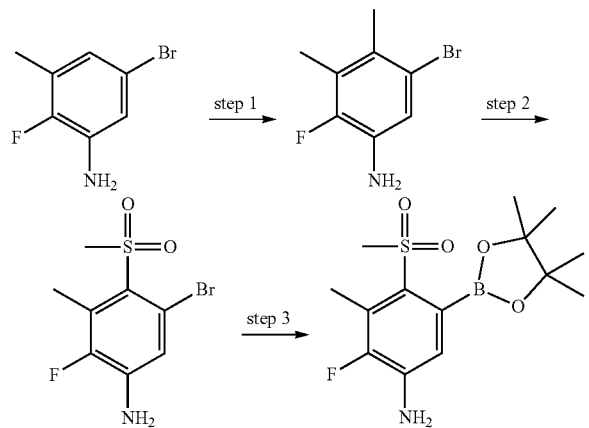

Step 1: 5-Bromo-2-fluoro-4-iodo-3-methylaniline

A solution of 5-bromo-2-fluoro-3-methylaniline (2.00 g, 9.80 mmol) and NIS (2.65 g, 11.8 mmol) in AcOH (50 mL) was stirred for 1 hour at room temperature. The solution was quenched with $Na_2S_2O_3$ aqueous and extracted with EtOAc. The combined organic layers were dried over anhydrous sodium sulfate and concentrated under vacuum. The residue was purified by flash chromatography on silica gel (gradient: 0-20% EtOAc in petroleum ether) to afford the title compound (1.90 g) as an off-white solid. LC-MS: (ESI, m/z): [M+H]$^+$=330.

Step 2: 5-Bromo-2-fluoro-3-methyl-4-(methylsulfonyl)aniline

Under nitrogen, a mixture of 5-bromo-2-fluoro-4-iodo-3-methylaniline (1.90 g, 5.76 mmol), sodium methanesulfinate (705 mg, 6.91 mmol), L-proline sodium salt (158 mg, 1.15 mmol) and CuI (110 mg, 0.578 mmol) in DMSO (30 mL) was stirred overnight at 80° C. The reaction mixture was diluted with water and extracted with EtOAc. The combined organic layers were dried over anhydrous sodium sulfate and concentrated under vacuum. The residue was purified by flash chromatography on silica gel (gradient: 0-40% EtOAc in petroleum ether) to afford the title compound (320 mg) as an off-white solid. LC-MS: (ESI, m/z): [M+H]$^+$=282.

Step 3: 2-Fluoro-3-methyl-4-(methylsulfonyl)-5-(4,4,5,5-tetramethyl-1,3,2-dioxaborolan-2-yl)aniline Under nitrogen, a solution of 5-bromo-2-fluoro-3-methyl-4-(methylsulfonyl)aniline (320 mg, 1.13 mmol), $B_2Pin_2$ (432 mg, 1.70 mmol), KOAc (334 mg, 3.40 mmol) and $Pd(dppf)Cl_2 \cdot CH_2Cl_2$ (277 mg, 0.342 mmol) in dioxane (3 mL) was stirred for 2 hours at 90° C. The reaction mixture was diluted with water and extracted with EtOAc. The combined organic layer was dried over anhydrous sodium sulfate and concentrated under vacuum. The residue was purified by flash chromatography on silica gel (gradient: 0-50% EtOAc in petroleum ether) to afford the title compound (140 mg) as a colorless oil. LC-MS: (ESI, m/z): [M+H]$^+$=330.

Intermediate 129: 6-(Allylsulfonyl)-3-fluoro-N,N-bis(4-methoxybenzyl)-4-methyl-5-(trifluoromethyl)pyridin-2-amine

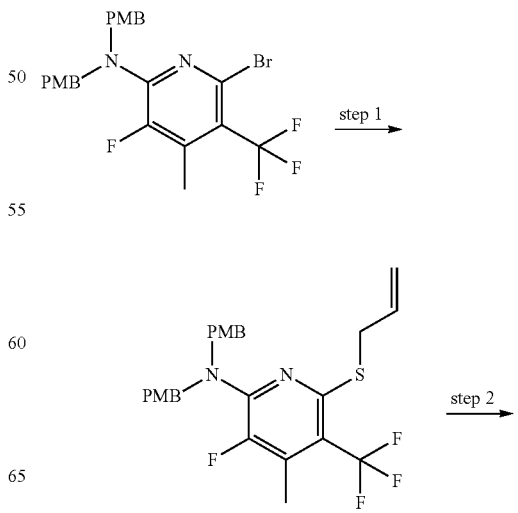

489
-continued

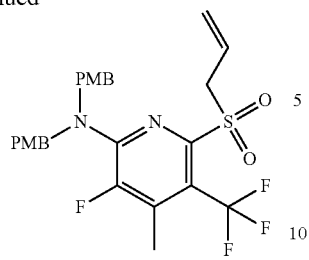

Step 1: 6-(Allylthio)-3-fluoro-N,N-bis(4-methoxybenzyl)-4-methyl-5-(trifluoromethyl)pyridin-2-amine To a solution of prop-2-ene-1-thiol (0.190 mL, 2.44 mmol) in DMF (2.5 mL) was added K$_2$CO$_3$ (134 mg, 0.970 mmol) and 6-bromo-3-fluoro-N,N-bis(4-methoxybenzyl)-4-methyl-5-(trifluoromethyl)pyridin-2-amine (250 mg, 0.490 mmol) at room temperature. The resulting solution was stirred overnight at room temperature. The resulting reaction was diluted with EtOAc, washed with water. The separated organic layer was dried over anhydrous sodium sulfate and concentrated under vacuum. The residue was purified by flash chromatography on silica gel (gradient: 0%-16% EtOAc/petroleum ether) to afford 234 mg of the title compound as a yellow oil. LC-MS: (ESI, m/z): [M+H]$^+$=507.

Step 2: 6-(Allylsulfonyl)-3-fluoro-N,N-bis(4-methoxybenzyl)-4-methyl-5-(trifluoromethyl) pyridin-2-amine Under nitrogen, a solution of 6-(allylthio)-3-fluoro-N,N-bis(4-methoxybenzyl)-4-methyl-5-(trifluoromethyl) pyridin-2-amine (234 mg, 0.460 mmol) and m-CPBA (240 mg, 1.39 mmol) in DCM (3 mL) was stirred overnight at room temperature. The reaction was quenched with NaHCO$_3$ aqueous and extracted with DCM. The combined organic layers were dried over anhydrous sodium sulfate and concentrated under vacuum. The residue was purified by flash chromatography on silica gel (gradient: 0%-43% EtOAc/petroleum ether) to afford 99.7 mg of the title compound as a yellow oil. LC-MS: (ESI, m/z): [M+H]$^+$=539.

Intermediate 130: 4-(1,1-Difluoropropan-2-yl)-2-fluoro-N,N-bis(4-methoxybenzyl)-5-(4,4,5,5-tetramethyl-1,3,2-dioxaborolan-2-yl)aniline

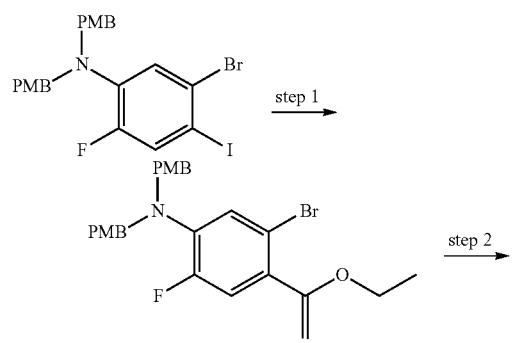

490
-continued

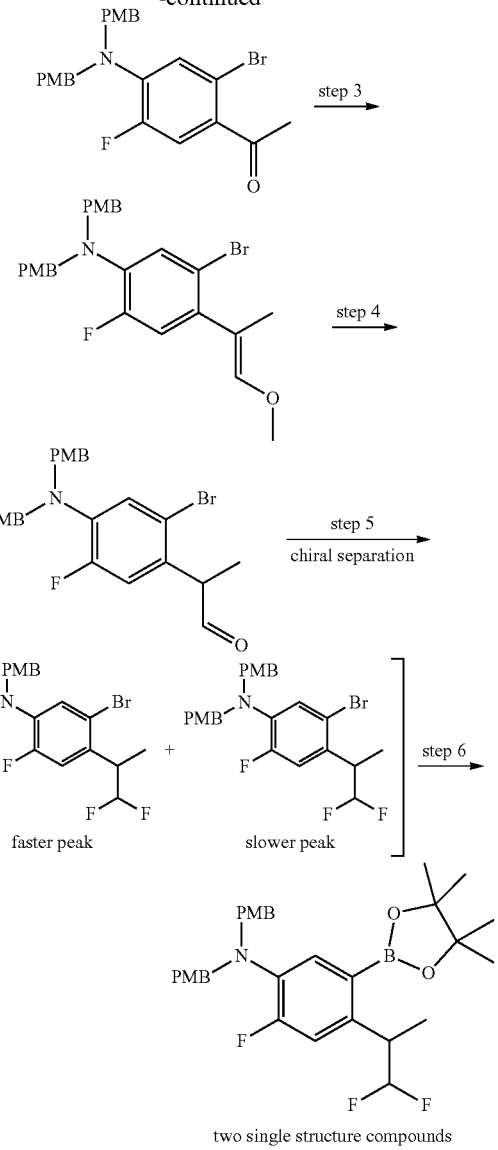

Step 1: 5-Bromo-4-(1-ethoxyvinyl)-2-fluoro-N,N-bis(4-methoxybenzyl) aniline

Under nitrogen, a solution of 5-bromo-2-fluoro-4-iodo-N,N-bis(4-methoxybenzyl) aniline (3.01 g, 5.41 mmol), tributyl(1-ethoxyvinyl) stannane (2.74 mL, 8.11 mmol) and PdCl$_2$(PPh$_3$)$_2$ (406 mg, 0.578 mmol) in DMF (15 mL) was stirred for 6 hours at 80° C. The resulting mixture was diluted with ethyl acetate and washed with water. The organic layer was concentrated under vacuum to afford 2.98 g (crude) of the title compound as a white solid. LC-MS: (ESI, m/z): [M+H]$^+$=500.

Step 2: 1-(4-(Bis(4-methoxybenzyl) amino)-2-bromo-5-fluorophenyl) ethan-1-one

To a solution of 5-bromo-4-(1-ethoxyvinyl)-2-fluoro-N,N-bis(4-methoxybenzyl) aniline (2.98 g, 5.96 mmol) in DMF (15 mL) was added HCl (3 mL, 12 M), and the mixture was stirred at room temperature for 2 h. The resulting mixture was diluted with ethyl acetate and washed with water. The organic layer was dried over anhydrous sodium sulfate and concentrated under vacuum. The residue was purified by flash chromatography on silica gel (gradient: 0-50% EtOAc/petroleum ether) to afford 1.71 g of the title compound as a white solid. LC-MS: (ESI, m/z): [M+H]$^+$= 472.

Step 3: (E)-5-Bromo-2-fluoro-N,N-bis(4-methoxybenzyl)-4-(1-methoxyprop-1-en-2-yl)aniline Under nitrogen, to a solution of 1-(4-(bis(4-methoxybenzyl)amino)-2-bromo-5-fluorophenyl)ethan-1-one (1.69 g, 3.58 mmol) in THF (20 mL) was added t-BuOK (10.6 mL, 1 M in THF) at 0° C. The resulting solution was stirred for 0.5 h at 0° C. Then (methoxymethyl)triphenylphosphonium chloride (4.01 g, 11.7 mmol) was added, and the mixture was stirred at 0° C. for 1.5 h. The reaction was quenched with NH$_4$Cl aqueous and extracted with EtOAc. The combined organic layers were dried over anhydrous sodium sulfate and concentrated under vacuum. The residue was purified by flash chromatography on silica gel (gradient: 0-50% EtOAc/petroleum ether) to afford 1.31 g of the title compound as a yellow solid. LC-MS: (ESI, m/z): [M+H]$^+$= 500.

Step 4: 2-(4-(Bis(4-methoxybenzyl)amino)-2-bromo-5-fluorophenylproopanal

A solution of (E)-5-bromo-2-fluoro-N,N-bis(4-methoxybenzyl)-4-(1-methoxyprop-1-en-2-yl)aniline (1.31 g, 2.62 mmol) in THF (4 mL) was added HCl (1 mL, 12 M), and the mixture was stirred at room temperature for 2 h. The solvent was concentrated under vacuum. The resulting mixture was diluted with ethyl acetate and washed with water. The organic layer was dried over anhydrous sodium sulfate and concentrated under vacuum. The residue was purified by flash chromatography on-silica gel (gradient: 0-70% EtOAc/petroleum ether) to afford 763 mg of the title compound as a yellow solid. LC-MS: (ESI, m/z): [M+H]$^+$=486.

Step 5: 5-Bromo-4-(1,1-difluoropropan-2-yl)-2-fluoro-N,N-bis(4-methoxybenzyl)aniline Under nitrogen, to a solution of 2-(4-(bis(4-methoxybenzyl)amino)-2-bromo-5-fluorophenyl)propanal (763 mg, 1.56 mmol) in DCM (10 mL) was added DAST (1.26 g, 7.83 mmol) at 0° C. The resulting solution was stirred for 2 h at room temperature. The reaction was quenched with NH$_4$Cl aqueous. The resulting mixture was diluted with ethyl acetate and washed with water. The organic layer was dried over anhydrous sodium sulfate and concentrated under vacuum. The residue was purified by flash chromatography on silica gel (gradient: 0-50% EtOAc/petroleum ether) to afford 716 mg of the title compound as a yellow solid. The mixture product was purified by Chiral-Prep-HPLC (Column: Lux 5 µm Cellulose-3 5×25 cm, 5 µm; Mobile Phase—Hex(0.1% 2 M NH$_3$—MeOH)—H—, Mobile Phase B: EtOH—HPLC; Flow rate: 20 mL/min; Gradient: isocratic; Wave Length: 220/254 nm; R$_{T1}$(min): 14.182; R$_{T2}$(min): 20-; Sample Solvent: EtOH—HPLC) afford 191 mg of the faster peak and 175 mg of the slower peak as white solids. LC-MS: (ESI, m/z): [M+H]$^+$=508.

Step 6: 4-(1,1-Difluoropropan-2-yl)-2-fluoro-N,N-bis(4-methoxybenzyl)-5-(4,4,5,5-tetramethyl-1,3,2-dioxaborolan-2-yl)aniline Under nitrogen, a solution of 5-bromo-4-(1,1-difluoropropan-2-yl)-2-fluoro-N,N-bis(4-methoxybenzyl)aniline (171 mg, 0.340 mmol, faster perk from last step), Pin$_2$B$_2$ (256 mg, 1.01 mmol), KOAc (99.2 mg, 1.01 mmol) and Pd(dppf)Cl$_2$ (49.6 mg, 0.0700 mmol) in 1,4-dioxane (10 mL) was stirred for 3 h at 100° C. The resulting mixture was diluted with ethyl acetate and washed with water. The separated organic layer was concentrated under vacuum. The residue was purified by flash chromatography on silica gel (gradient: 0-50% EtOAc/petroleum ether) to afford 132 mg of the title compound as a yellow solid. LC-MS: (ESI, m/z): [M+H]$^+$=556.

Analogous to method described as above, the enantiomer 113 mg was prepared from 5-bromo-4-(1,1-difluoropropan-2-yl)-2-fluoro-N,N-bis(4-methoxybenzyl)aniline (slower perk from last step)

Intermediate 131: (3-(Bis(4-methoxybenzyl)amino)-2-fluoro-5-methyl-6-(2,2,2-trifluoroethyl)phenyl) boronic acid

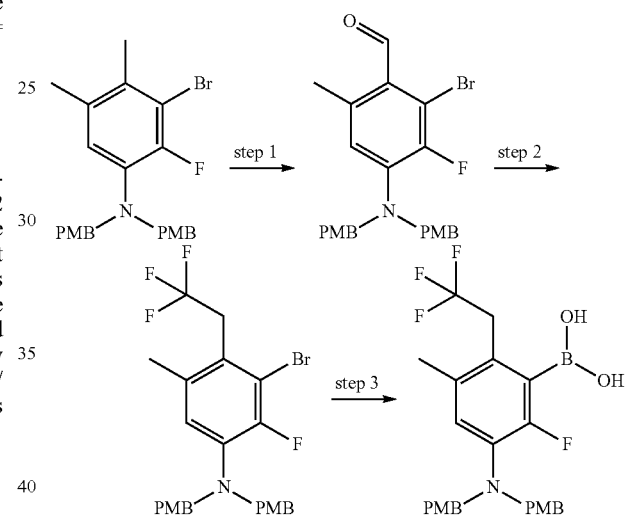

Step 1: 4-(Bis(4-methoxybenzyl) amino)-2-bromo-3-fluoro-6-methylbenzaldehyde

Under nitrogen, to a solution of 3-bromo-2-fluoro-4-iodo-N,N-bis(4-methoxybenzyl)-5-methylaniline (500 mg, 0.880 mmol) in tetrahydrofuran (5 mL) was added 2 M iPrMgCl in THF (1.32 mL, 2.63 mmol) at −20° C. The resulting solution was stirred for 1 hour at −20° C. Then DMF (640 mg, 8.77 mmol) was added, and the mixture was stirred at room temperature for 1 h. The reaction was quenched with water, extracted with EtOAc. The combined organic layers were dried over anhydrous sodium sulfate and concentrated under vacuum. The residue was purified by flash chromatography on silica gel (gradient: 0-20% EtOAc in petroleum ether) to afford the title compound (202 mg) as a yellow solid. LC-MS: (ESI, m/z): [M+H]$^+$=472.

Step 2: 3-Bromo-2-fluoro-N,N-bis(4-methoxybenzyl)-5-methyl-4-(2,2,2-trifluoroethyl)aniline Under nitrogen, to a solution of 4-(bis(4-methoxybenzyl) amino)-2-bromo-3-fluoro-6-methylbenzaldehyde (200 mg, 0.420 mmol) in N,N-dimethylacetamide (2 mL) was added 2,2-difluoro-2-(triphenylphosphonio)acetate (301 mg, 0.850 mmol) at room temperature. The resulting solution was stirred at 60° C. overnight. Then TBAF (6.35 mL, 6.35 mmol) was added, and the mixture was stirred at 60° C. for 3 hours. The resulting solution was diluted with EtOAc and washed with water. The organic layer was dried over anhydrous sodium sulfate and concentrated under vacuum. The residue was purified by flash chromatography on silica gel (gradient: 0-10% EtOAc in petroleum ether) to afford the title compound (85 mg) as a yellow oil. LC-MS: (ESI, m/z): [M+H]$^+$=526.

Step 3: (3-(Bis(4-methoxybenzyl)amino)-2-fluoro-5-methyl-6-(2,2,2-trifluoroethyl) phenyl) boronic acid Under nitrogen, to a solution of 3-bromo-2-fluoro-N,N-bis(4-methoxybenzyl)-5-methyl-4-(2,2,2-trifluoroethyl)aniline (65.0 mg, 0.123 mmol) and triisopropyl borate (0.04 mL, 0.190 mmol) in tetrahydrofuran (1 mL) was added n-BuLi (1.6 M in hexane, 0.09 mL, 0.150 mmol) at −78° C. The solution was stirred at −78° C. for 1 hour. The reaction was quenched by MeOH and concentrated under vacuum. The residue was purified by flash chromatography on silica gel (gradient: 0-25% EtOAc in petroleum ether) to afford the title compound (23 mg) as a white oil. LC-MS: (ESI, m/z): [M+H]$^+$=492.

Intermediate 132: 2,3-Difluoro-N,N-bis(4-methoxybenzyl)-5-(4,4,5,5-tetramethyl-1,3,2-dioxaborolan-2-yl)-4-(2,2,2-trifluoroethyl)aniline

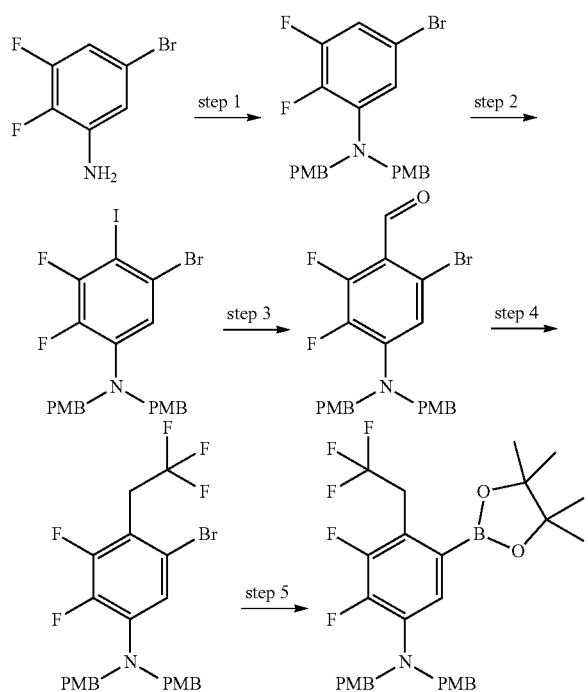

Step 1: 5-Bromo-2,3-difluoro-N,N-bis(4-methoxybenzyl)aniline

Under nitrogen, to a solution of 5-bromo-2,3-difluoroaniline (5.01 g, 24.1 mmol) in DMF (50 mL) was added NaH (3.69 g, 92.3 mmol, 60% dispersion in mineral oil) at 0° C. The solution was stirred for 30 min at 0° C. Then PMB-Cl (9.39 g, 60.2 mmol) was added at 0° C., and the mixture was stirred at room temperature for 1 hour. The solution was quenched by saturated NH$_4$Cl aqueous and extracted with EtOAc. The combined organic layers were dried over anhydrous sodium sulfate and concentrated under vacuum. The residue was purified by flash chromatography on silica gel (gradient: 0%-~5% EtOAc/petroleum ether) to afford 9.70 g of the title compound as a yellow solid. LC-MS: (ESI, m/z): [M+H]$^+$=448.

Step 2: 5-Bromo-2,3-difluoro-4-iodo-N,N-bis(4-methoxybenzyl)aniline

To a solution of 5-bromo-2,3-difluoro-N,N-bis(4-methoxybenzyl)aniline (4.51 g, 10.1 mmol) in AcOH (45 mL) was added NIS (3.37 g, 15.1 mmol), and the mixture was stirred for 30 min at room temperature. The reaction was quenched by Na$_2$S$_2$O$_3$ aqueous and extracted with EtOAc. The combined organic layers were dried over anhydrous sodium sulfate and concentrated under vacuum. The residue was purified by flash chromatography on silica gel (gradient: 00%-6%0 EtOAc/petroleum ether) to afford 4.74 g of the title compound as a yellow solid. LC-MS: (ESI, m/z): [M+H]$^+$=574.

Step 3: 4-(bis(4-Methoxybenzyl)amino)-6-bromo-2,3-difluorobenzaldehyde

Under nitrogen, to a solution of 5-bromo-2,3-difluoro-4-iodo-N,N-bis(4-methoxybenzyl) aniline (2.62 g, 4.56 mmol) in THF (26 mL) was added 2 M iPr-MgCl (2.74 mL, 5.48 mmol) in THF at −60° C. The resulting solution was stirred for 1 h at −60° C. Then DMF (3.33 g, 45.6 mmol) was added at −60° C., and the mixture was stirred at room temperature for 30 min. The reaction was quenched by NH$_4$Cl aqueous, extracted with EtOAc. The combined organic layers were dried over anhydrous sodium sulfate and concentrated under vacuum. The residue was purified by flash chromatography on silica gel (gradient: 0%-20% EtOAc/petroleum ether) to afford 1.11 g of the title compound as a yellow solid. LC-MS: (ESI, m/z): [M+H]$^+$=476; 478.

Step 4: 5-Bromo-2,3-difluoro-N,N-bis(4-methoxybenzyl)-4-(2,2,2-trifluoroethyl)aniline Under nitrogen, a solution of 4-(bis(4-methoxybenzyl) amino)-6-bromo-2,3-difluorobenzaldehyde (1.41 g, 2.95 mmol) and 2,2-difluoro-2-triphenylphosphaniumyl-acetate (2.10 g, 5.91 mmol) in DMF (18 mL) was stirred for 2.5 h at 60° C. Then TBAF (26.6 mL, 1 M in THF) was added, and the mixture was stirred at 60° C. for 3 h. The resulting reaction was diluted with EtOAc, washed with water. The organic layer was dried over anhydrous sodium sulfate and concentrated under vacuum. The residue was purified by flash chromatography on silica gel (gradient: 0%-10% EtOAc/petroleum ether) to afford 940 mg of the title compound as a white solid. LC-MS: (ESI, m/z): [M+H]$^+$=530.

Step 5: 2,3-Difluoro-N,N-bis(4-methoxybenzyl)-5-(4,4,5,5-tetramethyl-1,3,2-dioxaborolan-2-yl)-4-(2,2,2-trifluoroethyl)aniline Under nitrogen, a solution of 5-bromo-2,3-difluoro-N,N-bis(4-methoxybenzyl)-4-(2,2,2-trifluoroethyl) aniline (810 mg, 1.53 mmol), Pin$_2$B$_2$(776 mg, 3.06 mmol), KOAc (449 mg, 4.58 mmol) and Pd(dppf)Cl$_2$ (234 mg, 0.310 mmol) in 1,4-dioxane (8 mL) was stirred for 8 hours at 90° C. The solution was cooled to room temperature and concentrated under vacuum. The residue was purified by flash chromatography on silica gel (gradient: 0%-40% EtOAc/petroleum ether) to afford 741 mg of the title compound as a yellow oil. LC-MS: (ESI, m/z): [M+H]$^+$=578.

Intermediate 133: (5-(Bis(4-methoxybenzyl)amino)-1-methyl-6-oxo-2-(trifluoromethyl)-1,6-dihydropyridin-3-yl)boronic acid

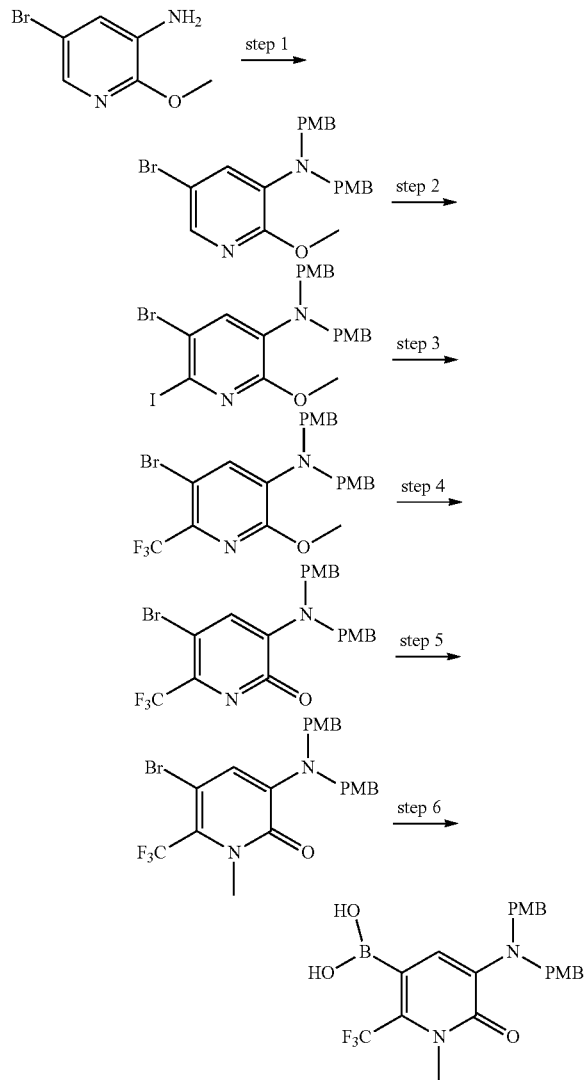

Step 1: 5-Bromo-2-methoxy-N,N-bis(4-methoxybenzyl)pyridin-3-amine

To a solution of 5-bromo-2-methoxypyridin-3-amine (2.01 g, 9.90 mmol) in DMF (25 mL) was added NaH (1.19 g, 29.7 mmol) at 0° C. under nitrogen. After 30 min, PMBCl (3.86 g, 24.7 mmol) was added, and the reaction mixture was warmed to room temperature for 1.5 h. The reaction was quenched with saturated aqueous NH$_4$Cl and extracted with EtOAc. The combined organic extracts were dried over anhydrous sodium sulfate and concentrated under vacuum. Purification by flash column chromatography on silica gel (gradient: 0%-30% EtOAc/petroleum ether) afforded the title compound as a white solid (4.81 g). LC-MS: (ESI, m/z): [M+H]$^+$=443.

Step 2: 5-Bromo-6-iodo-2-methoxy-N,N-bis(4-methoxybenzyl)pyridin-3-amine

To a solution of 5-bromo-2-methoxy-N,N-bis(4-methoxybenzyl)pyridin-3-amine (2.47 g, 5.57 mmol) in AcOH (15 mL) was added NIS (2.51 g, 11.1 mmol) at room temperature. After 1.5 h, the resulting mixture was diluted with ethyl acetate and washed with water and brine. The organic layer was concentrated under vacuum. The residue was purified by flash column chromatography on silica gel (gradient: 0-20% EtOAc/petroleum ether) to afford 2.21 g of the title compound as a yellow solid. LC-MS: (ESI, m/z): [M+H]$^+$=569.

Step 3: 5-Bromo-2-methoxy-N,N-bis(4-methoxybenzyl)-6-(trifluoromethyl)pyridin-3-amine Under nitrogen, to a mixture of 5-bromo-6-iodo-2-methoxy-N,N-bis(4-methoxybenzyl)pyridin-3-amine (2.01 g, 3.53 mmol), Cu(O$_2$CCF$_2$SO$_2$F)$_2$ (14.6 g, 35.0 mmol) and Cu powder (2.25 g, 35.2 mmol) was added DMF (20 mL) at 0° C., and the mixture was stirred at room temperature for 1.5 h. The reaction was diluted with ethyl acetate, and the resulting mixture was washed with water and brine. The organic layer was concentrated under vacuum. The residue was purified by flash column chromatography on silica gel (gradient: 0-20% EtOAc/petroleum ether) to afford 1.35 g the title compound as a yellow oil. LC-MS: (ESI, m/z): [M+H]$^+$=511.

Step 4: 3-(Bis(4-methoxybenzyl)amino)-5-bromo-6-(trifluoromethyl)pyridin-2(1H)-one A solution of 5-bromo-2-methoxy-N,N-bis(4-methoxybenzyl)-6-(trifluoromethyl)pyridin-3-amine (1.21 g, 2.35 mmol), LiCl (492 mg, 11.7 mmol) and PTSA (2.13 g, 12.4 mmol) in DMF (5 mL) was heated at 120° C. for 16 h. The reaction was diluted with ethyl acetate, and the resulting mixture was washed with water and brine. The organic layer was concentrated under vacuum. The residue was purified by flash column chromatography on silica gel (gradient: 0-20% EtOAc/petroleum ether) to afford 570 mg of the title compound as a yellow solid. LC-MS: (ESI, m/z): [M+H]$^+$=497.

Step 5: 3-(Bis(4-methoxybenzyl)amino)-5-bromo-1-methyl-6-(trifluoromethyl)pyridin-2(1H)-one A solution of 3-(bis(4-methoxybenzyl)amino)-5-bromo-6-(trifluoromethyl)pyridin-2(1H)-one (516 mg, 1.04 mmol), CH$_3$I (728 mg, 5.13 mmol) and K$_2$CO$_3$ (732 mg, 5.30 mmol) in MeOH (8 mL) was stirred at 65° C. for 2 h. The reaction was cooled to room temperature, and the solvent was concentrated under vacuum. The residue was purified by C18 column (solvent gradient: 0-80% ACN in water (0.05% NH$_4$HCO$_3$)) to afford 136 mg of the title compound as a white solid. LC-MS: (ESI, m/z): [M+H]$^+$=511.

Step 6: (5-(Bis(4-methoxybenzyl)amino)-1-methyl-6-oxo-2-(trifluoromethyl)-1,6-dihydropyridin-3-yl)boronic acid To a solution of 3-(bis(4-methoxybenzyl)amino)-5-bromo-1-methyl-6-(trifluoromethyl)pyridin-2(1H)-one (136 mg, 0.270 mmol) and triisopropyl borate (249 mg, 1.32 mmol) in THF (5 mL) was added n-BuLi (0.5 mL, 1.25 mmol) at −78° C. under nitrogen. The resulting solution was stirred for 1 h at −78° C. The reaction was quenched with MeOH at −78° C. and concentrated under vacuum. Purification by flash column chromatography on silica gel (gradient: 0-30% EtOAc (0.1% Et$_3$N)/petroleum ether (10% DCM)) afforded the titled compound as a yellow oil (32.1 mg). LC-MS: (ESI, m/z): [M+H]$^+$=476.

Intermediate 134: N, N-Bis(4-methoxybenzyl)-6-methyl-4-(4,4,5,5-tetramethyl-1,3,2-dioxaborolan-2-yl)-5-(2,2,2-trifluoroethyl)pyridin-2-amine

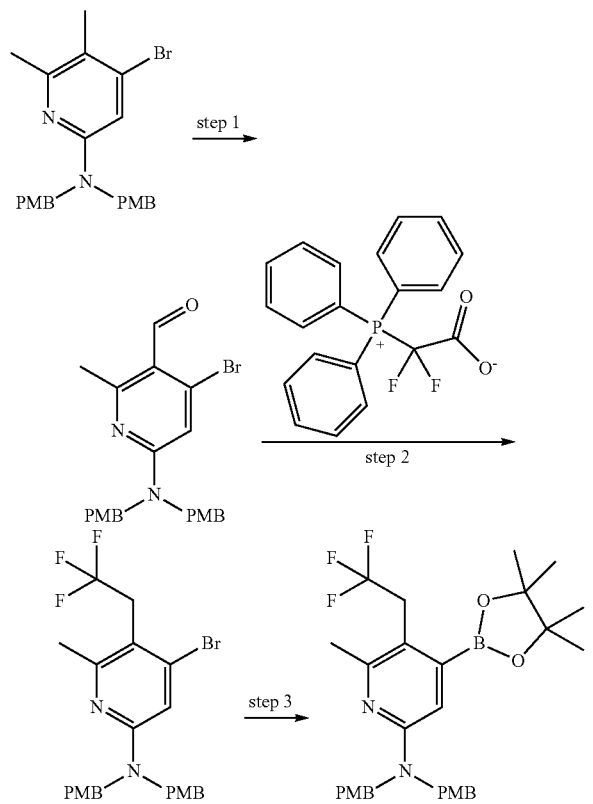

Step 1: 6-(Bis(4-methoxybenzyl)amino)-4-bromo-2-methylnicotinaldehyde

To a solution of 4-bromo-5-iodo-N, N-bis(4-methoxybenzyl)-6-methylpyridin-2-amine (1.00 g, 1.80 mmol, intermediate 138, step 2) in THF (10.0 mL) at −15° C. was added iPrMgCl (2.72 mL, 2 M in THF) under nitrogen. After 1 h, DMF (2.00 mL) was added, and the reaction mixture was warmed to room temperature for 1 h. The reaction was quenched with saturated aqueous NH$_4$Cl solution, and the resulting mixture was extracted with EtOAc. The combined organic extracts were dried over anhydrous sodium sulfate, filtered, and concentrated under vacuum. Purification by flash column chromatography on silica gel (gradient: 0%-50% EtOAc in petroleum ether) afforded the titled compound as a yellow solid (576 mg). LC-MS: (ESI, m/z): [M+H]$^+$=509.

Step 2: 4-Bromo-N,N-bis(4-methoxybenzyl)-6-methyl-5-(2,2,2-trifluoroethyl)pyridin-2-amine A solution of 2,2-difluoro-2-(triphenylphosphonio)acetate (530 mg, 1.49 mmol) and 6-(bis(4-methoxybenzyl)amino)-4-bromo-2-methylnicotinaldehyde (339 mg, 0.740 mmol) in DMF (3.00 mL) was stirred under an atmosphere of nitrogen for 2.5 h at room temperature. TBAF (11.2 mL, 1 M in THF) was then added, and the resulting mixture was heated at 60° C. After 12 h, the reaction was cooled to room temperature, and EtOAc was added. The resulting solution was washed with water. The organic was dried over anhydrous sodium sulfate, filtered, and concentrated under vacuum. Purification by flash column chromatography on silica gel (gradient: 0%-50% EtOAc in petroleum ether) afforded the titled compound as a white solid (506 mg). LC-MS: (ESI, m/z): [M+H]$^+$=509.

Step 3: N,N-Bis(4-methoxybenzyl)-6-methyl-4-(4,4,5,5-tetramethyl-1,3,2-dioxaborolan-2-yl)-5-(2,2,2-trifluoroethyl)pyridin-2-amine A solution of 4-bromo-N,N-bis(4-methoxybenzyl)-6-methyl-5-(2,2,2-trifluoroethyl)pyridin-2-amine (100 mg, 0.200 mmol), bis(pinacolato)diboron (149 mg, 0.590 mmol), PdCl$_2$(dppf) (28.5 mg, 0.0400 mmol) and KOAc (57.7 mg, 0.590 mmol) in 1,4-dioxane (1.00 mL) was heated at 90° C. under nitrogen. After 18 h, the reaction was concentrated under vacuum. Purification by flash column chromatography on silica gel (gradient: 0%-50% EtOAc in petroleum ether) afforded the titled compound as a colorless oil (97.8 mg). LC-MS: (ESI, m/z): [M+H]$^+$=557.

Intermediate 135: 3-Chloro-4-(2,2-difluoroethyl)-2-fluoro-N,N-bis(4-methoxybenzyl)-5-(4,4,5,5-tetramethyl-1,3,2-dioxaborolan-2-yl)aniline

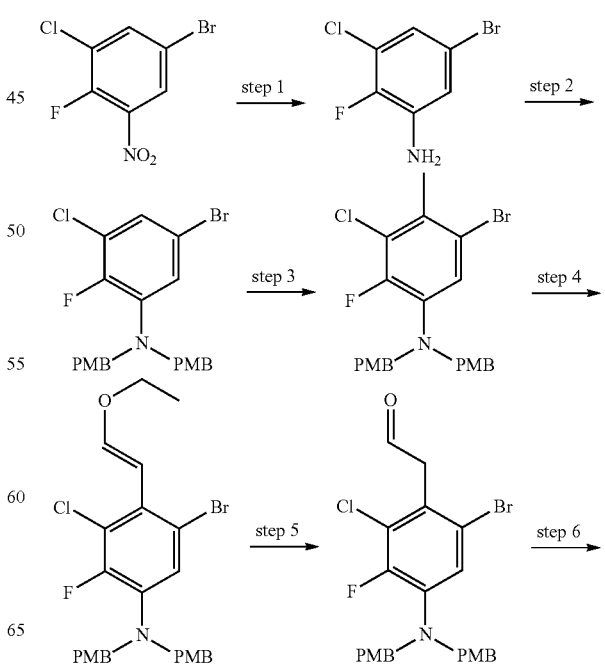

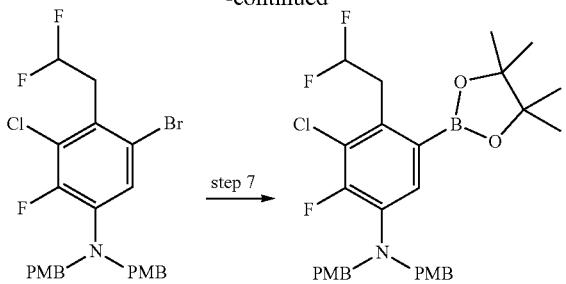

Step 1: 5-Bromo-3-chloro-2-fluoroaniline

A solution of 5-bromo-1-chloro-2-fluoro-3-nitrobenzene (10.1 g, 39.7 mmol), Fe (11.1 g, 198 mmol) and NH$_4$Cl (21.2 g, 399 mmol) in EtOH (70 mL) and water (30 mL) was heated at 80° C. for 2 h. The resulting solution was partitioned between water and EtOAc. The organic was dried over anhydrous sodium sulfate, filtered, and concentrated under vacuum. Purification by flash column chromatography on silica gel (gradient: 0%-20% EtOAc in petroleum ether) afforded the titled compound as a yellow solid (7.22 g). LC-MS: (ESI, m/z): [M+H]$^+$=224. $^1$H NMR (400 MHz, DMSO-d$_6$, ppm): δ 6.92-6.85 (m, 1H), 6.85-6.78 (m, 1H), 5.82 (s, 2H).

Step 2: 5-Bromo-3-chloro-2-fluoro-N,N-bis(4-methoxybenzyl)aniline

To an ice-cooled solution of 5-bromo-3-chloro-2-fluoroaniline (7.81 g, 34.8 mmol) in DMF (80 mL) was added NaH (4.20 g, 105 mmol). After 30 min, PMBCl (11.5 g, 73.5 mmol) was added at 0° C., and the mixture was warmed to room temperature for 2 h. The reaction was quenched by the addition of saturated aqueous NH$_4$Cl solution, and the mixture was extracted with EtOAc. The combined organics were dried over anhydrous sodium sulfate, filtered, and concentrated under vacuum. Purification by flash column chromatography on silica gel (gradient: 0%-10% EtOAc in petroleum ether) afforded the titled compound as a yellow solid (14.3 g). LC-MS: (ESI, m/z): [M+H]$^+$=464.

Step 3: 5-Bromo-3-chloro-2-fluoro-4-iodo-N,N-bis(4-methoxybenzyl)aniline

To a solution of 5-5-bromo-3-chloro-2-fluoro-N,N-bis(4-methoxybenzyl)aniline (13.1 g, 28.1 mmol) in AcOH (150 mL) was added NIS (7.31 g, 32.5 mmol) at room temperature. After 2 h, the reaction was quenched with saturated aqueous Na$_2$S$_2$O$_3$ solution and extracted with EtOAc. The combined organics were dried over anhydrous sodium sulfate, filtered, and concentrated under vacuum. Purification by flash column chromatography on silica gel (gradient: 0%-10% EtOAc in petroleum ether) afforded the titled compound as a yellow oil (11.0 g). LC-MS: (ESI, m/z): [M+H]$^+$=590. $^1$H NMR (400 MHz, DMSO-d$_6$, ppm): δ 7.29-7.13 (m, 5H), 6.94-6.82 (m, 4H), 4.31 (s, 4H), 3.72 (s, 6H).

Step 4: (E)-5-Bromo-3-chloro-4-(2-ethoxyvinyl)-2-fluoro-N,N-bis(4-methoxybenzyl)aniline A solution of 5-bromo-3-chloro-2-fluoro-4-iodo-N,N-bis(4-methoxybenzyl)aniline (4.01 g, 6.77 mmol), (E)-2-(2-ethoxyvinyl)-4,4,5,5-tetramethyl-1,3,2-dioxaborolane (2.69 g, 13.6 mmol), Pd(dppf)Cl$_2$ (1.04 g, 1.36 mmol) and K$_2$CO$_3$ (2.81 g, 20.4 mmol) in 1,4-dioxane (40 mL) and water (8 mL) was heated at 60° C. under nitrogen. After 48 h, the resulting solution was partitioned between water and EtOAc. The collected organic was dried over anhydrous sodium sulfate, filtered, and concentrated under vacuum. Purification by flash column chromatography on silica gel (gradient: 0%-30% DCM in petroleum ether) afforded the titled compound as a yellow oil (976 mg). LC-MS: (ESI, m/z): [M+H]$^+$=534.

Step 5: 2-(4-(Bis(4-methoxybenzyl)amino)-6-bromo-2-chloro-3-fluorophenyl)acetaldehyde To a solution of (E)-5-bromo-3-chloro-4-(2-ethoxyvinyl)-2-fluoro-N,N-bis(4-methoxybenzyl)aniline (1.22 g, 2.28 mmol) in THF (15 mL) was added aqueous HCl (1.5 mL, 12 M) at room temperature. After 3 h, the solution was cooled to 0° C., and the pH was adjusted to 7 with saturated aqueous NaHCO$_3$ solution. The resulting mixture was partitioned between water and EtOAc. The organic was dried over anhydrous sodium sulfate, filtered, and concentrated under vacuum. Purification by flash column chromatography on silica gel (gradient: 0%-10% EtOAc in petroleum ether) afforded the titled compound as a yellow oil (568 mg). LC-MS: (ESI, m/z): [M+H]$^+$=506.

Step 6: 5-Bromo-3-chloro-4-(2,2-difluoroethyl)-2-fluoro-N,N-bis(4-methoxybenzyl)aniline To a solution of 2-(4-(bis(4-methoxybenzyl)amino)-6-bromo-2-chloro-3-fluorophenyl)acetaldehyde (558 mg, 1.10 mmol) in DCM (8 mL) was added DAST (3.56 g, 22.1 mmol) at −10° C. The reaction mixture was warmed to room temperature for 2.5 h. The reaction was quenched with saturated aqueous NaHCO$_3$ solution, and resulting mixture was extracted with DCM. The combined organics were dried over anhydrous sodium sulfate, filtered, and concentrated under vacuum. Purification by flash column chromatography on silica gel (gradient: 0%-15% EtOAc in petroleum ether) afforded the titled compound as a yellow oil (542 mg). LC-MS: (ESI, m/z): [M+H]$^+$=528.

Step 7: 3-Chloro-4-(2,2-difluoroethyl)-2-fluoro-N,N-bis(4-methoxybenzyl)-5-(4,4,5,5-tetramethyl-1,3,2-dioxaborolan-2-yl)aniline A solution of 5-bromo-3-chloro-4-(2,2-difluoroethyl)-2-fluoro-N,N-bis(4-methoxybenzyl)aniline (1.42 g, 3.19 mmol), bis(pinacolato)diboron (1.22 g, 4.8 mmol), Pd(dppf)Cl$_2$ (491 mg, 0.640 mmol) and KOAc (614 mg, 6.4 mmol) in 1,4-dioxane (14 mL) was heated at 80° C. under nitrogen overnight. The resulting solution was partitioned between water and EtOAc. The organic layer was dried over anhydrous sodium sulfate, filtered, and concentrated under vacuum. Purification by flash column chromatography on silica gel (gradient: 0%-80% EtOAc in petroleum ether) afforded the titled compound as a yellow oil (1.73 g). LC-MS: (ESI, m/z): [M+H]$^+$=576. $^1$H NMR (400 MHz, CDCl$_3$, ppm): δ 7.29-7.11 (m, 5H), 6.96-6.78 (m, 4H), 6.35-5.85 (m, 1H), 4.24 (s, 4H), 3.71 (s, 6H), 3.65-3.44 (m, 2H), 1.26 (s, 12H).

Intermediate 136: 5-(Difluoromethoxy)-N,N-bis(4-methoxybenzyl)-6-methyl-4-(4,4,5,5-tetramethyl-dioxaborolan-2-yl)pyridin-2-amine

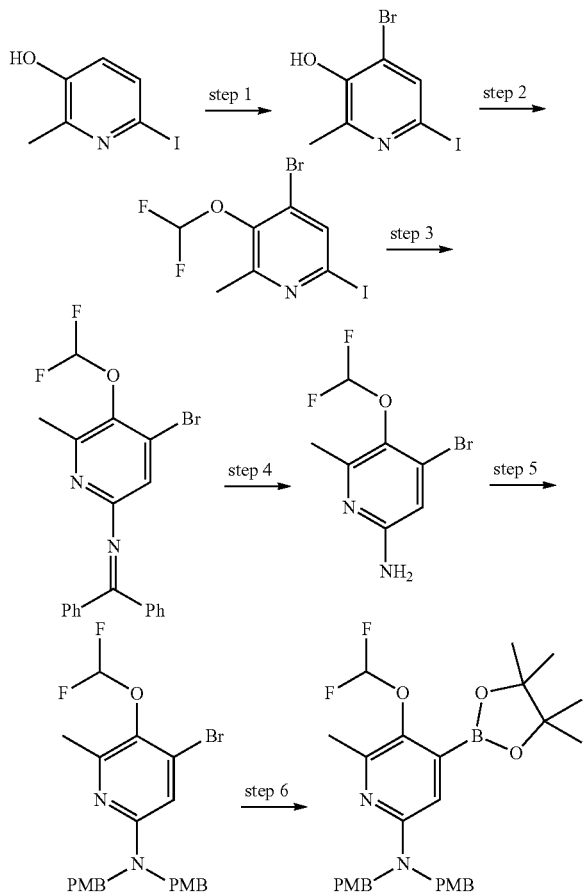

Step 1: 4-Bromo-6-iodo-2-methylpyridin-3-ol

To a solution of 6-iodo-2-methylpyridin-3-ol (1.90 g, 8.09 mmol) in ACN (20 mL) was added NBS (2.16 g, 12.1 mmol) at room temperature. After 2 h, the reaction was quenched with saturated aqueous $Na_2S_2O_3$, and the mixture was extracted with EtOAc. The combined organics were dried over anhydrous sodium sulfate, filtered, and concentrated under vacuum. Purification by flash column chromatography on silica gel (gradient: 0%-20% EtOAc in petroleum ether) provided the titled compound as a yellow solid (1.35 g). LC-MS: (ESI, m/z): $[M+H]^+=314$.

Step 2: 4-Bromo-3-(difluoromethoxy)-6-iodo-2-methylpyridine

A solution of 4-bromo-6-iodo-2-methylpyridin-3-ol (600 mg, 1.91 mmol), sodium 2-chloro-2,2-difluoroacetate (728 mg, 4.78 mmol) and $Cs_2CO_3$ (1.56 g, 4.79 mmol) in DMF (8 mL) was heated at 100° C. under nitrogen for 2 h. The reaction was cooled to room temperature, diluted with EtOAc, and washed with water. The organic was dried over anhydrous sodium sulfate, filtered, and concentrated under vacuum. Purification by flash column chromatography on silica gel (gradient: 0%-10% EtOAc in petroleum ether) yielded a white solid (583 mg). LC-MS: (ESI, m/z): $[M+H]^+=364$.

Step 3: N-(4-Bromo-5-(difluoromethoxy)-6-methylpyridin-2-yl)-1,1-diphenylmethanimine A solution of 4-bromo-3-(difluoromethoxy)-6-iodo-2-methylpyridine (500 mg, 1.37 mmol), diphenylmethanimine (274 mg, 1.51 mmol), Xantphos (160 mg, 0.280 mmol), $Pd_2(dba)_3$ (126 mg, 0.140 mmol) and $Cs_2CO_3$ (1.23 g, 3.76 mmol) in 1,4-dioxane (8 mL) was heated under nitrogen at 80° C. overnight. The resulting solution was partitioned between water and EtOAc. The collected organic was dried over anhydrous sodium sulfate, filtered, and concentrated under vacuum. Purification by flash column chromatography on silica gel (gradient: 0%-10% EtOAc in petroleum ether) provided a yellow oil (138 mg). LC-MS: (ESI, m/z): $[M+H]^+=417$.

Step 4: 4-Bromo-5-(difluoromethoxy)-6-methylpyridin-2-amine

To a solution of N-(4-Bromo-5-(difluoromethoxy)-6-methylpyridin-2-yl)-1,1-diphenylmethanimine (613 mg, 1.47 mmol) in DCM (6 mL) was added TFA (3 mL) at room temperature. After 1 h, the solution was concentrated under vacuum. The resulting mixture was cooled to 0° C. and added saturated aqueous $NaHCO_3$ solution until the measured pH was 7. The resulting solution was partitioned between water and DCM. The organic was dried over anhydrous sodium sulfate, filtered, and concentrated under vacuum. Purification by flash column chromatography on silica gel (gradient: 0%-50% EtOAc in petroleum ether) furnished a white solid (191 mg). LC-MS: (ESI, m/z): $[M+H]^+=253$.

Step 5: 4-Bromo-5-(difluoromethoxy)-N,N-bis(4-methoxybenzyl)-6-methylpyridin-2-amine To an ice-cooled solution of 4-bromo-5-(difluoromethoxy)-6-methylpyridin-2-amine (207 mg, 0.820 mmol) in DMF (3 mL) was added NaH (82.2 mg, 2.06 mmol) under nitrogen. After 30 min, PMBCl (219 mg, 1.40 mmol) was added at 0° C., and the suspension was stirred at room temperature for 1.5 h. The reaction was quenched with saturated aqueous $NH_4Cl$ solution and extracted with EtOAc. The combined organic extracts were dried over anhydrous sodium sulfate, filtered, and concentrated under vacuum. Purification by flash column chromatography on silica gel (gradient: 0%-15% EtOAc in petroleum ether) provided a yellow solid (313 mg). LC-MS: (ESI, m/z): $[M+H]^+=493$.

Step 6: 5-(Difluoromethoxy)-N,N-bis(4-methoxybenzyl)-6-methyl-4-(4,4,5,5-tetramethyl-dioxaborolan-2-yl)pyridin-2-amine A solution of 4-bromo-5-(difluoromethoxy)-N,N-bis(4-methoxybenzyl)-6-methylpyridin-2-amine (319 mg, 0.650 mmol), bis(pinacolato)diboron (823 mg, 3.24 mmol), $Pd(dppf)Cl_2$ (99.6 mg, 0.130 mmol) and KOAc (190 mg, 1.94 mmol) in 1,4-dioxane (5 mL) was heated at 100° C. under nitrogen overnight. The reaction was cooled to room temperature and concentrated under vacuum. Purification by flash column chromatography on silica gel (gradient: 0%-25% EtOAc in petroleum ether) furnished a yellow solid (211 mg). LC-MS: (ESI, m/z): [M+H]$^+$=541. $^1$H NMR (400 MHz, DMSO-d$_6$, ppm): δ 7.23-6.44 (m, 10H), 4.63 (s, 4H), 3.70 (s, 6H), 2.30 (s, 3H), 1.22 (s, 12H).

Intermediate 137: 4-Fluoro-N$^3$,N$^3$-bis(4-methoxybenzyl)-N$^1$-methylbenzene-1,3-diamine

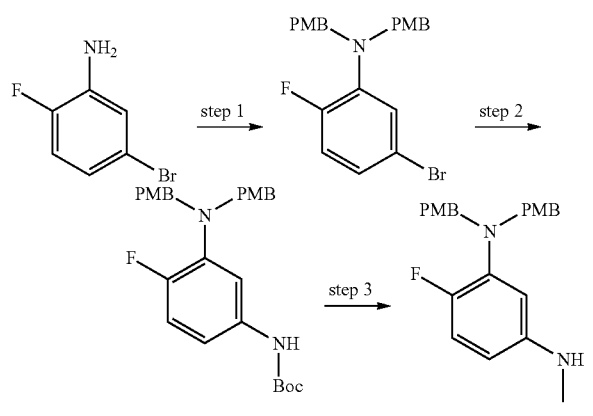

Step 1:
5-Bromo-2-fluoro-N,N-bis(4-methoxybenzyl)aniline

To an ice-cooled solution of 5-bromo-2-fluoroaniline (2.00 g, 10.5 mmol) in DMF (20 mL) was added NaH (2.11 g, 52.6 mmol, 60% dispersion in mineral oil) portion wise. The suspension was warmed to room temperature. After 30 min, PMBCl (4.11 g, 26.3 mmol) was added. After another hour, the reaction was quenched with saturated aqueous NH$_4$Cl solution and diluted with water. The mixture was extracted with ethyl acetate. The combined organics were washed with brine, dried over anhydrous sodium sulfate, filtered, and concentrated under vacuum. Purification by flash column chromatography on silica gel (gradient: 0-20% ethyl acetate in petroleum ether) yielded a yellow oil (3.40 g). LC-MS: (ESI, m/z): [M+H]$^+$=430.

Step 2: tert-Butyl (3-(bis(4-methoxybenzyl)amino)-4-fluorophenyl)carbamate

Under nitrogen, a solution of 5-bromo-2-fluoro-N,N-bis(4-methoxybenzyl)aniline (1.00 g, 2.33 mmol), BocNH$_2$ (760 mg, 6.50 mmol), Cs$_2$CO$_3$ (3.04 g, 9.32 mmol), Pd(OAc)$_2$ (125 mg, 0.560 mmol) and Xantphos (269 mg, 0.466 mmol) in 1,4-dioxane (50 mL) was heated for 2 hours at 110° C. The reaction mixture was cooled to room temperature, diluted with water, and extracted with ethyl acetate. The combined organics were washed with brine, dried over anhydrous sodium sulfate, filtered, and concentrated under vacuum. Purification by flash column chromatography on silica gel (gradient: 0-20% ethyl acetate in petroleum ether) provided a yellow solid (570 mg). LC-MS: (ESI, m/z): [M+H]$^+$=467.

Step 3: 4-Fluoro-N$^3$,N$^3$-bis(4-methoxybenzyl)-N$^1$-methylbenzene-1,3-diamine To an ice-cooled solution of tert-butyl (3-(bis(4-methoxybenzyl)amino)-4-fluorophenyl)carbamate (0.550 g, 1.18 mmol) in tetrahydrofuran (30 mL) was added LiAlH$_4$ (112 mg, 2.95 mmol) portion wise. The suspension was heated to 60° C. for 1 h. The reaction was cooled to room temperature and quenched with Na$_2$SO$_4$·10H$_2$O. After filtration, the filtrate was collected and concentrated under vacuum to afford the titled compound (490 mg,) as a yellow solid. LC-MS: (ESI, m/z): [M+H]$^+$=381. The crude material was used without further purification.

Intermediate 138: 5-(2,2-Difluoroethyl)-N,N-bis(4-methoxybenzyl)-6-methyl-4-(4,4,5,5-tetramethyl-dioxaborolan-2-yl) pyridin-2-amine

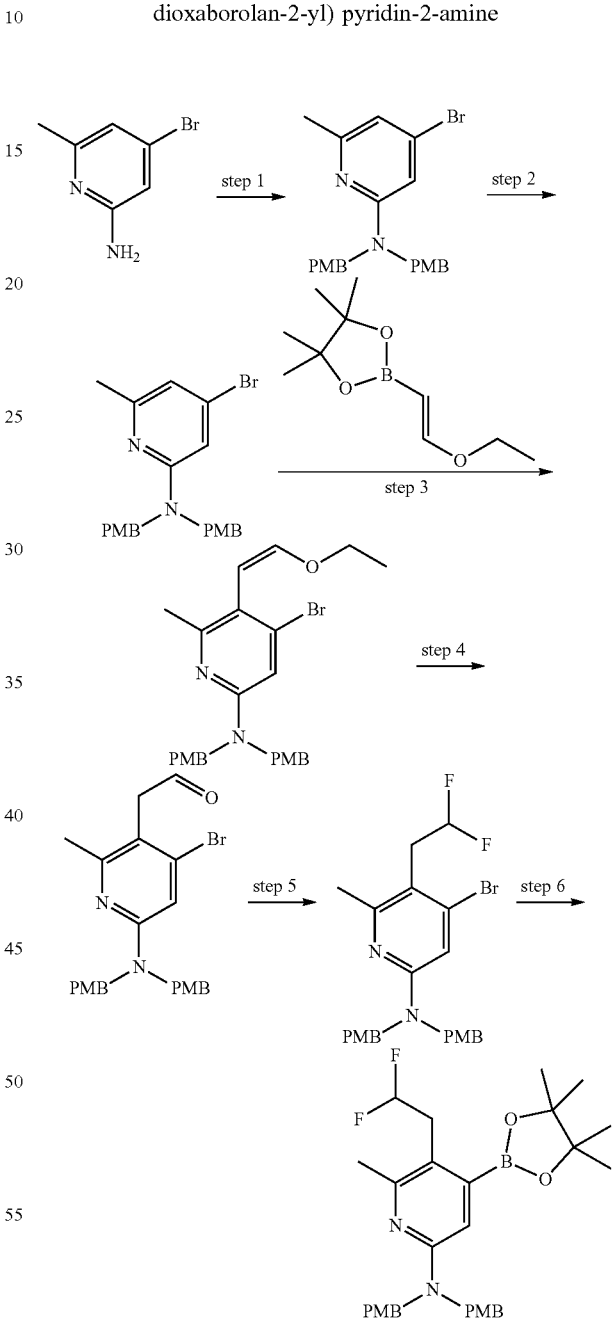

Step 1: 4-Bromo-N,N-bis(4-methoxybenzyl)-6-methylpyridin-2-amine

To an ice-cooled solution of 4-bromo-6-methylpyridin-2-amine (4.00 g, 21.4 mmol) in DMF (40.0 mL) was added NaH (2.57 g, 64.1 mmol, 60% in mineral oil) under nitrogen.

The resulting suspension was warmed to room temperature. After 30 min, 1-(chloromethyl)-4-methoxybenzene (7.03 g, 44.9 mmol) was added. After an additional 2 h, the reaction was quenched with saturated aqueous NH$_4$Cl solution and extracted with EtOAc. The organic extracts were dried over anhydrous sodium sulfate, filtered, and concentrated under vacuum. Purification by flash column chromatography on silica gel (gradient: 0-50% EtOAc in petroleum ether) afforded a white solid (8.00 g). LC-MS: (ESI, m/z): [M+H]$^+$= 427.

Step 2: 4-Bromo-5-iodo-N, N-bis(4-methoxybenzyl)-6-methylpyridin-2-amine

To a solution of 4-bromo-N, N-bis(4-methoxybenzyl)-6-methylpyridin-2-amine (6.80 g, 15.9 mmol) in AcOH (68.0 mL) was added NIS (3.58 g, 15.9 mmol) at room temperature under nitrogen. After 30 min, the reaction was quenched with saturated aqueous sodium thiosulfate solution and extracted with EtOAc. The collected organic extracts were dried over anhydrous sodium sulfate, filtered, and concentrated under vacuum. Purification by flash column chromatography on silica gel (gradient: 0-50% EtOAc in petroleum ether) provided a white solid (7.20 g). LC-MS: (ESI, m/z): [M+H]$^+$=553.

Step 3: (Z)-4-Bromo-5-(2-ethoxyvinyl)-N,N-bis(4-methoxybenzyl)-6-methylpyridin-2-amine A solution of 4-bromo-5-iodo-N, N-bis(4-methoxybenzyl)-6-methylpyridin-2-amine (1.30 g, 2.35 mmol), (E)-2-(2-ethoxyvinyl)-4,4,5,5-tetramethyl-1,3,2-dioxaborolane (0.470 g, 2.35 mmol), Cs$_2$CO$_3$ (1.53 g, 4.70 mmol) and PdCl$_2$(dppf) (170 mg, 0.23 mmol) in 1,4-dioxane (6 mL) and H$_2$O (0.6 mL) was heated at 72° C. for 4 h under nitrogen. The reaction was cooled to room temperature and extracted with EtOAc. The organic extracts were combined and dried over anhydrous sodium sulfate, filtered, and concentrated under vacuum. Purification by flash column chromatography on silica gel (gradient: 0-50% EtOAc in petroleum ether) afforded a colorless oil (408 mg). LC-MS: (ESI, m/z): [M+H]$^+$=497.

Step 4: 2-(6-(Bis(4-methoxybenzyl)amino)-4-bromo-2-methylpyridin-3-yl)acetaldehyde To a solution of (Z)-4-bromo-5-(2-ethoxyvinyl)-N, N-bis(4-methoxybenzyl)-6-methylpyridin-2-amine (0.400 g, 0.800 mmol) in THF (4 mL) was added aqueous HCl (1.00 mL, 12 M in water) at room temperature. After 3 h, the reaction was neutralized with saturated aqueous NaHCO$_3$ solution and extracted with EtOAc. The organic extracts were collected, dried over anhydrous sodium sulfate, filtered, and concentrated under vacuum. Purification by flash column chromatography on silica gel (gradient: 0-50% EtOAc in petroleum ether) afforded a white solid (218 mg). LC-MS: (ESI, m/z): [M+H]$^+$=469.

Step 5: 4-Bromo-5-(2,2-difluoroethyl)-N,N-bis(4-methoxybenzyl)-6-methylpyridin-2-amine To a solution of 2-(6-(bis(4-methoxybenzyl)amino)-4-bromo-2-methylpyridin-3-yl)acetaldehyde (218 mg, 0.470 mmol) in DCM (10.0 mL) was added DAST (764 mg, 4.75 mmol) at room temperature. After 2 h, the reaction was quenched with EtOH and partitioned between water and EtOAc. The collected organic was dried over anhydrous sodium sulfate, filtered, and concentrated under vacuum. Purification by flash column chromatography on silica gel (gradient: 0-50% EtOAc in petroleum ether) afforded a white solid (215 mg). LC-MS: (ESI, m/z): [M+H]$^+$=491.

Step 6: 5-(2,2-Difluoroethyl)-N,N-bis(4-methoxybenzyl)-6-methyl-4-(4,4,5,5-tetramethyl-dioxaborolan-2-yl) pyridin-2-amine A solution of 4-bromo-5-(2,2-difluoroethyl)-N, N-bis(4-methoxybenzyl)-6-methylpyridin-2-amine (215 mg, 0.440 mmol), bis(pinacolato)diboron (333 mg, 1.31 mmol), PdCl$_2$(dppf) (63.5 mg, 0.0900 mmol) and KOAc (128 mg, 1.31 mmol) in 1,4-dioxane (10.0 mL) was heated at 90° C. for 12 h under nitrogen. The resulting solution was cooled to room temperature and partitioned between water and EtOAc. The organic layer was dried over anhydrous sodium sulfate, filtered, and concentrated under vacuum. Purification by flash column chromatography on silica gel (gradient: 0-50% EtOAc in petroleum ether) furnished a colorless oil (0.10 g). LC-MS: (ESI, m/z): [M+H]$^+$=539.

Intermediate 139: 4-(2,2-Difluoroethyl)-2,3-difluoro-N,N-bis(4-methoxybenzyl)-5-(4,4,5,5-tetramethyl-1,3,2-dioxaborolan-2-yl)aniline

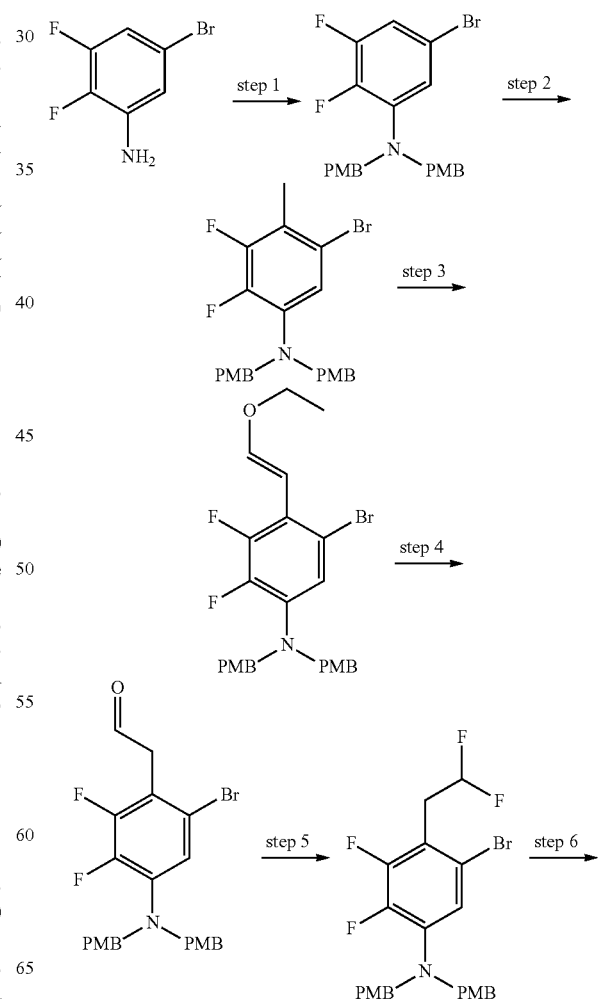

-continued

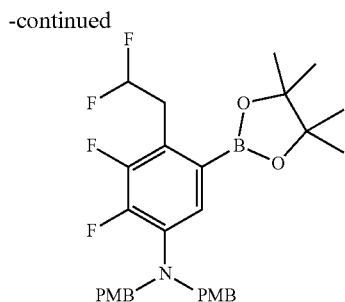

Step 1: 5-Bromo-2,3-difluoro-N,N-bis(4-methoxybenzyl)aniline

To an ice-cooled solution of 5-bromo-2,3-difluoroaniline (5.01 g, 24.1 mmol) in DMF (50 mL) was added NaH (3.69 g, 96.3 mmol). After 30 min, PMB-Cl (9.39 g, 60.2 mmol) was added, and the reaction was warmed to room temperature for 1 h. Excess sodium hydride was quenched by the slow addition of saturated aqueous NH$_4$Cl solution, and the resulting mixture was extracted with EtOAc. The combined organic extracts were dried over anhydrous sodium sulfate, filtered, and concentrated under vacuum. Purification by flash column chromatography on silica gel (gradient: 0%-5% EtOAc in petroleum ether) afforded a yellow solid (9.70 g). LC-MS: (ESI, m/z): [M+H]$^+$=448.

Step 2: 5-Bromo-2,3-difluoro-4-iodo-N,N-bis(4-methoxybenzyl)aniline

To a solution of 5-bromo-2,3-difluoro-N,N-bis(4-methoxybenzyl)aniline (4.51 g, 10.1 mmol) in AcOH (45 mL) was added NIS (3.37 g, 15.1 mmol) at room temperature. After 30 min, excess NIS was quenched by saturated aqueous Na$_2$S$_2$O$_3$ solution, and the resulting mixture was extracted with EtOAc. The combined organic extracts were dried over anhydrous sodium sulfate, filtered, and concentrated under vacuum. Purification by flash column chromatography on silica gel (gradient: 0%-6% EtOAc in petroleum ether) afforded a yellow solid (4.74 g). LC-MS: (ESI, m/z): [M+H]$^+$=574.

Step 3: (E)-5-Bromo-4-(2-ethoxyvinyl)-2,3-difluoro-N,N-bis(4-methoxybenzyl)aniline A solution of 5-bromo-2,3-difluoro-4-iodo-N,N-bis(4-methoxybenzyl)aniline (2.01 g, 3.48 mmol), (E)-2-(2-ethoxyvinyl)-4,4,5,5-tetramethyl-1,3,2-dioxaborolane (1.38 g, 6.97 mmol), Pd(dppf)Cl$_2$ (535 mg, 0.700 mmol) and K$_2$CO$_3$ (961 mg, 6.97 mmol) in 1,4-dioxane (20 mL) and water (4 mL) was heated at 60° C. under nitrogen. After 4 h, the resulting solution cooled to room temperature and concentrated under vacuum. Purification by flash column chromatography on silica gel (gradient: 0%-37% DCM in petroleum ether) afforded a yellow solid (1.23 g). LC-MS: (ESI, m/z): [M+H]$^+$=518.

Step 4: 2-(4-(bis(4-Methoxybenzyl) amino)-6-bromo-2,3-difluorophenyl) acetaldehyde To a solution of (E)-5-bromo-4-(2-ethoxyvinyl)-2,3-difluoro-N,N-bis(4-methoxybenzyl)aniline (1.23 g, 2.55 mmol) in THF (12 mL) was added aqueous HCl (2.00 mL, 12 M) at room temperature. After 2 h, the reaction was neutralized with saturated aqueous NaHCO$_3$ solution, and the mixture was extracted with EtOAc. The combined organic extracts were dried over anhydrous sodium sulfate, filtered, and concentrated under vacuum. Purification by flash column chromatography on silica gel (gradient: 0%-100% EtOAc in petroleum ether) afforded a yellow oil (0.20 g). LC-MS: (ESI, m/z): [M+H]$^+$=490.

Step 5: 5-Bromo-4-(2,2-difluoroethyl)-2,3-difluoro-N,N-bis(4-methoxybenzyl)aniline To a solution of 2-(4-(bis(4-methoxybenzyl) amino)-6-bromo-2,3-difluorophenyl)acetaldehyde (190 mg, 0.390 mmol) in DCM (2 mL) was added DAST (1.25 g, 7.75 mmol) at −10° C. under nitrogen. The reaction was warmed to room temperature for 2 h. The reaction was diluted with saturated aqueous NaHCO$_3$ solution, and the resulting mixture was extracted with DCM. The combined organic extracts were dried over anhydrous sodium sulfate, filtered, and concentrated under vacuum. Purification by flash column chromatography on silica gel (gradient: 0%-13% EtOAc in petroleum ether) afforded a yellow oil (130 mg). LC-MS: (ESI, m/z): [M+H]$^+$=512.

Step 6: 4-(2,2-Difluoroethyl)-2,3-difluoro-N,N-bis(4-methoxybenzyl)-5-(4,4,5,5-tetramethyl-1,3,2-dioxaborolan-2-yl)aniline A solution of 5-bromo-4-(2,2-difluoroethyl)-2,3-difluoro-N,N-bis(4-methoxybenzyl) aniline (110 mg, 0.21 mmol), bis(pinacolato)diboron (109 mg, 0.430 mmol), KOAc (63.2 mg, 0.640 mmol) and Pd(dppf)Cl$_2$ (33 mg, 0.040 mmol) in 1,4-dioxane (1.2 mL) was heated at 90° C. under nitrogen. After 2 h, the reaction was cooled to room temperature and concentrated under vacuum. Purification by flash column chromatography on silica gel (gradient: 0%-18% EtOAc in petroleum ether) afforded a yellow oil (60.1 mg). LC-MS: (ESI, m/z): [M+H]$^+$=560.

Intermediate 140: 7-Fluoro-1-methoxy-8-(4,4,5,5-tetramethyl-1,3,2-dioxaborolan-2-yl) isoquinoline

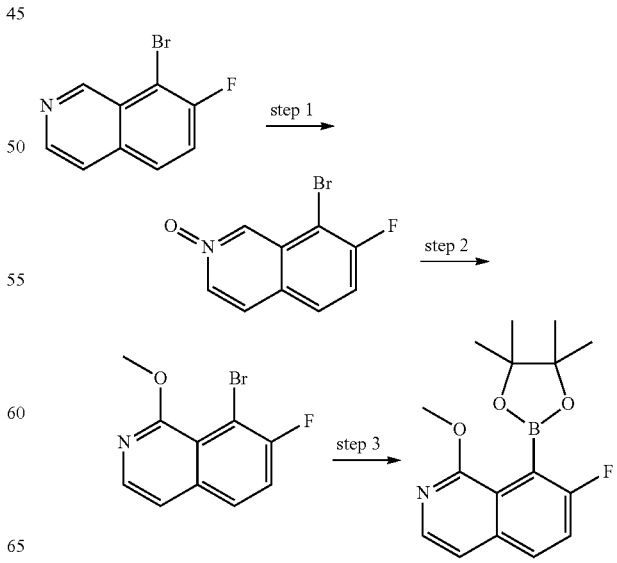

Step 1: 8-Bromo-7-fluoroisoquinoline 2-oxide

A solution of 3-chloroperbenzoic acid (839 mg, 4.87 mmol) and 8-bromo-7-fluoroisoquinoline (1.00 g, 4.42 mmol) in dichloromethane (10 mL) was stirred at room temperature for 2 h. The reaction was diluted with DCM and washed with brine. The collected organic was concentrated under vacuum to afford the titled compound (1.89 g, crude) as a light yellow solid. LC-MS: (ESI, m/z): [M+H]$^+$=242.

Step 2: 8-Bromo-7-fluoro-1-methoxyisoquinoline

To a solution of 8-bromo-7-fluoroisoquinoline 2-oxide (2.20 g, 9.09 mmol) and Et$_3$N (1.73 g, 17.1 mmol) in methanol (20 mL) was added methyl chloroformate (1.3 mL, 13.6 mmol) at room temperature. The resulting solution was stirred overnight at room temperature. The resulting mixture was diluted with EtOAc, washed with brine, dried over anhydrous sodium sulfate, filtered, and concentrated under vacuum. Purification by flash column chromatography on silica gel (gradient: 0-20% EtOAc in petroleum ether) afforded a white solid (586 mg,). LC-MS: (ESI, m/z): [M+H]$^+$=256.

Step 3: 7-Fluoro-1-methoxy-8-(4,4,5,5-tetramethyl-1,3,2-dioxaborolan-2-yl)isoquinoline A solution of 8-bromo-7-fluoro-1-methoxyisoquinoline (0.450 g, 1.76 mmol), bis(pinacolato)diboron (669 mg, 2.64 mmol), Pd(dppf)Cl$_2$ (257 mg, 0.350 mmol) and KOAc (344 mg, 3.51 mmol) in 1,4-dioxane (5 mL) was heated at 80° C. under nitrogen. After 2 h, the mixture cooled to room temperature and filtered. The filtrate was concentrated in vacuo. The resulting residue was diluted with EtOAc and washed with water. The collected organic was dried over anhydrous Na$_2$SO$_4$, filtered and concentrated in vacuo. Purification of the residue by flash column chromatography on silica gel (gradient: 0-20% EtOAc in petroleum ether) afforded a white solid (270 mg). LC-MS: (ESI, m/z): [M+H]$^+$=304.

Intermediate 141: (2-(Bis(4-methoxybenzyl)amino)-3-chloro-6-methylpyridin-4-yl)boronic acid

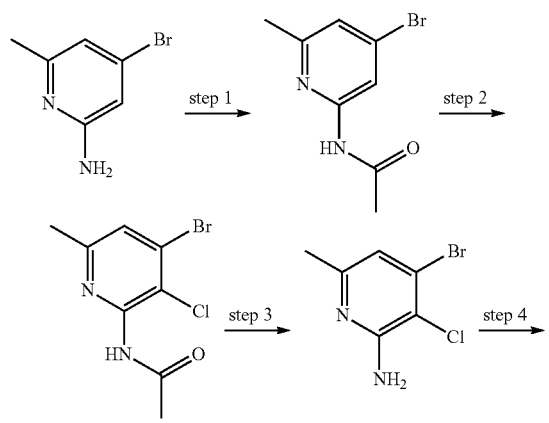

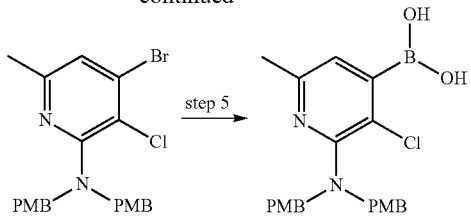

Step 1: N-(4-Bromo-6-methylpyridin-2-yl)acetamide

A solution of 4-bromo-6-methylpyridin-2-amine (5.01 g, 26.9 mmol), acetic anhydride (7.50 mL, 72.7 mmol) and Et$_3$N (2.99 g, 29.6 mmol) in THF (30 mL) was heated at 65° C. After 15 h, the mixture was cooled to room temperature. The precipitated solids were collected by filtration and rinsed with petroleum ether to afford a white solid (5.41 g, crude). LC-MS: (ESI, m/z): [M+H]$^+$=229.

Step 2: N-(4-Bromo-3-chloro-6-methylpyridin-2-yl)acetamide

Under nitrogen, a solution of N-(4-bromo-6-methylpyridin-2-yl) acetamide (2.08 g, 7.89 mmol), NaCl (1.01 g, 17.3 mmol) and oxone (6.91 g, 11.2 mmol) in H$_2$O (4.0 mL) and ACN (28 mL) was stirred at room temperature for 15 h. The resulting solution was partitioned between water and EtOAc. The collected organic layer was dried over anhydrous sodium sulfate, filtered, and concentrated under vacuum. The residue was purified by C18 column (solvent gradient: 0-80% ACN in water (0.05% formic acid)) to afford a white solid (502 mg). LC-MS: (ESI, m/z): [M+H]$^+$=263.

Step 3: 4-Bromo-3-chloro-6-methylpyridin-2-amine

A solution of N-(4-bromo-3-chloro-6-methylpyridin-2-yl) acetamide (0.800 g, 3.04 mmol) and NaOH (1.22 g, 30.5 mmol) in MeOH (10 mL) was heated at 60° C. under nitrogen. After 50 min, the solution was cooled to room temperature and concentrated in vacuo. The resulting residue was partitioned between water and EtOAc. The collected organic was dried over anhydrous sodium sulfate, filtered, and concentrated under vacuum to afford a white solid (650 mg, crude). LC-MS: (ESI, m/z): [M+H]$^+$=221.

Step 4: 4-Bromo-3-chloro-N,N-bis(4-methoxybenzyl)-6-methylpyridin-2-amine

To an ice-cooled solution of 4-bromo-3-chloro-6-methylpyridin-2-amine (0.600 g, 2.71 mmol) in DMF (8 mL) was added NaH (273 mg, 6.82 mmol). The reaction was warmed to room temperature. After 0.5 h, the reaction was cooled to 0° C. before the addition of PMBCl (936 mg, 6.00 mmol). The reaction was warmed to room temperature again for 3 h. Excess NaH was quenched by the addition of saturated aqueous NH$_4$Cl solution, and the mixture was extracted with DCM. The combined organic extracts were dried over anhydrous sodium sulfate, filtered, and concentrated under vacuum. Purification of the resulting residue by flash column chromatography on silica gel (gradient: 0-30% EtOAc in petroleum ether) afforded a white solid (1.21 g). LC-MS: (ESI, m/z): [M+H]$^+$=461.

Step 5: (2-(Bis(4-methoxybenzyl) amino)-3-chloro-6-methylpyridin-4-yl)boronic acid To a solution of 4-bromo-3-chloro-N,N-bis(4-methoxybenzyl)-6-methylpyridin-2-amine (0.300 g, 0.650 mmol) and triisopropyl borate (613 mg, 3.31 mmol) in THF (5 mL) was added n-BuLi (1.1 mL, 2.5 M in THF) at −78° C. After 1 h, the reaction was quenched with MeOH and concentrated under vacuum to afford a yellow oil (672 mg, crude). LC-MS: (ESI, m/z): [M+H]$^+$=427. The crude product was used without further purification.

Intermediate 142: N,N-Bis(4-methoxybenzyl)-3,6-dimethyl-4-(4,4,5,5-tetramethyl-dioxaborolan-2-yl)pyridin-2-amine

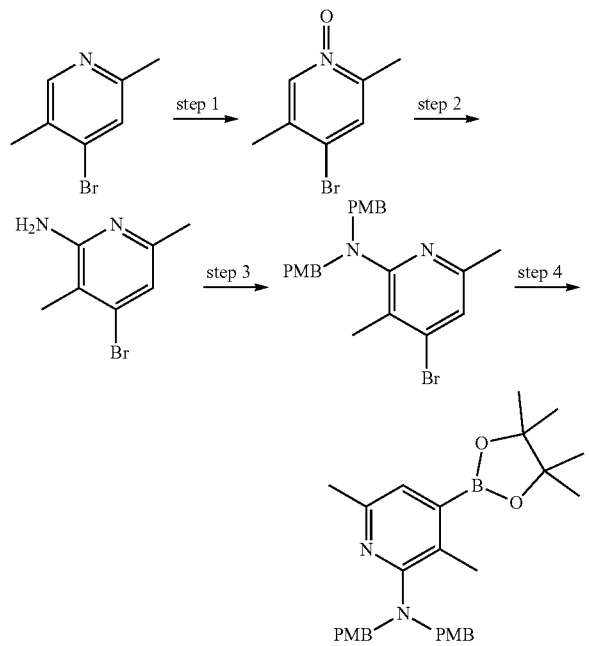

Step 1: 4-Bromo-2,5-dimethylpyridine 1-oxide

To an ice-cooled solution of 4-bromo-2,5-dimethylpyridine (1.01 g, 5.43 mmol) in EtOAc (20 mL) was added 3-chloroperbenzoic acid (1.88 g, 10.8 mmol). The reaction was warmed to room temperature for 2 h. Excess 3-chloroperbenzoic acid was quenched with aqueous Na$_2$S$_2$O$_3$, and resulting mixture was extracted with EtOAc. The combined organic extracts were dried over anhydrous sodium sulfate, filtered, and concentrated under vacuum. Purification of the resulting residue by flash column chromatography on silica gel (gradient: 0-10% EtOAc in petroleum ether) afforded a yellow solid (932 mg). LC-MS: (ESI, m/z): [M+H]$^+$=202.

Step 2: 4-Bromo-3,6-dimethylpyridin-2-amine

To a solution of 4-bromo-2,5-dimethylpyridine 1-oxide (491 mg, 2.43 mmol) and pyridine (962 mg, 12.2 mmol) in ACN (15 mL) was added TFAA (1.02 g, 4.86 mmol). The resulting solution was heated at 70° C. for 1.5 h. before the addition of NH$_2$—NH$_2$·H$_2$O (1.23 g, 24.6 mmol). After 2 h, the resulting mixture was cooled to room temperature, diluted with ethyl acetate, and washed with water. The collected organic was concentrated under vacuum to afford a yellow solid (359 mg, crude). LC-MS: (ESI, m/z): [M+H]$^+$= 201.

Step 3: 4-Bromo-N,N-bis(4-methoxybenzyl)-3,6-dimethylpyridin-2-amine

To an ice-cooled solution of 4-bromo-3,6-dimethylpyridin-2-amine (341 mg, 1.7 mmol) in DMF (10 mL) was added NaH (205 mg, 5.13 mmol, 60%). The suspension was warmed to room temperature for 0.5 h. PMBCl (559 mg, 3.58 mmol) was added to the reaction. After an additional 1.5 h, excess sodium hydride was quenched with saturated aqueous NH$_4$Cl solution and extracted with EtOAc. The organic extracts were dried over anhydrous sodium sulfate, filtered, and concentrated under vacuum. Purification of the residue by flash column chromatography on silica gel (gradient: 0-45% EtOAc in petroleum ether) afforded a yellow solid (507 mg). LC-MS: (ESI, m/z): [M+H]$^+$=441.

Step 4: N,N-Bis(4-methoxybenzyl)-3,6-dimethyl-4-(4,4,5,5-tetramethyl-dioxaborolan-2-yl)pyridin-2-amine Under nitrogen, a solution of 4-bromo-N,N-bis(4-methoxybenzyl)-3,6-dimethylpyridin-2-amine (507 mg, 1.15 mmol), bis(pinacolato)diboron (875 mg, 3.44 mmol), KOAc (338 mg, 3.45 mmol) and Pd(dppf)Cl$_2$ (168 mg, 0.230 mmol) in 1,4-dioxane (10 mL) was heated at 80° C. After 4 h, the resulting mixture was cooled to room temperature, diluted with ethyl acetate and washed with water. The organic layer was dried over anhydrous sodium sulfate, filtered, and concentrated under vacuum. Purification of the residue by flash column chromatography on silica gel (gradient: 0-60% EtOAc in petroleum ether) afforded a yellow solid (417 mg). LC-MS: (ESI, m/z): [M+H]$^+$=489.

Intermediate 143: N,N-Bis(4-methoxybenzyl)-3-methyl-5-(4,4,5,5-tetramethyl-1,3,2-dioxaborolan-2-yl)-4-(trifluoromethyl)aniline

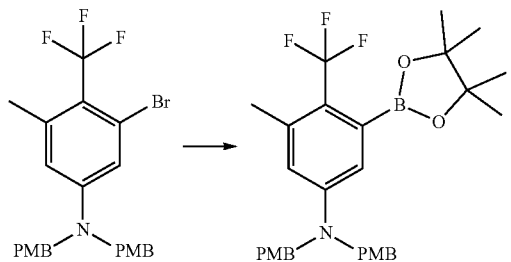

A solution of 3-bromo-N,N-bis(4-methoxybenzyl)-5-methyl-4-(trifluoromethyl)aniline (1.50 g, 3.03 mmol), bis(pinacolato)diboron (1.16 g, 4.56 mmol), KOAc (895 mg, 9.13 mmol) and Pd(dppf)Cl$_2$·CH$_2$Cl$_2$ (497 mg, 0.610 mmol) in 1,4-dioxane (50 mL) was heated at 110° C. under nitrogen. After 4 h, the reaction mixture was cooled to room temperature, diluted with water, and extracted with EtOAc. The collected organic extracts were dried over anhydrous sodium sulfate, filtered, and concentrated under vacuum. The residue was purified by flash column chromatography on silica gel (gradient: 0-20% dichloromethane in petroleum ether) to afford a yellow oil (0.50 mg). LC-MS: (ESI, m/z): [M+H]$^+$=542.

Intermediate 144: 4,4,5,5-Tetramethyl-2-(4-nitrobicyclo[4.2.0]octa-1(6),2,4-trien-2-yl)-1,3,2-dioxaborolane

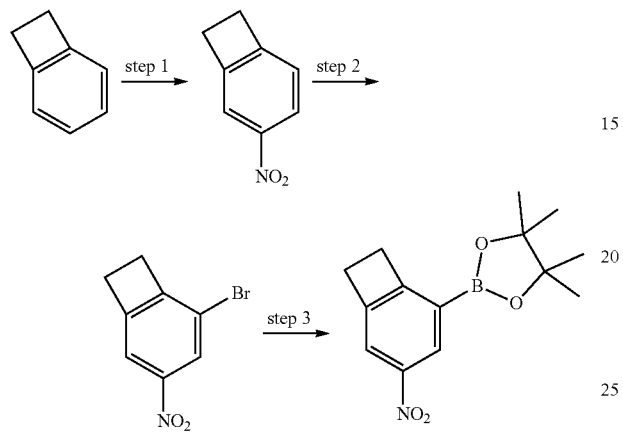

Step 1: 3-Nitrobicyclo[4.2.0]octa-1(6),2,4-triene

To a precooled mixture of H$_2$SO$_4$ (3.00 mL, 98.0%) and HNO$_3$ (3.78 mL, 68.0%) was added bicyclo[4.2.0]octa-1(6),2,4-triene (3.00 g, 28.8 mmol) at 5-10° C. The mixture was stirred for 2 h at 10° C. The solution was poured into ice-water and extracted with ether. The combined organic extracts were washed with 5% aqueous NaHCO$_3$ solution, dried over anhydrous sodium sulfate, and concentrated under vacuum. The residue was purified by flash column chromatography on silica gel (gradient: 0%-50% EtOAc in petroleum ether) to afford a yellow oil (1.50 g).

Step 2: 2-Bromo-4-nitrobicyclo [4.2.0]octa-1(6),2,4-triene

To a solution of 3-nitrobicyclo [4.2.0] octa-1(6),2,4-triene (1.00 g, 6.70 mmol) in H$_2$SO$_4$ (10 mL, 98%) and H$_2$O (10 mL) was added NBS (1.19 g, 6.70 mmol). The resulting solution was stirred for 12 h at room temperature. The reaction was diluted with water and extracted with EtOAc. The combined organic extracts were dried over anhydrous sodium sulfate, filtered, and concentrated under vacuum. The residue was purified by flash column chromatography on silica gel (gradient: 0%-50% EtOAc in petroleum ether) to afford a yellow oil (0.50 g).

Step 3: 4,4,5,5-Tetramethyl-2-(4-nitrobicyclo[4.2.0]octa-1(6),2,4-trien-2-yl)-1,3,2-dioxaborolane A solution of 2-bromo-4-nitrobicyclo [4.2.0] octa-1(6),2,4-triene (0.500 g, 2.19 mmol), bis(pinacolato)diboron (835 mg, 3.28 mmol), PdCl$_2$(dppf) (168 mg, 0.218 mmol) and KOAc (644 mg, 6.56 mmol) in 1,4-dioxane (5 mL) was heated at 100° C. under nitrogen. After 2 h, the reaction was cooled to room temperature, and filtered. The filtrate was concentrated under reduced pressure, and the resulting residue was purified by flash column chromatography on silica gel (gradient: 0%-50% EtOAc in petroleum ether) to afford the titled compound as a yellow oil (87.5 mg). LC-MS: (ESI, m/z): [M+H]$^+$=276.

Intermediate 145: (1-((Tetrahydro-1H-furo[3,4-c] pyrrol-5(3H)-yl)methyl)cyclopropyl)methanol

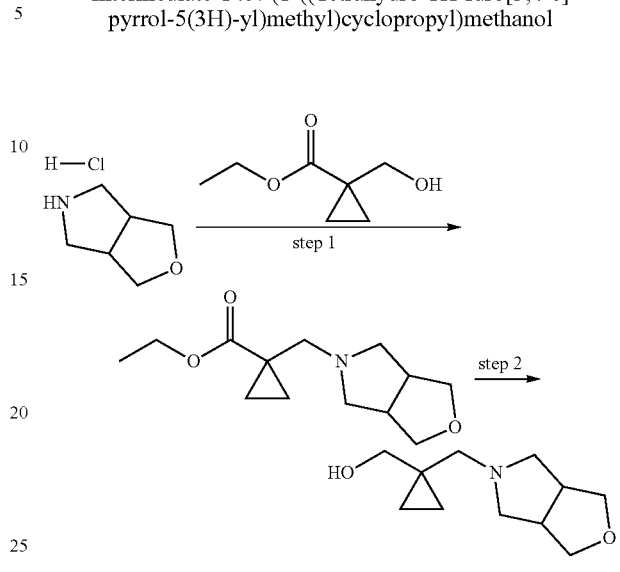

Step 1: Ethyl 1-((tetrahydro-1H-furo[3,4-c] pyrrol-5(3H)-yl)methyl) cyclopropane-1-carboxylate To a solution of ethyl 1-(hydroxymethyl) cyclopropane-1-carboxylate (0.300 g, 2.08 mmol) and DIPEA (1.03 mL, 6.24 mmol) in dichloromethane (3 mL) under nitrogen was added Tf$_2$O (0.70 mL, 4.16 mmol) dropwise at −10° C. After 5 min, a solution of hexahydro-1H-furo[3,4-c] pyrrole (311 mg, 2.08 mmol) and DIPEA (0.74 mL, 4.16 mmol) in dichloromethane (3 mL) was added at −10° C., and the reaction was warmed to room temperature. After an hour, the solvent was concentrated under vacuum to afford the crude titled compound (1.00 g, crude) as a yellow solid. LC-MS: (ESI, m/z): [M+H]$^+$=240.

Step 2: (1-((Tetrahydro-1H-furo[3,4-c] pyrrol-5(3H)-yl)methyl)cyclopropyl)methanol To an ice-cooked solution of ethyl 1-((tetrahydro-1H-furo[3,4-c] pyrrol-5(3H)-yl)methyl) cyclopropane-1-carboxylate (1.00 g, crude) in THF (40 mL) was added LiAlH$_4$ (336 g, 8.85 mmol) portion wise, and the reaction was warmed to room temperature. After an hour, Na$_2$SO$_4$·10H$_2$O was added, and the resulting suspension was filtered. The filtrate was concentrated under reduced pressure to afford the titled compound (1.50 g, crude) as a yellow oil. LC-MS: (ESI, m/z): [M+H]$^+$=198. The crude material was used without further purification.

Intermediate 146: (1-((3-Oxa-8-azabicyclo [3.2.1]octan-8-yl)methyl)cyclopropyl)methanol

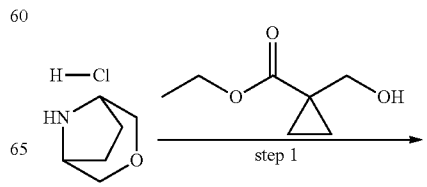

-continued

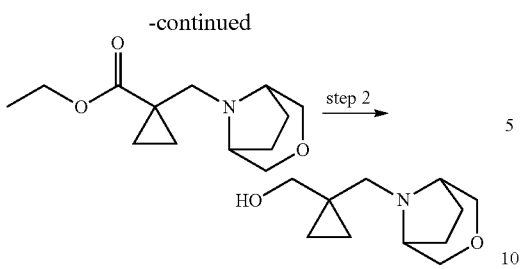

Step 1: Ethyl 1-((3-oxa-8-azabicyclo[3.2.1]octan-8-yl)methyl)cyclopropane-1-carboxylate To a solution of ethyl 1-(hydroxymethyl) cyclopropane-1-carboxylate (0.500 g, 3.47 mmol) and DIPEA (1.84 mL, 10.4 mmol) in dichloromethane (5 mL) under nitrogen was added Tf$_2$O (1.2 mL, 6.94 mmol) dropwise at −10° C. After 5 min, a solution of 3-oxa-8-azabicyclo[3.2.1]octane (518 mg, 3.47 mmol) and DIPEA (1.23 mL, 6.94 mmol) in dichloromethane (5 mL)) was added at −10° C., and the reaction mixture was warmed to room temperature. After 1 h, the solvent was concentrated under vacuum to afford the titled compound (3 g, crude) as a yellow solid. LC-MS: (ESI, m/z): [M+H]$^+$=240.

Step 2: (1-((3-Oxa-8-azabicyclo [3.2.1] octan-8-yl)methyl)cyclopropyl)methanol To an ice-cooled solution of ethyl 1-((3-oxa-8-azabicyclo [3.2.1] octan-8-yl)methyl)cyclopropane-1-carboxylate (3.0 g, crude) in THF (40 mL) was added LiAlH$_4$ (1.00 g, 25.0 mmol) portion wise, and the reaction was warmed to room temperature. After 1 h, Na$_2$SO$_4$·10H$_2$O was added, and the resulting suspension was filtered. The filtrate was concentrated under reduced pressure to afford the titled compound (2 g, crude) as a yellow oil. LC-MS: (ESI, m/z): [M+H]$^+$=198. The crude was used without further purification.

Intermediate 147: (1-((8-Oxa-3-azabicyclo[3.2.1]octan-3-yl)methyl) cyclopropyl) methanol

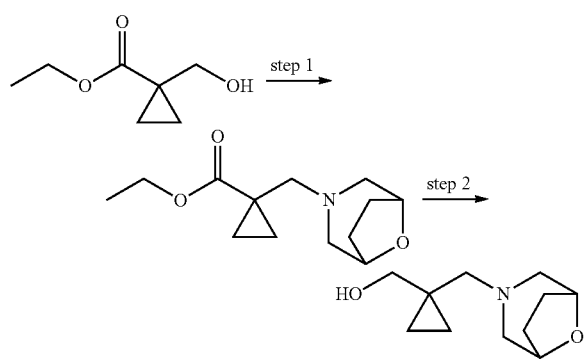

Step 1: Ethyl 1-((8-oxa-3-azabicyclo[3.2.1]octan-3-yl)methyl cyclopropane-1-carboxylate To a solution of ethyl 1-(hydroxymethyl)cyclopropane-1-carboxylate (0.600 g, 4.16 mmol) and DIPEA (1.61 g, 12.5 mmol) in DCM (6.0 mL) under nitrogen was added Tf$_2$O (1.76 g, 6.24 mmol) at −78° C. After 5 min, 8-oxa-3-azabicyclo[3.2.1]octane hydrogen chloride (621 mg, 4.15 mmol) was added at −78° C. After 1 h, the reaction was warmed to room temperature and concentrated under vacuum to afford the titled compound as brown solid (4 g, crude). LC-MS: (ESI, m/z): [M+H]$^+$=240.

Step 2: (1-((8-Oxa-3-azabicyclo[3.2.1]octan-3-yl)methyl)cyclopropyl)methanol To an ice-cooled solution of ethyl 1-((8-oxa-3-azabicyclo [3.2.1]octan-3-yl)methyl)cyclopropane-1-carboxylate (1.0 g, 4.2 mmol) in THF (10.0 mL) was added LiAlH$_4$ (1.67 mL, 2.5 M in THF), and the reaction was warmed to room temperature. After 1 h, Na$_2$SO$_4$·10H$_2$O was added, and the resulting suspension was filtered. The filtrate was concentrated under reduced pressure to afford the titled compound as colorless oil (0.9 g, crude) which was used without further purification. LC-MS: (ESI, m/z): [M+H]$^+$=198.

Intermediate 148: (1-((2-Oxa-5-azabicyclo[2.2.2]octan-5-yl)methyl)cyclopropyl)methanol

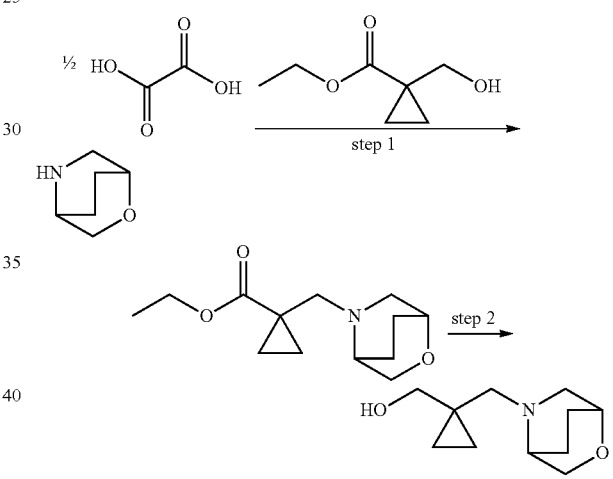

Step 1: Ethyl 1-((2-Oxa-5-azabicyclo[2.2.2]octan-5-yl)methyl)cyclopropane-1-carboxylate To a solution of ethyl 1-(hydroxymethyl)cyclopropane-1-carboxylate (0.500 g, 3.47 mmol) and DIPEA (1.84 mL, 10.4 mmol) in dichloromethane (5 mL) under nitrogen was added Tf$_2$O (1.2 mL, 6.9 mmol) dropwise at −10° C. After 5 min a solution of 2-oxa-5-azabicyclo[2.2.2]octane (393 mg, 3.47 mmol) in dichloromethane (5 mL) (pretreated 2-oxa-5-azabicyclo[2.2.2]octane hemioxalate with ion exchange resin column to remove oxalic acid) was added, and the reaction was warmed to room temperature. After 1 h, the reaction was concentrated under vacuum to afford the crude titled compound (2 g) as a yellow solid. LC-MS: (ESI, m/z): [M+H]$^+$=240.

Step 2: (1-((2-Oxa-5-azabicyclo[2.2.2]octan-5-yl)methyl)cyclopropyl)methanol To an ice-cooled solution of ethyl 1-(2-oxa-5-azabicyclo [2.2.2]octan-5-ylmethyl)cyclopropanecarboxylate (2 g, crude) in THF (30 mL) was added LiAlH$_4$ (627 mg, 16.5 mmol) portion wise. The reaction was warmed to room temperature for 1 h. Na$_2$SO$_4$·10H$_2$O was added to the reaction, and the resulting suspension was filtered. The filtrate was concentrated under reduced pressure to afford the crude titled compound (580 mg) as a colorless oil. LC-MS: (ESI, m/z): [M+H]$^+$=198. The crude product was used without further purification.

Intermediate 149: (1-((4-Oxa-7-azaspiro[2.5]octan-7-yl)methyl)cyclopropyl)methanol

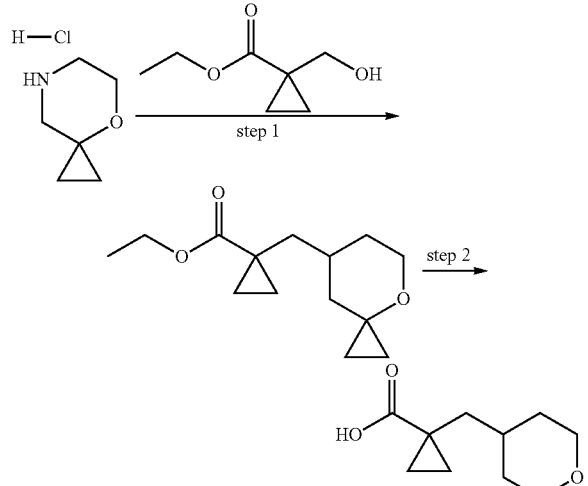

Step 1: Ethyl 1-((4-oxa-7-azaspiro[2.5]octan-7-yl)methyl)cyclopropane-1-carboxylate To a solution of ethyl 1-(hydroxymethyl)cyclopropane-1-carboxylate (300 mg, 2.08 mmol) and DIPEA (1.03 mL, 6.24 mmol) in dichloromethane (3 mL) under nitrogen was added Tf$_2$O (0.70 mL, 4.16 mmol) dropwise at −10° C. After 5 min, a solution of 4-oxa-7-azaspiro[2.5]octane hydrochloride (311 mg, 2.08 mmol) and DIPEA (0.74 mL, 4.16 mmol) in dichloromethane (3 mL) was added, and the reaction was warmed to room temperature. After 1 h, the solvent was concentrated under vacuum to afford the crude titled compound (1 g) as a yellow solid. LC-MS: (ESI, m/z): [M+H]$^+$= 240.

Step 2: (1-((4-Oxa-7-azaspiro[2.5]octan-7-yl)methyl)cyclopropyl)methanol

To an ice-cooled solution of ethyl 1-((4-oxa-7-azaspiro[2.5]octan-7-yl)methyl)cyclopropane-1-carboxylate (1 g, crude) in THF (40 mL) was added LiAlH$_4$ (316 g, 8.85 mmol) portion wise. The reaction mixture was warmed to room temperature for 1 h. Na$_2$SO$_4$·10H$_2$O was added to the reaction, and the resulting suspension was filtered. The filtrate was concentrated under reduced pressure to afford the crude product as a yellow oil (1.4 g). LC-MS: (ESI, m/z): [M+H]$^+$=198. The crude was used without further purification.

Intermediate 150: tert-Butyl (5S,5aS,6S,9R)-2-(6-(bis(4-methoxybenzyl)amino)-2-methyl-3-(trifluoromethyl)pyridin-4-yl)-1-fluoro-12-((1-(hydroxymethyl)cyclopropyl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate

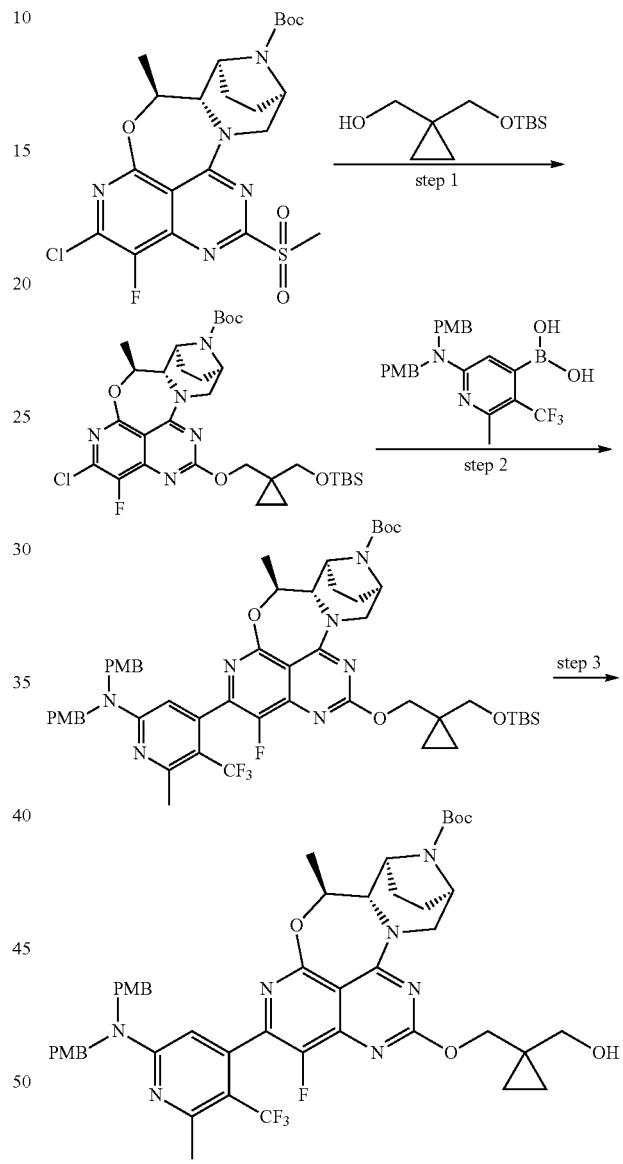

Step 1: tert-Butyl (5S,5aS,6S,9R)-12-((1-(((tert-butyldimethylsilyl)oxy)methyl)cyclopropyl)methoxy)-2-chloro-1-fluoro-5-methyl-5a,6,7,8,9,10-hexahydro-5H-4-oxa-3,10a,11,13,14-pentaaza-6,9-methanonaphtho[1,8-ab]heptalene-14-carboxylate To an ice-cooled solution of (1-(((tert-butyldimethylsilyl)oxy)methyl)cyclopropyl)methanol (784 mg, 3.63 mmol) in tetrahydrofuran (12.5 mL) was added NaH (435 mg, 10.9 mmol, 60% in mineral oil). The resulting solution was warmed to room temperature. After 30 min, tert-butyl (5S,5aS,6S,9R)-2-chloro-1-fluoro-5-methyl-12-(methylsulfonyl)-5a,6,7,8,9,10-hexahydro-5H-4-oxa-3,10a,11,13,14-pentaaza-6,9-methanonaphtho[1,8-ab]heptalene-14-carboxylate (931 mg, 1.81 mmol) was added. After an additional hour, excess NaH was quenched with saturated aqueous NH₄Cl solution, and the resulting mixture was extracted with EtOAc. The combined organic extracts were dried over anhydrous sodium sulfate, filtered, and concentrated under vacuum. Purification of the residue by flash column chromatography on silica gel (gradient: 0%-20% EtOAc in petroleum ether) afforded product a white solid (826 mg). LCMS: (ESI, m/z): [M+H]⁺=650.

Step 2: tert-Butyl (5S,5aS,6S,9R)-2-(6-(bis(4-methoxybenzyl)amino)-2-methyl-3-(trifluoromethyl)pyridin-4-yl)-12-((1-(((tert-butyldimethylsilyl)oxy)methyl)cyclopropyl)methoxy)-1-fluoro-5-methyl-5a,6,7,8,9,10-hexahydro-5H-4-oxa-3,10a,11,13,14-pentaaza-6,9-methanonaphtho[1,8-ab]heptalene-14-carboxylate A solution of tert-butyl (5S,5aS,6S,9R)-12-((1-(((tert-butyldimethylsilyl)oxy)methyl)cyclopropyl)methoxy)-2-chloro-1-fluoro-5-methyl-5a,6,7,8,9,10-hexahydro-5H-4-oxa-3,10a,11,13,14-pentaaza-6,9-methanonaphtho[1,8-ab]heptalene-14-carboxylate (826 mg, 1.27 mmol), (6-(bis(4-methoxybenzyl)amino)-2-methyl-3-(trifluoromethyl)pyridin-4-yl)boronic acid (1.56 g, 3.39 mmol), cataCXium A Pd G₃ (185 mg, 0.254 mmol) and K₃PO₄ (2.54 mL, 1.5 M in water) in tetrahydrofuran (12.7 mL) was heated at 60° C. under nitrogen. After 1 h, the reaction was cooled to room temperature, and the solution was partitioned between water and EtOAc. The collected organic layer was dried over anhydrous sodium sulfate, filtered, and concentrated under vacuum. Purification of the residue by flash column chromatography on silica gel (gradient: 0-20% MeOH in DCM) afforded product as a brown solid (1.30 g). LCMS: (ESI, m/z): [M+H]⁺=1030.

Step 3: tert-Butyl (5S,5aS,6S,9R)-2-(6-(bis(4-methoxybenzyl)amino)-2-methyl-3-(trifluoromethyl)pyridin-4-yl)-1-fluoro-12-((1-(hydroxymethyl)cyclopropyl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate To a solution of tert-butyl (5S,5aS,6S,9R)-2-(6-(bis(4-methoxybenzyl)amino)-2-methyl-3-(trifluoromethyl)pyridin-4-yl)-12-((1-(((tert-butyldimethylsilyl)oxy)methyl)cyclopropyl)methoxy)-1-fluoro-5-methyl-5a,6,7,8,9,10-hexahydro-5H-4-oxa-3,10a,11,13,14-pentaaza-6,9-methanonaphtho[1,8-ab]heptalene-14-carboxylate (1.30 g, 1.27 mmol) in tetrahydrofuran (12.0 mL) was added TBAF (2.60 mL, 1 M in THF) at room temperature. After 5 h, the reaction was concentrated in vacuo, and the resulting residue was purified by flash column chromatography on silica gel (gradient: 0%-55% EtOAc/petroleum ether) to afford product as a tawny solid (926 mg). LC-MS: (ESI, m/z): [M+H]⁺=916.

Intermediate 151: 4-(2,2-Difluoroethyl)-N,N-bis(4-methoxybenzyl)-3-methyl-5-(4,4,5,5-tetramethyl-1,3,2-dioxaborolan-2-yl)aniline

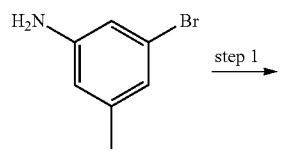

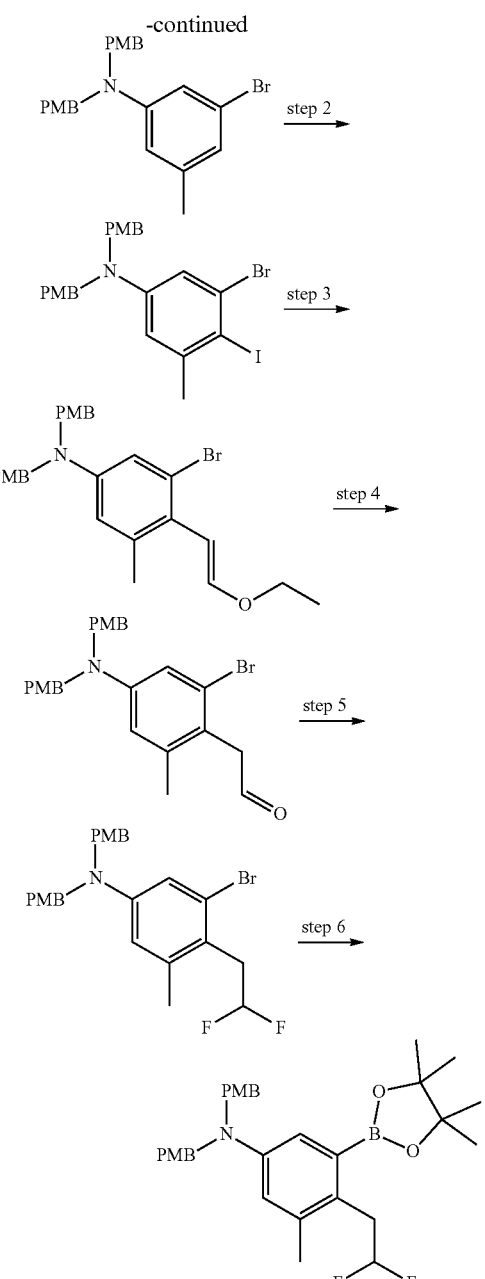

Step 1: 3-Bromo-N,N-bis(4-methoxybenzyl)-5-methylaniline

To an ice-cooled solution of 3-bromo-5-methylaniline (3.51 g, 18.8 mmol) in DMF (30 mL) was added NaH (2.27 g, 56.7 mmol, 60% in mineral oil) under nitrogen. After 0.5 h, PMBCl (6.23 g, 39.6 mmol) was added, and the resulting mixture was warmed to room temperature for 3 h. Excess NaH was quenched with saturated aqueous NH₄Cl solution, and the mixture was extracted with EtOAc. The combined organics were dried over anhydrous sodium sulfate, filtered, and concentrated under vacuum. The residue was purified by flash column chromatography on silica gel (gradient: 0%-30% EtOAc/petroleum ether) to afford product as a yellow solid (3.81 g). LC-MS: (ESI, m/z): [M+H]⁺=426.

Step 2: 3-Bromo-4-iodo-N,N-bis(4-methoxybenzyl)-5-methylaniline

A solution of 3-bromo-N,N-bis(4-methoxybenzyl)-5-methylaniline (3.81 g, 8.96 mmol) and NIS (2.11 g, 9.33 mmol) in AcOH (30 mL) was stirred at room temperature for 1 h. Excess NIS was quenched with saturated aqueous Na$_2$S$_2$O$_3$ solution, and the mixture was extracted with EtOAc. The combined organic layers were dried over anhydrous sodium sulfate, filtered, and concentrated under vacuum. The residue was purified by flash column chromatography on silica gel (gradient: 0%-30% EtOAc in petroleum ether) to yield product as a yellow solid (2.61 g). LC-MS: (ESI, m/z): [M+H]$^+$=552.

Step 3: (E)-3-Bromo-4-(2-ethoxyvinyl)-N,N-bis(4-methoxybenzyl)-5-methylaniline A solution of (E)-2-(2-ethoxyvinyl)-4,4,5,5-tetramethyl-1,3,2-dioxaborolane (1.87 g, 9.44 mmol), K$_2$CO$_3$ (1.31 g, 9.49 mmol), Pd(dppf)Cl$_2$ (351 mg, 0.480 mmol) and 3-bromo-4-iodo-N,N-bis[(4-methoxyphenyl)methyl]-5-methyl-aniline (2.61 g, 4.71 mmol) in 1,4-dioxane (5 mL) and water (1 mL) was heated under nitrogen at 90° C. After 2 h, the reaction was cooled to room temperature, diluted with EtOAc, and washed with water. The organic layer was concentrated under vacuum. Purification by flash column chromatography on silica gel (gradient: 0-10% EtOAc in petroleum ether) afforded product as a yellow solid (893 mg). LC-MS: (ESI, m/z): [M+H]$^+$=496.

Step 4: 2-(4-(Bis(4-methoxybenzyl)amino)-2-bromo-6-methylphenyl)acetaldehyde To a solution of (E)-3-bromo-4-(2-ethoxyvinyl)-N,N-bis(4-methoxybenzyl)-5-methylaniline (891 mg, 1.79 mmol) in THF (5 mL) was added aqueous HCl (1.4 mL, 12 M) at room temperature. After 1 h, aqueous NaHCO$_3$ solution was added until the solution was neutral pH. The resulting mixture was extracted with EtOAc. The organic extracts were combined, dried over anhydrous sodium sulfate, filtered, and concentrated under vacuum. The residue was purified by flash column chromatography on silica gel (gradient: 0-30% EtOAc in petroleum ether) to afford product as a yellow solid (311 mg). LC-MS: (ESI, m/z): [M+H]$^+$=468.

Step 5: 3-Bromo-4-(2,2-difluoroethyl)-N,N-bis(4-methoxybenzyl)-5-methylaniline To an ice-cooled solution of 2-(4-(bis(4-methoxybenzyl)amino)-2-bromo-6-methylphenyl)acetaldehyde (450 mg, 0.960 mmol) in DCM (15 mL) was added DAST (1.24 g, 7.70 mmol). After 1 h at 0° C., saturated aqueous NaHCO$_3$ solution was added, and the resulting mixture was extracted with EtOAc. The organic extracts were combined, dried over anhydrous sodium sulfate, filtered, and concentrated under vacuum. The residue was purified by flash column chromatography on silica gel (gradient: 0-15% EtOAc in petroleum ether) to afford product as a yellow solid (215 mg). LC-MS: (ESI, m/z): [M+H]$^+$=490.

Step 6: 4-(2,2-Difluoroethyl)-N,N-bis(4-methoxybenzyl)-3-methyl-5-(4,4,5,5-tetramethyl-1,3,2-dioxaborolan-2-yl)aniline A solution of 3-bromo-4-(2,2-difluoroethyl)-N,N-bis(4-methoxybenzyl)-5-methylaniline (215 mg, 0.440 mmol), Pin$_2$B$_2$ (224 mg, 0.880 mmol), Pd(dppf)Cl$_2$ (32.3 mg, 0.0400 mmol) and K$_2$CO$_3$ (129 mg, 1.32 mmol) in 1,4-doxane (8 mL) under nitrogen was heated at 110° C. After 3 h, the reaction was cooled to room temperature and diluted with EtOAc. The resulting mixture was washed with water. The organic layer was concentrated under vacuum. Purification by flash column chromatography on silica gel (gradient: 0-40% EtOAc in petroleum ether) provided the product as a yellow solid (168 mg). LC-MS: (ESI, m/z): [M+H]$^+$=538.

Intermediate 152: (3-(Bis(4-methoxybenzyl)amino)-6-(2,2-difluoroethyl)-2-fluoro-5-methylphenyl)boronic acid

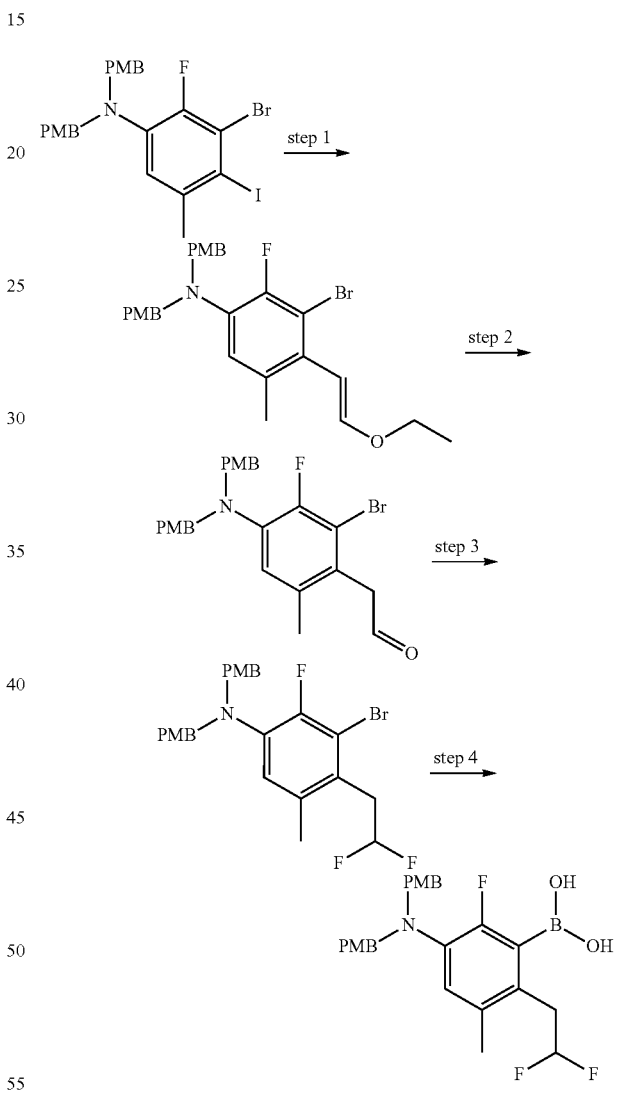

Step 1: (E)-3-Bromo-4-(2-ethoxyvinyl)-2-fluoro-N,N-bis(4-methoxybenzyl)-5-methylaniline A solution of 3-bromo-2-fluoro-4-iodo-N,N-bis(4-methoxybenzyl)-5-methylaniline (5.03 g, 8.82 mmol), (E)-2-(2-ethoxyvinyl)-4,4,5,5-tetramethyl-1,3,2-dioxaborolane (4.37 g, 22.1 mmol), K$_2$CO$_3$ (2.42 g, 17.5 mmol) and Pd(dppf)Cl$_2$ (642 mg, 0.880 mmol) in 1,4-dioxane (50 mL) and water (10 mL) was heated at 90° C. under nitrogen. After 4 h, the reaction was cooled to room temperature and diluted with EtOAc. The mixture was washed with water, and the organic was concentrated under vacuum. Purification by flash column chromatography on silica gel (gradient: 0-10% EtOAc in petroleum ether) afforded product as a yellow solid (3.36 g). LC-MS: (ESI, m/z): [M+H]$^+$=514.

Step 2: 2-(4-(Bis(4-methoxybenzyl)amino)-2-bromo-3-fluoro-6-methylphenyl)acetaldehyde To an ice-cooled solution of (E)-3-bromo-4-(2-ethoxyvinyl)-2-fluoro-N,N-bis(4-methoxybenzyl)-5-methylaniline (2.12 g, 4.12 mmol) in THF (12 mL) under nitrogen was added aqueous HCl (3 mL, 12 M). The reaction was warmed to room temperature for 2 h. The resulting mixture was diluted with EtOAc and washed with water. The organic layer was concentrated under vacuum. Purification by flash column chromatography on silica gel (gradient: 0-30% EtOAc in petroleum ether) furnished product as a yellow oil (667 mg). LC-MS: (ESI, m/z): [M+H]$^+$=486.

Step 3: 3-Bromo-4-(2,2-difluoroethyl)-2-fluoro-N,N-bis(4-methoxybenzyl)-5-methylaniline To an ice-cooled solution of 2-[4-[bis[(4-methoxyphenyl)methyl]amino]-2-bromo-3-fluoro-6-methyl-phenyl]acetaldehyde (667 mg, 1.37 mmol) in DCM (8 mL) under nitrogen was added DAST (1.55 g, 9.63 mmol). The reaction was warmed to room temperature for 30 min. Saturated aqueous NH$_4$Cl solution was added, and the mixture was extracted with EtOAc. The organic extracts were combined, dried over anhydrous sodium sulfate, filtered, and concentrated under vacuum. Purification by flash column chromatography on silica gel (gradient: 0-50% EtOAc in petroleum ether) provided product as a yellow oil (574 mg). LC-MS: (ESI, m/z): [M+H]$^+$=508.

Step 4: (3-(Bis(4-methoxybenzyl)amino)-6-(2,2-difluoroethyl)-2-fluoro-5-methylphenyl)boronic acid To a solution of 3-bromo-4-(2,2-difluoroethyl)-2-fluoro-N,N-bis(4-methoxybenzyl)-5-methylaniline (1.21 g, 2.38 mmol) and (iPrO)$_3$B (2.23 g, 11.8 mmol) in THF (15 mL) was added n-BuLi (4.84 mL, 12.1 mmol) at −60° C. After 30 min, MeOH was added, and the reaction was warmed to room temperature. The mixture was concentrated under vacuum. Purification by flash column chromatography on silica gel (gradient: 0-10% MeOH in DCM) afforded product as a yellow solid (821 mg). LC-MS: (ESI, m/z): [M+H]$^+$= 474.

Intermediate 153: 2,3-Difluoro-N,N-bis(4-methoxybenzyl)-5-(4,4,5,5-tetramethyl-1,3,2-dioxaborolan-2-yl)-4-(trifluoromethyl)aniline

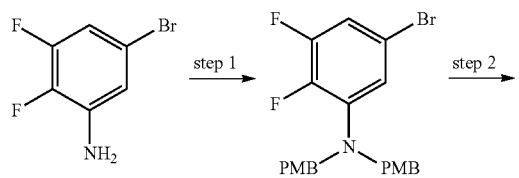

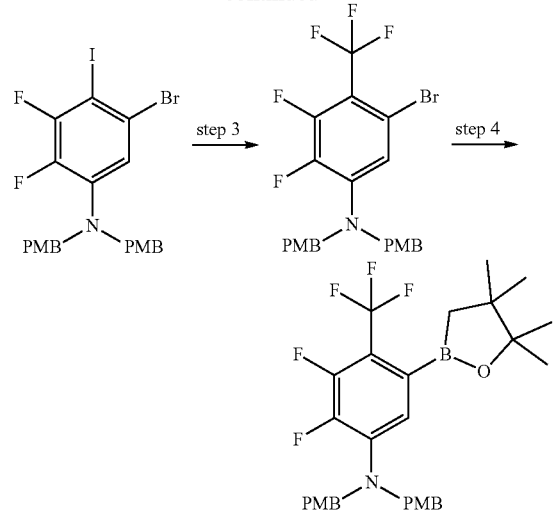

Step 1: 5-Bromo-2,3-difluoro-N,N-bis(4-methoxybenzyl)aniline

To an ice-cooled solution of 5-bromo-2,3-difluoro-aniline (0.50 g, 2.4 mmol) in DMF (10 mL) was added NaH (384 mg, 9.6 mmol, 60% in mineral oil). The solution was warmed to room temperature for 1 hour. PMBCl (1.13 g, 7.21 mmol) was then added. After 4 h, the excess NaH was quenched by the addition of saturated aqueous NH$_4$Cl solution, and the resulting mixture was extracted with EtOAc. The organic extracts were combined, dried over anhydrous Na$_2$SO$_4$, filtered, and concentrated under vacuum. Purification by flash column chromatography on silica gel (gradient: 0-5% ethyl acetate in petroleum ether) furnished product as an oil (0.90 g). LC-MS: (ESI, m/z): [M+H]$^+$=448.

Step 2: 5-Bromo-2,3-difluoro-4-iodo-N,N-bis(4-methoxybenzyl)aniline

A solution of 5-bromo-2,3-difluoro-N,N-bis[(4-methoxyphenyl)methyl]aniline (0.90 g, 2.0 mmol) and NIS (676 mg, 3.02 mmol) in acetic acid (10 mL) was stirred at room temperature for 2 hours. The reaction was concentrated under vacuum, and the resulting residue was purified by flash column chromatography on silica gel (gradient: 0-5% ethyl acetate in petroleum ether) to yield as a yellow oil (0.80 g). LC-MS: (ESI, m/z): [M+H]$^+$=574.

Step 3: 5-Bromo-2,3-difluoro-N,N-bis(4-methoxybenzyl)-4-(trifluoromethyl)aniline To a solution of 5-bromo-2,3-difluoro-4-iodo-N,N-bis[(4-methoxyphenyl)methyl]aniline (0.900 g, 1.57 mmol) and methyl 2,2-difluoro-2-(fluorosulfonyl)acetate (1.50 g, 7.85 mmol) in DMA (9 mL) was added CuI (0.30 g, 1.6 mmol) under nitrogen at room temperature. The reaction was heated to 90° C. for 4 hours. The reaction mixture was cooled to room temperature and partitioned between water and EtOAc. The separated organic layer was dried over anhydrous sodium sulfate, filtered, and concentrated under vacuum. Purification by flash column chromatography on silica gel (gradient: 0-10% ethyl acetate in petroleum ether) afforded the product as a brown oil (0.60 g). LC-MS: (ESI, m/z): [M+H]⁺=516.

Step 4: 2,3-Difluoro-N,N-bis(4-methoxybenzyl)-5-(4,4,5,5-tetramethyl-1,3,2-dioxaborolan-2-yl)-4-(trifluoromethyl)aniline A solution of 5-bromo-2,3-difluoro-N,N-bis[(4-methoxyphenyl)methyl]-4-(trifluoromethyl)aniline (0.50 mg, 0.97 mmol), Pin₂B₂ (739 mg, 2.91 mmol), PdCl₂(dppf) (71 mg, 0.10 mmol) and KOAc (285 mg, 2.91 mmol) in 1,4-dioxane (5 mL) was heated at 100° C. under nitrogen for 4 hours. The reaction was cooled to room temperature, diluted with water, and extracted with EtOAc. The organic extracts were dried over anhydrous sodium sulfate, filtered, and concentrated under vacuum. Purification by flash column chromatography on silica gel (gradient: 0-10% ethyl acetate in petroleum ether) provided product as a white solid (260 mg). LC-MS: (ESI, m/z): [M+H]⁺=564.

Intermediate 154: 4-(2,2-Difluoroethyl)-2-fluoro-N,N-bis(4-methoxybenzyl)-3-methyl-5-(4,4,5,5-tetramethyl-1,3,2-dioxaborolan-2-yl)aniline

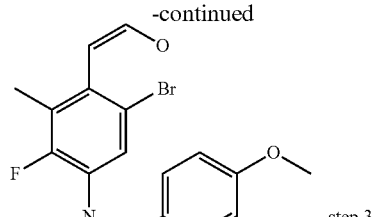

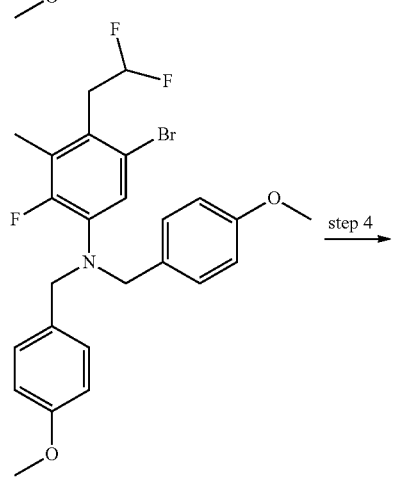

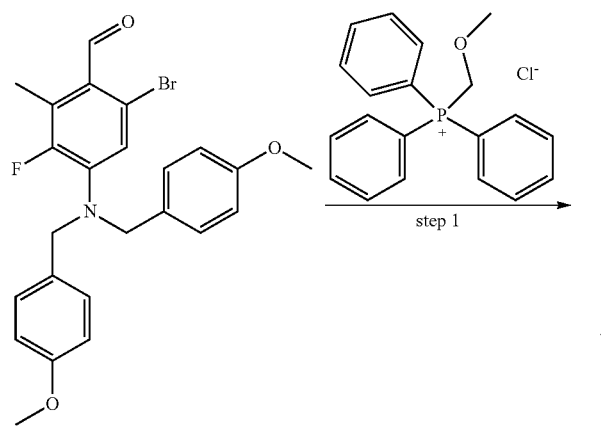

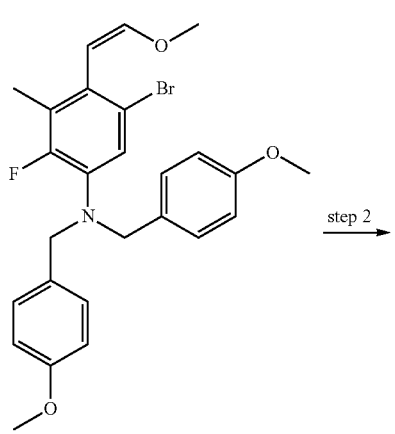

Step 1: 5-Bromo-2-fluoro-N,N-bis(4-methoxybenzyl)-4-(2-methoxyvinyl)-3-methylaniline To an ice-cooled solution of (methoxymethyl)triphenylphosphonium chloride (2.04 g, 5.95 mmol) in tetrahydrofuran (30 mL) was added t-BuOK (7.40 mL, 7.40 mmol, 1 M in THF). The reaction was warmed to room temperature for 0.5 hour. The reaction was cooled to 0° C. before the addition of 4-(bis(4-methoxybenzyl)amino)-6-bromo-3-fluoro-2-methylbenzaldehyde (1.41 g, 2.99 mmol, Intermediate 114, step 3). The solution was then warmed to room temperature for 2 hours. Saturated aqueous NH₄Cl solution was added, and the resulting mixture was extracted with EtOAc. The combined organic was dried over anhydrous sodium sulfate, filtered, and concentrated under vacuum. Purification by flash column chromatography on silica gel (gradient: 0-11% EtOAc in petroleum ether) provided product as a yellow oil (1.44 g). LC-MS: (ESI, m/z): [M+H]$^+$= 500/502. $^1$H NMR (400 MHz, CDCl$_3$, ppm) δ 7.26-7.22 (m, 4H), 6.82 (d, J=8.8 Hz, 4H), 6.55 (d, J=13.2 Hz, 1H), 6.14 (d, J=6.8 Hz, 0.5H), 5.55 (d, J=13.2 Hz, 1H), 5.18 (d, J=6.8 Hz, 0.5H), 4.27-4.23 (m, 4H), 3.78 (s, 6H), 3.71-3.67 (m, 3H), 2.28-2.21 (m, 3H).

Step 2: 2-(4-(Bis(4-methoxybenzyl)amino)-6-bromo-3-fluoro-2-methylphenyl)acetaldehyde To a solution of 5-bromo-2-fluoro-N,N-bis(4-methoxybenzyl)-4-(2-methoxyvinyl)-3-methylaniline (1.29 g, 2.58 mmol) in tetrahydrofuran (15 mL) was added concentrated hydrochloric acid (1.5 mL, 36%) at −15° C. After 1 h, the solution was warmed to room temperature for 5 h. The reaction was quenched with saturated aqueous NaHCO$_3$ solution and extracted with EtOAc. The combined organics were dried over anhydrous sodium sulfate, filtered, and concentrated under vacuum. Purification by flash column chromatography on silica gel (gradient: 0-11% EtOAc in petroleum ether) provided product as a colorless oil (890 mg). LC-MS: (ESI, m/z): [M+H]$^+$=486/488.

Step 3: 5-Bromo-4-(2,2-difluoroethyl)-2-fluoro-N,N-bis(4-methoxybenzyl)-3-methylaniline To a solution of 2-(4-(bis(4-methoxybenzyl)amino)-6-bromo-3-fluoro-2-methylphenyl)acetaldehyde (0.50 g, 1.0 mmol) in dichloromethane (15 mL) under nitrogen was added DAST (3.20 mL, 26.2 mmol) at −10° C. The solution was warmed to room temperature for 3 hours. Saturated aqueous NaHCO$_3$ solution was added, and the resulting mixture was extracted with DCM. The combined organics were dried over anhydrous sodium sulfate, filtered, and concentrated under vacuum. Purification by flash column chromatography on silica gel (gradient: 0-7% EtOAc in petroleum ether) afforded product as a white solid (518 mg). LC-MS: (ESI, m/z): [M+H]$^+$=508/510.

Step 4: 4-(2,2-Difluoroethyl)-2-fluoro-N,N-bis(4-methoxybenzyl)-3-methyl-5-(4,4,5,5-tetramethyl-1,3,2-dioxaborolan-2-yl)aniline Under nitrogen, a solution of 5-bromo-4-(2,2-difluoroethyl)-2-fluoro-N,N-bis(4-methoxybenzyl)-3-methylaniline (518 mg, 1.02 mmol), PdCl$_2$(dppf) (140 mg, 0.18 mmol), Pin$_2$B$_2$(712 mg, 2.80 mmol) and KOAc (0.30 g, 3.1 mmol) in 1,4-dioxane (12 mL) was stirred at 85° C. After 7 h, the reaction was cooled to room temperature and filtered. The filtrate was washed with brine, dried over anhydrous sodium sulfate, filtered, and concentrated under vacuum. Purification by flash column chromatography on silica gel eluting (gradient: 0-5% EtOAc in petroleum ether) afforded product as an colorless oil (504 mg). LC-MS: (ESI, m/z): [M+H]$^+$= 556. $^1$H NMR (400 MHz, CDCl$_3$, ppm) δ 7.44-7.29 (m, 4H), 6.81-6.76 (m, 4H), 6.-1-5.72 (m, 2H), 4.47-4.26 (m, 4H), 3.77 (s, 6H), 3.50-3.43 (m, 2H), 2.25 (s, 3H), 1.27-2.26 (m, 12H).

Intermediate 155: 3-Chloro-2-fluoro-5-(4,4,5,5-tetramethyl-1,3,2-dioxaborolan-2-yl)aniline

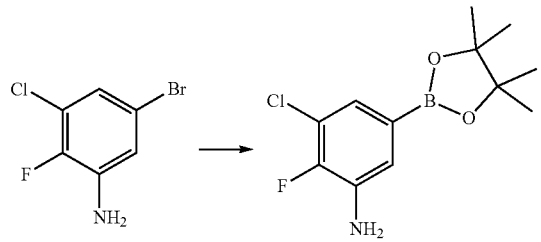 [SMILES: Nc1cc(Br)cc(Cl)c1F ; CC1(C)OB(c2cc(N)c(F)c(Cl)c2)OC1(C)C]

Under nitrogen, a solution of 5-bromo-3-chloro-2-fluoroaniline (0.20 g, 0.89 mmol, intermediate 135, step 1), Pin$_2$B$_2$(339 mg, 1.34 mmol), Pd(dppf)Cl$_2$ (65 mg, 0.090 mmol) and KOAc (175 mg, 1.78 mmol) in 1,2-dimethoxyethane (8 mL) was stirred at 100° C. overnight. The mixture cooled to room temperature and concentrated under vacuum. Purification by flash column chromatography on silica gel (gradient: 0-20% EtOAc in petroleum ether) afforded product as a yellow oil (230 mg). LC-MS: (ESI, m/z): [M+H]$^+$= 272.

Intermediate 156: tert-Butyl 3-(1-hydroxyethyl)-2-methylpiperazine-1-carboxylate

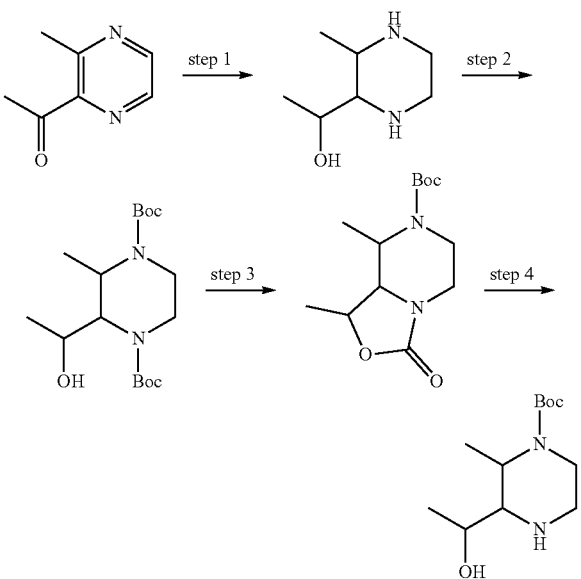

Step 1: 1-(3-Methylpiperazin-2-yl)ethan-1-ol

Under hydrogen (20 atm), a mixture of 1-(3-methylpyrazin-2-yl)ethan-1-one (10.0 g, 73.5 mmol) and PtO$_2$ (3.34 g, 14.7 mmol) in methanol (150 mL) was stirred overnight at 80° C. The resulting mixture was cooled to room temperature and filtered over Celite. The filter cake was washed with methanol, and the filtrate was concentrated under vacuum to afford the crude titled compound as a light yellow oil (10 g). LC-MS: (ESI, m/z): [M+H]$^+$=145.

Step 2: Di-tert-butyl 2-(1-hydroxyethyl)-3-methylpiperazine-1,4-dicarboxylate To an ice-cooled solution of 1-(3-methylpiperazin-2-yl)ethan-1-ol (10.0 g, 69.4 mmol) and DIPEA (57.2 mL, 347 mmol) in dichloromethane (200 mL) was added a solution of (Boc)₂O (45.4 g, 208 mmol) in dichloromethane (100 mL) dropwise. The solution was warmed to room temperature for 2 hours. The reaction mixture was diluted with water and extracted with dichloromethane. The combined organic was washed with brine, dried over anhydrous sodium sulfate, filtered, and concentrated under vacuum. Purification by flash column chromatography on silica gel (gradient: 0-10% methanol in dichloromethane) afforded product as a light yellow oil (15 g). LC-MS: (ESI, m/z): [M+H]⁺=345.

Step 3: tert-Butyl 1,8-dimethyl-3-oxotetrahydro-3H-oxazolo[3,4-a]pyrazine-7(1H)-carboxylate To an ice-cooled solution of di-tert-butyl 2-(1-hydroxyethyl)-3-methylpiperazine-1,4-dicarboxylate (5.00 g, 14.5 mmol) in tetrahydrofuran (10 mL) was added NaH (1.16 g, 29.0 mmol, 60% dispersion in mineral oil) in 3 portions. The reaction was warmed to room temperature. After 3 h, the saturated aqueous NH₄Cl solution was added. The reaction mixture was diluted with water and extracted with ethyl acetate. The combined organic layers were washed with brine, dried over anhydrous sodium sulfate, filtered, and concentrated under vacuum to afford the crude product as a brown solid (3.5 g). LC-MS: (ESI, m/z): [M+H]⁺=271.

Step 4: tert-Butyl 3-(1-hydroxyethyl)-2-methylpiperazine-1-carboxylate

To a solution of tert-butyl 1,8-dimethyl-3-oxotetrahydro-3H-oxazolo[3,4-a]pyrazine-7(1H)-carboxylate (3.5 g, crude) in ethanol (60 mL) was added a solution of NaOH (2.60 g, 65.0 mmol) in water (20 mL) at room temperature. The reaction was heated at 80° C. for 3 h. Ethanol was removed under reduced pressure, and the resulting residue was diluted with water. The solution was neutralized to pH=8 with HCl (1 M) and extracted with ethyl acetate. The combined organic layer was dried over anhydrous Na₂SO₄, filtered, and concentrated under vacuum to afford the crude product as an off white solid (2.6 g). LC-MS: (ESI, m/z): [M+H]⁺=245.

Intermediate 157: tert-Butyl (S)-3-((S)-1-hydroxyethyl)piperazine-1-carboxylate

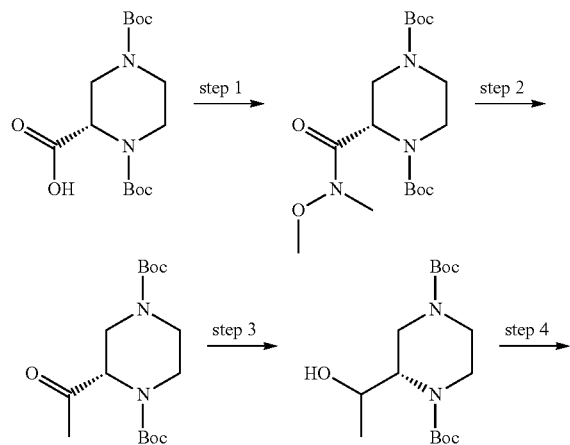

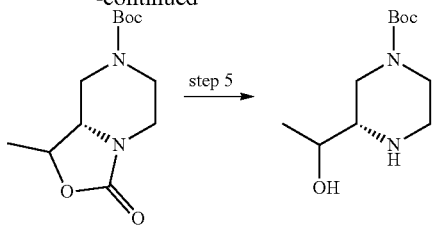

Step 1: Di-tert-butyl (S)-2-(methoxy(methyl)carbamoyl)piperazine-1,4-dicarboxylate Under nitrogen, a solution of (S)-1,4-bis(tert-butoxycarbonyl)piperazine-2-carboxylic acid (5.01 g, 15.2 mmol), N,O-dimethylhydroxylamine (1.63 g, 16.7 mmol), HATU (7.50 g, 19.7 mmol) and DIPEA (3.91 g, 30.3 mmol) in DCM (2 mL) was stirred overnight at room temperature. Saturated aqueous NH₄Cl solution was added to the reaction, and resulting mixture was extracted with DCM. The combined organic was dried over anhydrous sodium sulfate, filtered, and concentrated under vacuum. Purification by flash column chromatography on silica gel (gradient: 0%-70% EtOAc in petroleum ether) afforded product as a white solid (5.41 g). LC-MS: (ESI, m/z): [M+H]⁺=374.

Step 2: Di-tert-butyl (S)-2-acetylpiperazine-1,4-dicarboxylate

To an ice-cooled solution of di-tert-butyl (S)-2-(methoxy(methyl)carbamoyl) piperazine-1,4-dicarboxylate (5.41 g, 14.5 mmol) in Et₂O (50 mL) was added MeMgBr (24.2 mL, 3 M in Et₂O) under nitrogen. After 2 h, the reaction was quenched by saturated aqueous NH₄Cl solution and extracted with EtOAc. The combined organic was dried over anhydrous sodium sulfate, filtered, and concentrated under vacuum. Purification by flash column chromatography on silica gel (gradient: 0%-50% EtOAc in petroleum ether) afforded the product as a white solid (2.24 g). LC-MS: (ESI, m/z): [M+H]⁺=329.

Step 3: Di-tert-butyl (S)-2-((R)-1-hydroxyethyl)piperazine-1,4-dicarboxylate To an ice-cooled solution of di-tert-butyl (S)-2-acetylpiperazine-1,4-dicarboxylate (2.21 g, 6.70 mmol) in CH₃OH (22 mL) was added NaBH₄ (380 mg, 10.1 mmol). The reaction was warmed to room temperature for 1 h. Water was added to the reaction, and the reaction was concentrated under vacuum to remove CH₃OH. The resulting solution was partitioned between water and EtOAc. The separated organic layer was dried over anhydrous sodium sulfate, filtered, and concentrated under vacuum. Purification by flash column chromatography on silica gel (gradient: 0%-50% EtOAc in petroleum ether) to afford the titled compound as a white solid (2.21 g). LC-MS: (ESI, m/z): [M+H]⁺=331.

Step 4: tert-Butyl (1S,8aS)-1-methyl-3-oxotetrahydro-3H-oxazolo[3,4-a]pyrazine-7(1H)-carboxylate To an ice-cooled solution of di-tert-butyl (S)-2-((R)-1-hydroxyethyl)piperazine-1,4-dicarboxylate (2.28 g, 6.90 mmol) in THF (25 mL) was added NaH (553 mg, 13.8 mmol) under nitrogen. The solution was warmed to room temperature for 1 h, before the addition of saturated aqueous NH₄Cl solution and extracted with EtOAc. The combined organic was dried over anhydrous sodium sulfate, filtered, and concentrated under vacuum. The residue was purified by C18 column (solvent gradient: 0-60% ACN in water (0.05% NH₄HCO₃)) to afford the titled compound as a white solid (1.46 g). LC-MS: (ESI, m/z): [M+H]⁺=201.

Step 5: tert-Butyl (3S)-3-(1-hydroxyethyl)piperazine-1-carboxylate

A solution of tert-butyl (1S,8aS)-1-methyl-3-oxotetrahydro-3H-oxazolo[3,4-a] pyrazine-7(1H)-carboxylate (1.45 g, 5.67 mmol) and NaOH (2.27 g, 56.8 mmol) in EtOH (15 mL) and water (3 mL) was stirred at 80° C. for 2 h. The reaction was cooled to room temperature, and the resulting solution was concentrated under vacuum, and filtered. t The solid was washed with DCM, and the filtrate was concentrated under vacuum to afford crude product as a white oil (1.48 g), which was used without further purification. LC-MS: (ESI, m/z): [M+H]⁺=231.

Intermediate 158: tert-Butyl (1R,4S,5S)-4-(hydroxymethyl)-3,6-diazabicyclo[3.2.2]nonane-6 carboxylate

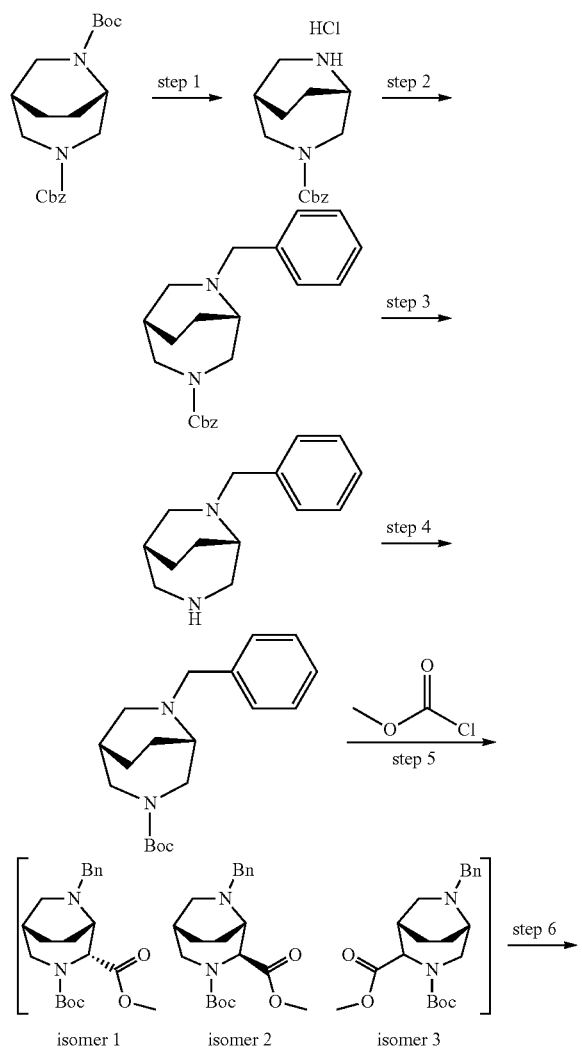

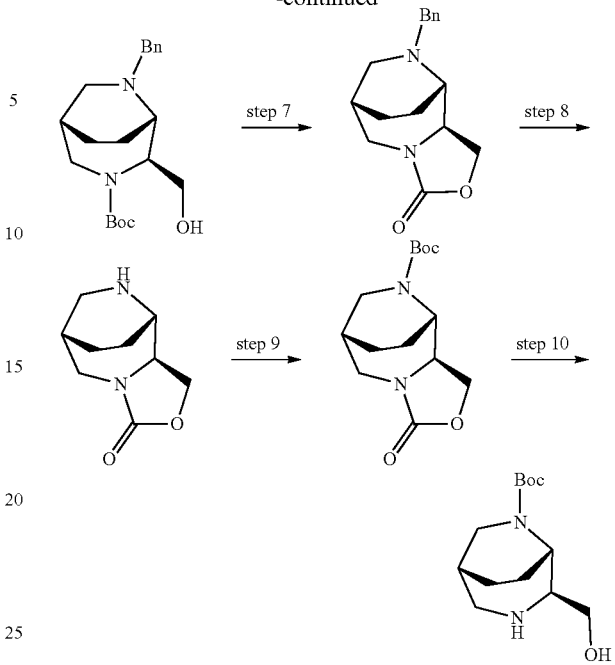

Step 1: Benzyl (1S,5S)-3,6-diazabicyclo[3.2.2]nonane-3-carboxylate HCl salt

To a solution of 3-benzyl 6-(tert-butyl) (1R,5S)-3,6-diazabicyclo[3.2.2]nonane-3,6-dicarboxylate (40.0 g, 111 mmol) in dichloromethane (40 mL) was added HCl (40 mL, 4 M in 1,4-dioxane). The resulting solution was stirred for 3 h at room temperature. The solvent was concentrated under vacuum to afford 43 g (crude) of the title compound as a yellow oil. LC-MS: (ESI, m/z): [M+H]⁺=261.

Step 2: Benzyl (1S,5S)-6-benzyl-3,6-diazabicyclo[3.2.2]nonane-3-carboxylate

A solution of benzyl (1S,5S)-3,6-diazabicyclo[3.2.2]nonane-3-carboxylate HCl salt (43 g, 146 mmol), benzyl bromide (23.6 mL, 198 mmol) and N-ethyl-N-isopropylpropan-2-amine (42.0 g, 326 mmol) in N,N-dimethylformamide (40 mL) was stirred at 80° C. for 1 h. The reaction was cooled to room temperature, diluted with EtOAc and washed with water. The organic layers were dried over anhydrous sodium sulfate and concentrated under vacuum. The residue was purified by flash chromatography on silica gel (gradient: 0-50% EtOAc/petroleum ether) to afford 50 g of the title compound as a yellow oil. LC-MS: (ESI, m/z): [M+H]⁺=351.

Step 3: (1R,5S)-6-Benzyl-3,6-diazabicyclo[3.2.2]nonane

A solution of benzyl (1S,5S)-6-benzyl-3,6-diazabicyclo[3.2.2]nonane-3-carboxylate (30.0 g, 85.6 mmol) in TFA (300 mL) was stirred for 3 h at 70° C. The solvent was concentrated under vacuum to afford 27 g (crude) of the title compound as a yellow oil. LC-MS: (ESI, m/z): [M+H]⁺=217.

Step 4: tert-Butyl (1S,5S)-6-benzyl-3,6-diazabicyclo[3.2.2]nonane-3-carboxylate

To a solution of (1R,5S)-6-benzyl-3,6-diazabicyclo[3.2.2]nonane (27 g, 125 mmol) and N-ethyl-N-isopropylpropan- 2-amine (95.2 g, 437 mmol) in dichloromethane (270 mL) was added (Boc)₂O (24.2 g, 187 mmol). The resulting solution was stirred for 30 min at room temperature. The solvent was concentrated under vacuum. The residue was purified by flash chromatography on silica gel (gradient: 0-50% EtOAc/petroleum ether) to afford 16 g of the title compound as a yellow oil. LC-MS: (ESI, m/z): [M+H]⁺= 317.

Step 5: 3-(tert-Butyl) 4-methyl (1S,4S,5S)-6-benzyl-3,6-diazabicyclo[3.2.2]nonane-3,4-dicarboxylate, 3-(tert-butyl) 4-methyl (1S,4R,5S)-6-benzyl-3,6-diazabicyclo[3.2.2]nonane-3,4-dicarboxylate and 3-(tert-butyl) 2-methyl (1S,5S)-6-benzyl-3,6-diazabicyclo[3.2.2]nonane-2,3-dicarboxylate (mixture of two isomers)

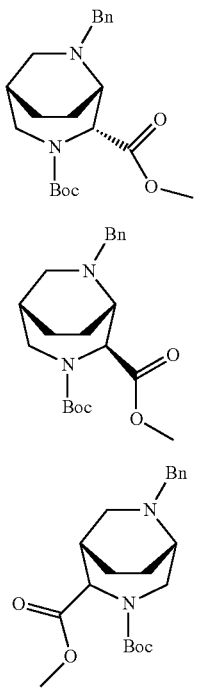

isomer 1 isomer 2 isomer 3

Under nitrogen, to a solution of tert-butyl (1S,5S)-6-benzyl-3,6-diazabicyclo[3.2.2]nonane-3-carboxylate (15 g, 47 mmol) and N¹,N¹N²,N²-tetramethylethane-1,2-diamine (11.0 g, 94.9 mmol) in diethyl ether (150 mL) was added s-BuLi (73.1 mL, 1.3 M in cHex) at −78° C. The resulting solution was stirred for 1.5 h at −55° C. The reaction system was recooled to −78° C. and methyl chloroformate (11.2 g, 118 mmol) in diethyl ether (100 mL) was added. The reaction was stirred overnight at room temperature. The reaction was quenched with NH₄Cl aqueous and extracted with EtOAc. The combined organic layers were dried over anhydrous sodium sulfate and concentrated under vacuum. The crude was purified by flash chromatography on silica gel (gradient: 0-10% EtOAc/petroleum ether) to afford 1.2 g of isomer 1 (the first peak), 1.7 g of isomer 2 (the second peak) and 2.0 g of isomer 3 (the third peak) as yellow oil. LC-MS: (ESI, m/z): [M+H]⁺=375.

isomer 1: ¹H NMR (300 MHz, DMSO-d₆) δ 7.37-7.01 (m, 5H), 4.82-4.66 (m, 1H), 4.25-3.95 (m, 1H), 3.71-3.57 (m, 5H), 3.52-3.47 (m, 1H), 3.24-3.12 (m, 1H), 2.61- 2.49 (m, 1H), 2.20-1.98 (m, 2H), 1.99-1.94 (m, 1H), 1.77-1.43 (m, 3H), 1.37 (d, J=15.0 Hz, 9H).

isomer 2: ¹H NMR (300 MHz, DMSO-d₆) δ 7.52-7.09 (m, 5H), 5.13-4.94 (m, 1H), 4.28-4.13 (m, 1H), 3.76-3.70 (m, 1H), 3.64-3.52 (m, 4H), 3.30-3.25 (m, 1H), 3.15-2.99 (m, 1H), 2.84-2.80 (m, 1H), 2.46-2.38 (m, 1H), 2.22-2.16 (m, 1H), 2.02-1.84 (m, 1H), 1.59-1.46 (m, 3H), 1.41 (d, J=7.1 Hz, 9H).

isomer 3: ¹H NMR (300 MHz, DMSO-d₆) δ 7.41-7.12 (m, 5H), 4.99-4.65 (m, 1H), 4.19-3.80 (m, 1H), 3.77-3.68 (m, 1H), 3.67-3.57 (m, 4H), 3.52-3.29 (m, 1H), 3.06-2.60 (m, 3H), 2.55-2.40 (m, 1H), 1.93-1.50 (m, 4H), 1.45-1.34 (m, 9H).

Step 6: tert-Butyl (1S,4S,5S)-6-benzyl-4-(hydroxymethyl)-3,6-diazabicyclo[3.2.2]nonane-3-carboxylate Under nitrogen, to a solution of 3-(tert-butyl) 4-methyl (1S,4S,5S)-6-benzyl-3,6-diazabicyclo[3.2.2]nonane-3,4-dicarboxylate (isomer 2, 1.6 g, 4.3 mmol) in tetrahydrofuran (20 mL) was added LiAlH₄ (1.7 mL, 2.5 M in THF) at 0° C. The resulting solution was stirred for 30 min at 0° C. The mixture was quenched by Na₂SO₄·10H₂O and filtered. The filtrate was evaporated under vacuum to afford 1.4 g (crude) of the title compound as a yellow oil. LC-MS: (ESI, m/z): [M+H]⁺=347.

Step 7: (6S,9S,9aS)-10-Benzylhexahydro-1H,3H-9,6-(epiminomethano)oxazolo[3,4-a]azepin-3-one Under nitrogen, to a solution of tert-butyl (1S,4S,5S)-6-benzyl-4-(hydroxymethyl)-3,6-diazabicyclo[3.2.2]nonane-3-carboxylate (1.4 g, 4.0 mmol) in tetrahydrofuran (20 mL) was added NaH (324 mg, 8.09 mmol, 60% in mineral oil) at 0° C. The resulting solution was stirred for 2 h at room temperature. The reaction was quenched with NH₄Cl aqueous and extracted with EtOAc. The combined organic layers were dried over anhydrous sodium sulfate and concentrated under vacuum. The residue was purified by C18 column (solvent gradient: 0-80% MeOH in water (0.05% NH₄HCO₃)) to afford 781 mg of the title compound as a white solid. LC-MS: (ESI, m/z): [M+H]⁺=273.

Step 8: (6S,9S,9aS)-Hexahydro-1H,3H-9,6-(epiminomethano)oxazolo[3,4-a]azepin-3-one Under hydrogen (1 atm), a solution of (6S,9S,9aS)-10-benzylhexahydro-1H,3H-9,6-(epiminomethano) oxazolo [3,4-a] azepin-3-one (680 mg, 2.50 mmol) in methyl alcohol (20.0 mL) was added Pd/C (136 mg). The resulting solution was stirred for 1 h at room temperature. The solids were filtered. The solvent was evaporated under vacuum to afford 475 mg (crude) of the title compound as a yellow solid. LCMS: (ESI): [M+H]⁺=183.

Step 9: tert-Butyl (6S,9S,9aS)-3-oxohexahydro-1H,3H-9,6-(epiminomethano)oxazolo[3,4-a]azepine-10-carboxylate A solution of (6S,9S,9aS)-hexahydro-1H,3H-9,6-(epiminomethano)oxazolo[3,4-a]azepin-3-one (475 mg, 2.61 mmol), (Boc)₂O (853 mg, 3.91 mmol) and N-ethyl-N-isopropylpropan-2-amine (1.01 g, 7.83 mmol) in dichloromethane (10 mL) was stirred for 30 min at room temperature. The reaction was diluted with water and extracted with DCM. The combined organic layers were dried over anhydrous sodium sulfate and concentrated under vacuum to afford 706 mg (crude) of the title compound as a white solid. LC-MS: (ESI, m/z): [M+H]⁺=283.

Step 10: tert-Butyl (1R,4S,5S)-4-(hydroxymethyl)-3,6-diazabicyclo[3.2.2]nonane-6-carboxylate To a solution of tert-butyl (6S,9S,9aS)-3-oxohexahydro-1H,3H-9,6-(epiminomethano) oxazolo[3,4-a]azepine-10-carboxylate (173 mg, 0.610 mmol) in ethanol (5.0 mL) was added NaOH (244 mg, 6.10 mmol) in water (1.0 mL). The resulting solution was stirred for 1 h at 80° C. Solvent was evaporated under vacuum. The solid was washed with DCM several times. The combined DCM layers were evaporated under vacuum to afford 85 mg (crude) of the title compound as a yellow oil. LC-MS: (ESI, m/z): [M+H]⁺=257. The crude was used for next step without further purification.

Intermediate 159: tert-Butyl (1S,2S,5R)-2-(2-((tert-butyldiphenylsilyl)oxy)-1-hydroxyethyl)-3,8-diazabicyclo[3.2.1]octane-8-carboxylate

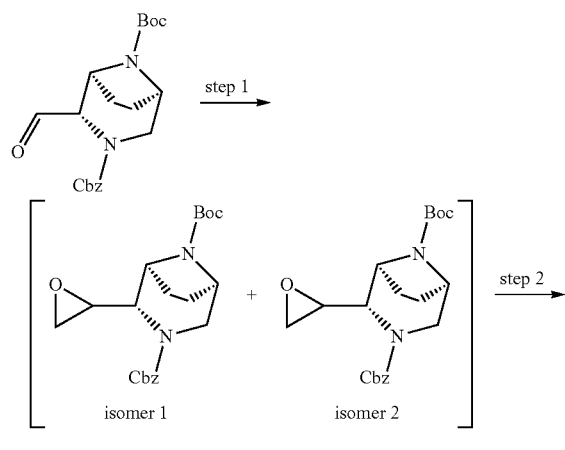

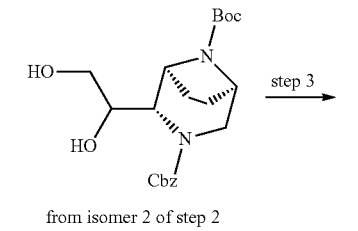

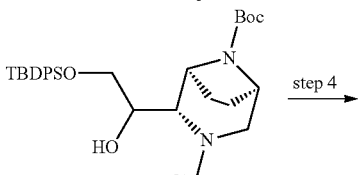

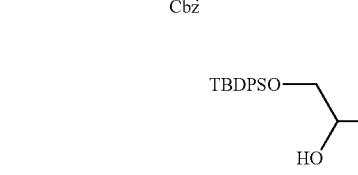

Step 1: 3-Benzyl 8-(tert-butyl) (1S,2S,5R)-2-(oxiran-2-yl)-3,8-diazabicyclo[3.2.1]octane-3,8-dicarboxylate (two isomers)

To a solution of trimethylsulfonium iodide (12.0 g, 58.9 mmol) in dimethyl sulfoxide (100 mL) and tetrahydrofuran (20 mL) was added NaH (2.17 g, 54.3 mmol, 60% in mineral oil) at room temperature. The solution was stirred for 1 hour at room temperature. A solution of 3-benzyl 8-(tert-butyl) (1S,2S,5R)-2-formyl-3,8-diazabicyclo [3.2.1]octane-3,8-dicarboxylate (5.01 g, 13.4 mmol, intermediate 163, the faster peak of step 2) in tetrahydrofuran (20 mL) was then added at room temperature, and the mixture was stirred for an additional 2 hours. The reaction was quenched by aqueous NH₄Cl solution and extracted with EtOAc. The combined organic layers were dried over anhydrous sodium sulfate and concentrated under vacuum. The residue was purified by flash chromatography on silica gel eluting (gradient: 0-30% EtOAc/petroleum ether) to afford 0.83 g isomer 1 (the faster peak) and 2.01 g isomer 2 (the slower peak) as light yellow oil. LC-MS: (ESI, m/z): [M+H]⁺=389.

Step 2: 3-Benzyl 8-(tert-butyl) (1S,2S,5R)-2-(1,2-dihydroxyethyl)-3,8-diazabicyclo[3.2.1]octane-3,8-dicarboxylate (isomer 2)

To a solution of 3-benzyl 8-(tert-butyl) (1S,2S,5R)-2-(oxiran-2-yl)-3,8-diazabicyclo[3.2.1]octane-3,8-dicarboxylate (1.96 g, 5.05 mmol) (isomer 2 of last step) in tetrahydrofuran (18 mL) was added aqueous $H_2SO_4$ solution (10%, 2 mL). The solution was stirred at 50° C. for 16 hours. The solution was cooled to room temperature and adjusted pH to ~10 by aqueous NaOH solution (10%). DIPEA (2.31 g, 17.9 mmol) and (Boc)₂O (1.64 g, 7.59 mmol) was then added. The resulting solution was stirred at room temperature for 2 hours. The solution was diluted with water, extracted with EtOAc. The combined organic layers were dried over anhydrous sodium sulfate and concentrated under vacuum. The residue was purified by flash chromatography on silica gel eluting (gradient: 0-4% MeOH/DCM) to afford 1.52 g of the title compound as light yellow oil. LC-MS: (ESI, m/z): [M+H]⁺=407.

Step 3: 3-Benzyl 8-(tert-butyl) (1S,2S,5R)-2-(2-((tert-butyldiphenylsilyl)oxy)-1-hydroxyethyl)-3,8-diazabicyclo[3.2.1]octane-3,8-dicarboxylate (isomer 2)

To a solution of 3-benzyl 8-(tert-butyl) (1S,2S,5R)-2-(1,2-dihydroxyethyl)-3,8-diazabicyclo[3.2.1]octane-3,8-dicarboxylate (1.51 g, 3.71 mmol), DMAP (0.91 g, 7.46 mmol) and DIPEA (2.45 g, 19.0 mmol) in N,N-Dimethylformamide (20 mL) was added tert-butylchlorodiphenylsilane (2.24 g, 8.15 mmol). The solution was stirred at room temperature for 16 hours. The solution was diluted with water, extracted with EtOAc. The combined organic layers were dried over anhydrous sodium sulfate and concentrated under vacuum. The residue was purified by flash chromatography on silica gel (gradient: 0-25% EtOAc/petroleum ether) to afford 2.22 g of the title compound as a colorless oil. LC-MS: (ESI, m/z): [M+H]⁺=645.

Step 4: tert-Butyl (1S,2S,5R)-2-(2-((tert-butyldiphenylsilyl)oxy)-1-hydroxyethyl)-3,8-diazabicyclo[3.2.1]octane-8-carboxylate Under hydrogen (1 atm), a solution of 3-benzyl 8-(tert-butyl) (1S,2S,5R)-2-(2-((tert-butyldiphenylsilyl)oxy)-1-hydroxyethyl)-3,8-diazabicyclo[3.2.1]octane-3,8-dicarboxylate (2.22 g, 3.44 mmol) and Pd/C (10%, 517 mg, 0.490 mmol) in methyl alcohol (50 mL) was stirred at room temperature for 1.5 hours. The reaction was filtered, and the filtrate was concentrated under vacuum to afford 1.57 g (crude) of the title compound as crude white solid. LC-MS: (ESI, m/z): [M+H]$^+$=511. The crude was used for next step without further purification.

Intermediate 160: tert-Butyl (1R,2R,5S)-2-(1-hydroxyethyl)-3,8-diazabicyclo[3.2.1]octane-8-carboxylate

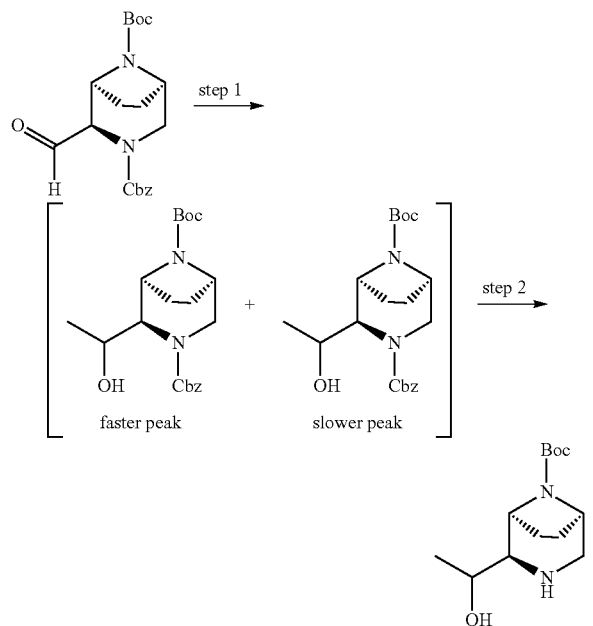

Step 1: 3-Benzyl 8-(tert-butyl) (1R,2R,5S)-2-(1-hydroxyethyl)-3,8-diazabicyclo[3.2.1]octane-3,8-dicarboxylate Under nitrogen, to a solution of 3-benzyl 8-(tert-butyl) (1R,2R,5S)-2-formyl-3,8-diazabicyclo[3.2.1]octane-3,8-dicarboxylate (1.51 g, 4.01 mmol, intermediate 159, step 1, the slower peak) in THF (15 mL) was added MeMgBr (10 mL, 3 M in Et$_2$O) at −40° C., and the mixture was stirred for 2 h at −40° C. The resulting solution was partitioned between water and EtOAc. The separated organic layer was dried over anhydrous sodium sulfate and concentrated under vacuum. The residue was purified by flash chromatography on-silica gel (gradient: 0-45% EtOAc/petroleum ether) to afford 780 mg of the faster peak and 488 mg of the slower peak as a yellow oil. LC-MS: (ESI, m/z): [M+H]$^+$=391.

Step 2: tert-Butyl (1R,2R,5S)-2-(1-hydroxyethyl)-3,8-diazabicyclo[3.2.1]octane-8-carboxylate Under hydrogen, a solution of 3-benzyl 8-(tert-butyl) (1R,2R,5S)-2-(1-hydroxyethyl)-3,8-diazabicyclo[3.2.1]octane-3,8-dicarboxylate (2.74 g, 7.02 mmol) (the faster peak from last step) in MeOH (18 mL) was added Pd/C (880 mg, 10%), and the mixture was stirred at room temperature for 2.5 h. After filtration, the filtrate was concentrated under vacuum to afford 1.64 g (crude) of the title compound as a white solid LC-MS: (ESI, m/z): [M+H]$^+$=257.

Analogous to method described as above, the other isomers were prepared from the slower peak of step 1.

Intermediate 161: tert-Butyl (1R,5S)-8-benzyl-2-(2,2-difluoro-1-hydroxyethyl)-3,8-diazabicyclo [3.2.1] octane-3-carboxylate

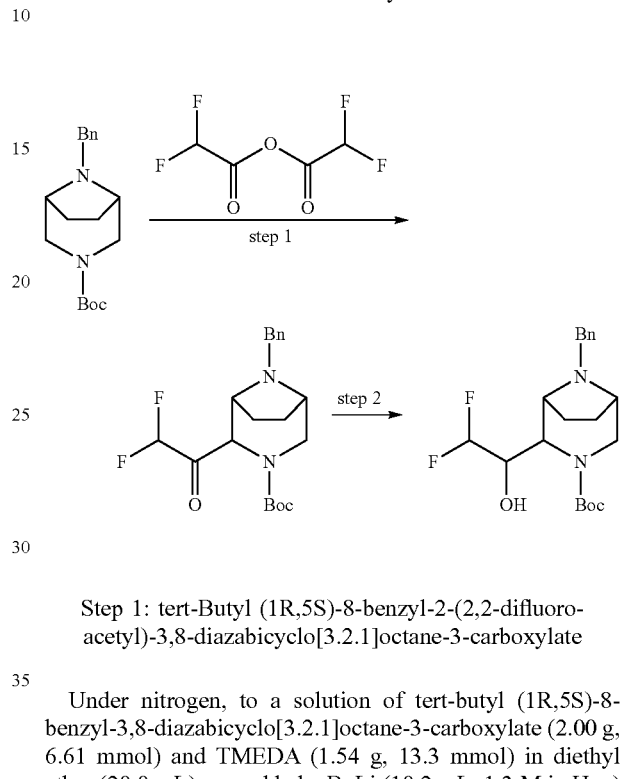

Step 1: tert-Butyl (1R,5S)-8-benzyl-2-(2,2-difluoroacetyl)-3,8-diazabicyclo[3.2.1]octane-3-carboxylate Under nitrogen, to a solution of tert-butyl (1R,5S)-8-benzyl-3,8-diazabicyclo[3.2.1]octane-3-carboxylate (2.00 g, 6.61 mmol) and TMEDA (1.54 g, 13.3 mmol) in diethyl ether (20.0 mL) was added s-BuLi (10.2 mL, 1.3 M in Hex) at −78° C. The resulting solution was stirred for 1.5 h at −78° C. Then 2,2-difluoroacetic anhydride (2.88 g, 16.5 mmol) in diethyl ether (5.00 mL) was added at −78° C., and the mixture was stirred overnight at room temperature. The reaction was quenched with NH$_4$Cl aqueous and extracted with EtOAc. The combined organic layers were dried over anhydrous sodium sulfate and concentrated under vacuum The residue was purified by flash chromatography on silica gel eluting (gradient: 0%-50% EtOAc in petroleum ether) to afford 1.3 g of the title compound as a yellow oil. LC-MS: (ESI, m/z): [M+H]$^+$=381.

Step 2: tert-Butyl (1R,5S)-8-benzyl-2-(2,2-difluoro-1-hydroxyethyl)-3,8-diazabicyclo [3.2.1]octane-3-carboxylate Under nitrogen, to a solution of tert-butyl (1R,5S)-8-benzyl-2-(2,2-difluoroacetyl)-3,8-diazabicyclo [3.2.1] octane-3-carboxylate (6.0 g, 15.7 mmol) in tetrahydrofuran (60 mL) was added LiAlH$_4$ (4.7 mL, 1 M in THF) at 0° C. The resulting solution was stirred at 0° C. for 1 h. The mixture was quenched by Na$_2$SO$_4$·10H$_2$O and filtered. The filtrate was concentrated under vacuum to afford 4.6 g (crude) of the title compound as a yellow oil. LC-MS: (ESI, m/z): [M+H]$^+$=383. The crude was used for next step without further purification.

Intermediate 162: tert-Butyl (5S,5aS,6S,9R)-1,2-dichloro-5-methyl-12-(methylsulfonyl)-5a,6,7,8,9,10-hexahydro-5H-4-oxa-3,10a,11,13,14-pentaaza-6,9-methanonaphtho[1,8-ab]heptalene-14-carboxylate

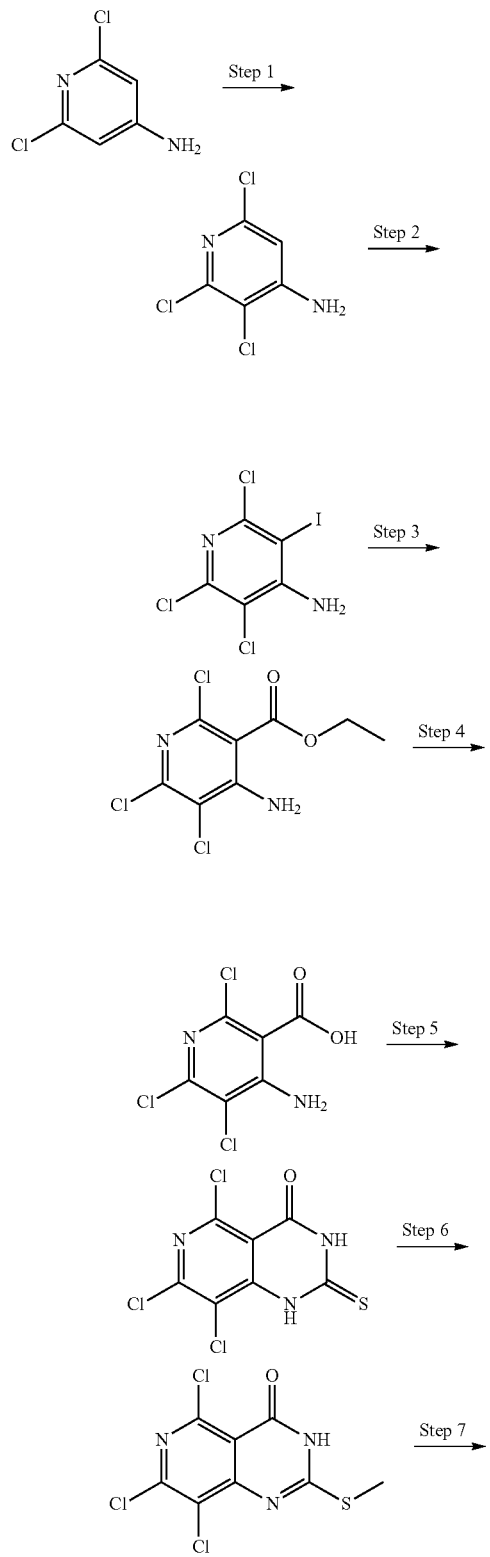

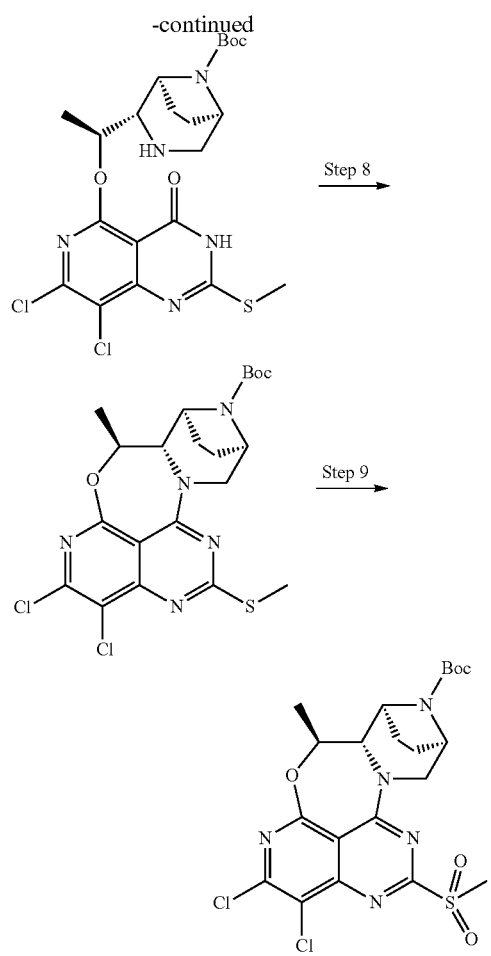

Step 1: 2,3,6-Trichloropyridin-4-amine

A solution of 2,6-dichloropyridin-4-amine (20.0 g, 123 mmol) and NCS (16.4 g, 123 mmol) in tetrahydrofuran (500 mL) was stirred at 50° C. for 24 hours. The solvent was concentrated under vacuum. The residue was diluted with water, and the resulting solution was extracted with EtOAc. The combined organic layers were concentrated under vacuum. The crude product was slurried with ether/EtOAc (10:1) and filtered to afford 21 g of the title compound (crude) as an off-white solid. LC-MS: (ESI, m/z): [M+H]$^+$=197.

Step 2: 2,3,6-Trichloro-5-iodopyridin-4-amine

To a stirred mixture of 2,3,6-trichloropyridin-4-amine (22 g, 111 mmol) in ACN (200 mL) was added NIS (30 g, 134 mmol) and TsOH (2.18 g, 11 mmol) at room temperature. The solution was stirred for 2 h at 70° C. The reaction system was cooled to room temperature, diluted with aqueous Na$_2$SO$_3$ and extracted with EtOAc. The combined organic layers were washed sequentially with water and brine, dried over anhydrous Na$_2$SO$_4$ and concentrated under vacuum. The residue was purified by silica gel column chromatography (gradient: 0%-30% EtOAc/petroleum ether) to afford 35 g of the title compound as a white solid. LC-MS: (ESI, m/z): [M+H]$^+$=323.

Step 3: Ethyl 4-amino-2,5,6-trichloronicotinate

Under carbon monoxide atmosphere, a solution of 2,3,6-trichloro-5-iodo-pyridin-4-amine (8.0 g, 24.7 mmol), Pd(PPh$_3$)$_2$Cl$_2$ (1.74 g, 2.47 mmol) and triethylamine (7.51 g, 74.2 mmol) in ethanol (80 mL) was stirred for 48 h at 80° C. The resulting mixture was concentrated under vacuum. The residue was purified by flash chromatography on silica gel (gradient: 0%-20% EtOAc/DCM) to yield 3.7 g of the title compound as a white solid. LC-MS: (ESI, m/z): [M+H]$^+$=269.

Step 4: 4-Amino-2,5,6-trichloronicotinic acid

A solution of ethyl 4-amino-2,5,6-trichloro-pyridine-3-carboxylate (3.0 g, 11 mmol) and NaOH (890 mg, 22 mmol) in EtOH (20 mL) and water (60 mL) was stirred for 2 h at room temperature. The resulting mixture was filtered. The filtrate was acidified to pH ~3 with HCl. The precipitated solids were collected by filtration to afford 1.5 g of the title compound as a yellow solid. LC-MS: (ESI, m/z): [M+H]$^+$=241.

Step 5: 5,7,8-Trichloro-2-thioxo-2,3-dihydropyrido[4,3-d]pyrimidin-4(1H)-one

To a solution of 4-amino-2,5,6-trichloropyridine-3-carboxylic acid (8.5 g, 35 mmol) and pyridine (20 mL) in ACN (100 mL) was added ethoxycarbonyl isothiocyanate (18.5 g, 141 mmol). The solution was stirred for 2 h at room temperature. The resulting mixture was concentrated under vacuum. The residue was diluted with water and the precipitated solid was collected by filtration to afford 8.7 g of the title compound as a yellow solid. LC-MS: (ESI, m/z): [M+H]$^+$=282.

Step 6: 5,7,8-Trichloro-2-(methylthio)pyrido[4,3-d]pyrimidin-4(3H)-one

To a stirred mixture of 5,7,8-trichloro-2-sulfanylidene-1H,3H-pyrido[4,3-d]pyrimidin-4-one (8.7 g, 31 mmol) and NaOMe (4.99 g, 92.4 mmol) in DMF (100 mL) was added CH$_3$I (3.06 g, 21.6 mmol) dropwise at 0° C. The solution was stirred for 2 h at room temperature. The resulting mixture was diluted with water, and the resulting solution was extracted with CH$_2$Cl$_2$. The combined organic layers were concentrated under vacuum to afford 6.3 g (crude) of the title compound as a yellow solid. LC-MS: (ESI, m/z): [M+H]$^+$=296.

Step 7: tert-Butyl (1S,2S,5R)-2-((S)-1-((7,8-dichloro-2-(methylthio)-4-oxo-3,4-dihydropyrido[4,3-d]pyrimidin-5-yl)oxy)ethyl)-3,8-diazabicyclo[3.2.1]octane-8-carboxylate Under nitrogen, to a solution of tert-butyl (1S,2S,5R)-2-((S)-1-hydroxyethyl)-3,8-diazabicyclo[3.2.1]octane-8-carboxylate (156 mg, 0.610 mmol) in tetrahydrofuran (4 mL) was added NaH (81 mg, 2.02 mmol, 60% in mineral oil) at 0° C. The resulting solution was stirred at room temperature for 0.5 h. Then 5,7,8-trichloro-2-methylsulfanyl-3H-pyrido[4,3-d] pyrimidin-4-one (0.20 g, 0.67 mmol) was added, and the mixture was stirred at room temperature for 2 h. The reaction was quenched with water, extracted with EtOAc. The combined organic layers were dried over anhydrous sodium sulfate and concentrated under vacuum. The residue was purified by flash chromatography on silica gel (gradient: 0%-60% EA/PE) to yield 180 mg of the title compound as a white solid. LC-MS: (ESI, m/z): [M+H]$^+$=516.

Step 8: tert-Butyl (5S,5aS,6S,9R)-1,2-dichloro-5-methyl-12-(methylthio)-5a,6,7,8,9,10-hexahydro-5H-4-oxa-3,10a,11,13,14-pentaaza-6,9-methanonaphtho[1,8-ab]heptalene-14-carboxylate To a solution of tert-butyl (1S,2S,5R)-2-((S)-1-((7,8-dichloro-2-(methylthio)-4-oxo-3,4-dihydropyrido[4,3-d]pyrimidin-5-yl)oxy)ethyl)-3,8-diazabicyclo[3.2.1]octane-8-carboxylate (2.0 g, 3.87 mmol) and DIPEA (2.5 g, 19 mmol) in dichloromethane (20 mL) was added BOPCl (2.95 g, 11.6 mmol) at room temperature. The resulting solution was stirred at room temperature for 2 h. The solvent was concentrated under vacuum, and the residue was purified by flash chromatography on silica gel (gradient: 0%-20% EtOAc/petroleum ether) to yield 1.5 g of the title compound as a yellow solid. LC-MS: (ESI, m/z): [M+H]$^+$=498.

Step 9: tert-Butyl (5S,5aS,6S,9R)-1,2-dichloro-5-methyl-12-(methylsulfonyl)-5a,6,7,8,9,10-hexahydro-5H-4-oxa-3,10a,11,13,14-pentaaza-6,9-methanonaphtho[1,8-ab]heptalene-14-carboxylate Under nitrogen, to a solution of tert-Butyl (5S,5aS,6S,9R)-1,2-dichloro-5-methyl-12-(methylthio)-5a,6,7,8,9,10-hexahydro-5H-4-oxa-3,10a,11,13,14-pentaaza-6,9-methanonaphtho[1,8-ab]heptalene-14-carboxylate (0.050 g, 0.10 mmol) in ethyl acetate (2 mL) was added m-CPBA (17.3 mg, 0.10 mmol) at 0° C. The resulting solution was stirred at room temperature for 2 hours. The reaction mixture was diluted with water and extracted with ethyl acetate. The combined organic layers were dried over Na$_2$SO$_4$ and concentrated under vacuum. The residue was purified by flash chromatography on silica (gradient: 0%-20% EtOAc/petroleum ether) to afford 45 mg as a yellow solid. LC-MS: (ESI, m/z): [M+H]$^+$=530.

Intermediate 163: tert-Butyl (1R,2S,5S)-2-((R)-2,2,2-trifluoro-1-hydroxyethyl)-3,8-diazabicyclo [3.2.1] octane-8-carboxylate

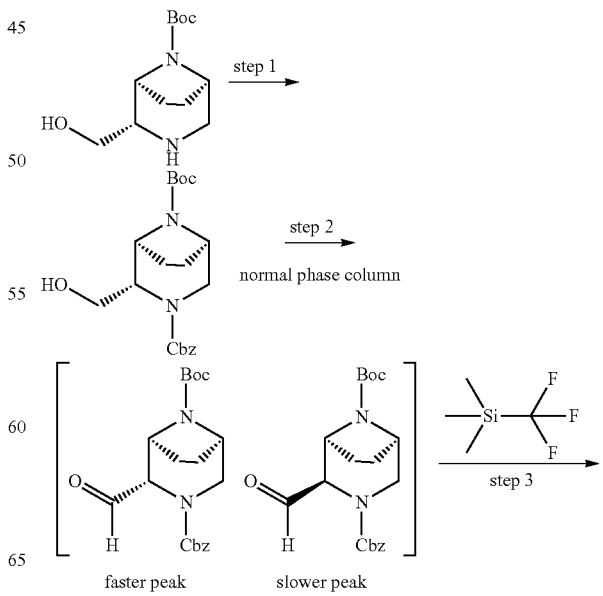

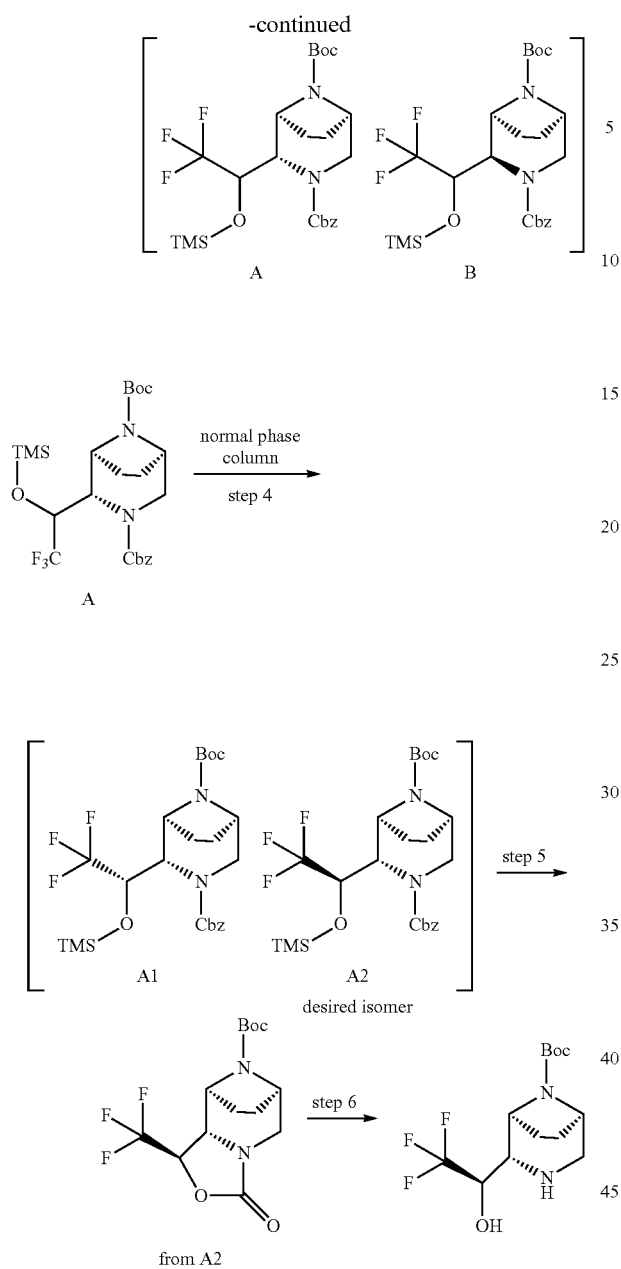

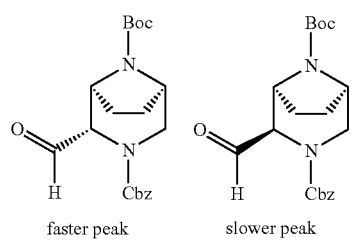

faster peak    slower peak

Step 2: 3-Benzyl 8-(tert-butyl) (1R,2S,5S)-2-formyl-3,8-diazabicyclo[3.2.1]octane-3,8-dicarboxylate and 3-benzyl 8-(tert-butyl) (1R,2R,5S)-2-formyl-3,8-diazabicyclo[3.2.1]octane-3,8-dicarboxylate Under nitrogen, to a solution of oxalyl dichloride (18.4 mL, 2 M in DCM) in dichloromethane (10 mL) was added DMSO (5.73 g, 73.5 mmol) in dichloromethane (10.0 mL) at −78° C. The resulting solution was stirred for 30 min at −78° C. Then 3-benzyl 8-(tert-butyl) (1R,2S,5S)-2-(hydroxymethyl)-3,8-diazabicyclo[3.2.1]octane-3,8-dicarboxylate (6.9 g, 18 mmol) in dichloromethane (70 mL) was added at −78° C., and the mixture was stirred for 1 h. Triethylamine (11.1 g, 110 mmol) was added at −78° C. The reaction system was warmed to room temperature and stirred an additional 1 h. The reaction was diluted with water and extracted with DCM. The combined organic layers were dried over anhydrous sodium sulfate and concentrated under vacuum. The residue was purified by flash chromatography on silica gel (gradient: 0-30% EtOAc/petroleum ether) to afford 1.46 g of the faster peak and 2.9 g of the slower peak as colorless oil. LC-MS: (ESI, m/z): [M+H]⁺=375. Note: crude material does not epimerize.

Faster peak: ¹H NMR (300 MHz, DMSO-d₆) δ 9.43 (d-J=3.8 Hz, 1H), 7.38-736 (s, 5H), 5.12 (s, 2H), 4.23 (s, 1H), 4.08 (s, 1H), 3.78 (s, 1H), 3.57 (d, J=12.1 Hz, 1H), 3.16-3.20 (m, 1H), 2.00-1.86 (m, 2H), 1.79-1.73 (m, 2H), 1.42 (s, 9H).

Slower peak: ¹H NMR (300 MHz, DMSO-d₆) δ 9.58 (s, 1H), 7.45-7.23 (m, 5H), 5.15-5.00 (m, 2H), 4.76 (t, J=8.1 Hz, 1H), 4.60-4.64 (m, 1H), 4.22-3.98 (m, 1H), 3.75-3.58 (m, 1H), 3.18-3.06 (m, 1H), 2.09-1.80 (m, 2H), 1.82-1.52 (m, 2H), 1.36 (s, 9H).

Step 3: 3-Benzyl 8-(tert-butyl) (1R,2S,5S)-2-(2,2,2-trifluoro-1-((trimethylsilyl)oxy)ethyl)-3,8-diazabicyclo[3.2.1]octane-3,8-dicarboxylate and 3-benzyl 8-(tert-butyl) (1R,2R,5S)-2-(2,2,2-trifluoro-1-((trimethylsilyl)oxy)ethyl)-3,8-diazabicyclo[3.2.1]octane-3,8-dicarboxylate

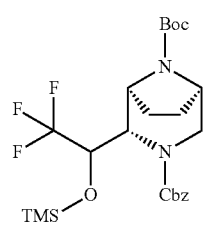

Step 1: 3-Benzyl 8-(tert-butyl) (1R,2S,5S)-2-(hydroxymethyl)-3,8-diazabicyclo[3.2.1]octane-3,8-dicarboxylate To a solution of tert-butyl (1R,2S,5S)-2-(hydroxymethyl)-3,8-diazabicyclo[3.2.1]octane-8-carboxylate (5.00 g, 20.6 mmol) and N-ethyl-N-isopropylpropan-2-amine (5.33 g, 41.3 mmol) in dichloromethane (50 mL) was added CbzCl (4.57 g, 26.9 mmol) at 0° C. The resulting solution was stirred for 1 h at room temperature. The reaction was quenched with water and extracted with DCM. The combined organic layers were dried over anhydrous sodium sulfate and concentrated under vacuum. The residue was purified by flash chromatography on silica gel (gradient: 0-50% EtOAc/petroleum ether) to afford 7.7 g of the title compound as a colorless oil. LC-MS: (ESI, m/z): [M+H]⁺=377.

-continued

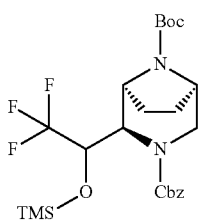
B

A solution of 3-benzyl 8-(tert-butyl) (1R,2S,5S)-2-formyl-3,8-diazabicyclo[3.2.1]octane-3,8-dicarboxylate (faster peak of step 2) (1.46 g, 3.90 mmol), trimethyl (trifluoromethyl)silane (1.11 g, 7.82 mmol) and LiOAc (258 mg, 3.90 mmol) in N,N-dimethylformamide (15.0 mL) was stirred for 1 h at room temperature. The reaction was diluted with EtOAc and washed with water. The organic layers were dried over anhydrous sodium sulfate and concentrated under vacuum to afford 2 g (crude) of the compound A as a yellow oil. LC-MS: (ESI, m/z): [M+H]$^+$=517.

Analogous to method described as above, 3.80 g crude compound B was prepared from 2.80 g of slower peak of step 2.

Step 4: 3-Benzyl 8-(tert-butyl) (1R,2S,5S)-2-((S)-2,2,2-trifluoro-1-((trimethylsilyl)oxy)ethyl)-3,8-diazabicyclo[3.2.1]octane-3,8-dicarboxylate and 3-benzyl 8-(tert-butyl) (1R,2S,5S)-2-((R)-2,2,2-trifluoro-1-((trimethylsilyl)oxy)ethyl)-3,8-diazabicyclo[3.2.1]octane-3,8-dicarboxylate

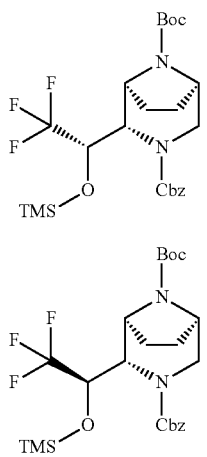

desired isomer

The mixture of diastereomers of 3-Benzyl 8-(tert-butyl) (1R,2S,5S)-2-(2,2,2-trifluoro-1-((trimethylsilyl)oxy)ethyl)-3,8-diazabicyclo[3.2.1]octane-3,8-dicarboxylate (6.5 g crude, compound A of last step) was separated by flash chromatography on silica gel (gradient: 0-15% EtOAc in petroleum ether) to afford 3.2 g compound A1 (the faster peak) and 810 mg compound A2 (the slower peak, desired isomer) as yellow oil. LC-MS: (ESI, m/z): [M+H]$^+$=517.

Compound A1 $^1$H NMR (300 MHz, DMSO-d$_6$) δ 7.46-7.11 (m, 5H), 5.07 (s, 2H), 4.87 (s, 1H), 4.38 (d, J=46.1 Hz, 1H), 4.24-3.93 (m, 3H), 3.17-2.83 (m, 1H), 2.43 (d, J=8.9 Hz, 1H), 1.86 (s, 2H), 1.56 (s, 1H), 1.33 (s, 9H), 0.09 (s, 9H).

Compound A2: $^1$H NMR (300 MHz, DMSO-d$_6$) δ 7.49-7.19 (m, 5H), 4.99 (d, J=8.0 Hz, 2H), 4.70 (d, J=29.2 Hz, 2H), 4.28 (d, J=16.8 Hz, 1H), 4.11 (s, 2H), 2.69 (d, J=16.1 Hz, 1H), 2.02 (d, J=13.2 Hz, 1H), 1.88 (d, J=27.8 Hz, 2H), 1.54 (d, J=10.9 Hz, 1H), 1.31 (d, J=9.6 Hz, 9H), 0.07 (s, 9H).

Step 5: tert-Butyl (1R,6S,9R,9aS)-3-oxo-1-(trifluoromethyl)hexahydro-1H,3H-6,9-epiminooxazolo[3,4-a]azepine-10-carboxylate A solution of 3-benzyl 8-(tert-butyl) (1R,2S,5S)-2-((R)-2,2,2-trifluoro-1-((trimethylsilyl) oxy) ethyl)-3,8-diazabicyclo[3.2.1]octane-3,8-dicarboxylate (compound A2 of last step) (0.80 g, 1.6 mmol) and TBAF (1.60 mL, 1 M in THF) in tetrahydrofuran (10.0 mL) was stirred for overnight at room temperature. The reaction system was diluted with EtOAc and washed with water. The organic layers were dried over anhydrous sodium sulfate and concentrated under vacuum. The residue was purified by C18 column (solvent gradient: 0-100% MeOH in water (0.05% NH$_4$HCO$_3$)) to afford 480 mg of the title compound as a white solid. LC-MS: (ESI, m/z): [M+H]$^+$=337.

Step 6: tert-Butyl (1R,2S,5S)-2-((R)-2,2,2-trifluoro-1-hydroxyethyl)-3,8-diazabicyclo[3.2.1]octane-8-carboxylate To a solution of tert-butyl (1R,6S,9R,9aS)-3-oxo-1-(trifluoromethyl)hexahydro-1H,3H-6,9-epiminooxazolo[3,4-a]azepine-10-carboxylate (480 mg, 1.4 mmol) in ethanol (5.0 mL) was added NaOH (571 mg, 14.3 mmol) in water (1.0 mL). The resulting solution was stirred for 1 h at 80° C. Solvent was evaporated under vacuum. The residue was dissolved in DCM, and the suspension was filtered. The solvent was evaporated under vacuum to afford 460 mg (crude) of the title compound as a yellow solid. LC-MS: (ESI, m/z): [M+H]$^+$=311. $^1$H NMR (300 MHz, DMSO-d$_6$) δ 3.95 (br, 2H), 3.67 (br, 1H), 2.90-2.80 (br, 1H), 2.80-2.70 (m, 1H), 2.68-2.60 (m, 1H), 2.25 (br, 1H), 1.95-1.85 (m, 1H), 1.82-1.52 (m, 3H), 1.40 (s, 9H).

Intermediate 164: tert-Butyl (5R,5aS,6S,9R)-2-chloro-1-fluoro-12-(methylthio)-5-(trifluoromethyl)-5a,6,7,8,9,10-hexahydro-5H-4-oxa-3,10a,11,13,14-pentaaza-6,9-methanonaphtho[1,8-ab]heptalene-14-carboxylate

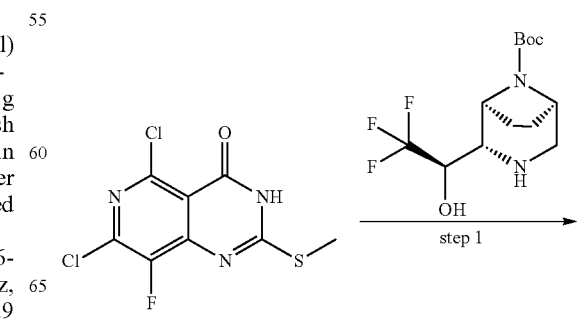
step 1

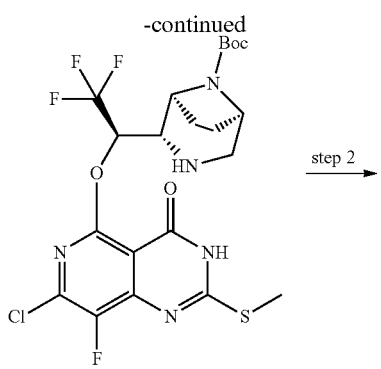

→ step 2

Step 1: tert-Butyl (1S,2S,5R)-2-((R)-1-((7-chloro-8-fluoro-2-(methylthio)-4-oxo-3,4-dihydropyrido[4,3-d]pyrimidin-5-yl)oxy)-2,2,2-trifluoroethyl)-3,8-diazabicyclo[3.2.1]octane-8-carboxylate Under nitrogen, to a solution of tert-butyl (1R,2S,5S)-2-((R)-2,2,2-trifluoro-1-hydroxyethyl)-3,8-diazabicyclo[3.2.1]octane-8-carboxylate (460 mg, 1.5 mmol, intermediate 163) in tetrahydrofuran (10.0 mL) was added NaH (356 mg, 8.90 mmol, 60% in mineral oil) at 0° C. The resulting solution was stirred for 30 min at room temperature. Then 5,7-dichloro-8-fluoro-2-(methylthio)pyrido[4,3-d]pyrimidin-4(3H)-one (621 mg, 2.22 mmol) was added at 0° C. The solution was stirred overnight at room temperature. The mixture was quenched with NH₄Cl aqueous and extracted with EtOAc. The combined organic layers were dried over anhydrous sodium sulfate and concentrated under vacuum to afford 1.10 g (crude) of the title compound as a yellow solid. LC-MS: (ESI, m/z): [M+H]⁺=554.

Step 2: tert-Butyl (5R,5aS,6S,9R)-2-chloro-1-fluoro-12-(methylthio)-5-(trifluoromethyl)-5a,6,7,8,9,10° hexahydro-5H-4-oxa-3,10a,11,13,14-pentaaza-6,9-methanonaphtho[1,8-ab]heptalene-14-carboxylate A solution of tert-butyl (1S,2S,5R)-2-((R)-1-((7-chloro-8-fluoro-2-(methylthio)-4-oxo-3,4-dihydropyrido[4,3-d]pyrimidin-5-yl)oxy)-2,2,2-trifluoroethyl)-3,8-diazabicyclo[3.2.1]octane-8-carboxylate (0.70 g, 1.3 mmol), BOPCl (1.2 g, 5.06 mmol) and DIPEA (2.46 g, 19.0 mmol) in dichloromethane (15.0 mL) was stirred overnight at room temperature. The solvent was concentrated under vacuum. The residue was purified by flash chromatography on silica gel (gradient: 0-25% EtOAc in petroleum ether) to afford 548 mg of the title compound as a yellow solid. LC-MS: (ESI, m/z): [M+H]⁺=536. ¹H NMR (300 MHz, DMSO-d₆) δ 5.74-5.69 (m, 1H), 5.24 (d, J=13.3 Hz, 1H), 4.44 (d, J=10.0 Hz, 1H), 4.31 (d, J=18.1 Hz, 2H), 3.20 (d, J=13.3 Hz, 1H), 2.58 (s, 3H), 1.89 (s, 4H), 1.46 (s, 9H).

Intermediate 165: tert-Butyl (5R,5aS,6S,9R)-2-chloro-1-fluoro-12-(methylsulfonyl)-5-(trifluoromethyl)-5a,6,7,8,9,10-hexahydro-5H-4-oxa-3,10a,11,13,14-pentaaza-6,9-methanonaphtho[1,8-ab]heptalene-14-carboxylate

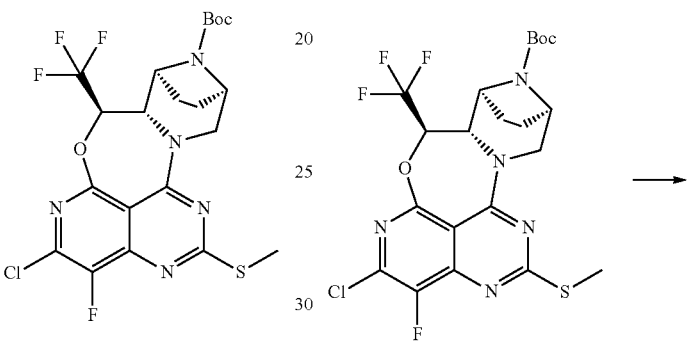

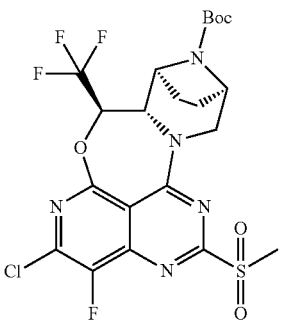

Under nitrogen, to a solution of tert-butyl (5R,5aS,6S,9R)-2-chloro-1-fluoro-12-(methylthio)-5-(trifluoromethyl)-5a,6,7,8,9,10° hexahydro-5H-4-oxa-3,10a,11,13,14-pentaaza-6,9-methanonaphtho[1,8-ab]heptalene-14-carboxylate (80.0 mg, 0.150 mmol, intermediate 164) in ethyl acetate (2.0 mL) was added 3-chlorobenzoperoxoic acid (77.2 mg, 0.450 mmol) at 0° C. The resulting solution was stirred for 1 h at room temperature. The solution was quenched with Na₂S₂O₃ aqueous and extracted with EtOAc. The combined organic layers were dried over anhydrous sodium sulfate and concentrated under vacuum. The residue was purified by flash chromatography on silica gel (gradient: 0-50% EtOAc/petroleum ether) to afford 51.0 mg of the title compound as a white solid. LC-MS: (ESI, m/z): [M+H]⁺=568.

Intermediate 166: tert-Butyl (5S,5aS,6S,9R)-2-chloro-1-fluoro-12-(methylthio)-5-(trifluoromethyl)-5a,6,7,8,9,10-hexahydro-5H-4-oxa-3,10a,11,13,14-pentaaza-6,9-methanonaphtho[1,8-ab]heptalene-14-carboxylate

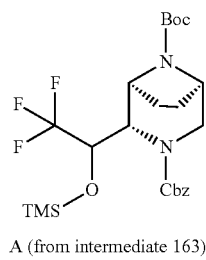

A (from intermediate 163)

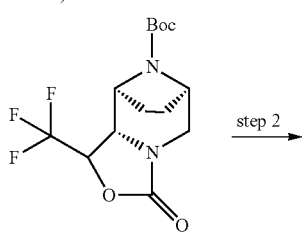

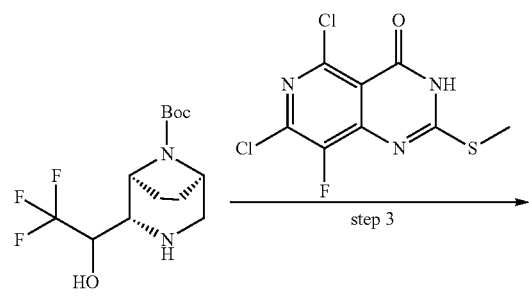

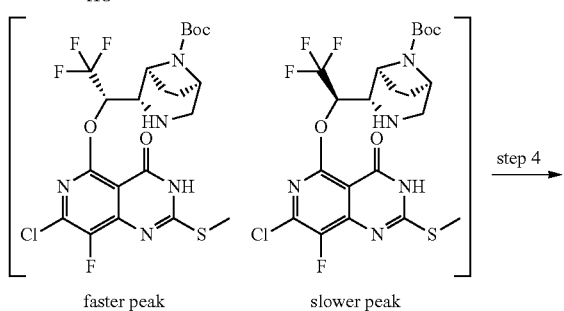

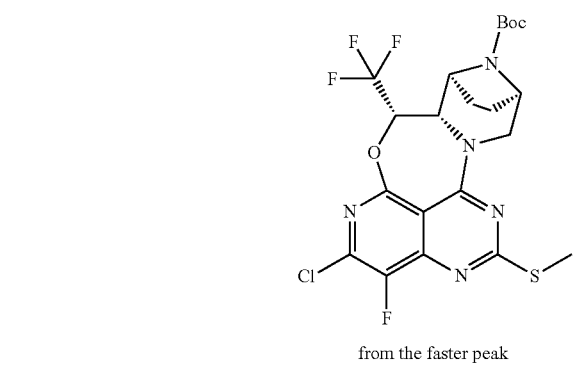

from the faster peak

Step 1: tert-Butyl (6S,9R,9aS)-3-oxo-1-(trifluoromethyl)hexahydro-1H,3H-6,9-epiminooxazolo[3,4-a]azepine-10-carboxylate To a solution of 3-benzyl 8-(tert-butyl) (1R,2S,5S)-2-(2,2,2-trifluoro-1-((trimethylsilyl)oxy)ethyl)-3,8-diazabicyclo[3.2.1]octane-3,8-dicarboxylate (2.00 g, 3.87 mmol, intermediate 163, step 3, compound A) in tetrahydrofuran (15.0 mL) was added tetrabutylammonium fluoride (3.90 mL, 1 M in THF) at room temperature. The resulting solution was stirred overnight at room temperature. The reaction system was diluted with EtOAc, washed with water. The organic layer was dried over anhydrous sodium sulfate and concentrated under vacuum. The residue was purified by C18 column (solvent gradient: 0-100% MeOH in water (0.05% NH$_4$HCO$_3$)) to afford 1.80 g (minor TBAF contaminant) of the title compound as a yellow solid. LC-MS: (ESI, m/z): [M+H]$^+$=337.

Step 2: tert-Butyl (1R,2S,5S)-2-(2,2,2-trifluoro-1-hydroxyethyl)-3,8-diazabicyclo[3.2.1]octane-8-carboxylate A solution of tert-butyl (6S,9R,9aS)-3-oxo-1-(trifluoromethyl)hexahydro-1H,3H-6,9-epiminooxazolo[3,4-a]azepine-10-carboxylate (1.70 g, 5.05 mmol) and NaOH (2.01 g, 50.2 mmol) in ethanol (25.0 mL) and water (5.0 mL) was stirred for 1 h at 80° C. Solid was filtered, and the filtrate was evaporated under vacuum to afford 850 mg (crude) the title compound as a yellow solid. LC-MS: (ESI, m/z): [M+H]$^+$=311. The crude was use for next step without further purification.

Step 3: tert-Butyl (1S,2S,5R)-2-((S)-1-((7-chloro-8-fluoro-2-(methylthio)-4-oxo-3,4-dihydropyrido[4,3-d]pyrimidin-5-yl)oxy)-2,2,2-trifluoroethyl)-3,8-diazabicyclo[3.2.1]octane-8-carboxylate & tert-butyl (1S,2S,5R)-2-((R)-1-((7-chloro-8-fluoro-2-(methylthio)-4-oxo-3,4-dihydropyrido[4,3-d]pyrimidin-5-yl)oxy)-2,2,2-trifluoroethyl)-3,8-diazabicyclo[3.2.1]octane-8-carboxylate

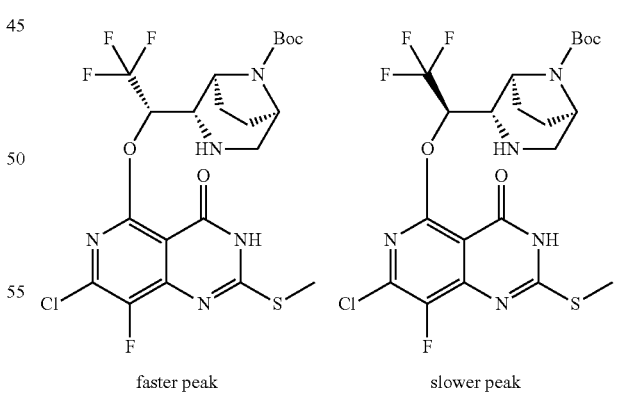

faster peak    slower peak

Under nitrogen, to a solution of tert-butyl (1R,2S,5S)-2-(2,2,2-trifluoro-1-hydroxyethyl)-3,8-diazabicyclo[3.2.1]octane-8-carboxylate (0.30 g, 0.97 mmol) in tetrahydrofuran (10.0 mL) was added NaH (232 mg, 5.81 mmol, 60% in mineral oil) at 0° C. The resulting solution was stirred for 30 min at 0° C. Then 5,7-dichloro-8-fluoro-2-(methylthio)pyrido[4,3-d]pyrimidin-4(3H)-one (405 mg, 1.45 mmol)

was added at 0° C., and the mixture was stirred for 3 h at room temperature, the reaction was quenched with NH₄Cl aqueous and extracted with EtOAc. The combined organic layers were dried over anhydrous sodium sulfate and concentrated under vacuum. The residue was purified by flash chromatography on silica gel (gradient: 0-50% EtOAc/petroleum ether and then 10% MeOH/DCM) to afford 0.40 g of the faster peak (EtOAc/petroleum ether fraction) and 0.17 g of the slower peak (MeOH/DCM fraction) as yellow solids. LC-MS: (ESI, m/z): [M+H]⁺=554.

Faster peak: ¹H NMR (500 MHz, DMSO-$d_6$) δ 5.41 (s, 1H), 4.15-3.91 (m, 3H), 3.28 (s, 1H), 2.81 (s, 1H), 2.64-2.58 (m, 1H), 2.39 (d, J=4.7 Hz, 3H), 1.75-1.64 (m, 4H), 1.43 (s, 9H).

Slower peak: ¹H NMR (3-0 MHz, DMSO-$d_6$) δ 6.06-5.63 (m, 1H), 4.13-3.94 (m, 3H), 3.17 (s, 2H), 2.87-2.75 (m, 1H), 2.59 (d, J=2.7 Hz, 3H), 2.28-2.05 (m, 1H), 1.85-1.61 (m, 3H), 1.41 (d, J=9.7 Hz, 9H).

Step 4: tert-Butyl (5S,5aS,6S,9R)-2-chloro-1-fluoro-12-(methylthio)-5-(trifluoromethyl)-5a,6,7,8,9,10-hexahydro-5H-4-oxa-3,10a,11,13,14-pentaaza-6,9-methanonaphtho[1,8-ab]heptalene-14-carboxylate A solution of tert-butyl (1S,2S,5R)-2-((S)-1-((7-chloro-8-fluoro-2-(methylthio)-4-oxo-3,4-dihydropyrido[4,3-d]pyrimidin-5-yl)oxy)-2,2,2-trifluoroethyl)-3,8-diazabicyclo[3.2.1]octane-8-carboxylate and tert-butyl (1S,2S,5R)-2-((R)-1-((7-chloro-8-fluoro-2-(methylthio)-4-oxo-3,4-dihydropyrido[4,3-d]pyrimidin-5-yl)oxy)-2,2,2-trifluoroethyl)-3,8-diazabicyclo[3.2.1]octane-8-carboxylate (the faster peak of last step) (400 mg, 0.724 mmol), bis(2-oxooxazolidin-3-yl)phosphinic chloride (735 mg, 2.89 mmol) and N-ethyl-N-isopropylpropan-2-amine (1.40 g, 10.8 mmol) in 1,2-dichloroethane (10.0 mL) was stirred for 8 h at 60° C. The solid was filtered, and the filtrate was evaporated under vacuum. The residue was purified by flash chromatography on silica gel (gradient: 0-30% EtOAc/petroleum ether) to afford 0.080 g of the title compound as a yellow solid. LC-MS: (ESI, m/z): [M+H]⁺=536.

Intermediate 167: tert-Butyl (5S,5aS,6S,9R)-2-chloro-1-fluoro-12-(methylsulfonyl)-5-(trifluoromethyl)-5a,6,7,8,9,10-hexahydro-5H-4-oxa-3,10a,11,13,14-pentaaza-6,9-methanonaphtho[1,8-ab]heptalene-14-carboxylate

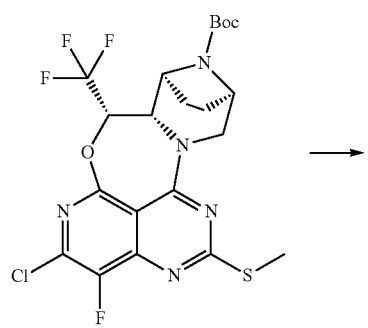

→

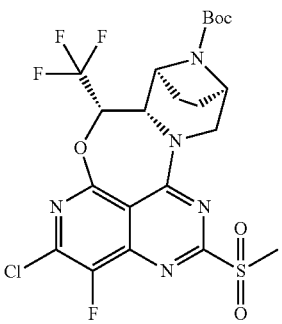

Under nitrogen, to a solution of tert-butyl (5S,5aS,6S,9R)-2-chloro-1-fluoro-12-(methylthio)-5-(trifluoromethyl)-5a,6,7,8,9,10-hexahydro-5H-4-oxa-3,10a,11,13,14-pentaaza-6,9-methanonaphtho[1,8-ab]heptalene-14-carboxylate (0.080 g, 0.15 mmol) in ethyl acetate (2.0 mL) was added 3-chlorobenzoperoxoic acid (77.2 mg, 0.450 mmol) at 0° C. The resulting solution was stirred for 1 h at room temperature. The reaction was quenched with Na₂S₂O₃ aqueous and extracted with EtOAc. The combined organic layers were dried over anhydrous sodium sulfate and concentrated under vacuum. The residue was purified by flash chromatography on silica gel (gradient: 0-50% EtOAc/petroleum ether) to afford 51.0 mg of the title compound as a white solid. LC-MS: (ESI, m/z): [M+H]⁺=568.

Intermediate 168: tert-Butyl (5aR,6S,9R)-2-chloro-1-fluoro-12-(methylthio)-5-(trifluoromethyl)-5a,6,7,8,9,10-hexahydro-5H-4-oxa-3,10a,11,13,14-pentaaza-6,9-methanonaphtho[1,8-ab]heptalene-14-carboxylate

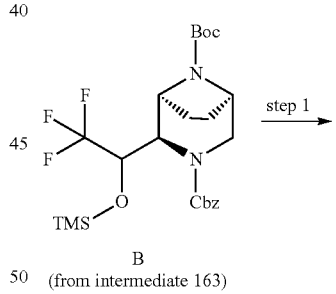

B
(from intermediate 163)

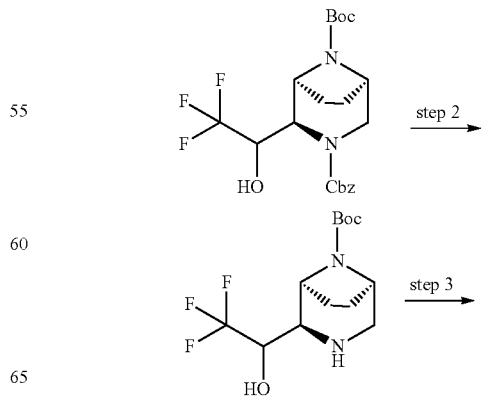

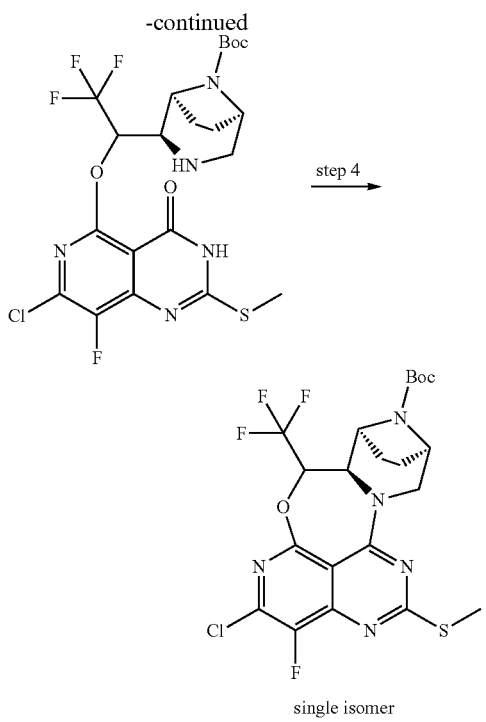

Step 1: 3-Benzyl 8-(tert-butyl) (1R,2R,5S)-2-(2,2,2-trifluoro-1-hydroxyethyl)-3,8-diazabicyclo[3.2.1]octane-3,8-dicarboxylate (mixture of two isomers, ~1:15 by FNMR)

To a solution of 3-benzyl 8-(tert-butyl) (1R,2R,5S)-2-(2,2,2-trifluoro-1-((trimethylsilyl)oxy)ethyl)-3,8-diazabicyclo[3.2.1]octane-3,8-dicarboxylate (intermediate 163, step 3, compound B) (3.80 g, 7.36 mmol) in tetrahydrofuran (40.0 mL) was added tetrabutylammonium fluoride (7.4 mL, 1 M in THF) at room temperature. The solution was stirred overnight at room temperature. The reaction system was diluted with EtOAc and washed with water. The organic layer was dried over anhydrous sodium sulfate and concentrated under vacuum. The crude was purified by C18 column (solvent gradient: 0-100% MeOH in water (0.05% NH$_4$HCO$_3$)) to afford 2.4 g of the title compound as a yellow oil. LC-MS: (ESI, m/z): [M+H]$^+$=445.

Step 2: tert-Butyl (1R,2R,5S)-2-(2,2,2-trifluoro-1-hydroxyethyl)-3,8-diazabicyclo[3.2.1]octane-8-carboxylate Under hydrogen (1 atm), to a solution of 3-benzyl 8-(tert-butyl) (1R,2R,5S)-2-(2,2,2-trifluoro-1-hydroxyethyl)-3,8-diazabicyclo[3.2.1]octane-3,8-dicarboxylate (2.35 g, 5.29 mmol) in methyl alcohol (30.0 mL) was added Pd/C (522 mg, 10%). The resulting solution was stirred for 1 h at room temperature. The solid was filtered, and the filtrate was evaporated under vacuum to afford 1.6 g (crude) of the title compound as a yellow oil. LC-MS: (ESI, m/z): [M+H]$^+$=311.

Step 3: tert-Butyl (1S,2R,5R)-2-(1-((7-chloro-8-fluoro-2-(methylthio)-4-oxo-3,4-dihydropyrido[4,3-d]pyrimidin-5-yl)oxy)-2,2,2-trifluoroethyl)-3,8-diazabicyclo[3.2.1]octane-8-carboxylate Under nitrogen, to a solution of tert-butyl (1R,2R,5S)-2-(2,2,2-trifluoro-1-hydroxyethyl)-3,8-diazabicyclo[3.2.1]octane-8-carboxylate (1.0 g, 3.2 mmol) in tetrahydrofuran (20.0 mL) was added NaH (774 mg, 19.4 mmol, 60% in mineral oil) at 0° C. The resulting solution was stirred for 30 min at 0° C. Then 5,7-dichloro-8-fluoro-2-(methylthio)pyrido[4,3-d]pyrimidin-4(3H)-one (1.35 g, 4.82 mmol) was added at 0° C., and the mixture was stirred for 3 h at room temperature. The reaction system was quenched with NH$_4$Cl aqueous and extracted with EtOAc. The combined organic layers were dried over anhydrous sodium sulfate and concentrated under vacuum. The residue was purified by flash chromatography on silica gel (gradient: 0-10% MeOH/DCM) to afford 1.5 g of the title compound as a yellow solid. LC-MS: (ESI, m/z): [M+H]$^+$=554.

Step 4: tert-Butyl (5aR,6S,9R)-2-chloro-1-fluoro-12-(methylthio)-5-(trifluoromethyl)-5a,6,7,8,9,10-hexahydro-5H-4-oxa-3,10a,11,13,14-pentaaza-6,9-methanonaphtho[1,8-ab]heptalene-14-carboxylate A solution of tert-butyl (1S,2R,5R)-2-(1-((7-chloro-8-fluoro-2-(methylthio)-4-oxo-3,4-dihydropyrido[4,3-d]pyrimidin-5-yl)oxy)-2,2,2-trifluoroethyl)-3,8-diazabicyclo[3.2.1]octane-8-carboxylate (1.5 g, 2.7 mmol), bis(2-oxooxazolidin-3-yl)phosphinic chloride (2.76 g, 10.9 mmol) and N-ethyl-N-isopropylpropan-2-amine (5.25 g, 40.7 mmol) in dichloromethane (30 mL) was stirred overnight at room temperature. The solvent was evaporated under vacuum. The residue was purified by flash chromatography on silica gel (gradient: 0-30% EtOAc/petroleum ether) to afford 764 mg of the title compound as a yellow solid. LC-MS: (ESI, m/z): [M+H]$^+$=536. Note: only one isomer was obtained.

Intermediate 169: tert-Butyl (5aR,6S,9R)-2-chloro-1-fluoro-12-(methylsulfonyl)-5-(trifluoromethyl)-5a,6,7,8,9,10-hexahydro-5H-4-oxa-3,10a,11,13,14-pentaaza-6,9-methanonaphtho[1,8-ab]heptalene-14-carboxylate

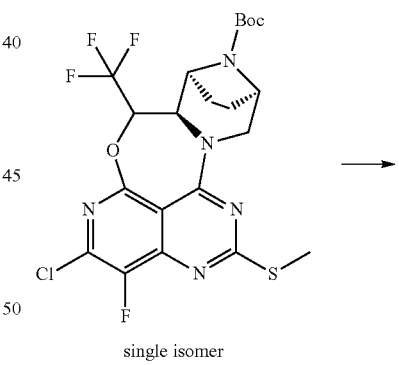

single isomer

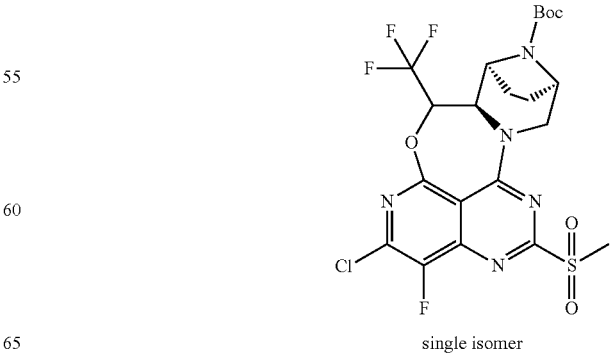

single isomer

Under nitrogen, to a solution of tert-butyl (5aR,6S,9R)-2-chloro-1-fluoro-12-(methylthio)-5-(trifluoromethyl)-5a,6,7,8,9,10-hexahydro-5H-4-oxa-3,10a,11,13,14-pentaaza-6,9-methanonaphtho[1,8-ab]heptalene-14-carboxylate (0.70 g, 1.3 mmol) in ethyl acetate (15 mL) was added 3-chlorobenzoperoxoic acid (679 mg, 3.93 mmol) at 0° C. The resulting solution was stirred for 1 h at room temperature. The reaction was quenched with Na$_2$S$_2$O$_3$ aqueous and extracted with EtOAc. The combined organic layers were dried over anhydrous sodium sulfate and concentrated under vacuum. The residue was purified by flash chromatography on silica gel (gradient: 0-50% EtOAc/petroleum ether) to afford 430 mg of the title compound as a white solid. LC-MS: (ESI, m/z): [M+H]$^+$=568.

Intermediates 170 & 171: (1-Methyltetrahydro-1H-furo[3,4-b]pyrrol-3a(4H)-yl)methanol (two isomers

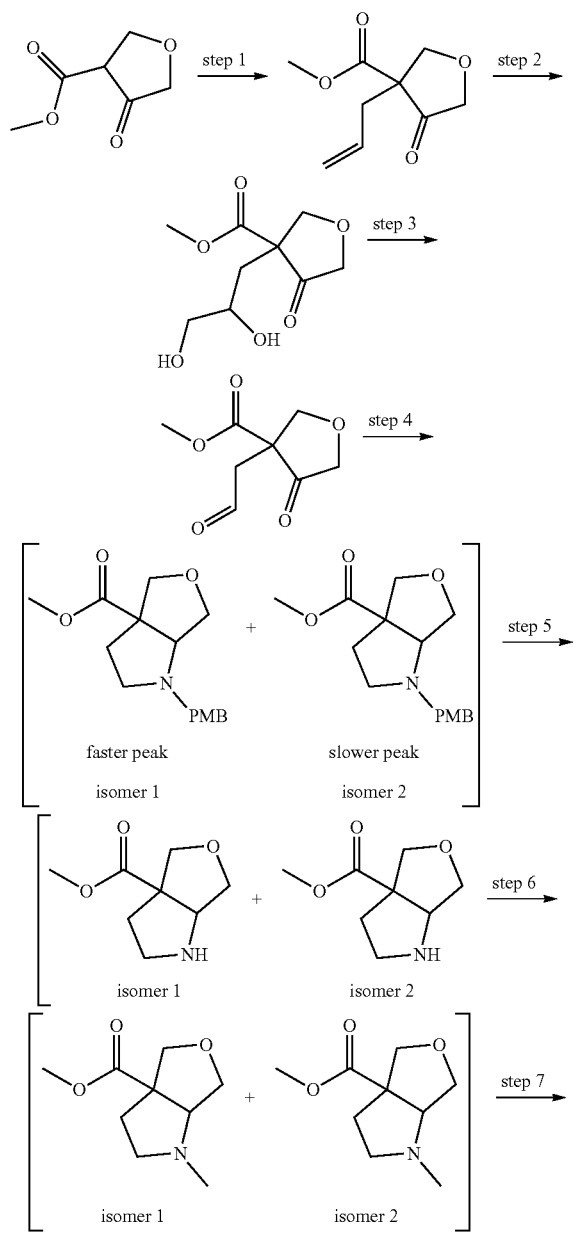

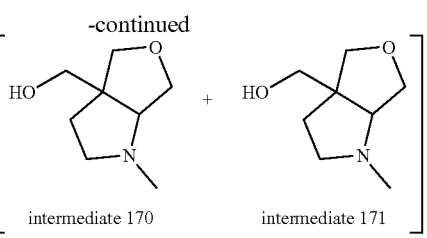

Step 1: Methyl 3-allyl-4-oxotetrahydrofuran-3-carboxylate

Under nitrogen, a mixture of methyl 4-oxotetrahydrofuran-3-carboxylate (25.0 g, 173 mmol), 3-bromoprop-1-ene (45.0 mL, 520 mmol) and K$_2$CO$_3$ (47.9 g, 347 mmol) in tetrahydrofuran (600 mL) was stirred overnight at 60° C. The resulting mixture was filtered and the filtrate was concentrated under vacuum. The residue was purified by flash chromatography on silica gel (gradient: 0-60% ethyl acetate in petroleum ether) to afford the title compound (20.3 g, 63.5% yield) as a colorless oil. LC-MS: (ESI, m/z): [M+H]$^+$=185. $^1$H NMR (400 MHz, DMSO-d6, ppm) δ 5.80-5.61 (m, 1H), 5.18-5.03 (m, 2H), 4.48 (d, J=9.6 Hz, 1H), 4.16-3.95 (m, 3H), 3.67 (s, 3H), 2.69-2.56 (m, 1H), 2.48-2.37 (m, 1H). $^{13}$C NMR (101 MHz, DMSO-d6, ppm) δ 210.45, 169.08, 132.80, 119.79, 73.40, 70.75, 59.20, 53.17, 36.08.

Step 2: Methyl 3-(2,3-dihydroxypropyl)-4-oxotetrahydrofuran-3-carboxylate

To a solution of methyl 3-allyl-4-oxotetrahydrofuran-3-carboxylate (5.00 g, 27.2 mmol) and NMO (6.36 g, 54.3 mmol) in acetone (40 mL) and water (5 mL) was added K$_2$OsO$_4$·2H$_2$O (500 mg, 1.36 mmol) at 0° C., and the mixture was stirred for 6 hours at room temperature. The reaction was quenched with solid Na$_2$S$_2$O$_3$. The resulting mixture was filtered and the filtrate was concentrated under vacuum to afford the title compound (6.50 g, crude) as a brown solid. LC-MS: (ESI, m/z): [M+H]$^+$=219.

Step 3: Methyl 4-oxo-3-(2-oxoethyl)tetrahydrofuran-3-carboxylate

To a mixture of methyl 3-(2,3-dihydroxypropyl)-4-oxo-tetrahydrofuran-3-carboxylate (6.50 g, crude) in acetone (54 mL) and water (6 mL) and was added NaIO$_4$ (8.82 g, 41.2 mmol) at 0° C. and stirred for 3 hours at 50° C. The resulting mixture was filtered and the filtrate was concentrated under vacuum. The residue was re-dissolved in dichloromethane, dried over anhydrous sodium sulfate and concentrated under vacuum to afford the title compound (4.20 g, crude) as a light yellow oil. LC-MS: (ESI, m/z): [M+H]$^+$=187.

Step 4: Methyl 1-(4-methoxybenzyl)tetrahydro-1H-furo[3,4-b]pyrrole-3a(4H)-carboxylate (two isomers)

To a solution of methyl 4-oxo-3-(2-oxoethyl) tetrahydrofuran-3-carboxylate (2.00 g, crude) and (4-methoxyphenyl)methanamine (1.47 g, 10.7 mmol) in dichloromethane (10 mL) was added NaBH$_3$CN (2.03 g, 32.2 mmol) in portions at 0° C. and stirred for 1 hour at room temperature. The reaction was quenched with water and extracted with ethyl acetate. The combined organic layers were washed with brine, dried over anhydrous sodium sulfate and concentrated under vacuum. The residue was purified by flash chromatography on silica gel (gradient: 0-60% ethyl acetate in petroleum ether) to afford a mixture of isomers (990 mg, 31.7% yield) as a colorless oil. Two isomers were separated by chiral prep. HPLC with the following conditions: (Column: CHIRALPAK IH, 2*25 cm, 5 µm; Mobile Phase A: Hex (0.1% DEA)-H—C, Mobile Phase B: IPA-HPLC; Flow rate: 20 mL/min; Gradient: isocratic 70; Wave Length: 220/254 nm; RT1(min): 6.443; RT2(min): 8.6-; Sample Solvent: EtOH—HPLC; Injection Volume: 0.5 mL; Number Of Runs: 21) to afford isomer 1 (340 mg, 10.9% yield, the faster peak) and isomer 2 (300 mg, 9.60% yield, the slower peak) as colorless oil. LC-MS: (ESI, m/z): [M+H]⁺=292.

Step 5: Methyl tetrahydro-1H-furo[3,4-b]pyrrole-3a (4H)-carboxylate (two isomers)

Under hydrogen, a mixture of methyl 1-(4-methoxybenzyl)tetrahydro-1H-furo[3,4-b]pyrrole-3a(4H)-carboxylate (340 mg, 1.16 mmol, isomer 1 of last Step) and 10% Pd/C (124. mg, 0.120 mmol) in methanol (30 mL) was stirred overnight at room temperature. The resulting mixture was filtered over celite. The filtrate was concentrated under vacuum to afford the title compound (230 mg, crude) as a light yellow oil. LC-MS: (ESI, m/z): [M+H]⁺=172.

Analogous to method described as above, isomer 2 (200 mg, crude) was prepared from isomer 2 of the last step (300 mg, 1.03 mmol) as a light yellow oil. LC-MS: (ESI, m/z): [M+H]⁺=172.

Step 6: Methyl 1-methyltetrahydro-1H-furo[3,4-b] pyrrole-3a(4H)-carboxylate (two isomers)

To a mixture of methyl tetrahydro-1H-furo[3,4-b]pyrrole-3a(4H)-carboxylate (100 mg, crude, isomer 1 of last step) and polyformaldehyde (87.2 mg, 0.968 mmol) in dichloromethane (5 mL) was added NaBH(OAc)₃ (618 mg, 2.92 mmol) in portions at 0° C., and the mixture was stirred for 1 hour at room temperature. The reaction was quenched with Na₂SO₄·10H₂O and filtered. The filtrate was concentrated under vacuum to afford the title compound (140 mg, crude) as a light yellow oil. LC-MS: (ESI, m/z): [M+H]⁺=186.

Analogous to the method described as above, isomer 2 (150 mg, crude) was prepared from isomer 2 of the last step (100 mg, crude) as a light yellow oil. LC-MS: (ESI, m/z): [M+H]⁺=186.

Step 7: (1-methyltetrahydro-1H-furo[3,4-b]pyrrol-3a (4H)-yl)methanol(two isomers)

To a solution of methyl-1-methyltetrahydro-1H-furo[3,4-b]pyrrole-3a(4H)-carboxylate (140 mg, crude, isomer 1 of the last step) in tetrahydrofuran (5 mL) was added LiAlH₄ (2.5 M solution in tetrahydrofuran, 0.3 mL, 0.750 mmol) at 0° C., and the mixture was stirred for 1 hour at room temperature. The reaction was quenched with Na₂SO₄·10H₂O and filtered over celite. The filtrate was concentrated under vacuum to afford intermediate 170 (90.0 mg, crude) as a light yellow oil. LC-MS: (ESI, m/z): [M+H]⁺=158.

Analogous to the method described as above, intermediate 171 (100 mg, crude) was prepared from isomer 2 of the last step (150 mg, crude) as a light yellow oil. LC-MS: (ESI, m/z): [M+H]⁺=158.

Intermediates 172, 173, 174, & 175: (1,1-Difluoro-5-methyl-5-azaspiro[2.3] hexan-4-yl)methanol (4 isomers

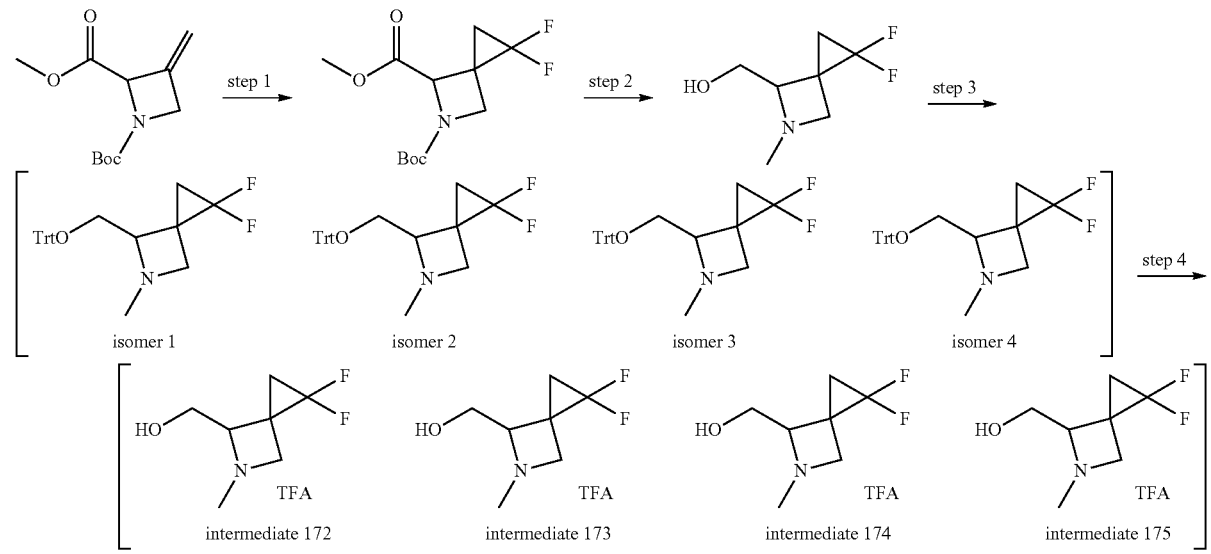

Step 1: 5-(tert-Butyl) 4-methyl 1,1-difluoro-5-azaspiro[2.3]hexane-4,5-dicarboxylate A solution of 1-(tert-butyl) 2-methyl 3-methyleneazetidine-1,2-dicarboxylate (750 mg, 3.30 mmol), TMSCF₃ (1.88 g, 13.2 mmol) and NaI (248 mg, 1.65 mmol) in tetrahydrofuran (5.00 mL) was stirred for overnight at 70° C. The reaction was cooled to room temperature, quenched with water and extracted with EtOAc. The combined organic layers were dried over anhydrous sodium sulfate and concentrated under vacuum. The residue was purified by flash chromatography on silica gel (gradient: 0-40% EtOAc in petroleum ether) to afford 541 mg (59.1% yield) of the title compound as a yellow oil. LC-MS: (ESI, m/z): [M+H]⁺= 278.

Step 2: (1,1-Difluoro-5-methyl-5-azaspiro[2.3]hexan-4-yl)methanol

Under nitrogen, to a solution of 5-(tert-butyl) 4-methyl 1,1-difluoro-5-azaspiro[2.3]hexane-4,5-dicarboxylate (541 mg, 1.95 mmol) in tetrahydrofuran (5.00 mL) was added LiAlH$_4$ (1.9 mL, 1 M in THF) at 0° C. The resulting solution was stirred for 2 h at 60° C. The mixture was quenched by Na$_2$SO$_4$·10H$_2$O and filtrated. The solvent was remove by blowing N$_2$ to afford 259 mg (81.3% yield) of the title compound as a yellow crude oil. LC-MS: (ESI, m/z): [M+H]$^+$=164.

Step 3: 1,1-Difluoro-5-methyl-4-((trityloxy)methyl)-5-azaspiro[2.3]hexane

To a solution of (1,1-difluoro-5-methyl-5-azaspiro[2.3]hexan-4-yl)methanol (259 mg, 1.59 mmol) and Et$_3$N (482 mg, 4.77 mmol) in dichloromethane (5.00 mL) was added (chloromethanetriyl)tribenzene (663 mg, 2.38 mmol). The resulting solution was stirred overnight at room temperature. The reaction was diluted with water and extracted with ethyl acetate. The combined organic layers were dried over anhydrous sodium sulfate and concentrated under vacuum. The residue was purified by flash chromatography on silica gel (gradient: 0-30% EtOAc in petroleum ether) to afford 61.0 mg of the faster peak (mixture of two isomers) and 326 mg of the slower peak (mixture of two isomers) as yellow solids. The faster peak was separated by chiral prep. HPLC (Column: CHIRAL ART Cellulose-SB, 2*25 cm, 5 μm; Mobile Phase—Hex(0.5% 2 M NH$_3$—MeOH)—HP—, Mobile Phase B: EtOH—HPLC; Flow rate: 20 mL/min; Gradient: isocratic 99; Wave Length: 220/254 n; RT1(min): 5.907; RT2(min): 6.8-; Sample Solvent: EtOH—HPLC; Injection Volume: 0.3 mL; Number Of Runs: 24) to afford 20.0 mg (3.10% yield) of isomer 1 and 23 mg (3.60% yield) of isomer 2. The slower peak was separated by chiral prep. HPLC (Column: SB 2 cm Hex(0.05% DEA): IPA=1000:1; Mobil-Phase A: Hex(0.1% DEA)—H—C, Mobile Phase B: IPA-HPLC; Flow rate: 20 mL/min; Gradient: isocratic 1000:1; Wave Length: 220/254 nm; RT1(min): 12.27; RT2(min): 16.-; Sample Solvent: EtOH—HPLC; Number Of Runs: 10) to afford 113 mg (17.6% yield) of isomer 3 and 105 mg (16.3% yield) of isomer 4.

Isomer 1: $^1$H NMR (500 MHz, DMSO-d$_6$, ppm) δ 7.42-7.36 (m, 6H), 7.35-7.33 (m, 6H), 7.30-7.23 (m, 3H), 3.51 (s, 1H), 3.44 (d, J=7.4 Hz, 1H), 3.15 (t, J=9.0 Hz, 1H), 2.97 (t, J=7.3 Hz, 1H), 2.90-2.83 (m, 1H), 2.53 (s, 3H), 1.47-1.42 (m, 2H).

Isomer 2: $^1$H NMR (500 MHz, DMSO-d$_6$, ppm) δ 7.41-7.37 (m, 6H), 7.35-7.33 (m, 6H), 7.30-7.23 (m, 3H), 3.51 (s, 1H), 3.44 (d, J=7.4 Hz, 1H), 3.15 (t, J=9.0 Hz, 1H), 2.97 (t, J=7.3 Hz, 1H), 2.90-2.84 (m, 1H), 2.53 (s, 3H), 1.47-1.42 (m, 2H).

Isomer 3: $^1$H NMR (500 MHz, DMSO-d$_6$, ppm) δ 7.40-7.32 (m, 12H), 7.32-7.24 (m, 3H), 3.39 (t, J=6.0 Hz, 1H), 3.35-3.29 (m, 1H), 3.16-3.12 (m, 1H), 3.08 (d, J=7.6 Hz, 1H), 2.84-2.81 (m, 1H), 2.36 (s, 3H), 1.40-1.33 (m, 2H).

Isomer 4: $^1$H NMR (500 MHz, DMSO-d$_6$, ppm) δ 7.40-7.32 (m, 12H), 7.32-7.24 (m, 3H), 3.39 (t, J=6.1 Hz, 1H), 3.34 (s, 1H), 3.16-3.12 (m, 1H), 3.08 (d, J=7.6 Hz, 1H), 2.84-2.81 (m, 1H), 2.36 (s, 3H), 1.42-1.29 (m, 2H).

Step 4: (1,1-Difluoro-5-methyl-5-azaspiro[2.3]hexan-4-yl)methanol

To a solution of 1,1-difluoro-5-methyl-4-((trityloxy)methyl)-5-azaspiro[2.3]hexane (20.0 mg, 0.0500 mmol) (isomer 1 of step 3) in dichloromethane (1.50 mL) was added TFA (0.500 mL). The resulting solution was stirred for 1 h at room temperature. Solvent was evaporated under vacuum to afford 44.0 mg (crude) intermediate 172 as a yellow solid. LC-MS: (ESI, m/z): [M+H]$^+$=164. The crude was used for next step without further purification.

Analogous to the method described above, intermediates 173, 174, and 175 were prepared from isomers 2, 3, and 4, respectively, of step 3.

Intermediate 176: 6-(Difluoromethyl)-N,N-bis(4-methoxybenzyl)-4-(4,4,5,5-tetramethyl-dioxaborolan-2-yl)pyridin-2-amine

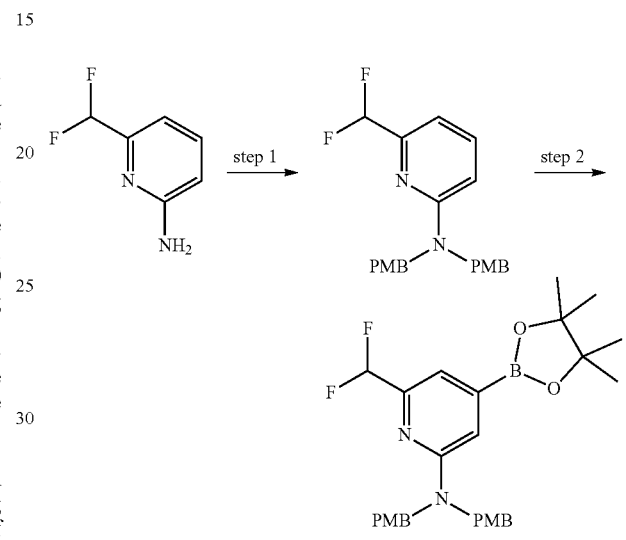

Step 1: 6-(Difluoromethyl)-N,N-bis(4-methoxybenzyl)pyridin-2-amine

To a solution of 6-(difluoromethyl)pyridin-2-amine (200 mg, 1.39 mmol) in N,N-dimethylformamide (8 mL) was added NaH (60% dispersion in mineral oil, 278 mg, 6.94 mmol) in portions at 0° C. and stirred for 30 minutes at room temperature. Then PMBCl (541 mg, 3.47 mmol) was added and stirred for 2 hours at room temperature. The reaction was quenched with saturated NH$_4$Cl aqueous solution. The reaction mixture was diluted with water and extracted with ethyl acetate. The combined organic layers were washed with brine, dried over anhydrous sodium sulfate and concentrated under vacuum. The residue was purified by flash chromatography on silica gel (gradient: 0-10% methanol in dichloromethane) to afford the title compound (500 mg, 93.7% yield) as a brown solid. LC-MS: (ESI, m/z): [M+H]$^+$= 385.

Step 2: 6-(Difluoromethyl)-N,N-bis(4-methoxybenzyl)-4-(4,4,5,5-tetramethyl-dioxaborolan-2-yl)pyridin-2-amine Under nitrogen, a solution of Pin$_2$B$_2$ '661 mg, 2.60 mmol)'4,4'-di-tert-butyl-2,2'-bipyridine (69.8 mg, 0.260 mmol) and methoxy(cyclooctadiene)iridium(I) dimer (86.2 mg, 0.130 mmol) in hexane (30 mL) was stirred for 10 minutes at 50° C. to afford a dark-red solution. Then a suspension of 6-(difluoromethyl)-N,N-bis(4-methoxybenzyl)pyridin-2-amine (500 mg, 1.3 mmol) in hexane (10 mL) was added, and the mixture was stirred for 3 hours at 50° C.

The solvent was concentrated under vacuum. The residue was purified by flash chromatography on silica gel (gradient: 0-10% methanol in dichloromethane) to afford the title compound (370 mg, 55.7% yield) as a colorless oil. LC-MS: (ESI, m/z): [M+H]⁺=511. ¹H NMR (300 MHz, DMSO-d6, ppm) δ 7.23-7.12 (m, 4H), 7.02 (s, 1H), 6.98-6.55 (m, 6H), 4.70 (s, 4H), 3.72 (s, 6H), 1.26 (s, 12H).

Intermediate 177: (6-(Bis(4-methoxybenzyl)amino)-2-methyl-3-(trifluoromethyl) pyridin-4-yl) boronic acid

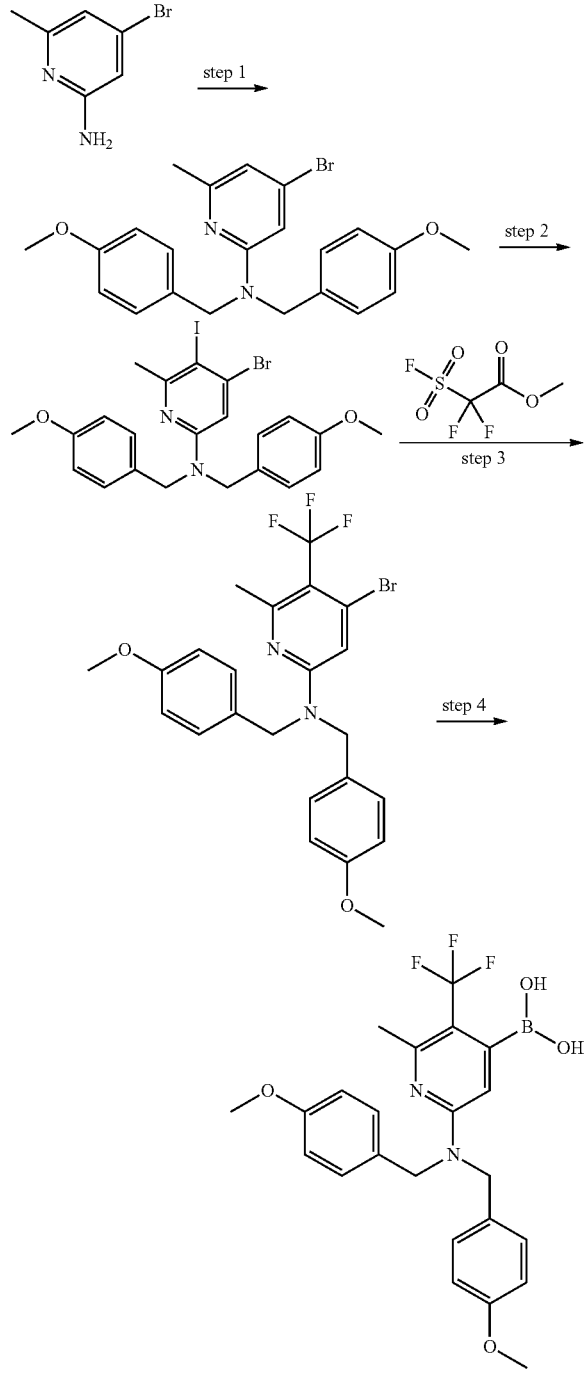

Step 1: 4-Bromo-N, N-bis(4-methoxybenzyl)-6-methylpyridin-2-amine

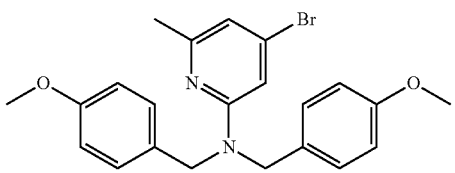

Under nitrogen, to a solution of 4-bromo-6-methylpyridin-2-amine (1.0 g, 5.35 mmol) was added NaH (535 mg, 13.4 mmol, 60% oil suspension) at 0° C. The mixture was stirred for 20 min. PMBCl (1.85 g, 11.8 mmol) was added and the mixture was allowed to warm to room temperature and stirred additional 1 hour. The reaction was quenched with water. The resulting mixture was extracted with EtOAc. The combined organic layers were washed with brine, dried over anhydrous sodium sulfate and concentrated under vacuum. The residue was purified by flash chromatography on silica gel (gradient: 0-20% EtOAc in petroleum ether) to afford the title compound (2.20 g, 94.7% yield) as a white solid. LC-MS: (ESI, m/z): [M+H]⁺=427.

Step 2: 4-Bromo-5-iodo-N, N-bis(4-methoxybenzyl)-6-methylpyridin-2-amine

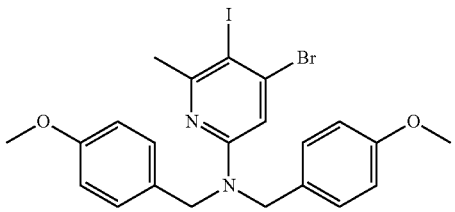

A solution of 4-bromo-N N-bis(4-methoxybenzyl)-6-methylpyridin-2-amine (2.10 g, 4.91 mmol) and NIS (1.11 g, 4.91 mmol) in acetic acid (20 mL) was stirred at room temperature for 30 min. The reaction was quenched by water. The resulting mixture was extracted with EtOAc. The combined organic layers were washed with brine, dried over anhydrous sodium sulfate and concentrated under vacuum. The residue was purified by flash chromatography on silica gel (gradient: 0-20% EtOAc in petroleum ether) to afford the title compound (2.60 g, 89% yield) as a white solid. LC-MS: (ESI, m/z): [M+H]⁺=553.

Step 3: 4-Bromo-N,N-bis(4-methoxybenzyl)-6-methyl-5-(trifluoromethyl)pyridin-2-amine

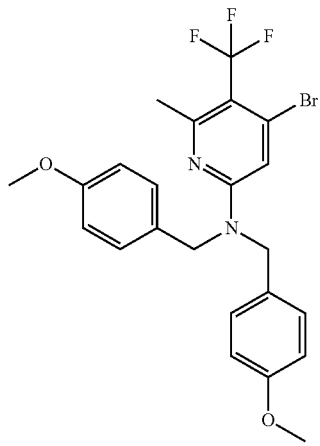

Under nitrogen, a solution of 4-bromo-5-iodo-N, N-bis(4-methoxybenzyl)-6-methylpyridin-2-amine (2.58 g, 4.66 mmol), methyl 2,2-difluoro-2-(fluorosulfonyl) acetate (5.94 mL, 46.6 mmol) and CuI (8.86 g, 46.6 mmol) in N, N-dimethylacetamide (25 mL) was stirred at 90° C. for 1 hour. The solution was cooled to room temperature. The resulting mixture was filtered. The filtrate was concentrated under reduced pressure. The crude product was diluted with EtOAc, washed with water. The organic layer was dried over anhydrous Na$_2$SO$_4$ and concentrated under vacuum. The residue was purified by flash chromatography on silica gel (gradient: 0-20% EtOAc in petroleum ether) to afford the title compound (1.92 g, 71% yield) as a white solid. LC-MS: (ESI, m/z): [M+H]$^+$=495.

Step 4: (6-(Bis(4-methoxybenzyl) amino)-2-methyl-3-(trifluoromethyl) pyridin-4-yl) boronic acid

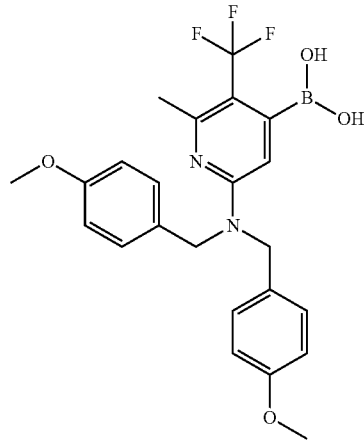 [SMILES: COc1ccc(CN(Cc2ccc(OC)cc2)c2cc(B(O)O)c(C(F)(F)F)c(C)n2)cc1]

Under nitrogen, to a solution of 4-bromo-N, N-bis(4-methoxybenzyl)-6-methyl-5-(trifluoromethyl) pyridin-2-amine (1.83 g, 3.69 mmol) and triisopropyl borate (1.28 mL, 5.54 mmol) in tetrahydrofuran (20 mL) was added a solution of n-BuLi (2.77 mL, 1.6 M in hexane) at −78° C., and the mixture was stirred at −78° C. for 1 hour. The reaction was quenched with water. The resulting mixture was extracted with EtOAc. The combined organic layers were washed with brine, dried over anhydrous sodium sulfate and concentrated under vacuum. The residue was purified by flash chromatography on silica gel (gradient: 0-40% EtOAc in petroleum ether) to afford the title compound (562 mg, 31.3% yield) as a white oil. LC-MS: (ESI, m/z): [M+H]$^+$=461.

COMPOUNDS

Example 1: Compound 1

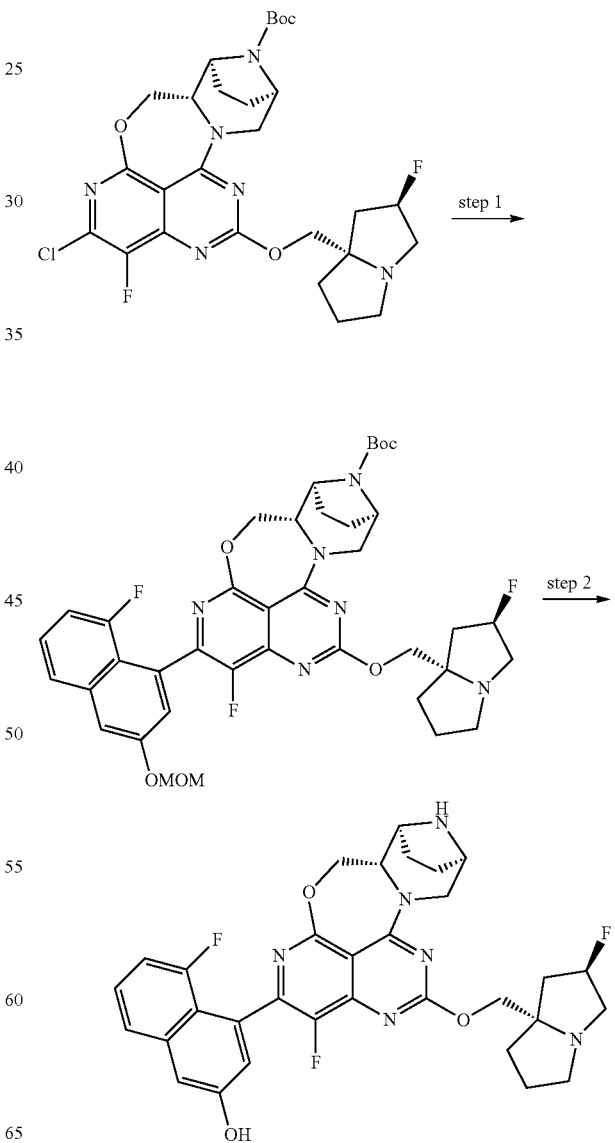

Step 1: tert-Butyl (5aS,6S,9R)-1-fluoro-2-(8-fluoro-3-(methoxymethoxy)naphthalen-1-yl)-12-(((2R,7aS)-2-fluorotetrahydro-1H-pyrrolizin-7a(5H)-yl)methoxy)-5a,6,7,8,9,10-hexahydro-5H-4-oxa-3,10a,11,13,14-pentaaza-6,9-methanonaphtho[1,8-ab]heptalene-14-carboxylate

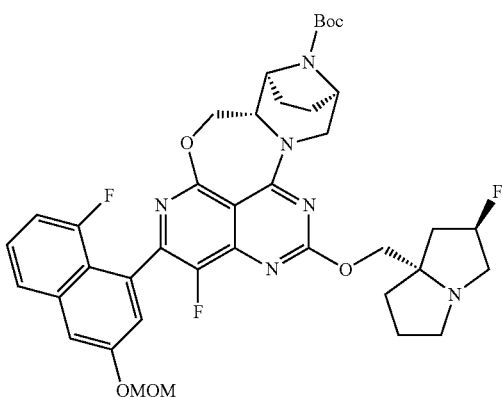

Under nitrogen, a solution of tert-butyl (5aS,6S,9R)-2-chloro-1-fluoro-12-(((2R,7aS)-2-fluorotetrahydro-1H-pyrrolizin-7a(5H)-yl)methoxy)-5a,6,7,8,9,10-hexahydro-5H-4-oxa-3,10a,11,13,14-pentaaza-6,9-methanonaphtho[1,8-ab]heptalene-14-carboxylate (40.6 mg, 0.0700 mmol, intermediate 9), Pd(PPh$_3$)$_4$ (39.5 mg, 0.0300 mmol), 2-(8-fluoro-3-(methoxymethoxy)naphthalen-1-yl)-4,4,5,5-tetramethyl-1,3,2-dioxaborolane (34.1 mg, 0.100 mmol, intermediate 25), Cs$_2$CO$_3$ (66.9 mg, 0.210 mmol) and H$_2$O (0.5 mL) in 1,4-dioxane (5 mL) was stirred for 1.5 h at 95° C. The reaction mixture was diluted with water (20 mL) and extracted with EtOAc (30 mL*2). The combined organic layers were dried over anhydrous sodium sulfate and concentrated under vacuum. The residue was purified by flash chromatography on silica gel eluting with CH$_3$OH/DCM (0-10%) to afford the title compound (40.6 mg, 77.7%) as white solid. LC-MS: (ESI, m/z): [M+H]$^+$=750.

Step 2: 5-Fluoro-4-((5aS,6S,9R)-1-fluoro-12-(((2R,7aS)-2-fluorotetrahydro-1H-pyrrolizin-7a(5H)-yl)methoxy)-5a,6,7,8,9,10-hexahydro-5H-4-oxa-3,10a,11,13,14-pentaaza-6,9-methanonaphtho[1,8-ab]heptalen-2-yl)naphthalen-2-ol (Compound 1)

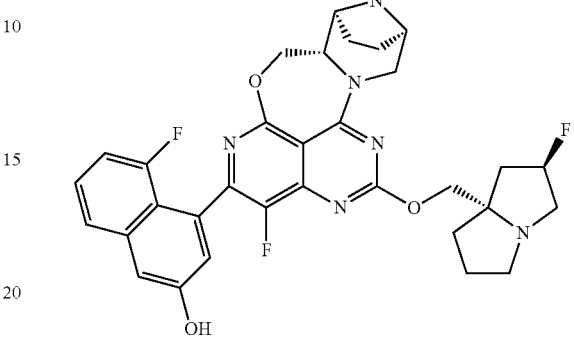

A solution of tert-butyl (5aS,6S,9R)-1-fluoro-2-(8-fluoro-3-(methoxymethoxy)naphthalen-1-yl)-12-(((2R,7aS)-2-fluorotetrahydro-1H-pyrrolizin-7a(5H)-yl)methoxy)-5a,6,7,8,9,10-hexahydro-5H-4-oxa-3,10a,11,13,14-pentaaza-6,9-methanonaphtho[1,8-ab]heptalene-14-carboxylate (40.6 mg, 0.0542 mmol) in TFA (1 mL) and DCM (4 mL) was stirred at room temperature for 1.5 hours and then concentrated under vacuum. The residue was purified by Prep-HPLC (Column: XBridge Prep OBD C18 Column, 30×150 mm 5 μm; Mobile Phase A: water (10 mmol/L NH$_4$HCO$_3$), Mobile Phase B: ACN; Flow rate:60 mL/min; Gradient:14B to 48B in 7 min; 254 nm; R$_{T1}$:6.7) to afford the title compound 12.3 mg (37.5% yield) as a white solid. LC-MS: (ESI, m/z): [M+H]$^+$=604. $^1$H NMR (400 MHz, DMSO-d$_6$, ppm) δ 10.18 (s, 1H), 7.65 (d, J=8.3 Hz, 1H), 7.49-7.30 (m, 2H), 7.22-6.86 (m, 2H), 5.50-5.08 (m, 1H), 4.86-4.76 (m, 1H), 4.53 (d, J=13.0 Hz, 1H), 4.46-4.34 (m, 1H), 4.16-4.06 (m, 1H), 4.05-3.95 (m, 2H), 3.61 (d, J=5.9 Hz, 1H), 3.55-3.49 (m, 1H), 3.16-2.99 (m, 4H), 2.88-2.89 (m, 2H), 2.17-2.10 (m, 1H), 2.11-1.94 (m, 2H), 1.93-1.49 (m, 7H).

Each compound in the Table below was prepared following a similar experimental procedure (using appropriately substituted reagents) as described for Example 1.

| Cmpd. No. | $^1$H NMR | MS (M + H)$^+$ |
|---|---|---|
| 2 | $^1$H NMR (300 MHz, DMSO-d$_6$, ppm) δ 8.21-8.14 (m, 1H), 8.08 (d, J = 8.1 Hz, 1H), 7.76-7.48 (m, 4H), 5.28 (d, J = 54.3 Hz, 1H), 4.84 (d, J = 13.2 Hz, 1H), 4.58-4.31(m, 2H), 4.16-3.96 (m, 3H), 3.68-3.58 (m, 2H), 3.16-3.01 (m, 4H), 2.83-2.77 (m, 2H), 2.15 (d, J = 5.5 Hz, 1H), 2.07-1.92 (m, 2H), 1.92-1.50 (m, 7H). | 606 |
| 3 | $^1$H NMR (400 MHz, DMSO-d$_6$, ppm) δ 10.12 (s, 1H), 7.87-7.85 (m, 1H), 7.45-7.42 (m, 2H), 7.31 (s, 1H), 7.08 (dd, J = 39.0, 2.6 Hz, 1H), 5.56-5.09 (m, 1H), 4.94-4.73 (m, 1H), 4.59-4.46 (m, 1H), 4.48-4.34 (m, 1H), 4.09 (dd, J = 10.3, 5.6 Hz, 1H), 4.04-3.94 (m, 2H), 3.74 (d, J = 46.7 Hz, 1H), 3.61 (d, J = 5.9 Hz, 1H), 3.51 (d, J = 5.9 Hz, 1H), 3.16-2.99 (m, 4H), 2.86-2.81 (m, 2H), 2.09-1.92 (m, 3H), 1.83-1.51 (m, 7H). | 611 |
| 4 | $^1$H NMR (300 MHz, DMSO-d$_6$, ppm): δ 8.16 (d, J = 2.8 Hz, 1H), 7.95 (dd, J = 8.8, 5.2 Hz, 1H), 7.24-7.11 (m, 1H), 5.27 (d, J = 54 Hz, 1H), 4.82 (dd, J = 12.9, 2.2 Hz, 1H), 4.51-4.35 (m, 2H), 4.21-4.17 (m, 1H), 4.01 (d, J = 10.3 Hz, 2H), 3.78-3.69 (m, 3H), 3.51-3.59 (m, 3H), 3.15-3.01 (m, 3H), 2.98-2.93 (m, 1H), 2.82 (q, J = 8.5, 8.0 Hz, 1H), 2.13 (s, 1H), 2.06-1.92 (m, 2H), 1.92-1.66 (m, 7H). | 593 |
| 5 | $^1$H NMR (300 MHz, DMSO-d$_6$, ppm): δ 9.89 (s, 1H), 7.65 (d, J = 9 Hz, 1H), 7.42-7.31 (m, 1H), 7.26 (t, J = 2.5 Hz, 1H), 7.13 (t, J = 9 Hz, 1H), 7.00 (d, J = 2.6 Hz, 1H), 6.89 (d, J = 2.6 Hz, 1H), 5.38 (s, 1H), 5.20 (s, 1H), 4.78-4.28 (m, 2H), 4.14-4.01 (m, 3H), 3.63 (s, 2H), 3.12-3.01 (m, 4H), 2.90-2.77 (m, 1H), 2.46-2.33 (m, 1H), 2.32-2.18 (m, 2H), 2.08-1.98 (m, 2H), 1.94-1.65 (m, 7H), 0.92-0.83 (m, 3H). | 615 |

Example 6: Compound 6

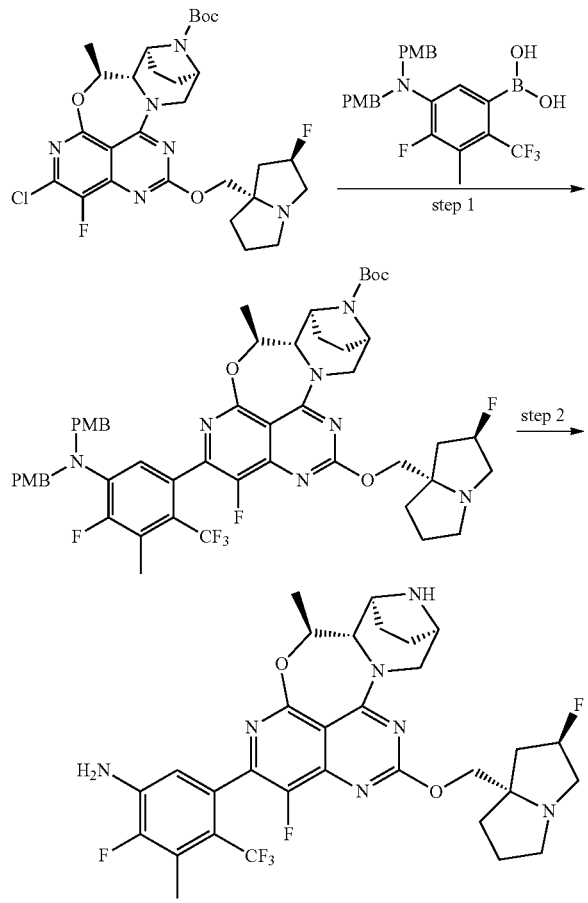

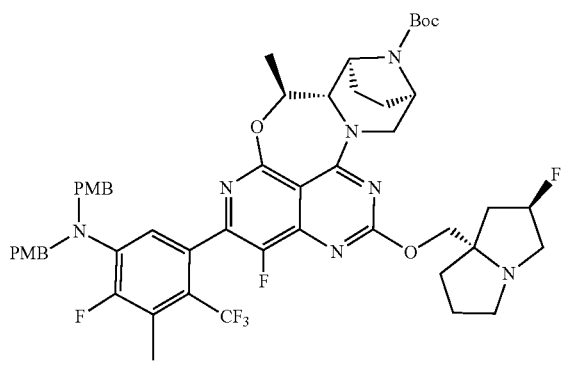

Step 1: tert-Butyl (5S,5aS,6S,9R)-2-(5-(bis(4-methoxybenzyl)amino)-4-fluoro-3-methyl-2-(trifluoromethyl)phenyl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate Under nitrogen, a solution of (5-(bis(4-methoxybenzyl)amino)-4-fluoro-3-methyl-2-(trifluoromethyl)phenyl)boronic acid (161 mg, 0.338 mmol, intermediate 20), tert-butyl (5S,5aS,6S,9R)-2-chloro-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (80.2 mg, 0.131 mmol, intermediate 12), K$_3$PO$_4$ (1.6 mL, 1.5 M in water) and cataCXium A Pd G3 (19.9 mg, 0.0300 mmol) in THF (8 mL) was stirred for 6 hours at 60° C. The reaction mixture was diluted with H$_2$O (5 mL) and extracted with EtOAc. The combined organic layers were dried over anhydrous sodium sulfate and concentrated under vacuum. The residue was purified by flash chromatography on silica gel eluting with MeOH/DCM (0-10%) to yield 130 mg (77.9% yield) of the title compound as a white solid. LC-MS: (ESI, m/z): [M+H]$^+$=990.

Step 2: 2-Fluoro-5-((5S,5aS,6S,9R)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-3-methyl-4-(trifluoromethyl)aniline (Compound 6)

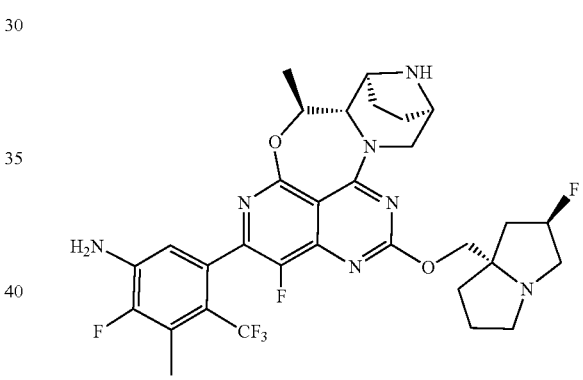

A solution of tert-butyl (5S,5aS,6S,9R)-2-(5-(bis(4-methoxybenzyl)amino)-4-fluoro-3-methyl-2-(trifluoromethyl)phenyl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (130 mg, 0.130 mmol) in TFA (4 mL) was stirred at 50° C. for 3 hours and then concentrated under vacuum. The residue was purified by Prep-HPLC with the following conditions: (Column: XBridge Prep OBD C18 Column, 30×150 mm, 5 μm; Mobile Phase A: Water(10 mmol/L NH$_4$HCO$_3$), Mobile Phase B: ACN; Flow rate: 60 mL/min; Gradient: 33% B to 59% B in 10 min, 59% B; Wave Length: 254/220 nm; R$_{T1}$(min): 7.35) to yield 29.1 mg (33.4% yield) of the title compound as a light yellow solid. LC-MS: (ESI, m/z): [M+H]$^+$=650. $^1$H NMR (300 MHz, DMSO-d$_6$) δ 6.59 (d, J=3.0 Hz, 1H), 6.02 (s, 2H), 5.28 (d, J=55.5 Hz, 1H), 5.08 (d, J=12.6 Hz, 1H), 4.51 (t, J=7.6 Hz, 1H), 4.10-3.93 (m, 3H), 3.56 (s, 1H), 3.44 (d, J=4.8 Hz, 1H), 3.08-2.99 (m, 4H), 2.88-2.81 (m, 1H), 2.31 (s, 3H), 2.13 (s, 1H), 2.07-1.94 (m, 2H), 1.85-1.76 (m, 4H), 1.70-1.50 (m, 3H), 1.42 (d, J=6.2 Hz, 3H).

Example 7: Compound 7

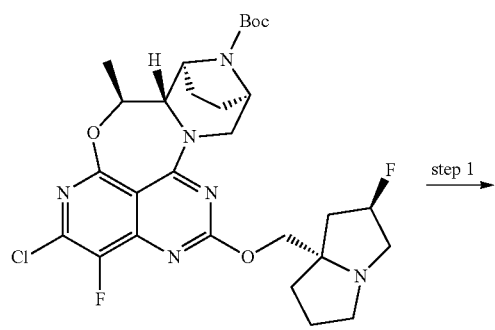

step 1 →

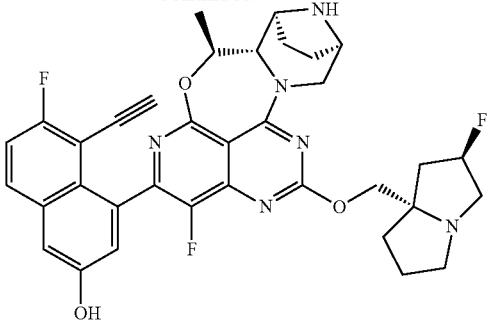

Step 1: tert-Butyl (5S,5aS,6S,9R)-1-fluoro-2-(7-fluoro-3-(methoxymethoxy)-8-((triisopropylsilyl)ethynyl)naphthalen-1-yl)-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate

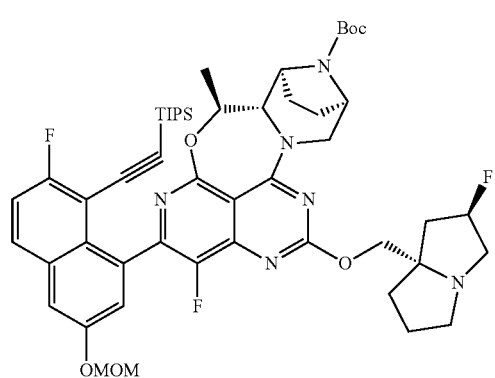

step 2 →

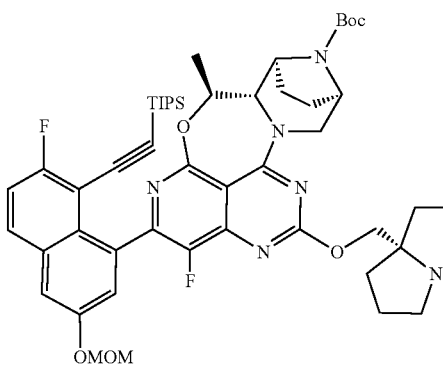

Under nitrogen, a solution of tert-butyl (5S,5aS,6S,9R)-2-chloro-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (280 mg, 0.470 mmol, intermediate 12), ((2-fluoro-6-(methoxymethoxy)-8-(4,4,5,5-tetramethyl-1,3,2-dioxaborolan-2-yl)naphthalen-1-yl)ethynyl)triisopropylsilane (363 mg, 0.710 mmol, intermediate 43), cataCXium A Pd G3 (68.9 mg, 0.0900 mmol) and K$_3$PO$_4$ (0.6 mL, 1.5 M in H$_2$O) in THF (5 mL) was stirred for 3 h at 60° C. The reaction mixture was diluted with water (15 mL) and extracted with EtOAc. The combined organic layers were dried over anhydrous sodium sulfate and concentrated under vacuum. The residue was purified by flash chromatography on silica gel (gradient: 0%-7% MeOH/DCM) to afford 315 mg (70.7% yield) of the title compound as a yellow solid. LC-MS: (ESI, m/z): [M+H]$^+$=943.

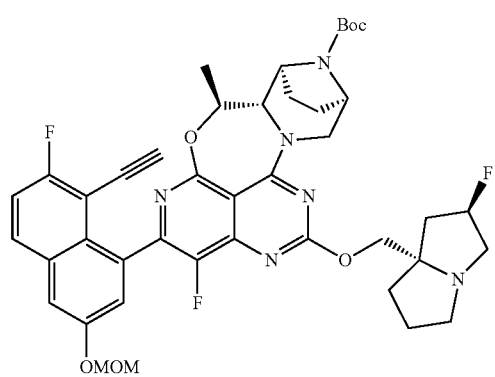

step 3 →

Step 2: tert-Butyl (5S,5aS,6S,9R)-2-(8-ethynyl-7-fluoro-3-(methoxymethoxy)naphthalen-1-yl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate

Step 3: 5-Ethynyl-6-fluoro-4-((5S,5aS,6S,9R)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)naphthalen-2-ol (Compound 7)

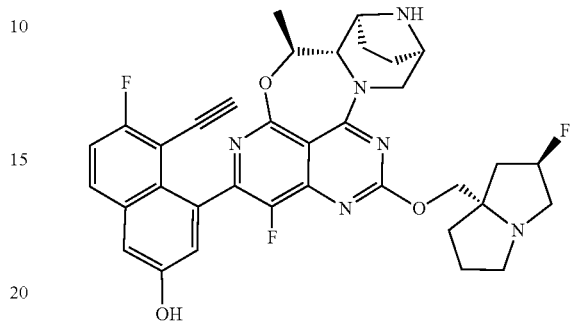

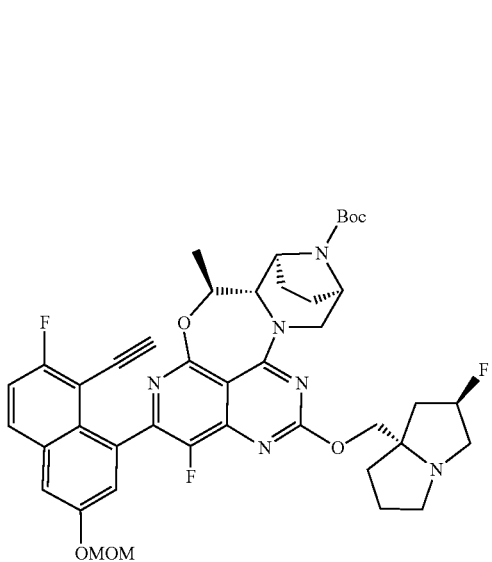

A solution of tert-butyl (5S,5aS,6S,9R)-1-fluoro-2-(7-fluoro-3-(methoxymethoxy)-8-((triisopropylsilyl)ethynyl)naphthalen-1-yl)-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (315 mg, 0.334 mmol) and CsF (257 mg, 1.69 mmol) in DMF (3 mL) was stirred at room temperature for 1 hour. The resulting solution was diluted with EtOAc and washed with water. The organic phase was dried over anhydrous sodium sulfate and concentrated under reduced pressure to afford the title compound (320 mg, crude) as a yellow solid which was used for next step without further purification. LC-MS: (ESI, m/z): [M+H]$^+$=787.

A solution of tert-butyl (5S,5aS,6S,9R)-2-(8-ethynyl-7-fluoro-3-(methoxymethoxy)naphthalen-1-yl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (311 mg, 0.390 mmol) and HCl/1,4-dioxane (1.0 mL, 4 M) in ACN (3 mL) was stirred at 0° C. for 2 hours. The reaction mixture was adjusted to pH ~ 8 with solid NaHCO$_3$. The solid was filtered off and the filtrate was concentrated under reduced pressure. The residue was purified by C18 column (solvent gradient: 0-70% CH$_3$OH in water (0.05% NH$_4$HCO$_3$)) to afford 116.1 mg (45.9% yield) of the title compound as a yellow solid. LC-MS: (ESI, m/z): [M+H]$^+$=643. $^1$H NMR (300 MHz, DMSO-d$_6$, ppm): δ 10.13 (s, 1H), 8.01-7.97 (m, 1H), 7.49-7.43 (m, 1H), 7.37 (s, 1H), 7.19 (d, J=2.5 Hz, 1H), 5.38 (s, 1H), 5.23-5.09 (m, 1H), 4.48-4.41 (m, 1H), 4.25 (d, J=1.1 Hz, 1H), 4.14-4.09 (m, 1H), 4.04-3.93 (m, 2H), 3.60 (s, 1H), 3.46 (s, 1H), 3.15-3.09 (m, 2H), 3.05-2.85 (m, 2H), 2.95-2.83 (m, 1H), 2.15 (s, 1H), 2.03-1.98 (m, 2H), 1.96-1.77 (m, 5H), 1.69-1.57 (m, 3H), 1.53-1.41 (m, 3H).

Each compound in the Table below was prepared following a similar experimental procedure

| Cmpd. No. | $^1$H NMR | MS (M + H)$^+$ |
|---|---|---|
| 8 | $^1$H NMR (400 MHz, DMSO-d$_6$, ppm) δ 8.22-8.14 (m, 1H), 8.13-8.04 (m, 1H), 7.76-7.47 (m, 4H), 5.43-5.05 (m, 2H), 4.64-4.64 (m, 1H), 4.17-3.91 (m, 3H), 3.65-3.41 (m, 2H), 3.19-2.93 (m, 4H), 2.91-2.75 (m, 1H), 2.24-1.92 (m, 3H), 1.92-1.34 (m, 5H). | 619 |
| 9 | $^1$H NMR (400 MHz, DMSO-d$_6$, ppm) δ 10.22 (s, 1H), 7.65 (dd, J = 8.4, 4.9 Hz, 1H), 7.47-7.38 (m, 1H), 7.36-7.31 (m, 1H), 7.21-6.91 (m, 2H), 5.28 (d, J = 54.2 Hz, 1H), 5.10 (d, J = 12.6 Hz, 1H), 4.63-4.48 (m, 1H), 4.11 (dd, J = 10.3, 2.6 Hz, 1H), 4.05-3.93 (m, 2H), 3.58 (d, J = 5.6 Hz, 1H), 3.45 (d, J = 6.1 Hz, 1H), 3.15-3.02 (m, 3H), 3.01 (s, 1H), 2.92-2.74 (m, 2H), 2.21-2.08 (m, 1H), 2.15-2.01 (m, 2H), 1.81 (dd, J = 22.8, 11.2 Hz, 4H), 1.69-1.63 (m, 1H), 1.63-1.52 (m, 2H), 1.44 (dd, J = 6.4, 2.7 Hz, 3H). | |
| 10 | $^1$H NMR (400 MHz, DMSO-d$_6$, ppm) δ 9.95-9.79 (m, 1H), 7.70-7.58 (m, 1H), 7.42-7.28 (m, 1H), 7.27-7.20 (m, 1H), 7.18-7.04 (m, 1H), 7.03-6.78 (m, 1H), 5.45-5.00 (m, 2H), 4.64-4.39 (m, 1H), 4.10 (d, J = 10.4 Hz, 1H), 4.05-3.90 (m, 2H), 3.63-3.40 (m, 2H), 3.16-2.94 (m, 4H), 2.89-2.74 (m, 1H), 2.46-2.34 (m, 1H), 2.32-2.09 (m, 2H), 2.07-1.92 (m, 2H), 1.91-1.73 (m, 4H), 1.72-1.49 (m, 3H), 1.46-1.35 (m, 3H), 1.22 (s, 1H), 1.00-0.89 (m, 1H), 0.86-0.71 (m, 2H). | 629 |

-continued

| Cmpd. No. | ¹H NMR | MS (M + H)⁺ |
|---|---|---|
| 11 | ¹H NMR (400 MHz, DMSO-d₆, ppm) δ 10.11 (s, 1H), 7.93-7.82 (m, 1H), 7.52-7.36 (m, 2H), 7.35-7.25 (m, 1H), 7.16-6.95 (m, 1H), 5.39-5.08 (m, 2H), 4.56-4.39 (m, 1H), 4.16-4.04 (m, 1H), 4.03-3.93 (m, 2H), 3.90 (s, 1H), 3.67-3.55 (m, 2H), 3.53-3.44 (m, 1H), 3.16-2.95 (m, 4H), 2.88-2.78 (m, 1H), 2.19-1.94 (m, 3H), 1.90-1.51 (m, 7H), 1.49-1.37 (m, 3H). | 625 |
| 12 | ¹H NMR (300 MHz, DMSO-d₆, ppm): δ 6.97 (t, J = 7.8 Hz, 1H), 6.86 (dd, J = 8.2, 1.8 Hz, 1H), 6.71-6.63 (m, 1H), 5.56-5.27 (m, 3H), 5.07 (dd, J = 12.9, 2.5 Hz, 1H), 4.52 (dd, J = 8.4, 6.1 Hz, 1H), 4.10 (d, J = 10.3 Hz, 1H), 4.00 (d, J = 10.3 Hz, 1H), 3.93 (dd, J = 8.8, 1.4 Hz, 1H), 3.55 (s, 1H), 3.43 (d, J = 5.7 Hz, 1H), 3.18-3.00 (m, 4H), 2.88-2.77 (m, 1H), 2.18-2.01 (m, 3H), 1.88-1.72 (m, 4H), 1.79-1.61 (m, 3H), 1.43 (d, J = 6.3 Hz, 3H). | 568 |
| 13 | ¹H NMR (300 MHz, DMSO-d₆, ppm) δ 7.19 (d, J = 8.0 Hz, 1H), 6.94 (d, J = 6.4 Hz, 1H), 5.37-5.19 (m, 3H), 5.00-4.89 (m, 1H), 4.54-4.49 (m, 1H), 4.00 (d, J = 10.3 Hz, 1H), 3.89 (d, J = 10.3 Hz, 1H), 3.81 (d, J = 8.6 Hz, 1H), 3.44 (s, 1H), 3.34 (d, J = 5.4 Hz, 1H), 2.99 (d, J = 6.2 Hz, 2H), 2.88 (d, J = 9.2 Hz, 2H), 2.72 (d, J = 7.6 Hz, 1H), 2.12 (d, J = 2.1 Hz, 3H), 2.04 (d, J = 5.9 Hz, 1H), 1.91 (d, J = 12.5 Hz, 2H), 1.80-1.73 (m, 4H), 1.50 (d, J = 14.3 Hz, 3H), 1.34 (d, J = 6.3 Hz, 3H). | 582 |
| 14 | ¹H NMR (300 MHz, DMSO-d₆, ppm): δ 7.45 (d, J = 12.0 Hz, 1H), 6.76 (d, J = 8.6 Hz, 1H), 6.09 (s, 2H), 5.36-5.18 (s, 1H), 5.07 (dd, J = 12.8, 2.6 Hz, 1H), 4.52 (dd, J = 8.7, 6.3 Hz, 1H), 4.08 (d, J = 10.4 Hz, 1H), 4.03-3.90 (m, 2H), 3.56 (s, 1H), 3.44 (d, J = 5.8 Hz, 1H), 3.17-2.96 (m, 4H), 2.86-2.74 (m, 1H), 2.14 (d, J = 4.5 Hz, 1H), 2.11-1.91 (m, 2H), 1.90-1.71 (m, 4H), 1.72-1.50 (m, 3H), 1.42 (d, J = 6.3 Hz, 3H). | 636 |
| 15 | ¹H NMR (300 MHz, DMSO-d₆) δ 6.67-6.48 (m, 3H), 5.37-5.19 (m, 1H), 5.10-5.01 (m, 1H), 4.58-4.46 (m, 1H), 4.11-3.95 (m, 3H), 3.60-3.51 (m, 1H), 3.49-3.41 (m, 1H), 3.12-2.94 (m, 4H), 2.87-2.68 (m, 2H), 2.16-1.90 (m, 3H), 1.88-1.70 (m, 4H), 1.68-1.50 (m, 3H), 1.43 (d, J = 6.3 Hz, 3H) | 654 |
| 16 | ¹H NMR (300 MHz, DMSO-d₆) δ 6.57 (s, 1H), 6.41-6.16 (m, 1H), 5.86 (s, 2H), 5.41-5.16 (m, 1H), 5.08 (d, J = 11.4 Hz, 1H), 4.57-4.44 (m, 1H), 4.13-3.86 (m, 3H), 3.61-3.53 (m, 1H), 3.48-3.39 (m, 1H), 3.16-2.93 (m, 4H), 2.88-2.68 (m, 2H), 2.33 (s, 3H), 2.19-1.90 (m, 3H), 1.89-1.71 (m, 4H), 1.69-1.49 (m, 3H), 1.43 (d, J = 6.3 Hz, 3H). | 632 |
| 17 | ¹H NMR (300 MHz, DMSO-d₆) δ 6.55 (d, J = 14.4 Hz, 1H), 6.45-6.30 (m, 3H), 5.41-5.29 (m, 1H), 5.12-5.03 (m, 1H), 4.60-4.47 (m, 1H), 4.14-3.92 (m, 3H), 3.62-3.52 (m, 1H), 3.50-3.42 (m, 1H), 3.17-3.06 (m, 2H), 3.05-2.97 (m, 2H), 2.89-2.77 (m, 1H), 2.19-2.11 (m, 1H), 2.08-1.94 (m, 2H), 1.90-1.73 (m, 4H), 1.71-1.51 (m, 3H), 1.44 (d, J = 6.3 Hz, 3H). | 636 |
| 18 | ¹H NMR (300 MHz, DMSO-d₆) δ 6.53-6.30 (m, 1H), 5.45-5.15 (m, 3H), 5.15-5.00 (m, 1H), 4.60-4.47 (m, 1H), 4.11 (d, J = 10.2 Hz, 1H), 4.05-3.87 (m, 2H), 3.61-3.55 (m, 1H), 3.50-3.41 (m, 1H), 3.13-3.05 (m, 4H), 2.92-2.67 (m, 2H), 2.32-2.11 (m, 4H), 2.07-2.02 (m, 2H), 1.89-1.71 (m, 4H), 1.70-1.57 (m, 3H), 1.44 (d, J = 6.3 Hz, 3H). | 600 |

Example 19: Compound 19

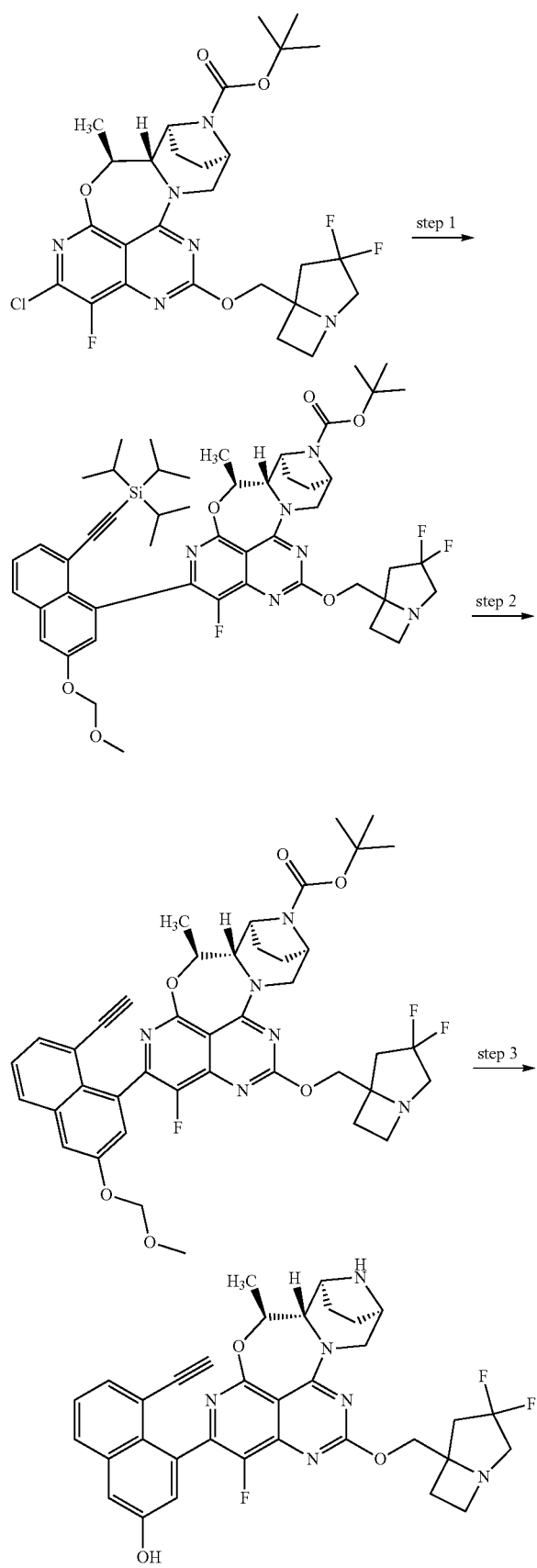

Step 1: tert-Butyl (5S,5aS,6S,9R)-12-((3,3-difluoro-1-azabicyclo[3.2.0]heptan-5-yl)methoxy)-1-fluoro-2-(3-(methoxymethoxy)-8-((triisopropylsilyl)ethynyl)naphthalen-1-yl)-5-methyl-5a,6,7,8,9,10-hexahydro-5H-4-oxa-3,10a,11,13,14-pentaaza-6,9-methanonaphtho[1,8-ab]heptalene-14-carboxylate Under nitrogen, a solution of tert-butyl (5S,5aS,6S,9R)-2-chloro-12-((3,3-difluoro-1-azabicyclo[3.2.0]heptan-5-yl)methoxy)-1-fluoro-5-methyl-5a,6,7,8,9,10-hexahydro-5H-4-oxa-3,10a,11,13,14-pentaaza-6,9-methanonaphtho[1,8-ab]heptalene-14-carboxylate (150 mg, 0.250 mmol, intermediate 13, the faster peak), triisopropyl((6-(methoxymethoxy)-8-(4,4,5,5-tetramethyl-1,3,2-dioxaborolan-2-yl)naphthalen-1-yl)ethynyl)silane (311 mg, 0.630 mmol, intermediate 26), cataCXium A Pd G3 (36.6 mg, 0.0500 mmol) and $K_3PO_4$ (0.5 mL, 1.5 M in water) in THF (2.5 mL) was stirred at 60° C. overnight. The solid was filtered off and the filtrate was concentrated under vacuum. The residue was purified by reverse phase chromatography (gradient: 0-80% ACN in water (0.05% $NH_4HCO_3$)) to afford 215 mg, (92.1% yield) of the title compound as a yellow solid. LC-MS: (ESI, m/z): $[M+H]^+$=929.

Step 2: tert-Butyl (5S,5aS,6S,9R)-12-((3,3-difluoro-1-azabicyclo[3.2.0]heptan-5-yl)methoxy)-2-(8-ethynyl-3-(methoxymethoxy)naphthalen-1-yl)-1-fluoro-5-methyl-5a,6,7,8,9,10-hexahydro-5H-4-oxa-3,10a,11,13,14-pentaaza-6,9-methanonaphtho[1,8-ab]heptalene-14-carboxylate A solution of tert-butyl (5S,5aS,6S,9R)-12-((3,3-difluoro-1-azabicyclo[3.2.0]heptan-5-yl)methoxy)-1-fluoro-2-(3-(methoxymethoxy)-8-((triisopropylsilyl)ethynyl)naphthalen-1-yl)-5-methyl-5a,6,7,8,9,10-hexahydro-5H-4-oxa-3,10a,11,13,14-pentaaza-6,9-methanonaphtho[1,8-ab]heptalene-14-carboxylate (215 mg, 0.230 mmol) and CsF (341 mg, 2.24 mmol) in DMF (2 mL) was stirred at room temperature for 1.5 h. The resulting reaction mixture was purified directly by reverse phase chromatography (gradient: 0-80% ACN in water (0.05% $NH_4HCO_3$)) to afford 181 mg, (96.2% yield) of the title compound as a yellow solid. LC-MS: (ESI, m/z): $[M+H]^+$=773.

Step 3: 4-((5S,5aS,6S,9R)-12-((3,3-Difluoro-1-azabicyclo[3.2.0]heptan-5-yl)methoxy)-1-fluoro-5-methyl-5a,6,7,8,9,10-hexahydro-5H-4-oxa-3,10a,11,13,14-pentaaza-6,9-methanonaphtho[1,8-ab]heptalen-2-yl)-5-ethynylnaphthalen-2-ol (Compound 19)

A solution of tert-butyl (5S,5aS,6S,9R)-12-((3,3-difluoro-1-azabicyclo[3.2.0]heptan-5-yl)methoxy)-2-(8-ethynyl-3-(methoxymethoxy)naphthalen-1-yl)-1-fluoro-5-methyl-5a,6,7,8,9,10-hexahydro-5H-4-oxa-3,10a,11,13,14-pentaaza-6,9-methanonaphtho[1,8-ab]heptalene-14-carboxylate (170 mg, 0.220 mmol) in HCl/1,4-dioxane (0.8 mL, 4 M) and ACN (2.5 mL) was stirred at 0° C. for 1 h and then concentrated under vacuum at 0° C. The crude product was purified by reverse phase chromatography (gradient: 0-50% ACN in water (0.05% $NH_4HCO_3$)) to afford 83.1 mg (59.1% yield) of the title compound as a yellow solid. LC-MS: (ESI, m/z): $[M+H]^+$=629. $^1$H NMR (400 MHz, DMSO-$d_6$, ppm) δ 10.09 (s, 1H), 7.90-7.81 (m, 1H), 7.51-7.36 (m, 2H), 7.30 (d, J=2.6 Hz, 1H), 7.16-6.95 (m, 1H), 5.14 (d, J=12.7 Hz, 1H), 4.57-4.40 (m, 1H), 4.39-4.24 (m, 2H), 4.01-3.92 (m, 1H), 3.75 (d, J=87.3 Hz, 1H), 3.59-3.41 (m, 3H), 3.27-2.76 (m, 5H), 2.74-2.52 (m, 1H), 2.46-2.23 (m, 3H), 1.92-1.49 (m, 4H), 1.43 (t, J=6.0 Hz, 3H).

Example 20: Compound 20

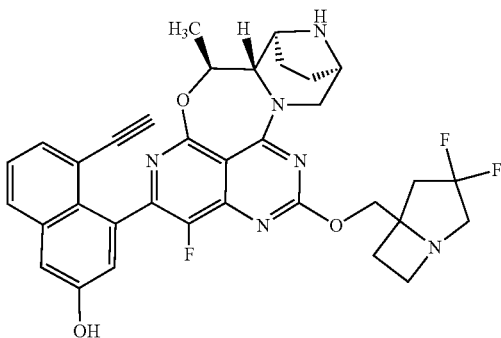 [SMILES: C#Cc1cccc2cc(O)cc(-c3nc4c5c(nc(OCC67CCN6CC(F)(F)C7)nc5c3F)N3C[C@H]5CC[C@H](N5)[C@H]3[C@H](C)O4)c12]

Analogous to the method described for Example 19, 84.4 mg Example 20 were prepared from tert-butyl (5S,5aS,6S,9R)-2-chloro-12-((3,3-difluoro-1-azabicyclo[3.2.0]heptan-5-yl)methoxy)-1-fluoro-5-methyl-5a,6,7,8,9,10-hexahydro-5H-4-oxa-3,10a,11,13,14-pentaaza-6,9-methanonaphtho[1,8-ab]heptalene-14-carboxylate (150 mg, 0.250 mmol, intermediate 13, the slower peak). LC-MS: (ESI, m/z): [M+H]$^+$=629. $^1$H NMR (400 MHz, DMSO-d$_6$, ppm) δ 10.10 (s, 1H), 7.91-7.81 (m, 1H), 7.51-7.35 (m, 2H), 7.31 (d, J=2.6 Hz, 1H), 7.15-6.97 (m, 1H), 5.21-5.10 (m, 1H), 4.58-4.41 (m, 1H), 4.401-4.22 (m, 2H), 3.98 (d, J=8.7 Hz, 1H), 3.90-3.59 (m, 2H), 3.59-3.42 (m, 2H), 3.27-2.97 (m, 4H), 2.74-2.52 (m, 1H), 2.46-2.23 (m, 3H), 1.95-1.50 (m, 4H), 1.43 (t, J=6.0 Hz, 3H).

Each compound in the Table below was prepared following a similar experimental procedure (using appropriately substituted reagents) as described for Examples 19 and 20.

| Cmpd. No. | $^1$H NMR | MS (M + H)$^+$ |
|---|---|---|
| 21 (Isomer 1) | $^1$H NMR (400 MHz, DMSO-d$_6$, ppm) δ 8.23-8.14 (m, 1H), 8.12-8.04 (m, 1H), 7.76-7.47 (m, 4H), 5.21-5.08 (m, 1H), 4.65-4.47 (m, 1H), 4.39 (d, J = 10.9 Hz, 1H), 4.35-4.26 (m, 1H), 3.99 (t, J = 8.0 Hz, 1H), 3.65-3.43 (m, 3H), 3.22 (d, J = 8.5 Hz, 1H), 3.14 (s, 1H), 3.12-3.00 (m, 2H), 2.75-2.57 (m, 1H), 2.47-2.24 (m, 3H), 1.93-1.79 (m, 1H), 1.78-1.52 (m, 3H), 1.44 (t, J = 6.7 Hz, 3H), 1.23 (s, 1H). | 623 |
| 21 (Isomer 2) | $^1$H NMR (400 MHz, DMSO-d$_6$, ppm) δ 8.23-8.14 (m, 1H), 8.12-8.05 (m, 1H), 7.77-7.47 (m, 4H), 5.22 (d, J = 13.5 Hz, 1H), 4.75-4.57 (m, 1H), 4.45-4.28 (m, 2H), 4.26-4.15 (m, 1H), 3.94 (s, 1H), 3.85-3.72 (m, 1H), 3.54 (s, 1H), 3.28-2.99 (m, 4H), 2.75-2.54 (m, 1H), 2.48-2.24 (m, 3H), 2.05-1.62 (m, 4H), 1.46 (t, J = 6.5 Hz, 3H), 1.23 (s, 1H). | 623 |
| 22 | $^1$H NMR (300 MHz, DMSO-d$_6$, ppm): δ 8.29-8.14 (m, 2H), 7.74-7.50 (m, 3H), 5.21-5.11 (m, 1H), 4.51 (dd, J = 9.1, 6.4 Hz, 1H), 4.51-4.24 (m, 2H), 4.08 (t, J = 1.3 Hz, 1H), 3.98 (d, J = 8.8 Hz, 1H), 3.71-3.58 (m, 2H), 3.47 (s, 1H), 3.23 (d, J = 8.7 Hz, 1H), 3.19 (dd, J = 22.5, 15.5 Hz, 1H), 2.98-2.78 (m, 2H), 2.72-2.61 (m, 2H), 2.43-2.30 (m, 3H), 1.85 (d, J = 10.1 Hz, 1H), 1.68-1.59 (m, 3H), 1.45 (t, J = 6.8 Hz, 3H). | 630 |
| 23 | $^1$H NMR (300 MHz, DMSO-d$_6$, ppm): δ 6.69 (dd, J = 8.2, 2.2 Hz, 1H), 6.46 (dd, J = 5.7, 2.2 Hz, 1H), 5.20 (s, 2H), 5.11 (dd, J = 12.9, 2.5 Hz, 1H), 4.54 (dd, J = 8.5, 6.2 Hz, 1H), 4.40 (d, J = 11.0 Hz, 2H), 4.32 (d, J = 11.0 Hz, 1H), 3.96 (dd, J = 8.7, 1.4 Hz, 2H), 3.49-3.16 (m, 2H), 3.10-2.98 (m, 2H), 2.79 (s, 1H), 2.74-2.53 (m, 1H), 2.51-2.35 (m, 2H), 2.31-2.29(m, 1H), 2.21 (s, 3H), 1.82 (s, 1H), 1.60 (dd, J = 23.7, 8.2 Hz, 3H), 1.46 (d, J = 6.3 Hz, 3H). | 586 |
| 23 | $^1$H NMR (300 MHz, DMSO-d$_6$, ppm): δ 6.69 (dd, J = 8.3, 2.2 Hz, 1H), 6.46 (dd, J = 5.7, 2.2 Hz, 1H), 5.20 (s, 2H), 5.11 (dd, J = 12.8, 2.5 Hz, 1H), 4.62-4.47 (m, 1H), 4.40 (d, J = 11.0 Hz, 1H), 4.31 (d, J = 11.1 Hz, 1H), 3.96 (dd, J = 8.8, 1.4 Hz, 1H), 3.56 (dd, J = 5.4, 4.2 Hz, 2H), 3.49-3.41 (m, 1H), 3.30-3.18 (m, 2H), 3.12-2.98 (m, 2H), 2.78 (s, 1H), 2.74-2.52 (m, 1H), 2.50-2.27 (m, 2H), 2.25 (s, 1H), 2.2-2.1 (m, 3H), 1.85-1.74 (m, 1H), 1.60 (dd, J = 23.7, 8.2 Hz, 3H), 1.46 (d, J = 6.3 Hz, 3H). | 586 |
| 24 | $^1$H NMR (300 MHz, DMSO-d6, ppm) δ 8.25 (s, 1H), 6.60 (d, J = 6.0 Hz, 1H), 6.01 (s, 2H), 5.09 (d, J = 12.6 Hz, 1H), 4.53 (s, 1H), 4.36-4.29 (m, 2H), 3.96 (d, J = 8.6 Hz, 1H), 3.61-3.44 (m, 3H), 3.28-3.03 (d, J = 14.3 Hz, 4H), 2.71-2.50 (m, 1H), 2.48-2.32 (m, 2H), 2.30 (s, 4H), 1.81 (s, 1H), 1.63 (s, 3H), 1.42 (d, J = 6.3 Hz, 3H) | 654 |
| 25 | $^1$H NMR (400 MHz, DMSO-d6, ppm): δ 9.95 (s, 1H), 7.79 (d, J = 7.9 Hz, 1H), 7.53 (d, J = 8.3 Hz, 1H), 7.43 (t, J = 8.1 Hz, 1H), 7.29-7.20 (m, 2H), 7.18 (d, J = 2.5 Hz, 1H), 5.14 (dd, J = 12 Hz, J = 4 Hz, 1H), 4.66-4.54 (m, 1H), 4.43-4.22 (m, 2H), 3.99 (d, J = 8.7 Hz, 1H), 3.59 (m, 3H), 3.23 (d, J = 8.8 Hz, 1H), 3.14 (m, 1H), 3.11-3.02 (m, 2H), 2.65 (m, 1H), 2.46-2.33 (m, 3H), 1.84 (m 1H), 1.67 (m, 3H), 1.46 (d, J = 6.3 Hz, 3H). | 605 |

Example 26: Compound 26

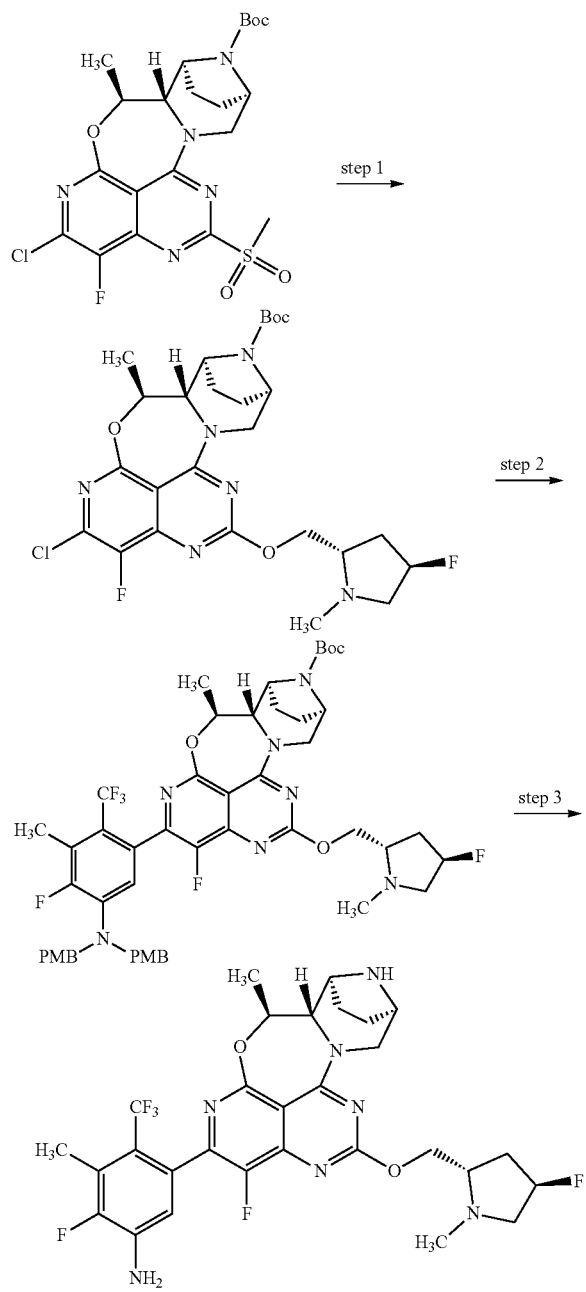

Step 1: tert-Butyl (5S,5aS,6S,9R)-2-chloro-1-fluoro-12-(((2S,4R)-4-fluoro-1-methylpyrrolidin-2-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate To a solution of tert-butyl (5S,5aS,6S,9R)-2-chloro-1-fluoro-5-methyl-12-(methylsulfonyl)-5a,6,7,8,9,10-hexahydro-5H-4-oxa-3,10a,11,13,14-pentaaza-6,9-methanonaphtho[1,8-ab]heptalene-14-carboxylate (100 mg, 0.190 mmol, intermediate 11) and ((2S,4R)-4-fluoro-1-methylpyrrolidin-2-yl)methanol (31.1 mg, 0.230 mmol, intermediate 35) in toluene (1 mL) was added t-BuONa (37.4 mg, 0.390 mmol) at 0° C. The reaction was stirred at room temperature for 1 hour. Water was added and the resulting mixture was extracted with EtOAc. The combined organic layers were washed with brine and dried over anhydrous $Na_2SO_4$. The solvent was concentrated under reduced pressure. The residue was purified by flash chromatography on silica gel (gradient: 0-4% MeOH in DCM) to afford 112 mg (85.7% yield) of the title compound as a white solid. LC-MS: (ESI, m/z): $[M+H]^+$=567.

Step 2: tert-Butyl (5S,5aS,6S,9R)-2-(5-(bis(4-methoxybenzyl)amino)-4-fluoro-3-methyl-2-(trifluoromethyl)phenyl)-1-fluoro-12-(((2S,4R)-4-fluoro-1-methylpyrrolidin-2-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate Under nitrogen, a mixture of tert-butyl (5S,5aS,6S,9R)-2-chloro-1-fluoro-12-(((2S,4R)-4-fluoro-1-methylpyrrolidin-2-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (25.3 mg, 0.0400 mmol), (5-(bis(4-methoxybenzyl)amino)-4-fluoro-3-methyl-2-(trifluoromethyl)phenyl)boronic acid (50.0 mg, 0.105 mmol, intermediate 20), $K_3PO_4$ (1.5 M in $H_2O$, 0.2 mL) and cataCXium A Pd G3 (6.5 mg, 0.0100 mmol) in tetrahydrofuran (1 mL) was stirred at 60° C. for 1 hour. Water was added and the resulting mixture was extracted with EtOAc. The combined organic layers were washed with brine, dried over anhydrous $Na_2SO_4$ and concentrated under reduced pressure. The residue was purified by flash chromatography on silica gel (gradient: 0-100% EtOAc/petroleum ether) to afford 12 mg (23.8% yield) of the title compound as a brown solid. LC-MS: (ESI, m/z): $[M+H]^+$=965.

Step 3: 2-Fluoro-5-((5S,5aS,6S,9R)-1-fluoro-12-(((2S,4R)-4-fluoro-1-methylpyrrolidin-2-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-3-methyl-4-(trifluoromethyl)aniline (Compound 26)

A solution of tert-butyl (5S,5aS,6S,9R)-2-(5-(bis(4-methoxybenzyl)amino)-4-fluoro-3-methyl-2-(trifluoromethyl)phenyl)-1-fluoro-12-(((2S,4R)-4-fluoro-1-methylpyrrolidin-2-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (12.0 mg, 0.0100 mmol) in 2,2,2-trifluoroacetic acid (1 mL) was stirred at 50° C. for 1 hour. Concentrated under reduced pressure. The residue was purified by Prep-HPLC (XBridge Prep OBD C18 Column, 30×150 mm 5 μm; Mobile Phase A:Water(10 mmol/L $NH_4HCO_3$), Mobile Phase B:ACN; Flow rate:60 mL/min; Gradient:31% B to 53% B in 8 min; 53% B; Wavelength: 254/220 n; $R_T$(min): 8) to yield 2.5 mg (32.2% yield) of the title compound as a white solid. LC-MS: (ESI, m/z): $[M+H]^+$=624. $^1$H NMR (300 MHz, DMSO-$d_6$) δ 6.54 (m, 1H), 6.02 (s, 2H), 5.32-5.07 (m, 2H), 4.54 (m, 1H), 4.44 (m, 1H), 4.29 (m, 1H), 3.95 (m, 1H), 3.59-3.50 (m, 1H), 3.49-3.36 (m, 2H), 3.03 (m, 1H), 2.93 (m, 1H), 2.77 (s, 1H), 2.41 (s, 3H), 2.32 (s, 3H), 2.22-1.92 (m, 2H), 1.92-1.75 (m, 2H), 1.59 (m, 3H), 1.44 (m, 3H).

Each compound in the Table below was prepared following a similar experimental procedure (using appropriately substituted reagents) as described for Example 26.

| Cmpd. No. | ¹H NMR | MS (M + H)⁺ |
|---|---|---|
| 27 | ¹H NMR (400 MHz, DMSO-$d_6$, ppm): δ 8.22-8.15 (m, 1H), 8.12-8.05 (m, 1H), 7.76-7.47 (m, 4H), 5.13 (d, J = 12.7 Hz, 1H), 4.54 (dd, J = 13.8, 7.7, 6.8 Hz, 1H), 4.23-4.12 (m, 2H), 3.98 (t, J = 8.9 Hz, 1H), 3.59 (s, 1H), 3.45 (d, J = 6.1 Hz, 1H), 3.15-3.00 (m, 3H), 2.81 (s, 1H), 2.72 (d, J = 12.0 Hz, 1H), 2.13 (d, J = 11.7 Hz, 1H), 2.09 (d, J = 5.5 Hz, 1H), 1.91 (d, J = 13.1 Hz, 1H), 1.82 (s, 2H), 1.67-1.55 (m, 6H), 1.44-1.26 (m, 4H). | 663 |
| 28 | ¹H NMR (300 MHz, DMSO-d6, ppm) δ 9.88 (s, 1H), 7.63-7.63 (m, 1H), 7.37-7.32 (m, 1H), 7.26-7.24 (m, 1H), 7.18-7.04 (m, 1H), 7.00 (d, J = 2.6 Hz, 1H), 5.16-5.11 (m, 1H), 4.66 (d, J = 2.8 Hz, 2H), 4.54-4.51 (m, 2H), 3.96 (t, J = 8.3 Hz, 1H), 3.60 (s, 3H), 3.44 (s, 1H), 3.04 (t, J = 11.1 Hz, 1H), 2.84 (s, 1H), 2.39 (t, J = 7.4 Hz, 1H), 2.32-2.04 (m, 1H), 1.83 (d, J = 4.8 Hz, 3H), 1.73-1.61 (m, 3H), 1.60 (s, 2H), 1.56-1.36 (m, 3H), 0.94 (t, J = 7.4 Hz, 1H), 0.77 (t, J = 7.4 Hz, 2H). | 585 |
| 29 | ¹H NMR (300 MHz, DMSO-$d_6$, ppm): δ 6.61 (s, 1H), 6.02 (s, 2H), 5.69 (s, 1H), 5.51 (s, 1H), 5.11 (d, J = 11.2 Hz, 1H), 4.54 (s, 1H), 4.36 (d, J = 11.0 Hz, 1H), 4.13 (d, J = 10.9 Hz, 1H), 3.65 (m, 2H), 3.45 (d, J = 5.7 Hz, 1H), 3.05-3.01 (m, 3H), 2.99-2.84 (m, 2H), 2.45-2.40 (m, 1H), 2.36-2.29 (m, 4H), 2.28-2.06 (m, 1H), 1.88-1.77 (m, 1H), 1.75-1.63 (m, 3H), 1.44 (dd, J = 6.3 Hz, 3H). | 636 |
| 30 | ¹H NMR (400 MHz, DMSO-$d_6$, ppm) δ 9.46 (s, 1H), 8.61 (d, J = 1.1 Hz, 1H), 8.30-8.23 (m, 1H), 7.90-7.71 (m, 3H), 5.21-5.07 (m, 1H), 4.68-4.54 (m, 1H), 4.27-4.14 (m, 2H), 4.00 (d, J = 8.8 Hz, 1H), 3.60 (s, 1H), 3.53-3.43 (m, 1H), 3.17-2.97 (m, 3H), 2.84 (s, 1H), 2.73 (d, J = 11.9 Hz, 1H), 2.63-2.54 (m, 1H), 2.18-2.05 (m, 1H), 2.05-1.96 (m, 1H), 1.96-1.88 (m, 1H), 1.88-1.54 (m, 8H), 1.53-1.42 (m, 4H). | 630 |
| 31 | ¹H NMR (400 MHz, DMSO-$d_6$) 6.60 (m, 1H), 6.46 (s, 2H), 5.09 (m, 1H), 4.53 (m, 1H), 4.40 (m, 1H), 4.13 (m, 1H), 3.97 (m, 1H), 3.61 (m. 6H), 3.50 (m, 5H), 2.32 (s, 3H), 2.14-2.01 (m, 1H), 1.84-1.69 (m, 6H), 1.44 (d, J = 6.3 Hz, 3H), 1.31 (m, 1H). | 648 |
| 32 | ¹H NMR (300 MHz, DMSO-$d_6$) δ 7.99-7.90 (m, 1H), 7.85-7.73 (m, 1H), 7.65-7.51 (m, 4H), 7.46 (d, J = 8.1 Hz, 2H), 6.68-6.40 (m, 1H), 6.01 (s, 2H), 5.16-5.00 (m, 1H), 4.59-4.45 (m, 3H), 4.28-4.18 (m, 1H), 4.11-4.00 (m, 2H), 3.97-3.87 (m, 1H), 3.60-3.54 (m, 1H), 3.50-3.41 (m, 1H), 3.20-3.12 (m, 1H), 3.08-2.95 (m, 2H), 2.90-2.77 (m, 2H), 2.30 (s, 3H), 2.25-2.14 (m, 1H), 1.97-1.70 (m, 6H), 1.70-1.51 (m, 3H), 1.42 (d, J = 6.3 Hz, 3H). | 839 |

Example 33: Compound 33

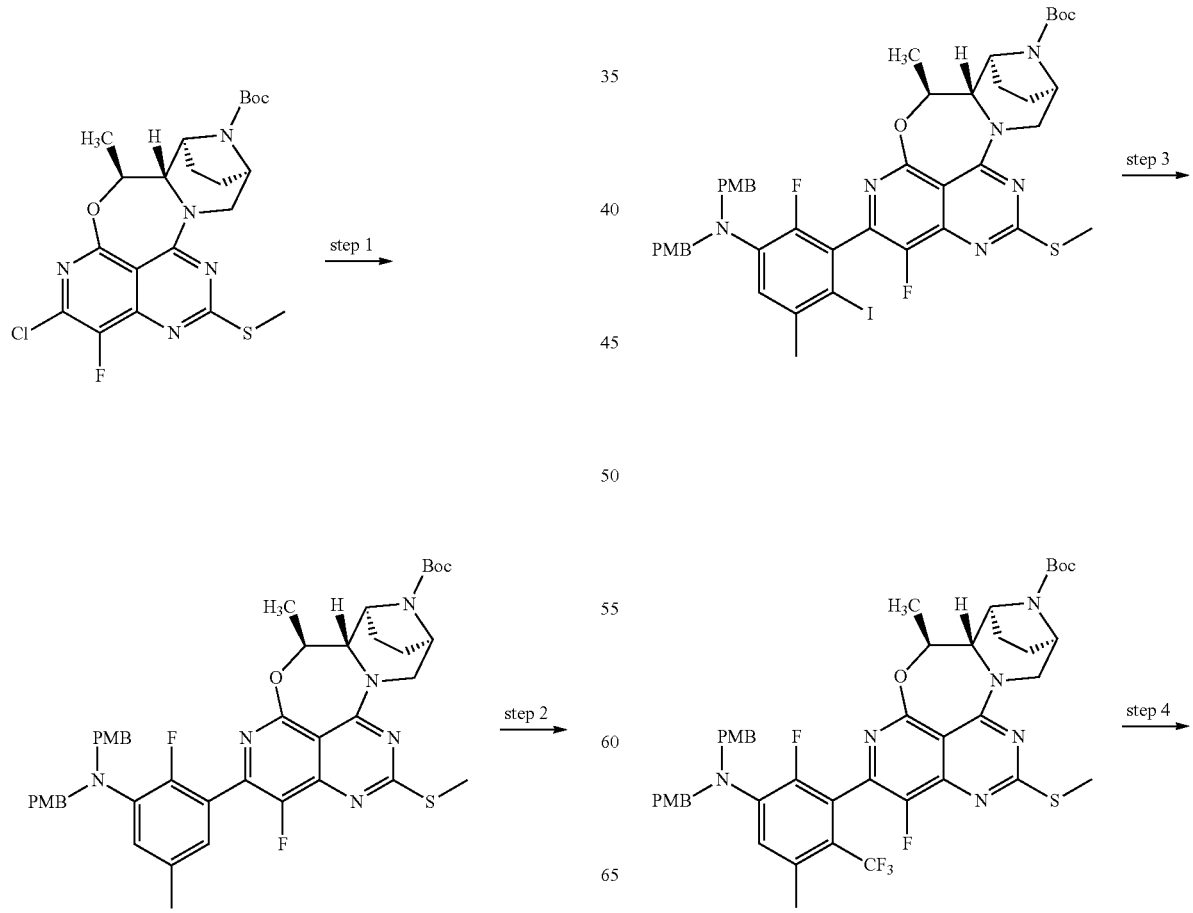

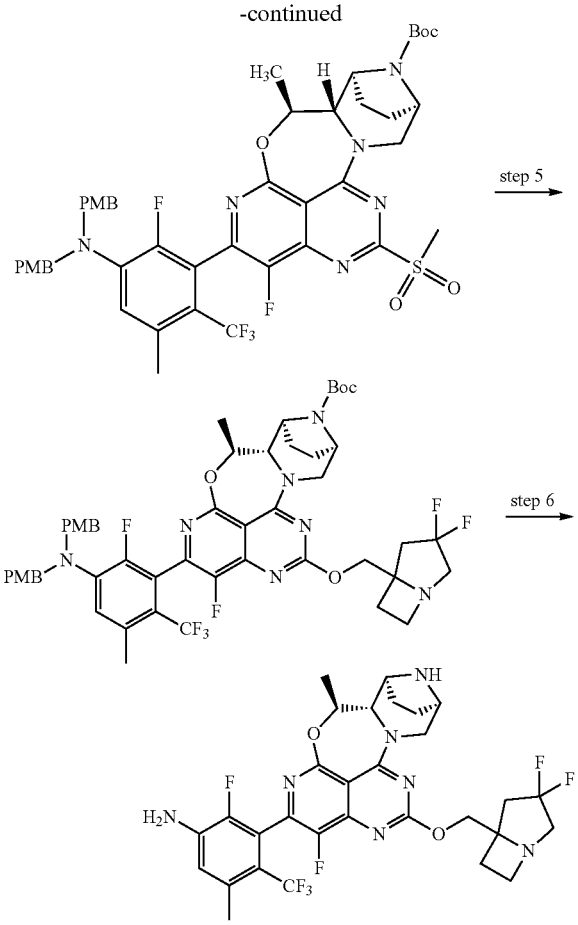

Step 1: tert-Butyl (5S,5aS,6S,9R)-2-(3-(bis(4-methoxybenzyl)amino)-2-fluoro-5-methylphenyl)-1-fluoro-5-methyl-12-(methylthio)-5a,6,7,8,9,10-hexahydro-5H-4-oxa-3,10a,11,13,14-pentaaza-6,9-methanonaphtho[1,8-ab]heptalene-14-carboxylate Under nitrogen, a solution of tert-butyl (5S,5aS,6S,9R)-2-chloro-1-fluoro-5-methyl-12-(methylthio)-5a,6,7,8,9,10-hexahydro-5H-4-oxa-3,10a,11,13,14-pentaaza-6,9-methanonaphtho[1,8-ab]heptalene-14-carboxylate (300 mg, 0.620 mmol, intermediate 10), 2-fluoro-N,N-bis(4-methoxybenzyl)-5-methyl-3-(4,4,5,5-tetramethyl-1,3,2-dioxaborolan-2-yl)aniline and (612 mg, 0.124 mmol, intermediate 19), $K_3PO_4$ (0.5 mL, 1.5 M in $H_2O$) and cataCXium A Pd G3 (90.8 mg, 0.120 mmol) in THF (2.5 mL) was stirred for 3 h at 60° C. The resulting solution was partitioned between water and EtOAc. The combined organic layers were dried over anhydrous sodium sulfate and concentrated under vacuum. The residue was purified by C18 column (solvent gradient: 0-80% ACN in water (0.05% $NH_4HCO_3$)) to afford 219 mg (43.4% yield) of the title compound as a yellow solid. LC-MS: (ESI, m z): $[M+H]^+$=811.

Step 2: tert-Butyl (5S,5aS,6S,9R)-2-(3-(bis(4-methoxybenzyl)amino)-2-fluoro-6-iodo-5-methylphenyl)-1-fluoro-5-methyl-12-(methylthio)-5a,6,7,8,9,10-hexahydro-5H-4-oxa-3,10a,11,13,14-pentaaza-6,9-methanonaphtho[1,8-ab]heptalene-14-carboxylate To a solution of tert-butyl (5S,5aS,6S,9R)-2-(3-(bis(4-methoxybenzyl)amino)-2-fluoro-5-methylphenyl)-1-fluoro-5-methyl-12-(methylthio)-5a,6,7,8,9,10-hexahydro-5H-4-oxa-3,10a,11,13,14-pentaaza-6,9-methanonaphtho[1,8-ab]heptalene-14-carboxylate (206 mg, 0.250 mmol) in AcOH (2.5 mL) was added NIS (63.9 mg, 0.280 mmol). The solution was stirred at room temperature for 1.5 hours, quenched with $Na_2S_2O_3$ aqueous and extracted with EtOAc. The combined organic layers were dried over anhydrous sodium sulfate and concentrated under vacuum. The residue was purified by flash chromatography on silica gel (gradient: 0%-40% EtOAc/petroleum ether) to afford 203 mg (85.3% yield) of the title compound as a yellow solid. LC-MS: (ESI, m/z): $[M+H]^+$=937.

Step 3: tert-Butyl (5S,5aS,6S,9R)-2-(3-(bis(4-methoxybenzyl)amino)-2-fluoro-5-methyl-6-(trifluoromethyl)phenyl)-1-fluoro-5-methyl-12-(methylthio)-5a,6,7,8,9,10-hexahydro-5H-4-oxa-3,10a,11,13,14-pentaaza-6,9-methanonaphtho[1,8-ab]heptalene-14-carboxylate Under nitrogen, a solution of tert-butyl (5S,5aS,6S,9R)-2-(3-(bis(4-methoxybenzyl)amino)-2-fluoro-6-iodo-5-methylphenyl)-1-fluoro-5-methyl-12-(methylthio)-5a,6,7,8,9,10-hexahydro-5H-4-oxa-3,10a,11,13,14-pentaaza-6,9-methanonaphtho[1,8-ab]heptalene-14-carboxylate (195 mg, 0.210 mmol), $Cu(O_2CCF_2SO_2F)_2$ (1.30 g, 3.12 mmol) and Cu powder (200 mg, 3.14 mmol) was stirred for 30 min at 90° C. The resulting mixture was cooled to room, diluted with EtOAc (30 mL), washed with water. The organic layers were dried over anhydrous sodium sulfate and concentrated under vacuum. The residue was purified by flash chromatography on silica gel (gradient: 0%-40% EtOAc/petroleum ether) to afford 149 mg (81.4% yield) of the title compound as a yellow solid. LC-MS: (ESI, m/z): $[M+H]^+$=879.

Step 4: tert-Butyl (5S,5aS,6S,9R)-2-(3-(bis(4-methoxybenzyl)amino)-2-fluoro-5-methyl-6-(trifluoromethyl)phenyl)-1-fluoro-5-methyl-12-(methylsulfonyl)-5a,6,7,8,9,10-hexahydro-5H-4-oxa-3,10a,11,13,14-pentaaza-6,9-methanonaphtho[1,8-ab]heptalene-14-carboxylate Under nitrogen, a solution of tert-Butyl (5S,5aS,6S,9R)-2-(3-(bis(4-methoxybenzyl)amino)-2-fluoro-5-methyl-6-(trifluoromethyl)phenyl)-1-fluoro-5-methyl-12-(methylthio)-5a,6,7,8,9,10-hexahydro-5H-4-oxa-3,10a,11,13,14-pentaaza-6,9-methanonaphtho[1,8-ab]heptalene-14-carboxylate (129 mg, 0.150 mmol) and m-CPBA (76.1 mg, 0.440 mmol) in EtOAc (3 mL) was stirred for 3 h at room temperature. The reaction was quenched with saturated aq. $NaHCO_3$, extracted with EtOAc. The combined organic layers were dried over anhydrous sodium sulfate and concentrated under vacuum. The residue was purified by flash chromatography on silica gel (gradient: 0%-50% EtOAc/petroleum ether) to afford 120 mg (89.8% yield) of the title compound as a yellow solid. LC-MS: (ESI, m/z): $[M+H]^+$= 911.

Step 5: tert-Butyl (5S,5aS,6S,9R)-2-(3-(bis(4-methoxybenzyl)amino)-2-fluoro-5-methyl-6-(trifluoromethyl)phenyl)-12-((3,3-difluoro-1-azabicyclo[3.2.0]heptan-5-yl)methoxy)-1-fluoro-5-methyl-5a,6,7,8,9,10-hexahydro-5H-4-oxa-3,10a,11,13,14-pentaaza-6,9-methanonaphtho[1,8-ab]heptalene-14-carboxylate Under nitrogen, to a solution of tert-Butyl (5S,5aS,6S,9R)-2-(3-(bis(4-methoxybenzyl)amino)-2-fluoro-5-methyl- 6-(trifluoromethyl)phenyl)-1-fluoro-5-methyl-12-(methylsulfonyl)-5a,6,7,8,9,10-hexahydro-5H-4-oxa-3,10a,11,13,14-pentaaza-6,9-methanonaphtho[1,8-ab]heptalene-14-carboxylate (101 mg, 0.110 mmol) and ((3,3-difluoro-1-azabicyclo[3.2.0]heptan-5-yl)methanol (21.0 mg, 0.130 mmol, intermediate 6) in PhMe (2.5 mL) was added t-BuONa (21.0 mg, 0.220 mmol) at 0° C. The resulting solution was stirred for 1 h at room temperature. The resulting solution was added water (10 mL), extracted with EtOAc. The combined organic layers were dried over anhydrous sodium sulfate and concentrated under vacuum. The residue was purified by flash chromatography on silica gel (gradient: 0%-7% MeOH/DCM) to afford 88.0 mg (80.6% yield) of the title compound as a yellow solid. LC-MS: (ESI, m/z): [M+H]$^+$=994.

Step 6: 3-((5S,5aS,6S,9R)-12-((3,3-Difluoro-1-azabicyclo[3.2.0]heptan-5-yl)methoxy)-1-fluoro-5-methyl-5a,6,7,8,9,10-hexahydro-5H-4-oxa-3,10a,11,13,14-pentaaza-6,9-methanonaphtho[1,8-ab]heptalen-2-yl)-2-fluoro-5-methyl-4-(trifluoromethyl)aniline (Compound 33)

A solution of tert-butyl (5S,5aS,6S,9R)-2-(3-(bis(4-methoxybenzyl)amino)-2-fluoro-5-methyl-6-(trifluoromethyl)phenyl)-12-((3,3-difluoro-1-azabicyclo[3.2.0]heptan-5-yl)methoxy)-1-fluoro-5-methyl-5a,6,7,8,9,10-hexahydro-5H-4-oxa-3,10a,11,13,14-pentaaza-6,9-methanonaphtho[1,8-ab]heptalene-14-carboxylate (88.0 mg, 0.0900 mmol) in TFA (2.5 mL) was stirred at 50° C. for 3.5 hours. The solvent was concentrated under vacuum. The residue was purified by C18 column (solvent gradient: 0-90% ACN in water (0.05% NH$_4$HCO$_3$)) to yield 23.5 mg (40.6% yield) of the title compound as a white solid. LC-MS: (ESI, m/z): [M+H]$^+$=654. $^1$H NMR (300 MHz, DMSO-d$_6$, ppm): δ 6.82 (d, J=8.8 Hz, 1H), 5.99 (d, J=11.6 Hz, 2H), 5.19-5.07 (m, 1H), 4.69-4.58 (m, 1H), 4.45-4.31 (m, 2H), 4.00 (t, J=8.1 Hz, 1H), 3.72-3.63 (m, 1H), 3.53 (d, J=5.9, 5.3 Hz, 2H), 3.23-3.07 (m, 4H), 2.73-2.52 (m, 1H), 2.50-2.24 (m, 6H), 1.85 (s, 1H), 1.72-1.67 (m, 3H), 1.57-1.44 (m, 3H)

This compound was evaluated as a mixture of diastereomers.

Example 34: Compound 34

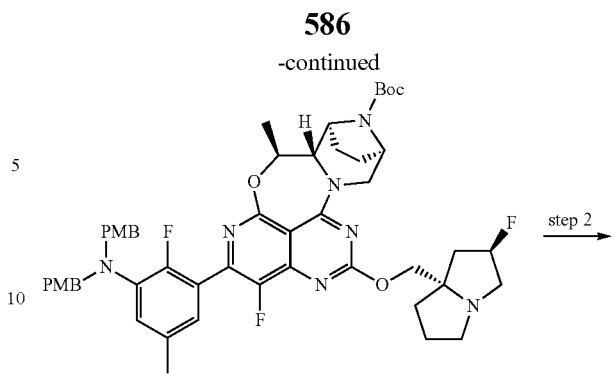

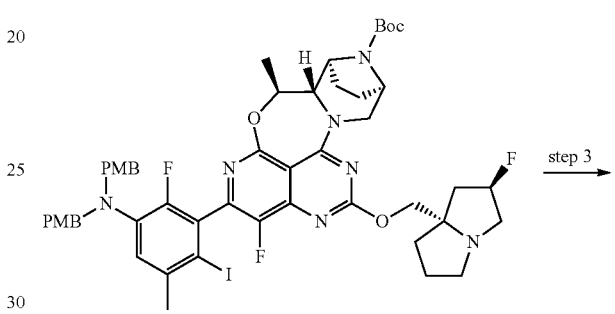

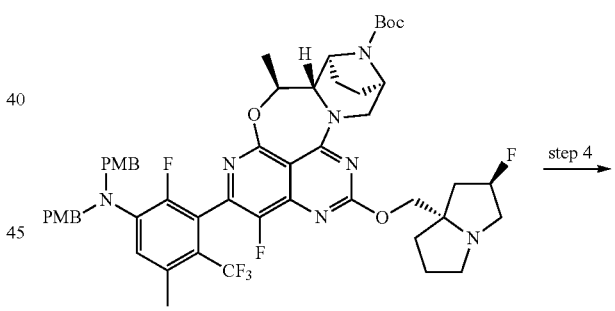

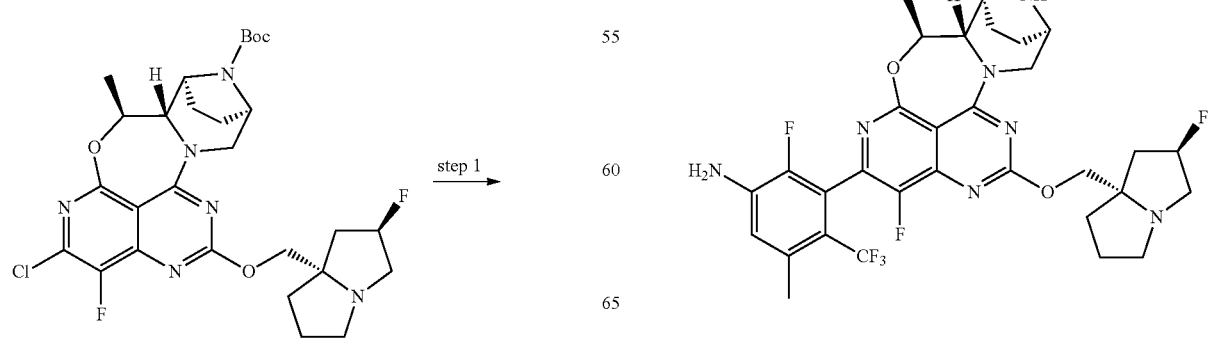

Step 1: tert-Butyl (5S,5aS,6S,9R)-2-(3-(bis(4-methoxybenzyl)amino)-2-fluoro-5-methylphenyl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate Under nitrogen, a solution of tert-butyl (5S,5aS,6S,9R)-2-chloro-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (410 mg, 0.690 mmol, intermediate 12), 2-fluoro-N,N-bis(4-methoxybenzyl)-5-methyl-3-(4,4,5,5-tetramethyl-1,3,2-dioxaborolan-2-yl)aniline (680 mg, 1.39 mmol, intermediate 19), K$_3$PO$_4$ aqueous (0.5 mL, 1.5 M in H$_2$O) and cat a CXium A Pd G3 (102 mg, 0.140 mmol) in THF (2.5 mL) was stirred for 3 h at 60° C. The resulting solution was cooled to room temperature, diluted with water (10 mL), and extracted with EtOAc. The combined organic layers were dried over anhydrous sodium sulfate and concentrated under vacuum. The residue was purified by flash chromatography on silica gel (gradient: 0%-10% MeOH/DCM) to afford 383 mg (59.7% yield) of the title compound as a brown solid. LC-MS: (ESI, m/z): [M+H]$^+$=922.

Step 2: tert-Butyl (5S,5aS,6S,9R)-2-(3-(bis(4-methoxybenzyl)amino)-2-fluoro-6-iodo-5-methylphenyl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate A solution of tert-butyl (5S,5aS,6S,9R)-2-(3-(bis(4-methoxybenzyl)amino)-2-fluoro-5-methylphenyl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (371 mg, 0.400 mmol) and NIS (90.7 mg, 0.400 mmol) in acetic acid (2.5 mL) was stirred at room temperature for 2 hours. The resulting solution was quenched with aq. Na$_2$S$_2$O$_3$, extracted with EtOAc. The combined organic layers were dried over anhydrous sodium sulfate and concentrated under vacuum. The residue was purified by flash chromatography on silica gel (gradient: 0%-9% MeOH/DCM) to afford 144 mg (34.2% yield) of the title compound as a brown solid. LC-MS: (ESI, m/z): [M+H]$^+$=1048.

Step 3: tert-Butyl (5S,5aS,6S,9R)-2-(3-(bis(4-methoxybenzyl)amino)-2-fluoro-5-methyl-6-(trifluoromethyl)phenyl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate Under nitrogen, a solution of tert-butyl (5S,5aS,6S,9R)-2-(3-(bis(4-methoxybenzyl)amino)-2-fluoro-6-iodo-5-methylphenyl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (133 mg, 0.130 mmol), Cu(O$_2$CCF$_2$SO$_2$F)$_2$ (794 mg, 1.90 mmol) and Cu (123 mg, 1.92 mmol) in DMF (2.5 mL) was stirred for 30 min at 90° C. The resulting solution was cooled to room temperature, diluted with EtOAc and washed with water. The organic layers were dried over anhydrous sodium sulfate and concentrated under vacuum. The residue was purified by reverse phase chromatography (solvent gradient: 0-100% MeOH in water (0.05% NH$_4$HCO$_3$)) to yield 86.0 mg (68.4% yield) of the title compound as a yellow solid. LC-MS: (ESI, m/z): [M+H]$^+$=990.

Step 4: 2-Fluoro-3-((5S,5aS,6S,9R)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-5-methyl-4-(trifluoromethyl)aniline (Compound 34)

A solution of tert-butyl (5S,5aS,6S,9R)-2-(3-(bis(4-methoxybenzyl)amino)-2-fluoro-5-methyl-6-(trifluoromethyl)phenyl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (72.1 mg, 0.0729 mmol) in TFA (3.5 mL) was stirred at 50° C. for 4 hours and then concentrated under vacuum. The residue was purified by reverse phase chromatography (solvent gradient: 0-40% MeOH in water (0.1% FA)) to yield 1.2 mg (2.5% yield) of the title compound as a yellow solid. LC-MS: (ESI, m/z): [M+H]$^+$=650. $^1$H NMR (300 MHz, DMSO-d$_6$, ppm): δ 8.22 (s, 2H), 6.79 (d, J=8.8 Hz, 1H), 5.97 (d, J=11.3 Hz, 2H), 5.36 (s, 1H), 5.18-5.05 (m, 1H), 4.60-4.47 (m, 1H), 4.09 (dd, J=10.3, 4.7 Hz, 1H), 4.05-3.90 (m, 1H), 3.59 (s, 1H), 3.46 (s, 1H), 3.12-3.02 (m, 4H), 2.99 (s, 1H), 2.35-2.31 (m, 3H), 2.13 (s, 1H), 2.00 (d, J=16.1 Hz, 2H), 1.88-1.46 (m, 7H), 1.42 (d, J=6.3 Hz, 3H).

Each compound in the Table below was prepared following a similar experimental procedure (using appropriately substituted reagents) as described for Example 34.

| Cmpd. No. | $^1$H NMR | MS (M + H)$^+$ |
| --- | --- | --- |
| 35 | $^1$H NMR (300 MHz, DMSO-d$_6$, ppm): δ 7.37 (dd, J = 8.7, 5.7 Hz, 1H), 6.96 (t, J = 8.6 Hz, 1H), 6.10 (d, J = 9.8 Hz, 2H), 5.38 (s, 1H), 5.16-5.03 (m, 1H), 4.56 (s, 2H), 4.17-3.96 (m, 3H), 3.50 (s, 2H), 3.12-3.05 (m, 3H), 3.01-2.93 (m, 1H), 2.91-2.83 (m, 1H), 2.29-2.23 (m, 1H), 2.01 (s, 2H), 1.93-1.73 (m, 4H), 1.65-1.52 (m, 3H), 1.59-1.42 (m, 3H). | 636 |
| 36 | $^1$H NMR (400 MHz, DMSO-d$_6$, ppm) δ 6.82 (d, J = 8.8 Hz, 1H), 6.01 (d, J = 8.6 Hz, 2H), 5.41 (d, J = 54.4 Hz, 1H), 5.14-4.99 (m, 1H), 4.72-4.54 (m, 2H), 4.44-4.11 (m, 5H), 3.57-3.47 (m, 1H), 3.46-3.35 (m, 3H), 3.03 (s, 2H), 2.34 (m, 3H), 2.25-2.11 (m, 2H), 2.07-1.75 (m, 8H). | 636 |

Example 38 and 39: Compounds 38 and 39

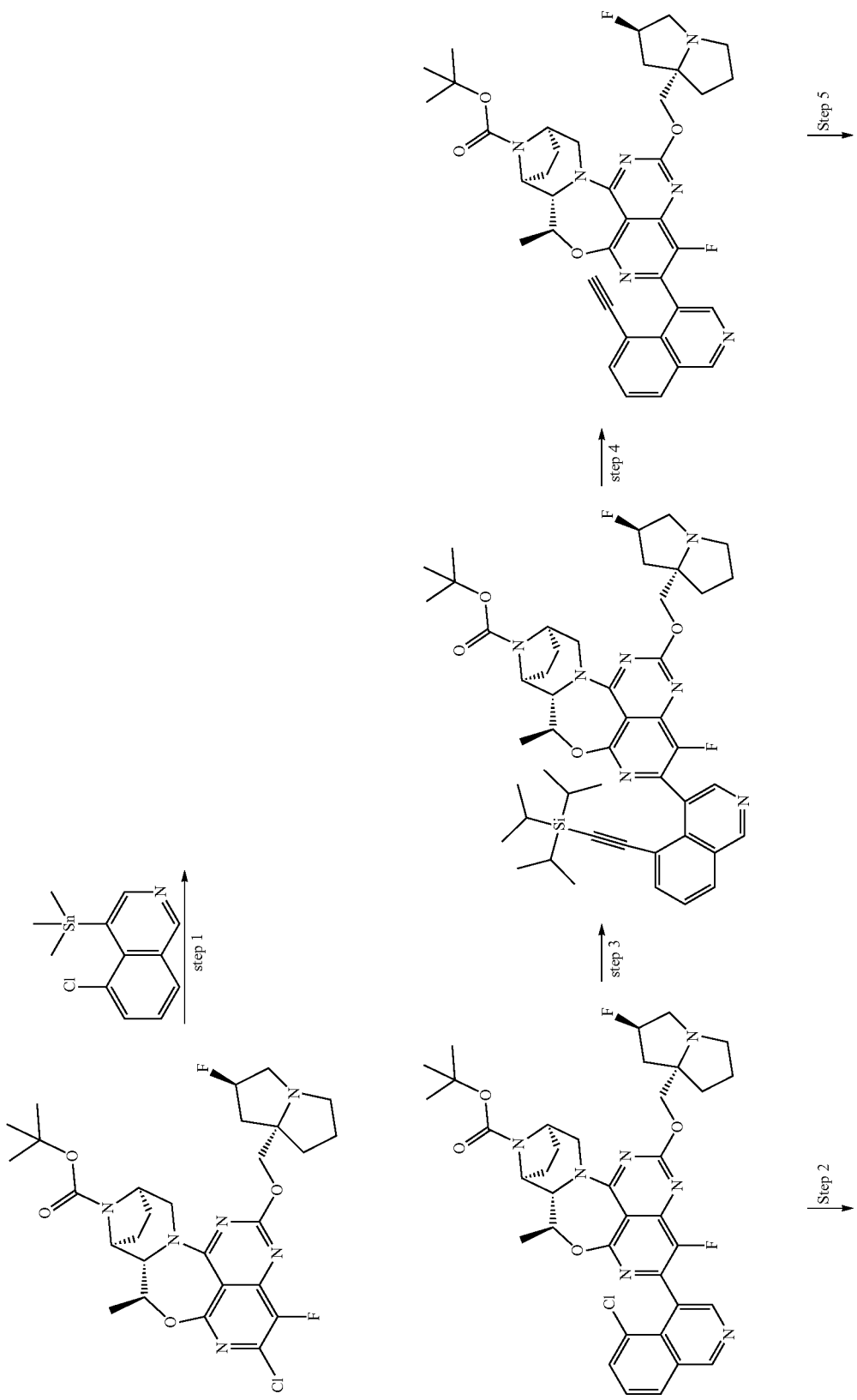

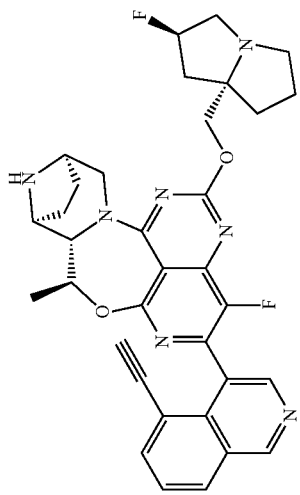
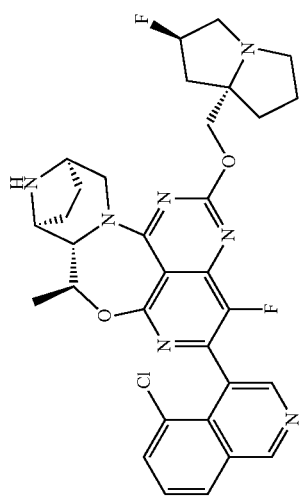

Step 1: tert-Butyl (5S,5aS,6S,9R)-2-(5-chloroisoquinolin-4-yl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate Under nitrogen, a solution of tert-butyl (5S,5aS,6S,9R)-2-chloro-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (150 mg, 0.250 mmol, intermediate 12), 5-chloro-4-(trimethylstannyl)isoquinoline (301 mg, 0.920 mmol, intermediate 21), BINAP (31.6 mg, 0.0500 mmol), CuI (14.4 mg, 0.0800 mmol) and Pd(dppf)Cl$_2$ (19.5 mg, 0.0300 mmol) in toluene (2 mL) was stirred at 90° C. overnight. The resulting reaction mixture was extracted with EtOAc (20 mL), washed with water (2*20 mL) and brine (20 mL). The organic layer was dried over anhydrous sodium sulfate and concentrated under vacuum. The residue was purified by reverse phase chromatography (gradient: 0-100% ACN in water (0.1% FA)) to afford 145 mg (79.5% yield) of the title compound as a yellow solid. LC-MS: (ESI, m/z): [M+H]$^+$=720.

Step 2: (5S,5aS,6S,9R)-2-(5-Chloroisoquinolin-4-yl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene (Compound 38)

A solution of tert-butyl (5S,5aS,6S,9R)-2-(5-chloroisoquinolin-4-yl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (20.0 mg, 0.0300 mmol) in HCl/1,4-dioxane (0.3 mL, 4 M) and ACN (1 mL) was stirred at 0° C. for 1.5 h. Then the mixture was concentrated under vacuum at 0° C. The residue was adjusted to pH ~8 with NaHCO$_3$ (aq.) and extracted with EtOAc. The combined organic layers were dried over anhydrous Na$_2$SO$_4$ and concentrated under vacuum. The residue was purified by reverse phase chromatography (gradient: 0-80% ACN in water (0.05% NH$_4$HCO$_3$)) to afford 7.4 mg, (42.3% yield) of the title compound as a white solid. LC-MS: (ESI, m/z): [M+H]$^+$=620. $^1$H NMR (400 MHz, DMSO-d$_6$, ppm) δ 9.53 (d, J=3.6 Hz, 1H), 8.50 (d, J=36.9 Hz, 1H), 8.33-8.26 (m, 1H), 7.97-7.88 (m, 1H), 7.80-7.70 (m, 1H), 5.41-5.03 (m, 2H), 4.64-4.44 (m, 1H), 4.09 (d, J=10.3 Hz, 1H), 4.05-3.90 (m, 2H), 3.70-3.53 (m, 1H), 3.51-3.41 (m, 1H), 3.16-2.91 (m, 4H), 2.89-2.75 (m, 1H), 2.22-2.09 (m, 1H), 2.08-1.92 (m, 2H), 1.90-1.50 (m, 7H), 1.43 (t, J=5.7 Hz, 3H).

Step 3: tert-Butyl (5S,5aS,6S,9R)-1-fluoro-12-(((2R,7aS)-2-fluorotetrahydro-1H-pyrrolizin-7a(5H)-yl)methoxy)-5-methyl-2-(5-((triisopropylsilyl)ethynyl)isoquinolin-4-yl)-5a,6,7,8,9,10-hexahydro-5H-4-oxa-3,10a,11,13,14-pentaaza-6,9-methanonaphtho[1,8-ab]heptalene-14-carboxylate Under nitrogen, a solution of tert-butyl (5S,5aS,6S,9R)-2-(5-chloroisoquinolin-4-yl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (110 mg, 0.150 mmol, from step 1), ethynyltriisopropylsilane (139 mg, 0.760 mmol), Pd(CH$_3$CN)$_2$Cl$_2$ (7.90 mg, 0.0300 mmol), X-Phos (43.8 mg, 0.0900 mmol) and Cs$_2$CO$_3$ (99.7 mg, 0.310 mmol) in ACN (2 mL) was stirred at 95° C. overnight, then concentrated under vacuum. The residue was purified by flash chromatography on silica gel (gradient: 0-18% MeOH/DCM) to afford 40.0 mg (30.2% yield) of the title compound as a yellow solid. LC-MS: (ESI, m/z): [M+H]$^+$=866.

Step 4: tert-Butyl (5S,5aS,6S,9R)-2-(5-ethynylisoquinolin-4-yl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate A solution of tert-butyl (5S,5aS,6S,9R)-1-fluoro-12-(((2R,7aS)-2-fluorotetrahydro-1H-pyrrolizin-7a(5H)-yl)methoxy)-5-methyl-2-(5-((triisopropylsilyl)ethynyl)isoquinolin-4-yl)-5a,6,7,8,9,10-hexahydro-5H-4-oxa-3,10a,11,13,14-pentaaza-6,9-methanonaphtho[1,8-ab]heptalene-14-carboxylate (37.1 mg, 0.0400 mmol) and CsF (64.9 mg, 0.424 mmol) in DMF (1.5 mL) was stirred at room temperature for 1 h. The reaction mixture was purified directly by reverse phase chromatography (gradient: 0-80% ACN in water (0.05% NH$_4$HCO$_3$)) to afford the title compound 29.2 mg (74.4% yield) as a white solid. LC-MS: (ESI, m/z): [M+H]$^+$=710.

Step 5: (5S,5aS,6S,9R)-2-(5-Ethynylisoquinolin-4-yl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene (Compound 39)

A solution of tert-butyl (5S,5aS,6S,9R)-2-(5-ethynylisoquinolin-4-yl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (21.3 mg, 0.0300 mmol) in HCl/1,4-dioxane (0.5 mL, 4 M) and ACN (1.5 mL) was stirred at 0° C. for 1.5 h. Then the mixture was concentrated under vacuum at 0° C. The mixture was adjusted to pH ~ 8 with NaHCO$_3$ (aq.) and extracted with EtOAc. The combined organic layers were dried over anhydrous Na$_2$SO$_4$ and concentrated under vacuum. The crude product was purified by reverse phase chromatography (gradient: 0-50% ACN in water (0.050% NH$_4$HCO$_3$)) to afford 7.9 mg (42.7% yield) of the title compound as a white solid. LC-MS: (ESI, m/z): [M+H]$^+$= 610. $^1$H NMR (400 MHz, DMSO-d$_6$, ppm) δ 9.49 (s, 1H), 8.49 (d, J=29.7 Hz, 1H), 8.36-8.28 (m, 1H), 8.03-7.92 (m, 1H), 7.84-7.70 (m, 1H), 5.46-5.00 (m, 2H), 4.61-4.37 (m, 1H), 4.16-3.80 (m, 4H), 3.58 (s, 1H), 3.45 (s, 1H), 3.25-2.94 (m, 4H), 2.90-2.69 (m, 1H), 2.21-2.10 (m, 1H), 2.09-1.92 (m, 2H), 1.91-1.50 (m, 7H), 1.43 (t, J=6.1 Hz, 3H).

Each compound in the Table below was prepared following a similar experimental procedure (using appropriately substituted reagents) as described for Examples 38 and 39.

| Cmpd. No. | ¹H NMR | MS (M + H)⁺ |
|---|---|---|
| 40 | ¹H NMR (400 MHz, DMSO-d₆, ppm) δ 9.49 (s, 1H), 8.49 (d, J = 29.7 Hz, 1H), 8.37-8.29 (m, 1H), 8.04-7.91 (m, 1H), 7.80-7.68 (m, 1H), 5.24-5.13 (m, 1H), 4.64-4.43 (m, 1H), 4.17 (d, J = 2.8 Hz, 3H), 4.12-3.84 (m, 1H), 3.80 (s, 1H), 3.70-3.61 (m, 1H), 3.22-2.96 (m, 3H), 2.77-2.67 (m, 1H), 2.60-2.52 (m, 1H), 2.14-1.49 (m, 12H), 1.48-1.37 (m, 3H). | 654 |
| 41 | ¹H NMR (300 MHz, DMSO-d₆, ppm) δ 7.62 (d, J = 8.4 Hz, 1H), 7.53-7.39 (m, 2H), 7.12-7.03 (m, 1H), 6.76 (s, 1H), 6.09 (s, 2H), 5.45-5.04 (m, 2H), 4.64-4.47 (m, 1H), 4.13 (d, J = 10.3 Hz, 1H), 4.04-3.91 (m, 2H), 3.64-3.42 (m, 2H), 3.11-3.05 (m, 3H), 3.02 (d, J = 5.5 Hz, 1H), 2.92-2.81 (m, 1H), 2.16 (d, J = 5.4 Hz, 1H), 2.07-1.95 (m, 2H), 1.93-1.74 (m, 4H), 1.73-1.48 (m, 3H), 1.45 (d, J = 6.3 Hz, 3H). | 601 |
Example 42: Compound 42
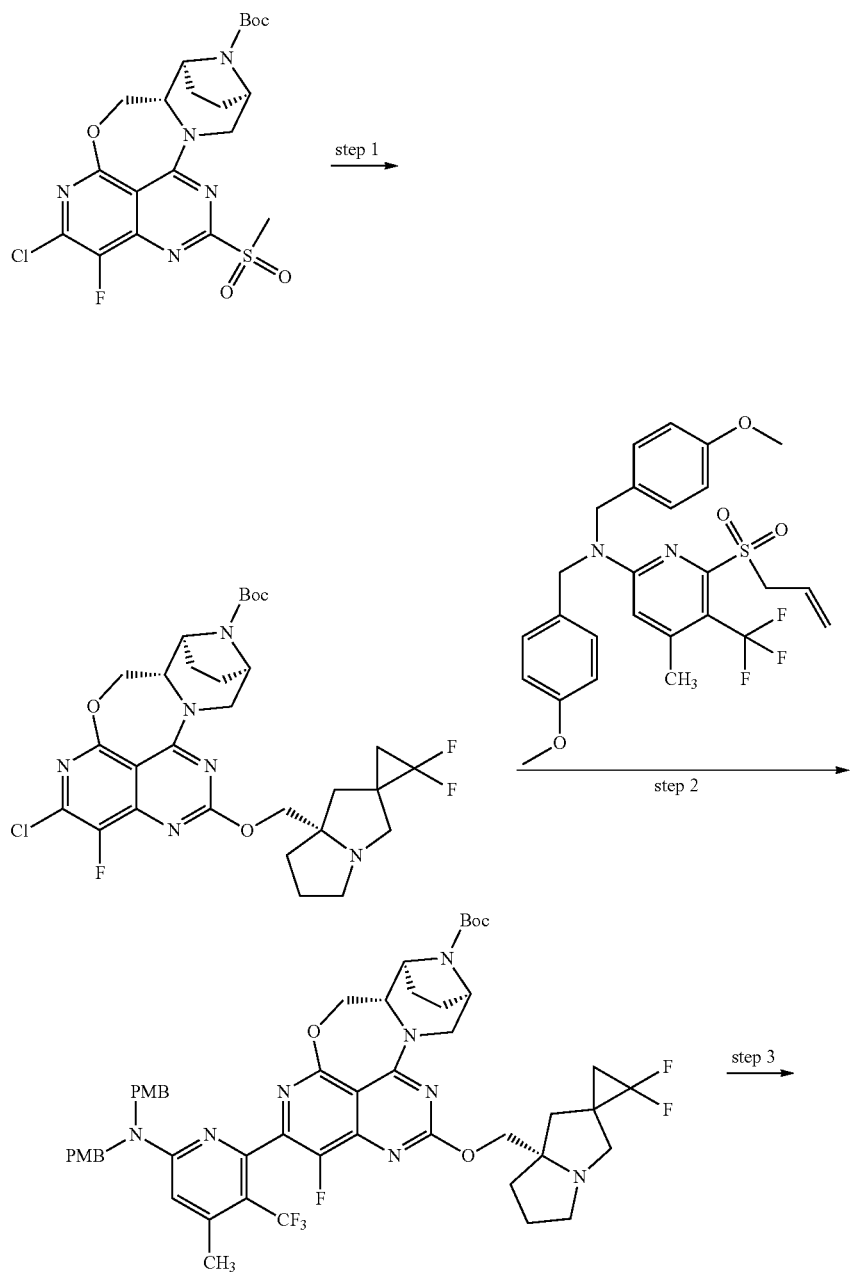

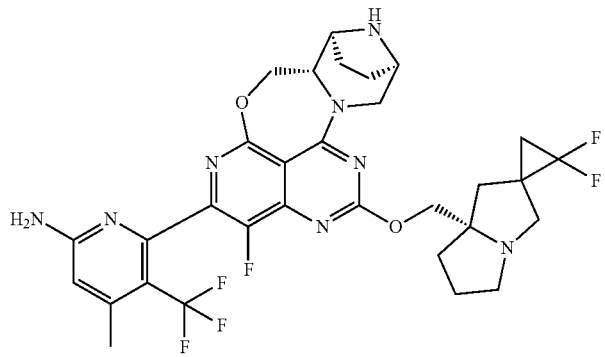

Step 1: tert-Butyl (5aS,6S,9R)-2-chloro-12-(((7a'S)-2,2-difluorodihydro-1'H,3'H-spiro[cyclopropane-1,2'-pyrrolizin]-7a'(5'H)-yl)methoxy)-1-fluoro-5a,6,7,8,9,10-hexahydro-5H-4-oxa-3,10a,11,13,14-pentaaza-6,9-methanonaphtho[1,8-ab]heptalene-14-carboxylate To a solution of ((7a'S)-2,2-difluorodihydro-1'H,3'H-spiro[cyclopropane-1,2'-pyrrolizin]-7a'(5'H)-yl)methanol (163 mg, 0.800 mmol, intermediate 33), tert-butyl (5aS,6S,9R)-2-chloro-1-fluoro-12-(methylsulfonyl)-5a,6,7,8,9,10-hexahydro-5H-4-oxa-3,10a,11,13,14-pentaaza-6,9-methanonaphtho[1,8-ab]heptalene-14-carboxylate (201 mg, 0.400 mmol, intermediate 8) in toluene (2 mL) was added t-BuONa (77.1 mg, 0.800 mmol) at 0° C. The reaction mixture was stirred at room temperature for 1 hour, water (20 mL) and extracted with EtOAc. The combined organic layers were dried over anhydrous sodium sulfate and concentrated under vacuum. The resulting residue was purified by flash chromatography on silica gel eluting with CH$_3$OH/DCM (0-10%) to afford the title compound (301 mg, crude) as light yellow solid. LC-MS: (ESI, m/z): [M+H]$^+$=624.

Step 2: tert-Butyl (5aS,6S,9R)-2-(6-(bis(4-methoxybenzyl)amino)-4-methyl-3-(trifluoromethyl)pyridin-2-yl)-12-(((7a'S)-2,2-difluorodihydro-1'H,3'H-spiro[cyclopropane-1,2'-pyrrolizin]-7a'(5'H)-yl)methoxy)-1-fluoro-5a,6,7,8,9,10-hexahydro-5H-4-oxa-3,10a,11,13,14-pentaaza-6,9-methanonaphtho[1,8-ab]heptalene-14-carboxylate Under nitrogen, a solution of 6-(allylsulfonyl)-N,N-bis(4-methoxybenzyl)-4-methyl-5-(trifluoromethyl)pyridin-2-amine (501 mg, 0.0300 mmol, intermediate 17), Pd(OAc)$_2$ (5.60 mg, 0.0250 mmol), Pt-Bu$_2$MeHBF$_4$ (35.6 mg, 0.144 mmol), Cs$_2$CO$_3$ (357 mg, 0.0400 mmol) and tert-butyl (5aS,6S,9R)-2-chloro-12-(((7a'S)-2,2-difluorodihydro-1'H,3'H-spiro[cyclopropane-1,2'-pyrrolizin]-7a'(5'H)-yl)methoxy)-1-fluoro-5a,6,7,8,9,10-hexahydro-5H-4-oxa-3,10a,11,13,14-pentaaza-6,9-methanonaphtho[1,8-ab]heptalene-14-carboxylate (301 mg, 0.0200 mmol) in 1,4-dioxane (5 mL) was stirred overnight at 120° C. The reaction mixture was cooled to room temperature, diluted with water (20 mL) and extracted with EtOAc. The combined organic layers were dried over anhydrous sodium sulfate and concentrated under vacuum. The residue was purified by flash chromatography on silica gel eluting with CH$_3$OH/DCM (0-10%) to afford the title compound (206 mg, 48.6% yield) as yellow solid. LC-MS: (ESI, m/z): [M+H]$^+$=1003.

Step 3: 6-((5aS,6S,9R)-12-(((7a'S)-2,2-difluorodihydro-1'H,3'H-spiro[cyclopropane-1,2'-pyrrolizin]-7a'(5'H)-yl)methoxy)-1-fluoro-5a,6,7,8,9,10-hexahydro-5H-4-oxa-3,10a,11,13,14-pentaaza[6,9]methanonaphtho[1,8-ab]heptalen-2-yl)-4-methyl-5-(trifluoromethyl)pyridin-2-amine (Compound 42)

A solution of tert-butyl (5aS,6S,9R)-2-(6-(bis(4-methoxybenzyl)amino)-4-methyl-3-(trifluoromethyl)pyridin-2-yl)-12-(((7a'S)-2,2-difluorodihydro-1'H,3'H-spiro[cyclopropane-1,2'-pyrrolizin]-7a'(5'H)-yl)methoxy)-1-fluoro-5a,6,7,8,9,10-hexahydro-5H-4-oxa-3,10a,11,13,14-pentaaza-6,9-methanonaphtho[1,8-ab]heptalene-14-carboxylate (70.6 mg, 0.0700 mmol) in TFA (3 mL) was stirred at 50° C. for 3 hours. Then the mixture was concentrated under vacuum. The residue was purified by Prep-HPLC (Column: XBridge Prep OBD C18 Column, 30×150 mm 5 µm; Mobile Phase A:water (10 mmol/L NH$_4$HCO$_3$), Mobile Phase B:ACN; Flow rate:60 mL/min; Gradient:14B to 47B in 7 min; 254 nm; R$_{T1}$:6.8) to afford the title compound (21.5 mg, 46.1% yield) as a white solid. LC-MS: (ESI, m/z): [M+H]$^+$=663. $^1$H NMR (300 MHz, DMSO-d$_6$, ppm) δ 6.76 (s, 2H), 6.46 (s, 1H), 4.77 (dd, J=13.1, 2.2 Hz, 1H), 4.49 (dd, J=13.3, 2.0 Hz, 1H), 4.33 (dd, J=13.3, 7.6 Hz, 1H), 4.15 (d, J=1.8 Hz, 2H), 3.97 (d, J=7.2 Hz, 1H), 3.58 (d, J=5.6 Hz, 1H), 3.54-3.45 (m, 1H), 3.14-2.93 (m, 3H), 2.75-2.65 (m, 2H), 2.59-2.50 (m, 1H), 2.33 (d, J=2.2 Hz, 3H), 2.12-1.38 (m, 11H).

Example 43: 6 Compound 43
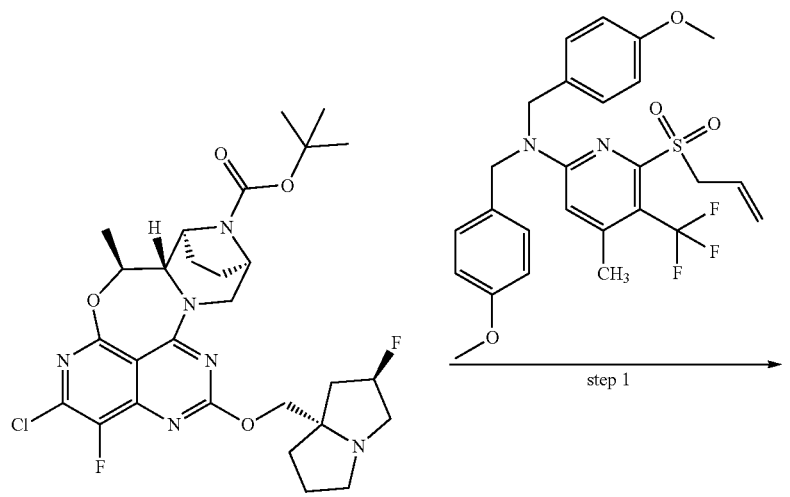
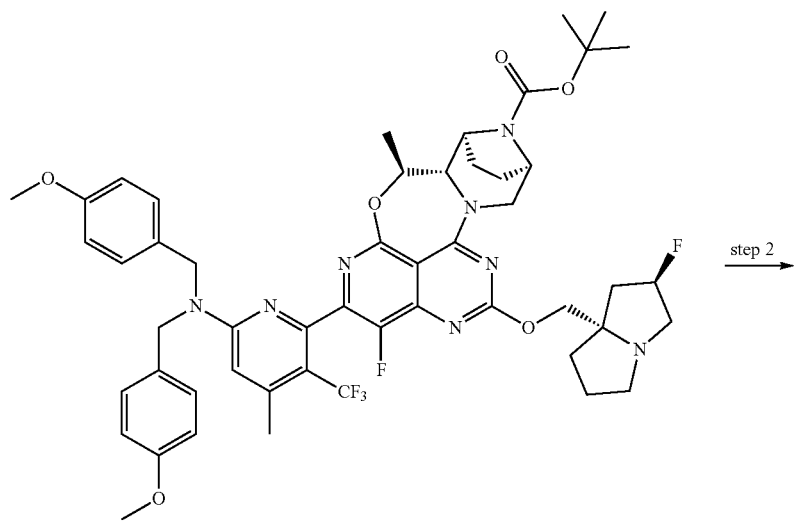
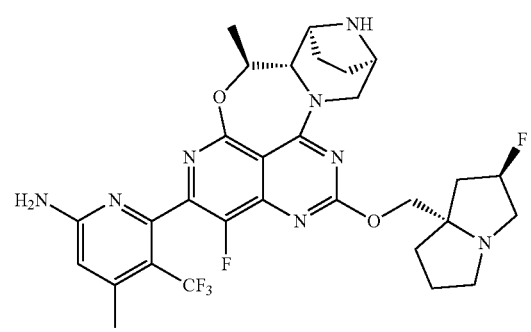

Step 1: tert-Butyl (5S,5aS,6S,9R)-2-(6-(bis(4-methoxybenzyl)amino)-4-methyl-3-(trifluoromethyl)pyridin-2-yl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate

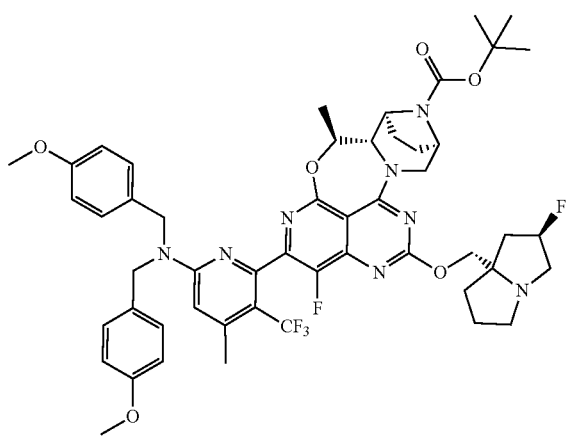

Under nitrogen, a solution of tert-butyl (5S,5aS,6S,9R)-2-chloro-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (300 mg, 0.510 mmol, intermediate 12), 6-(allylsulfonyl)-N,N-bis(4-methoxybenzyl)-4-methyl-5-(trifluoromethyl)pyridin-2-amine (395 mg, 0.760 mmol, intermediate 17), Pd(OAc)$_2$ (11.4 mg, 0.0500 mmol), P(t-Bu)$_2$MeHBF$_4$ (25.1 mg, 0.100 mmol) and Cs$_2$CO$_3$ (330 mg, 1.01 mmol) in 1,4-dioxane (3.5 mL) was stirred at 120° C. overnight. Then the mixture was concentrated under vacuum. The residue was purified by reverse phase chromatography (gradient: 0-100% ACN in water (0.05% NH$_4$HCO$_3$)) to afford 158 mg (32.1% yield) of the title compound as a yellow solid. LC-MS: (ESI, m/z): [M+H]$^+$=973.

Step 2: 6-((5S,5aS,6S,9R)-1-Fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-4-methyl-5-(trifluoromethyl)pyridin-2-amine (Compound 43)

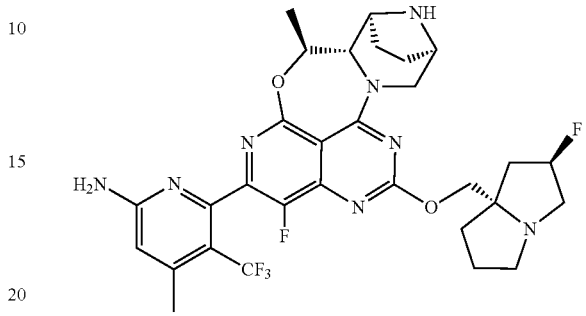

A solution of tert-butyl (5S,5aS,6S,9R)-2-(6-(bis(4-methoxybenzyl)amino)-4-methyl-3-(trifluoromethyl)pyridin-2-yl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (153 mg, 0.160 mmol) in TFA (5 mL) was stirred at 50° C. for 4 h. Then the mixture was concentrated under vacuum. The residue was purified by Prep-HPLC (Column: XBridge Prep OBD C18 Column, 30*150 mm, 5 μM; Mobile Phase A: Water(10 mmol/L NH$_4$HCO$_3$), Mobile Phase B: ACN; Flow rate: 60 mL/min; Gradient: 23% B to 48% B in 9 min, 48% B; Wave Length: 254/220 nm; R$_{T1}$(min): 8.9) to afford 58.8 mg (56.9% yield) of the title compound as a white solid. LC-MS: (ESI, m/z): [M+H]$^+$=633. $^1$HNMR (400 MHz, DMO-d$_6$, ppm) δ 6.82 (s, 2H), 6.48 (s, 1H), 5.29 (d, J=54.4 Hz, 1H), 5.15-5.03 (3, 1H), 4.56-4.43 (m, 1H), 4.09 (d, J=10.3 Hz, 1H), 4.04-3.90 (m, 2H), 3.57 (s, 1H), 3.49-3.41 (m, 1H), 3.17-3.03 (m, 3H), 3.00 (s, 1H), 2.92-2.75 (m, 1H), 2.40-2.31 (m, 3H), 2.18-2.12 (m, 1H), 2.08-1.97 (m, 2H), 1.93-1.72 (m, 4H), 1.71-1.51 (m, 3H), 1.43 (d, J=6.3 Hz, 3H).

Each compound in Table below was prepared following a similar experimental procedure (using appropriately substituted reagents) as described for Examples 42 and 43.

| Cmpd. No. | $^1$H NMR | MS (M + H)$^+$ |
|---|---|---|
| 44 | $^1$H NMR (400 MHz, DMSO-d$_6$, ppm) δ 6.79 (s, 2H), 6.47 (s, 1H), 5.39-5.18 (m, 1H), 4.78 (d, J = 12.8 Hz, 1H), 4.50 (dd, J = 13.3, 2.0 Hz, 1H), 4.34 (dd, J = 13.2, 7.6 Hz, 1H), 4.09 (d, J = 10.4 Hz, 1H), 4.02-3.95 (m, 2H), 3.59 (d, J = 5.8 Hz, 1H), 3.53-3.47 (m, 1H), 3.12-2.93 (m, 4H), 2.88-2.77 (m, 1H), 2.73 (s, 1H), 2.37-2.32 (m, 3H), 2.12 (d, J = 4.5 Hz, 1H), 2.11-1.90 (m, 2H), 1.87-1.51 (m, 7H). | 619 |
| 45 (Isomer 1) | $^1$H NMR (300 MHz, DMSO-d$_6$, ppm): δ 6.68 (s, 2H), 6.36 (s, 1H), 4.99 (dd, J = 12.9, 2.5 Hz, 1H), 4.42-4.54 (m, 1H), 4.40-4.25 (m, 2H), 3.84 (d, J = 8.7 Hz, 1H), 3.50-3.43 (m, 2H), 3.33 (d, J = 5.7 Hz, 1H), 3.28-3.21 (m, 1H), 3.10-3.02 (m, 3H), 2.78-2.86 (m, 1H), 2.62-2.40 (m, 2H), 2.38-2.16 (m, 4H), 1.88-1.78 (m, 1H) 1.68-1.58 (m, 3H), 1.31 (d, J = 6.3 Hz, 3H) | 637 |
| 45 (Isomer 2) | $^1$H NMR (300 MHz, DMSO-d$_6$, ppm): δ 6.86 (s, 2H), 6.46 (s, 1H), 5.12 (dd, J = 12.9, 2.5 Hz, 1H), 4.62-4.44 (m, 1H), 4.40-4.25 (m, 2H), 3.86 (d, J = 8.7 Hz, 1H), 3.68-3.57 (m, 3H), 3.33-3.02 (m, 4H), 2.78-2.86 (m, 1H), 2.52-2.30 (m, 6H), 1.88-1.78 (m, 1H) 1.78-1.58 (m, 3H), 1.46-1.37 (d, J = 6.3 Hz, 3H) | 637 |
| 47 | $^1$H NMR (300 MHz, DMSO-d$_6$, ppm): δ 6.80 (s, 2H), 6.48 (s, 1H), 5.10 (d, J = 12.2 Hz, 1H), 4.49 (s, 1H), 4.21-4.10 (m, 2H), 3.96 (d, J = 8.7 Hz, 1H), 3.68-3.57 (m, 1H), 3.44 (d, J = 5.7 Hz, 1H), 3.16-2.98 (m, 3H), 2.72 (d, J = 11.6 Hz, 1H), 2.35 (s, 3H), 2.10 (dd, J = 13.4, 5.6 Hz, 1H), 2.08-1.99 (m, 1H), 1.95-1.86 (d, J = 13.3 Hz, 1H), 1.84-1.76 (m, 4H), 1.72-1.51 (m, 6H), 1.59-1.40 (m, 3H). | 677 |

| Cmpd. No. | 1H NMR | MS (M + H)+ |
|---|---|---|
| 48 | 1H NMR (300 MHz, DMSO-d6, ppm): δ 6.80 (s, 2H), 6.48 (s, 1H), 5.08 (d, J = 12.6 Hz, 1H), 4.91 (s, 2H), 4.49 (dd, J = 8.6, 6.3 Hz, 1H), 4.07-3.91 (m, 3H), 3.56 (m, 2H), 3.44 (d, J = 5.7 Hz, 1H), 3.19 (d, J = 14.1 Hz, 1H), 3.07-2.94 (m, 2H), 2.65-2.55 (m, 2H), 2.30-2.24 (m, 4H), 2.03-1.90 (m, 1H), 1.88-1.57 (m, 7H), 1.43 (d, J = 6.3 Hz, 3H). | 627 |
Example 49: Compound 49 (Two Unknown Single Isomers
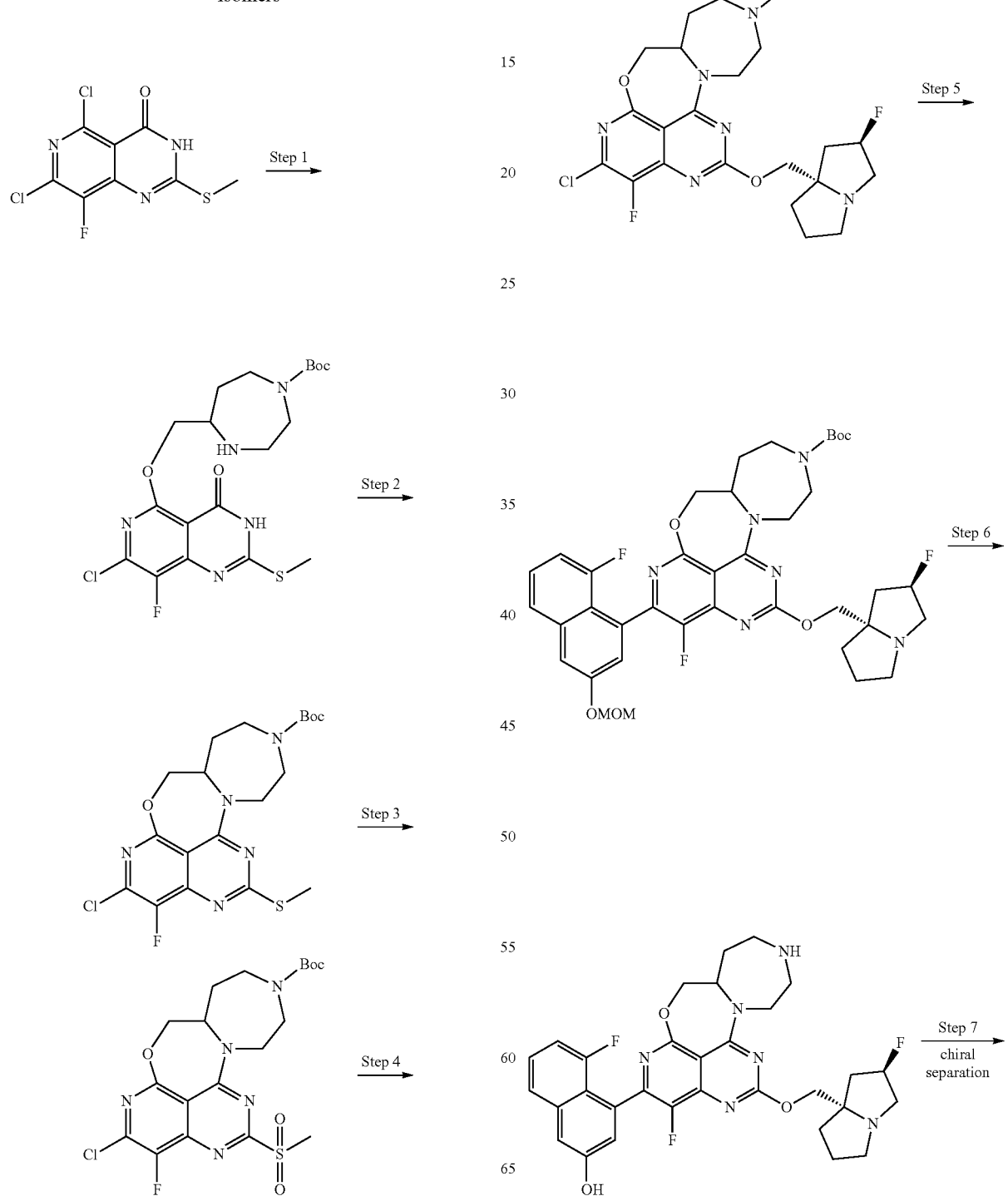

-continued

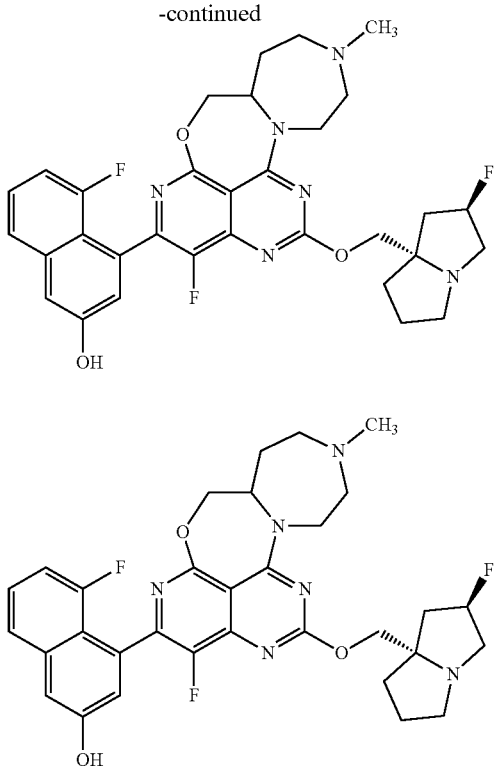

Step 1: tert-Butyl 5-(((7-chloro-8-fluoro-2-(methyl-thio)-4-oxo-4-pyrido[3,4-e]pyrimidin-5-yl)oxy)methyl)-1,4-diazepane-1-carboxylate Under nitrogen, to a solution of tert-butyl 5-(hydroxymethyl)-1,4-diazepane-1-carboxylate (280 mg, 1.22 mmol, intermediate 38) in tetrahydrofuran (2 mL) was added NaH (316 mg, 4.86 mmol, 60% in mineral oil) at 0° C. The resulting solution was stirred at room temperature for 0.5 h. Then 5,7-dichloro-8-fluoro-2-methylsulfanyl-3H-pyrido[4,3-d]pyrimidin-4-one (409 mg, 1.46 mmol, intermediate 2) was added. The resulting mixture was stirred for 2 hours at room temperature. The reaction mixture was partitioned between saturated aqueous NH$_4$Cl and EtOAc. The organic layer was washed with saturated aqueous NaHCO$_3$, water and brine, dried over MgSO$_4$ and concentrated under vacuum. The residue was purified by flash chromatography on silica gel (gradient: 0%-20% MeOH/DCM) to yield 480 mg (83.6% yield) of the title compound as a white solid. LC-MS: (ESI, m/z): [M+H]$^+$=473.

Step 2: tert-Butyl 2-chloro-1-fluoro-12-(methyl-thio)-5,5a,6,7,9,10-hexahydro-8H-4-oxa-3,8,10a,11,13-pentaazanaphtho[1,8-ab]heptalene-8-carboxylate A mixture of tert-butyl rac-(5S)-5-[(7-chloro-8-fluoro-2-methylsulfanyl-4-oxo-3H-pyrido[4,3-d]pyrimidin-5-yl)oxymethyl]-1,4-diazepane-1-carboxylate (100 mg, 0.210 mmol), BOPCl (80.6 mg, 0.320 mmol) and DIEPA (136 mg, 1.05 mmol) in DCE (2 mL) was stirred overnight at room temperature. The resulting mixture was diluted with water and extracted with EtOAc. The combined organic layers were dried over anhydrous Na$_2$SO$_4$ and concentrated under reduced pressure to afford 120 mg (crude) as brown solid which was used for next step without further purification. LC-MS: (ESI, m/z): [M+H]$^+$=456.

Step 3: tert-Butyl 2-chloro-1-fluoro-12-(methylsulfonyl)-5,5a,6,7,9,10-hexahydro-8H-4-oxa-3,8,10a,11,13-pentaazanaphtho[1,8-ab]heptalene-8-carboxylate To a solution of tert-butyl 13-chloro-14-fluoro-17-methylsulfanyl-10-oxa-2,5,12,16,18-pentazatetracyclo[9.7.1.02,8.015,19]nonadeca-1(18),11(19),12,14,16-pentaene-5-carboxylate (104 mg, 0.230 mmol) in EtOAc (3 mL) was added m-CPBA (118 mg, 0.680 mmol) at 0° C. The resulting mixture was stirred overnight at room temperature. The reaction mixture was partitioned between saturated aqueous NH$_4$Cl and EtOAc. The organic layer was washed with saturated aqueous NaHCO$_3$, water and brine, dried over MgSO$_4$ and concentrated under vacuum. The residue was purified by flash chromatography on silica gel (gradient: 0%-50% EtOAc/petroleum ether) to yield 61 mg (54% yield) of the title compound as a yellow solid. LC-MS: (ESI, m/z): [M+H]$^+$=488.

Step 4: tert-Butyl 2-chloro-1-fluoro-12-(((2R,7aS)-2-fluorotetrahydro-1H-pyrrolizin-7a(5H)-yl)methoxy)-5,5a,6,7,9,10-hexahydro-8H-4-oxa-3,8,10a,11,13-pentaazanaphtho[1,8-ab]heptalene-8-carboxylate To a solution of tert-butyl 13-chloro-14-fluoro-17-methylsulfonyl-10-oxa-2,5,12,16,18-pentazatetracyclo[9.7.1.02,8.015,19]nonadeca-1(18),11(19),12,14,16-pentaene-5-carboxylate (105 mg, 0.220 mmol), [rac-(2R,8S)-2-fluoro-1,2,3,5,6,7-hexahydropyrrolizin-8-yl]methanol (68.5 mg, 0.430 mmol, intermediate 5) in toluene (3 mL) was added t-BuONa (41.4 mg, 0.430 mmol) at 0° C. The resulting mixture was stirred overnight at room temperature. The reaction mixture was partitioned between saturated aqueous NH$_4$Cl and EtOAc. The organic layer was washed with saturated aqueous NaHCO$_3$, water and brine, dried over MgSO$_4$ and concentrated under vacuum. The residue was purified by flash chromatography on silica gel (gradient: 0%-20% MeOH/DCM) to yield 40 mg (32.8% yield) of the title compound as a yellow solid. LC-MS: (ESI, m/z): [M+H]$^+$=567.

Step 5: tert-Butyl 1-fluoro-2-(8-fluoro-3-(methoxymethoxy)naphthalen-1-yl)-12-(((2R,7aS)-2-fluorotetrahydro-1H-pyrrolizin-7a(5H)-yl)methoxy)-5,5a,6,7,9,10-hexahydro-8H-4-oxa-3,8,10a,11,13-pentaazanaphtho[1,8-ab]heptalene-8-carboxylate A solution of tert-butyl 13-chloro-14-fluoro-17-[[rac-(2R,8S)-2-fluoro-1,2,3,5,6,7-hexahydropyrrolizin-8-yl]methoxy]-10-oxa-2,5,12,16,18-pentazatetracyclo[9.7.1.02,8.015,19]nonadeca-1(18),11(19),12,14,16-pentaene-5-carboxylate (50 mg, 0.09 mmol), 2-(8-fluoro-3-(methoxymethoxy)naphthalen-1-yl)-4,4,5,5-tetramethyl-1,3,2-dioxaborolane (44 mg, 0.13 mmol, intermediate 25), Cs$_2$CO$_3$ (86.2 mg, 0.260 mmol), Pd(PPh$_3$)$_4$(51 mg, 0.040 mmol) in 1,4-dioxane (2 mL) and water (0.4 mL) was stirred for 3 hours at 95° C. The reaction mixture was partitioned between water and EtOAc. The organic layer was washed with saturated aqueous NaHCO$_3$, water and brine, dried over MgSO$_4$ and concentrated under vacuum. The residue was purified by flash chromatography on silica gel (gradient: 0%-20% MeOH/

DCM) to yield 45 mg (69.3% yield) of the title compound as a yellow solid. LC-MS: (ESI, m/z): [M+H]⁺=737.

Step 6: 5-Fluoro-4-(1-fluoro-12-(((2R,7aS)-2-fluorotetrahydro-1H-pyrrolizin-7a(5H)-yl)methoxy)-5a,6,7,8,9,10-hexahydro-5H-4-oxa-3,8,10a,11,13-pentaazanaphtho[1,8-ab]heptalen-2-yl)naphthalen-2-ol A solution of tert-butyl 14-fluoro-13-[8-fluoro-3-(methoxymethoxy)-1-naphthyl]-17-[[rac-(2R,8S)-2-fluoro-1,2,3,5,6,7-hexahydropyrrolizin-8-yl]methoxy]-10-oxa-2,5,12,16,18-pentazatetracyclo[9.7.1.02,8.015,19]nonadeca-1(18),11(19),12,14,16-pentaene-5-carboxylate (80 mg, 0.110 mmol) and HCl (1 mL, 4 M in dioxane) in DCE (2 mL) was stirred for 2 hours at room temperature. The resulting mixture was concentrated under reduced pressure to afford 60 mg (crude) which was used for next step without further purification. LC-MS: (ESI, m/z): [M+H]⁺=593.

Step 7: 5-Fluoro-4-(1-fluoro-12-(((2R,7aS)-2-fluorotetrahydro-1H-pyrrolizin-7a(5H)-yl)methoxy)-8-methyl-5a,6,7,8,9,10-hexahydro-5H-4-oxa-3,8,10a,11,13-pentaazanaphtho[1,8-ab]heptalen-2-yl)naphthalen-2-ol (two unknown single isomers)

A solution of 5-fluoro-4-[14-fluoro-17-[[rac-(2R,8S)-2-fluoro-1,2,3,5,6,7-hexahydropyrrolizin-8-yl]methoxy]-10-oxa-2,5,12,16,18-pentazatetracyclo[9.7.1.02,8.015,19]nonadeca-1(18),11(19),12,14,16-pentaen-13-yl]naphthalen-2-ol (60.0 mg, 0.1 mmol), HCHO (0.1 mL, 40% in water) and NaOAc (8.3 mg, 0.1 mmol) in DCM (2 mL) was stirred 1 h at room temperature. Then NaBH(AcO)₃ (32.2 mg, 0.150 mmol) was added. The resulting mixture was stirred overnight at room temperature. The reaction mixture was partitioned between water and DCM. The organic layer was dried over sodium sulfate and concentrated under vacuum. The crude product was separated by Prep-CHIRAL HPLC with the following conditions: (Column: CHIRAL ART Cellulose-SC, 2*25 cm, 5 μm; Mobile Phase A: Hex:DCM=3:1 (0.5% 2 M NH₃-MeOH)-HPLC, Mobile Phase B: EtOH—HPLC; Flow rate: 20 mL/min; Gradient: 15% B to 15% B in 21 min; Wave Length: 220/254 nm; RT1(min): 12.52; RT2(min): 17.38; Sample Solvent: EtOH-HPLC; Injection Volume: 1 mL; Number Of Runs: 1) to yield 5.7 mg (9.3% yield) Compound 49a and 7.8 mg (12.7% yield) of Compound 49b as white solids.

Compound 49a: LC-MS: (ESI, m/z): [M+H]⁺=607. ¹H NMR (300 MHz, DMSO-d₆, ppm): δ 10.22 (d, J=9.4 Hz, 1H), 7.66 (d, J=8.3 Hz, 1H), 7.44 (m, 1H), 7.34 (d, J=2.2 Hz, 1H), 7.14 (m, 1H), 7.02 (m, 1H), 5.29 (d, J=54.5 Hz, 1H), 4.84 (t, J=12.6 Hz, 1H), 4.52 (m, 2H), 4.15 (m, 2H), 4.02 (m, 1H), 3.54-3.41 (m, 1H), 3.10 (d, J=6.7 Hz, 2H), 3.01 (s, 1H), 2.82 (t, J=8.1 Hz, 2H), 2.67 (d, J=11.5 Hz, 3H), 2.30 (d, J=2.3 Hz, 3H), 2.15 (d, J=6.7 Hz, 1H), 2.10-1.93 (m, 3H), 1.93-1.63 (m, 4H).

Compound 49b: LC-MS: (ESI, m/z): [M+H]⁺=607. ¹H NMR (300 MHz, DMSO-d4, ppm): δ 10.22 (d, J=9.1 Hz, 1H), 7.66 (d, J=8.3 Hz, 1H), 7.43 (m, 1H), 7.34 (d, J=2.2 Hz, 1H), 7.18 (d, J=2.4 Hz, 1H), 7.02 (m, 1H), 5.28 (d, J=54.3 Hz, 1H), 4.93-4.80 (m, 1H), 4.65-4.41 (m, 2H), 4.26-4.09 (m, 2H), 4.04 (d, J=10.6 Hz, 1H), 3.54-3.41 (m, 1H), 3.10 (s, 2H), 3.00 (s, 1H), 2.89-2.75 (m, 2H), 2.69 (s, 3H), 2.30 (s, 3H), 2.14 (s, 1H), 2.06-1.89 (m, 3H), 1.89-1.61 (m, 4H).

Example of 50: Compound 50

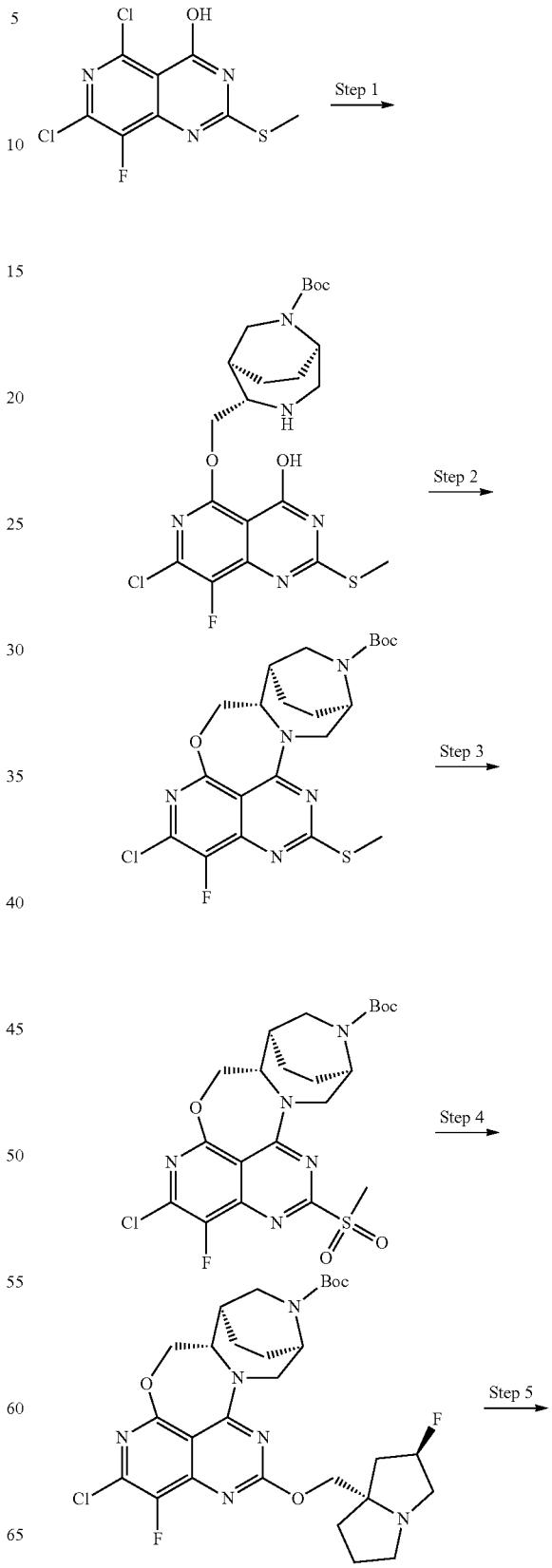

-continued

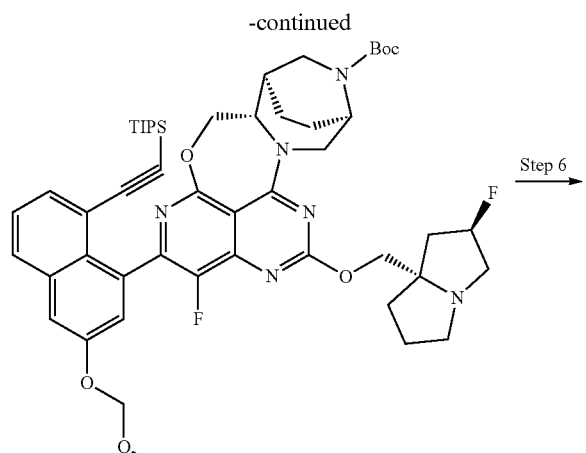

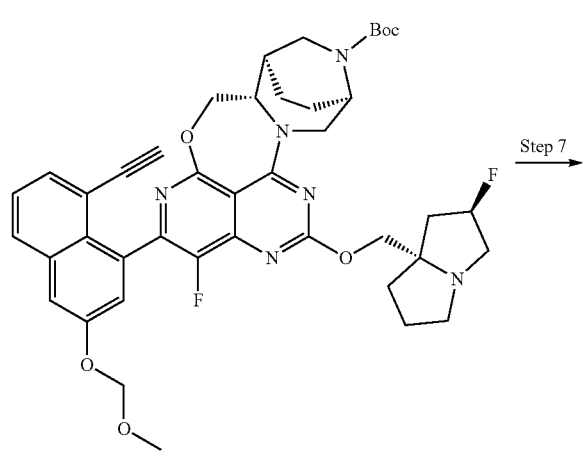

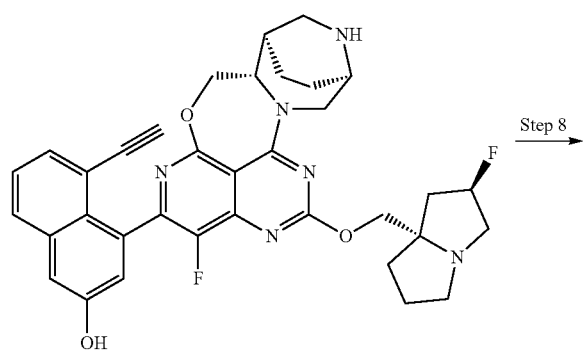

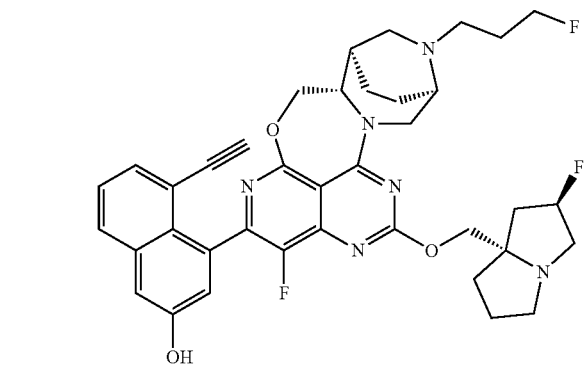

Step 1: tert-Butyl (1R,2S,5R)-2-(((7-chloro-8-fluoro-4-hydroxy-2-(methylthio)pyrido[4,3-d]pyrimidin-5-yl)oxy)methyl)-3,6-diazabicyclo[3.2.2]nonane-6-carboxylate To a solution of tert-butyl (1R,2S,5R)-2-(hydroxymethyl)-3,6-diazabicyclo[3.2.2]nonane-6-carboxylate (460 mg, 1.79 mmol, intermediate 39) in tetrahydrofuran (10 mL) was added NaH (431 mg, 10.8 mmol, 60% in mineral oil) at 0° C. The mixture was stirred at room temperature for 20 min. Then 5,7-dichloro-8-fluoro-2-(methylthio)pyrido[4,3-d]pyrimidin-4-ol (600 mg, 2.15 mmol, intermediate 2) was added and the mixture was allowed to warm to room temperature and stirred at room temperature overnight. The reaction mixture was quenched with water. The precipitated solids were collected by filtration, washed with water and dried in oven to yield 1.20 g (crude) the title compound as a yellow solid which was used for next step without further purification. LC-MS: (ESI, m/z): [M+H]$^+$=500.

Step 2: tert-Butyl (5aS,6R,9R)-2-chloro-1-fluoro-12-(methylthio)-5a,6,7,8,9,10-hexahydro-5H-4-oxa-3,10a,11,13,14-pentaaza-6,9-ethanonaphtho[1,8-ab]heptalene-14-carboxylate A solution of tert-butyl (1R,2S,5R)-2-(((7-chloro-8-fluoro-4-hydroxy-2-(methylthio)pyrido[4,3-d]pyrimidin-5-yl)oxy)methyl)-3,6-diazabicyclo[3.2.2]nonane-6-carboxylate (1.17 g, 2.34 mmol), BOPCl (2.97 g, 11.7 mmol) and DIPEA (3.02 g, 23.4 mmol) in DCE (12 mL) was stirred at room temperature for 4 hours. The resulting mixture was partitioned between water and EtOAc. The combined organic layers were washed with brine, dried over anhydrous Na$_2$SO$_4$ and concentrated under reduced pressure. The residue was purified by flash chromatography on silica gel (gradient:0-40% EtOAc/petroleum ether) to afford 600 mg (46.9% yield) of the title compound as a light yellow solid. LC-MS: (ESI, m/z): [M+H]$^+$=482

Step 3: tert-Butyl (5aS,6R,9R)-2-chloro-1-fluoro-12-(methylsulfonyl)-5a,6,7,8,9,10-hexahydro-5H-4-oxa-3,10a,11,13,14-pentaaza-6,9-ethanonaphtho[1,8-ab]heptalene-14-carboxylate To a solution of tert-butyl (5aS,6R,9R)-2-chloro-1-fluoro-12-(methylthio)-5a,6,7,8,9,10-hexahydro-5H-4-oxa-3,10a,11,13,14-pentaaza-6,9-ethanonaphtho[1,8-ab]heptalene-14-carboxylate (430 mg, 0.894 mmol) in ethyl acetate (10 mL) was added mCPBA (308 mg, 1.79 mmol) portion wise at 0° C. The resulting solution was stirred at room temperature for 1 h. The reaction mixture was quenched with aqueous NaHCO$_3$ and extracted with EtOAc. The combined organic layers were dried over anhydrous Na$_2$SO$_4$ and concentrated under reduced pressure. The residue was purified by flash chromatography on silica gel (gradient:0-50% EtOAc/petroleum ether) to afford 422 mg (92.0% yield) of the title compound as a light yellow solid. LC-MS: (ESI, m/z): [M+H]$^+$=514.

Step 4: tert-Butyl (5aS,6R,9R)-2-chloro-1-fluoro-12-(((2R,7aS)-2-fluorotetrahydro-1H-pyrrolizin-7a(5H)-yl)methoxy)-5a,6,7,8,9,10-hexahydro-5H-4-oxa-3,10a,11,13,14-pentaaza-6,9-ethanonaphtho[1,8-ab]heptalene-14-carboxylate To a solution of tert-butyl (5aS,6R,9R)-2-chloro-1-fluoro-12-(methylsulfonyl)-5a,6,7,8,9,10-hexahydro-5H-4-oxa-3, 10a,11,13,14-pentaaza-6,9-ethanonaphtho[1,8-ab]heptalene-14-carboxylate (400 mg, 0.780 mmol) and ((2R,7aS)-2-fluorotetrahydro-1H-pyrrolizin-7a(5H)-yl)methanol (149 mg, 0.930 mmol, intermediate 5) in toluene (5 mL) was added t-BuONa (149 mg, 1.56 mmol) at 0° C. The reaction was stirred at room temperature for 1 hour. The resulting mixture was diluted with water and extracted with EtOAc. The combined organic layers were washed with brine, dried over anhydrous $Na_2SO_4$ and concentrated under reduced pressure. The residue was purified by flash chromatography on silica gel (gradient: 0-5% MeOH in DCM) to afford 370 mg (78.4% yield) of the title compound as a white solid. LC-MS: (ESI, m/z): $[M+H]^+$=593.

Step 5: tert-Butyl (5aS,6R,9R)-1-fluoro-12-(((2R,7aS)-2-fluorotetrahydro-1H-pyrrolizin-7a(5H)-yl)methoxy)-2-(3-(methoxymethoxy)-8-((triisopropylsilyl)ethynyl)naphthalen-1-yl)-5a,6,7,8,9,10-hexahydro-5H-4-oxa-3,10a,11,13,14-pentaaza-6,9-ethanonaphtho[1,8-ab]heptalene-14-carboxylate Under nitrogen, a solution of tert-butyl (5aS,6R,9R)-2-chloro-1-fluoro-12-(((2R,7aS)-2-fluorotetrahydro-1H-pyrrolizin-7a(5H)-yl)methoxy)-5a,6,7,8,9,10-hexahydro-5H-4-oxa-3,10a,11,13,14-pentaaza-6,9-ethanonaphtho[1,8-ab]heptalene-14-carboxylate (180 mg, 0.300 mmol), triisopropyl((6-(methoxymethoxy)-8-(4,4,5,5-tetramethyl-1,3,2-dioxaborolan-2-yl)naphthalen-1-yl)ethynyl)silane (300 mg, 0.610 mmol), $K_3PO_4$(1.5 M in water, 0.4 ml) and cataCXium A Pd G3 (44.2 mg, 0.0600 mmol) in tetrahydrofuran (5 mL) was stirred at 60° C. for 2 hours. The solid was filtered off and the filtrate was concentrated under reduced pressure. The residue was partitioned between water and EtOAc. The combined organic layers were washed with brine, dried over anhydrous $Na_2SO_4$ and concentrated under reduced pressure. The residue was purified by flash chromatography on silica gel (gradient: 0-5% MeOH in DCM) to afford 259 mg (91.6% yield) of the title compound as a yellow solid. LC-MS: (ESI, m/z): $[M+H]^+$= 926.

Step 6: tert-Butyl (5aS,6R,9R)-2-(8-ethynyl-3-(methoxymethoxy)naphthalen-1-yl)-1-fluoro-12-(((2R,7aS)-2-fluorotetrahydro-1H-pyrrolizin-7a(5H)-yl)methoxy)-5a,6,7,8,9,10-hexahydro-5H-4-oxa-3,10a,11,13,14-pentaaza-6,9-ethanonaphtho[1,8-ab]heptalene-14-carboxylate A solution of tert-butyl (5aS,6R,9R)-1-fluoro-12-(((2R,7aS)-2-fluorotetrahydro-1H-pyrrolizin-7a(5H)-yl)methoxy)-2-(3-(methoxymethoxy)-8-((triisopropylsilyl)ethynyl)naphthalen-1-yl)-5a,6,7,8,9,10-hexahydro-5H-4-oxa-3,10a,11,13,14-pentaaza-6,9-ethanonaphtho[1,8-ab]heptalene-14-carboxylate (249 mg, 0.270 mmol) and CsF (409 mg, 2.69 mmol) in N,N-dimethylacetamide (2 mL) was stirred at room temperature for 2 hours. The solid was filtered off. The filtrate was purified by reverse phase chromatography on pre-packed C18 column (solvent gradient: 0-100% ACN in water (0.05% $NH_4HCO_3$)) to yield 198 mg (95.7% yield) of the title compound as a white solid. LC-MS: (ESI, m/z): $[M+H]^+$=769.

Step 7: 5-Ethynyl-4-((5aS,6R,9R)-1-fluoro-12-(((2R,7aS)-2-fluorotetrahydro-1H-pyrrolizin-7a(5H)-yl)methoxy)-5a,6,7,8,9,10-hexahydro-5H-4-oxa-3,10a,11,13,14-pentaaza-6,9-ethanonaphtho[1,8-ab]heptalen-2-yl)naphthalen-2-ol To a solution of tert-butyl (5aS,6R,9R)-2-(8-ethynyl-3-(methoxymethoxy)naphthalen-1-yl)-1-fluoro-12-(((2R,7aS)-2-fluorotetrahydro-1H-pyrrolizin-7a(5H)-yl)methoxy)-5a,6,7,8,9,10-hexahydro-5H-4-oxa-3,10a,11,13,14-pentaaza-6,9-ethanonaphtho[1,8-ab]heptalene-14-carboxylate (188 mg, 0.250 mmol) in acetonitrile (1.5 mL) was added 4 M HCl/dioxane (0.5 mL) at 0° C. The reaction was stirred at 0° C. for 3 hours and concentrated under reduced pressure. The residue was purified by reverse phase chromatography on pre-packed C18 column (solvent gradient: 0-50% ACN in water (0.05% $NH_4HCO_3$)) to yield 147 mg (89.7% yield) of the title compound as a yellow solid. LC-MS: (ESI, m/z): $[M+H]^+$=625.

Step 8: 5-Ethynyl-4-((5aS,6R,9R)-1-fluoro-14-(3-fluoropropyl)-12-(((2R,7aS)-2-fluorotetrahydro-1H-pyrrolizin-7a(5H)-yl)methoxy)-5a,6,7,8,9,10-hexahydro-5H-4-oxa-3,10a,11,13,14-pentaaza-6,9-ethanonaphtho[1,8-ab]heptalen-2-yl)naphthalen-2-ol (Compound 50)

A solution of 5-ethynyl-4-((5aS,6R,9R)-1-fluoro-12-(((2R,7aS)-2-fluorotetrahydro-1H-pyrrolizin-7a(5H)-yl)methoxy)-5a,6,7,8,9,10-hexahydro-5H-4-oxa-3,10a,11,13,14-pentaaza-6,9-ethanonaphtho[1,8-ab]heptalen-2-yl)naphthalen-2-ol (75.0 mg, 0.120 mmol), 1-iodo-3-fluoropropane (45.1 mg, 0.240 mmol) and DIPEA (77.4 mg, 0.600 mmol) in acetonitrile (1.5 mL) was stirred at 50° C. overnight. Then the mixture was concentrated under vacuum. The crude was purified by Prep-HPLC (XBridge Prep OBD C18 Column, 30×150 mm 5 μm; Mobile Phase A:Water(10 mmol/L $NH_4HCO_3$), Mobile Phase B:ACN; Flow rate:60 mL/min; Gradient:32% B to 57% B in 9 min; 57% B; Wavelength: 254/220 nm; $R_T$(min): 7.9) to yield 24.4 mg (29.6% yield) of the title compound as a yellow solid. LC-MS: (ESI, m/z): $[M+H]^+$=685. $^1$H NMR (300 MHz, DMSO-d6) δ 10.12 (m, 1H), 7.87 (m, 1H), 7.51-7.35 (m, 2H), 7.31 (m, 1H), 7.10 (m, 1H), 5.28 (m, 1H), 5.10-4.93 (m, 1H), 4.66-4.41 (m, 4H), 4.24 (s, 1H), 4.13 (m, 1H), 3.97 (m, 1H), 3.49 (s, 1H), 3.25 (m, 1H), 3.07 (m, 5H), 2.88-2.69 (m, 3H), 2.56 (m, 1H), 2.38 (s, 1H), 2.17-1.96 (m, 3H), 1.83 (m, 6H), 1.51 (m, 3H).

The compound in the Table below was prepared following a similar experimental procedure (using appropriately substituted reagents) as described for Examples 49 and 50.

| Cmpd. No. | $^1$H NMR | MS (M + H)$^+$ |
|---|---|---|
| 51 | $^1$H NMR (300 MHz, DMSO-d$_6$) δ 10.10 (s, 1H), 7.85 (m, 1H), 7.48-7.35 (m, 2H), 7.30 (m, 1H), 7.09 (m, 1H), 5.27 (m, 1H), 5.07-4.92 (m, 1H), 4.65 (m, 2H), 4.56-4.37 (m, 2H), 4.28 m, 2H), 4.24-4.05 (m, 2H), 3.96 (m, 1H), 3.73 (s, 1H), 3.47 (s, 1H), 3.24-2.67 (m, 10H), 2.35 (s, 1H), 2.13 (m, 1H), 2.01 (m, 2H), 1.94-1.65 (m, 4H), 1.65-1.30 (m, 3H). | 695 |

Example 52: Compound 52

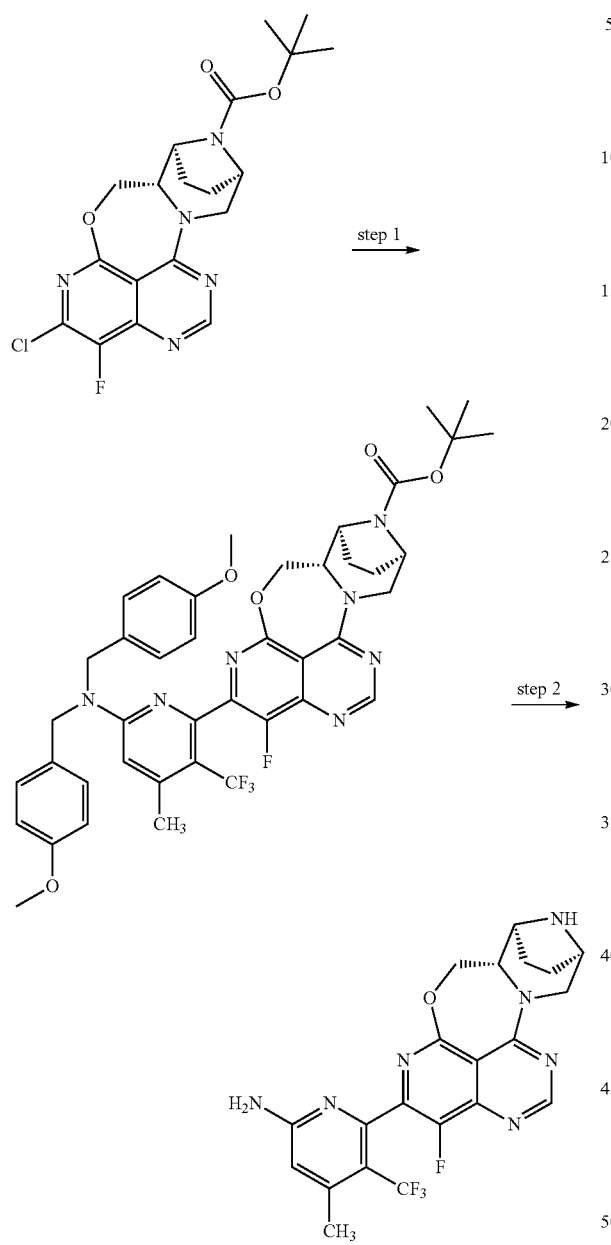

Step 1: tert-Butyl (5aS,6S,9R)-2-(6-(bis(4-methoxybenzyl)amino)-4-methyl-3-(trifluoromethyl)pyridin-2-yl)-1-fluoro-5a,6,7,8,9,10-hexahydro-5H-4-oxa-3,10a,11,13,14-pentaaza-6,9-methanonaphtho[1,8-ab]heptalene-14-carboxylate Under nitrogen, a solution of tert-butyl (5aS,6S,9R)-2-chloro-1-fluoro-5a,6,7,8,9,10-hexahydro-5H-4-oxa-3,10a,11,13,14-pentaaza-6,9-methanonaphtho[1,8-ab]heptalene-14-carboxylate (55.1 mg, 0.130 mmol, intermediate 14), N,N-bis(4-methoxybenzyl)-4-methyl-6-(tributylstannyl)-5-(trifluoromethyl)pyridin-2-amine (168 mg, 0.240 mmol, intermediate 42), Pd(PPh$_3$)$_4$(30.1 mg, 0.0300 mmol), LiCl (14.1 mg, 0.340 mmol) and CuI (3.20 mg, 0.0200 mmol) in 1,4-dioxane (1 mL) was stirred for 2 days at 110° C. Then the mixture was concentrated under vacuum. The residue was purified by flash chromatography on silica gel eluting with EtOAc/petroleum ether (0-65%) to afford the title compound (63.9 mg, 42.7% yield) as a light yellow solid. LC-MS: (ESI, m/z): [M+H]$^+$=802.

Step 2: 6-((5aS,6S,9R)-1-Fluoro-5a,6,7,8,9,10-hexahydro-5H-4-oxa-3,10a,11,13,14-pentaaza-6,9-methanonaphtho[1,8-ab]heptalen-2-yl)-4-methyl-5-(trifluoromethyl)pyridin-2-amine (Compound 52)

A solution of tert-butyl (5aS,6S,9R)-2-(6-(bis(4-methoxybenzyl)amino)-4-methyl-3-(trifluoromethyl)pyridin-2-yl)-1-fluoro-5a,6,7,8,9,10-hexahydro-5H-4-oxa-3,10a,11,13,14-pentaaza-6,9-methanonaphtho[1,8-ab]heptalene-14-carboxylate (63.9 mg, 0.0558 mmol) in TFA (3 mL) was stirred at 50° C. for 4 hours. Then the mixture was concentrated under vacuum. The residue was purified by Prep-HPLC (Column: XBridge Prep OBD C18 Column, 30×150 mm 5 μm; Mobile Phase A:Water (10 mmol/L NH$_4$HCO$_3$), Mobile Phase B:ACN; Flow rate:60 mL/min; Gradient:12B to 42B in 7 min; 254 nm; R$_{T1}$:6.5) to afford the title compound (9.7 mg, 26.4% yield) as a white solid. LC-MS: (ESI, m/z): [M+H]$^+$=462. $^1$H NMR (300 MHz, DMSO-d$_6$, ppm) δ 8.63 (s, 1H), 6.81 (s, 2H), 6.47 (s, 1H), 4.91 (dd, J=13.1, 2.2 Hz, 1H), 4.52 (dd, J=13.3, 2.1 Hz, 1H), 4.39 (dd, J=13.3, 7.7 Hz, 1H), 4.00 (d, J=7.4 Hz, 1H), 3.56 (d, J=5.3 Hz, 1H), 3.50 (d, J=5.7 Hz, 1H), 3.03 (d, J=12.3 Hz, 1H), 2.37-2.30 (m, 3H), 1.67 (d, J=10.5 Hz, 2H), 1.64-1.41 (m, 2H).

Example 53: Compound 53

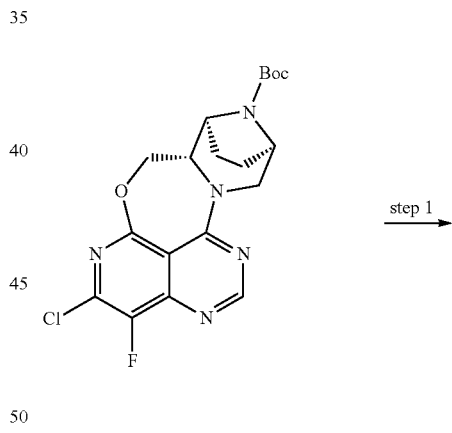

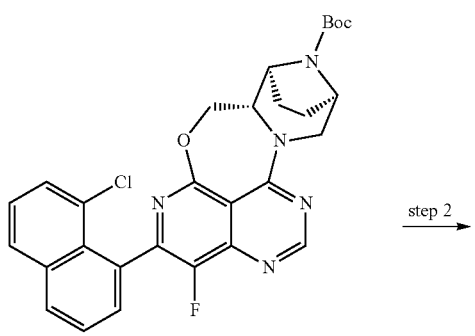

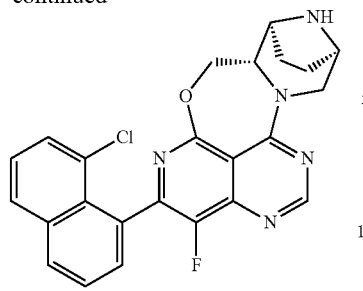

Step 1: tert-Butyl (5aS,6S,9R)-2-(8-chloronaphthalen-1-yl)-1-fluoro-5a,6,7,8,9,10-hexahydro-5H-4-oxa-3,10a,11,13,14-pentaaza-6,9-methanonaphtho[1,8-ab]heptalene-14-carboxylate Under nitrogen, a solution of tert-butyl (5aS,6S,9R)-2-chloro-1-fluoro-5a,6,7,8,9,10-hexahydro-5H-4-oxa-3,10a,11,13,14-pentaaza-6,9-methanonaphtho[1,8-ab]heptalene-14-carboxylate (60.2 mg, 0.140 mmol, intermediate 14), 2-(8-chloronaphthalen-1-yl)-4,4,5,5-tetramethyl-1,3,2-dioxaborolane (103 mg, 0.360 mmol, intermediate 41), Pd(PPh$_3$)$_2$Cl$_2$ (20.1 mg, 0.0300 mmol) and KF (24.8 mg, 0.430 mmol) in acetonitrile (1.5 mL) and water (0.3 mL) was stirred overnight at 100° C. Then the mixture was concentrated under vacuum. The residue was purified by flash chromatography on silica gel eluting with EtOAc/petroleum ether (0-75%) to afford the title compound (37.3 mg, 47.7% yield) as a yellow solid. LC-MS: (ESI, m/z): [M+H]$^+$=548.

Step 2: (5aS,6S,9R)-2-(8-Chloronaphthalen-1-yl)-1-fluoro-5a,6,7,8,9,10-hexahydro-5H-4-oxa-3,10a,11,13,14-pentaaza-6,9-methanonaphtho[1,8-ab]heptalene (Compound 53)

A solution of tert-butyl (5aS,6S,9R)-2-(8-chloronaphthalen-1-yl)-1-fluoro-5a,6,7,8,9,10-hexahydro-5H-4-oxa-3,10a,11,13,14-pentaaza-6,9-methanonaphtho[1,8-ab]heptalene-14-carboxylate (37.3 mg, 0.0700 mmol) and TFA (0.5 mL) in DCM (2 mL) was stirred at room temperature for 1 hour. Then the mixture was concentrated under vacuum. The residue was purified by Prep-HPLC (Column: Xselect CSH F-Phenyl OBD column, 19*250, 5 μm; Mobile Phase A: Water (0.05% FA), Mobile Phase B: ACN; Flow rate:25 mL/min; Gradient:3B to 20B in 9 min; 254 nm; R$_{T1}$:7.55) to afford the title compound (11.3 mg, 33.6% yield) as a white solid. LC-MS: (ESI, m/z): [M+H]$^+$=448. $^1$H NMR (300 MHz, DMSO-d$_6$, ppm) δ 8.68 (d, J=1.8 Hz, 1H), 8.25-8.14 (m, 1H), 8.10 (dd, J=8.1, 1.4 Hz, 1H), 7.79-7.50 (m, 4H), 5.04-4.94 (m, 1H), 4.63-4.37 (m, 2H), 4.08 (t, J=9.5 Hz, 1H), 3.64 (s, 1H), 3.57 (s, 1H), 3.16-3.03 (m, 1H), 1.80-1.54 (m, 4H).

Example 54: Compound 54

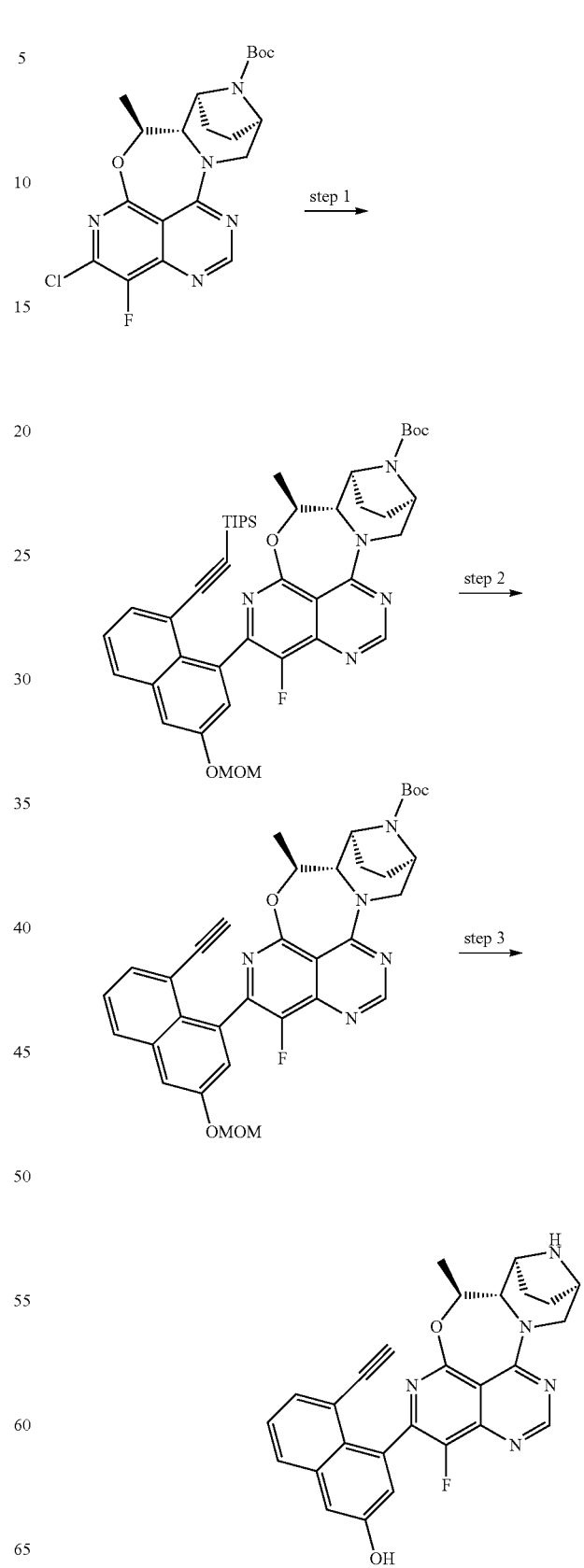

Step 1: tert-Butyl (5S,5aS,6S,9R)-1-fluoro-2-(3-(methoxymethoxy)-8-((triisopropylsilyl)ethynyl) naphthalen-1-yl)-5-methyl-5a,6,7,8,9,10-hexahydro-5H-4-oxa-3,10a,11,13,14-pentaaza-6,9-methanonaphtho[1,8-ab]heptalene-14-carboxylate Under nitrogen, a solution of tert-butyl (5S,5aS,6S,9R)-2-chloro-1-fluoro-5-methyl-5a,6,7,8,9,10-hexahydro-5H-4-oxa-3,10a,11,13,14-pentaaza-6,9-methanonaphtho[1,8-ab] heptalene-14-carboxylate (90.6 mg, 0.210 mmol, intermediate 15), Pd(dppf)Cl$_2$ (15.9 mg, 0.0200 mmol), triisopropyl((6-(methoxymethoxy)-8-(4,4,5,5-tetramethyl-1,3,2-dioxaborolan-2-yl)naphthalen-1-yl)ethynyl)silane (133 mg, 0.270 mmol, intermediate 26) and Cs$_2$CO$_3$ (230 mg, 0.710 mmol) in 1,4-dioxane (1.5 mL) and H$_2$O (0.4 mL) was stirred for 1.5 h at 95° C. The reaction mixture was partitioned between water and EtOAc. The combined organic layers were dried over anhydrous sodium sulfate and concentrated under vacuum. The residue was purified by flash chromatography on silica gel eluting with EtOAc/ petroleum ether (0-65%) to afford the title compound (131 mg, 81.8% yield) as a yellow solid. LC-MS: (ESI, m/z): [M+H]$^+$=768.

Step 2: tert-Butyl (5S,5aS,6S,9R)-2-(8-ethynyl-3-(methoxymethoxy)naphthalen-1-yl)-1-fluoro-5-methyl-5a,6,7,8,9,10-hexahydro-5H-4-oxa-3,10a,11,13,14-pentaaza-6,9-methanonaphtho[1,8-ab]heptalene-14-carboxylate A solution of tert-butyl (5S,5aS,6S,9R)-1-fluoro-2-(3-(methoxymethoxy)-8-((triisopropylsilyl)ethynyl)naphthalen-1-yl)-5-methyl-5a,6,7,8,9,10-hexahydro-5H-4-oxa-3,10a,11,13,14-pentaaza-6,9-methanonaphtho[1,8-ab] heptalene-14-carboxylate (111 mg, 0.140 mmol) and CsF (219 mg, 1.44 mmol) in DMF (2 mL) was stirred at room temperature for 1 h. The reaction mixture was diluted with EtOAc (15 mL) and washed with H$_2$O. The organic layer was dried over anhydrous sodium sulfate and concentrated under vacuum. The residue was purified by flash chromatography on silica gel eluting with EtOAc/petroleum ether (0-75%) to afford the title compound (80.6 mg, 91.5% yield) as a yellow solid. LC-MS: (ESI, m/z): [M+H]$^+$=612.

Step 3: 5-ethynyl-4-((5S,5aS,6S,9R)-1-fluoro-5-methyl-5a,6,7,8,9,10-hexahydro-5H-4-oxa-3,10a,11,13,14-pentaaza-6,9-methanonaphtho[1,8-ab]heptalen-2-yl)naphthalen-2-ol (Compound 54)

To a solution of tert-butyl (5S,5aS,6S,9R)-2-(8-ethynyl-3-(methoxymethoxy)naphthalen-1-yl)-1-fluoro-5-methyl-5a,6,7,8,9,10-hexahydro-5H-4-oxa-3,10a,11,13,14-pentaaza-6,9-methanonaphtho[1,8-ab]heptalene-14-carboxylate (80.6 mg, 0.130 mmol) in ACN (2 mL) was added HCl (1 mL, 4 M in dioxane) at 0° C. The reaction mixture was stirred at 0° C. for 1 hour. Then the mixture was concentrated under vacuum. The residue was purified by Prep-HPLC (Column: XBridge Shield RP18 OBD Column, 30*150 mm, 5 μm; Mobile Phase A: Water(10 mmol/L NH$_4$HCO$_3$), Mobile Phase B: ACN; Flow rate: 60 mL/min; Gradient: 10% B to 40% B in 10 min, 40% B; Wave Length: 220/254 nm; R$_{T1}$(min): 11.93;) to afford the title compound (14.1 mg, 22.9% yield) as a yellow solid. LC-MS: (ESI, m/z): [M+H]$^+$=468. $^1$H NMR (400 MHz, DMSO-d$_6$, ppm) δ 10.14 (s, 1H), 8.67 (s, 1H), 7.88-7.86 (m, 1H), 7.53-7.37 (m, 2H), 7.33 (t, J=2.1 Hz, 1H), 7.10 (dd, J=54.9, 2.6 Hz, 1H), 5.29-5.27 (m, 1H), 4.60-4.46 (m, 1H), 4.04-3.96 (m, 1H), 3.72 (d, J=136.1 Hz, 2H), 3.46 (t, J=6.8 Hz, 1H), 3.04 (t, J=11.7 Hz, 1H), 2.82 (s, 1H), 1.84-1.80 (m, 1H), 1.78-1.62 (m, 2H), 1.62-1.51 (m, 1H), 1.45 (dd, J=8.0, 6.3 Hz, 3H).

Each compound in the Table below was prepared following a similar experimental procedure (using appropriately substituted reagents) as described for Examples 53 and 54.

| Cmpd. No. | $^1$H NMR | MS (M + H)$^+$ |
| --- | --- | --- |
| 55 | $^1$H NMR (300 MHz, DMSO-d$_6$, ppm) δ 8.66 (s, 1H), 7.93 (s, 2H), 7.36 (dd, J = 8.5, 5.8 Hz, 1H), 7.04 (t, J = 8.8 Hz, 1H), 4.94 (dd, J = 13.3, 2.3 Hz, 1H), 4.55 (dd, J = 13.4, 2.2 Hz, 1H), 4.44 (dd, J = 13.3, 7.3 Hz, 1H), 4.05 (d, J = 7.0 Hz, 1H), 3.71-3.59 (m, 2H), 3.18-3.03 (m, 1H), 1.85-1.48 (m, 4H). | 454 |
| 56 | $^1$H NMR (400 MHz, DMSO-d$_6$, ppm) δ 8.69 (s, 1H), 8.28-8.15 (m, 2H), 7.73-7.52 (m, 3H), 5.31-5.21 (m, 1H), 4.60-4.45 (m, 1H), 4.36-3.91 (m, 2H), 3.56 (d, J = 5.3 Hz, 1H), 3.47 (t, J = 7.5 Hz, 1H), 3.05 (t, J = 12.6 Hz, 1H), 2.81-2.76 (m, 1H), 1.91-1.51 (m, 4H), 1.46 (dd, J = 9.9, 6.3 Hz, 3H). | 470 |

621

Example 57: Compound 57

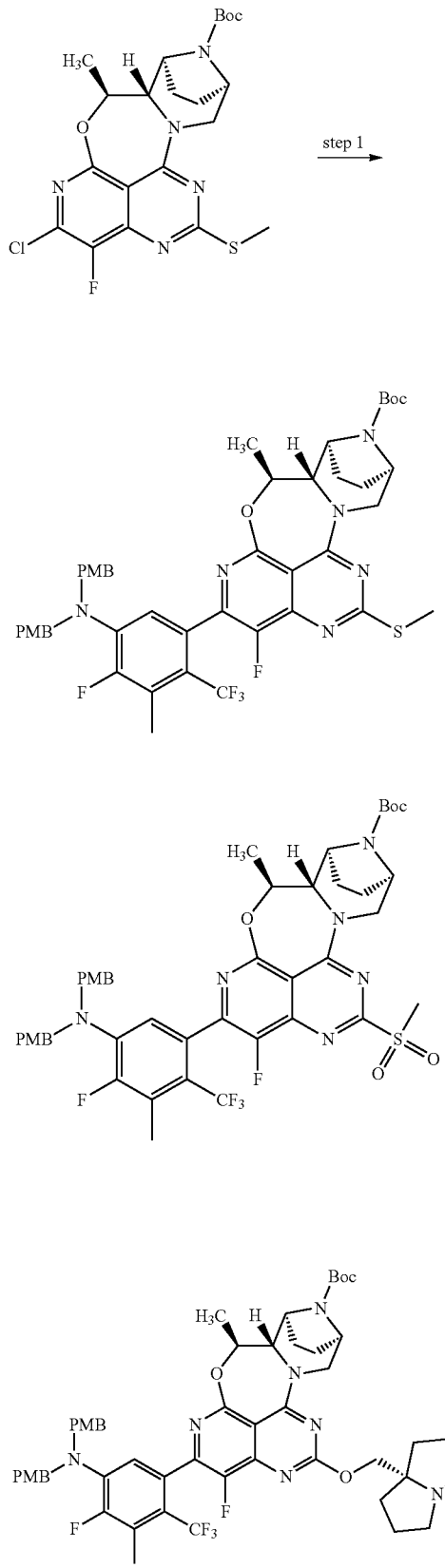

622

-continued

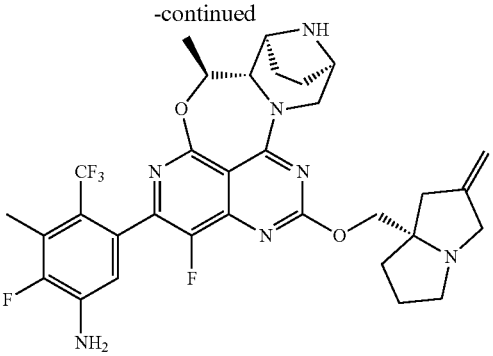

Step 1: tert-Butyl (5S,5aS,6S,9R)-2-(5-(bis(4-methoxybenzyl)amino)-4-fluoro-3-methyl-2-(trifluoromethyl)phenyl)-1-fluoro-5-methyl-12-(methylthio)-5a,6,7,8,9,10-hexahydro-5H-4-oxa-3,10a,11,13,14-pentaaza-6,9-methanonaphtho[1,8-ab]heptalene-14-carboxylate Under nitrogen, to a solution of tert-butyl (5S,5aS,6S,9R)-2-chloro-1-fluoro-5-methyl-12-(methylthio)-5a,6,7,8,9,10-hexahydro-5H-4-oxa-3,10a,11,13,14-pentaaza-6,9-methanonaphtho[1,8-ab]heptalene-14-carboxylate (701 mg, 1.45 mmol, intermediate 46) and (5-(bis(4-methoxybenzyl)amino)-4-fluoro-3-methyl-2-(trifluoromethyl)phenyl)boronic acid (1.73 g, 3.63 mmol, intermediate 20) in THF (9 mL) was added cataCXium A Pd $G_3$ (317 mg, 0.440 mmol) and $K_3PO_4$ (1.8 mL, 1.5 M in $H_2O$) at room temperature. The resulting solution was stirred for 3 h at 60° C. The reaction mixture was cooled to room temperature and concentrated under vacuum. The residue was purified by reverse phase flash chromatography on a pre-packed C18 column (gradient: 0-100% $CH_3CN$ in water (0.05% $NH_4HCO_3$)) to yield 941 mg (73.7% yield) of the title compound as a yellow solid. LC-MS: (ESI, m/z): $[M+H]^+=879$.

Step 2: tert-Butyl (5S,5aS,6S,9R)-2-(5-(bis(4-methoxybenzyl)amino)-4-fluoro-3-methyl-2-(trifluoromethyl)phenyl)-1-fluoro-5-methyl-12-(methylsulfonyl)-5a,6,7,8,9,10-hexahydro-5H-4-oxa-3,10a,11,13,14-pentaaza-6,9-methanonaphtho[1,8-ab]heptalene-14-carboxylate Under nitrogen, to a solution of tert-butyl (5S,5aS,6S,9R)-2-(5-(bis(4-methoxybenzyl)amino)-4-fluoro-3-methyl-2-(trifluoromethyl)phenyl)-1-fluoro-5-methyl-12-(methylthio)-5a,6,7,8,9,10-hexahydro-5H-4-oxa-3,10a,11,13,14-pentaaza-6,9-methanonaphtho[1,8-ab]heptalene-14-carboxylate (910 mg, 1.04 mmol) in DCM (10 mL) was added m-CPBA (537 mg, 3.11 mmol) at 0° C. The resulting solution was stirred for 2 h at room temperature. The solution was diluted with $NaHCO_3$ solution and extracted with DCM. The combined organic layers were washed with brine, dried over anhydrous sodium sulfate and concentrated under vacuum. The residue was purified by flash chromatography on silica gel (gradient: 0-51% EtOAc in petroleum ether) to afford 378 mg (33.3% yield) of the title compound as a yellow solid. LC-MS: (ESI, m/z): $[M+H]^+=911$.

Step 3: tert-Butyl (5S,5aS,6S,9R)-2-(5-(bis(4-methoxybenzyl)amino)-4-fluoro-3-methyl-2-(trifluoromethyl)phenyl)-1-fluoro-5-methyl-12-(((S)-2-methylenetetrahydro-1H-pyrrolizin-7a(5H)-yl)methoxy)-5a,6,7,8,9,10-hexahydro-5H-4-oxa-3,10a,11,13,14-pentaaza-6,9-methanonaphtho[1,8-ab]heptalene-14-carboxylate Under nitrogen, to a solution of tert-butyl (5S,5aS,6S,9R)-2-(5-(bis(4-methoxybenzyl)amino)-4-fluoro-3-methyl-2-(trifluoromethyl)phenyl)-1-fluoro-5-methyl-12-(methylsulfonyl)-5a,6,7,8,9,10-hexahydro-5H-4-oxa-3,10a,11,13,14-pentaaza-6,9-methanonaphtho[1,8-ab] heptalene-14-carboxylate (100 mg, 0.110 mmol) and (S)-(2-methylenetetrahydro-1H-pyrrolizin-7a(5H)-yl) methanol (20.2 mg, 0.130 mmol, intermediate 36) in toluene (1.5 mL) was added t-BuONa (21.1 mg, 0.220 mmol) at 0° C. The resulting solution was stirred for 1 h at room temperature. The solution was diluted with water and extracted with EtOAc. The combined organic layers were washed with brine, dried over anhydrous sodium sulfate and concentrated under vacuum. The residue was purified by flash chromatography on silica gel (gradient: 0-8% MeOH in DCM) to yield 91 mg (84.1% yield) of the title compound as a yellow oil. LC-MS: (ESI, m/z): [M+H]$^+$=984.

Step 4: 2-Fluoro-5-((5S,5aS,6S,9R)-1-fluoro-5-methyl-12-(((S)-2-methylenetetrahydro-1H-pyrrolizin-7a(5H)-yl)methoxy)-5a,6,7,8,9,10-hexahydro-5H-4-oxa-3,10a,11,13,14-pentaaza-6,9-methanonaphtho[1,8-ab]heptalen-2-yl)-3-methyl-4-(trifluoromethyl) aniline (Compound 57) Under nitrogen, a solution of tert-butyl (5S,5aS,6S,9R)-2-(5-(bis(4-methoxybenzyl)amino)-4-fluoro-3-methyl-2-(trifluoromethyl)phenyl)-1-fluoro-5-methyl-2-(((S)-2-methylenetetrahydro-1H-pyrrolizin-7a(5H)-yl)methoxy)-5a,6,7,8,9,10-hexahydro-5H-4-oxa-3,10a,11,13,14-pentaaza-6,9-methanonaphtho[1,8-ab]heptalene-14-carboxylate (90.8 mg, 0.0900 mmol) in TFA (5 mL) was stirred for 3 h at 50° C. The resulting solution was concentrated under vacuum. The crude product was purified by Prep-HPLC(Column: XBridge Prep OBD C18 Column, 30*150 mm, 5 μm; Mobile Phase A: Water(10 mmol/L NH$_4$HCO$_3$), Mobile Phase B: ACN; Flow rate: 60 mL/min; Gradient: 30% B to 55% B in 9 min, 55% B; Wave Length: 254/220 nm; R$_{T1}$(min): 8.6;) to yield 20.1 mg (33.1% yield) of the title compound as a while solid. LC-MS: (ESI, m/z): [M+H]$^+$=634. $^1$H NMR (300 MHz, DMSO-d6, ppm) δ 6.61 (s, 1H), 6.02 (s, 2H), 5.10 (dd, J=13.1, 2.5 Hz, 1H), 4.93 (s, 2H), 4.58-4.52 (m, 1H), 4.03-3.94 (m, 3H), 3.66-3.55 (m, 3H), 3.23 (s, 1H), 3.11-2.98 (m, 2H), 2.67-2.56 (m, 2H), 2.41 (s, 1H), 2.32 (s, 3H), 1.98-1.33 (m, 8H), 1.44 (d, J=6.3 Hz, 3H).

Example 58 and 59: Compounds 58 and 59

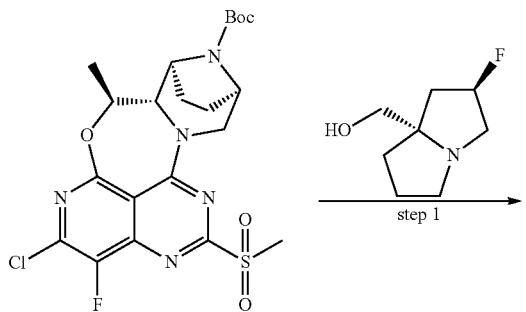

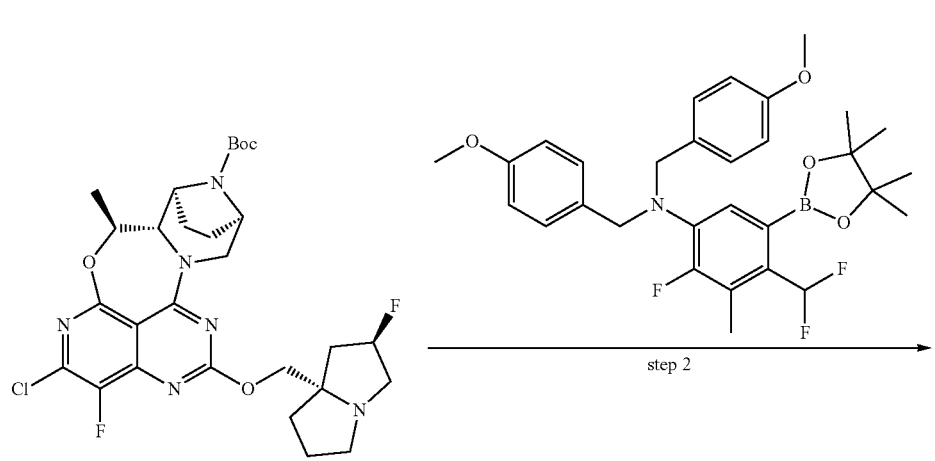

-continued

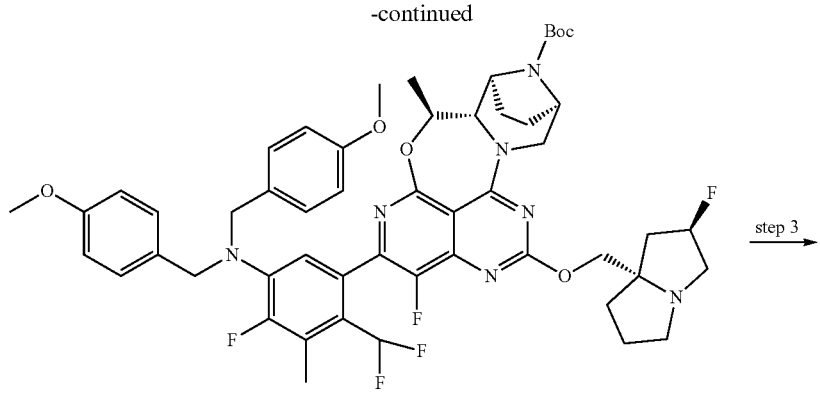

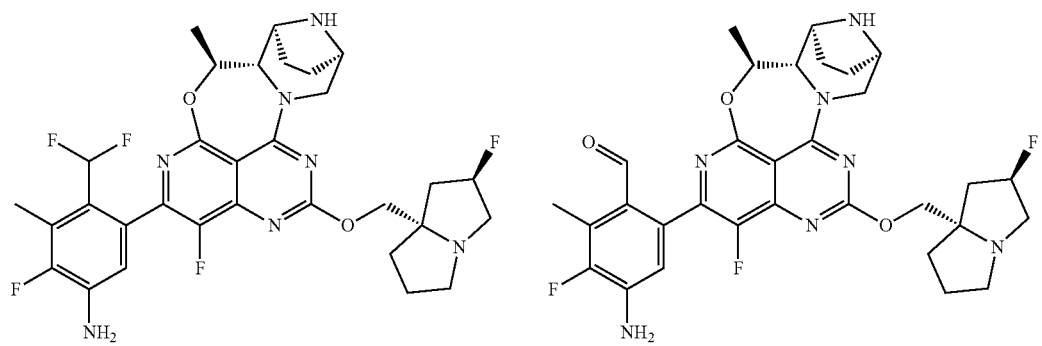

Step 1: tert-Butyl (5S,5 aS,6S,9R)-2-chloro-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate Under nitrogen, to a solution of ((2R,7aS)-2-fluorotetrahydro-1H-pyrrolizin-7a(5H)-yl)methanol (37.5 mg, 0.240 mmol, intermediate 5) and tert-butyl (5S,5aS,6S,9R)-2-chloro-1-fluoro-5-methyl-12-(methylsulfonyl)-5a,6,7,8,9,10-hexahydro-5H-4-oxa-3,10a,11,13,14-pentaaza-6,9-methanonaphtho[1,8-ab]heptalene-14-carboxylate (60.6 mg, 0.120 mmol, intermediate 11) in toluene (1.5 mL) was added t-BuONa (22.6 mg, 0.240 mmol) at 0° C. The reaction mixture was stirred at room temperature for 1 hour, quenched with water and extracted with EtOAc. The combined organic layers were dried over anhydrous sodium sulfate and concentrated under vacuum. The residue was purified by flash chromatography on silica gel eluting with $CH_3OH/DCM$ (0-10%) to afford the title compound (40.6 mg, 58.1% yield) as light yellow solid. LC-MS: (ESI, m/z): $[M+H]^+$=593.

Step 2: tert-Butyl (5S,5aS,6S,9R)-2-(5-(bis(4-methoxybenzyl)amino)-2-(difluoromethyl)-4-fluoro-3-methylphenyl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate Under nitrogen, a solution of tert-butyl (5S,5aS,6S,9R)-2-chloro-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (100 mg, 0.170 mmol), 4-(difluoromethyl)-2-fluoro-N,N-bis(4-methoxybenzyl)-3-methyl-5-(4,4,5,5-tetramethyl-1,3,2-dioxaborolan-2-yl)aniline (201 mg, 0.370 mmol, intermediate 56), cataCXium A Pd G3 (28.7 mg, 0.0400 mmol) and $K_3PO_4$ (313 mg, 1.47 mmol) in Tetrahydrofuran (6 mL) and Water (1 mL) was stirred at 60° C. for 3 hours. The solution was concentrated under vacuum. The residue was purified by flash chromatography on silica gel eluting (gradient: 0-7% MeOH in DCM) to afford 136 mg (83% yield) of the title compound as yellow oil. LC-MS: (ESI, m/z): $[M+H]^+$= 972.

Step 3: 4-(Difluoromethyl)-2-fluoro-5-((5S,5aS,6S,9R)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-3-methylaniline (Compound 58) and 4-Amino-3-fluoro-6-((5S,5aS,6S,9R)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-2-methylbenzaldehyde(Compound 59)

58
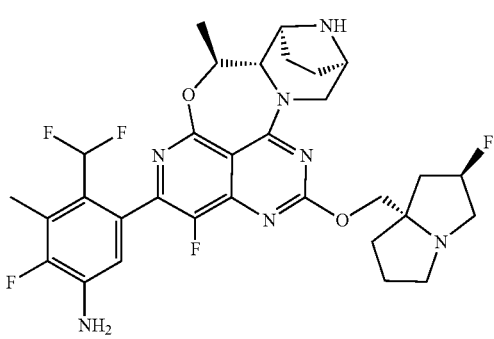

59
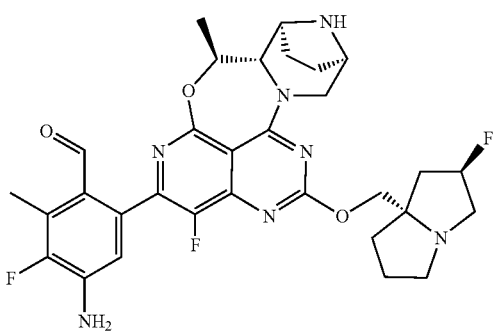

A solution of tert-butyl (5S,5aS,6S,9R)-2-(5-(bis(4-methoxybenzyl)amino)-2-(difluoromethyl)-4-fluoro-3-methylphenyl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (80.3 mg, 0.0800 mmol) in 2,2,2-trifluoroacetic acid (1 mL) was stirred at room temperature for 1 hour. The solution was concentrated under vacuum in cold water. The residue was purified by reverse phase flash chromatography on pre-packed C18 column (gradient: 0-55% CH$_3$CN in water (0.05% NH$_4$HCO$_3$)). The fraction that contained desired product (Compound 58) was extracted with DCM, dried over anhydrous sodium sulfate and concentrated under vacuum (in cold water) to afford 10.2 mg (20% yield) of the title compound as a light yellow solid.

When the solvent was concentrated under reduce pressure after reverse phase column directly, compound 58 hydrolyzed to 59.

58: LC-MS: (ESI, m/z): [M+H]$^+$=632. $^1$H NMR (400 MHz, DMSO-d6, ppm) δ 6.71-6.45 (m, 2H), 5.78 (s, 2H), 5.29 (d, J=54.0 Hz, 1H), 5.13-5.10 (m, 1H), 4.56-4.52 (m, 1H), 4.13-3.97 (m, 3H), 3.66-3.51 (m, 2H), 3.18-3.02 (m, 4H), 2.90-2.83 (m, 1H), 2.35 (s, 3H), 2.17-2.00 (m, 3H), 1.88-1.61 (m, 7H), 1.46-1.44 (m, 3H).

59: LC-MS: (ESI, m/z): [M+H]$^+$=610. $^1$H NMR (300 MHz, DMSO-d6, ppm) δ 9.63 (s, 1H), 6.70 (d, J=8.4 Hz, 1H), 6.41 (s, 2H), 5.27 (d, J=54.0 Hz, 1H), 5.11-5.08 (m, 1H), 4.54-4.51 (m, 1H), 4.13-3.94 (m, 3H), 3.58-3.44 (m, 2H), 3.16-3.00 (m, 4H), 2.90-2.78 (m, 2H), 2.49 (s, 3H), 2.16-2.00 (m, 3H), 1.91-1.58 (m, 7H), 1.48-1.46 (m, 3H).

Example 60: Compound 60

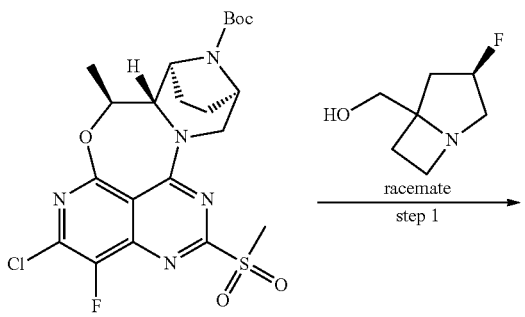

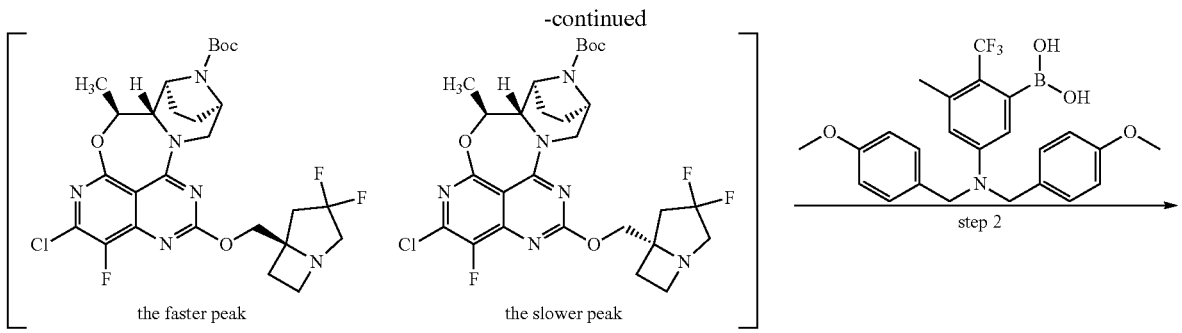

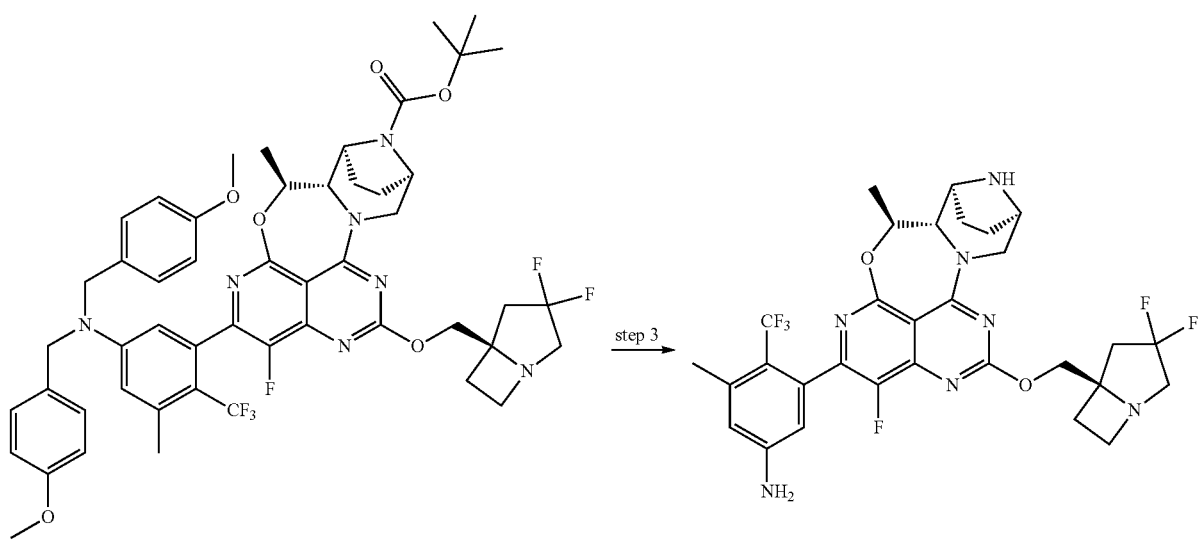

Step 1: tert-Butyl (5S,5aS,6S,9R)-2-chloro-12-((3,3-difluoro-1-azabicyclo[3.2.0]heptan-5-yl)methoxy)-1-fluoro-5-methyl-5a,6,7,8,9,10-hexahydro-5H-4-oxa-3,10a,11,13,14-pentaaza-6,9-methanonaphtho[1,8-ab]heptalene-14-carboxylate

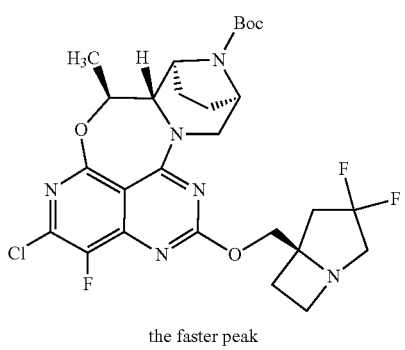

the faster peak

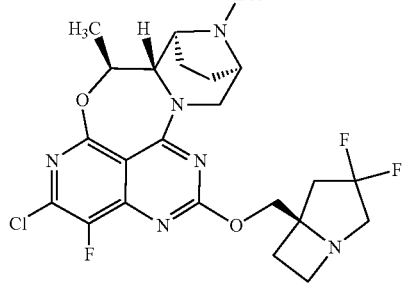

the slower peak

Under nitrogen, to a solution of tert-butyl (5S,5aS,6S,9R)-2-chloro-1-fluoro-5-methyl-12-(methylsulfonyl)-5a,6,7,8,9,10-hexahydro-5H-4-oxa-3,10a,11,13,14-pentaaza-6,9-methanonaphtho[1,8-ab]heptalene-14-carboxylate (3.50 g, 6.81 mmol, intermediate 11) and (3,3-difluoro-1-azabicyclo[3.2.0]heptan-5-yl)methanol (1.30 g, 7.97 mmol, intermediate 6A) in toluene (35 mL) was added t-BuONa (1.30 g, 13.5 mmol) at 0° C. The resulting solution was stirred at room temperature for 1 h, the reaction was quenched with water and extracted with EtOAc. The combined organic layers were dried over anhydrous sodium sulfate and concentrated under vacuum. The residue was purified by flash chromatography on silica gel eluting (gradient: 0%-6% MeOH/DCM) to afford 2.06 g (50.7% yield) of a mixture of two diastereoisomers as a white solid. The diastereoisomers were separated by Chiral-Prep-HPLC (Column: CHIRALPAK IE-3, 4.6*50 mm, 3 μm; Mobile Phase A: Hex(0.1% DEA): EtOH=50:50; Flow rate: 1 mL/min; Gradient: 0% B to 0% B; Injection Volume: 5 ul mL) to afford yield 643 mg of the faster peak and 676 mg of the slower peak as white solid. LC-MS: (ESI, m z): [M+H]$^+$=597.

The faster peak (desired isomer): $^1$H NMR (300 MHz, DMSO-$d_6$, ppm): δ 5.18 (d, J=13.2 Hz, 1H), 4.64 (t, J=7.6 Hz, 1H), 4.44-4.29 (m, 3H), 4.16 (s, 1H), 3.99 (d, J=9.0 Hz, 1H), 3.54 (dd, J=9.0, 4.7 Hz, 1H), 3.33-3.15 (m, 1H), 3.15 (d, J=4.4 Hz, 1H), 3.13-2.98 (m, 2H), 2.75-2.52 (m, 1H), 2.50-2.38 (m, 1H), 2.41-2.25 (m, 1H), 1.87 (s, 3H), 1.73 (s, 1H), 1.50 (d, J=6.3 Hz, 3H), 1.47 (s, 9H).

The slower peak: $^1$H NMR (300 MHz, DMSO-$d_6$, ppm): $^1$H NMR (300 MHz, DMSO-$d_6$, ppm): δ 5.18 (d, J=13.2 Hz, 1H), 4.64 (t, J=7.6 Hz, 1H), 4.44-4.29 (m, 3H), 4.16 (s, 1H), 3.99 (d, J=9.0 Hz, 1H), 3.54 (dd, J=9.0, 4.7 Hz, 1H), 3.33-3.15 (m, 1H), 3.15 (d, J=4.4 Hz, 1H), 3.13-2.98 (m, 2H), 2.75-2.52 (m, 1H), 2.50-2.38 (m, 1H), 2.41-2.25 (m, 1H), 1.87 (s, 3H), 1.73 (s, 1H), 1.50 (d, J=6.3 Hz, 3H), 1.47 (s, 9H).

Step 2: tert-Butyl (5S,5aS,6S,9R)-2-(5-(bis(4-methoxybenzyl)amino)-3-methyl-2-(trifluoromethyl)phenyl)-12-(((R)-3,3-difluoro-1-azabicyclo[3.2.0]heptan-5-yl)methoxy)-1-fluoro-5-methyl-5a,6,7,8,9,10-hexahydro-5H-4-oxa-3,10a,11,13,14-pentaaza-6,9-methanonaphtho[1,8-ab]heptalene-14-carboxylate Under nitrogen, a solution of (5-(bis(4-methoxybenzyl)amino)-3-methyl-2-(trifluoromethyl)phenyl)boronic acid (84.6 mg, 0.180 mmol, intermediate 52), tert-butyl (5S,5aS,6S,9R)-2-chloro-12-((3,3-difluoro-1-azabicyclo[3.2.0]heptan-5-yl)methoxy)-1-fluoro-5-methyl-5a,6,7,8,9,10-hexahydro-5H-4-oxa-3,10a,11,13,14-pentaaza-6,9-methanonaphtho[1,8-ab]heptalene-14-carboxylate (55.0 mg, 0.0900 mmol, the faster peak of from step 1), cataCXium A Pd G$_3$ (13.4 mg, 0.0200 mmol) and K$_3$PO$_4$(1.5 M in water) (0.2 mL) in tetrahydrofuran (2 mL) was stirred at 60° C. for 1 hour. The resulting mixture was filtered. The filtrate was concentrated under reduced pressure. The crude product was diluted with water and was extracted with EtOAc. The combined organic layers were washed with brine, dried over anhydrous sodium sulfate and concentrated under reduced pressure. The residue was purified by flash chromatography on silica gel (gradient: 0-90% EtOAc in petroleum ether) to afford the title compound (75 mg, 82.6% yield) as a yellow solid. LC-MS: (ESI, m/z): [M+H]$^+$=976.

Step 3: 3-((5S,5aS,6S,9R)-12-(((R)-3,3-Difluoro-1-azabicyclo[3.2.0]heptan-5-yl)methoxy)-1-fluoro-5-methyl-5a,6,7,8,9,10-hexahydro-5H-4-oxa-3,10a,11,13,14-pentaaza-6,9-methanonaphtho[1,8-ab]heptalen-2-yl)-5-methyl-4-(trifluoromethyl)aniline (Compound 60)

A solution of tert-butyl (5S,5aS,6S,9R)-2-(5-(bis(4-methoxybenzyl)amino)-3-methyl-2-(trifluoromethyl)phenyl)-12-((3,3-difluoro-1-azabicyclo[3.2.0]heptan-5-yl)methoxy)-1-fluoro-5-methyl-5a,6,7,8,9,10-hexahydro-5H-4-oxa-3,10a,11,13,14-pentaaza-6,9-methanonaphtho[1,8-ab]heptalene-14-carboxylate (75.0 mg, 0.0800 mmol) in 2,2,2-trifluoroacetic acid (1 mL) was stirred at 50° C. for 1 hour. The solvent was concentrated under vacuum. The crude was purified by Prep-HPLC with the following conditions: (Column: XBridge Prep OBD C18 Column, 30*150 mm, 5 μm; Mobile Phase A: Water(10 mmol/L NH$_4$HCO$_3$), Mobile Phase B: ACN; Flow rate: 60 mL/min; Gradient: 26% B to 51% B in 9 min, 51% B; Wave Length: 254/220 nm; R$_{T1}$(min): 8.18) to afford the title compound (28.1 mg, 57.4% yield) as a white solid. LC-MS: (ESI, m/z): [M+H]$^+$= 636. $^1$H NMR (300 MHz, DMSO-d6) δ 6.60 (d, J=2.2 Hz, 1H), 6.30 (d, J=43.8 Hz, 1H), 5.89 (s, 2H), 5.13 (d, J=13.0 Hz, 1H), 4.56 (dd, J=8.6, 6.3 Hz, 1H), 4.48-4.24 (m, 2H), 4.00 (d, J=8.7 Hz, 1H), 3.67 (s, 1H), 3.54 (d, J=5.5 Hz, 2H), 3.23 (d, J=8.8 Hz, 1H), 3.20-3.03 (m, 3H), 2.78-2.56 (m, 2H), 2.39 (d, J=23.0 Hz, 6H), 1.84 (d, J=10.7 Hz, 1H), 1.80-1.55 (m, 3H), 1.45 (d, J=6.3 Hz, 3H).

Example 61: Compound 61

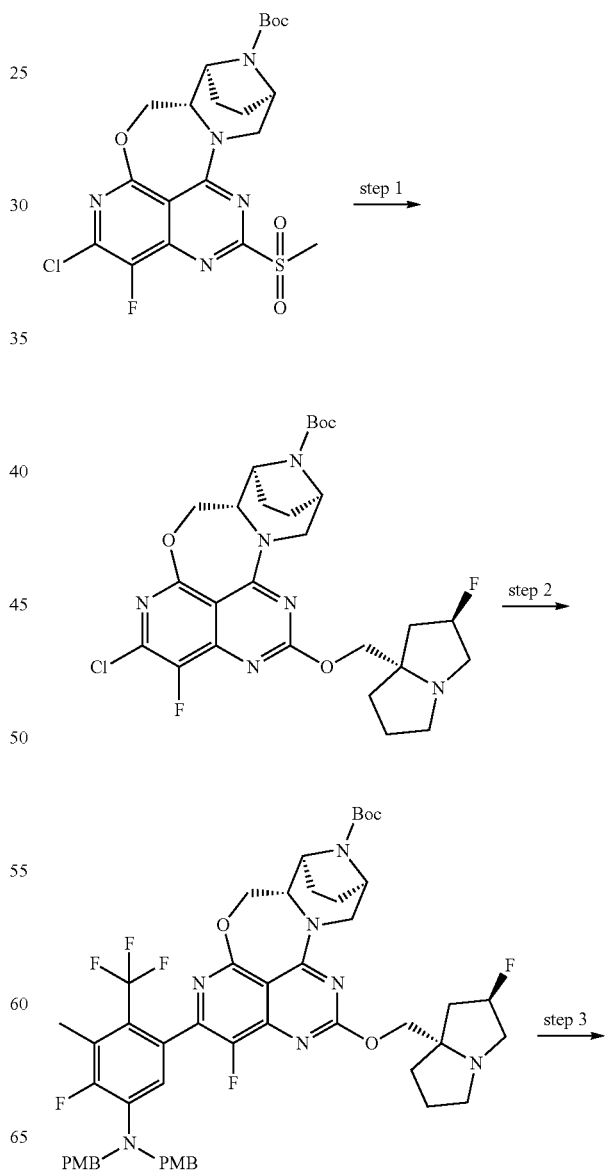

-continued

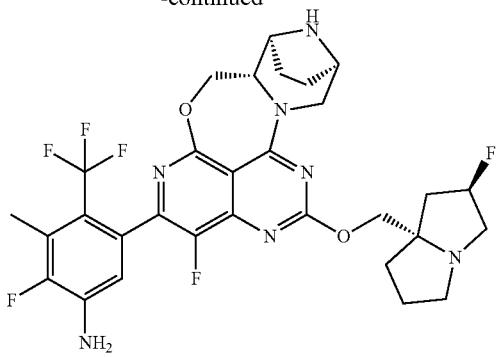

Step 1: tert-Butyl (5aS,6S,9R)-2-chloro-1-fluoro-12-(((2R,7aS)-2-fluorotetrahydro-1H-pyrrolizin-7a(5H)-yl)methoxy)-5a,6,7,8,9,10-hexahydro-5H-4-oxa-3,10a,11,13,14-pentaaza-6,9-methanonaphtho[1,8-ab]heptalene-14-carboxylate Under nitrogen, to a mixture of tert-butyl (5aS,6S,9R)-2-chloro-1-fluoro-12-(methylsulfonyl)-5a,6,7,8,9,10-hexahydro-5H-4-oxa-3,10a,11,13,14-pentaaza-6,9-methanonaphtho[1,8-ab]heptalene-14-carboxylate (201 mg, 0.401 mmol, intermediate 11) and ((2R,7aS)-2-fluorotetrahydro-1H-pyrrolizin-7a(5H)-yl)methanol (128 mg, 0.802 mmol, intermediate 5) in toluene (2 mL) was added t-BuONa (77.1 mg, 0.802 mmol) at 0° C. The solution was stirred at room temperature for 1 hour. The reaction system was diluted with water, extracted with EtOAc. The combined organic layers were dried over anhydrous sodium sulfate and concentrated under vacuum. The resulting residue was purified by flash chromatography on silica gel eluting with CH$_3$OH/DCM (0-10%) to afford the title compound (151 mg, 64.8% yield) as light yellow solid. LC-MS: (ESI, m/z): [M+H]$^+$=579. $^1$H NMR (300 MHz, DMSO-d6, ppm) δ 5.29 (d, J=54.2 Hz, 1H), 4.89 (d, J=13.4 Hz, 1H), 4.72-4.62 (m, 1H), 4.48 (dd, J=13.3, 7.3 Hz, 1H), 4.40-4.25 (m, 2H), 4.19-3.95 (m, 3H), 3.15-2.97 (m, 4H), 2.89-2.76 (m, 1H), 2.17-2.11 (m, 1H), 2.07-2.02 (m, 1H), 1.94-1.62 (m, 8H), 1.45 (s, 9H).

Step 2: tert-Butyl (5aS,6S,9R)-2-(5-(bis(4-methoxybenzyl)amino)-4-fluoro-3-methyl-2-(trifluoromethyl)phenyl)-1-fluoro-12-(((2R,7aS)-2-fluorotetrahydro-1H-pyrrolizin-7a(5H)-yl)methoxy)-5a,6,7,8,9,10-hexahydro-5H-4-oxa-3,10a,11,13,14-pentaaza-6,9-methanonaphtho[1,8-ab]heptalene-14-carboxylate Under nitrogen, a solution of tert-butyl (5aS,6S,9R)-2-chloro-1-fluoro-12-(((2R,7aS)-2-fluorotetrahydro-1H-pyrrolizin-7a(5H)-yl)methoxy)-5a,6,7,8,9,10-hexahydro-5H-4-oxa-3,10a,11,13,14-pentaaza-6,9-methanonaphtho[1,8-ab]heptalene-14-carboxylate (150 mg, 0.260 mmol), (5-(bis(4-methoxybenzyl)amino)-4-fluoro-3-methyl-2-(trifluoromethyl)phenyl)boronic acid (371 mg, 0.780 mmol, intermediate 20), cataCXium A Pd G3 (37.8 mg, 0.0500 mmol) and K$_3$PO$_4$ (0.4 mL, 1.5 M in water) in THF (2 mL) was stirred at 60° C. for 3 h. The solvent was concentrated under vacuum. The resulting residue was purified by reverse phase chromatography (gradient: 0-100% acetonitrile in water (0.1% FA)) to yield 202 mg (79.8% yield) of the title compound as a yellow solid. LC-MS: (ESI, m/z): [M+H]$^+$= 956.

Step 3: 2-Fluoro-5-((5aS,6S,9R)-1-fluoro-12-(((2R,7aS)-2-fluorotetrahydro-1H-pyrrolizin-7a(5H)-yl)methoxy)-5a,6,7,8,9,10-hexahydro-5H-4-oxa-3,10a,11,13,14-pentaaza-6,9-methanonaphtho[1,8-ab]heptalen-2-yl)-3-methyl-4-(trifluoromethyl)aniline (Compound 61)

A solution of tert-butyl (5aS,6S,9R)-2-(5-(bis(4-methoxybenzyl)amino)-4-fluoro-3-methyl-2-(trifluoromethyl)phenyl)-1-fluoro-12-(((2R,7aS)-2-fluorotetrahydro-1H-pyrrolizin-7a(5H)-yl)methoxy)-5a,6,7,8,9,10-hexahydro-5H-4-oxa-3,10a,11,13,14-pentaaza-6,9-methanonaphtho[1,8-ab]heptalene-14-carboxylate (201 mg, 0.210 mmol) in TFA (9.5 mL) was stirred at 50° C. for 4 h. The reaction mixture was concentrated under vacuum. The crude product was purified by Prep-HPLC (Column: XBridge Prep OBD C18 Column, 30*150 mm, 5 μm; Mobile Phase A: Water (10 mmol/L NH$_4$HCO$_3$), Mobile Phase B: ACN; Flow rate: 60 mL/min; Gradient: 27% B to 45% B in 10 min, 45% B; Wave Length: 254/220 nm; R$_{T1}$(min): 8.9) to yield 50.3 mg (37.7% yield) of the title compound as a light yellow solid. LC-MS: (ESI, m/z): [M+H]$^+$=636. $^1$H NMR (400 MHz, DMSO-d$_6$, ppm) δ 6.57 (s, 1H), 5.99 (s, 2H), 5.44-5.11 (m, 1H), 4.78 (d, J=12.9 Hz, 1H), 4.59-4.44 (m, 1H), 4.42-4.27 (m, 1H), 4.08 (d, J=10.4 Hz, 1H), 3.97 (d, J=10.3 Hz, 2H), 3.65-3.54 (m, 1H), 3.54-3.43 (m, 1H), 3.18-2.93 (m, 4H), 2.90-2.68 (m, 2H), 2.39-2.23 (m, 3H), 2.19-2.08 (m, 1H), 2.07-1.91 (m, 2H), 1.90-1.40 (m, 7H).

Example 62: Compound 62

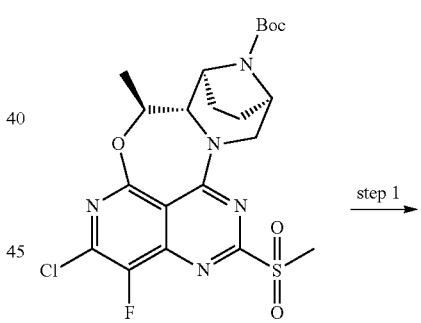

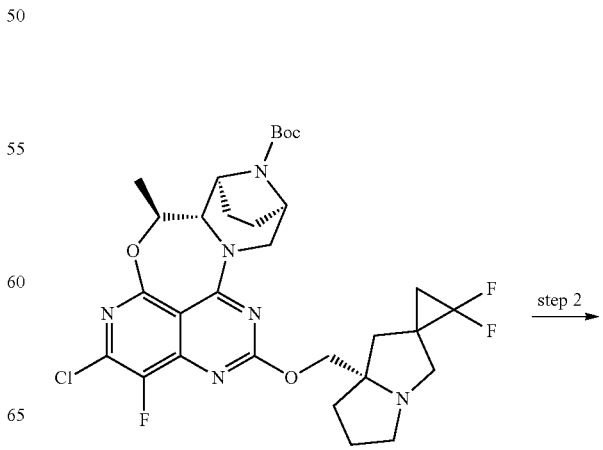

-continued

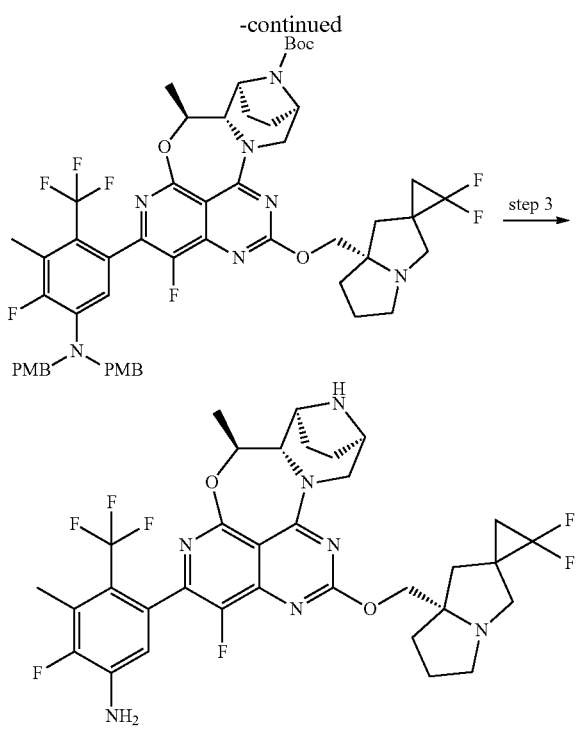

Step 1: tert-Butyl (5S,5aS,6S,9R)-2-chloro-12-(((7a'S)-2,2-difluorodihydro-1'H,3'H-spiro[cyclopropane-1,2'-pyrrolizin]-7a'(5'H)-yl)methoxy)-1-fluoro-5-methyl-5a,6,7,8,9,10-hexahydro-5H-4-oxa-3,10a,11,13,14-pentaaza-6,9-methanonaphtho[1,8-ab]heptalene-14-carboxylate Under nitrogen, to a solution of tert-butyl (5S,5aS,6S,9R)-2-chloro-1-fluoro-5-methyl-12-(methylsulfonyl)-5a,6,7,8,9,10-hexahydro-5H-4-oxa-3,10a,11,13,14-pentaaza-6,9-methanonaphtho[1,8-ab]heptalene-14-carboxylate (301 mg, 0.590 mmol, intermediate 11) and [rac-(8S)-1',1'-difluorospiro[2,3,5,7-tetrahydro-1H-pyrrolizine-6,2'-cyclopropane]-8-yl]methanol (238 mg, 1.17 mmol, intermediate 33) in toluene (3 mL) was added t-BuONa (111 mg, 1.16 mmol) at 0° C. The resulting solution was stirred for 1 h at room temperature. The solution was diluted with water and extracted with EtOAc. The combined organic layers were dried over anhydrous sodium sulfate and concentrated under vacuum. The residue was purified by flash chromatography on silica gel eluting (gradient: 0%-10% MeOH/DCM) to afford 231 mg (61.9% yield) of the title compound as white solid. LC-MS: (ESI, m/z): [M+H]$^+$=637.

Step 2: tert-Butyl (5S,5aS,6S,9R)-2-(5-(bis(4-methoxybenzyl)amino)-4-fluoro-3-methyl-2-(trifluoromethyl)phenyl)-12-(((7a'S)-2,2-difluorodihydro-1'H,3'H-spiro[cyclopropane-1,2'-pyrrolizin]-7a'(5'H)-yl)methoxy)-1-fluoro-5-methyl-5a,6,7,8,9,10-hexahydro-5H-4-oxa-3,10a,11,13,14-pentaaza-6,9-methanonaphtho[1,8-ab]heptalene-14-carboxylate Under nitrogen, a solution of tert-butyl (5S,5aS,6S,9R)-2-chloro-12-(((7a'S)-2,2-difluorodihydro-1'H,3'H-spiro[cyclopropane-1,2'-pyrrolizin]-7a'(5'H)-yl)methoxy)-1-fluoro-5-methyl-5a,6,7,8,9,10-hexahydro-5H-4-oxa-3,10a,11,13,14-pentaaza-6,9-methanonaphtho[1,8-ab]heptalene-14-carboxylate (121 mg, 0.190 mmol), (5-(bis(4-methoxybenzyl)amino)-4-fluoro-3-methyl-2-(trifluoromethyl)phenyl)boronic acid (217 mg, 0.450 mmol, intermediate 20), cataCXium A Pd G3 (29.2 mg, 0.0400 mmol) and K$_3$PO$_4$ (0.4 mL, 1.5 M in H$_2$O) in THF (2 mL) was stirred for 3 hours at 60° C. The solution was cooled to room temperature, diluted with water and extracted with ethyl acetate. The combined organic layers were washed with brine, dried over anhydrous sodium sulfate and concentrated under vacuum. The residue was purified by flash chromatography on silica gel (gradient: 0-10% MeOH in DCM) to afford 141 mg (71.8% yield) of the title compound as a yellow solid. LC-MS: (ESI, m/z): [M+H]$^+$=1034.

Step 3: 5-(((5S,5aS,6S,9R)-12-(((7a'S)-2,2-Difluorodihydro-1'H,3'H-spiro[cyclopropane-1,2'-pyrrolizin]-7a'(5'H)-yl)methoxy)-1-fluoro-5-methyl-5a,6,7,8,9,10-hexahydro-5H-4-oxa-3,10a,11,13,14-pentaaza[6,9]methanonaphtho[1,8-ab]heptalen-2-yl)-2-fluoro-3-methyl-4-(trifluoromethyl)aniline (Compound 62)

A solution of tert-butyl (5S,5aS,6S,9R)-2-(5-(bis(4-methoxybenzyl)amino)-4-fluoro-3-methyl-2-(trifluoromethyl)phenyl)-12-(((7a'S)-2,2-difluorodihydro-1'H,3'H-spiro[cyclopropane-1,2'-pyrrolizin]-7a (5')-yl)methoxy)-1-fluoro-5-methyl-5a,6,7,8,9,0-hexahydro-5H-4-oxa-3,10a,11,13,14-pentaaza-6,9-methanonaphtho[1,8-ab]heptalene-14-carboxylate (141 mg, 0.140 mmol) in TFA (5 mL) was stirred at 50° C. for 4 hours. The solvent was concentrated under vacuum. The crude product was purified by Prep-HPLC with the following conditions: (Column: XBridge Shield RP18 OBD Column, 30×150 mm, 5 μm; Mobile Phase A: Water(10 mmol/L NH$_4$HCO$_3$), Mobile Phase B: ACN; Flow rate: 60 mL/min; Gradient: 39% B to 59% B in 10 min 59% B; Wave Length: 254/220 nm; RT1(min): 10.0) to afford 17.8 mg (18.6% yield) of the title compound as a yellow solid. LC-MS: (ESI, m/z): [M+H]$^+$=694. $^1$H NMR (400 MHz, DMSO-d$_6$, ppm) δ 6.53 (d, J=56.7 Hz, 1H), 6.01 (s, 2H), 5.13-5.03 (m, 1H), 4.59-4.47 (m, 1H), 4.22-4.10 (m, 2H), 3.95 (d, J=8.7 Hz, 1H), 3.56 (d, J=5.5 Hz, 1H), 3.44 (d, J=6.1 Hz, 1H), 3.09 (s, 1H), 3.01 (s, 2H), 2.72 (d, J=11.9 Hz, 1H), 2.55 (d, J=8.6 Hz, 1H), 2.32 (d, J=3.3 Hz, 3H), 2.11-2.03 (m, 1H), 2.02-1.93 (m, 1H), 1.90 (d, J=13.3 Hz, 1H), 1.86-1.71 (m, 3H), 1.70-1.51 (m, 5H), 1.50-1.39 (n, 4H).

Each compound in the Table below was prepared following a similar experimental procedure (using appropriately substituted reagents) as described for Examples 60, 61, and 62.

| Cmpd. No. | ¹H NMR | MS (M + H)⁺ |
|---|---|---|
| 64 | ¹H NMR (400 MHz, DMSO-d₆, ppm) δ 6.86-6.39 (m, 2H), 6.02 (s, 2H), 5.14-5.00 (m, 1H), 4.54-4.51 (m, 1H), 4.13-3.89 (m, 3H), 3.70 (d, J = 14.8 Hz, 1H), 3.60-3.52 (m, 1H), 3.45 (d, J = 6.1 Hz, 1H), 3.27 (s, 1H), 3.09-2.85 (m, 3H), 2.62-2.53 (m, 2H), 2.32 (s, 4H), 1.95 (m, 1H), 1.90-1.52 (m, 7H), 1.43 (m, 3H). | 662 |
| 65 | ¹H NMR (300 MHz, DMSO-d6, ppm) δ 6.70-6.37 (m, 1H), 6.02 (s, 2H), 5.18-5.01 (m, 1H), 4.60-4.28 (m, 3H), 3.96 (d, J = 8.7 Hz, 1H), 3.61-3.51 (m, 1H), 3.49-3.43 (m, 1H), 3.42-3.35 (m, 1H), 3.03 (d, J = 13.2 Hz, 1H), 2.99-2.89 (m, 1H), 2.81 (s, 1H), 2.76-2.62 (m, 1H), 2.61-2.53 (m, 1H), 2.38 (s, 3H), 2.32 (t, J = 2.5 Hz, 3H), 2.29-2.07 (m, 1H), 1.89-1.75 (m, 1H), 1.68-1.52 (m, 3H), 1.44 (d, 3H). | 642 |
| 66 | ¹H NMR (300 MHz, DMSO-d6, ppm) δ 6.53 (d, J = 58.5 Hz, 1H), 6.01 (s, 2H), 5.17-5.04 (m, 1H), 4.57-4.50 (m, 1H), 4.47-4.29 (m, 2H), 3.95 (d, J = 8.8 Hz, 1H), 3.63-3.50 (m, 1H), 3.44 (d, J = 6.1 Hz, 1H), 3.41-3.34 (m, 1H), 3.03 (d, J = 12.8 Hz, 1H), 2.99-2.79 (m, 1H), 2.74-2.59 (m, 1H), 2.59-2.53 (m, 1H), 2.48-2.42 (m, 1H), 2.37 (s, 3H), 2.32 (d, J = 3.4 Hz, 3H), 2.27-2.12 (m, 1H), 1.87-1.74 (m, 1H), 1.73-1.48 (m, 3H), 1.43 (d, 3H). | 642 |
| 67 | ¹H NMR (300 MHz, DMSO-d6, ppm) δ 6.57 (s, 1H), 6.35-6.16 (m, 1H), 5.87 (s, 2H), 5.08 (dd, J = 12.8, 2.5 Hz, 1H), 4.55-4.49 (m, 1H), 4.41-4.36 (m, 1H), 4.13-4.09 (m, 1H), 3.95 (d, J = 8.8 Hz, 1H), 3.61-.40 (m, 6H), 3.13 (t, J = 10.4 Hz, 1H), 3.06-2.81 (m, 4H), 2.33 (s, 3H), 2.13-2.00 (m, 1H), 1.83-1.50 (m, 6H), 1.42 (d, J = 6.3 Hz, 3H), 1.35-1.19 (m, 1H), 1.13 (s, 1H). | 630 |
| 68 | ¹H NMR (300 MHz, DMSO-d₆, ppm) δ 6.63-6.56 (s, 1H), 6.37-6.23 (m, 1H), 5.88 (s, 2H), 5.09 (dd, J = 12.8, 2.5 Hz, 1H), 4.60-4.45 (m, 1H), 4.17 (d, J = 2.6 Hz, 2H), 3.95 (d, J = 8.8 Hz, 1H), 3.58 (s, 1H), 3.45 (d, J = 5.7 Hz, 1H), 3.12-3.00 (m, 3H), 2.78-2.64 (m, 2H), 2.56 (d, J = 7.8 Hz, 1H), 2.35 (d, J = 2.6 Hz, 3H), 2.15-1.85 (m, 2H), 1.92-1.81 (m, 1H), 1.75-1.71 (m, 2H), 1.69-1.54 (m, 6H), 1.58-1.40 (m, 4H). | 676 |
| 69 | ¹H NMR (400 MHz, DMSO-d₆, ppm) δ 6.64-6.51 (m, 1H), 6.28 (d, J = 45.1 Hz, 1H), 5.87 (s, 2H), 5.16-4.99 (m, 1H), 4.62-4.44 (m, 1H), 4.19-4.02 (m, 2H), 4.00-3.89 (m, 1H), 3.60 (s, 1H), 3.53-3.43 (m, 1H), 3.41-3.34 (m, 1H), 3.30-3.23 (m, 1H), 3.17-2.96 (m, 3H), 2.78-2.62 (m, 1H), 2.46-2.22 (m, 5H), 2.09-1.95 (m, 1H), 1.93-1.50 (m, 7H), 1.48-1.36 (m, 3H). | 650 |
| 70 | ¹H NMR (300 MHz, DMSO-d6, ppm) δ 7.45 (d, J = 12.0 Hz, 1H), 6.76 (d, J = 8.6 Hz, 1H), 6.09 (s, 2H), 5.12-5.02 (m, 1H), 4.54-4.49 (m, 1H), 4.41-4.36 (m, 1H), 4.14-4.08 (m, 1H), 3.94 (d, J = 8.4 Hz, 1H), 3.65-3.40 (m, 6H), 3.13 (t, J = 10.4 Hz, 1H), 3.06-2.83 (m, 4H), 2.74-2.71 (m, 1H), 2.12-2.01 (m, 1H), 1.84-1.52 (m, 6H), 1.42 (d, J = 6.3 Hz, 3H), 1.34-1.22 (m, 1H). | 634 |
| 71 | ¹H NMR (300 MHz, DMSO-d6) δ 7.48 (d, J = 12.0 Hz, 1H), 6.78 (d, J = 8.6 Hz, 1H), 6.11 (s, 2H), 5.13 (dd, J = 13.1, 2.5 Hz, 1H), 4.57 (dd, J = 8.7, 6.3 Hz, 1H), 4.42-4.26 (m, 2H), 4.01 (d, J = 8.5 Hz, 1H), 3.66 (s, 1H), 3.54 (d, J = 5.4 Hz, 2H), 3.23 (d, J = 8.9 Hz, 1H), 3.19-3.13 (m, 1H), 3.13-3.02 (m, 2H), 2.75-2.56 (m, 2H), 2.47-2.22 (m, 3H), 1.84 (d, J = 10.3 Hz, 1H), 1.77-1.54 (m, 3H), 1.45 (d, J = 6.3 Hz, 3H). | 640 |
| 72 | ¹H-NMR (300 MHz, CDCl₃, ppm) δ 7.50 (d, J = 6 Hz, 1H), 6.73 (d, J = 9 Hz, 1H), 6.64 (s, 1H), 5.46-5.35 (m, 1H), 5.22 (s, 1H), 4.41-4.14 (m, 3H), 4.02 (s, 3H), 3.8-3.53 (m, 2H), 3.46-3.17 (m, 3H), 3.16-2.93 (m, 2H), 2.43-2.13 (m, 3H), 2.11-1.87 (m, 4H), 1.85-1.65 (m, 3H), 1.57 (d, J = 6 Hz, 3H). | 618 |
| 73 | ¹H NMR (300 MHz, DMSO-d6, ppm) δ 7.23 (d, J = 13.6 Hz, 1H), 6.68 (d, J = 9.0 Hz, 1H), 5.70 (s, 2H), 5.40-5.15 (m, 2H), 4.66-4.61 (m, 1H), 4.17-4.04 (m, 3H), 3.89-3.74 (m, 2H), 3.27-3.09 (m, 6H), 2.92-2.88 (m, 1H), 2.19-1.69 (m, 9H), 1.53-1.47 (m, 3H), 1.33-1.24 (m, 2H). | 632 |
| 74 | ¹H NMR (300 MHz, DMSO-d6, ppm) δ 6.62 (d, J = 2.7 Hz, 1H), 6.47 (d, J = 2.7 Hz, 1H), 5.40-5.17 (m, 3H), 5.08 (d, J = 12 Hz, 1H), 4.61-4.48 (m, 1H), 4.14-3.91 (m, 3H), 3.57 (s, 1H), 3.45 (d, J = 5.4 Hz, 1H), 3.20-3.07 (m, 2H), 3.06-2.97 (m, 2H), 2.86-2.74 (m, 2H), 2.25 (s, 3H), 2.16 (d, J = 4.4 Hz, 1H), 2.02 (m, 2H), 1.93-1.75 (m, 4H), 1.72-1.52 (m, 3H), 1.44 (d, J = 6.3 Hz, 3H). | 598 |
| 75 | ¹H NMR (300 MHz, DMSO-d6, ppm) δ 6.65-6.62 (m, 1H), 6.30-5.92 (m, 1H), 5.38-5.09 (m, 4H), 4.57-4.52 (m, 1H), 4.10-3.97 (m, 3H), 3.63-3.49 (m, 2H), 3.18-3.01 (m, 6H), 2.89-2.83 (m, 1H), 2.22 (s, 3H), 2.21-1.99 (m, 3H), 1.87-1.60 (m, 7H), 1.45-1.43 (m, 3H). | 646 |
| 76 | ¹H NMR (300 MHz, DMSO-d₆, ppm) δ 6.71 (d, J = 9.4 Hz, 1H), 5.40 (d, J = 10.2 Hz, 2H), 5.20 (s, 1H), 5.08 (dd, J = 12.8, 2.5 Hz, 1H), 4.62-4.47 (m, 1H), 4.16-3.98 (m, 2H), 3.95 (d, J = 8.7 Hz, 1H), 3.58 (s, 1H), 3.45 (d, J = 5.8 Hz, 1H), 3.15-3.07 (m, 2H), 3.07-2.97 (m, 2H), 2.89-2.80 (m, 2H), 2.26 (d, J = 2.6 Hz, 3H), 2.16 (d, J = 4.7 Hz, 1H), 2.02 (dd, J = 14.4, 4.9 Hz, 2H), 1.91-1.69 (m, 4H), 1.73-1.50 (m, 3H), 1.45 (d, J = 6.3 Hz, 3H). | 616 |
| 77 | ¹H NMR (300 MHz, DMSO-d6, ppm) δ 6.55 (d, J = 14.3 Hz, 1H), 6.37 (s, 3H), 5.09 (dd, J = 12.9, 2.6 Hz, 1H), 4.56-4.52 (m, 1H), 4.43-4.33 (m, 1H), 4.16-4.13 (m, 1H), 3.96 (d, J = 8.8 Hz, 1H), 3.64-3.41 (m, 6H), 3.15 (t, J = 10.4 Hz, 1H), 3.08-2.78 (m, 4H), 2.14-1.99 (m, 1H), 1.82-1.73 (m, 2H), 1.66-1.54 (m, 4H), 1.44 (d, J = 6.3 Hz, 3H), 1.37-1.24 (m, 1H). | 634 |
| 78 | ¹H NMR (300 MHz, DMSO-d6, ppm) δ 9.01 (d, J = 5.2 Hz, 1H), 8.85 (s, 1H), 7.96 (d, J = 5.2 Hz, 1H), 5.11 (d, J = 9 Hz, 1H), 4.65-4.52 (m, 1H), 4.48-4.25 (m, 2H), 3.99 (d, J = 8.6 Hz, 1H), 3.62-3.50 (m, 2H), 3.46 (d, J = 5.8 Hz, 1H), 3.27-3.17 (m, 1H), 3.15 (d, J = 4.5 Hz, 1H), 3.06 (d, J = 13.3 Hz, 2H), 2.81 (s, 1H), 2.75-2.58 (m, 2H), 2.44-2.30 (m, 2H), 1.81 (d, J = 10.5 Hz, 1H), 1.73-1.52 (m, 3H), 1.45 (d, J = 6.3 Hz, 3H). | 608 |

-continued

| Cmpd. No. | $^1$H NMR | MS $(M + H)^+$ |
|---|---|---|
| 79 | $^1$H NMR (300 MHz, DMSO-d6, ppm) δ 7.60-7.46 (m, 2H), 7.40 (d, J = 8.1 Hz, 1H), 7.28-7.15(m, 1H), 6.85 (s, 1H), 6.60 (s, 2H), 5.19-5.08 (m, 1H), 4.66-4.52 (m, 1H), 4.45-4.28 (m, 2H), 3.98 (d, J = 8.6 Hz, 1H), 3.65-3.49 (m, 2H), 3.46 (d, J = 5.5 Hz, 1H), 3.22 (d, J = 8.8 Hz, 1H), 3.14 (s, 1H), 3.05 (d, J = 14.1 Hz, 2H), 2.74 (d, J = 18.8 Hz, 1H), 2.69-2.57 (m, 1H), 2.47-2.21 (m, 3H), 1.92-1.78 (m, 1H), 1.74-1.51 (m, 3H), 1.45 (d, J = 6.3 Hz, 3H). | 605 |
| 80 | $^1$H NMR (300 MHz, DMSO-$d_6$, ppm) δ 9.88 (s, 1H), 7.65 (d, J = 8.2 Hz, 1H), 7.43-7.30 (m, 1H), 7.26 (t, J = 3.3 Hz, 1H), 7.13 (dd, J = 15.2, 7.1 Hz, 1H), 7.01 (d, J = 2.6 Hz, 1H), 5.12 (d, J = 12.5 Hz, 1H), 4.91 (s, 2H), 4.59-4.53 (m, 1H), 4.06-3.95 (m, 3H), 3.56 (d, J = 13.9 Hz, 3H), 3.45 (s, 1H), 3.12-2.94 (m, 2H), 2.79 (s, 1H), 2.67-2.53 (m, 1H), 2.47-2.31 (m, 2H), 2.29-2.09 (m, 2H), 1.97-1.83 (m, 3H), 1.70-1.65 (m, 4H), 1.43 (t, J = 5.1 Hz, 3H), 1.25 (s, 1H), 0.96 (t, J = 7.4 Hz, 1H), 0.80 (t, J = 7.4 Hz, 2H). | 623 |
| 81 | $^1$H NMR (300 MHz, DMSO-$d_6$, ppm) δ 10.15 (s, 1H), 8.01-7.92 (m, 1H), 7.52-7.45 (m, 1H), 7.40-7.34 (m, 1H), 7.19 (d, J = 2.5 Hz, 1H), 5.29 (d, J = 54 Hz, 1H), 4.83 (dd, J = 18.4, 13.2 Hz, 1H), 4.54 (dd, J = 14.2, 12.1 Hz, 1H), 4.38-4.31 (m, 2H), 4.17-4.05 (m, 2H), 4.05-3.94 (m, 2H), 3.62 (s, 1H), 3.53 (s, 1H), 3.11-3.01 (m, 4H), 2.85-2.76 (m, 2H), 2.14 (s, 1H), 2.03 (d, J = 9.7 Hz, 2H), 1.90-1.61 (m, 7H). | 629 |
| 82 | $^1$H NMR (400 MHz, DMSO-$d_6$, ppm) δ 7.90 (d, J = 8.3 Hz, 1H), 7.63-7.48 (m, 1H), 7.47-7.19 (m, 2H), 5.29 (d, J = 54.4 Hz, 1H), 5.16-5.05 (m, 1H), 4.65-4.47 (m, 1H), 4.12 (d, J = 10.4 Hz, 1H), 4.06-3.91 (m, 2H), 3.64-3.53 (m, 1H), 3.51-3.42 (m, 1H), 3.17-3.03 (m, 3H), 3.01 (s, 1H), 2.91-2.77 (m, 1H), 2.24-2.12 (m, 1H), 2.11-1.93 (m, 2H), 1.91-1.73 (m, 4H), 1.72-1.51 (m, 3H), 1.50-1.37 (m, 3H). | 637 |
| 83 | $^1$H NMR (300 MHz, DMSO-d6, ppm) δ 6.57 (s, 2H), 5.27 (d, 1H), 5.14-5.04 (m, 1H), 4.98 (s, 2H), 4.60-4.43 (m, 1H), 4.17-3.98 (m, 2H), 3.94 (d, J = 8.8 Hz, 1H), 3.62-3.53 (m, 1H), 3.49-3.41 (m, 1H), 3.20-3.07 (m, 2H), 3.07-2.95 (m, 2H), 2.90-2.72 (m, 4H), 2.72-2.55 (m, 2H), 2.30-2.11 (m, 1H), 2.10-1.98 (m, 2H), 1.97-1.73 (m, 6H), 1.72-1.51 (m, 3H), 1.45 (d, J = 6.3 Hz, 3H). | 590 |

Example 84: Compound 84

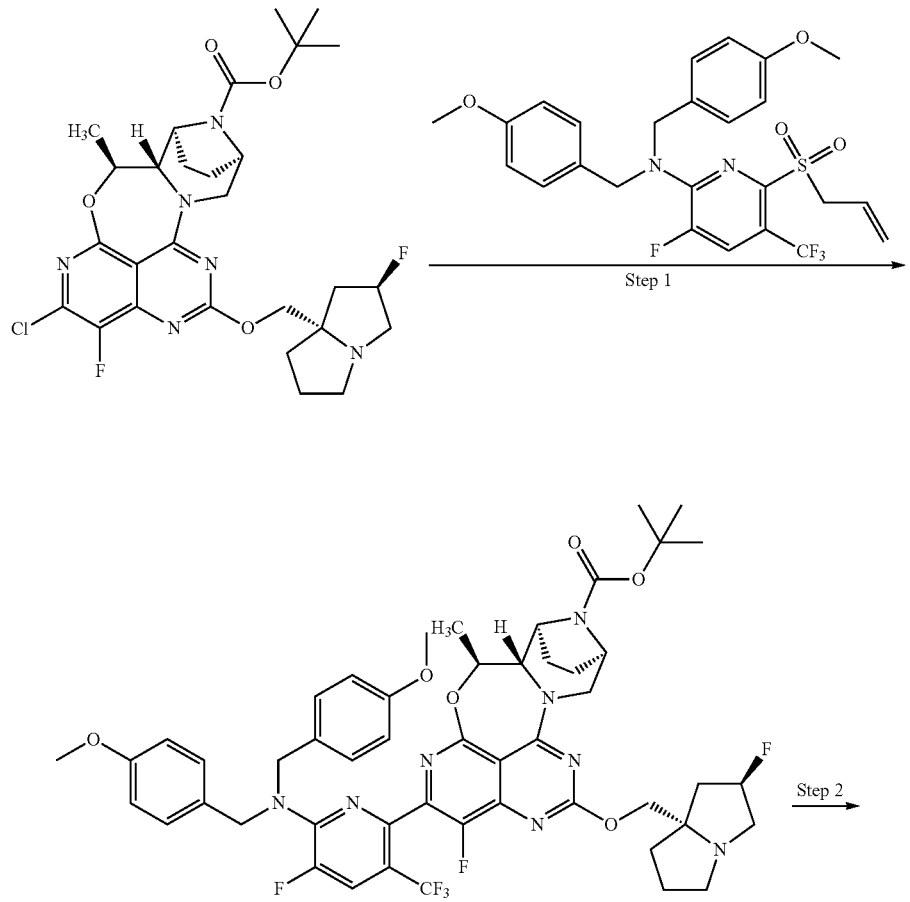

-continued

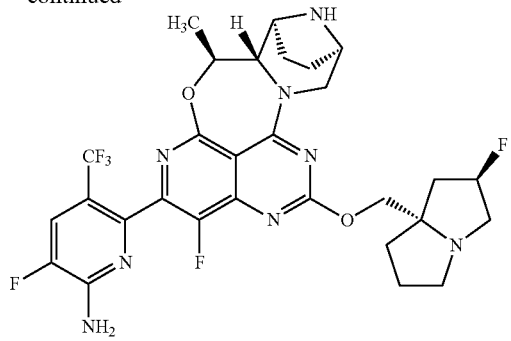

Step 1: tert-Butyl (5S,5aS,6S,9R)-2-(6-(bis(4-methoxybenzyl)amino)-5fluoro-3-(trifluoromethyl)pyridin-2-yl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate Under nitrogen, a solution of tert-butyl rac-(4R,7S,8S,9S)-13-chloro-14-fluoro-9-methyl-17-[[rac-(2R,8S)-2-fluoro-1,2,3,5,6,7-hexahydropyrrolizin-8-yl]methoxy]-10-oxa-2,12,16,18,20-pentazapentacyclo[9.7.1.14,7.02,8.015,19]icosa-1(18),11(19),12,14,16-pentaene-20-carboxylate (10.0 mg, 0.02 mmol), Pd(OAc)$_2$ (1.89 mg, 0.01 mmol, Example 58, step 1), 6-allylsulfonyl-3-fluoro-N,N-bis[(4-methoxyphenyl)methyl]-5-(trifluoromethyl)pyridin-2-amine (13.3 mg, 0.03 mmol, intermediate 64), P(t-Bu)$_2$Me·HBF$_4$ (0.42 mg) and Cs$_2$CO$_3$ (10.9 mg, 0.03 mmol) in 1,4-dioxane (2 mL) was stirred at 120° C. overnight. The resulting mixture was cooled to room temperature, diluted with water and extracted with EtOAc. The combined organic layers were dried over anhydrous Na$_2$SO$_4$ and concentrated under reduced pressure. The residue was purified by flash chromatography on silica gel (gradient: 0%-5% MeOH/DCM) to yield 12 mg (72.8% yield) of the title compound as a yellow solid. LC-MS: (ESI, m z): [M+H]$^+$=977.

Step 2: 3-Fluoro-6-((5S,5aS,6S,9R)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-5-(trifluoromethyl)pyridin-2-amine (Compound 84)

A solution of tert-Butyl (5S,5aS,6S,9R)-2-(6-(bis(4-methoxybenzyl)amino)-5-fluoro-3-(trifluoromethyl)pyridin-2-yl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (12.0 mg, 0.01 mmol) in TFA (2 mL) was stirred at 50° C. for 4 hours. The solvent was concentrated under vacuum. The crude product was purified by Prep-HPLC (conditions: Column: XBridge Prep OBD C18 Column, 30×150 mm 5 μm; Mobile Phase A:Water(10 mmol/L NH$_4$HCO$_3$), Mobile Phase B:ACN; Flow rate: 60 mL/min; Gradient: 12B to 42B in 7 min; 254 nm; RTL:6.5) to afford the title compound (1.5 mg, 19.2% yield) as a white solid. LC-MS: (ESI, m/z): [M+H]$^+$=637. H NMR (400 MHz, DMSO-d$_6$, ppm): δ 7.86 (m, 1H), 7.26 (s, 2H), 5.34 (s, 1H), 5.17-5.06 (m, 1H), 4.50 (m, 1H), 4.09 (m, 1H), 4.05-3.89 (m, 2H), 3.56 (s, 2H), 3.09 (s, 2H), 3.02 (d, J=13.2 Hz, 2H), 2.82 (d, J=7.9 Hz, 2H), 2.25-1.94 (m, 3H), 1.81 (i, 4H), 1.64 (s, 2H), 1.55 (s, 1H), 1.43 (in, 3H).

Each compound in the Table below was prepared following a similar experimental procedure (using appropriately substituted reagents) as described for Example 84.

| Cmpd. No. | $^1$H NMR | MS (M + H)$^+$ |
|---|---|---|
| 85 | $^1$H NMR (400 MHz, DMSO-d$_6$, ppm): δ 7.76 (d, J = 8.9 Hz, 1H), 7.42-7.20 (m, 1H), 6.91 (s, 2H), 6.62 (d, J = 8.8 Hz, 1H), 5.43-5.19 (m, 1H), 5.09 (m, 1H), 4.49 (m, 1H), 4.09 (d, J = 10.3 Hz, 1H), 4.06-3.93 (m, 2H), 3.50-3.37 (m, 1H), 3.18-3.04 (m, 1H), 3.03 (d, J = 12.5 Hz, 2H), 2.91-2.75 (m, 2H), 2.22-2.10 (m, 2H), 2.10-2.02 (m, 1H), 1.99 (m, 1H), 1.91-1.72 (m, 4H), 1.65 (m, 2H), 1.55 (m, 1H), 1.43 (d, J = 6.3 Hz, 3H). | 619 |
| 86 | $^1$H NMR (300 MHz, DMSO-d6, ppm) δ 7.87-7.78 (m, 1H), 7.27 (s, 2H), 5.10 (d, J = 12.0 Hz, 1H), 4.56-4.45 (m, 1H), 4.22-4.11 (m, 2H), 3.96 (d, J = 8.7 Hz, 1H), 3.60-3.55 (m, 1H), 3.44 (d, J = 6.2 Hz, 1H), 3.09-2.97 (m, 3H), 2.75-2.68 (m, 2H), 2.56-2.53 (m, 1H), 2.13-2.05 (m, 1H), 2.02-1.94 (m, 1H), 1.93-1.86 (m, 1H), 1.84-1.76 (m, 2H), 1.74-1.71(m, 1H), 1.66-1.45 (m, 5H), 1.48-1.45 (d, J = 6.3 Hz, 4H). | 681 |

| Cmpd. No. | ¹H NMR | MS (M + H)⁺ |
|---|---|---|
| 87 | ¹H NMR (300 MHz, DMSO-d6, ppm) δ 7.87 (d, J = 11.2 Hz, 1H), 7.28 (s, 2H), 5.17-5.07 (m, 1H), 4.54-4.48 (m, 1H), 4.35 (q, J = 12.0 Hz, 2H), 4.02-3.93 (m, 1H), 3.71-3.57 (m, 2H), 3.45 (d, J = 5.4 Hz, 1H), 3.25-3.17 (m, 1H), 3.14-2.99 (m, 3H), 2.77-2.60 (m, 2H), 2.46-2.29 (m, 3H), 1.91-1.78 (m, 1H), 1.75-1.51 (m, 3H), 1.44 (d, J = 6.3 Hz, 3H). | 641 |
| 88 | ¹H NMR (300 MHz, DMSO-d₆, ppm) δ 8.79 (dd, J = 6.5, 5.0 Hz, 1H), 7.68 (dd, J = 9.8, 5.0 Hz, 1H), 5.32-5.06 (m, 1H), 4.52 (m, 1H), 4.35 (q, J = 11.0 Hz, 1H), 4.00 (dd, J = 12.6, 9.5 Hz, 2H), 3.60-3.51 (m, 1H), 3.45-3.37 (m, 1H), 3.23-3.03 (m, 3H), 3.03-2.90 (m, 2H), 2.84-2.64 (m, 2H), 2.59 (d, J = 2.3 Hz, 3H), 2.48-2.26 (m, 2H), 1.99-1.78 (m, 1H), 1.75-1.53 (m, 4H), 1.45 (dd, J = 8.2, 6.3 Hz, 3H). | 622 |
| 89 | ¹H NMR (300 MHz, DMSO-d6, ppm) δ 7.93 (d, J = 8.4 Hz, 1H), 7.83-7.59 (m, 2H), 7.50-7.29 (m, 2H), 5.15 (dd, J = 12.8, 2.5 Hz, 1H), 4.72-4.53 (m, 1H), 4.37 (m, 2H), 4.10-3.90 (m, 4H), 3.60-3.45 (m, 4H), 3.26-3.00 (m, 4H), 2.82-2.59 (m, 2H), 2.42-2.25 (m, 2H), 1.83 (d, J = 10.9 Hz, 1H), 1.64 (m, 3H), 1.45 (d, J = 6.3 Hz, 3H). | 620 |
Example 90: Compound 90
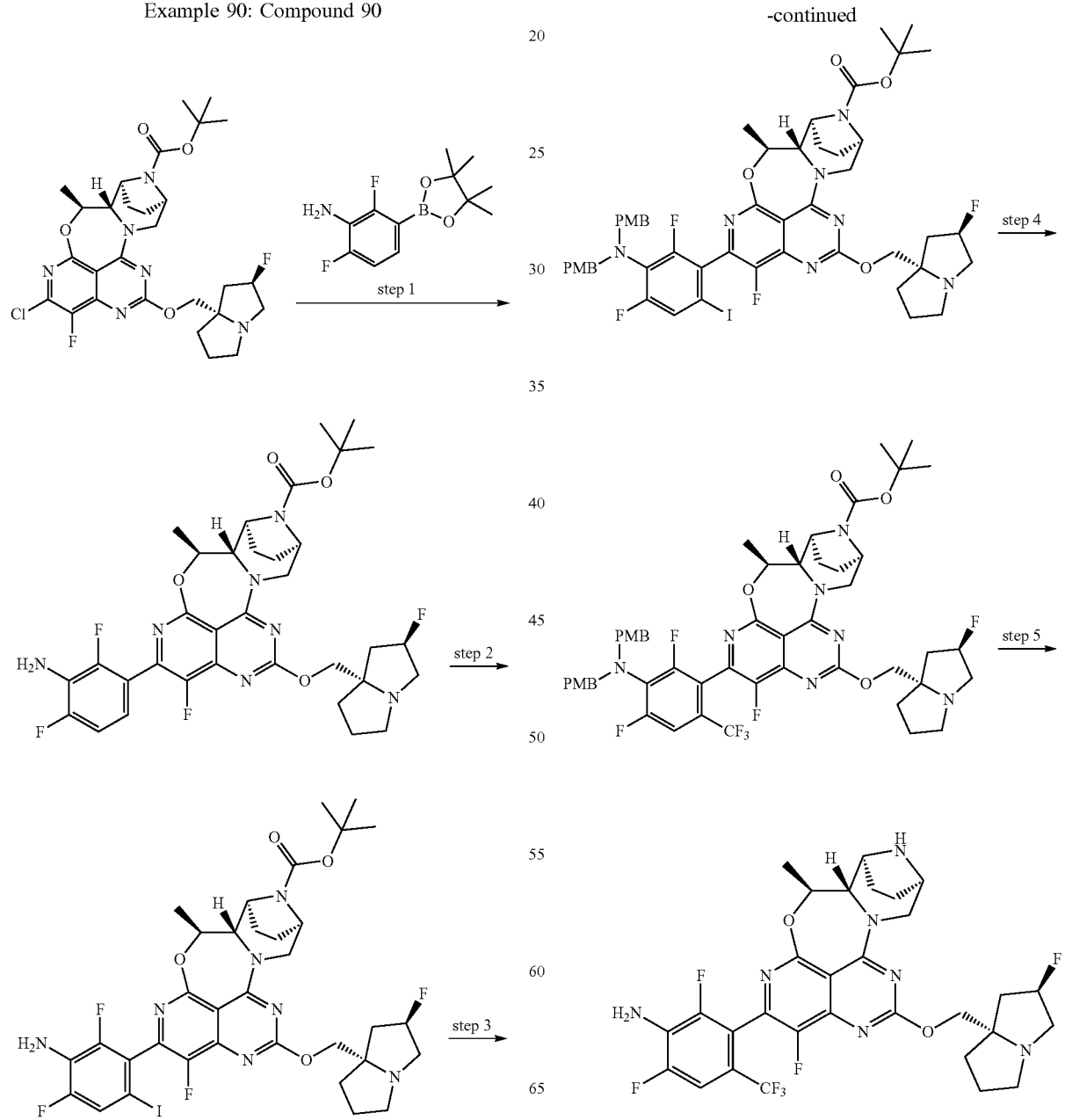

Step 1: tert-Butyl (5S,5aS,6S,9R)-2-(3-amino-2,4-difluorophenyl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate Under nitrogen, a solution of 2,6-difluoro-3-(4,4,5,5-tetramethyl-1,3,2-dioxaborolan-2-yl)aniline (305 mg, 1.19 mmol, intermediate 62), tert-butyl (5S,5aS,6S,9R)-2-chloro-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (354 mg, 0.597 mmol, Example 58, step 1), cataCXium A Pd G$_3$ (86.9 mg, 0.120 mmol) and K$_3$PO$_4$ (1.5 M in water) (1.2 mL) in tetrahydrofuran (6 mL) was stirred at 60° C. for 1 hour. The resulting mixture was filtered. The filtrate was concentrated under reduced pressure. The crude product was diluted with water and extracted with EtOAc. The combined organic layers were washed with brine, dried over anhydrous sodium sulfate and concentrated under reduced pressure. The residue was purified by flash chromatography on silica gel (gradient: 0-5% MeOH in DCM) to afford the title compound (390 mg, 95.3% yield) as a yellow solid. LC-MS: (ESI, m/z): [M+H]$^+$=686.

Step 2: tert-Butyl (5S,5aS,6S,9R)-2-(3-amino-2,4-difluoro-6-iodophenyl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate A solution of tert-butyl (5S,5aS,6S,9R)-2-(3-amino-2,4-difluorophenyl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (390 mg, 0.570 mmol), NIS (384 mg, 1.71 mmol) and TsOH (78.3 mg, 0.460 mmol) in N,N-dimethylacetamide (6 mL) was stirred at room temperature overnight. Additional NIS (384 mg, 1.71 mmol) and TsOH (78.3 mg, 0.460 mmol) were added, and the mixture was stirred at room temperature for another 1 hour. The solution was loaded to reverse phase column directly and eluted with 0-90% acetonitrile in water (0.5% NH$_4$HCO$_3$) to afford the title compound (486 mg, 94.1% yield) as a yellow solid. LC-MS: (ESI, m/z): [M+H]$^+$=812.

Step 3: tert-Butyl (5S,5aS,6S,9R)-2-(3-(bis(4-methoxybenzyl)amino)-2,4-difluoro-6-iodophenyl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate To a solution of tert-butyl (5S,5aS,6S,9R)-2-(3-amino-2,4-difluoro-6-iodophenyl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (580 mg, 0.710 mmol) was added NaH (71.5 mg, 1.79 mmol, 60% suspension in oil) at 0° C. The mixture was stirred for 15 min before PMBCl (247 mg, 1.57 mmol) was added. The mixture was allowed to warm to room temperature and stirred for 3 hours. The reaction mixture was quenched with water and extracted with EtOAc. The combined organic layers were dried over anhydrous sodium sulfate and concentrated under vacuum. The residue was purified by flash chromatography on silica gel (gradient: 0-5% MeOH in DCM) to afford the title compound (320 mg, 39.4% yield) as a yellow solid. LC-MS: (ESI, m/z): [M+H]$^+$=1052.

Step 4: tert-Butyl (5S,5aS,6S,9R)-2-(3-(bis(4-methoxybenzyl)amino)-2,4-difluoro-6-(trifluoromethyl)phenyl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate Under nitrogen, to a solution of tert-butyl (5S,5aS,6S,9R)-2-(3-(bis(4-methoxybenzyl)amino)-2,4-difluoro-6-iodophenyl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (320 mg, 0.300 mmol) in N,N-dimethylacetamide (10 mL) was added copper 2,2-difluoro-2-(fluorosulfonyl)acetate (1.90 g, 4.56 mmol) and Cu (292 mg, 4.56 mmol) at 0° C. was added. The reaction was stirred at 90° C. for 30 min. The solution was cooled to room temperature. The reaction mixture was extracted with EtOAc and washed with water. The combined organic layers were dried over anhydrous sodium sulfate and concentrated under vacuum. The residue was purified by flash chromatography on silica gel (gradient: 0-5% MeOH in DCM) to afford the title compound (200 mg, 58.7% yield) as a yellow solid. LC-MS: (ESI, m/z): [M+H]$^+$=994.

Step 5: 2,6-Difluoro-3-((5S,5aS,6S,9R)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-4-(trifluoromethyl)aniline (Compound 90)

A solution of tert-butyl (5S,5aS,6S,9R)-2-(3-(bis(4-methoxybenzyl)amino)-2,4-difluoro-6-(trifluoromethyl)phenyl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (120 mg, 0.120 mmol) in 2,2,2-trifluoroacetic acid (1.5 mL) was stirred at 50° C. for 1 hour. The solvent was concentrated under vacuum. The crude were purified by Prep-HPLC with the following conditions: (Column: XBridge Prep OBD C18 Column, 19*250 mm, 5 μm; Mobile Phase A: Water(10 mmol/L NH$_4$HCO$_3$), Mobile Phase B: MeOH; Flow rate: 25 mL/min; Gradient: 60% B to 85% B in 9 min, 85% B; Wave Length: 220/254 nm; R$_{T1}$(min): 9.03) to afford the title compound (24.1 mg, 30.5% yield) as a white solid. LC-MS: (ESI, m/z): [M+H]$^+$=654. $^1$H NMR (300 MHz, DMSO-d6) δ 7.55-7.39 (m, 1H), 6.23 (d, J=9.3 Hz, 2H), 5.27 (d, J=54.4 Hz, 1H), 5.14-5.00 (m, 1H), 4.62-4.46 (m, 1H), 4.14-3.90 (m, 3H), 3.56 (s, 1H), 3.43 (d, J=5.9 Hz, 1H), 3.16-2.92 (m, 4H), 2.92-2.67 (m, 2H), 2.28-1.93 (m, 3H), 1.93-1.48 (m, 7H), 1.42 (dd, J=6.4, 3.1 Hz, 3H).

647

Example 91: Compound 91

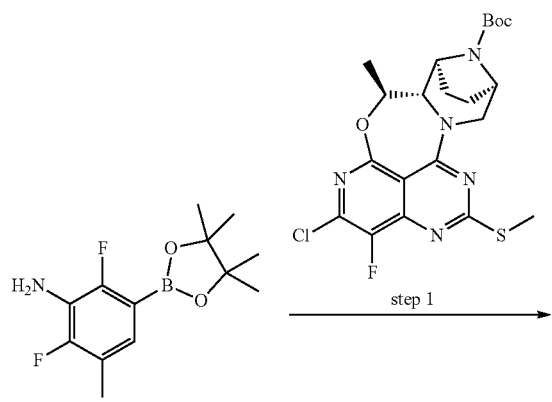

step 1 →

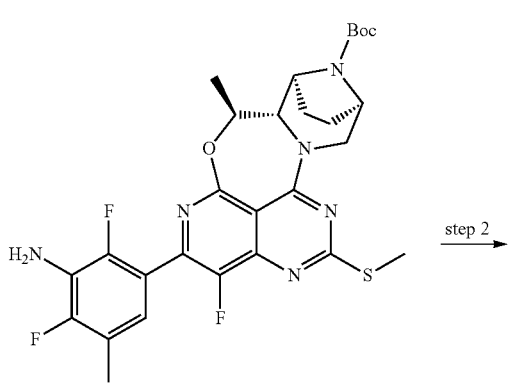

step 2 →

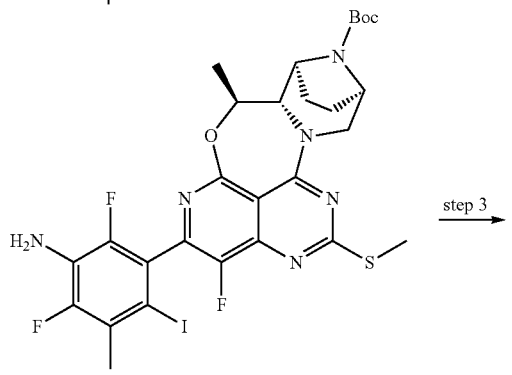

step 3 →

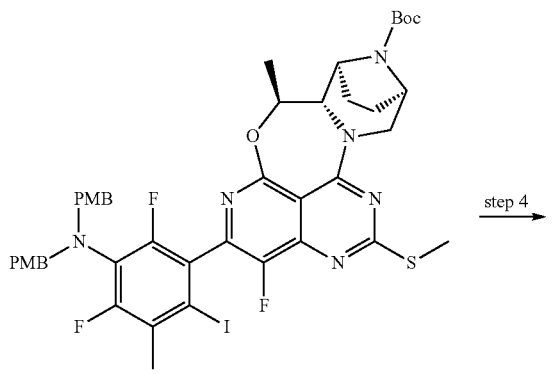

step 4 →

648

-continued

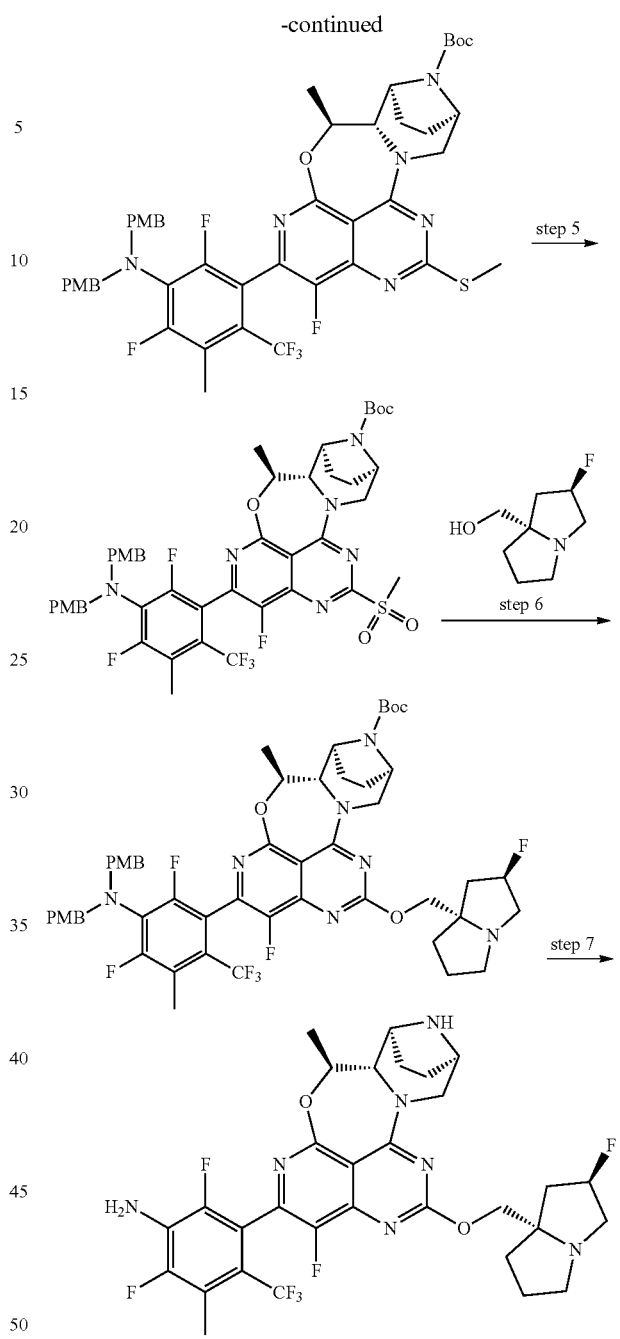

Step 1: tert-Butyl (5S,5aS,6S,9R)-2-(3-amino-2,4-difluoro-5-methylphenyl)-1-fluoro-5-methyl-12-(methylthio)-5a,6,7,8,9,10-hexahydro-5H-4-oxa-3,10a,11,13,14-pentaaza-6,9-methanonaphtho[1,8-ab]heptalene-14-carboxylate Under nitrogen, to a solution of 2,6-difluoro-3-methyl-5-(4,4,5,5-tetramethyl-1,3,2-dioxaborolan-2-yl)aniline (280 mg, 1.04 mmol, intermediate 31), tert-butyl (5S,5aS,6S,9R)-2-chloro-1-fluoro-5-methyl-12-(methylthio)-5a,6,7,8,9,10-hexahydro-5H-4-oxa-3,10a,11,13,14-pentaaza-6,9-methanonaphtho[1,8-ab]heptalene-14-carboxylate (501 mg, 1.04 mmol, intermediate 46) and cataCXium A Pd G3 (75.7 mg, 0.100 mmol) in tetrahydrofuran (5.4 mL) and Water (1.1 mL) was added K₃PO₄ (1.5 M solution in H₂O, 1.1 mL, 1.65 mmol) at room temperature. The resulting mixture was stirred for 3 hours at 90° C. The reaction mixture was diluted with water and extracted with EtOAc. The combined organic layers were dried over anhydrous sodium sulfate and concentrated under vacuum. The residue was purified by flash chromatography on silica gel (gradient: 0-26% EtOAc in petroleum ether) to afford the title compound (260 mg, 42.5% yield) as a yellow solid. LC-MS: (ESI, m/z): [M+H]⁺= 589.

Step 2: tert-Butyl (5S,5aS,6S,9R)-2-(3-amino-2,4-difluoro-6-iodo-5-methylphenyl)-1-fluoro-5-methyl-12-(methylthio)-5a,6,7,8,9,10-hexahydro-5H-4-oxa-3,10a,11,13,14-pentaaza-6,9-methanonaphtho[1,8-ab]heptalene-14-carboxylate A solution of tert-butyl (5S,5aS,6S,9R)-2-(3-amino-2,4-difluoro-5-methylphenyl)-1-fluoro-5-methyl-12-(methylthio)-5a,6,7,8,9,10-hexahydro-5H-4-oxa-3,10a,11,13,14-pentaaza-6,9-methanonaphtho[1,8-ab]heptalene-14-carboxylate (260 mg, 0.440 mmol), TsOH (9.2 mg, 0.0500 mmol and NIS (130 mg, 0.580 mmol) in N,N-dimethylformamide (3 mL) was stirred at room temperature for 1 hour. The solvent was concentrated under vacuum. The residue was purified by flash chromatography on silica gel (gradient: 0-14% EtOAc in petroleum ether) to afford the title compound (320 mg, 98.3% yield) as a brown solid. LC-MS: (ESI, m/z): [M+H]⁺=715.

Step 3: tert-Butyl (5S,5aS,6S,9R)-2-(3-(bis(4-methoxybenzyl)amino)-2,4-difluoro-6-iodo-5-methylphenyl)-1-fluoro-5-methyl-12-(methylthio)-5a,6,7,8,9,10-hexahydro-5H-4-oxa-3,10a,11,13,14-pentaaza-6,9-methanonaphtho[1,8-ab]heptalene-14-carboxylate Under nitrogen, to a solution of tert-butyl (5S,5aS,6S,9R)-2-(3-amino-2,4-difluoro-6-iodo-5-methylphenyl)-1-fluoro-5-methyl-12-(methylthio)-5a,6,7,8,9,10-hexahydro-5H-4-oxa-3,10a,11,13,14-pentaaza-6,9-methanonaphtho[1,8-ab]heptalene-14-carboxylate (320 mg, 0.448 mmol) in N,N-dimethylformamide (5 mL) was added NaH (90.0 mg, 2.25 mmol, 60% suspension in oil) and the mixture was stirred at 0° C. for 30 minutes. Then PMBCl (175 mg, 1.12 mmol) was added and the mixture was stirred at room temperature for 5 hours. The reaction was quenched with saturated NH₄Cl solution and extracted with EtOAc. The combined organic layers were dried over anhydrous sodium sulfate and concentrated under vacuum. The residue was purified by flash chromatography on silica gel (gradient: 0-14% EtOAc in petroleum ether) to afford the title compound (400 mg, 65.5% yield) as a yellow oil. LC-MS: (ESI, m/z): [M+H]⁺=955.

Step 4: tert-Butyl (5S,5aS,6S,9R)-2-(3-(bis(4-methoxybenzyl)amino)-2,4-difluoro-5-methyl-6-(trifluoromethyl)phenyl)-1-fluoro-5-methyl-12-(methylthio)-5a,6,7,8,9,10-hexahydro-5H-4-oxa-3,10a,11,13,14-pentaaza-6,9-methanonaphtho[1,8-ab]heptalene-14-carboxylate Under nitrogen, to a solution of tert-butyl (5S,5aS,6S,9R)-2-(3-(bis(4-methoxybenzyl)amino)-2,4-difluoro-6-iodo-5-methylphenyl)-1-fluoro-5-methyl-12-(methylthio)-5a,6,7,8,9,10-hexahydro-5H-4-oxa-3,10a,11,13,14-pentaaza-6,9-methanonaphtho[1,8-ab]heptalene-14-carboxylate (370 mg, 0.390 mmol) and CuI (74.0 mg, 0.390 mmol) in N,N-dimethylacetamide (5 mL) was added methyl 2,2-difluoro-2-(fluorosulfonyl)acetate (0.25 mL, 1.93 mmol). The resulting solution was stirred at 90° C. for 3 hours. The reaction mixture was diluted with water and extracted with EtOAc. The combined organic layer was dried over anhydrous sodium sulfate and concentrated under vacuum. The residue was purified by flash chromatography on silica gel (gradient: 0-30% EtOAc in petroleum ether) to afford the title compound (280 mg, 74.9% yield) as a yellow oil. LC-MS: (ESI, m/z): [M+H]⁺=897.

Step 5: tert-Butyl (5S,5aS,6S,9R)-2-(3-(bis(4-methoxybenzyl)amino)-2,4-difluoro-5-methyl-6-(trifluoromethyl)phenyl)-1-fluoro-5-methyl-12-(methylsulfonyl)-5a,6,7,8,9,10-hexahydro-5H-4-oxa-3,10a,11,13,14-pentaaza-6,9-methanonaphtho[1,8-ab]heptalene-14-carboxylate To a solution of tert-butyl (5S,5aS,6S,9R)-2-(3-(bis(4-methoxybenzyl)amino)-2,4-difluoro-5-methyl-6-(trifluoromethyl)phenyl)-1-fluoro-5-methyl-12-(methylthio)-5a,6,7,8,9,10-hexahydro-5H-4-oxa-3,10a,11,13,14-pentaaza-6,9-methanonaphtho[1,8-ab]heptalene-14-carboxylate (300 mg, 0.330 mmol) in EtOAc (5 mL) was added m-CPBA (174 mg, 1.01 mmol) at 0° C. The solution was stirred at room temperature for 3 hours. The reaction was quenched with saturated NaHCO₃ solution and extracted with EtOAc. The combined organic layers were dried over anhydrous sodium sulfate and concentrated under vacuum. The residue was purified by flash chromatography on silica gel eluting with 0-54% EtOAc in petroleum ether to afford the title compound (192 mg, 49.4% yield) as a yellow solid. LC-MS: (ESI, m/z): [M+H]⁺=929.

Step 6: tert-Butyl (5S,5aS,6S,9R)-2-(3-(bis(4-methoxybenzyl)amino)-2,4-difluoro-5-methyl-6-(trifluoromethyl)phenyl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate To a solution of ((2R,7aS)-2-fluorotetrahydro-1H-pyrrolizin-7a(5H)-yl)methanol (42.8 mg, 0.270 mmol, intermediate 14) in tetrahydrofuran (3 mL) was added NaH (30.0 mg, 0.75 mmol, 60% suspension in oil) at 0° C. and the mixture was stirred for 30 minutes at room temperature. Then tert-butyl (5S,5aS,6S,9R)-2-(3-(bis(4-methoxybenzyl)amino)-2,4-difluoro-5-methyl-6-(trifluoromethyl)phenyl)-1-fluoro-5-methyl-12-(methylsulfonyl)-5a,6,7,8,9,10-hexahydro-5H-4-oxa-3,10a,11,13,14-pentaaza-6,9-methanonaphtho[1,8-ab]heptalene-14-carboxylate (192 mg, 0.210 mmol) was added and the mixture was stirred at room temperature for 2 hours. The reaction system was quenched with aqueous NH₄Cl and concentrated under vacuum. The residue was purified by flash chromatography on silica gel (gradient: 0-55% EtOAc in petroleum ether) to afford the title compound (120 mg, 57.6% yield) as a yellow oil. LC-MS: (ESI, m/z): [M+H]⁺=1008.

Step 7: 2,6-Difluoro-3-((5S,5aS,6S,9R)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-5-methyl-4-(trifluoromethyl)aniline A solution of tert-butyl (5S,5aS,6S,9R)-2-(3-(bis(4-methoxybenzyl)amino)-2,4-difluoro-5-methyl-6-(trifluoromethyl)phenyl)-1-fluoro-12-(((2R,7aS)-2-fluorotetrahydro-1H-pyrrolizin-7a(5H)-yl)methoxy)-5-methyl-5a,6,7, 8,9,10-hexahydro-5H-4-oxa-3,10a,11,13,14-pentaaza-6,9-methanonaphtho[1,8-ab]heptalene-14-carboxylate (120 mg, 0.120 mmol) in TFA (5 mL) was stirred at 50° C. for 2 hours. The solvent was concentrated under vacuum. The crude product was purified by Prep-HPLC with the following conditions: (Column: XBridge Prep OBD C18 Column, 30*150 mm, 5 μm; Mobile Phase A: Water(10 mmol/L NH$_4$HCO$_3$), Mobile Phase B: ACN; Flow rate: 60 mL/min; Gradient: 30% B to 55% B in 9 min, 55% B; Wave Length: 254/220 nm; R$_{T1}$(min): 8.8) to afford the title compound (18.2 mg, 22.6% yield) as a white solid. LC-MS: (ESI, m/z): [M+H]$^+$=668. $^1$H NMR (300 MHz, DMSO-d6, ppm) δ 6.16 (d, J=10.7 Hz, 2H), 5.29 (d, J=54.3 Hz, 1H), 5.16-5.01 (m, 1H), 4.66-4.50 (m, 1H), 4.18-3.94 (m, 3H), 3.71-3.46 (m, 2H), 3.07 (dd, J=24.1, 9.1 Hz, 4H), 2.92-2.71 (m, 1H), 2.30 (s, 3H), 2.23-2.12 (m, 1H), 2.11-1.94 (m, 2H), 1.93-1.52 (m, 7H), 1.44 (d, J=6.3 Hz, 3H).

Each compound in the Table below was prepared following a similar experimental procedure (using appropriately substituted reagents) as described for Example 91.

| Cmpd. No. | $^1$H NMR | MS (M + H)$^+$ |
| --- | --- | --- |
| 92 (Isomer 1) | $^1$H NMR (300 MHz, CD$_3$OD-d6, ppm) δ 6.87 (d, J = 8.8 Hz, 1H), 5.37 (d, J = 13.3 Hz, 1H), 4.58-4.56 (m, 1H), 4.51 (s, 2H), 4.09 (m, 1H), 3.79-3.67 (m, 2H), 3.63-3.55 (s, 1H), 3.42-3.35 (m, 2H), 3.29-3.20 (m, 1H), 3.18-3.10 (m, 1H), 2.79-2.49 (m, 4H), 2.53-2.38 (m, 3H), 2.13-2.07 (m, 1H), 1.82-1.73 (m, 3H), 1.59 (dd, J = 6.4, 2.2 Hz, 3H), 1.31 (s, 1H) | 654 |
| 92 (Isomer 2) | $^1$H NMR (300 MHz, CD$_3$OD-d6, ppm) δ 6.87 (d, J = 8.8 Hz, 1H), 5.44-5.39 (m, 1H), 4.61-4.46 (m, 3H), 4.16-4.11 (m, 1H), 3.83-3.63 (m, 3H), 3.52-3.35 (m, 2H), 3.30-3.16 (m, 2H), 2.74-2.46 (m, 4H), 2.46-2.35 (m, 3H), 2.18-2.04 (m, 1H), 1.98-1.73 (m, 3H), 1.62-1.57 (m, 3H), 1.31 (s, 1H). | 654 |

Examples 93, 94, and 95: Compounds 93, 94, and 95

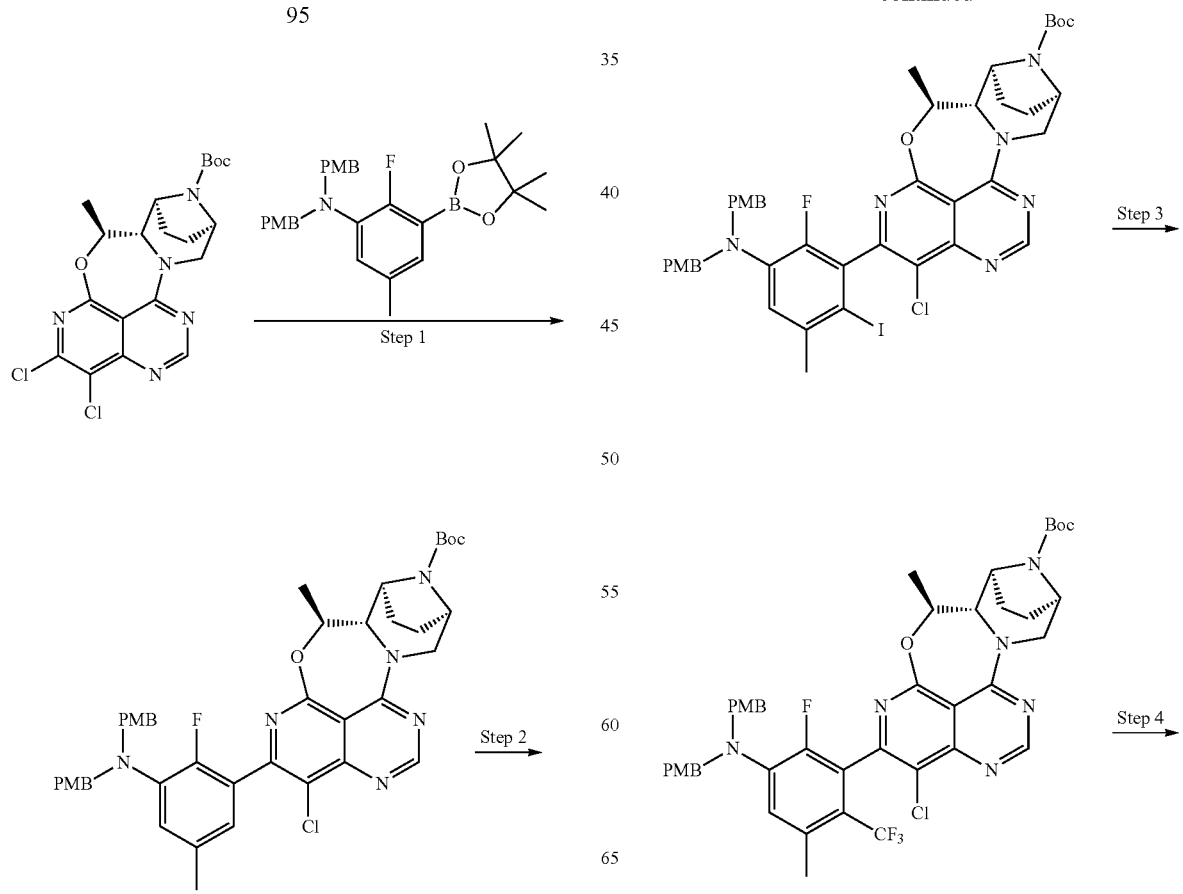

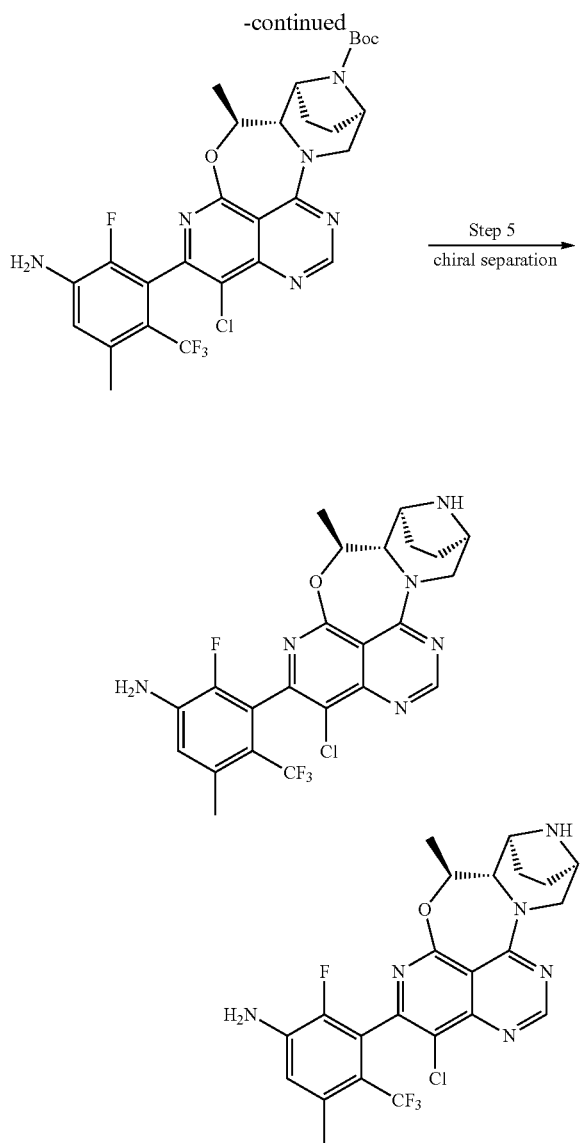

Step 1: tert-Butyl(5S,5aS,6S,9R)-2-(3-(bis(4-methoxybenzyl)amino)-2-fluoro-5-methylphenyl)-1-chloro-5-methyl-5a,6,7,8,9,10-hexahydro-5H-4-oxa-3,10a,11,13,14-pentaaza-6,9-methanonaphtho[1,8-ab]heptalene-14-carboxylate Under nitrogen, a solution of 2-fluoro-N,N-bis[(4-methoxyphenyl)methyl]-5-methyl-3-(4,4,5,5-tetramethyl-1,3,2-dioxaborolan-2-yl)aniline (217 mg, 0.44 mmol, intermediate 19), tert-butyl rac-(4R,7S,8S,9S)-13,14-dichloro-9-methyl-10-oxa-2,12,16,18,20-pentazapentacyclo[9.7.1.14,7.02,8.015,19]icosa-1(18),11(19),12,14,16-pentaene-20-carboxylate (100 mg, 0.22 mmol, intermediate 47), Cs$_2$CO$_3$ (216 mg, 0.66 mmol) and Pd(PPh$_3$)$_4$(128 mg, 0.11 mmol) in dioxane and water (0.5 mL) was stirred for 1 h at 95° C. After filtration, the filtrate was concentrated under reduced pressure. The residue was purified by flash chromatography on silica gel (gradient: 0%-10% MeOH/DCM) to yield 160 mg (92.6% yield) of the title compound as a yellow solid. LC-MS: (ESI, m/z): [M+H]$^+$=781.

Step 2: tert-Butyl(5S,5aS,6S,9R)-2-(3-(bis(4-methoxybenzyl)amino)-2-fluoro-6-iodo-5-methylphenyl)-1-chloro-5-methyl-5a,6,7,8,9,10-hexahydro-5H-4-oxa-3,10a,11,13,14-pentaaza-6,9-methanonaphtho[1,8-ab]heptalene-14-carboxylate To a solution of tert-butyl rac-(4R,7S,8S,9S)-13-[3-[bis[(4-methoxyphenyl)methyl]amino]-2-fluoro-5-methyl-phenyl]-14-chloro-9-methyl-10-oxa-2,12,16,18,20-pentazapentacyclo[9.7.1.14,7.02,8.015,19]icosa-1(18),11(19),12,14,16-pentaene-20-carboxylate (200 mg, 0.26 mmol) in acetic acid (3 mL) was added NIS (57.6 mg, 0.26 mmol). The resulting mixture was stirred for 1 h at room temperature. The reaction system was diluted with water, extracted with EtOAc. The combined organic layers were dried over anhydrous Na$_2$SO$_4$. After filtration, the filtrate was concentrated under reduced pressure. The residue was purified by flash chromatography on silica gel (gradient: 0%-20% MeOH/DCM) to yield 165 mg (71.1% yield) of the title compound as a yellow solid. LC-MS: (ESI, m/z): [M+H]$^+$=907.

Step 3: tert-Butyl(5S,5aS,6S,9R)-2-(3-(bis(4-methoxybenzyl)amino)-2-fluoro-5-methyl-6-(trifluoromethyl)phenyl)-1-chloro-5-methyl-5a,6,7,8,9,10-hexahydro-5H-4-oxa-3,10a,11,13,14-pentaaza-6,9-methanonaphtho[1,8-ab]heptalene-14-carboxylate Under nitrogen, to a solution of methyl 2,2-difluoro-2-(fluorosulfonyl)acetate (1.1 g, 26.5 mmol) in N,N-dimethylformamide (6 mL) was added tert-butyl rac-(4R,7S,8S,9S)-13-[3-[bis[(4-methoxyphenyl)methyl]amino]-2-fluoro-6-iodo-5-methyl-phenyl]-14-chloro-9-methyl-10-oxa-2,12,16,18,20-pentazapentacyclo[9.7.1.14,7.02,8.015,19]icosa-1(18),11(19),12,14,16-pentaene-20-carboxylate (160 mg, 0.18 mmol) and CuI (34.2 mg, 0.18 mmol) at 0° C. The resulting solution was stirred at 90° C. for 30 min. The resulting mixture was cooled to room temperature, diluted with water and extracted with EtOAc. The combined organic layers were dried over anhydrous Na$_2$SO$_4$ and concentrated under reduced pressure. The crude product was purified by reverse phase chromatography (gradient: 0-60% acetonitrile in water (0.1% NH$_4$HCO$_3$)) to afford 120 mg (80.1% yield) of the title compound as a yellow solid. LC-MS: (ESI, m/z): [M+H]$^+$=849.

Step 4: 3-((5S,5aS,6S,9R)-1-chloro-5-methyl-5a,6,7,8,9,10-hexahydro-5H-4-oxa-3,10a,11,13,14-pentaaza-6,9-methanonaphtho[1,8-ab]heptalen-2-yl)-2-fluoro-5-methyl-4-(trifluoromethyl)aniline (mixture of two atropisomers) (Compound 93)

A solution of tert-butyl rac-(4R,7S,8S,9S)-13-[3-[bis[(4-methoxyphenyl)methyl]amino]-2-fluoro-5-methyl-6-(trifluoromethyl)phenyl]-14-chloro-9-methyl-10-oxa-2,12,16,18,20-pentazapentacyclo[9.7.1.14,7.02,8.015,19]icosa-1(18),11(19),12,14,16-pentaene-20-carboxylate (30.0 mg, 0.04 mmol) in TFA (1.5 mL) was stirred at 50° C. for 4 hours. The solvent was concentrated under vacuum and the residue was purified by Prep-HPLC ((Column: XSelect CSH Fluoro Phenyl, 30*150 mm, 5 μm; Mobile Phase A: Water (10 mmol/L NH$_4$HCO$_3$), Mobile Phase B: ACN; Flow rate: 60 mL/min; Gradient: 30% B to 55% B in 9.5 min, 55% B; Wave Length: 254/220 nm; RT1(min): 7.98; Number Of Runs: 0) to afford 8.2 mg (45.6% yield) of Compound 93 (mixture of atropisomers) as a white solid. LC-MS: (ESI, m/z): [M+H]$^+$=509. $^1$H NMR (300 MHz, DMSO-d6, ppm) δ 8.71 (s, 1H), 6.89-6.64 (m, 1H), 5.95 (d, J=13.0 Hz, 2H), 5.24-5.08 (m, 1H), 4.75-4.51 (m, 1H), 4.00 (t, J=8.3 Hz, 1H), 3.54 (s, 1H), 3.43 (s, 1H), 3.02 (d, J=12.7 Hz, 1H), 2.76 (s, 1H), 2.38-2.21 (m, 3H), 1.79 (d, J=8.9 Hz, 1H), 1.65 (m, 3H), 1.44 (d, J=6.3 Hz, 3H).

Step 5: 3-((5S,5aS,6S,9R)-1-chloro-5-methyl-5a,6,7,8,9,10-hexahydro-5H-4-oxa-3,10a,11,13,14-pentaaza-6,9-methanonaphtho[1,8-ab]heptalen-2-yl)-2-fluoro-5-methyl-4-(trifluoromethyl)aniline (two single atropisomers)

94

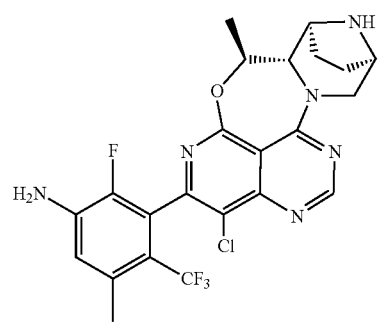

95

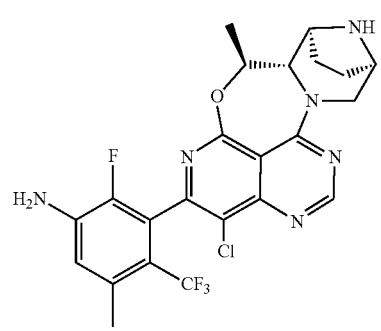

60 mg the product from step 4 was separated by Chiral Prep-HPLC Column: (CHIRALPAK ID, 2*25 cm, 5 M; Mobile Phase A: Hex(0.5% 2 M NH₃—MeOH)-HPLC, Mobile Phase B: EtOH—HPLC; Flow rate: 20 mL/min; Gradient: 30% B to 30% B in 20 min; Wave Length: 220/254 nm; RT1(min): 10.613; RT2(min): 16.407; Sample Solvent: EtOH—HPLC; Injection Volume: 0.8 mL; Number Of Runs: 4) to afford 18.5 mg (17.2% yield) faster peak and 20.5 mg (19% yield) slower peak as a white solid. LC-MS: (ESI, m/z): [M+H]⁺=509.

94: ¹H NMR (400 MHz, DMSO-d6, ppm) δ 8.73 (s, 1H), 6.80 (m, 1H), 5.97 (d, J=17.4 Hz, 2H), 5.22 (m, 1H), 4.66 (m, 1H), 4.02 (t, J=9.6 Hz, 1H), 3.64-3.42 (m, 2H), 3.05 (d, J=12.5 Hz, 1H), 2.34 (m, 3H), 1.84 (m, 1H), 1.79-1.51 (m, 3H), 1.45 (d, J=6.3 Hz, 3H).

95: ¹H NMR (400 MHz, DMSO-d6, ppm) δ 8.73 (s, 1H), 6.80 (d, J=8.8 Hz, 1H), 5.95 (s, 2H), 5.21 (m, 1H), 4.65 (m, 1H), 4.00 (dd, J=8.7, 1.5 Hz, 1H), 3.51 (m, 5.9 Hz, 2H), 3.04 (d, J=12.7 Hz, 1H), 2.82 (s, 1H), 2.36 (m, 3H), 1.93-1.79 (m, 1H), 1.74-1.51 (m, 3H), 1.45 (d, J=6.4 Hz, 3H).

Example 96: Compound 96

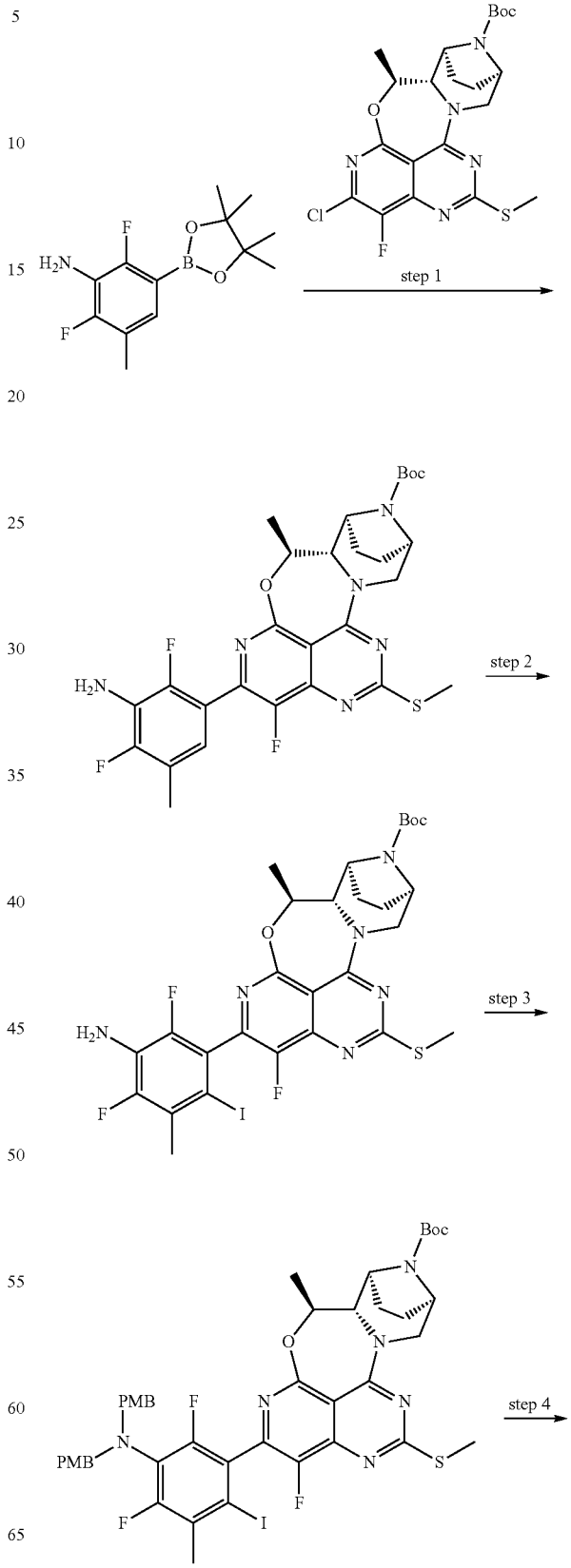

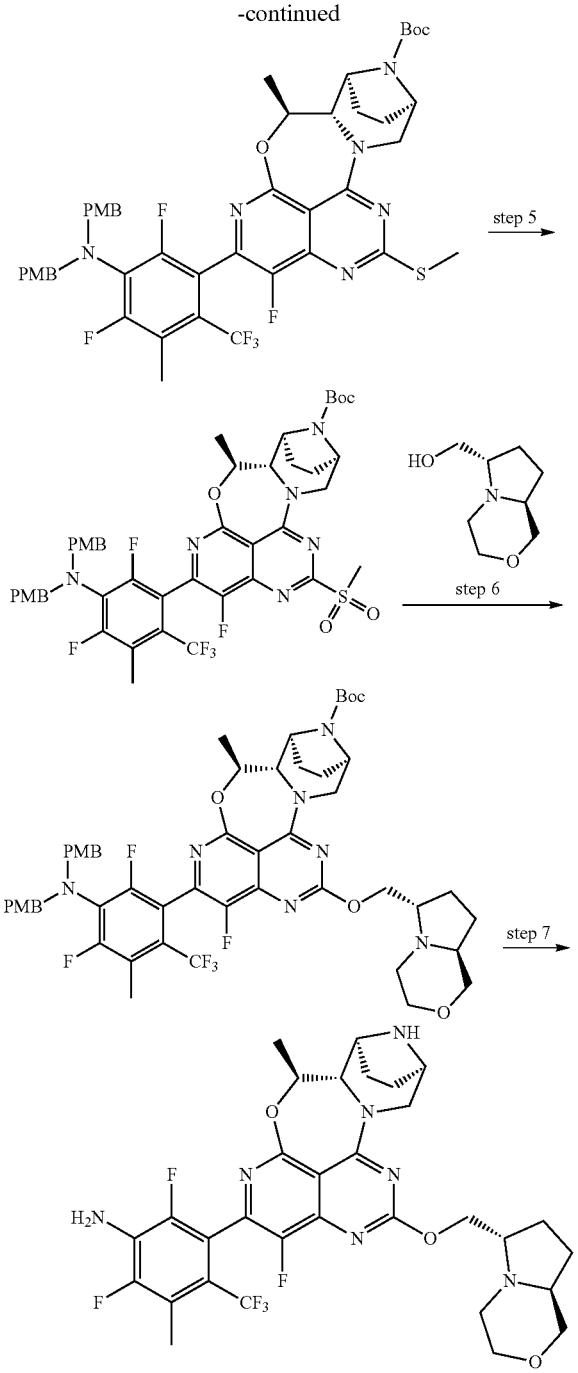

furan (5.4 mL) and water (1.1 mL) was added $K_3PO_4$ (1.5 M in $H_2O$, 1.1 mL). The resulting mixture was stirred for 3 hours at 90° C. The reaction mixture was diluted with water and extracted with EtOAc. The combined organic layer was dried over anhydrous sodium sulfate and concentrated under vacuum. The residue was purified by flash chromatography on silica gel (gradient: 0-26% EtOAc in petroleum ether) to afford the title compound (260 mg, 42.5% yield) as a yellow solid. LC-MS: (ESI, m/z): $[M+H]^+$=589.

Step 2: tert-Butyl (5S,5aS,6S,9R)-2-(3-amino-2,4-difluoro-6-iodo-5-methylphenyl)-1-fluoro-5-methyl-12-(methylthio)-5a,6,7,8,9,10-hexahydro-5H-4-oxa-3,10a,11,13,14-pentaaza-6,9-methanonaphtho[1,8-ab]heptalene-14-carboxylate A solution of tert-butyl (5S,5aS,6S,9R)-2-(3-amino-2,4-difluoro-5-methylphenyl)-1-fluoro-5-methyl-12-(methylthio)-5a,6,7,8,9,10-hexahydro-5H-4-oxa-3,10a,11,13,14-pentaaza-6,9-methanonaphtho[1,8-ab]heptalene-14-carboxylate (260 mg, 0.440 mmol), TsOH (9.2 mg, 0.0500 mmol and NIS (130 mg, 0.580 mmol) in N,N-dimethylformamide (3 mL) was stirred at room temperature for 1 hour. The solvent was concentrated under vacuum. The residue was purified by flash chromatography on silica gel (gradient: 0-14% EtOAc in petroleum ether) to afford the title compound (320 mg, 98.3% yield) as a brown solid. LC-MS: (ESI, m/z): $[M+H]^+$=715.

Step 3: tert-Butyl (5S,5aS,6S,9R)-2-(3-(bis(4-methoxybenzyl)amino)-2,4-difluoro-6-iodo-5-methylphenyl)-1-fluoro-5-methyl-12-(methylthio)-5a,6,7,8,9,10-hexahydro-5H-4-oxa-3,10a,11,13,14-pentaaza-6,9-methanonaphtho[1,8-ab]heptalene-14-carboxylate To a solution of tert-butyl (5S,5aS,6S,9R)-2-(3-amino-2,4-difluoro-6-iodo-5-methylphenyl)-1-fluoro-5-methyl-12-(methylthio)-5a,6,7,8,9,10-hexahydro-5H-4-oxa-3,10a,11,13,14-pentaaza-6,9-methanonaphtho[1,8-ab]heptalene-14-carboxylate (320 mg, 0.448 mmol) in N,N-dimethylformamide (5 mL) was added NaH (90.0 mg, 2.25 mmol, 60% suspension in mineral oil), and the mixture was stirred at 0° C. for 30 minutes. Then PMBCl (175 mg, 1.12 mmol) was added, and the mixture was stirred at room temperature for 5 hours. The reaction was quenched with saturated $NH_4Cl$ solution and extracted with EtOAc. The combined organic layers were dried over anhydrous sodium sulfate and concentrated under vacuum. The residue was purified by flash chromatography on silica gel (gradient: 0-14% EtOAc in petroleum ether) to afford the title compound (400 mg, 65.5% yield) as a yellow oil. LC-MS: (ESI, m/z): $[M+H]^+$=955.

Step 4: tert-Butyl (5S,5aS,6S,9R)-2-(3-(bis(4-methoxybenzyl)amino)-2,4-difluoro-5-methyl-6-(trifluoromethyl)phenyl)-1-fluoro-5-methyl-12-(methylthio)-5a,6,7,8,9,10-hexahydro-5H-4-oxa-3,10a,11,13,14-pentaaza-6,9-methanonaphtho[1,8-ab]heptalene-14-carboxylate Under nitrogen, to a solution of tert-butyl (5S,5aS,6S,9R)-2-(3-(bis(4-methoxybenzyl)amino)-2,4-difluoro-6-iodo-5-methylphenyl)-1-fluoro-5-methyl-12-(methylthio)-5a,6,7,8,9,10-hexahydro-5H-4-oxa-3,10a,11,13,14-pentaaza-6,9-methanonaphtho[1,8-ab]heptalene-14-carboxylate (370 mg, 0.390 mmol) and CuI (74.0 mg, 0.390

Step 1: tert-Butyl (5S,5aS,6S,9R)-2-(3-amino-2,4-difluoro-5-methylphenyl)-1-fluoro-5-methyl-12-(methylthio)-5a,6,7,8,9,10-hexahydro-5H-4-oxa-3,10a,11,13,14-pentaaza-6,9-methanonaphtho[1,8-ab]heptalene-14-carboxylate Under nitrogen, to a mixture of 2,6-difluoro-3-methyl-5-(4,4,5,5-tetramethyl-1,3,2-dioxaborolan-2-yl)aniline (280 mg, 1.04 mmol), tert-butyl (5S,5aS,6S,9R)-2-chloro-1-fluoro-5-methyl-12-(methylthio)-5a,6,7,8,9,10-hexahydro-5H-4-oxa-3,10a,11,13,14-pentaaza-6,9-methanonaphtho[1,8-ab]heptalene-14-carboxylate (501 mg, 1.04 mmol) and cataCXium A Pd G3 (75.7 mg, 0.100 mmol) in tetrahydrommol) in N,N-dimethylacetamide (5 mL) was added methyl 2,2-difluoro-2-(fluorosulfonyl)acetate (0.25 mL, 1.93 mmol), and the mixture was stirred at 90° C. for 3 hours. The reaction mixture was diluted with water and extracted with EtOAc. The combined organic layers were dried over anhydrous sodium sulfate and concentrated under vacuum. The residue was purified by flash chromatography on silica gel (gradient: 0-30% EtOAc in petroleum ether) to afford the title compound (280 mg, 74.9% yield) as a yellow oil. LC-MS: (ESI, m/z): [M+H]⁺=897.

Step 5: tert-Butyl (5S,5aS,6S,9R)-2-(3-(bis(4-methoxybenzyl)amino)-2,4-difluoro-5-methyl-6-(trifluoromethyl)phenyl)-1-fluoro-5-methyl-12-(methylsulfonyl)-5a,6,7,8,9,10-hexahydro-5H-4-oxa-3,10a,11,13,14-pentaaza-6,9-methanonaphtho[1,8-ab]heptalene-14-carboxylate To a solution of tert-butyl (5S,5aS,6S,9R)-2-(3-(bis(4-methoxybenzyl)amino)-2,4-difluoro-5-methyl-6-(trifluoromethyl)phenyl)-1-fluoro-5-methyl-12-(methylthio)-5a,6,7,8,9,10-hexahydro-5H-4-oxa-3,10a,11,13,14-pentaaza-6,9-methanonaphtho[1,8-ab]heptalene-14-carboxylate (300 mg, 0.330 mmol) in EtOAc (5 mL) was added m-CPBA (174 mg, 1.01 mmol) in batches at 0° C., and the mixture was stirred at room temperature for 3 hours. The reaction was quenched with saturated NaHCO₃ solution and extracted with EtOAc. The combined organic layers were dried over anhydrous sodium sulfate and concentrated under vacuum. The residue was purified by flash chromatography on silica gel (gradient: 0-54% EtOAc in petroleum ether) to afford the title compound (192 mg, 49.4% yield) as a yellow solid. LC-MS: (ESI, m/z): [M+H]⁺=929.

Step 6: tert-Butyl (5S,5aS,6S,9R)-2-(3-(bis(4-methoxybenzyl)amino)-2,4-difluoro-5-methyl-6-(trifluoromethyl)phenyl)-1-fluoro-12-(((6S,8aS)-hexahydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate Under nitrogen, to a solution of ((6S,8aS)-hexahydro-1H-pyrrolo[2,1-c][1,4]oxazin-6-yl)methanol (55.0 mg, 0.350 mmol) in tetrahydrofuran (3 mL) was added NaH (65.0 mg, 1.63 mmol, 60% suspension in mineral oil) at 0° C. The solution was stirred for 30 minutes at room temperature. Then tert-butyl (5S,5aS,6S,9R)-2-(3-(bis(4-methoxybenzyl)amino)-2,4-difluoro-5-methyl-6-(trifluoromethyl)phenyl)-1-fluoro-5-methyl-12-(methylsulfonyl)-5a,6,7,8,9,10-hexahydro-5H-4-oxa-3,10a,11,13,14-pentaaza-6,9-methanonaphtho[1,8-ab]heptalene-14-carboxylate (192 mg, 0.210 mmol) was added and the mixture was stirred at room temperature for 2 hours. The solvent was concentrated under vacuum. The residue was purified by flash chromatography on silica gel (gradient: 0-55% EtOAc in petroleum ether) to afford the title compound (190 mg, 37.9% yield) as a yellow oil. LC-MS: (ESI, m/z): [M+H]⁺=1009.

Step 7: 2,6-Difluoro-3-((5S,5aS,6S,9R)-1-fluoro-12-(((6S,8aS)-hexahydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-5-methyl-4-(trifluoromethyl)aniline (Compound 96)

A solution of tert-butyl (5S,5aS,6S,9R)-2-(3-(bis(4-methoxybenzyl)amino)-2,4-difluoro-5-methyl-6-(trifluoromethyl)phenyl)-1-fluoro-12-(((6S,8aS)-hexahydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (190 mg, 0.120 mmol) in TFA (5 mL) was stirred at 50° C. for 2 hours. The solvent was concentrated under vacuum. The crude product was purified by Prep-HPLC with the following conditions: (Column: XBridge Prep OBD C18 Column, 30*150 mm, 5 µm; Mobile Phase A: Water (10 mmol/L NH₄HCO₃), Mobile Phase B: ACN; Flow rate: 60 mL/min; Gradient: 17% B to 42% B in 9 min, 42% B; Wave Length: 254/220 nm; R_{T1}(min): 8.9) to afford the title compound (32.5 mg, 30.2% yield) as a white solid. LC-MS: (ESI, m/z): [M+H]⁺=668. ¹H NMR (300 MHz, DMSO-d6) δ 6.14 (d, J=10.6 Hz, 2H), 5.13-5.01 (m, 1H), 4.61-4.47 (m, 1H), 4.45-4.34 (m, 1H), 4.18-4.08 (m, 1H), 4.00-3.90 (m, 1H), 3.65-3.38 (m, 6H), 3.19-2.64 (m, 6H), 2.30 (s, 3H), 2.14-1.97 (m, 1H), 1.87-1.48 (m, 6H), 1.42 (d, J=6.3 Hz, 3H), 1.36-1.17 (m, 1H).

Example 97: Compound 97

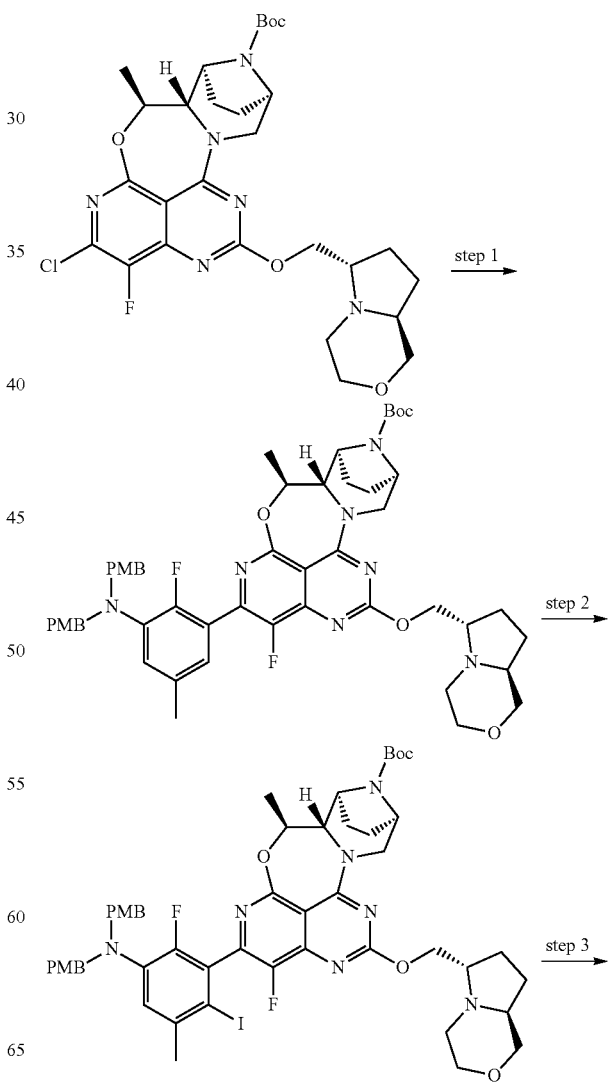

-continued

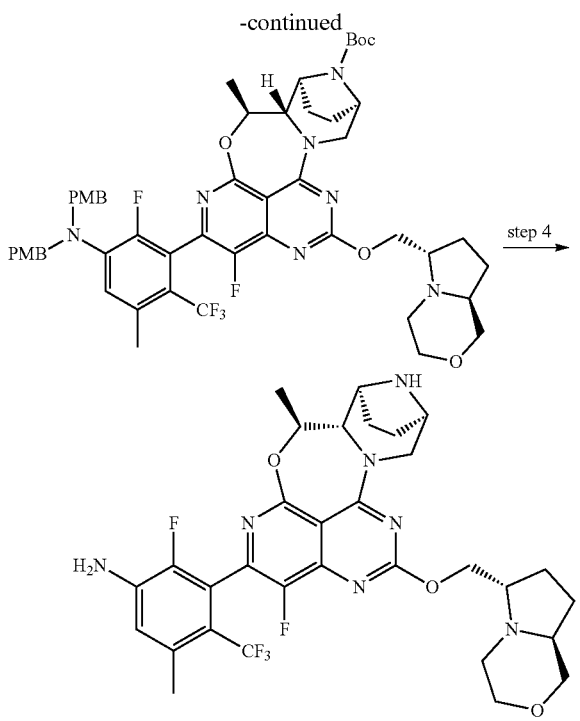

Step 1: tert-Butyl (5S,5aS,6S,9R)-2-(3-(bis(4-methoxybenzyl)amino)-2-fluoro-5-methylphenyl)-1-fluoro-12-(((6S,8aS)-hexahydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate Under nitrogen, a solution of tert-butyl (5S,5aS,6S,9R)-2-chloro-1-fluoro-12-(((6S,8aS)-hexahydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (700 mg, 1.18 mmol), 2-fluoro-N,N-bis(4-methoxybenzyl)-5-methyl-3-(4,4,5,5-tetramethyl-1,3,2-dioxaborolan-2-yl)aniline (1.16 g, 2.37 mmol), cataCXium A Pd G3 (173 mg, 0.240 mmol) and K$_3$PO$_4$ (2.5 mL, 1.5 M in water) in THF (10 mL) was stirred at 60° C. for 3 h. The solution was cooled to room temperature, diluted with water and extracted with ethyl acetate. The combined organic layers were washed with brine, dried over anhydrous sodium sulfate and concentrated under vacuum. The residue was purified by flash chromatography on silica gel (gradient: 0-10% MeOH in DCM) to yield 1.18 g (93.1% yield) of the title compound as a yellow solid. LC-MS: (ESI, m/z): [M+H]$^+$=920.

Step 2: tert-Butyl (5S,5aS,6S,9R)-2-(3-(bis(4-methoxybenzyl)amino)-2-fluoro-6-iodo-5-methylphenyl)-1-fluoro-12-(((6S,8aS)-hexahydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate To a solution of tert-butyl (5S,5aS,6S,9R)-2-(3-(bis(4-methoxybenzyl)amino)-2-fluoro-5-methylphenyl)-1-fluoro-12-(((6S,8aS)-hexahydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (1.08 g, 1.01 mmol) in AcOH (10 mL) was added NIS (239 mg, 1.06 mmol) at room temperature. The mixture was stirred at room temperature for 0.5 h. The solution was cooled to 0° C. and quenched with saturated Na$_2$S$_2$O$_3$ solution. The solution diluted with water and extracted with ethyl acetate. The combined organic layers were washed with brine, dried over anhydrous sodium sulfate and concentrated under vacuum. The residue was purified by flash chromatography on silica gel (gradient: 0-10% MeOH in DCM) to yield 845 mg (71.8% yield) of the title compound as a yellow solid. LC-MS: (ESI, m/z): [M+H]$^+$=1046.

Step 3: tert-Butyl (5S,5aS,6S,9R)-2-(3-(bis(4-methoxybenzyl)amino)-2-fluoro-5-methyl-6-(trifluoromethyl)phenyl)-1-fluoro-12-(((6S,8aS)-hexahydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate Under nitrogen, a solution of tert-butyl (5S,5aS,6S,9R)-2-(3-(bis(4-methoxybenzyl)amino)-2-fluoro-6-iodo-5-methylphenyl)-1-fluoro-12-(((6S,8aS)-hexahydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (150 mg, 0.140 mmol), Cu(O$_2$CCF$_2$SO$_2$F)$_2$ (898 mg, 1.46 mmol) and Cu (138 mg, 2.15 mmol) in DMF (5 mL) was stirred at room temperature for 1 h. The solution was diluted with water and extracted with ethyl acetate. The combined organic layers were washed with brine, dried over anhydrous sodium sulfate and concentrated under vacuum. The crude product was purified by reverse phase chromatography (gradient: 0-100% MeOH in water (0.05% ammonium acid carbonate) to yield 129 mg (91% yield) of the title compound as a yellow solid. LC-MS: (ESI, m/z): [M+H]$^+$=988.

Step 4: 2-Fluoro-3-((5S,5aS,6S,9R)-1-fluoro-12-(((6S,8aS)-hexahydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-5-methyl-4-(trifluoromethyl)aniline (Compound 97)

A solution of tert-butyl (5S,5aS,6S,9R)-2-(3-(bis(4-methoxybenzyl)amino)-2-fluoro-5-methyl-6-(trifluoromethyl)phenyl)-1-fluoro-12-(((6S,8aS)-hexahydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (129 mg, 0.130 mmol) in TFA (5.5 mL) was stirred at 50° C. for 4 h. The solution was concentrated under vacuum. The crude product was purified by Prep-HPLC with the following conditions: (Column: Xselect CSH C18 OBD Column 30*150 mm 5 m, n; Mobile Phase A: Water(0.1% FA), Mobile Phase B: ACN; Flow rate: 60 mL/min; Gradient: 7% B to 20% B in 8 min, 20% B; Wave Length: 254/220 nm; R$_{T1}$(min): 8; Number Of Runs: 0) to yield 37.7 mg (44.3% yield) of the title compound as a white solid. LC-MS: (ESI, m/z): [M+H]$^+$=648. $^1$H NMR (400 MHz, DMSO-d$_6$, ppm) δ 6.80 (d, J=8.8 Hz, 1H), 5.97 (d, J=11.3 Hz, 2H), 5.17-4.98 (m, 1H), 4.64-4.46 (m, 1H), 4.45-4.32 (m, 1H), 4.19-4.06 (m, 1H), 4.01-3.88 (m, 1H), 3.68-3.38 (m, 6H), 3.13 (t, J=10.4 Hz, 1H), 3.08-2.91 (m, 2H), 2.90-2.77 (m, 2H), 2.39-2.28 (m, 3H), 2.15-1.98 (m, 1H), 1.88-1.48 (m, 6H), 1.42 (d, J=6.3 Hz, 3H), 1.37-1.24 (m, 1H).

Example 98: Compound 98

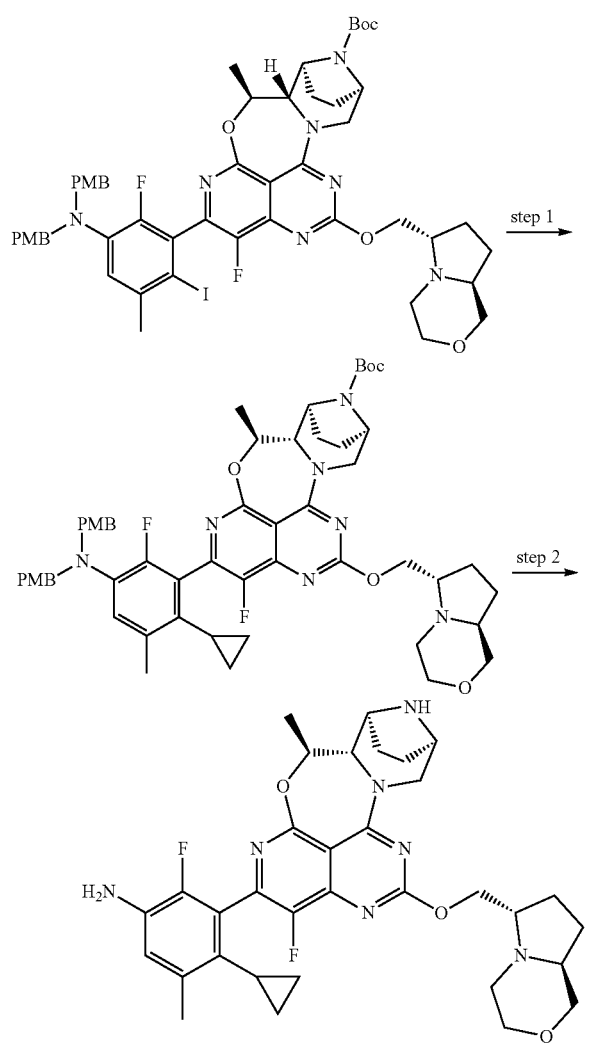

Step 1: tert-Butyl (5S,5aS,6S,9R)-2-(3-(bis(4-methoxybenzyl)amino)-6-cyclopropyl-2-fluoro-5-methylphenyl)-1-fluoro-12-(((6S,8aS)-hexahydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate Under nitrogen, a solution of tert-butyl (5S,5aS,6S,9R)-2-(3-(bis(4-methoxybenzyl)amino)-2-fluoro-6-iodo-5-methylphenyl)-1-fluoro-12-(((6S,8aS)-hexahydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (112 mg, 0.110 mmol, Example 97, step 2), 2-cyclopropyl-4,4,5,5-tetramethyl-1,3,2-dioxaborolane (26.6 mg, 0.160 mmol), K$_2$CO$_3$ (14.6 mg, 0.110 mmol) and Pd(dppf)Cl$_2$ (3.9 mg, 0.0100 mmol) in 1,4-dioxane (1 mL) and water (0.2 mL) was stirred for 16 hours at 90° C. The solution was cooled to room temperature, diluted with water and extracted with ethyl acetate. The combined organic layers were washed with brine, dried over anhydrous sodium sulfate and concentrated under vacuum. The residue was purified by flash chromatography on silica gel (gradient: 0-10% MeOH in DCM) to afford 43.1 mg (25.5% yield) of the title compound as a yellow solid. LC-MS: (ESI, m/z): [M+H]$^+$=960.

Step 2: 4-Cyclopropyl-2-fluoro-3-((5S,5aS,6S,9R)-1-fluoro-12-(((6S,8aS)-hexahydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-5-methylaniline (Compound 98)

A solution of tert-butyl (5S,5aS,6S,9R)-2-(3-(bis(4-methoxybenzyl)amino)-6-cyclopropyl-2-fluoro-5-methylphenyl)-1-fluoro-12-(((6S,8aS)-hexahydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (34.8 mg, 0.0100 mmol) in TFA (4 mL) was stirred at 50° C. for 3 hours. The solvent was concentrated under vacuum. The crude product was purified by Prep-HPLC with the following conditions: (Column: YMC-Actus Triart C18 ExRS, 30×150 mm, 5 μm; Mobile Phase A: Water(10 mmol/L NH$_4$HCO$_3$), Mobile Phase B: ACN; Flow rate: 60 mL/min; Gradient: 17% B to 42% B in 9 min, 42% B; Wave Length: 254/220 nm; R$_{T1}$(min): 8.9) to afford 2.8 mg (12.4% yield) of the title compound as a white solid. LC-MS: (ESI, m/z): [M+H]$^+$=620. $^1$H NMR (300 MHz, DMSO-d$_6$) δ 6.67 (d, J=9.2 Hz, 1H), 5.12 (d, J=12.6 Hz, 1H), 5.01 (d, J=9.1 Hz, 2H), 4.65-4.31 (m, 2H), 4.15-4.13 (m, 1H), 3.97 (d, J=9.0 Hz, 1H), 3.64-3.82 (m, 1H), 3.54 (d, J=12.7 Hz, 3H), 3.45 (t, J=5.5 Hz, 2H), 3.15 (t, J=10.4 Hz, 1H), 3.09-2.79 (m, 5H), 2.28 (d, J=6.7 Hz, 3H), 2.08 (s, 1H), 1.91-1.74 (m, 2H), 1.72-1.48 (m, 5H), 1.44 (d, J=6.2 Hz, 3H), 1.31-1.24 (m, 1H), 0.53 (t, J=8.2 Hz, 1H), 0.40-0.18 (m, 1H), 0.17-0.01 (m, 1H), −0.18 (d, J=5.5 Hz, 1H).

Example 99: Compound 99

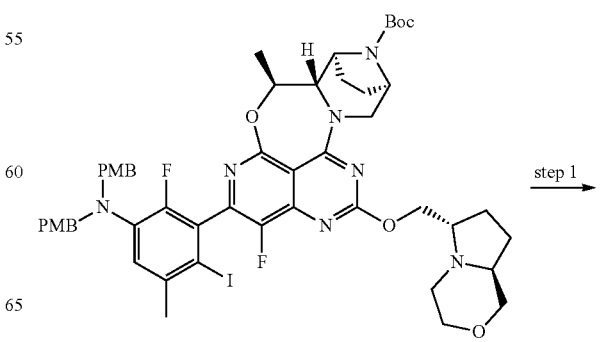

-continued

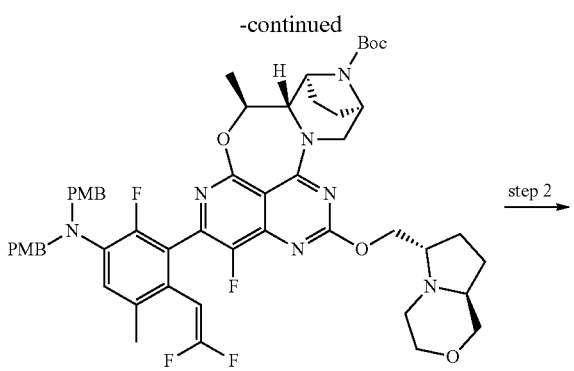

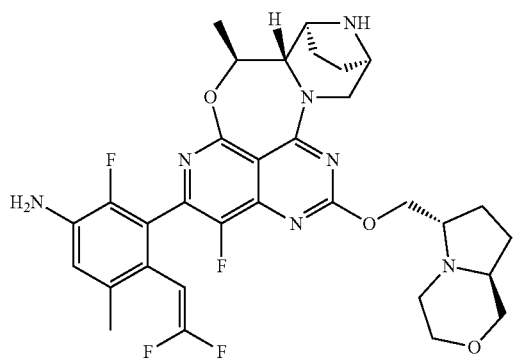

Step 1: tert-Butyl (5S,5aS,6S,9R)-2-(3-(bis(4-methoxybenzyl)amino)-6-(2,2-difluorovinyl)-2-fluoro-5-methylphenyl)-1-fluoro-12-(((6S,8aS)-hexahydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate Under nitrogen, a solution of tert-butyl (5S,5aS,6S,9R)-2-(3-(bis(4-methoxybenzyl)amino)-2-fluoro-6-iodo-5-methylphenyl)-1-fluoro-12-(((6S,8aS)-hexahydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (112 mg, 0.110 mmol, Example 97, step 2), 2-(2,2-difluorovinyl)-4,4,5,5-tetramethyl-1,3,2-dioxaborolane (40.6 mg, 0.210 mmol), K$_2$CO$_3$ (29.6 mg, 0.210 mmol) and Pd(dppf)Cl$_2$ (7.83 mg, 0.0100 mmol) in 1,4-dioxane (1.5 mL) and water (0.2 mL) was stirred for 2 hours at 90° C. The solution was cooled to room temperature, diluted with water and extracted with ethyl acetate. The combined organic layers were washed with brine, dried over anhydrous sodium sulfate and concentrated under vacuum. The residue was purified by flash chromatography on silica gel (gradient: 0-10% MeOH in DCM) to afford the title compound 104 mg (85.1% yield) as a yellow solid. LC-MS: (ESI, m/z): [M+H]$^+$=982.

Step 2: 4-(2,2-Difluorovinyl)-2-fluoro-3-((5S,5aS,6S,9R)-1-fluoro-12-(((6S,8aS)-hexahydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-5-methylaniline (Compound 99)

A solution of tert-butyl (5S,5aS,6S,9R)-2-(3-(bis(4-methoxybenzyl)amino)-6-(2,2-difluorovinyl)-2-fluoro-5-methylphenyl)-1-fluoro-12-(((6S,8aS)-hexahydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (30.1 mg, 0.0305 mmol) in TFA (4 mL) stirred at 50° C. for 3 hours. The solvent was concentrated under vacuum. The crude product was purified by Prep-HPLC with the following conditions: (Column: XBridge Prep Phenyl OBD Column, 19×250 mm, 5 µm; Mobile Phase A: Water (10 mmol/L NH$_4$HCO$_3$), Mobile Phase B: MeOH-HPLC; Flow rate: 25 mL/min; Gradient: 40% B to 70% B in 7 min, 70% B; Wave Length: 254/220 nm; R$_{T1}$(min): 6.5) to afford 4.6 mg (23.5% yield) of the title compound as a yellow solid. LC-MS: (ESI, m/z): [M+H]$^+$=642. $^1$H NMR (400 MHz, DMSO-d$_6$) δ 6.76-6.73 (m, 1H), 5.48-5.27 (m, 3H), 5.10 (d, J=12.9 Hz, 1H), 4.57 (d, J=28.9 Hz, 1H), 4.41-4.39 (m, 1H), 4.15-4.12 (m, 1H), 3.97 (d, J=8.3 Hz, 1H), 3.67-3.59 (m, 1H), 3.55 (s, 2H), 3.52 (d, J=3.2 Hz, 1H), 3.49-3.40 (m, 2H), 3.15 (t, J=10.4 Hz, 1H), 3.07-2.94 (m, 2H), 2.88 (d, J=14.1 Hz, 2H), 2.36-2.18 (m, 1H), 2.14 (d, J=8.3 Hz, 4H), 1.78-1.73 (m, 2H), 1.64 (d, J=7.8 Hz, 4H), 1.51-1.39 (m, 3H), 1.38-1.20 (m, 1H).

Example 100: Compound 100

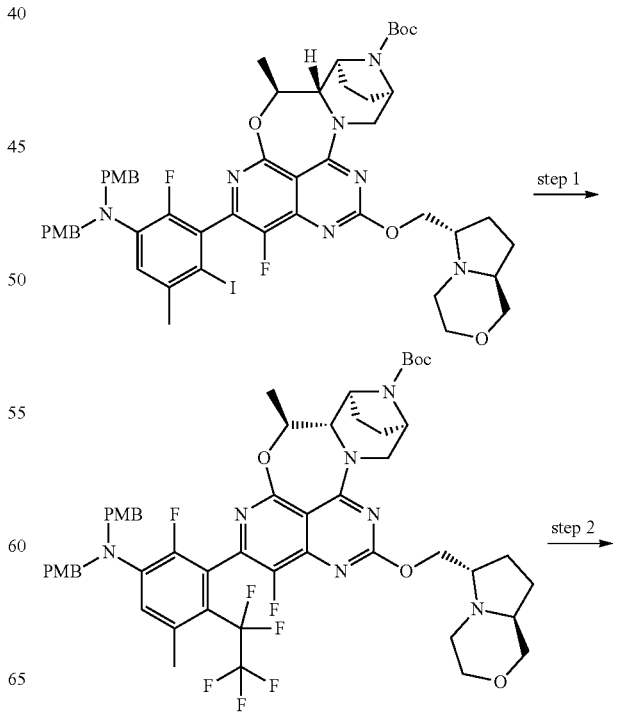

-continued

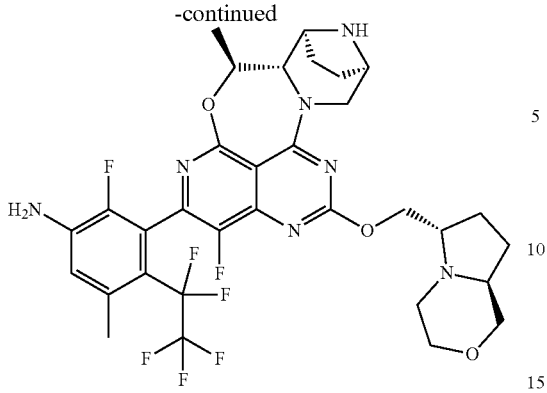

Step 1: tert-Butyl (5S,5aS,6S,9R)-2-(3-(bis(4-methoxybenzyl)amino)-2-fluoro-5-methyl-6-(perfluoroethyl)phenyl)-1-fluoro-12-(((6S,8aS)-hexahydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate Under nitrogen, a solution of tert-butyl (5S,5aS,6S,9R)-2-(3-(bis(4-methoxybenzyl)amino)-2-fluoro-6-iodo-5-methylphenyl)-1-fluoro-12-(((6S,8aS)-hexahydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (143 mg, 0.140 mmol, Example 97, step 2), trimethyl(perfluoroethyl)silane (525 mg, 2.73 mmol), KF (15.9 mg, 0.270 mmol) and CuI (143 mg, 0.750 mmol) in DMF (5 mL) was stirred for 3 hours at 50° C. The solution was cooled to room temperature, diluted with ethyl acetate and washed with water. The separated organic layer was washed with brine, dried over anhydrous sodium sulfate and concentrated under vacuum. The residue was purified by flash chromatography on silica gel (gradient: 0-15% MeOH in DCM) to afford 152 mg (84.4% yield) of the title compound as a yellow solid. LC-MS: (ESI, m/z): [M+H]$^+$=1038.

Step 2: 2-Fluoro-3-((5S,5aS,6S,9R)-1-fluoro-12-(((6S,8aS)-hexahydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-5-methyl-4-(perfluoroethyl)aniline (Compound 100)

A solution of tert-butyl (5S,5aS,6S,9R)-2-(3-(bis(4-methoxybenzyl)amino)-2-fluoro-5-methyl-6-(perfluoroethyl)phenyl)-1-fluoro-12-(((6S,8aS)-hexahydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (136 mg, 0.130 mmol) in TFA (5 mL) was stirred at 50° C. for 3 hours. The solvent was concentrated under vacuum. The crude product was purified by Prep-HPLC with the following conditions: (Column: XBridge Shield RP18 OBD Column, 30×150 mm, 5 μm; Mobile Phase A: Water (10 mmol/L NH$_4$HCO$_3$), Mobile Phase B: ACN; Flow rate: 60 mL/min; Gradient: 32% B to 44% B in 10 min, 44% B; Wave Length: 254/220 nm; R$_{T1}$(min): 10) to afford 11.2 mg (12.3% yield) of the title compound as a yellow solid. LC-MS: (ESI, m/z): [M+H]$^+$=698. $^1$H NMR (300 MHz, DMSO-d$_6$) δ 6.82 (d, J=9.1 Hz, 1H), 6.04 (d, J=10.3 Hz, 2H), 5.09 (t, J=10.8 Hz, 1H), 4.69-4.30 (m, 2H), 4.14 (s, 1H), 3.96 (d, J=8.5 Hz, 1H), 3.59-3.50 (m, 6H), 3.22-2.78 (m, 6H), 2.33 (s, 3H), 2.08 (s, 1H), 1.91-1.49 (m, 6H), 1.50-1.36 (m, 3H), 1.31 (s, 1H).

Examples 101 & 102: Compounds 101 and 102

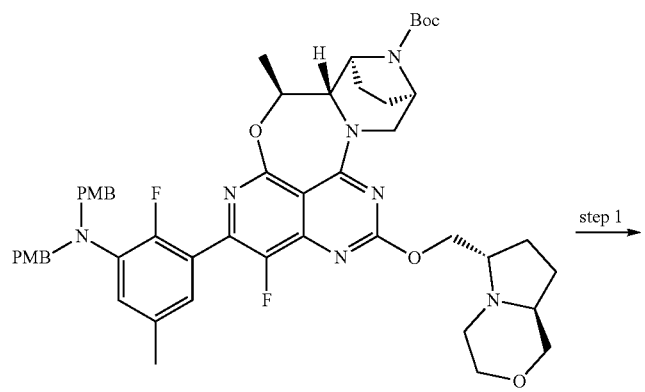

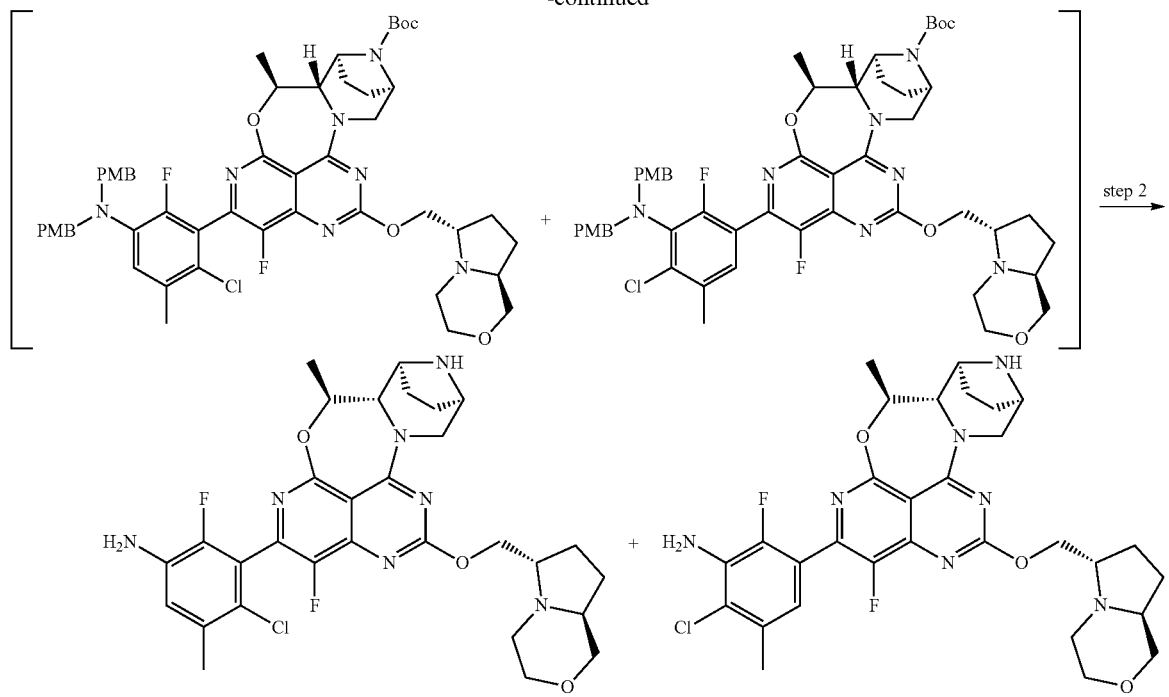

Step 1: tert-Butyl (5S,5aS,6S,9R)-2-(3-(bis(4-methoxybenzyl)amino)-6-chloro-2-fluoro-5-methylphenyl)-1-fluoro-12-(((6S,8aS)-hexahydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate tert-Butyl (5S,5aS,6S,9R)-2-(3-(bis(4-methoxybenzyl)amino)-4-chloro-2-fluoro-5-methylphenyl)-1-fluoro-12-(((6S,8aS)-hexahydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate To a solution of tert-butyl (5S,5aS,6S,9R)-2-(3-(bis(4-methoxybenzyl)amino)-2-fluoro-5-methylphenyl)-1-fluoro-12-(((6S,8aS)-hexahydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (100 mg, 0.110 mmol, Example 97, step 1) in AcOH (1.5 mL) was added NCS (17.5 mg, 0.130 mmol). The mixture was stirred at room temperature overnight. The solution was cooled to 0° C. and quenched with saturated Na$_2$S$_2$O$_3$ solution. The solution diluted with water and extracted with ethyl acetate. The combined organic layers were washed with brine, dried over anhydrous sodium sulfate and concentrated under vacuum. The residue was purified by flash chromatography on silica gel (gradient: 0-10% MeOH in DCM) to yield 78.9 mg (76.1% yield) of the mixture title compound as a yellow solid. LC-MS: (ESI, m/z): [M+H]$^+$=955.

Step 2: 4-Chloro-2-fluoro-3-((5S,5aS,6S,9R)-1-fluoro-12-(((6S,8aS)-hexahydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-5-methylaniline (Compound 101) & 2-Chloro-6-fluoro-5-((5S,5aS,6S,9R)-1-fluoro-12-(((6S,8aS)-hexahydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-3-methylaniline (Compound 102)

A solution of tert-Butyl (5S,5aS,6S,9R)-2-(3-(bis(4-methoxybenzyl)amino)-6-chloro-2-fluoro-5-methylphenyl)-1-fluoro-12-(((6S,8aS)-hexahydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate and tert-Butyl (5S,5aS,6S,9R)-2-(3-(bis(4-methoxybenzyl)amino)-4-chloro-2-fluoro-5-methylphenyl)-1-fluoro-12-(((6S,8aS)-hexahydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate mixture (78.9 mg, 0.0827 mmol) in TFA (3.5 mL) was stirred at 50° C. for 4 h. The solution was concentrated under vacuum. The crude product was purified by Prep-HPLC with the following conditions: (Column: XBridge Prep OBD C18 Column, 30*150 mm, 5 μm; Mobile Phase A: Water(10 mmol/L NH$_4$HCO$_3$), Mobile Phase B: ACN; Flow rate: 60 mL/min; Gradient: 17% B to 42% B in 9 min, 42% B; Wave Length: 254/220 nm; R$_{T1}$(min): 8.9) to yield 14.5 mg (28.5% yield) of 101 and 1.0 mg (1.7% yield) of 101 as a white solid.

101: LC-MS: (ESI, m/z): [M+H]$^+$=614. $^1$H NMR (400 MHz, DMSO-d$_6$, ppm) δ 6.84 (d, J=9.4 Hz, 1H), 5.37 (d, J=8.7 Hz, 2H), 5.20-5.01 (m, 1H), 4.67-4.52 (m, 1H), 4.50-4.33 (m, 1H), 4.24-4.08 (m, 1H), 4.03-3.91 (m, 1H), 3.70-3.39 (m, 6H), 3.15 (t, J=10.3 Hz, 1H), 3.08-2.92 (m, 2H), 2.92-2.78 (m, 2H), 2.24 (d, J=8.6 Hz, 3H), 2.16-1.99 (m, 1H), 1.91-1.50 (m, 6H), 1.45 (d, J=6.3 Hz, 3H), 1.38-1.26 (m, 1H).
102: LC-MS: (ESI, m/z): [M+H]$^+$=614. $^1$H NMR (400 MHz, DMSO-d$_6$, ppm) δ 6.70 (d, J=6.9 Hz, 1H), 5.49 (s, 2H), 5.17-5.03 (m, 1H), 4.68-4.49 (m, 1H), 4.48-4.37 (m, 1H), 4.22-4.07 (m, 1H), 4.03-3.92 (m, 1H), 3.68-3.41 (m, 6H), 3.15 (t, J=10.3 Hz, 1H), 3.09-2.93 (m, 2H), 2.93-2.80 (m, 2H), 2.30 (s, 3H), 2.17-1.97 (m, 1H), 1.90-1.52 (m, 6H), 1.46 (d, J=6.4 Hz, 3H), 1.39-1.26 (m, 1H).
Example 103: Compound 103
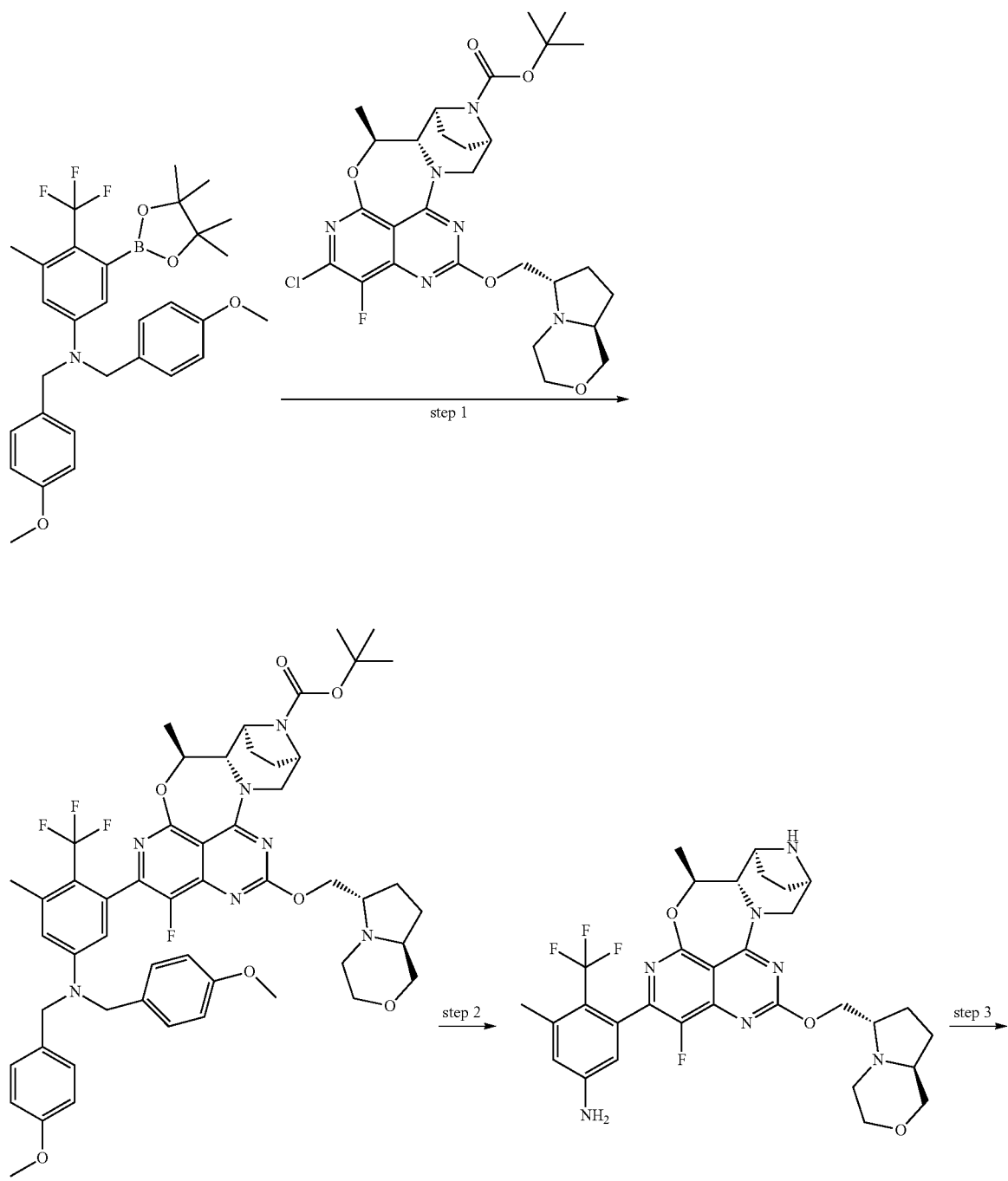

-continued

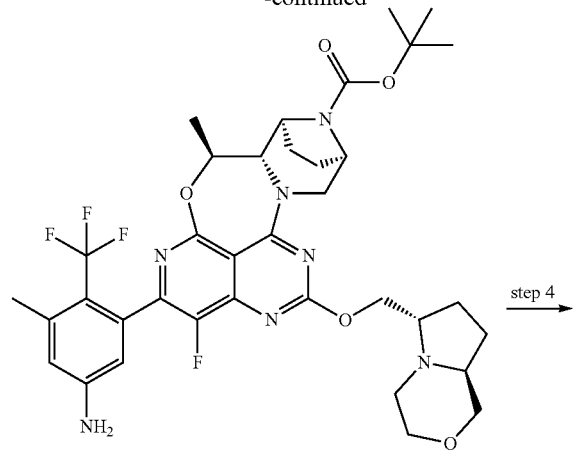

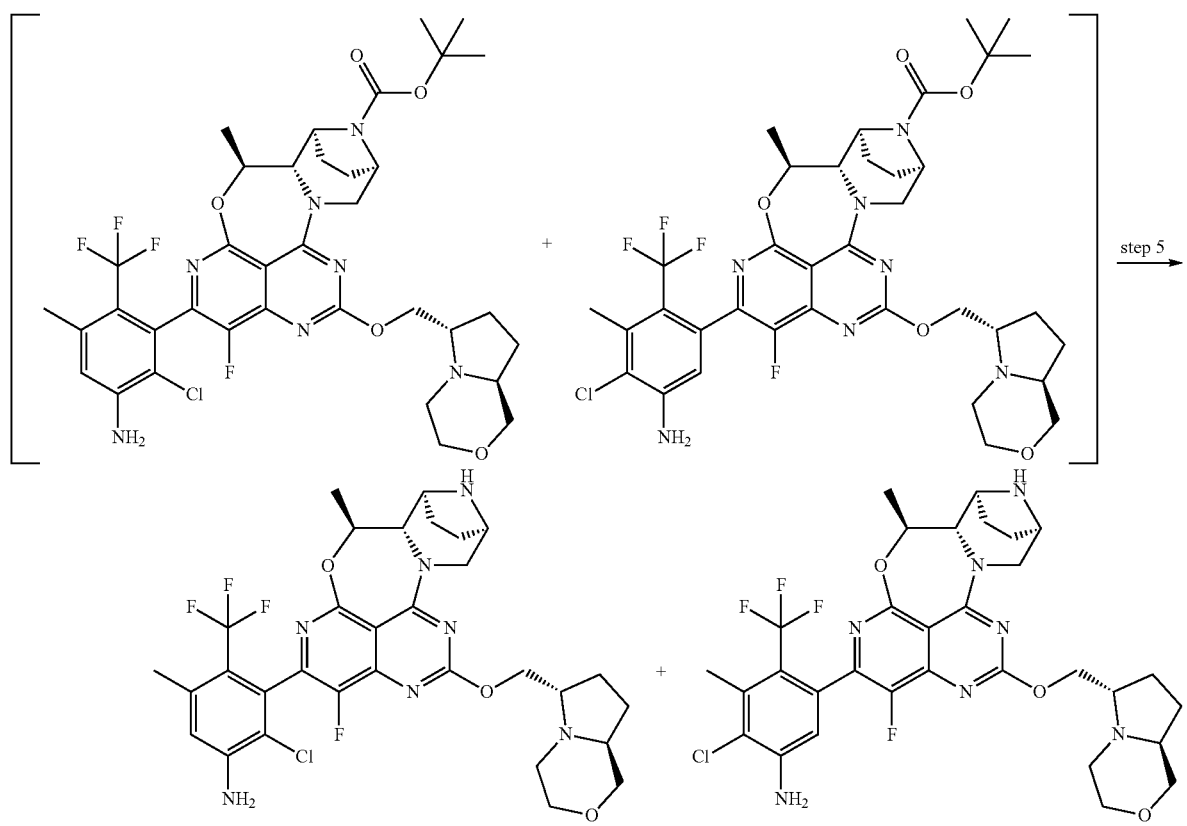

Step 1: tert-Butyl (5S,5aS,6S,9R)-2-(5-(bis(4-methoxybenzyl)amino)-3-methyl-2-(trifluoromethyl)phenyl)-1-fluoro-12-(((6S,8aS)-hexahydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate Under nitrogen, a mixture of N,N-bis(4-methoxybenzyl)-3-methyl-S-(4,4,5,5-tetramethyl-1,3,2-dioxaborolan-2-yl)-4-(trifluoromethyl)aniline (90.0 mg, 0.170 mmol), tert-butyl (5S,5aS,6S,9R)-2-chloro-1-fluoro-12-(((6S,8aS)-hexa- hydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (39.3 mg, 0.0700 mmol), cataCXium A Pd G3 (9.70 mg, 0.0100 mmol) and K$_3$PO$_4$ (70.6 mg, 0.330 mmol) in tetrahydrofuran (1 mL) and water (0.2 mL) was stirred at 60° C. for 1 hour. The resulting solution was extracted with ethyl acetate. The combined organic layers were dried over anhydrous sodium sulfate and concentrated under vacuum. The residue was purified by flash chromatography on silica gel (gradient: 0-20% ethyl acetate in petroleum ether) to afford 70.5 mg (42.8% yield) of the title compound as a yellow oil. LC-MS: (ESI, m/z): [M+H]$^+$=970.

Step 2: 3-((5S,5aS,6S,9R)-1-Fluoro-12-(((6S,8aS)-hexahydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-5-methyl-4-(trifluoromethyl)aniline Under nitrogen, a solution of tert-butyl (5S,5aS,6S,9R)-2-(5-(bis(4-methoxybenzyl)amino)-3-methyl-2-(trifluoromethyl)phenyl)-1-fluoro-12-(((6S,8aS)-hexahydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (60.5 mg, 0.0600 mmol) in 2,2,2-trifluoroacetic acid (5 mL) was stirred at 50° C. for 3 hours. The solvent was concentrated under vacuum. The residue was neutralized by saturated NaHCO₃ aqueous solution and extracted with ethyl acetate. The combined organic layer was dried over anhydrous sodium sulfate and concentrated under vacuum. The residue was purified by reverse phase flash chromatography on a pre-packed C18 column (gradient: 0-100% CH₃CN in water (0.05% NH₄HCO₃)) to afford 33.5 mg (76.2% yield) of the title compound as a yellow solid. LC-MS: (ESI, m/z): [M+H]⁺=630.

Step 3: tert-Butyl (5S,5aS,6S,9R)-2-(5-amino-3-methyl-2-(trifluoromethyl)phenyl)-1-fluoro-12-(((6S,8aS)-hexahydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate A solution of 3-((5S,5aS,6S,9R)-1-fluoro-12-(((6S,8aS)-hexahydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-5-methyl-4-(trifluoromethyl)aniline (33.5 mg, 0.0500 mmol), Boc₂0 (13.9 mg, 0.0600 mmol) and DIPEA (13.7 mg, 0.110 mmol) in dichloromethane (1 mL) was stirred at room temperature for 1 hour. The solvent was concentrated under vacuum. The residue was purified by flash chromatography on silica gel (gradient: 0-10% methanol in dichloromethane) to afford 25.0 mg (64.4% yield) of the title compound as a yellow solid. LC-MS: (ESI, m/z): [M+H]⁺=730.

Step 4: tert-butyl (5S,5aS,6S,9R)-2-(3-amino-2-chloro-5-methyl-6-(trifluoromethyl)phenyl)-1-fluoro-12-(((6S,8aS)-hexahydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate & tert-butyl (5S,5aS,6S,9R)-2-(5-amino-4-chloro-3-methyl-2-(trifluoromethyl)phenyl)-1-fluoro-12-(((6S,8aS)-hexahydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate A solution of tert-butyl (5S,5aS,6S,9R)-2-(5-amino-3-methyl-2-(trifluoromethyl)phenyl)-1-fluoro-12-(((6S,8aS)-hexahydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (14.6 mg, 0.0200 mmol) and NCS (4.0 mg, 0.0300 mmol) in acetic acid (1 mL) was stirred at room temperature for 36 hours. The reaction was quenched with saturated Na₂S₂O₃ aqueous solution. The resulting solution was extracted with ethyl acetate. The combined organic layers were dried over anhydrous sodium sulfate and concentrated under vacuum. The residue was purified by flash chromatography on silica gel (gradient: 0-10% methanol in dichloromethane) to yield 12.9 mg (mixture, 85.6% yield) of the title compounds as a yellow solid. LC-MS: (ESI, m/z): [M+H]⁺=764.

Step 5: 2-Chloro-3-((5S,5aS,6S,9R)-1-fluoro-12-(((6S,8aS)-hexahydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-5-methyl-4-(trifluoromethyl)aniline & 2-chloro-5-((5S,5aS,6S,9R)-1-fluoro-12-(((6S,8aS)-hexahydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-3-methyl-4-(trifluoromethyl)aniline To a solution of tert-butyl (5S,5aS,6S,9R)-2-(3-amino-2-chloro-5-methyl-6-(trifluoromethyl)phenyl)-1-fluoro-12-(((6S,8aS)-hexahydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate and tert-butyl (5S,5aS,6S,9R)-2-(5-amino-4-chloro-3-methyl-2-(trifluoromethyl)phenyl)-1-fluoro-12-(((6S,8aS)-hexahydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (mixture, 12.9 mg, 0.0169 mmol) in dichloromethane (1 mL) was added 2,2,2-trifluoroacetic acid (0.2 mL). The resulting solution was stirred at room temperature for 1 hour. The solvent was concentrated under vacuum. The residue was neutralized by saturated NaHCO₃ aqueous solution and extracted with ethyl acetate. The combined organic layer was dried over anhydrous sodium sulfate and concentrated under vacuum. The crude product was purified by Prep-HPLC with the following conditions: Column: XBridge Prep OBD C18 Column, 30*150 mm, 5 μm; Mobile Phase A: Water (10 mmol/L NH₄HCO₃), Mobile Phase B: ACN; Flow rate: 60 mL/min; Gradient: 17% B to 42% B in 9 min, 42% B; Wave Length: 254/220 nm; RT1(min): 8.9; RT2(min): 9.0) to yield 1.2 mg (10.7% yield, the faster peak) of 103a and 1.2 mg (10.7% yield, the slower peak) of 103b as while solids.

103a: LC-MS: (ESI, m/z): [M+H]⁺=664. ¹H NMR (300 MHz, DMSO-d6, ppm,) δ 6.86 (s, 1H), 6.16 (d, J=9.9 Hz, 2H), 5.09 (d, J=12.4 Hz, 1H), 4.53 (t, J=6.2 Hz, 1H), 4.46-4.37 (m, 1H), 4.18-4.10 (m, 1H), 3.96 (d, J=8.7 Hz, 1H), 3.64-3.59 (m, 1H), 3.57-3.45 (m, 4H), 3.15 (t, J=10.3 Hz, 2H), 3.07-2.94 (m, 2H), 2.87 (d, J=12.5 Hz, 2H), 2.74 (s, 1H), 2.44-2.30 (m, 3H), 2.14-2.02 (m, 1H), 1.82-1.57 (m, 5H), 1.44 (d, J=6.3 Hz, 3H), 1.38-1.27 (m, 1H), 1.24 (s, 1H).

103b: LC-MS: (ESI, m/z): [M+H]⁺=664. ¹H NMR (300 MHz, DMSO-d6, ppm,) δ 6.68-6.53 (m, 1H), 6.22 (s, 2H), 5.09 (d, J=11.5 Hz, 1H), 4.58-4.48 (m, 1H), 4.45-4.35 (m, 1H), 4.18-4.09 (m, 1H), 3.96 (d, J=8.7 Hz, 1H), 3.64-3.44 (m, 5H), 3.20-3.09 (m, 2H), 3.07-2.95 (m, 2H), 2.89 (s, 2H), 2.46 (s, 3H), 2.08 (s, 1H), 1.78 (t, J=7.9 Hz, 2H), 1.62 (d, J=12.6 Hz, 3H), 1.44 (d, J=6.3 Hz, 3H), 1.37-1.29 (m, 1H), 1.24 (s, 1H).

Example 104: Compound 104

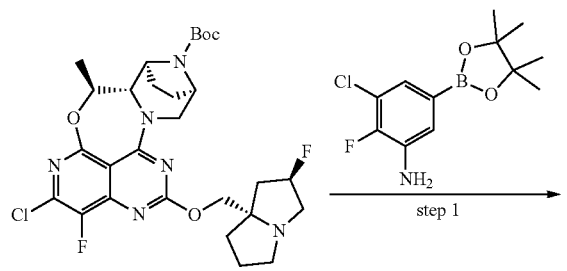

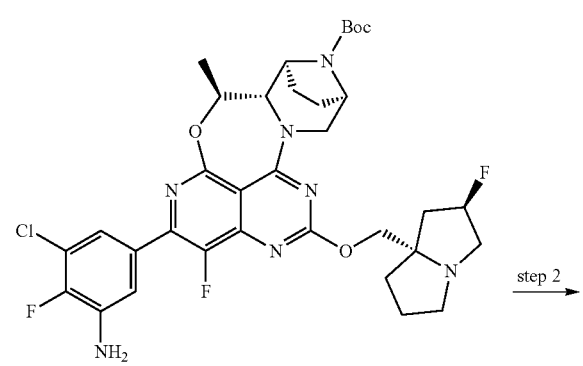

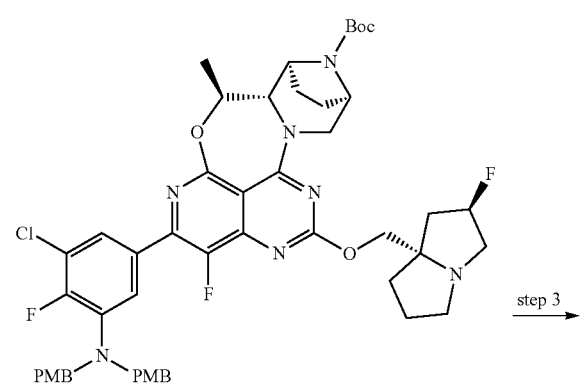

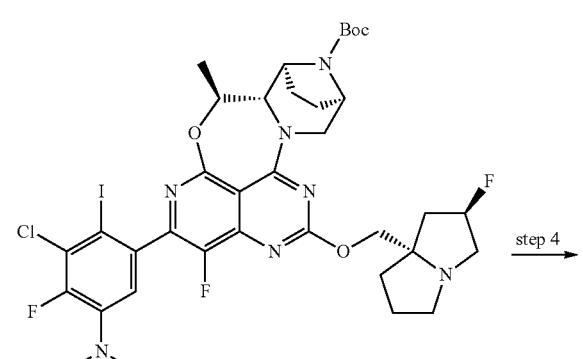

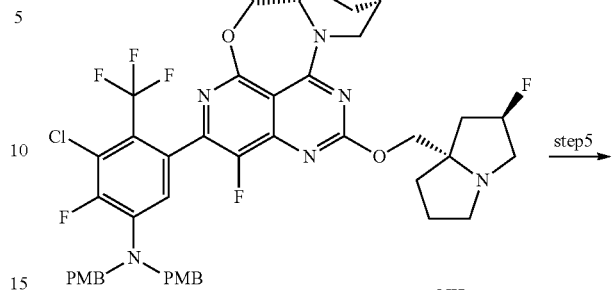

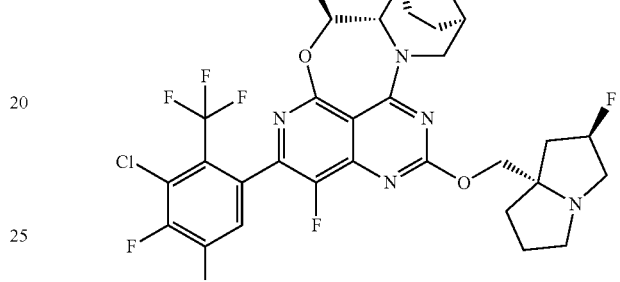

Step 1: tert-Butyl (5S,5aS,6S,9R)-2-(3-amino-5-chloro-4-fluorophenyl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate Under nitrogen, a stirred solution of 3-chloro-2-fluoro-5-(4,4,5,5-tetramethyl-1,3,2-dioxaborolan-2-yl)aniline (220 mg, 0.810 mmol, intermediate 76), tert-butyl (5S,5aS,6S,9R)-2-chloro-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (400 mg, 0.670 mmol), Catacxium A Pd G$_3$ (98.2 mg, 0.130 mmol) and aqueous K$_3$PO$_4$ (2.25 mL, 1.5 mol/L in water) in tetrahydrofuran (11.2 mL) was stirred at 60° C. overnight. The reaction system was cooled to room temperature, diluted with water and extracted with EtOAc. The combined organic layers were dried over anhydrous sodium sulfate and concentrated under vacuum. The residue was purified by flash chromatography on silica gel (gradient: 0-20% MeOH in CH$_2$Cl$_2$) to afford 250 mg (52.8% yield) of the title compound as a yellow solid. LC-MS: (ESI, m/z): [M+H]$^+$= 702.

Step 2: tert-Butyl (5S,5aS,6S,9R)-2-(3-(bis(4-methoxybenzyl)amino)-5-chloro-4-fluorophenyl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate Under nitrogen, to a stirred solution of tert-butyl (5S,5aS, 6S,9R)-2-(3-amino-5-chloro-4-fluorophenyl)-1-fluoro-12-(((2R,7aS)-2-fluorotetrahydro-1H-pyrrolizin-7a(5H)-yl) methoxy)-5-methyl-5a,6,7,8,9,10-hexahydro-5H-4-oxa-3, 10a,11,13,14-pentaaza-6,9-methanonaphtho[1,8-ab] heptalene-14-carboxylate (250 mg, 0.360 mmol) in N,N-dimethylformamide (5 mL) was added NaH (42.7 mg, 1.78 mmol, 60% suspension in mineral oil) at 0° C. The solution was stirred at 25° C. for 0.5 h, then PMB-Cl (126 mg, 0.800 mmol) was added and the resulting solution was stirred at 25° C. for 5 h. The resulting solution was quenched with aqueous NH$_4$Cl solution and extracted with EtOAc. The combined organic layers were washed with brine, dried over anhydrous sodium sulfate and concentrated under vacuum. The residue was purified by reverse phase flash chromatography on a pre-packed C18 column (gradient: 0-100% CH$_3$CN in water (0.05% TFA)) to afford of the title compound 170 mg (50.7% yield) as a white solid. LC-MS: (ESI, m/z): [M+H]$^+$=942.

Step 3: tert-Butyl (5S,5aS,6S,9R)-2-(5-(bis(4-methoxybenzyl)amino)-3-chloro-4-fluoro-2-iodophenyl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate Under nitrogen, to a stirred solution of tert-butyl (5S,5aS,6S,9R)-2-(3-(bis(4-methoxybenzyl)amino)-5-chloro-4-fluorophenyl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (170 mg, 0.180 mmol) in N,N-dimethylformamide (5 mL) was added I$_2$ (183 mg, 0.720 mmol) and AgOAc (120 mg, 0.720 mmol). The solution was stirred for 1 h at 25° C. The resulting solution was quenched with aqueous Na$_2$S$_2$O$_3$ solution and extracted with EtOAc. The combined organic layers were washed with saturated NaCl solution, dried over anhydrous sodium sulfate and concentrated under vacuum. The residue was purified by reverse phase flash chromatography on a pre-packed C18 column (gradient: 0-100% CH$_3$CN in water (0.05% TFA)) to afford of the title compound 88.0 mg (45.7% yield) as a white solid. LC-MS: (ESI, m/z): [M+H]$^+$= 1068.

Step 4: tert-Butyl (5S,5aS,6S,9R)-2-(5-(bis(4-methoxybenzyl)amino)-3-chloro-4-fluoro-2-(trifluoromethyl)phenyl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab] heptalene-14-carboxylate Under nitrogen, to a stirred solution of Cu(FSO$_2$CF$_2$COO)$_2$ (297 mg, 1.24 mmol), Cu (78.5 mg, 1.24 mmol) in N,N-dimethylformamide (2.5 mL) was added tert-butyl (5S,5aS,6S,9R)-2-(5-(bis(4-methoxybenzyl) amino)-3-chloro-4-fluoro-2-iodophenyl)-1-fluoro-12-(((2R, 7aS)-2-fluorotetrahydro-1H-pyrrolizin-7a(5H)-yl) methoxy)-5-methyl-5a,6,7,8,9,10-hexahydro-5H-4-oxa-3, 10a,11,13,14-pentaaza-6,9-methanonaphtho[1,8-ab] heptalene-14-carboxylate (88.0 mg, 0.0800 mmol) at 0° C. The solution was stirred for 1 h at 25° C. The resulting solution was diluted with H$_2$O and extracted with EtOAc. The combined organic layers were washed with saturated NaCl solution, dried over anhydrous sodium sulfate and concentrated under vacuum. The residue was purified by reverse phase flash chromatography on a pre-packed C18 column (gradient: 0-100% CH$_3$CN in water (0.05% TFA)) to afford of the title compound 32.0 mg (38.4% yield) as a white solid. LC-MS: (ESI, m/z): [M+H]$^+$=1010.

Step 5: 3-Chloro-2-fluoro-5-((5S,5aS,6S,9R)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-4-(trifluoromethyl)aniline (Compound 104)

Under nitrogen, a solution of tert-butyl (5S,5aS,6S,9R)-2-(5-(bis(4-methoxybenzyl)amino)-3-chloro-4-fluoro-2-(trifluoromethyl)phenyl)-1-fluoro-12-(((2R,7aS)-2-fluorotetrahydro-1H-pyrrolizin-7a(5H)-yl)methoxy)-5-methyl-5a, 6,7,8,9,10-hexahydro-5H-4-oxa-3,10a,11,13,14-pentaaza-6, 9-methanonaphtho[1,8-ab]heptalene-14-carboxylate (32.0 mg, 0.0300 mmol) in 2,2,2-trifluoroacetic acid (3 mL) was stirred for 1 h at 25° C. The mixture was concentrated under vacuum. The crude product was purified by Prep-HPLC with the following conditions: (Column: XBridge Prep OBD C18 Column, 30*150 mm, 5 µm; Mobile Phase A: Water (10 mmol/L NH$_4$HCO$_3$), Mobile Phase B: ACN; Flow rate: 60 mL/min; Gradient: 11% to 41% B in 7 min, 41% B; Wave Length: 254/220 nm; R$_{T1}$(min): 5.72) to afford 4.7 mg (22.1% yield) of the title compound as a white solid. LC-MS: (ESI, m/z): [M+H]$^+$=670. $^1$H NMR (300 MHz, DMSO-d6, ppm) δ 6.66 (d, J=39.8 Hz, 1H), 6.47 (s, 2H), 5.28 (d, J=54.3 Hz, 1H), 5.07 (d, J=12.7 Hz, 1H), 4.53 (m, 1H), 4.17-3.86 (m, 3H), 3.57 (s, 1H), 3.44 (s, 1H), 3.16-2.95 (m, 4H), 2.90-2.55 (m, 2H), 2.15 (d, J=4.9 Hz, 1H), 2.02 (d, J=13.5 Hz, 2H), 1.90-1.70 (m, 4H), 1.69-1.5 (m, 3H), 1.43 (d, J=6.3 Hz, 3H).

Example 105: Compound 105

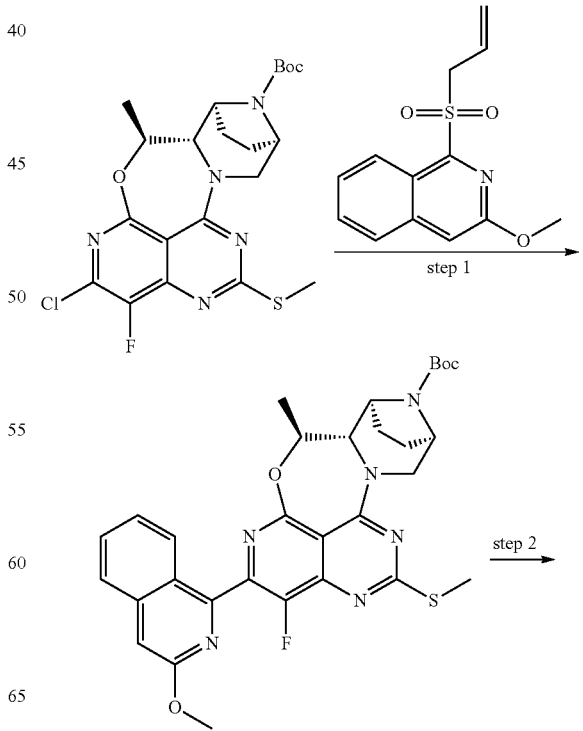

681

-continued

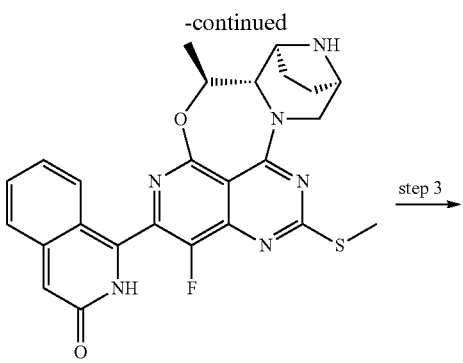

step 3

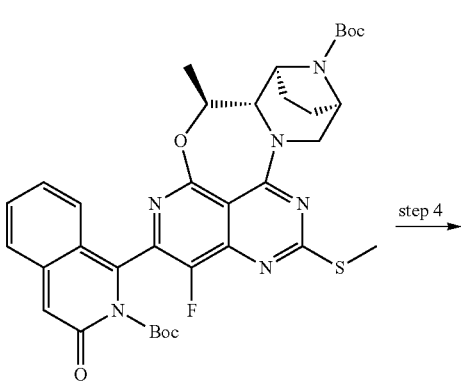

step 4

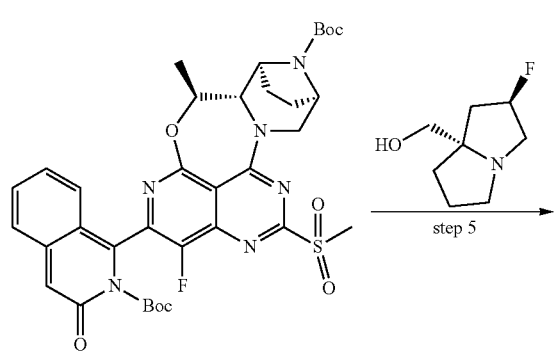

step 5

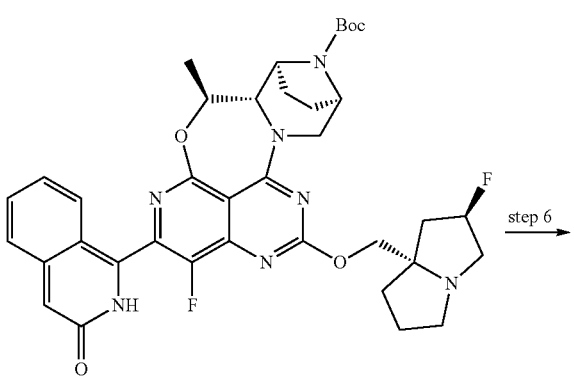

step 6

682

-continued

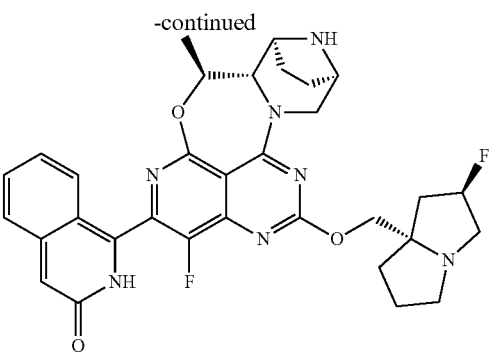

Step 1: tert-Butyl (5S,5aS,6S,9R)-1-fluoro-2-(3-methoxyisoquinolin-1-yl)-5-methyl-12-(methylthio)-5a,6,7,8,9,10-hexahydro-5H-4-oxa-3,10a,11,13,14-pentaaza-6,9-methanonaphtho[1,8-ab]heptalene-14-carboxylate Under nitrogen, a solution of 1-(allylsulfonyl)-3-methoxyisoquinoline (82.0 mg, 0.310 mmol, intermediate 77), tert-butyl (5S,5aS,6S,9R)-2-chloro-1-fluoro-5-methyl-12-(methylthio)-5a,6,7,8,9,10-hexahydro-5H-4-oxa-3,10a, 11,13,14-pentaaza-6,9-methanonaphtho[1,8-ab]heptalene-14-carboxylate (100 mg, 0.210 mmol), Pd(OAc)$_2$ (4.7 mg, 0.0200 mmol), P(t-Bu)$_2$Me·HBF$_4$ (10.3 mg, 0.0400 mmol), Cs$_2$CO$_3$ (135 mg, 0.410 mmol) in 1,4-dioxane (3 mL) was stirred at 120° C. overnight. The mixture was concentrated under vacuum. The residue was purified by flash chromatography on silica gel (gradient: 0-60% EtOAc in petroleum ether) to afford 58.0 mg (46.2% yield) of the title compound as a yellow solid. LC-MS: (ESI, m/z): [M+H]$^+$=605.

Step 2: 1-((5S,5aS,6S,9R)-1-Fluoro-5-methyl-12-(methylthio)-5a,6,7,8,9,10-hexahydro-5H-4-oxa-3,10a,11,13,14-pentaaza-6,9-methanonaphtho[1,8-ab]heptalen-2-yl)isoquinolin-3(2H)-one A stirred solution of tert-butyl (5S,5aS,6S,9R)-1-fluoro-2-(3-methoxyisoquinolin-1-yl)-5-methyl-12-(methylthio)-5a,6,7,8,9,10-hexahydro-5H-4-oxa-3,10a,11,13,14-pentaaza-6,9-methanonaphtho[1,8-ab]heptalene-14-carboxylate (200 mg, 0.332 mmol) in HBr/AcOH (8 mL, 36% in AcOH) was stirred overnight at 80° C. The mixture was concentrated under vacuum. The residue was purified by reverse phase flash chromatography on a pre-packed C18 column (gradient: 0-100% CH$_3$CN in water (0.05% TFA)) to yield 110 mg (67.9% yield) as a yellow solid. LC-MS: (ESI, m/z): [M+H]$^+$=491.

Step 3: tert-Butyl (5S,5aS,6S,9R)-2-(2-(tert-butoxycarbonyl)-3-oxo-2,3-dihydroisoquinolin-1-yl)-1-fluoro-5-methyl-12-(methylthio)-5a,6,7,8,9,10-hexahydro-5H-4-oxa-3,10a,11,13,14-pentaaza-6,9-methanonaphtho[1,8-ab]heptalene-14-carboxylate Under nitrogen, to a stirred solution of 1-((5S,5aS,6S,9R)-1-fluoro-5-methyl-12-(methylthio)-5a,6,7,8,9,10-hexahydro-5H-4-oxa-3,10a,11,13,14-pentaaza-6,9-methanonaphtho[1,8-ab]heptalen-2-yl)isoquinolin-3(2H)-one (90.0 mg, 0.183 mmol) in DMF (3 mL) was added DMAP (2.3 mg, 0.0180 mmol) and di-tert-butyl dicarbonate (80.1 mg, 0.365 mmol) at 0° C. The resulting solution was stirred at 25° C. for 5 h. The mixture was concentrated under vacuum.

The residue was purified by flash chromatography on silica gel (gradient: 0-40% EtOAc in petroleum ether) to afford 120 mg (87.4% yield) of the title compound as a white solid. LC-MS: (ESI, m/z): [M+H]$^+$=691.

Step 4: tert-Butyl (5S,5aS,6S,9R)-2-(2-(tert-butoxycarbonyl)-3-oxo-2,3-dihydroisoquinolin-1-yl)-1-fluoro-5-methyl-12-(methylsulfonyl)-5a,6,7,8,9,10-hexahydro-5H-4-oxa-3,10a,11,13,14-pentaaza-6,9-methanonaphtho[1,8-ab]heptalene-14-carboxylate To a solution of tert-butyl (5S,5aS,6S,9R)-2-(2-(tert-butoxycarbonyl)-3-oxo-2,3-dihydroisoquinolin-1-yl)-1-fluoro-5-methyl-12-(methylthio)-5a,6,7,8,9,10-hexahydro-5H-4-oxa-3,10a,11,13,14-pentaaza-6,9-methanonaphtho[1,8-ab]heptalene-14-carboxylate (100 mg, 0.169 mmol) in CH$_2$Cl$_2$ (8 mL) was added m-CPBA (87.6 mg, 0.507 mmol) in batches at 0° C. The resulting solution was stirred at 25° C. for 3 h. The reaction mixture was quenched with aqueous Na$_2$S$_2$O$_3$ solution and extracted with EtOAc. The combined organic layers were washed with brine and dried over anhydrous sodium sulfate. The solvent was concentrated under vacuum. The residue was purified by flash chromatography on silica gel (gradient: 0-60% EtOAc in petroleum ether) to afford 90 mg (85.4% yield) of the title compound as a yellow solid. LC-MS: (ESI, m/z): [M+H]$^+$=723.

Step 5: tert-Butyl (5S,5aS,6S,9R)-1-Fluoro-12-(((2R,7aS)-2-fluorotetrahydro-1H-pyrrolizin-7a(5H)-yl)methoxy)-5-methyl-2-(3-oxo-2,3-dihydroisoquinolin-1-yl)-5a,6,7,8,9,10-hexahydro-5H-4-oxa-3,10a,11,13,14-pentaaza-6,9-methanonaphtho[1,8-ab]heptalene-14-carboxylate Under nitrogen, to a solution of tert-butyl (5S,5aS,6S,9R)-2-(2-(tert-butoxycarbonyl)-3-oxo-2,3-dihydroisoquinolin-1-yl)-1-fluoro-5-methyl-12-(methylsulfonyl)-5a,6,7,8,9,10-hexahydro-5H-4-oxa-3,10a,11,13,14-pentaaza-6,9-methanonaphtho[1,8-ab]heptalene-14-carboxylate (75.0 mg, 0.104 mmol) in toluene (5 mL) were added t-BuONa (19.9 mg, 0.208 mmol) and ((2R,7aS)-2-fluorotetrahydro-1H-pyrrolizin-7a(5H)-yl)methanol (24.8 mg, 0.156 mmol) at 0° C. The resulting solution was stirred at 25° C. for 1 h. The solvent was concentrated under vacuum. The residue was purified by flash chromatography on silica gel (gradient: 0-60% MeOH in CH$_2$Cl$_2$) to afford 82.0 mg (95.2% yield) of the title compound as a yellow solid. LC-MS: (ESI, m/z): [M+H]$^+$=702.

Step 6: 1-((5S,5aS,6S,9R)-1-Fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)isoquinolin-3(2H)-one (Compound 105)

Under nitrogen, to a stirred solution of tert-butyl (5S,5aS,6S,9R)-1-Fluoro-12-(((2R,7aS)-2-fluorotetrahydro-1H-pyrrolizin-7a(5H)-yl)methoxy)-5-methyl-2-(3-oxo-2,3-dihydroisoquinolin-1-yl)-5a,6,7,8,9,10-hexahydro-5H-4-oxa-3,10a,11,13,14-pentaaza-6,9-methanonaphtho[1,8-ab]heptalene-14-carboxylate (82.0 mg, 0.117 mmol) in CH$_2$Cl$_2$ (3 mL) was added TFA (0.6 mL). The resulting solution was stirred at 25° C. for 1 h. The solvent was concentrated under vacuum. The crude product was purified by Prep-HPLC with the following conditions: (Column: XBridge Prep C18 OBD Column, 30*100 mm, 5 μm; Mobile Phase A: Water (10 mmol/L NH$_4$HCO$_3$), Mobile Phase B: ACN; Flow rate: 60 mL/min; Gradient: 30% B to 60% B in 10 min, 60% B; Wavelength: 254/220 nm; R$_{T1}$(min): 7.5) to yield 9.4 mg (0.120% yield) of the title compound as yellow solid. LC-MS: (ESI, m/z): [M+H]$^+$=602. $^1$H NMR (300 MHz, DMSO-d6, ppm) δ 11.5-10.5 (m, 1H), 7.92-7.78 (m, 1H), 7.62 (dd, J=8.3, 6.5 Hz, 2H), 7.39-7.21 (m, 1H), 7.08 (s, 1H), 5.45-5.03 (m, 2H), 4.66-4.49 (m, 1H), 4.13 (d, J=10.3 Hz, 1H), 4.09-3.86 (m, 2H), 3.59 (s, 1H), 3.46 (d, J=5.6 Hz, 1H), 3.19-2.96 (m, 4H), 2.92-2.79 (m, 1H), 2.16 (d, J=5.4 Hz, 1H), 2.13-1.97 (m, 2H), 1.97-1.75 (m, 4H), 1.75-1.54 (m, 3H), 1.45 (d, J=6.3 Hz, 3H).

Example 106: Compound 106

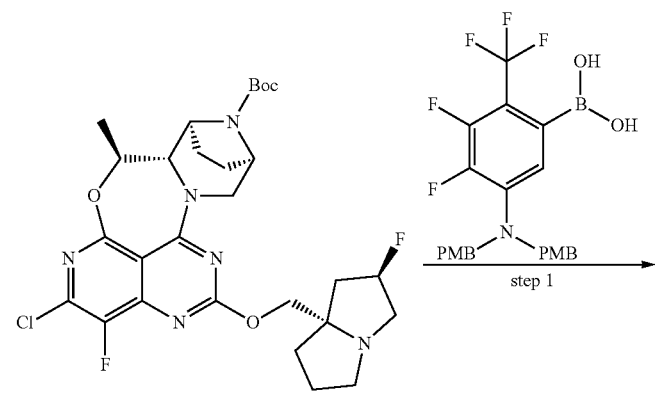

-continued

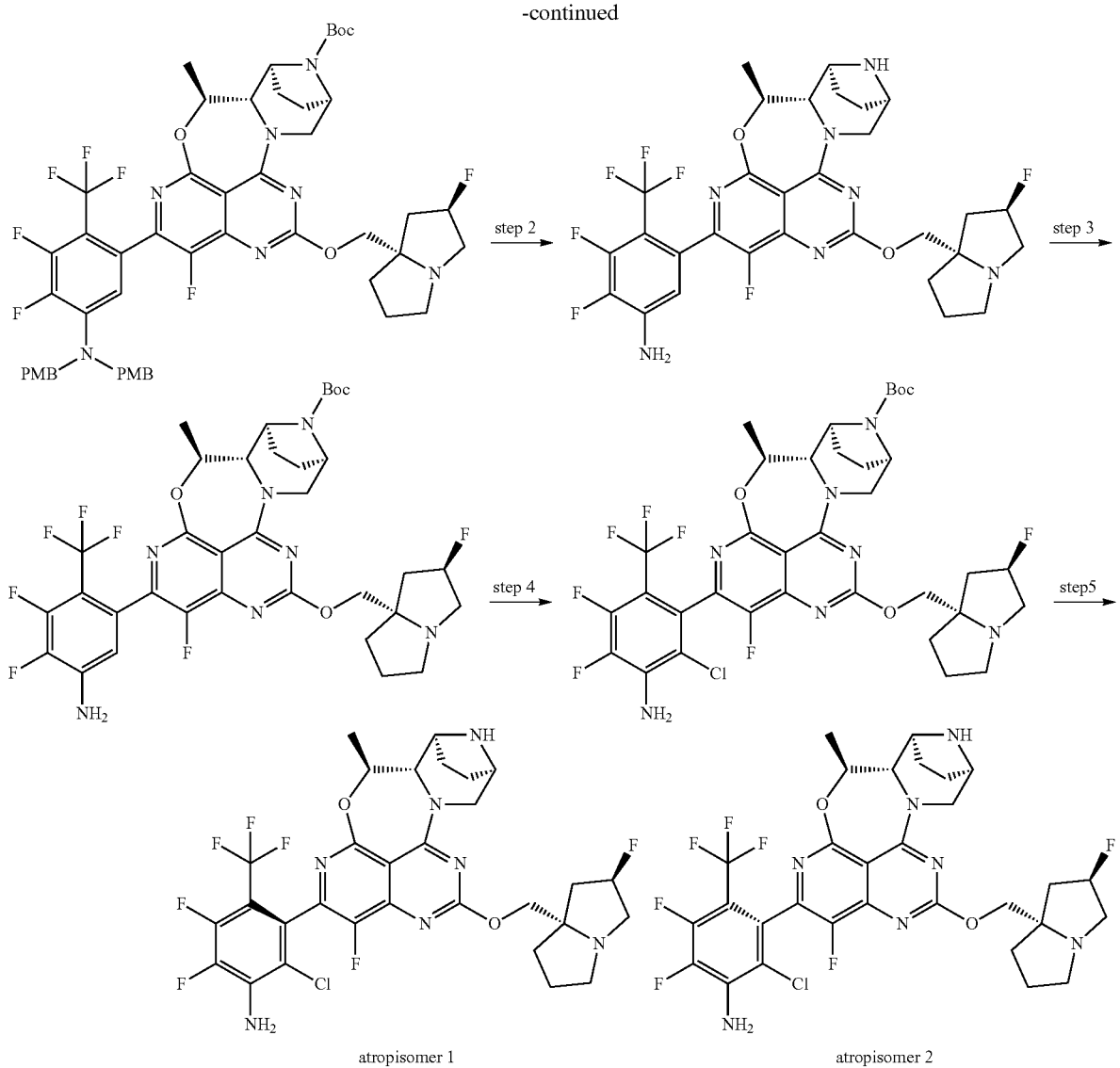

atropisomer 1                            atropisomer 2

Step 1: tert-Butyl (5S,5aS,6S,9R)-2-(5-(bis(4-methoxybenzyl)amino)-3,4-difluoro-2-(trifluoromethyl)phenyl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate Under nitrogen, a solution of tert-butyl (5S,5aS,6S,9R)-2-chloro-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (308 mg, 0.520 mmol), (5-(bis(4-methoxybenzyl)amino)-3,4-difluoro-2-(trifluoromethyl)phenyl)boronic acid (500 mg, 1.04 mmol), cataCXium A Pd $G_3$ (75.7 mg, 0.100 mmol) and $K_3PO_4$ (1.5 M in water) (1.1 mL, 1.65 mmol) in tetrahydrofuran (5 mL) was stirred at 60° C. for 2 h. The solution was concentrated under vacuum. The residual was purified by reverse phase flash chromatography on a pre-packed C18 column (gradient: 0-100% MeOH in water (0.05% $NH_4HCO_3$)) to afford the title compound (299 mg, 57.9% yield) as a white solid. LC-MS: (ESI, m/z): $[M+H]^+$=994.

Step 2: 2,3-Difluoro-5-((5S,5aS,6S,9R)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-4-(trifluoromethyl)aniline A solution of tert-butyl (5S,5aS,6S,9R)-2-(5-(bis(4-methoxybenzyl)amino)-3,4-difluoro-2-(trifluoromethyl)phenyl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (200 mg, 0.200 mmol) in 2,2,2-trifluoroacetic acid (2 mL) was stirred at 50° C. for 1.5 h. The solvent was evaporated under vacuum to afford the title compound (150 mg, crude) as a yellow solid. The crude product was used for the next step without further purification. LC-MS: (ESI, m/z): $[M+H]^+$= 654.

Step 3: tert-Butyl (5S,5aS,6S,9R)-2-(5-amino-3,4-difluoro-2-(trifluoromethyl)phenyl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate A solution of 2,3-difluoro-5-((5S,5aS,6S,9R)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-4-(trifluoromethyl)aniline (150 mg, 0.230 mmol), Boc$_2$O (75.0 mg, 0.340 mmol) and DIPEA (88.9 mg, 0.690 mmol) in dichloromethane (2 mL) was stirred at room temperature for 1 h. The solvent was evaporated under vacuum. The residue was purified by reverse phase flash chromatography on a pre-packed C18 column (gradient: 0-100% MeOH in water (0.05% NH$_4$HCO$_3$)) to afford the title compound (75.0 mg, 43.4% yield) as a white solid. LC-MS: (ESI, m/z): [M+H]$^+$=754.

Step 4: tert-Butyl (5S,5aS,6S,9R)-2-(3-amino-2-chloro-4,5-difluoro-6-(trifluoromethyl)phenyl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate A solution of tert-butyl (5S,5aS,6S,9R)-2-(5-amino-3,4-difluoro-2-(trifluoromethyl)phenyl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (50.0 mg, 0.0700 mmol) and NCS (53.0 mg, 0.400 mmol) in 1-methyl-2-pyrrolidinone (1 mL) was stirred at 80° C. for 2 h. The resulting mixture was purified by reverse phase flash chromatography on a pre-packed C18 column (gradient: 0-100% MeOH in water (0.05% NH$_4$HCO$_3$)) to afford the title compound (49.0 mg, 93.7% yield) as a yellow solid. LC-MS: (ESI, m/z): [M+H]$^+$= 788.

Step 5: 2-Chloro-5,6-difluoro-3-((5S,5aS,6S,9R)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-4-(trifluoromethyl)aniline

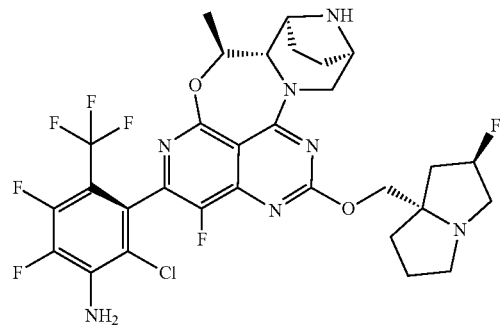

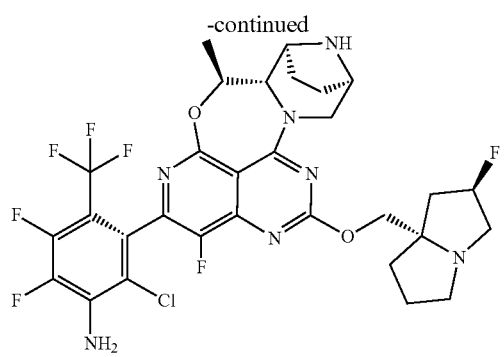

To a solution of tert-butyl (5S,5aS,6S,9R)-2-(3-amino-2-chloro-4,5-difluoro-6-(trifluoromethyl)phenyl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (49.0 mg, 0.0600 mmol) in dichloromethane (1.5 mL) was added TFA (0.5 mL). The solution was stirred at room temperature for 30 min. Solvent was evaporated under vacuum. The residue was purified by prep HPLC with the following conditions: (Column: XBridge BEH130 Prep C18 OBD Column, 19*150 mm, 5 μm; Mobile Phase A: Water(10 mmol/L NH$_4$HCO$_3$), Mobile Phase B: ACN; Flow rate: 60 mL/min; Gradient: 33% B to 50% B in 10 min; Wave Length: 254 nm; R$_{T1}$(min): 8.4, R$_{T2}$(min): 9.1; Number Of Runs: 2) to afford 106a (7.30 mg, 17.1% yield) (the faster peak, atropisomer 1) and 106b (5.00 mg, 11.7% yield) (the slower peak, atropisomer 2) as white solids. LC-MS: (ESI, m/z): [M+H]$^+$=688.

106a: $^1$H NMR (400 MHz, DMSO-d$_6$) δ 6.86 (s, 2H), 5.28 (d, J=54 Hz, 1H), 5.09-5.05 (m, 1H), 4.57-4.53 (m, 1H), 4.14-3.89 (m, 3H), 3.58 (d, J=5.6 Hz, 1H), 3.45 (d, J=6.2 Hz, 1H), 3.20-2.99 (m, 4H), 2.84-2.82 (m, 1H), 2.76 (s, 1H), 2.20-1.93 (m, 3H), 1.91-1.73 (m, 4H), 1.74-1.64 (m, 2H), 1.56-1.53 (m, 1H), 1.44 (d, J=6.3 Hz, 3H).

106b: $^1$H NMR (400 MHz, DMSO-d$_6$) δ 6.83 (s, 2H), 5.28 (d, J=54 Hz, 1H), 5.09-5.06 (m, 1H), 4.57-4.53 (m, 1H), 4.14-3.92 (m, 3H), 3.58-3.44 (m, 2H), 3.16-2.97 (m, 4H), 2.84-2.80 (m, 1H), 2.76 (s, 1H), 2.19-1.95 (m, 3H), 1.90-1.73 (m, 4H), 1.75-1.61 (m, 2H), 1.61-1.49 (m, 1H), 1.44 (d, J=6.3 Hz, 3H).

Example 107: Compound 107

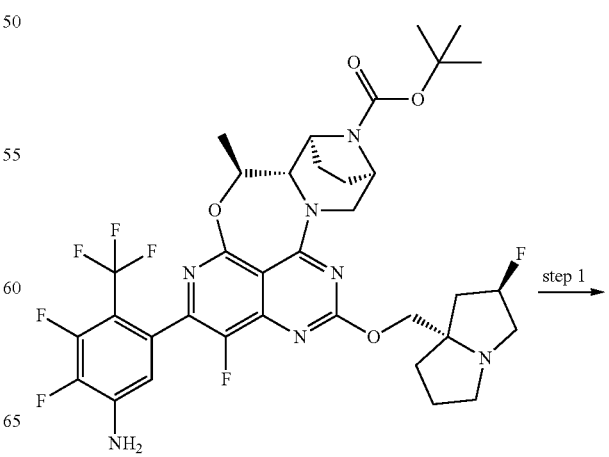

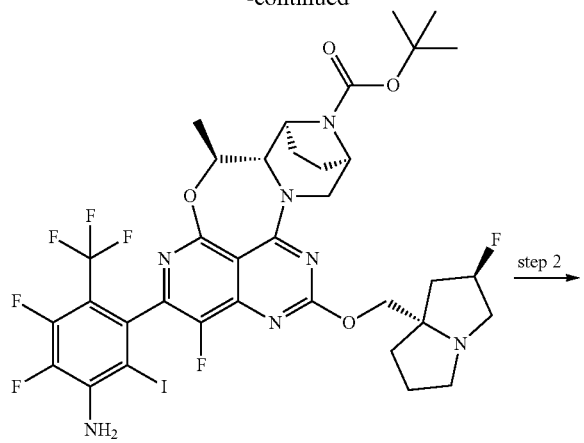

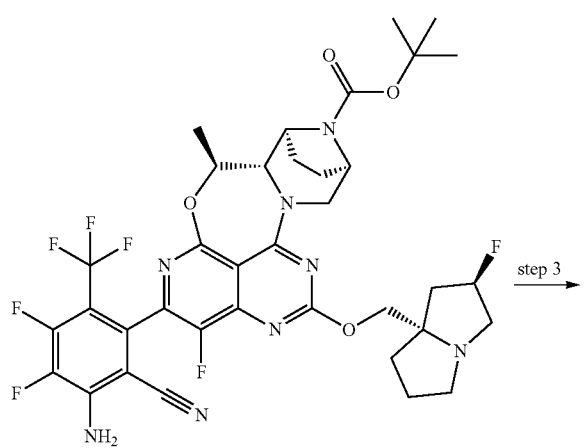

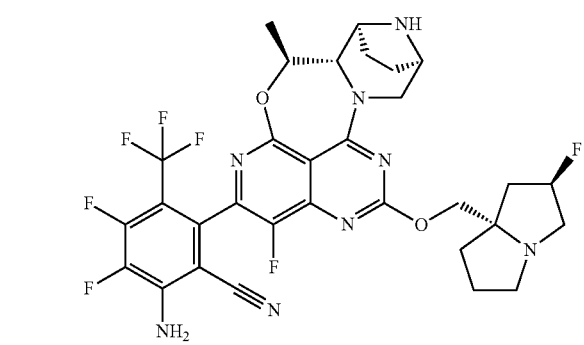

Step 1: tert-Butyl (5S,5aS,6S,9R)-2-(3-amino-4,5-difluoro-2-iodo-6-(trifluoromethyl)phenyl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate A solution of tert-butyl (5S,5aS,6S,9R)-2-(5-amino-3,4-difluoro-2-(trifluoromethyl)phenyl)-1-fluoro-12-(((2R,7aS)-2-fluorotetrahydro-1H-pyrrolizin-7a(5H)-yl) methoxy)-5-methyl-5a,6,7,8,9,10-hexahydro-5H-4-oxa-3,10a,11,13,14-pentaaza-6,9-methanonaphtho[1,8-ab]heptalene-14-carboxylate (150 mg, 0.200 mmol, Example 97, step 1) and NIS (537.8 mg, 2.39 mmol) in acetic acid (2 mL) was stirred at room temperature for overnight. The mixture was poured into water. The product was extracted with DCM, and the combined organic layers were washed with aqueous saturated aqueous sodium thiosulfate. The combined organic layers were dried over anhydrous sodium sulfate and concentrated under vacuum. The residue was purified by flash chromatography on silica gel (gradient: 0-10% MeOH in DCM) to yield the title compound (91.0 mg, 52% yield) as a yellow solid. LC-MS (ESI, m/z): $[M+H]^+=880$.

Step 2: tert-Butyl (5S,5aS,6S,9R)-2-(3-amino-2-cyano-4,5-difluoro-6-(trifluoromethyl)phenyl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate Under nitrogen, to a solution of tert-butyl (5S,5aS,6S,9R)-2-(3-amino-4,5-difluoro-2-iodo-6-(trifluoromethyl)phenyl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (80.0 mg, 0.0900 mmol) in 1-methyl-2-pyrrolidinone (1.5 mL) was added $Zn(CN)_2$ (46.4 mg, 0.400 mmol) and $Pd(PPh_3)_4$ (20.1 mg, 0.0200 mmol). The solution was reacted under microwave irradiation at 100° C. for 2 h. The resulting mixture was purified by reverse phase flash chromatography on a pre-packed C18 column (gradient: 0-100% ACN in water (0.05% $NH_4HCO_3$)) to yield the title compound (46.0 mg, 64.9% yield) as a white solid. LC-MS (ESI, m/z): $[M+H]^+=779$.

Step 3: 2-Amino-3,4-difluoro-6-((5S,5aS,6S,9R)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-5-(trifluoromethyl)benzonitrile To a solution of tert-butyl (5S,5aS,6S,9R)-2-(3-amino-2-cyano-4,5-difluoro-6-(trifluoromethyl)phenyl)-1-fluoro-12-(((2R,7aS)-2-fluorotetrahydro-1H-pyrrolizin-7a(5H)-yl) methoxy)-5-methyl-5a,6,7,8,9,10-hexahydro-5H-4-oxa-3,10a,11,13,14-pentaaza-6,9-methanonaphtho[1,8-ab] heptalene-14-carboxylate (46.0 mg, 0.0600 mmol) in dichloromethane (5 mL) was added TFA (1 mL). The solution was stirred at room temperature for 1 h. Solvent was evaporated under vacuum. The residue was purified by reverse phase flash chromatography on a pre-packed C18 column (gradient:0-100% ACN in water (0.05% $NH_4HCO_3$)) to yield the title compound (5.80 mg, 14.5% yield) as a white solid. LC-MS (ESI, m/z): $[M+H]^+=679$. $^1$H NMR (300 MHz, DMSO-$d_6$) δ 7.55 (s, 2H), 5.28 (d, J=54.3 Hz, 1H), 5.08 (d, J=12.9 Hz, 1H), 4.58 (s, 1H), 4.18-3.88 (m, 3H), 3.57 (s, 1H), 3.45 (s, 1H), 3.04 (d, J=24.9 Hz, 4H), 2.83 (s, 1H), 2.15 (s, 1H), 2.04 (s, 2H), 1.79-1.53 (m, 7H), 1.44 (s, 3H).

Example 108: Compound 108

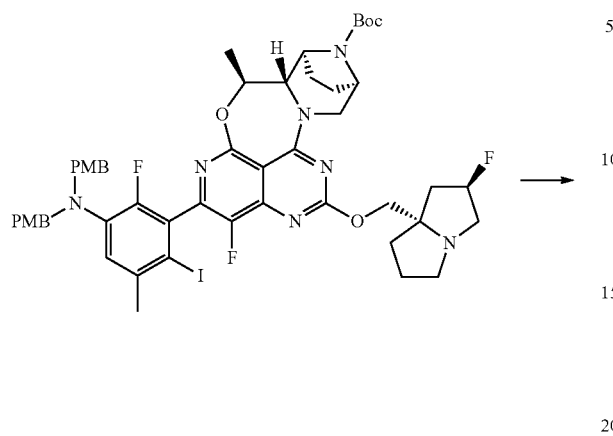

Example 109: tert-Butyl (5S,5aS,6S,9R)-2-(5-(bis(4-methoxybenzyl)amino)-4-fluoro-3-methyl-2-(trifluoromethyl)phenyl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate

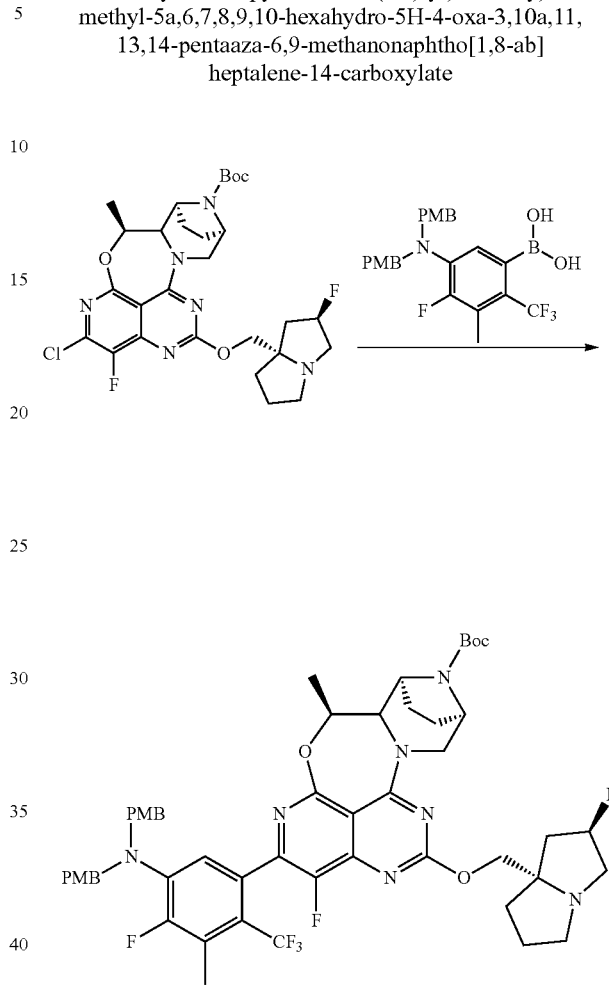

A solution of tert-butyl (5S,5aS,6S,9R)-2-(3-(bis(4-methoxybenzyl)amino)-2-fluoro-6-iodo-5-methylphenyl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (71.0 mg, 0.0700 mmol) in TFA (2.5 mL) was stirred at 50° C. for 4 hours. The reaction was concentrated under vacuum. The crude product was purified by Prep-HPLC with the following conditions (Column: XBridge Prep OBD C18 Column, 30*150 mm, 5 μm; Mobile Phase A: Water (10 mmol/L NH$_4$HCO$_3$), Mobile Phase B: ACN; Flow rate: 60 mL/min; Gradient: 27% B to 47% B in 10 min, 47% B; Wave Length: 254/220 nm; R$_{T1}$(min): 9.13) to yield 17.0 mg (35.5% yield) of the title compound as a white solid. LC-MS: (ESI, m/z): [M+H]$^+$= 623. $^1$H NMR (300 MHz, DMSO-d$_6$, ppm) δ 6.89 (d, J=8.8 Hz, 1H), 5.39 (d, J=11.3 Hz, 2H), 5.36 (s, 1H), 5.18-5.02 (m, 1H), 4.60-4.47 (m, 1H), 4.15-3.95 (m, 3H), 3.59 (s, 1H), 3.46 (s, 1H), 3.19-3.02 (m, 4H), 2.99-2.82 (m, 2H), 2.32 (d, J=2.7 Hz, 3H), 2.13 (s, 1H), 2.05 (d, J=16.1 Hz, 2H), 1.89-1.75 (m, 4H), 1.71-1.52 (m, 3H), 1.42 (d, J=6.3 Hz).

Under nitrogen, to a solution of (5-(bis(4-methoxybenzyl)amino)-4-fluoro-3-methyl-2-(trifluoromethyl)phenyl)boronic acid (130.5 mg, 0.274 mmol), tert-butyl (5S,5aS,6S,9R)-2-chloro-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (80.7 mg, 0.136 mmol) and cataCXium A Pd G3 (20.1 mg, 0.0276 mmol) in THF (8 mL) was added K$_3$PO$_4$ (1.6 mL, 1.5 M in water). The resulting solution was stirred for 4 hours at 60° C. The solution was cooled to room temperature, diluted with water and extracted with ethyl acetate. The combined organic layers were washed with brine, dried over anhydrous sodium sulfate and concentrated under vacuum. The residue was purified by reverse phase chromatography (gradient: 0-95% acetonitrile in water (0.05% NH$_4$HCO$_3$) to afford 118 mg (87.5% yield) of the title compound as a white solid. LC-MS: (ESI, m/z): [M+H]$^+$=990. $^1$H NMR (300 MHz, DMSO-d$_6$) δ 7.16 (d, J=8.1 Hz, 4H), 6.86 (d, J=8.1 Hz, 4H), 6.71 (d, J=29.2 Hz, 1H), 5.44-5.04 (m, 2H), 4.56 (s, 1H), 4.33 (d, J=19.3 Hz, 5H), 4.17-3.98 (m, 3H), 3.94 (s, 1H), 3.71 (s, 6H), -3.16-2.92 (m, 4H), 2.88-2.75 (m, 1H), 2.35 (s, 3H), 2.16-2.09 (m, 1H), 2.07-1.94 (m, 2H), 1.92-1.62 (m, 7H), 1.45 (s, 12H).

693

Example 110: Compound 110

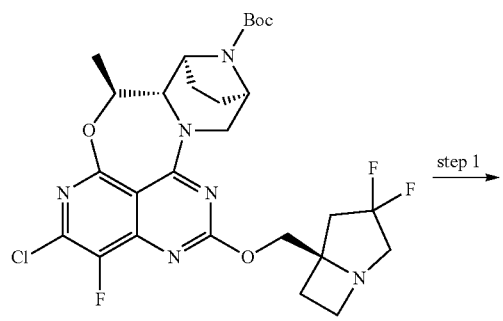

↓ step 1

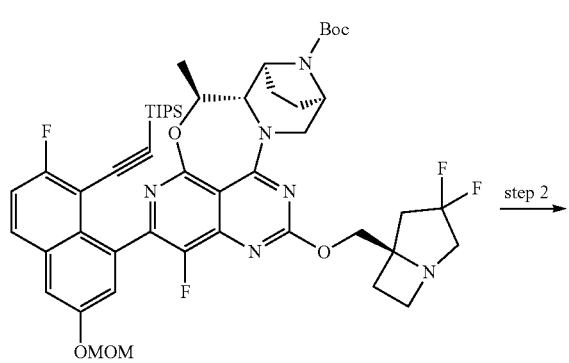

↓ step 2

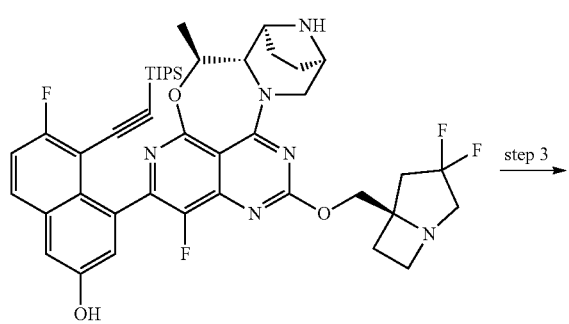

↓ step 3

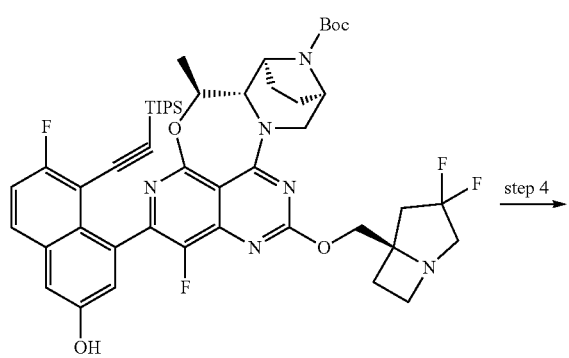

↓ step 4

694

-continued

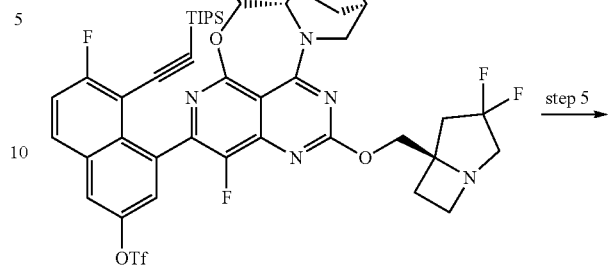

↓ step 5

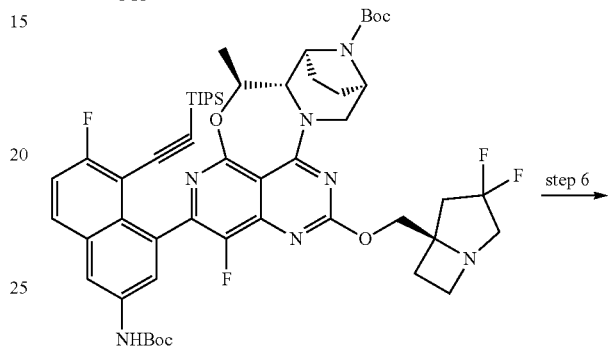

↓ step 6

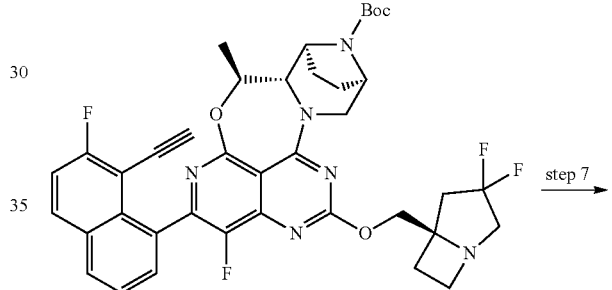

↓ step 7

Step 1: tert-Butyl (5S,5 aS,6S,9R)-12-(((R)-3,3-difluoro-1-azabicyclo[3.2.0]heptan-5-yl)methoxy)-1-fluoro-2-(7-fluoro-3-(methoxymethoxy)-8-((triisopropylsilyl)ethynyl)naphthalen-1-yl)-5-methyl-5a,6,7,8,9,10-hexahydro-5H-4-oxa-3,10a,11,13,14-pentaaza-6,9-methanonaphtho[1,8-ab]heptalene-14-carboxylate Under nitrogen, to a solution of tert-butyl (5S,5aS,6S, 9R)-2-chloro-12-(((R)-3,3-difluoro-1-azabicyclo[3.2.0]heptan-5-yl)methoxy)-1-fluoro-5-methyl-5a,6,7,8,9,10-hexahydro-5H-4-oxa-3,10a,11,13,14-pentaaza-6,9- methanonaphtho[1,8-ab]heptalene-14-carboxylate (100 mg, 0.168 mmol), ((2-fluoro-6-(methoxymethoxy)-8-(4,4,5,5-tetramethyl-1,3,2-dioxaborolan-2-yl)naphthalen-1-yl)ethynyl)triisopropylsilane (215 mg, 0.420 mmol) and cataCXium A Pd G3 (24.1 mg, 0.0331 mmol) in THF (2 mL) was added $K_3PO_4$ (0.4 mL, 1.5 M in $H_2O$) at room temperature. The resulting solution was stirred for 16 hours at 60° C. The solution was cooled to room temperature, diluted with water and extracted with ethyl acetate. The combined organic layers were washed with brine, dried over anhydrous sodium sulfate and concentrated under vacuum. The residue was purified by flash chromatography on silica gel (gradient: 0-10% MeOH in DCM) to afford the title compound 141 mg (88.9% yield) as a yellow solid. LC-MS: (ESI, m/z): $[M+H]^+=947$.

Step 2: 4-((5S,5aS,6S,9R)-12-(((R)-3,3-Difluoro-1-azabicyclo[3.2.0]heptan-5-yl)methoxy)-1-fluoro-5-methyl-5a,6,7,8,9,10-hexahydro-5H-4-oxa-3,10a,11,13,14-pentaaza-6,9-methanonaphtho[1,8-ab]heptalen-2-yl)-6-fluoro-5-((triisopropylsilyl)ethynyl)naphthalen-2-ol To a solution of tert-butyl (5S,5aS,6S,9R)-12-(((R)-3,3-difluoro-1-azabicyclo[3.2.0]heptan-5-yl)methoxy)-1-fluoro-2-(7-fluoro-3-(methoxymethoxy)-8-((triisopropylsilyl)ethynyl)naphthalen-1-yl)-5-methyl-5a,6,7,8,9,10-hexahydro-5H-4-oxa-3,10a,11,13,14-pentaaza-6,9-methanonaphtho[1,8-ab]heptalene-14-carboxylate (141 mg, 0.149 mmol) in DCM (3 mL) was added HCl in 1,4-dioxane (1 mL, 4 M), and the mixture was stirred at room temperature for 3 hours. The solvent was concentrated under vacuum. The residue was purified by reverse phase flash chromatography on a pre-packed C18 column (gradient: 0-80% acetonitrile in water (0.05% $NH_4HCO_3$) to afford the title compound 102 mg (85.9% yield) as a yellow solid. LC-MS: (ESI, m/z): $[M+H]^+=803$.

Step 3: tert-Butyl (5S,5aS,6S,9R)-12-(((R)-3,3-difluoro-1-azabicyclo[3.2.0]heptan-5-yl)methoxy)-1-fluoro-2-(7-fluoro-3-hydroxy-8-((triisopropylsilyl)ethynyl)naphthalen-1-yl)-5-methyl-5a,6,7,8,9,10-hexahydro-5H-4-oxa-3,10a,11,13,14-pentaaza-6,9-methanonaphtho[1,8-ab]heptalene-14-carboxylate To a solution of 4-((5S,5aS,6S,9R)-12-(((R)-3,3-difluoro-1-azabicyclo[3.2.0]heptan-5-yl)methoxy)-1-fluoro-5-methyl-5a,6,7,8,9,10-hexahydro-5H-4-oxa-3,10a,11,13,14-pentaaza-6,9-methanonaphtho[1,8-ab]heptalen-2-yl)-6-fluoro-5-((triisopropylsilyl)ethynyl)naphthalen-2-ol (102 mg, 0.125 mmol) and DIPEA (48.1 mg, 0.372 mmol) in DCM (2 mL) was added $(Boc)_2O$ (41.2 mg, 0.190 mmol) at 0° C., and the mixture was stirred at room temperature for 3 hours. The solution was diluted with water and extracted with DCM. The combined organic layers were washed with brine, dried over anhydrous sodium sulfate and concentrated under vacuum. The residue was purified by flash chromatography on silica gel (gradient: 0-70% EtOAc/petroleum ether) to afford the title compound 81.0 mg (72.0% yield) as a yellow solid. LC-MS: (ESI, m/z): $[M+H]^+=903$.

Step 4: tert-Butyl (5S,5aS,6S,9R)-12-(((R)-3,3-difluoro-1-azabicyclo[3.2.0]heptan-5-yl)methoxy)-1-fluoro-2-(7-fluoro-3-(((trifluoromethyl)sulfonyl)oxy)-8-((triisopropylsilyl)ethynyl)naphthalen-1-yl)-5-methyl-5a,6,7,8,9,10-hexahydro-5H-4-oxa-3,10a,11,13,14-pentaaza-6,9-methanonaphtho[1,8-ab]heptalene-14-carboxylate To a solution of tert-butyl (5S,5aS,6S,9R)-12-(((R)-3,3-difluoro-1-azabicyclo[3.2.0]heptan-5-yl)methoxy)-1-fluoro-2-(7-fluoro-3-hydroxy-8-((triisopropylsilyl)ethynyl)naphthalen-1-yl)-5-methyl-5a,6,7,8,9,10-hexahydro-5H-4-oxa-3,10a,11,13,14-pentaaza-6,9-methanonaphtho[1,8-ab]heptalene-14-carboxylate (50.2 mg, 0.0554 mmol) and DIPEA (42.6 mg, 0.222 mmol) in DCM (2 mL) was added $Tf_2O$ (15.6 mg, 0.0554 mmol) at −60° C. and the mixture was stirred at −60° C. for 1 hour. The solution was warmed to room temperature, diluted with water and extracted with ethyl acetate. The combined organic layers were washed with brine, dried over anhydrous sodium sulfate and concentrated under vacuum The residue was purified by flash chromatography on silica gel (gradient: 0-10% MeOH in DCM) to afford the title compound 23.4 mg (40.1% yield) as a yellow solid. LC-MS: (ESI, m/z): $[M+H]^+=1035$.

Step 5: tert-Butyl (5S,5aS,6S,9R)-2-(3-((tert-butoxycarbonyl)amino)-7-fluoro-8-((triisopropylsilyl)ethynyl)naphthalen-1-yl)-12-(((R)-3,3-difluoro-1-azabicyclo[3.2.0]heptan-5-yl)methoxy)-1-fluoro-5-methyl-5a,6,7,8,9,10-hexahydro-5H-4-oxa-3,10a,11,13,14-pentaaza-6,9-methanonaphtho[1,8-ab]heptalene-14-carboxylate Under nitrogen, a solution of tert-butyl (5S,5aS,6S,9R)-12-(((R)-3,3-difluoro-1-azabicyclo[3.2.0]heptan-5-yl)methoxy)-1-fluoro-2-(7-fluoro-3-(((trifluoromethyl)sulfonyl)oxy)-8-((triisopropylsilyl)ethynyl)naphthalen-1-yl)-5-methyl-5a,6,7,8,9,10-hexahydro-5H-4-oxa-3,10a,11,13,14-pentaaza-6,9-methanonaphtho[1,8-ab]heptalene-14-carboxylate (21.5 mg, 0.0208 mmol), $Pd_2(dba)_3$ (0.5 mg, 0.546 μmol), Xantphos (1.0 mg, 1.73 μmol), $Cs_2CO_3$ (20.3 mg, 0.0623 mmol) and $BocNH_2$ (3.7 mg, 0.0316 mmol) in 1,4-dioxane (2 mL) was stirred for 3 hours at 100° C. The solution was cooled to room temperature, diluted with water and extracted with ethyl acetate. The combined organic layers were washed with brine, dried over anhydrous sodium sulfate and concentrated under vacuum. The residue was purified by flash chromatography on silica gel (gradient: 0-10% MeOH in DCM) to afford 15.3 mg (73.5% yield) of the title compound as a yellow solid. LC-MS: (ESI, m/z): $[M+H]^+=1002$.

Step 6: tert-Butyl (5S,5aS,6S,9R)-2-(3-((tert-butoxycarbonyl)amino)-8-ethynyl-7-fluoronaphthalen-1-yl)-12-(((R)-3,3-difluoro-1-azabicyclo[3.2.0]heptan-5-yl)methoxy)-1-fluoro-5-methyl-5a,6,7,8,9,10-hexahydro-5H-4-oxa-3,10a,11,13,14-pentaaza-6,9-methanonaphtho[1,8-ab]heptalene-14-carboxylate To a solution of tert-butyl (5S,5aS,6S,9R)-2-(3-((tert-butoxycarbonyl)amino)-7-fluoro-8-((triisopropylsilyl)ethynyl)naphthalen-1-yl)-12-(((R)-3,3-difluoro-1-azabicyclo[3.2.0]heptan-5-yl)methoxy)-1-fluoro-5-methyl-5a,6,7,8,9,10-hexahydro-5H-4-oxa-3,10a,11,13,14-pentaaza-6,9-methanonaphtho[1,8-ab]heptalene-14-carboxylate (15.3 mg, 0.0153 mmol) in DMF (1.5 mL) was added CsF (11.3 mg, 0.0745 mmol). The solution was stirred at room temperature for 1 hour. The solution was diluted with ethyl acetate and washed with water. The separated organic layer was washed with brine, dried over anhydrous sodium sulfate and concentrated under vacuum to afford the title compound 11 mg (crude) as a yellow solid. LC-MS: (ESI, m/z): $[M+H]^+=846$.

Step 7: 4-((5S,5aS,6S,9R)-12-(((R)-3,3-Difluoro-1-azabicyclo[3.2.0]heptan-5-yl)methoxy)-1-fluoro-5-methyl-5a,6,7,8,9,10-hexahydro-5H-4-oxa-3,10a,11,13,14-pentaaza-6,9-methanonaphtho[1,8-ab]heptalen-2-yl)-5-ethynyl-6-fluoronaphthalen-2-amine (Compound 110)

To a solution of TFA (0.05 mL) in HFIP (1 mL) was added tert-butyl (5S,5aS,6S,9R)-2-(3-((tert-butoxycarbonyl)amino)-8-ethynyl-7-fluoronaphthalen-1-yl)-12-(((R)-3,3-difluoro-1-azabicyclo[3.2.0]heptan-5-yl)methoxy)-1-fluoro-5-methyl-5a,6,7,8,9,10-hexahydro-5H-4-oxa-3,10a,11,13,14-pentaaza-6,9-methanonaphtho[1,8-ab]heptalene-14-carboxylate (9.1 mg, 0.0106 mmol), and the mixture was stirred for 2 hours at room temperature. The reaction mixture was concentrated under vacuum. The crude product was purified by Prep-HPLC with the following conditions: (Column: XBridge Prep OBD C18 Column, 30×150 mm, 5 μm; Mobile Phase A: Water (10 mmol/L NH$_4$HCO$_3$), Mobile Phase B: ACN; Flow rate: 60 mL/min; Gradient: 23% B to 48% B in 9.5 min, 48% B; Wave Length: 254/220 nm; R$_{T1}$(min): 8.2) to afford the title compound 4.9 mg (69.6% yield) as a yellow solid. LC-MS: (ESI, m/z): [M+H]$^+$=646. $^1$H NMR (400 MHz, DMSO-d$_6$) δ 7.77-7.72 (m, 1H), 7.35-7.29 (m, 1H), 7.11-6.90 (m, 2H), 5.63 (d, J=12.1 Hz, 2H), 5.17-5.13 (m, 1H), 4.49-4.43 (m, 1H), 4.40-4.27 (m, 2H), 4.20-3.87 (m, 2H), 3.56 (d, J=15.7 Hz, 2H), 3.46 (t, J=6.2 Hz, 1H), 3.32-3.21 (m, 1H), 3.17-3.00 (m, 3H), 2.81 (s, 1H), 2.71-2.59 (m, 1H), 2.48-2.28 (m, 3H), 1.84 (t, J=10.1 Hz, 1H), 1.79-1.52 (m, 3H), 1.45 (t, J=6.9 Hz, 3H).

Example 111: Compound 111

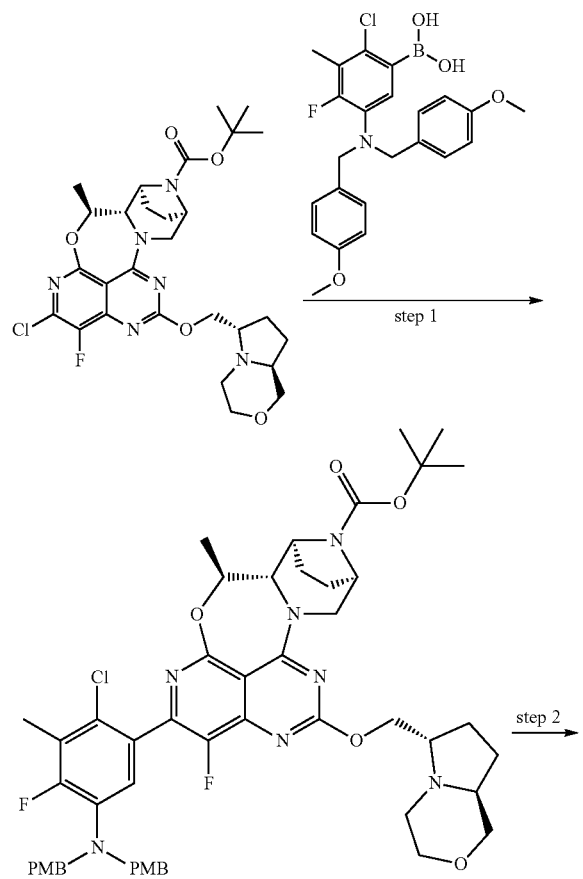

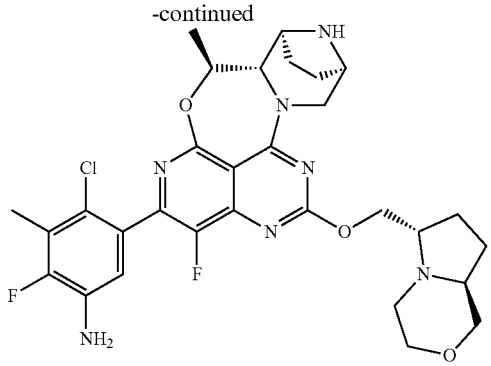

Step 1: tert-Butyl (5S,5aS,6S,9R)-2-(5-(bis(4-methoxybenzyl)amino)-2-chloro-4-fluoro-3-methylphenyl)-1-fluoro-12-(((6S,8aS)-hexahydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate Under nitrogen, a solution of tert-butyl (5S,5aS,6S,9R)-2-chloro-1-fluoro-12-(((6S,8aS)-hexahydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (150 mg, 0.250 mmol), (5-(bis(4-methoxybenzyl)amino)-2-chloro-4-fluoro-3-methylphenyl)boronic acid (224 mg, 0.500 mmol, Intermediate 69), cataCXium A Pd G$_3$ (36.8 mg, 0.0500 mmol) and K$_3$PO$_4$ (1.5 M in water) (0.5 mL, 0.750 mmol) in tetrahydrofuran (2.5 mL) was stirred at 60° C. for 1.5 h. The solvent was concentrated under vacuum. The crude product was purified by reverse phase flash chromatography on a pre-packed C18 column (gradient: 0-100% CH$_3$CN in water (0.05% NH$_4$HCO$_3$)) to afford 290 mg the title compound (60% purity). The crude product was repurified by flash chromatography on silica gel (gradient: 0-50% EtOAc in petroleum ether, 0-10% MeOH in DCM) to afford the title compound (180 mg, 74.3% yield) as a yellow solid. LC-MS: (ESI, m/z): [M+H]$^+$=954.

Step 2: 4-Chloro-2-fluoro-5-((5S,5aS,6S,9R)-1-fluoro-12-((((6S,8aS)-hexahydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-3-methylaniline ((Compound 111)

A solution of tert-butyl (5S,5aS,6S,9R)-2-(5-(bis(4-methoxybenzyl)amino)-2-chloro-4-fluoro-3-methylphenyl)-1-fluoro-12-((((6S,8aS)-hexahydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (175 mg, 0.180 mmol) in 2,2,2-trifluoroacetic acid (2 mL) was stirred at 50° C. for 1 h. The solvent was concentrated under vacuum. The crude product was purified by Prep-HPLC with the following conditions: (Column: XBridge BEH C18 OBD Prep Column, 19*250 mm, 5 μm; Mobile Phase A: Water(10 mmol/L NH$_4$HCO$_3$), Mobile Phase B: MeOH-HPLC; Flow rate: 25 mL/min; Gradient: 50% B to 80% B in 7 min, 80% B; Wave Length: 254/220 nm; R$_T$(min): 6.4) to yield the title compound (19.3 mg, 17.1% yield) as a white solid. LC-MS:

(ESI, m/z): [M+H]⁺=614. ¹H NMR (300 MHz, DMSO-d₆) δ 6.70 (d, J=9.3 Hz, 1H), 5.40 (s, 2H), 5.10-5.06 (m, 1H), 4.63-4.48 (m, 1H), 4.43-4.38 (m, 1H), 4.16-4.10 (m, 1H), 3.94 (d, J=8.7 Hz, 1H), 3.64-3.60 (m, 1H), 3.59-3.43 (m, 5H), 3.14 (t, J=10.4 Hz, 1H), 3.04-2.86 (m, 5H), 2.26 (d, J=2.4 Hz, 3H), 2.17-1.99 (m, 1H), 1.90-1.70 (m, 2H), 1.64-1.58 (m, 4H), 1.44 (d, J=6.3 Hz, 3H), 1.37-1.24 (m, 1H).

Each compound in the Table below was prepared following a similar experimental procedure (using appropriately substituted reagents) as described for Example 111.

| Cmpd. No. | ¹H NMR | MS (M + H)⁺ |
|---|---|---|
| 112 | ¹H NMR (300 MHz, DMSO-d6) δ 6.82 (s, 2H), 6.23 (s, 1H), 5.09 (d, J = 12.0 Hz, 1H), 4.61-4.48 (m, 1H), 4.41 (dd, J = 10.9, 5.3 Hz, 1H), 4.14 (dd, J = 10.9, 5.9 Hz, 1H), 3.96 (d, J = 8.7 Hz, 1H), 3.62 (dd, J = 10.9, 3.5 Hz, 1H), 3.53 (d, J = 12.8 Hz, 3H), 3.45 (s, 2H), 3.21-3.15 (m, 1H), 3.09-2.92 (m, 2H), 2.94-2.79 (m, 2H), 2.74 (s, 1H), 2.49-2.43 (m, 3H), 2.19-1.99 (m, 1H), 1.90-1.73 (m, 2H), 1.76-1.54 (m, 4H), 1.44 (d, J = 6.3 Hz, 3H), 1.35-1.20 (m, 1H). | 631 |
| 113 | ¹H NMR (300 MHz, DMSO-d6, ppm) δ 6.66 (d, J = 8.7 Hz, 1H), 5.37 (br, 2H), 5.12-5.08 (m, 1H), 4.54-4.52 (m, 1H), 4.44-4.42 (m, 1H), 4.16-4.13 (m, 1H), 3.97-3.94 (m, 1H), 3.77-3.43 (m, 8H), 3.19-2.86 (m, 5H), 2.24 (s, 3H), 2.17-2.08 (m, 1H), 1.83-1.55 (m, 6H), 1.44 (d, J = 6.3 Hz, 3H), 1.40-1.33 (m, 1H). | 662 |

Example 114: Compound 114

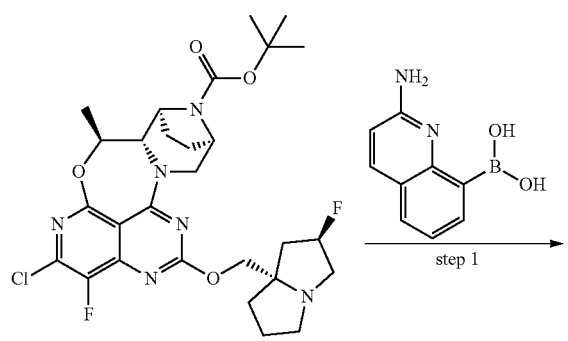

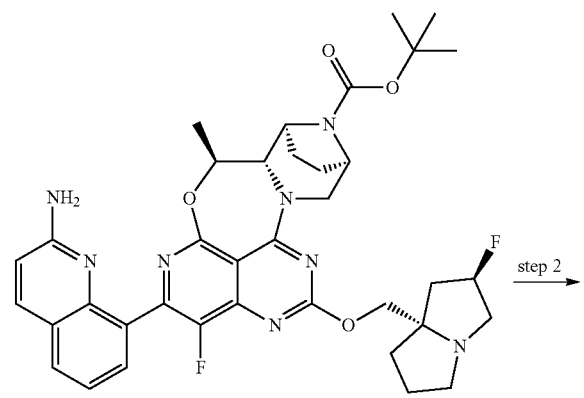

Step 1: tert-Butyl (5S,5aS,6S,9R)-2-(2-aminoquinolin-8-yl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate Under nitrogen, to a mixture of tert-butyl (5S,5aS,6S,9R)-2-chloro-12-((3,3-difluoro-1-azabicyclo[3.2.0]heptan-5-yl)methoxy)-1-fluoro-5-methyl-5a,6,7,8,9,10-hexahydro-5H-4-oxa-3,10a,11,13,14-pentaaza-6,9-methanonaphtho[1,8-ab]heptalene-14-carboxylate (62.7 mg, 0.110 mmol), (2-aminoquinolin-8-yl)boronic acid (40.0 mg, 0.210 mmol, intermediate 72) and cataCXium A Pd G3 (15.4 mg, 0.0200 mmol) in tetrahydrofuran (2.5 mL) was added a solution of K₃PO₄ (67.4 mg, 0.320 mmol) in water (0.5 mL) at room temperature. The solution was stirred at 60° C. for 5 hours. The resulting solution was diluted with water and extracted with ethyl acetate. The combined organic layers were dried over anhydrous sodium sulfate and concentrated under vacuum. The residue was purified by reverse phase flash chromatography on a pre-packed C18 column (gradient: 0-70% CH₃CN in water (0.05% NH₄HCO₃) to afford 21.0 mg (28.3% yield) of the title compound as a white solid. LC-MS: (ESI, m/z): [M+H]⁺=701.

Step 2: 8-((5S,5aS,6S,9R)-1-Fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)quinolin-2-amine (Compound 114)

To a solution of tert-butyl (5S,5aS,6S,9R)-2-(2-aminoquinolin-8-yl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (20.0 mg, 0.0500 mmol) in dichloromethane was added 2,2,2-trifluoroacetic acid (3 mL) at room temperature. The solution was stirred for 1 hour. The solvent was concentrated under vacuum. The crude product was purified by Prep-HPLC with the following conditions: (Column: XBridge Prep OBD C18 Column, 30*150 mm, 5 μm; Mobile Phase A: Water(10 mmol/L NH$_4$HCO$_3$), Mobile Phase B: ACN; Flow rate: 60 mL/min; Gradient: 20% B to 45% B in 7 min; Wave Length: 254 nm; RT1(min): 8.3; Number Of Runs: 2) to yield 4.4 mg (25.7% yield) of the title compound as a white solid. LC-MS: (ESI, m/z): [M+H]$^+$=601. $^1$H NMR (300 MHz, DMSO-d6, ppm) δ 7.96 (d, J=8.9 Hz, 1H), 7.78-7.70 (m, 1H), 7.51-7.43 (m, 1H), 7.25 (t, J=7.5 Hz, 1H), 6.78 (d, J=8.9 Hz, 1H), 6.32 (s, 2H), 5.29 (d, J=54.4 Hz, 1H), 5.18-5.06 (m, 1H), 4.58-4.45 (m, 1H), 4.13 (d, J=10.3 Hz, 1H), 4.06-3.93 (m, 2H), 3.59 (s, 1H), 3.46 (d, J=5.6 Hz, 1H), 3.15-2.98 (m, 4H), 2.84 (d, J=6.7 Hz, 1H), 2.21-2.12 (m, 1H), 2.10-1.97 (m, 2H), 1.89-1.59 (m, 7H), 1.46 (d, J=6.3 Hz, 3H), 1.24 (s, 1H).

Each compound in the Table below was prepared following a similar experimental procedure (using appropriately substituted reagents) as described for Example 114.

| Cmpd. No. | $^1$H NMR | MS (M + H)$^+$ |
|---|---|---|
| 115 | $^1$H NMR (300 MHz, DMSO-d6) δ 7.20 (d, J = 2.3 Hz, 1H), 6.75 (s, 1H), 6.52 (d, J = 2.5 Hz, 2H), 5.27 (d, J = 54.2 Hz, 1H), 5.07 (d, J = 12.1 Hz, 1H), 4.51 (dd, J = 8.7, 6.3 Hz, 1H), 4.09 (d, J = 10.3 Hz, 1H), 3.97 (dd, J = 14.4, 9.5 Hz, 2H), 3.56 (s, 1H), 3.51-3.40 (m, 1H), 3.18-2.89 (m, 4H), 2.82 (d, J = 6.4 Hz, 1H), 2.14 (d, J = 5.2 Hz, 1H), 2.01 (d, J = 12.7 Hz, 2H), 1.95-1.44 (m, 7H), 1.42 (d, J = 6.3 Hz, 3H). | 686 |
| 116 | $^1$H NMR (300 MHz, DMSO-d6, ppm) δ 7.79-7.76 (m, 1H), 7.60 (s, 2H), 7.31-7.26 (m, 1H), 7.13 (t, J = 7.7 Hz, 1H), 5.39-5.20 (m, 1H), 5.13-5.05 (m, 1H), 4.57-4.46 (m, 1H), 4.11 (d, J = 10.3 Hz, 1H), 4.02 (d, J = 10.3 Hz, 1H), 3.97-3.93 (m, 1H), 3.57 (d, J = 5.6 Hz, 1H), 3.46 (d, J = 5.9 Hz, 1H), 3.15-3.07 (m, 2H), 3.06-2.99 (m, 2H), 2.88-2.79 (m, 1H), 2.75 (s, 1H), 2.20-2.11 (m, 1H), 2.10-2.04 (m, 1H), 2.03-1.96 (m, 1H), 1.89-1.73 (m, 4H), 1.70-1.54 (m, 3H), 1.45 (d, J = 6.3 Hz, 3H). | 607 |
| 117 | $^1$H NMR (300 MHz, DMSO-d6, ppm) δ 7.19 (d, J = 8.6 Hz, 1H), 6.63-6.56 (m, 1H), 6.36-6.09 (m, 1H), 5.42-5.30 (m, 1H), 5.24-4.92 (m, 3H), 4.58-4.44 (m, 1H), 4.16-3.89 (m, 3H), 3.63-3.54 (m, 1H), 3.44 (d, J = 5.9 Hz, 1H), 3.19-2.95 (m, 4H), 2.92-2.71 (m, 1H), 2.24-2.12 (m, 1H), 2.11-1.94 (m, 2H), 1.93-1.51 (m, 6H), 1.43 (d, J = 6.3 Hz, 3H), 1.24 (s, 2H), 1.04 (s, 9H). | 606 |

Example 118: Compound 118

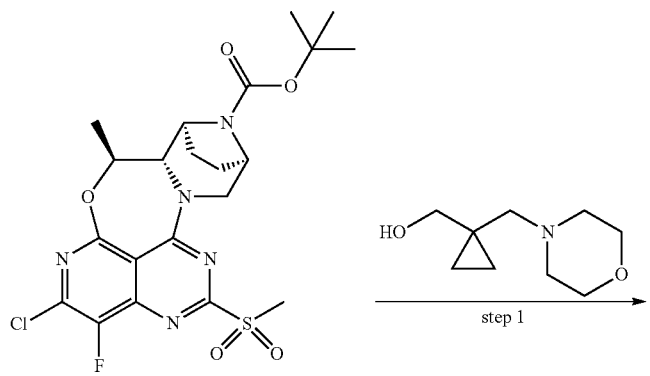

-continued
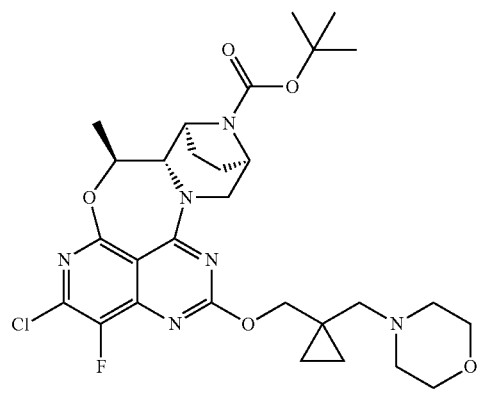
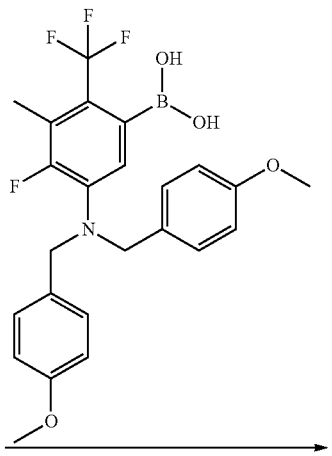
step 2
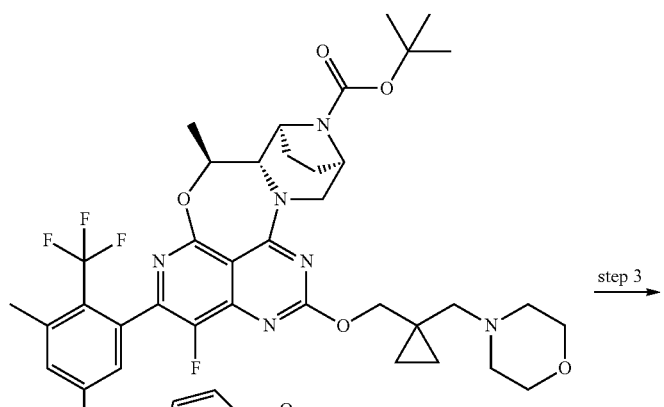
step 3
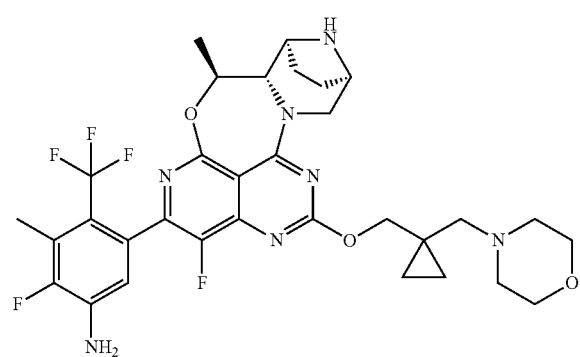

Step 1: tert-Butyl (5S,5aS,6S,9R)-2-chloro-1-fluoro-5-methyl-12-((1-(morpholinomethyl)cyclopropyl)methoxy)-5a,6,7,8,9,10-hexahydro-5H-4-oxa-3,10a,11,13,14-pentaaza-6,9-methanonaphtho[1,8-ab]heptalene-14-carboxylate To a solution of tert-butyl (5S,5aS,6S,9R)-2-chloro-1-fluoro-5-methyl-12-(methylsulfonyl)-5a,6,7,8,9,10-hexahydro-5H-4-oxa-3,10a,11,13,14-pentaaza-6,9-methanonaphtho[1,8-ab]heptalene-14-carboxylate (200 mg, 0.389 mmol) and (1-(morpholinomethyl)cyclopropyl)methanol (80.0 mg, 0.467 mmol) in toluene (10 mL) was added tert-butoxysodium (75.0 mg, 0.780 mmol) at 0° C. The solution was stirred at room temperature for 2 hours. The reaction mixture was diluted with water and extracted with ethyl acetate. The combined organic layer was dried over anhydrous sodium sulfate and concentrated under vacuum. The residue was purified by flash chromatography on silica gel (gradient: 0-15% methanol in dichloromethane) to afford 176 mg (74.7% yield) of the title compound as a yellow solid. LC-MS: (ESI, m/z): [M+H]⁺=605.

Step 2: tert-Butyl (5S,5aS,6S,9R)-2-(5-(bis(4-methoxybenzyl)amino)-4-fluoro-3-methyl-2-(trifluoromethyl)phenyl)-1-fluoro-5-methyl-12-((1-(morpholinomethyl)cyclopropyl)methoxy)-5a,6,7,8,9,10-hexahydro-5H-4-oxa-3,10a,11,13,14-pentaaza-6,9-methanonaphtho[1,8-ab]heptalene-14-carboxylate Under nitrogen, to a solution of tert-butyl (5S,5aS,6S,9R)-2-chloro-1-fluoro-5-methyl-12-((1-(morpholinomethyl)cyclopropyl)methoxy)-5a,6,7,8,9,10-hexahydro-5H-4-oxa-3,10a,11,13,14-pentaaza-6,9-methanonaphtho[1,8-ab]heptalene-14-carboxylate (136 mg, 0.225 mmol), (5-(bis(4-methoxybenzyl)amino)-4-fluoro-3-methyl-2-(trifluoromethyl)phenyl)boronic acid (214 mg, 0.449 mmol) and cataCXium A Pd G3 (32.8 mg, 0.0451 mmol) in tetrahydrofuran (4 mL) was added a solution of $K_3PO_4$ (143 mg, 0.674 mmol) in water (0.8 mL). This solution was stirred at 60° C. for 5 hours. The resulting solution was diluted with water and extracted with ethyl acetate. The combined organic layers were dried over anhydrous sodium sulfate and concentrated under vacuum. The residue was purified by flash chromatography on silica gel (gradient: 0-15% methanol in dichloromethane) to afford 186 mg (82.6% yield) of the title compound as a white solid. LC-MS: (ESI, m/z): [M+H]⁺=1002.

Step 3: 2-Fluoro-5-((5S,5aS,6S,9R)-1-fluoro-5-methyl-12-((1-(morpholinomethyl)cyclopropyl)methoxy)-5a,6,7,8,9,10-hexahydro-5H-4-oxa-3,10a,11,13,14-pentaaza-6,9-methanonaphtho[1,8-ab]heptalen-2-yl)-3-methyl-4-(trifluoromethyl)aniline (Compound 118)

A solution of tert-butyl (5S,5aS,6S,9R)-2-(5-(bis(4-methoxybenzyl)amino)-4-fluoro-3-methyl-2-(trifluoromethyl)phenyl)-1-fluoro-5-methyl-12-((1-(morpholinomethyl)cyclopropyl)methoxy)-5a,6,7,8,9,10-hexahydro-5H-4-oxa-3,10a,11,13,14-pentaaza-6,9-methanonaphtho[1,8-ab]heptalene-14-carboxylate (170 mg, 0.170 mmol) in 2,2,2-trifluoroacetic acid (5 mL) was stirred at 50° C. for 1 hour. The solvent was concentrated under vacuum. The crude product was purified by Prep-HPLC with the following conditions: (Column: YMC-Actus Triart C18 ExRS, 30*150 mm, 5 μm; Mobile Phase A: Water (10 mmol/L $NH_4HCO_3$), Mobile Phase B: ACN; Flow rate: 60 mL/min; Gradient: 17% B to 42% B in 9 min, 42% B; Wave Length: 254/220 nm; RT1(min): 8.5) to yield 47.7 mg (42.5% yield) of the title compound as a white solid. LC-MS: (ESI, m/z): [M+H]⁺=662. ¹H NMR (300 MHz, DMSO-d6, ppm) δ 6.64-6.40 (m, 1H), 6.00 (s, 2H), 5.11-5.04 (m, 1H), 4.58-4.43 (m, 1H), 4.34-4.18 (m, 2H), 3.93 (d, J=8.7 Hz, 1H), 3.63-3.39 (m, 6H), 3.00 (d, J=12.8 Hz, 1H), 2.75 (s, 1H), 2.44-32.20 (i, 9H), 1.80 (s, 1H), 1.57 (d, J=26.3 Hz, 3H), 1.42 (d, J=6.3 Hz, 3H), 0.63 (d, J=5.2 Hz, 2H), 0.41 (t, J=2.9 Hz, 2H).

Each compound in the Table below was prepared following a similar experimental procedure (using appropriately substituted reagents) as described for Example 118.

| Cmpd. No. | ¹H NMR | MS (M + H)⁺ |
| --- | --- | --- |
| 119 (isomer 1) | ¹H NMR (300 MHz, DMSO-d6, ppm) δ 6.67-6.45 (m, 1H), 6.02 (br, 2H), 5.12-5.07 (m, 1H), 4.55-4.50 (m, 1H), 4.42-4.37 (m, 1H), 4.31-4.27 (m, 1H), 3.98-3.95 (m, 1H), 3.59-3.57 (m, 1H), 3.48-3.46 (m, 1H), 3.06-3.02 (m, 1H), 2.83-2.78 (m, 1H), 2.32-2.28 (m, 4H), 2.27-2.19 (m, 2H), 2.08-1.53 (m, 11H), 1.45-1.39 (m, 4H). | 682 |
| 119 (isomer 2) | ¹H NMR (300 MHz, DMSO-d6, ppm) δ 6.68-6.45 (m, 1H), 6.02 (br, 2H), 5.11-5.06 (m, 1H), 4.55-4.50 (m, 1H), 4.40-4.35 (m, 1H), 4.16-4.10 (m, 1H), 3.98-3.94 (m, 1H), 3.56-3.53 (m, 1H), 3.45-3.40 (m, 2H), 3.31-3.23 (m, 1H), 3.10-3.00 (m, 2H), 2.86-2.78 (m, 2H), 2.32 (s, 3H), 2.16-1.45 (m, 12H), 1.43 (d, J = 6.3 Hz, 3H). | 682 |
| 120 | ¹H NMR (300 MHz, DMSO-d6, ppm) δ 6.67-6.46 (m, 1H), 6.01 (br, 2H), 5.27-5.21 (m, 1H), 5.11-5.07 (m, 1H), 4.55-4.39 (m, 2H), 4.21-4.16 (m, 1H), 3.97-3.94 (m, 1H), 3.75-3.18 (m, 6H), 3.05-3.01 (m, 1H), 2.32 (s, 3H), 2.16-1.94 (m, 4H), 1.82-1.46 (m, 6H), 1.43 (d, J = 6.3 Hz, 3H). | 662 |
| 121 (isomer 1) | ¹H NMR (400 MHz, DMSO-d6, ppm) δ 6.61-6.47 (m, 1H), 6.02 (br, 2H), 5.10-5.06 (m, 1H), 4.55-4.51 (m, 1H), 4.38-4.32 (m, 2H), 3.96-3.92 (m, 2H), 3.82-3.78 (m, 1H), 3.55-3.54 (m, 1H), 3.44-3.43 (m, 1H), 3.24-3.20 (m, 1H), 3.06-2.99 (m, 3H), 2.82-2.78 (m, 1H), 2.32 (s, 3H), 2.08-1.95 (m, 3H), 1.87-1.54 (m, 7H), 1.43 (d, J = 6.4 Hz, 3H), 1.28-1.23 (m, 1H). | 648 |
| 121 (isomer 2) | ¹H NMR (400 MHz, DMSO-d6, ppm) δ 6.65-6.44 (m, 1H), 6.02 (br, 2H), 5.10-5.07 (m, 1H), 4.84-4.79 (m, 1H), 4.55-4.51 (m, 1H), 4.36-4.32 (m, 1H), 4.05-3.94 (m, 2H), 3.74-3.71 (m, 1H), 3.60-3.54 (m, 2H), 3.44-3.43 (m, 1H), 3.03-2.77 (m, 4H), 2.37-2.32 (m, 4H), 2.21-2.06 (m, 2H), 1.87-1.55 (m, 7H), 1.43 (d, J = 6.4 Hz, 3H), 1.38-1.34 (m, 1H). | 648 |
| 122 | ¹H NMR (300 MHz, DMSO-d6, ppm) δ 6.68-6.40 (m, 1H), 6.01 (s, 2H), 5.36-4.99 (m, 2H), 4.61-4.44 (m, 1H), 4.09 (s, 2H), 3.95 (d, J = 8.7 Hz, 1H), 3.62-3.41 (m, 2H), 3.19 (s, 1H), 3.11-2.96 (m, 3H), 2.46-2.25 (m, 5H), 1.99-1.71 (m, 4H), 1.70-1.51 (m, 4H), 1.44 (d, J = 6.3 Hz, 3H), 1.12 (d, J = 6.7 Hz, 3H). | 664 |

| Cmpd. No. | $^1$H NMR | MS (M + H)$^+$ |
|---|---|---|
| 123 | $^1$H NMR (300 MHz, DMSO-d6, ppm) δ 6.74-6.37 (m, 1H), 6.02 (s, 2H), 5.19-5.00 (m, 1H), 4.62-4.46 (m, 1H), 4.41-4.28 (m, 1H), 4.23-4.10 (m, 1H), 3.96 (d, J = 8.8 Hz, 1H), 3.69-3.53 (m, 3H), 3.50-3.35 (m, 2H), 3.20-3.09 (m, 2H), 3.09-2.98 (m, 2H), 2.84 (s, 3H), 2.33 (s, 3H), 2.13-1.76 (m, 4H), 1.74-1.52 (m, 4H), 1.44 (d, J = 6.3 Hz, 3H). | 67 |
| 124 | $^1$H NMR (300 MHz, DMSO-d6, ppm) δ 6.67-6.39 (m, 1H), 6.02 (s, 2H), 5.09 (d, J = 13.0 Hz, 1H), 4.60-4.47 (m, 1H), 4.44-4.19 (m, 2H), 3.96 (d, J = 8.8 Hz, 1H), 3.58 (s, 1H), 3.50-3.41 (m, 3H), 3.40-3.35 (m, 1H), 3.31-3.27 (m, 1H), 3.27-3.14 (m, 2H), 3.03 (d, J = 13.0 Hz, 1H), 2.83 (s, 3H), 2.32 (s, 3H), 2.19-2.04 (m, 1H), 2.02-1.75 (m, 2H), 1.74-1.48 (m, 5H), 1.44 (d, J = 6.3 Hz, 3H) | 675 |
| 125 | $^1$H NMR (300 MHz, DMSO-d6) δ 6.54 (dd, J = 14.3, 2.2 Hz, 1H), 6.34 (d, J = 5.0 Hz, 3H), 5.07 (dd, J = 12.9, 2.5 Hz, 1H), 4.62-4.32 (m, 2H), 4.23-4.07 (m, 1H), 3.94 (d, J = 8.8 Hz, 1H), 3.70-3.39 (m, 4H), 3.34 (s, 1H), 3.28 (s, 1H), 3.01 (d, J = 12.7 Hz, 1H), 2.86-2.65 (m, 3H), 2.14-1.94 (m, 1H), 1.78 (d, J = 7.3 Hz, 2H), 1.73-1.46 (m, 4H), 1.42 (d, J = 6.3 Hz, 3H), 1.38-1.26 (m, 1H), 1.19 (d, J = 1.6 Hz, 3H), 1.06 (s, 3H). | 662 |
Example 126: Compound 126 (four isomers
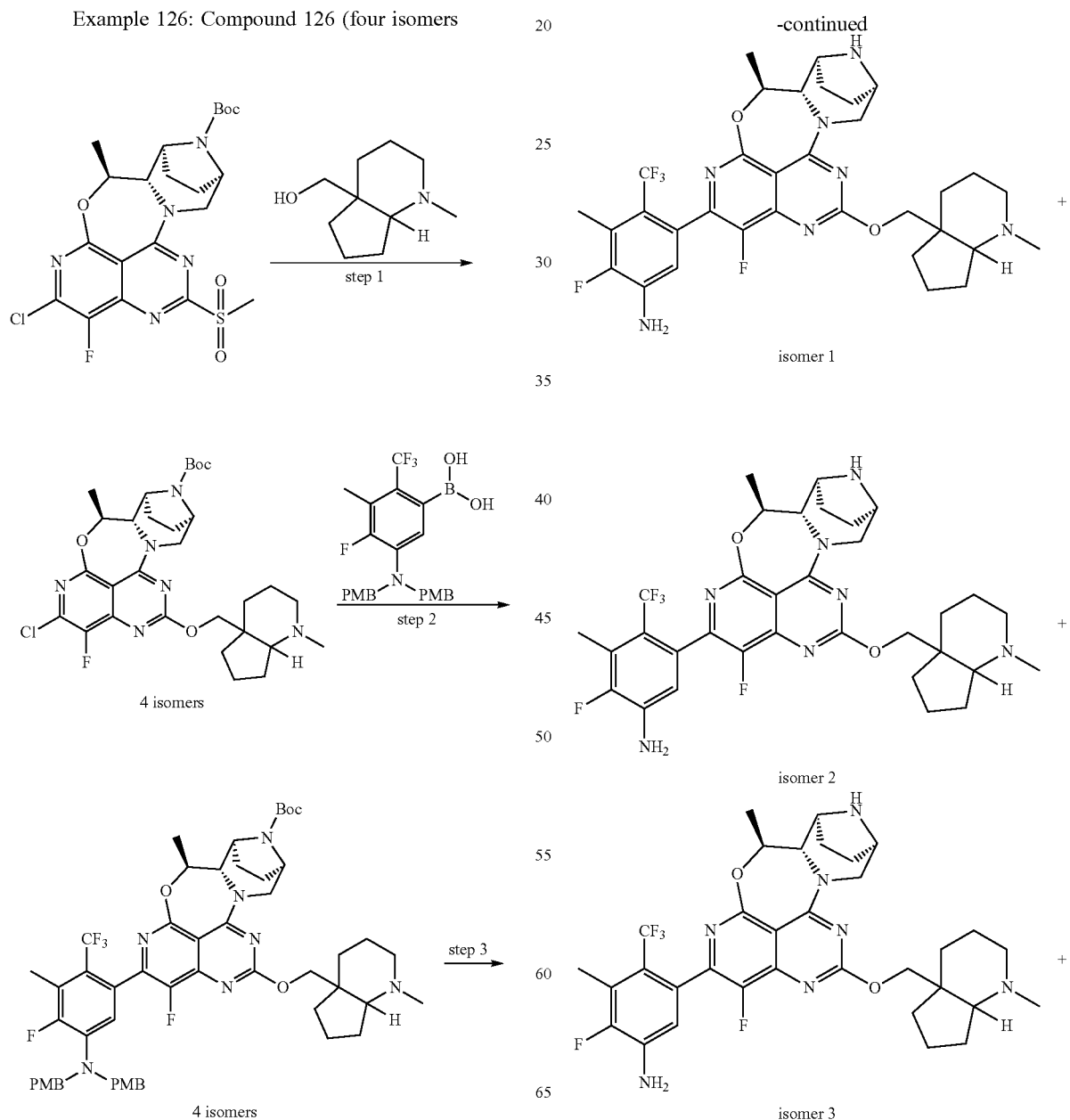

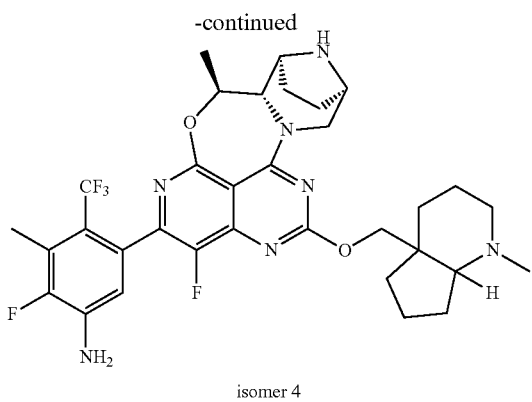

isomer 4

Step 1: tert-Butyl (5S,5aS,6S,9R)-2-chloro-1-fluoro-5-methyl-12-((1-methyloctahydro-4aH-cyclopenta[b]pyridin-4a-yl)methoxy)-5a,6,7,8,9,10-hexahydro-5H-4-oxa-3,10a,11,13,14-pentaaza-6,9-methanonaphtho[1,8-ab]heptalene-14-carboxylate (four isomers)

To a solution of (1-methyloctahydro-4aH-cyclopenta[b]pyridin-4a-y)methanol (0.60 g, 3.5 mmol, intermediate 95) in tetrahydrofuran (20 mL) was added NaH (60% dispersion in mineral oil, 425 mg, 10.6 mmol) at 0° C., and the mixture was stirred for 30 minutes at room temperature. Then tert-butyl (5S,5aS,6S,9R)-2-chloro-1-fluoro-5-methyl-12-(methylsulfonyl)-5a,6,7,8,9,10-hexahydro-5H-4-oxa-3,10a,11,13,14-pentaaza-6,9-methanonaphtho[1,8-ab]heptalene-14-carboxylate (907 mg, 1.77 mmol) was added at room temperature, and the mixture was stirred for 2 hours. The reaction was quenched with NH$_4$Cl solution. The resulting solution was extracted with ethyl acetate. The combined organic layers were dried over anhydrous sodium sulfate and concentrated under vacuum. The residue was purified by flash chromatography on silica gel (gradient: 0-15% methanol in dichloromethane) to afford two fractions as yellow solids. The faster peak (80 mg, mixture of isomer 1 and isomer 2). The slower peak (380 mg, mixture of isomer 3 and isomer 4). Isomer 1 and isomer 2 was separated by Chiral-Prep-HPLC with the following conditions (Column: CHI-LPAK ID, 2*25 cm, 5 μm; Mo-1e Phase A: Hex(0.1% 2 M NH$_3$-MeOH)-HPLC, Mobile Phase B: EtOH—HPLC; Flow rate: 20 mL/min; Gradient: isocratic 15; Wave Length: 220/254 nm; RT1(min): 13.88; RT2(min): 17.661; Injection Volume: 0.4 mL; Number Of Runs: 11) to afford isomer 1 (35 mg, the faster peak) and isomer 2 (30 mg, the slower peak) as white solids. Isomer 3 and isomer 4 was separated by Chiral-Prep-HPLC with the following conditions: (Column: CHI-LPAK ID, 2*25 cm, 5 M; Mo-1e Phase A: Hex(0.1% 2 M NH$_3$—MeOH)-HPLC, Mobile Phase B: EtOH—HPLC; Flow rate: 20 mL/min; Gradient: isocratic 10; Wave Length: 220/254 nm; RT1(min): 12.978; RT2(min): 15.578; Injection Volume: 0.8 mL; Number Of Runs: 16) to afford isomer 3 (150 mg, the faster peak) and isomer 4 (150 mg, the slower peak) as white solids. LC-MS: (ESI, m/z): [M+H]$^+$=603.

Step 2: tert-Butyl (5S,5aS,6S,9R)-2-(5-(bis(4-methoxybenzyl)amino)-4-fluoro-3-methyl-2-(trifluoromethyl)phenyl)-1-fluoro-5-methyl-12-((1-methyloctahydro-4aH-cyclopenta[b]pyridin-4a-yl)methoxy)-5a,6,7,8,9,10-hexahydro-5H-4-oxa-3,10a,11,13,14-pentaaza-6,9-methanonaphtho[1,8-ab]heptalene-14-carboxylate (four isomers)

Under nitrogen, a solution of tert-butyl (5S,5aS,6S,9R)-2-chloro-1-fluoro-5-methyl-12-((1-methyloctahydro-4aH-cyclopenta[b]pyridin-4a-yl)methoxy)-5a,6,7,8,9,10-hexahydro-5H-4-oxa-3,10a,11,13,14-pentaaza-6,9-methanonaphtho[1,8-ab]heptalene-14-carboxylate (35 mg, 0.058 mmol, isomer 1 of last step), (5-(bis(4-methoxybenzyl)amino)-4-fluoro-3-methyl-2-(trifluoromethyl)phenyl) boronic acid (55.4 mg, 0.116 mmol), K$_3$PO$_4$ (1.5 M aqueous solution, 0.2 mL, 0.300 mmol) and cataCXium A Pd G3 (8.50 mg, 0.0116 mmol) in tetrahydrofuran (1 mL) was stirred for 3 hours at 60° C. The reaction mixture was diluted with water and extracted with ethyl acetate. The combined organic layers were dried over anhydrous sodium sulfate and concentrated under vacuum. The residue was purified by flash chromatography on silica gel (gradient: 0-15% methanol in dichloromethane) to afford the title compound (31 mg, 53%, isomer 1) as a brown solid. LC-MS: (ESI, m/z): [M+H]$^+$=1000.

Analogous to method described as above, isomer 2 (42 mg), isomer 3 (185 mg) and isomer 4 (180 mg) were obtained as brown solids.

Step 3: 2-Fluoro-5-((5S,5aS,6S,9R)-1-fluoro-5-methyl-12-((1-methyloctahydro-4aH-cyclopenta[b]pyridin-4a-yl)methoxy)-5a,6,7,8,9,10-hexahydro-5H-4-oxa-3,10a,11,13,14-pentaaza-6,9-methanonaphtho[1,8-ab]heptalen-2-yl)-3-methyl-4-(trifluoromethyl)aniline (four isomers)

A solution of tert-butyl (5S,5aS,6S,9R)-2-(5-(bis(4-methoxybenzyl) amino)-4-fluoro-3-methyl-2-(trifluoromethyl) phenyl)-1-fluoro-5-methyl-12-((1-methyloctahydro-4aH-cyclopenta[b]pyridin-4a-yl) methoxy)-5a,6,7,8,9,10-hexahydro-5H-4-oxa-3,10a,11,13,14-pentaaza-6,9-methanonaphtho[1,8-ab]heptalene-14-carboxylate (31 mg, 0.031 mmol, isomer 1 of last step) in TFA (10 mL) was stirred for 1 hour at room temperature. The solvent was concentrated under vacuum. The residue was purified by Prep-HPLC (Column: XBridge Prep OBD C18 Column, 30*150 mm, 5 μm; Mobile Phase A: Water (10 mmol/L NH$_4$HCO$_3$), Mobile Phase B: ACN; Flow rate: 60 mL/min mL/min; Gradient: 43% B to 67% B in 9 min; Wave Length: 254 nm/220 nm nm; RT1(min): 8) to afford Isomer 1 (6.4 mg) as a white solid. LC-MS: (ESI, m/z): [M+H]$^+$=660.

Analogous to method described as above, Isomer 2, (5.9 mg), Isomer 3 (116 mg) and Isomer 4 (62.9 mg) were obtained as white solids. LC-MS: (ESI, m/z): [M+H]$^+$=660.

Isomer 1: $^1$H NMR (300 MHz, CD$_3$OD, ppm) δ 6.74-6.47 (m, 1H), 5.68-5.53 (m, 1H), 4.81-4.69 (m, 1H), 4.64 (d, J=11.1 Hz, 1H), 4.52 (d, J=11.0 Hz, 1H), 4.43-4.30 (m, 3H), 4.30-4.20 (m, 1H), 3.58-3.40 (m, 2H), 3.30-3.15 (m, 1H), 2.99-2.83 (m, 3H), 2.41 (s, 3H), 2.37-2.28 (m, 1H), 2.27-2.02 (m, 6H), 2.02-1.83 (m, 5H), 1.83-1.70 (m, 2H), 1.63 (d, J=6.3 Hz, 3H).

Isomer 2: $^1$H NMR (300 MHz, DMSO-d6, ppm) δ 6.71-6.38 (m, 1H), 6.02 (s, 2H), 5.08 (d, J=12.9, 2.5 Hz, 1H), 4.63-4.48 (m, 1H), 4.40 (d, J=10.7 Hz, 1H), 4.15 (d, J=10.7 Hz, 1H), 3.95 (d, J=8.6 Hz, 1H), 3.61-3.50 (m, 1H), 3.45 (d, J=5.7 Hz, 1H), 3.03 (d, J=12.8 Hz, 1H), 2.71-2.60 (m, 1H), 2.48-2.40 (m, 2H), 2.32 (s, 3H), 2.29-2.11 (s, 4H), 1.903-1.75 (m, 2H), 1.74-1.47 (m, 10H), 1.47-1.33 (m, 4H).

Isomer 3: ¹H NMR (300 MHz, DMSO-d6, ppm) δ 6.67-6.41 (m, 1H), 6.02 (s, 2H), 5.08 (d, J=12.8 Hz, 1H), 4.80-4.62 (m, 1H), 4.60-4.45 (m, 1H), 4.20-3.99 (m, 1H), 3.94 (d, J=8.6 Hz, 1H), 3.63-3.50 (m, 1H) (m, 1H), 3.50-3.40 (m, 1H), 3.02 (d, J=12.8 Hz, 1H), 2.97-2.76 (m, 2H), 2.33 (s, 3H), 2.17-2.01 (m, 4H), 1.98-21.88 (m, 1H), 1.87-1.51 (m, 10H), 1.51-1.32 (m, 5H), 1.28-1.09 (m, 1H), 1.08-0.91 (m, 1H).

Isomer 4: ¹H NMR (300 MHz, DMSO-d6, ppm) δ 6.71-6.38 (m, 1H), 6.02 (s, 2H), 5.16-4.99 (m, 1H), 4.70-4.48 (m, 2H), 4.13 (d, J=11.2 Hz, 1H), 3.94 (d, J=8.6 Hz, 1H), 3.62-3.40 (m, 2H), 3.11-2.76 (m, 3H), 2.32 (s, 3H), 2.19-2.02 (m, 4H), 1.99-1.87 (m, 1H), 1.87-1.51 (m, 10H), 1.51-1.32 (m, 5H), 1.29-0.91 (m, 2H).

Each compound in Table below was prepared following a similar experimental procedure (using appropriately substituted reagents) as described for Example 126.

| Cmpd. No. | ¹H NMR | MS (M + H)⁺ |
|---|---|---|
| 127 (isomer 1) | ¹H NMR (300 MHz, DMSO-d6, ppm) δ 6.65-6.44 (m, 1H), 6.04 (br, 2H), 5.12-5.08 (m, 1H), 4.72-4.51 (m, 3H), 4.27-4.25 (m, 2H), 4.00-3.97 (m, 1H), 3.62-3.61 (m, 1H), 3.50-3.48 (m, 1H), 3.08-3.04 (m, 1H), 2.82-2.76 (m, 2H), 2.34-2.32 (m, 6H), 2.03-1.58 (m, 10H), 1.44 (d, J = 6.3 Hz, 3H). | 652 |
| 127 (isomer 2) | ¹H NMR (300 MHz, DMSO-d6, ppm) δ 6.65-6.43 (m, 1H), 6.04 (br, 2H), 5.13-5.08 (m, 1H), 4.72-4.51 (m, 3H), 4.29-4.27 (m, 2H), 4.02-3.99 (m, 1H), 3.65-3.63 (m, 1H), 3.53-3.49 (m, 1H), 3.10-3.06 (m, 1H), 2.83-2.77 (m, 2H), 2.34-2.32 (m, 6H), 2.03-1.60 (m, 10H), 1.44 (d, J = 6.3 Hz, 3H). | 652 |
| 128 | ¹H NMR (300 MHz, DMSO-d6, ppm) δ 6.70-6.40 (m, 1H), 6.30-5.79 (m, 3H), 5.15-4.94 (m, 1H), 4.64-4.33 (m, 3H), 4.33-4.05 (m, 1H), 3.99-3.89 (m, 1H), 3.69-3.48 (m, 3H), 3.16-2.99 (m, 3H), 2.89-2.79 (m, 2H), 2.79-2.72 (m, 1H), 2.32 (s, 3H), 1.98-1.56 (m, 4H), 1.43 (d, J = 6.3 Hz, 3H). | 642 |
| 129 | ¹H NMR (300 MHz, DMSO-d6, ppm) δ 6.67-6.43 (m, 1H), 6.03 (s, 2H), 5.17-5.06 (m, 1H), 4.61-4.45 (m, 2H), 3.96 (d, J = 8.7 Hz, 2H), 3.65 (d, J = 11.6 Hz, 1H), 3.55-3.48 (m, 2H), 3.47-3.42 (m, 1H), 3.26-3.20 (m, 3H), 3.10-2.89 (m, 4H), 2.37-2.21 (m, 4H), 2.17-2.05 (m, 1H), 1.94-1.73 (m, 1H), 1.65-1.52 (m, 3H), 1.44 (d, J = 6.3 Hz, 3H), 0.82 (d, J = 6.1 Hz, 3H), 0.72-0.63 (m, 1H), 0.60-0.45 (m, 2H), 0.40-0.30 (m, 1H). | 676 |
| 130 (isomer 1) | ¹H NMR (300 MHz, DMSO-d6, ppm) δ 6.76-6.38 (m, 1H), 6.03 (s, 2H), 5.77-5.52 (m, 1H), 5.13-5.04 (m, 1H), 4.60-4.46 (m, 1H), 4.15-4.01 (m, 2H), 3.95 (d, J = 8.8 Hz, 1H), 3.61-3.53 (m, 1H), 3.46-3.42 (m, 1H), 3.08-2.88 (m, 3H), 2.77-2.64 (m, 1H), 2.32 (s, 3H), 2.13-1.94 (m, 2H), 1.93-1.74 (m, 5H), 1.74-1.50 (m, 5H), 1.44 (d, J = 6.3 Hz, 3H). | 682 |
| 130 (isomer 2) | ¹H NMR (300 MHz, DMSO-d6, ppm) δ 6.69-6.38 (m, 1H), 6.02 (s, 2H), 5.78-5.51 (m, 1H), 5.15-5.02 (m, 1H), 4.59-4.46 (m, 1H), 4.13-4.01 (m, 2H), 4.00-3.92 (m, 1H), 3.61-3.50 (m, 1H), 3.45 (d, J = 5.7 Hz, 1H), 3.09-2.92 (m, 3H), 2.75-2.64 (m, 1H), 2.33 (s, 3H), 2.12-1.93 (m, 2H), 1.92-1.75 (m, 5H), 1.73-1.51 (m, 5H), 1.44 (d, J = 6.3 Hz, 3H). | 682 |
| 131 (isomer 1) | ¹H NMR (400 MHz, DMSO-d6, ppm) δ 6.71-6.38 (m, 1H), 6.03 (s, 2H), 5.16-5.03 (m, 1H), 4.62-4.46 (m, 1H), 4.44-4.32 (m, 1H), 4.32-4.20 (m, 1H), 3.96 (d, J = 8.7 Hz, 1H), 3.61-3.54 (m, 1H), 3.49-3.41 (m, 3H), 3.41-3.36 (m, 1H), 3.30-3.16 (m, 3H), 3.04 (d, J = 12.8 Hz, 1H), 2.83 (s, 3H), 2.33 (s, 3H), 2.19-2.05 (m, 1H), 2.05-1.88 (m, 2H), 1.88-1.75 (m, 1H), 1.75-1.60 (m, 3H), 1.60-1.46 (m, 2H), 1.44 (d, J = 6.4 Hz, 3H). | 675 |
| 131 (isomer 2) | ¹H NMR (400 MHz, DMSO-d6, ppm) δ 6.67-6.42 (m, 1H), 6.02 (s, 2H), 5.14-5.03 (m, 1H), 4.61-4.48 (m, 1H), 4.45-4.31 (m, 1H), 4.31-4.17 (m, 1H), 3.96 (d, J = 8.8 Hz, 1H), 3.67-3.54 (m, 1H), 3.46 (d, J = 6.5 Hz, 1H), 3.44-3.36 (m, 3H), 3.31-3.29 (m, 1H), 3.29-3.15 (m, 2H), 3.03 (d, J = 12.8 Hz, 1H), 2.83 (s, 3H), 2.33 (s, 3H), 2.18-2.05 (m, 1H), 2.05-1.89 (m, 1H), 1.89-1.77 (m, 1H), 1.75-1.61 (m, 3H), 1.61-1.47 (m, 2H), 1.44 (d, J = 6.3 Hz, 3H). | 675 |
| 131 (isomer 3) | ¹H NMR (300 MHz, DMSO-d6, ppm) δ 6.70-6.38 (m, 1H), 6.02 (s, 2H), 5.08 (d, J = 12.2 Hz, 1H), 4.63-4.46 (m, 1H), 4.42-4.28 (m, 1H), 4.22-4.07 (m, 1H), 4.03-3.86 (m, 1H), 3.69-3.50 (m, 3H), 3.50-3.36 (m, 2H), 3.22-2.96 (m, 5H), 2.83 (s, 3H), 2.32 (s, 3H), 2.09-1.95 (m, 1H), 1.95-1.76 (m, 3H), 1.74-1.50 (m, 4H), 1.44 (d, J = 6.3 Hz, 3H). | 675 |
| 131 (isomer 4) | ¹H NMR (300 MHz, DMSO-d6, ppm) δ 6.74-6.37 (m, 1H), 6.03 (s, 2H), 5.22-5.00 (m, 1H), 4.66-4.47 (m, 1H), 4.44-4.28 (m, 1H), 4.25-4.10 (m, 1H), 3.97 (d, J = 8.8 Hz, 1H), 3.72-3.35 (m, 5H), 3.22-2.97 (m, 4H), 2.84 (s, 3H), 2.32 (s, 3H), 2.12-1.75 (m, 4H), 1.75-1.50 (m, 4H), 1.44 (d, J = 6.3 Hz, 3H). | 675 |

-continued

| Cmpd. No. | ¹H NMR | MS (M + H)⁺ |
|---|---|---|
| 132 | ¹H NMR (300 MHz, DMSO-d₆) δ 6.52 (d, J = 40.6 Hz, 1H), 6.03 (s, 2H), 5.09 (d, J = 12.3 Hz, 1H), 4.65-4.54 (m, 3H), 4.29 (s, 1H), 4.08 (d, J = 7.5 Hz, 1H), 3.95 (d, J = 9.0 Hz, 1H), 3.62-3.51 (m, 3H), 3.44 (d, J = 5.4 Hz, 1H), 3.17 (d, J = 1.2 Hz, 1H), 3.03 (d, J = 12.6 Hz, 1H), 2.35 (s, 6H), 1.88-1.75 (m, 3H), 1.64 (s, 3H), 1.42 (d, J = 6.3 Hz, 3H) | 634 |
| 133 (isomer 1) | 1H NMR (400 MHz, DMSO-d6, ppm) δ 6.72-6.46 (m, 1H), 6.03 (br, 2H), 5.11-5.07 (m, 1H), 4.55-4.53 (m, 1H), 4.41-4.38 (m, 1H), 4.11-4.07 (m, 1H), 3.97-3.95 (m, 1H), 3.58-3.57 (m, 1H), 3.47-3.41 (m, 2H), 3.13-3.11 (m, 1H), 3.07-3.05 (m, 1H), 3.05 (s, 3H), 2.90-2.88 (m, 1H), 2.82 (s, 3H), 2.80-2.65 (m, 2H), 2.32 (s, 3H), 2.08-2.05 (m, 1H), 1.90-1.82 (m, 2H), 1.66-1.33 (m, 8H), 1.43 (d, J = 6.0 Hz, 3H), 1.22-1.18 (m, 1H). | 717 |
| 133 (isomer 2) | ¹H NMR (400 MHz, DMSO-d6, ppm) δ 6.71-6.46 (m, 1H), 6.02 (br, 2H), 5.11-5.08 (m, 1H), 4.55-4.53 (m, 1H), 4.40-4.38 (m, 1H), 4.27-4.24 (m, 1H), 3.96-3.94 (m, 1H), 3.58-3.57 (m, 1H), 3.44-3.43 (m, 1H), 3.29-3.27 (m, 1H), 3.13-3.11 (m, 1H), 3.04-3.02 (m, 1H), 3.02 (s, 3H), 2.80 (s, 3H), 2.67-2.61 (m, 2H), 2.32 (s, 3H), 2.10-2.07 (m, 2H), 1.89-1.50 (m, 10H), 1.43 (d, J = 6.0 Hz, 3H), 1.35-1.26 (m, 2H). | 717 |
| 133 (isomer 3) | ¹H NMR (400 MHz, DMSO-d6, ppm) δ 6.66-6.42 (m, 1H), 6.05 (br, 2H), 5.11-5.09 (m, 1H), 4.55-4.53 (m, 1H), 4.39-4.37 (m, 1H), 4.24-4.21 (m, 1H), 3.97-3.95 (m, 1H), 3.57-3.56 (m, 1H), 3.46-3.45 (m, 1H), 3.05-2.97 (m, 3H), 3.01 (s, 3H), 2.83-2.79 (m, 4H), 2.65-2.62 (m, 1H), 2.50-2.46 (m, 1H), 2.38-2.32 (m, 4H), 1.88-1.51 (m, 10H), 1.44 (d, J = 6.4 Hz, 3H), 1.41-1.35 (m, 1H), 1.26-1.22 (m, 1H). | 717 |
| 133 (isomer 4) | 1H NMR (400 MHz, DMSO-d6, ppm) δ 6.64-6.46 (m, 1H), 6.02 (br, 2H), 5.10-5.06 (m, 1H), 4.55-4.53 (m, 1H), 4.36-4.34 (m, 1H), 4.05-4.03 (m, 1H), 3.96-3.94 (m, 1H), 3.55-3.53 (m, 1H), 3.44-3.42 (m, 1H), 3.21-3.19 (m, 1H), 3.03-2.98 (m, 4H), 2.90-2.87 (m, 2H), 2.80 (s, 3H), 2.80-2.73 (m, 2H), 2.32 (s, 3H), 2.06-2.03 (m, 1H), 1.85-1.43 (m, 11H), 1.43 (d, J = 6.0 Hz, 3H). | 717 |
| 134 (isomer 1) | ¹H NMR (300 MHz, DMSO-d6, ppm) δ 6.73-6.34 (m, 1H), 6.01 (s, 2H), 5.16-5.01 (m, 1H), 4.62-4.40 (m, 2H), 4.30 (d, J = 11.1 Hz, 1H), 3.99-3.76 (m, 3H), 3.62-3.51 (m, 1H), 3.51-3.35 (m, 3H), 3.01 (d, J = 12.7 Hz, 1H), 2.86-2.77 (m, 1H), 2.73-2.57 (m, 2H), 2.39-2.24 (m, 5H), 1.96-1.72 (m, 3H), 1.71-1.46 (m, 4H), 1.41 (d, J = 6.5 Hz, 3H). | 648 |
| 134 (isomer 2) | ¹H NMR (300 MHz, DMSO-d6, ppm) δ 6.69-6.36 (m, 1H), 6.01 (s, 2H), 5.08 (d, J = 12.7 Hz, 1H), 4.64-4.24 (m, 3H), 4.01-3.73 (m, 3H), 3.59-3.51 (m, 1H), 3.50-3.36 (m, 3H), 3.01 (d, J = 12.7 Hz, 1H), 2.87-2.76 (m, 1H), 2.73-2.58 (m, 2H), 2.39-2.23 (m, 6H), 2.00-1.72 (m, 2H), 1.72-1.45 (m, 4H), 1.42 (d, J = 6.3 Hz, 3H). | 648 |
| 135 | ¹H NMR (300 MHz, DMSO-d6) δ 6.52 (d, J = 39.5 Hz, 1H), 6.01 (s, 2H), 5.09 (dd, J = 12.9, 2.5 Hz, 1H), 4.65-4.37 (m, 3H), 4.17 (d, J = 4.6 Hz, 1H), 3.94 (d, J = 8.8 Hz, 1H), 3.81 (dd, J = 12.4, 4.9 Hz, 1H), 3.53 (s, 1H), 3.43-3.39 (m, 1H), 3.35 (s, 1H), 3.23 (d, J = 12.3 Hz, 1H), 3.01 (d, J = 12.5 Hz, 2H), 2.92-2.78 (m, 2H), 2.74 (s, 1H), 2.30 (s, 3H), 2.11-1.96 (m, 2H), 1.86-1.48 (m, 5H), 1.42 (d, J = 6.3 Hz, 3H). | 634 |
| 136 | ¹H NMR (300 MHz, DMSO-d₆) δ 6.52 (d, J = 39.4 Hz, 1H), 6.01 (s, 2H), 5.07 (d, J = 11.7 Hz, 1H), 4.62-4.46 (m, 1H), 4.23 (d, J = 4.2 Hz, 1H), 4.08 (d, J = 8.0 Hz, 1H), 3.93 (d, J = 8.9 Hz, 2H), 3.76-3.68 (m, 1H), 3.53 (s, 1H), 3.46-3.36 (m, 3H), 3.1--2.85 (m, 4H), 2.56 (d, J = 4.1 Hz, 1H), 2.30 (s, 3H), 2.05-1.89 (m, 2H), 1.78 (d, J = 10.3 Hz, 1H), 1.58 (d, J = 32.3 Hz, 3H), 1.42 (d, J = 6.3 Hz, 3H). | 634 |
| 137 (isomer 1) | ¹H NMR (300 MHz, DMSO-d6, ppm) δ 6.70-6.39 (m, 1H), 6.03 (s, 2H), 5.15-5.01 (m, 1H), 4.61 (d, J = 10.1 Hz, 1H), 4.55 (t, J = 7.6 Hz, 1H), 4.25 (d, J = 10.1 Hz, 1H), 3.97 (d, J = 8.7 Hz, 1H), 3.78-3.68 (m, 1H), 3.60 (s, 1H), 3.49 (s, 1H), 3.46-3.37 (m, 1H), 3.19 (m, 1H), 3.03 (d, J = 13.0 Hz, 1H), 2.99-2.89 (m, 5H), 2.86-2.77 (m, 1H), 2.34 (s, 3H), 1.90 (m, 3H), 1.78-1.51 (m, 5H), 1.44 (d, J = 6.3 Hz, 3H). | 675 |
| 137 (isomer 2) | ¹H NMR (300 MHz, DMSO-d6, ppm) δ 6.72-6.42 (m, 1H), 6.03 (s, 2H), 5.14-5.01 (m, 1H), 4.61-4.55 (m, 2H), 4.25 (d, J = 10.1 Hz, 1H), 3.97 (d, J = 8.7 Hz, 1H), 3.78-3.70 (m, 1H), 3.62 (s, 1H), 3.49 (s, 1H), 3.44-3.37 (m, 1H), 3.20 (m, 1H), 3.04 (d, J = 13.0 Hz, 1H), 2.98-2.89 (m, 5H), 2.85-2.76 (m, 1H), 2.33 (s, 3H), 1.91 (m, 3H), 1.78-1.52 (m, 5H), 1.43 (d, J = 6.3 Hz, 3H). | 675 |
| 138 | ¹H NMR (300 MHz, DMSO-d6, ppm) δ 6.68-6.32 (m, 1H), 6.02 (s, 2H), 5.16-5.04 (m, 1H), 4.61-4.46 (m, 1H), 4.43-4.31 (m, 2H), 3.95 (d, J = 8.8 Hz, 1H), 3.64-3.50 (m, 5H), 3.44 (d, J = 5.6 Hz, 1H), 3.02 (d, J = 12.8 Hz, 1H), 2.83-2.68 (m, 1H), 2.48-2.42 (m, 2H), 2.42-2.35 (m, 4H), 2.32 (s, 3H), 1.98-1.86 (m, 2H), 1.84-1.75 (m, 1H), 1.71-1.50 (m, 3H), 1.44 (d, J = 6.3 Hz, 3H). | 636 |

| Cmpd. No. | ¹H NMR | MS (M + H)⁺ |
|---|---|---|
| 139 | ¹H NMR (400 MHz, DMSO-d₆) δ 6.54 (d, J = 60.8 Hz, 1H), 6.03 (s, 2H), 5.49 (s, 1H), 5.35 (d, J = 4.7 Hz, 1H), 5.08 (dd, J = 13.1, 2.5 Hz, 1H), 4.54 (dd, J = 8.7, 6.2 Hz, 1H), 4.16 (s, 2H), 3.95 (d, J = 8.8 Hz, 1H), 3.57 (d, J = 5.4 Hz, 2H), 3.44 (d, J = 6.2 Hz, 1H), 3.28 (s, 1H), 3.03 (d, J = 12.7 Hz, 1H), 2.92 (dd, J = 12.5, 4.0 Hz, 1H), 2.87-2.79 (m, 1H), 2.43-2.28 (m, 5H), 2.05 (dd, J = 14.7, 4.7 Hz, 1H), 2.00-1.88 (m, 1H), 1.79 (d, J = 10.9 Hz, 1H), 1.64 (s, 2H), 1.54 (t, J = 5.7 Hz, 1H), 1.44 (d, J = 6.3 Hz, 3H). | 668 |
| 140 | ¹H NMR (300 MHz, DMSO-d6) δ 6.54 (d, J = 40.2 Hz, 1H), 6.02 (s, 2H), 5.43 (s, 1H), 5.26 (s, 1H), 5.09 (dd, J = 12.9, 2.5 Hz, 1H), 4.53 (dd, J = 8.7, 6.3 Hz, 1H), 4.27-4.08 (m, 2H), 3.95 (d, J = 8.8 Hz, 1H), 3.56 (d, J = 4.9 Hz, 1H), 3.49-3.38 (m, 2H), 3.25-3.06 (m, 2H), 3.06-2.95 (m, 2H), 2.83 (s, 1H), 2.35 (d, J = 18.0 Hz, 4H), 2.26-2.12 (m, 2H), 2.12-1.99 (m, 1H), 1.78 (d, J = 10.0 Hz, 1H), 1.72-1.49 (m, 3H), 1.44 (d, J = 6.3 Hz, 3H). | 668 |
| 141 | ¹H NMR (400 MHz, DMSO-d₆, ppm) δ 6.53 (d, J = 60.5 Hz, 1H), 6.03 (s, 2H), 5.55-5.25 (m 2H), 5.20-5.01 (m, 1H), 4.64-4.41 (m, 1H), 4.28-4.06 (m, 2H), 3.95 (d, J = 8.8 Hz, 1H), 3.56 (d, J = 4.9 Hz, 1H), 3.48-3.39 (m, 2H), 3.22-3.15 (m, 1H), 3.11 (d, J = 10.2 Hz, 1H), 3.08-2.97 (m, 2H), 2.67 (s,1H), 2.43-2.25 (m, 4H), 2.19 (t, J = 12.0 Hz, 2H), 2.12-1.99 (m, 1H), 1.80 (s, 1H), 1.59 (d, J = 40.5 Hz, 3H), 1.43 (dd, J = 6.5, 3.1 Hz, 3H). | 668 |
| 142 | ¹H NMR (300 MHz, DMSO-d6) δ 6.53 (d, J = 38.0 Hz, 1H), 6.02 (s, 2H), 5.42 (s, 1H), 5.24 (s, 1H), 5.08 (d, J = 13.2 Hz, 1H), 4.52 (d, J = 6.6 Hz, 1H), 4.04 (d, J = 5.1 Hz, 2H), 3.95 (d, J = 7.2 Hz, 1H), 3.57 (d, J = 5.6 Hz, 1H), 3.44 (s, 1H), 3.24 (s, 2H), 3.19-2.97 (m, 3H), 2.32 (s, 4H), 2.22 (d, J = 22.5 Hz, 3H), 1.88-1.73 (m, 1H), 1.63 (s, 3H), 1.45 (d, J = 6.2 Hz, 3H), 1.24 (s, 1H). | 668 |
| 143 (isomer 1) | ¹H NMR (300 MHz, DMSO-d₆, ppm): δ 6.54 (d, J = 41.3 Hz, 1H), 6.03 (s, 2H), 5.50-5.19 (m, 1H), 5.19-4.80 (m, 2H), 4.71-4.49 (m, 1H), 4.35 (d, J = 10.6 Hz, 1H), 4.10 (d, J = 10.9 Hz, 1H), 3.96 (d, J = 8.8 Hz, 1H), 3.58 (s, 1H), 3.45 (d, J = 5.8 Hz, 1H), 3.24-3.07 (m, 2H), 3.08-2.84 (m, 3H), 2.68-2.55 (m, 1H), 2.32 (s, 3H), 2.14-1.97 (m, 1H), 1.89-1.73 (m, 3H), 1.72-1.50 (m, 4H), 1.44 (d, J = 6.3 Hz, 3H). | 668 |
| 143 (isomer 2) | ¹H NMR (300 MHz, DMSO-d₆, ppm): δ 6.54 (d, J = 40.8 Hz, 1H), 6.03 (s, 2H), 5.55-5.04 (m, 3H), 4.56 (dd, J = 8.6, 6.3 Hz, 1H), 4.27-4.12 (m, 2H), 3.99 (d, J = 8.8 Hz, 1H), 3.64 (s, 1H), 3.51 (d, J = 5.7 Hz, 1H), 3.29-3.16 (m, 1H), 3.07 (d, J = 12.2 Hz, 2H), 3.02-2.89 (m, 1H), 2.82-2.69 (m, 1H), 2.52 (s, 1H), 2.32 (s, 3H), 2.02 (s, 1H), 1.93-1.76 (m, 4H), 1.75-1.52 (m, 3H), 1.44 (d, J = 6.3 Hz, 3H). | 668 |
| 143 (isomer 3) | ¹H NMR (300 MHz, DMSO-d₆, ppm): δ 6.54 (d, J = 40.8 Hz, 1H), 6.03 (s, 2H), 5.53-5.01 (m, 3H), 4.62-4.46 (m, 1H), 4.26-4.18 (m, 1H), 4.14 (dd, J = 10.7, 3.6 Hz, 1H), 3.96 (d, J = 8.7 Hz, 1H), 3.57 (s, 1H), 3.52-3.41 (m, 1H), 3.24 (d, J = 13.3 Hz, 1H), 3.03 (d, J = 12.4 Hz, 2H), 2.97 (d, J = 6.5 Hz, 1H), 2.86-2.68 (m, 1H), 2.30 (d, J = 13.3 Hz, 3H), 2.02 (d, J = 9.6 Hz, 1H), 1.92-1.73 (m, 4H), 1.72-1.51 (m, 3H), 1.44 (d, J = 6.3 Hz, 3H). | 668 |
| 144 | ¹H NMR (300 MHz, DMSO-d6, ppm) δ 6.80-6.25 (m, 1H), 6.03 (s, 2H), 5.16-5.00 (m, 1H), 4.93-4.69 (m, 1H), 4.60 (s, 4H), 4.57-4.36 (m, 3H), 3.96 (d, J = 8.7 Hz, 1H), 3.58-3.50 (m, 1H), 3.48-3.38 (m, 2H), 3.35 (s, 4H), 3.02 (d, J = 12.8 Hz, 1H), 2.87-2.70 (m, 1H), 2.70-2.62 (m, 1H), 2.32 (s, 3H), 1.90-1.75 (m, 1H), 1.73-1.50 (m, 3H), 1.44 (d, J = 6.3 Hz, 3H). | 666 |
| 145 | ¹H NMR (300 MHz, DMSO-d6, ppm) δ 6.68-6.37 (m, 1H), 6.02 (s, 2H), 5.06 (d, J = 12.8, 2.5 Hz, 1H), 4.94-4.67 (m, 1H), 4.58 (s, 4H), 4.55-4.35 (m, 3H), 3.94 (d, J = 8.7 Hz, 1H), 3.56-3.48 (m, 1H), 3.48-3.39 (m, 2H), 3.35 (s, 4H), 3.01 (d, J = 12.8 Hz, 1H), 2.73 (d, J = 5.1 Hz, 1H), 2.65 (d, J = 5.2 Hz, 1H) , 2.30 (s, 3H), 1.82-1.71 (m, 1H), 1.71-1.48 (m, 3H), 1.42 (d, J = 6.3 Hz, 3H). | 666 |
| 146 | ¹H NMR (300 MHz, DMSO-d6, ppm) 6.67-6.37 (m, 1H), 6.02 (s, 2H), 5.07 (m, 1H), 4.95-4.68 (m, 1H), 4.66-4.35 (m, 5H), 3.94 (d, J = 8.8 Hz, 1H), 3.59-3.40 (m, 6H), 3.09-2.91 (m, 5H), 2.86-2.65 (m, 3H), 2.30 (s, 3H), 1.87-1.73 (m, 1H), 1.71-1.49 (m, 3H), 1.42 (d, J = 6.3 Hz, 3H). | 684 |
| 149 | ¹H NMR (400 MHz, DMSO-d6, ppm) δ 6.67-6.46 (m, 1H), 6.03 (s, 2H), 5.10-5.06 (m, 1H), 4.61-4.50 (m, 5H), 4.36-4.35 (m, 2H), 3.96-3.94 (m, 1H), 3.60-3.43 (m, 6H), 3.03-3.00 (m, 1H), 2.76-2.75 (m, 1H), 2.54-2.51 (m, 4H), 2.35-2.23 (m, 5H), 1.88-1.84 (m, 1H), 1.72-1.55 (m, 3H), 1.44 (d, J = 6.4 Hz, 3H). | 678 |
| 150 (isomer 1) | ¹H NMR (300 MHz, DMSO-d6, ppm) δ 6.68-6.38 (m, 1H), 6.37-6.15 (m, 1H), 6.14-5.91 (m, 2H), 5.17-5.03 (m, 1H), 4.64-4.46 (m, 1H), 4.39-4.20 (m, 2H), 3.96 (d, J = 8.7 Hz, 1H), 3.56 (d, J = 5.5 Hz, 1H), 3.49-3.40 (m, 1H), 3.03 (d, J = 12.8 Hz, 1H), 2.91-2.64 (m, 3H), 2.41-2.27 (m, 6H), 2.24-1.99 (m, 2H), 1.96-1.77 (m, 2H), 1.76-1.68 (m, 3H), 1.68-1.49 (m, 3H), 1.44 (d, J = 6.3 Hz, 3H). | 670 |
| 150 (isomer 2) | ¹H NMR (300 MHz, DMSO-d6, ppm) δ 6.68-6.40 (m, 1H), 6.38-6.13 (m, 1H), 6.09-5.91 (m, 2H), 5.16-4.99 (m, 1H), 4.60-4.44 (m, 1H), 4.39-4.17 (m, 2H), 3.94 (d, J = 8.7 Hz, 1H), 3.55 (d, J = 5.3 Hz, 1H), 3.43 (d, J = 5.7 Hz, 1H), 3.01 (d, J = 12.7 Hz, 1H), 2.91-2.66 (m, 3H), 2.41-2.23 (m, 6H), 2.21-1.97 (m, 2H), 1.95-1.48 (m, 8H), 1.42 (d, J = 6.3 Hz, 3H). | 670 |

-continued

| Cmpd. No. | ¹H NMR | MS (M + H)⁺ |
|---|---|---|
| 151 (isomer 1) | ¹H NMR (400 MHz, DMSO-d₆, ppm): δ 6.54 (d, J = 57.1 Hz, 1H), 6.04 (s, 2H), 5.18-5.03 (m, 1H), 4.76 (s, 1H), 4.66 (s, 1H), 4.59-4.50 (m, 1H), 4.31-4.22 (m, 1H), 3.97 (d, J = 8.8 Hz, 1H), 3.84-3.71 (m, 1H), 3.59 (s, 1H), 3.53-3.38 (m, 4H), 3.11-2.92 (m, 3H), 2.81-2.65 (m, 1H), 2.46 (d, J = 11.5 Hz, 1H), 2.38-2.28 (m, 3H), 2.12-1.98 (m, 1H), 1.93-1.74 (m, 2H), 1.73-1.51 (m, 3H), 1.44 (d, J = 6.3 Hz, 3H). | 634 |
| 151 (isomer 2) | ¹H NMR (400 MHz, DMSO-d₆, ppm): δ 6.52 (d, J = 40.7 Hz, 1H), 6.01 (s, 2H), 5.07 (d, J = 12.7 Hz, 1H), 4.62-4.43 (m, 1H), 4.37-4.16 (m, 2H), 4.07-3.88 (m, 2H), 3.85-3.68 (m, 1H), 3.66-3.49 (m, 2H), 3.47-3.36 (m, 2H), 3.08-2.89 (m, 2H), 2.89-2.78 (m, 1H), 2.60-2.52 (m, 2H), 2.30 (s, 3H), 2.27-2.14 (m, 1H), 1.93-1.71 (m, 1H), 1.70-1.48 (m, 4H), 1.42 (d, J = 6.3 Hz, 3H). | 634 |
| 152 (isomer 1) | ¹H NMR (400 MHz, DMSO-d₆, ppm): δ 6.54 (d, J = 56.7 Hz, 1H), 6.03 (s, 2H), 5.40-5.17 (m, 1H), 5.14-5.01 (m, 1H), 4.64-4.37 (m, 3H), 4.02-3.89 (m, 1H), 3.62-3.49 (m, 2H), 3.48-3.41 (m, 1H), 3.09-2.95 (m, 2H), 2.94-2.82 (m, 2H), 2.39-2.27 (m, 3H), 2.24-2.07 (m, 1H), 1.93-1.75 (m, 4H), 1.74-1.60 (m, 3H), 1.60-1.47 (m, 2H), 1.44 (d, J = 6.3 Hz, 3H). | 650 |
| 152 (isomer 2) | ¹H NMR (400 MHz, DMSO-d₆, ppm): δ 6.54 (d, J = 58.4 Hz, 1H), 6.03 (s, 2H), 5.39-5.15 (m, 1H), 5.13-5.04 (m, 1H), 4.61-4.49 (m, 1H), 4.48-4.35 (m, 2H), 4.02-3.86 (m, 1H), 3.60-3.49 (m, 1H), 3.47-3.41 (m, 1H), 3.30-3.23 (m, 1H), 3.22-3.14 (m, 1H), 3.12-2.97 (m, 2H), 2.84-2.80 (m, 1H), 2.37-2.30 (m, 3H), 2.29-2.20 (m, 1H), 1.93-1.71 (m, 4H), 1.71-1.50 (m, 5H), 1.44 (d, J = 6.3 Hz, 3H). | 650 |
| 153 (isomer 1) | ¹H NMR (300 MHz, DMSO-d6, ppm) δ 6.53 (d, J = 57.7 Hz, 1H), 6.03 (s, 2H), 5.09 (m, 1H), 4.53 (m, 1H), 4.22 (m, 2H), 3.96 (d, J = 8.8 Hz, 1H), 3.68 (m, 1H), 3.50 (m, 2H), 3.31-3.14 (m, 3H), 3.02 (d, J = 12.8 Hz, 1H), 2.84 (s, 1H), 2.48-2.28 (m, 4H), 2.23-2.01 (m, 3H), 1.80 (d, J = 11.5 Hz, 1H), 1.76-1.49 (m, 4H), 1.44 (d, J = 6.3 Hz, 3H). | 668 |
| 153 (isomer 2) | ¹H NMR (300 MHz, DMSO-d6, ppm) δ 6.55 (d, J = 57.7 Hz, 1H), 6.04 (s, 2H), 5.09 (m, 1H), 4.53 (m, 1H), 4.23 (m, 2H), 3.97 (d, J = 8.8 Hz, 1H), 3.68 (m, 1H), 3.52 (m, 2H), 3.31-3.15 (m, 3H), 3.01 (d, J = 12.8 Hz, 1H), 2.85 (s, 1H), 2.48-2.29 (m, 4H), 2.23-2.02 (m, 3H), 1.81 (d, J = 11.5 Hz, 1H), 1.76-1.47 (m, 4H), 1.43 (d, J = 6.3 Hz, 3H). | 668 |
| 153 (isomer 3) | ¹H NMR (300 MHz, DMSO-d6, ppm) δ 6.54 (d, J = 40.3 Hz, 1H), 6.03 (s, 2H), 5.09 (m, 1H), 4.65-4.32 (m, 2H), 3.96 (d, J = 8.7 Hz, 1H), 3.68-3.41 (m, 2H), 3.32-3.15 (m, 2H), 3.06-2.86 (m, 2H), 2.84-2.72 (m, 1H), 2.30 (d, J = 13.6 Hz, 4H), 2.15-1.98 (m, 3H), 1.97-1.72 (m, 4H), 1.80-1.47 (m, 4H), 1.44 (d, J = 6.3 Hz, 3H). | 668 |
| 154 | ¹H NMR (300 MHz, DMSO-d6, ppm) δ 6.53 (d, J = 55.9 Hz, 1H), 6.03 (s, 2H), 5.09 (m, 1H), 4.53 (m, 1H), 4.48-4.29 (m, 2H), 3.95 (d, J = 8.8 Hz, 1H), 3.66-3.53 (m, 4H), 3.52-3.40 (m, 2H), 3.32-3.13 (m, 3H), 3.02 (d, J = 12.8 Hz, 1H), 2.89 (m, 1H), 2.84-2.66 (m, 2H), 2.32 (d, J = 3.5 Hz, 3H), 2.11-1.93 (m, 1H), 1.89-1.48 (m, 5H), 1.44 (d, J = 6.3 Hz, 3H), 1.35-1.17 (m, 3H). | 662 |
| 155 | ¹H NMR (400 MHz, DMSO-d₆) δ 6.58 (d, J = 20.7 Hz, 3H), 5.11-5.08 (m, 1H), 4.64-4.48 (m, 1H), 4.44-4.23 (m, 2H), 3.97 (d, J = 8.8 Hz, 1H), 3.56-3.52 (m, 2H), 3.45 (d, J = 6.0 Hz, 1H), 3.25-3.21(m, 1H), 3.15-2.99 (m, 3H), 2.77 (s, 1H), 2.71-2.58 (m, 1H), 2.49-2.26 (m, 3H), 1.80 (d, J = 11.7 Hz, 1H), 1.74-1.52 (m, 3H), 1.45 (d, J = 6.3 Hz, 3H). | 658 |
| 156 | ¹H NMR (300 MHz, DMSO-d6, ppm) δ 6.70-6.55 (m, 1H), 6.28-5.83 (m, 1H), 5.24 (s, 2H), 5.05-5.17 (m, 1H), 4.61-4.44 (m, 1H), 4.36-4.16 (m, 2H), 3.97 (d, J = 8.9 Hz, 1H), 3.67-3.60 (m, 1H), 3.54-3.49 (m, 6H), 3.13-2.91 (m, 3H), 2.45-2.32 (m, 4H), 2.32-2.23 (m, 2H), 2.20 (s, 3H), 1.92-1.74 (m, 1H), 1.74-1.52 (m, 3H), 1.43 (d, J = 6.3 Hz, 3H), 0.68-0.59 (m, 2H), 0.48-0.38 (m, 2H). | 658 |
| 157 | ¹H NMR (300 MHz, DMSO-d6, ppm) δ 6.62-6.50 (m, 2H), 6.37 (s, 2H), 5.09 (d, J = 12.6 Hz, 1H), 4.62-4.40 (m, 2H), 4.27-4.17 (m, 1H), 4.01-3.92 (m, 1H), 3.66-3.39 (m, 5H), 3.14-2.80 (m, 3H), 2.67-2.52 (m, 2H), 2.15-1.70 (m, 4H), 1.70-1.47 (m, 4H), 1.44 (d, J = 6.3 Hz, 3H), 1.14 (s, 3H), 1.08 (s, 3H). | 662 |
| 158 | ¹H NMR (400 MHz, DMSO-d₆, ppm): δ 6.78-6.58 (m, 1H), 6.41-5.91 (m, 1H), 5.73 (s, 2H), 5.12 (d, J = 12.0 Hz, 1H), 4.64-4.50 (m, 1H), 4.48-4.36 (m, 1H), 4.21-4.09 (m, 1H), 3.99 (d, J = 8.9 Hz, 1H), 3.74-3.41 (m, 7H), 3.22-2.93 (m, 5H), 2.92-2.81 (m, 2H), 2.20-1.99 (m, 1H), 1.94-1.52 (m, 6H), 1.45 (d, J = 6.3 Hz, 3H), 1.39-1.20 (m, 1H). | 648 |

Example 159: Compound 159 (two diastereomers

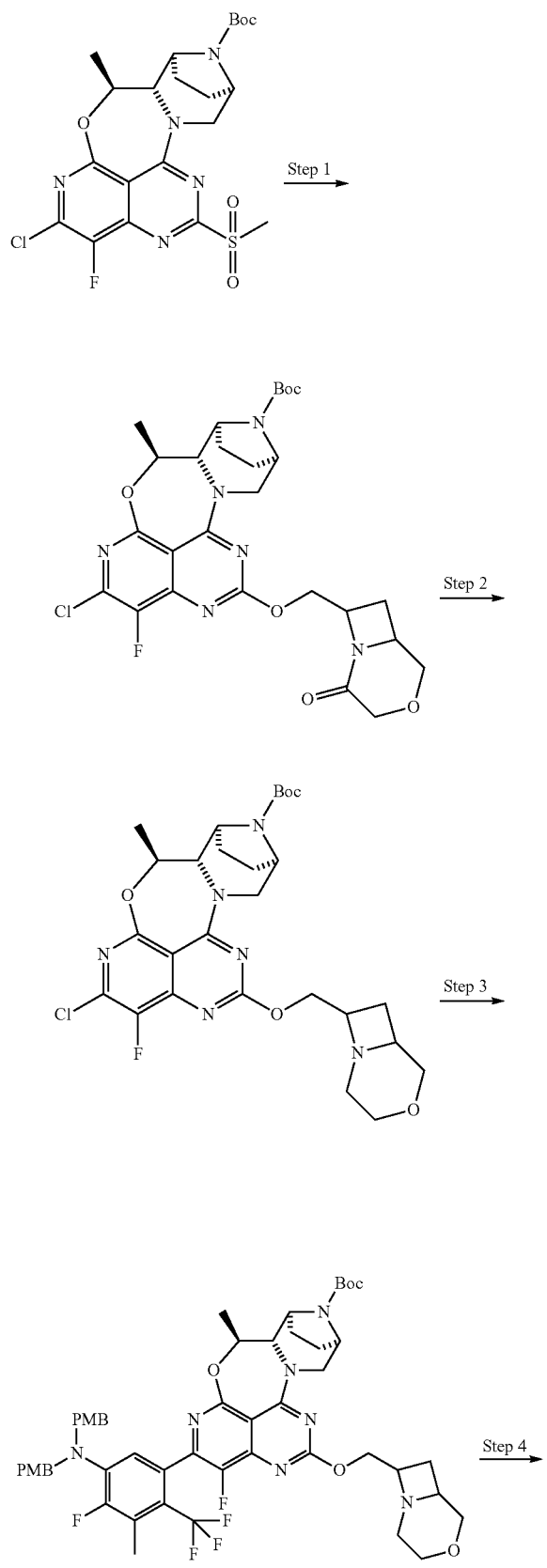

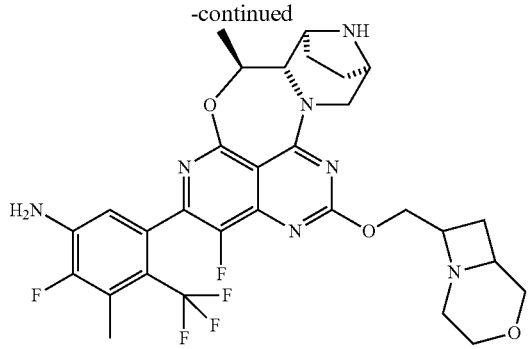

Step 1: tert-Butyl (5S,5aS,6S,9R)-2-chloro-1-fluoro-5-methyl-12-((2-oxo-4-oxa-1-azabicyclo[4.2.0]octan-8-yl)methoxy)-5a,6,7,8,9,10-hexahydro-5H-4-oxa-3,10a,11,13,14-pentaaza-6,9-methanonaphtho[1,8-ab]heptalene-14-carboxylate Under nitrogen, to a solution of tert-butyl rac-(4R,7S,8S,9S)-13-chloro-14-fluoro-9-methyl-17-methylsulfonyl-10-oxa-2,12,16,18,20-pentazapentacyclo[9.7.1.14,7.02,8.015,19] icosa-1(18),11(19),12,14,16-pentaene-20-carboxylate (300 mg, 0.580 mmol) and 8-(hydroxymethyl)-4-oxa-1-azabicyclo[4.2.0]octan-2-one (175 mg, 1.11 mmol, intermediate 111) in toluene (3 mL) was added t-BuONa (112 mg, 1.17 mmol) at 0° C. The resulting solution was stirred for 1 h at room temperature. The resulting solution was dilute with water and extracted with EtOAc. The combined organic layers were dried over anhydrous sodium sulfate and concentrated under vacuum. The residue was purified by flash chromatography on silica gel (gradient: 0%-6% MeOH/DCM) to afford 257 mg of the title compound as a yellow solid. LC-MS: (ESI, m z): [M+H]$^+$=591.

Step 2: tert-Butyl (5S,5aS,6S,9R)-12-((4-oxa-1-azabicyclo[4.2.0]octan-8-yl)methoxy)-2-chloro-1-fluoro-5-methyl-5a,6,7,8,9,10-hexahydro-5H-4-oxa-3,10a,11,13,14-pentaaza-6,9-methanonaphtho[1,8-ab]heptalene-14-carboxylate Under nitrogen, to a solution of tert-butyl (5S,5aS,6S,9R)-2-chloro-1-fluoro-5-methyl-12-((2-oxo-4-oxa-1-azabicyclo[4.2.0]octan-8-yl)methoxy)-5a,6,7,8,9,10-hexahydro-5H-4-oxa-3,10a,11,13,14-pentaaza-6,9-methanonaphtho[1,8-ab]heptalene-14-carboxylate (257 mg, 0.430 mmol) in THF (6 mL) was added DIBAL-H (6.0 mL, 1 M in THF) at −20° C. The resulting solution was slowly warmed to room temperature and stirred at room temperature for 1 h. The reaction was quenched by $Na_2SO_4 \cdot 10\ H_2O$. After filtration, the filtrate was concentrated under reduced pressure. The residue was purified by flash chromatography on silica gel (gradient: 0%-6% MeOH/DCM) to afford 83.0 mg of the title compound as a yellow oil. LC-MS: (ESI, m/z): [M+H]$^+$= 577.

Step 3: tert-Butyl (5S,5aS,6S,9R)-12-((4-oxa-1-azabicyclo[4.2.0]octan-8-yl)methoxy)-2-(5-(bis(4-methoxybenzyl)amino)-4-fluoro-3-methyl-2-(trifluoromethyl)phenyl)-1-fluoro-5-methyl-5a,6,7,8,9,10-hexahydro-5H-4-oxa-3,10a,11,13,14-pentaaza-6,9-methanonaphtho[1,8-ab]heptalene-14-carboxylate Under nitrogen, a solution of tert-butyl (5S,5aS,6S,9R)-12-((4-oxa-1-azabicyclo[4.2.0]octan-8-yl)methoxy)-2- chloro-1-fluoro-5-methyl-5a,6,7,8,9,10-hexahydro-5H-4-oxa-3,10a,11,13,14-pentaaza-6,9-methanonaphtho[1,8-ab]heptalene-14-carboxylate (83.0 mg, 0.140 mmol), [5-[bis[(4-methoxyphenyl)methyl]amino]-4-fluoro-3-methyl-2-(trifluoromethyl)phenyl]boronic acid (137 mg, 0.290 mmol), cataCXium A Pd G3 (21.0 mg, 0.0300 mmol) and $K_3PO_4$ (0.5 mL, 1.5 M in $H_2O$) in THF (2.5 mL) was stirred for 3 h at 60° C. The resulting solution was diluted with water and extracted with EtOAc. The combined organic layers were dried over anhydrous sodium sulfate and concentrated under vacuum. The resulting residue was purified by C18 column (solvent gradient: 0-70% ACN in water (0.05% $NH_4HCO_3$)) to yield 94.1 mg of the title compound as a yellow oil. LC-MS: (ESI, m/z): $[M+H]^+$=974.

Step 4: 5-((5S,5aS,6S,9R)-12-((4-Oxa-1-azabicyclo[4.2.0]octan-8-yl)methoxy)-1-fluoro-5-methyl-5a,6,7,8,9,10-hexahydro-5H-4-oxa-3,10a,11,13,14-pentaaza-6,9-methanonaphtho[1,8-ab]heptalen-2-yl)-2-fluoro-3-methyl-4-(trifluoromethyl)aniline (two diastereomers)

A solution of tert-butyl (5S,5aS,6S,9R)-12-((4-oxa-1-azabicyclo[4.2.0]octan-8-yl)methoxy)-2-(5-(bis(4-methoxybenzyl)amino)-4-fluoro-3-methyl-2-(trifluoromethyl)phenyl)-1-fluoro-5-methyl-5a,6,7,8,9,10-hexahydro-5H-4-oxa-3,10a,11,13,14-pentaaza-6,9-methanonaphtho[1,8-ab]heptalene-14-carboxylate (94.1 mg, 0.100 mmol) in TFA (3.5 mL) was stirred at room temperature for 1 hour. The solvent was concentrated under vacuum. The residue was purified by Prep-HPLC (Column: XBridge Prep OBD C18 Column, 30*150 mm, 5 μm; Mobile Phase A: water(10 mmol/L $NH_4HCO_3$), Mobile Phase B: ACN; Flow rate: 60 mL/min; Gradient: 21% B to 41% B in 10.5 min; Wave Length: 220 nm; $R_{T1}$(min): 10) to afford product 18.1 mg (mixture of two diastereomers) as a white solid. The two diastereomers were separated by Chiral-Prep-HPLC (conditions: Column: CHIR-PAK IE, 2*25 cm, 5 μm; Mob-e Phase A: MtBE(0.5% 2 M $NH_3$—MeOH)-HPLC, Mobile Phase B: EtOH—HPLC; Flow rate: 20 mL/min; 25% B; Wave Length: 220/-4 nm; $R_{T1}$(min): 9.377; $R_{T2}$(min): 11.805; Sample Solvent: EtOH—HPLC) to afford 3.1 mg 159 (diastereomer 1) and 2.8 mg 159 (diastereomer 2) as white solids.

159 (diastereomer 1): LC-MS: (ESI, m/z): $[M+H]^+$=634. $^1$H NMR (300 MHz, DMSO-$d_6$, ppm): δ 6.60 (s, 1H), 6.02 (s, 2H), 5.09 (d, J=12.7 Hz, 1H), 4.53 (dd, J=8.7, 6.3 Hz, 1H), 4.40-4.17 (m, 3H), 3.96 (d, J=8.6 Hz, 1H), 3.80-3.74 (m, 1H), 3.74-3.57 (m, 2H), 3.57-3.42 (m, 4H), 3.02 (d, J=12.8 Hz, 1H), 2.83-2.67 (m, 2H), 2.32 (d, J=2.8 Hz, 3H), 2.10 (dt, J=10.5, 7.2 Hz, 1H), 1.81 (s, 1H), 1.75-1.44 (m, 8H).

159 (diastereomer 2): LC-MS: (ESI, m/z): $[M+H]^+$=634. $^1$H NMR (300 MHz, DMSO-$d_6$, ppm): δ 6.61 (s, 1H), 6.03 (s, 2H), 5.09 (d, J=12.7 Hz, 1H), 4.54 (dd, J=8.7, 6.3 Hz, 1H), 4.41-4.18 (m, 3H), 3.97 (d, J=8.6 Hz, 1H), 3.81-3.75 (m, 1H), 3.74-3.41 (m, 6H), 3.01 (d, J=12.8 Hz, 1H), 2.81-2.68 (m, 2H), 2.31 (d, J=2.8 Hz, 3H), 2.10 (dt, J=10.5, 7.2 Hz, 1H), 1.80 (s, 1H), 1.74-1.43 (m, 8H).

Example 160: Compound 160 (two diastereomers

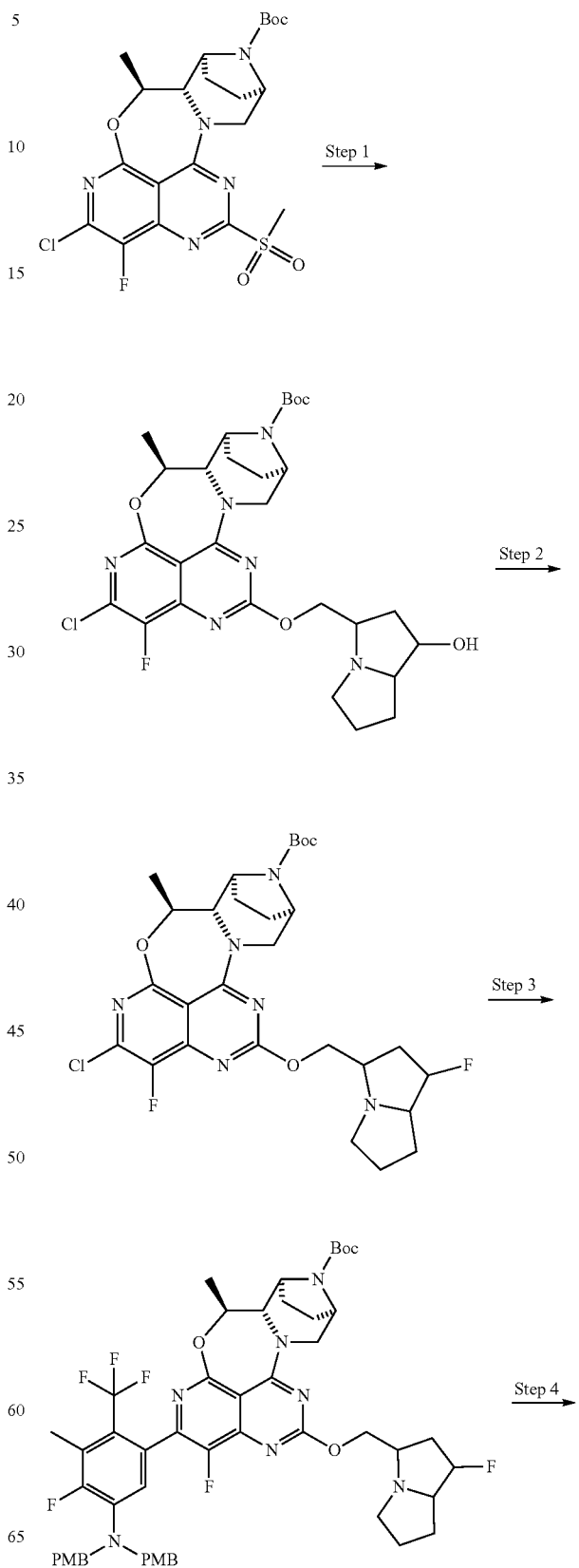

-continued

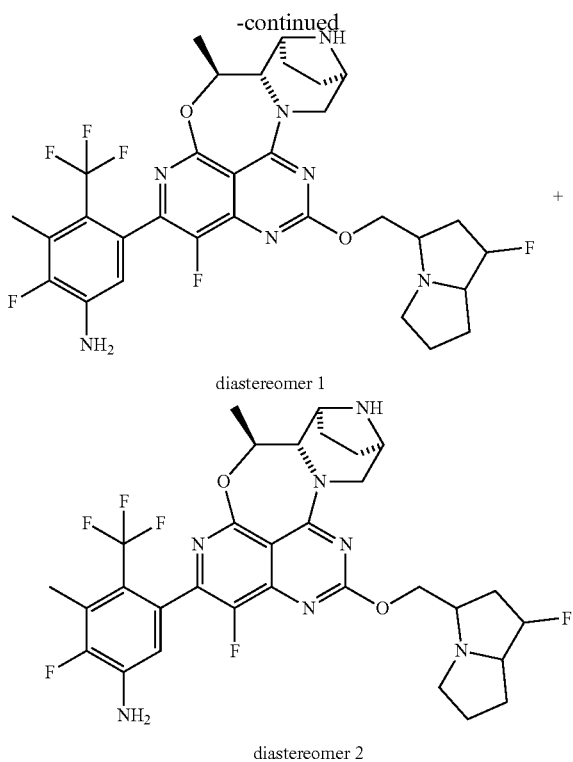

diastereomer 1 diastereomer 2

Step 1: tert-Butyl (5S,5aS,6S,9R)-2-chloro-1-fluoro-12-((1-hydroxyhexahydro-1H-pyrrolizin-3-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate Under nitrogen, to a solution of 3-(hydroxymethyl)-2,3,5,6,7,8-hexahydro-1H-pyrrolizin-1-ol (459 mg, 2.92 mmol, intermediate 112) in THF (15 mL) was added NaH (312 mg, 7.80 mmol) at 0° C., and the mixture was stirred for 30 min at 0° C. Then tert-butyl (5S,5aS,6S,9R)-2-chloro-1-fluoro-5-methyl-12-(methylsulfonyl)-5a,6,7,8,9,10-hexahydro-5H-4-oxa-3,10a,11,13,14-pentaaza-6,9-methanonaphtho[1,8-ab]heptalene-14-carboxylate (1.00 g, 1.95 mmol) was added, and the mixture was stirred at room temperature for 1 h. The reaction was quenched with saturated $NH_4Cl$ aqueous, extracted with EtOAc. The combined organic layers were dried over anhydrous sodium sulfate and concentrated under vacuum. The residue was purified by flash chromatography on silica gel eluting (gradient: 0%-20% MeOH/DCM) to afford 246 mg of the title compound as a yellow solid. LC-MS: (ESI, m/z): $[M+H]^+$=591

Step 2: tert-butyl (5S,5aS,6S,9R)-2-chloro-1-fluoro-12-((1-fluorohexahydro-1H-pyrrolizin-3-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate Under nitrogen, to a solution of tert-butyl (5S,5aS,6S,9R)-2-chloro-1-fluoro-12-((1-hydroxyhexahydro-1H-pyrrolizin-3-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (246 mg, 0.420 mmol) in DCM (2.5 mL) was added DAST (408 mg, 2.53 mmol) at −78° C. The resulting solution was slowly warmed to room temperature and stirred for 2 h at room temperature. The reaction was quenched with saturated $NH_4Cl$ aqueous, extracted with DCM. The combined organic layers were dried over anhydrous sodium sulfate and concentrated under vacuum. The residue was purified by C18 column (solvent gradient: 0-95% MeOH in water (0.05% $NH_4HCO_3$)) to afford 54.2 mg of the title compound as a yellow solid. LC-MS: (ESI, m/z): $[M+H]^+$=592.

Step 3: tert-Butyl (5S,5aS,6S,9R)-2-(5-(bis(4-methoxybenzyl)amino)-4-fluoro-3-methyl-2-(trifluoromethyl)phenyl)-1-fluoro-12-((1-fluorohexahydro-1H-pyrrolizin-3-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate Under nitrogen, a solution of tert-butyl (5S,5aS,6S,9R)-2-chloro-1-fluoro-12-((1-fluorohexahydro-1H-pyrrolizin-3-yl)methoxy)-5-methyl-5a,6,7,8,9,10-hexahydro-5H-4-oxa-3,10a,11,13,14-pentaaza-6,9-methanonaphtho[1,8-ab] heptalene-14-carboxylate (54.2 mg, 0.0900 mmol), [5-[bis[(4-methoxyphenyl)methyl]amino]-4-fluoro-3-methyl-2-(trifluoromethyl)phenyl]boronic acid (87.5 mg, 0.180 mmol), cataCXium A Pd G3 (13.4 mg, 0.0200 mmol) and $K_3PO_4$ (0.2 mL, 1.5 M in $H_2O$) in THF (0.5 mL) was stirred for 1.5 h at 60° C. The resulting solution was partitioned between water and EtOAc. The separated organic layer was dried over anhydrous sodium sulfate and concentrated under vacuum. The residue was purified by flash chromatography on silica gel (gradient: 0%-10% MeOH/DCM) to afford 63.3 mg of the title compound as a brown solid. LC-MS: (ESI, m/z): $[M+H]^+$=990.

Step 7: 2-Fluoro-5-((5S,5aS,6S,9R)-1-fluoro-12-((1-fluorohexahydro-1H-pyrrolizin-3-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-3-methyl-4-(trifluoromethyl)aniline (two diastereomers)

A solution of tert-butyl (5S,5aS,6S,9R)-2-(5-(bis(4-methoxybenzyl)amino)-4-fluoro-3-methyl-2-(trifluoromethyl)phenyl)-1-fluoro-12-((1-fluorohexahydro-1H-pyrrolizin-3-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (63.3 mg, 0.0600 mmol) in TFA (2.5 mL) was stirred at room temperature for 40 min. The solvent was concentrated under vacuum. The residue was purified by C18 column (solvent gradient: 0-85% $CH_3OH$ in water (0.05% $NH_4HCO_3$)) to afford 35.6 mg as the mixture of two diastereomers. The mixture diastereomers were separated by Chiral-Prep-HPLC (conditions: Column: CHIRALPAK IE, −25 cm, 5 μm; Mobile Phase—Hex: DCM=3:1(0.5% 2 M $NH_3$—MeOH)-HPLC, Mobile Phase B: EtOH—HPLC; Flow rate: 20 mL/min; 20% in 24 min; Wave Length: 220/2-nm; $R_{T1}$(min): 16.594; $R_{T2}$(min): 19.762; Sample Solvent: EtOH—HPLC) to afford 6.9 mg of 160 (diastereomer 1) and 6.8 mg of 160 (diastereomer 2) as white solids.

160 (diastereomer 1):LC-MS: (ESI, m/z): $[M+H]^+$=650. $^1$H NMR (300 MHz, DMSO-$d_6$, ppm): δ 6.51 (d, J=41.4 Hz, 1H), 6.01 (s, 2H), 5.18-4.77 (m, 2H), 4.60-4.46 (m, 1H), 4.39-4.28 (m, 1H), 4.12-4.01 (m, 1H), 3.9-(d, J=8.8 Hz, 1H), 3.56 (s, 1H), 3.52-3.40 (m, 2H), 3.25-3.11 (m, 1H), 3.02 (d, J=12.8 Hz, 1H), 2.95-2.83 (m, 1H), 2.79-2.66 (m, 1H), 2.30 (s, 4H), 1.99-1.76 (m, 3H), 1.74-1.49 (m, 5H), 1.51-1.30 (m, 4H).
160 (diastereomer 2): LC-MS: (ESI, m/z): [M+H]$^+$=650. $^1$H NMR (300 MHz, DMSO-d$_6$, ppm): δ 6.52 (d, J=40.4 Hz, 1H), 6.01 (s, 2H), 5.16-4.80 (m, 2H), 4.61-4.43 (m, 1H), 4.43-4.27 (m, 1H), 4.17-4.03 (m, 1H), 3.94 (d, J=8.8 Hz, 1H), 3.57-3.46 (m, 1H), 3.48-3,37-(m, 2H), 3.23-3.09 (m, 1H), 3.01 (d, J=12.7 Hz, 1H), 2.94-2.82 (m, 1H), 2.84-2.63 (m, 1H), 2.44-2.19 (m, 4H), 1.99-1.73 (m, 3H), 1.73-1.48 (m, 5H), 1.50-1.29 (m, 4H).
Example 161: Compound 161
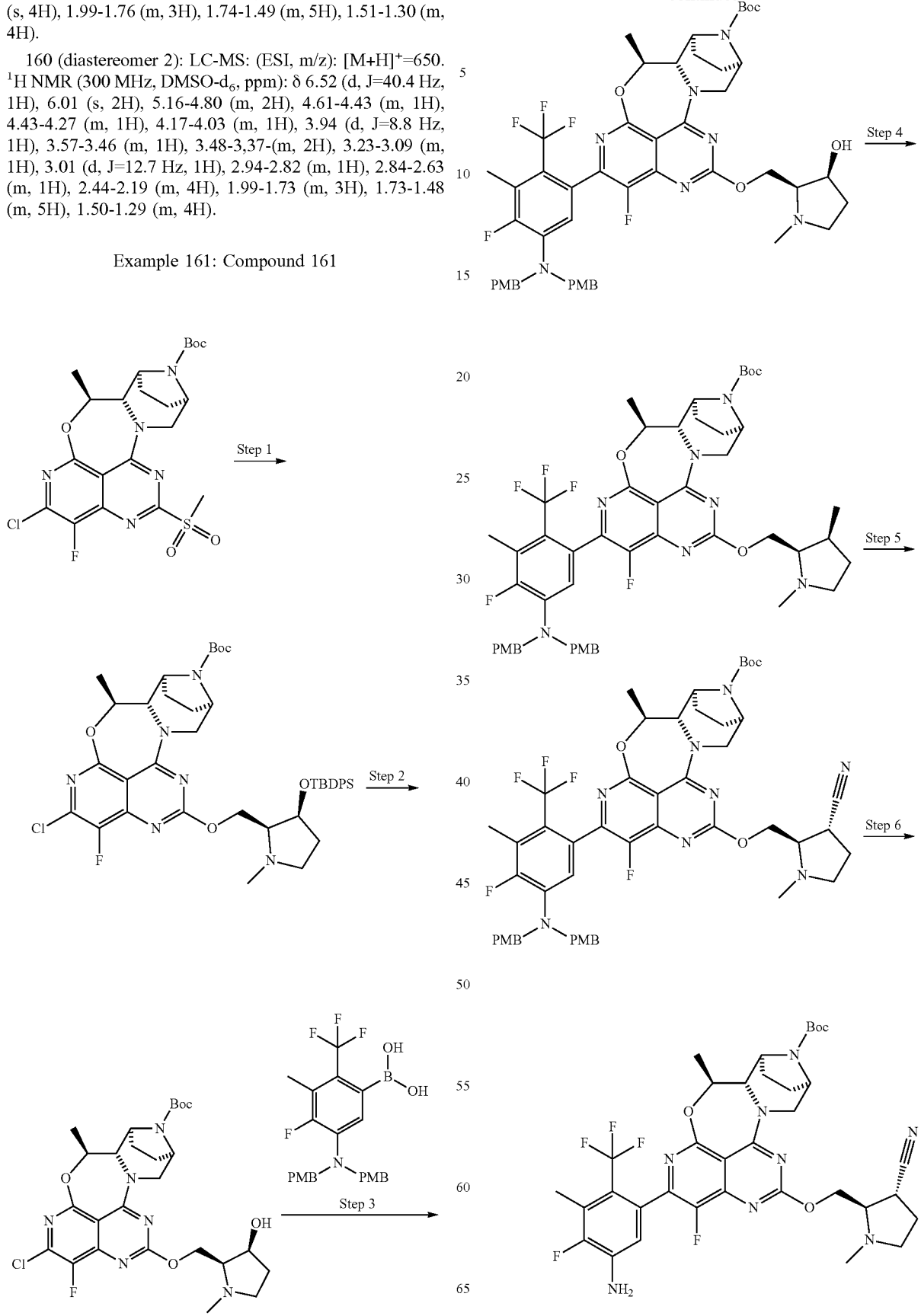

Step 1: tert-Butyl (5S,5aS,6S,9R)-12-(((2S,3S)-3-((tert-butyldiphenylsilyl)oxy)-1-methylpyrrolidin-2-yl)methoxy)-2-chloro-1-fluoro-5-methyl-5a,6,7,8,9,10-hexahydro-5H-4-oxa-3,10a,11,13,14-pentaaza-6,9-methanonaphtho[1,8-ab]heptalene-14-carboxylate Under nitrogen, to a solution of ((2S,3S)-3-((tert-butyldiphenylsilyl)oxy)-1-methylpyrrolidin-2-yl)methanol (400 mg, 1.08 mmol, intermediate 113) and tert-butyl (5S,5aS,6S,9R)-2-chloro-1-fluoro-5-methyl-12-(methylsulfonyl)-5a,6,7,8,9,10-hexahydro-5H-4-oxa-3,10a,11,13,14-pentaaza-6,9-methanonaphtho[1,8-ab]heptalene-14-carboxylate (463 mg, 0.900 mmol) in toluene (1 mL) was added t-BuONa (173 mg, 1.80 mmol) at 0° C., and the mixture was stirred at room temperature overnight. The solvent was concentrated under vacuum. The crude product was diluted with water and extracted with EtOAc. The combined organic layers were washed with brine, dried over anhydrous sodium sulfate and concentrated under reduced pressure. The residue was purified by flash chromatography on silica gel (gradient: 0-80% EtOAc/petroleum ether) to afford the title compound (413 mg) as a yellow oil. LC-MS: (ESI, m/z): [M+H]$^+$=803.

Step 2: tert-Butyl (5S,5aS,6S,9R)-2-chloro-1-fluoro-12-(((2S,3S)-3-hydroxy-1-methylpyrrolidin-2-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate A solution of tert-butyl (5S,5aS,6S,9R)-12-(((2S,3S)-3-((tert-butyldiphenylsilyl)oxy)-1-methylpyrrolidin-2-yl)methoxy)-2-chloro-1-fluoro-5-methyl-5a,6,7,8,9,10-hexahydro-5H-4-oxa-3,10a,11,13,14-pentaaza-6,9-methanonaphtho[1,8-ab]heptalene-14-carboxylate (390 mg, 0.490 mmol) and TBAF (2.43 mL, 2.43 mmol) in tetrahydrofuran (5 mL) was stirred at room temperature for 1 hour. The reaction was quenched by water and extracted with EtOAc. The combined organic layers were washed with brine, dried over anhydrous sodium sulfate and concentrated under vacuum. The residue was purified by flash chromatography on silica gel eluting (gradient: 0-5% MeOH/DCM) to afford the title compound (190 mg) as a yellow solid. LC-MS: (ESI, m/z): [M+H]$^+$=565.

Step 3: tert-Butyl (5S,5aS,6S,9R)-2-(5-(bis(4-methoxybenzyl)amino)-4-fluoro-3-methyl-2-(trifluoromethyl)phenyl)-1-fluoro-12-(((2S,3S)-3-hydroxy-1-methylpyrrolidin-2-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate Under nitrogen, a solution of tert-butyl (5S,5aS,6S,9R)-2-chloro-1-fluoro-12-(((2S,3S)-3-hydroxy-1-methylpyrrolidin-2-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (170 mg, 0.300 mmol), (5-(bis(4-methoxybenzyl)amino)-4-fluoro-3-methyl-2-(trifluoromethyl)phenyl)boronic acid (287.18 mg, 0.6000 mmol), cataCXium A Pd G$_3$ (43.8 mg, 0.0600 mmol) and K$_3$PO$_4$ (1.5 M in water) (0.1 mL) in tetrahydrofuran (5 mL) was stirred at 60° C. for 2 hours. The resulting mixture was filtered. The filtrate was concentrated under reduced pressure. The crude product was diluted with water and extracted with EtOAc. The combined organic layers were washed with brine, dried over anhydrous sodium sulfate and concentrated under reduced pressure. The residue was purified by flash chromatography on silica gel (gradient: 0-10% MeOH in DCM) to afford the title compound (224 mg) as a yellow solid. LC-MS: (ESI, m/z): [M+H]$^+$=962.

Step 4: tert-Butyl (5S,5aS,6S,9R)-2-(5-(bis(4-methoxybenzyl)amino)-4-fluoro-3-methyl-2-(trifluoromethyl)phenyl)-1-fluoro-5-methyl-12-(((2S,3S)-1-methyl-3-(tosyloxy)pyrrolidin-2-yl)methoxy)-5a,6,7,8,9,10-hexahydro-5H-4-oxa-3,10a,11,13,14-pentaaza-6,9-methanonaphtho[1,8-ab]heptalene-14-carboxylate To a solution of tert-butyl (5S,5aS,6S,9R)-2-(5-(bis(4-methoxybenzyl)amino)-4-fluoro-3-methyl-2-(trifluoromethyl)phenyl)-1-fluoro-12-(((2S,3S)-3-hydroxy-1-methylpyrrolidin-2-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (180 mg, 0.190 mmol) in dichloromethane (4 mL) was added Et$_3$N (56.7 mg, 0.560 mmol), TsCl (39.1 mg, 0.210 mmol) and 4-DMAP (1.1 mg, 0.0090 mmol) at 0° C. The reaction was stirred at room temperature overnight. The reaction was quenched with water and extracted with EtOAc. The combined organic layers were washed with brine, dried over anhydrous sodium sulfate and concentrated under reduced pressure. The residue was purified by flash chromatography on silica gel (gradient: 0-5% MeOH in DCM) to afford the title compound (126 mg) as a yellow solid. LC-MS: (ESI, m/z): [M+H]$^+$=1116.

Step 5: tert-Butyl (5S,5aS,6S,9R)-2-(5-(bis(4-methoxybenzyl)amino)-4-fluoro-3-methyl-2-(trifluoromethyl)phenyl)-12-(((2R,3R)-3-cyano-1-methylpyrrolidin-2-yl)methoxy)-1-fluoro-5-methyl-5a,6,7,8,9,10-hexahydro-5H-4-oxa-3,10a,11,13,14-pentaaza-6,9-methanonaphtho[1,8-ab]heptalene-14-carboxylate Under nitrogen, to a solution of tert-butyl (5S,5aS,6S,9R)-2-(5-(bis(4-methoxybenzyl)amino)-4-fluoro-3-methyl-2-(trifluoromethyl)phenyl)-1-fluoro-5-methyl-12-(((2S,3S)-1-methyl-3-(tosyloxy)pyrrolidin-2-yl)methoxy)-5a,6,7,8,9,10-hexahydro-5H-4-oxa-3,10a,11,13,14-pentaaza-6,9-methanonaphtho[1,8-ab]heptalene-14-carboxylate (100 mg, 0.103 mmol) in dimethyl sulfoxide (1 mL) was added NaCN (21.9 mg, 0.450 mmol) at room temperature. The resulting solution was stirred for 2 hours at 55° C. Then additional NaCN (219 mg, 4.50 mmol) was added, and the mixture was stirred at 55° C. overnight. The reaction was quenched with water, extracted with Et$_2$O. The combined organic layers were dried over anhydrous sodium sulfate and concentrated under vacuum. The residue was purified by flash chromatography on silica gel (gradient: 0-70% EtOAc/petroleum ether) to afford the title compound (28 mg) as a yellow solid. LC-MS: (ESI, m/z): [M+H]$^+$=971.

Step 6: (2R,3R)-2-((((5S,5aS,6S,9R)-2-(5-Amino-4°fluoro-3-methyl-2-(trifluoromethyl)°henyl)-1-fluoro-5-methyl-5a,6,7,8,9,10-hexahydro-5H-4-oxa-3,10a,11,13,14-pentaaza-6,9-methanonaphtho[1,8-ab]heptalen-12-yl)oxy)methyl)-1-methylpyrrolidine-3-carbonitrile A solution of tert-butyl (5S,5aS,6S,9R)-2-(5-(bis(4-methoxybenzyl)amino)-4-fluoro-3-methyl-2-(trifluoromethyl)phenyl)-12-(((2R,3R)-3-cyano-1-methylpyrrolidin-2- yl)methoxy)-1-fluoro-5-methyl-5a,6,7,8,9,10-hexahydro-5H-4-oxa-3,10a,11,13,14-pentaaza-6,9-methanonaphtho[1,8-ab]heptalene-14-carboxylate (31.0 mg, 0.0300 mmol) in 2,2,2-trifluoroacetic acid (2 mL) was stirred at room temperature for 1 hour. The solvent was concentrated under vacuum. The residue was purified by Prep-HPLC (Column: Xselect CSH F-Phenyl OBD column, 30*250 mm, 5 μm; Mobile Phase A: Water(10 mmol/L NH$_4$HCO$_3$), Mobile Phase B: ACN; Flow rate: 60 mL/min; Gradient: 39% B to 61% B in 10 min, 61% B; Wave Length: 254/220 n; R$_{T1}$(min): 8.5) to afford the title compound (3.8 mg) as a white solid. LC-MS: (ESI, m/z): [M+H]$^+$=631. $^1$H NMR (300 MHz, DMSO-d6) δ 6.55 (d, J=37.2 Hz, 1H), 6.02 (s, 2H), 5.11 (d, J=12.3 Hz, 1H), 4.59-4.29 (m, 3H), 3.97 (d, J=8.8 Hz, 1H), 3.71 (s, 1H), 3.45 (d, J=5.6 Hz, 1H), 3.25 (s, 2H), 3.10-2.99 (m, 2H), 2.85 (d, J=5.2 Hz, 1H), 2.39 (s, 4H), 2.32 (s, 3H), 2.24-2.08 (m, 1H), 2.05-1.90 (m, 1H), 1.82 (s, 1H), 1.62 (d, J=12.2 Hz, 3H), 1.44 (d, J=6.3 Hz, 3H).

Example 162: Compound 162

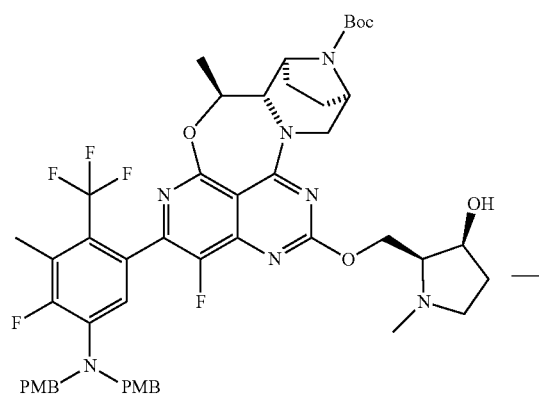

A solution of tert-butyl (5S,5aS,6S,9R)-2-(5-(bis(4-methoxybenzyl)amino)-4-fluoro-3-methyl-2-(trifluoromethyl)phenyl)-1-fluoro-12-(((2S,3S)-3-hydroxy-1-methylpyrrolidin-2-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (20.0 mg, 0.0208 mmol, from compound 161) in 2,2,2-trifluoroacetic acid (2 mL) was stirred at room temperature for 1 hours. The solvent was concentrated under vacuum. The residue was purified by Prep-HPLC (Column: XBridge Prep OBD C18 Column, 30*150 mm, 5 μm; Mobile Phase A: Water (10 mmol/L NH$_4$HCO$_3$), Mobile Phase B: ACN; Flow rate: 60 mL/min; Gradient: 26% B to 42% B in 9 min, 42% B; Wave Length: 254/220 nm; R$_{T1}$(min): 8.9) to afford the title compound (1.2 mg) as a white solid. LC-MS: (ESI, m/z): [M+H]$^+$=622. $^1$H NMR (300 MHz, DMSO-d6) δ 6.54 (d, J=40.0 Hz, 1H), 6.03 (s, 2H), 5.20-5.05 (m, 1H), 4.81 (d, J=6.1 Hz, 1H), 4.62-4.47 (m, 2H), 4.35-4.18 (m, 2H), 3.96 (d, J=8.8 Hz, 1H), 3.53 (d, J=10.0 Hz, 1H), 3.44 (d, J=5.7 Hz, 1H), 3.09-2.93 (m, 2H), 2.76 (s, 1H), 2.46-2.37 (m, 1H), 2.32 (d, J=3.7 Hz, 6H), 2.16-1.98 (m, 2H), 1.82 (s, 1H), 1.74-1.51 (m, 4H), 1.44 (d, J=6.3 Hz, 3H).

Example 163: Compound 163

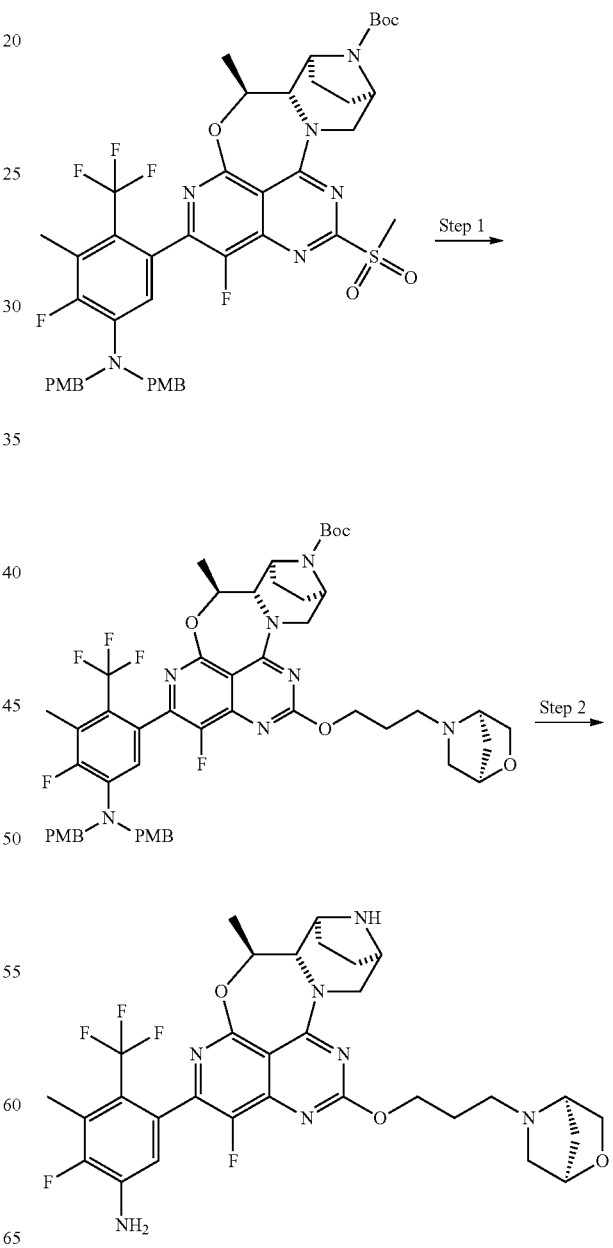

Step 1: tert-Butyl (5S,5aS,6S,9R)-12-(3-((1R,4R)-2-oxa-5-azabicyclo[2.2.1]heptan-5-yl)propoxy)-2-(5-(bis(4-methoxybenzyl)amino)-4-fluoro-3-methyl-2-(trifluoromethyl)phenyl)-1-fluoro-5-methyl-5a,6,7,8,9,10-hexahydro-5H-4-oxa-3,10a,11,13,14-pentaaza-6,9-methanonaphtho[1,8-ab]heptalene-14-carboxylate Under nitrogen, to a solution of 3-((1R,4R)-2-oxa-5-azabicyclo[2.2.1]heptan-5-yl)propan-1-ol (62.1 mg, 0.400 mmol, intermediate 114) in THF (2.5 mL) was added NaH (35.2 mg, 0.880 mmol) at 0° C., and the mixture was stirred for 20 min. Then tert-butyl (5S,5aS,6S,9R)-2-(5-(bis(4-methoxybenzyl) amino)-4-fluoro-3-methyl-2-(trifluoromethyl) phenyl)-1-fluoro-5-methyl-12-(methylsulfonyl)-5a,6,7,8,9,10-hexahydro-5H-4-oxa-3,10a,11,13,14-pentaaza-6,9-methanonaphtho[1,8-ab]heptalene-14-carboxylate (80.1 mg, 0.0900 mmol, intermediate 113) was added at 0° C., and the mixture was stirred at room temperature for 1 h. The reaction system was quenched with NH₄Cl aqueous and extracted with EtOAc. The combined organic layers were dried over anhydrous sodium sulfate and concentrated under vacuum. The residue was purified by flash chromatography on silica gel (gradient: 0%-10% MeOH/DCM) to afford 52.5 mg of the title compound as a yellow solid. LC-MS: (ESI, m/z): [M+H]⁺=988.

Step 2: 5-((5S,5aS,6S,9R)-12-(3-((1R,4R)-2-Oxa-5-azabicyclo[2.2.1]heptan-5-yl)propoxy)-1-fluoro-5-methyl-5a,6,7,8,9,10-hexahydro-5H-4-oxa-3,10a,11,13,14-pentaaza-6,9-methanonaphtho[1,8-ab]heptalen-2-yl)-2-fluoro-3-methyl-4-(trifluoromethyl)aniline A solution of tert-butyl (5S,5aS,6S,9R)-12-(3-((1R,4R)-2-oxa-5-azabicyclo[2.2.1]heptan-5-yl)propoxy)-2-(5-(bis(4-methoxybenzyl)amino)-4-fluoro-3-methyl-2-(trifluoromethyl)phenyl)-1-fluoro-5-methyl-5a,6,7,8,9,10-hexahydro-5H-4-oxa-3,10a,11,13,14-pentaaza-6,9-methanonaphtho[1,8-ab]heptalene-14-carboxylate (52.5 mg, 0.0500 mmol) in TFA (2.5 mL) was stirred at room temperature for 1 h. Then the solution was concentrated under vacuum. The crude product was purified by Prep-HPLC (Column: XBridge Prep OBD C18 Column, 30*150 mm, 5 μm; Mobile Phase A: water (10 mmol/L NH₄HCO₃), Mobile Phase B: ACN; Flow rate: 60 mL/min; Gradient: 26% B to 42% B in 9 min, 42% B; Wave Length: 254/220 nm; R$_{T1}$(min): 9 to afford 10.4 mg of the title compound as a white solid. LC-MS: (ESI, m/z): [M+H]⁺=648. ¹H NMR (400 MHz, DMSO-d₆, ppm): δ 6.52 (d, J=38.2 Hz, 1H), 6.00 (s, 2H), 5.17-5.01 (m, 1H), 4.59-4.44 (m, 1H), 4.38 (t, J=6.5 Hz, 2H), 4.33-4.26 (m, 1H), 3.93 (d, J=8.8 Hz, 1H), 3.81 (d, J=7.4 Hz, 1H), 3.53 (s, 1H), 3.49-3.39 (m, 3H), 3.00 (d, J=12.7 Hz, 1H), 2.84-2.70 (m, 2H), 2.70-2.54 (m, 2H), 2.37 (d, J=9.8 Hz, 1H), 2.31 (s, 3H), 1.90-1.49 (m, 8H), 1.42 (d, J=6.3 Hz, 3H).

Example 164: Compound 164 was prepared following a similar experimental procedure (using appropriately substituted reagents) as described for Example 163

164: ¹H NMR (400 MHz, DMSO-d6, ppm): δ 6.54 (d, J=40.3 Hz, 1H), 6.02 (s, 2H), 5.19-5.03 (m, 1H), 4.67-4.48 (m, 1H), 4.46-4.26 (m, 3H), 3.97 (d, J=8.8 Hz, 1H), 3.84 (d, J=7.4 Hz, 1H), 3.58 (s, 1H), 3.55-3.45 (m, 3H), 3.04 (d, J=12.9 Hz, 1H), 2.81 (d, J=9.8 Hz, 1H), 2.77-2.58 (m, 2H), 2.44 (d, J=9.9 Hz, 1H), 2.37-2.28 (m, 3H), 1.93-1.78 (m, 3H), 1.77-1.50 (m, 5H), 1.44 (d, J=6.3 Hz, 3H).

Example 165: Compound 165 (Mixture and Two Separate Diastereomers

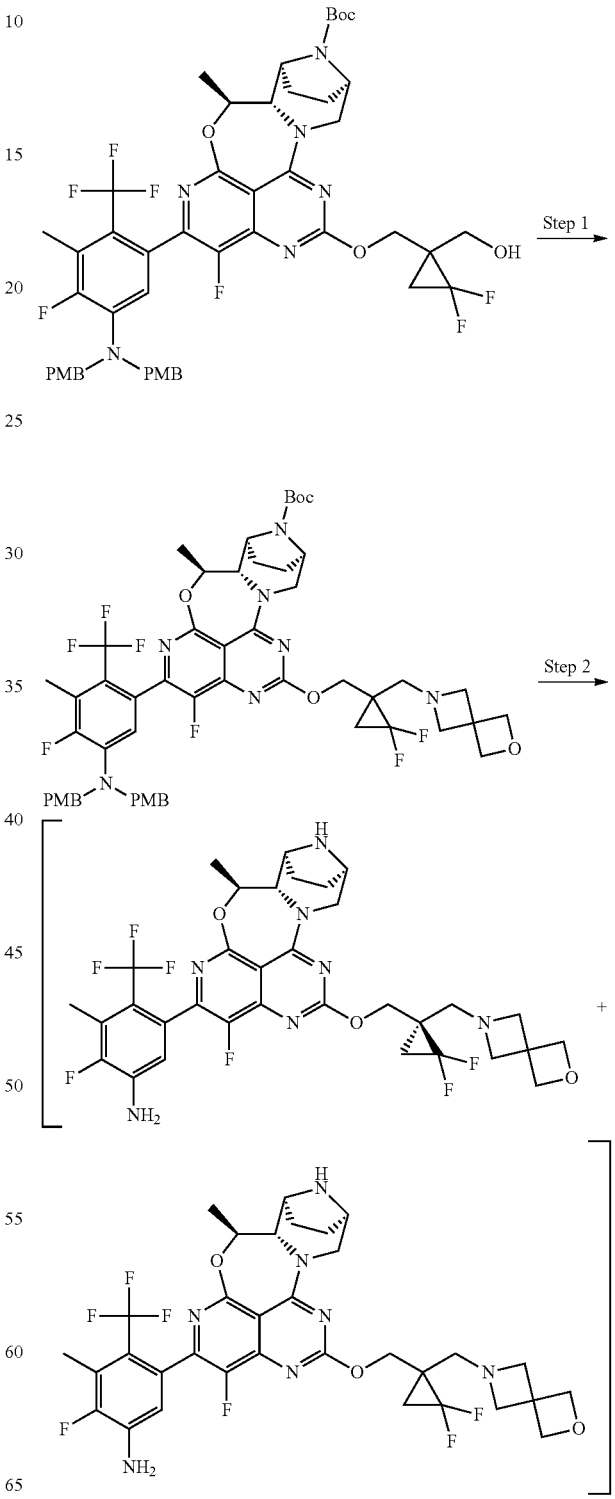

Step 1: tert-Butyl (5S,5aS,6S,9R)-12-((1-((2-oxa-6-azaspiro[3.3]heptan-6-yl)methyl)-2,2-difluorocyclopropyl)methoxy)-2-(5-(bis(4-methoxybenzyl)amino)-4-fluoro-3-methyl-2-(trifluoromethyl)phenyl)-1-fluoro-5-methyl-5a,6,7,8,9,10-hexahydro-5H-4-oxa-3,10a,11,13,14-pentaaza-6,9-methanonaphtho[1,8-ab]heptalene-14-carboxylate (two isomers)

To a solution of tert-butyl (5S,5aS,6S,9R)-2-(5-(bis(4-methoxybenzyl)amino)-4-fluoro-3-methyl-2-(trifluoromethyl)phenyl)-12-((2,2-difluoro-1-(hydroxymethyl)cyclopropyl)methoxy)-1-fluoro-5-methyl-5a,6,7,8,9,10-hexahydro-5H-4-oxa-3,10a,11,13,14-pentaaza-6,9-methanonaphtho[1,8-ab]heptalene-14-carboxylate (240 mg, 0.248 mmol, intermediate 118) and NMO (58.0 mg, 0.496 mmol) in dichloromethane (5 mL) was added TPAP (43.6 mg, 0.124 mmol) at 0° C., and the mixture was stirred for 1 hour at room temperature. The resulting mixture was filtered and the filter cake was washed with dichloromethane. To the combined filtrate was added NaOAc (305 mg, 3.72 mmol) and 2-oxa-6-azaspiro [3.3]heptane (369 mg, 3.72 mmol) at room temperature, and the mixture was stirred for 1 hour at 60° C. Then the mixture was cooled to ambient temperature and NaBH$_3$CN (234 mg, 3.72 mmol) was added, and the mixture was stirred overnight at room temperature. The reaction was quenched with water and extracted with ethyl acetate. The combined organic layers were washed with brine, dried over anhydrous sodium sulfate and concentrated under vacuum. The residue was purified by reverse phase flash chromatography on pre-packed C18 column (gradient: 0-100% CH$_3$CN in water (0.05% NH$_4$HCO$_3$)) to afford the title compound (200 mg) as a white solid. LC-MS: (ESI, m/z): [M+H]$^+$=1050.

Step 2: ((5S,5aS,6S,9R)-12-((1-((2-Oxa-6-azaspiro[3.3]heptan-6-yl)methyl)-2,2-difluorocyclopropyl)methoxy)-1-fluoro-5-methyl-5a,6,7,8,9,10-hexahydro-5H-4-oxa-3,10a,11,13,14-pentaaza[6,9]methanonaphtho[1,8-ab]heptalen-2-yl)-2-fluoro-3-methyl-4-(trifluoromethyl)aniline (two isomers)

A solution of tert-Butyl (5S,5aS,6S,9R)-12-((1-((2-oxa-6-azaspiro[3.3]heptan-6-yl)methyl)-2,2-difluorocyclopropyl)methoxy)-2-(5-(bis(4-methoxybenzyl)amino)-4-fluoro-3-methyl-2-(trifluoromethyl)phenyl)-1-fluoro-5-methyl-5a,6,7,8,9,10-hexahydro-5H-4-oxa-3,10a,11,13,14-pentaaza-6,9-methanonaphtho[1,8-ab]heptalene-14-carboxylate (200 mg, 0.190 mmol, mixture of diastereomers) in 2,2,2-trifluoroacetic acid (20 mL) was stirred for 30 minutes at room temperature. The solvent was concentrated under vacuum. The residue was purified by Prep-HPLC (Column: XBridge Prep OBD C18 Column, 30*150 mm, 5 µm; Mobile Phase A: Water (10 mmol/L NH$_4$HCO$_3$), Mobile Phase B: ACN; Flow rate: 60 mL/min mL/min; Gradient: 17% B to 42% B in 9 min; Wave Length: 254 nm/220 nm; RT1(min): 9.6) to afford 165 (mixture of diastereomers with respect to the difluorocyclopropyl stereogenic center) (25.1 mg). LC-MS: (ESI, m/z): [M+H]$^+$=710. $^1$H NMR (300 MHz, DMSO-d6, ppm) δ 6.68-6.37 (m, 1H), 6.04 (s, 2H), 5.14-5.02 (m, 1H), 4.70-4.42 (m, 6H), 4.32-4.21 (m, 1H), 3.96 (d, J=8.6 Hz, 1H), 3.56 (d, J=5.6 Hz, 1H), 3.45 (d, J=6.1 Hz, 1H), 3.38-3.35 (m, 1H), 3.33-3.30 (m, 1H), 3.03 (d, J=12.8 Hz, 1H), 2.91-2.69 (m, 1H), 2.67-2.52 (m, 3H), 2.32 (s, 3H), 1.85-1.75 (m, 1H), 1.75-1.58 (m, 3H), 1.58-1.47 (m, 2H), 1.44 (d, J=6.3 Hz, 3H).

Each compound in the Table below was prepared following a similar experimental procedure (using appropriately substituted reagents) as described for Example 165.

| Cmpd. No. | $^1$H NMR | MS (M + H)$^+$ |
|---|---|---|
| 166 | $^1$H NMR (400 MHz, DMSO-d$_6$, ppm): δ 6.54 (d, J = 39.0 Hz, 1H), 6.03 (s, 2H), 5.17-5.02 (m, 1H), 4.66-4.48 (m, 2H), 4.42 (t, J = 11.2 Hz, 1H), 4.31 (s, 1H), 3.97 (d, J = 8.7 Hz, 1H), 3.78 (t, J = 6.9 Hz, 1H), 3.63-3.54 (m, 1H), 3.53-3.38 (m, 3H), 3.04 (d, J = 12.8 Hz, 1H), 2.92-2.68 (m, 3H), 2.48-2.40 (m, 2H), 2.32 (s, 3H), 1.90-1.48 (m, 8H), 1.44 (d, J = 6.3 Hz, 3H). | 710 |
| 167 | $^1$H NMR (300 MHz, DMSO-d6, ppm) δ 6.54 (d, J = 59.6 Hz, 1H), 6.04 (s, 2H), 5.11 (m, 1H), 4.72-4.35 (m, 3H), 3.99 (d, J = 8.8 Hz, 1H), 3.68-3.44 (m, 6H), 3.06 (d, J = 12.9 Hz, 1H), 2.79-2.65 (m, 1H), 2.47-2.23 (m, 8H), 1.88-1.49 (m, 6H), 1.45 (d, J = 6.3 Hz, 3H). | 698 |

Example 168: Compound 168

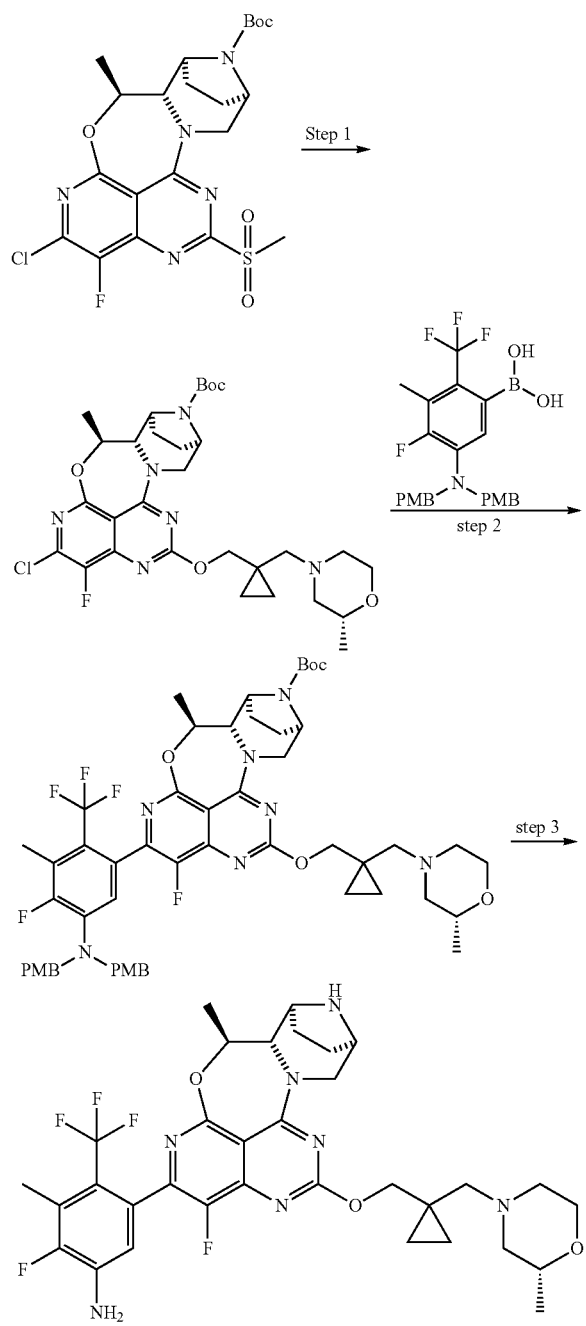

Step 1: tert-Butyl (5S,5aS,6S,9R)-2-chloro-1-fluoro-5-methyl-12-((1-(((R)-2-methylmorpholino)methyl)cyclopropyl)methoxy)-5a,6,7,8,9,10-hexahydro-5H-4-oxa-3,10a,11,13,14-pentaaza-6,9-methanonaphtho[1,8-ab]heptalene-14-carboxylate To a solution of (R)-(1-((3-methylmorpholino)methyl)cyclopropyl)methanol (360 mg, crude) in THF (5 mL) was added NaH (60% dispersion in mineral oil, 156 mg, 3.90 mmol) in portions at 0° C., and the mixture was stirred for 30 minutes at room temperature. Then tert-butyl (5S,5aS, 6S,9R)-2-chloro-1-fluoro-5-methyl-12-(methylsulfonyl)-5a, 6,7,8,9,10-hexahydro-5H-4-oxa-3,10a,11,13,14-pentaaza-6, 9-methanonaphtho[1,8-ab]heptalene-14-carboxylate (200 mg, 0.390 mmol) was added, and the mixture was stirred for 1 hour at room temperature. The reaction was quenched with saturated NH$_4$Cl aqueous solution. The reaction mixture was diluted with water and extracted with ethyl acetate. The combined organic layers were washed with brine, dried over anhydrous sodium sulfate and concentrated under vacuum. The residue was purified by flash chromatography on silica gel (gradient: 0-20% EtOAc in petroleum ether) to afford the title compound (139 mg) as a white solid. LC-MS: (ESI, m/z): [M+H]$^+$=619.

Step 2: tert-Butyl (5S,5aS,6S,9R)-2-(5-(bis(4-methoxybenzyl)amino)-4-fluoro-3-methyl-2-(trifluoromethyl)phenyl)-1-fluoro-5-methyl-12-((1-(((R)-2-methylmorpholino)methyl)cyclopropyl)methoxy)-5a,6,7,8,9,10-hexahydro-5H-4-oxa-3,10a,11,13,14-pentaaza-6,9-methanonaphtho[1,8-ab]heptalene-14-carboxylate Under nitrogen, a solution of tert-butyl (5S,5aS,6S,9R)-2-chloro-1-fluoro-5-methyl-12-((1-(((R)-2-methylmorpholino)methyl)cyclopropyl)methoxy)-5a,6,7,8,9,10-hexahydro-5H-4-oxa-3,10a,11,13,14-pentaaza-6,9-methanonaphtho[1,8-ab]heptalene-14-carboxylate (139 mg, 0.225 mmol), (5-(bis(4-methoxybenzyl)amino)-4-fluoro-3-methyl-2-(trifluoromethyl)phenyl)boronic acid (215 mg, 0.450 mmol), K$_3$PO$_4$ (1.5 M aqueous solution, 0.8 mL, 1.20 mmol) and cataCXium A Pd G3 (32.8 mg, 0.0450 mmol) in THF (4 mL) was stirred for 1 hour at 60° C. The reaction mixture was diluted with water and extracted with ethyl acetate. The combined organic layers were dried over anhydrous sodium sulfate and concentrated under vacuum. The residue was purified by flash chromatography on silica gel (gradient: 0-60% ethyl acetate in petroleum ether) to afford the title compound (210 mg) as a yellow solid. LC-MS: (ESI, m/z): [M+H]$^+$=1016.

Step 3: 2-Fluoro-5-((5S,5aS,6S,9R)-1-fluoro-5-methyl-12-((1-(((R)-2-methylmorpholino) methyl) cyclopropyl) methoxy)-5a,6,7,8,9,10-hexahydro-5H-4-oxa-3,10a,11,13,14-pentaaza-6,9-methanonaphtho [1,8-ab]heptalen-2-yl)-3-methyl-4-(trifluoromethyl) aniline A solution of tert-butyl (5S,5aS,6S,9R)-2-(5-(bis(4-methoxybenzyl) amino)-4-fluoro-3-methyl-2-(trifluoromethyl)phenyl)-1-fluoro-5-methyl-12-((1-(((R)-2-methylmorpholino)methyl)cyclopropyl)methoxy)-5a,6,7,8,9,10-hexahydro-5H-4-oxa-3,10a,11,13,14-pentaaza-6,9-methanonaphtho[1,8-ab]heptalene-14-carboxylate (210 mg, 0.207 mmol) in 2,2,2-trifluoroacetic acid (20 mL) was stirred for 30 minutes at room temperature. The solvent was concentrated under vacuum. The residue was purified by Prep-HPLC (Column: XBridge Prep OBD C18 Column, 19*250 mm, 5 µm; Mobile Phase A: Water (10 mmol/L NH$_4$HCO$_3$), Mobile Phase B: MeOH-HPLC; Flow rate: 25 mL/min; Gradient: 62% B to 84% B in 9 min, 84% B; Wave Length: 220/254 nm; RT1(min): 6.77) to afford the title compound (20.0 mg) as a white solid. LC-MS: (ESI, m/z): [M+H]$^+$=676. $^1$H NMR (300 MHz, DMSO-d6, ppm) δ 6.64-6.38 (m, 1H), 6.01 (s, 2H), 5.16-4.99 (m, 1H), 4.56-4.44 (m, 1H), 4.26 (s, 2H), 3.93 (d, J=8.7 Hz, 1H), 3.73-3.63 (m, 1H), 3.57-3.50 (m, 1H), 3.50-3.39 (m, 4H), 3.00 (d, J=12.7 Hz, 1H), 2.84-2.68 (m, 2H), 2.35-2.17 (m, 5H), 1.97-1.85 (m, 1H), 1.85-1.73 (m, 1H), 1.69-1.50 (m, 4H), 1.42 (d, J=6.3 Hz, 3H), 0.99 (d, J=6.2 Hz, 3H), 0.70-0.54 (m, 2H), 0.51-0.29 (m, 2H). Each compound in the Table below was prepared following a similar experimental procedure (using appropriately substituted reagents) as described for Example 168.

| Cmpd. No. | ¹H NMR | MS (M + H)⁺ |
|---|---|---|
| 169 | ¹H NMR (300 MHz, DMSO-d6, ppm) δ 6.68-6.41 (m, 1H), 6.03 (s, 2H), 5.09 (d, J = 12.7 Hz, 1H), 4.60-4.45 (m, 1H), 4.40-4.26 (m, 2H), 4.20 (d, J = 10.8 Hz, 1H), 3.94 (d, J = 8.7 Hz, 1H), 3.78 (d, J = 7.5 Hz, 1H), 3.65-3.52 (m, 1H), 3.52-3.40 (m, 3H), 3.01 (d, J = 12.8 Hz, 1H), 2.91-2.73 (m, 2H), 2.65 (d, J = 12.6 Hz, 1H), 2.48-2.36 (m, 1H), 2.32 (s, 3H), 1.91-1.74 (m, 1H), 1.74-1.50 (m, 5H), 1.44 (d, J = 6.3 Hz, 3H), 0.66-0.54 (m, 2H), 0.54-0.34 (m, 2H). | 674 |
| 170 | ¹H NMR (300 MHz, DMSO-d6, ppm) δ 6.75-6.30 (m, 1H), 6.01 (s, 2H), 5.13-5.02 (m, 1H), 4.58-4.43 (m, 1H), 4.38-4.10 (m, 3H), 3.93 (d, J = 8.7 Hz, 1H), 3.76 (d, J = 7.5 Hz, 1H), 3.50-3.38 (m, 4H), 3.00 (d, J = 12.8 Hz, 1H), 2.88-2.78 (m, 2H), 2.60 (d, J = 12.6 Hz, 1H), 2.54-2.48 (m, 1H), 2.30 (s, 3H), 1.90-1.75 (m, 1H), 1.74-1.48 (m, 5H), 1.51 (d, J = 8.7 Hz, 3H), 0.65-0.50 (m, 2H), 0.50-0.34 (m, 2H). | 674 |

Example 171: Compound 171

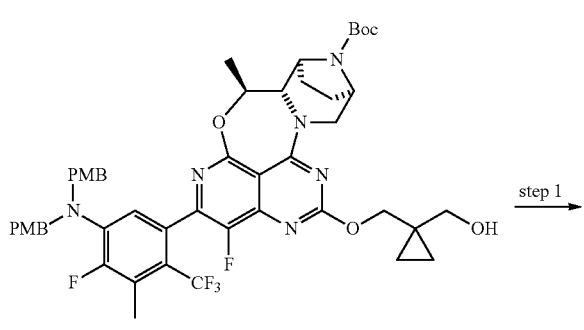

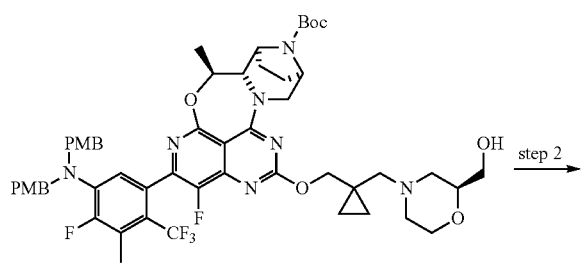

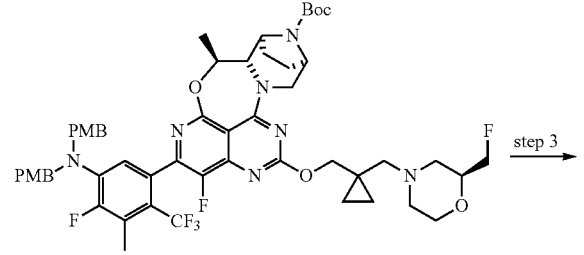

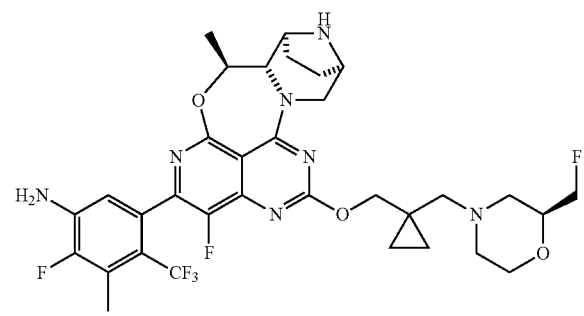

Step 1: tert-Butyl (5S,5aS,6S,9R)-2-(5-(bis(4-methoxybenzyl)amino)-4-fluoro-3-methyl-2-(trifluoromethyl)phenyl)-1-fluoro-12-((1-(((S)-2-(hydroxymethyl)morpholino)methyl)cyclopropyl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate To a solution of tert-butyl (5S,5aS,6S,9R)-2-(5-(bis(4-methoxybenzyl)amino)-4-fluoro-3-methyl-2-(trifluoromethyl)phenyl)-1-fluoro-12-((1-(hydroxymethyl)cyclopropyl)methoxy)-5-methyl-5a,6,7,8,9,10-hexahydro-5H-4-oxa-3,10a,11,13,14-pentaaza-6,9-methanonaphtho[1,8-ab] heptalene-14-carboxylate (200 mg, 0.214 mmol, intermediate 122) and NMO (50.2 mg, 0.428 mmol) in dichloromethane (4 mL) was added TPAP (37.6 mg, 0.107 mmol) at 0° C., and the mixture was stirred for 1 hour at room temperature. The resulting mixture was filtered and the filter cake was washed with dichloromethane. To the combined filtrate were added NaOAc (264 mg, 3.22 mmol) and a solution of (S)-morpholin-2-ylmethanol in dichloromethane (4 mL) at room temperature, and the mixture was stirred for 1 hour. Then NaBH₃CN (202 mg, 3.22 mmol) was added at room temperature, and the mixture was stirred overnight. The reaction was quenched with water and extracted with ethyl acetate. The combined organic layers were washed with brine, dried over anhydrous sodium sulfate and concentrated under vacuum. The residue was purified twice by flash chromatography on silica gel (gradient: 0-10% methanol in dichloromethane) and reverse phase flash chromatography on pre-packed C18 column (gradient: 0-50% CH₃CN in water (0.05% NH₄HCO₃)) to afford the title compound (85.0 mg) as a white solid. LC-MS: (ESI, m/z): [M+H]⁺= 1032.

Step 2: tert-Butyl (5S,5aS,6S,9R)-2-(5-(bis(4-methoxybenzyl)amino)-4-fluoro-3-methyl-2-(trifluoromethyl)phenyl)-1-fluoro-12-((1-(((S)-2-(fluoromethyl)morpholino)methyl)cyclopropyl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate Under nitrogen, to a solution of tert-butyl (5S,5aS,6S,9R)-2-(5-(bis(4-methoxybenzyl) amino)-4-fluoro-3-methyl-2-(trifluoromethyl) phenyl)-1-fluoro-12-((1-(((S)-2-(hydroxymethyl)morpholino)methyl)cyclopropyl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (85.0 mg, 0.0824 mmol) in dichloromethane (2 mL) was added DAST (66.4 mg, 0.412 mmol) dropwise at −60° C., and the mixture was stirred for 1 hour at room temperature. The reaction was quenched by saturated NaHCO₃ solution at 0° C. The reaction mixture was diluted with water and extracted with ethyl acetate. The combined organic layers were washed with brine, dried over anhydrous sodium sulfate and concentrated under vacuum. The residue was purified twice by flash chromatography on silica gel (gradient: 0-10% methanol in dichloromethane) and reverse phase flash chromatography on pre-packed C18 column (gradient: 0-50% CH₃CN in water (0.05% NH₄HCO₃)) to afford the title compound (32.0 mg) as a white solid. LC-MS: (ESI, m/z): [M+H]⁺=1034.

Step 3: 2-Fluoro-5-((5S,5aS,6S,9R)-1-fluoro-12-((1-(((S)-2-(fluoromethyl)morpholino)methyl)cyclopropyl)methoxy)-5-methyl-5a,6,7,8,9,10-hexahydro-5H-4-oxa-3,10a,11,13,14-pentaaza-6,9-methanonaphtho[1,8-ab]heptalen-2-yl)-3-methyl-4-(trifluoromethyl)aniline A solution of tert-butyl (5S,5aS,6S,9R)-2-(5-(bis(4-methoxybenzyl)amino)-4-fluoro-3-methyl-2-(trifluoromethyl)phenyl)-1-fluoro-12-((1-(((S)-2-(fluoromethyl)morpholino)methyl)cyclopropyl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (32.0 mg, 0.0309 mmol) in 2,2,2-trifluoroacetic acid (10 mL) was stirred for 1 hour at room temperature. The solvent was concentrated under vacuum. The residue was purified by Prep-HPLC (Column: XBridge Prep OBD C18 Column, 30*150 mm, 5 μm; Mobile Phase A: Water (10 mmol/L NH₄HCO₃), Mobile Phase B: ACN; Flow rate: 60 mL/min; Gradient: 17% B to 42% B in 9 min, 42% B; Wave Length: 254/220 nm; RT1(min): 9) to afford the title compound (7.0 mg) as a white solid. LC-MS: (ESI, m/z): [M+H]⁺=694. ¹H NMR (300 MHz, DMSO-d6, ppm) δ 6.70-6.40 (m, 1H), 6.03 (s, 2H), 5.09 (d, J=12.9 Hz, 1H), 4.56-4.49 (m, 1H), 4.49-4.43 (m, 1H), 4.34-4.22 (m, 3H), 3.95 (d, J=8.7 Hz, 1H), 3.78 (d, J=11.1 Hz, 1H), 3.70-3.59 (m, 1H), 3.59-3.48 (m, 2H), 3.48-3.40 (m, 2H), 3.02 (d, J=12.9 Hz, 1H), 2.92-2.76 (m, 2H), 2.30-2.23 (m, 5H), 2.06-1.93 (m, 1H), 1.90-1.74 (m, 2H), 1.73-1.52 (m, 3H), 1.44 (d, J=6.3 Hz, 3H), 0.72-0.61 (m, 2H), 0.48-0.38 (m, 2H).

Each compound in the Table below was prepared following a similar experimental procedure (using appropriately substituted reagents) as described for Example 171.

| Cmpd. No. | ¹H NMR | MS (M + H)⁺ |
|---|---|---|
| 172 | ¹H NMR (300 MHz, DMSO-d6, ppm) δ 6.71-6.39 (m, 1H), 6.04 (s, 2H), 5.09 (d, J = 12.9 Hz, 1H), 4.60-4.49 (m, 1H), 4.48-4.42 (m, 1H), 4.38-4.16 (m, 3H), 3.95 (d, J = 8.7 Hz, 1H), 3.78 (d, J = 11.1 Hz, 1H), 3.69-3.40 (m, 5H), 3.02 (d, J = 12.6 Hz, 1H), 2.85 (d, J = 11.1 Hz, 1H), 2.76 (d, J = 11.7 Hz, 1H), 2.34-2.28 (m, 5H), 2.06-1.92 (m, 1H), 1.89-1.74 (m, 2H), 1.72-1.52 (m, 3H), 1.44 (d, J = 6.3 Hz, 3H), 0.70-0.62 (m, 2H), 0.49-0.39 (m, 2H). | 694 |
| 173 | ¹H NMR (300 MHz, DMSO-d6, ppm) δ 6.68-6.38 (m, 1H), 6.03 (s, 2H), 5.36-4.94 (m, 2H), 4.62-4.44 (m, 1H), 4.17 (s, 2H), 3.94 (d, J = 8.7 Hz, 1H), 3.69-3.52 (m, 3H), 3.46-3.42 (m, 1H), 3.17-3.08 (m, 1H), 3.07-2.96 (m, 2H), 2.47 (s, 2H), 2.32 (s, 3H), 1.88-1.72 (m, 1H), 1.72-1.49 (m, 3H), 1.43 (d, J = 6.3 Hz, 3H), 0.60-0.39 (m, 4H). | 650 |
| 174 | ¹H NMR (300 MHz, DMSO-d6, ppm) δ 1H NMR (300 MHz, DMSO-d6) δ 6.70-6.34 (m, 1H), 6.01 (s, 2H), 5.06 (d, J = 12.7 Hz, 1H), 4.66-4.41 (m, 6H), 4.14 (s, 2H), 3.92 (d, J = 8.7 Hz, 1H), 3.59-3.48 (m, 1H), 3.42 (d, J = 5.8 Hz, 1H), 3.26 (s, 4H), 2.99 (d, J = 12.9 Hz, 1H), 2.38-2.24 (m, 5H), 1.86-1.72 (m, 1H), 1.72-1.48 (m, 3H), 1.42 (d, J = 6.3 Hz, 3H), 0.55-0.46 (m, 2H), 0.44-0.35 (m, 2H). | 674 |

Example 175: Compound 175

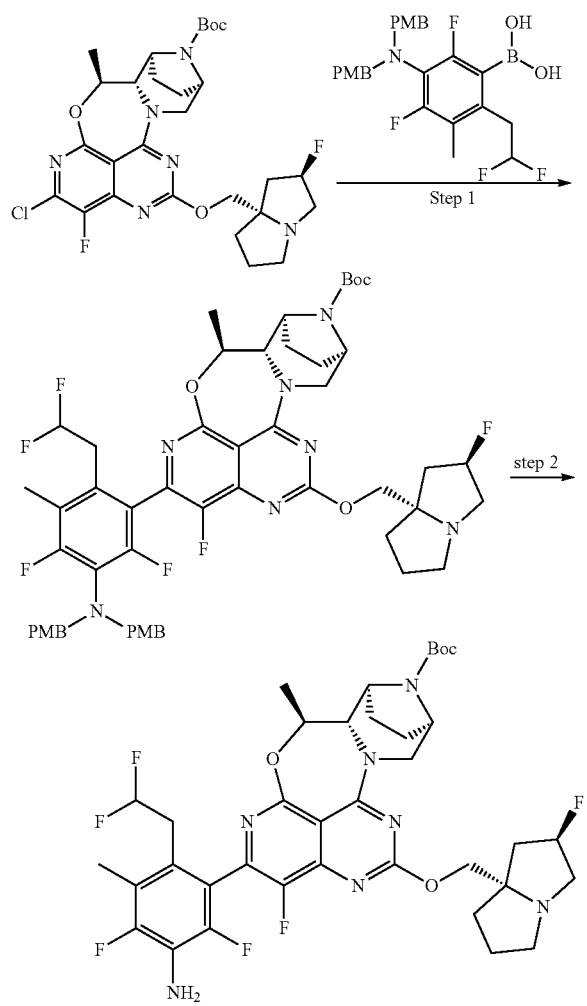

Step 1: tert-Butyl (5S,5aS,6S,9R)-2-(3-(bis(4-methoxybenzyl)amino)-6-(2,2-difluoroethyl)-2,4-difluoro-5-methylphenyl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate Under nitrogen, a solution of tert-butyl (5S,5aS,6S,9R)-2-chloro-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (75.1 mg, 0.130 mmol), (3-(bis(4-methoxybenzyl)amino)-6-(2,2-difluoroethyl)-2,4-difluoro-5-methylphenyl) boronic acid (155 mg, 0.321 mmol, intermediate 124), $K_3PO_4$ (0.19 mL, 1.5 M in $H_2O$) and Xphos Pd G3 (21.4 mg, 0.0300 mmol) in 2-methyl-2-butanol (1 mL) was stirred for 3 h at room temperature. The resulting solution was partitioned between water and EtOAc. The organic layers were dried over anhydrous sodium sulfate and concentrated under vacuum. The residue was purified by flash chromatography on silica gel eluting (gradient: 0%-10% MeOH/DCM) to afford 84.1 mg of the title compound as a yellow oil. LC-MS: (ESI, m/z): $[M+H]^+$=764.

Step 2: 4-(2,2-Difluoroethyl)-2,6-difluoro-3-((5S,5aS,6S,9R)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-5-methylaniline A solution of tert-butyl (5S,5aS,6S,9R)-2-(3-(bis(4-methoxybenzyl) amino)-6-(2,2-difluoroethyl)-2,4-difluoro-5-methylphenyl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (80.1 mg, 0.0800 mmol) in TFA (3 mL) was stirred for 30 min at room temperature. The resulting solution was concentrated under vacuum. The residue was purified by Prep-HPLC (Column: XBridge Prep OBD C18 Column, 30*150 mm, 5 µm; Mobile Phase A: Water(10 mmol/L $NH_4HCO_3$), Mobile Phase B: ACN; Flow rate: 60 mL/min; Gradient: 17% B to 42% B in 9 min, 42% B; Wave Length: 254/220 nm; $R_{T1}$(min): 8.9) to yield 40.5 mg of the title compound as a white solid. LC-MS: (ESI, m/z): $[M+H]^+$=664. $^1H$ NMR (300 MHz, DMSO-$d_6$, ppm): δ 5.80-6.47 (m, 1H), 5.41-5.21 (m, 3H), 5.16-5.07 (m, 1H), 4.78-4.57 (m, 1H), 4.18-3.92 (m, 3H), 3.62-3.54 (m, 1H), 3.45 (d, J=5.8 Hz, 1H), 3.25-3.04 (m, 4H), 3.03-2.98 (m, 2H), 2.85-2.73 (m, 2H), 2.25-2.17 (m, 3H), 2.12-2.09 (m, 1H), 2.02-1.94 (m, 2H), 1.92-1.74 (m, 4H), 1.69-1.54 (m, 3H), 1.52-1.44 (m, 3H).

Each compound in the Table below was prepared following a similar experimental procedure (using appropriately substituted reagents) as described for Example 175.

| Cmpd. No. | $^1H$ NMR | MS $(M + H)^+$ |
|---|---|---|
| 176 | $^1H$ NMR (300 MHz, DMSO-$d_6$, ppm): δ 13.30 (s, 1H), 7.78-7.63 (m, 2H), 5.29 (d, J = 54.3 Hz, 1H), 5.12 (d, J = 12.6 Hz, 1H), 4.59 (s, 1H), 4.15-3.98 (m, 3H), 3.59 (s, 1H), 3.47 (s, 1H), 3.12-3.01 (m, 4H), 2.87-2.78 (m, 2H), 2.54 (s, 3H), 2.16 (d, J = 4.9 Hz, 1H), 2.06-1.95 (m, 2H), 1.91-1.74 (m, 4H), 1.77-1.51 (m, 3H), 1.46 (s, 3H). | 623 |
| 177 | $^1H$ NMR (300 MHz, DMSO-d6) δ 6.48 (d, J = 3.8 Hz, 1H), 6.31 (s, 2H), 5.29 (d, J = 54.4 Hz, 1H), 5.17-5.00 (m, 1H), 4.56 (dd, J = 8.7, 6.2 Hz, 1H), 4.12 (d, J = 10.3 Hz, 1H), 3.99 (dd, J = 18.2, 9.5 Hz, 2H), 3.57 (s, 1H), 3.45 (d, J = 5.7 Hz, 1H), 3.14-2.92 (m, 4H), 2.88-2.77 (m, 1H), 2.29 (s, 3H), 2.23-1.93 (m, 3H), 1.93-1.72 (m, 4H), 1.58 (dd, J = 25.2, 7.1 Hz, 3H), 1.46 (d, J = 6.3 Hz, 3H). | 583 |

-continued

| Cmpd. No. | ¹H NMR | MS (M + H)⁺ |
|---|---|---|
| 178 | ¹H NMR (400 MHz, DMSO-d6, ppm) δ 8.09 (s, 1H), 6.93 (s, 1H), 6.29 (s, 2H), 5.28 (d, J = 54.0 Hz, 1H), 5.09-5.06 (m, 1H), 4.56-4.52 (m, 1H), 4.11-4.08 (m, 1H), 4.02-3.95 (m, 2H), 3.57-3.56 (m, 1H), 3.45-3.43 (m, 1H), 3.13-3.01 (m, 4H), 2.84-2.79 (m, 2H), 2.14-1.98 (m, 3H), 1.86-1.54 (m, 7H), 1.44 (d, J = 6.4 Hz, 3H). | 619 |
| 179 | ¹H NMR (400 MHz, DMSO-d6, ppm) δ 7.44-7.42 (m, 2H), 7.01-6.96 (m, 1H), 6.68 (s, 1H), 6.54-6.48 (m, 2H), 5.27 (d, J = 54.0 Hz, 1H), 5.14-5.11 (m, 1H), 4.57-4.55 (m, 1H), 4.13-3.97 (m, 3H), 3.59-3.44 (m, 2H), 3.10-3.01 (m, 4H), 2.84-2.82 (m, 1H), 2.38-2.36 (m, 1H), 2.28-2.06 (m, 4H), 1.87-1.56 (m, 7H), 1.43 (d, J = 6.4 Hz, 3H), 0.95 (t, J = 7.6 Hz, 1H), 0.78 (t, J = 7.6 Hz, 2H). | 629 |
| 180 | ¹H NMR (300 MHz, DMSO-d6, ppm) δ 6.73-6.46 (m, 1H), 6.38-6.18 (m, 2H), 5.29 (d, J = 54.3 Hz, 1H), 5.02-5.18 (m, 1H), 4.60-4.31 (m, 1H), 4.19-3.86 (m, 3H), 3.61-3.52 (m, 1H), 3.50-3.35 (m, 3H), 3.28 (s, 1H), 3.19 (s, 3H), 3.14-2.95 (m, 4H), 2.90-2.77 (m, 1H), 2.21-2.11 (m, 1H), 2.10-1.95 (m, 2H), 1.92-1.72 (m, 4H), 1.70-1.50 (m, 3H), 1.49-1.36 (m, 3H). | 660 |
| 181 (isomer 1) | ¹H NMR (400 MHz, DMSO-d₆) δ 7.15 (d, J = 13.0 Hz, 1H), 6.82-6.66 (m, 1H), 6.06 (t, J = 4.5 Hz, 1H), 5.38-5.20 (s, 3H), 5.09 (d, J = 12.0 Hz, 1H), 4.61-4.52 (m, 1H), 4.11 (d, J = 10.3 Hz, 1H), 4.05-3.91 (m, 2H), 3.57 (s, 1H), 3.44 (s, 1H), 3.11-3.02 (m, 5H), 2.82 (s, 2H), 2.16 (d, J = 4.9 Hz, 1H), 2.03 (d, J = 12.2 Hz, 2H), 1.82-1.69 (m, 4H), 1.62-1.53 (m, 2H), 1.51-1.49 (m, 1H), 1.44 (d, J = 6.3 Hz, 3H), 1.27-1.15 (m, 3H). | 646 |
| 181 (isomer 2) | ¹H NMR (400 MHz, DMSO-d₆) δ 7.15 (d, J = 13.0 Hz, 1H), 6.82-6.66 (m, 1H), 6.06 (t, J = 4.5 Hz, 1H), 5.38-5.20 (s, 3H), 5.09 (d, J = 12.0 Hz, 1H), 4.61-4.52 (m, 1H), 4.11 (d, J = 10.3 Hz, 1H), 4.09-4.02 (m, 1H), 4.00-3.92 (m, 1H), 3.57 (s, 1H), 3.44 (s, 1H), 3.11-3.06 (m, 2H), 3.14-2.92 (m, 3H), 2.85-2.82 (m, 1H), 2.77 (s, 1H), 2.16 (d, J = 4.9 Hz, 1H), 2.03 (d, J = 12.2 Hz, 2H), 1.82-1.69 (m, 4H), 1.62-1.49 (m, 3H), 1.44 (d, J = 6.3 Hz, 3H), 1.27-1.15 (m, 3H). | 646 |
| 182 | ¹H NMR (300 MHz, DMSO-d6) δ 6.75 (dd, J = 9.3, 2.0 Hz, 1H), 5.44-5.18 (m, 3H), 5.18-5.03 (m, 1H), 4.66-4.48 (m, 1H), 4.15-3.92 (m, 3H), 3.66-3.43 (m, 4H), 3.14-2.97 (m, 4H), 2.91-2.77 (m, 1H), 2.25 (d, J = 6.5 Hz, 3H), 2.20-2.12 (m, 1H), 2.10-1.96 (m, 2H), 1.90-1.73 (m, 5.3 Hz, 4H), 1.70-1.50 (m, 3H), 1.44 (dd, J = 6.4, 2.6 Hz, 3H). | 664 |
| 183 | ¹H NMR (300 MHz, DMSO-d₆, ppm): δ 6.67 (d, J = 8.0 Hz, 1H), 5.88 (s, 2H), 5.36-5.21 (m, 1H), 5.14-5.07 (m, 1H), 4.62-4.50 (m, 1H), 4.11 (d, J = 10.2 Hz, 1H), 4.05-3.96 (m, 2H), 3.73-3.54 (m, 3H), 3.50 (d, J = 6.3 Hz, 1H), 3.14-2.99 (m, 4H), 2.86-2.81 (m, 1H), 2.21-2.12 (m, 1H), 2.11-2.04 (m, 1H), 2.03-1.95 (m, 1H), 1.93-1.76 (m, 4H), 1.73-1.53 (m, 3H), 1.44 (d, J = 6.3 Hz, 3H). | 668 |
| 184 | ¹H NMR (400 MHz, DMSO-d₆, ppm) δ 6.28 (d, J = 35.8 Hz, 3H), 5.29 (d, J = 54.3 Hz, 1H), 5.12-5.06 (m, 1H), 4.58-4.51 (m, 1H), 4.10 (d, J = 10.3 Hz, 1H), 3.99-3.93 (m, 2H), 3.63 (s, 3H), 3.57 (d, J = 5.6 Hz, 1H), 3.45 (d, J = 6.0 Hz, 1H), 3.16-3.07 (m, 2H), 3.02 (d, J = 9.5 Hz, 2H), 2.84 (t, J = 8.0 Hz, 1H), 2.14 (d, J = 4.8 Hz, 1H), 2.06 (s, 1H), 1.98 (d, J = 15.6 Hz, 1H), 1.87-1.81 (m, 4H), 1.71-1.50 (m, 3H), 1.45 (d, J = 6.4 Hz, 3H). | 649 |
| 185 | ¹H NMR (300 MHz, DMSO-d6) δ 6.32 (s, 1H), 6.17 (s, 2H), 5.30 (d, J = 54.4 Hz, 1H), 5.14 (d, J = 13.0 Hz, 1H), 4.62-4.57 (m, 1H), 4.19-3.98 (m, 3H), 3.75 (d, J = 5.1 Hz, 1H), 3.69-3.60 (m, 2H), 3.54 (d, J = 15.1 Hz, 2H), 3.13 (d, J = 10.3 Hz, 3H), 3.03 (s, 1H), 2.85 (d, J = 7.3 Hz, 1H), 2.38 (s, 2H), 2.17 (d, J = 5.0 Hz, 1H), 2.04 (d, J = 12.5 Hz, 2H), 1.91-1.70 (m, 7H), 1.68-1.42 (m, 3H). | 647 |
| 186 | ¹H NMR (400 MHz, DMSO-d₆, ppm): δ 6.84-6.69 (m 1H), 6.37-5.83 (m, 1H), 5.72 (s, 2H), 5.48-5.08 (m, 2H), 4.74-4.57 (m, 1H), 4.22-4.12 (m, 2H), 4.08 (d, J = 10.5 Hz, 1H), 3.98 (s, 1H), 3.90-3.78 (m, 1H), 3.23 (s, 1H), 3.21-3.07 (m, 4H), 3.07 (s, 1H), 2.94-2.80 (m, 1H), 2.22-2.15 (m, 1H), 2.14-1.99 (m, 2H), 1.98-1.60 (m, 7H), 1.45 (d, J = 6.3 Hz, 3H). | 666 |
| 187 | ¹H NMR (400 MHz, DMSO-d₆, ppm): δ 7.12 (d, J = 12.4 Hz, 1H), 6.92-6.74 (m, 1H), 6.43-5.82 (m, 1H), 5.62-5.16 (m, 4H), 4.84-4.60 (m, 1H), 4.47-4.16 (m, 4H), 4.15-4.02 (m, 1H), 3.44-3.31 (m, 4H), 3.15-2.81 (m, 3H), 2.42-2.11 (m, 3H), 2.09-1.69 (m, 8H), 1.49 (d, J = 6.3 Hz, 3H). | 632 |
| 188 | ¹H NMR (400 MHz, DMSO-d₆, ppm): δ 6.67 (t, J = 74.4 Hz, 1H), 6.39 (s, 1H), 6.18 (s, 2H), 5.29 (d, J = 54.3 Hz, 1H), 5.14-5.02 (m, 1H), 4.61-4.44 (m, 1H), 4.11 (d, J = 10.3 Hz, 1H), 4.06-3.89 (m, 2H), 3.57 (s, 1H), 3.49-3.42 (m, 1H), 3.19-2.97 (m, 4H), 2.92-2.70 (m, 2H), 2.30 (s, 3H), 2.24-2.12 (m, 1H), 2.11-2.93 (m, 2H), 1.92-1.73 (m, 4H), 1.72-1.51 (m, 3H), 1.45 (d, J = 6.3 Hz, 3H). | 631 |
| 189 | ¹H NMR (300 MHz, DMSO-d₆) δ 6.30 (d, J = 1.3 Hz, 1H), 6.12-5.81 (m, 3H), 5.43-5.14 (m, 1H), 5.12-5.07 (m, 1H), 4.56-4.51 (m, 1H), 4.16-4.03 (m, 2H), 3.99-3.94 (m, 1H), 3.57 (d, J = 5.3 Hz, 1H), 3.44 (d, J = 5.7 Hz, 1H), 3.19-3.03 (m, 4H), 3.03-2.86 (m, 3H), 2.84-2.81 (m, 1H), 2.37 (s, 3H), 2.16 (d, J = 4.5 Hz, 1H), 2.04-1.98 (m, 2H), 1.91-1.67 (m, 4H), 1.62 (d, J = 9.3 Hz, 3H), 1.44 (d, J = 6.3 Hz, 3H). | 629 |
| 190 | ¹H NMR (300 MHz, DMSO-d₆, ppm): δ 6.71-6.62 (m, 1H), 6.36-5.95 (m, 1H), 5.72 (s, 2H), 5.36-5.18 (m, 1H), 5.13-5.04 (m, 1H), 4.62-4.44 (m, 1H), 4.09 (d, J = 10.3 Hz, 1H), 4.02-3.83 (m, 2H), 3.42-3.59 (m, 3H), 3.13-2.92 (m, 6H), 2.86-2.75 (m, 1H), 2.17-1.96 (m, 3H), 1.92-1.73 (m, 4H), 1.71-1.49 (m, 3H), 1.43 (d, J = 6.3 Hz, 3H). | 650 |

Example 191: Compound 191

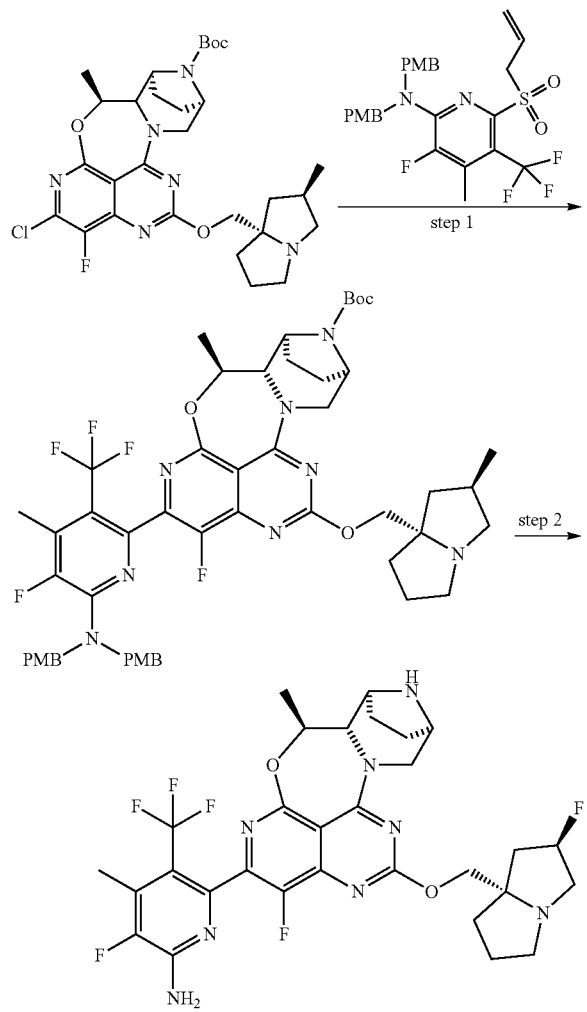

Step 1: tert-Butyl (5S,5aS,6S,9R)-2-(6-(bis(4-methoxybenzyl)amino)-5-fluoro-4-methyl-3-(trifluoromethyl)pyridin-2-yl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate Under nitrogen, a solution of tert-butyl (5S,5aS,6S,9R)-2-chloro-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (60.2 mg, 0.100 mmol), 6-(allylsulfonyl)-3-fluoro-N,N-bis(4-methoxybenzyl)-4-methyl-5-(trifluoromethyl)pyridin-2-amine (82.0 mg, 0.150 mmol, intermediate 129), Pd(OAc)$_2$ (1.14 mg, 0.010 mmol), P(t-Bu)$_2$MeHBF$_4$ (2.52 mg, 0.0100 mmol) and Cs$_2$CO$_3$ (66.2 mg, 0.200 mmol) in 1,4-doxane (1 mL) was stirred for 2 h at 120° C. The resulting reaction was cooled to room and concentrated under vacuum. The residue was purified by C18 column (solvent gradient: 0-90% ACN in water (0.05% NH$_4$HCO$_3$)) to afford 35.1 mg of the title compound as a yellow oil. LC-MS: (ESI, m/z): [M+H]$^+$= 991.

Step 2: 3-Fluoro-6-((5S,5aS,6S,9R)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-4-methyl-5-(trifluoromethyl)pyridin-2-amine A solution of tert-butyl (5S,5aS,6S,9R)-2-(6-(bis(4-methoxybenzyl)amino)-5-fluoro-4-methyl-3-(trifluoromethyl)pyridin-2-yl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (35.1 mg, 0.0400 mmol) in TFA (2 mL) was stirred at 50° C. for 4 h. The solvent was concentrated under vacuum. The residue was purified by Prep-HPLC (Column: XBridge Prep OBD C18 Column, 30*150 mm, 5 µm; Mobile Phase A: Water(10 mmol/L NH$_4$HCO$_3$), Mobile Phase B: ACN; Flow rate: 60 mL/min; Gradient: 31% B to 47% B in 8.5 min; Wave Length: 254/220 n; R$_{T1}$(min): 6.5) to yield 9.30 mg of the title compound as a white solid. LC-MS: (ESI, m/z): [M+H]$^+$=651. $^1$H NMR (300 MHz, DMSO-d$_6$, ppm): δ 7.15 (s, 2H), 5.36-5.18 (m, 1H), 5.07 (d, J=12.7 Hz, 1H), 4.53-4.46 (m, 1H), 4.07-3.96 (m, 3H), 3.55-3.42 (m, 2H), 3.12-3.01 (m, 4H), 2.80-2.71 (m, 2H), 2.35-2.26 (m, 3H), 2.13-2.07 (m, 1H), 2.04-1.96 (m, 2H), 1.95-1.76 (m, 4H), 1.69-1.59 (m, 3H), 1.41 (d, J=6.3 Hz, 3H).

Example 192: Compound 192 was Prepared Following a Similar Experimental Procedure (Using Appropriately Substituted Reagents) as Described for Example 191

$^1$H NMR (300 MHz, DMSO-d6, ppm): δ 7.18 (s, 2H), 5.15-5.07 (m, 1H), 4.54-4.45 (m, 1H), 4.21-4.13 (m, 2H), 3.96 (d, J=8.7 Hz, 1H), 3.58-3.55 (m, 1H), 3.44 (d, J=6.1 Hz, 1H), 3.10-2.97 (m, 3H), 2.83-2.85 (m, 1H), 2.72 (d, J=11.9 Hz, 1H), 2.45-2.23 (m, 3H), 2.13-2.03 (m, 1H), 2.01-1.97 (m, 1H), 1.90 (d, J=13.3 Hz, 1H), 1.85-1.73 (m, 3H), 1.78-1.56 (m, 5H), 1.48-1.38 (m, 4H). MS (M+H)+695.

Example 193: Compound 193

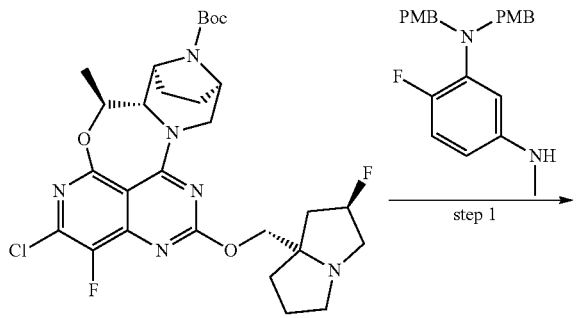

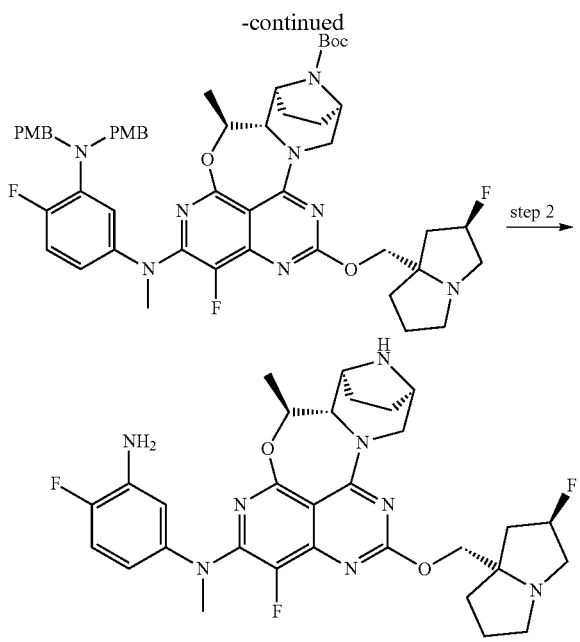

Step 1: tert-Butyl (5S,5aS,6S,9R)-2-((3-(bis(4-methoxybenzyl) amino)-4-fluorophenyl)(methyl) amino)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate Under nitrogen, a solution of tert-butyl (5S,5aS,6S,9R)-2-chloro-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (150 mg, 0.250 mmol), 4-fluoro-$N^3$,$N^3$-bis(4-methoxybenzyl)-$N^1$-methylbenzene-1,3-diamine (190 mg, crude, intermediate 137), $Cs_2CO_3$ (326 mg, 1.00 mmol), $Pd(OAc)_2$ (28.0 mg, 0.125 mmol) and Xantphos (57.8 mg, 0.100 mmol) in 1,4-dioxane (5 mL) was stirred for 1 hour at 110° C. The reaction mixture was cooled to room temperature, diluted with water and extracted with ethyl acetate. The combined organic layers were washed with brine, dried over anhydrous sodium sulfate and concentrated under vacuum. The residue was purified by flash chromatography on silica gel (gradient: 0-10% methanol in dichloromethane) to afford the title compound (110 mg) as a yellow solid. LC-MS: (ESI, m/z): $[M+H]^+$=938.

Step 2: 4-fluoro-$N^1$-((5S,5aS,6S,9R)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-$N^1$-methylbenzene-1,3-diamine A solution of tert-butyl (5S,5aS,6S,9R)-2-((3-(bis(4-methoxybenzyl)amino)-4-fluorophenyl)(methyl)amino)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (100 mg, 0.110 mmol) in 2,2,2-trifluoroacetic acid (10 mL) was stirred for 1 hour at room temperature. The solvent was concentrated under vacuum. The residue was purified by Prep-HPLC (Column: XBridge Prep OBD C18 Column, 30*150 mm, 5 μm; Mobile Phase A: Water (10 mmol/L $NH_4HCO_3$), Mobile Phase B: ACN; Flow rate: 60 mL/min mL/min; Gradient: 17% B to 42% B in 9 min; Wave Length: 254 nm/220 nm; RT1(min): 8.9) to afford the title compound (23.3 mg) as a white solid. LC-MS: (ESI, m/z): $[M+H]^+$=597. $^1$H NMR (300 MHz, DMSO-d6, ppm) δ 7.04-6.82 (m, 1H), 6.58-6.41 (m, 1H), 6.38-6.26 (m, 1H), 5.35 (d, J=53.5 Hz, 1H), 5.16 (s, 2H), 5.07-4.96 (m, 1H), 4.53-4.41 (m, 1H), 4.07-3.84 (m, 3H), 3.62-3.54 (m, 1H), 3.54-3.45 (m, 1H), 3.30 (s, 3H), 3.14-3.02 (m, 2H), 3.01-2.92 (m, 2H), 2.87-2.73 (m, 1H), 2.15-2.04 (m, 1H), 2.04-1.92 (m, 2H), 1.88-1.69 (m, 4H), 1.68-1.51 (m, 3H), 1.44 (d, J=6.3 Hz, 3H).

Example 194: Compound 194

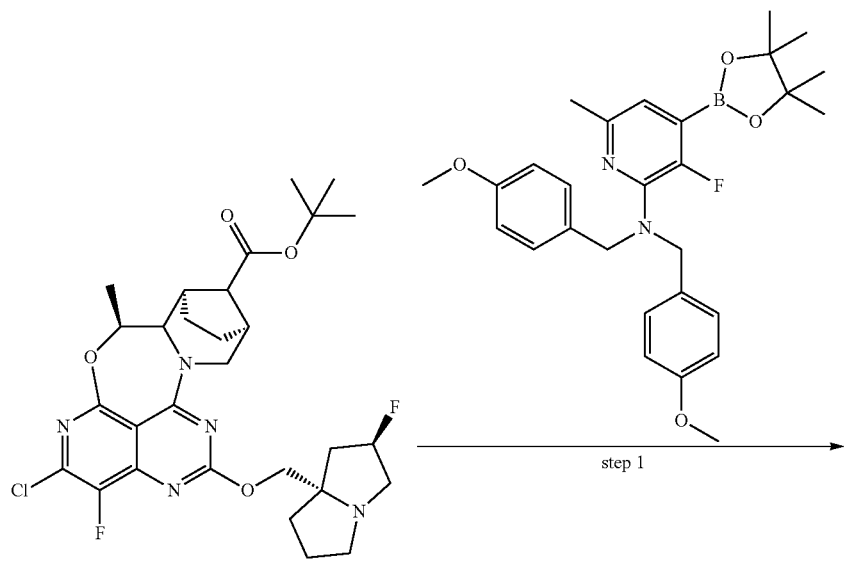

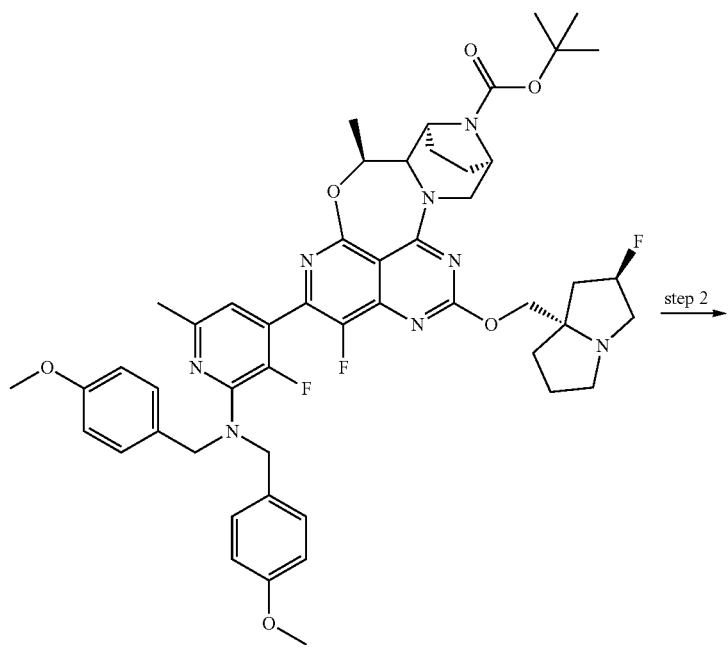
step 2
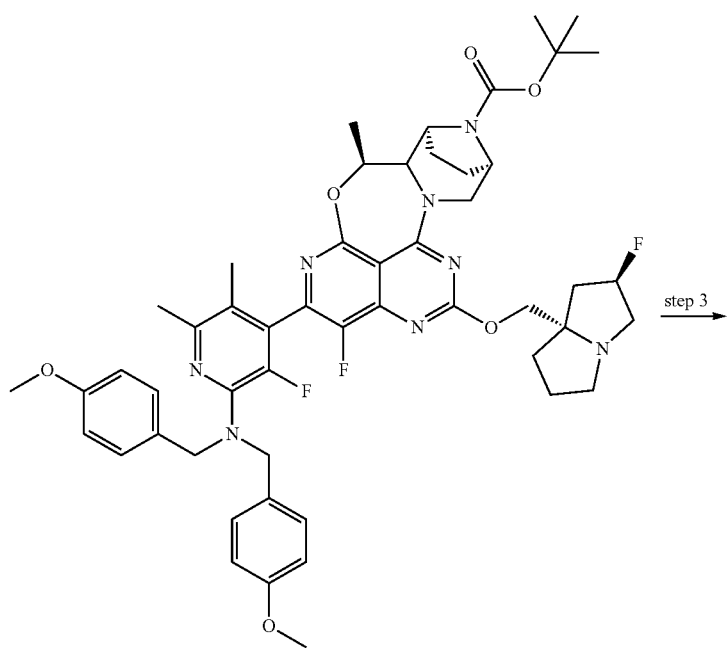
step 3

-continued

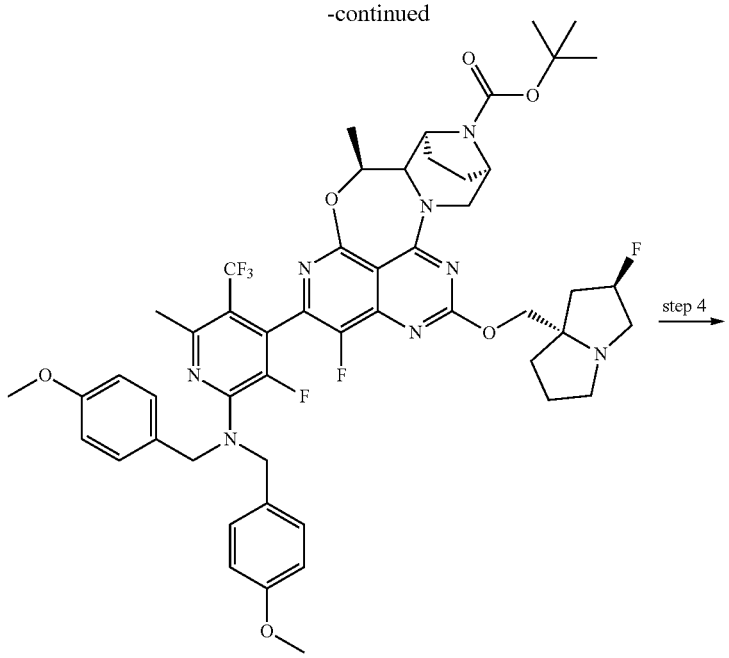

step 4 →

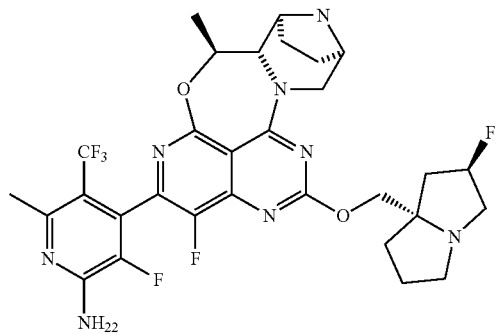

Step 1: tert-Butyl (5S,5aS,6S,9R)-2-(2-(bis(4-methoxybenzyl)amino)-3-fluoro-6-methylpyridin-4-yl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate Under nitrogen, a solution of tert-butyl (5S,5aS,6S,9R)-2-chloro-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (93.9 mg, 0.160 mmol), 3-fluoro-N,N-bis(4-methoxybenzyl)-6-methyl-4-(4,4,5,5-tetramethyl-1,3,2-dioxaborolan-2-yl)pyridin-2-amine (130 mg, 0.263 mmol, intermediate 125), cataCXium A Pd $G_3$ (23.1 mg, 0.0300 mmol) and $K_3PO_4$ (1.5 M in water, 0.3 mL) in tetrahydrofuran (1.5 mL) was stirred at 60° C. for 2 hours. The resulting mixture was filtered. The filtrate was concentrated under reduced pressure. The crude product was diluted with water and extracted with EtOAc. The combined organic layers were washed with brine, dried over anhydrous sodium sulfate and concentrated under reduced pressure. The residue was purified by flash chromatography on silica gel (gradient: 0-100% EtOAc in petroleum ether) to afford the title compound (180 mg) as a yellow solid. LC-MS: (ESI, m/z): $[M+H]^+=923$.

Step 2: tert-Butyl (5S,5aS,6S,9R)-2-(2-(bis(4-methoxybenzyl)amino)-3-fluoro-5-iodo-6-methylpyridin-4-yl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate A solution of tert-butyl (5S,5aS,6S,9R)-2-(2-(bis(4-methoxybenzyl)amino)-3-fluoro-6-methylpyridin-4-yl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (170 mg, 0.180 mmol) and NIS (41.4 mg, 0.180 mmol) in acetic acid (2 mL) was stirred at room temperature for 1 hour. The solvent was concentrated under vacuum. The residue was purified by flash chromatography on silica gel (gradient: 0-5% MeOH in DCM) to afford the title compound (141 mg) as a yellow solid. LC-MS: (ESI, m/z): $[M+H]^+=1049$.

Step 3: tert-Butyl (5S,5aS,6S,9R)-2-(2-(bis(4-methoxybenzyl)amino)-3-fluoro-6-methyl-5-(trifluoromethyl)pyridin-4-yl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate Under nitrogen, to a solution of tert-butyl (5S,5aS,6S,9R)-2-(2-(bis(4-methoxybenzyl) amino)-3-fluoro-5-iodo-6-methylpyridin-4-yl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (120 mg, 0.110 mmol), copper(II) 2,2-difluoro-2-(fluorosulfonyl)acetate (716 mg, 1.72 mmol) and Cu (110 mg, 1.72 mmol) was added N,N-Dimethylacetamide (2 mL) at 0° C. The reaction was stirred at room temperature for 1 hour. The resulting mixture was filtered. The filtrate was concentrated under reduced pressure. The crude product was diluted with water and extracted with EtOAc. The combined organic layers were washed with brine, dried over anhydrous sodium sulfate and concentrated under reduced pressure. The residue was purified by flash chromatography on silica gel (gradient: 0-100% EtOAc in petroleum ether) to afford the title compound (75 mg) as a yellow solid. LC-MS: (ESI, m/z): [M+H]$^+$=991.

Step 4: 3-Fluoro-4-((5S,5aS,6S,9R)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-6-methyl-5-(trifluoromethyl)pyridin-2-amine A solution of tert-butyl (5S,5aS,6S,9R)-2-(2-(bis(4-methoxybenzyl)amino)-3-fluoro-6-methyl-5-(trifluoromethyl)pyridin-4-yl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (70.0 mg, 0.0700 mmol) in 2,2,2-trifluoroacetic acid (2 mL) was stirred at 50° C. for 1 hour. The solvent was concentrated under vacuum. The residue was purified by Prep-HPLC (Column: XBridge Prep OBD C18 Column, 30*150 mm, 5 µm; Mobile Phase A: Water(10 mmol/L NH$_4$HCO$_3$), Mobile Phase B: ACN; Flow rate: 60 mL/min; Gradient: 22% B to 42% B in 10 min; Wave Length: 220 nm; R$_{T1}$(min): 9.7) to afford the title compound (17.1 mg) as a white solid. LC-MS: (ESI, m/z): [M+H]$^+$=651. $^1$H NMR (300 MHz, DMSO-d6) δ 7.18 (d, J=10.9 Hz, 2H), 5.27 (d, J=54.4 Hz, 1H), 5.11-5.03 (m, 1H), 4.63-4.50 (m, 1H), 4.16-3.88 (m, 3H), 3.53 (d, J=17.8 Hz, 1H), 3.43 (s, 1H), 3.16-2.92 (m, 4H), 2.86-2.76 (m, 1H), 2.46-2.38 (m, 3H), 2.14 (d, J=5.2 Hz, 1H), 2.01 (d, J=11.8 Hz, 2H), 1.92-1.48 (m, 7H), 1.42 (d, J=6.3 Hz, 3H).

Example 195: Compound 195

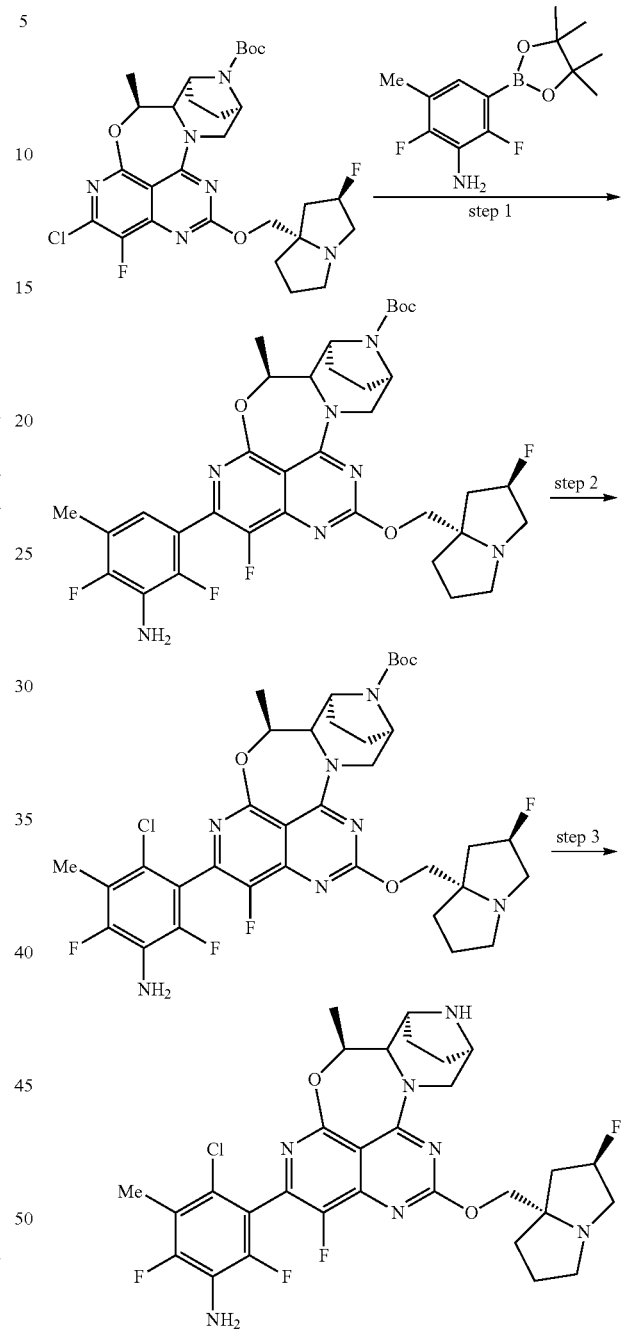

Step 1: tert-Butyl (5S,5aS,6S,9R)-2-(3-amino-2,4-difluoro-5-methylphenyl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate Under nitrogen, a solution of tert-butyl (5S,5aS,6S,9R)-2-chloro-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9- methanonaphtho[1,8-ab]heptalene-14-carboxylate (100 mg, 0.169 mmol), 2,6-difluoro-3-methyl-5-(4,4,5,5-tetramethyl-1,3,2-dioxaborolan-2-yl)aniline (68.1 mg, 0.253 mmol), $K_3PO_4$ (1.5 M in $H_2O$, 0.6 mL, 0.900 mmol) and cataCXium A Pd G3 (24.6 mg, 0.0338 mmol) in tetrahydrofuran (3 mL) was stirred for 3 hours at 90° C. The reaction mixture was diluted with water and extracted with EtOAc. The combined organic layer was dried over anhydrous sodium sulfate and concentrated under vacuum. The residue was purified by flash chromatography on silica gel (gradient: 0-10% methanol in dichloromethane) to afford the title compound (77.0 mg) as a yellow solid. LC-MS: (ESI, m/z): $[M+H]^+=700$.

Step 2: tert-Butyl (5S,5aS,6S,9R)-2-(3-amino-6-chloro-2,4-difluoro-5-methylphenyl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate To a solution of tert-butyl (5S,5aS,6S,9R)-2-(3-amino-2,4-difluoro-5-methylphenyl)-1-fluoro-5-methyl-12-(methylthio)-5a,6,7,8,9,10-hexahydro-5H-4-oxa-3,10a,11,13,14-pentaaza-6,9-methanonaphtho[1,8-ab]heptalene-14-carboxylate (110 mg, 0.157 mmol) in AcOH (10 mL) was added NCS (41.9 mg, 0.314 mmol) at room temperature and the solution was stirred for 24 hours at room temperature. The reaction was quenched with saturated $Na_2S_2O_3$ aqueous solution. The reaction mixture was diluted with water and extracted with EtOAc. The combined organic layers were washed with brine, dried over anhydrous sodium sulfate and concentrated under vacuum. The residue was purified by flash chromatography on silica gel (gradient: 0-10% methanol in dichloromethane) to afford the title compound (110 mg) as a brown solid. LC-MS: (ESI, m/z): $[M+H]^+=734$.

Step 3: 4-Chloro-2,6-difluoro-3-((5S,5aS,6S,9R)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-5-methylaniline To a solution of tert-Butyl (5S,5aS,6S,9R)-2-(3-amino-6-chloro-2,4-difluoro-5-methylphenyl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (110 mg, 0.149 mmol) in dichloromethane (10 mL) was added 2,2,2-trifluoroacetic acid (2 mL) at room temperature, and the mixture was stirred for 1 hour. The solvent was concentrated under vacuum. The residue was purified by Prep-HPLC (Column: XBridge Prep OBD C18 Column, 30*150 mm, 5 μm; Mobile Phase A: Water(10 mmol/L $NH_4HCO_3$), Mobile Phase B: ACN; Flow rate: 60 mL/min; Gradient: 17% B to 42% B in 9 min; Wave Length: 254/220 nm; RT1(min): 8.9) to afford the title compound (29.5 mg) as a white solid. LC-MS: (ESI, m/z): $[M+H]^+=635$. $^1$H NMR (300 MHz, DMSO-d6, ppm) δ 5.52 (d, J=8.2 Hz, 2H), 5.29 (d, J=54.3 Hz, 1H), 5.08 (d, J=12.6 Hz, 1H), 4.67-4.50 (m, 1H), 4.17-3.91 (m, 3H), 3.63-3.41 (m, 2H), 3.18-2.94 (m, 4H), 2.91-2.68 (m, 3H), 2.32-2.19 (m, 3H), 2.19-2.12 (m, 1H), 2.10-1.94 (m, 2H), 1.91-1.73 (m, 4H), 1.73-1.51 (m, 3H), 1.44 (d, J=6.3 Hz, 3H).

Example 196: Compound 196

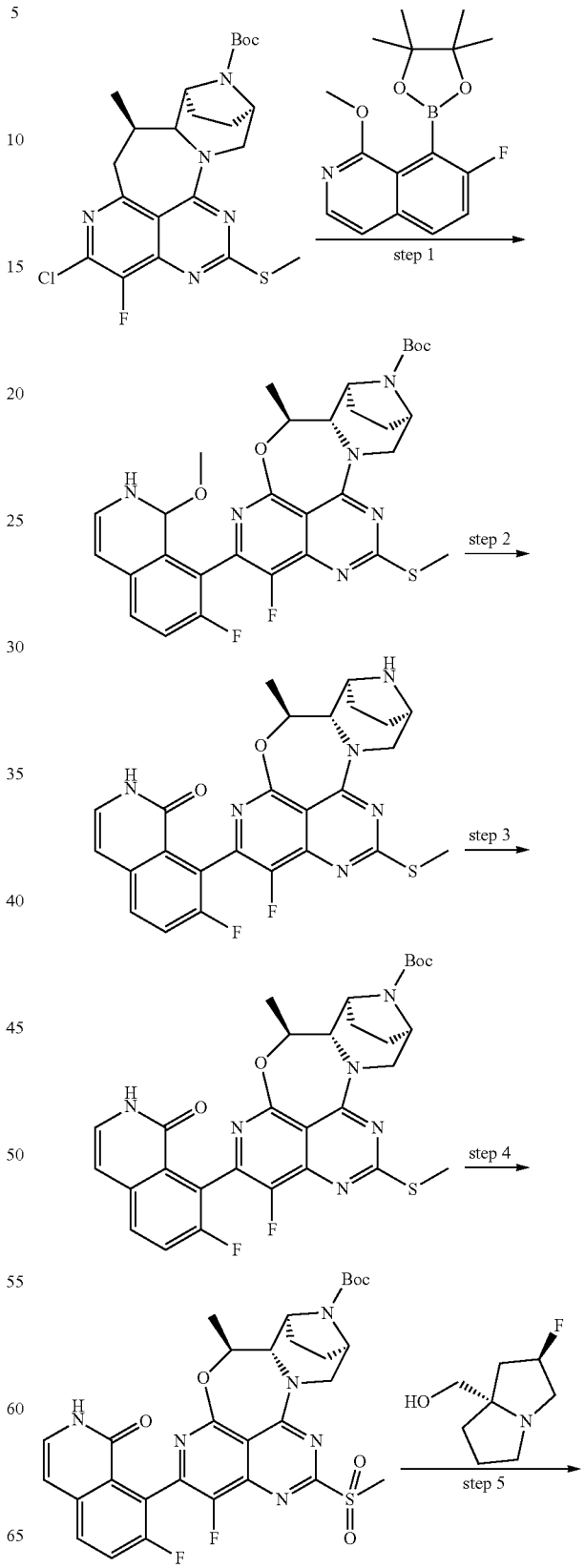

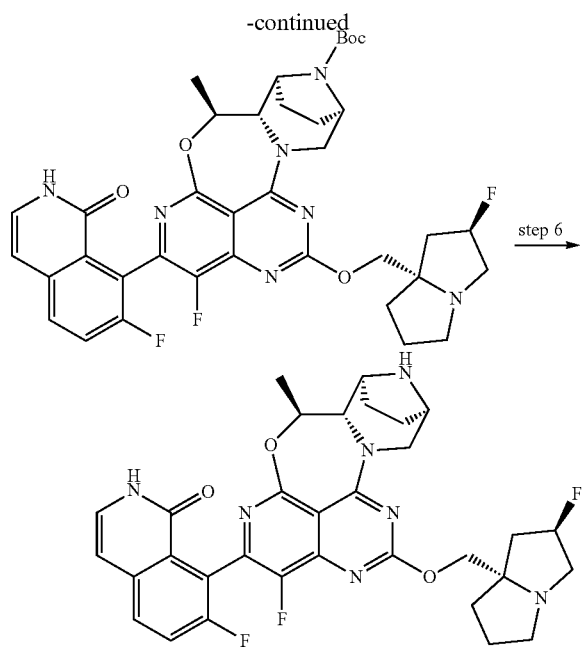

Step 1: tert-Butyl (5S,5aS,6S,9R)-1-fluoro-2-(7-fluoro-1-methoxyisoquinolin-8-yl)-5-methyl-12-(methylthio)-5a,6,7,8,9,10-hexahydro-5H-4-oxa-3,10a,11,13,14-pentaaza-6,9-methanonaphtho[1,8-ab]heptalene-14-carboxylate Under nitrogen, a solution of 7-fluoro-1-methoxy-8-(4,4,5,5-tetramethyl-1,3,2-dioxaborolan-2-yl)isoquinoline (269 mg, 0.890 mmol, intermediate 140), tert-butyl (5S,5aS,6S,9R)-2-chloro-1-fluoro-5-methyl-12-(methylthio)-5a,6,7,8,9,10-hexahydro-5H-4-oxa-3,10a,11,13,14-pentaaza-6,9-methanonaphtho[1,8-ab]heptalene-14-carboxylate (357 mg, 0.740 mmol) and cataCXium A Pd G$_3$ (107 mg, 0.150 mmol) in tetrahydrofuran (7.5 mL) and K$_3$PO$_4$ (1.5 M in water, 1.5 mL) was stirred at 60° C. overnight. The resulting mixture was filtered. The filtrate was concentrated under reduced pressure. The residue was dissolved in EtOAc, washed with water and dried over anhydrous Na$_2$SO$_4$. The solvent was concentrated under vacuum. The residue was purified by flash chromatography on silica gel (gradient: 0-70% EtOAc in petroleum ether) to afford the title compound (255 mg) as a yellow solid. LC-MS: (ESI, m/z): [M+H]$^+$=623.

Step 2: 7-Fluoro-8-((5S,5aS,6S,9R)-1-fluoro-5-methyl-12-(methylthio)-5a,6,7,8,9,10-hexahydro-5H-4-oxa-3,10a,11,13,14-pentaaza-6,9-methanonaphtho[1,8-ab]heptalen-2-yl)isoquinolin-1-ol A solution of tert-butyl (5S,5aS,6S,9R)-1-fluoro-2-(7-fluoro-1-methoxyisoquinolin-8-yl)-5-methyl-12-(methylthio)-5a,6,7,8,9,10-hexahydro-5H-4-oxa-3,10a,11,13,14-pentaaza-6,9-methanonaphtho[1,8-ab]heptalene-14-carboxylate (255 mg, 0.410 mmol) in 40% HBr/AcOH (5 mL) was stirred at 80° C. for 1 hour. Solvent was evaporated and the residue was purified by flash chromatography on silica gel (gradient: 0-20% MeOH in DCM) to afford the title compound (175 mg) as a yellow solid. LC-MS: (ESI, m/z): [M+H]$^+$=509.

Step 3: tert-Butyl (5S,5aS,6S,9R)-1-fluoro-2-(7-fluoro-1-hydroxyisoquinolin-8-yl)-5-methyl-12-(methylthio)-5a,6,7,8,9,10-hexahydro-5H-4-oxa-3,10a,11,13,14-pentaaza-6,9-methanonaphtho[1,8-ab]heptalene-14-carboxylate A solution of 7-fluoro-8-((5S,5aS,6S,9R)-1-fluoro-5-methyl-12-(methylthio)-5a,6,7,8,9,10-hexahydro-5H-4-oxa-3,10a,11,13,14-pentaaza-6,9-methanonaphtho[1,8-ab]heptalen-2-yl)isoquinolin-1-ol (230 mg, 0.450 mmol), Boc$_2$O (197 mg, 0.900 mmol) and DIPEA (875 mg, 6.78 mmol) in dichloromethane (5 mL) was stirred at room temperature for 1 hour. The resulting mixture was diluted with EtOAc, washed with brine and dried over anhydrous sodium sulfate. The solvent was concentrated under vacuum. The residue was purified by flash chromatography on silica gel (gradient: 0-100% EtOAc in petroleum ether) to afford the title compound (148 mg) as a yellow solid. LC-MS: (ESI, m/z): [M+H]$^+$=609.

Step 4: tert-Butyl (5S,5aS,6S,9R)-1-fluoro-2-(7-fluoro-1-hydroxyisoquinolin-8-yl)-5-methyl-12-(methylsulfonyl)-5a,6,7,8,9,10-hexahydro-5H-4-oxa-3,10a,11,13,14-pentaaza-6,9-methanonaphtho[1,8-ab]heptalene-14-carboxylate To a solution of tert-butyl (5S,5aS,6S,9R)-1-fluoro-2-(7-fluoro-1-hydroxyisoquinolin-8-yl)-5-methyl-12-(methylthio)-5a,6,7,8,9,10-hexahydro-5H-4-oxa-3,10a,11,13,14-pentaaza-6,9-methanonaphtho[1,8-ab]heptalene-14-carboxylate (135 mg, 0.220 mmol) in ethyl acetate (2 mL) was added 3-chlorobenzoperoxoic acid (38.3 mg, 0.220 mmol) in EtOAc (0.5 ml) at 0° C. The resulting solution was stirred for 3 h at room temperature. The reaction was quenched with NaHCO$_3$ aqueous and extracted with EtOAc. The combined organic layers were dried over anhydrous sodium sulfate and concentrated under vacuum. The residue was purified by flash chromatography on silica gel (gradient: 0-50% EtOAc/petroleum ether) afford the title compound (136 mg) as a pink solid. LC-MS: (ESI, m/z): [M+H]$^+$=641.

Step 5: tert-Butyl (5S,5aS,6S,9R)-1-fluoro-2-(7-fluoro-1-oxo-1,2-dihydroisoquinolin-8-yl)-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate To a solution of tert-butyl (5S,5aS,6S,9R)-1-fluoro-2-(7-fluoro-1-hydroxyisoquinolin-8-yl)-5-methyl-12-(methylsulfonyl)-5a,6,7,8,9,10-hexahydro-5H-4-oxa-3,10a,11,13,14-pentaaza-6,9-methanonaphtho[1,8-ab] heptalene-14-carboxylate(125 mg, 0.200 mmol) and ((2R,7aS)-2-fluorotetrahydro-1H-pyrrolizin-7a(5H)-yl)methanol (37.2 mg, 0.230 mmol) in toluene (1.5 mL) was added t-BuONa (37.4 mg, 0.390 mmol) at 0° C. The reaction was stirred at room temperature for 2 hours. Then the solvent was evaporated and the residue was purified by C18 column (solvent gradient: 0-100% ACN in water (0.05% NH$_4$HCO$_3$)) to afford the title compound (62 mg) as a yellow solid. LC-MS: (ESI, m/z): [M+H]$^+$=720.

Step 6: 7-Fluoro-8-((5S,5aS,6S,9R)-1-fluoro-12-(((2R,7aS)-2-fluorotetrahydro-1H-pyrrolizin-7a(5H)-yl) methoxy)-5-methyl-5a,6,7,8,9,10-hexahydro-5H-4-oxa-3,10a,11,13,14-pentaaza-6,9-methanonaphtho[1,8-ab]heptalen-2-yl)isoquinolin-1(2H)-one A solution of tert-butyl (5S,5aS,6S,9R)-1-fluoro-2-(7-fluoro-1-oxo-1,2-dihydroisoquinolin-8-yl)-12-(((2R,7aS)-2- fluorotetrahydro-1H-pyrrolizin-7a(5H)-yl) methoxy)-5-methyl-5a,6,7,8,9,10-hexahydro-5H-4-oxa-3,10a,11,13,14-pentaaza-6,9-methanonaphtho[1,8-ab]heptalene-14-carboxylate (62.0 mg, 0.0900 mmol) in 2,2,2-trifluoroacetic acid (2 mL) and DCM (4 mL) was stirred at room for 1 hour. The solvent was concentrated under vacuum. The residue was purified by Prep-HPLC (Column: XBridge Prep OBD C18 Column, 30*150 mm, 5 μm; Mobile Phase A: Water(10 mmol/L NH$_4$HCO$_3$), Mobile Phase B: ACN; Flow rate: 60 mL/min; Gradient: 17% B to 42% B in 9 min, 42% B; Wave Length: 254/220 nm; RT1(min): 8.9) to afford the title compound (19.9 mg) as a light yellow solid. LC-MS: (ESI, m/z): [M+H]$^+$=620. $^1$H NMR (300 MHz, DMSO-d6) δ 11.18-11.04 (m, 1H), 7.88 (dd, J=8.9, 5.4 Hz, 1H), 7.79-7.61 (m, 1H), 7.24-7.09 (m, 1H), 6.64 (dd, J=7.1, 5.0 Hz, 1H), 5.38-5.02 (m, 2H), 4.57-4.41 (m, 1H), 4.18-3.86 (m, 3H), 3.57 (s, 1H), 3.44 (t, J=6.6 Hz, 1H), 3.21-2.93 (m, 4H), 2.81 (q, J=8.0 Hz, 2H), 2.16 (dd, J=12.2, 8.2 Hz, 1H), 2.10-1.95 (m, 2H), 1.99-1.46 (m, 7H), 1.41 (t, J=6.3 Hz, 3H).

Example 197: Compound 197

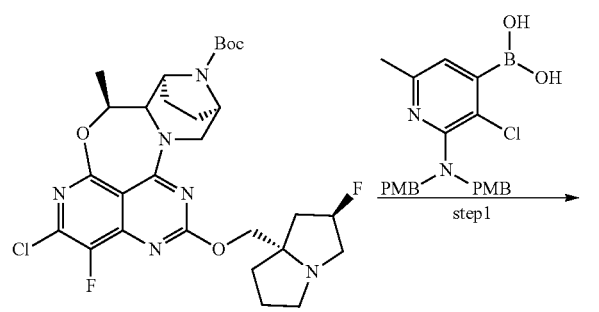

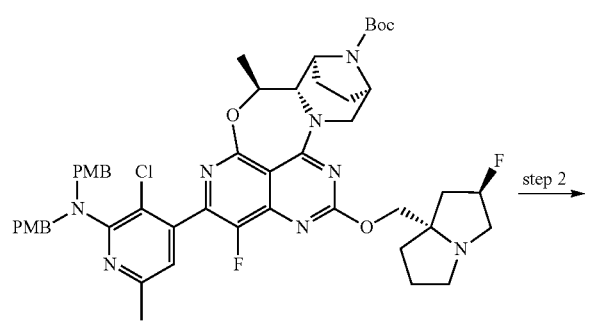

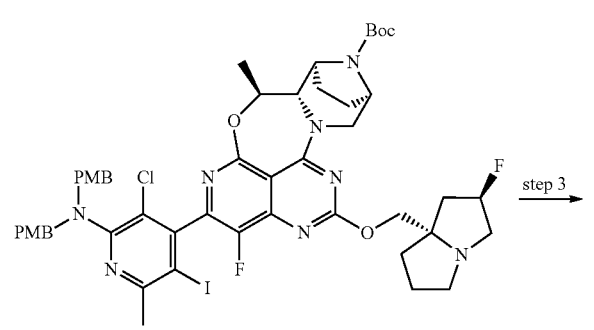

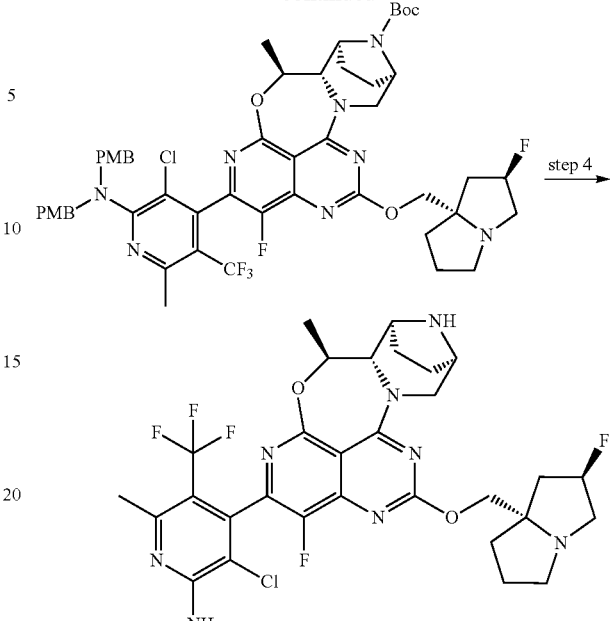

Step 1: tert-Butyl (5S,5aS,6S,9R)-2-(2-(bis(4-methoxybenzyl)amino)-3-chloro-6-methylpyridin-4-yl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate Under nitrogen, a solution of tert-butyl (5S,5aS,6S,9R)-2-chloro-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (300 mg, 0.620 mmol), (2-(bis(4-methoxybenzyl)amino)-3-chloro-6-methylpyridin-4-yl)boronic acid (1.01 g, 2.34 mmol, intermediate 141), K$_3$PO$_4$ (1.0 mL, 1.5 M in H$_2$O) and cataCXium A Pd G3 (50.1 mg, 0.0700 mmol) in THF (5 mL) was stirred for 1.5 h at 60° C. The resulting solution was partitioned between water and EtOAc. The separated organic layer was dried over anhydrous sodium sulfate and concentrated under vacuum. The residue was purified by flash chromatography on silica gel (gradient: 0-12% MeOH/DCM) to afford 280 mg of the title compound as a white solid. LC-MS: (ESI, m/z): [M+H]$^+$=939.

Step 2: tert-Butyl (5S,5aS,6S,9R)-2-(2-(bis(4-methoxybenzyl)amino)-3-chloro-5-iodo-6-methylpyridin-4-yl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate Under nitrogen, a solution of tert-butyl (5S,5aS,6S,9R)-2-(2-(bis(4-methoxybenzyl) amino)-3-chloro-6-methylpyridin-4-yl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (270 mg, 0.290 mmol) and NIS (97.0 mg, 0.430 mmol) in AcOH (3 mL) was stirred for 25 min at room temperature. The reaction was quenched with Na₂S₂O₃ aqueous and extracted with EtOAc. The combined organic layers were dried over anhydrous sodium sulfate and concentrated under vacuum. The residue was purified by flash chromatography on silica gel (gradient: 0-13% MeOH/DCM) to afford 281 mg of the title compound as a yellow solid. LC-MS: (ESI, m/z): [M+H]⁺=1065.

Step 3: tert-Butyl (5S,5aS,6S,9R)-2-(2-(bis(4-methoxybenzyl)amino)-3-chloro-6-methyl-5-(trifluoromethyl)pyridin-4-yl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate Under nitrogen, to a mixture of tert-butyl (5S,5aS,6S,9R)-2-(2-(bis(4-methoxybenzyl)amino)-3-chloro-5-iodo-6-methylpyridin-4-yl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (270 mg, 0.250 mmol), Cu powder (162 mg, 2.53 mmol) and Cu(O₂CCF₂SO₂F)₂ (1.06 g, 2.54 mmol) was added DMF (4 mL) at 0° C., and the mixture was stirred for 1 h at room temperature. The resulting mixture was diluted with EtOAc, washed with water. The organic layers were dried over anhydrous sodium sulfate and concentrated under vacuum. The residue was purified by flash chromatography on silica gel (gradient: 0-13% MeOH/DCM) to afford 196 mg of the title compound as a yellow solid. LC-MS: (ESI, m/z): [M+H]⁺=1007.

Step 4: 3-Chloro-4-((5S,5aS,6S,9R)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-6-methyl-5-(trifluoromethyl)pyridin-2-amine A solution of tert-butyl (5S,5aS,6S,9R)-2-(2-(bis(4-methoxybenzyl)amino)-3-chloro-6-methyl-5-(trifluoromethyl)pyridin-4-yl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (180 mg, 0.180 mmol) in TFA (4 mL) was stirred at 50° C. for 1.5 h. The solvent was concentrated under vacuum. The crude product was purified by Prep-HPLC (conditions: Column: XBridge Prep OBD C18 Column, 30×150 mm, 5 μm; Mobile Phase A: Water (10 mmol/L NH₄HCO₃), Mobile Phase B: ACN; Flow rate: 60 mL/min; Gradient: 17% B to 42% B in 9 min; Wave Length: 254/220 nm; $R_{T1}$ (min): 8.9) to afford 11.1 mg of the title compound as a white solid. LC-MS: (ESI, m/z): [M+H]⁺=668 LC-MS: (ESI, m/z): [M+H]⁺=668 ¹H NMR (400 MHz, DMSO-d₆) δ 7.28 (s, 2H), 5.29 (d, J=54.5 Hz, 1H), 5.15-4.91 (m, 1H), 4.55 (d, J=2.1 Hz, 1H), 4.10 (d, J=10.2 Hz, 1H), 4.01 (d, J=10.4 Hz, 2H), 3.51 (d, J=53.3 Hz, 2H), 3.29-2.91 (m, 4H), 2.83 (d, J=8.1 Hz, 2H), 2.48 (d, J=2.5 Hz, 2H), 2.09 (d, J=30.1 Hz, 2H), 2.00 (d, J=6.3 Hz, 1H), 1.93-1.69 (m, 4H), 1.61 (d, J=54.3 Hz, 2H), 1.52-1.46 (m, 1H), 1.44 (d, J=6.3 Hz, 3H).

Example 198: Compound 198

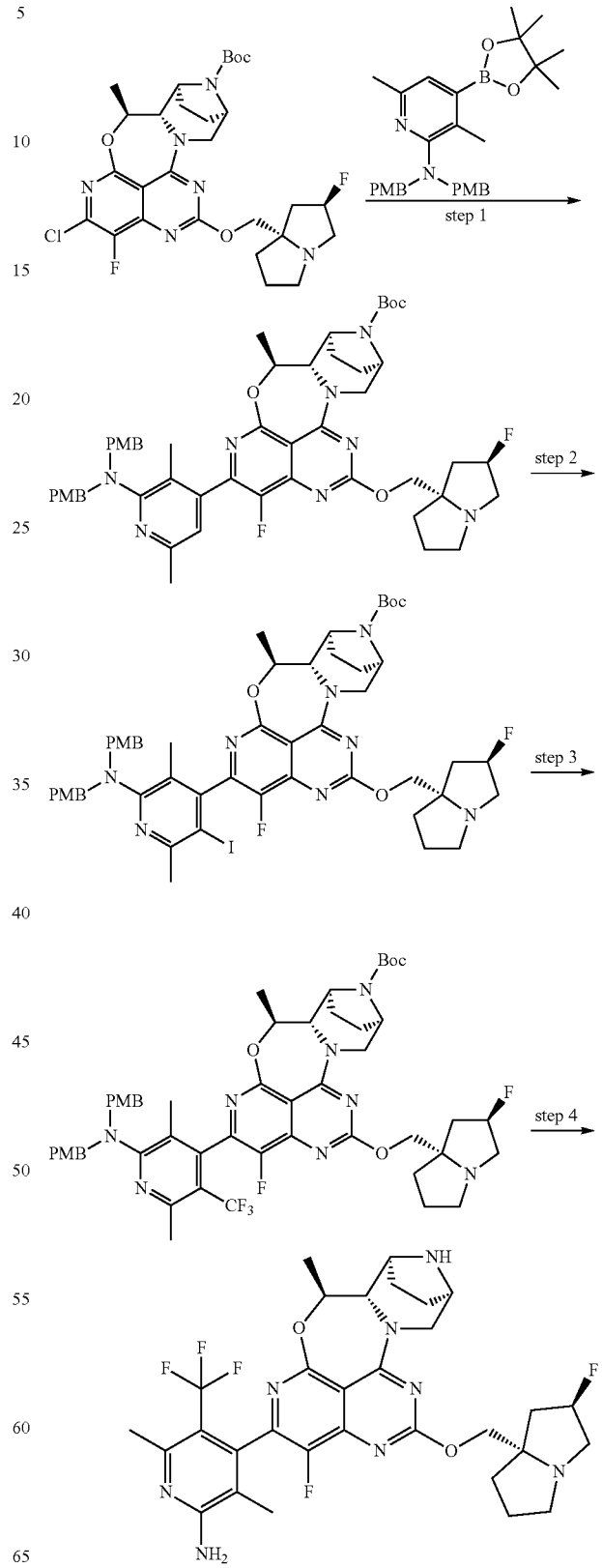

Step 1: tert-Butyl (5S,5aS,6S,9R)-2-(2-(bis(4-methoxybenzyl)amino)-3,6-dimethylpyridin-4-yl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate Under nitrogen, a solution of N,N-bis(4-methoxybenzyl)-3,6-dimethyl-4-(4,4,5,5-tetramethyl-1,3,2-dioxaborolan-2-yl)pyridin-2-amine (417 mg, 0.850 mmol, intermediate 142), tert-butyl (5S,5aS,6S,9R)-2-chloro-1-fluoro-12-(((2R,7aS)-2-fluorotetrahydro-1H-pyrrolizin-7a(5H)-yl) methoxy)-5-methyl-5a,6,7,8,9,10-hexahydro-5H-4-oxa-3,10a,11,13,14-pentaaza-6,9-methanonaphtho[1,8-ab]heptalene-14-carboxylate (251 mg, 0.420 mmol), cataCXium A Pd G3 (69.2 mg, 0.0900 mmol) and K$_3$PO$_4$ (3 mL, 1.5 M in H$_2$O) in THF (15 mL) was stirred for 3 hours at 60° C. The resulting mixture was diluted with ethyl acetate and washed with water. The organic layer was dried over anhydrous sodium sulfate and concentrated under vacuum. The residue was purified by flash chromatography on silica gel (gradient: 0-15% MeOH/DCM) to afford 286 mg of the title compound as a yellow solid. LC-MS: (ESI, m/z): [M+H]$^+$=919.

Step 2: tert-Butyl (5S,5aS,6S,9R)-2-(2-(bis(4-methoxybenzyl) amino)-5-iodo-3,6-dimethylpyridin-4-yl)-1-fluoro-12-(((2R,7aS)-2-fluorotetrahydro-1H-pyrrolizin-7a(5H)-yl) methoxy)-5-methyl-5a,6,7,8,9,10-hexahydro-5H-4-oxa-3,10a,11,13,14-pentaaza-6,9-methanonaphtho[1,8-ab]heptalene-14-carboxylate A solution of tert-butyl (5S,5aS,6S,9R)-2-(2-(bis(4-methoxybenzyl) amino)-3,6-dimethylpyridin-4-yl)-1-fluoro-12-(((2R,7aS)-2-fluorotetrahydro-1H-pyrrolizin-7a (5H)-yl)methoxy)-5-methyl-5a,6,7,8,9,10-hexahydro-5H-4-oxa-3,10a,11,13,14-pentaaza-6,9-methanonaphtho[1,8-ab] heptalene-14-carboxylate (356 mg, 0.390 mmol) and NIS (123 mg, 0.550 mmol) in AcOH (3 mL) was stirred at room temperature for 0.5 h. The solution was quenched by Na$_2$S$_2$O$_3$ aqueous and extracted with EtOAc. The combined organic layers were dried over anhydrous sodium sulfate and concentrated under vacuum. The residue was purified by flash chromatography on silica gel (gradient: 0-15% MeOH/DCM) to afford 382 mg of the title compound as white solid. LC-MS: (ESI, m/z): [M+H]$^+$=1045.

Step 3: tert-Butyl (5S,5aS,6S,9R)-2-(2-(bis(4-methoxybenzyl)amino)-3,6-dimethyl-5-(trifluoromethyl)pyridin-4-yl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab] heptalene-14-carboxylate Under nitrogen, to a mixture of tert-butyl (5S,5aS,6S,9R)-2-(2-(bis(4-methoxybenzyl)amino)-5-iodo-3,6-dimethylpyridin-4-yl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (305 mg, 0.290 mmol), Cu(O$_2$CCF$_2$SO$_2$F)$_2$ (608 mg, 1.46 mmol) and Cu powder (149 mg, 2.33 mmol) was added DMF (15 mL) at 0° C., and the mixture was stirred at room temperature for 1.5 h. The resulting reaction was diluted with EtOAc, washed with water. The organic layers were dried over anhydrous sodium sulfate and concentrated under vacuum. The residue was purified by flash (0-70% EtOAc in petroleum ether and then 0-15% MeOH/DCM) to afford 289 mg of the title compound as a white solid. LC-MS: (ESI, m/z): [M+H]$^+$=987.

Step 4: 4-((5S,5aS,6S,9R)-1-Fluoro-12-(((2R,7aS)-2-fluorotetrahydro-1H-pyrrolizin-7a(5H)-yl) methoxy)-5-methyl-5a,6,7,8,9,10-hexahydro-5H-4-oxa-3,10a,11,13,14-pentaaza-6,9-methanonaphtho[1,8-ab]heptalen-2-yl)-3,6-dimethyl-5-(trifluoromethyl) pyridin-2-amine A solution of tert-butyl (5S,5aS,6S,9R)-2-(2-(bis(4-methoxybenzyl)amino)-3,6-dimethyl-5-(trifluoromethyl) pyridin-4-yl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (286 mg, 0.290 mmol) in TFA (5 mL) was stirred at 50° C. for 3 h. The solvent was concentrated under vacuum. The crude product was purified by Prep-HPLC with the following conditions: (Column: XBridge Prep OBD C18 Column, 30×150 mm, 5 μm; Mobile Phase A: Water (10 mmol/L NH$_4$HCO$_3$), Mobile Phase B: ACN; Flow rate: 60 mL/min mL/min; Gradient: 23% B to 48% B in 9 min; Wave Length: 254 nm/220 nm; R$_{T1}$(min): 8.7) to afford 25.8 mg of the title compound as a white solid. LC-MS: (ESI, m/z): [M+H]$^+$=647. $^1$H NMR (400 MHz, DMSO-d$_6$) δ 6.63 (d, J=13.2 Hz, 2H), 5.42-5.18 (m, 1H), 5.12-5.04 (m, 1H), 4.54-4.49 (m, 1H), 4.13-4.07 (m, 1H), 4.06-3.87 (m, 2H), 3.58 (d, J=5.6 Hz, 1H), 3.45 (d, J=6.1 Hz, 1H), 3.16-2.98 (m, 4H), 2.89-2.77 (m, 2H), 2.45-2.37 (m, 3H), 2.18-1.93 (m, 3H), 1.91-1.85 (m, 3H), 1.79 (d, J=22.4 Hz, 3H), 1.71-1.60 (m, 2H), 1.57 (s, 2H), 1.43 (d, J=6.3 Hz, 3H).

Examples 199 and 200: Compound 199 and 200

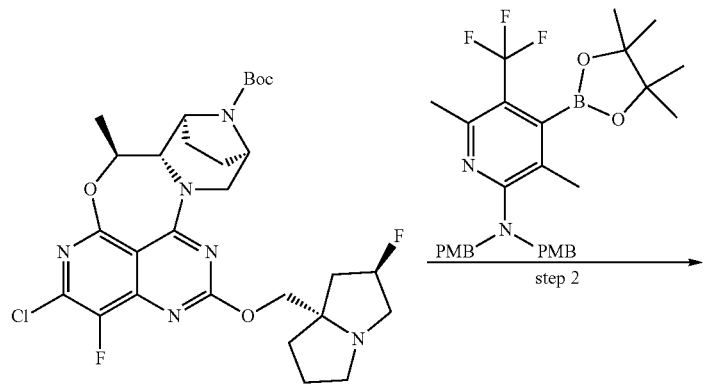

-continued
765 766
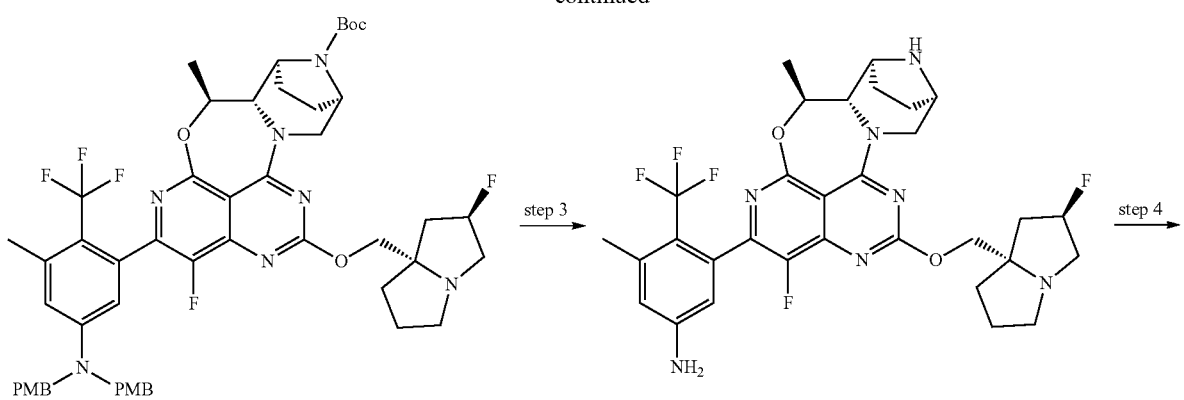
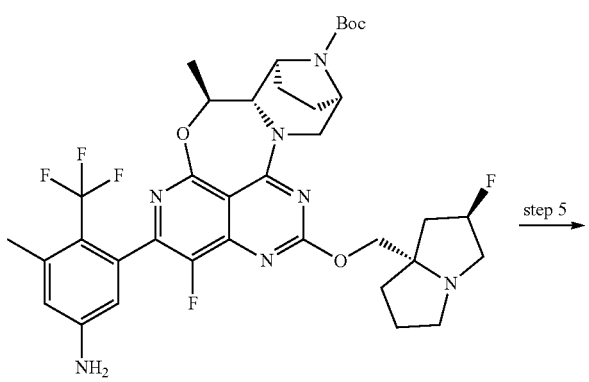
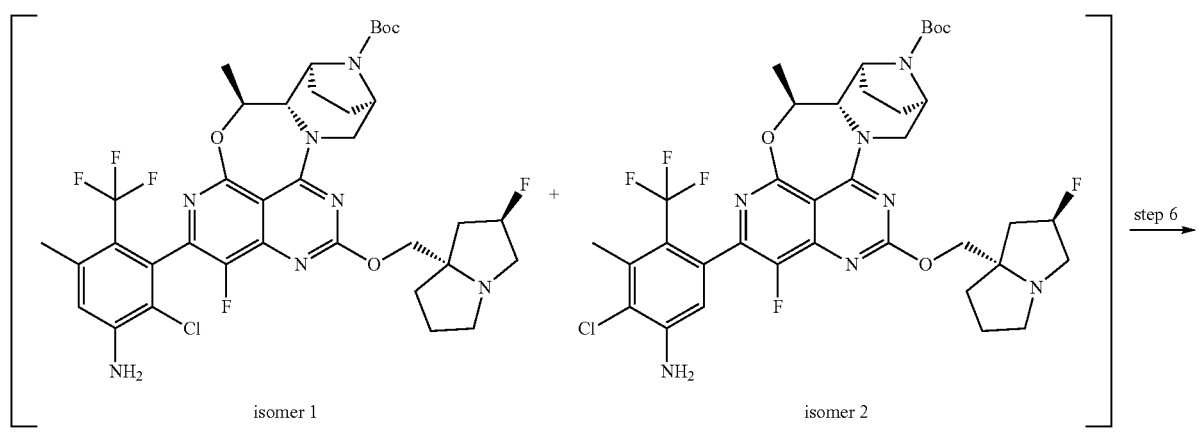
isomer 1      isomer 2
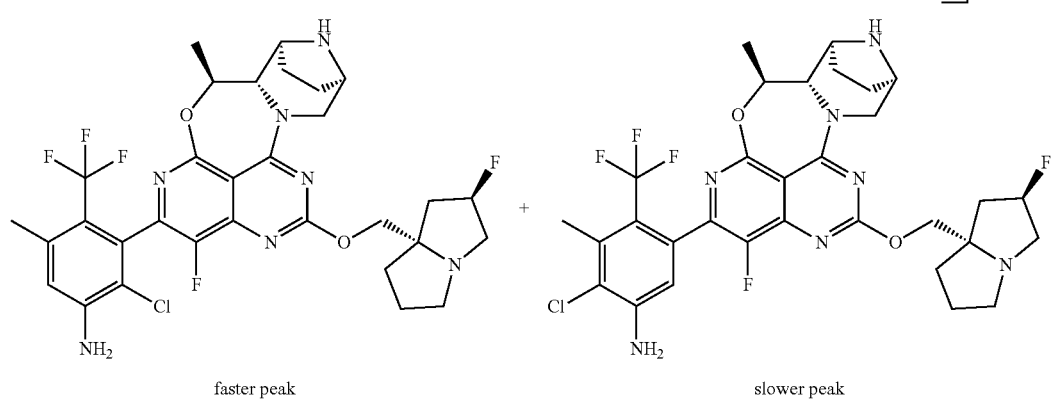
faster peak      slower peak Step 1: tert-Butyl (5S,5aS,6S,9R)-2-(5-(bis(4-methoxybenzyl)amino)-3-methyl-2-(trifluoromethyl)phenyl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate Under nitrogen, a mixture of tert-butyl (5S,5aS,6S,9R)-2-chloro-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (190 mg, 0.320 mmol), N,N-bis(4-methoxybenzyl)-3-methyl-5-(4,4,5,5-tetramethyl-1,3,2-dioxaborolan-2-yl)-4-(trifluoromethyl)aniline (434 mg, 0.800 mmol, intermediate 143), $K_3PO_4$ (1.5 M in $H_2O$, 1.1 mL, 1.65 mmol) and cataCXium A Pd G3 (46.6 mg, 0.0640 mmol) in tetrahydrofuran (5.5 mL) was stirred for 1 hour at 60° C. The reaction mixture was diluted with water and extracted with EtOAc. The combined organic layer was dried over anhydrous sodium sulfate and concentrated under vacuum. The residue was purified by flash chromatography on silica gel (gradient: 0-10% methanol in dichloromethane) to afford the title compound (354 mg) as a yellow solid. LC-MS: (ESI, m/z): $[M+H]^+$=972.

Step 2: 3-((5S,5aS,6S,9R)-1-Fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-5-methyl-4-(trifluoromethyl)aniline A solution of tert-butyl (5S,5aS,6S,9R)-2-(5-(bis(4-methoxybenzyl) amino)-3-methyl-2-(trifluoromethyl)phenyl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (354 mg, 0.364 mmol) in 2,2,2-trifluoroacetic acid (20 mL) was stirred for 1 hour at room temperature. The solvent was concentrated under vacuum. The residue was neutralized by saturated $NaHCO_3$ aqueous solution and extracted with ethyl acetate. The combined organic layer was dried over anhydrous sodium sulfate and concentrated under vacuum to afford the title compound (240 mg, crude) as a yellow solid. LC-MS: (ESI, m/z): $[M+H]^+$=632.

Step 3: tert-Butyl (5S,5aS,6S,9R)-2-(5-amino-3-methyl-2-(trifluoromethyl)phenyl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate To a solution of 3-((5S,5aS,6S,9R)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-5-methyl-4-(trifluoromethyl)aniline (220 mg, 0.350 mmol) and DIPEA (90.0 mg, 0.700 mmol) in dichloromethane (5 mL) was added a solution of $(Boc)_2O$ (91.3 mg, 0.420 mmol) in dichloromethane (1 mL) at 0° C., and the mixture was stirred at room temperature for 1 hour. The reaction mixture was diluted with water and extracted with ethyl acetate. The combined organic layers were washed with brine, dried over anhydrous sodium sulfate and concentrated under vacuum. The residue was purified by flash chromatography on silica gel (gradient: 0-10% methanol in dichloromethane) to afford the title compound (181 mg) as a yellow solid. LC-MS: (ESI, m/z): $[M+H]^+$=732.

Step 4: Mixture of tert-Butyl (5S,5aS,6S,9R)-2-(3-amino-2-chloro-5-methyl-6-(trifluoromethyl)phenyl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (isomer 1) & (isomer 2)

To a solution of tert-butyl (5S,5aS,6S,9R)-2-(5-amino-3-methyl-2-(trifluoromethyl)phenyl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (160 mg, 0.220 mmol) in acetic acid (2 mL) was added NCS (35.1 mg, 0.260 mmol) at room temperature, and the mixture was stirred for 48 hours at room temperature. The reaction was quenched by saturated $Na_2S_{203}$ aqueous solution. The reaction mixture was diluted with water and extracted with ethyl acetate. The combined organic layers were washed with brine, dried over anhydrous sodium sulfate and concentrated under vacuum. The residue was purified by flash chromatography on silica gel (gradient: 0-10% methanol in dichloromethane) to afford the title compound (136 mg, mixture of isomer 1 and isomer 2) as a yellow solid. LC-MS: (ESI, m/z): $[M+H]^+$=766.

Step 5: 2-Chloro-3-((5S,5aS,6S,9R)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-5-methyl-4-(trifluoromethyl)aniline (199) and 2-chloro-5-((5S,5aS,6S,9R)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-3-methyl-4-(trifluoromethyl)aniline (200)

To a solution of mixture of tert-butyl (5S,5aS,6S,9R)-2-(3-amino-2-chloro-5-methyl-6-(trifluoromethyl)phenyl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate and tert-butyl (5S,5aS,6S,9R)-2-(5-amino-4-chloro-3-methyl-2-(trifluoromethyl)phenyl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (136 mg, 0.177 mmol) in dichloromethane (5 mL) was added 2,2,2-trifluoroacetic acid (1 mL) at room temperature, and the mixture was stirred for 1 hour. The solvent was concentrated under vacuum. The residue was purified by Prep-HPLC (Column: XBridge Prep OBD C18 Column, 30*150 mm, 5 μm; Mobile Phase A: Water (10 mmol/L $NH_4HCO_3$), Mobile Phase B: ACN; Flow rate: 60 mL/min; Gradient: 17% B to 42% B in 9 min, 42% B; Wave Length: 254/220 nm; RT1(min): 8.9; RT2(min): 9.0) to afford 199 (19.0 mg, the faster peak) and 200 (24.2 mg, the slower peak) as white solids.

199: LC-MS: (ESI, m/z): $[M+H]^+$=666 $^1H$ NMR (300 MHz, DMSO-d6, ppm) δ 6.86 (s, 1H), 6.18 (d, J=10.0 Hz, 2H), 5.30 (d, J=54.4 Hz, 1H), 5.11 (d, J=13.0 Hz, 1H), 4.69-4.49 (m, 1H), 4.14-3.99 (m, 3H), 3.72-3.68 (m, 1H), 3.59-3.53 (m, 1H), 3.15-3.05 (m, 3H), 3.04-2.99 (m, 1H), 2.92-2.77 (m, 2H), 2.42-2.32 (m, 3H), 2.20-2.15 (m, 1H), 2.10-2.00 (m, 2H), 1.96-1.56 (m, 7H), 1.44 (d, J=6.3 Hz, 3H).

200: LC-MS (ESI, m/z): [M+H]$^+$=666 $^1$H NMR (300 MHz, DMSO-d6, ppm) δ 6.71-6.50 (m, 1H), 6.24 (s, 2H), 5.29 (d, J=54.5 Hz, 1H), 5.15-5.03 (m, 1H), 4.59-4.49 (m, 1H), 4.15-3.91 (m, 3H), 3.61-3.54 (m, 1H), 3.48-3.42 (m, 1H), 3.18-2.98 (m, 4H), 2.90-2.71 (m, 2H), 2.46 (s, 3H), 2.23-2.11 (m, 1H), 2.11-1.94 (m, 2H), 1.93-1.73 (m, 4H), 1.73-1.51 (m, 3H), 1.44 (d, J=6.3 Hz, 3H).

Example 201: Compound 201

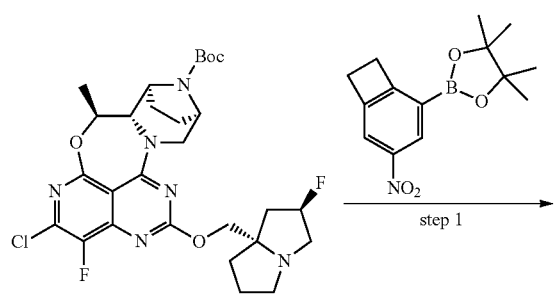

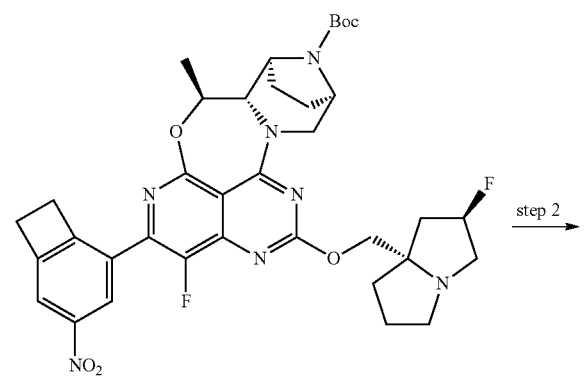

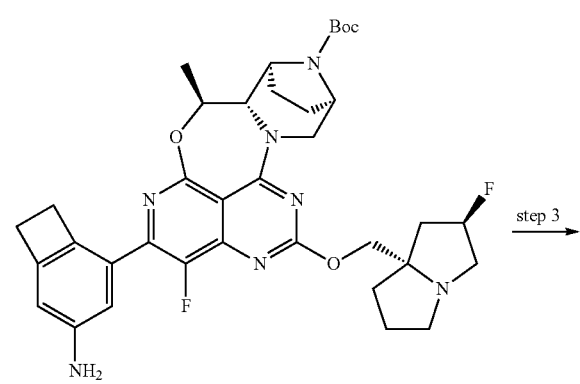

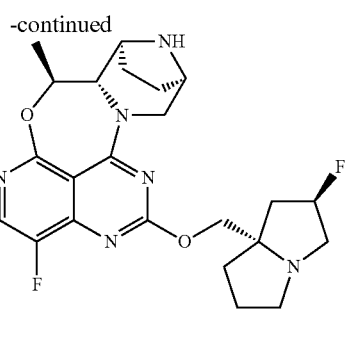

Step 1: tert-Butyl (5S,5aS,6S,9R)-1-fluoro-12-(((2R, 7aS)-2-fluorotetrahydro-1H-pyrrolizin-7a(5H)-yl)methoxy)-5-methyl-2-(4-nitrobicyclo[4.2.0]octa-1 (6),2,4-trien-2-yl)-5a,6,7,8,9,10-hexahydro-5H-4-oxa-3,10a,11,13,14-pentaaza-6,9-methanonaphtho[1, 8-ab]heptalene-14-carboxylate Under nitrogen, a solution of 4,4,5,5-tetramethyl-2-(4-nitrobicyclo[4.2.0]octa-1(6),2,4-trien-2-yl)-1,3,2-dioxaborolane (87.5 mg, 0.324 mmol, intermediate 144), tert-butyl (5S,5aS,6S,9R)-2-chloro-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate(76.3 mg, 0.131 mmol), K$_3$PO$_4$ (0.254 mL, 1.5 M in water) and cataCXium A Pd G$_3$ (18.6 mg, 0.0260 mmol) in THF (1.27 mL) was stirred for 1 h at 60° C. The resulting solution was partitioned between water and EtOAc. The separated organic layer was dried over anhydrous sodium sulfate and concentrated under vacuum. The residue was purified by flash chromatography on silica gel (gradient: 0%-20% MeOH/DCM) to afford 114 mg of the title compound as a yellow solid. LC-MS: (ESI, m/z): [M+H]$^+$=706.

Step 2: tert-Butyl (5S,5aS,6S,9R)-2-(4-aminobicyclo[4.2.0]octa-1(6),2,4-trien-2-yl)-1-fluoro-12-(((2R, 7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1, 8-ab]heptalene-14-carboxylate A solution of tert-butyl (5S,5aS,6S,9R)-1-fluoro-12-(((2R,7aS)-2-fluorotetrahydro-1H-pyrrolizin-7a(5H)-yl)methoxy)-5-methyl-2-(4-nitrobicyclo[4.2.0]octa-1(6),2,4-trien-2-yl)-5a,6,7,8,9,10-hexahydro-5H-4-oxa-3,10a,11,13, 14-pentaaza-6,9-methanonaphtho[1,8-ab]heptalene-14-carboxylate (50.0 mg, 0.0700 mmol), Fe (19.8 mg, 0.350 mmol) and NH$_4$Cl (37.5 mg, 0.710 mmol) in EtOH (1.40 mL) and H$_2$O (0.600 mL) was stirred for 1 h at 80° C. After filtration, the filtrate was concentrated under vacuum. The residue was purified by flash chromatography on silica gel (gradient: 0%-10% MeOH/DCM) to afford 40.0 mg of the title compound as a yellow solid. LC-MS: (ESI, m/z): [M+H]$^+$=676.

Step 3: 5-((5S,5aS,6S,9R)-1-Fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1, 8-ab]heptalen-2-yl)bicyclo[4.2.0]octa-1(6),2,4-trien-3-amine A solution of tert-butyl (5S,5aS,6S,9R)-2-(4-aminobicyclo[4.2.0]octa-1(6),2,4-trien-2-yl)-1-fluoro-12-(((2R,7aS)-

2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (30.0 mg, 0.0400 mmol) in DCM (1 mL) and TFA (1 mL) was stirred for 1 h at room temperature. The solvent was concentrated under vacuum. The residue was purified by PREP-HPLC (Column: XBridge Prep OBD C18 Column, 30*150 mm, 5 μm; Mobile Phase A: Water (10 mmol/L NH$_4$HCO$_3$), Mobile Phase B: ACN; Flow rate: 60 mL/min mL/min; Gradient: 17% B to 42% B in 9 min; Wave Length: 254 nm/220 nm; RT1(min): 9.6) to afford 3.10 mg of the title compound as a white solid. LC-MS: (ESI, m/z): [M+H]$^+$=576. $^1$H NMR (300 MHz, DMSO-d$_6$) δ 7.07 (d, J=1.8 Hz, 1H), 6.45 (d, J=1.8 Hz, 1H), 5.29 (d, J=54.9 Hz, 2H), 5.06 (s, 2H), 4.52 (p, J=6.3 Hz, 1H), 4.11 (d, J=10.3 Hz, 1H), 4.01 (d, J=10.3 Hz, 1H), 3.93 (d, J=8.7 Hz, 1H), 3.57 (s, 1H), 3.45 (d, J=5.5 Hz, 1H), 3.19-3.07 (m, 4H), 3.00 (d, J=9.3 Hz, 5H), 2.84 (q, J=8.4, 7.9 Hz, 1H), 2.16 (d, J=5.4 Hz, 1H), 2.03 (d, J=10.3 Hz, 2H), 1.80 (dd, J=12.0, 7.2 Hz, 4H), 1.60 (q, J=15.9, 12.7 Hz, 3H), 1.46 (d, J=6.3 Hz, 3H).

Examples 202 and 203: Compounds 202 and 203

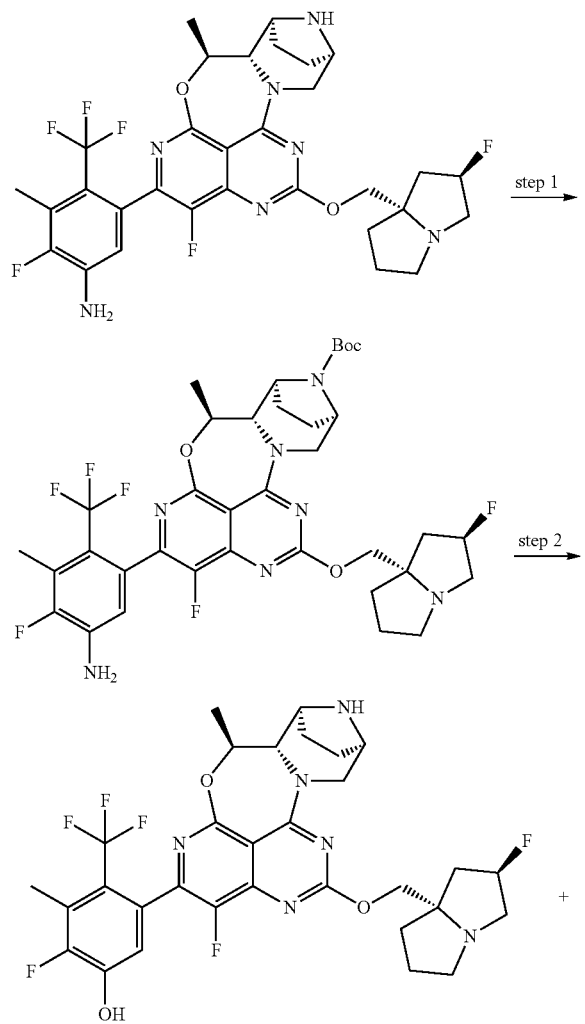

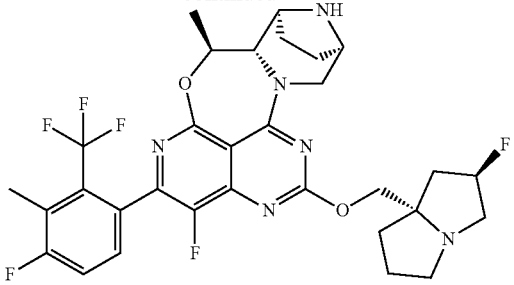

Step 1: tert-Butyl (5S,5aS,6S,9R)-2-(5-amino-4-fluoro-3-methyl-2-(trifluoromethyl)phenyl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate A solution of 2-fluoro-5-((5S,5aS,6S,9R)-1-fluoro-12-(((2R,7aS)-2-fluorotetrahydro-1H-pyrrolizin-7a(5H)-yl) methoxy)-5-methyl-5a,6,7,8,9,10-hexahydro-5H-4-oxa-3,10a,11,13,14-pentaaza-6,9-methanonaphtho[1,8-ab]heptalen-2-yl)-3-methyl-4-(trifluoromethyl)aniline (200 mg, 0.310 mmol, Example 6), di-tert-butyl dicarbonate (100 mg, 0.460 mmol) and N-ethyl-N-isopropylpropan-2-amine (119 mg, 0.920 mmol) in dichloromethane (2 mL) was stirred for 30 min at room temperature. The solvent was evaporated under vacuum and the residual was purified by flash chromatography on silica gel (gradient: 0%-10% MeOH/DCM) to afford 181 mg of the title compound as a white solid. LC-MS: (ESI, m/z): [M+H]$^+$=750. Step 2: 2-Fluoro-5-((5S,5aS,6S,9R)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-3-methyl-4-(trifluoromethyl)phenol and (5S,5aS,6S,9R)-1-fluoro-2-(4-fluoro-3-methyl-2-(trifluoromethyl)phenyl)-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene To a solution of tert-butyl (5S,5aS,6S,9R)-2-(5-amino-4-fluoro-3-methyl-2-(trifluoromethyl) phenyl)-1-fluoro-12-(((2R,7aS)-2-fluorotetrahydro-1H-pyrrolizin-7a(5H)-yl) methoxy)-5-methyl-5a,6,7,8,9,10-hexahydro-5H-4-oxa-3,10a,11,13,14-pentaaza-6,9-methanonaphtho[1,8-ab] heptalene-14-carboxylate (150 mg, 0.200 mmol) and 35% H$_2$SO$_4$ (2.50 mL) in water (1.76 mL) was added NaNO$_2$ (15.2 mg, 0.220 mmol) at −5~0° C. Then Cu(NO$_3$)$_2$.3H$_2$O (676 mg, 2.80 mmol) in water (1.80 mL) and Cu$_2$O (34.4 mg, 0.240 mmol) was added, and the mixture was stirred for 15 min at room temperature. The reaction was quenched by NaHCO$_3$ aqueous and extracted with DCM. The combined organic layers were dried over anhydrous sodium sulfate and concentrated under vacuum. The residue was purified by prep. HPLC (Column: XBridge BEH C18 OBD Prep Column, 19*250 mm, 5 μm; Mobile Phase A: Water (10 mmol/L NH$_4$HCO$_3$), Mobile Phase B: MeOH-HPLC; Flow rate: 25 mL/min; Gradient: 20% B to 54% B in 10 min, 54% B; Wave Length: 254/220 nm; RT1(min): 9.68) to yield 202 4.50 mg and 203 5.30 mg of as white solids.

202: LC-MS: (ESI, m/z): [M+H]$^+$=651. $^1$H NMR (300 MHz, DMSO-d$_6$) δ 6.80 (d, J=31.5 Hz, 1H), 5.29 (d, J=54.3 Hz, 1H), 5.09 (d, J=12.7 Hz, 1H), 4.55 (s, 1H), 4.19-3.88 (m,

3H), 3.72-3.49 (m, 2H), 3.20-2.91 (m, 5H), 2.90-2.79 (m, 1H), 2.38 (s, 3H), 2.15 (d, J=4.9 Hz, 1H), 2.08-1.98 (m, 2H), 1.94-1.73 (m, 4H), 1.65 (s, 3H), 1.44 (d, J=6.3 Hz, 3H).

203: LC-MS: (ESI, m/z): [M+H]⁺=635. ¹H NMR (300 MHz, DMSO-d₆) δ 7.63 (t, J=8.9 Hz, 1H), 7.36 (d, J=40.8 Hz, 1H), 5.29 (d, J=54.2 Hz, 1H), 5.08 (d, J=12.6 Hz, 1H), 4.54 (s, 1H), 4.10 (d, J=10.4 Hz, 1H), 4.06-3.80 (m, 2H), 3.58 (s, 1H), 3.45 (s, 1H), 3.17-2.95 (m, 5H), 2.83 (m, 1H), 2.46-2.39 (m, 3H), 2.15 (d, J=4.9 Hz, 1H), 2.12-1.97 (m, 2H), 1.90-1.72 (m, 4H), 1.63 (d, J=14.4 Hz, 3H), 1.44 (d, J=6.3 Hz, 3H).

Example 204: Compound 204

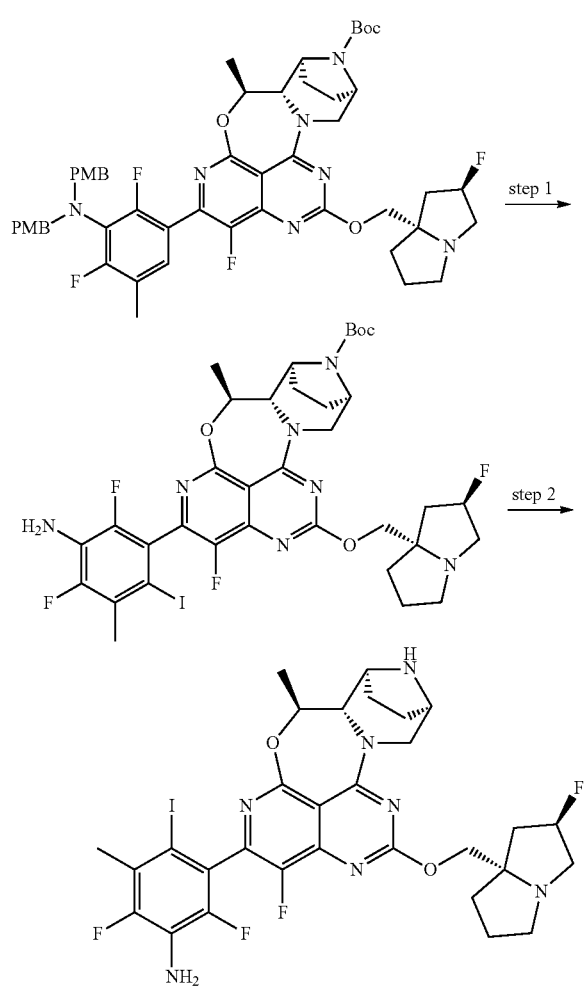

Step 1: tert-Butyl (5S,5aS,6S,9R)-2-(3-amino-2,4-difluoro-6-iodo-5-methylphenyl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate A solution of tert-butyl (4R,7S,8S,9S)-13-[3-[bis[(4-methoxyphenyl) methyl] amino]-2,4-difluoro-5-methylphenyl]-14-fluoro-17-[[(2R,8S)-2-fluoro-1,2,3,5,6,7-hexahydropyrrolizin-8-yl]methoxy]-9-methyl-10-oxa-2,12,16,18,20-pentazapentacyclo[9.7.1.14,7.02,8.015,19]icosa-1(18),11(19),12,14,16-pentaene-20-carboxylate (90.5 mg, 0.100 mmol) and NIS (109 mg, 0.480 mmol) in AcOH (1.5 mL) was stirred at room temperature for 1 h. The reaction was quenched by Na₂S₂O₃ aqueous and extracted with EtOAc. The combined organic layers were dried over anhydrous sodium sulfate and concentrated under vacuum. The residue was purified by flash chromatography on silica gel (gradient: 0%-10% MeOH/DCM) to afford 66.1 mg of the title compound as a brown solid. LC-MS: (ESI, m/z): [M+H]⁺=826.

Step 2: 2,6-Difluoro-3-((5S,5aS,6S,9R)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-4-iodo-5-methylaniline A solution of tert-butyl (5S,5aS,6S,9R)-2-(3-amino-2,4-difluoro-6-iodo-5-methylphenyl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (66.2 mg, 0.0800 mmol) and TFA (1 mL) in DCM (4 mL) was stirred at room temperature for 1 h. The solvent was concentrated under vacuum. The crude product was purified by Prep-HPLC (conditions: Column: XBridge Prep OBD C18 Column, 30*150 mm, 5 μm; Mobile Phase A: Water (10 mmol/L NH₄HCO₃), Mobile Phase B: ACN; Flow rate: 60 mL/min; Gradient: 17% B to 42% B in 9 min, 42% B; Wave Length: 254/220 n; R_{T1}(min): 8.9) to afford 26.2 mg of the title compound as a white solid. LC-MS: (ESI, m/z): [M+H]⁺=726. ¹H NMR (300 MHz, DMSO-d₆, ppm): δ 5.56-5.47 (m, 1H), 5.29 (d, J=54.4 Hz, 1H), 5.16-5.03 (m, 1H), 4.66-4.49 (m, 1H), 4.21-3.94 (m, 3H), 3.61 (s, 1H), 3.48 (d, J=5.5 Hz, 1H), 3.17-2.97 (m, 4H), 2.91-2.79 (m, 1H), 2.32-2.25 (m, 3H), 2.20-2.13 (m, 1H), 2.09-1.95 (m, 2H), 1.92-1.57 (m, 7H), 1.45 (d, J=6.2 Hz, 3H).

Example 205: Compound 205

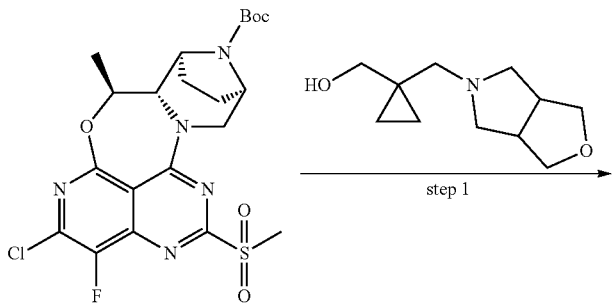

-continued

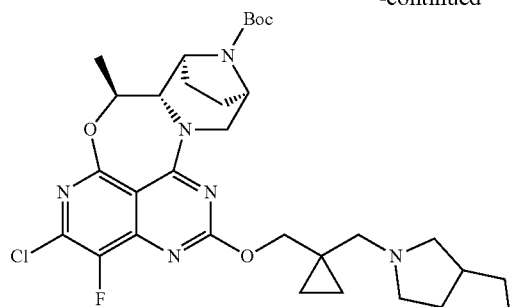
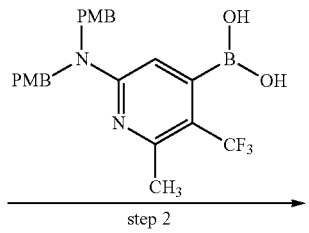

step 2

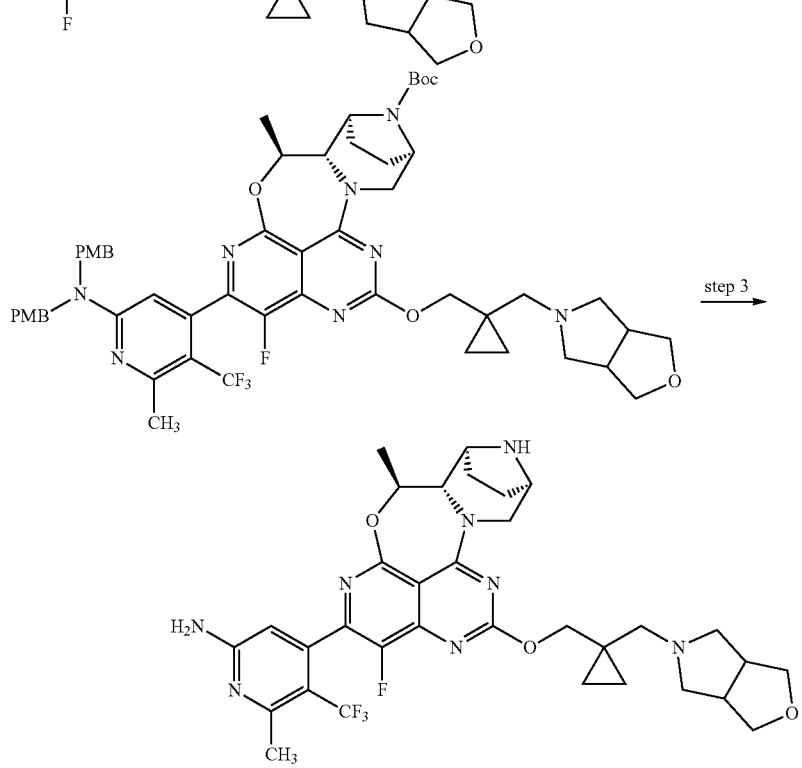

Step 1: tert-Butyl (5S,5aS,6S,9R)-2-chloro-1-fluoro-5-methyl-12-((1-((tetrahydro-1H-furo[3,4-c]pyrrol-5(3H)-yl)methyl)cyclopropyl)methoxy)-5a,6,7,8,9,10-hexahydro-5H-4-oxa-3,10a,11,13,14-pentaaza-6,9-methanonaphtho[1,8-ab]heptalene-14-carboxylate To a solution of (1-((tetrahydro-1H-furo[3,4-c]pyrrol-5(3H)-yl)methyl)cyclopropyl)methanol (360 mg, crude, intermediate 145) in THF (5 mL) was added NaH (60% dispersion in mineral oil, 156 mg, 3.90 mmol) in portions at 0° C., and the mixture was stirred for 30 minutes at room temperature. Then tert-butyl (5S,5aS,6S,9R)-2-chloro-1-fluoro-5-methyl-12-(methylsulfonyl)-5a,6,7,8,9,10-hexahydro-5H-4-oxa-3,10a,11,13,14-pentaaza-6,9-methanonaphtho[1,8-ab] heptalene-14-carboxylate (200 mg, 0.390 mmol) was added, and the mixture was stirred for 1 hour at room temperature. The reaction was quenched with saturated NH4Cl aqueous solution. The reaction mixture was diluted with water and extracted with ethyl acetate. The combined organic layers were washed with brine, dried over anhydrous sodium sulfate and concentrated under vacuum. The residue was purified by flash chromatography on silica gel (gradient: 0-90% ethyl acetate in petroleum ether) to afford the title compound (100 mg) as a yellow solid. LC-MS: (ESI, m/z): [M+H]⁺=632.

Step 2: tert-Butyl (5S,5aS,6S,9R)-2-(6-(bis(4-methoxybenzyl)amino)-2-methyl-3-(trifluoromethyl)pyridin-4-yl)-1-fluoro-5-methyl-12-((1-((tetrahydro-1H-furo[3,4-c]pyrrol-5(3H)-yl)methyl)cyclopropyl)methoxy)-5a,6,7,8,9,10-hexahydro-5H-4-oxa-3,10a,11,13,14-pentaaza-6,9-methanonaphtho[1,8-ab]heptalene-14-carboxylate Under nitrogen, a solution of tert-butyl (5S,5aS,6S,9R)-2-chloro-1-fluoro-5-methyl-12-((1-((tetrahydro-1H-furo[3,4-c]pyrrol-5(3H)-yl)methyl)cyclopropyl)methoxy)-5a,6,7,8,9,10-hexahydro-5H-4-oxa-3,10a,11,13,14-pentaaza-6,9-methanonaphtho[1,8-ab]heptalene-14-carboxylate (100 mg, 0.158 mmol), (6-(bis(4-methoxybenzyl)amino)-2-methyl-3-(trifluoromethyl)pyridin-4-yl)boronic acid (190 mg, 0.412 mmol), K3PO4 (1.5 M aqueous solution, 0.5 mL, 0.75 mmol) and cataCXium A Pd G3 (23.0 mg, 0.0316 mmol) in THF (2.5 mL) was stirred for 3 hours at 60° C. The reaction mixture was diluted with water and extracted with ethyl acetate. The combined organic layers were dried over anhydrous sodium sulfate and concentrated under vacuum. The residue was purified by flash chromatography on silica gel (gradient: 0-100% ethyl acetate in petroleum ether) to afford the title compound (140 mg) as a yellow solid. LC-MS: (ESI, m/z): [M+H]⁺=1011.

Step 3: 4-((5S,5aS,6S,9R)-1-Fluoro-5-methyl-12-((1-((tetrahydro-1H-furo[3,4-c]pyrrol-5(3H)-yl)methyl)cyclopropyl)methoxy)-5a,6,7,8,9,10-hexahydro-5H-4-oxa-3,10a,11,13,14-pentaaza-6,9-methanonaphtho[1,8-ab]heptalen-2-yl)-6-methyl-5-(trifluoromethyl)pyridin-2-amine A solution of tert-butyl (5S,5aS,6S,9R)-2-(6-(bis(4-methoxybenzyl) amino)-2-methyl-3-(trifluoromethyl)pyridin-4-yl)-1-fluoro-5-methyl-12-((1-((tetrahydro-1H-furo[3,4-c]pyrrol-5 (3H)-yl)methyl)cyclopropyl)methoxy)-5a,6,7,8,9,10-hexahydro-5H-4-oxa-3, a, 11,3,14-pentaaza-6,9-methanonaphtho[1,8-ab]heptalene-14-carboxylate (140 mg, 0.138 mmol) in 2,2,2-trifluoroacetic acid (20 mL) was stirred for 3 hours at 50° C. The solvent was concentrated under vacuum. The residue was purified by reverse phase chromatography (gradient: 0-50% acetonitrile in water (0.05% NH₄HCO₃)) and Prep-HPLC (Column: XBridge Prep OBD C18 Column, 30*150 mm, 5 μm; Mobile Phase A: Water (10 mmol/L NH₄HCO₃), Mobile Phase B: ACN; Flow rate: 60 mL/min; Gradient: 17% B to 42% B in 9 min; Wave Length: 254/220 nm; RT1(min): 9) to afford the title compound (8.20 mg) as a white solid. LC-MS: (ESI, m/z): [M+H]⁺=671. ¹H NMR (300 MHz, DMSO-d6, ppm) δ 6.83 (s, 2H), 6.23 (s, 1H), 5.17-5.02 (m, 1H), 4.60-14.46 (m, 1H), 4.36-4.20 (m, 2H), 3.95 (d, J=8.7 Hz, 1H), 3.72 (t, J=7.4 Hz, 2H), 3.62-3.51 (i, 1H), 3.49-3.36 (m, 2H), 3.02 (d, J=12.7 Hz, 1H), 3.71-3.58 (i, 3H), 2.48-2.43 (m, 5H), 2.41-2.25 (m, 4H), 1.88-1.73 (d, 1H), 1.71-1.49 (s, 3H), 1.44 (d, J=6.3 Hz, 3H), 0.69-0.57 (m, 2H), 0.48-0.32 (in, 2H).

Each compound in the Table below was prepared following a similar experimental procedure (using appropriately substituted reagents) as described for Example 205.

| Cmpd. No. | ¹H NMR | MS (M + H)⁺ |
|---|---|---|
| 206 | ¹H NMR (300 MHz, DMSO-d6, ppm) δ 6.83 (s, 2H), 6.23 (s, 1H), 5.16-5.04 (m, 1H), 4.60-4.48 (m, 1H), 4.44 (d, J = 10.8 Hz, 1H), 4.31 (d, J = 10.8 Hz, 1H), 3.99-3.92 (m, 1H), 3.58-3.43 (m, 6H), 3.18-2.92 (m, 4H), 2.49-2.44 (m, 3H), 2.37-2.23 (m, 2H), 1.84-1.53 (m, 8H), 1.44 (d, J = 6.3 Hz, 3H), 0.66-0.55 (m, 2H), 0.50-0.41 (m, 2H). | 671 |
| 207 | ¹H NMR (300 MHz, DMSO-d₆) δ 6.83 (s, 2H), 6.23 (s, 1H), 5.11 (d, J = 12.6 Hz, 1H), 4.51 (m, 1H), 4.40 (d, J = 10.7 Hz, 1H), 4.25 (d, J = 10.9 Hz, 1H), 4.16 (s, 2H), 3.96 (d, J = 8.8 Hz, 1H), 3.55 (s, 1H), 3.52 (d, J = 12.6 Hz, 2H), 3.02 (m, 1H), 2.62 (t, J = 10.8 Hz, 2H), 2.47 (d, J = 2.3 Hz, 2H), 2.31 (d, J = 12.7 Hz, 1H), 2.25-2.07 (m, 3H), 1.73 (d, J = 9.7 Hz, 3H), 1.61 (s, 4H), 1.44 (d, J = 6.3 Hz, 3H), 0.61 (s, 2H), 0.38 (s, 2H). | 671 |
| 208 | ¹H NMR (300 MHz, DMSO-d6, ppm) δ 6.83 (s, 2H), 6.23 (s, 1H), 5.16-5.04 (m, 1H), 4.60-4.48 (m, 1H), 4.39-4.26 (m, 2H), 4.20 (d, J = 10.8 Hz, 1H), 3.96 (d, J = 8.5 Hz, 1H), 3.78 (d, J = 7.5 Hz, 1H), 3.65-3.53 (m, 1H), 3.53-3.37 (m, 4H), 3.02 (d, J = 12.7 Hz, 1H), 2.85 (d, J = 9.8 Hz, 1H), 2.76-2.59 (m, 1H), 2.48-2.32 (m, 5H), 1.88-1.74 (m, 1H), 1.73-1.57 (m, 3H), 1.57-1.48 (m, 2H), 1.44 (d, J = 6.3 Hz, 3H), 0.79-0.52 (m, 2H), 0.52-0.36 (m, 2H). | 657 |
| 209 | ¹H NMR (300 MHz, DMSO-d6, ppm) δ 6.84 (s, 2H), 6.23 (s, 1H), 5.19-4.97 (m, 1H), 4.61-4.45 (m, 1H), 4.37-4.16 (m, 3H), 3.95 (d, J = 8.7 Hz, 1H), 3.78 (d, J = 7.4 Hz, 1H), 3.59-3.52 (m, 1H), 3.52-3.41 (m, 3H), 3.02 (d, J = 12.7 Hz, 1H), 2.88-2.77 (m, 1H), 2.62 (d, J = 12.6 Hz, 1H), 2.51-2.43 (m, 4H), 2.42-2.37 (m, 1H), 1.91-1.76 (m, 1H), 1.76-1.45 (m, 5H), 1.44 (d, J = 6.3 Hz, 3H), 0.65-0.53 (m, 2H), 0.51-0.45 (m, 1H), 0.45-0.37 (m, 1H). | 657 |
| 210 | ¹H NMR (400 MHz, DMSO-d₆, ppm): δ 6.84 (s, 2H), 6.23 (s, 1H), 5.20-5.00 (m, 1H), 4.63-4.46 (m, 1H), 4.38-4.17 (m, 3H), 3.97 (d, J = 8.7 Hz, 1H), 3.68-3.44 (m, 6H), 3.04 (d, J = 12.8 Hz, 1H), 2.49-2.44 (m, 3H), 2.39 (s, 4H), 2.30 (s, 2H), 1.90-1.77 (m, 1H), 1.75-1.51 (m, 3H), 1.44 (d, J = 6.3 Hz, 3H), 0.71-0.60 (m, 2H), 0.48-0.37 (m, 2H). | 645 |
| 211 | ¹H NMR (300 MHz, DMSO-d6, ppm) δ 6.83 (s, 2H), 6.23 (s, 1H), 5.09 (d, J = 12.6 Hz, 1H), 4.58-4.48 (m, 1H), 4.38-4.20 (m, 2H), 4.06-3.92 (m, 2H), 3.75-3.60 (m, 1H), 3.64-3.60 (m, 1H), 3.28-3.49 (m, 1H), 3.44 (d, J = 6.0 Hz, 1H), 3.02 (d, J = 12.7 Hz, 1H), 2.96-2.84 (m, 3H), 2.71-2.58 (m, 2H), 2.55-2.52 (m, 1H), 2.48 (s, 3H), 1.90-1.77 (m, 3H), 1.70-1.52 (m, 5H), 1.44 (d, J = 6.3 Hz, 3H), 0.67-0.55 (m, 2H), 0.52-0.38 (m, 2H). | 671 |
| 212 | ¹H NMR (300 MHz, DMSO-d6, ppm) δ 6.83 (s, 2H), 6.23 (s, 1H), 5.10 (d, J = 12.8 Hz, 1H), 4.61-4.45 (m, 1H), 4.36-4.18 (m, 2H), 3.96 (d, J = 8.8 Hz, 1H), 3.66-3.50 (m, 3H), 3.48-3.41 (m, 1H), 3.02 (d, J = 12.7 Hz, 1H), 2.48-2.41 (m, 6H), 2.37 (s, 3H), 2.36-2.24 (m, 1H), 1.89-1.74 (m, 1H), 1.74-1.50 (m, 3H), 1.44 (d, J = 6.3 Hz, 3H), 0.68-0.61 (m, 2H), 0.61-0.54 (m, 2H), 0.48-0.36 (m, 4H). | 671 |
| 213 | ¹H NMR (300 MHz, DMSO-d6, ppm): δ 6.84 (s, 2H), 6.23 (s, 1H), 5.13-5.04 (m, 1H), 4.57-4.49 (m, 1H), 4.28 (s, 2H), 3.95 (d, J = 8.6 Hz, 1H), 3.70 (d, J = 10.9 Hz, 1H), 3.56 (s, 1H), 3.44 (d, J = 6.1 Hz, 2H), 3.02 (d, J = 12.7 Hz, 1H), 2.88-2.67 (m, 3H), 2.47 (d, J = 2.4 Hz, 3H), 2.35-2.20 (m, 2H), 1.99-1.88 (m, 1H), 1.80 (d, J = 10.8 Hz, 1H), 1.69-1.58 (m, 3H), 1.44 (d, J = 6.3 Hz, 3H), 1.01 (d, J = 6.2 Hz, 3H), 0.64 (d, J = 4.3 Hz, 2H), 0.43 (d, J = 4.5 Hz, 2H). | 659 |
| 214 | ¹H NMR (300 MHz, DMSO-d6) δ 6.84 (s, 2H), 6.23 (s, 1H), 5.10 (dd, J = 12.9, 2.5 Hz, 1H), 4.63-4.47 (m, 1H), 4.41-4.27 (m, 2H), 3.97 (d, J = 8.7 Hz, 1H), 3.55 (d, J = 11.0 Hz, 2H), 3.45 (d, J = 5.4 Hz, 1H), 3.27-3.17 (m, 1H), 3.15 (d, J = 3.8 Hz, 1H), 3.11-2.98 (m, 2H), 2.87 (s, 1H), 2.75-2.57 (m, 1H), 2.49-2.44 (m, 3H), 2.36 (d, J = 33.4 Hz, 3H), 1.80 (d, J = 10.6 Hz, 1H), 1.58 (dd, J = 28.5, 8.2 Hz, 3H), 1.44 (d, J = 6.3 Hz, 3H). | 637 |
| 215 | ¹H NMR (300 MHz, DMSO-d6) δ 6.81 (s, 2H), 6.21 (s, 1H), 5.27 (d, J = 54.4 Hz, 1H), 5.06 (dd, J = 12.9, 2.5 Hz, 1H), 4.57-4.46 (m, 1H), 4.08 (d, J = 10.3 Hz, 1H), | 633 |

| Cmpd. No. | ¹H NMR | MS (M + H)⁺ |
|---|---|---|
| | 3.96 (dd, J = 14.8, 9.5 Hz, 2H), 3.55 (s, 1H), 3.43 (d, J = 5.8 Hz, 1H), 3.18-2.89 (m, 4H), 2.89-2.78 (m, 1H), 2.75 (d, J = 12.0 Hz, 1H), 2.48-2.40 (m, 3H), 2.19-2.05 (m, 1H), 2.00 (dd, J = 14.8, 4.8 Hz, 2H), 1.90-1.70 (m, 4H), 1.70-1.46 (m, 3H), 1.42 (d, J = 6.3 Hz, 3H). | |
| 216 | ¹H NMR (400 MHz, DMSO-d6, ppm): δ 6.84 (s, 1H), 6.23 (s, 2H), 5.16-4.99 (m, 1H), 4.63-4.45 (m, 1H), 4.24-4.09 (m, 2H), 3.96 (d, J = 8.8 Hz, 1H), 3.57 (s, 1H), 3.45 (d, J = 5.7 Hz, 1H), 3.18-2.94 (m, 3H), 2.80-2.66 (m, 1H), 2.57 (s, 1H), 2.47 (d, J = 2.4 Hz, 3H), 2.15-2.04 (m, 1H), 2.03-1.94 (m, 1H), 1.90 (d, J = 13.3 Hz, 1H), 1.86-1.74 (m, 3H), 1.74-1.49 (m, 6H), 1.44 (d, J = 6.2 Hz, 3H). | 677 |
| 217 | ¹H NMR (400 MHz, DMSO-d6, ppm) δ 6.84 (s, 2H), 6.23 (s, 1H), 5.09 (m, 1H), 4.55 (m, 1H), 4.14-4.08 (d, J = 10.5 Hz, 1H), 3.97 (d, J = 8.8 Hz, 1H), 3.58 (s, 1H), 3.45 (d, J = 6.1 Hz, 1H), 3.16-3.06 (m, 1H), 3.03 (d, J = 12.6 Hz, 3H), 2.72 (m, 1H), 2.50-2.42 (m, 4H), 2.42-2.27 (m, 2H), 2.06-1.99 (m, 1H), 1.96-1.85 (m, 1H), 1.79 (m, 3H), 1.65 (s, 2H), 1.60-1.51 (m, 1H), 1.44 (d, J = 6.3 Hz, 3H). | 651 |

Example 218. Compound 218

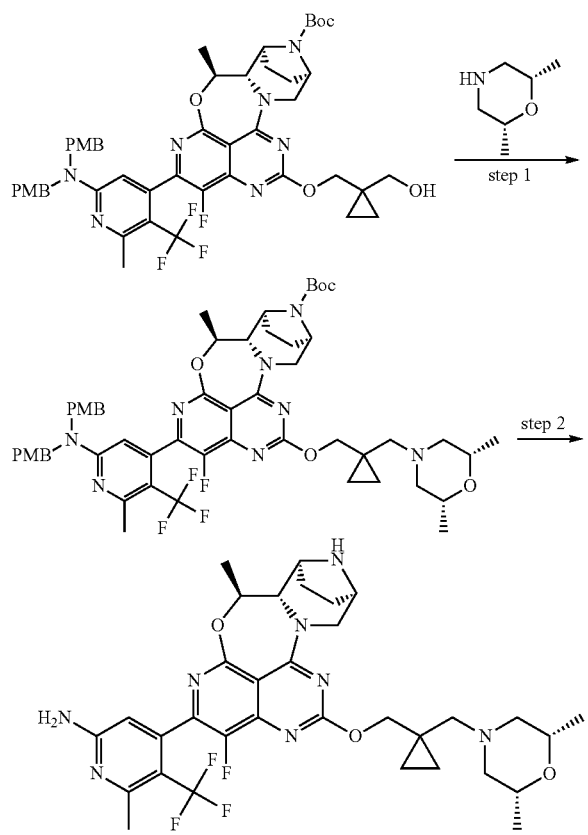

Step 1: tert-Butyl (5S,5aS,6S,9R)-2-(6-(bis(4-methoxybenzyl)amino)-2-methyl-3-(trifluoromethyl)pyridin-4-yl)-12-((1-(((2R,6S)-2,6-dimethylmorpholino)methyl)cyclopropyl)methoxy)-1-fluoro-5-methyl-5a,6,7,8,9,10-hexahydro-5H-4-oxa-3,10a,11,13,14-pentaaza-6,9-methanonaphtho[1,8-ab]heptalene-14-carboxylate Under nitrogen, to a solution of tert-butyl (5S',5aS,6S',9R)-2-(6-(bis(4-methoxybenzyl)amino)-2-methyl-3-(trifluoromethyl)pyridin-4-yl)-1-fluoro-12-((1-(hydroxymethyl)cyclopropyl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (250 mg, 0.274 mmol, intermediate 150) in DCM (3.00 mL) was added NMO (64.0 mg, 0.548 mmol) in DCM (1.00 mL) and TPAP (48.0 mg, 0.550 mmol) in DCM (1.00 mL) at 0° C. The resulting solution was stirred for 1 h at room temperature. After filtration, to the filtrate was added (2R,6S)-2,6-dimethylmorpholine (472 mg, 4.10 mmol) and NaOAc (336 mg, 4.10 mmol) at room temperature, and the mixture was stirred for 30 min. Then NaBH₃CN (257 mg, 4.10 mmol) was added and the solution was stirred overnight. The resulting solution was quenched with water and extracted with DCM. The combined organic layers were dried over anhydrous sodium sulfate and concentrated under vacuum. The residue was purified by C18 column (solvent gradient: 0-100% MeOH in water (0.05% NH₄HCO₃)) to afford 144 mg of the title compound as a white solid. LC-MS: (ESI, m/z): [M+H]⁺= 1013.

Step 2: 4-((5S,5aS,6S,9R)-12-((1-(((2R,6S)-2,6-Dimethylmorpholino)methyl)cyclopropyl)methoxy)-1-fluoro-5-methyl-5a,6,7,8,9,10-hexahydro-5H-4-oxa-3,10a,11,13,14-pentaaza-6,9-methanonaphtho[1,8-ab]heptalen-2-yl)-6-methyl-5-(trifluoromethyl)pyridin-2-amine A solution of tert-butyl (5S,5aS,6S,9R)-2-(6-(bis(4-methoxybenzyl) amino)-2-methyl-3-(trifluoromethyl)pyridin-4-yl)-12-((1-(((2R,6S)-2,6-dimethylmorpholino)methyl)cyclopropyl)methoxy)-1-fluoro-5-methyl-5a,6,7,8,9,10-hexahydro-5H-4-oxa-3,10a,11,13,14-pentaaza-6,9-methanonaphtho[1,8-ab]heptalene-14-carboxylate (63.4 mg, 0.0626 mmol) in TFA (0.300 mL) was stirred for overnight at room temperature. The solvent was evaporated under vacuum. The residue was purified by C18 column (solvent gradient: 0-100% ACN in water (0.05% NH₄HCO₃)) to yield 2.6 mg of the title compound as a white solid. LC-MS: (ESI, m/z): [M+H]⁺=673. ¹H NMR (300 MHz, DMSO-d₆, ppm): δ 6.84 (s, 2H), 6.23 (s, 1H), 5.09 (d, J=12.3 Hz, 1H), 4.60-4.44 (m, 1H), 4.27 (q, J=10.9 Hz, 2H), 3.95 (d, J=8.8 Hz, 1H), 3.60-3.38 (m, 5H), 3.01 (d, J=12.7 Hz, 1H), 2.87-2.69 (m, 3H), 2.49-2.44 (m, 3H), 2.27 (s, 2H), 1.81 (s, 1H), 1.63 (s, 1H), 1.55 (t, J=10.7 Hz, 2H), 1.44 (d, J=6.3 Hz, 3H), 1.24 (s, 1H), 1.02 (d, J=6.2 Hz, 5H), 0.64 (d, J=4.5 Hz, 2H), 0.41 (d, J=5.2 Hz, 2H).

Example 219: Compound 219

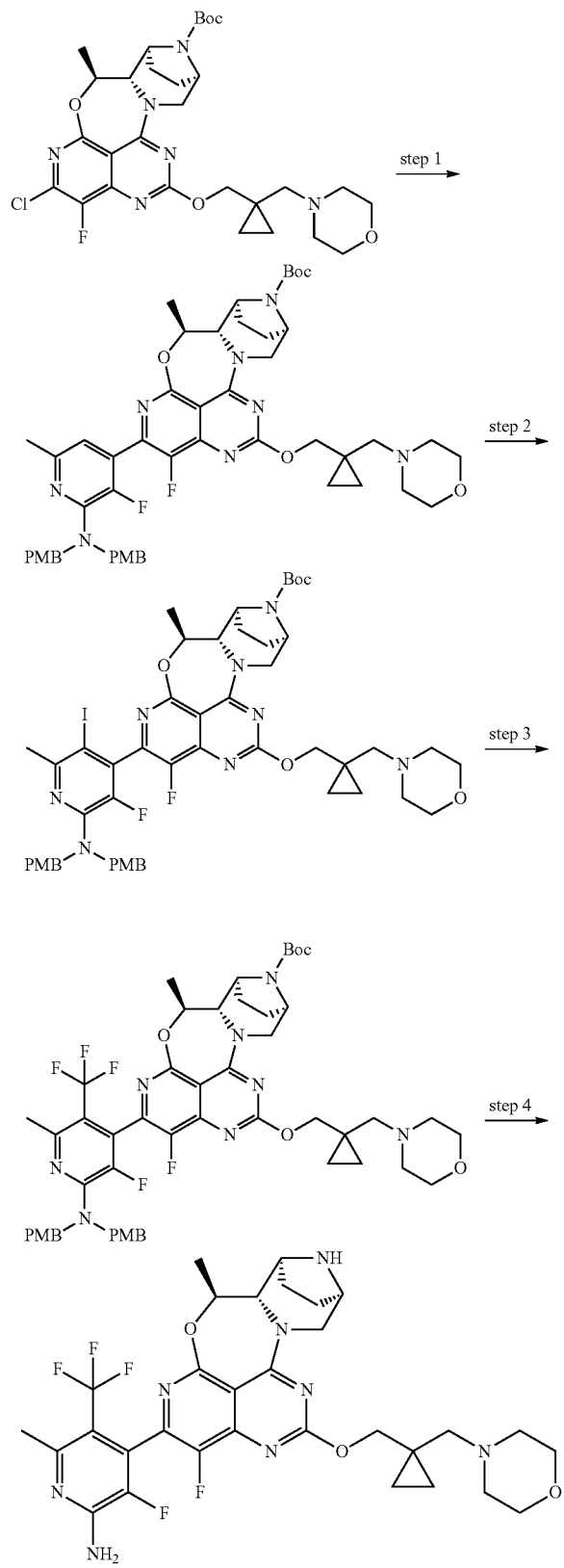

Step 1: tert-Butyl (5S,5aS,6S,9R)-2-(2-(bis(4-methoxybenzyl)amino)-3-fluoro-6-methylpyridin-4-yl)-1-fluoro-5-methyl-12-((1-(morpholinomethyl)cyclopropyl)methoxy)-5a,6,7,8,9,10-hexahydro-5H-4-oxa-3,10a,11,13,14-pentaaza-6,9-methanonaphtho[1,8-ab]heptalene-14-carboxylate Under nitrogen, a solution of tert-butyl (5S,5aS,6S,9R)-2-chloro-1-fluoro-5-methyl-12-((1-(morpholinomethyl)cyclopropyl)methoxy)-5a,6,7,8,9,10-hexahydro-5H-4-oxa-3,10a,11,13,14-pentaaza-6,9-methanonaphtho[1,8-ab]heptalene-14-carboxylate (150 mg, 0.263 mmol, from Compound 210), 3-fluoro-N,N-bis(4-methoxybenzyl)-6-methyl-4-(4,4,5,5-tetramethyl-1,3,2-dioxaborolan-2-yl)pyridin-2-amine (245 mg, 0.500 mmol), cataCXium A Pd G3 (36.1 mg, 0.0500 mmol) and $K_3PO_4$ (0.5 mL, 1.5 M in water) in THF (2.5 mL) was stirred at 60° C. for 2 h. The resulting solution was partitioned between water and EtOAc. The separated organic layer was dried over anhydrous sodium sulfate and concentrated under vacuum. The residue was purified by C18 column (solvent gradient: 0-100% ACN in water (0.05% $NH_4HCO_3$)) to afford 159 mg of the title compound as a yellow solid. LC-MS: (ESI, m/z): $[M+H]^+$=935.

Step 2: tert-Butyl (5S,5aS,6S,9R)-2-(2-(bis(4-methoxybenzyl)amino)-3-fluoro-5-iodo-6-methylpyridin-4-yl)-1-fluoro-5-methyl-12-((1-(morpholinomethyl)cyclopropyl)methoxy)-5a,6,7,8,9,10-hexahydro-5H-4-oxa-3,10a,11,13,14-pentaaza-6,9-methanonaphtho[1,8-ab]heptalene-14-carboxylate Under nitrogen, to a solution of tert-butyl (5S,5aS,6S,9R)-2-(2-(bis(4-methoxybenzyl) amino)-3-fluoro-6-methylpyridin-4-yl)-1-fluoro-5-methyl-12-((1-(morpholinomethyl)cyclopropyl)methoxy)-5a,6,7,8,9,10-hexahydro-5H-4-oxa-3,10a,11,13,14-pentaaza-6,9-methanonaphtho[1,8-ab]heptalene-14-carboxylate (147 mg, 0.157 mmol) in AcOH (1.5 mL) was added NIS (38.9 mg, 0.170 mmol) and the solution was stirred at room temperature for 30 min. The resulting solution was quenched by $Na_2S_{2O3}$ aqueous and extracted with EtOAc. The combined organic layers were dried over anhydrous sodium sulfate and concentrated under vacuum. The residue was purified by flash chromatography on silica gel eluting (gradient: 0%-10% MeOH/DCM) to afford 142 mg of the title compound as a yellow solid. LC-MS: (ESI, m/z): $[M+H]^+$=1061.

Step 3: tert-Butyl (5S,5aS,6S,9R)-2-(2-(bis(4-methoxybenzyl) amino)-3-fluoro-6-methyl-5-(trifluoromethyl)pyridin-4-yl)-1-fluoro-5-methyl-12-((1-(morpholinomethyl)cyclopropyl)methoxy)-5a,6,7,8,9,10-hexahydro-5H-4-oxa-3,10a,11,13,14-pentaaza-6,9-methanonaphtho[1,8-ab]heptalene-14-carboxylate Under nitrogen, to a mixture of tert-butyl (5S,5aS,6S,9R)-2-(2-(bis(4-methoxybenzyl) amino)-3-fluoro-5-iodo-6-methylpyridin-4-yl)-1-fluoro-5-methyl-12-((1-(morpholinomethyl) cyclopropyl) methoxy)-5a,6,7,8,9,10-hexahydro-5H-4-oxa-3,10a,11,13,14-pentaaza-6,9-methanonaphtho[1,8-ab]heptalene-14-carboxylate (130.1 mg, 0.123 mmol), $Cu(O_2CCF_2SO_2F)_2$ (511 mg, 1.23 mmol) and Cu powder (78.5 mg, 1.23 mmol) was added DMF (3 mL) at 0° C., and the mixture was stirred at room temperature for 1 h. The resulting reaction was diluted with EtOAc, washed with water. The organic layers were dried over anhydrous sodium sulfate and concentrated under vacuum. The residue was purified by C18 column (solvent gradient: 0-90% MeOH in water (0.05% NH$_4$HCO$_3$)) to afford 116 mg of the title compound as a yellow solid. LC-MS: (ESI, m/z): [M+H]$^+$= 1003.

Step 4: 3-Fluoro-4-((5S,5aS,6S,9R)-1-fluoro-5-methyl-12-((1-(morpholinomethyl)cyclopropyl)methoxy)-5a,6,7,8,9,10-hexahydro-5H-4-oxa-3,10a,11,13,14-pentaaza-6,9-methanonaphtho[1,8-ab]heptalen-2-yl)-6-methyl-5-(trifluoromethyl)pyridin-2-amine A solution of tert-butyl (5S,5aS,6S,9R)-2-(2-(bis(4-methoxybenzyl) amino)-3-fluoro-6-methyl-5-(trifluoromethyl)pyridin-4-yl)-1-fluoro-5-methyl-12-((1-(morpholinomethyl)cyclopropyl)methoxy)-5a,6,7,8,9,10-hexahydro-5H-4-oxa-3,10a,11,13,14-pentaaza-6,9-methanonaphtho[1,8-ab]heptalene-14-carboxylate (115 mg, 0.115 mmol) in TFA (6 mL) was stirred at 50° C. for 4 h. Then the solution was concentrated under vacuum. The crude product was purified by Prep-HPLC (Column: XBridge Prep OBD C18 Column, 30*150 mm, 5 μm; Mobile Phase A: water (10 mmol/L NH$_4$HCO$_3$), Mobile Phase B: ACN; Flow rate: 60 mL/min; Gradient: 26% B to 45% B in 9 min, 45% B; Wave Length: 254/220 nm; R$_{T1}$(min): 8.8) to afford 27.8 mg of the title compound as a white solid. LC-MS: (ESI, m/z): [M+H]$^+$=663. $^1$H NMR (400 MHz, DMSO-d$_6$, ppm): δ 7.31-7.01 (m, 2H), 5.15-4.97 (m, 1H), 4.64-4.43 (m, 1H), 4.39-4.13 (m, 2H), 3.95 (t, J=8.2 Hz, 1H), 3.62-3.39 (m, 6H), 3.01 (d, J=12.8 Hz, 1H), 2.82 (s, 1H), 2.47-2.41 (m, 3H), 2.36 (s, 4H), 2.29 (s, 2H), 1.89-1.72 (m, 1H), 1.71-1.48 (m, 3H), 1.42 (d, J=6.2 Hz, 3H), 0.69-0.57 (m, 2H), 0.45-0.35 (m, 2H).

Each compound in the Table below was prepared following a similar experimental procedure (using appropriately substituted reagents) as described for Example 219.

| Cmpd. No. | $^1$H NMR | MS (M + H)$^+$ |
|---|---|---|
| 220 | $^1$H NMR (400 MHz, DMSO-d$_6$, ppm): δ 7.32-7.08 (m, 2H), 5.17-4.98 (m, 1H), 4.66-4.47 (m, 1H), 4.44-4.24 (m, 2H), 4.03-3.88 (m, 1H), 3.61-3.40 (m, 3H), 3.21 (d, J = 8.7 Hz, 1H), 3.15-2.97 (m, 3H), 2.73-2.52 (m, 1H), 2.47-2.24 (m, 6H), 1.71 (m, 4H), 1.92-1.48 (d, J = 6.3 Hz, 3H). | 655 |
| 221 | $^1$H NMR (400 MHz, DMSO-d$_6$, ppm): δ 7.19 (d, J = 11.4 Hz, 2H), 5.07 (d, J = 13.2 Hz, 1H), 4.69-4.44 (m, 1H), 4.27-4.06 (m, 2H), 3.95 (t, J = 8.2 Hz, 1H), 3.50 (d, J = 40.1 Hz, 2H), 3.16-2.92 (m, 3H), 2.82 (s, 1H), 2.70 (d, J = 11.8 Hz, 1H), 2.59-2.52 (m, 1H), 2.47-2.39 (m, 3H), 2.12-1.89 (m, 3H), 1.87-1.45 (m, 9H), 1.42 (d, J = 6.2 Hz, 3H). | 695 |
| 222 | $^1$H NMR (300 MHz, DMSO-d6, ppm) δ 7.32-7.02 (m, 2H), 5.07 (d, J = 12.4 Hz, 1H), 4.65-4.42 (m, 1H), 4.39-4.12 (m, 3H), 4.02-3.87 (m, 1H), 3.76 (d, J = 7.6 Hz, 1H), 3.59-3.49 (m, 1H), 3.50-3.33 (m, 3H), 3.01 (d, J = 13.1 Hz, 1H), 2.83 (d, J = 9.7 Hz, 1H), 2.74-2.58 (m, 1H), 2.47-2.22 (m, 5H), 1.85-1.71 (m, 1H), 1.70-1.58 (m, 3H), 1.55-1.46 (m, 2H), 1.42 (d, J = 6.3 Hz, 3H), 0.62-0.34 (m, 4H). | 675 |
| 223 | $^1$H NMR (300 MHz, DMSO-d6, ppm) δ 7.33-7.07 (m, 2H), 5.18-5.00 (m, 1H), 4.67-4.49 (m, 1H), 4.40-4.18 (m, 3H), 3.97 (t, J = 8.1 Hz, 1H), 3.78 (d, J = 7.4 Hz, 1H), 3.64-3.54 (m, 1H), 3.54-3.39 (m, 4H), 3.04 (d, J = 12.9 Hz, 1H), 2.85 (d, J = 9.7 Hz, 1H), 2.70-2.56 (m, 2H), 2.49-2.30 (m, 4H), 1.90-1.75 (m, 1H), 1.75-1.59 (m, 3H), 1.59-1.49 (m, 2H), 1.44 (d, J = 6.3 Hz, 3H), 0.66-0.53 (m, 2H), 0.53-0.37 (m, 2H). | 675 |

Example 224: Compound 224

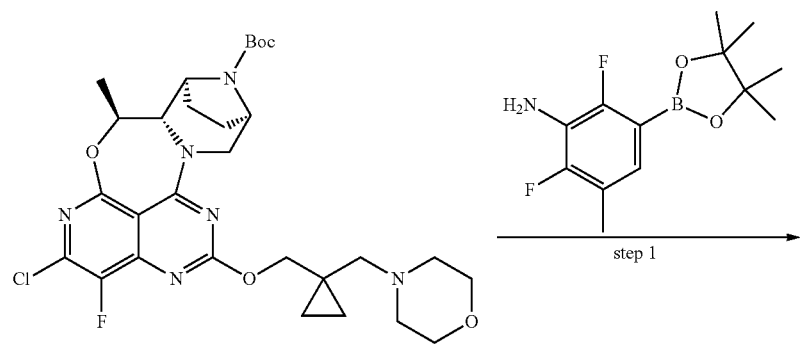

-continued
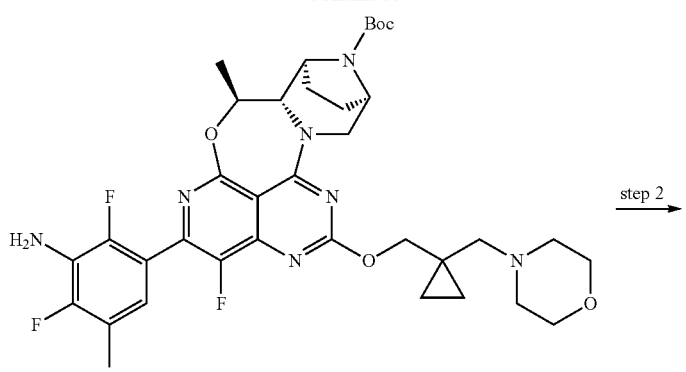
step 2
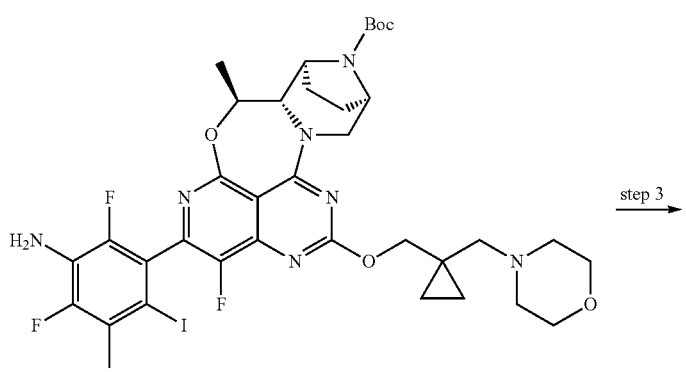
step 3
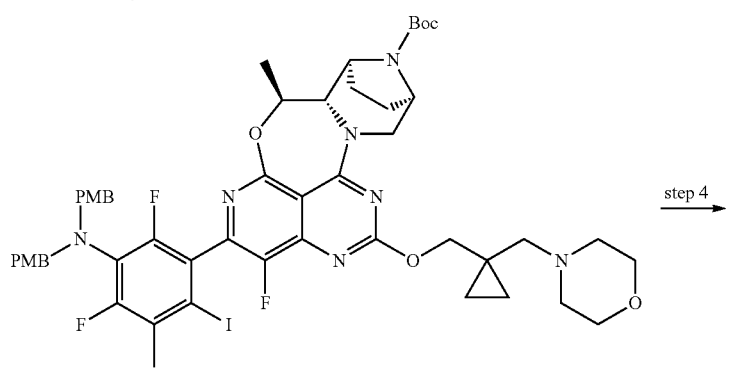
step 4
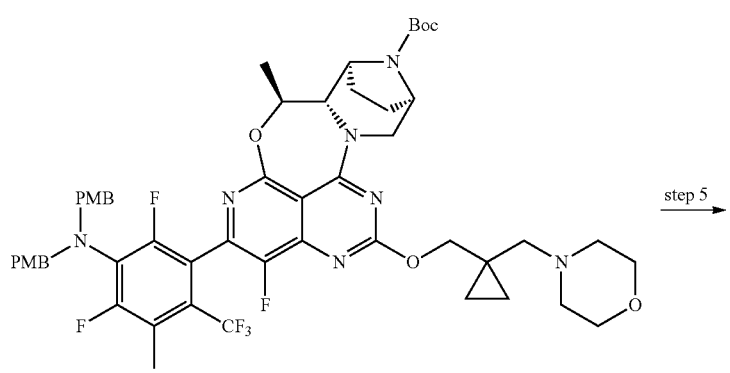
step 5

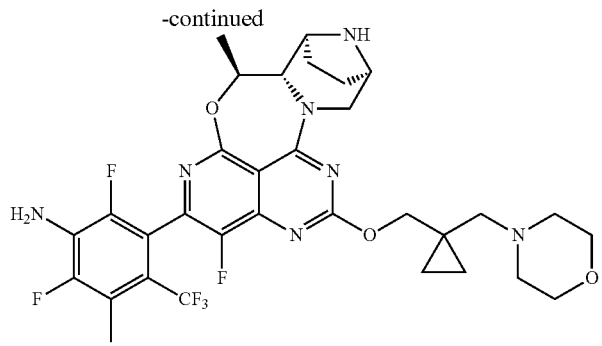

Step 1: tert-Butyl (5S,5aS,6S,9R)-2-(3-amino-2,4-difluoro-5-methylphenyl)-1-fluoro-5-methyl-12-((1-(morpholinomethyl)cyclopropyl)methoxy)-5a,6,7,8,9,10-hexahydro-5H-4-oxa-3,10a,11,13,14-pentaaza-6,9-methanonaphtho[1,8-ab]heptalene-14-carboxylate Under nitrogen, a solution of tert-butyl (5S,5aS,6S,9R)-2-chloro-1-fluoro-5-methyl-12-((1-(morpholinomethyl)cyclopropyl)methoxy)-5a,6,7,8,9,10-hexahydro-5H-4-oxa-3,10a,11,13,14-pentaaza-6,9-methanonaphtho[1,8-ab]heptalene-14-carboxylate (300 mg, 0.496 mmol, from Compound 210), 2,6-difluoro-3-methyl-5-(4,4,5,5-tetramethyl-1,3,2-dioxaborolan-2-yl)aniline (266.8 mg, 0.990 mmol), $K_3PO_4$ (1.5 M in $H_2O$, 2 mL, 0.600 mmol) and cataCXium A Pd G3 (72.2 mg, 0.100 mmol) in tetrahydrofuran (10 mL) was stirred for 3 hours at 60° C. The reaction mixture was diluted with water and extracted with EtOAc. The combined organic layer was dried over anhydrous sodium sulfate and concentrated under vacuum. The residue was purified by flash chromatography on silica gel (gradient: 0-60% ethyl acetate in petroleum ether) to afford the title compound (250 mg) as a yellow solid. LC-MS: (ESI, m/z): $[M+H]^+=712$.

Step 2: tert-Butyl (5S,5aS,6S,9R)-2-(3-amino-2,4-difluoro-6-iodo-5-methylphenyl)-1-fluoro-5-methyl-12-((1-(morpholinomethyl)cyclopropyl)methoxy)-5a,6,7,8,9,10-hexahydro-5H-4-oxa-3,10a,11,13,14-pentaaza-6,9-methanonaphtho[1,8-ab]heptalene-14-carboxylate To a solution of tert-butyl (5S,5aS,6S,9R)-2-(3-amino-2,4-difluoro-5-methylphenyl)-1-fluoro-5-methyl-12-((1-(morpholinomethyl) cyclopropyl)methoxy)-5a,6,7,8,9,10-hexahydro-5H-4-oxa-3,10a,11,13,14-pentaaza-6,9-methanonaphtho[1,8-ab]heptalene-14-carboxylate (250 mg, 0.352 mmol) in acetic acid (10 mL) was added NIS (94.8 mg, 0.420 mmol) at room temperature. The mixture was stirred at room temperature for 1 hour. The reaction was quenched with $Na_2S_2O_3$ aqueous and extracted with EtOAc. The combined organic layers were dried over anhydrous sodium sulfate and concentrated under vacuum. The residue was purified by flash chromatography on silica gel (gradient: 0-10% methanol in dichloromethane) to afford the title compound (180 mg) as a yellow solid. LC-MS: (ESI, m/z): $[M+H]^+=838$.

Step 3: tert-Butyl (5S,5aS,6S,9R)-2-(3-(bis(4-methoxybenzyl)amino)-2,4-difluoro-6-iodo-5-methylphenyl)-1-fluoro-5-methyl-12-((1-(morpholinomethyl)cyclopropyl)methoxy)-5a,6,7,8,9,10-hexahydro-5H-4-oxa-3,10a,11,13,14-pentaaza-6,9-methanonaphtho[1,8-ab]heptalene-14-carboxylate To a solution of tert-butyl (5S,5aS,6S,9R)-2-(3-amino-2,4-difluoro-6-iodo-5-methylphenyl)-1-fluoro-5-methyl-12-((1-(morpholinomethyl)cyclopropyl)methoxy)-5a,6,7,8,9,10-hexahydro-5H-4-oxa-3,10a,11,13,14-pentaaza-6,9-methanonaphtho[1,8-ab]heptalene-14-carboxylate (180 mg, 0.215 mmol)] in N,N-dimethylformamide (10 mL) was added NaH (60% dispersion in mineral oil, 43.0 mg, 1.08 mmol) at 0° C., and the mixture was stirred for 30 minutes at room temperature. Then PMBCl (86.5 mg, 0.550 mmol) was added, and the mixture was stirred overnight at room temperature. The reaction was quenched with saturated $NH_4Cl$ aqueous solution. The reaction mixture was diluted with water and extracted with ethyl acetate. The combined organic layers were washed with brine, dried over anhydrous sodium sulfate and concentrated under vacuum. The residue was purified by flash chromatography on silica gel (gradient: 0-10% methanol in dichloromethane) to afford the title compound (150 mg) as a yellow solid. LC-MS: (ESI, m/z): $[M+H]^+=1078$.

Step 4: tert-Butyl (5S,5aS,6S,9R)-2-(3-(bis(4-methoxybenzyl)amino)-2,4-difluoro-5-methyl-6-(trifluoromethyl)phenyl)-1-fluoro-5-methyl-12-((1-(morpholinomethyl)cyclopropyl)methoxy)-5a,6,7,8,9,10-hexahydro-5H-4-oxa-3,10a,11,13,14-pentaaza-6,9-methanonaphtho[1,8-ab]heptalene-14-carboxylate Under nitrogen, to a mixture of $Cu(O_2CCF_2SO_2F)_2$ (551 mg, 1.32 mmol) and copper (84.3 mg, 1.32 mmol) was added an ice cooled solution of tert-butyl (5S,5aS,6S,9R)-2-(3-(bis(4-methoxybenzyl) amino)-2,4-difluoro-6-iodo-5-methylphenyl)-1-fluoro-5-methyl-12-((1-(morpholinomethyl)cyclopropyl)methoxy)-5a,6,7,8,9,10-hexahydro-5H-4-oxa-3,10a,11,13,14-pentaaza-6,9-methanonaphtho[1,8-ab]heptalene-14-carboxylate (142 mg, 0.132 mmol) in DMF (10 mL) at 0° C., and the mixture was stirred for 1 hour at room temperature. The reaction mixture was diluted with water and extracted with ethyl acetate. The combined organic layers were dried over anhydrous sodium sulfate and concentrated under vacuum. The residue was purified by flash chromatography on silica gel (gradient: 0-10% methanol in dichloromethane) to afford the title compound (105 mg) as a yellow solid. LC-MS: (ESI, m/z): $[M+H]^+=1020$.

Step 5: 2,6-Difluoro-3-((5S,5aS,6S,9R)-1-fluoro-5-methyl-12-((1-(morpholinomethyl)cyclopropyl)methoxy)-5a,6,7,8,9,10-hexahydro-5H-4-oxa-3,10a,11,13,14-pentaaza-6,9-methanonaphtho[1,8-ab]heptalen-2-yl)-5-methyl-4-(trifluoromethyl)aniline A solution of tert-butyl (5S,5aS,6S,9R)-2-(3-(bis(4-methoxybenzyl)amino)-2,4-difluoro-5-methyl-6-(trifluoromethyl)phenyl)-1-fluoro-5-methyl-12-((1-(morpholinomethyl)cyclopropyl)methoxy)-5a,6,7,8,9,10-hexahydro-5H-4-oxa-3,10a,11,13,14-pentaaza-6,9-methanonaphtho[1,8-ab]heptalene-14-carboxylate (100 mg, 0.098 mmol) in 2,2,2-trifluoroacetic acid (10 mL) was stirred for 1 hour at room temperature. The solvent was concentrated under vacuum. The residue was purified by Prep-HPLC (Column: XBridge Prep OBD C18 Column, 30*150 mm, 5 μm; Mobile Phase A: Water (10 mmol/L $NH_4HCO_3$), Mobile Phase B: ACN; Flow rate: 60 mL/min; Gradient: 26% B to 42% B in 9 min, 42% B; Wave Length: 254/220 nm; RT1(min): 8.9) to afford the title compound (9.5 mg) as a white solid. LC-MS: (ESI, m/z): $[M+H]^+$=680. $^1$H NMR (300 MHz, DMSO-d6, ppm) δ 6.28-6.10 (m, 2H), 5.10 (d, J=13.3 Hz, 1H), 4.60-4.50 (m, 1H), 4.37-4.19 (m, 2H), 4.01-3.90 (m, 1H), 3.61-3.49 (m, 5H), 3.48-3.41 (m, 2H), 3.03 (d, J=12.8 Hz, 1H), 2.90-2.75 (m, 1H), 2.42-2.32 (m, 5H), 2.31 (s, 3H), 1.90-1.74 (m, 1H), 1.72-1.51 (m, 3H), 1.44 (d, J=6.3 Hz, 3H), 0.72-0.59 (m, 2H), 0.47-0.32 (m, 2H).

Each compound in the Table below was prepared following a similar experimental procedure (using appropriately substituted reagents) as described for Example 224.

| Cmpd. No. | $^1$H NMR | MS $(M + H)^+$ |
|---|---|---|
| 225 | $^1$H NMR (300 MHz, DMSO-d6, ppm) δ 6.18-6.14 (m, 1H), 5.16-5.12 (m, 1H), 4.67-4.62 (m, 1H), 4.22-4.04 (m, 3H), 3.81-3.62 (m, 2H), 3.19-3.03 (m, 3H), 2.77-2.72 (m, 1H), 2.38-2.31 (m, 4H), 2.10-1.46 (m, 15H). | 712 |
| 226 | $^1$H NMR (400 MHz, DMSO-$d_6$, ppm): δ 6.79 (d, J = 8.8 Hz, 1H), 5.97 (d, J = 11.5 Hz, 2H), 5.17-4.96 (m, 1H), 4.61-4.43 (m, 1H), 4.38-4.15 (m, 2H), 3.94 (t, J = 7.9 Hz, 1H), 3.57-3.48 (m, 5H), 3.47-3.39 (m, 1H), 3.01 (d, J = 13.1 Hz, 1H), 2.43-2.23 (m, 9H), 1.89-1.72 (m, 1H), 1.71-1.47 (m, 3H), 1.42 (d, J = 6.3 Hz, 3H), 0.69-0.53 (m, 2H), 0.47-0.32 (m, 2H). | 662 |
| 227 | $^1$H NMR (300 MHz, DMSO-$d_6$, ppm): δ 6.81 (d, J = 8.8 Hz, 1H), 5.54-5.38 (m, 1H), 4.66-4.48 (m, 2H), 4.37-4.23 (m, 2H), 4.09-3.91 (m, 3H), 3.82 (s, 1H), 3.73-3.42 (m, 2H), 3.32-3.26 (m, 1H), 3.06-2.97 (m, 1H), 2.84-2.73 (m, 1H), 2.60-2.53 (m, 4H), 2.37-2.24 (m, 2H), 2.19-2.08 (m, 2H), 1.86-1.69 (m, 3H), 1.65-1.52 (m, 3H), 1.54-1.45 (m, 2H), 1.28 (s, 2H). | 694 |

Example 228: Compound 228

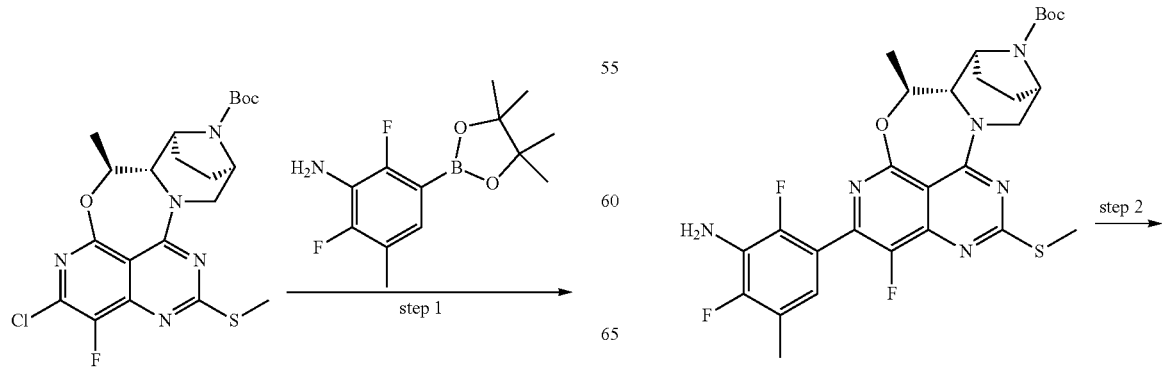

-continued

791
-continued

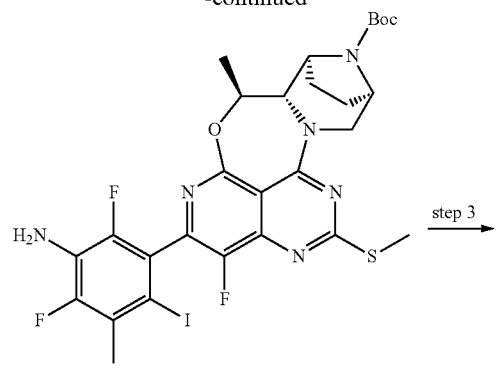
step 3

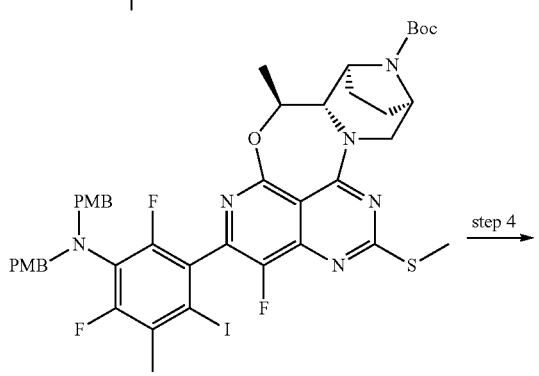
step 4

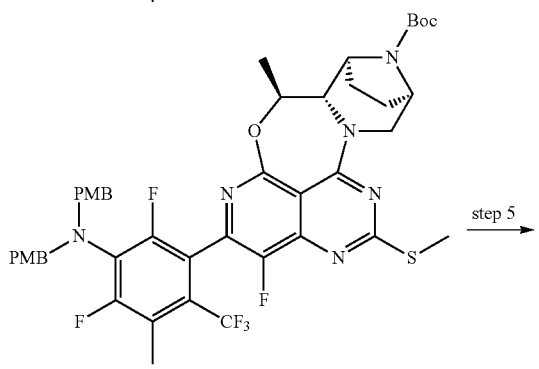
step 5

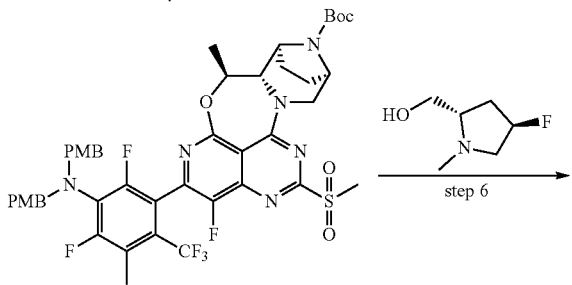
step 6

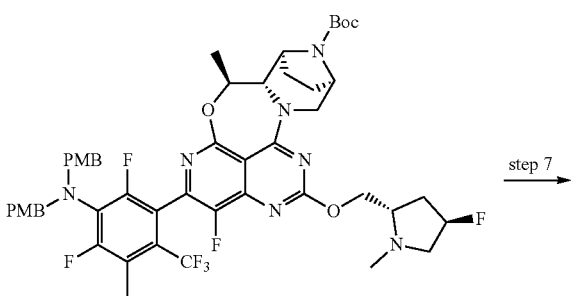
step 7

792
-continued

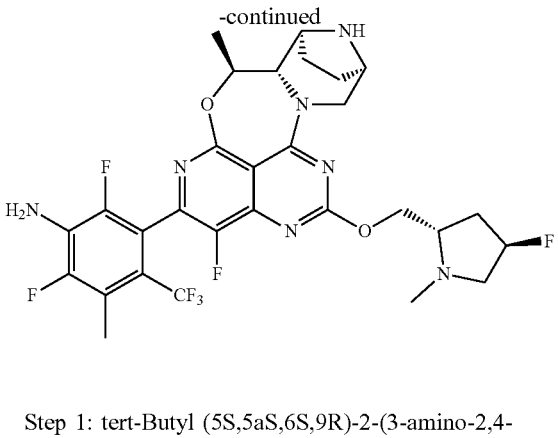

Step 1: tert-Butyl (5S,5aS,6S,9R)-2-(3-amino-2,4-difluoro-5-methylphenyl)-1-fluoro-5-methyl-12-(methylthio)-5a,6,7,8,9,10-hexahydro-5H-4-oxa-3,10a,11,13,14-pentaaza-6,9-methanonaphtho[1,8-ab]heptalene-14-carboxylate Under nitrogen, a solution of tert-butyl (5S,5aS,6S,9R)-2-chloro-1-fluoro-5-methyl-12-(methylthio)-5a,6,7,8,9,10-hexahydro-5H-4-oxa-3,10a,11,13,14-pentaaza-6,9-methanonaphtho[1,8-ab]heptalene-14-carboxylate (501 mg, 1.04 mmol), 2,6-difluoro-3-methyl-5-(4,4,5,5-tetramethyl-1,3,2-dioxaborolan-2-yl)aniline (280 mg, 1.04 mmol), $K_3PO_4$ (1.5 M in $H_2O$, 1.1 mL) and cataCXium A Pd G3 (75.7 mg, 0.100 mmol) in tetrahydrofuran (5.5 mL) was stirred for 3 hours at 90° C. The reaction mixture was diluted with water and extracted with EtOAc. The combined organic layers were dried over anhydrous sodium sulfate and concentrated under vacuum. The residue was purified by flash chromatography on silica gel (gradient: 0-30% EtOAc in petroleum ether) to afford the title compound (260 mg) as a yellow solid. LC-MS: (ESI, m z): $[M+H]^+=589$.

Step 2: tert-Butyl (5S,5aS,6S,9R)-2-(3-amino-2,4-difluoro-6-iodo-5-methylphenyl)-1-fluoro-5-methyl-12-(methylthio)-5a,6,7,8,9,10-hexahydro-5H-4-oxa-3,10a,11,13,14-pentaaza-6,9-methanonaphtho[1,8-ab]heptalene-14-carboxylate To a solution of tert-butyl (5S,5aS,6S,9R)-2-(3-amino-2,4-difluoro-5-methylphenyl)-1-fluoro-5-methyl-12-(methylthio)-5a,6,7,8,9,10-hexahydro-5H-4-oxa-3,10a,11,13,14-pentaaza-6,9-methanonaphtho[1,8-ab]heptalene-14-carboxylate (260 mg, 0.441 mmol) and TsOH·$H_2O$ (9.2 mg, 0.050 mmol) in N,N-dimethylformamide (3 mL) was added and NIS (130 mg, 0.580 mmol) at room temperature. The solution was stirred for 1 hour at room temperature. The reaction was quenched with saturated $Na_2S_2O_3$ aqueous solution. The reaction mixture was diluted with water and extracted with EtOAc. The combined organic layers were washed with brine, dried over anhydrous sodium sulfate and concentrated under vacuum. The residue was purified by flash chromatography on silica gel (gradient: 0-20% EtOAc in petroleum ether) to afford the title compound (320 mg) as a brown solid. LC-MS: (ESI, m/z): $[M+H]^+=715$.

Step 3: tert-Butyl (5S,5aS,6S,9R)-2-(3-(bis(4-methoxybenzyl)amino)-2,4-difluoro-6-iodo-5-methylphenyl)-1-fluoro-5-methyl-12-(methylthio)-5a,6,7,8,9,10-hexahydro-5H-4-oxa-3,10a,11,13,14-pentaaza-6,9-methanonaphtho[1,8-ab]heptalene-14-carboxylate To a solution of tert-butyl (5S,5aS,6S,9R)-2-(3-amino-2,4-difluoro-6-iodo-5-methylphenyl)-1-fluoro-5-methyl-12-

(methylthio)-5a,6,7,8,9,10-hexahydro-5H-4-oxa-3,10a,11,13,14-pentaaza-6,9-methanonaphtho[1,8-ab] heptalene-14-carboxylate (320 mg, 0.447 mmol) in N,N-dimethylformamide (5 mL) was added NaH (60% dispersion in mineral oil, 90.0 mg, 2.25 mmol) at 0° C., and the mixture was stirred for 30 minutes at room temperature. Then PMBCl (175 mg, 1.12 mmol) was added, and the mixture was stirred for 5 hours at room temperature. The reaction was quenched with saturated NH$_4$Cl solution and extracted with EtOAc. The combined organic layers were dried over anhydrous sodium sulfate and concentrated under vacuum. The residue was purified by flash chromatography on silica gel (gradient: 0-20% EtOAc in petroleum ether) to afford the title compound (400 mg) as a yellow oil. LC-MS: (ESI, m/z): [M+H]$^+$=955.

Step 4: tert-Butyl (5S,5aS,6S,9R)-2-(3-(bis(4-methoxybenzyl)amino)-2,4-difluoro-5-methyl-6-(trifluoromethyl)phenyl)-1-fluoro-5-methyl-12-(methylthio)-5a,6,7,8,9,10-hexahydro-5H-4-oxa-3,10a,11,13,14-pentaaza-6,9-methanonaphtho[1,8-ab]heptalene-14-carboxylate Under nitrogen, a solution of tert-butyl (5S,5aS,6S,9R)-2-(3-(bis(4-methoxybenzyl) amino)-2,4-difluoro-6-iodo-5-methylphenyl)-1-fluoro-5-methyl-12-(methylthio)-5a,6,7,8,9,10-hexahydro-5H-4-oxa-3,10a,11,13,14-pentaaza-6,9-methanonaphtho[1,8-ab]heptalene-14-carboxylate (370 mg, 0.387 mmol), methyl 2,2-difluoro-2-(fluorosulfonyl)acetate (0.25 mL, 1.93 mmol) and CuI (74.0 mg, 0.390 mmol) in N,N-dimethylacetamide (5 mL) was stirred for 3 hours at 90° C. The reaction mixture was diluted with water and extracted with EtOAc. The combined organic layers were dried over anhydrous sodium sulfate and concentrated under vacuum. The residue was purified by flash chromatography on silica gel (gradient: 0-30% EtOAc in petroleum ether) to afford the title compound (280 mg) as a yellow oil. LC-MS: (ESI, m/z): [M+H]$^+$=897.

Step 5: tert-Butyl (5S,5aS,6S,9R)-2-(3-(bis(4-methoxybenzyl)amino)-2,4-difluoro-5-methyl-6-(trifluoromethyl)phenyl)-1-fluoro-5-methyl-12-(methylsulfonyl)-5a,6,7,8,9,10-hexahydro-5H-4-oxa-3,10a,11,13,14-pentaaza-6,9-methanonaphtho[1,8-ab]heptalene-14-carboxylate To a solution of tert-butyl (5S,5aS,6S,9R)-2-(3-(bis(4-methoxybenzyl) amino)-2,4-difluoro-5-methyl-6-(trifluoromethyl)phenyl)-1-fluoro-5-methyl-12-(methylthio)-5a,6,7,8,9,10-hexahydro-5H-4-oxa-3,10a,11,13,14-pentaaza-6,9-methanonaphtho[1,8-ab]heptalene-14-carboxylate (300 mg, 0.334 mmol) in EtOAc (5 mL) was added mCPBA (174 mg, 1.01 mmol) at 0° C. in 3 portions, and the mixture was stirred for 3 hours at room temperature. The reaction was quenched with saturated Na$_2$S$_2$O$_3$ aqueous solution, diluted with water and extracted with EtOAc. The combined organic layers were washed with brine, dried over anhydrous sodium sulfate and concentrated under vacuum. The residue was purified by flash chromatography on silica gel (gradient: 0-60% EtOAc in petroleum ether) to afford the title compound (192 mg) as a yellow solid. LC-MS: (ESI, m/z): [M+H]$^+$=929.

Step 6: tert-Butyl (5S,5aS,6S,9R)-2-(3-(bis(4-methoxybenzyl)amino)-2,4-difluoro-5-methyl-6-(trifluoromethyl)phenyl)-1-fluoro-12-(((2S,4R)-4-fluoro-1-methylpyrrolidin-2-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate To a solution of ((2S,4R)-4-fluoro-1-methylpyrrolidin-2-yl)methanol (21.6 mg, 0.162 mmol) in tetrahydrofuran (2 mL) was added NaH (60% dispersion in mineral oil, 25.9 mg, 0.648 mmol) at 0° C., and the mixture was stirred for 30 minutes at room temperature. Then tert-butyl (5S,5aS,6S,9R)-2-(3-(bis(4-methoxybenzyl) amino)-2,4-difluoro-5-methyl-6-(trifluoromethyl)phenyl)-1-fluoro-5-methyl-12-(methylsulfonyl)-5a,6,7,8,9,10-hexahydro-5H-4-oxa-3,10a,11,13,14-pentaaza-6,9-methanonaphtho[1,8-ab]heptalene-14-carboxylate (100 mg, 0.108 mmol) was added, and the mixture was stirred for 2 hours at room temperature. The reaction was quenched with saturated NH$_4$Cl aqueous solution, diluted with water and extracted with ethyl acetate. The combined organic layers were washed with brine, dried over anhydrous sodium sulfate and concentrated under vacuum. The residue was purified by flash chromatography on silica gel (gradient: 0-100% EtOAc in petroleum ether) to afford the title compound (100 mg) as a yellow solid. LC-MS: (ESI, m/z): [M+H]$^+$=982.

Step 7: 2,6-Difluoro-3-((5S,5aS,6S,9R)-1-fluoro-12-(((2S,4R)-4-fluoro-1-methylpyrrolidin-2-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-5-methyl-4-(trifluoromethyl)aniline A solution of tert-butyl (5S,5aS,6S,9R)-2-(3-(bis(4-methoxybenzyl) amino)-2,4-difluoro-5-methyl-6-(trifluoromethyl)phenyl)-1-fluoro-12-(((2S,4R)-4-fluoro-1-methylpyrrolidin-2-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (100 mg, 0.102 mmol) in 2,2,2-trifluoroacetic acid (10 mL) was stirred for 1 hour at room temperature. The solvent was concentrated under vacuum. The residue was purified by Prep-HPLC (Column: XBridge Prep OBD C18 Column, 30*150 mm, 5 μm; Mobile Phase A: Water (10 mmol/L NH$_4$HCO$_3$), Mobile Phase B: ACN; Flow rate: 60 mL/min; Gradient: 17% B to 42% B in 9 min; Wave Length: 254/220 nm; RT1(min): 8) to afford the title compound (8.9 mg) as a white solid. LC-MS: (ESI, m/z): [M+H]$^+$=642. $^1$H NMR (300 MHz, DMSO-d6, ppm) δ 6.56-6.11 (m, 2H), 5.38-4.70 (m, 2H), 4.49-4.25 (m, 1H), 4.25-4.10 (m, 1H), 4.09-3.87 (m, 1H), 3.84-3.61 (m, 1H), 3.59-3.34 (m, 4H), 3.06-2.70 (m, 2H), 2.42-2.35 (m, 3H), 2.32 (s, 3H), 2.26-2.00 (m, 2H), 2.00-1.89 (m, 1H), 1.89-1.75 (m, 1H), 1.75-1.50 (m, 2H), 1.39-1.13 (m, 3H).

Example 229: Compound 229, was prepared following a similar experimental procedure (using appropriately substituted reagents) as described for Example 228

229: $^1$H NMR: (400 MHz, DMSO-d6, ppm) δ 6.76 (d, J=86.0 Hz, 1H), 6.18-6.15 (m, 2H), 5.09-5.06 (m, 1H), 4.57-4.54 (m, 1H), 4.08-3.96 (m, 3H), 3.72-3.69 (m, 1H), 3.57-3.55 (m, 1H), 3.45-3.43 (m, 1H), 3.27-3.25 (m, 1H), 3.05-2.99 (m, 2H), 2.58-2.54 (m, 2H), 2.34-2.30 (m, 4H), 1.96-1.54 (m, 8H), 1.43 (d, J=6.4 Hz, 3H). MS (M+H)+: 680

Example 230: Compound 230

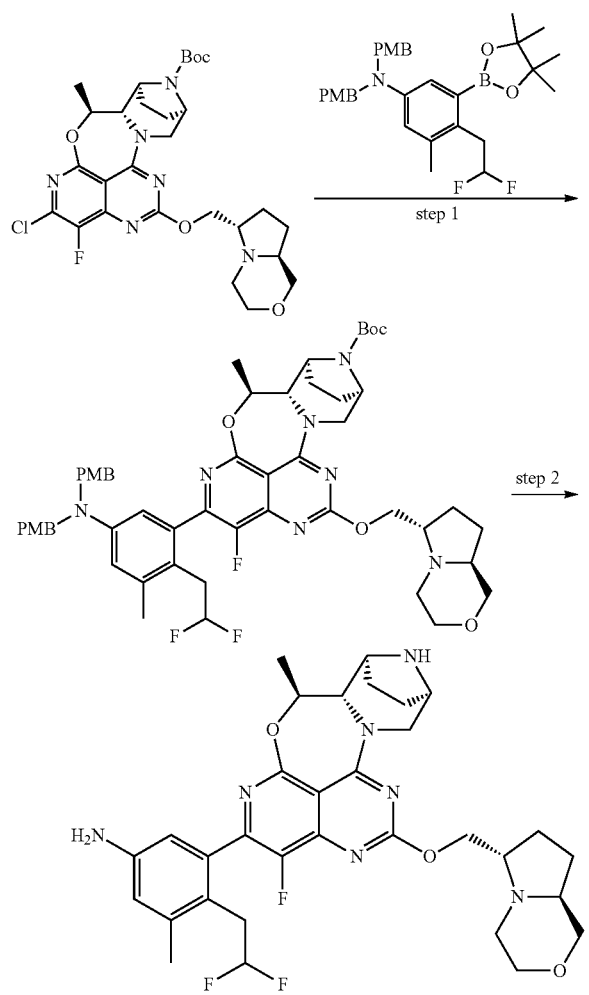

Step 1: tert-Butyl (5S,5aS,6S,9R)-2-(5-(bis(4-methoxybenzyl)amino)-2-(2,2-difluoroethyl)-3-methylphenyl)-1-fluoro-12-(((6S,8aS)-hexahydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate Under nitrogen, a solution of tert-butyl (5S,5aS,6S,9R)-2-chloro-1-fluoro-12-(((6S,8aS)-hexahydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (261 mg, 0.440 mmol), 4-(2,2-difluoroethyl)-N,N-bis(4-methoxybenzyl)-3-methyl-5-(4,4,5,5-tetramethyl-1,3,2-dioxaborolan-2-yl)aniline (220 mg, 0.372 mmol, intermediate 151), cataCXium A Pd G3 (60.1 mg, 0.0800 mmol) and K₃PO₄ (1 mL, 1.5 M in H₂O) in THF (5 mL) was stirred for 3 h at 60° C. The resulting mixture was diluted with EtOAc and washed with water. The organic layer was concentrated under vacuum. The residue was purified by flash chromatography on silica gel (gradient: 0-15% MeOH/DCM) to afford 315 mg of the title compound as a yellow solid. LC-MS: (ESI, m/z): [M+H]⁺=996.

Step 2: 4-(2,2-Difluoroethyl)-3-((5S,5aS,6S,9R)-1-fluoro-12-(((6S,8aS)-hexahydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-5-methylaniline A solution of tert-butyl (5S,5aS,6S,9R)-2-(5-(bis(4-methoxybenzyl)amino)-2-(2,2-difluoroethyl)-3-methylphenyl)-1-fluoro-12-(((6S,8aS)-hexahydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (20.1 mg, 0.0208 mmol) in TFA (2 mL) was stirred at room temperature for 1 h. The solvent was concentrated under vacuum. The residue was purified by C18 column (solvent gradient: 0-90% ACN in water (0.05% NH₄HCO₃)) to afford 9.8 mg of the title compound as a white solid. LC-MS: (ESI, m/z): [M+H]⁺=626. ¹H NMR (400 MHz, DMSO-d₆) δ 6.60-6.47 (m, 1H), 6.42 (s, 1H), 6.26-5.79 (m, 1H), 5.29-5.00 (m, 3H), 4.63-4.47 (m, 1H), 4.42 (dd, J=11.0, 5.3 Hz, 1H), 4.14 (dd, J=10.9, 5.9 Hz, 1H), 3.97 (d, J=9.0 Hz, 1H), 3.63 (dd, J=11.0, 3.6 Hz, 1H), 3.59-3.48 (m, 3H), 3.45 (t, J=5.2 Hz, 2H), 3.15 (t, J=10.5 Hz, 1H), 3.01 (dd, J=19.2, 9.7 Hz, 4H), 2.95-2.80 (m, 3H), 2.25 (s, 3H), 2.14-1.97 (m, 1H), 1.90-1.71 (m, 2H), 1.70-1.50 (m, 4H), 1.44 (d, J=6.3 Hz, 3H), 1.37-1.19 (m, 1H).

Example 231: Compound 231

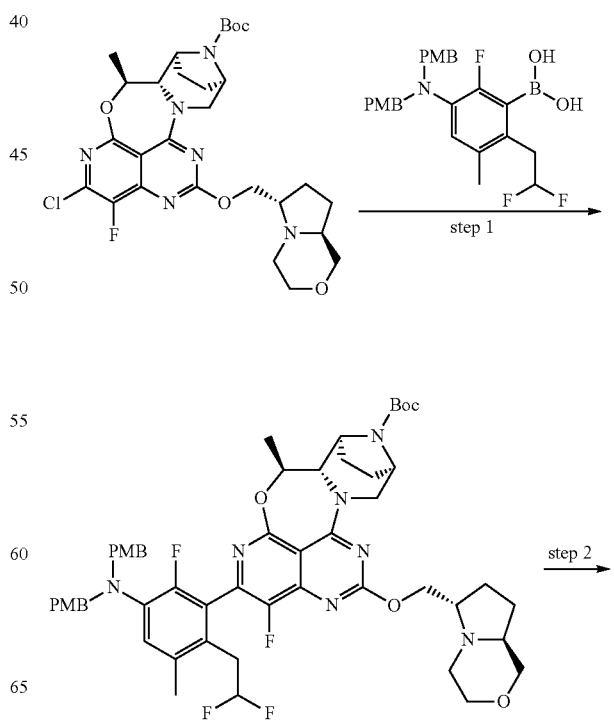

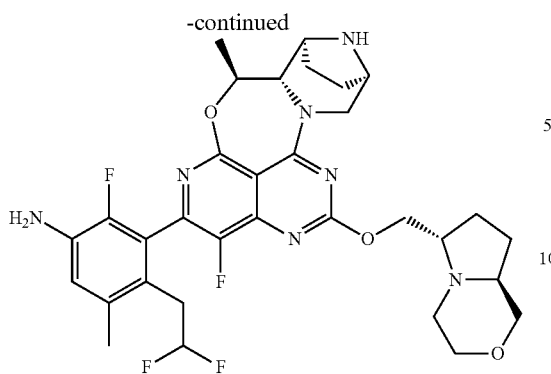

Step 1: tert-Butyl (5S,5aS,6S,9R)-2-(3-(bis(4-methoxybenzyl)amino)-6-(2,2-difluoroethyl)-2-fluoro-5-methylphenyl)-1-fluoro-12-(((6S,8aS)-hexahydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate Under nitrogen, a solution of tert-butyl (5S,5aS,6S,9R)-2-chloro-1-fluoro-12-(((6S,8aS)-hexahydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (20.2 mg, 0.0342 mmol), (3-(bis(4-methoxybenzyl)amino)-6-(2,2-difluoroethyl)-2-fluoro-5-methylphenyl)boronic acid (120 mg, 0.203 mmol, intermediate 152), cataCXium A Pd G3 (5.1 mg, 0.00700 mmol) and K$_3$PO$_4$ (0.3 mL, 1.5 M in H$_2$O) in THF (1.5 mL) was stirred at 60° C. for 3 h. The resulting solution was partitioned between water and EtOAc. The organic layer was dried over anhydrous sodium sulfate and concentrated under vacuum. The residue was purified by flash chromatography on silica gel eluting (gradient: 0-15% MeOH/DCM) to afford 28.0 mg of the title compound as a yellow solid. LC-MS: (ESI, m/z): [M+H]$^+$=984.

Step 2: 4-(2,2-Difluoroethyl)-2-fluoro-3-((5S,5aS,6S,9R)-1-fluoro-12-(((6S,8aS)-hexahydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-5-methylaniline A solution of tert-butyl (5S,5aS,6S,9R)-2-(3-(bis(4-methoxybenzyl) amino)-6-(2,2-difluoroethyl)-2-fluoro-5-methylphenyl)-1-fluoro-12-(((6S,8aS)-hexahydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (28.0 mg, 0.0285 mmol) in TFA (3 mL) was stirred at room temperature for 1.5 h. The solvent was concentrated under vacuum. The crude product was purified by Prep-HPLC with the following conditions: (Column: XBridge Prep OBD C18 Column, 30×150 mm, 5 μm; Mobile Phase A: Water (10 mmol/L NH$_4$HCO$_3$), Mobile Phase B: ACN; Flow rate: 60 mL/min; Gradient: 17% B to 42% B in 9 min, 42% B; Wave Length: 254/220 nm; R$_{T1}$(min): 9) to afford 4.7 mg of the title compound as a white solid LC-MS: (ESI, m/z): [M+H]$^+$= 644. $^1$H NMR (400 MHz, DMSO-d$_6$) δ 6.74 (d, J=9.2 Hz, 1H), 6.40-5.74 (m, 1H), 5.23 (s, 2H), 5.11 (dd, J=12.9, 2.6 Hz, 1H), 4.64-4.52 (m, 1H), 4.50-4.36 (m, 1H), 4.14 (dd, J=10.9, 5.8 Hz, 1H), 3.98 (d, J=9.1 Hz, 1H), 3.70-3.39 (m, 6H), 3.23-2.67 (m, 8H), 2.23 (d, J=7.5 Hz, 3H), 2.18-1.94 (m, 1H), 1.93-1.51 (m, 6H), 1.44 (dd, J=6.4, 2.1 Hz, 3H), 1.39-1.25 (m, 1H).

Example 232: Compound 232

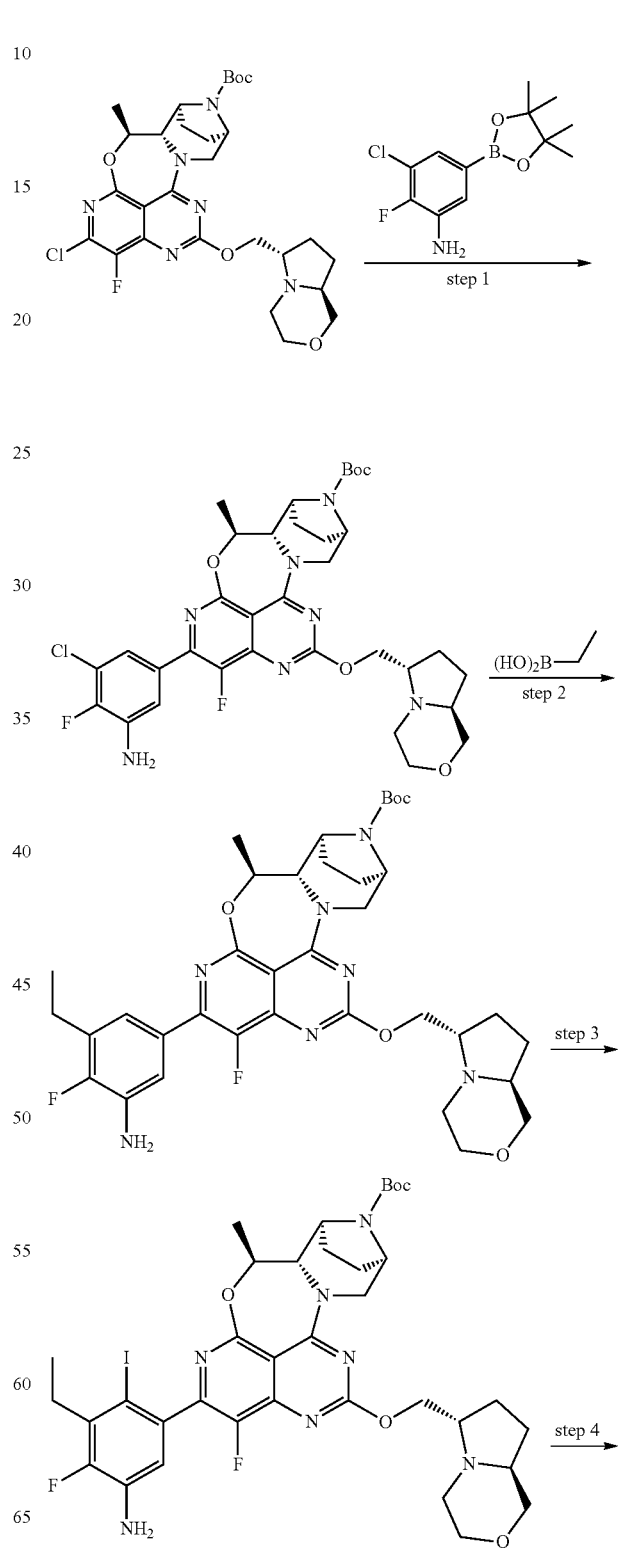

-continued

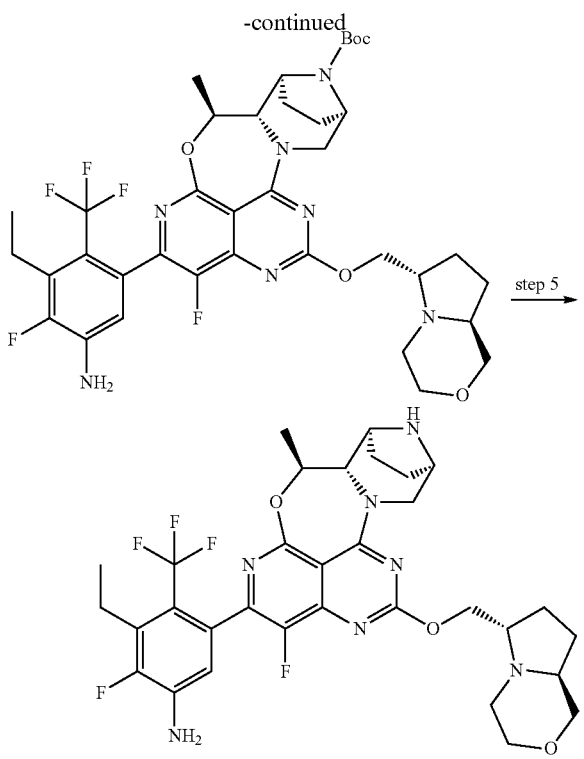

Step 1: tert-Butyl (5S,5aS,6S,9R)-2-(3-amino-5-chloro-4-fluorophenyl)-1-fluoro-12-(((6S,8aS)-hexahydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate Under nitrogen, a solution of 3-chloro-2-fluoro-5-(4,4,5,5-tetramethyl-1,3,2-dioxaborolan-2-yl)aniline (55.0 mg, 0.200 mmol, intermediate 155), tert-butyl (5S,5aS,6S,9R)-2-chloro-1-fluoro-12-(((6S,8aS)-hexahydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (120 mg, 0.203 mmol), K₃PO₄ (aqueous, 1 mL, 1.5 mmol) and cataCXium A Pd G3 (15.0 mg, 0.020 mmol) in THF (2 mL) was stirred at 60° C. for two hours. The reaction system was cooled to room temperature, diluted with water and extracted with ethyl acetate. The combined organic layers were concentrated under reduced pressure. The residue was purified by flash chromatography on silica gel (gradient: 0-12% methanol in dichloromethane) to yield 130 mg of the title compound as a white solid. LC-MS: (ESI, m z): [M+H]⁺=700.

Step 2: tert-Butyl (5S,5aS,6S,9R)-2-(3-amino-5-ethyl-4-fluorophenyl)-1-fluoro-12-(((6S,8aS)-hexahydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate Under nitrogen, a solution of ethylboronic acid (264.0 mg, 3.57 mmol), tert-butyl (5S,5aS,6S,9R)-2-(3-amino-5-chloro-4-fluorophenyl)-1-fluoro-12-(((6S,8aS)-hexahydro-1H-pyrrolo[2,1-c][1,4]oxazin-6-yl)methoxy)-5-methyl-5a, 6,7,8,9,10-hexahydro-5H-4-oxa-3,10a,11,13,14-pentaaza-6,9-methanonaphtho[1,8-ab]heptalene-14-carboxylate (500 mg, 0.714 mmol), BI-DIME (47.0 mg, 0.140 mmol), Pd₂(dba)₃ (66.0 mg, 0.070 mmol) and K₃PO₄ (1.52 g, 7.14 mmol) in toluene (8 mL) was stirred at 110° C. for two hours. The solvent was concentrated under reduced pressure. The residue was purified by flash chromatography on silica gel (gradient: 0-12% methanol in dichloromethane) to yield 537 mg (crude) of the title compound as a yellow solid. LC-MS: (ESI, m z): [M+H]⁺=694.

Step 3: tert-Butyl (5S,5aS,6S,9R)-2-(5-amino-3-ethyl-4-fluoro-2-iodophenyl)-1-fluoro-12-(((6S,8aS)-hexahydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate A solution of tert-butyl (5S,5aS,6S,9R)-2-(3-amino-5-ethyl-4-fluorophenyl)-1-fluoro-12-(((6S,8aS)-hexahydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (119.0 mg, 0.170 mmol) and NIS (42.0 mg, 0.190 mmol) in acetic acid (2 mL) was stirred for two hours at room temperature. The reaction was quenched with Na₂S₂O₃, diluted with water and extracted with ethyl acetate. The combined organic layers were concentrated under reduced pressure. The residual was purified by flash chromatography on silica gel (gradient: 0-15% methanol in dichloromethane) to yield 30 mg of the title compound as a brown solid. LC-MS: (ESI, m/z): [M+H]⁺=820.

Step 4: tert-Butyl (5S,5aS,6S,9R)-2-(5-amino-3-ethyl-4-fluoro-2-(trifluoromethyl)phenyl)-1-fluoro-12-(((6S,8aS)-hexahydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate Under nitrogen, to a solution of 2,2-difluoro-2-(fluorosulfonyl) acetate copper(II) (81.0 mg, 0.190 mmol) and Cu (12.0 mg, 0.190 mmol) in N,N-dimethyl formamide (1.5 mL) was added tert-butyl (5S,5aS,6S,9R)-2-(5-amino-3-ethyl-4-fluoro-2-iodophenyl)-1-fluoro-12-(((6S,8aS)-hexahydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (30.0 mg, 0.0366 mmol) at −78° C. The reaction was warmed to room temperature and stirred additional 1 h. The solution was loaded on C18 column and eluted with acetonitrile and water containing 0.05% NH₄HCO₃ (gradient:0-70% ACN in water) to yield 30 mg of the title compound as brown solid. LC-MS: (ESI, m/z): [M+H]⁺= 762.

Step 5: 3-Ethyl-2-fluoro-5-((5S,5aS,6S,9R)-1-fluoro-12-(((6S,8aS)-hexahydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-4-(trifluoromethyl)aniline A solution of tert-butyl (5S,5aS,6S,9R)-2-(5-amino-3-ethyl-4-fluoro-2-(trifluoromethyl) phenyl)-1-fluoro-12-(((6S,8aS)-hexahydro-1H-pyrrolo[2,1-c][1,4]oxazin-6-yl)methoxy)-5-methyl-5a,6,7,8,9,10-hexahydro-5H-4-oxa-3, 10a,11,13,14-pentaaza-6,9-methanonaphtho[1,8-ab]heptalene-14-carboxylate (30.0 mg, 0.0394 mmol) in TFA (3 mL) was stirred for 10 minutes at room temperature. The solvent was removed under vacuum. The residual was purified by reverse phase chromatography eluting with acetonitrile and water containing 0.05% NH$_4$HCO$_3$ (0-60%) to yield 30 mg crude product. The crude was further purified by prep-HPLC to afford 1 mg of title compound as a white solid. LC-MS: (ESI, m/z): [M+H]$^+$=662. $^1$H-NMR (300 MHz, DMSO-d6) δ 6.69-6.39 (m, 1H), 6.01 (s, 2H), 5.06 (d, J=12.9 Hz, 1H), 4.58-4.42 (m, 1H), 4.43-4.31 (m, 1H), 4.17-4.04 (m, 1H), 3.93 (d, J=8.9 Hz, 1H), 3.71-3.63 (m, 2H), 3.64-3.59 (m, 2H), 3.59-3.55 (m, 1H), 3.55-3.50 (m, 1H), 3.50-3.45 (m, 1H), 3.13 (t, J=10.4 Hz, 1H), 3.07-2.88 (m, 2H), 2.89-2.79 (m, 2H), 2.79-2.66 (m, 2H), 2.16-1.94 (m, 2H), 1.87-1.69 (m, 2H), 1.68-1.49 (m, 4H), 1.48-1.37 (m, 3H), 1.19-1.17 (m, 3H).

Example 233: Compound 233

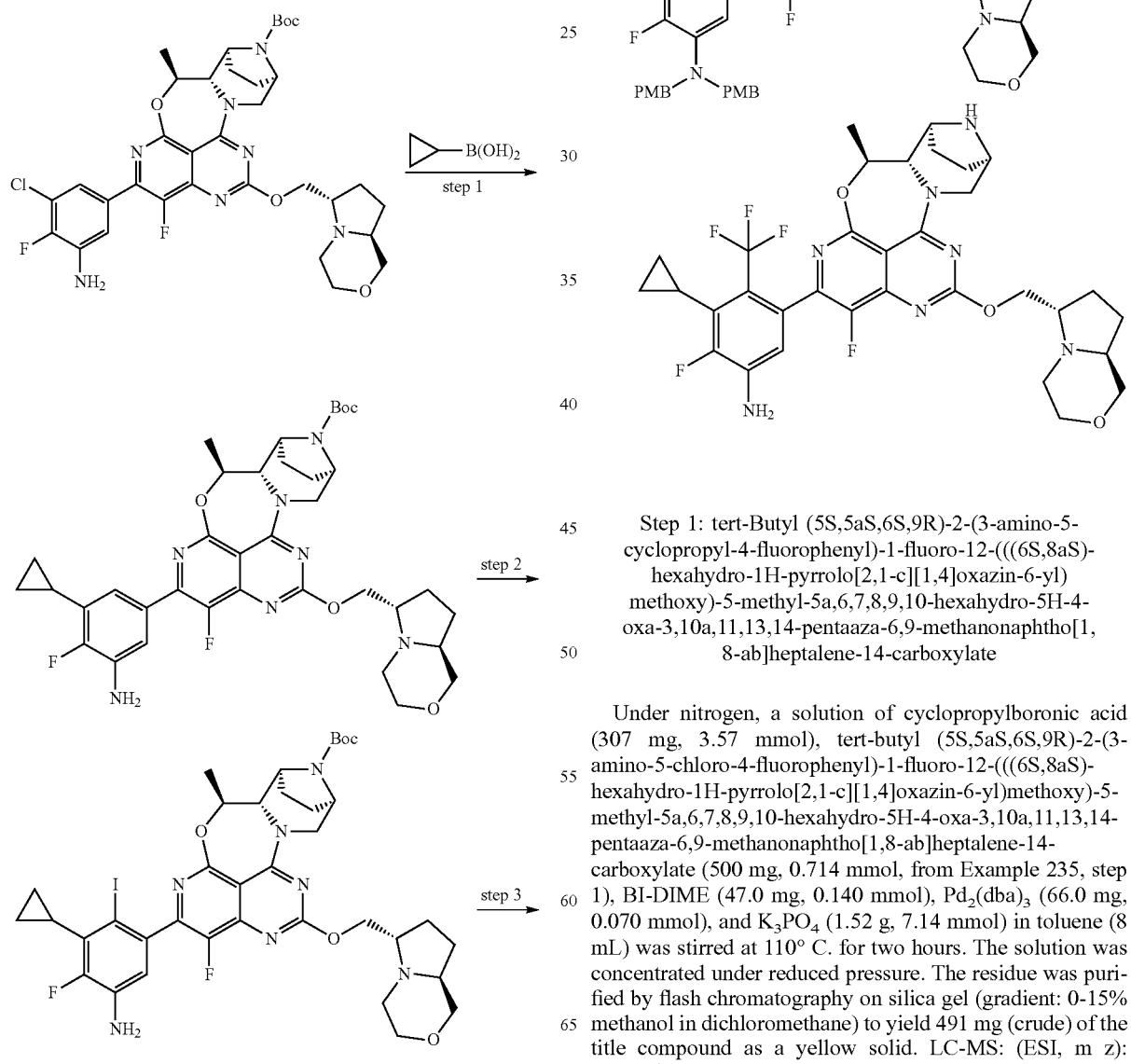

Step 1: tert-Butyl (5S,5aS,6S,9R)-2-(3-amino-5-cyclopropyl-4-fluorophenyl)-1-fluoro-12-(((6S,8aS)-hexahydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate Under nitrogen, a solution of cyclopropylboronic acid (307 mg, 3.57 mmol), tert-butyl (5S,5aS,6S,9R)-2-(3-amino-5-chloro-4-fluorophenyl)-1-fluoro-12-(((6S,8aS)-hexahydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (500 mg, 0.714 mmol, from Example 235, step 1), BI-DIME (47.0 mg, 0.140 mmol), Pd$_2$(dba)$_3$ (66.0 mg, 0.070 mmol), and K$_3$PO$_4$ (1.52 g, 7.14 mmol) in toluene (8 mL) was stirred at 110° C. for two hours. The solution was concentrated under reduced pressure. The residue was purified by flash chromatography on silica gel (gradient: 0-15% methanol in dichloromethane) to yield 491 mg (crude) of the title compound as a yellow solid. LC-MS: (ESI, m/z): [M+H]$^+$=706.

Step 2: tert-Butyl (5S,5aS,6S,9R)-2-(5-amino-3-cyclopropyl-4-fluoro-2-iodophenyl)-1-fluoro-12-(((6S,8aS)-hexahydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate A solution of tert-butyl (5S,5aS,6S,9R)-2-(3-amino-S-cyclopropyl-4-fluorophenyl)-1-fluoro-12-(((6S,8aS)-hexahydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (490 mg, 0.694 mmol), NIS (187.7 mg, 0.830 mmol) in acetic acid (2.5 mL) was stirred for two hours at room temperature. The reaction was quenched with $Na_2S_2O_3$, diluted with water and extracted with ethyl acetate. The combined organic layers were concentrated under reduced pressure. The residual was purified by flash chromatography on silica gel (gradient: 0-9 methanol in dichloromethane) to yield 280 mg crude product as a white solid. LC-MS: (ESI, m z): $[M+H]^+$=832.

Step 3: tert-Butyl (5S,5aS,6S,9R)-2-(5-(bis(4-methoxybenzyl)amino)-3-cyclopropyl-4-fluoro-2-iodophenyl)-1-fluoro-12-(((6S,8aS)-hexahydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate Under nitrogen, to a solution of tert-butyl (5S,5aS,6S,9R)-2-(5-amino-3-cyclopropyl-4-fluoro-2-iodophenyl)-1-fluoro-12-(((6S,8aS)-hexahydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (220.4 mg, 0.312 mmol) in N,N-dimethylformamide (8 mL) was added NaH (80.0 mg, 3.33 mmol) at 0° C. The solution was stirred at 0° C. for 30 min, then PMBCl (230.0 mg, 1.47 mmol) was added. The solution was stirred additional 1 h at room temperature. The reaction was quenched with ice water, extracted with ethyl acetate. The concentrated organic layers were concentrated under reduced pressure. The residue was purified by flash chromatography on silica gel (gradient: 0-9% methanol in dichloromethane) to yield 230 mg crude product as a brown solid. LC-MS: (ESI, m/z): $[M+H]^+$=1072.

Step 4: tert-Butyl (5S,5aS,6S,9R)-2-(5-(bis(4-methoxybenzyl)amino)-3-cyclopropyl-4-fluoro-2-(trifluoromethyl)phenyl)-1-fluoro-12-(((6S,8aS)-hexahydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate Under nitrogen, to a solution of 2,2-difluoro-2-(fluorosulfonyl) acetate copper(II) (1.06 g, 2.54 mmol) and Cu (156.8 mg, 2.49 mmol) in N, N-dimethylformamide (5 mL) was added tert-butyl (5S,5aS,6S,9R)-2-(5-(bis(4-methoxybenzyl)amino)-3-cyclopropyl-4-fluoro-2-iodophenyl)-1-fluoro-12-(((6S,8aS)-hexahydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (230.0 mg, 0.214 mmol) at −78° C. The reaction was allowed to warm to room temperature and stirred additional 1 h. The solution was diluted with water, extracted with EtOAc. The combined organic layers were concentrated under vacuum. The residue was purified by flash chromatography on silica gel (gradient: 0-10% methanol in dichloromethane) to yield 220 mg crude product as a brown solid. LC-MS: (ESI, m/z): $[M+H]^+$=1014.

Step 5: 3-Cyclopropyl-2-fluoro-5-((5S,5aS,6S,9R)-1-fluoro-12-(((6S,8aS)-hexahydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-4-(trifluoromethyl)aniline A solution of tert-butyl (5S,5aS,6S,9R)-2-(5-(bis(4-methoxybenzyl) amino)-3-cyclopropyl-4-fluoro-2-(trifluoromethyl)phenyl)-1-fluoro-12-(((6S,8aS)-hexahydro-1H-pyrrolo[2,1-c][1,4]oxazin-6-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (220.0 mg, 0.217 mmol) in 2,2,2-trifluoroacetic acid (5 mL) was stirred for one hour at room temperature. The reaction was concentrated under reduced pressure. The residual was purified by prep-HPLC to yield 10.3 mg product as a white solid. LC-MS: (ESI, m/z): $[M+H]^+$=674. $^1$H-NMR (300 MHz, DMSO-d6) δ: 6.11 (s, 1H), 5.70 (s, 2H), 5.07 (dd, J=12.8, 2.5 Hz, 1H), 4.49 (s, 1H), 4.39 (dd, J=10.9, 5.4 Hz, 1H), 4.12 (dd, J=10.9, 5.9 Hz, 1H), 3.94 (d, J=8.7 Hz, 1H), 3.62 (dd, J=10.9, 3.5 Hz, 1H), 3.58-3.47 (m, 3H), 3.47-3.38 (m, 1H), 3.14 (t, J=10.3 Hz, 1H), 3.07-2.76 (m, 5H), 2.23-1.94 (m, 2H), 1.91-1.50 (m, 6H), 1.43 (d, J=6.3 Hz, 3H), 1.39-1.15 (m, 2H), 1.01 (d, J=8.4 Hz, 2H), 0.73 (s, 2H).

Example 234: Compound 234 (Four Isomers)

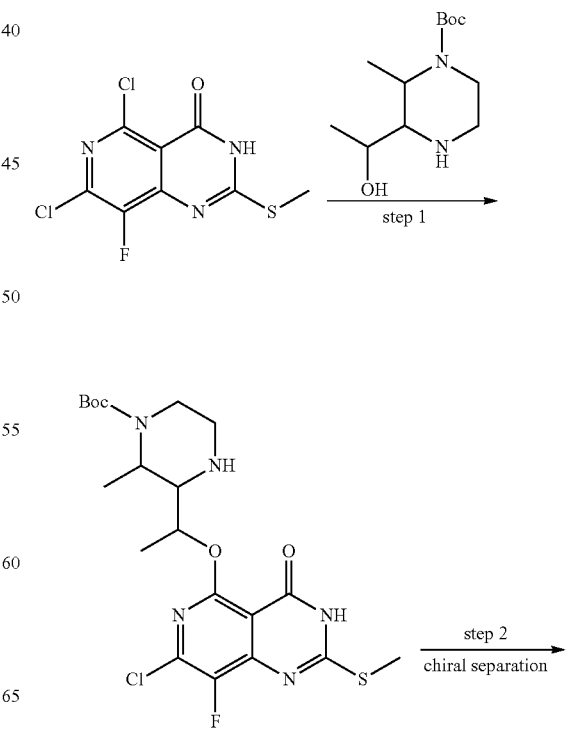

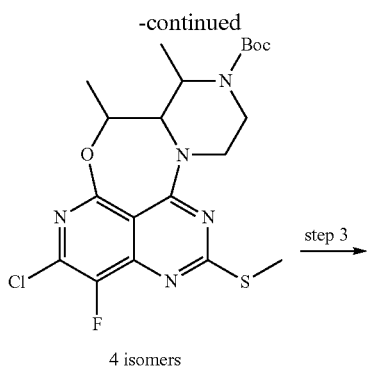

805

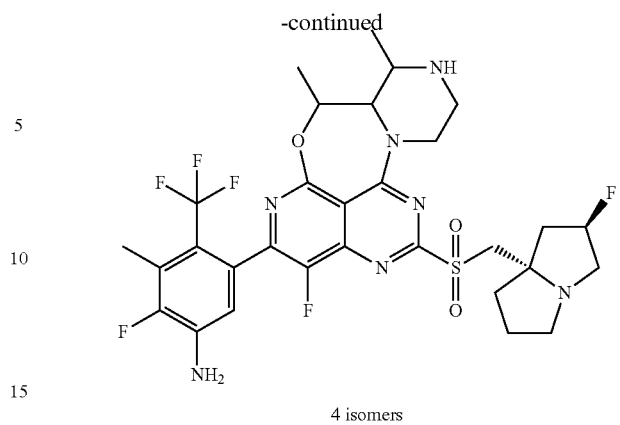

806

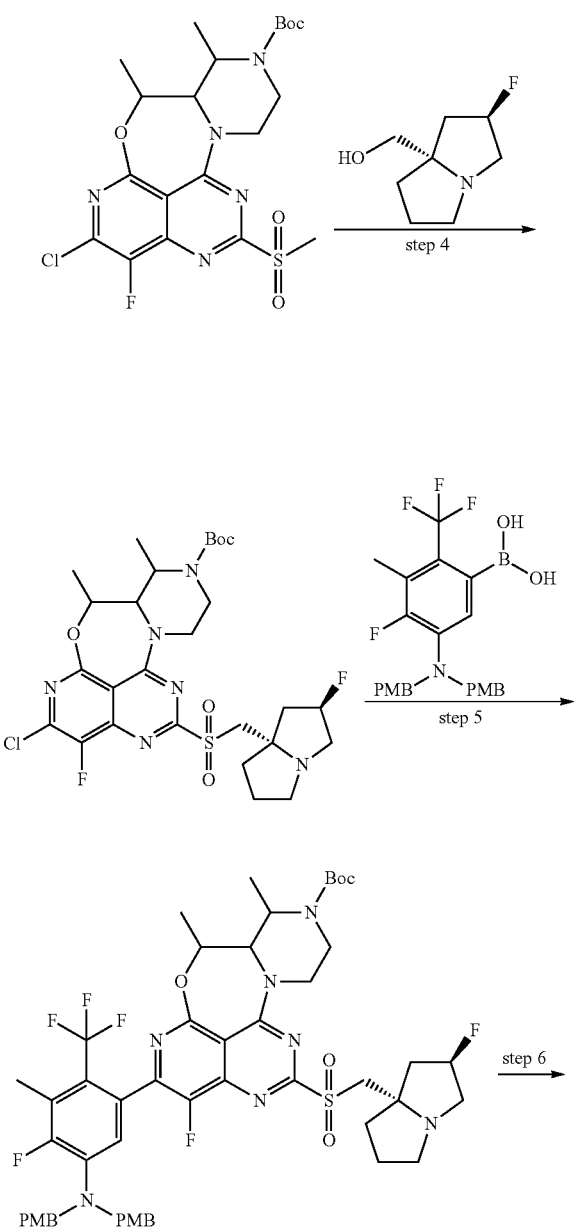

Step 1: tert-Butyl 3-(1-((7-chloro-8-fluoro-2-(methylthio)-4-oxo-3,4-dihydropyrido[4,3-d]pyrimidin-5-yl)oxy)ethyl)-2-methylpiperazine-1-carboxylate To a solution of tert-butyl 3-(1-hydroxyethyl)-2-methylpiperazine-1-carboxylate (1.30 g, crude, intermediate 156) in tetrahydrofuran (50 mL) was added NaH (60% dispersion in mineral oil, 1.28 g, 32.0 mmol) in 3 portions at 0° C., and the mixture was stirred for 30 minutes at room temperature. Then 5,7-dichloro-8-fluoro-2-methylsulfanyl-3H-pyrido[4,3-d]pyrimidin-4-one (2.24 g, 8.00 mmol) was added at room temperature, and the mixture was stirred for 2 hours. The reaction was quenched with saturated NH₄Cl aqueous solution. The reaction mixture was diluted with water and extracted with ethyl acetate. The combined organic layers were washed with brine, dried over anhydrous sodium sulfate and concentrated under vacuum to afford the title compound (1.65 g, crude) as a brown solid. LC-MS: (ESI, m/z): [M+H]⁺=488.

Step 2: tert-Butyl 2-chloro-1-fluoro-5,6-dimethyl-11-(methylthio)-5a,6,8,9-tetrahydro-4-oxa-3,7,9a,10,12-pentaazabenzo[4,5]cyclohepta[1,2,3-de]naphthalene-7(5H)-carboxylate (four isomers)

To a mixture of tert-butyl 3-(1-((7-chloro-8-fluoro-2-(methylthio)-4-oxo-3,4-dihydropyrido[4,3-d]pyrimidin-5-yl)oxy)ethyl)-2-methylpiperazine-1-carboxylate (1.65 g, crude) and DIPEA (9.00 mL, 54.5 mmol) in dichloromethane (150 mL) was added BOPCl (3.44 g, 13.5 mmol) at room temperature, and the mixture was stirred overnight. The reaction mixture was diluted with water and extracted with ethyl acetate. The combined organic layer was dried over anhydrous sodium sulfate and concentrated under vacuum. The residue was purified by flash chromatography on silica gel eluting (gradient: 0-50% ethyl acetate in petroleum ether) to afford 130 mg of the faster peak (mixture of isomer 1 and isomer 2) and 700 mg of the slower peak (mixture of isomer 3 and isomer 4) as yellow solids. Isomer 1 and isomer 2 was separated by Chiral-Prep-HPLC with the following conditions: (Column: CHIRALPAK IG, 2*25 cm, 5 μm; Mobile Phase A: Hex(0.5% 2 M NH₃—MeOH)-HPLC, Mobile Phase B: EtOH—HPLC; Flow rate: 20 mL/min; Gradient: 20% B to 20% B in 21 min; Wave Length: 220/254 nm; RT1(min): 10.91; RT2(min): 15.006; Sample Solvent: EtOH—HPLC; Injection Volume: 0.8 mL; Number Of Runs: 9) to afford isomer 1 (50.0 mg, the faster peak) and isomer 2 (50.0 mg, the slower peak) as white solids. Isomer 3 and isomer 4 was separated by Chiral-Prep-HPLC with the following conditions: (Column: CHIRAL ART Cellulose-SB, 2*25 cm, 5 M; Mobile Phase A: Hex (0.5% 2 M NH$_3$—MeOH)-HPLC, Mobile Phase B: EtOH—HPLC; Flow rate: 20 mL/min; Gradient: 15% B to 15% B in 16 min; Wave Length: 220/254 nm; RT1(min): 9.282; RT2(min): 10.762; Sample Solvent: EtOH—HPLC; Injection Volume: 0.3 mL; Number Of Runs: 54) to afford isomer 3 (230 mg, the faster peak) and isomer 4 (150 mg, the slower peak) as white solids.

Isomer 1: LC-MS: (ESI, m/z): [M+H]$^+$=470. $^1$H NMR (300 MHz, CDCl$_3$, ppm) δ 5.39-5.14 (m, 1H), 4.93-4.52 (m, 2H), 4.17-3.87 (m, 1H), 3.85-3.61 (m, 1H), 3.21-2.88 (m, 2H), 2.61 (s, 3H), 1.75-1.59 (m, 3H), 1.50 (d, J=4.9 Hz, 9H), 1.24 (d, J=6.4 Hz, 3H).

Isomer 2: LC-MS: (ESI, m/z): [M+H]$^+$=470. $^1$H NMR (300 MHz, CDCl$_3$, ppm) 5.44-5.11 (m, 1H), 4.95-4.48 (m, 2H), 4.21-3.90 (m, 1H), 3.86-3.58 (m, 1H), 3.04 (s, 2H), 2.61 (s, 3H), 1.72-1.57 (m, 3H), 1.50 (s, 9H), 1.25 (d, J=6.4 Hz, 3H).

Isomer 3: LC-MS: (ESI, m/z): [M+H]$^+$=470. $^1$H NMR (300 MHz, DMSO-d6, ppm) δ 5.19-5.00 (m, 1H), 4.90-4.76 (m, 1H), 4.68-4.46 (m, 1H), 4.09-3.98 (m, 1H), 3.98-3.76 (m, 1H), 3.16-2.90 (m, 2H), 2.54 (s, 3H), 1.48 (d, J=6.6 Hz, 3H), 1.42 (s, 9H), 1.16-1.02 (m, 3H).

Isomer 4: LC-MS: (ESI, m/z): [M+H]$^+$=470. $^1$H NMR (300 MHz, DMSO-d6, ppm) δ 5.21-5.01 (m, 1H), 4.93-4.76 (m, 1H), 4.70-4.44 (m, 1H), 4.09-3.97 (m, 1H), 3.97-3.75 (m, 1H), 3.17-2.88 (m, 2H), 2.54 (s, 3H), 1.48 (d, J=6.6 Hz, 3H), 1.42 (s, 9H), 1.18-0.99 (m, 3H).

Step 3: tert-Butyl 2-chloro-1-fluoro-5,6-dimethyl-11-(methylsulfonyl)-5a,6,8,9-tetrahydro-4-oxa-3,7,9a,10,12-pentaazabenzo [4,5] cyclohepta[1,2,3-de]naphthalene-7(5H)-carboxylate (four isomers)

To a solution of tert-butyl 2-chloro-1-fluoro-5,6-dimethyl-11-(methylthio)-5a,6,8,9-tetrahydro-4-oxa-3,7,9a,10,12-pentaazabenzo[4,5]cyclohepta[1,2,3-de]naphthalene-7(5H)-carboxylate (50.0 mg, 0.106 mmol, isomer 1 of last step) in ethyl acetate (3 mL) was added mCPBA (85% purity, 64.6 mg, 0.318 mmol) at 0° C., and the mixture was stirred for 3 hours at room temperature. The reaction was quenched with saturated Na$_2$S$_2$O$_3$ solution, diluted with water and extracted with ethyl acetate. The combined organic layers were dried over anhydrous sodium sulfate and concentrated under vacuum. The residue was purified by flash chromatography on silica gel eluting with (gradient: 0-60% ethyl acetate in petroleum ether) to afford the title compound (52.0 mg) as a yellow solid. LC-MS: (ESI, m/z): [M+H]$^+$=503.

Analogous to method described as above, another 3 isomers were prepared with the corresponding isomers of last step.

Step 4: tert-Butyl 2-chloro-1-fluoro-11-(((2R,7aS)-2-fluorotetrahydro-1H-pyrrolizin-7a(5H)-yl)methoxy)-5,6-dimethyl-5a,6,8,9-tetrahydro-4-oxa-3,7,9a,10,12-pentaazabenzo[4,5]cyclohepta[1,2,3-de]naphthalene-7(5H)-carboxylate (four isomers)

To a solution of ((2R,7aS)-2-fluorotetrahydro-1H-pyrrolizin-7a(5H)-yl) methanol (32.9 mg, 0.207 mmol) in tetrahydrofuran (2 mL) was added NaH (60% dispersion in mineral oil, 24.7 mg, 0.618 mmol) at 0° C. and stirred for 30 minutes at room temperature. Then tert-butyl 2-chloro-1-fluoro-5,6-dimethyl-11-(methylsulfonyl)-5a,6,8,9-tetrahydro-4-oxa-3,7,9a,10,12-pentaazabenzo[4,5]cyclohepta[1,2,3-de]naphthalene-7(5H)-carboxylate (52.0 mg, 0.103 mmol, the first isomer of last step) was added at room temperature and stirred for 2 hours. The reaction was quenched with NH$_4$Cl solution. The resulting solution was extracted with ethyl acetate. The combined organic layers were dried over anhydrous sodium sulfate and concentrated under vacuum. The residue was purified by flash chromatography on silica gel (gradient: 0-10% methanol in dichloromethane) to afford the title compound (55.0 mg) as a yellow solid. LC-MS: (ESI, m/z): [M+H]$^+$=581.

Analogous to method described as above, another 3 isomers were prepared with the corresponding isomers of last step.

Step 5: tert-Butyl 2-(5-(bis(4-methoxybenzyl)amino)-4-fluoro-3-methyl-2-(trifluoromethyl)phenyl)-1-fluoro-11-(((2R,7aS)-2-fluorotetrahydro-1H-pyrrolizin-7a(5H)-yl)methoxy)-5,6-dimethyl-5a,6,8,9-tetrahydro-4-oxa-3,7,9a,10,12-pentaazabenzo[4,5]cyclohepta[1,2,3-de]naphthalene-7(5H)-carboxylate (four isomers)

Under nitrogen, a solution of tert-butyl 2-chloro-1-fluoro-11-(((2R,7aS)-2-fluorotetrahydro-1H-pyrrolizin-7a(5H)-yl)methoxy)-5,6-dimethyl-5a,6,8,9-tetrahydro-4-oxa-3,7,9a,10,12-pentaazabenzo[4,5]cyclohepta[1,2,3-de]naphthalene-7(5H)-carboxylate (55.0 mg, 0.0947 mmol, the first isomer of last step), (5-(bis(4-methoxybenzyl)amino)-4-fluoro-3-methyl-2-(trifluoromethyl)phenyl)boronic acid (90.8 mg, 0.190 mmol), K$_3$PO$_4$ (1.5 M aqueous solution, 0.3 mL, 0.450 mmol) and cataCXium A Pd G3 (13.8 mg, 0.0189 mmol) in tetrahydrofuran (1.5 mL) was stirred for 3 hours at 60° C. The reaction mixture was diluted with water and extracted with ethyl acetate. The combined organic layers were dried over anhydrous sodium sulfate and concentrated under vacuum. The residue was purified by flash chromatography on silica gel (gradient: 0-10% methanol in dichloromethane) to afford the title compound (35.0 mg) as a brown solid. LC-MS: (ESI, m/z): [M+H]$^+$=978.

Analogous to the method described above, another 3 isomers were prepared with the corresponding isomers of last step.

Step 6: 2-Fluoro-5-(1-fluoro-11-(((2R,7aS)-2-fluorotetrahydro-1H-pyrrolizin-7a(5H)-yl)methoxy)-5,6-dimethyl-5,5a,6,7,8,9-hexahydro-4-oxa-3,7,9a,10,12-pentaazabenzo[4,5]cyclohepta[1,2,3-de]naphthalen-2-yl)-3-methyl-4-(trifluoromethyl)aniline (four isomers)

A solution of tert-butyl 2-(5-(bis(4-methoxybenzyl)amino)-4-fluoro-3-methyl-2-(trifluoromethyl)phenyl)-1-fluoro-11-(((2R,7aS)-2-fluorotetrahydro-1H-pyrrolizin-7a (5H)-yl)methoxy)-5,6-dimethyl-5a,6,8,9-tetrahydro-4-oxa-3,7,9a,10,12-pentaazabenzo[4,5]cyclohepta[1,2,3-de]naphthalene-7(5H)-carboxylate (35.0 mg, 0.0358 mmol, the first isomer of last step) in TFA (10 mL) was stirred for 1 hour at room temperature. The solvent was concentrated under vacuum. The residue was purified by Prep-HPLC (Column: XBridge Prep OBD C18 Column, 30*150 mm, 5 μm; Mobile Phase A: Water (10 mmol/L NH₄HCO₃), Mobile Phase B: ACN; Flow rate: 60 mL/min; Gradient: 15% B to 45% B in 9 min, 45% B; Wave Length: 254/220 nm; RT1(min): 8.6) to afford 234 (isomer 1) (2.0 mg) as a white solid.

Analogous to method described as above, another 3 isomers were prepared with the corresponding isomers of the last step.

234 (isomer 1): LC-MS: (ESI, m/z): [M+H]⁺=638. ¹H NMR (300 MHz, DMSO-d6, ppm) δ 6.72-6.44 (m, 1H), 6.01 (s, 2H), 5.28 (d, J=54.3 Hz, 1H), 5.04 (d, J=12.2 Hz, 1H), 4.80-4.70 (m, 1H), 4.15-3.95 (m, 3H), 3.60-3.49 (m, 1H), 3.20-2.91 (m, 4H), 2.90-2.71 (m, 3H), 2.31 (s, 3H), 2.19-2.12 (m, 1H), 2.10-1.94 (m, 2H), 1.92-1.70 (m, 2H), 1.46 (d, J=6.6 Hz, 3H), 1.27-1.22 (m, 1H), 1.13 (d, J=6.6 Hz, 3H).

234 (isomer 2): LC-MS: (ESI, m/z): [M+H]⁺=638. ¹H NMR (300 MHz, DMSO-d6, ppm) δ 6.70-6.43 (m, 1H), 6.01 (s, 2H), 5.28 (d, J=54.3 Hz, 1H), 5.03 (d, J=12.2 Hz, 1H), 4.79-4.68 (m, 1H), 4.11 (d, J=10.3 Hz, 1H), 4.04-3.93 (m, 2H), 3.58-3.46 (m, 1H), 3.19-2.98 (m, 4H), 2.98-2.69 (m, 3H), 2.32 (s, 3H), 2.21-2.12 (m, 1H), 2.07-1.93 (m, 2H), 1.92-1.69 (m, 2H), 1.46 (d, J=6.6 Hz, 3H), 1.28-1.22 (m, 1H), 1.12 (d, J=6.6 Hz, 3H).

234 (isomer 3): LC-MS: (ESI, m/z): [M+H]⁺=638. ¹H NMR (300 MHz, DMSO-d6, ppm) δ 6.66-6.46 (d, 1H), 5.99 (s, 2H), 5.46-4.77 (m, 2H), 4.771-4.62 (m, 1H), 4.14-3.93 (m, 2H), 3.54 (d, J=9.0 Hz, 1H), 3.16-2.74 (m, 7H), 2.71-2.57 (m, 1H), 2.51-2.50 (m, 1H), 2.31 (s, 3H), 2.15-2.07 (m, 1H), 2.07-1.90 (m, 2H), 1.89-1.66 (7, 3H), 1.61-1.40 (m, 3H), 1.19 (d, J=6.2 Hz, 3H).

234 (isomer 4): LC-MS: (ESI, n/z): [M+H]⁺=638. ¹H NMR (300 MHz, DMSO-d6, ppm) δ 6.70-6.41 (m, 1H), 6.01 (s, 2H), 5.49-4.83 (m, 2H), 4.78-4.62 (m, 1H), 4.12 (d, J=10.4 Hz, 1H), 3.98 (d, J=10.4 Hz, 1H), 3.56 (d, J=9.0 Hz, 1H), 3.18-2.76 (m, 7H), 2.70-2.52 (m, 2H), 2.34 (s, 3H), 2.21-2.11 (m, 1H), 2.10-1.92 (m, 2H), 1.92-1.66 (m, 3H), 1.60-1.39 (m, 3H), 1.21 (d, J=6.2 Hz, 3H).

Each compound in the Table below was prepared following a similar experimental procedure (using appropriately substituted reagents) as described for Example 234.

| Cmpd. No. | ¹H NMR | MS (M + H)⁺ |
|---|---|---|
| 235 (isomer 1) | ¹H NMR (400 MHz, DMSO-d₆, ppm): δ 6.54 (d, J = 30.2 Hz, 1H), 5.98 (s, 2H), 5.26 (d, J = 54.3 Hz, 1H), 5.02 (d, J = 12.8 Hz, 1H), 4.80-4.67 (m, 1H), 4.11 (d, J = 10.4 Hz, 1H), 3.97 (d, J = 10.4 Hz, 1H), 3.81 (d, J = 10.2 Hz, 1H), 3.23 (s, 1H), 3.17-2.90 (m, 5H), 2.89-2.57 (m, 3H), 2.35-2.27 (m, 3H), 2.16-2.08 (d, J = 4.7 Hz, 1H), 2.06-1.92 (m, 2H), 1.87-1.71 (m, 3H), 1.42 (d, J = 6.6 Hz, 3H). | 624 |
| 235 (isomer 2) | ¹H NMR (400 MHz, DMSO-d₆, ppm): δ 6.56 (s, 1H), 5.98 (s, 2H), 5.27 (d, J = 54.2 Hz, 1H), 4.90 (s, 1H), 4.59-4.41 (m, 1H), 4.11 (d, J = 10.4 Hz, 1H), 3.99 (d, J = 10.4 Hz, 1H), 3.87 (t, J = 9.3 Hz, 1H), 3.17-2.92 (m, 6H), 2.89-2.74 (m, 2H), 2.54 (s, 1H), 2.35-2.27 (m, 3H), 2.17-1.92 (m, 3H), 1.90-1.67 (m, 3H), 1.35 (d, J = 6.4 Hz, 3H). | 624 |
| 236 | ¹H NMR (300 MHz, DMSO-d₆) δ 6.57 (s, 1H), 6.01 (s, 2H), 5.38 (s, 1H), 5.27-5.20 (m, 1H), 4.61-4.55 (m, 1H), 4.44 (d, J = 13.1 Hz, 1H), 4.16 (d, J = 10.4 Hz, 1H), 4.08 (d, J = 4.4 Hz, 1H), 4.00 (d, J = 10.4 Hz, 1H), 3.32-3.18 (m, 2H), 3.18-2.92 (m, 5H), 2.87-2.79 (m, 1H), 2.32 (s, 3H), 2.24-2.11 (m, 2H), 2.11-1.91 (m, 2H), 1.86-1.74 (m, 4H), 1.62-1.46 (m, 2H), 1.26 (d, J = 12.0 Hz, 1H). | 650 |
| 237 (isomer 1) | ¹H NMR (400 MHz, DMSO-d6) δ 6.55 (d, J = 50.4 Hz, 1H), 5.98 (s, 2H), 5.44-5.14 (m, 1H), 4.97-4.52 (m, 1H), 4.28 (d, J = 13.3 Hz, 1H), 4.11 (d, J = 10.3 Hz, 1H), 3.99 (d, J = 10.3 Hz, 1H), 3.85-3.63 (m, 3H), 3.41 (dd, J = 13.3, 4.1 Hz, 1H), 3.17-3.04 (m, 2H), 3.01 (s, 1H), 2.89-2.76 (m, 1H), 2.72-2.57 (m, 1H), 2.32 (t, J = 2.6 Hz, 3H), 2.21-2.08 (m, 1H), 2.07-1.97 (m, 2H), 1.91-1.6 (m, 7H), 1.41 (d, J = 6.6 Hz, 3H). | 650 |
| 237 (isomer 2) | ¹H NMR (400 MHz, DMSO-d₆) δ 6.55 (d, J = 54.4 Hz, 1H), 6.00 (s, 2H), 5.45-5.09 (m, 1H), 4.66 (s, 1H), 4.41 (d, J = 13.1 Hz, 1H), 4.12 (d, J = 10.4 Hz, 1H), 3.98 (d, J = 10.4 Hz, 1H), 3.77 (s, 1H), 3.65 (s, 1H), 3.38 (s, 1H), 3.25 (s, 1H), 3.17-3.04 (m, 2H), 3.02 (s, 1H), 2.89-2.78 (m, 1H), 2.39-2.27 (m, 3H), 2.21-2.10 (m, 1H), 2.09-1.94 (m, 2H), 1.91-1.63 (m, 7H), 1.56 (d, J = 6.4 Hz, 3H). | 650 |

811    812
Example 238: Compound 238 (two isomers
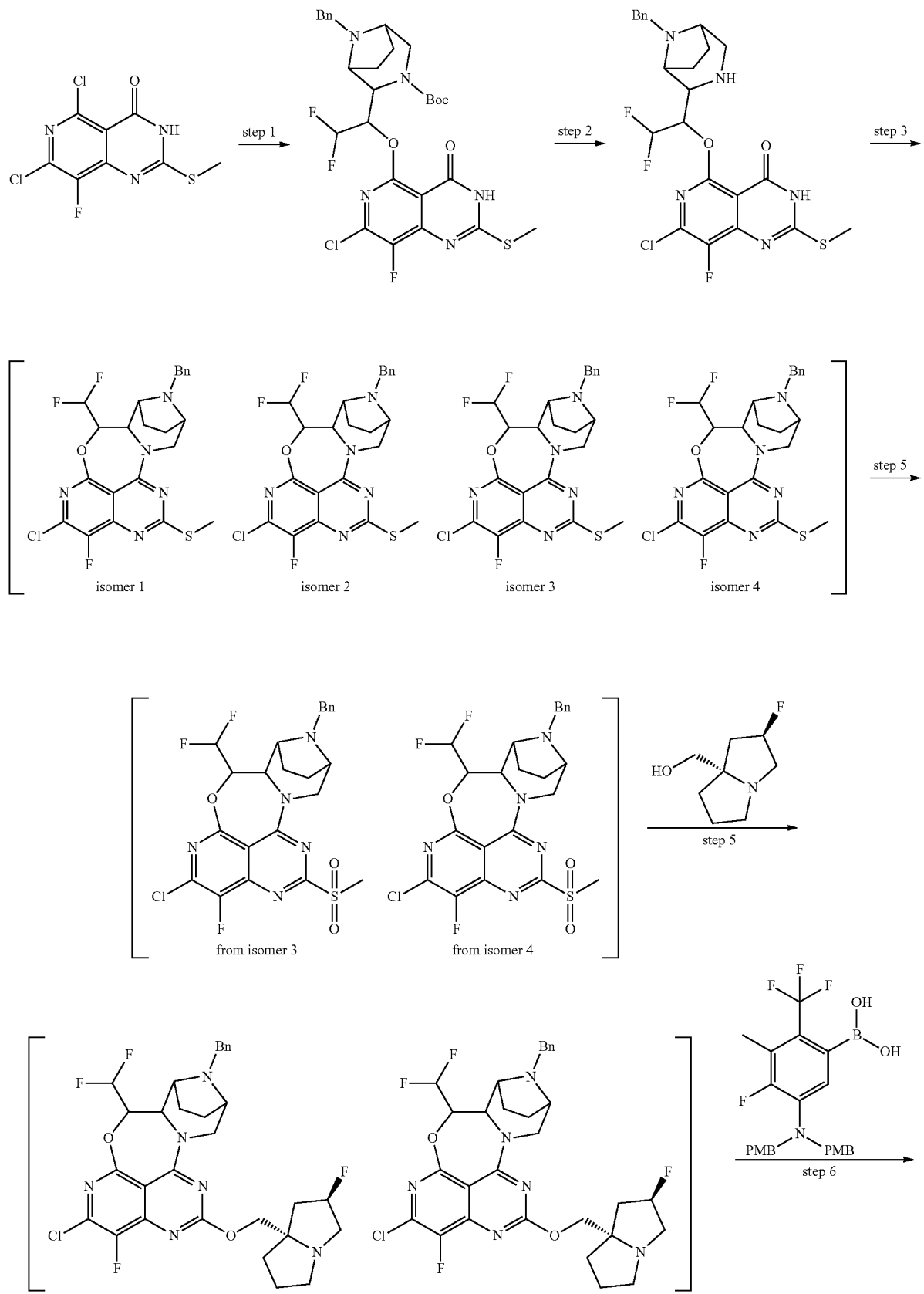

813

814

-continued

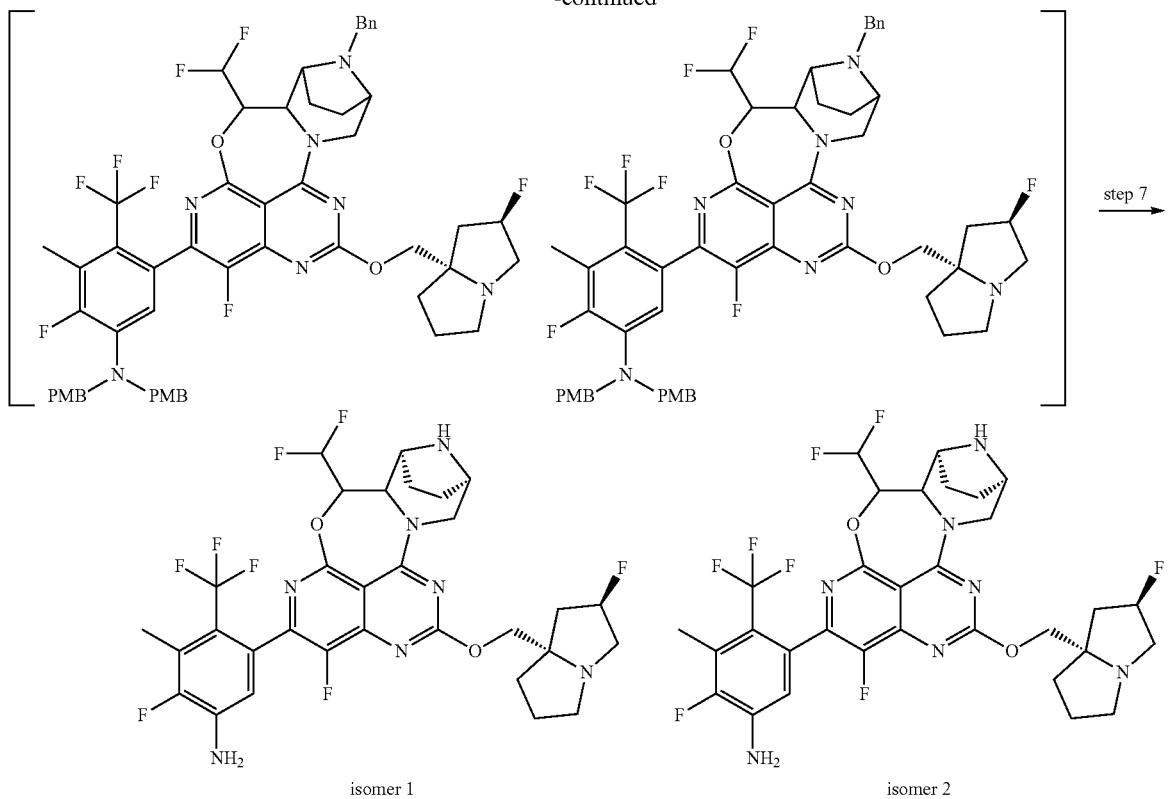

isomer 1 isomer 2

Step 1: tert-Butyl 8-benzyl-2-(1-((7-chloro-8-fluoro-2-(methylthio)-4-oxo-3,4-dihydropyrido[4,3-d]pyrimidin-5-yl)oxy)-2,2-difluoroethyl)-3,8-diazabicyclo[3.2.1]octane-3-carboxylate Under nitrogen, to a solution of tert-butyl (1R,5S)-8-benzyl-2-(2,2-difluoro-1-hydroxyethyl)-3,8-diazabicyclo[3.2.1] octane-3-carboxylate (4.60 g, 12.0 mmol, intermediate 161) in tetrahydrofuran (50.0 mL) was added NaH (2.89 g, 72.2 mmol, 60% in mineral oil) at 0° C. The resulting solution was stirred for 30 min at 0° C. Then 5,7-dichloro-8-fluoro-2-(methylthio) pyrido[4,3-d] pyrimidin-4(3H)-one (4.60 g, 12.0 mmol) was added at 0° C. The solution was stirred for 3 h at room temperature. The reaction was quenched with NH$_4$Cl aqueous and extracted with EtOAc. The combined organic layers were dried over anhydrous sodium sulfate and concentrated under vacuum. The residue was purified by flash chromatography on silica gel eluting (gradient: 0-10% MeOH/DCM) to afford 2.90 g of the title compound as a yellow oil. LC-MS: (ESI, m z): [M+H]$^+$=626.

Step 2: 5-(1-(8-Benzyl-3,8-diazabicyclo[3.2.1]octan-2-yl)-2,2-difluoroethoxy)-7-chloro-8-fluoro-2-(methylthio)pyrido[4,3-d]pyrimidin-4(3H)-one To a solution of tert-butyl 8-benzyl-2-(1-((7-chloro-8-fluoro-2-(methylthio)-4-oxo-3,4-dihydropyrido[4,3-d]pyrimidin-5-yl)oxy)-2,2-difluoroethyl)-3,8-diazabicyclo[3.2.1]octane-3-carboxylate (2.90 g, 4.63 mmol) in dichloromethane (60.0 mL) was added TFA (20.0 mL). The resulting solution was stirred for 30 min at room temperature. The solvent was evaporated under vacuum. The residue was dissolved in DCM, washed with aqueous NaHCO$_3$. The organic layers were dried over anhydrous sodium sulfate and concentrated under vacuum to afford 2.60 g (crude) of the title compound as a yellow solid. LC-MS: (ESI, m/z): [M+H]$^+$=526.

Step 3: 14-Benzyl-2-chloro-5-(difluoromethyl)-1-fluoro-12-(methylthio)-5a,6,7,8,9,10-hexahydro-5H-4-oxa-3,10a,11,13,14-pentaaza-6,9-methanonaphtho[1,8-ab]heptalene A solution of 5-(1-(8-benzyl-3,8-diazabicyclo[3.2.1]octan-2-yl)-2,2-difluoroethoxy)-7-chloro-8-fluoro-2-(methylthio)pyrido[4,3-d]pyrimidin-4(3H)-one (2.60 g, 4.94 mmol), bis(2-oxooxazolidin-3-yl)phosphinic chloride (5.04 g, 19.8 mmol) and DIPEA (9.60 g, 74.4 mmol) in 1,2-dichloroethane (30.0 mL) was stirred for 2 h at 60° C. The solvent was evaporated under vacuum. The residue was purified by flash chromatography on silica gel eluting (gradient: 0%-30% EtOAc/petroleum ether) to afford 230 mg of the faster peak and 610 mg of the slower peak as yellow solids. The faster peak was separated by PREP_SFC (Column: Lux 3 Cellulose-4 4.6*50 mm, 3 µm; Mobile Phase A: CO$_2$, Mobile Phase B: MeOH:ACN=1:1; Flow rate: 100 mL/min; Gradient: isocratic 50% B; Column Temperature (° C.): 35; Back Pressure(bar): 100; Wave Length: 220 nm; RT1(min): 3.42; RT2(min): 4.43; Sample Solvent: MeOH; Injection Volume: 4 mL) to yield 174.0 mg isomer 1 and 92.0 mg isomer 2. The slower peak was separated by PREP_SFC (Column: CHIRALPAK IG 3*25 cm, 5 µm; Mobile Phase A: CO$_2$, Mobile Phase B: MeOH:ACN=2:1; Flow rate: 100 mL/min; Gradient: isocratic 40% B; Column Temperature (° C.): 35; Back Pressure(bar): 100; Wave Length: 220 nm; RT1(min): 3.87;

RT2(min): 5.27; Sample Solvent: MeOH; Injection Volume: 1.5 mL; Number of Runs: 22) to yield 312 mg isomer 3 and 310 mg isomer 4.

Step 4: 14-Benzyl-2-chloro-5-(difluoromethyl)-1-fluoro-12-(methylsulfonyl)-5a,6,7,8,9,10-hexahydro-5H-4-oxa-3,10a,11,13,14-pentaaza-6,9-methanonaphtho[1,8-ab]heptalene To a solution of 14-benzyl-2-chloro-5-(difluoromethyl)-1-fluoro-12-(methylthio)-5a,6,7,8,9,10-hexahydro-5H-4-oxa-3,10a,11,13,14-pentaaza-6,9-methanonaphtho[1,8-ab]heptalene (isomer 3 of last step) (265 mg, 0.522 mmol) in EtOAc (2.00 mL) was added m-CPBA (269 mg, 1.57 mmol) at 0° C. The resulting solution was stirred for 1 h at room temperature. The reaction was quenched with $Na_2O_3S_2$ aqueous and extracted with EtOAc. The combined organic layers were dried over anhydrous sodium sulfate and concentrated under vacuum to afford 501 mg (crude) of the title compound as a white solid. LC-MS: (ESI, m/z): $[M+H]^+$= 540.

Analogous to the method described as above, another isomer was prepared with isomer 4 of last step.

Step 5: 14-Benzyl-2-chloro-5-(difluoromethyl)-1-fluoro-12-(((2R,7aS)-2-fluorotetrahydro-1H-pyrrolizin-7a(5H)-yl)methoxy)-5a,6,7,8,9,10-hexahydro-5H-4-oxa-3,10a,11,13,14-pentaaza-6,9-methanonaphtho[1,8-ab]heptalene (two isomers)

To a solution of 14-benzyl-2-chloro-5-(difluoromethyl)-1-fluoro-12-(methylsulfonyl)-5a,6,7,8,9,10-hexahydro-5H-4-oxa-3,10a,11,13,14-pentaaza-6,9-methanonaphtho[1,8-ab] heptalene (501 mg, 0.930 mmol) and ((2R,7aS)-2-fluorotetrahydro-1H-pyrrolizin-7a(5H)-yl) methanol (178 mg, 1.86 mmol) in toluene (5.00 mL) was added t-BuONa (178 mg, 1.86 mmol) at 0° C. The resulting solution was stirred for 30 min at room temperature. The solvent was concentrated under vacuum at 0° C. The residue was purified by flash chromatography on silica gel eluting (gradient: 0%-20% MeOH/DCM) to afford 225 mg of the title compound as a yellow solid. LC-MS: (ESI, m/z): $[M+H]^+$=619.

Analogous to method described as above, the other isomers were prepared with the corresponding isomers of last step.

Step 6: 5-(14-Benzyl-5-(difluoromethyl)-1-fluoro-12-(((2R,7aS)-2-fluorotetrahydro-1H-pyrrolizin-7a(5H)-yl)methoxy)-5a,6,7,8,9,10-hexahydro-5H-4-oxa-3,10a,11,13,14-pentaaza-6,9-methanonaphtho[1,8-ab]heptalen-2-yl)-2-fluoro-N,N-bis(4-methoxybenzyl)-3-methyl-4-(trifluoromethyl)aniline (two isomers)

Under nitrogen, a solution of 14-benzyl-2-chloro-5-(difluoromethyl)-1-fluoro-12-(((2R,7aS)-2-fluorotetrahydro-1H-pyrrolizin-7a(5H)-yl) methoxy)-5a,6,7,8,9,10-hexahydro-5H-4-oxa-3,10a,11,13,14-pentaaza-6,9-methanonaphtho[1,8-ab] heptalene (256 mg, 0.414 mmol), (5-(bis(4-methoxybenzyl)amino)-4-fluoro-3-methyl-2-(trifluoromethyl)phenyl) boronic acid (493 mg, 1.03 mmol), $K_3PO_4$ (0.830 mL, 1.5 M in water) and cataCXium A Pd G$_3$ (60.2 mg, 0.0800 mmol) in THF (4.00 mL) was stirred for 1 h at 60° C. The resulting solution was partitioned between water and EtOAc. The separated organic layer was dried over anhydrous sodium sulfate and concentrated under vacuum. The residue was purified by flash chromatography on silica gel (gradient: 0%-20% MeOH/DCM) to afford 306 mg of the title compound as a brown solid. LC-MS: (ESI, m/z): $[M+H]^+$=1016.

Analogous to method described as above, the other isomers were prepared with the corresponding isomers of last step.

Step 7: 5-((6S,9R)-5-(difluoromethyl)-1-fluoro-12-(((2R,7aS)-2-fluorotetrahydro-1H-pyrrolizin-7a(5H)-yl)methoxy)-5a,6,7,8,9,10-hexahydro-5H-4-oxa-3,10a,11,13,14-pentaaza-6,9-methanonaphtho[1,8-ab]heptalen-2-yl)-2-fluoro-3-methyl-4-(trifluoromethyl)aniline (two isomers)

To a solution of 5-(14-benzyl-5-(difluoromethyl)-1-fluoro-12-(((2R,7aS)-2-fluorotetrahydro-1H-pyrrolizin-7a (5H)-yl) methoxy)-5a,6,7,8,9,10-hexahydro-5H-4-oxa-3, 10a,11,13,14-pentaaza-6,9-methanonaphtho[1,8-ab]heptalen-2-yl)-2-fluoro-N,N-bis(4-methoxybenzyl)-3-methyl-4-(trifluoromethyl)aniline (240 mg, 0.236 mmol) in MeOH (30.0 mL) was added 10% Pd/C (240 mg) and HCl (0.300 ml, 12 M in water). The resulting solution was stirred for 1 h at room temperature. After filtration, the filtrate was concentrated under reduced pressure. The residue was purified by prep. HPLC (Column: XBridge Prep OBD C18, Column, 30*150 mm: 5 μm; Mobile Phase A: Water (10 mmol/L $NH_4HCO_3$), Mobile Phase B: CAN; Flow rate: 60 mL/min; Gradient: 39% B to 56% B in 9 min; Wave Length: 254/220 nm; RT1(min): 8.6) to afford 21.2 mg of 238 (isomer 1) (head piece from isomer 3 of step 3) as a white solid.

Analogous to method described as above, the other isomer 238 (isomer 2) (head piece from isomer 4 of step 3) was prepared.

238 (isomer 1): LC-MS: (ESI, m/z): $[M+H]^+$=686. $^1$H NMR (300 MHz, DMSO-d$_6$) δ 7.06 (t, J=53.2 Hz, 1H), 6.69-6.63 (m, 1H), 6.01 (s, 2H), 5.54-5.07 (m, 2H), 4.38 (d, J=13.2 Hz, 1H), 4.12 (d, J=10.4 Hz, 1H), 4.07 (s, 1H), 3.98 (d, J=10.4 Hz, 1H), 3.91 (s, 1H), 3.73 (s, 1H), 3.10 (d, J=8.2 Hz, 2H), 3.00 (s, 1H), 2.90 (s, 1H), 2.82 (d, J=6.8 Hz, 1H), 2.37-2.31 (m, 3H), 2.14 (d, J=7.8 Hz, 1H), 2.03 (s, 1H), 1.99 (s, 1H), 1.93-1.53 (m, 7H).

238 (isomer 2): LC-MS: (ESI, m/z): $[M+H]^+$=686. $^1$H NMR (300 MHz, Methanol-d$_4$) δ 7.08 (t, J=53.1 Hz, 1H), 6.80-6.47 (m, 1H), 5.31 (d, J=53.9 Hz, 1H), 5.11 (dd, J=20.5, 9.8 Hz, 1H), 4.57 (d, J=13.4 Hz, 1H), 4.26 (d, J=1.7 Hz, 2H), 4.08 (d, J=5.4 Hz, 1H), 3.93 (d, J=6.2 Hz, 1H), 3.81 (s, 1H), 3.50 (d, J=13.4 Hz, 1H), 3.28-3.10 (m, 3H), 3.09-2.90 (m, 1H), 2.55-2.31 (m, 3H), 2.29-2.19 (m, 3H), 2.13-1.99 (m, 3H), 1.99-1.70 (m, 4H).

Example 239: Compound 239

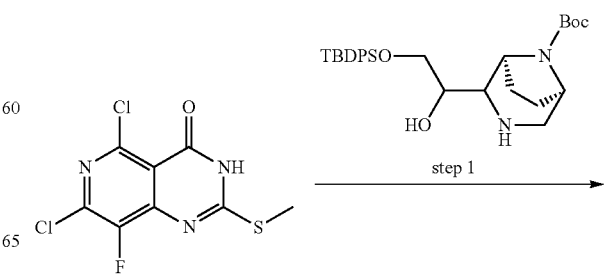

817
-continued
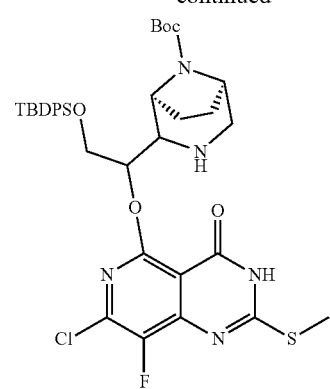
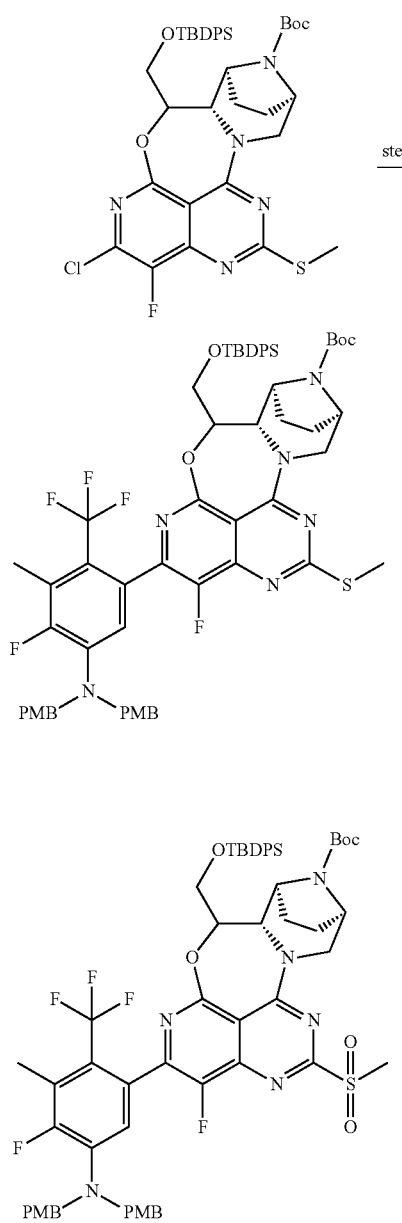
818
-continued
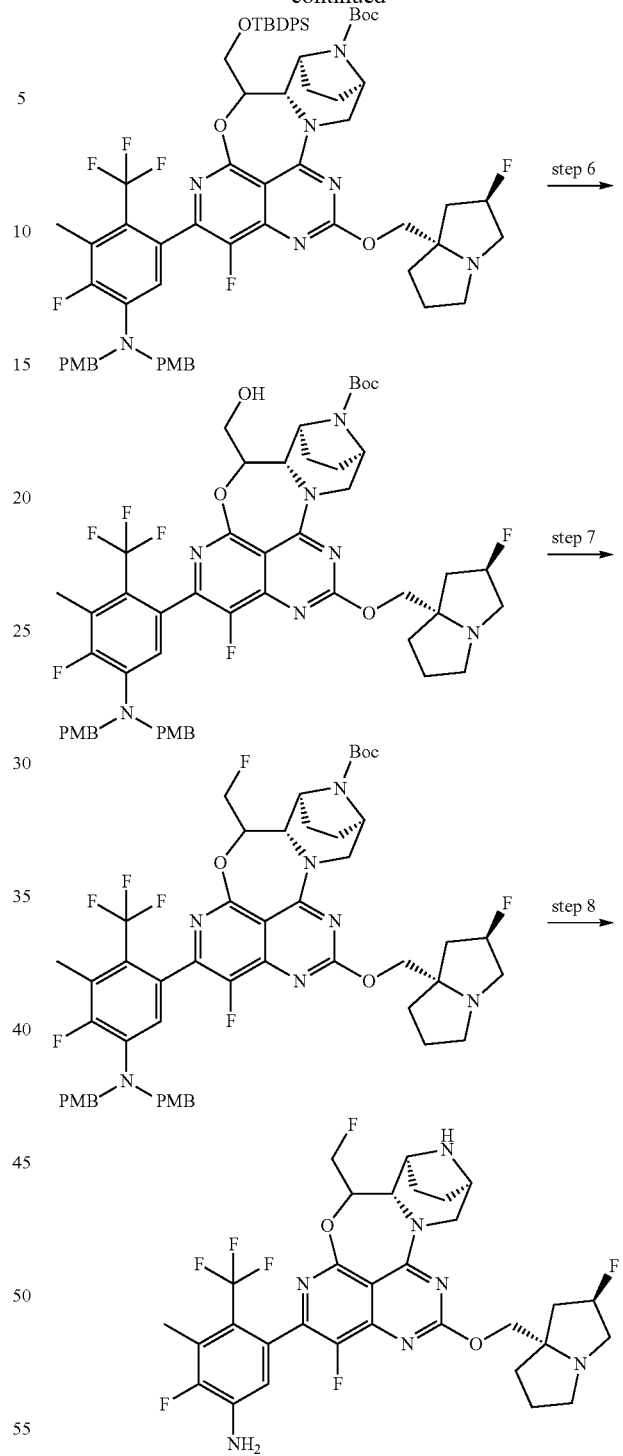
Step 1: tert-Butyl (1S,2S,5R)-2-(2-((tert-butyldiphenylsilyl)oxy)-1-((7-chloro-8-fluoro-2-(methylthio)-4-oxo-3,4-dihydropyrido[4,3-d]pyrimidin-5-yl)oxy)ethyl)-3,8-diazabicyclo[3.2.1]octane-8-carboxylate
Under nitrogen, to a solution of tert-butyl (1S,2S,5R)-2-(2-((tert-butyldiphenylsilyl)oxy)-1-hydroxyethyl)-3,8-diazabicyclo [3.2.1] octane-8-carboxylate (1.56 g, 3.05 mmol, intermediate 159) in tetrahydrofuran (35 mL) was added NaH (60%) (1.03 g, 25.8 mmol) at 0° C. The solution was stirred at room temperature for 0.5 hour. Then 5,7-dichloro-8-fluoro-2-(methylthio) pyrido [4,3-d] pyrimidin-4(3H)-one (2.11 g, 7.53 mmol) was added and the solution was stirred at room temperature for 16 hours. The reaction was quenched with aqueous NH$_4$Cl and extracted with EtOAc. The combined organic layers were dried over anhydrous sodium sulfate and concentrated under vacuum. The residue was purified by flash chromatography on silica gel (gradient: 0-7% MeOH/DCM) to afford 1.44 g of the title compound as a brown solid. LC-MS: (ESI, m/z): [M+H]$^+$=754.

Step 2: tert-Butyl (5aS,6S,9R)-5-(((tert-butyldiphenylsilyl)oxy)methyl)-2-chloro-1-fluoro-12-(methylthio)-5a,6,7,8,9,10-hexahydro-5H-4-oxa-3,10a,11,13,14-pentaaza-6,9-methanonaphtho[1,8-ab]heptalene-14-carboxylate A solution of tert-butyl (1S,2S,5R)-2-(2-((tert-butyldiphenylsilyl)oxy)-1-((7-chloro-8-fluoro-2-(methylthio)-4-oxo-3,4-dihydropyrido[4,3-d]pyrimidin-5-yl)oxy)ethyl)-3,8-diazabicyclo[3.2.1]octane-8-carboxylate (1.44 g, 1.98 mmol), BOPCl (1.11 g, 4.35 mmol) and DIPEA (1.49 g, 11.6 mmol) in dichloromethane (40 mL) was stirred at room temperature for 16 hours. The reaction was quenched with water and extracted with DCM. The combined organic layers were dried over anhydrous sodium sulfate and concentrated under vacuum. The residue was purified by flash chromatography on silica gel (gradient: 0-20% EtOAc/petroleum ether) to afford 1.14 g of the title compound as a yellow solid. LC-MS: (ESI, m/z): [M+H]$^+$=736.

Step 3: tert-Butyl (5aS,6S,9R)-2-(5-(bis(4-methoxybenzyl)amino)-4-fluoro-3-methyl-2-(trifluoromethyl)phenyl)-5-(((tert-butyldiphenylsilyl)oxy)methyl)-1-fluoro-12-(methylthio)-5a,6,7,8,9,10-hexahydro-5H-4-oxa-3,10a,11,13,14-pentaaza-6,9-methanonaphtho[1,8-ab]heptalene-14-carboxylate Under nitrogen, a solution of tert-butyl (5aS,6S,9R)-5-(((tert-butyldiphenylsilyl)oxy) methyl)-2-chloro-1-fluoro-12-(methylthio)-5a,6,7,8,9,10-hexahydro-5H-4-oxa-3,10a,11,13,14-pentaaza-6,9-methanonaphtho[1,8-ab] heptalene-14-carboxylate (400 mg, 0.543 mmol), (5-(bis(4-methoxybenzyl)amino)-4-fluoro-3-methyl-2-(trifluoromethyl)phenyl)boronic acid (674 mg, 1.41 mmol), cataCxium A Pd G3 (115 mg, 0.160 mmol) and K$_3$PO$_4$ (2 mL, 1.5 M in H$_2$O) in tetrahydrofuran (10 mL) was stirred at 60° C. for 3 hours. The solution was diluted with water, extracted with EtOAc. The combined organic layers were dried over anhydrous sodium sulfate and concentrated under vacuum. The residue was purified by flash chromatography on silica gel (gradient: 0-20% EtOAc/petroleum ether) to afford 497 mg of the title compound as a yellow solid. LC-MS: (ESI, m/z): [M+H]$^+$=1133.

Step 4: tert-Butyl (5aS,6S,9R)-2-(5-(bis(4-methoxybenzyl) amino)-4-fluoro-3-methyl-2-(trifluoromethyl)phenyl)-5-(((tert-butyldiphenylsilyl)oxy) methyl)-1-fluoro-12-(methylsulfonyl)-5a,6,7,8,9,10-hexahydro-5H-4-oxa-3,10a,11,13,14-pentaaza-6,9-methanonaphtho[1,8-ab]heptalene-14-carboxylate Under nitrogen, to a solution of tert-butyl (5aS,6S,9R)-2-(5-(bis(4-methoxybenzyl) amino)-4-fluoro-3-methyl-2-(trifluoromethyl)phenyl)-5-(((tert-butyldiphenylsilyl)oxy)methyl)-1-fluoro-12-(methylthio)-5a,6,7,8,9,10-hexahydro-5H-4-oxa-3,10a,11,13,14-pentaaza-6,9-methanonaphtho[1,8-ab]heptalene-14-carboxylate (497 mg, 0.439 mmol) in dichloromethane (8 mL) was added m-CPBA (232 mg, 1.34 mmol) at 0° C. The solution was stirred at room temperature for 1 hour. The reaction was quenched with aqueous Na$_2$S$_2$O$_3$ solution, extracted with DCM. The combined organic layers were dried over anhydrous sodium sulfate and concentrated under vacuum. The residue was purified by flash chromatography on silica gel (gradient: 0-40% EtOAc/petroleum ether) to afford 383 mg of the title compound as a brown solid. LC-MS: (ESI, m/z): [M+H]$^+$=1165.

Step 5: tert-Butyl (5aS,6S,9R)-2-(5-(bis(4-methoxybenzyl)amino)-4-fluoro-3-methyl-2-(trifluoromethyl)phenyl)-5-(((tert-butyldiphenylsilyl)oxy)methyl)-1-fluoro-12-(((2R,7aS)-2-fluorotetrahydro-1H-pyrrolizin-7a(5H)-yl)methoxy)-5a,6,7,8,9,10-hexahydro-5H-4-oxa-3,10a,11,13,14-pentaaza-6,9-methanonaphtho[1,8-ab]heptalene-14-carboxylate Under nitrogen, to a solution of ((2R,7aS)-2-fluorotetrahydro-1H-pyrrolizin-7a(5H)-yl) methanol (95.3 mg, 0.600 mmol) in tetrahydrofuran (8 mL) was added NaH (60%) (76.2 mg, 1.91 mmol) at 0° C. and stirred at room temperature for 0.5 hour. Then tert-butyl (5aS,6S,9R)-2-(5-(bis(4-methoxybenzyl) amino)-4-fluoro-3-methyl-2-(trifluoromethyl)phenyl)-5-(((tert-butyldiphenylsilyl)oxy)methyl)-1-fluoro-12-(methylsulfonyl)-5a,6,7,8,9,10-hexahydro-5H-4-oxa-3,10a,11,13,14-pentaaza-6,9-methanonaphtho[1,8-ab] heptalene-14-carboxylate (370 mg, 0.318 mmol) was added. The solution was stirred at room temperature for 2 hours. The reaction was quenched with aqueous NH$_4$Cl and extracted with EtOAc. The combined organic layers were dried over anhydrous sodium sulfate and concentrated under vacuum. The residue was purified by flash chromatography on silica gel (gradient: 04% MeOH/DCM) to afford 251 mg of the title compound as a white solid. LC-MS: (ESI, m/z): [M+H]$^+$=1244.

Step 6: tert-Butyl (5aS,6S,9R)-2-(5-(bis(4-methoxybenzyl) amino)-4-fluoro-3-methyl-2-(trifluoromethyl)phenyl)-1-fluoro-12-(((2R,7aS)-2-fluorotetrahydro-1H-pyrrolizin-7a(5H)-yl)methoxy)-5-(hydroxymethyl)-5a,6,7,8,9,10-hexahydro-5H-4-oxa-3,10a,11,13,14-pentaaza-6,9-methanonaphtho[1,8-ab]heptalene-14-carboxylate To a solution of tert-butyl (5aS,6S,9R)-2-(5-(bis(4-methoxybenzyl) amino)-4-fluoro-3-methyl-2-(trifluoromethyl) phenyl)-5-(((tert-butyldiphenylsilyl)oxy)methyl)-1-fluoro-12-(((2R,7aS)-2-fluorotetrahydro-1H-pyrrolizin-7a(5H)-yl)methoxy)-5a,6,7,8,9,10-hexahydro-5H-4-oxa-3,10a,11,13,14-pentaaza-6,9-methanonaphtho[1,8-ab]heptalene-14-carboxylate (250 mg, 0.201 mmol) in tetrahydrofuran (6 mL) was added TBAF (1 M in THF, 1.5 mL) and the solution was stirred at room temperature for 2 hours. Then the reaction was diluted with water, extracted with EtOAc. The combined organic layers were dried over anhydrous sodium sulfate and concentrated under vacuum. The residue was purified by flash chromatography on silica gel (gradient: 0-5% MeOH/DCM) to afford 170 mg of the title compound as a white solid. LC-MS: (ESI, m/z): [M+H]$^+$=1006.

Step 7: tert-Butyl (5aS,6S,9R)-2-(5-(bis(4-methoxybenzyl) amino)-4-fluoro-3-methyl-2-(trifluoromethyl) phenyl)-1-fluoro-5-(fluoromethyl)-12-(((2R,7aS)-2-fluorotetrahydro-1H-pyrrolizin-7a(5H)-yl)methoxy)-5a,6,7,8,9,10-hexahydro-5H-4-oxa-3,10a,11,13,14-pentaaza-6,9-methanonaphtho[1,8-ab]heptalene-14-carboxylate Under nitrogen, to a solution of tert-butyl (5aS,6S,9R)-2-(5-(bis(4-methoxybenzyl)amino)-4-fluoro-3-methyl-2-(trifluoromethyl)phenyl)-1-fluoro-12-(((2R,7aS)-2-fluorotetrahydro-1H-pyrrolizin-7a(5H)-yl)methoxy)-5-(hydroxymethyl)-5a,6,7,8,9,10-hexahydro-5H-4-oxa-3,10a,11,13,14-pentaaza-6,9-methanonaphtho[1,8-ab]heptalene-14-carboxylate (170 mg, 0.169 mmol) in dichloromethane (5 mL) was added DAST (854 mg, 5.30 mmol) at 0° C. The solution was stirred at room temperature for 16 hours. The reaction was quenched with aqueous NaHCO$_3$ solution and extracted with DCM. The combined organic layers were dried over anhydrous sodium sulfate and concentrated under vacuum. The residue was purified by flash chromatography on silica gel (gradient: 0-6% MeOH/DCM) to afford 80 mg of the title compound as a white solid. LC-MS: (ESI, m/z): [M+H]$^+$=1008.

Step 8: 2-Fluoro-5-((5aS,6S,9R)-1-fluoro-5-(fluoromethyl)-12-(((2R,7aS)-2-fluorotetrahydro-1H-pyrrolizin-7a(5H)-yl)methoxy)-5a,6,7,8,9,10-hexahydro-5H-4-oxa-3,10a,11,13,14-pentaaza-6,9-methanonaphtho[1,8-ab]heptalen-2-yl)-3-methyl-4-(trifluoromethyl)aniline A solution of tert-butyl (5aS,6S,9R)-2-(5-(bis(4-methoxybenzyl)amino)-4-fluoro-3-methyl-2-(trifluoromethyl)phenyl)-1-fluoro-5-(fluoromethyl)-12-(((2R,7aS)-2-fluorotetrahydro-1H-pyrrolizin-7a(5H)-yl)methoxy)-5a,6,7,8,9,10-hexahydro-5H-4-oxa-3,10a,11,13,14-pentaaza-6,9-methanonaphtho[1,8-ab]heptalene-14-carboxylate (75.1 mg, 0.0745 mmol) in 2,2,2-trifluoroacetic acid (4 mL) was stirred at room temperature for 2 hours. The solution was concentrated under vacuum. The residue was purified by prep-HPLC with the following conditions: (Column: XBridge Prep OBD C18 Column, 30*150 mm, 5 μm; Mobile Phase A: Water (10 mmol/L NH$_4$HCO$_3$), Mobile Phase B: ACN; Flow rate: 60 mL/min; Gradient: 36% B to 55% B in 9 min; Wave Length: 254/220 nm; RT1(min): 8.2; Number of Runs:2) to afford 22.6 mg of the title compound as a white solid. LC-MS: (ESI, m/z): [M+H]$^+$=668. $^1$H NMR (400 MHz, DMSO-d6, ppm) δ 6.56 (d, J=50.4 Hz, 1H), 6.01 (s, 2H), 5.27 (d, J=54.0 Hz, 1H), 5.08-4.80 (m, 3H), 4.45-4.42 (m, 1H), 4.13-4.11 (m, 1H), 3.98-3.96 (m, 1H), 3.77-3.61 (m, 3H), 3.38-3.35 (m, 1H), 3.13-3.01 (m, 3H), 2.85-2.75 (m, 2H), 2.33 (s, 3H), 2.14-1.95 (m, 3H), 1.87-1.65 (m, 7H).

Examples 240 and 241: Compounds 240 (two atropisomers) and 241

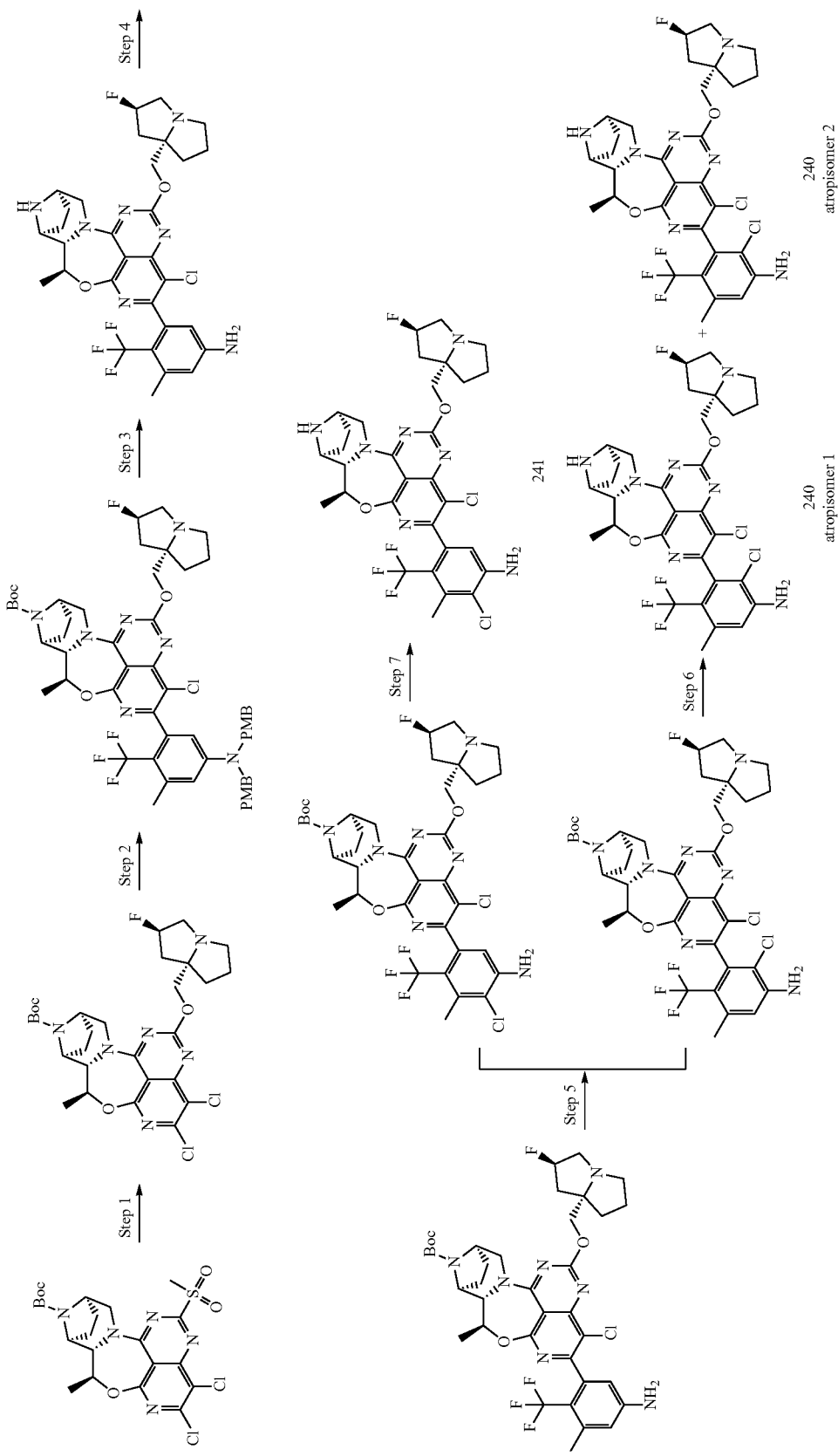

Step 1: tert-Butyl (5S,5aS,6S,9R)-1,2-dichloro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate Under nitrogen, to a solution of ((2R,7aS)-2-fluorotetrahydro-1H-pyrrolizin-7a(5H)-yl) methanol (225 mg, 1.41 mmol) in tetrahydrofuran (2 mL) was added 60% NaH (189 mg, 4.71 mmol) at 0° C. The resulting solution was stirred at room temperature for 30 min. Then tert-butyl rac-(4R,7S,8S,9S)-13,14-dichloro-9-methyl-17-methylsulfonyl-10-oxa-2,12,16,18,20-pentazapentacyclo[9.7.1.14,7.02,8.015,19]icosa-1(18),11(19),12,14,16-pentaene-20-carboxylate (500 mg, 0.94 mmol, intermediate 162) was added. The solution was stirred at 25° C. for 2 hours. The reaction mixture was partitioned between saturated aqueous NH$_4$Cl and EtOAc. The separated organic layer was concentrated under reduced pressure. The residue was purified by flash chromatography on silica gel (gradient: 0%-20% MeOH/DCM) to yield 400 mg of the title compound as a white solid. LC-MS: (ESI, m/z): [M+H]$^+$=609.

Step 2: tert-Butyl (5S,5aS,6S,9R)-2-(5-(bis(4-methoxybenzyl) amino)-3-methyl-2-(trifluoromethyl)phenyl)-1-chloro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate Under nitrogen, a solution of tert-butyl rac-(4R,7S,8S,9S)-13,14-dichloro-9-methyl-17-[[rac-(2R,8S)-2-fluoro-1,2,3,5,6,7-hexahydropyrrolizin-8-yl]methoxy]-10-oxa-2,12,16,18,20-pentazapentacyclo[9.7.1.14,7.02,8.015,19]icosa-1(18),11(19),12,14,16-pentaene-20-carboxylate (257 mg, 0.42 mmol), [5-[bis[(4-methoxyphenyl)methyl]amino]-3-methyl-2-(trifluoromethyl)phenyl]boronic acid (490 mg, 0.53 mmol), cataCxium A Pd G3 (61.4 mg, 0.08 mmol) and K$_3$PO$_4$ (1 mL, 1.5 M in H$_2$O) in tetrahydrofuran (5 mL) was stirred at 60° C. for 2 hours. The reaction mixture was diluted with water, extracted with EtOAc. The combined organic layers were concentrated under vacuum. The residue was purified by flash chromatography on silica (gradient: 0%-10% MeOH/DCM) to afford 380 mg as a yellow solid. LC-MS: (ESI, m/z): [M+H]$^+$=988.

Step 3: 3-((5S,5aS,6S,9R)-1-Chloro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-5-methyl-4-(trifluoromethyl)aniline A solution of tert-butyl rac-(4R,7S,8S,9S)-13-[5-[bis[(4-methoxyphenyl) methyl]amino]-3-methyl-2-(trifluoromethyl)phenyl]-14-chloro-9-methyl-17-[[rac-(2R,8S)-2-fluoro-1,2,3,5,6,7-hexahydropyrrolizin-8-yl]methoxy]-10-oxa-2,12,16,18,20-pentazapentacyclo[9.7.1.14,7.02,8.015,19]icosa-1(18),11(19),12,14,16-pentaene-20-carboxylate (260 mg, 0.30 mmol) in TFA (2.5 mL) was stirred at 25° C. for hours. The resulting mixture was concentrated under reduced pressure. The residue was purified by flash chromatography on silica gel (gradient: 0%-20% MeOH/DCM) to yield 100 mg of the title compound as a yellow liquid. LC-MS: (ESI, m/z): [M+H]$^+$=648.

Step 4: tert-Butyl (5S,5aS,6S,9R)-2-(5-amino-3-methyl-2-(trifluoromethyl)phenyl)-1-chloro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate Under nitrogen, to a solution of 3-((5S,5aS,6S,9R)-1-chloro-12-(((2R,7aS)-2-fluorotetrahydro-1H-pyrrolizin-7a (5H)-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-5-methyl-4-(trifluoromethyl)aniline (10 mg, 0.02 mmol) in DCM (5 mL) was added DIPEA (9.95 mg, 0.08 mmol) and (Boc)$_2$O (6.73 mg, 0.03 mmol). The resulting mixture was stirred for 2 h at room temperature. The solution was diluted with water, extracted with DCM. The combined organic layers were dried over anhydrous Na$_2$SO$_4$ and concentrated under reduced pressure. The residue was purified by flash chromatography on silica gel (gradient: 0%-20% MeOH/DCM) to yield 11 mg of the title compound as a yellow liquid. LC-MS: (ESI, m/z): [M+H]$^+$=748.

Step 5: tert-Butyl (5S,5aS,6S,9R)-2-(3-amino-2-chloro-5-methyl-6-(trifluoromethyl)phenyl)-1-chloro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate & tert-Butyl (5S,5aS,6S,9R)-2-(5-amino-4-chloro-3-methyl-2-(trifluoromethyl)phenyl)-1-chloro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (two isomers)

A solution of tert-butyl rac-(4R,7S,8S,9S)-13-[5-amino-3-methyl-2-(trifluoromethyl) phenyl]-14-chloro-9-methyl-17-[[rac-(2R,8S)-2-fluoro-1,2,3,5,6,7-hexahydropyrrolizin-8-yl]methoxy]-10-oxa-2,12,16,18,20-pentazapentacyclo[9.7.1.14,7.02,8.015,19]icosa-1(18),11(19),12,14,16-pentaene-20-carboxylate (160 mg, 0.21 mmol) and NCS (34 mg, 0.26 mmol) in acetic acid (2 mL) was stirred at 25 degrees C. for 36 hours. The solvent was evaporated and the residue was purified by flash chromatography on silica gel (gradient: 0%-20% MeOH/DCM) to yield 110 mg (isomer 1) and 25 mg (isomer 2) as yellow solids. LC-MS: (ESI, m/z): [M+H]$^+$=782.

Step 6: 2-Chloro-3-((5S,5aS,6S,9R)-1-chloro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-5-methyl-4-(trifluoromethyl) aniline (two atropisomers)

A solution of tert-butyl (5S,5aS,6S,9R)-2-(3-amino-2-chloro-5-methyl-6-(trifluoromethyl) phenyl)-1-chloro-12-(((2R,7aS)-2-fluorotetrahydro-1H-pyrrolizin-7a(5H)-yl) methoxy)-5-methyl-5a,6,7,8,9,10-hexahydro-5H-4-oxa-3,10a,11,13,14-pentaaza-6,9-methanonaphtho[1,8-ab]

heptalene-14-carboxylate (30 mg, 0.05 mmol) in TFA (3 mL) was stirred at 25° C. for 1 hour. The residue was purified by Prep-HPLC ((Column: XBridge Prep OBD C18 Column, 30*150 mm, 5 µm; Mobile Phase A: Water (10 mmol/L NH$_4$HCO$_3$), Mobile Phase B: ACN; Flow rate: 60 mL/min; Gradient: 52% B to 82% B in 7 min, 82% B; Wave Length: 254 nm; RT1(min): 6.5) to afford 2.3 mg 240 (atropisomer 1) and 3.0 mg 240 (atropisomer 2) as white solids. LC-MS: (ESI, m/z): [M+H]$^+$=682.

240 (atropisomer 1): $^1$H NMR (300 MHz, DMSO-d6, ppm) δ 6.84 (s, 1H), 6.15 (s, 2H), 5.41-4.96 (m, 2H), 4.64-4.46 (m, 1H), 4.21-3.93 (m, 3H), 3.51 (m, 2H), 3.21-2.93 (m, 5H), 2.34 (m, 3H), 2.21-1.95 (m, 3H), 1.94-1.52 (m, 7H), 1.52-1.43 (m, 3H).

240 (atropisomer 2): $^1$H NMR (300 MHz, DMSO-d6, ppm) δ 6.84 (s, 1H), 6.16 (s, 2H), 5.45-4.97 (m, 2H), 4.64-4.40 (m, 1H), 4.25-3.90 (m, 3H), 3.53 (m, 2H), 3.24-2.94 (m, 5H), 2.37 (m, 3H), 2.21-1.94 (m, 2H), 1.93-1.55 (m, 8H), 1.54-1.41 (m, 3H).

Step 7: 2-Chloro-5-((5S,5aS,6S,9R)-1-chloro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-3-methyl-4-(trifluoromethyl)aniline A solution of tert-butyl (5S,5aS,6S,9R)-2-(5-amino-4-chloro-3-methyl-2-(trifluoromethyl)phenyl)-1-chloro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (25 mg, 0.03 mmol) in TFA (3 mL) was stirred at 25° C. for 1 hour. The solvent was remove under reduce pressure. The residue was purified by Prep-HPLC ((Column: XBridge Prep OBD C18 Column, 30*150 mm, 5 µm; Mobile Phase A: Water (10 mmol/L NH$_4$HCO$_3$), Mobile Phase B: ACN; Flow rate: 60 mL/min; Gradient: 52% B to 82% B in 7 min, 82% B; Wave Length: 254 nm; RT1(min): 6.5) to afford 3.0 mg of Compound 241 as a white solid. LC-MS: (ESI, m/z): [M+H]$^+$=682. $^1$H NMR (300 MHz, DMSO-d6, ppm) δ 6.56 (s, 1H), 6.30 (d, J=41.4 Hz, 2H), 5.42-4.99 (m, 3H), 4.70-4.50 (m, 1H), 4.22-3.90 (m, 2H), 3.62 (d, J=5.2 Hz, 1H), 3.50 (t, J=5.5 Hz, 1H), 3.19-2.77 (m, 5H), 2.48-2.39 (m, 4H), 2.24-1.96 (m, 3H), 1.95-1.53 (m, 7H), 1.44 (d, J=6.3 Hz, 3H).

Example 242: Compounds 242

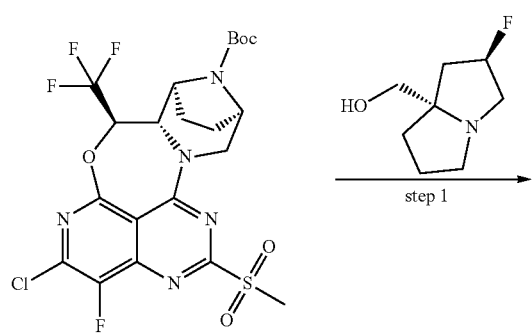

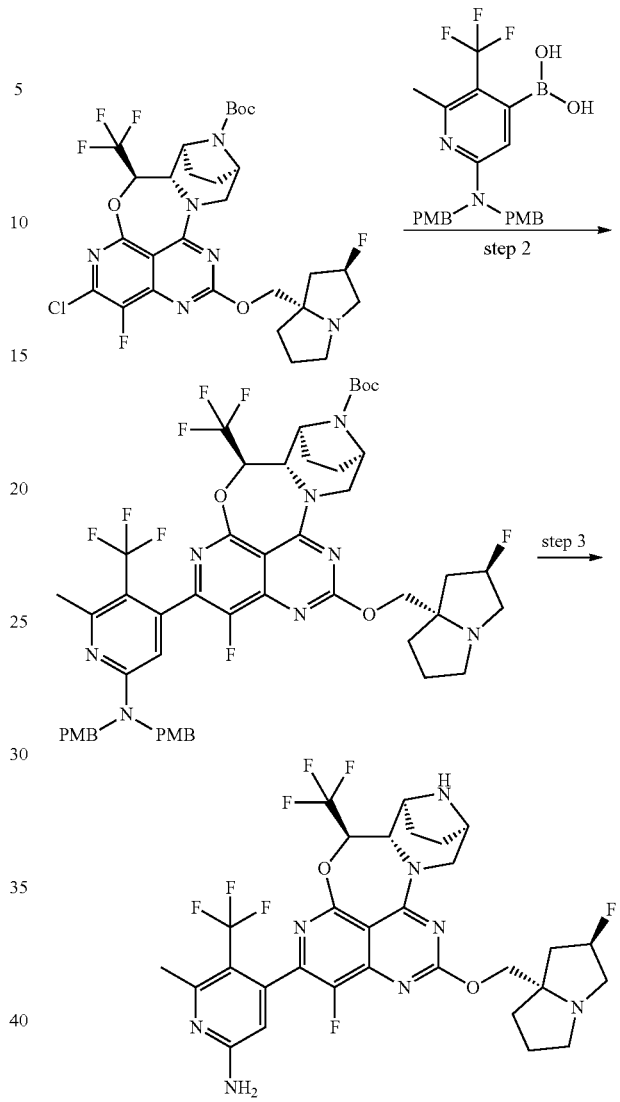

Step 1: tert-Butyl (5R,5aS,6S,9R)-2-chloro-1-fluoro-12-(((2R,7aS)-2-fluorotetrahydro-1H-pyrrolizin-7a(5H)-yl)methoxy)-5-(trifluoromethyl)-5a,6,7,8,9,10-hexahydro-5H-4-oxa-3,10a,11,13,14-pentaaza-6,9-methanonaphtho[1,8-ab]heptalene-14-carboxylate Under nitrogen, a solution of tert-butyl (5R,5aS,6S,9R)-2-chloro-1-fluoro-12-(methylsulfonyl)-5-(trifluoromethyl)-5a,6,7,8,9,10-hexahydro-5H-4-oxa-3,10a,11,13,14-pentaaza-6,9-methanonaphtho[1,8-ab]heptalene-14-carboxylate (40.0 mg, 0.0704 mmol, intermediate 165) and ((2R,7aS)-2-fluorotetrahydro-1H-pyrrolizin-7a(5H)-yl)methanol (12.3 mg, 0.0800 mmol) in toluene (1.00 mL) was added t-BuONa (13.5 mg, 0.140 mmol) at 0° C. The resulting solution was stirred for 20 min at room temperature. The solvent was evaporated under vacuum at 0° C. The residue was purified by flash chromatography on silica gel (gradient: 0-10% MeOH/DCM) to afford 25.0 mg of the title compound as a white solid. LC-MS: (ESI, m/z): [M+H]$^+$=674.

Step 2: tert-Butyl (5R,5aS,6S,9R)-2-(6-(bis(4-methoxybenzyl)amino)-2-methyl-3-(trifluoromethyl)pyridin-4-yl)-1-fluoro-12-(((2R,7aS)-2-fluorotetrahydro-1H-pyrrolizin-7a(5H)-yl)methoxy)-5-(trifluoromethyl)-5a,6,7,8,9,10-hexahydro-5H-4-oxa-3,10a,11,13,14-pentaaza-6,9-methanonaphtho[1,8-ab]heptalene-14-carboxylate Under nitrogen, a solution of tert-butyl (5R,5aS,6S,9R)-2-chloro-1-fluoro-12-(((2R,7aS)-2-fluorotetrahydro-1H-pyrrolizin-7a(5H)-yl)methoxy)-5-(trifluoromethyl)-5a,6,7,8,9,10-hexahydro-5H-4-oxa-3,10a,11,13,14-pentaaza-6,9-methanonaphtho[1,8-ab]heptalene-14-carboxylate (73.0 mg, 0.112 mmol), (6-(bis(4-methoxybenzyl)amino)-2-methyl-3-(trifluoromethyl)pyridin-4-yl)boronic acid (104 mg, 0.230 mmol), cataCXium A Pd $G_3$ (16.4 mg, 0.0200 mmol) and $K_3PO_4$ (0.230 mL, 1.5 M in water) in tetrahydrofuran (1.10 mL) was stirred for 1 h at 60° C. Solvent was evaporated under vacuum. The residue was purified by flash chromatography on silica gel (gradient: 0-10% MeOH/DCM) to afford 89.0 mg of the title compound as a yellow solid. LC-MS: (ESI, m/z): [M+H]$^+$=1027.

Step 3: 4-((5R,5aS,6S,9R)-1-Fluoro-12-(((2R,7aS)-2-fluorotetrahydro-1H-pyrrolizin-7a(5H)-yl)methoxy)-5-(trifluoromethyl)-5a,6,7,8,9,10-hexahydro-5H-4-oxa-3,10a,11,13,14-pentaaza-6,9-methanonaphtho[1,8-ab]heptalen-2-yl)-6-methyl-5-(trifluoromethyl)pyridin-2-amine A solution of tert-butyl (5R,5aS,6S,9R)-2-(6-(bis(4-methoxybenzyl)amino)-2-methyl-3-(trifluoromethyl)pyridin-4-yl)-1-fluoro-12-(((2R,7aS)-2-fluorotetrahydro-1H-pyrrolizin-7a(5H)-yl)methoxy)-5-(trifluoromethyl)-5a,6,7,8,9,10-hexahydro-5H-4-oxa-3,10a,11,13,14-pentaaza-6,9-methanonaphtho[1,8-ab]heptalene-14-carboxylate (85.0 mg, 0.0828 mmol) in 2,2,2-trifluoroacetic acid (1.00 mL) was stirred for 3 h at 50° C. The solvent was evaporated under vacuum. The residue was purified by prep. HPLC (Column: XBridge Prep OBD C18 Column, 30*150 mm, 5 μm; Mobile Phase A: Water (10 mmol/L $NH_4HCO_3$), Mobile Phase B: ACN; Flow rate: 60 mL/min; Gradient: 17% B to 42% B in 9 min, 42% B; Wave Length: 254/220 nm; RT1(min): 8.9) to afford 16.2 mg of the title compound as a white solid. LC-MS: (ESI, m/z): [M+H]$^+$=687. $^1$H NMR (300 MHz, DMSO-$d_6$) δ 6.88 (s, 2H), 6.22 (s, 1H), 5.66-5.61 (m, 1H), 5.38 (s, 1H), 5.20-5.13 (m, 1H), 4.39 (d, J=9.6 Hz, 1H), 4.15-4.03 (m, 2H), 3.60-3.52 (m, 2H), 3.17-3.01 (m, 5H), 2.87-2.82 (m, 1H), 2.48 (d, J=2.3 Hz, 3H), 2.15 (s, 1H), 2.05-1.96 (m, 2H), 1.92-1.75 (m, 5H), 1.75-1.52 (m, 2H).

Each compound in the Table below was prepared following a similar experimental procedure (using appropriately substituted reagents) as described for Example 242.

| Cmpd. No. | $^1$H NMR | MS (M + H)$^+$ |
|---|---|---|
| 243 | $^1$H NMR (300 MHz, DMSO-$d_6$, ppm) δ 6.87 (s, 2H), 6.28 (s, 1H), 5.73 (d, J = 7.2 Hz, 1H), 5.28 (d, J = 54 Hz, 1H), 4.60 (d, J = 2.1 Hz, 1H), 4.25-3.99 (m, 3H), 3.67-3.53 (m, 2H), 3.28 (s, 1H), 3.16-3.00 (m, 4H), 2.84-2.82 (m, 1H), 2.48 (d, J = 2.3 Hz, 3H), 2.15 (d, J = 4.1 Hz, 1H), 2.08-1.97 (m, 2H), 1.86-1.62 (m, 6H), 1.40 (t, J = 9.5 Hz, 1H) | 687 |
| 244 | $^1$H NMR (300 MHz, DMSO-$d_6$, ppm): δ 6.70-6.43 (m, 1H), 6.25-5.93 (m, 2H), 5.80-5.58 (m, 1H), 5.19 (d, J = 13.1, 2.5 Hz, 1H), 4.52-4.25 (m, 3H), 3.66-3.49 (m, 3H), 3.27-3.19 (m, 1H), 3.18-3.03 (m, 3H), 2.72-2.60 (m, 1H), 2.48-2.38 (m, 2H), 2.38-2.28 (m, 4H), 1.96-1.75 (m, 2H), 1.72-1.50 (m, 2H). | 708 |
| 245 | $^1$H NMR (400 MHz, DMSO-$d_6$, ppm): δ 6.56 (s, 1H), 6.07 (s, 2H), 5.63 (s, 1H), 5.16 (d, J = 12.8 Hz, 1H), 4.52-4.29 (m, 2H), 4.24-4.08 (m, 1H), 3.70-3.39 (m, 6H), 3.21-3.06 (m, 2H), 3.05-2.92 (m, 1H), 2.92-2.78 (m, 2H), 2.39-2.26 (m, 3H), 2.19-1.98 (m, 1H), 1.96-1.71 (m, 3H), 1.70-1.48 (m, 3H), 1.40-1.19 (m, 1H). | 702 |
| 246 | $^1$H NMR (300 MHz, DMSO-$d_6$) δ 6.60 (s, 1H), 6.04 (s, 2H), 5.73 (s, 1H), 5.28 (d, J = 53.7 Hz, 1H), 4.58 (d, J = 10.8 Hz, 1H), 4.24 (s, 1H), 4.15 (d, J = 10.2 Hz, 1H), 3.96 (d, J = 10.2 Hz, 1H), 3.66-3.53 (m, 2H), 3.27 (s, 1H), 3.16-3.04 (m, 3H), 3.00 (s, 1H), 2.86-2.82 (m, 1H), 2.33 (s, 3H), 2.15-2.14 (s, 1H), 2.04 (s, 1H), 2.00-1.96 (m, 1H), 1.85-1.61 (m, 6H), 1.42-1.39 (s, 1H). | 704 |
| 247 | $^1$H NMR (300 MHz, DMSO-$d_6$) δ 6.55 (s, 1H), 6.07 (s, 2H), 5.63 (s, 1H), 5.37-5.13 (m, 2H), 4.37 (d, J = 10.5 Hz, 1H), 4.14-3.05 (m, 2H), 3.59-3.51 (m, 2H), 3.09 (s, 3H), 3.00 (s, 1H), 2.84 (s, 1H), 2.32 (s, 3H), 2.14 (s, 1H), 2.04 (s, 1H), 2.00 (s, 1H), 1.87-1.77 (m, 5H), 1.68-1.56 (m, 2H). | 704 |
| 248 | $^1$H NMR (300 MHz, DMSO-$d_6$) δ 6.57 (d, J = 19.2 Hz, 1H), 6.05 (s, 2H), 5.67 (t, J = 8.7 Hz, 1H), 5.28 (d, J = 53.7 Hz, 1H), 4.58 (d, J = 12.6 Hz, 1H), 4.15 (d, J = 10.5 Hz, 1H), 3.99 (d, J = 10.5 Hz, 1H), 3.90 (s, 1H), 3.66 (s, 2H), 3.45 (d, J = 2.1 Hz, 1H), 3.11-3.08 (m, 2H), 3.00 (s, 1H), 2.83-2.80 (m, 2H), 2.33 (s, 3H), 2.15-2.13 (m, 1H), 2.04-1.99 (m, 2H), 1.94-1.56 (m, 7H). | 704 |
| 249 | $^1$H NMR (400 MHz, DMSO-$d_6$, ppm): δ 6.56 (s, 1H), 6.07 (s, 2H), 5.62 (s, 1H), 5.25-5.08 (m, 1H), 4.45-4.31 (m, 2H), 4.25 (d, J = 10.9 Hz, 1H), 3.64-3.47 (m, 6H), 3.10 (d, J = 12.8 Hz, 1H), 2.95 (s, 1H), 2.45-2.20 (m, 9H), 1.86 (s, 2H), 1.73-1.49 (m, 2H), 0.73-0.55 (m, 2H), 0.49-0.33 (m, 2H). | 716 |
| 250 | $^1$H NMR (400 MHz, DMSO-$d_6$) δ 6.73-6.56 (m, 1H), 6.31-5.82 (m, 1H), 5.79-5.61 (m, 1H), 5.43-5.09 (m, 4H), 4.39 (d, J = 9.8 Hz, 1H), 4.22-3.96 (m, 2H), 3.56 (d, J = 25.2 Hz, 2H), 3.32-2.92 (m, 7H), 2.89-2.82 (m, 1H), 2.23 (d, J = 2.6 Hz, 3H), 2.16 (d, J = 4.5 Hz, 1H), 2.10-1.91 (m, 2H), 1.88-1.71 (m, 5H), 1.69-1.45 (m, 2H). | 700 |

| Cmpd. No. | ¹H NMR | MS (M + H)⁺ |
|---|---|---|
| 251 | ¹H NMR (300 MHz, DMSO-d₆, ppm): δ 10.17 (s, 1H), 7.92-7.85 (m, 1H), 7.51-7.39 (m, 2H), 7.37-7.32 (m, 1H), 7.18-6.98 (m, 1H), 5.66-5.19 (m, 3H), 4.40 (d, J = 9.7 Hz, 1H), 4.16-4.09 (m, 1H), 4.03 (d, J = 10.4 Hz, 1H), 3.93 (s, 1H), 3.58 (d, J = 20.8 Hz, 2H), 3.17-2.99 (m, 5H), 2.91-2.78 (m, 1H), 2.23-2.13 (m, 1H), 2.10-1.99 (m, 2H), 1.94-1.64 (m, 7H). | 679 |

Example 252: Compound 252 (two isomers

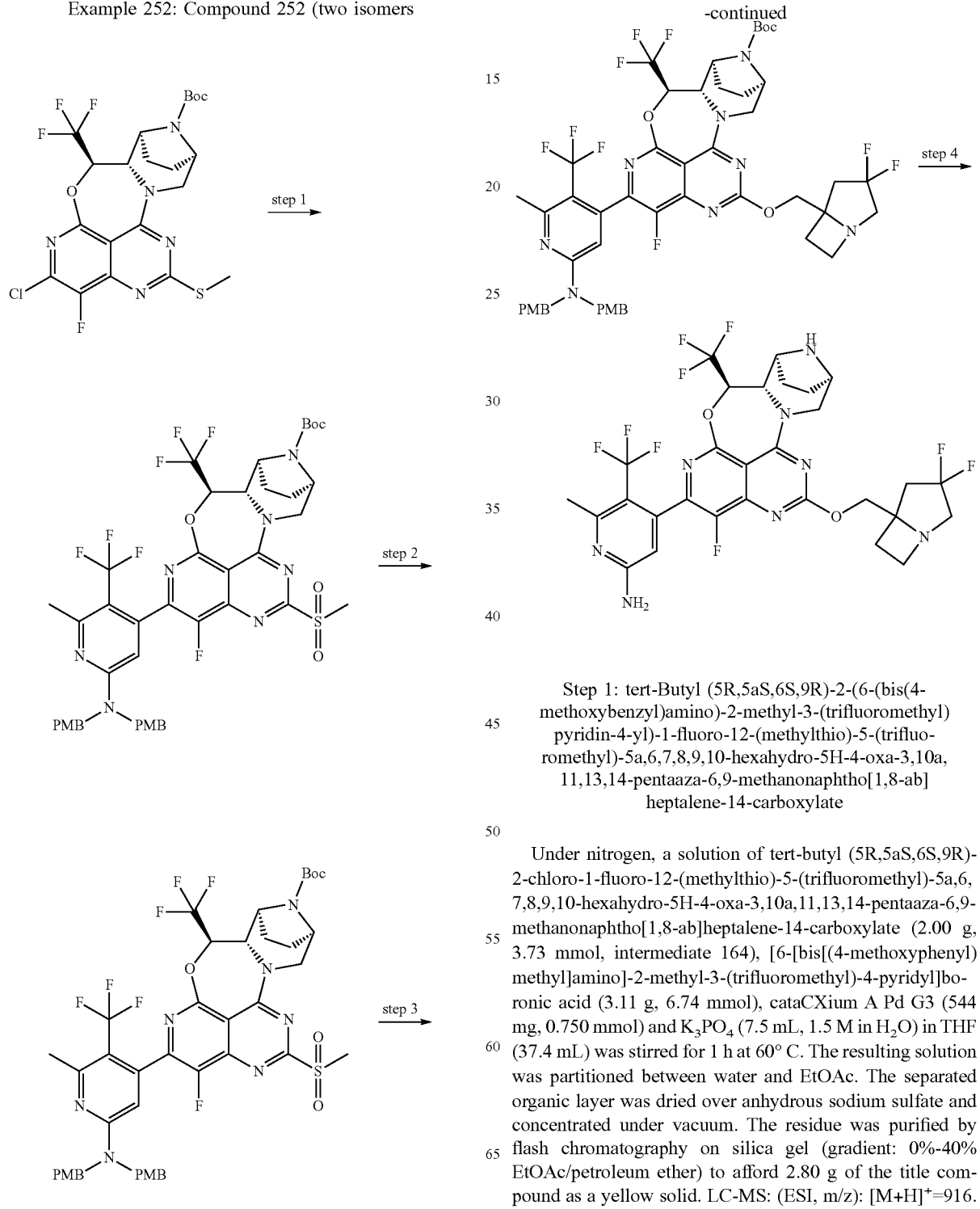

Step 1: tert-Butyl (5R,5aS,6S,9R)-2-(6-(bis(4-methoxybenzyl)amino)-2-methyl-3-(trifluoromethyl)pyridin-4-yl)-1-fluoro-12-(methylthio)-5-(trifluoromethyl)-5a,6,7,8,9,10-hexahydro-5H-4-oxa-3,10a,11,13,14-pentaaza-6,9-methanonaphtho[1,8-ab]heptalene-14-carboxylate Under nitrogen, a solution of tert-butyl (5R,5aS,6S,9R)-2-chloro-1-fluoro-12-(methylthio)-5-(trifluoromethyl)-5a,6,7,8,9,10-hexahydro-5H-4-oxa-3,10a,11,13,14-pentaaza-6,9-methanonaphtho[1,8-ab]heptalene-14-carboxylate (2.00 g, 3.73 mmol, intermediate 164), [6-[bis[(4-methoxyphenyl)methyl]amino]-2-methyl-3-(trifluoromethyl)-4-pyridyl]boronic acid (3.11 g, 6.74 mmol), cataCXium A Pd G3 (544 mg, 0.750 mmol) and K₃PO₄ (7.5 mL, 1.5 M in H₂O) in THF (37.4 mL) was stirred for 1 h at 60° C. The resulting solution was partitioned between water and EtOAc. The separated organic layer was dried over anhydrous sodium sulfate and concentrated under vacuum. The residue was purified by flash chromatography on silica gel (gradient: 0%-40% EtOAc/petroleum ether) to afford 2.80 g of the title compound as a yellow solid. LC-MS: (ESI, m/z): [M+H]⁺=916.

Step 2: tert-Butyl (5R,5aS,6S,9R)-2-(6-(bis(4-methoxybenzyl)amino)-2-methyl-3-(trifluoromethyl)pyridin-4-yl)-1-fluoro-12-(methylsulfonyl)-5-(trifluoromethyl)-5a,6,7,8,9,10-hexahydro-5H-4-oxa-3,10a,11,13,14-pentaaza-6,9-methanonaphtho[1,8-ab]heptalene-14-carboxylate To a solution of tert-butyl (5R,5aS,6S,9R)-2-(6-(bis(4-methoxybenzyl) amino)-2-methyl-3-(trifluoromethyl)pyridin-4-yl)-1-fluoro-12-(methylthio)-5-(trifluoromethyl)-5a,6,7,8,9,10-hexahydro-5H-4-oxa-3,10a,11,13,14-pentaaza-6,9-methanonaphtho[1,8-ab]heptalene-14-carboxylate (1.60 g, 1.75 mmol) in EtOAc (20 mL) was added m-CPBA (900 mg, 5.24 mmol) at 0° C. and stirred at room temperature for 1 h. The reaction was quenched with saturated Na$_2$S$_2$O$_3$ aqueous, extracted with EtOAc. The combined organic layers were dried over anhydrous sodium sulfate and concentrated under vacuum. The residue was purified by flash chromatography on silica gel eluting (gradient: 0%-55% EtOAc/petroleum ether) to afford 1.29 g of the title compound as a yellow solid. LC-MS: (ESI, m/z): [M+H]$^+$=948.

Step 3: tert-Butyl (5R,5aS,6S,9R)-2-(6-(bis(4-methoxybenzyl)amino)-2-methyl-3-(trifluoromethyl)pyridin-4-yl)-12-((3,3-difluoro-1-azabicyclo[3.2.0]heptan-5-yl)methoxy)-1-fluoro-5-(trifluoromethyl)-5a,6,7,8,9,10-hexahydro-5H-4-oxa-3,10a,11,13,14-pentaaza-6,9-methanonaphtho[1,8-ab]heptalene-14-carboxylate Under nitrogen, to a solution of tert-butyl (5R,5aS,6S,9I)-2-(6-(bis(4-methoxybenzyl) amino)-2-methyl-3-(trifluoromethyl)pyridin-4-yl)-1-fluoro-12-(methylsulfonyl)-5-(trifluoromethyl)-5a,6,7,8,9,10-hexahydro-5H-4-oxa-3,10a,11,13,14-pentaaza-6,9-methanonaphtho[1,8-ab]heptalene-14-carboxylate (120 mg, 0.130 mmol) and (3,3-difluoro-1-azabicyclo[3.2.0]heptan-5-yl)methanol (42.0 mg, 0.260 mmol) in toluene (5 mL) was added t-BuONa (24.0 mg, 0.250 mmol) at 0° C., and the mixture was stirred for 1 h at room temperature. The resulting solution was partitioned between water and EtOAc. The separated organic layer was dried over anhydrous sodium sulfate and concentrated under vacuum. The residue was purified by C18 column (solvent gradient: 0-89% MeOH in water (0.05% NH$_4$HCO$_3$)) to afford 102 mg of the title compound as a yellow solid. LC-MS: (ESI, m/z): [M+H]$^+$=1031.

Step 4: tert-Butyl (5R,5aS,6S,9R)-2-(6-(bis(4-methoxybenzyl)amino)-2-methyl-3-(trifluoromethyl)pyridin-4-yl)-12-((3,3-difluoro-1-azabicyclo[3.2.0]heptan-5-yl)methoxy)-1-fluoro-5-(trifluoromethyl)-5a,6,7,8,9,10-hexahydro-5H-4-oxa-3,10a,11,13,14-pentaaza-6,9-methanonaphtho[1,8-ab]heptalene-14-carboxylate A solution of tert-butyl (5R,5aS,6S,9R)-2-(6-(bis(4-methoxybenzyl) amino)-2-methyl-3-(trifluoromethyl)pyridin-4-yl)-12-((3,3-difluoro-1-azabicyclo[3.2.0]heptan-5-yl)methoxy)-1-fluoro-5-(trifluoromethyl)-5a,6,7,8,9,10-hexahydro-5H-4-oxa-3,10a,11,13,14-pentaaza-6,9-methanonaphtho[1,8-ab]heptalene-14-carboxylate (90.0 mg, 0.0900 mmol) in TFA (5 mL) was stirred at 50° C. for 3.5 h. The solvent was concentrated under vacuum. The crude product was purified by Prep-HPLC (Column: CHIRALPAK SB 2×25 cm, 5 M; Mobile Phase A: HEX(0.5% 2 M NH$_3$—MeOH), Mobile Phase B: ETOH; Flow rate: 20 mL/min; Gradient: isocratic 20; Wave Length: 220/254 nm; R$_{T1}$(min): 10.427; R$_{T2}$(min): 12.233; Sample Solvent: EtOH) to afford 252 (isomer 1) 10.4 mg (the faster peak) and 252 (isomer 2) 9.8 mg (the slower peak) as white solids. LC-MS: (ESI, m/z): [M+H]$^+$=691.

252 (isomer 1): $^1$H NMR (300 MHz, DMSO-d$_6$, ppm): δ 6.88 (s, 2H), 6.23 (s, 1H), 5.65 (t, J=8.2 Hz, 1H), 5.19 (d, J=12.7 Hz, 1H), 4.53-4.23 (m, 3H), 3.67-3.47 (m, 3H), 3.30-3.18 (m, 1H), 3.18-3.00 (m, 3H), 2.80-2.58 (m, 1H), 2.48-2.41 (m, 3H), 2.35 (dd, J=10.8, 6.2 Hz, 2H), 2.30-2.15 (m, 1H), 1.88 (d, J=19.6 Hz, 2H), 1.77-1.46 (m, 2H).

252 (isomer 2): $^1$H NMR (300 MHz, DMSO-d$_6$) δ 6.87 (s, 2H), 6.22 (s, 1H), 6.01-5.63 (m, 1H), 5.18 (dd, J=12.9, 2.6 Hz, 1H), 4.50-4.20 (m, 3H), 3.72-3.43 (m, 3H), 3.22 (d, J=8.7 Hz, 1H), 3.15 (d, J=4.3 Hz, 2H), 3.08 (t, J=5.3 Hz, 1H), 2.85-2.65 (m, 1H), 2.51-2.29 (m, 6H), 1.96-1.75 (m, 2H), 1.62 (dd, J=15.2, 7.3 Hz, 2H).

Each compound in the Table below was prepared following a similar experimental procedure (using appropriately substituted reagents) as described for Example 252.

| Cmpd. No. | $^1$H NMR | MS (M + H)$^+$ |
|---|---|---|
| 253 | $^1$H NMR (500 MHz, DMSO-d$_6$, ppm): δ 6.87 (s, 2H), 6.22 (s, 1H), 5.66-5.62 (m, 1H), 5.23-5.14 (m, 1H), 4.46-4.37 (m, 2H), 4.19-4.16 (m, 1H), 3.74-3.65 (m, 1H), 3.61-3.49 (m, 4H), 3.45-3.38 (m, 1H), 3.31-3.29 (m, 1H), 3.21-3.18 (m, 2H), 3.05-2.98 (m, 1H), 2.93-2.85 (m, 2H), 2.46-2.42 (m, 3H), 2.14-2.03 (m, 1H), 1.90-1.77 (m, 3H), 1.68-1.57 (m, 3H), 1.36-1.29 (m, 1H). | 685 |
| 254 | $^1$H NMR (400 MHz, DMSO-d$_6$, ppm): δ 6.87 (s, 2H), 6.22 (s, 1H), 5.75-5.53 (m, 1H), 5.24-5.08 (m, 1H), 4.39 (d, J = 9.7 Hz, 1H), 4.28-4.12 (m, 2H), 3.67-3.46 (m, 2H), 3.20-2.94 (m, 3H), 2.72 (d, J = 11.8 Hz, 1H), 2.59-2.53 (m, 1H), 2.48-2.42 (m, 3H), 2.18-2.02 (m, 1H), 2.03-1.91 (m, 2H), 1.90-1.88 (m, 1H), 1.87-1.77 (m, 3H), 1.76-1.68 (m, 1H), 1.68-1.55 (m, 3H), 1.54-1.41 (m, 1H). | 731 |

Example 255: Compound 255 (Mixture and Two Separate Diastereomers

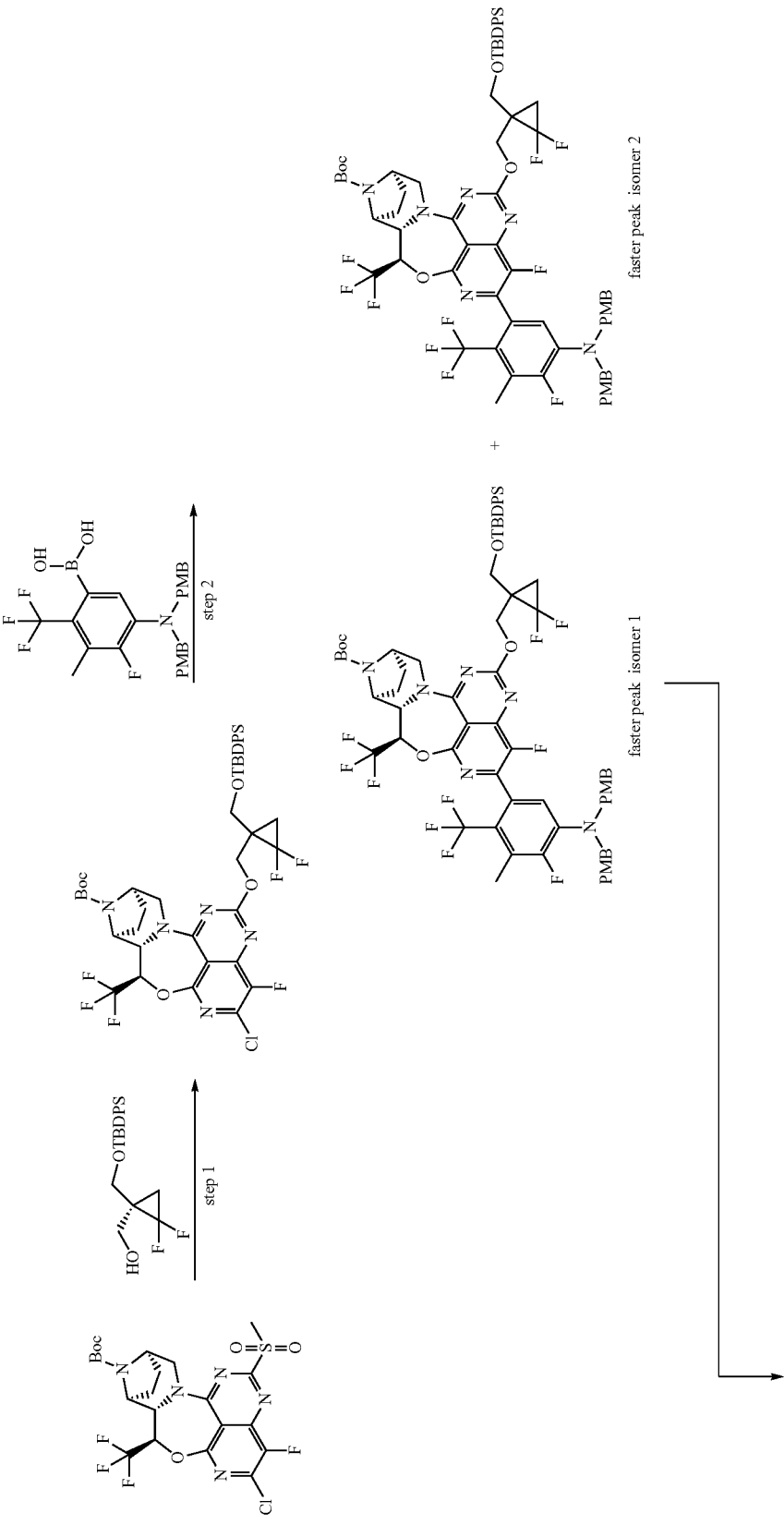

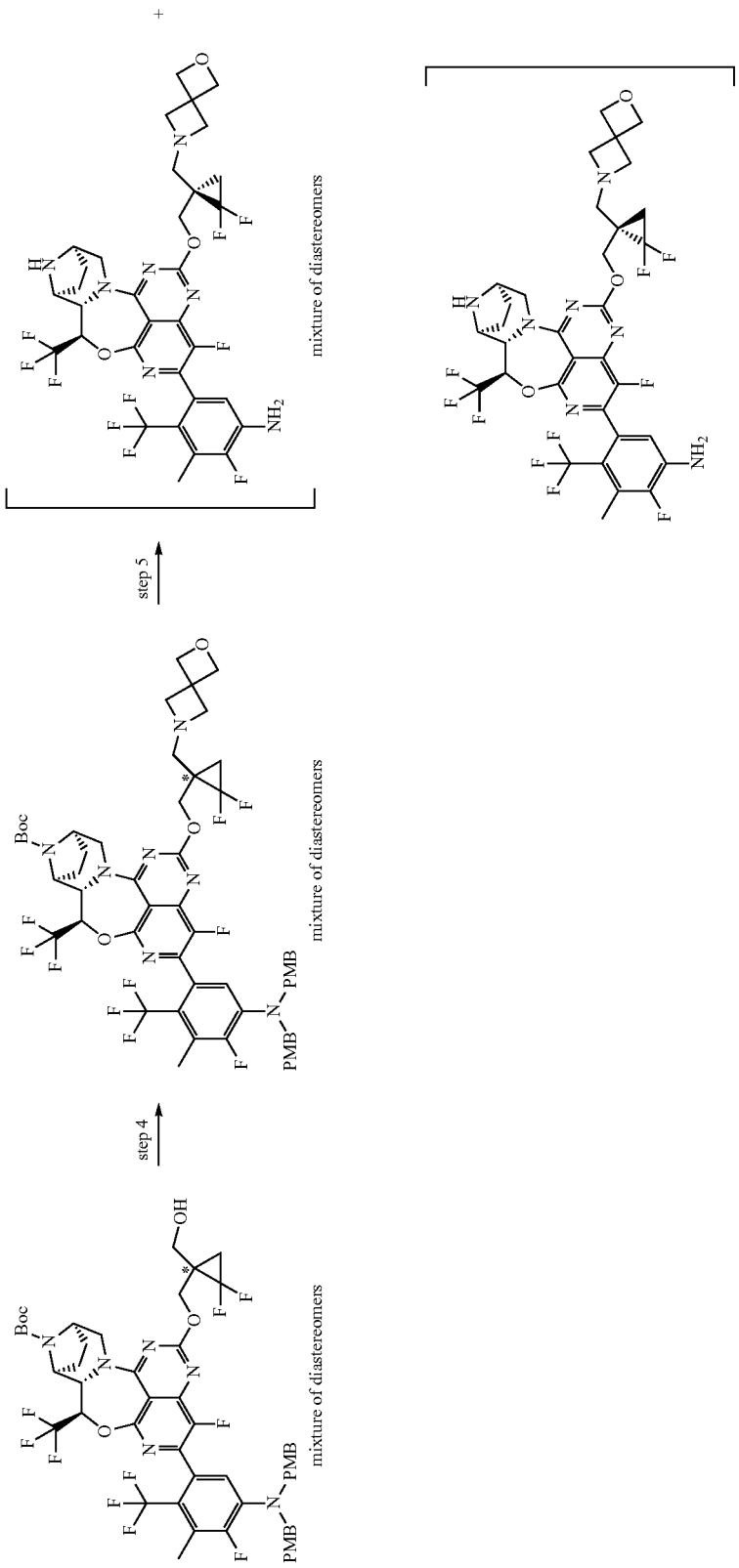

Step 1: tert-Butyl (5R,5aS,6S,9R)-12-((1-(((tert-butyldiphenylsilyl)oxy)methyl)-2,2-difluorocyclopropyl)methoxy)-2-chloro-1-fluoro-5-(trifluoromethyl)-5a,6,7,8,9,10-hexahydro-5H-4-oxa-3,10a,11,13,14-pentaaza-6,9-methanonaphtho[1,8-ab]heptalene-14-carboxylate To a solution of tert-butyl (5R,5aS,6S,9R)-2-chloro-1-fluoro-12-(methylsulfonyl)-5-(trifluoromethyl)-5a,6,7,8,9,10-hexahydro-5H-4-oxa-3,10a,11,13,14-pentaaza-6,9-methanonaphtho[1,8-ab]heptalene-14-carboxylate (500 mg, 0.880 mmol, intermediate 165) and (1-(((tert-butyldiphenylsilyl)oxy)methyl)-2,2-difluorocyclopropyl)methanol (497 mg, 1.32 mmol, intermediate 117) in toluene (3 mL) was added tBuONa (169 mg, 1.76 mmol) at 0° C. and the solution was stirred for 1 hour at room temperature. The reaction mixture was diluted with water and extracted with ethyl acetate. The combined organic layer was dried over anhydrous sodium sulfate and concentrated under vacuum. The residue was purified by flash chromatography on silica gel (gradient: 0-100% EtOAc in petroleum ether) to afford the title compound (640 mg) as a brown solid. LC-MS: (ESI, m/z): [M+H]$^+$=865.

Step 2: tert-Butyl (5R,5aS,6S,9R)-2-(5-(bis(4-methoxybenzyl)amino)-4-fluoro-3-methyl-2-(trifluoromethyl)phenyl)-12-((1-(((tert-butyldiphenylsilyl)oxy)methyl)-2,2-difluorocyclopropyl)methoxy)-1-fluoro-5-(trifluoromethyl)-5a,6,7,8,9,10-hexahydro-5H-4-oxa-3,10a,11,13,14-pentaaza-6,9-methanonaphtho[1,8-ab]heptalene-14-carboxylate (two isomers)

Under nitrogen, a solution of tert-butyl (5R,5aS,6S,9R)-12-((1-(((tert-butyldiphenylsilyl)oxy)methyl)-2,2-difluorocyclopropyl)methoxy)-2-chloro-1-fluoro-5-(trifluoromethyl)-5a,6,7,8,9,10-hexahydro-5H-4-oxa-3,10a,11,13,14-pentaaza-6,9-methanonaphtho[1,8-ab]heptalene-14-carboxylate (640 mg, 0.740 mmol), (5-(bis(4-methoxybenzyl)amino)-4-fluoro-3-methyl-2-(trifluoromethyl)phenyl)boronic acid (530 mg, 1.11 mmol), K$_3$PO$_4$ (1.5 M aqueous solution, 2.5 mL, 3.75 mmol) and cataCXium A Pd G3 (108 mg, 0.148 mmol) in THF (12.5 mL) was stirred for 3 hours at 60° C. The reaction mixture was diluted with water and extracted with ethyl acetate. The combined organic layers were dried over anhydrous sodium sulfate and concentrated under vacuum. The residue was purified by flash chromatography on silica gel (gradient: 0-10% methanol in dichloromethane) to afford a mixture of two diastereomers (840 mg) as a light brown solid. The two diastereomers were separated by Chiral-Prep-SFC with the following conditions: (Column:((S, S)-WHELK-01-Kromasil, 5*25 cm, 10 μm; Mobile Phase A: CO$_2$, Mobile Phase B: IPA; Flow rate: 90 mL/min; Gradient: isocratic 35% B; Column Temperature(° C.): 35; Back Pressure(bar): 100; Wave Length: 220 nm; RT1(min): 18.95; RT2(min): 21.17; Sample Solvent: MEOH; Injection Volume: 1 mL; Number Of Runs: 40) to afford isomer 1 (270 mg, the faster peak) and isomer 2 (250 mg, the slower peak) as white solids. LC-MS: (ESI, m/z): [M+H]$^+$=1262.

Step 3: tert-Butyl (5R,5aS,6S,9R)-2-(5-(bis(4-methoxybenzyl)amino)-4-fluoro-3-methyl-2-(trifluoromethyl)phenyl)-12-((2,2-difluoro-1-(hydroxymethyl)cyclopropyl)methoxy)-1-fluoro-5-(trifluoromethyl)-5a,6,7,8,9,10-hexahydro-5H-4-oxa-3,10a,11,13,14-pentaaza-6,9-methanonaphtho[1,8-ab]heptalene-14-carboxylate (two isomers)

To a solution of tert-butyl (5R,5aS,6S,9R)-2-(5-(bis(4-methoxybenzyl)amino)-4-fluoro-3-methyl-2-(trifluoromethyl)phenyl)-12-((1-(((tert-butyldiphenylsilyl)oxy)methyl)-2,2-difluorocyclopropyl)methoxy)-1-fluoro-5-(trifluoromethyl)-5a,6,7,8,9,10-hexahydro-5H-4-oxa-3,10a,11,13,14-pentaaza-6,9-methanonaphtho[1,8-ab]heptalene-14-carboxylate (200 mg, 0.158 mmol, isomer 1 of last step) in tetrahydrofuran (4 mL) was added TBAF (1 M solution in tetrahydrofuran, 0.5 mL), and the mixture was stirred for 2 hours at room temperature. The reaction mixture was diluted with water and extracted with ethyl acetate. The combined organic layer was dried over anhydrous sodium sulfate and concentrated under vacuum. The residue was purified by flash chromatography on silica gel (gradient: 0-10% methanol in dichloromethane) to afford the title compound (120 mg) as a light brown solid. LC-MS: (ESI, m/z): [M+H]$^+$= 1023. It appears that isomerization took place in the TBDPS deprotection step to give a mixture of diastereomers of the title compound with respect to the stereogenic center of the difluorocyclopropyl moiety. This mixture was used as such in the following steps.

Step 4: tert-Butyl (5R,5aS,6S,9R)-12-((1-((2-oxa-6-azaspiro[3.3]heptan-6-yl)methyl)-2,2-difluorocyclopropyl)methoxy)-2-(5-(bis(4-methoxybenzyl)amino)-4-fluoro-3-methyl-2-(trifluoromethyl)phenyl)-1-fluoro-5-(trifluoromethyl)-5a,6,7,8,9,10-hexahydro-5H-4-oxa-3,10a,11,13,14-pentaaza-6,9-methanonaphtho[1,8-ab]heptalene-14-carboxylate (mixture of diastereomers)

To a solution of tert-butyl (5R,5aS,6S,9R)-2-(5-(bis(4-methoxybenzyl)amino)-4-fluoro-3-methyl-2-(trifluoromethyl)phenyl)-12-((2,2-difluoro-1-(hydroxymethyl)cyclopropyl)methoxy)-1-fluoro-5-(trifluoromethyl)-5a,6,7,8,9,10-hexahydro-5H-4-oxa-3,10a,11,13,14-pentaaza-6,9-methanonaphtho[1,8-ab]heptalene-14-carboxylate (50.0 mg, 0.0489 mmol, mixture of diastereomers) and NMO (11.5 mg, 0.0978 mmol) in dichloromethane (2 mL) was added TPAP (3.44 mg, 0.00978 mmol) at 0° C. and the solution was stirred for 1 hour at room temperature. The resulting mixture was filtered and the filter cake was washed with dichloromethane. To the combined filtrate were added NaOAc (60.2 mg, 0.734 mmol) and 2-oxa-6-azaspiro [3.3] heptane (72.8 mg, 0.734 mmol) at room temperature and the solution was stirred for 1 hour at 60° C. Then the mixture was cooled to ambient temperature and NaBH$_3$CN (46.1 mg, 0.734 mmol) was added, and the mixture was stirred overnight at room temperature. The reaction was quenched with water and extracted with ethyl acetate. The combined organic layers were washed with brine, dried over anhydrous sodium sulfate and concentrated under vacuum. The residue was purified by reverse phase flash chromatography on pre-packed C18 column (gradient: 0-100% CH$_3$CN in water (0.05% NH$_4$HCO$_3$)) to afford the title compound (30.0 mg) as a mixture of diastereomers with respect to the stereogenic center of the difluorocyclopropyl moiety. LC-MS: (ESI, m/z): [M+H]$^+$=1105.

Step 5: 5-((5R,5aS,6S,9R)-12-((1-((2-Oxa-6-azaspiro[3.3]heptan-6-yl)methyl)-2,2-difluorocyclopropyl)methoxy)-1-fluoro-5-(trifluoromethyl)-5a,6,7,8,9,10-hexahydro-5H-4-oxa-3,10a,11,13,14-pentaaza[6,9]methanonaphtho[1,8-ab]heptalen-2-yl)-2-fluoro-3-methyl-4-(trifluoromethyl)aniline A solution of tert-butyl (5R,5aS,6S,9R)-12-((1-((2-oxa-6-azaspiro[3.3]heptan-6-yl)methyl)-2,2-difluorocyclopropyl)methoxy)-2-(5-(bis(4-methoxybenzyl)amino)-4-fluoro-3- methyl-2-(trifluoromethyl)phenyl)-1-fluoro-5-(trifluoromethyl)-5a,6,7,8,9,10-hexahydro-5H-4-oxa-3,10a,11,13,14-pentaaza-6,9-methanonaphtho[1,8-ab]heptalene-14-carboxylate (30.0 mg, 0.0271 mmol, mixture of diastereomers) in TFA (10 mL) was stirred for 30 minutes at room temperature. The solvent was concentrated under vacuum. The residue was purified by Prep-HPLC (Column: XBridge Prep OBD C18 Column, 30*150 mm, 5 μm; Mobile Phase A: Water (10 mmol/L $NH_4HCO_3$), Mobile Phase B: ACN; Flow rate: 60 mL/min mL/min; Gradient: 42% B to 56% B in 10 min; Wave Length: 254 nm/220 nm nm; RT1(min): 8.5) to afford 255 (mixture of diastereomers) (3.00 mg).

255 (mixture of diastereomers): LC-MS: (ESI, m/z): $[M+H]^+=764$. $^1$H NMR (300 MHz, DMSO-d6, ppm) δ 6.69-6.40 (m, 1H), 6.08 (s, 2H), 5.78-5.53 (m, 1H), 5.17 (d, J=12.8 Hz, 1H), 4.67-4.47 (m, 5H), 4.40 (d, J=9.6 Hz, 1H), 4.36-4.22 (m, 1H), 3.66-3.48 (m, 2H), 3.43-3.37 (m, 1H), 3.13 (d, J=12.9 Hz, 1H), 2.66-2.55 (m, 1H), 2.53 (s, 4H), 2.33 (s, 3H), 1.92-1.79 (m, 2H), 1.79-1.41 (m, 4H).

Example 256: Compound 256

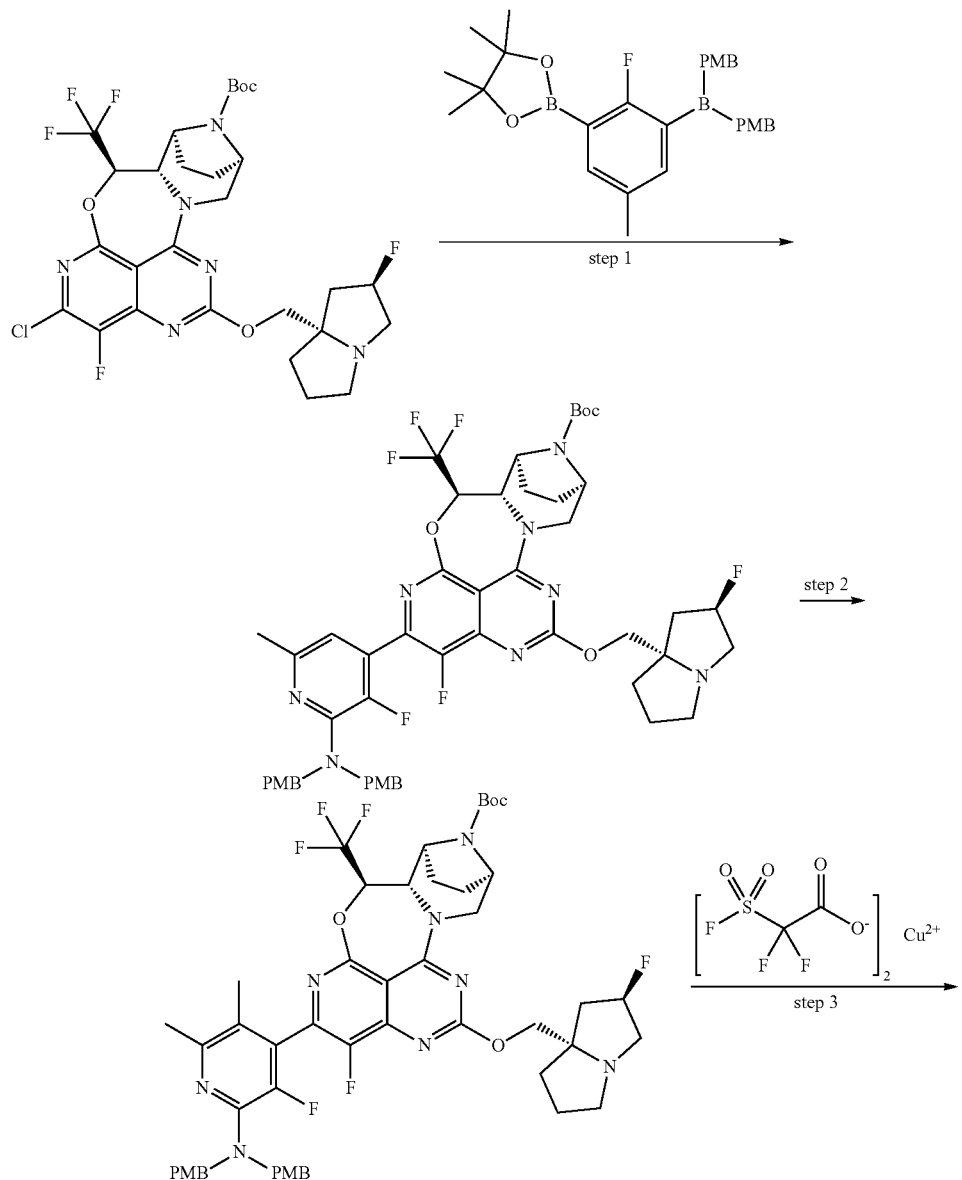

845 846

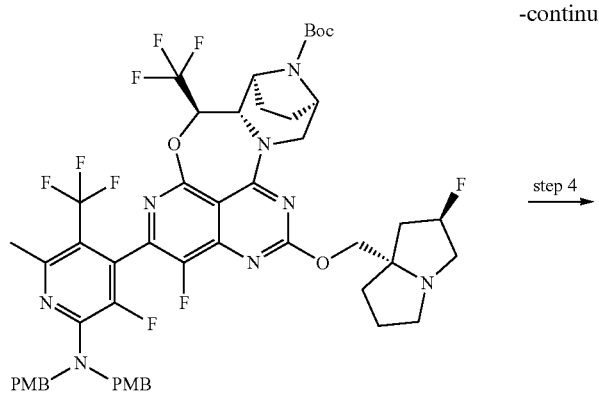
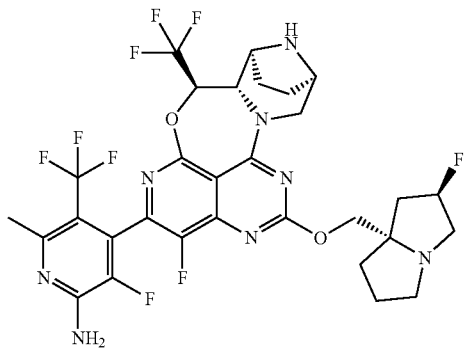

-continued step 4

Step 1: tert-Butyl (5R,5aS,6S,9R)-2-(2-(bis(4-methoxybenzyl)amino)-3-fluoro-6-methylpyridin-4-yl)-1-fluoro-12-(((2R,7aS)-2-fluorotetrahydro-1H-pyrrolizin-7a(5H)-yl)methoxy)-5-(trifluoromethyl)-5a,6,7,8,9,10-hexahydro-5H-4-oxa-3,10a,11,13,14-pentaaza-6,9-methanonaphtho[1,8-ab]heptalene-14-carboxylate Under nitrogen, a solution of tert-butyl (5R,5aS,6S,9R)-2-chloro-1-fluoro-12-(((2R,7aS)-2-fluorotetrahydro-1H-pyrrolizin-7a(5H)-yl)methoxy)-5-(trifluoromethyl)-5a,6,7,8,9,10-hexahydro-5H-4-oxa-3,10a,11,13,14-pentaaza-6,9-methanonaphtho[1,8-ab]heptalene-14-carboxylate (100 mg, 0.155 mmol, Example 245, step 1), 3-fluoro-N,N-bis(4-methoxybenzyl)-6-methyl-4-(4,4,5,5-tetramethyl-1,3,2-dioxaborolan-2-yl)pyridin-2-amine (153 mg, 0.312 mmol), cataCxium A Pd G$_3$ (22.5 mg, 0.0309 mmol) and K$_3$PO$_4$ (0.310 mL, 1.5 M in water) in tetrahydrofuran (1.55 mL) was stirred for 1 h at 60° C. The resulting solution was partitioned between water and EtOAc. The separated organic layer was dried over anhydrous sodium sulfate and concentrated under vacuum. The residue was purified by flash chromatography on silica gel (gradient: 0-50% 0-10% MeOH/DCM) to afford 140 mg of the title compound as a yellow solid. LC-MS: (ESI, m/z): [M+H]$^+$=977.

Step 2: tert-Butyl (5R,5aS,6S,9R)-2-(2-(bis(4-methoxybenzyl)amino)-3-fluoro-5-iodo-6-methylpyridin-4-yl)-1-fluoro-12-(((2R,7aS)-2-fluorotetrahydro-1H-pyrrolizin-7a(5H)-yl)methoxy)-5-(trifluoromethyl)-5a,6,7,8,9,10-hexahydro-5H-4-oxa-3,10a,11,13,14-pentaaza-6,9-methanonaphtho[1,8-ab]heptalene-14-carboxylate A solution of tert-butyl (5R,5aS,6S,9R)-2-(2-(bis(4-methoxybenzyl) amino)-3-fluoro-6-methylpyridin-4-yl)-1-fluoro-12-(((2R,7aS)-2-fluorotetrahydro-1H-pyrrolizin-7a(5H)-yl)methoxy)-5-(trifluoromethyl)-5a,6,7,8,9,10-hexahydro-5H-4-oxa-3,10a,11,13,14-pentaaza-6,9-methanonaphtho[1,8-ab]heptalene-14-carboxylate (140 mg, 0.140 mmol) and 1-iodopyrrolidine-2,5-dione (32.3 mg, 0.140 mmol) in acetic acid (2.00 mL) was stirred for 1 h at room temperature. The solvent was evaporated under vacuum. The residue was purified by flash chromatography on silica gel (gradient: 0-10% MeOH/DCM) to afford 150 mg of the title compound as a yellow solid. LC-MS: (ESI, m/z): [M+H]$^+$=1103.

Step 3: tert-Butyl (5R,5aS,6S,9R)-2-(2-(bis(4-methoxybenzyl)amino)-3-fluoro-6-methyl-5-(trifluoromethyl)pyridin-4-yl)-1-fluoro-12-(((2R,7aS)-2-fluorotetrahydro-1H-pyrrolizin-7a(5H)-yl)methoxy)-5-(trifluoromethyl)-5a,6,7,8,9,10-hexahydro-5H-4-oxa-3,10a,11,13,14-pentaaza-6,9-methanonaphtho[1,8-ab]heptalene-14-carboxylate Under nitrogen, to a mixture of tert-butyl (5R,5aS,6S,9R)-2-(2-(bis(4-methoxybenzyl) amino)-3-fluoro-5-iodo-6-methylpyridin-4-yl)-1-fluoro-12-(((2R,7aS)-2-fluorotetrahydro-1H-pyrrolizin-7a(5H)-yl)methoxy)-5-(trifluoromethyl)-5a,6,7,8,9,10-hexahydro-5H-4-oxa-3,10a,11,13,14-pentaaza-6,9-methanonaphtho[1,8-ab]heptalene-14-carboxylate (184 mg, 0.170 mmol), Cu(O$_2$CCF$_2$SO$_2$F)$_2$ (1.05 g, 2.51 mmol) and copper (160 mg, 2.50 mmol) was added N,N-dimethylacetamide (5.00 mL) at 0° C. The resulting solution was stirred for 1 h at room temperature. The resulting mixture was diluted with water and extracted with EtOAc. The combined organic layers were dried over anhydrous sodium sulfate and concentrated under vacuum. The residue was purified by flash chromatography on silica gel (gradient: 0-100% EtOAc/petroleum ether) to afford 90.0 mg of the title compound as a yellow solid. LC-MS: (ESI, m/z): [M+H]$^+$=1045.

Step 4: 3-Fluoro-4-((5R,5aS,6S,9R)-1-fluoro-12-(((2R,7aS)-2-fluorotetrahydro-1H-pyrrolizin-7a(5H)-yl)methoxy)-5-(trifluoromethyl)-5a,6,7,8,9,10-hexahydro-5H-4-oxa-3,10a,11,13,14-pentaaza-6,9-methanonaphtho[1,8-ab]heptalen-2-yl)-6-methyl-5-(trifluoromethyl)pyridin-2-amine A solution of tert-butyl (5R,5aS,6S,9R)-2-(2-(bis(4-methoxybenzyl) amino)-3-fluoro-6-methyl-5-(trifluoromethyl)pyridin-4-yl)-1-fluoro-12-(((2R,7aS)-2-fluorotetrahydro-1H-pyrrolizin-7a(5H)-yl)methoxy)-5-(trifluoromethyl)-5a,6,7,8,9,10-hexahydro-5H-4-oxa-3,10a,11,13,14-pentaaza-6,9-methanonaphtho[1,8-ab]heptalene-14-carboxylate (85.0 mg, 0.0800 mmol) in 2,2,2-trifluoroacetic acid (1.00 mL) was stirred for 1 h at 50° C. Solvent was evaporated under vacuum. The residue was purified by prep. HPLC (Column: XBridge Prep OBD C18 Column, 30*150 mm, 5 μm; Mobile Phase A: Water (10 mmol/L NH$_4$HCO$_3$), Mobile Phase B: ACN; Flow rate: 60 mL/min; Gradient: 17% B to 42% B in 9 min; Wave Length: 254 nm/220 nm; RT1(min): 8.6) to afford 23.4 mg of the title compound as a white solid. LC-MS: (ESI, m/z): [M+H]$^+$= 705. $^1$H NMR (300 MHz, DMSO-d$_6$) δ 7.23 (d, J=13.1 Hz, 2H), 5.68-5.65 (m, 1H), 5.38-5.13 (m, 2H), 4.39 (t, J=9.9 Hz, 1H), 4.16-4.03 (m, 2H), 3.59-3.51 (m, 2H), 3.15-3.00 (m, 5H), 2.84-2.82 (m, 1H), 2.46 (s, 3H), 2.15 (s, 1H), 2.07-1.86 (m, 2H), 1.83-1.77 (m, 5H), 1.68-1.56 (m, 2H).

Example 257: Compound 257

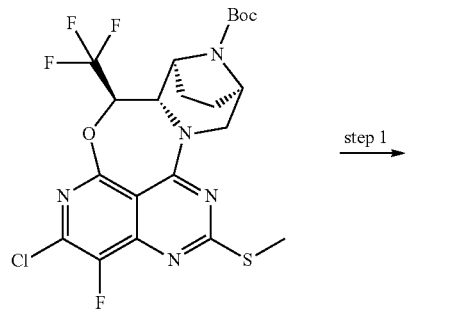

step 1

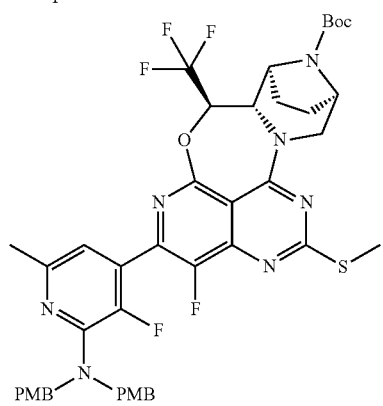

step 2

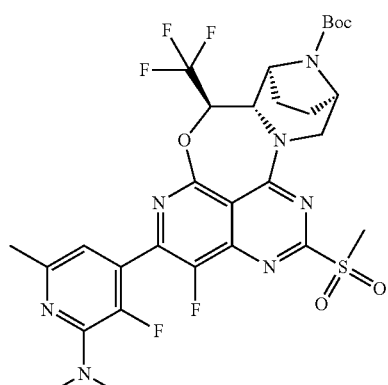

step 3

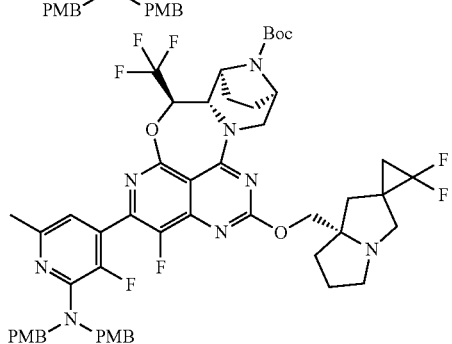

step 4

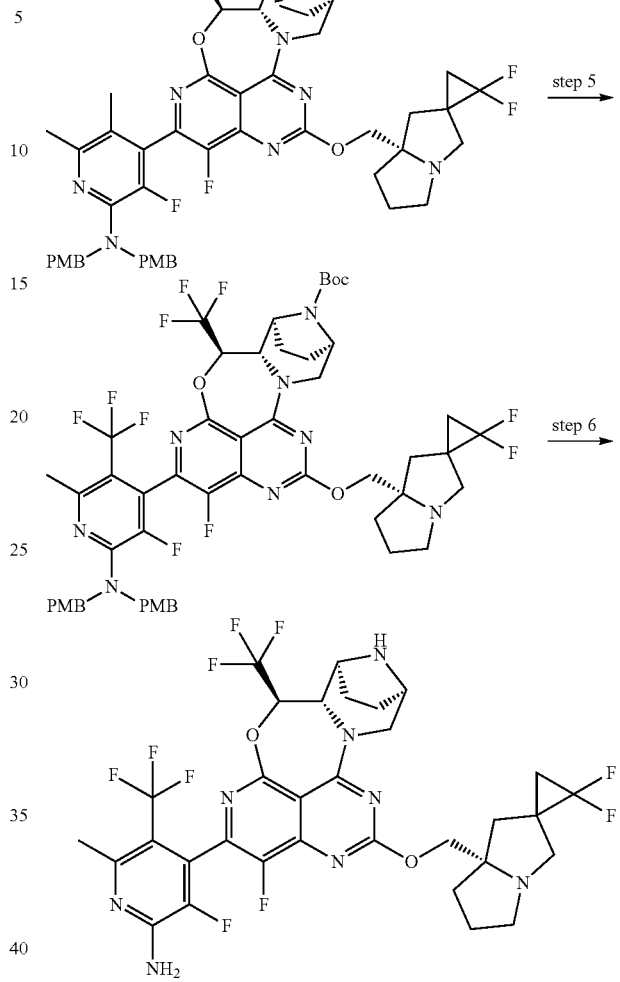

Step 1: tert-Butyl (5R,5aS,6S,9R)-2-(2-(bis(4-methoxybenzyl)amino)-3-fluoro-6-methylpyridin-4-yl)-1-fluoro-12-(methylthio)-5-(trifluoromethyl)-5a,6,7,8,9,10-hexahydro-5H-4-oxa-3,10a,11,13,14-pentaaza-6,9-methanonaphtho[1,8-ab]heptalene-14-carboxylate Under nitrogen, a solution of tert-butyl (5R,5aS,6S,9R)-2-chloro-1-fluoro-12-(methylthio)-5-(trifluoromethyl)-5a,6,7,8,9,10-hexahydro-5H-4-oxa-3,10a,11,13,14-pentaaza-6,9-methanonaphtho[1,8-ab]heptalene-14-carboxylate (250 mg, 0.470 mmol, intermediate 164), 3-fluoro-N,N-bis(4-methoxybenzyl)-6-methyl-4-(4,4,5,5-tetramethyl-1,3,2-dioxaborolan-2-yl)pyridin-2-amine (575 mg, 1.17 mmol), cataCXium A Pd G3 (68.1 mg, 0.0900 mmol) and $K_3PO_4$ (1 mL, 1.5 M in $H_2O$) in THF (5 mL) was stirred at 60° C. for 2 h. The resulting solution was partitioned between water and EtOAc. The organic layer was dried over anhydrous sodium sulfate and concentrated under vacuum. The residue was purified by flash chromatography on silica gel (gradient: 0%-50% EtOAc/petroleum ether) to afford 568 mg of the title compound as a yellow solid. LC-MS: (ESI, m/z): [M+H]$^+$=866.

Step 2: tert-Butyl (5R,5aS,6S,9R)-2-(2-(bis(4-methoxybenzyl)amino)-3-fluoro-6-methylpyridin-4-yl)-1-fluoro-12-(methylsulfonyl)-5-(trifluoromethyl)-5a,6,7,8,9,10-hexahydro-5H-4-oxa-3,10a,11,13,14-pentaaza-6,9-methanonaphtho[1,8-ab]heptalene-14-carboxylate To a solution of tert-butyl (5R,5aS,6S,9R)-2-(2-(bis(4-methoxybenzyl)amino)-3-fluoro-6-methylpyridin-4-yl)-1-fluoro-12-(methylthio)-5-(trifluoromethyl)-5a,6,7,8,9,10-hexahydro-5H-4-oxa-3,10a,11,13,14-pentaaza-6,9-methanonaphtho[1,8-ab]heptalene-14-carboxylate (558 mg, 0.623 mmol) in ethyl acetate (10 mL) was added m-CPBA (335 mg, 1.94 mmol) at 0° C. The solution was stirred at room temperature for 1 h. The reaction was quenched with aqueous $Na_2S_2O_3$ and extracted with EtOAc. The combined organic layers were dried over anhydrous sodium sulfate and concentrated under vacuum. The residue was purified by flash chromatography on silica gel (gradient: 0%-40% EtOAc/petroleum ether) to afford 355 mg of the title compound as a yellow solid. LC-MS: (ESI, m/z): [M+H]$^+$=898.

Step 3: tert-Butyl (5R,5aS,6S,9R)-2-(2-(bis(4-methoxybenzyl)amino)-3-fluoro-6-methylpyridin-4-yl)-12-(((7a'S)-2,2-difluorodihydro-1'H,3'H-spiro[cyclopropane-1,2'-pyrrolizin]-7a'(5'H)-yl)methoxy)-1-fluoro-5-(trifluoromethyl)-5a,6,7,8,9,10-hexahydro-5H-4-oxa-3,10a,11,13,14-pentaaza-6,9-methanonaphtho[1,8-ab]heptalene-14-carboxylate To a solution of tert-butyl (5R,5aS,6S,9R)-2-(2-(bis(4-methoxybenzyl) amino)-3-fluoro-6-methylpyridin-4-yl)-1-fluoro-12-(methylsulfonyl)-5-(trifluoromethyl)-5a,6,7,8,9,10-hexahydro-5H-4-oxa-3,10a,11,13,14-pentaaza-6,9-methanonaphtho[1,8-ab]heptalene-14-carboxylate (343 mg, 0.382 mmol) and ((7a'S)-2,2-difluorodihydro-1'H,3'H-spiro[cyclopropane-1,2'-pyrrolizin]-7a'(5'H)-yl)methanol (93.1 mg, 0.460 mmol) in toluene (5 mL) was added t-BuONa (73.4 mg, 0.760 mmol) at 0° C. The mixture was stirred at 0° C. for 0.5 h. The resulting solution was partitioned between water and EtOAc. The organic layer was dried over anhydrous sodium sulfate and concentrated under vacuum. The residue was purified by C18 column (solvent gradient: 0-80% ACN in water (0.05% $NH_4HCO_3$)) to afford 163 mg of the title compound as a yellow solid. LC-MS: (ESI, m/z): [M+H]$^+$=1021.

Step 4: tert-Butyl (5R,5aS,6S,9R)-2-(2-(bis(4-methoxybenzyl)amino)-3-fluoro-5-iodo-6-methylpyridin-4-yl)-12-(((7a'S)-2,2-difluorodihydro-1'H,3'H-spiro[cyclopropane-1,2'-pyrrolizin]-7a'(5'H)-yl)methoxy)-1-fluoro-5-(trifluoromethyl)-5a,6,7,8,9,10-hexahydro-5H-4-oxa-3,10a,11,13,14-pentaaza-6,9-methanonaphtho[1,8-ab]heptalene-14-carboxylate To a solution of tert-butyl (5R,5aS,6S,9R)-2-(2-(bis(4-methoxybenzyl)amino)-3-fluoro-6-methylpyridin-4-yl)-12-(((7a'S)-2,2-difluorodihydro-1'H,3'H-spiro[cyclopropane-1,2'-pyrrolizin]-7a'(5'H)-yl)methoxy)-1-fluoro-5-(trifluoromethyl)-5a,6,7,8,9,10-hexahydro-5H-4-oxa-3,10a,11,13,14-pentaaza-6,9-methanonaphtho[1,8-ab]heptalene-14-carboxylate (139 mg, 0.136 mmol) in AcOH (1.5 mL) was added NIS (30.6 mg, 0.140 mmol). The reaction was stirred at room temperature for 20 min. The reaction was quenched with aqueous $Na_2S_2O_3$ and extracted with EtOAc. The combined organic layers were dried over anhydrous sodium sulfate and concentrated under vacuum. The residue was purified by flash chromatography on silica gel (gradient: 0%-10% MeOH/DCM) to afford 128 mg of the title compound as a yellow solid. LC-MS: (ESI, m/z): [M+H]$^+$=1147.

Step 5: tert-Butyl (5R,5aS,6S,9R)-2-(2-(bis(4-methoxybenzyl)amino)-3-fluoro-6-methyl-5-(trifluoromethyl)pyridin-4-yl)-12-(((7a'S)-2,2-difluorodihydro-1'H,3'H-spiro[cyclopropane-1,2'-pyrrolizin]-7a'(5'H)-yl)methoxy)-1-fluoro-5-(trifluoromethyl)-5a,6,7,8,9,10-hexahydro-5H-4-oxa-3,10a,11,13,14-pentaaza-6,9-methanonaphtho[1,8-ab]heptalene-14-carboxylate Under nitrogen, to a mixture of tert-butyl (5R,5aS,6S,9R)-2-(2-(bis(4-methoxybenzyl) amino)-3-fluoro-5-iodo-6-methylpyridin-4-yl)-12-(((7a'S)-2,2-difluorodihydro-1'H,3'H-spiro[cyclopropane-1,2'-pyrrolizin]-7a'(5'H)-yl)methoxy)-1-fluoro-5-(trifluoromethyl)-5a,6,7,8,9,10-hexahydro-5H-4-oxa-3,10a,11,13,14-pentaaza-6,9-methanonaphtho[1,8-ab]heptalene-14-carboxylate (115 mg, 0.100 mmol), $Cu(O_2CCF_2SO_2F)_2$ (419 mg, 1.00 mmol) and Cu (64.2 mg, 1.00 mmol) was added DMF (2.5 mL) at 0° C. The solution was stirred at room temperature for 1 h. The resulting reaction was diluted with EtOAc and washed with water. The organic layer was dried over anhydrous sodium sulfate and concentrated under vacuum. The residue was purified by C18 column (solvent gradient: 0-80% MeOH in water (0.05% $NH_4HCO_3$)) to afford 135 mg of the title compound as a yellow solid. LC-MS: (ESI, m/z): [M+H]$^+$=1088.

Step 6: 4-((5R,5aS,6S,9R)-12-(((7a'S)-2,2-Difluorodihydro-1'H,3'H-spiro[cyclopropane-1,2'-pyrrolizin]-7a'(5'H)-yl)methoxy)-1-fluoro-5-(trifluoromethyl)-5a,6,7,8,9,10-hexahydro-5H-4-oxa-3,10a,11,13,14-pentaaza[6,9]methanonaphtho[1,8-ab]heptalen-2-yl)-3-fluoro-6-methyl-5-(trifluoromethyl)pyridin-2-amine A solution of tert-butyl (5R,5aS,6S,9R)-2-(2-(bis(4-methoxybenzyl) amino)-3-fluoro-6-methyl-5-(trifluoromethyl)pyridin-4-yl)-12-(((7a'S)-2,2-difluorodihydro-1'H,3'H-spiro[cyclopropane-1,2'-pyrrolizin]-7a'(5'H)-yl)methoxy)-1-fluoro-5-(trifluoromethyl)-5a,6,7,8,9,10-hexahydro-5H-4-oxa-3,10a,11,13,14-pentaaza-6,9-methanonaphtho[1,8-ab]heptalene-14-carboxylate (116 mg, 0.107 mmol) in TFA (6 mL) was stirred at 50° C. for 3 h. Then the solution was concentrated under vacuum. The crude product was purified by Prep-HPLC (Column: XBridge Prep OBD C18 Column, 30*150 mm, 5 μm; Mobile Phase A: Water (10 mmol/L $NH_4HCO_3$), Mobile Phase B: ACN; Flow rate: 60 mL/min mL/min; Gradient: 31% B to 53% B in 10 min; Wave Length: 254 nm/220 nm nm; $R_{T1}$(min): 8) to afford 54.4 mg of the title compound as a white solid. LC-MS: (ESI, m/z): [M+H]$^+$=749. $^1$H NMR (400 MHz, DMSO-d$_6$, ppm): δ 7.24 (d, J=22.4 Hz, 2H), 5.78-5.63 (m, 1H), 5.25-5.11 (m, 1H), 4.50-4.33 (m, 1H), 4.29-4.15 (m, 2H), 3.65-3.57 (m, 1H), 3.56-3.49 (m, 1H), 3.20-3.07 (m, 2H), 3.06-2.98 (m, 1H), 2.96 (s, 1H), 2.72 (d, J=11.8 Hz, 1H), 2.58-2.52 (m, 1H), 2.49-2.44 (m, 2.6 Hz, 3H), 2.14-2.04 (m, 1H), 2.03-1.96 (m, 1H), 1.91 (d, J=13.3 Hz, 1H), 1.88-1.79 (m, 3H), 1.78-1.53 (m, 5H), 1.54-1.44 (m, 1H).

Example 258: Compound 258 (two isomers
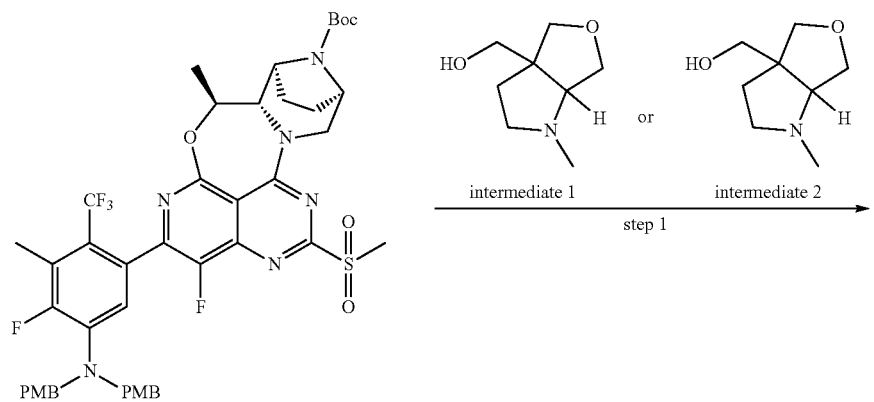
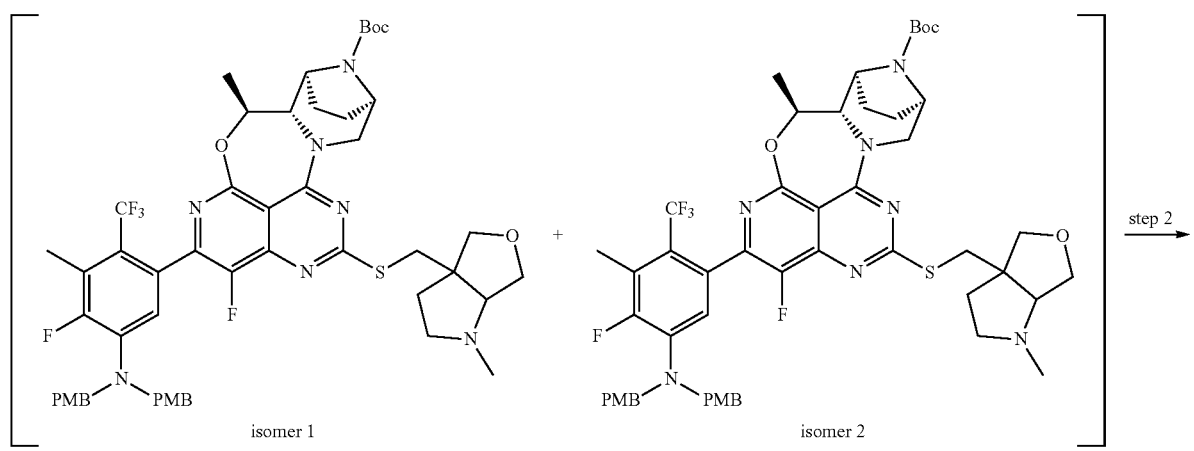
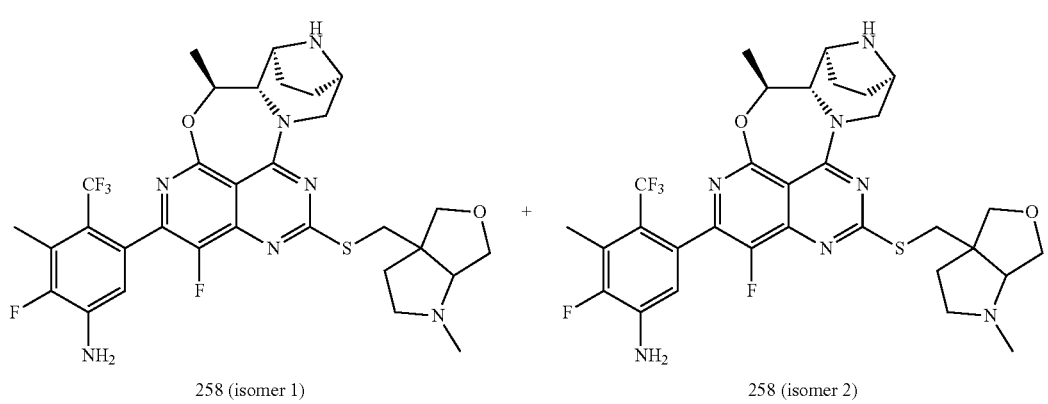
258 (isomer 1)   258 (isomer 2)

Step 1: tert-Butyl (5S,5aS,6S,9R)-2-(5-(bis(4-methoxybenzyl)amino)-4-fluoro-3-methyl-2-(trifluoromethyl)phenyl)-1-fluoro-5-methyl-12-((1-methyltetrahydro-1H-furo[3,4-b]pyrrol-3a(4H)-yl)methoxy)-5a,6,7,8,9,10-hexahydro-5H-4-oxa-3,10a,11,13,14-pentaaza-6,9-methanonaphtho[1,8-ab]heptalene-14-carboxylate (two isomers)

To a solution of tert-butyl (5S,5aS,6S,9R)-2-(5-(bis(4-methoxybenzyl)amino)-4-fluoro-3-methyl-2-(trifluoromethyl)phenyl)-1-fluoro-5-methyl-12-(methylsulfonyl)-5a,6,7,8,9,10-hexahydro-5H-4-oxa-3,10a,11,13,14-pentaaza-6,9-methanonaphtho[1,8-ab]heptalene-14-carboxylate (60.0 mg, 0.0659 mmol, procedure has been included in previous version) and (1-methyltetrahydro-1H-furo[3,4-b]pyrrol-3a(4H)-yl)methanol (90.0 mg, crude, intermediate 170) in toluene (2 mL) was added tBuONa (12.7 mg, 0.132 mmol) at 0° C., and the mixture was stirred for 1 hour at room temperature. The reaction mixture was diluted with water and extracted with ethyl acetate. The combined organic layer was dried over anhydrous sodium sulfate and concentrated under vacuum. The residue was purified by flash chromatography on silica gel (gradient: 0-10% methanol in dichloromethane) to afford the title compound (60.0 mg, 92.2% yield, isomer 1) as a light yellow solid. LC-MS: (ESI, m/z): $[M+H]^+$=989.

Analogous to the method described above, isomer 2 (35.0 mg, 53.8% yield) was prepared from tert-butyl (5S,5aS,6S,9R)-2-(5-(bis(4-methoxybenzyl)amino)-4-fluoro-3-methyl-2-(trifluoromethyl)phenyl)-1-fluoro-5-methyl-12-(methylsulfonyl)-5a,6,7,8,9,10-hexahydro-5H-4-oxa-3,10a,11,13,14-pentaaza-6,9-methanonaphtho[1,8-ab]heptalene-14-carboxylate (60.0 mg, 0.0659 mmol) and intermediate 171 (100 mg, crude) as a light yellow solid. LC-MS: (ESI, m/z): $[M+H]^+$=989.

Step 2: 2-Fluoro-5-((5S,5aS,6S,9R)-1-fluoro-5-methyl-12-((1-methyltetrahydro-1H-furo[3,4-b]pyrrol-3a(4H)-yl)methoxy)-5a,6,7,8,9,10-hexahydro-5H-4-oxa-3,10a,11,13,14-pentaaza-6,9-methanonaphtho[1,8-ab]heptalen-2-yl)-3-methyl-4-(trifluoromethyl)aniline (two isomers)

A solution of tert-butyl (5S,5aS,6S,9R)-2-(5-(bis(4-methoxybenzyl)amino)-4-fluoro-3-methyl-2-(trifluoromethyl)phenyl)-1-fluoro-5-methyl-12-((1-methyltetrahydro-1H-furo[3,4-b]pyrrol-3a(4H)-yl)methoxy)-5a,6,7,8,9,10-hexahydro-5H-4-oxa-3,10a,11,13,14-pentaaza-6,9-methanonaphtho[1,8-ab]heptalene-14-carboxylate (60.0 mg, 0.0607 mmol, isomer 1 of the last step) in 2,2,2-trifluoroacetic acid (10 mL) was stirred for 30 minutes at room temperature. The solvent was concentrated under vacuum. The residue was purified by prep. HPLC (Column: XBridge Prep OBD C18 Column, 30*150 mm, 5 μm; Mobile Phase A: Water (10 mmol/L $NH_4HCO_3$), Mobile Phase B: ACN; Flow rate: 60 mL/min; Gradient: 27% B to 50% B in 10 min; Wave Length: 254 nm/220 nm; RT1(min): 8.6) to afford 258 (isomer 1) (18.3 mg, 46.5% yield) as a white solid. LC-MS: (ESI, m/z): $[M+H]^+$=648. $^1$H NMR (300 MHz, DMSO-d6, ppm) δ 6.67-6.41 (m, 1H), 6.03 (s, 2H), 5.09 (d, J=12.6 Hz, 1H), 4.59-4.48 (m, 1H), 4.43-4.27 (m, 2H), 3.95 (d, J=8.6 Hz, 1H), 3.80-3.67 (m, 2H), 3.59-3.53 (m, 2H), 3.54-3.40 (m, 2H), 3.03 (d, J=12.9 Hz, 1H), 2.96-2.86 (m, 1H), 2.75-2.68 (m, 1H), 2.47-2.37 (m, 1H), 2.32 (s, 3H), 2.27 (s, 3H), 2.01-1.91 (m, 1H), 1.87-1.51 (m, 5H), 1.44 (d, J=6.3 Hz, 3H).

Analogous to method described as above, 258 (isomer 2) (10.1 mg, 44.0% yield) was prepared from (35.0 mg, 0.0354 mmol, isomer 2 of the last step) after purification by prep. HPLC (Column: XBridge Prep OBD C18 Column, 30*150 mm, 5 μm; Mobile Phase A: Water (10 mmol/L $NH_4HCO_3$), Mobile Phase B: ACN; Flow rate: 60 mL/min; Gradient: 27% B to 50% B in 10 min; Wave Length: 254 nm/220 nm; RT1(min): 8.1) as a white solid. LC-MS: (ESI, m/z): $[M+H]^+$=648. $^1$H NMR (300 MHz, DMSO-d6, ppm) δ 6.68-6.43 (m, 1H), 6.02 (s, 2H), 5.09 (d, J=12.7 Hz, 1H), 4.60-4.48 (m, 1H), 4.45-4.25 (m, 2H), 3.95 (d, J=8.7 Hz, 1H), 3.73 (d, J=9.1 Hz, 2H), 3.62-3.43 (m, 4H), 3.03 (d, J=12.8 Hz, 1H), 2.96-2.87 (m, 1H), 2.76-2.68 (m, 1H), 2.45-2.37 (m, 1H), 2.32 (s, 3H), 2.27 (s, 3H), 2.00-1.90 (m, 1H), 1.83-1.53 (m, 5H), 1.44 (d, J=6.3 Hz, 3H).

Example 259: Compound 259

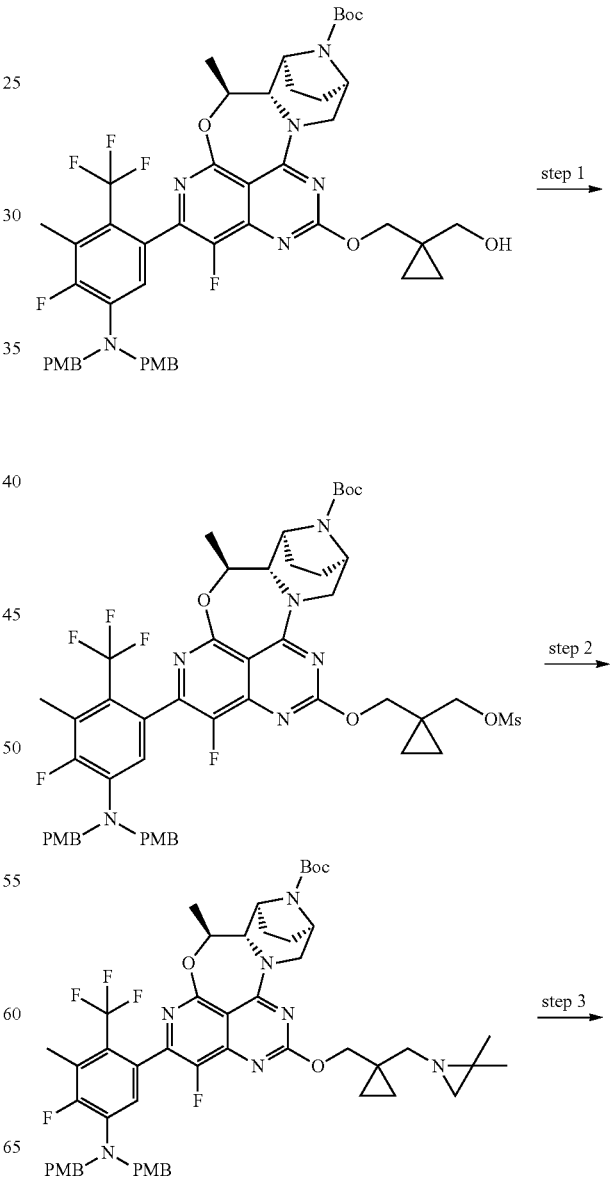

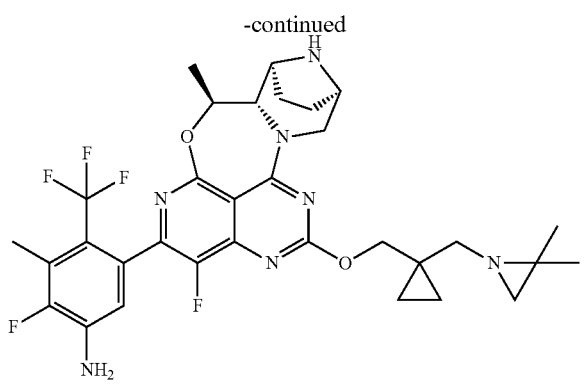

Step 1: tert-Butyl (5S,5aS,6S,9R)-2-(5-(bis(4-methoxybenzyl)amino)-4-fluoro-3-methyl-2-(trifluoromethyl)phenyl)-1-fluoro-5-methyl-12-((1-(((methylsulfonyl) oxy)methyl) cyclopropyl) methoxy)-5a, 6,7,8,9,10-hexahydro-5H-4-oxa-3,10a,11,13,14-pentaaza-6,9-methanonaphtho[1,8-ab]heptalene-14-carboxylate Under nitrogen, a solution of tert-butyl (4R,7S,8S,9S)-13-[5-[bis[(4-methoxyphenyl) methyl]amino]-4-fluoro-3-methyl-2-(trifluoromethyl) phenyl]-14-fluoro-17-[[1-(hydroxymethyl) cyclopropyl]methoxy]-9-methyl-10-oxa-2,12,16,18,20-pentazapentacyclo[9.7.1.14,7.02,8.015,19]icosa-1(18),11(19),12,14,16-pentaene-20-carboxylate (80.4 mg, 0.0900 mmol) in DCM (3 mL) was added DIPEA (55.3 mg, 0.430 mmol) at room temperature. Then Ms$_2$O (29.8 mg, 0.170 mmol) was added at 0° C. and stirred at room temperature for 1 hour. The solvent was concentrated under vacuum to afford 80.1 mg (crude) of the title compound as a yellow oil. LC-MS: (ESI, m/z): [M+H]$^+$=1011.

Step 2: tert-Butyl (5S,5aS,6S,9R)-2-(5-(bis(4-methoxybenzyl)amino)-4-fluoro-3-methyl-2-(trifluoromethyl)phenyl)-12-((1-((2,2-dimethylaziridin-1-yl) methyl)cyclopropyl)methoxy)-1-fluoro-5-methyl-5a, 6,7,8,9,10-hexahydro-5H-4-oxa-3,10a,11,13,14-pentaaza-6,9-methanonaphtho[1,8-ab]heptalene-14-carboxylate A solution of tert-butyl (4R,7S,8S,9S)-13-[5-[bis[(4-methoxyphenyl) methyl] amino]-4-fluoro-3-methyl-2-(trifluoromethyl) phenyl]-14-fluoro-9-methyl-17-[[1-(methylsulfonyloxymethyl) cyclopropyl]methoxy]-10-oxa-2,12,16,18,20-pentazapentacyclo [9.7.1.14,7.02,8.015,19] icosa-1(18),11(19),12,14,16-pentaene-20-carboxylate (80.1 mg, 0.0800 mmol), 2,2-dimethylaziridine (123 mg, 1.74 mmol) and K$_2$CO$_3$ (32.7 mg, 0.240 mmol) in DMF (3 mL) was stirred for 12 h at 70° C. The resulting solution was partitioned between water and EtOAc. The organic layers were dried over anhydrous sodium sulfate and concentrated under vacuum. The residue was purified by flash chromatography on silica gel eluting (gradient: 0%-15% MeOH/DCM) to afford 44.7 mg (57.2% yield) of the title compound as a yellow solid. LC-MS: (ESI, m/z): [M+H]$^+$=986.

Step 3: 5-((5S,5aS,6S,9R)-12-((1-((2,2-Dimethylaziridin-1-yl)methyl)cyclopropyl)methoxy)-1-fluoro-5-methyl-5a,6,7,8,9,10-hexahydro-5H-4-oxa-3,10a, 11,13,14-pentaaza-6,9-methanonaphtho[1,8-ab] heptalen-2-yl)-2-fluoro-3-methyl-4-(trifluoromethyl) aniline A solution of tert-butyl (4R,7S,8S,9S)-13-[5-[bis[(4-methoxyphenyl) methyl] amino]-4-fluoro-3-methyl-2-(trifluoromethyl)phenyl]-17-[[1-[(2,2-dimethylaziridin-1-yl) methyl]cyclopropyl]methoxy]-14-fluoro-9-methyl-10-oxa-2,12,16,18,20-pentazapentacyclo[9.7.1.14,7.02,8.015,19] icosa-1(18),11(19),12,14,16-pentaene-20-carboxylate (41.3 mg, 0.0400 mmol) in TFA (1.5 mL) was stirred at room temperature for 0.5 h. The solvent was concentrated under vacuum. The crude product was purified by prep. HPLC with the following conditions: (Column: XSelect CSH Fluoro Phenyl 30×150 mm, 5 μm; Mobile Phase A: Water (10 mmol/L NH$_4$HCO$_3$), Mobile Phase B: ACN; Flow rate: 60 mL/min mL/min; Gradient: 14% B to 38% B in 10 min; Wave Length: 254 nm/220 nm nm; R$_{T1}$(min): 9.3) to afford 1.4 mg (5.17% yield) of the title compound as a white solid. LC-MS: (ESI, m/z): [M+H]$^+$=646. $^1$H NMR (300 MHz, DMSO-d$_6$, ppm) δ 6.73-6.36 (m, 1H), 6.02 (s, 2H), 5.10 (d, J=12.7 Hz, 1H), 4.62-4.47 (m, 1H), 4.45-4.32 (m, 1H), 4.31-4.15 (m, 1H), 3.95 (d, J=8.7 Hz, 1H), 3.55 (s, 1H), 3.52 (s, 1H), 3.48-3.41 (m, 1H), 3.02 (d, J=12.9 Hz, 1H), 2.82-2.64 (m, 1H), 2.32 (s, 3H), 2.22-2.06 (m, 1H), 1.82 (s, 1H), 1.75-1.51 (m, 4H), 1.44 (d, J=6.3 Hz, 3H), 1.14 (s, 3H), 1.08 (s, 1H), 1.04 (s, 3H), 0.65-0.40 (m, 4H).

Example 260: Compound 260

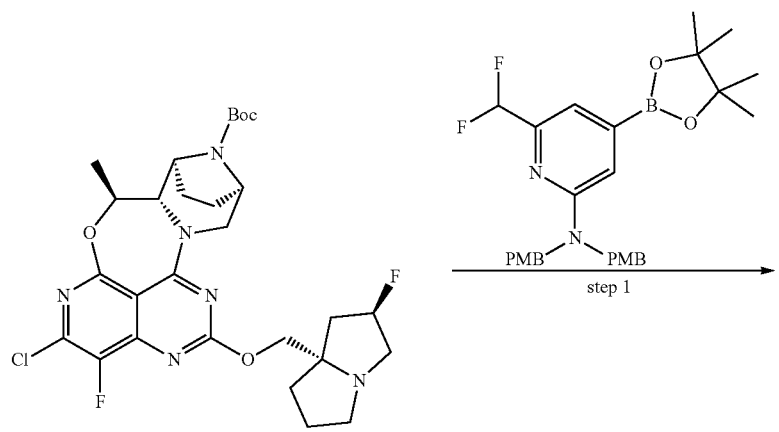

step 1

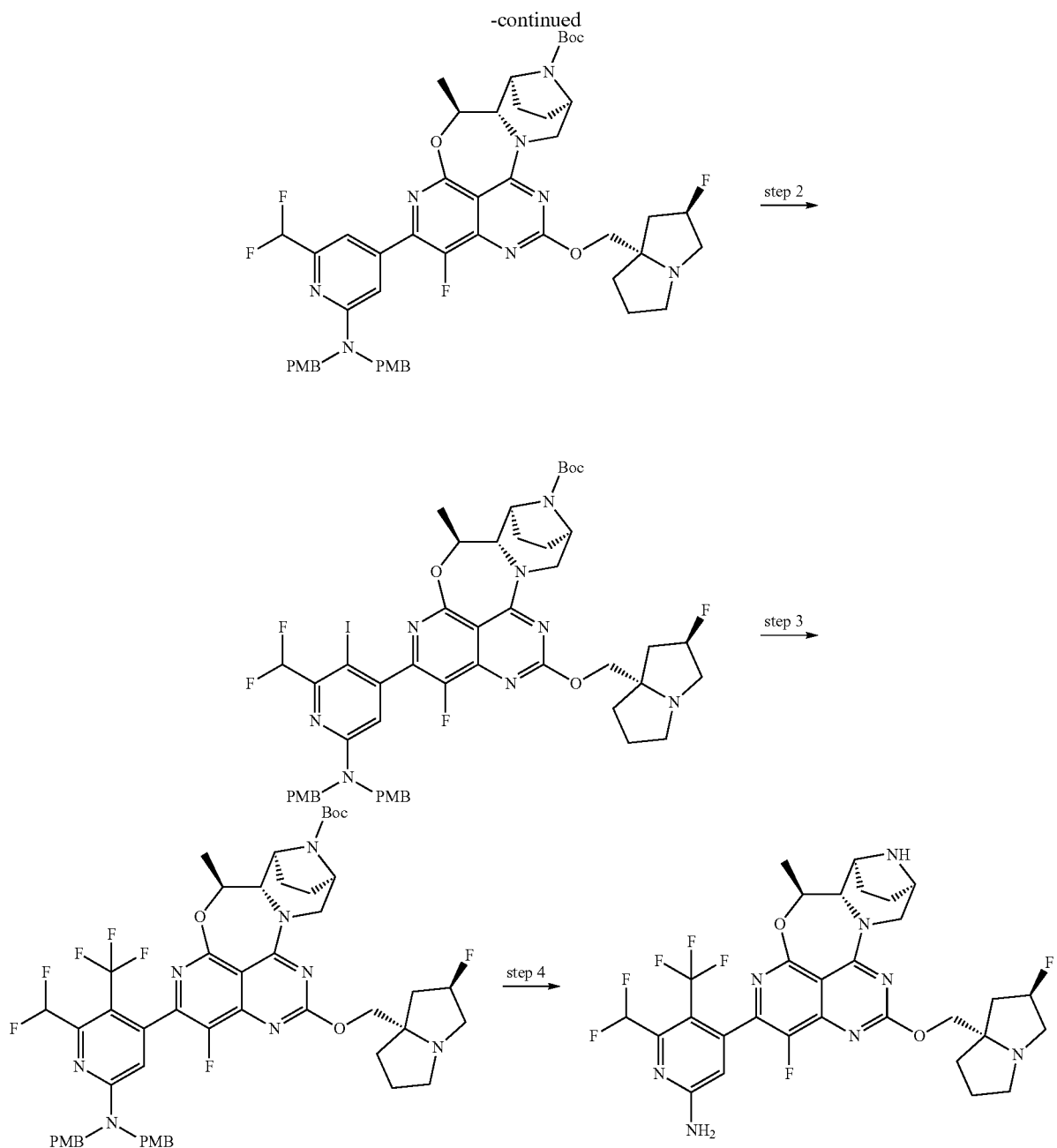

Step 1: tert-Butyl (5S,5aS,6S,9R)-2-(2-(bis(4-methoxybenzyl)amino)-6-(difluoromethyl)pyridin-4-yl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate Under nitrogen, a solution of tert-butyl (5S,5aS,6S,9R)-2-chloro-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (390 mg, 0.724 mmol), 6-(difluoromethyl)-N,N-bis(4-methoxybenzyl)-4-(4,4,5,5-tetramethyl-1,3,2-dioxaborolan-2-yl)pyridin-2-amine (370 mg, 0.724 mmol, intermediate 7), $K_3PO_4$ (1.5 M solution in $H_2O$, 2.4 mL, 3.60 mmol) and cataCXium A Pd G3 (105 mg, 0.145 mmol) in tetrahydrofuran (12 mL) was stirred for 2 hours at 60° C. The reaction mixture was diluted with water and extracted with ethyl acetate. The combined organic layers were dried over anhydrous sodium sulfate and concentrated under vacuum. The residue was purified by flash chromatography on silica gel (gradient: 0-10% methanol in dichloromethane) to afford the title compound (400 mg, 58.7% yield) as a brown solid. LC-MS: (ESI, m/z): $[M+H]^+$=941. $^1H$ NMR (300 MHz, DMSO-d6, ppm) δ 7.38 (s, 1H), 7.31-7.13 (m, 5H), 7.10-6.66 (m, 5H), 5.44-5.03 (m, 2H), 4.77 (s, 4H), 4.67-4.52 (m, 1H), 4.28 (d, J=9.8 Hz, 1H), 4.19-3.91 (m, 4H), 3.72 (s, 6H), 3.17-2.93 (m, 4H), 2.90-2.75 (m, 1H), 2.27-1.60 (m, 10H), 1.57-1.37 (m, 12H).

Step 2: tert-Butyl (5S,5aS,6S,9R)-2-(6-(bis(4-methoxybenzyl)amino)-2-(difluoromethyl)-3-iodopyridin-4-yl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate A solution of tert-butyl (5S,5aS,6S,9R)-2-(2-(bis(4-methoxybenzyl)amino)-6-(difluoromethyl)pyridin-4-yl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (100 mg, 0.106 mmol) and NIS (47.7 mg, 0.212 mmol) in acetic acid (2 mL) was stirred for 1 hour at room temperature. The reaction was quenched with saturated Na$_2$S$_2$O$_3$ aqueous solution. The reaction system was diluted with water and extracted with ethyl acetate. The combined organic layers were washed with brine, dried over anhydrous sodium sulfate and concentrated under vacuum. The residue was purified by flash chromatography on silica gel (gradient: 0-5% methanol in dichloromethane) to afford the title compound (80.0 mg, 70.6% yield) as a light brown solid. LC-MS: (ESI, m/z): [M+H]$^+$=1067. $^1$H NMR (300 MHz, DMSO-d6, ppm) δ 7.20 (d, J=8.3 Hz, 4H), 7.12-6.71 (m, 6H), 5.43-5.05 (m, 2H), 4.86-4.65 (m, 4H), 4.65-4.48 (m, 1H), 4.36-4.27 (m, 1H), 4.22-3.90 (m, 4H), 3.72 (s, 6H), 3.20-2.97 (m, 4H), 2.90-2.77 (m, 1H), 2.20-2.11 (m, 1H), 2.07-1.96 (m, 2H), 1.96-1.65 (m, 7H), 1.55-1.37 (m, 12H).

Step 3: tert-Butyl (5S,5aS,6S,9R)-2-(6-(bis(4-methoxybenzyl)amino)-2-(difluoromethyl)-3-(trifluoromethyl)pyridin-4-yl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate Under nitrogen, to a solid mixture of Cu(O$_2$CCF$_2$SO$_2$F)$_2$ (313 mg, 0.750 mmol) and Cu power (47.7 mg, 0.750 mmol) was added an ice-cold solution of tert-butyl (5S,5aS,6S,9R)-2-(6-(bis(4-methoxybenzyl)amino)-2-(difluoromethyl)-3-iodopyridin-4-yl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (80.0 mg, 0.0750 mmol) in N,N-dimethylacetamide (5 mL) at 0° C. and stirred for 1 hour at room temperature. The reaction mixture was diluted with water and extracted with ethyl acetate. The combined organic layer was dried over anhydrous sodium sulfate and concentrated under vacuum. The residue was purified by flash chromatography on silica gel (gradient: 0-10% methanol in dichloromethane) to afford the title compound (50.0 mg, 66.1% yield) as a yellow solid. LC-MS: (ESI, m/z): [M+H]$^+$=1009

Step 4: 6-(Difluoromethyl)-4-((5S,5aS,6S,9R)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalen-2-yl)-5-(trifluoromethyl)pyridin-2-amine A solution of tert-butyl (5S,5aS,6S,9R)-2-(6-(bis(4-methoxybenzyl)amino)-2-(difluoromethyl)-3-(trifluoromethyl)pyridin-4-yl)-1-fluoro-12-(((2R,7aS)-2-fluorotetrahydro-1H-pyrrolizin-7a(5H)-yl)methoxy)-5-methyl-5a,6,7,8,9,10-hexahydro-5H-4-oxa-3,10a,11,13,14-pentaaza-6,9-methanonaphtho[1,8-ab]heptalene-14-carboxylate (50.0 mg, 0.0496 mmol) in 2,2,2-trifluoroacetic acid (10 mL) was stirred for 1 hour at 50° C. The solvent was concentrated under vacuum. The residue was purified by prep. HPLC (Column: XBridge Prep OBD C18 Column, 30*150 mm, 5 µm; Mobile Phase A: Water (10 mmol/L NH$_4$HCO$_3$); Mobile Phase B: ACN; Flow rate: 60 mL/min; Gradient: 27% B to 50% B in 10 min; Wave Length: 254 nm; RT1(min): 8.6) to afford the title compound (8.20 mg, 24.7% yield) as a white solid. LC-MS: (ESI, m/z): [M+H]$^+$=669. $^1$H NMR (300 MHz, DMSO-d6, ppm) δ 7.36 (s, 2H), 6.98 (t, J=53.4 Hz, 1H), 6.58 (s, 1H), 5.29 (d, J=54.4 Hz, 1H), 5.08 (d, J=12.7 Hz, 1H), 4.63-4.45 (m, 1H), 4.17-3.99 (m, 2H), 3.99-3.90 (m, 1H), 3.63-3.53 (m, 1H), 3.45 (d, J=5.7 Hz, 1H), 3.17-3.08 (m, 2H), 3.07-2.96 (m, 2H), 2.93-2.76 (m, 1H), 2.20-2.11 (m, 1H), 2.08-1.94 (m, 2H), 1.91-1.73 (m, 4H), 1.73-1.52 (m, 4H), 1.44 (d, J=6.3 Hz, 3H).

Example 261: Compound 261

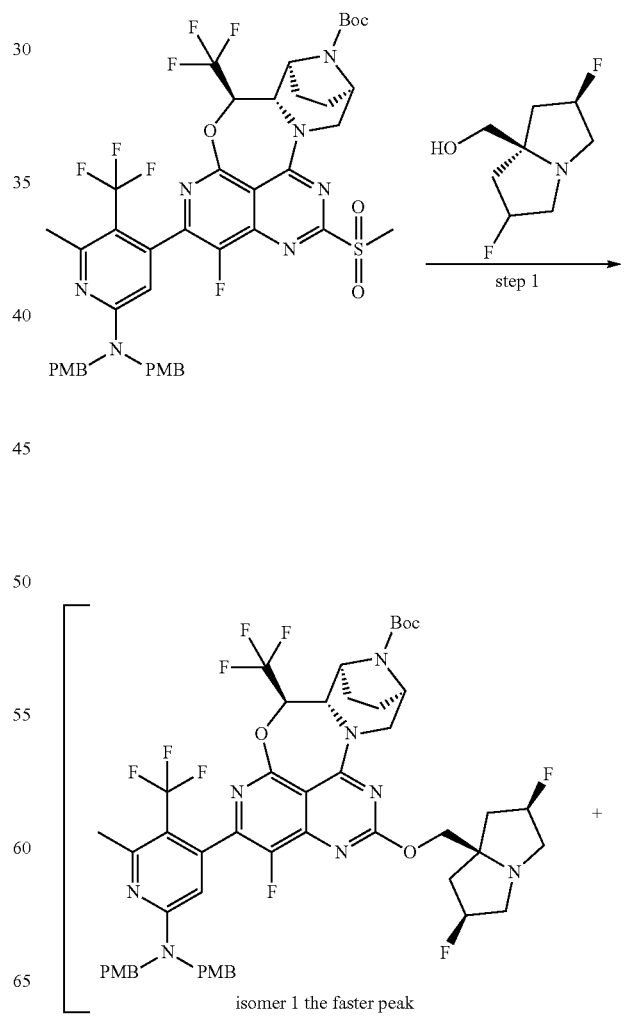

isomer 1 the faster peak

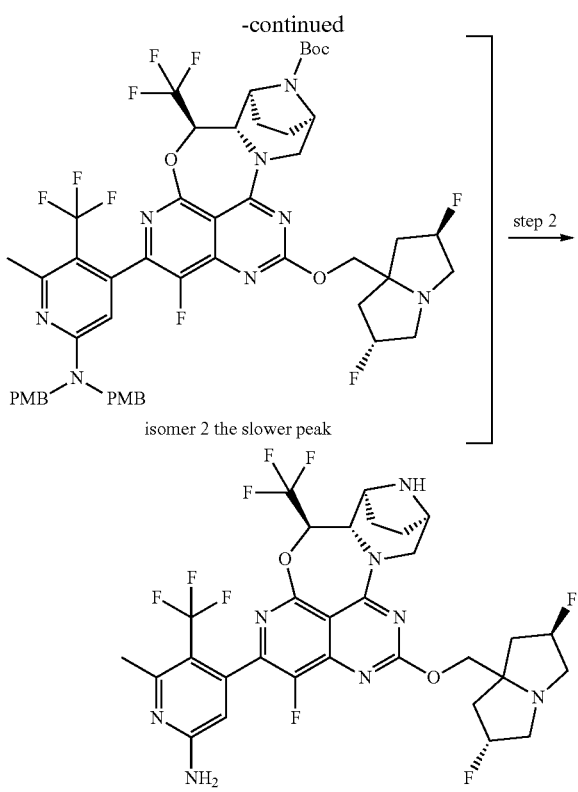

isomer 2 the slower peak

Step 1: tert-Butyl (5R,5aS,6S,9R)-2-(6-(bis(4-methoxybenzyl)amino)-2-methyl-3-(trifluoromethyl)pyridin-4-yl)-12-(((2R,6S,7ar)-2,6-difluorotetrahydro-1H-pyrrolizin-7a(5H)-yl)methoxy)-1-fluoro-5-(trifluoromethyl)-5a,6,7,8,9,10-hexahydro-5H-4-oxa-3,10a,11,13,14-pentaaza-6,9-methanonaphtho[1,8-ab]heptalene-14-carboxylate & tert-butyl (5R,5aS,6S,9R)-2-(6-(bis(4-methoxybenzyl)amino)-2-methyl-3-(trifluoromethyl)pyridin-4-yl)-12-(((2R,6R)-2,6-difluorotetrahydro-1H-pyrrolizin-7a(5H)-yl)methoxy)-1-fluoro-5-(trifluoromethyl)-5a,6,7,8,9,10-hexahydro-5H-4-oxa-3,10a,11,13,14-pentaaza-6,9-methanonaphtho[1,8-ab]heptalene-14-carboxylate To a solution of ((2R,7aR)-2,6-difluorotetrahydro-1H-pyrrolizin-7a(5H)-yl)methanol (120 mg, 0.677 mmol, the procedure has been included in previous version) in tetrahydrofuran (4 mL) was added NaH (60% dispersion in mineral oil, 52.8 mg, 1.32 mmol) at 0° C., and the mixture was stirred for 30 minutes at room temperature. Then tert-butyl (5R,5aS,6S,9R)-2-(6-(bis(4-methoxybenzyl)amino)-2-methyl-3-(trifluoromethyl)pyridin-4-yl)-1-fluoro-12-(methylsulfonyl)-5-(trifluoromethyl)-5a,6,7,8,9,10-hexahydro-5H-4-oxa-3,10a,11,13,14-pentaaza-6,9-methanonaphtho[1,8-ab]heptalene-14-carboxylate (250 mg, 0.264 mmol) was added, and the mixture was stirred for 1 hour at room temperature. The reaction was quenched with saturated NH$_4$Cl aqueous solution. The reaction mixture was diluted with water and extracted with ethyl acetate. The combined organic layers were washed with brine, dried over anhydrous sodium sulfate and concentrated under vacuum. The residue was purified by flash chromatography on silica gel (gradient: 0-50% ethyl acetate in petroleum ether) to afford a mixture of diastereomers (90.0 mg, 32.6% yield) as a yellow solid. Two diastereomers were separated by chiral prep. HPLC with the following conditions: (Column: CHIRALPAK ID, 2*25 cm, 5 μm; Mobile Phase A: Hex (0.1% TFA)-HPLC, Mobile Phase B: EtOH—HPLC; Flow rate: 20 mL/min; Gradient: isocratic 20; Wave Length: 220/254 nm; RT1(min): 8.461; RT2(min): 10.449; Sample Solvent: EtOH—HPLC; Injection Volume: 1.0 mL; Number Of Runs: 6) to afford isomer 1 (9.00 mg, 3.26% yield, the faster peak) and isomer 2 (50.0 mg, 18.1% yield, the slower peak) as white solids. LC-MS: (ESI, m/z): [M+H]$^+$=1045.

Step 2: 4-((5R,5aS,6S,9R)-12-(((2R,6R)-2,6-Difluorotetrahydro-1H-pyrrolizin-7a(5H)-yl)methoxy)-1-fluoro-5-(trifluoromethyl)-5a,6,7,8,9,10-hexahydro-5H-4-oxa-3,10a,11,13,14-pentaaza-6,9-methanonaphtho[1,8-ab]heptalen-2-yl)-6-methyl-5-(trifluoromethyl)pyridin-2-amine A solution of tert-butyl (5R,5aS,6S,9R)-2-(6-(bis(4-methoxybenzyl)amino)-2-methyl-3-(trifluoromethyl)pyridin-4-yl)-12-(((2R,6R)-2,6-difluorotetrahydro-1H-pyrrolizin-7a(5H)-yl)methoxy)-1-fluoro-5-(trifluoromethyl)-5a,6,7,8,9,10-hexahydro-5H-4-oxa-3,10a,11,13,14-pentaaza-6,9-methanonaphtho[1,8-ab]heptalene-14-carboxylate (50.0 mg, 0.0478 mmol, isomer 2 of last step) in 2,2,2-trifluoroacetic acid (10 mL) was stirred for 3 hours at 50° C. The solvent was concentrated under vacuum. The residue was purified by prep. HPLC (Column: XBridge Prep OBD C18 Column, 30*150 mm, 5 μm; Mobile Phase A: Water (10 mmol/L NH$_4$HCO$_3$), Mobile Phase B: ACN; Flow rate: 60 mL/min; Gradient: 28% B to 51% B in 9 min; Wave Length: 254 nm/220 nm; RT1(min): 8) to afford the title compound (12.3 mg, 36.5% yield) as a white solid. LC-MS: (ESI, m/z): [M+H]$^+$=705. $^1$H NMR (300 MHz, DMSO-d6, ppm) δ 6.87 (s, 2H), 6.23 (s, 1H), 5.73-5.56 (m, 1H), 5.51-5.41 (m, 1H), 5.33-5.23 (m, 1H), 5.23-5.11 (m, 1H), 4.40 (d, J=9.7 Hz, 1H), 4.30-4.12 (m, 2H), 3.64-3.49 (m, 2H), 3.49-3.34 (m, 1H), 3.26-2.93 (m, 5H), 2.48 (s, 3H), 2.44-2.29 (m, 1H), 2.29-2.13 (m, 2H), 2.11-2.00 (m, 1H), 1.91-1.76 (m, 2H), 1.74-1.49 (m, 2H).

Each compound in the Table below was prepared following a similar experimental procedure (using appropriately substituted reagents) as described for Example 261.

| Cmpd. No. | $^1$H NMR | MS (M + H)$^+$ |
|---|---|---|
| 262 (isomer 1) | $^1$H NMR (400 MHz, DMSO-d$_6$, ppm) δ 6.88 (s, 2H), 6.22 (s, 1H), 5.70-5.61 (m, 1H), 5.17-5.13 (m, 1H), 4.44-4.31 (m, 3H), 3.75 (q, J = 6.0 Hz, 1H), 3.57 (d, J = 5.9 Hz, 1H), 3.58-3.48 (m, 2H), 3.12 (d, J = 12.7 Hz, 1H), 3.05 (t, J = 7.2 Hz, 1H), 2.48 (d, J = 2.3 Hz, 3H), 2.42 (s, 3H), 1.84 (d, J = 8.7 Hz, 2H), 1.73-1.52 (m, 4H). | 691 |
| 262 (isomer 2) | $^1$H NMR (400 MHz, DMSO-d$_6$, ppm) δ 6.88 (s, 2H), 6.22 (s, 1H), 5.70-5.61 (m, 1H), 5.17-5.13 (m, 1H), 4.44-4.31 (m, 3H), 3.77-3.74 (m, 1H), 3.57 (d, J = 5.9 Hz, 1H), 3.58-3.48 (m, 2H), 3.12 (d, J = 12.7 Hz, 1H), 3.05 (t, J = 7.2 Hz, 1H), 2.48 (d, J = 2.3 Hz, 3H), 2.42 (s, 3H), 1.84 (d, J = 8.7 Hz, 2H), 1.73-1.52 (m, 4H). | 691 |

-continued

| Cmpd. No. | ¹H NMR | MS (M + H)⁺ |
|---|---|---|
| 262 (isomer 3) | ¹H NMR (300 MHz, DMSO-d₆, ppm) δ 6.86 (s, 2H), 6.21 (s, 1H), 5.67-5.62 (m, 1H), 5.17-5.12 (m, 1H), 4.45-4.35 (m, 3H), 3.67-3.52 (m, 3H), 3.44-3.40 (m, 1H), 3.18-3.08 (m, 2H), 2.46 (d, J = 2.3 Hz, 3H), 2.38 (s, 3H), 1.85 (d, J = 7.6 Hz, 2H), 1.81-1.49 (m, 4H). | 691 |
| 262 (isomer 4) | ¹H NMR (300 MHz, DMSO-d₆, ppm) δ 6.86 (s, 2H), 6.20 (s, 1H), 5.63 (t, J = 8.3 Hz, 1H), 5.16-5.12 (m, 1H), 4.47-4.29 (m, 3H), 3.65-3.47 (m, 3H), 3.44-3.40 (m, 1H), 3.18-3.05 (m, 2H), 2.46 (d, J = 2.3 Hz, 3H), 2.38 (s, 3H), 1.90-1.48 (m, 6H). | 691 |

Example 263: Compound 263 (Two Diastereomers

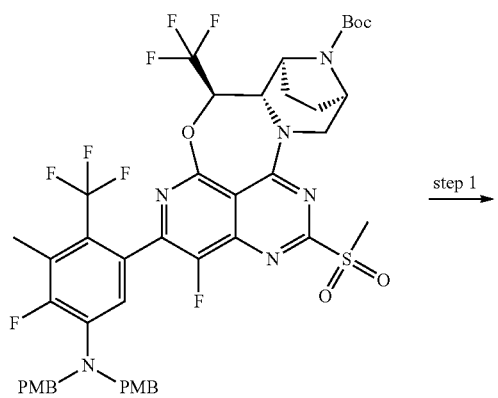

step 1

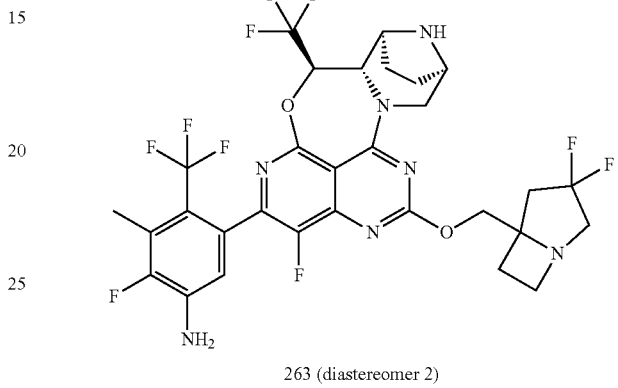

263 (diastereomer 2)

Step 1: tert-Butyl (5R,5aS,6S,9R)-2-(5-(bis(4-methoxybenzyl)amino)-4-fluoro-3-methyl-2-(trifluoromethyl)phenyl)-12-((3,3-difluoro-1-azabicyclo[3.2.0]heptan-5-yl)methoxy)-1-fluoro-5-(trifluoromethyl)-5a,6,7,8,9,10-hexahydro-5H-4-oxa-3,10a,11,13,14-pentaaza-6,9-methanonaphtho[1,8-ab]heptalene-14-carboxylate

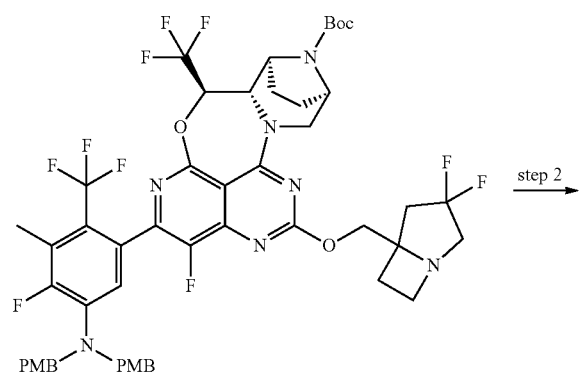

step 2

Under nitrogen, to a solution of tert-butyl (5R,5aS,6S,9R)-2-(5-(bis(4-methoxybenzyl)amino)-4-fluoro-3-methyl-2-(trifluoromethyl)phenyl)-1-fluoro-12-(methylsulfonyl)-5-(trifluoromethyl)-5a,6,7,8,9,10-hexahydro-5H-4-oxa-3,10a,11,13,14-pentaaza-6,9-methanonaphtho[1,8-ab]heptalene-14-carboxylate (300 mg, 0.310 mmol, the procedure has been included in previous version) and (3,3-difluoro-1-azabicyclo[3.2.0]heptan-5-yl)methanol (127 mg, 0.780 mmol, the procedure has been included in previous version) in toluene (5 mL) was added t-BuONa (74.7 mg, 0.780 mmol) at 0° C. The mixture was stirred at 0° C. for 1 h. Then solution was diluted with water and extracted with ethyl acetate. The combined organic layers were washed with brine, dried over anhydrous sodium sulfate and concentrated under vacuum. The residue was purified by C18 column (solvent gradient: 0-95% ACN in water (0.05% NH₄HCO₃)) to afford 198 mg (41.6% yield) of the title compound as a yellow solid. LC-MS: (ESI, m/z): [M+H]⁺=1048.

Step 2: 5-((5R,5aS,6S,9R)-12-((3,3-Difluoro-1-azabicyclo[3.2.0]heptan-5-yl)methoxy)-1-fluoro-5-(trifluoromethyl)-5a,6,7,8,9,10-hexahydro-5H-4-oxa-3,10a,11,13,14-pentaaza-6,9-methanonaphtho[1,8-ab]heptalen-2-yl)-2-fluoro-3-methyl-4-(trifluoromethyl)aniline

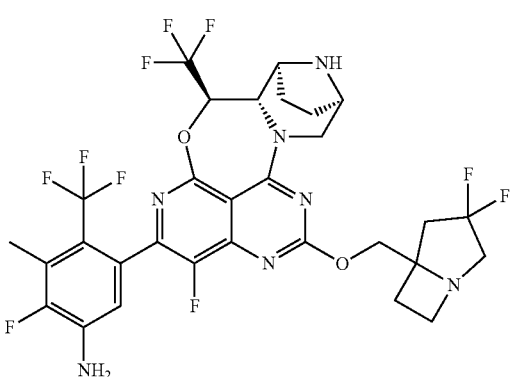

263 (diastereomer 1)

A solution of tert-butyl (5R,5aS,6S,9R)-2-(5-(bis(4-methoxybenzyl)amino)-4-fluoro-3-methyl-2-(trifluoromethyl)phenyl)-12-((3,3-difluoro-1-azabicyclo[3.2.0]heptan-5-yl)methoxy)-1-fluoro-5-(trifluoromethyl)-5a,6,7,8,9,10-hexahydro-5H-4-oxa-3,10a,11,13,14-pentaaza-6,9-methanonaphtho[1,8-ab]heptalene-14-carboxylate (364 mg, 0.230 mmol) in TFA (3 mL) was stirred at room temperature for 1 h. The solvent was concentrated under vacuum and the crude product was purified by prep. HPLC (Column: XSelect CSH Fluoro Phenyl 30*150 mm, 5 μm; Mobile Phase A: water (10 mmol/L NH$_4$HCO$_3$), Mobile Phase B: ACN; Flow rate: 60 mL/min mL/min; Gradient: 29% B to 54% B in 10 min; Wave Length: 254 nm/220 nm; R$_{T1}$(min): 8.6) to afford 83.2 mg of the mixture product as a white solid. The mixture product was purified by chiral prep. HPLC (Column: CHIRAL ART Cellulose-SB, 2*25 cm, 5 μm; Mobile Phase A: Hex:DCM=3:1 (0.5% 2 M NH$_3$—MeOH)-HPLC, Mobile Phase B: IPA-HPLC; Flow rate: 20 mL/min; Gradient: isocratic 5; Wave Length: 220/254 nm; R$_{T1}$(min): 13.123; R$_{T2}$(min): 18.513; Sample Solvent: EtOH—HPLC;) to afford 25.3 mg (15.6% yield) of 263 (diastereomer 1) and 26.4 mg (16.3% yield) of 263 (diastereomer 2) as white solids.

263 (diastereomer 1): LC-MS: (ESI, m/z): [M+H]$^+$=708. $^1$H NMR (400 MHz, DMSO-d$_6$, ppm): δ 6.54 (s, 1H), 6.08 (s, 2H), 5.65 (s, 1H), 5.28-5.09 (m, 1H), 4.51-4.24 (m, 3H), 3.67-3.42 (m, 3H), 3.29-3.18 (m, 1H), 3.14 (s, 2H), 3.12-2.95 (m, 2H), 2.77-2.58 (m, 1H), 2.46-2.37 (m, 2H), 2.37-2.25 (m, 4H), 1.95-1.76 (m, 2H), 1.75-1.51 (m, 2H).

263 (diastereomer 2): LC-MS: (ESI, m/z): [M+H]$^+$=708. $^1$H NMR (400 MHz, DMSO-d$_6$, ppm): δ 6.54 (s, 1H), 6.08 (s, 2H), 5.65 (s, 1H), 5.31-5.08 (m, 1H), 4.53-4.26 (m, 3H), 3.70-3.45 (m, 3H), 3.29-3.19 (m, 1H), 3.19-3.06 (m, 3H), 3.05-2.83 (m, 1H) 2.76-2.57 (m, 1H), 2.48-2.37 (m, 2H), 2.36-2.25 (m, 4H), 1.95-1.76 (m, 2H), 1.75-1.48 (m, 2H).

Examples 264-291: Compounds 264-291

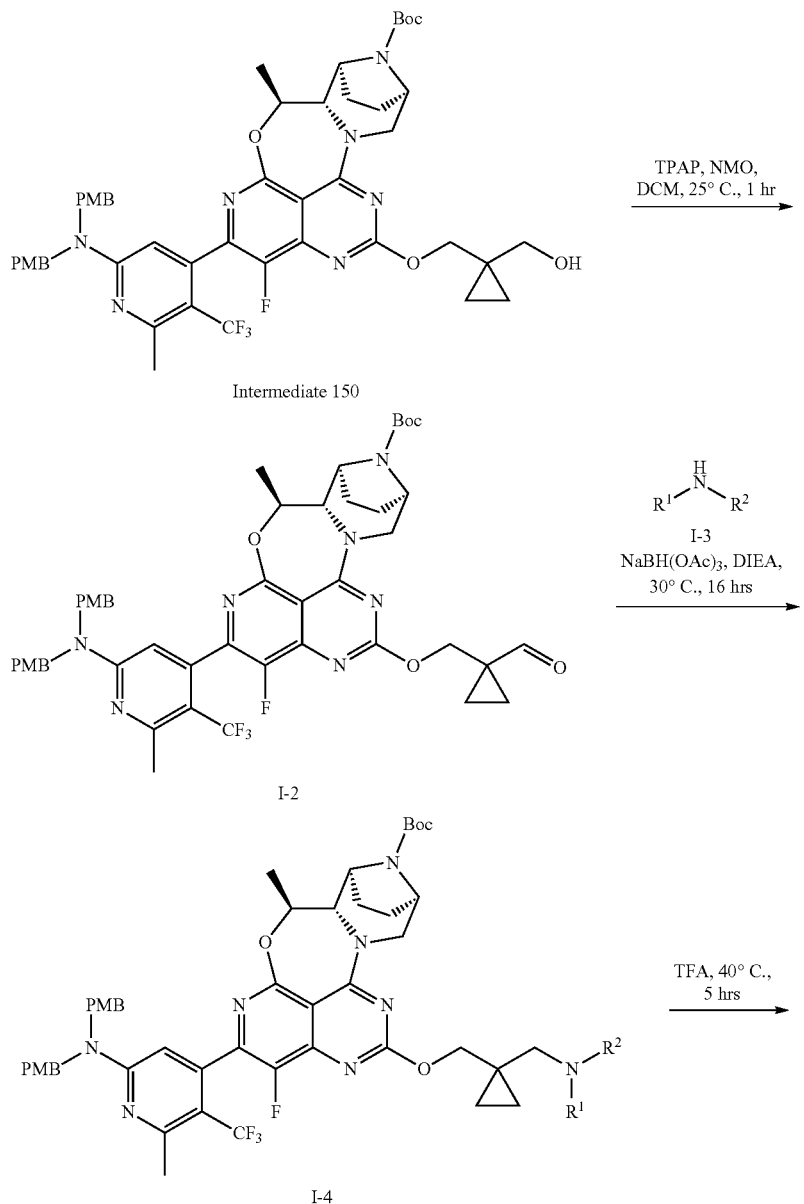

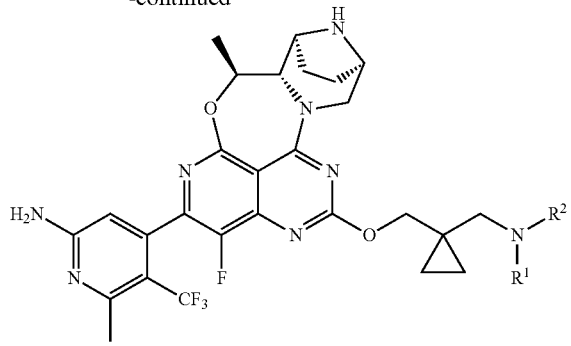

Examples 264-291

General Procedure

Step 1: To a vial containing a solution of Intermediate 150 (0.050 mmol, 1.0 eq) in DCM (0.50 mL) were added TPAP (0.030 mmol, 0.50 eq) and NMO (0.10 mmol, 2.0 eq) under nitrogen. The vial was capped and stirred at 25° C. for 1 hr. The solution was directly used for next step (Solution A).

Step 2: To Solution A were added amine I-3 (0.50 mmol, 10 eq), N,N-diisopropylethylamine (0.35 mmol, 7.0 eq) and NaBH(OAc)$_3$ (0.25 mmol, 5.0 eq). Then the reaction was stirred at 30° C. for 16 h. The solvent was concentrated under nitrogen gas flow. The residue was purified by prep-TLC (PE:EA=2:1, Rf=⅔) to give the protected reductive amination product I-4, which was directly used for next step.

Step 3: To a vial containing the residue of I-4 (0.030 mmol, 1.0 eq) was added TFA (0.15 mL). The reaction mixture was stirred at 40° C. for 5 hrs. The solution was concentrated under nitrogen flow gas. The residue was purified by prep-HPLC to give final product I-5 as the TFA salt (Examples 264-291).

| Cmpd. No. | $^1$H NMR | MS (M + H)$^+$ |
|---|---|---|
| 264 | N/A | 691 |
| 265 | N/A | 657 |
| 266 | N/A | 721 |
| 267 | N/A | 713 |
| 268 | N/A | 671 |
| 269 | N/A | 679 |
| 270 | N/A | 691 |
| 271 | N/A | 695 |
| 272 | N/A | 677 |
| 273 | $^1$H NMR (METHANOL-d4, 400 MHz) δ 6.5-6.6 (m, 1H), 5.5-5.6 (m, 1H), 4.7-4.8 (m, 1H), 4.3-4.5 (m, 7H), 4.2-4.3 (m, 1H), 4.0-4.1 (m, 2H), 3.7-3.8 (m, 1H), 3.4-3.5 (m, 2H), 3.38 (br s, 1H), 3.2-3.3 (m, 2H), 2.66 (s, 1H), 2.60 (d, 3H, J = 2.0 Hz), 2.3-2.4 (m, 1H), 2.0-2.2 (m, 3H), 1.4-1.7 (m, 7H), 1.3-1.4 (m, 3H), 0.90 (br s, 4H) | 659 |
| 274 | $^1$H NMR (METHANOL-d4, 400 MHz) δ 6.5-6.7 (m, 1H), 6.0-6.4 (m, 1H), 5.5-5.6 (m, 1H), 4.6-4.8 (m, 2H), 4.5-4.6 (m, 2H), 4.1-4.5 (m, 8H), 3.4-3.5 (m, 4H), 2.6-2.7 (m, 4H), 2.2-2.4 (m, 1H), 2.0-2.2 (m, 3H), 1.61 (d, 3H, J-6.4 Hz), 1.3-1.4 (m, 1H), 0.9-0.9 (m, 4H) | 665 |
| 275 | N/A | 691 |
| 276 | N/A | 679 |
| 277 | N/A | 677 |
| 278 | N/A | 657 |
| 279 | N/A | 691 |
| 280 | N/A | 671 |
| 281 | N/A | 671 |
| 282 | N/A | 685 |
| 283 | N/A | 647 |
| 284 | N/A | 647 |
| 285 | $^1$H NMR (DMSO-d6, 400 MHz) δ 10.0-10.3 (m, 1H), 9.3-9.5 (m, 2H), 6.9-6.9 (m, 1H), 6.1-6.3 (m, 1H), 5.2-5.4 (m, 1H), 4.7-4.8 (m, 1H), 4.49 (br dd, 1H, J = 6.3, 11.3 Hz), 4.1-4.3 (m, 7H), 3.3-3.4 (m, 6H), 2.47 (br d, 4H, J = 2.0 Hz), 1.8-2.2 (m, 6H), 1.4-1.5 (m, 3H), 0.6-0.9 (m, 4H) | 691 |
| 286 | N/A | 685 |
| 287 | N/A | 685 |
| 288 | N/A | 665 |
| 289 | N/A | 647 |
| 290 | N/A | 677 |
| 291 | $^1$H NMR (DMSO-d6, 400 MHz) δ 10.1-10.3 (m, 1H), 9.2-9.5 (m, 2H), 6.8-7.0 (m, 2H), 6.2-6.3 (m, 1H), 5.2-5.5 (m, 2H), 4.7-4.8 (m, 1H), 4.0-4.3 (m, 8H), 3.38 (br s, 5H), 2.46 (br d, 5H, J = 2.0 Hz), 1.8-2.1 (m, 5H), 1.5-1.5 (m, 3H), 1.0-1.1 (m, 1H), 0.7-1.0 (m, 4H) | 677 |

Example 500: KRAS G12D LoEnz Biochemical Assay, BODIPY-GDP Exchange TR-FRET. Biochemical compound potencies are assessed by evaluating inhibition of SOS1-mediated nucleotide exchange in KRAS G12D. In this assay, the SOS1-promoted exchange of fluorescently-labeled GDP (BOPIDY-GDP) is monitored by time-resolved fluorescence resonance energy transfer (TR-FRET). Compounds solubilized in DMSO are dispensed as concentration series into 384-well white assay plates. A preformed complex of biotin-tagged recombinant human KRAS (0.06 nM mutant G12D) and 0.06 nM terbium-labeled streptavidin (CisBIO) prepared in 10 uL/well assay buffer (20 mM HEPES, pH 7.5, 50 mM NaCl, 10 mM $MgCl_2$, 0.01% Tween-20 and 1 mM dithiothreitol) is added and allowed to incubate for 10-minutes at room temperature. The reaction is initiated with the addition of 5 uL 300 nM recombinant human SOS1 and 300 nM BODIPY-GDP in assay buffer. After a 120-minute incubation, the fluorescence is measured with excitation at 337 nm and emission at 490 and 520 nm. The TR-FRET ratio is determined as the fluorescence at 520 nm divided by the fluorescence at 490 nm multiplied by 10,000. The results are normalized to percent inhibition based on control samples: DMSO (0% inhibition) and control compound at a concentration that inhibits completely (100% inhibition). The normalized TR-FRET results are plotted against compound concentration, and the data are fit to a 4-parameter Hill equation to determine the $IC_{50}$ values.

Example 501: KRAS WI Biochemical Assay, BODIPY-GDP Exchange TR-FRET. Biochemical compound potencies are assessed by evaluating inhibition of SOS1-mediated nucleotide exchange in KRAS WT. In this assay, the SOS1-promoted exchange of fluorescently-labeled GDP (BOPIDY-GDP) is monitored by time-resolved fluorescence resonance energy transfer (TR-FRET). Compounds solubilized in DMSO are dispensed as concentration series into 384-well white assay plates, and 5 uL assay buffer (20 mM HEPES, pH 7.5, 50 mM NaCl, 10 mM $MgCl_2$, 0.01% Tween-20 and 1 mM dithiothreitol) is added just prior to the start of the assay. A preformed complex of 3 nM biotin-tagged recombinant human KRAS WT and 0.3 nM terbium-labeled streptavidin (CisBIO) prepared in 5 uL/well assay buffer is added and allowed to incubate for 10-minutes at room temperature. The reaction is initiated with the addition of 5 uL 3 nM recombinant human SOS1 and 300 nM BODIPY-GDP in assay buffer. After a 60-minute incubation, the fluorescence is measured with excitation at 337 nm and emission at 490 and 520 nm. The TR-FRET ratio is determined as the fluorescence at 520 nm divided by the fluorescence at 490 nm multiplied by 10,000. The results are normalized to percent inhibition based on control samples: DMSO (0% inhibition) and control compound at a concentration that inhibits completely (100% inhibition). The normalized TR-FRET results are plotted against compound concentration, and the data are fit to a 4-parameter Hill equation to determine the $IC_{50}$ values.

Example 502: KRAS WT Biochemical Assay, BODIPY-GDP Exchange TR-FRET. Biochemical compound potencies are assessed by evaluating inhibition of SOS1-mediated nucleotide exchange in KRAS WT. In this assay, the SOS1-promoted exchange of fluorescently-labeled GDP (BOPIDY-GDP) is monitored by time-resolved fluorescence resonance energy transfer (TR-FRET). Compounds solubilized in DMSO are dispensed as concentration series into 384-well white assay plates. A preformed complex of 0.06 nM biotin-tagged recombinant human KRAS WT, 15 nM GDP and 0.06 nM terbium-labeled streptavidin (CisBIO) prepared in 10 uL/well assay buffer (20 mM HEPES, pH 7.5, 50 mM NaCl, 10 mM $MgCl_2$, 0.01% Tween-20 and 1 mM dithiothreitol) is added and allowed to incubate for 10-minutes at room temperature. The reaction is initiated with the addition of 5 uL 300 nM recombinant human SOS1 and 300 nM BODIPY-GDP in assay buffer. After a 120-minute incubation, the fluorescence is measured with excitation at 337 nm and emission at 490 and 520 nm. The TR-FRET ratio is determined as the fluorescence at 520 nm divided by the fluorescence at 490 nm multiplied by 10,000. The results are normalized to percent inhibition based on control samples: DMSO (0% inhibition) and control compound at a concentration that inhibits completely (100% inhibition). The normalized TR-FRET results are plotted against compound concentration, and the data are fit to a 4-parameter Hill equation to determine the $IC_{50}$ values.

Example 503: KRAS 3D-Cell Proliferation Assays. Cellular potencies of compounds are assessed by evaluating inhibition of proliferation in 3D cultures of homozygous mutant KRAS G12D human pancreatic cell lines (AsPC-1 and HPAC) as compared to a KRAS wild type human lung adenocarcinoma cell line (PC-9 and/or H1975). Cells are seeded into 384-well black round-bottom, ultra-low attachment assay plates in 50 uL cell growth medium (RPMI-1640 with 10% fetal bovine serum and 2 mM L-glutamine). After overnight incubation at 37° C. and 5% $CO_2$, compounds solubilized in DMSO are added as dilution series to the wells in a total volume of 150 nL (0.3% DMSO final). The cells are incubated for 7 days at 37° C. and 5% $CO_2$. Cell proliferation is quantitated by addition of 40 uL/well of CellTiter-GloO 3D (Promega), and the well contents are mixed 20× at high speed using liquid handling automation workstation (Bravo with 384-well head) and centrifuged at 1500 rpm for 2 minutes to eliminate bubbles. This reagent in combination with mechanical disruption releases the cellular ATP to promote activity in a luciferase-based enzyme/substrate chemiluminescent detection system. After a 30-minute incubation under ambient conditions with shaking and an additional 10 minutes without shaking, the luminescence is read on a plate reader (e.g., EnVision [PerkinElmer]). The results are normalized to percent inhibition based on the following control samples: DMSO (0% inhibition) and 1 µM staurosporine (100% inhibition). The normalized luminescence results are plotted against compound concentration, and the data are fit to a 4-parameter Hill equation to determine the $IC_{50}$ values.

Table of Exemplary Compound Potencies.

| Cmpd. No. | KRas(wt) GDP HTRF IC50 | KRas (G12D) GDP HTRF IC50 | Prolif PC9 3D ATP IC50 | Prolif AsPC-1 3D ATP IC50 | KRas HTRF IC50 [uM] | Prolif HPAC 3D ATP IC50 [uM] | Prolif H1975 3D ATP IC50 [uM] |
|---|---|---|---|---|---|---|---|
| 1 | 0.008120 | 0.000120 | 16.900000 | 0.226000 | NT | NT | NT |
| 2 | 0.922000 | 0.015200 | 4.680000 | 0.565000 | NT | NT | NT |

-continued

Table of Exemplary Compound Potencies.

| Cmpd. No. | KRas(wt) GDP HTRF IC50 | KRas (G12D) GDP HTRF IC50 | Prolif PC9 3D ATP IC50 | Prolif AsPC-1 3D ATP IC50 | KRas HTRF IC50 [uM] | Prolif HPAC 3D ATP IC50 [uM] | Prolif H1975 3D ATP IC50 [uM] |
|---|---|---|---|---|---|---|---|
| 3 | 0.000517 | 0.000058 | 20.000000 | 0.006720 | 0.000757 | 0.0112000 | 0.2020 |
| 4 | 9.570000 | 0.899000 | 13.300000 | 9.750000 | NT | NT | NT |
| 5 | 0.002120 | 0.000060 | 9.050000 | 0.006280 | NT | 0.0070600 | 1.4000 |
| 6 | 0.000480 | 0.000074 | 4.210000 | 0.000561 | 0.000548 | 0.0002470 | 0.6920 |
| 7 | 0.000296 | 0.000059 | 10.200000 | 0.001920 | 0.000288 | 0.0013600 | 0.1300 |
| 8 | 0.146000 | 0.001780 | 3.920000 | 0.072000 | NT | 0.0873000 | 4.3100 |
| 9 | 0.006510 | 0.000057 | 7.790000 | 0.019300 | NT | 0.0116000 | 2.0200 |
| 10 | 0.006460 | 0.000082 | 6.670000 | 0.004930 | 0.013300 | 0.0059600 | 2.2700 |
| 11 | 0.000380 | 0.000060 | 20.000000 | 0.002300 | NT | 0.0024100 | 0.1690 |
| 12 | 37.400000 | 0.379000 | 13.900000 | 16.600000 | NT | NT | NT |
| 13 | 1.540000 | 0.030700 | 3.530000 | 1.870000 | 1.770000 | NT | NT |
| 14 | 0.006580 | 0.000260 | 6.210000 | 0.005620 | NT | 0.0113000 | 2.5100 |
| 15 | 0.000448 | 0.000070 | 2.900000 | 0.001570 | NT | NT | NT |
| 16 | 0.000668 | 0.000138 | 20.000000 | 0.001300 | 0.000484 | 0.0007000 | 0.2550 |
| 17 | 0.000559 | 0.000133 | 7.910000 | 0.001710 | 0.001050 | 0.0006200 | 1.3400 |
| 18 | 7.850000 | 0.175000 | 7.910000 | 5.590000 | NT | 5.2200000 | 20.0000 |
| 19 | 0.001830 | 0.000080 | 8.800000 | 0.005050 | NT | 0.0033100 | 0.2170 |
| 20 | 0.006550 | 0.000120 | 8.680000 | 0.028700 | NT | 0.0077800 | 2.2200 |
| 21 | 3.890000 | 0.069900 | 7.700000 | 1.090000 | NT | 0.6980000 | 12.2000 |
| 21 | 1.400000 | 0.020300 | 8.130000 | 0.330000 | NT | NT | NT |
| 22 | 0.145000 | 0.002990 | 7.410000 | 0.060300 | NT | 0.1390000 | 20.0000 |
| 23 | 39.500000 | 0.725000 | 9.400000 | 14.000000 | NT | NT | NT |
| 23 | 94.500000 | 2.500000 | 20.000000 | 20.000000 | NT | NT | NT |
| 24 | 0.003280 | 0.000290 | 7.870000 | 0.004290 | NT | 0.0018900 | 6.7100 |
| 25 | 0.126000 | 0.002040 | 11.000000 | 0.464000 | NT | 0.0788000 | 10.7000 |
| 26 | 0.006010 | 0.000260 | 7.640000 | 0.005190 | NT | 0.0032400 | 1.5400 |
| 27 | 0.065200 | 0.000720 | 2.780000 | 0.032100 | NT | 0.0681000 | 2.3900 |
| 28 | 0.751000 | 0.009380 | 11.000000 | 0.363000 | NT | 0.2570000 | 20.0000 |
| 29 | 0.002930 | 0.000086 | 8.190000 | 0.004980 | NT | 0.0077600 | 6.1100 |
| 30 | 0.598000 | 0.019400 | 3.810000 | 0.166000 | NT | 0.1540000 | 2.8900 |
| 31 | 0.001550 | 0.000087 | 3.790000 | 0.001640 | 0.007110 | 0.0008080 | 0.4230 |
| 32 | 0.000579 | 0.000200 | 0.821000 | 0.003380 | NT | NT | NT |
| 33 | 0.007530 | 0.000230 | 3.920000 | 0.003720 | NT | 0.0012900 | 1.8500 |
| 34 | 0.002130 | 0.000235 | 6.950000 | 0.000692 | 0.004290 | 0.0005400 | 0.3400 |
| 35 | 0.015800 | 0.000570 | 9.170000 | 0.010600 | NT | 0.0074000 | 5.8700 |
| 36 | 0.046500 | 0.000980 | 6.110000 | 0.052400 | NT | 0.0314000 | 1.1300 |
| 38 | 0.697000 | 0.013900 | 7.380000 | 0.270000 | NT | 0.0961000 | 2.8300 |
| 39 | 0.076100 | 0.001780 | 20.000000 | 0.055800 | NT | 0.0358000 | 3.9700 |
| 40 | 0.086800 | 0.001300 | 15.700000 | 0.027700 | NT | 0.0360000 | 20.0000 |
| 41 | 0.296000 | 0.006350 | 20.000000 | 0.980000 | NT | NT | NT |
| 42 | 0.045200 | 0.000470 | 7.040000 | 0.122000 | NT | NT | NT |
| 43 | 0.016600 | 0.000598 | 20.000000 | 0.043400 | NT | 0.0168000 | 4.2900 |
| 44 | 0.059000 | 0.000680 | 20.000000 | 0.337000 | NT | NT | NT |
| 45 | 0.069400 | 0.000730 | 20.000000 | 0.112000 | NT | NT | NT |
| 45 | 0.319000 | 0.003160 | 20.000000 | 0.345000 | NT | NT | NT |
| 47 | 0.004430 | 0.000443 | 8.840000 | 0.003970 | NT | 0.0029500 | 1.5300 |
| 48 | 0.010500 | 0.000491 | 20.000000 | 0.008240 | 0.028500 | 0.0055200 | 5.7600 |
| 49 | 0.561000 | 0.808000 | 2.370000 | 20.000000 | NT | NT | NT |
| 49 | 0.331000 | 3.460000 | 4.240000 | 20.000000 | NT | NT | NT |
| 50 | 0.001690 | 0.000240 | 4.910000 | 0.013000 | NT | 0.0258000 | 0.4550 |
| 51 | 0.005600 | 0.000300 | 19.500000 | 0.051200 | NT | 0.0730000 | 1.8200 |
| 52 | 194.00000 | 2.140000 | NT | NT | NT | NT | NT |
| 53 | 200.000 | 22.20000 | NT | NT | NT | NT | NT |
| 54 | 1.980000 | 0.017800 | 20.000000 | 2.090000 | NT | 3.4200000 | 20.0000 |
| 55 | 200.00000 | 22.20000 | 12.800000 | 20.000000 | NT | NT | NT |
| 56 | 46.500000 | 0.942000 | 20.000000 | 5.740000 | NT | NT | NT |
| 57 | NT | 0.000160 | 3.110000 | 0.000361 | 0.000633 | 0.0025900 | 0.2510 |
| 59 | NT | 0.000310 | NT | NT | 0.051400 | 0.1170000 | 10.5000 |
| 60 | NT | 0.000180 | 16.500000 | 0.003480 | 0.004550 | 0.0025900 | 0.7200 |
| 61 | NT | 0.000210 | NT | 0.044500 | 0.030500 | 0.0213000 | 2.6100 |
| 62 | NT | 0.000083 | NT | 0.000300 | 0.000290 | 0.0002610 | 0.1110 |
| 63 | NT | 0.000150 | NT | NT | 0.021700 | 0.0824000 | 20.8000 |
| 64 | NT | 0.000120 | NT | 0.000900 | 0.000738 | 0.0004600 | 0.2350 |
| 65 | NT | 0.001720 | 7.530000 | 0.064300 | 0.377000 | 0.0196000 | 7.9600 |
| 66 | NT | 0.002290 | 4.780000 | 0.041400 | 0.274000 | 0.0276000 | 7.1500 |
| 67 | NT | 0.000170 | NT | NT | 0.007530 | 0.0027900 | 0.6390 |
| 68 | NT | 0.000070 | NT | NT | 0.000112 | 0.0002050 | 0.1460 |
| 69 | NT | 0.000310 | NT | 0.021300 | 0.040900 | 0.0064200 | 1.2800 |
| 70 | NT | 0.000710 | NT | 0.044100 | 0.169000 | 0.0110000 | 1.7000 |
| 71 | NT | 0.003510 | 20.000000 | 0.132000 | 0.313000 | NT | NT |
| 72 | NT | 0.000280 | NT | NT | 0.012900 | 0.0031600 | 1.0600 |

-continued

Table of Exemplary Compound Potencies.

| Cmpd. No. | KRas(wt) GDP HTRF IC50 | KRas (G12D) GDP HTRF IC50 | Prolif PC9 3D ATP IC50 | Prolif AsPC-1 3D ATP IC50 | KRas HTRF IC50 [uM] | Prolif HPAC 3D ATP IC50 [uM] | Prolif H1975 3D ATP IC50 [uM] |
|---|---|---|---|---|---|---|---|
| 73 | NT | 0.002600 | NT | NT | 0.036300 | 0.0163000 | 4.0900 |
| 74 | NT | 0.000330 | NT | NT | 0.030800 | 0.0057000 | 2.0400 |
| 75 | NT | 0.000130 | NT | 0.005200 | 0.011800 | 0.0027700 | 0.7970 |
| 76 | NT | 0.000130 | 5.710000 | 0.014100 | 0.014300 | 0.0046200 | 0.2480 |
| 77 | NT | 0.000240 | NT | 0.011900 | 0.021100 | 0.0027900 | 0.3580 |
| 78 | NT | 0.867000 | 20.000000 | 15.900000 | 200.0000 | NT | NT |
| 79 | 0.954000 | 0.022700 | 20.000000 | 4.040000 | 1.530000 | NT | NT |
| 80 | 0.003390 | 0.000068 | 4.050000 | 0.005080 | 0.003480 | 0.0027600 | 0.9240 |
| 81 | NT | 0.000085 | 20.000000 | 0.014700 | 0.000448 | 0.0124000 | 4.7800 |
| 82 | NT | 0.360000 | NT | NT | 23.50000 | 20.000000 | 20.0000 |
| 83 | NT | 0.001150 | NT | NT | 0.123000 | 0.0237000 | 2.2300 |
| 84 | NT | 0.024900 | 20.000000 | 1.160000 | 4.310000 | NT | NT |
| 85 | NT | 0.003280 | 20.000000 | 0.975000 | 0.678000 | NT | NT |
| 86 | NT | 0.004670 | 8.750000 | 0.144000 | 0.248000 | 0.1260000 | 5.4300 |
| 87 | NT | 0.068900 | 20.000000 | 4.030000 | 16.10000 | 1.4000000 | 20.0000 |
| 88 | NT | 1.470000 | 20.000000 | 20.000000 | 1.620000 | NT | NT |
| 89 | NT | 0.912000 | NT | NT | 1.650000 | NT | NT |
| 90 | NT | 0.000470 | NT | 0.018900 | 0.071600 | 0.0073000 | 1.1400 |
| 91 | NT | 0.000182 | NT | 0.001300 | 0.005710 | 0.0012500 | 0.9530 |
| 92 | NT | 0.001010 | 8.130000 | 0.017300 | 0.148000 | 0.0126000 | 20.0000 |
| 92 | NT | 0.000760 | 11.200000 | 0.006040 | 0.034900 | 0.0031000 | 0.3830 |
| 93 | NT | 0.073400 | NT | NT | 14.40000 | 0.8360000 | 20.0000 |
| 94 | NT | 2.300000 | NT | NT | 200.0000 | 2.2300000 | 15.2000 |
| 95 | NT | 0.026600 | NT | 0.200000 | 3.570000 | 0.2470000 | 6.7000 |
| 96 | NT | 0.000433 | NT | 0.005800 | 0.075800 | 0.0036900 | 0.9820 |
| 97 | NT | 0.000370 | NT | 0.010100 | 0.043700 | 0.0032100 | 0.5730 |
| 98 | NT | 0.004250 | NT | NT | 0.553000 | 0.0262000 | 2.7500 |
| 99 | NT | 0.002090 | NT | NT | 0.506000 | 0.0400000 | 5.0600 |
| 100 | NT | 0.001490 | NT | NT | 0.495000 | 0.0218000 | 3.9700 |
| 101 | NT | 0.003190 | NT | NT | 0.906000 | 0.0415000 | 8.4900 |
| 103 | NT | 0.000860 | NT | NT | 0.224000 | 0.0092900 | 3.4600 |
| 104 | NT | 0.000050 | NT | 0.001400 | 0.000710 | 0.0006500 | 0.2210 |
| 105 | NT | 0.141000 | NT | NT | 9.700000 | 2.0000000 | 20.0000 |
| 106 | NT | 0.001890 | NT | NT | 0.210000 | 0.0314000 | 0.7700 |
| 106 | NT | 0.000180 | NT | 0.005400 | 0.031100 | 0.0041900 | 0.6220 |
| 107 | NT | 0.001390 | NT | NT | 0.167000 | 0.0435000 | 4.8700 |
| 108 | NT | 0.000325 | NT | NT | 0.037600 | 0.0028500 | 0.7720 |
| 110 | NT | 0.000150 | NT | NT | 0.007750 | 0.0025800 | 0.5870 |
| 111 | NT | 0.000310 | NT | NT | 0.108000 | 0.0141000 | 1.8400 |
| 112 | NT | 0.000480 | NT | 0.031600 | 0.062800 | 0.0075900 | 1.4700 |
| 113 | NT | 0.000310 | NT | NT | 0.065600 | 0.0029100 | 1.1700 |
| 114 | NT | 0.135000 | NT | NT | 36.70000 | 2.0000000 | 20.0000 |
| 115 | NT | 0.000390 | NT | NT | 0.034100 | 0.0157000 | 2.7100 |
| 116 | NT | 0.002410 | NT | NT | 0.213000 | 0.5130000 | 20.0000 |
| 117 | NT | 0.004840 | NT | NT | 0.638000 | 0.1480000 | 4.7400 |
| 118 | NT | 0.000090 | NT | 0.000600 | 0.001760 | 0.0004300 | 0.5190 |
| 119 (isomer 1) | NT | 0.004380 | NT | NT | 0.787000 | 0.0767000 | 3.1500 |
| 119 (isomer 2) | NT | 0.000370 | NT | NT | 0.075000 | 0.0079500 | 1.7000 |
| 120 | NT | 0.000240 | NT | NT | 0.044500 | 0.0106000 | 1.5300 |
| 121 (isomer 1) | NT | 0.000680 | NT | NT | 0.108000 | 0.0125000 | 1.3400 |
| 121 (isomer 2) | NT | 0.000270 | NT | 0.041000 | 0.049300 | 0.0175000 | 0.5330 |
| 122 | NT | 0.000110 | NT | NT | 0.003720 | 0.0018400 | 0.4870 |
| 123 | NT | 0.000700 | NT | NT | 0.181000 | 0.0630000 | 13.9000 |
| 124 | NT | 0.001740 | NT | NT | 0.619000 | 0.2930000 | 12.2000 |
| 125 | NT | 0.000230 | NT | 0.010200 | 0.014700 | 0.0021400 | 1.2200 |
| 126 (isomer 1) | NT | 0.000100 | NT | 0.000600 | 0.000420 | 0.0005100 | 0.7700 |
| 126 (isomer 2) | NT | 0.000090 | NT | NT | 0.008080 | 0.0051500 | 1.7700 |
| 126 (isomer 3) | NT | 0.000090 | NT | NT | 0.006310 | 0.0032800 | 1.4300 |
| 126 (isomer 4) | NT | 0.000370 | NT | NT | 0.090300 | 0.0249000 | 2.2500 |
| 127 (isomer 1) | NT | 0.000140 | NT | NT | 0.017900 | 0.0501000 | 6.0800 |
| 127 (isomer 2) | NT | 0.000190 | NT | NT | 0.037700 | 0.0575000 | 7.9700 |
| 128 | NT | 0.000480 | NT | NT | 0.156000 | 0.0515000 | 5.0600 |
| 129 | NT | 0.000180 | NT | 0.001000 | 0.003870 | 0.0011000 | 1.1500 |
| 130 (isomer 1) | NT | 0.002260 | NT | NT | 0.460000 | 0.0447000 | 2.8300 |
| 130 (isomer 2) | NT | 0.000920 | NT | NT | 0.174000 | 0.0158000 | 2.9000 |
| 131 (isomer 1) | NT | 0.013900 | NT | NT | 2.530000 | 1.4300000 | 20.0000 |
| 131 (isomer 2) | NT | 0.001310 | NT | NT | 0.293000 | 0.3420000 | 20.0000 |
| 131 (isomer 3) | NT | 0.002070 | NT | NT | 0.249000 | 0.0774000 | 8.8500 |
| 131 (isomer 4) | NT | 0.001140 | NT | NT | 0.195000 | 0.0900000 | 6.8100 |
| 132 | NT | 0.001470 | NT | NT | 0.291000 | 0.0704000 | 14.2000 |
| 133 (isomer 1) | NT | 0.000120 | NT | NT | 0.013600 | 0.0267000 | 2.6300 |

-continued

Table of Exemplary Compound Potencies.

| Cmpd. No. | KRas(wt) GDP HTRF IC50 | KRas (G12D) GDP HTRF IC50 | Prolif PC9 3D ATP IC50 | Prolif AsPC-1 3D ATP IC50 | KRas HTRF IC50 [uM] | Prolif HPAC 3D ATP IC50 [uM] | Prolif H1975 3D ATP IC50 [uM] |
|---|---|---|---|---|---|---|---|
| 133 (isomer 2) | NT | 0.000150 | NT | NT | 0.014400 | 0.0224000 | 1.6000 |
| 133 (isomer 3) | NT | 0.000140 | NT | NT | 0.023300 | 0.0363000 | 0.6590 |
| 133 (isomer 4) | NT | 0.000080 | NT | NT | 0.002300 | 0.0141000 | 2.0800 |
| 134 (isomer 1) | NT | 0.000190 | NT | NT | 0.039400 | 0.0085900 | 2.5500 |
| 134 (isomer 2) | NT | 0.000190 | NT | NT | 0.038100 | 0.0074500 | 1.9400 |
| 135 | NT | 0.000710 | NT | NT | 0.143000 | 0.0956000 | 20.0000 |
| 136 | NT | 0.000380 | NT | 0.200000 | 0.090800 | 0.0675000 | 12.3000 |
| 137 (isomer 1) | NT | 0.002310 | NT | NT | 0.283000 | 0.1270000 | 20.0000 |
| 137 (isomer 2) | NT | 0.002340 | NT | NT | 0.454000 | 0.1930000 | 20.0000 |
| 138 | NT | 0.000420 | NT | NT | 0.115000 | 0.0151000 | 2.5500 |
| 139 | NT | 0.002410 | NT | NT | 0.780000 | 0.1180000 | 8.5700 |
| 140 | NT | 0.000140 | NT | 0.004400 | 0.018400 | 0.0025300 | 2.0600 |
| 141 | NT | 0.000260 | NT | NT | 0.085000 | 0.0069200 | 6.2400 |
| 142 | NT | 0.000200 | NT | NT | 0.033200 | 0.0054500 | 3.5600 |
| 143 (isomer 1) | NT | 0.000220 | NT | NT | 0.028100 | 0.0047200 | 0.9720 |
| 143 (isomer 2) | NT | 0.000260 | NT | 0.004100 | 0.033500 | 0.0035200 | 1.1300 |
| 143 (isomer 3) | NT | 0.000430 | NT | NT | 0.047300 | 0.0047700 | 1.0900 |
| 144 | NT | 0.000500 | NT | NT | 0.099500 | 0.0212000 | 7.5100 |
| 145 | NT | 0.000670 | NT | NT | 0.171000 | 0.0687000 | 5.1200 |
| 146 | NT | 0.000760 | NT | NT | 0.114000 | 1.7400000 | 20.0000 |
| 149 | NT | 0.018400 | NT | NT | 5.450000 | 0.1860000 | 20.0000 |
| 150 (isomer 1) | NT | 0.000180 | NT | NT | 0.027500 | 0.0137000 | 3.7700 |
| 150 (isomer 2) | NT | 0.000250 | NT | NT | 0.064500 | 0.0239000 | 2.8500 |
| 151 (isomer 1) | NT | 0.001840 | NT | NT | 0.398000 | 0.3230000 | 20.0000 |
| 151 (isomer 2) | NT | 0.000120 | NT | NT | 0.025500 | 0.0080400 | 1.6900 |
| 152 (isomer 1) | NT | 0.000100 | NT | NT | 0.015700 | 0.0174000 | 0.7870 |
| 152 (isomer 2) | NT | 0.003230 | NT | NT | 0.526000 | 0.2990000 | 6.3300 |
| 153 (isomer 1) | NT | 0.000370 | NT | NT | 0.090900 | 0.0190000 | 4.7400 |
| 153 (isomer 2) | NT | 0.000320 | NT | NT | 0.087600 | 0.0134000 | 4.1800 |
| 153 (isomer 3) | NT | 0.000550 | NT | NT | 0.125000 | 0.0329000 | 4.4900 |
| 154 | NT | 0.000470 | NT | NT | 0.118000 | 0.0205000 | 4.1000 |
| 155 | NT | 0.000220 | NT | NT | 0.031500 | 0.0088400 | 4.7500 |
| 156 | NT | NT | NT | 0.009400 | NT | 0.0029400 | 0.7760 |
| 157 | NT | 0.000550 | NT | NT | 0.045600 | 0.0128000 | 2.1400 |
| 158 | NT | 0.003390 | NT | NT | 0.121000 | 0.0099400 | 13.8000 |
| 159 (diast. 1) | NT | 0.000280 | NT | NT | 0.064000 | 0.0369000 | 4.3100 |
| 159 (diast. 2) | NT | 0.000230 | NT | NT | 0.048100 | 0.0238000 | 1.2400 |
| 159 (mixture) | NT | 0.000230 | NT | NT | 0.045200 | 0.0179000 | 3.7400 |
| 160 (diast. 1) | NT | 0.000140 | NT | NT | 0.031300 | 0.0080700 | 1.0000 |
| 160 (diast. 2) | NT | 0.000120 | NT | NT | 0.022500 | 0.0069700 | 0.7550 |
| 161 | NT | 0.007610 | NT | NT | 1.330000 | 0.0689000 | 13.0000 |
| 162 | NT | 0.000130 | NT | 0.200000 | 0.041300 | 0.0487000 | 9.4500 |
| 163 | NT | 0.000110 | NT | NT | 0.019600 | 0.0102000 | 1.1400 |
| 164 | NT | 0.000150 | NT | NT | 0.030600 | 0.0438000 | 7.1100 |
| 165 a | NT | 0.000080 | NT | 0.000600 | 0.001140 | 0.0006300 | 0.3740 |
| 165 b | NT | 0.000100 | NT | 0.000849 | 0.001430 | 0.0006600 | 0.4990 |
| 165 c | NT | 0.000090 | NT | 0.001100 | 0.002190 | 0.0010900 | 0.4810 |
| 166 a | NT | 0.000100 | NT | NT | 0.003680 | 0.0014400 | 1.2700 |
| 166 b | NT | 0.000150 | NT | NT | 0.005380 | 0.0014900 | 0.4020 |
| 167 a | NT | 0.000170 | NT | NT | 0.013600 | 0.0015800 | 1.1400 |
| 167 b | NT | 0.000190 | NT | NT | 0.013800 | 0.0018200 | 1.0600 |
| 168 | NT | 0.000120 | NT | 0.000700 | 0.001680 | 0.0004720 | 0.6560 |
| 169 | NT | 0.000100 | NT | NT | 0.002310 | 0.0009200 | 0.4540 |
| 170 | NT | 0.000090 | NT | 0.000800 | 0.002160 | 0.0009200 | 0.5060 |
| 171 | NT | 0.000253 | NT | NT | 0.013700 | 0.0013300 | 0.9040 |
| 172 | NT | 0.000240 | NT | NT | 0.011100 | 0.0017200 | 0.8640 |
| 173 | NT | 0.000080 | NT | NT | 0.005950 | 0.0013300 | 0.9170 |
| 174 | NT | 0.003390 | NT | 0.001300 | 0.003040 | 0.0038600 | 0.2270 |
| 175 | NT | 0.003390 | NT | NT | 0.108000 | 0.0196000 | 2.3400 |
| 176 | NT | 0.002800 | NT | 0.200000 | 0.809000 | 0.1680000 | 15.2000 |
| 177 | NT | 0.126000 | NT | NT | 11.70000 | 4.4500000 | 20.0000 |
| 178 | NT | NT | NT | NT | NT | 0.1330000 | 9.2800 |
| 179 | NT | 0.006640 | NT | NT | 0.659000 | 0.2940000 | 8.4100 |
| 180 | NT | 0.017400 | NT | NT | 2.740000 | 2.0000000 | 20.0000 |
| 181 (isomer 1) | NT | 0.159000 | NT | NT | 10.90000 | 2.0000000 | 12.3000 |
| 181 (isomer 2) | NT | 0.050400 | NT | NT | 3.030000 | 0.9030000 | 7.2600 |
| 182 | NT | 0.000269 | NT | 0.008300 | 0.033900 | 0.0041200 | 1.9100 |
| 183 | NT | 0.000210 | NT | 0.004200 | 0.004460 | 0.0023200 | 0.8520 |
| 184 | NT | 0.001980 | NT | NT | 0.393000 | 0.1470000 | 20.0000 |
| 185 | NT | 0.001100 | NT | NT | 0.107000 | 0.0320000 | 4.9300 |
| 186 | NT | 0.000100 | NT | 0.008900 | 0.005610 | 0.0025800 | 1.0900 |

-continued

Table of Exemplary Compound Potencies.

| Cmpd. No. | KRas(wt) GDP HTRF IC50 | KRas (G12D) GDP HTRF IC50 | Prolif PC9 3D ATP IC50 | Prolif AsPC-1 3D ATP IC50 | KRas HTRF IC50 [uM] | Prolif HPAC 3D ATP IC50 [uM] | Prolif H1975 3D ATP IC50 [uM] |
|---|---|---|---|---|---|---|---|
| 187 | NT | 0.000510 | NT | NT | 0.163000 | 0.0348000 | 18.9000 |
| 188 | NT | 0.001260 | NT | NT | 0.225000 | 0.0660000 | 10.1000 |
| 189 | NT | 0.002310 | NT | NT | 0.252000 | 0.0954000 | 20.0000 |
| 190 | NT | 0.000110 | NT | 0.012600 | 0.010100 | 0.0022000 | 1.5600 |
| 191 | NT | 0.000460 | NT | NT | 0.091100 | 0.0296000 | 1.4100 |
| 192 | NT | NT | NT | NT | NT | 0.0071700 | 1.2800 |
| 193 | NT | 32.80000 | NT | NT | 128.0000 | 2.0000000 | 20.0000 |
| 194 | NT | 0.000420 | NT | 0.002700 | 0.028900 | 0.0049900 | 0.9190 |
| 195 | NT | 0.000440 | NT | NT | 0.108000 | 0.0221000 | 1.3400 |
| 196 | NT | 0.248000 | NT | NT | 20.10000 | 20.000000 | 20.0000 |
| 197 | NT | 0.000460 | NT | NT | 0.059800 | 0.0097900 | 0.4680 |
| 198 | NT | 0.000620 | NT | NT | 0.085800 | 0.0130000 | 3.7200 |
| 199 | NT | 0.000170 | NT | 0.004060 | 0.009630 | 0.0009800 | 1.0500 |
| 200 | NT | 0.000100 | NT | NT | 0.006700 | 0.0068300 | 0.5930 |
| 201 | NT | 0.009190 | NT | NT | 1.620000 | 0.4070000 | 10.6000 |
| 202 | NT | 0.001980 | NT | NT | 0.214000 | 2.0000000 | 20.0000 |
| 203 | NT | 0.026800 | NT | NT | 1.590000 | 0.5200000 | 20.0000 |
| 204 | NT | 0.000385 | NT | NT | 0.069100 | 0.0189000 | 1.4200 |
| 205 | NT | 0.003390 | NT | NT | 0.008610 | 0.0033500 | 1.1300 |
| 206 | NT | 0.000170 | NT | 0.003600 | 0.024200 | 0.0031600 | 2.8400 |
| 207 | NT | 0.000360 | NT | NT | 0.043100 | 0.0023600 | 1.4200 |
| 208 | NT | 0.000310 | NT | NT | 0.024700 | 0.0048900 | 3.6300 |
| 209 | NT | 0.000240 | NT | NT | 0.018500 | 0.0034700 | 0.2820 |
| 210 | NT | NT | NT | 0.003600 | NT | 0.0018100 | 0.8680 |
| 211 | NT | 0.000210 | NT | NT | 0.017800 | 0.0014500 | 1.1500 |
| 212 | NT | 0.000560 | NT | NT | 0.039100 | 0.0016400 | 0.3890 |
| 213 | NT | 0.000310 | NT | NT | 0.013600 | 0.0012500 | 0.2950 |
| 214 | NT | 0.000420 | NT | 0.025400 | 0.055700 | 0.0080400 | 7.0300 |
| 215 | NT | 0.000210 | NT | 0.007800 | 0.007100 | 0.0025000 | 0.8310 |
| 216 | NT | NT | NT | 0.000600 | NT | 0.0008930 | 0.1610 |
| 217 | NT | 0.003390 | NT | NT | 0.242000 | 0.0388000 | 12.6000 |
| 218 | NT | 0.000290 | NT | NT | 0.014100 | 0.0013600 | 0.3840 |
| 219 | NT | 0.000460 | NT | NT | 0.047300 | 0.0036700 | 8.2800 |
| 220 | NT | 0.000920 | NT | NT | 0.149000 | 0.0118000 | 20.0000 |
| 221 | NT | 0.000390 | NT | 0.001200 | 0.009950 | 0.0014500 | 0.4980 |
| 222 | NT | 0.003390 | NT | NT | 0.045700 | 0.0057600 | 1.4800 |
| 223 | NT | 0.003390 | NT | NT | 0.051300 | 0.0064600 | 1.2300 |
| 224 | NT | 0.000180 | NT | 0.003500 | 0.012000 | 0.0027200 | 0.7110 |
| 225 | NT | 0.000250 | NT | 0.002900 | 0.004200 | 0.0011900 | 0.5610 |
| 226 | NT | 0.000400 | NT | 0.001200 | 0.008110 | 0.0008600 | 0.5680 |
| 227 | NT | 0.000210 | NT | NT | 0.000938 | 0.0005160 | 0.6790 |
| 228 | NT | 0.370000 | NT | NT | 4.880000 | 2.0000000 | 20.0000 |
| 229 | NT | 0.000360 | NT | NT | 0.012000 | 0.0018200 | 0.6390 |
| 230 | NT | 0.001130 | NT | NT | 0.213000 | 0.0284000 | 5.8400 |
| 231 | NT | 0.004600 | NT | NT | 1.240000 | 0.0398000 | 13.2000 |
| 232 | NT | 0.002860 | NT | NT | 0.277000 | 0.0770000 | 10.5000 |
| 233 | NT | NT | NT | NT | NT | 2.0000000 | 5.4000 |
| 234 (isomer 1) | NT | 1.330000 | NT | NT | 23.30000 | 2.0000000 | 8.5700 |
| 234 (isomer 2) | NT | 0.209000 | NT | NT | 0.513000 | 2.0000000 | 9.7500 |
| 234 (isomer 3) | NT | 4.810000 | NT | NT | 4.570000 | 2.0000000 | 16.6000 |
| 234 (isomer 4) | NT | 0.589000 | NT | NT | 0.510000 | 2.0000000 | 8.5000 |
| 235 (isomer 1) | NT | 0.065800 | NT | NT | 0.143000 | 2.4200000 | 4.3400 |
| 235 (isomer 2) | NT | 0.000480 | NT | NT | 0.002630 | 0.1360000 | 0.2620 |
| 236 | NT | 0.068000 | NT | NT | 0.830000 | 2.0000000 | 14.5000 |
| 237 (isomer 1) | NT | 1.910000 | NT | NT | 1.020000 | NT | NT |
| 237 (isomer 2) | NT | 0.000150 | NT | 0.200000 | 0.000350 | 0.0036300 | 1.0400 |
| 238 (isomer 1) | NT | 7.700000 | NT | NT | 3.810000 | 2.0000000 | 13.5000 |
| 238 (isomer 2) | NT | 13.00000 | NT | NT | 4.800000 | 2.0000000 | 20.0000 |
| 239 | NT | 0.000580 | NT | NT | 0.000940 | 0.0334000 | 0.5690 |
| 240 (atrop. 1) | NT | 0.044900 | NT | NT | 1.080000 | 0.5940000 | 6.4800 |
| 240 (atrop. 2) | NT | 0.000140 | NT | 0.001500 | 0.015100 | 0.0018800 | 1.0600 |
| 241 | NT | 0.000130 | NT | NT | 0.015400 | 0.0162000 | 1.2000 |
| 242 | NT | 0.000330 | NT | 0.007800 | 0.005290 | 0.0051100 | 1.0400 |
| 243 | NT | 0.581000 | NT | NT | 3.960000 | 2.0000000 | 20.0000 |
| 244 | NT | 0.000520 | NT | NT | 0.011900 | 0.0061400 | 0.2580 |
| 245 | NT | 0.000249 | NT | 0.003600 | 0.007440 | 0.0041300 | 0.7390 |
| 246 | NT | 0.311000 | NT | NT | 1.200000 | 2.0000000 | 20.0000 |
| 247 | NT | 0.000210 | NT | 0.001000 | 0.000959 | 0.0016400 | 0.6430 |
| 248 | NT | 0.001100 | NT | 0.027900 | 0.000522 | 0.0125000 | 0.2440 |
| 249 | NT | 0.000220 | NT | 0.001100 | 0.001370 | 0.0013700 | 0.4170 |
| 250 | NT | 0.000390 | NT | NT | 0.013600 | 0.0169000 | 0.9940 |

-continued

Table of Exemplary Compound Potencies.

| Cmpd. No. | KRas(wt) GDP HTRF IC50 | KRas (G12D) GDP HTRF IC50 | Prolif PC9 3D ATP IC50 | Prolif AsPC-1 3D ATP IC50 | KRas HTRF IC50 [uM] | Prolif HPAC 3D ATP IC50 [uM] | Prolif H1975 3D ATP IC50 [uM] |
|---|---|---|---|---|---|---|---|
| 251 | NT | 0.000160 | NT | 0.001900 | 0.001050 | 0.0023000 | 0.2340 |
| 252 (isomer 1) | NT | 0.001170 | NT | NT | 0.025000 | 0.0204000 | 7.7100 |
| 252 (isomer 2) | NT | 0.005890 | NT | NT | 0.159000 | 0.1190000 | 20.0000 |
| 253 | NT | 0.001030 | NT | 0.064600 | 0.037100 | 0.0198000 | 5.0800 |
| 254 | NT | 0.000490 | NT | 0.002500 | 0.001250 | 0.0018600 | 0.1390 |
| 255 a | NT | 0.000410 | NT | 0.006600 | 0.001390 | 0.0016600 | 0.1200 |
| 255 b | NT | 0.000270 | NT | 0.004700 | 0.001170 | 0.0042100 | 0.3080 |
| 256 | NT | 0.000820 | NT | NT | 0.017000 | 0.0139000 | 0.0934 |
| 257 | NT | 0.000890 | NT | 0.008000 | 0.008410 | 0.0083700 | 5.0200 |
| 258 (isomer 1) | NT | 0.000090 | NT | 0.008100 | 0.014900 | 0.0050000 | 1.5600 |
| 258 (isomer 2) | NT | 0.000070 | NT | 0.006900 | 0.011000 | 0.0026800 | 1.5500 |
| 259 | NT | 0.000160 | NT | NT | 0.009710 | 0.0123000 | 1.9700 |
| 260 | NT | 0.000280 | NT | NT | 0.026200 | 0.0415000 | 3.2500 |
| 261 | NT | 0.002760 | NT | NT | 0.097100 | 0.1070000 | 6.1000 |
| 262 (isomer 1) | NT | 0.031900 | NT | NT | 0.668000 | 0.4750000 | 20.0000 |
| 262 (isomer 2) | NT | 0.007020 | NT | NT | 0.186000 | 0.1230000 | 20.0000 |
| 262 (isomer 3) | NT | 0.041100 | NT | NT | 1.080000 | 0.9710000 | 20.0000 |
| 262 (isomer 4) | NT | 0.001140 | NT | NT | 0.035100 | 0.0434000 | 4.3800 |
| 263 (diast. 1) | NT | 0.000260 | NT | 0.007100 | 0.005490 | 0.0061400 | 0.7890 |
| 263 (diast. 2) | NT | 0.000530 | NT | NT | 0.015400 | 0.0154000 | 0.3360 |
| 264 | NT | 0.000330 | NT | NT | 0.019200 | 0.0055600 | 11.0000 |
| 265 | NT | 0.000280 | NT | NT | 0.014100 | 0.0022400 | 6.2400 |
| 266 | NT | 0.003050 | NT | NT | 1.100000 | NT | NT |
| 267 | NT | 0.002980 | NT | NT | 0.609000 | NT | NT |
| 268 | NT | 0.000290 | NT | NT | 0.011900 | 0.0021700 | 1.7000 |
| 269 | NT | 0.000420 | NT | NT | 0.105000 | NT | NT |
| 270 | NT | 0.000260 | NT | NT | 0.010700 | 0.0025200 | 2.4800 |
| 271 | NT | 0.000510 | NT | NT | 0.056400 | 0.0044900 | 10.9000 |
| 272 | NT | 0.000380 | NT | NT | 0.024400 | 0.0045800 | 5.4800 |
| 273 | NT | 0.000290 | NT | NT | 0.017100 | 0.0065300 | 3.1900 |
| 274 | NT | 0.000340 | NT | NT | 0.025700 | 0.0075500 | 1.0700 |
| 275 | NT | 0.000480 | NT | NT | 0.023300 | 0.0032900 | 5.1800 |
| 276 | NT | 0.000260 | NT | NT | 0.008910 | 0.0018200 | 1.6200 |
| 277 | NT | NT | NT | NT | NT | 0.0020900 | 0.9740 |
| 278 | NT | NT | NT | NT | NT | NT | NT |
| 279 | NT | NT | NT | NT | NT | 0.0020200 | 1.2700 |
| 280 | NT | NT | NT | NT | NT | 0.0017700 | 1.3400 |
| 281 | NT | NT | NT | NT | NT | 0.0086000 | 2.4300 |
| 282 | NT | NT | NT | NT | NT | 0.0039600 | 2.4500 |
| 283 | NT | NT | NT | NT | NT | 0.0015800 | 0.5770 |
| 284 | NT | NT | NT | NT | NT | 0.0012300 | 0.4900 |
| 285 | NT | NT | NT | NT | NT | 0.0030500 | 0.6080 |
| 286 | NT | NT | NT | NT | NT | NT | NT |
| 287 | NT | NT | NT | NT | NT | 0.0057200 | 1.3800 |
| 288 | NT | NT | NT | NT | NT | 0.0188000 | 9.8100 |
| 289 | NT | NT | NT | NT | NT | 0.0031500 | 0.5730 |
| 290 | NT | NT | NT | NT | NT | 0.0025300 | 2.7800 |
| 291 | NT | NT | NT | NT | NT | 0.0040900 | 12.2000 |

NT = not tested

Example 504: Pharmacokinetic profiling

The pharmacokinetics of Compound 6 were evaluated following a single intravenous bolus (IV) of solution at doses of 0.5-1 mg/kg and oral administration (PO) of solution at doses of 5-30 mg/kg in female CD-1 mice or male Sprague Dawley rats using a parallel study design. Blood samples for the IV dose group in mice were collected at 0.033, 0.083, 0.25, 0.5, 1, 3, and 8 hours post-dose, and plasma samples for the same group were collected at 8 hours post-dose. Blood samples for the PO dose group in mice were collected at 0.25, 0.5, 1, 3, 8, and 24 hours post-dose. Blood and plasma samples for the IV dose group in rats were collected at 0.033, 0.083, 0.25, 0.5, 1, 2, 4, 8, and 24 hours post-dose. Blood and plasma samples for PO dose groups in rats were collected at 0.083, 0.25, 0.5, 1, 2, 4, 8, and 24 hours post-dose. The vehicle used for IV dose groups was 10% DMSO, 350% PEG400, 55% Water, and for PO groups was 80% PEG400/20% EtOH. Plasma and blood concentrations were quantitated at Wuxi Inc. using a non-validated LC/MS/MS method. The lower limits of quantitation (LLOQ) are 0.0079 µM for blood assays, and 0.0016 µM for plasma assays. Pharmacokinetic parameters were calculated by non-compartmental methods as described in Gibaldi and Perrier (Gibaldi and Perrier, 1982) using Phoenix® WinNonlin® version 8.3.4 (Certara L. P.). Following PO administration, percent bioavailability (% F) was determined for each animal by dividing the dose-normalized area under the plasma and blood concentration-time curve, extrapolated to infinity (AUCinf) obtained following each PO dose by the mean dose-normalized AUCinf of the animals dosed by IV injections. All PK parameters are presented as mean±standard deviation (SD).

The pharmacokinetics of Comparator Compound

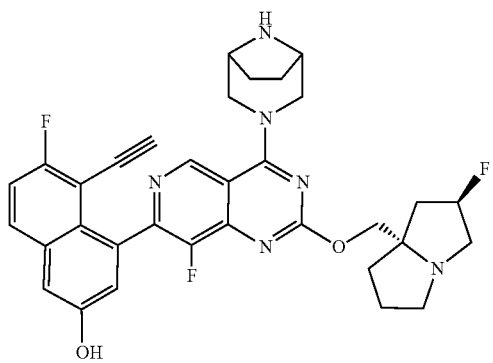 [SMILES: C#Cc1c(F)ccc2cc(O)cc(-c3ncc4c(N5CC6CCC(C5)N6)nc(OC[C@@]56CCCN5C[C@H](F)C6)nc4c3F)c12]

were evaluated following a single intravenous bolus (IV) of solution at a dose of 1 mg/kg and oral administration (PO) of solution at doses of 5-30 mg/kg in female CD-1 mice or male Sprague Dawley rats using a parallel study design. Blood samples for the IV dose group in mice were collected at 0.033, 0.083, 0.25, 0.5, 1, 3, and 8 hours post-dose, and plasma samples for the same group were collected at 8 hours post-dose. Blood samples for the PO dose group in mice were collected at 0.083, 0.25, 0.5, 1, 3, 8, and 24 hours post-dose. Blood and plasma samples for the IV dose group in rats were collected at 0.033, 0.083, 0.25, 0.5, 1, 2, 4, 8, and 24 hours post-dose. Blood and plasma samples for the PO dose group in rats were collected at 0.083, 0.25, 0.5, 1, 2, 4, 8, and 24 hours post-dose. For the IV group in rats, urine was collected from each animal from 0-8 and 8-24 hours post dose. The vehicle used for IV dose groups was 10% DMSO, 35% PEG400, 55% Water, and for PO groups was 80% PEG400/20% EtOH. Plasma and blood concentrations were quantitated at Wuxi Inc. using a non-validated LC/MS/MS method. The lower limits of quantitation (LLOQ) are 0.0085 µM for blood assays, 0.0017 µM for plasma assays (IV group in mice and PO group in rats), 0.0051 M for plasma assays (IV group in rats), and 0.017 M for urine assays. Pharmacokinetic parameters were calculated by non-compartmental methods as described in Gibaldi and Perrier (Gibaldi and Perrier, 1982) using Phoenix® WinNonlin® version 8.3.4 (Certara L. P.). Following PO administration, percent bioavailability (% F) was determined for each animal by dividing the dose-normalized area under the plasma and blood concentration-time curve, extrapolated to infinity (AUCinf) obtained following each PO dose by the mean dose-normalized AUCinf of the animals dosed by IV injections. All PK parameters are presented as mean±standard deviation (SD).

The pharmacokinetics of Compound 81 were evaluated following a single intravenous bolus (IV) of solution at a dose of 0.5 mg/kg and oral administration (PO) of solution at a dose of 5 mg/kg in female CD-1 mice using a parallel study design. Blood samples for the IV dose group were collected at 0.033, 0.083, 0.25, 0.5, 1, 3, and 8 hours post-dose, and plasma samples for the same group were collected at 8 hours post-dose. Blood samples for the PO dose group were collected at 0.25, 0.5, 1, 3, 8, and 24 hours post-dose. The vehicle used for IV dose groups was 10% DMSO, 35% PEG400, 55% Water, and for PO groups was 80% PEG400/20% EtOH. Plasma and blood concentrations were quantitated at Wuxi Inc. using a non-validated LC/MS/MS method. The lower limits of quantitation (LLOQ) are 0.0081 µM for blood assays, and 0.0049 µM for plasma assays. Pharmacokinetic parameters were calculated by non-compartmental methods as described in Gibaldi and Perrier (Gibaldi and Perrier, 1982) using Phoenix® WinNonlin® version 8.3.4 (Certara L. P.). Following PO administration, percent bioavailability (% F) was determined for each animal by dividing the dose-normalized area under the blood concentration-time curve, extrapolated to infinity (AUCinf) obtained following each PO dose by the mean dose-normalized AUCinf of the animals dosed by IV injections. All PK parameters are presented as mean±standard deviation (SD).

The pharmacokinetics of Compound 7 were evaluated following a single intravenous bolus (IV) of solution at doses of 0.5-1 mg/kg and oral administration (PO) of solution at doses of 5-30 mg/kg in female CD-1 mice or male Sprague Dawley rats using a parallel study design. Blood samples for the IV dose group in mice were collected at 0.033, 0.083, 0.25, 0.5, 1, 3, and 8 hours post-dose, and plasma samples for the same group were collected at 8 hours post-dose. Blood samples for the PO dose group in mice were collected at 0.25, 0.5, 1, 3, 8, and 24 hours post-dose. Blood and plasma samples for the IV dose group in rats were collected at 0.033, 0.083, 0.25, 0.5, 1, 2, 4, 8, and 24 hours post-dose. Blood and plasma samples for the PO dose group in rats were collected at 0.083, 0.25, 0.5, 1, 2, 4, 8, and 24 hours post-dose. The vehicle used for IV dose groups was 10% DMSO, 35% PEG400, 55% Water, and for PO groups was 80% PEG400/20% EtOH. Plasma and blood concentrations were quantitated at Wuxi Inc. using a non-validated LC/MS/MS method. The lower limits of quantitation (LLOQ) are 0.0079 µM for blood assays, and 0.0016 M for plasma assays. Pharmacokinetic parameters were calculated by non-compartmental methods as described in Gibaldi and Perrier (Gibaldi and Perrier, 1982) using Phoenix® WinNonlin® version 8.3.4 (Certara L. P.). Following PO administration, percent bioavailability (% F) was determined for each animal by dividing the dose-normalized area under the plasma and blood concentration-time curve, extrapolated to infinity (AUCinf) obtained following each PO dose by the mean dose-normalized AUCinf of the animals dosed by IV injections. All PK parameters are presented as mean±standard deviation (SD).

The pharmacokinetics of Compound 194 were evaluated following a single intravenous bolus (IV) of solution at a dose of 0.5 mg/kg and oral administration (PO) of solution at doses of 5-30 mg/kg in female CD-1 mice or male Sprague Dawley rats using a parallel study design. Blood samples for the IV dose group in mice were collected at 0.033, 0.083, 0.25, 0.5, 1, 3, and 8 hours post-dose, and plasma samples for the same group were collected at 8 hours post-dose. Blood samples for the PO dose group in mice were collected at 0.25, 0.5, 1, 3, 8, and 24 hours post-dose. Blood and plasma samples for the IV and PO dose groups in rats were collected at 0.033, 0.083, 0.25, 0.5, 1, 2, 4, 8, and 24 hours post-dose. The vehicle used for IV dose groups was 10% DMSO, 35% PEG400, 55% Water, and for PO groups was 80% PEG400/20% EtOH. Plasma and blood concentrations were quantitated at Pharmaron Inc. using a non-validated LC/MS/MS method. The lower limits of quantitation (LLOQ) are 0.0078 µM in mice and 0.0039 µM in rats for blood assays, and 0.0016 M in mice and 0.00078 µM in rats for plasma assays. Pharmacokinetic parameters were calculated by non-compartmental methods as described in Gibaldi and Perrier (Gibaldi and Perrier, 1982) using Phoenix® WinNonlin® version 8.3.4 (Certara L. P.). Following PO administration, percent bioavailability (% F) was determined for each animal by dividing the dose-normalized area under the plasma and blood concentration-time curve, extrapolated to infinity (AUCinf) obtained following each PO dose by the mean dose-normalized AUCinf of the animals dosed by IV injections. All PK parameters are presented as mean±standard deviation (SD).

The pharmacokinetics of compounds 6, 7, 81 and 194, and comparator compound are provided in the Drawing.

What is claimed is:
1. A compound of formula (I):

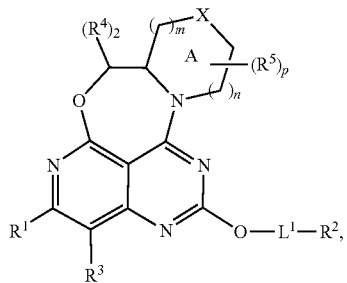

or an atropisomer, or pharmaceutically acceptable salt thereof,
wherein:
X is $NR^6$;
m is 1 or 2;
n is 1 or 2;
wherein n and m together make a 6- or 7-membered ring Ring A;
p is 0, 1, or 2;
$R^1$ is (E2) or (E3)

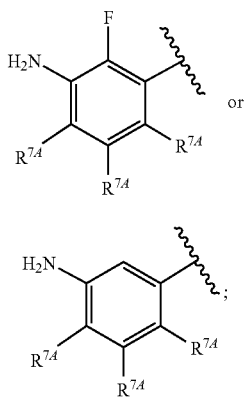

each $R^{7A}$ is independently hydrogen, halogen, unsubstituted $C_{1-3}$ alkyl or unsubstituted $C_{1-3}$ haloalkyl; wherein at least one $R^{7A}$ is unsubstituted $C_{1-3}$ haloalkyl;
$L^1$ is $R^{L1}$-substituted or unsubstituted $C_{1-4}$ alkylene;
$R^{L1}$ is halogen or unsubstituted $C_{1-3}$ alkyl, or two $R^{L1}$ together form an unsubstituted $C_{3-4}$ cycloalkyl;
$R^2$ is $R^9$-substituted or unsubstituted 4-10 membered heterocycle comprising one or more heteroatoms selected from N, S, and O;
each $R^9$ is independently halogen, CN, OH, $OCF_3$, $OCHF_2$, $OCH_2F$, $R^{10}$-substituted or unsubstituted $C_{1-3}$ alkyl, $R^{10}$-substituted or unsubstituted $C_{1-3}$ haloalkyl, unsubstituted $C_{1-3}$ alkoxy, $R^{10}$-substituted or unsubstituted $C_{1-3}$ alkylidene, $R^{10}$-substituted or unsubstituted $C_{3-4}$ cycloalkyl, or $R^{10}$-substituted or unsubstituted 3 or 4-membered heterocycle;
or two $R^9$ together form an $R^{10}$-substituted or unsubstituted $C_{3-5}$ cycloalkyl or an $R^{10}$-substituted or unsubstituted $C_{3-5}$ heterocycle comprising one or more oxygen atoms;
or two $R^9$ together form a bridge between two carbon atoms of the heterocycle, wherein the bridge comprises 1-3 carbons;
each $R^{10}$ is independently hydrogen, oxo, CN, halogen, or $C_{1-3}$ unsubstituted alkyl;
$R^3$ is hydrogen, —CN, halogen, unsubstituted $C_{1-3}$ alkyl, or unsubstituted cyclopropyl;
one $R^4$ is hydrogen and one $R^4$ is methyl;
each $R^5$ is independently halogen, oxo, unsubstituted $C_{1-3}$ alkyl, or unsubstituted $C_{1-3}$ haloalkyl;
or two $R^5$ together form a bridge between two carbon atoms of Ring A, wherein the bridge comprises 1-3 carbons and optionally one heteroatom selected from O and N;
or two $R^5$ together form a bridge between two carbon atoms of Ring A, wherein the bridge comprises one of O or $NR^{11}$;
$R^{11}$ is hydrogen, $C(O)CH_3$, or unsubstituted $C_{1-3}$ alkyl; and
$R^6$ is hydrogen.

2. The compound or an atropisomer, or pharmaceutically acceptable salt thereof of claim 1, wherein $L^1$ is methylene.

3. The compound or an atropisomer, or pharmaceutically acceptable salt thereof, of claim 1, wherein $R^2$ is

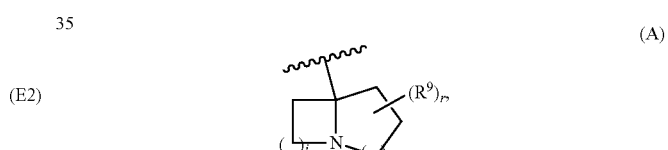

wherein:
each $R^9$ is independently halogen or $R^{10}$-substituted or unsubstituted $C_{1-3}$ alkylidene;
r is an integer of 0-12;
j is 1, 2, or 3; and
k is 1 or 2.

4. The compound or an atropisomer, or pharmaceutically acceptable salt thereof of claim 1, wherein $R^2$ is:

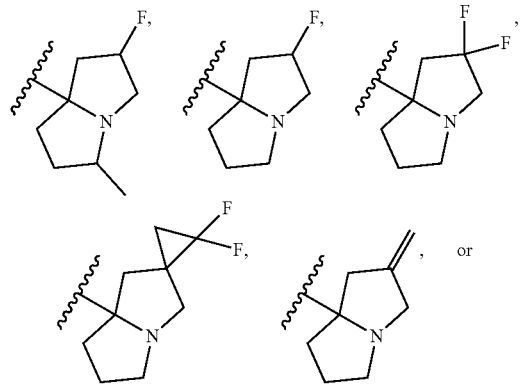

-continued

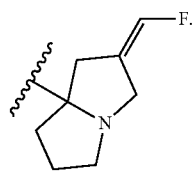

5. The compound or an atropisomer, or pharmaceutically acceptable salt thereof of claim 1, wherein $R^2$ is:

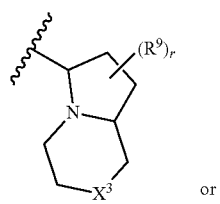
(D)

or

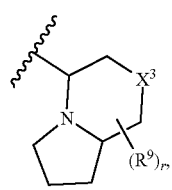
(D1)

wherein $X^3$ is $CR^9$, $NR^9$, or O; and r is 0 or 1.

6. The compound or an atropisomer, or pharmaceutically acceptable salt thereof of claim 1, wherein $R^2$ is:

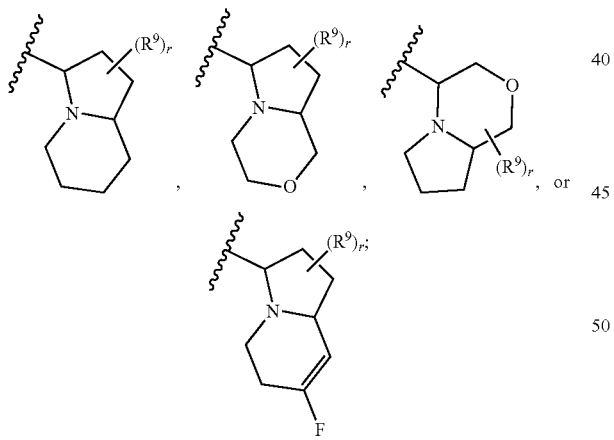

and r is 0 or 1.

7. The compound or an atropisomer, or pharmaceutically acceptable salt thereof of claim 1, wherein $R^3$ is fluoro.

8. The compound or an atropisomer, or pharmaceutically acceptable salt thereof of claim 1, wherein two $R^5$ together form a bridge between two carbon atoms of Ring A, wherein the bridge comprises 2 carbon atoms.

9. The compound or an atropisomer, or pharmaceutically acceptable salt thereof of claim 8, wherein the compound of formula (I) is a compound of the formula:

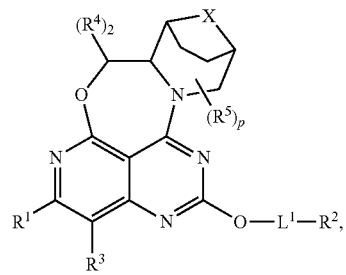

or an atropisomer, or pharmaceutically acceptable salt thereof.

10. A pharmaceutical composition comprising the compound of claim 4, or an atropisomer, or pharmaceutically acceptable salt thereof, and one or more pharmaceutically acceptable excipients.

11. The compound or an atropisomer, or pharmaceutically acceptable salt thereof, of claim 1, wherein $R^1$ is:

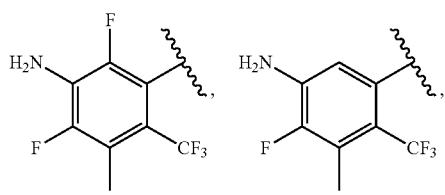

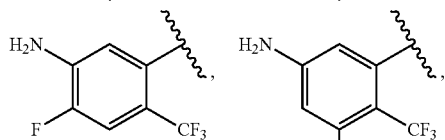

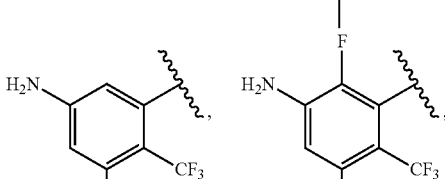

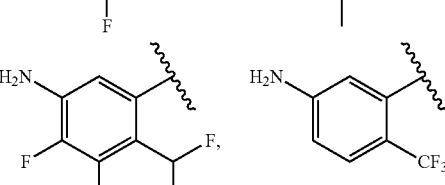

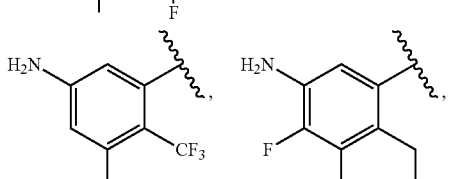

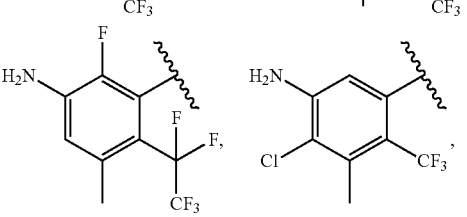

-continued

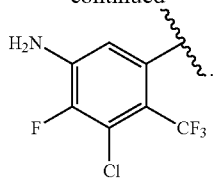

12. The compound or an atropisomer, pharmaceutically acceptable salt thereof, of claim 11, wherein $R^1$ is:

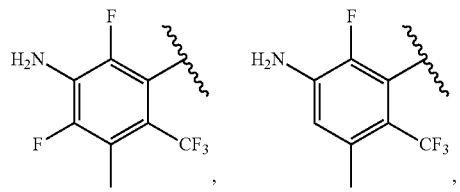

,

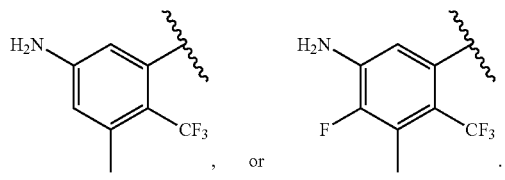

, or .

13. The compound or an atropisomer or pharmaceutically acceptable salt thereof, of claim 1, wherein m and n are both 1.

14. The compound or an atropisomer or pharmaceutically acceptable salt thereof, of claim 1, wherein m and n are both 1;

p is 2, and the two $R^5$ together form a bridge between two carbon atoms of Ring A, wherein the bridge comprises 2 carbon atoms;

$L^1$ is methylene;

$R^2$ is

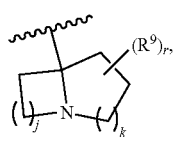 (A)

wherein:

each $R^9$ is independently halogen or $R^{10}$-substituted or unsubstituted $C_{1-3}$ alkylidene;

r is an integer of 0-12;

j is 1, 2, or 3; and k is 1 or 2;

and $R^3$ is fluoro.

15. A compound selected from the group consisting of:

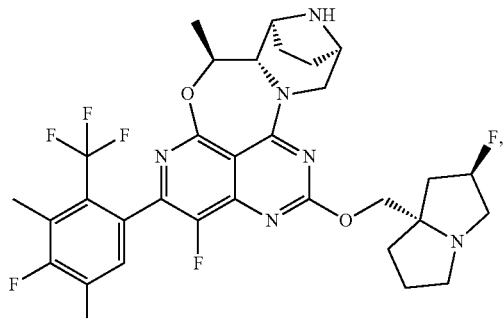

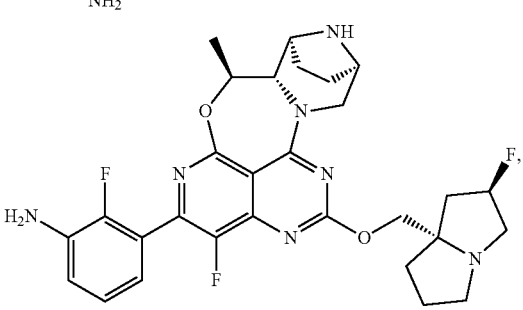

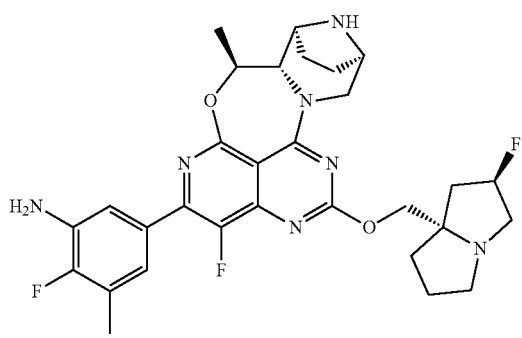

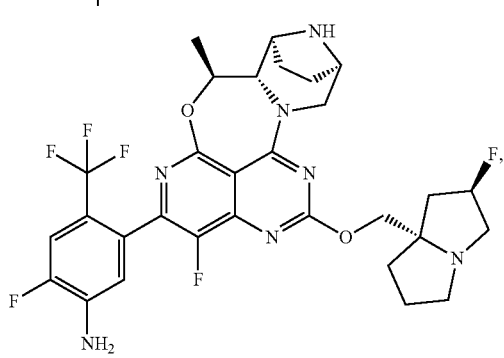

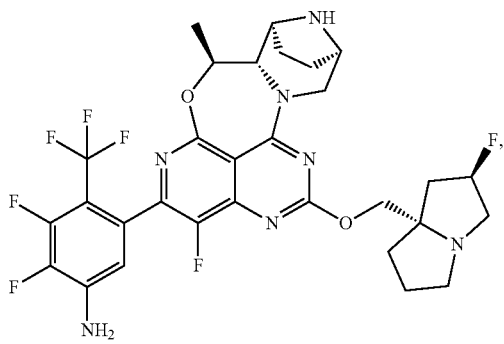

| 889 -continued | 890 -continued |
|---|---|
| 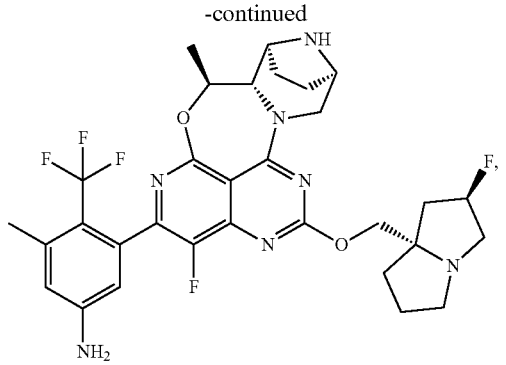 | 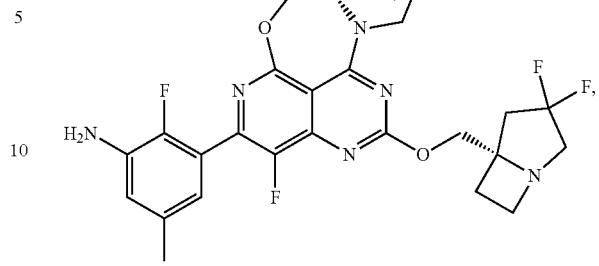 |
| 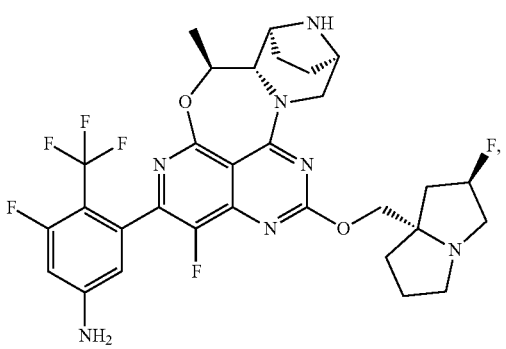 [SMILES: C[C@@H]1Oc2nc(-c3cc(N)cc(F)c3C(F)(F)F)c(F)c3nc(OC[C@@]45CCCN4C[C@H](F)C5)nc(c23)N2C[C@H]3CC[C@H](N3)[C@@H]12] | 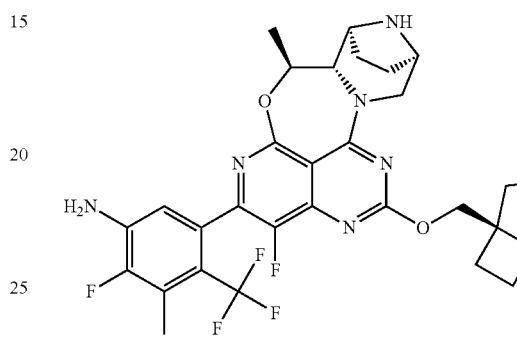 |
| 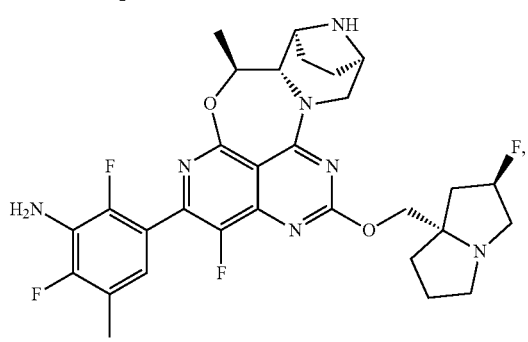 | 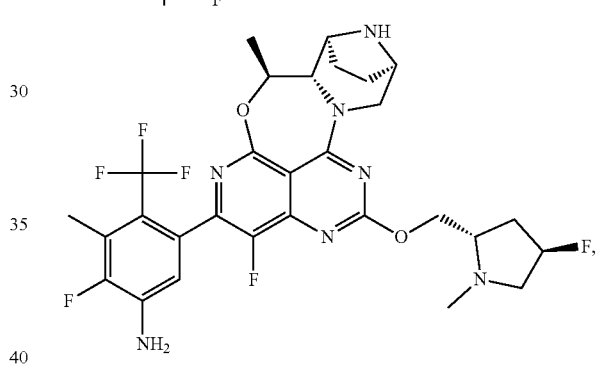 |
| 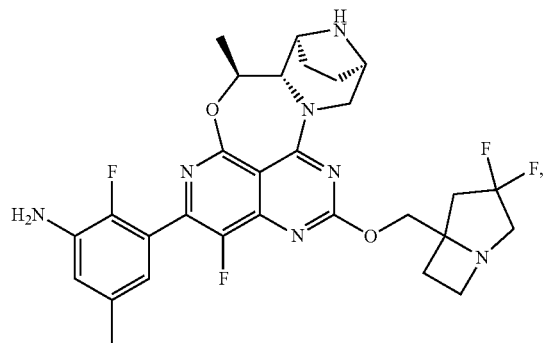 | 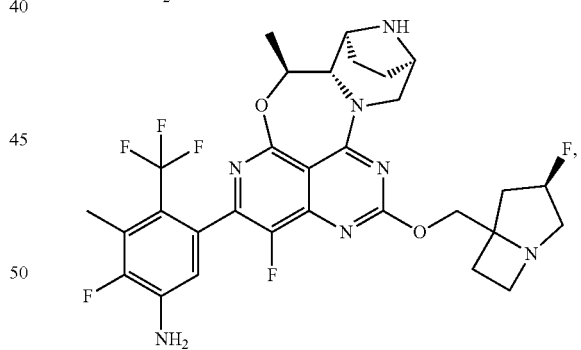 |
| 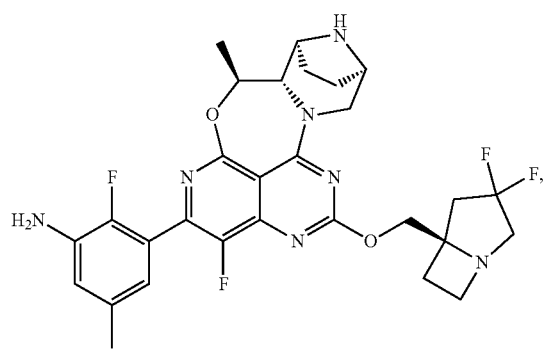 | 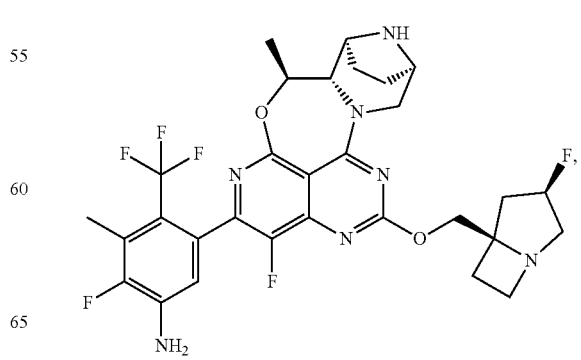 |

891
-continued
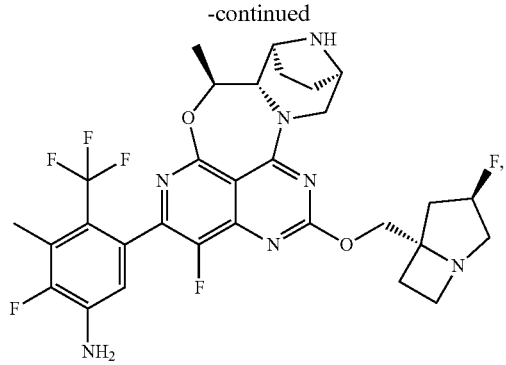
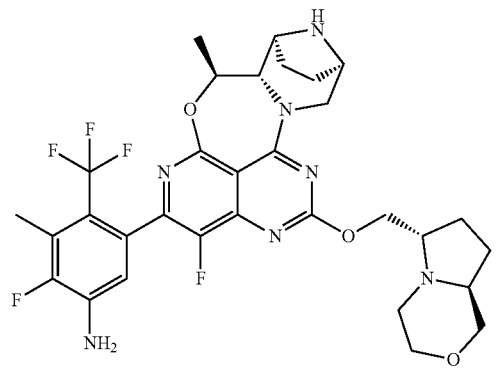
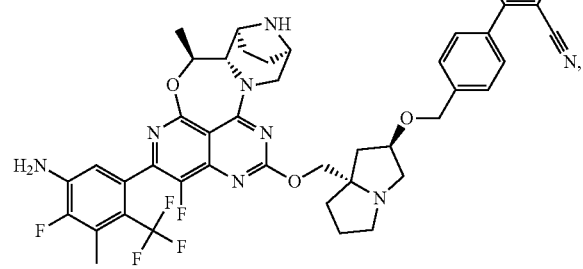
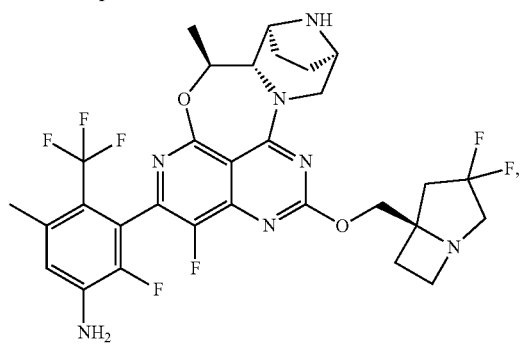
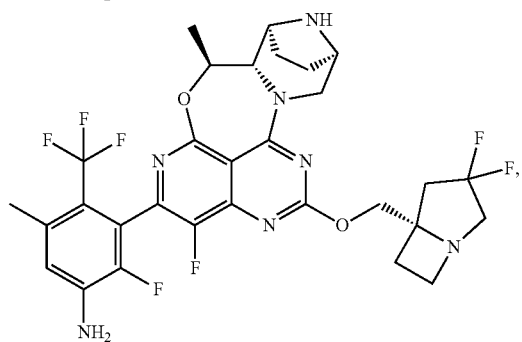
892
-continued
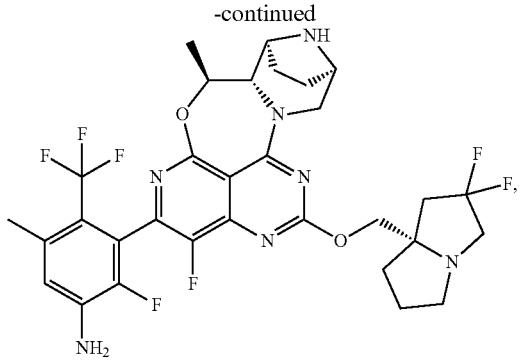
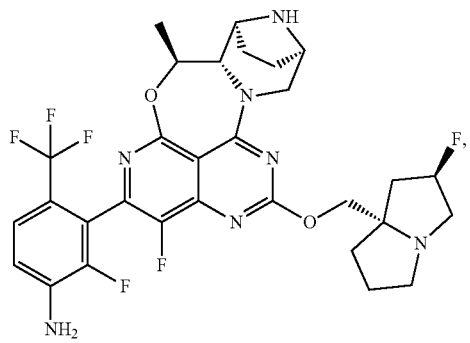
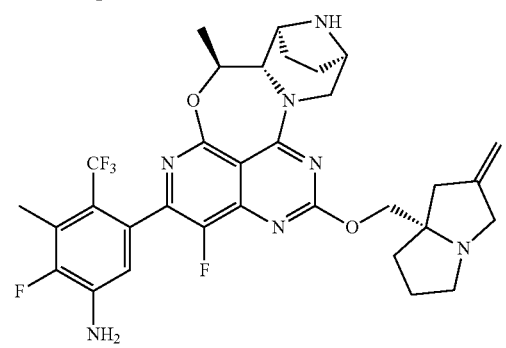
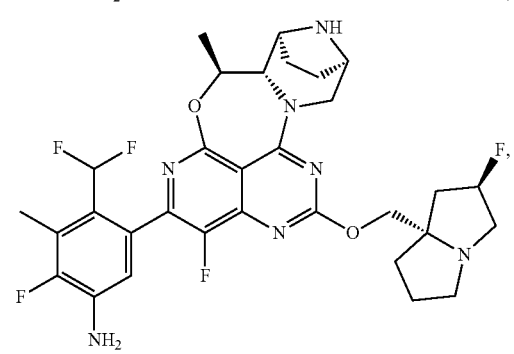
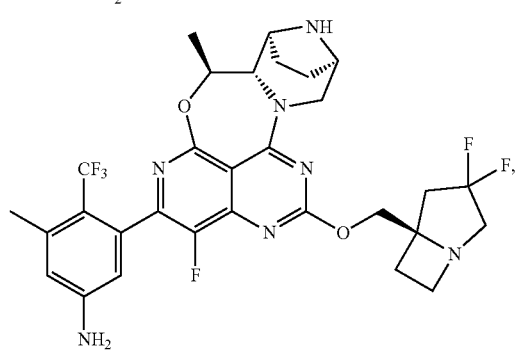

893
-continued
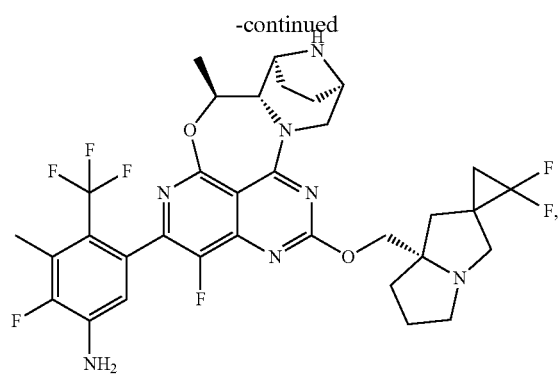
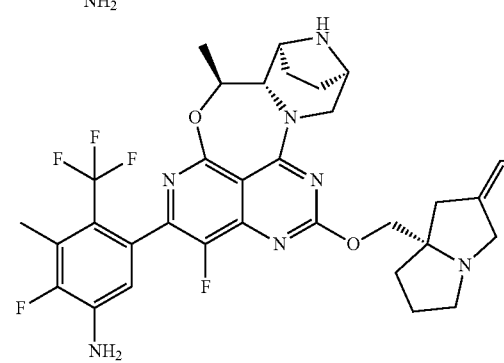
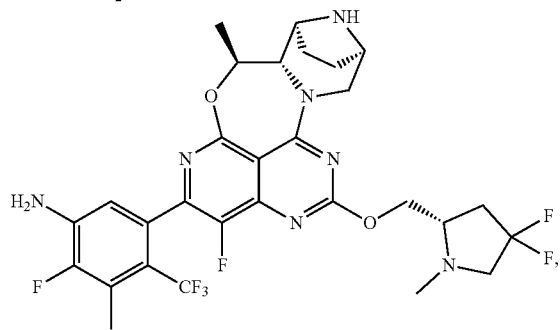
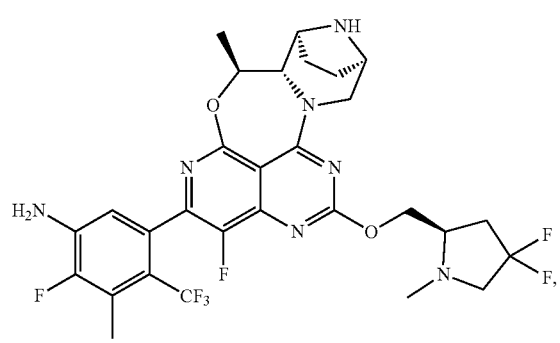
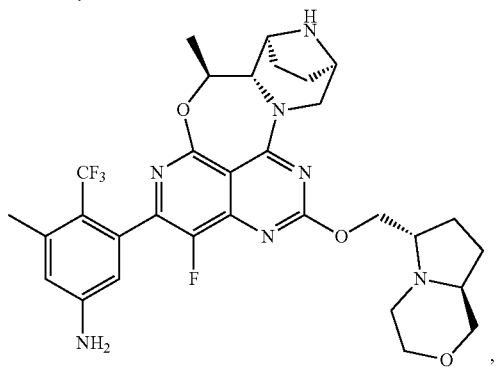
894
-continued
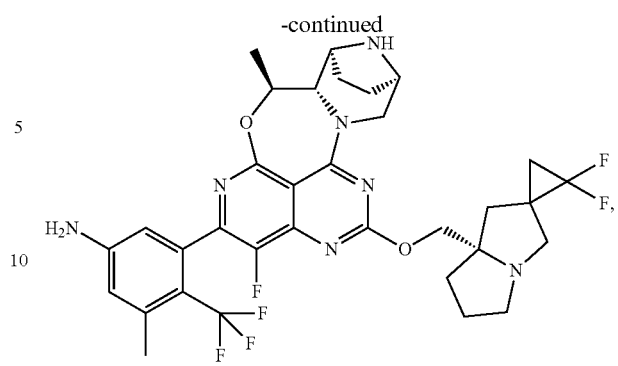
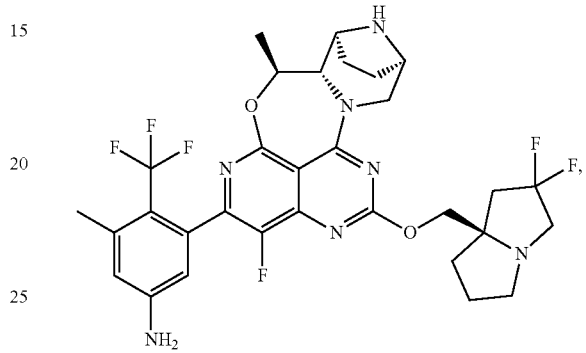
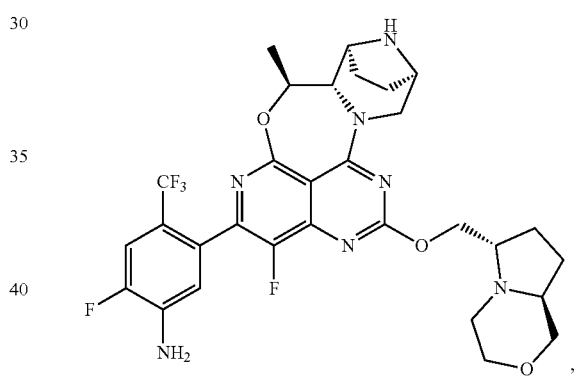
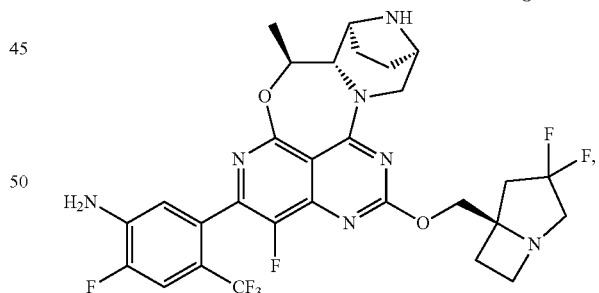
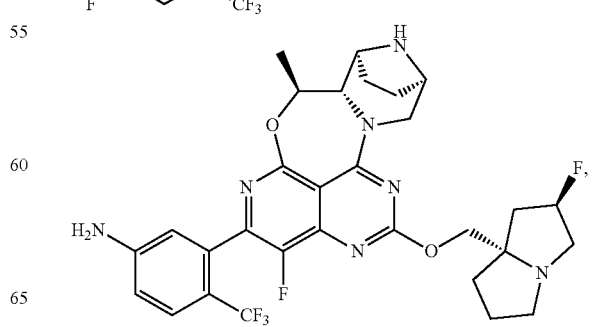

895
-continued
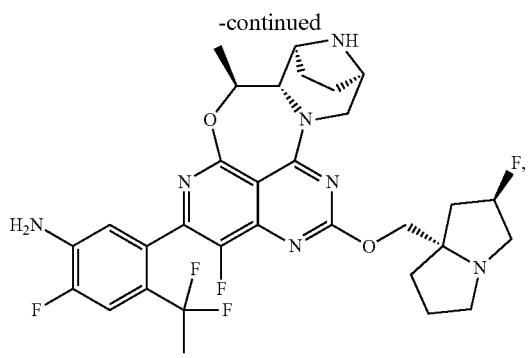
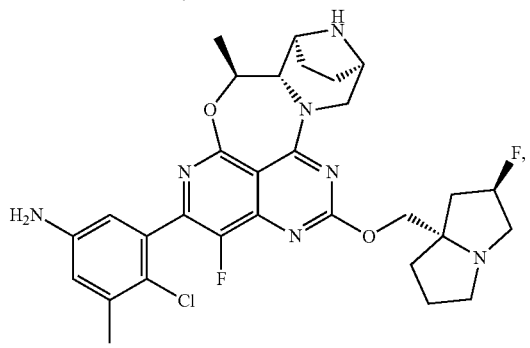
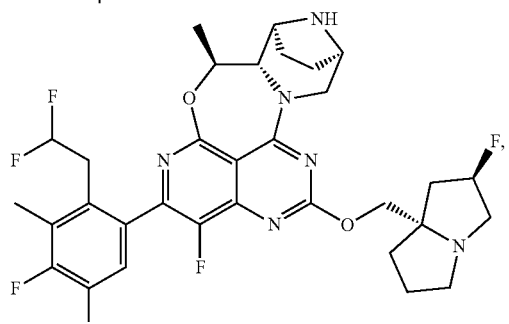
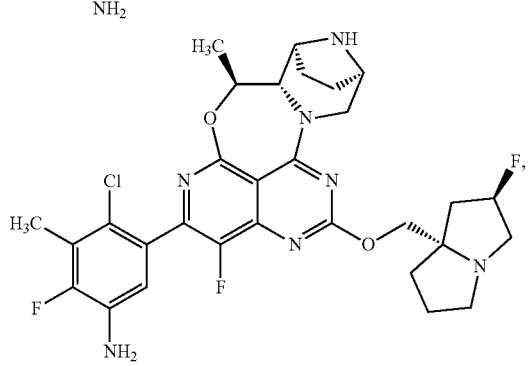
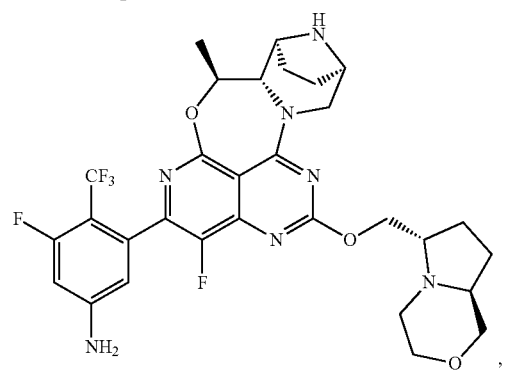
896
-continued
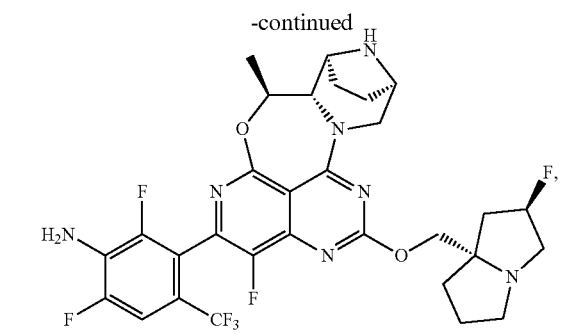
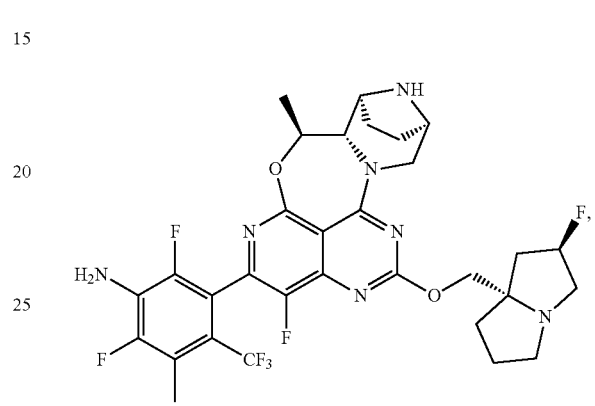
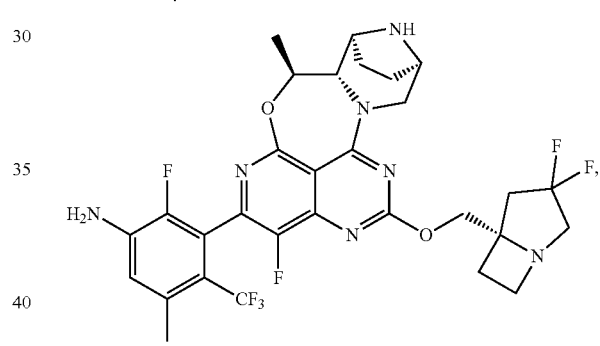
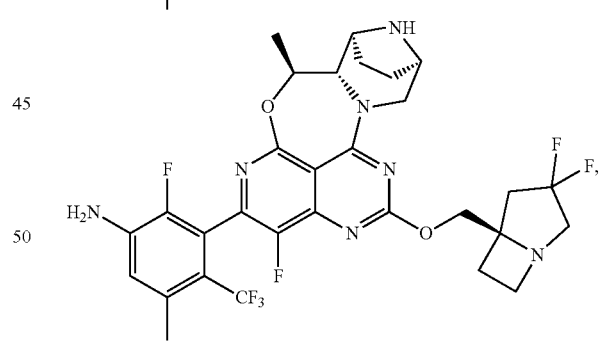
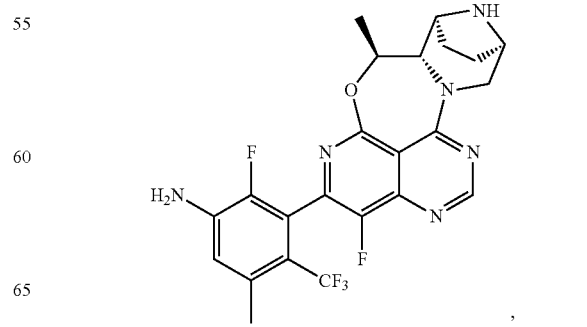

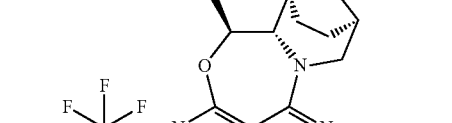

899
-continued
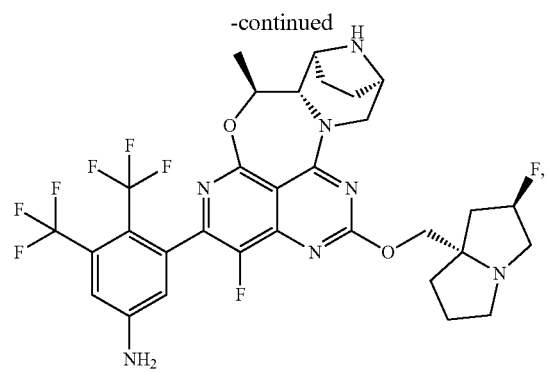
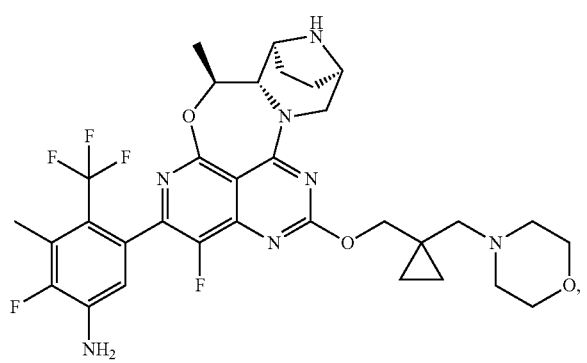
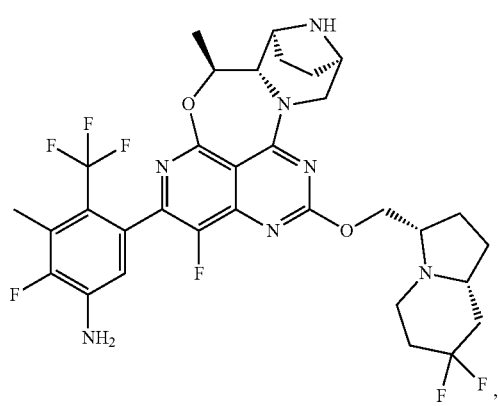
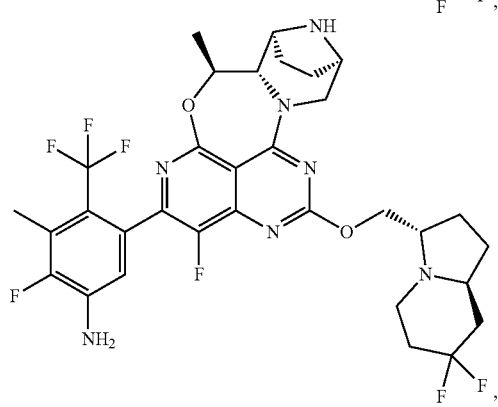
900
-continued
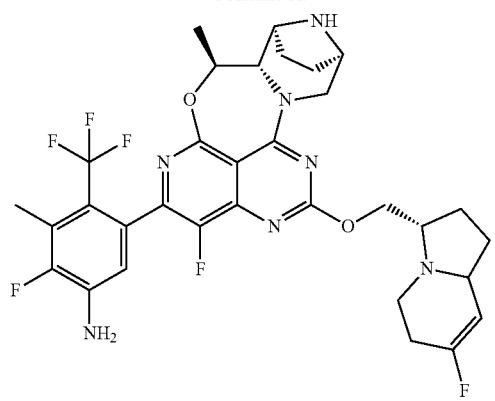
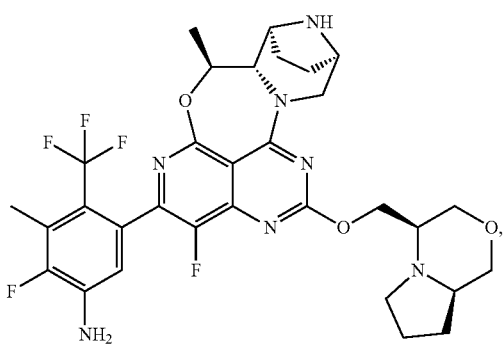
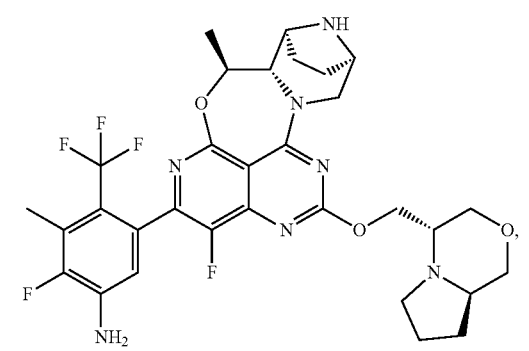
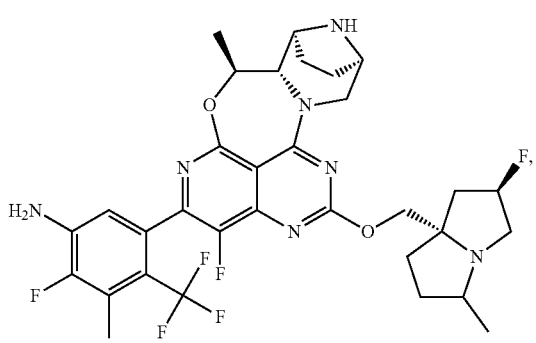

901
-continued
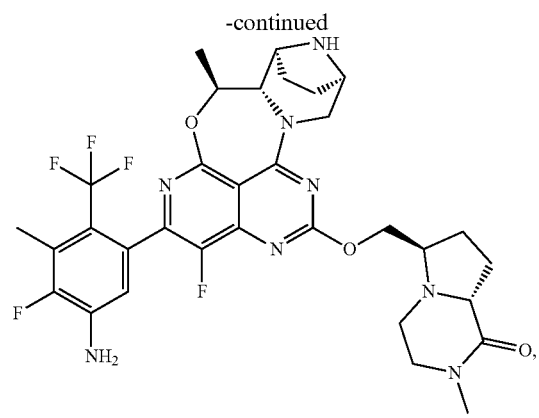
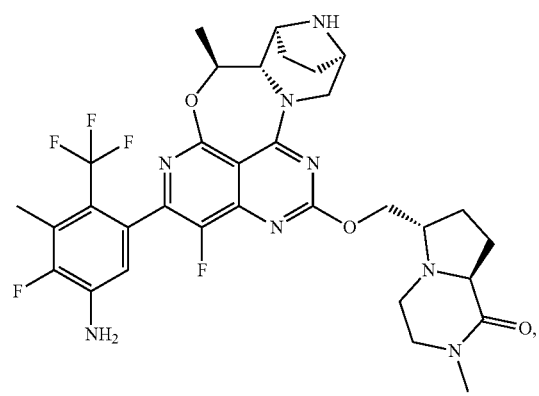
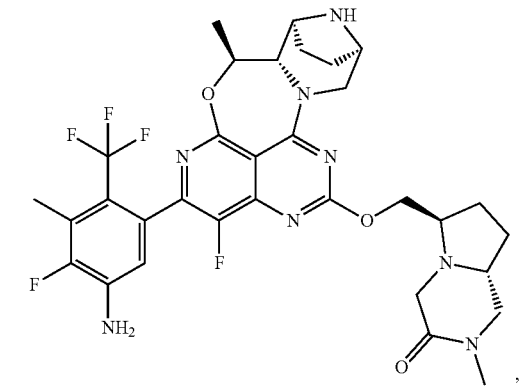
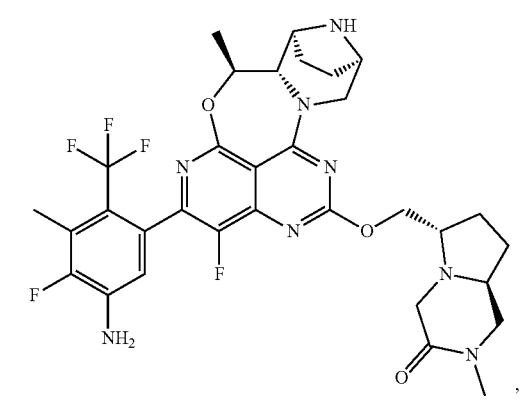
902
-continued
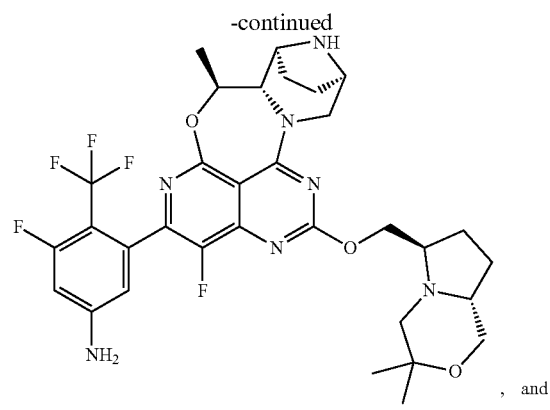
, and
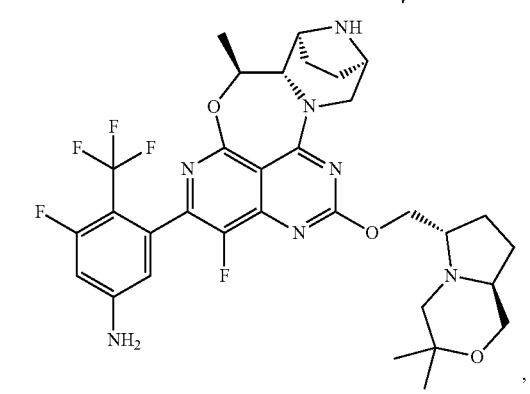
,
or an atropisomer, or pharmaceutically acceptable salt thereof.
16. The compound of claim 15, wherein the compound is selected from the group consisting of:
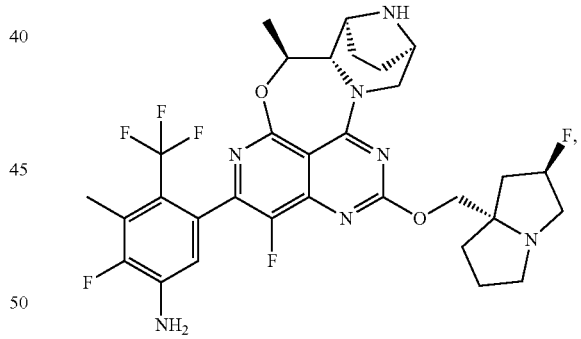
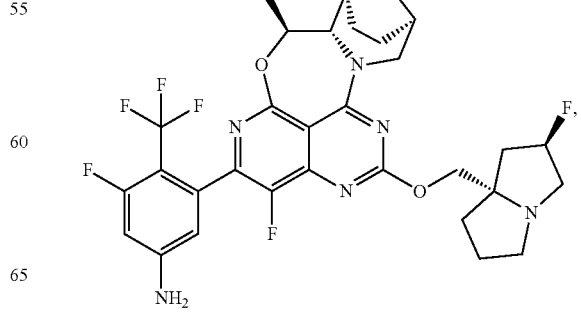

-continued
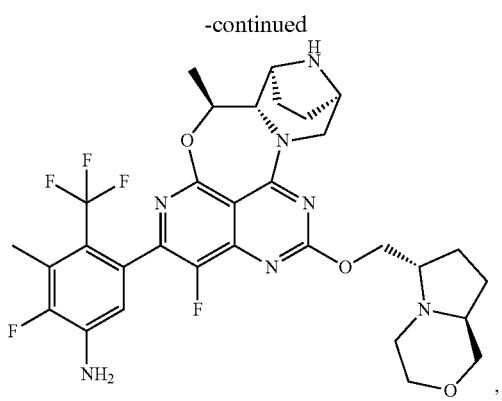
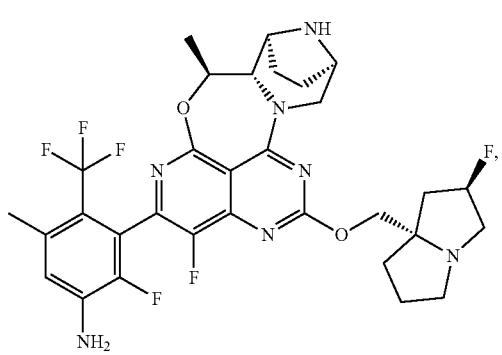 [SMILES: Cc1cc(N)c(F)c(-c2nc3c4c(nc(OC[C@@]56CCCN5C[C@H](F)C6)nc4c2F)N2C[C@H]4CC[C@H](N4)[C@H]2[C@H](C)O3)c1C(F)(F)F]
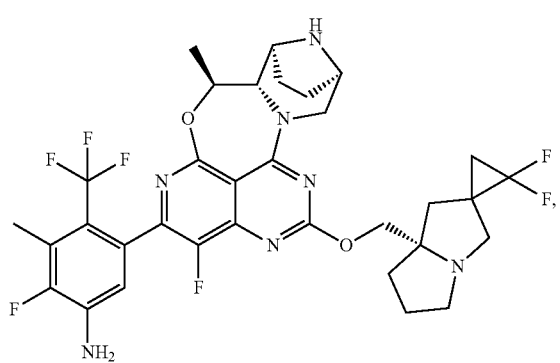
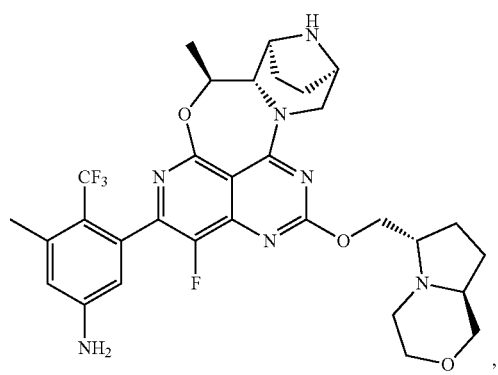
-continued
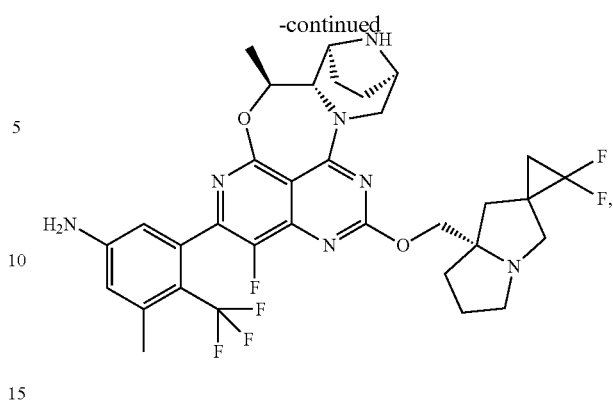
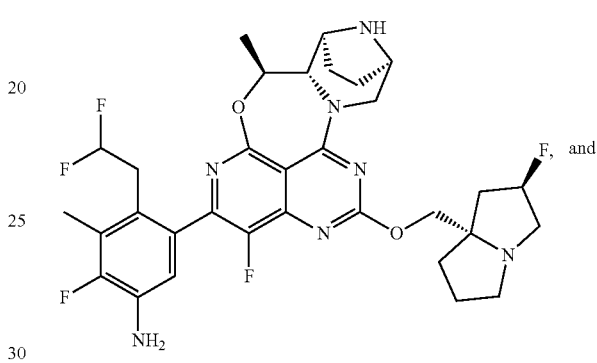
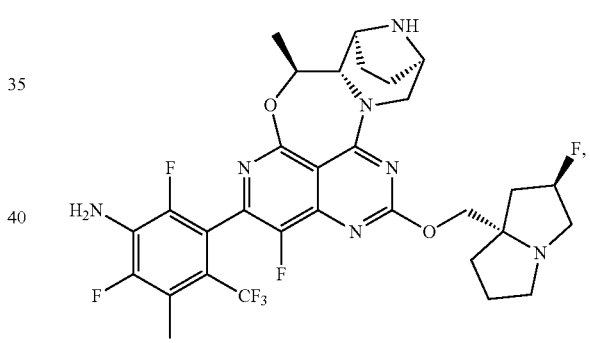
or an atropisomer, or pharmaceutically acceptable salt thereof.
17. The compound of claim 16, wherein the compound is:
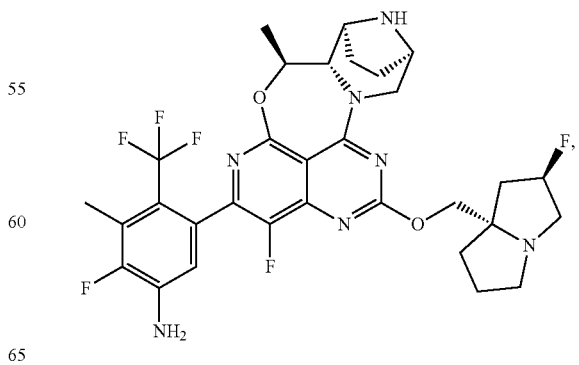
or a pharmaceutically acceptable salt thereof.

18. The compound of claim 16, wherein the compound is:

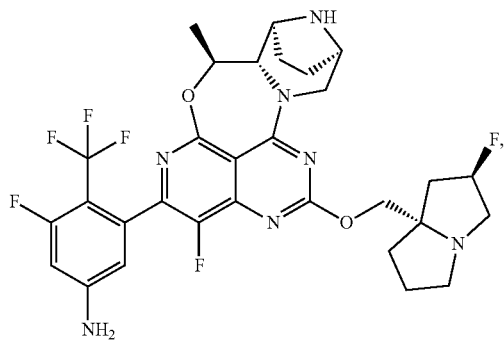

or a pharmaceutically acceptable salt thereof.

19. The compound of claim 16, wherein the compound is:

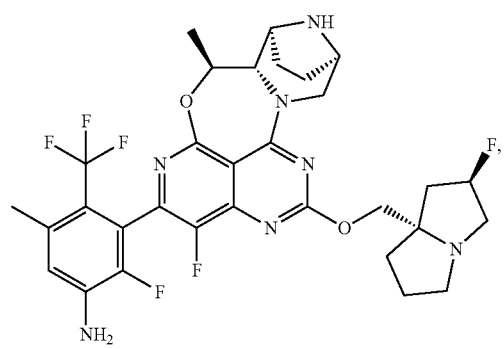

or a pharmaceutically acceptable salt thereof.

20. The compound of claim 16, wherein the compound is:

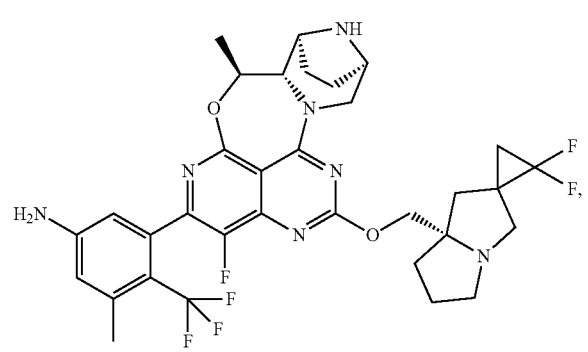 [SMILES: Cc1cc(N)cc(-c2nc3c4c(nc(OC[C@@]56CCCN5CC5(CC5(F)F)C6)nc4c2F)N2C[C@H]4CC[C@H](N4)[C@H]2[C@H](C)O3)c1C(F)(F)F]

or a pharmaceutically acceptable salt thereof.

21. The compound of claim 16, wherein the compound is:

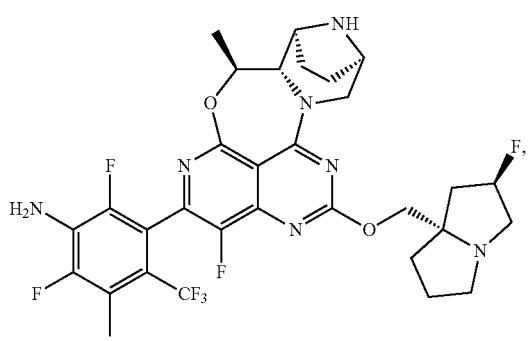 [SMILES: Cc1c(F)c(N)c(F)c(-c2nc3c4c(nc(OC[C@@]56CCCN5C[C@H](F)C6)nc4c2F)N2C[C@H]4CC[C@H](N4)[C@H]2[C@H](C)O3)c1C(F)(F)F]

or a pharmaceutically acceptable salt thereof.

22. A pharmaceutical composition comprising the compound of claim 16, or an atropisomer, or pharmaceutically acceptable salt thereof, and one or more pharmaceutically acceptable excipients.

23. The compound of claim 16, wherein the compound is:

24. The compound of claim 16, wherein the compound is:

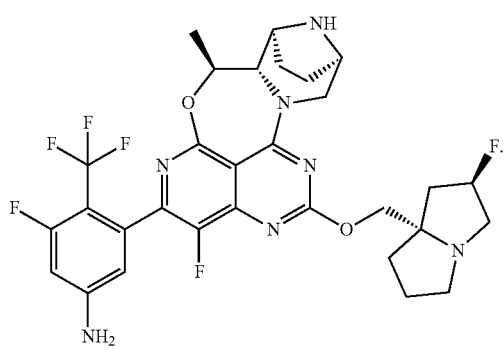 [SMILES: C[C@@H]1Oc2nc(-c3cc(N)cc(F)c3C(F)(F)F)c(F)c3nc(OC[C@@]45CCCN4C[C@H](F)C5)nc(c23)N2C[C@H]3CC[C@H](N3)[C@@H]12]

25. The compound of claim 16, wherein the compound is:

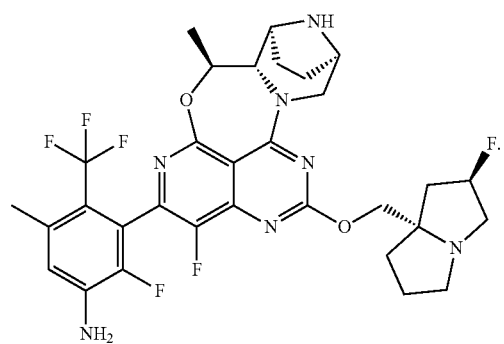 [SMILES: Cc1cc(N)c(F)c(-c2nc3c4c(nc(OC[C@@]56CCCN5C[C@H](F)C6)nc4c2F)N2C[C@H]4CC[C@H](N4)[C@H]2[C@H](C)O3)c1C(F)(F)F]

26. The compound of claim 16, wherein the compound is:

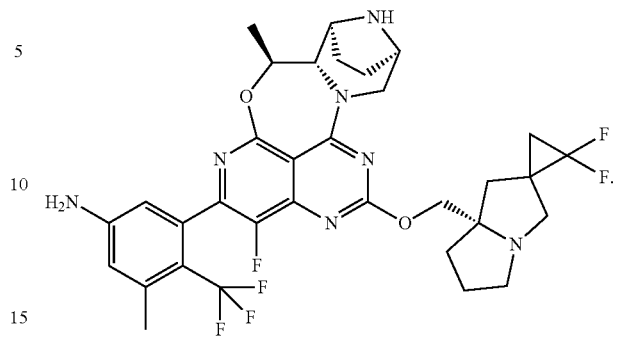

27. The compound of claim 16, wherein the compound is:

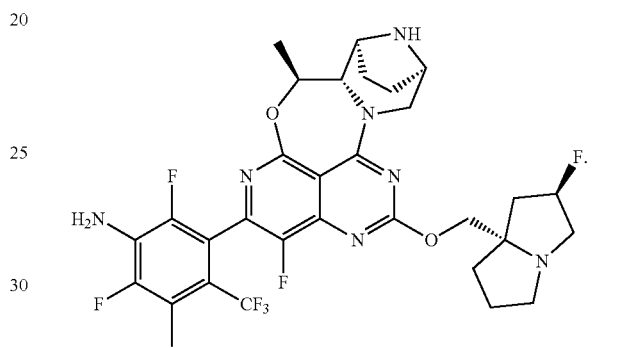

28. A pharmaceutical composition comprising the compound of claim 15, or an atropisomer, or pharmaceutically acceptable salt thereof, and one or more pharmaceutically acceptable excipients.

* * * * *